(12) United States Patent
Luo et al.

(10) Patent No.: US 8,877,900 B2
(45) Date of Patent: Nov. 4, 2014

(54) AX132 PCSK9 ANTAGONISTS

(75) Inventors: Peter Peizhi Luo, Lansdale, PA (US); Kevin Caili Wangr, Lansdale, PA (US); Pingyu Zhong, Blue Bell, PA (US); Mark Hsieh, Jenkintown, PA (US); Yan Li, San Jose, CA (US); Xinwei Wang, Germantown, MD (US); Feng Dong, Lansdale, PA (US); Andrei Golosov, Cambridge, MA (US); Yan Ni, Westfield, NJ (US); Weirong Wang, Harleysville, PA (US); Laurence B. Peterson, Westfield, NJ (US); Rose Cubbon, Fanwood, NJ (US); Sujata Sharma, Eagleville, PA (US); Jon Condra, Doylestown, PA (US); Jun Lu, Lansdale, PA (US); Gopalakrishnan Parthasarathy, Hillsborough, NJ (US); Stephen Soisson, Hillsborough, NJ (US); Noel Byrne, Doylestown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/503,729

(22) PCT Filed: Oct. 29, 2010

(86) PCT No.: PCT/US2010/054714
§ 371 (c)(1),
(2), (4) Date: Apr. 24, 2012

(87) PCT Pub. No.: WO2011/053783
PCT Pub. Date: May 5, 2011

(65) Prior Publication Data
US 2012/0213794 A1    Aug. 23, 2012

Related U.S. Application Data

(60) Provisional application No. 61/256,732, filed on Oct. 30, 2009, provisional application No. 61/323,148, filed on Apr. 12, 2010.

(51) Int. Cl.
*C07K 16/40* (2006.01)
*C07K 16/00* (2006.01)
*A61K 39/395* (2006.01)

(52) U.S. Cl.
USPC ............... 530/388.26; 530/387.1; 530/388.1; 424/146.1; 424/130.1

(58) Field of Classification Search
CPC .............. A61K 2300/00; A61K 45/06; A61K 39/3955; C07K 16/40; C07K 231/92
See application file for complete search history.

(56) References Cited

U.S. PATENT DOCUMENTS

| | | | |
|---|---|---|---|
| 5,977,322 A | 11/1999 | Marks et al. | |
| 8,080,243 B2 * | 12/2011 | Liang et al. | ................ 424/130.1 |
| 2002/0086014 A1 | 7/2002 | Korman et al. | |
| 2003/0040605 A1 | 2/2003 | Siegel | |
| 2003/0119038 A1 | 6/2003 | Bingham et al. | |
| 2004/0009178 A1 | 1/2004 | Bowdish et al. | |
| 2004/0009553 A1 | 1/2004 | Glucksmann et al. | |
| 2005/0118183 A1 | 6/2005 | Hoffee et al. | |
| 2005/0266008 A1 | 12/2005 | Graziano et al. | |
| 2006/0246506 A1 | 11/2006 | Pulli et al. | |
| 2006/0286112 A1 | 12/2006 | Kellermann et al. | |
| 2009/0169561 A1 | 7/2009 | Fischer et al. | |
| 2009/0232795 A1 | 9/2009 | Condra et al. | |
| 2009/0246192 A1 | 10/2009 | Condra et al. | |
| 2010/0068199 A1 | 3/2010 | Liang et al. | |
| 2010/0166768 A1 | 7/2010 | Sleeman et al. | |
| 2010/0233177 A1 | 9/2010 | Yowe et al. | |

FOREIGN PATENT DOCUMENTS

| | | |
|---|---|---|
| EP | 1 067 182 | 1/2001 |
| EP | 1 440 981 | 7/2004 |
| EP | 1 471 152 | 10/2004 |
| WO | WO 01/31007 | 5/2001 |
| WO | WO 01/34768 | 5/2001 |
| WO | WO 01/57081 | 8/2001 |
| WO | WO 01/77137 | 10/2001 |
| WO | WO 01/98468 | 12/2001 |
| WO | WO 02/14358 | 2/2002 |
| WO | WO 02/46383 | 6/2002 |
| WO | WO 02/090526 | 11/2002 |
| WO | WO 02/102993 | 12/2002 |
| WO | WO 02/102994 | 12/2002 |
| WO | WO 2009/026558 A1 | 2/2009 |
| WO | WO 2009/055783 A2 | 4/2009 |
| WO | WO 2009/100297 A1 | 8/2009 |
| WO | WO 2010/029513 A2 | 3/2010 |

OTHER PUBLICATIONS

Abifadel et al. (2003) *Nature Genetics* 34(2):154-156 "Mutations in PCSK9 cause autosomal dominant hypercholesterolemia".
Benjannet et al. (2004) *J Biol Chem.* 279(47):48865-75 "NARC-1/PCSK9 and its natural mutants: zymogen cleavage and effects on the low density lipoprotein (LDL) receptor and LDL cholesterol".
Cohen et al. (2006) *N. Engl. J. Med.* 354(12):1264-1272 "Sequence variations in PCSK9, low LDL, and protection against coronary heart disease".

(Continued)

*Primary Examiner* — Sharon Wen
(74) *Attorney, Agent, or Firm* — Sheela Mohan-Peterson

(57) ABSTRACT

Antagonists of human proprotein convertase subtilisin-kexin type 9 ("PCSK9") are disclosed. The disclosed antagonists are effective in the inhibition of PCSK9 function and, accordingly, present desirable antagonists for use in the treatment of conditions associated with PCSK9 activity. The present invention also discloses nucleic acid encoding said antagonists, vectors, host cells, and compositions comprising the antagonists. Methods of making PCSK9-specific antagonists as well as methods of using the antagonists for inhibiting or antagonizing PCSK9 function are also disclosed and form important additional aspects of the present disclosure.

9 Claims, 25 Drawing Sheets

(56) References Cited

OTHER PUBLICATIONS

Dubuc et al. (2004) *Arterioscler Thromb Vasc Biol.* 24(8):1454-9 "Statins upregulate PCSK9, the gene encoding the proprotein convertase neural apoptosis-regulated convertase-1 implicated in familial hypercholesterolemia".
Genbank Accession No. NP_777596.2, PRI Aug. 31, 2012 (Sharotri et al.).
Genbank Accession No. AX207686 PAT Aug. 31, 2001 (Chiang).
Genbank Accession No. NP_705793 ROD Nov. 25, 2012 (Fattori et al.).
Genbank Accession No. P59996 ROD Nov. 28, 2012 (Chiang).
Genbank Accession No. PH1492 ROD May 7, 1999 (Giusti and Manser).
Graham et al., (2007) *J. Lipid Res.* 48(4):763-767 "Antisense inhibition of proprotein convertase subtilisin/kexin type 9 reduces serum LDL in hyperlipidemic mice".
Lalanne et al. (2005) *J. Lipid Res.* 46:1312-1319 "Wild-type PCSK9 inhibits LDL clearance but does not affect apoB-containing lipoprotein production in mouse and cultured cells".
Leren (2004) *Clin. Genet.* 65(5):419-422 "Mutations in the PCSK9 gene in Norwegian subjects with autosomal dominant hypercholesterolemia".
Maxwell et al. (2003) *J Lipid Res.* 44(11):2109-19 "Novel putative SREBP and LXR target genes identified by microarray analysis in liver of cholesterol-fed mice".
Ouguerram et al. (2004) *Arterioscler. Thromb. Vasc. Biol.* 24:1448-1453 "Apolipoprotein B100 metabolism in autosomal-dominant hypercholesterolemia related to mutations in PCSK9".
Park et al. (2004) *J. Biol. Chem.* 279(48):50630-50638 Post-transcriptional regulation of low density lipoprotein receptor "protein by proprotein convertase subtilisin/kexin type 9a in mouse liver".
Rashid et al. (2005) *Proc Natl Acad Sci U S A.* 102(15):5374-9 "Decreased plasma cholesterol and hypersensitivity to statins in mice lacking Pcsk9".
Seidah, et al. (2003) *Proc Natl Acad Sci U S A.* 100(3):928-33 "The secretory proprotein convertase neural apoptosis-regulated convertase 1 (NARC-1): liver regeneration and neuronal differentiation".
Timms et al. (2004) *Hum. Genet.* 114(4):349-353 "A mutation in PCSK9 causing autosomal-dominant hypercholesterolemia in a Utah pedigree".

\* cited by examiner

```
          1234567890123456789012345678901234567890123456789012345678901234567890123456789012345678901234567890
          <-------FR1-------><--CDR1--><--X--FR2--X--><---CDR2---><--X------FR3------X----X--CDR3----X--FR4-->
          EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCAREGYGYYFDYWGQGTLVTVSSAS
                                                R.                                       G.V.S.         SEQ ID NO: 360
                              AT DFSYTRFSIS M    SV .DN RNRWHRVQCQVQSRV                S YKDYW.L N E
                              E   L    AQTFN    Q  YR SQ SPNQADS EDQF                    .FSA N  F
                              Q   Q    N AYT    S  Q KG TSQLEP          T                ANI   D
                              T        D YNH    L  S NY  S DR                            SHL
                                       T QQI    Q  D    Y YH                             HD.
                                       Y W                   S                           QSF
                                                             T                           DYA
```

EVQLLESGGGLVQPGGSLRLSCX1Y2SX3X4X5X6X7X8X9X10X11Y12WX13RQAPGKGLEX14X15GX16X17X18PX19X20X21X22X23X24X25X26X27X28X29X30X31
X32X33TISRDNSKNTLYLQMNSLRAEDTAVYYCX34RX35X36X57X38X39X40X41DX42WGX43GTLVTVSSAS SEQ ID NO: 591

```
                1234567890123456789012345678901234567890123456789012345678901234567890123456789012345678
                <----FR1------><---CDR1-----><---FR2---><--CDR2--><------FR3-------><-CDR3---><-FR4->
                EIVLTQSPATLSLSPGERATITCRASQYVGTYLMWYQQKPGQAPRLLIYDASNRATGIPARFSGSGSGTDFTLTISSLEPEDFAVYYCQVWDSSPPVAFGGGTKVEIK
                ...........................................................................  SEQ ID NO: 512
                                                                                                V
                             Q   I . S            A    A                                   AYGTNHAL. D
                             S                                                              G SNYASSM
                                                   S                                         N DDR I
                                                   T                                          TSG L
                                                                                                T
```

EIVLTQSPATLSLSPGERATITCX1ASQYX2GX3YLX4WYQQKPGQAPRLLIYDX5SNRAX6GIPARFSGSGSGTDFTLTISSLEPEDFAVYYCQX7X8X9X10X11
X12X

| Bin # | Amino acid residues in the bin |
|---|---|
| Bin 1 | 153-SIPW (SEQ ID NO: 579), 191-DHRE (SEQ ID NO: 580), 217-HRQAS (SEQ ID NO: 581), 237-RDA, 366-DIIGASSDCSTCFVS (SEQ ID NO: 582) |

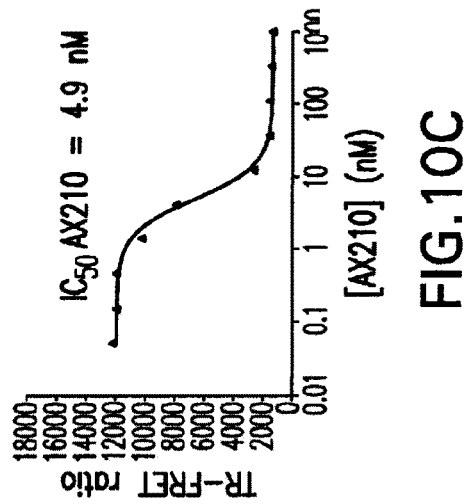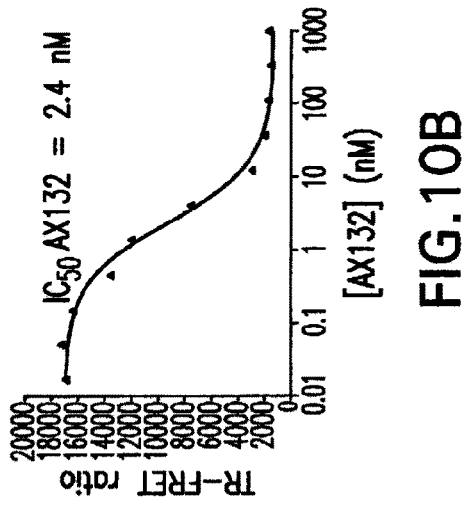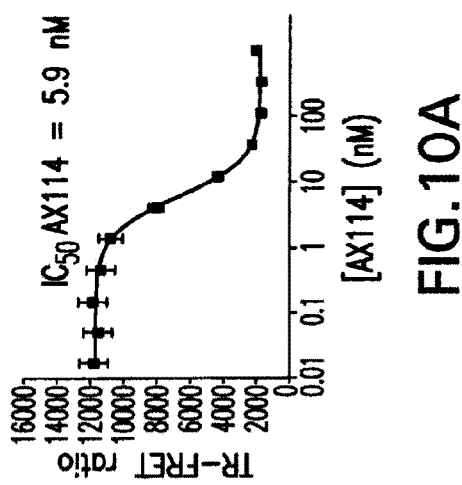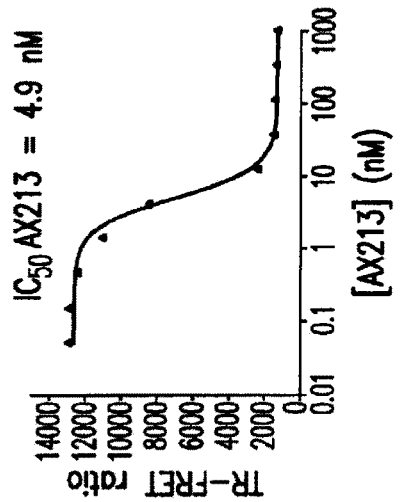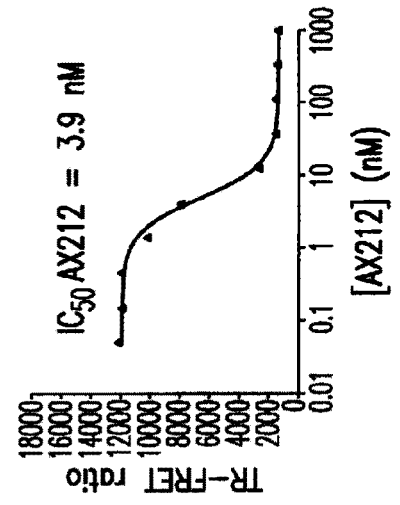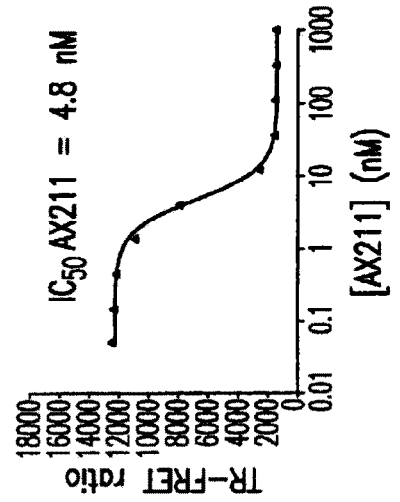

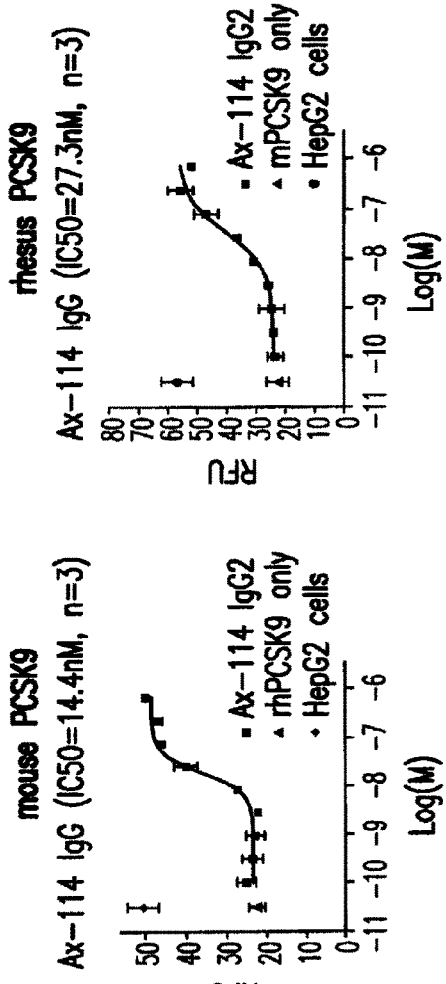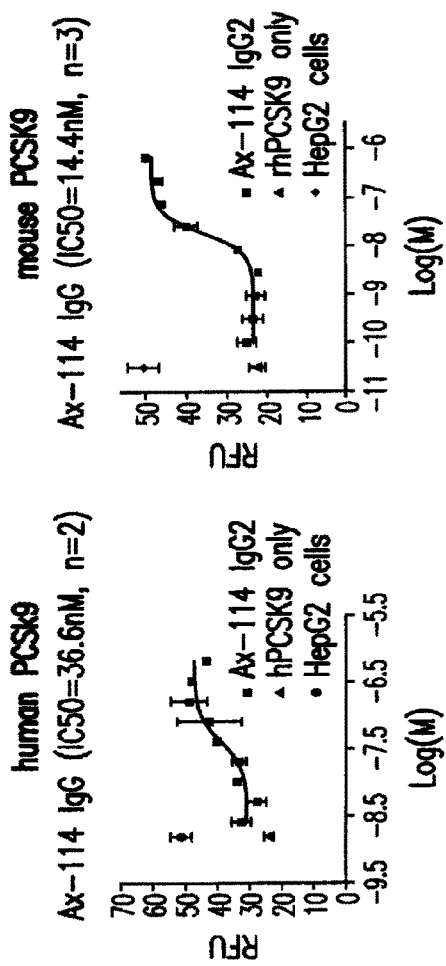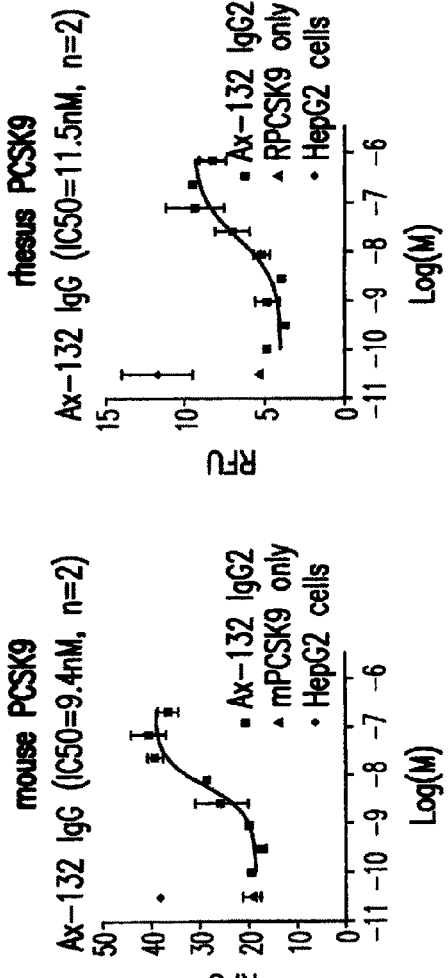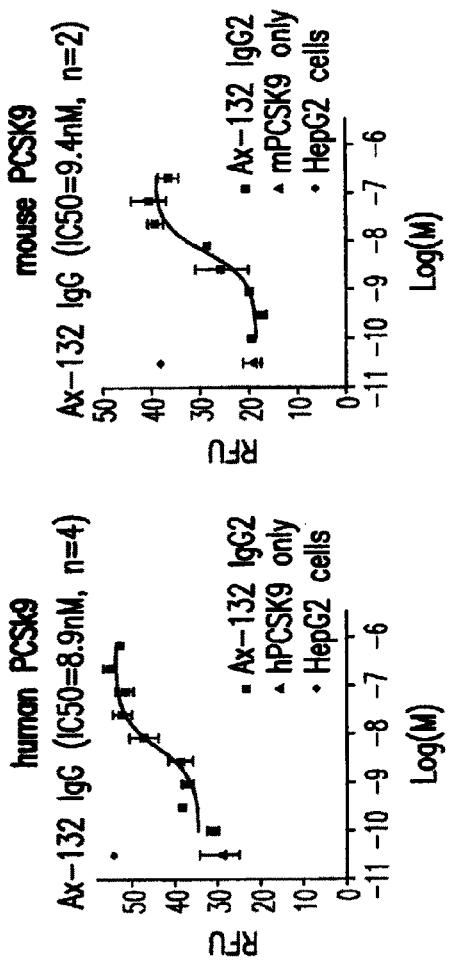
FIG. 11A  FIG. 11B  FIG. 11C
FIG. 11D  FIG. 11E  FIG. 11F

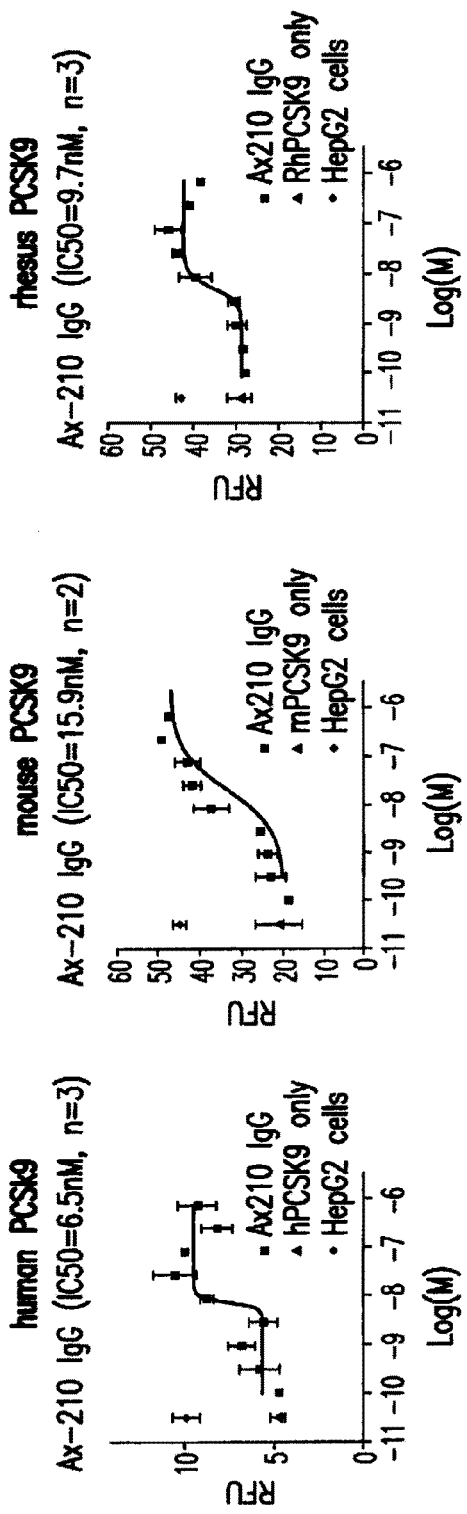
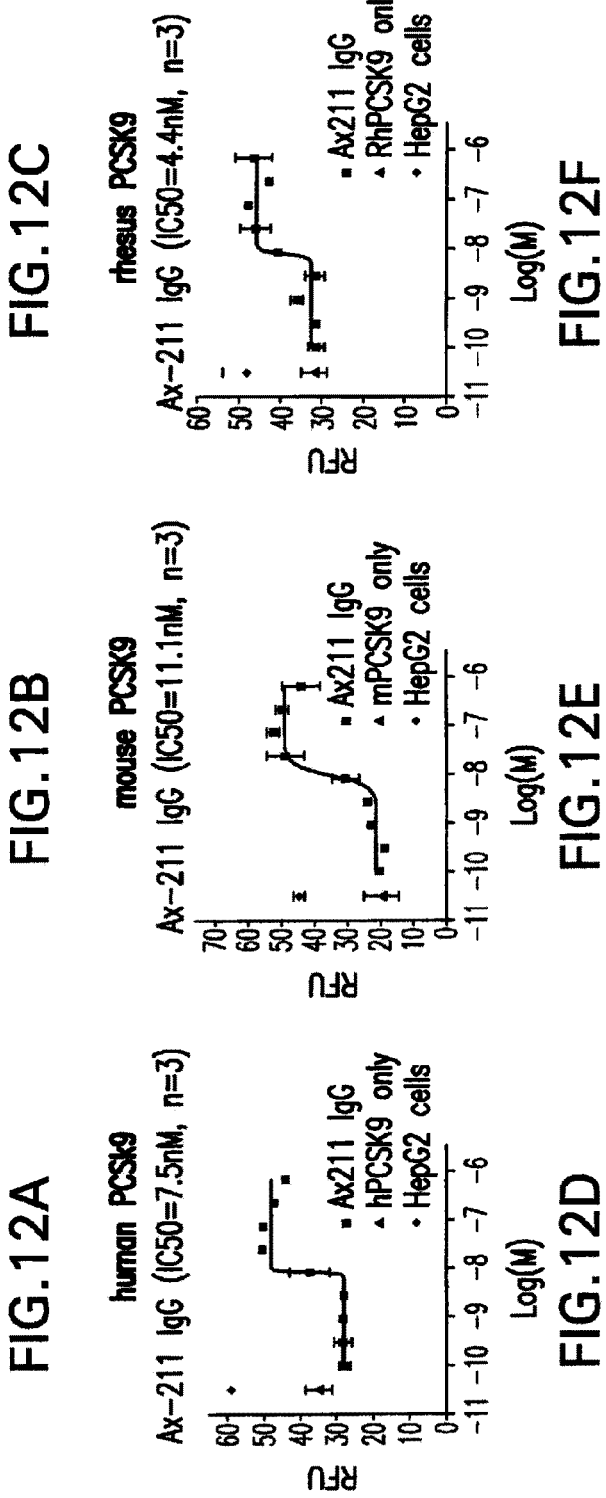
FIG. 12A, FIG. 12B, FIG. 12C, FIG. 12D, FIG. 12E, FIG. 12F

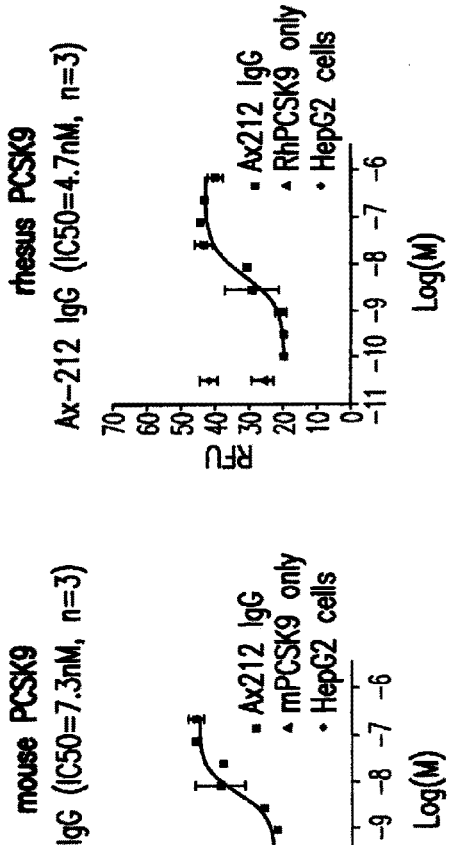
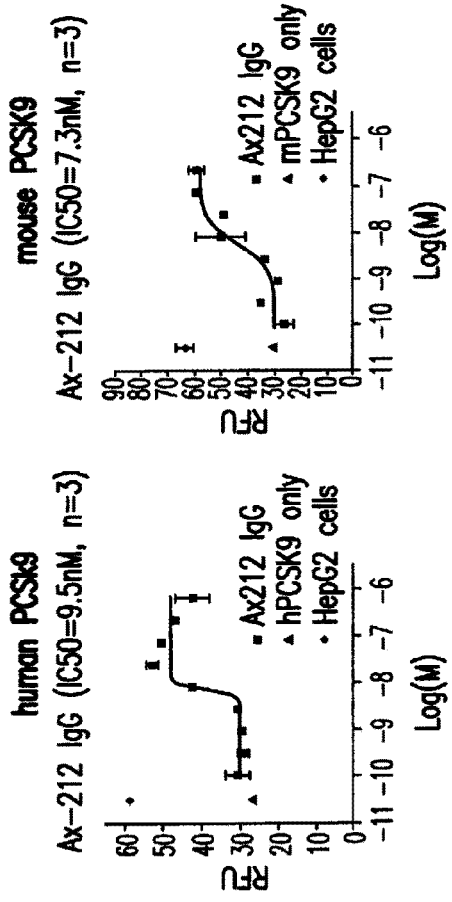
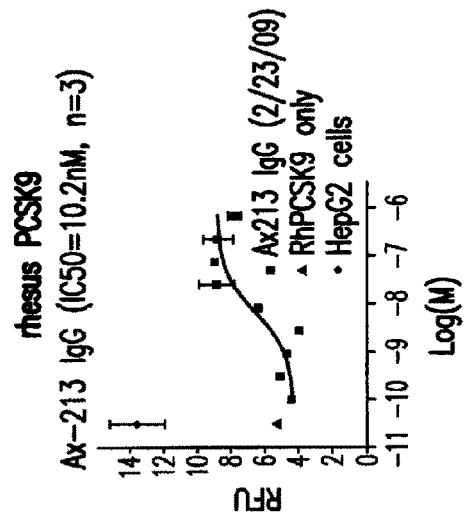
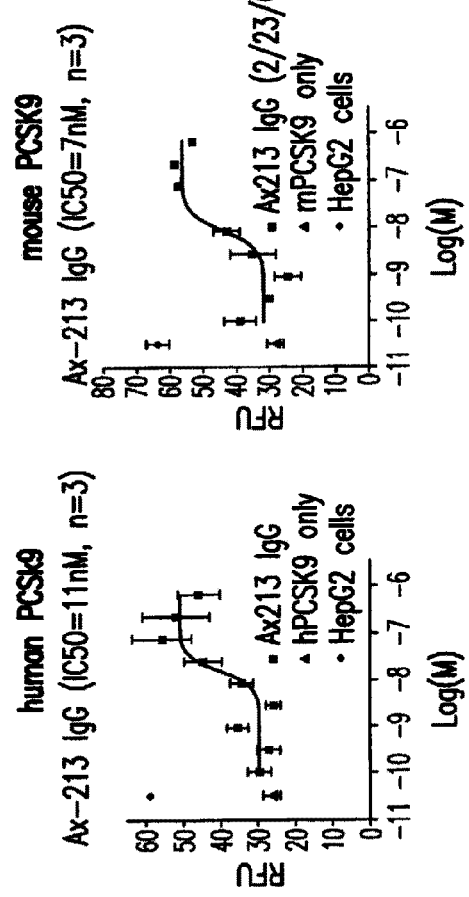

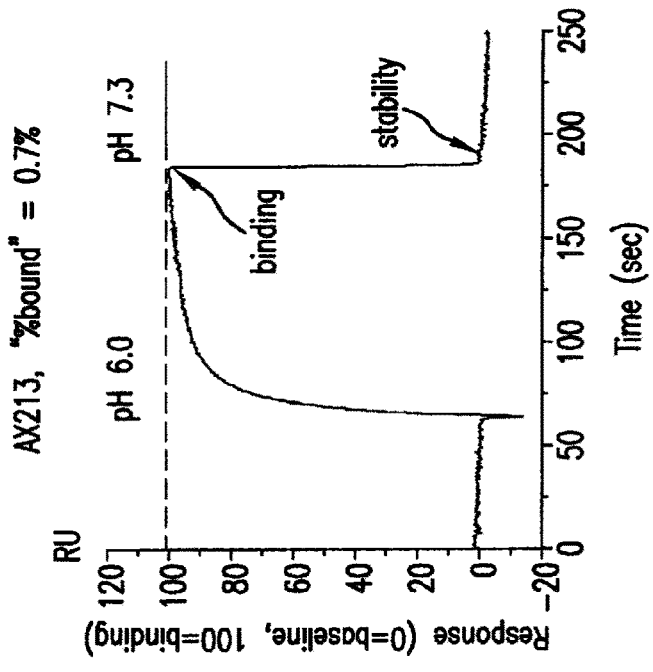
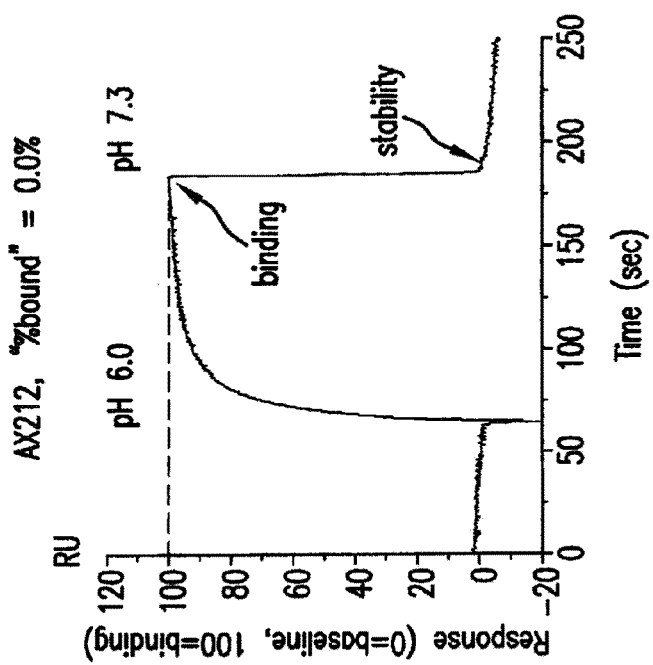

pMAB9-AX132
AM49 100.0%
lacP-35fa 100.0%

1   CGGCAACGCA ATTAATGTGA GTTAGCTCAC TCATTAGGCA CCCCAGGCTT TACACTTTAT GCTTCCGGCT CGTATGTTGT GTGGAATTGT GAGCGGATAA
    CGCGTTGCGT TAATTACACT CAGTCGAGTG AGTAATCCGT CGGGTCCGAA ATGTGAAATA CGAAGGCCGA GCATACAACA CACCTTAACA CTCGCCTATT

HindIII
p8 Leader 100.0%
BipI

101 CAATTTACCG GTCTTTAAG GAGGAATTAA AAATGAAAAA AGTCTTTAGT CCTCAAAGCC TCCGTAGCCG TTGCTACCCT CGTTCCGATG CTAAGCTTCG
    GTTAAATGGC CAAGAAATTC CTCCCTTAATT TTTACTTTT TCAGAAATCA GGAGTTCGG AGGCATCGGC AACGATGGGA GCAAGCTAC GATTCGAAGC

Xmal
Smal
VK3 FR1 100.0%
VK3 FR2 100.0%

201 CTGAAATCGT GCTGACCCAG TCTCCAGGCA CCCTGTCTCT GTCTCCCGGG GAACGTGCCA CCATCACCTG CCGTGCCTCT CAGTATGTCG GCAGCTACCT
    GACTTTAGCA CGACTGGGTC AGAGGTCCGT GGGACAGAGA CAGAGGGCCC CTTGCACGGT GGTAGTGGAC GGCACGGAGA GTCATACAGC CGTCGATGGA

VK3 FR3 100.0%

301 GAACTGGTAT CACCAGAAGC CAGGTCAGGC GCCAGTCCTG CTGATCTACG ACGCTCTAA CCGTGCCACC GGTATCCCAG CCCGTTCTC TGGTTCTGGT
    CTTGACCATA GTGGTCTTCG GTCCAGTCCG CGGTCAGGAC GACTAGATGC TGCGAGATT GGCACGGTGG CCATAGGGTC GGGCAAAGAG ACCAAGACCA

VK3 FR3 100.0%
BsiWI
VK3 FR4 100.0%
VK1 FR4 96.7%

401 TCTGGCACCG ACTTCACCCT GACCATCTCT TCTCTGGAAC CAGAAGACTT CGGCGTGTAC TACTGCCAGG TATGGGACAC CTCCCTGCCT GTGGTGTTCG
    AGACCGTGGC TGAAGTGGGA CTGGTAGAGA AGAGACCTTG GTCTTCTGAA GCCGCACATG ATGACGGTCC ATACCCTGTC GAGGGACGGA CACCACAAGC

VK3 FR4 100.0%
VK1 FR4 96.7%

501 GTGGTGGTAC CAAAGTGGAG ATCAAACGTA CGGTGGCTGC ACCATCTGTC TTCATCTTCC CGCCATCTGA TGAACAGTTG AAATCTGGAA CTGCCTCTGT
    CACCACCATG GTTTCACCTC TAGTTTGCAT GCCACCGACG TGGTAGACAG AAGTAGAAGG GCGGTAGACT ACTTGTCAAC TTTAGACCTT GACGGAGACA

FIG. 20A pMAB9-AX132

```
601  TGTGTGCCCTG CTGAATAACT TCTATCCCAG AGAGGCCAAA GTACACGTGA AGGTGGATAA CGCGCCTCCAA TCGGGTAACT CCCAGAGAG  TGTCACAGAG
     ACACAGGAC GACTTATTGA AGATAGGGTC TCTCCGGTTT CATGTCACCT TCCACCTATT GCGGGAGGTT AGCCATTGA GGGTCCTCTC ACAGTGTCTC
                                                       Blp I                                    SQ37 100.0%

701  CAGGACAGCA AGAGACCAC CTACAGCCTC AGCAGCAGCT TGAGCGCTGAG CAAAGCAGAC ACAAAGTCTA CGCCTGCGAA GTCACCCATC
     GTCCTGTCGT TCCTGTCGTG GATGTCGGAG TGTCGTCGA AGCTCGCGAC GTTTCGTCTG ATGCTCTTTG TGTTTCAGAT GCGGACGCTT CAGTGGGTAG
                                                                                                 p3 leader 100%

801  AGGGCCTGAG GACGGGGCAG CTGCCCGTC ACAAAGAGCT TCAAACGGAG AGAGTGTTGA TAAGGCGCGC CACAATTTCA CAGTAAGGAG GTTTAACTTA TGAAAAAATT
     TCCCGGACTC GACGGGCCAG TGTTCTCTGA AGTTGCTCCG TCTCACAACT ATTCCGCGCG GTGTTAAAGT GTCATTCCTC CAAATTGAAT ACTTTTTAA
                        p3 leader 100.0%                                                        VH3FR1 97.3%

901  ATTATTGGCA ATTCCTTTAG TGTGTCCTTT CTATTCTCAC TCCGAAGTGC AATTGCTGGA ATCTGCTGGT GGTCTGGTGT AGCCAGGTGG TTCTCTGCCT
     TAATAAGCGT TAAGGAAATC AACAAGGAAA GATAAGAGTG AGGCTTCACG TTAACGACCT TAGACGACCT ATCACGACCA CCAGACCACA TCGGTCCACC AAGAGACGGA
        VH3 FR1                                                                 MfeI               VH3 FR2 100.0%

1001 CTGTCTTGCA AGGGTCTCTG TTACCCTTC TTACACCTTC TCTCTTACG GGATGTACTG GCACCAGGTA AGGGTCTGGA ATGGATGGGT TGGATCGACC
     GACAAGACGT TCCCGAGACC AATGTCGAAG AGAAGAATGC CCTACATGAC CGTGGTCCAT TCCCAGACCT TACCTACCCA ACCTAGCTGG
                                                                        VH3 FR3 99.1%

1101 CAGGACAGCGG TGGCACCAAG TACAACGAAG AGTTCAAGGG TAAGGCCACC ATCTCCAGAG ACAACTCTAA GAACACCCTG TACTTGCAGA TGAACGTCT ACTTGAGAGA
     GTCCTGTCGCC ACCGTGGTTC ATGTTGCTTC TCAAGTTCCC ATTCCGGTGG TAGAGGTCTC TGTTGAGATT CTTGTGGGAC ATGAAGTCT ACTTCTCT
                                                        VH3 FR3                                         XhoI
                                                                                                 VH3 FR4 100.0%

1201 GCCTCCGAG GACACTGCAG TGTACTACTG CGGTACGGTT ACTACTTCGA CGTTACGGGT CAGGGTACGC TGGTGACTGT CTGGAGCGCA
     CGGAGGCTC CTGTGACGTC ACATGATGAC GCCATGCCAA TGATGAAGCT GCAATGCCCA GTCCCATGCG ACCACTGACA GACCTCGCGT

1301 AGCACCCAAAG GCCCATCGGT ATTCCCCCTG GCACCCTCCT CCAAGAGCAC CTCTGGGGGC ACAGCGGCGC TGGGCTGCCT GGTCAAGGAC TACTTCCCCG
     TCGTGGGTTTC CGGGTAGCCA TAAGGGGGAC CGTGGGAGGA GGTTCTCGTG GAGACCCCG TGTCGCCGGGG ACCGACGGA CCAGTTCCTG ATGAAGGGGC
                            SQ3 100.0%
```

FIG. 20B pMAB9-AX132
ApaLI

```
1401 AGCGCGTGAC GGTGTCGTCG AACTCAGGCG CCGGCTGCAC ACCTTCCCGG CTGTCCTACA GTCCTCAGGA CTCTACTCCC TCAGCAGCGT
     TCCGCCACTG CCACAGCAAC TTGAGTCCGC GAGACGTGTG GCCCACGTG TGAAGGGGCC GACACGGATGT CAGGAGTCCT GAGATGAGGG AGTCGTCGCA
     SQ35 100.0%
1501 CGTGACTGTC CCCTCGACGA GCTTGGGCCA CCAGACCTAC ATCTCGAACG TGAATCACAA GCCCAGCAAC ACTAAGGTGG ACAAGAAAGT TGAGCCCAAA
     CCACTGACAC GGGAGGTCGT CGAACCCGGT GGTCTGGATG TAGAGCTTGC ACTTAGTGTT CGGGTCGTTG TGATTCCACC TGTTCTTTCA ACTCGGGTTT
                                                        HA Tag 100.0%                        His Tag 100.0%
1601 TCTTGTGACA AAACTCACAC AGCGCGCGCT TATCCATACG AGGTACCAGA CTACCGCAGGA GGTCATCACC ATCATCACCA TTAATGAACC TGTGAAGTGA
     AGAACACTGT TTTGAGTGTG TCGCGCGCGA ATAGGTATGC TCCATGGTCT GATGGTCCT CCAGTAGTGG TAGTAGTGGT AATTACTTGG ACACTTCACT
1701 AAAATGGCGC AGATTGTGCC ACATGATCAT TGGGCTGCAA AACAAAACGG CCCTCGTGTCA GGAAGCCGCT TTTATCGGGT AGCCTCACTG CCCGCTTTCA
     TTTTACCGCG TCTAACACGC TGTACTAGTA ACCCGACGTT TTGTTTTGCC GGGAGACAGT CCTTCGGCGA AATAGCCCA TCGGAGTGAC GGGCGAAAGG
1801 AGTCGGGAAA CCTGCTGCGC GTCACAGCAC GTCGACGTAG TCACTTAGCC CGGTCGCGCG CCCTCTCCGC CAAACCCATA ACCCTCGGTC CCACCAAAA GAAAAGTGGT
     TCAGCCCTTT GGACAGCACG GTCAGCTGAC AGTGAATCGG GCAGAATCGG GGGAGAGGCG GGGAGAGGCG GTTTGCCTAT TGGGAGCCAG GGTGGTTTTT CTTTTCACCA
1601 GTGACACGGG CAACAGCTGA TTGCCCTTCA CCGGCTGCCC CTGAGAGAGT TGCACCAAGC GGTCCAGCCT GCTTTGCCCC AGCAGCGGAA AATCCTGTTT
     CACTGTGCCC GTTGTCGACT AACGGGAAGT GGCGGACCGG GACTCTCTCA AGTCGTTCG CCAGGTCGGA CGAAACGGGG TCGTCGCCTT TTAGGACAAA
2001 GATGGTGGTC AGCGGCGGGA TATAACATGA GCTGTCCTGG GTATCGTCGT ATCCACTACG CGGAGATGTCC GCACCAAGGC GAAGCCGGAA CTCGGTAATG
     CTACCACCAG TCGCCGCCCT ATATTGTACT CGACAGGACC CATAGCAGCA TAGGGTGATG GCTCTACAGG GGTGGTTGCG CGTCCGGCCT GACCCATTAC
2101 GCACCGCATTG CGCGCAGCGC TTGGCAACCA GCATCGCACT CATCTGATCG GTAGCGTGAG CCCTTGCTCA GCATTCGCAT CGTAAACGTA CCAAACAACT TTTGGCCTGT
     CGTGCGTAAC GCGGGTGCG AACCGTTGGT CGTAGCGTGA CGTAGCGTCA CCCTTGCTCA GGGAGTAAGT CGTAAACGTA CCAAACAACT TTTGGCCTGT
2201 TGGCACTCCA GTCGCCTGCA GCGCCCGAAG CGATTTGCTA TCGGCTGAAT TGATTCGGA GTGAGATATT TATGCGAGCC AGCCAGACGC AGACAGGCCG AGAACGAACT
     ACCCTGAGGT CAGCGGAAGG GCAAGGCGAT AGCCGACTTA ACCGACGGAT CACTCTATAA ATACCGTCGG TCGGTCTGCG TCTGGGCGGC TCTGTCTTGA
2301 TAATGCGCCA GCTAACAGCG CGATTTGCTG GTGCCCAAT CGACCAGAT GCTGCCACCC CAGTCCGGTA CGGTCCGGTA CGGTCCTGGT GGCAGGAGTA CCCTCTTTA AATACTGTTG
     ATTACCGGT CGATTCTGCG GCTAAAGCGAC CACGGGGTTA CCCTGGTCA CATTAGTGCA GTCAGCGCAT GCCAGGAGTA CCCTCTTTA TTATGACAAC
2401 ATGGTGTCT GGTCAGAGAC CCAGTCTCTG AGCAGCTTCC GGTCAGGAA CATTAGTGCA GGCAGCTTCC ACAGAATTGA CATCCTGGTC ATCCAGCGGA TAGTTAATAA
     TACCCACAGA CCAGTCTCTG GTAATCACCTT GTAATCACGT CCTTGGAAGG GCCTTGGAAGG TGTCGTTATC CATCGCTATC TAGTGCGCCT ATCAATTATT
```

FIG. 20E pMAB9-AX132

```
5001 AAGTTGGCCC AGGGCTTCCC GGTATCAACA GGGACACCAG GATTTATTTA TTCTGCGAAG TGATCTTCCG TCACACGGTAT TTATTCGGTC GAAAAGGATC
     TTCAACCGGG TCCCGAAGGG CCATAGTTGT CCCTGTGGTC CTAAATAAAT AAGACGCTTC ACTAGAAGGC AGTGTCCATA AATAAGCCAG CTTTTCCTAG
5101 TAGGTGAAGA TCCTTTTTGA TAATCTCATG ATTAGAGTAC CTAACGTGA GTTTTCGTTC CACTGACGT CAGACGCCCT AGAAAAGATC AAAGGATCTT
     ATCCACTTCT AGGAAAAACT ATTAGAGTAC CGGCTAATCT CAAAGCAAG GAATTGCACT CAAAAGCAAG GTGACTGCA TCTTTTCTAG TTTCCTAGAA
5201 CTTGAGATCC TTTTTTTTCTG CGCGTAATCT GCTGCTTGCA AACAAAAAAA CCACCGCTAC CAGCGGTGGT TTGTTTGCCG GATCAAGAGC TACCAACTCT
     GAACTCTACG AAAAAAAACAC GCGCATTAGA CGACGAACGT TGTTTTTTTT GGTGGCGATG GTCGCCACCA AACAAACGGC CTAGTTCTCG ATGGTTGAGA
5301 TTTTCCGAAG GTAACTGGCT TCAGCAGAGC GCAGATACCA AATACTGTTC TTCTAGTGTA GCCGTAGTTA GGCCACCACT TCAAGAACTC TGTAGCACCG
     AAAAGGCTTC CATTGACCGA AGTCGTCTCG CGTCTATGGT TTATGACAAG AAGATCACAT CGGCATCAAT CCGGTGGTGA AGTTCTTGAG ACATCGTGGC
5401 CCTACATACC TCGCTCTGCT AATCCTGTTA CCAGTGGCTG CTGCAGTGGC GATAAGTCG TGTCTTACCG GGTTGGACTC AAGACGATAG TTACCGGATA
                           ApaLI
     GGATGTATGG ACGAGACGA TTAGGACACA GTCAGCGGAC GACGGTCACC GCTATTCAGC ACAGAATGGC CCAACCTGAG TTCTGCTATC AATGGCCTAT
5501 ACGGGCAGCG GTCGGGCTGA ACGGGGGGTT CGTGCACACA GCCCAGCTTG GAGCGAACGA CCTACACCGA ACTGAGATAC CTACAGCGTG AGCTATGAGA
     TGCCCGTCGC CAGCCCGACT TGCCCCCCAA GCACGTGTGT CGGGTCGAAC CTCGCTTGCT TGACTCTATG GATGTCGCAC TCGATACTCT
5601 AAGCGCCACG CTTCCCGAAG GGAGAAAGGC GGACAGGTAT CCGGTAAGCG GCAGGGTCGG AACAGGAGAG AGCTTCCAGG GGGAAACGCC
     TTCGCGGTGC GAAGGGCTTC CCTCTTTCCG CCTGTCCATA GGCCATTCGC CGTCCCAGCC TTGTCCTCTC GGTGCTCCG TGAAGGTCC CCCTTTGCGG
5701 TGTATCTTT ATAGTCCTGT CGGGTTTCGC CACCTCTGAC TTGAGCGTCG ATTTTTGTGA TGCTCGTCAG GGGGGCGGAG CCTATGAAA AACCCCAGCA
     ACCATAGAAA TATCAGGACA GCCCAAAGCG GTGGAGACTG AACTCGCAGC TAAAAACACT ACGAGCAGTC CCCCGCCTC GGATACTTT TTGGGGTCGT
5801 ACGGGGCTT TTTTACGGTTC CTGGCCTTT CTGACCCGC AACGACGGAA ACGACCAGCC AAGAAAGGAC GCAATAGGGG ACTAAGACAC CTATTGGCAT AATGGCGGAA
     TGCCCCCGAA AAAATGCCAAG GACCGGAAA GACTGGGCG CGCCGACT TGCTGGTCGG TTCTTTCCTG CGTTATCCCC TGATTCTGTG GATAACCGTA CGCCTCCCC
5901 TGAGTGAGCT GATACCGCTC GCCGCAGCCG AACGACCGAG CAGTGACGCA GGAAGCGGAA GAGCGCCCAA TACGCAAACC GCCTCTCCCC CGGAGAGGG
     ACTCACTCGA CTATGGCGAG CGGCGTCGGC TTGCTGGCTC GTCACTGCGT CACTGCGT CCTTCGCCTT ATGCGTTTGG CGGAGAGGG
6001 GCGCGTTGGC CGATTCATTA ATGCACCTGGC TTCCGCGACT GAAAGCGGGC AGTGA
     CGCGCAACCG GCTAAGTAAT TACGTCGACC GTGCTGTCCA AAGGCGCTGA CTTTCGCCCG TCACT
```

AX132 PCSK9 ANTAGONISTS

CROSS-REFERENCE TO RELATED APPLICATIONS

This application is a 371 of PCT/US2010/054714, filed Oct. 29, 2010, which claims benefit of U.S. provisional application, U.S. Ser. No. 61/256,732, filed Oct. 30, 2009, and claims benefit of U.S. provisional application, U.S. Ser. No. 61/323,148, filed Apr. 12, 2010.

STATEMENT REGARDING FEDERALLY-SPONSORED R&D

Not Applicable.

REFERENCE TO MICROFICHE APPENDIX

Not Applicable.

BACKGROUND OF THE INVENTION

Proprotein convertase subtilisin-kexin type 9 (hereinafter called "PCSK9"), also known as neural apoptosis-regulated convertase 1 ("NARC-1"), is a proteinase K-like subtilase identified as the $9^{th}$ member of the secretory subtilase family; see Seidah et al., 2003 PNAS 100:928-933. The gene for PCSK9 localizes to human chromosome 1p33-p34.3; Seidah et al., supra. PCSK9 is expressed in cells capable of proliferation and differentiation including, for example, hepatocytes, kidney mesenchymal cells, intestinal ileum, and colon epithelia as well as embryonic brain telencephalon neurons; Seidah et al., supra.

Original synthesis of PCSK9 is in the form of an inactive enzyme precursor, or zymogen, of ~72-kDa which undergoes autocatalytic, intramolecular processing in the endoplasmic reticulum ("ER") to activate its functionality. This internal processing event has been reported to occur at the SSVFAQ↓SIPWNL$^{158}$ motif (SEQ ID NOs: 19 and 20, respectively); Benjannet et al., 2004 J. Biol. Chem. 279: 48865-48875. Such internal processing has been reported as a requirement of exit from the ER; Benjannet et al., supra; Seidah et al., supra. The cleaved and, thereby, activated protein is secreted in association with the cleaved peptide; supra.

The sequence for human PCSK9 (~22-kb long with 12 exons encoding a 692 amino acid protein) can be found in one instance at Deposit No. NP_777596.2. Human, mouse and rat PCSK9 nucleic acid sequences have been deposited; see, e.g., GenBank Accession Nos.: AX21327530 (also AX207686), NP_705793 (also Q80W65), and P59996, respectively. PCSK9 possesses several domains found in other proprotein convertases, including an N-terminal signal sequence, a pro domain, a catalytic domain and a cysteine-rich C terminal domain. The PCSK9 catalytic domain shares high sequence similarity with the proteinase K family of subtilases and, notably, a catalytic triad of D186, H226 and S386.

PCSK9 is disclosed and/or claimed in several patent publications including, but not limited to the following: PCT Publication Nos. WO 01/31007, WO 01/57081, WO 02/14358, WO 01/98468, WO 02/102993, WO 02/102994, WO 02/46383, WO 02/90526, WO 01/77137, and WO 01/34768; US Publication Nos. US 2004/0009553 and US 2003/0119038, and European Publication Nos. EP 1 440 981, EP 1 067 182, and EP 1 471 152.

PCSK9 has been ascribed a role in the differentiation of hepatic and neuronal cells (Seidah et al., supra.), is highly expressed in embryonic liver, and has been strongly implicated in cholesterol homeostasis. Studies have suggested a specific role for PCSK9 in cholesterol biosynthesis or uptake. In a study of cholesterol-fed rats, Maxwell et al. found that PCSK9 was downregulated in a similar manner to three other genes involved in cholesterol biosynthesis, Maxwell et al., 2003 J. Lipid Res. 44:2109-2119. The expression of PCSK9 has, in fact, been shown to be regulated by sterol regulatory element-binding proteins ("SREBP"), as seen with other genes involved in cholesterol metabolism; supra. Later support for these findings came about through a study of PCSK9 transcriptional regulation which demonstrated that such regulation was quite typical of other genes implicated in lipoprotein metabolism; Dubuc et al., 2004 Arterioscler. Thromb. Vasc. Biol. 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

Several lines of evidence demonstrate that PCSK9, in particular, lowers the amount of hepatic LDLR protein and thus compromises the liver's ability to remove LDL cholesterol from the circulation. Adenovirus-mediated overexpression of PCSK9 in the livers of mice results in the accumulation of circulating LDL-C due to a dramatic loss of hepatic LDLR protein, with no effect on LDLR mRNA levels; Benjannet et al., 2004 J. Biol. Chem. 279:48865-48875; Maxwell & Breslow, 2004 PNAS 101:7100-7105; Park et al., 2004 J. Biol. Chem. 279:50630-50638; and Lalanne et al., 2005 J. Lipid Res. 46:1312-1319. The effect of PCSK9 over-expression on raising circulating LDL-C levels in mice is completely dependent on the expression of LDLR, again, indicating that the regulation of LDL-C by PCSK9 is mediated through down-regulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid et al., 2005 PNAS 102:5374-5379; and Graham et al., 2007 J. Lipid Res. 48(4):763-767. In addition, lowering PCSK9 levels in cultured human hepatocytes by siRNA also results in higher LDLR protein levels and an increased ability to take up LDL-C; Benjannet et al., 2004 J. Biol. Chem. 279:48865-48875; and Lalanne et al., 2005 J. Lipid Res. 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 Nature Genetics 34:154-156; Timms et al., 2004 Hum. Genet. 114:349-353; Leren, 2004 Clin. Genet. 65:419-422. A later-published study on the S127R mutation of Abifadel et al., supra, reported that patients carrying such a mutation exhibited higher total cholesterol and apoB 100 in the plasma attributed to (1) an overproduction of apoB 100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Engl. J. Med.* 354:1264-1272.

The identification of compounds and/or agents effective in the treatment of cardiovascular affliction is highly desirable. In clinical trials, reductions in LDL cholesterol levels have been directly related to the rate of coronary events; Law et al., 2003 *BMJ* 326:1423-1427. More recently, the moderate lifelong reduction in plasma LDL cholesterol levels was found to correlate with a substantial reduction in the incidence of coronary events; Cohen et al., supra. This was the case even in populations with a high prevalence of non-lipid-related cardiovascular risk factors; supra. Accordingly, there is great benefit to be reaped from the managed control of LDL cholesterol levels.

The present invention advances these interests by providing antagonists of PCSK9 of use for inhibiting the activities of PCSK9 and the corresponding role PCSK9 plays in various therapeutic conditions.

SUMMARY OF THE INVENTION

The present invention relates to protein-specific antagonists of PCSK9 and, in particular embodiments, those antagonists that inhibit human PCSK9. Broadly, protein-specific antagonists of PCSK9 (or "PCSK9-specific antagonists" as referred to herein) are PCSK9 protein binding molecules or molecules effective in the selective binding of PCSK9 and inhibition of PCSK9 function. In particular embodiments, the present invention relates to monoclonal antibody variants having high affinity and desired properties from a therapeutic perspective. These molecules are of import in the treatment of conditions associated with or impacted by PCSK9 function, including, but not limited to hypercholesterolemia, coronary heart disease, metabolic syndrome, acute coronary syndrome and related conditions. PCSK9-specific antagonists are characterized by selective recognition and binding to PCSK9. PCSK9-specific antagonists do not show significant binding to proteins other than PCSK9, other than in those specific instances where the antagonist is supplemented or designed to confer an additional, distinct specificity to the PCSK9-specific binding component.

PCSK9-specific antagonists forming particular embodiments hereof comprise (a) a heavy chain variable region comprising a CDR3 domain comprising (in select embodiments, consisting of) a sequence selected from the group consisting of: SEQ ID NOs: 1-5, SEQ ID NO: 7, SEQ ID NO: 9, SEQ ID NO: 11, SEQ ID NOs: 13-63, residues 4-12 of the foregoing sequences that are 15 amino acids in length, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%); and/or (b) a light chain variable region comprising a CDR3 domain comprising (in select embodiments, consisting of) a sequence selected from the group consisting of: SEQ ID NOs: 295-301, SEQ ID NO: 303, SEQ ID NOs: 305-334, residues 4-13 of the foregoing sequences that are 16 amino acids in length, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%).

PCSK9-specific antagonists forming additional embodiments hereof comprise (a) a heavy chain variable region comprising a CDR2 domain comprising (in select embodiments, consisting of) a sequence selected from the group consisting of: SEQ ID NOs: 64-68, SEQ ID NO: 70, SEQ ID NO: 72, SEQ ID NO: 74, SEQ ID NOs: 76-182, residues 4-20 of the foregoing sequences that are 23 amino acids in length, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%); and/or (b) a light chain variable region comprising a CDR2 domain comprising (in select embodiments, consisting of) a sequence selected from the group consisting of: SEQ ID NOs: 335-339, SEQ ID NO: 341, SEQ ID NOs: 343-346, residues 4-10 of the foregoing sequences that are 13 amino acids in length, and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%).

In specific embodiments, PCSK9-specific antagonists bind to human PCSK9 with a $K_D$ of $1.2 \times 10^{-6}$ M or less. In more specific embodiments, PCSK9-specific antagonists bind to human PCSK9 with a $K_D$ of $1 \times 10^{-7}$ M or less. In additional embodiments, PCSK9-specific antagonists bind to human PCSK9 with a $K_D$ of $1 \times 10^{-8}$ M or less. In further embodiments, PCSK9-specific antagonists bind to human PCSK9 with a $K_D$ of $5 \times 10^{-9}$ M or less, or of $1 \times 10^{-9}$ M or less. In select embodiments, PCSK9-specific antagonists bind to human PCSK9 with a $K_D$ of $1 \times 10^{-10}$ M or less, a $K_D$ of $1 \times 10^{-11}$ M or less, or a $K_D$ of $1 \times 10^{-12}$ M or less. In specific embodiments, PCSK9-specific antagonists do not bind proteins other than PCSK9 at the above levels indicated for binding to PCSK9.

Particular embodiments of the present invention include PCSK9-specific antagonists which exhibit binding to PCSK9 at one of the above prescribed levels and compete for binding to PCSK9 with AX132 and its variants as described herein. AX132 and its disclosed variants, described as any antibody molecules fitting within the descriptions, sequence and/or functional limitations provided throughout the present disclosure, form important PCSK9-specific antagonists hereof.

AX132 antibody molecules are characterized as comprising a (i) heavy chain variable region ("VH") comprising SEQ ID NO: 360 or SEQ ID NO: 361; and (ii) a light chain variable region ("VL") comprising SEQ ID NO: 511. Said VH and VL regions comprise the full complement of disclosed CDRs 1, 2 and 3 for the VH [SEQ ID NOs: 189 (or SEQ ID NO: 191) as CDR1; SEQ ID NO: 68 (or SEQ ID NO: 70) as CDR2; and SEQ ID NO: 5 (or SEQ ID NO: 7) as CDR3] and VL regions [SEQ ID NOs: 349 (or SEQ ID NO: 351) as CDR1; SEQ ID NO: 339 (or SEQ ID NO: 341) as CDR2; and SEQ ID NO: 301 (or SEQ ID NO: 303) as CDR3], respectively. Examples of AX132 antibody molecules include without limitation: (i) a Fab which comprises a light chain comprising SEQ ID NO: 554 and an Fd chain comprising amino acids comprising amino acids 1-221 of SEQ ID NO: 552 (or SEQ ID NO: 552); (ii) a full length antibody molecule which comprises a light chain comprising SEQ ID NO: 558 and a heavy chain comprising SEQ ID NO: 556; and (iii) an antibody produced by the expression of SEQ ID NO: 560.

AX213 antibody molecules, an example of specific variants described herein, are characterized as comprising a (i) heavy chain variable region ("VH") comprising SEQ ID NO: 362 or SEQ ID NO: 363; and (ii) a light chain variable region ("VL") comprising SEQ ID NO: 511. Said VH and VL regions comprise the full complement of disclosed CDRs 1, 2 and 3 for the VH [SEQ ID NO: 193 (or SEQ ID NO: 195) as CDR1; SEQ ID NO: 72 (or SEQ ID NO: 74) as CDR2; and SEQ ID NO: 9 (or SEQ ID NO: 11) as CDR3)] and VL regions [SEQ ID NO: 349 (or SEQ ID NO: 351) as CDR1; SEQ ID NO: 339 (or SEQ ID NO: 341) as CDR2; and SEQ ID NO: 301 (or SEQ ID NO: 303) as CDR3], respectively. Examples of AX213 antibody molecules include without limitation: (i) a Fab which comprises a light chain comprising SEQ ID NO: 554 and an Fd chain comprising amino acids comprising amino acids 1-221 of SEQ ID NO: 562 (or SEQ ID NO: 562); (ii) a full length antibody molecule which comprises a light chain comprising SEQ ID NO: 566 and a heavy chain comprising SEQ ID NO: 564; and (iii) an antibody produced by the expression of SEQ ID NO: 569.

PCSK9-specific antagonists are effective in counteracting PCSK9-dependent inhibition of cellular LDL-uptake, and particularly human PCSK9-dependent inhibition of cellular LDL uptake. Repeatedly, PCSK9-specific antagonists as described herein have demonstrated dose-dependent inhibition of the effects of PCSK9 on LDL uptake. Accordingly, the disclosed PCSK9-specific antagonists are of import for lowering plasma LDL cholesterol levels. The disclosed antagonists also have utility for various diagnostic purposes, including the detection and quantification of PCSK9.

In particular embodiments, the present invention encompasses antibody molecules comprising the disclosed heavy and/or light chain variable regions, equivalents of said regions having one or more amino acid substitutions that do not substantially impact function, and homologs thereof. Select embodiments comprise isolated PCSK9-specific antagonists that comprise disclosed CDR domains or sets of the heavy and/or light chain CDR domains, and equivalents of such domains characterized as having one or more amino acid substitutions. As will be appreciated by those skilled in the art, fragments of PCSK9-specific antagonists that retain the ability to antagonize PCSK9 may be inserted into various frameworks; see, e.g., U.S. Pat. No. 6,818,418 and references contained therein, the collective disclosures of which are incorporated herein by reference, which discuss various scaffolds which may be used to display antibody loops previously selected on the basis of antigen binding. In the alternative, genes encoding for VL and VH may be joined, using recombinant methods, for example using a synthetic linker that enables them to be made as a single protein chain in which the VL and VH regions pair to form monovalent molecules, otherwise known as single chain Fvs ("ScFVs"); see, e.g., Bird et al., 1988 *Science* 242: 423-426, and Huston et al., 1988 *Proc. Natl. Acad. Sci. USA* 85:5879-5883, the disclosures of which are incorporated herein by reference. In another alternative, the VH and VL may be fused with two interactive domains, and form a Fab-like molecule, see, e.g., ccFv, Wang et al., U.S. Pat. No. 6,833,441 and U.S. Pat. No. 7,429,652.

PCSK-9 specific antagonists and fragments may be in the form of various non-antibody-based scaffolds, including but not limited to avimers (Avidia); DARPins (Molecular Partners); Adnectins (Adnexus), Anticalins (Pieris) and Affibodies (Affibody). The use of alternative scaffolds for protein binding is well appreciated in the scientific literature, see, e.g., Binz & Plückthun, 2005 *Curr. Opin. Biotech.* 16:1-11; the disclosure of which is incorporated herein by reference.

Accordingly, any PCSK9-specific antagonist, including antibody molecules and non-antibody-based scaffolds comprising (i) the disclosed heavy and/or light chain variable region CDR3 sequences (heavy chain variable region CDR3 sequence selected from SEQ ID NOs: 1-5, 7, 9, 11, 13-63, and residues 4-12 of the foregoing sequences that are 15 amino acids in length; light chain variable region CDR3 sequence selected from SEQ ID NOs: 295-301, 303, 305-334, and residues 4-13 of the foregoing sequences that are 16 amino acids in length), (ii) the disclosed heavy and/or light chain variable region CDR2 sequences (heavy chain variable region CDR2 sequence selected from SEQ ID NOs: 64-68, 70, 72, 74, 76-182, and residues 4-20 of the foregoing sequences that are 23 amino acids in length; light chain variable region CDR2 sequence selected from SEQ ID NOs: 335-339, 341, 343-346 and residues 4-10 of the foregoing sequences that are 13 amino acids in length), (iii) the disclosed heavy and/or light chain variable region CDR1 sequences (heavy chain variable region CDR1 sequence selected from SEQ ID NOs: 183-189, 191, 193, 195, 197-294, and residues 4-13 of the foregoing sequences that are 16 amino acids in length; light chain variable region CDR1 sequence selected from SEQ ID NOs: 347-349, 351, 353-359 and residues 4-14 of the foregoing sequences that are 17 amino acids in length), (iv) the disclosed heavy chain variable CDR1, CDR2 and CDR3 sequences or the disclosed light chain variable CDR1, CDR2 and CDR3 sequences, (v) a full complement (CDRs 1, 2 and 3) of the disclosed heavy and light chain CDRs within a variable region framework of a human heavy and/or light chain sequence, respectively, or (vi) the disclosed heavy and/or light chain variable regions (heavy chain variable sequence selected from SEQ ID NOs: 360-510; light chain variable sequence selected from SEQ ID NOs: 511-549) form important embodiments of the present invention; where antagonists, antibody molecules or scaffolds exhibit selectivity for PCSK9 and counteract PCSK9-dependent inhibition of cellular LDL-uptake.

In another aspect, the present invention provides nucleic acid encoding the disclosed PCSK9-specific antagonists and, in particular embodiments, PCSK9-specific antagonists which comprise the disclosed heavy and light chains, the disclosed variable heavy and light regions and select components thereof (including CDRs 1, 2 and/or 3), particularly the disclosed respective CDR3 or CDR2 regions. In another aspect, the present invention provides vectors comprising said nucleic acid. The present invention, additionally, provides isolated cell(s) comprising nucleic acid encoding disclosed PCSK9-specific antagonists. In another aspect, the present invention provides isolated cell(s) comprising a polypeptide or vector of the present invention.

The present invention provides methods for making PCSK9-specific antagonists disclosed herein including but not limited to antibodies, antigen binding fragments, derivatives, chimeric molecules, fusions of any of the foregoing with another polypeptide, or alternative structures/compositions capable of specifically binding PCSK9 which comprise the disclosed sequences. The methods comprise: (i) incubating a cell comprising nucleic acid encoding the PCSK9-specific antagonist(s), or which comprises individual nucleic acids encoding one or more components thereof, said nucleic acids which, when expressed, collectively produce the antagonist(s), under conditions that allow for the expression and/or assembly of the PCSK9-specific antagonist(s), and (ii) isolating said antagonist(s) from the cell. One of skill in the art can obtain PCSK9-specific antagonists disclosed herein using standard recombinant DNA techniques as well.

The present invention provides a method for antagonizing the activity or function of PCSK9 or a noted effect of PCSK9 which comprises contacting a cell, population of cells, or tissue sample of interest expressing PCSK9 (or treated with or having therein human PCSK9) with a PCSK9-specific antagonist disclosed herein under conditions that allow said antagonist to bind to PCSK9. Specific embodiments of the present invention include such methods wherein the cell is a human cell. Additional embodiments are wherein the cell expresses human-derived PCSK9.

In another aspect, the present invention provides a method for antagonizing the activity or function of PCSK9 or a noted effect of PCSK9 in a subject exhibiting a condition associated with PCSK9 activity, or a condition where the functioning of PCSK9 is contraindicated for a particular subject, which comprises administering to the subject a therapeutically effective amount of a PCSK9-specific antagonist of the present invention in a pharmaceutical or other composition.

The present invention, thus, encompasses a method of treating a condition associated with PCSK9 activity, or a condition wherein the functioning of PCSK9 is contraindicated for a particular subject, which comprises administering to the subject a therapeutically effective amount of a PCSK9-specific antagonist of the present invention in a pharmaceutical or other composition. In select embodiments, the condition is hypercholesterolemia, coronary heart disease, metabolic syndrome, acute coronary syndrome or related conditions.

In specific embodiments, the present invention encompasses a method of administering a disclosed PCSK9-specific antagonist to a subject which comprises delivering a therapeutically effective amount of a pharmaceutical or other composition comprising a PCSK9-specific antagonist as disclosed herein.

In another aspect, the present invention provides a pharmaceutical composition or other composition comprising a PCSK9-specific antagonist of the invention characterized as comprising a pharmaceutically acceptable carrier including but not limited to an excipient, diluent, stabilizer, buffer, or alternative designed to facilitate administration of the antagonist in the desired amount to the treated individual.

The following table offers a generalized outline of the sequences discussed in the present application. The Sequence Listing including all notations, sequences and features forms an express part of the disclosure hereof:

TABLE 1

| SEQ ID NO: | DESCRIPTION |
|---|---|
| SEQ ID NOs: 1-5, 7, 9, 11, 13-63 | HEAVY CHAIN CDR3 |
| SEQ ID NOs: 6, 8, 10, 12 | HEAVY CHAIN CDR3; NUCLEIC ACID |
| SEQ ID NOs: 64-68, 70, 72, 74, 76-182 | HEAVY CHAIN CDR2 |
| SEQ ID NOs: 69, 71, 73, 75 | HEAVY CHAIN CDR2; NUCLEIC ACID |
| SEQ ID NOs: 183-189, 191, 193, 195, 197-294 | HEAVY CHAIN CDR1 |
| SEQ ID NOs: 190, 192, 194, 196 | HEAVY CHAIN CDR1; NUCLEIC ACID |
| SEQ ID NOs: 295-301, 303, 305-334 | LIGHT CHAIN CDR3 |
| SEQ ID NOs: 302, 304 | LIGHT CHAIN CDR3; NUCLEIC ACID |
| SEQ ID NOs: 335-339, 341, 343-346 | LIGHT CHAIN CDR2 |
| SEQ ID NOs: 340, 342 | LIGHT CHAIN CDR2; NUCLEIC ACID |
| SEQ ID NOs: 347-349, 351, 353-359 | LIGHT CHAIN CDR1 |
| SEQ ID NOs: 350, 352 | LIGHT CHAIN CDR1; NUCLEIC ACID |
| SEQ ID NOs: 360-510 | VARIABLE HEAVY REGIONS |
| SEQ ID NOs: 550, 561 | VARIABLE HEAVY REGIONS; NUCLEIC ACID |
| SEQ ID NOs: 511-549 | VARIABLE LIGHT REGIONS |
| SEQ ID NO: 551 | VARIABLE LIGHT REGION; NUCLEIC ACID |
| SEQ ID NOs: 552, 562 | FAB HEAVY CHAIN |
| SEQ ID NOs: 553, 563 | FAB HEAVY CHAIN; NUCLEIC ACID |
| SEQ ID NO: 554 | FAB LIGHT CHAIN |

TABLE 1-continued

| SEQ ID NO: | DESCRIPTION |
|---|---|
| SEQ ID NO: 555 | FAB LIGHT CHAIN; NUCLEIC ACID |
| SEQ ID NOs: 556, 564 | IGG2 HEAVY CHAIN |
| SEQ ID NOs: 557, 565 | IGG2 HEAVY CHAIN; NUCLEIC ACID |
| SEQ ID NOs: 558, 566 | IGG2 LIGHT CHAIN |
| SEQ ID NOs: 559, 567, 568 | IGG2 LIGHT CHAIN; NUCLEIC ACID |
| SEQ ID NOs: 560, 569 | ANTIBODY EXPRESSION VECTOR SEQUENCE |
| SEQ ID NO: 570 | FRAGMENT OF PROCESSING SITE |
| SEQ ID NO: 571 | FRAGMENT OF PROCESSING SITE |
| SEQ ID NO: 572 | Constant domain of IgG1 |
| SEQ ID NO: 573 | Constant domain of IgG2 |
| SEQ ID NO: 574 | Constant domain of IgG4 |
| SEQ ID NO: 575 | Constant domain of IgG2m4 |
| SEQ ID NOs: 576-582 | AX132 EPITOPES |
| SEQ ID NOs: 583-590 | AX132 AND VARIANT FRAMEWORK REGIONS |
| SEQ ID NO: 591-592 | CONSENSUS VARIABLE HEAVY AND VARIABLE LIGHT REGIONS, RESPECTIVELY |
| SEQ ID NO: 593-641 | FIGURE SEQUENCES |
| SEQ ID NO: 642 | PCSK9 |
| SEQ ID NOs: 643-644 | AX132 CONTACT RESIDUES |
| SEQ ID NO: 645 | EGF_AB PEPTIDE |
| SEQ ID NOs: 646-647 | pMAB9-AX132; and complementary sequence; respectively |

BRIEF DESCRIPTION OF THE DRAWINGS

FIG. 2 illustrates amino acid substitutions in VH-CDR1, 2, 3 regions from 134 AX114 variants, which were isolated from 10 optimization libraries.

FIG. 3 illustrates amino acid substitutions in VK-CDR1, 2, 3 regions from 134 AX114 variants, which were isolated from 10 optimization libraries.

FIG. 6 illustrate the HD exchange profiles for AX132 and AX213 antibodies. The PCSK9 peptic fragments that exhibit the greatest deuteration difference upon AX213 or AX132 binding are 155-PWNL-158 (SEQ ID NO: 576) and 364-PGEDIIGASSDCSTC-378 (SEQ ID NO: 577).

FIG. 7 shows PCSK9 with the two peptic fragments containing the AX132 and AX213 epitope highlighted. These peptic fragments are 155-PWNL-158 (SEQ ID NO: 576) and 364-PGEDIIGASSDCSTC-378 (SEQ ID NO: 577). The HD exchange data is consistent with the PCSK9 mutagenesis data in Example 7. Both 155- and 364-peptides are located in the epitope Bin #1 as shown in FIG. 4.

FIG. 8 depicts the crystal structure of PCSK9 bound to the AX132 antibody.

Figure 9:
Figure 14A:
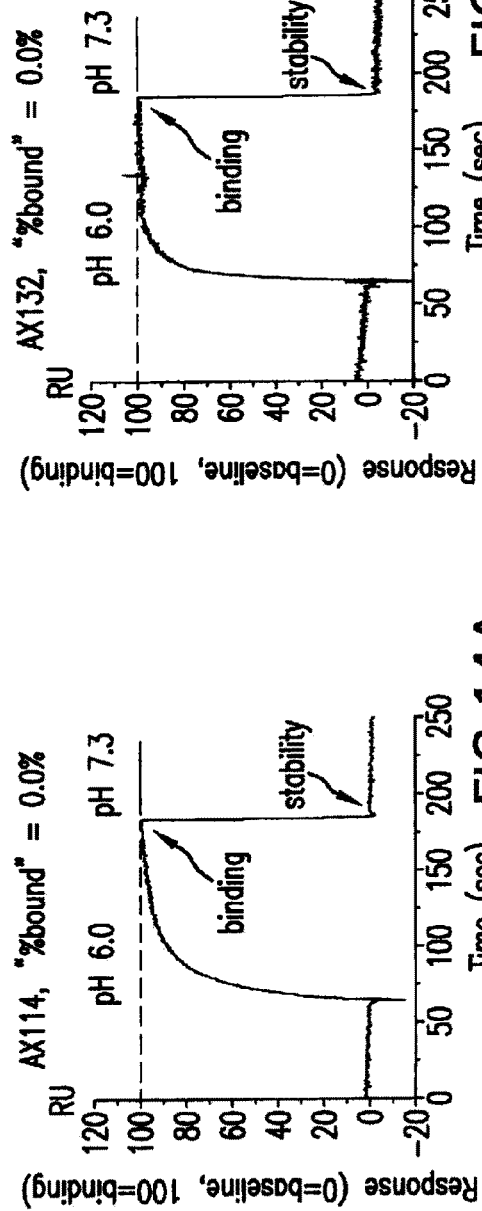
Figure 14B:
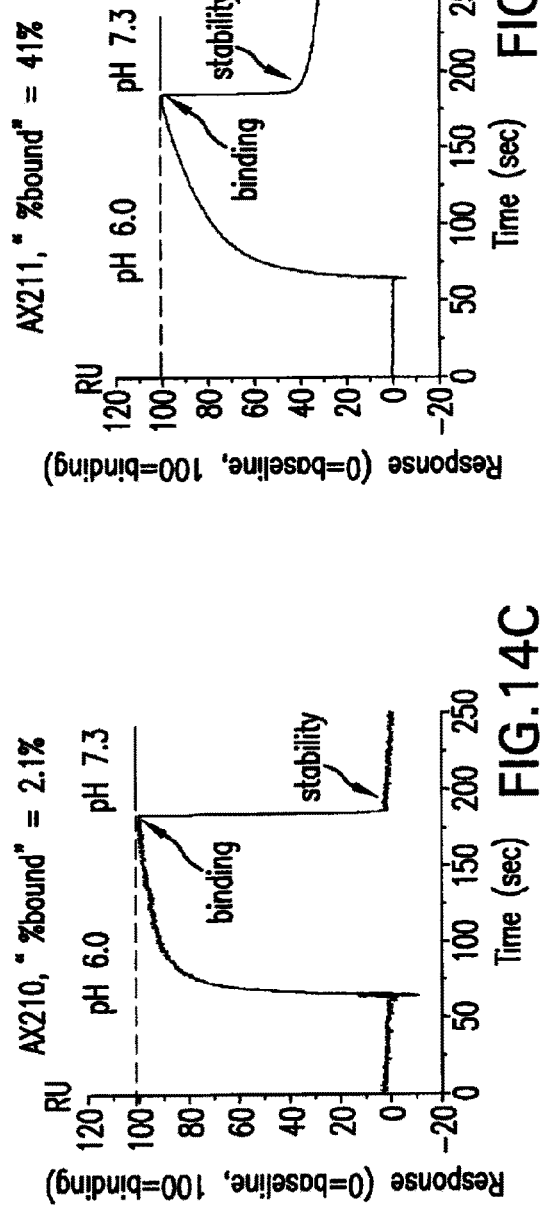
Figure 14C:
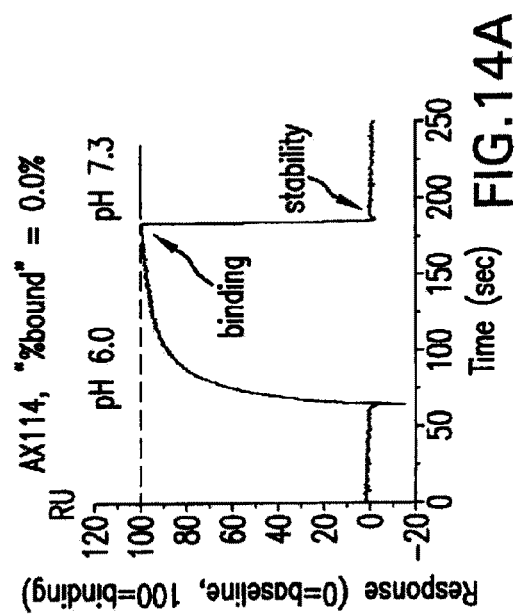
Figure 14D:
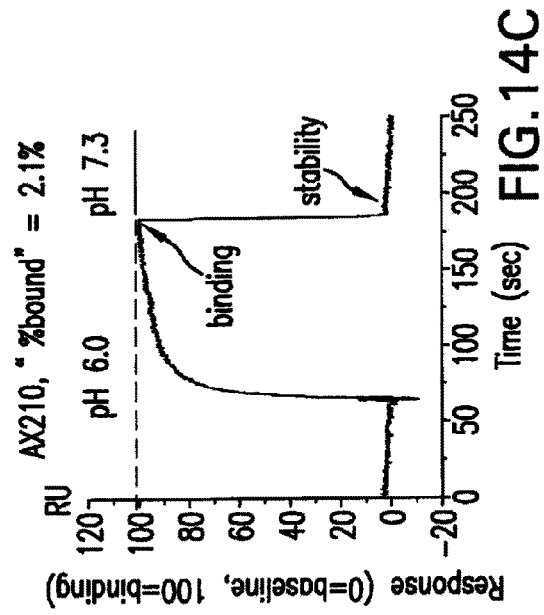

FIG. 9 shows the surface area representation of PCSK9 with AX132 epitope. FIG. 9 illustrates the involvement of F379 residue on PCSK9 in the AX132 binding.

FIGS. 10A-F illustrate the activities of AX114, AX132, AX210, AX211, AX212 and AX213 antibodies in a PCSK9-LDLR interaction TR-FRET format assay, respectively. All IgG2 antibodies tested are potent and inhibit the interaction of AF647-labeled wild type human PCSK9 and Eu8044-labeled LDL receptor [AF647 PCSK9=10 nM; [Eu 8044 sLDLR] ~5 nM (20,000 counts at F1620 nM).

FIGS. 11A-F illustrate AX114 and AX132 IgG's dose-dependent inhibition of human, murine and rhesus PCSK9-dependent loss of cellular LDL-uptake (FIGS. 11A, 11B and 11C, respectively for AX114; and FIGS. 11D, 11E and 11F, respectively for AX132). AX114 and AX132 IgGs cross-react with human, mouse and rhesus PCSK9.

FIGS. 12A-F illustrate AX210 and AX211 IgG's dose-dependent inhibition of human, murine and rhesus PCSK9-dependent loss of cellular LDL-uptake (FIGS. 12A, 12B and 12C, respectively for AX210; and FIGS. 12D, 12E and 12F, respectively for AX211). AX210 and AX211 IgGs cross-react with human, mouse and rhesus PCSK9.

FIGS. 13A-F illustrate AX212 and AX213 IgG's dose-dependent inhibition of human, murine and rhesus PCSK9-dependent loss of cellular LDL-uptake (FIGS. 13A, 13B and 13C, respectively for AX212; and FIGS. 13D, 13E and 13F, respectively for AX213). AX212 and AX213 IgGs cross-react with human, mouse and rhesus PCSK9.

FIGS. 14A-D illustrate binding of AX114, AX132, AX210 and AX211, respectively, to immobilized human FcRn with Biacore.

FIGS. 15A-B illustrate binding of AX212 and AX213, respectively, to immobilized human FcRn with Biacore.

Figure 16B:
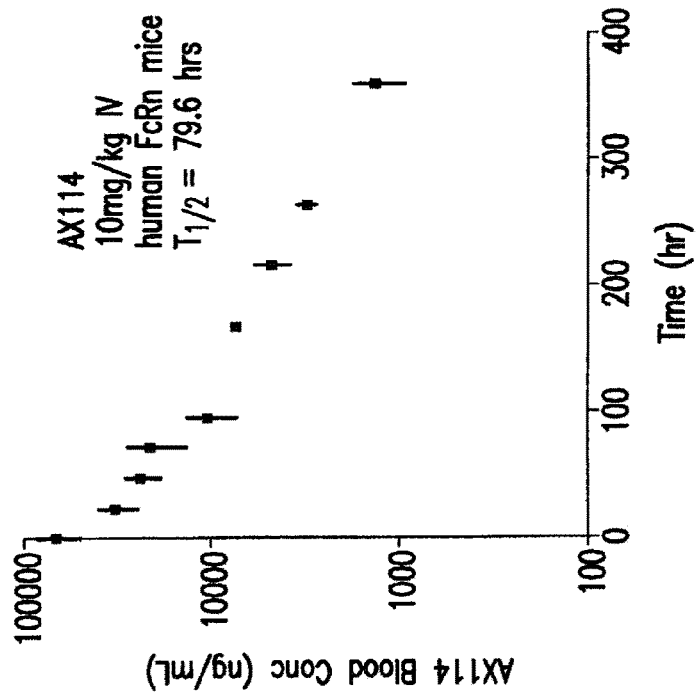
Figure 16A:
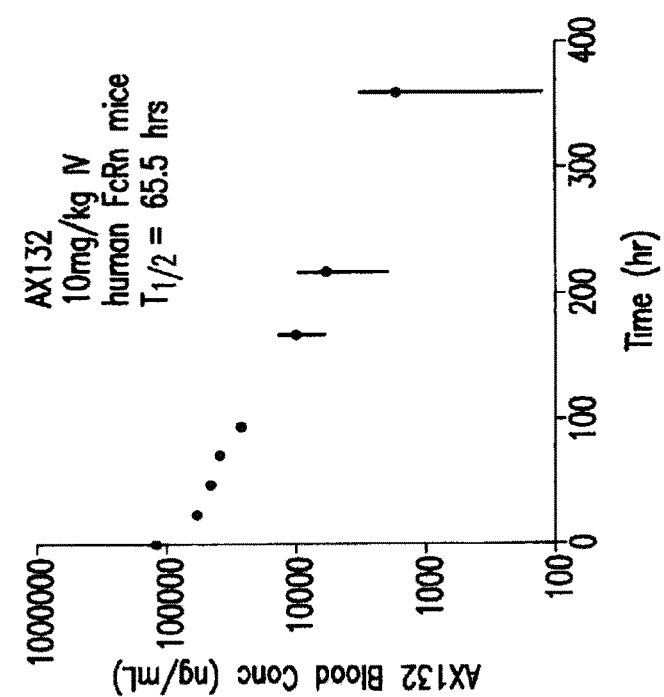

FIGS. 16A-B illustrate the pharmacokinetic profile of AX132 and AX114, respectively, in human FcRn mice following a single 10 mg/kg IV administration.

Figure 17:
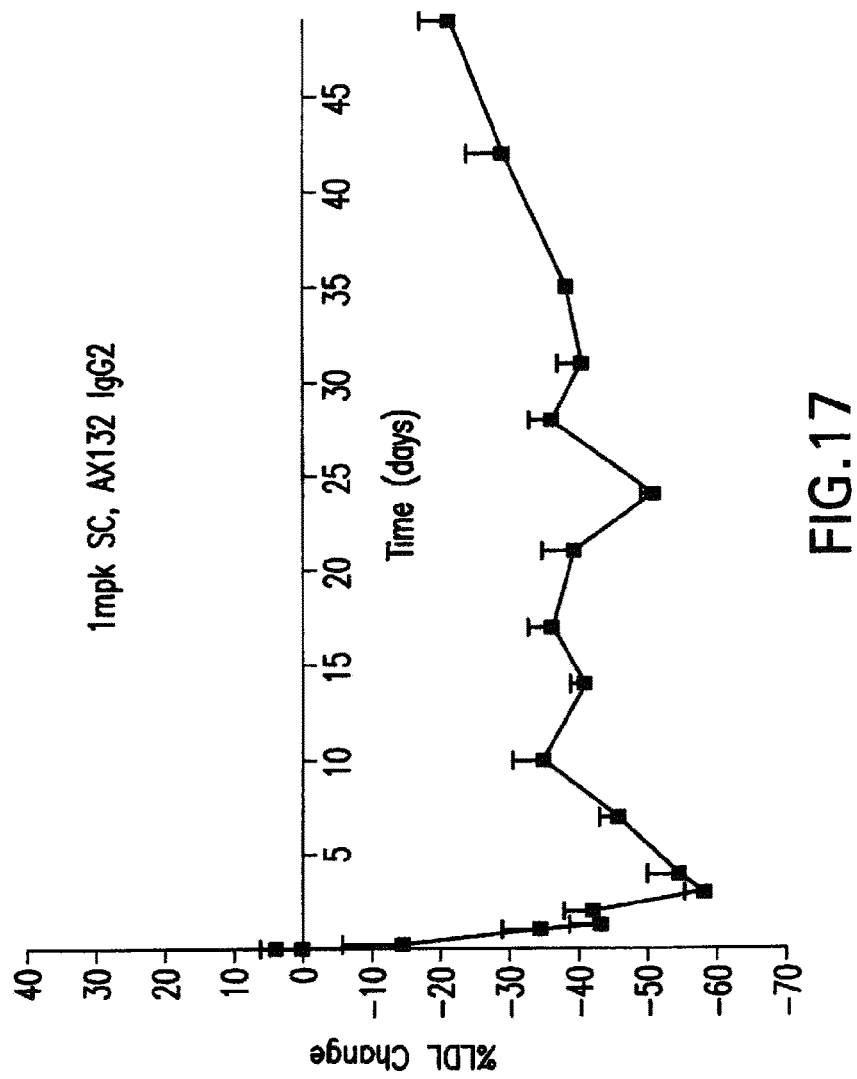

FIG. 17 illustrates the results of pharmacodynamics study in rhesus monkeys. AX132 significantly lowered LDL cholesterol following a single dose, with a maximum mean reduction of 60%, and >25% LDL-C lowering for 42 days.

Figure 18:
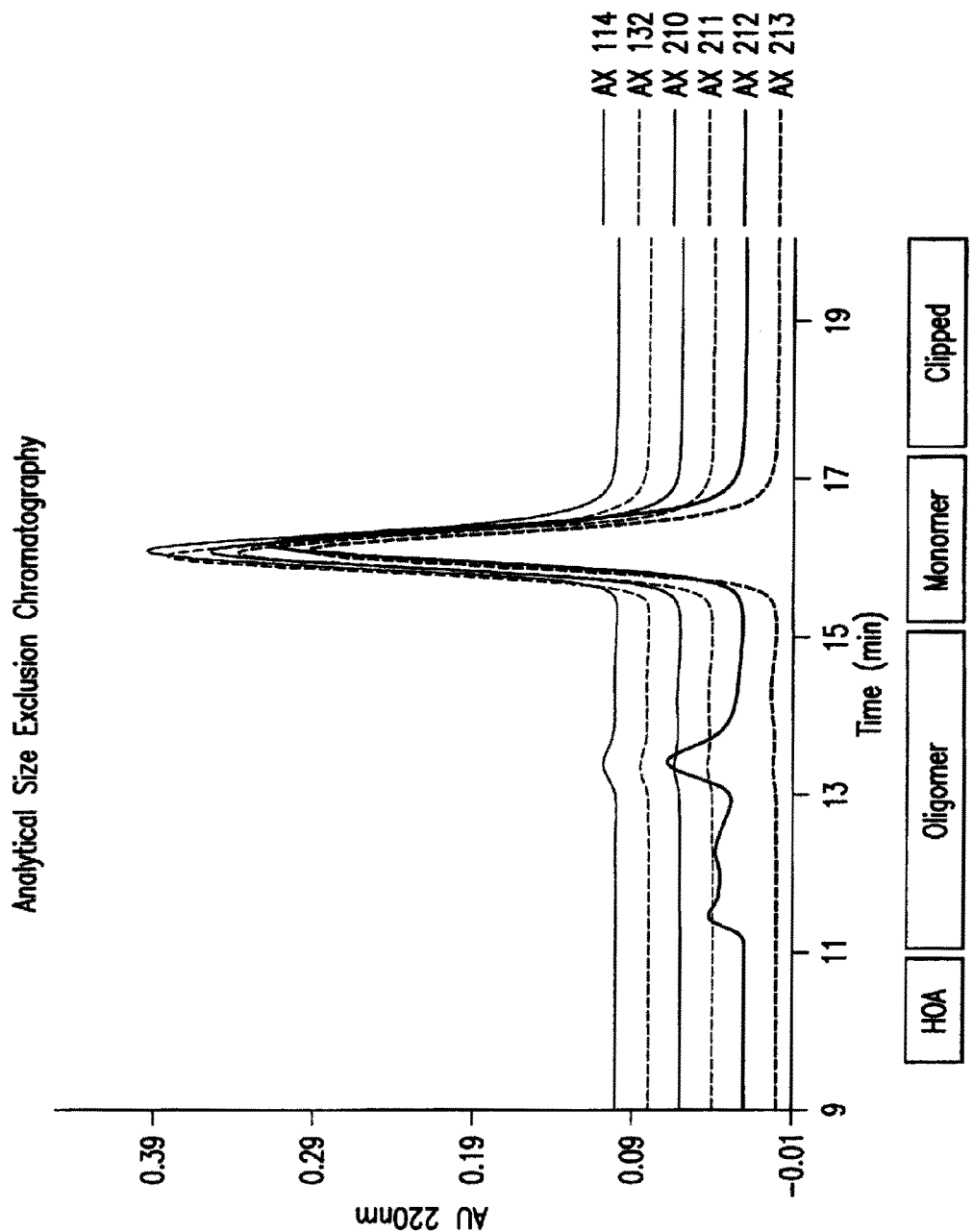

FIG. 18 illustrates size-exclusion chromatography for the time-zero product of monoclonal antibodies in the AX114 epitope bin.

Figure 19:
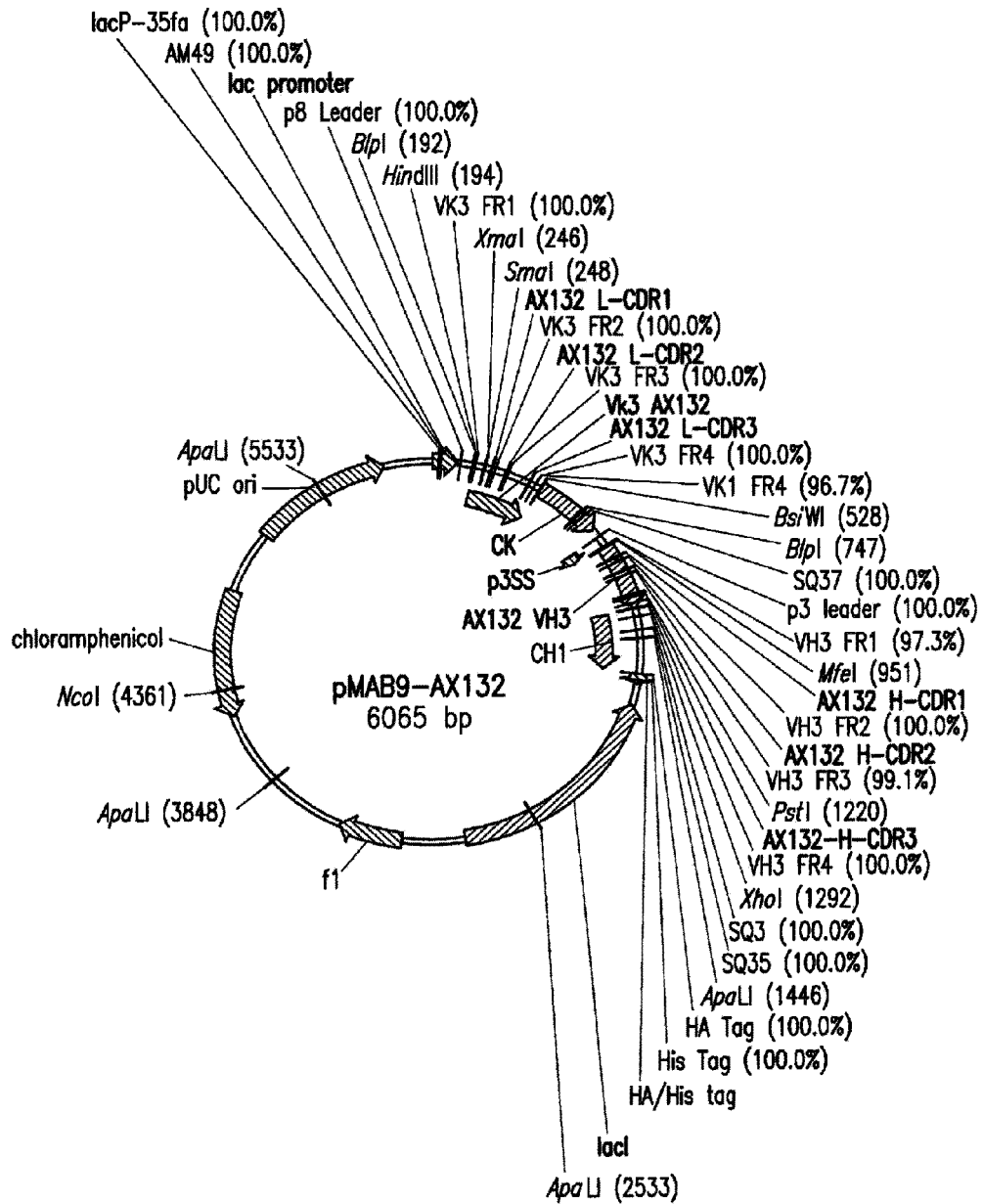

FIG. 19 illustrates a vector map for expression of AX132 antibody.

Figure 20D:
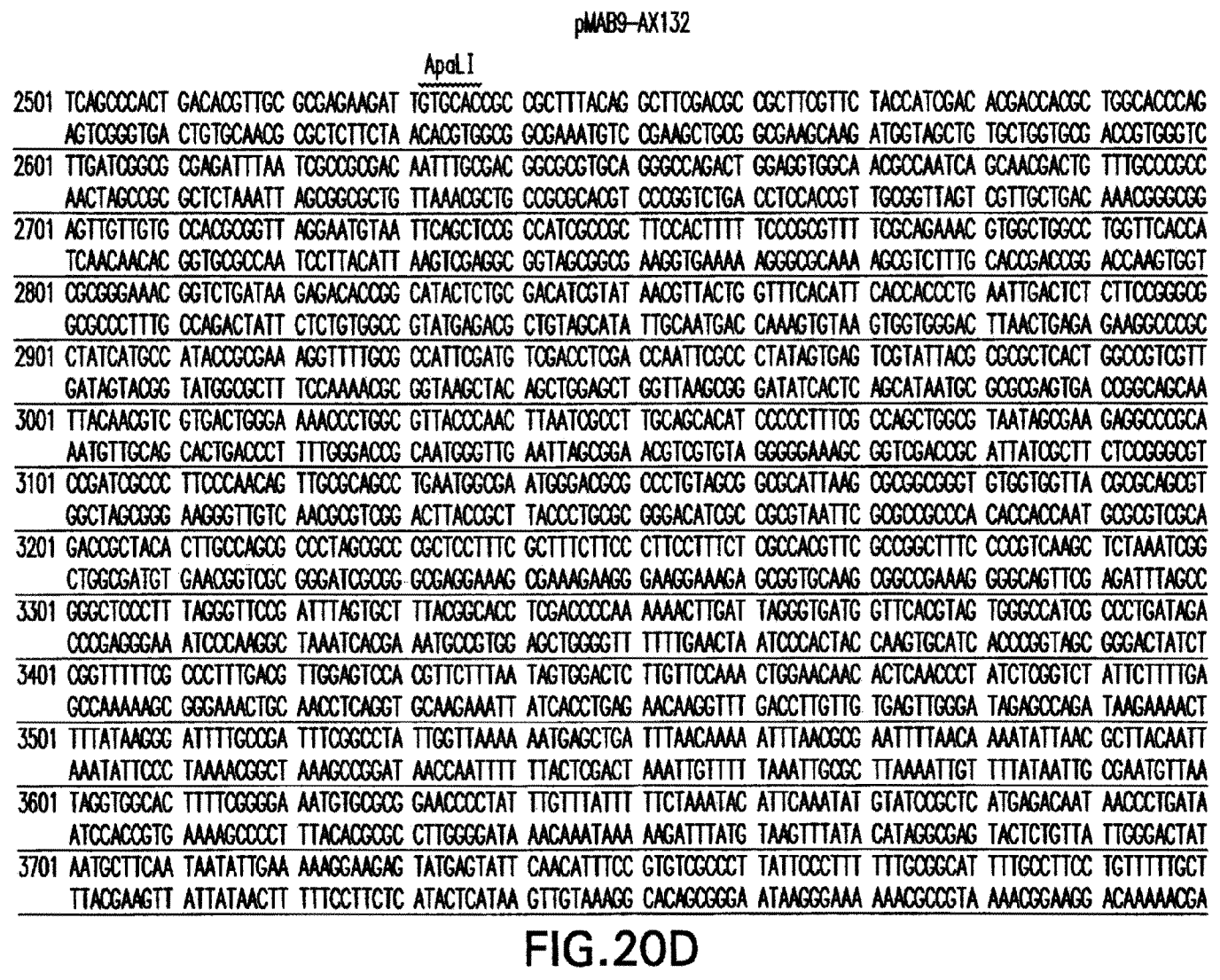
Figure 20E:
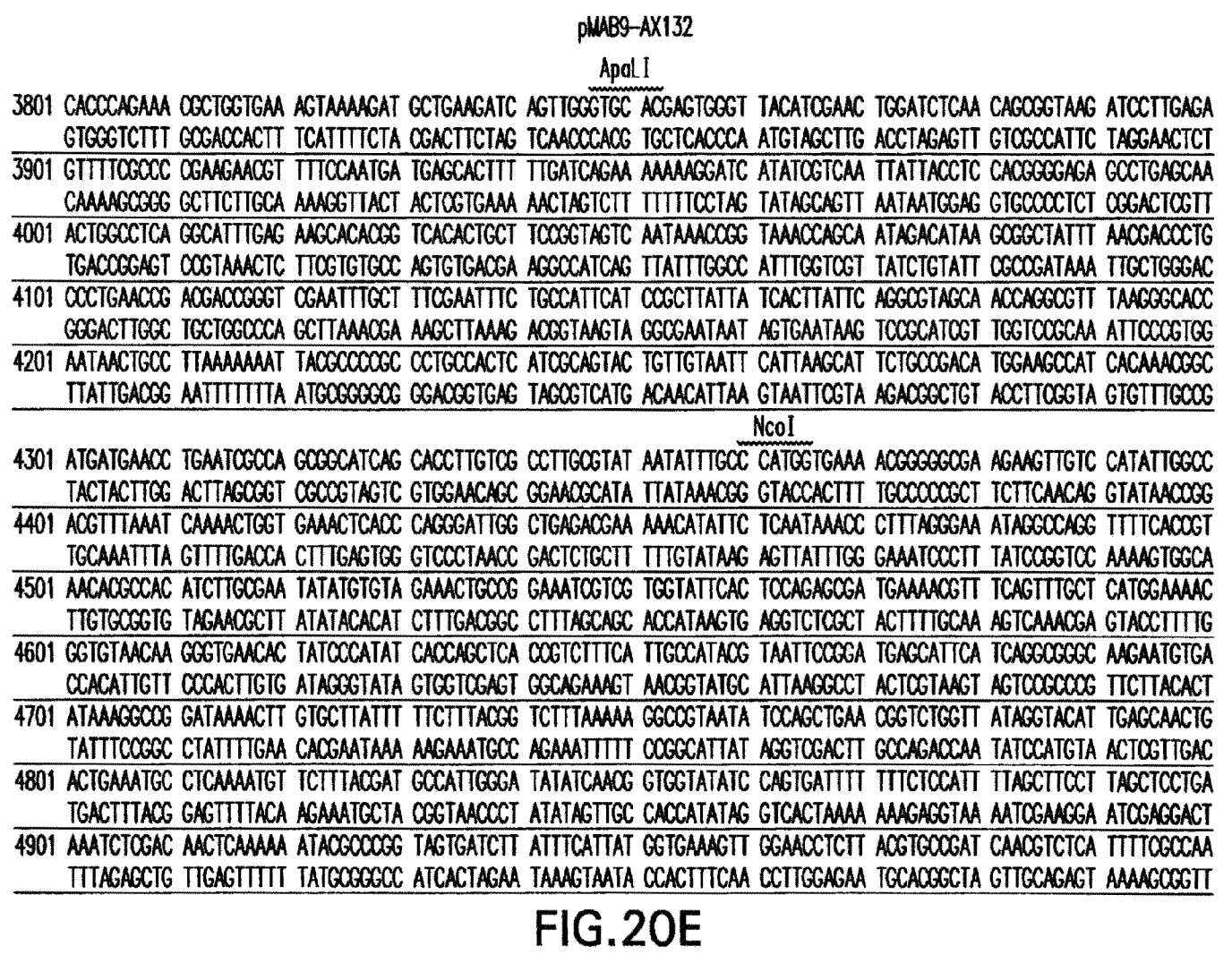

FIGS. 20A-F illustrate a sequence for an expression plasmid for AX132 antibody.

DETAILED DESCRIPTION OF THE INVENTION

The present invention relates to protein-specific antagonists of PCSK9 and, in particular embodiments, those antagonists that inhibit human PCSK9. Protein-specific antagonists of PCSK9 (or "PCSK9-specific antagonists") in accordance herewith are effective in the selective binding to and inhibition of PCSK9 function and, thus, are of import in the treatment of conditions associated with or impacted by PCSK9 function, including, but not limited to, hypercholesterolemia, coronary heart disease, metabolic syndrome, acute coronary syndrome and related conditions. Use of the term "antagonist" refers to the fact that the subject molecule can antagonize the functioning of PCSK9. Use of the term "antagonizing" or derivatives thereof refers to the act of opposing, counteracting, inhibiting, neutralizing or curtailing one or more functions of PCSK9. Reference herein to PCSK9 function or PCSK9 activity refers to any function or activity that is driven by, requires, or is exacerbated or enhanced by PCSK9. PCSK9-specific antagonists as described herein have proven to be effective for counteracting human PCSK9-dependent inhibition of cellular LDL-uptake.

One important embodiment hereof relates to AX132 antibody molecules and variants thereof. Specific embodiments of the present invention include AX132 antibody molecules characterized as comprising a (i) heavy chain variable region ("VH") comprising or consisting of SEQ ID NO: 360 or SEQ ID NO: 361; and (ii) a light chain variable region ("VL") comprising SEQ ID NO: 511. Said VH and VL regions comprise the full complement of disclosed CDRs 1, 2 and 3 for the VH [SEQ ID NOs: 189 (or SEQ ID NO: 191) as CDR1; SEQ ID NO: 68 (or SEQ ID NO: 70) as CDR2; and SEQ ID NO: 5 (or SEQ ID NO: 7) as CDR3] and VL regions [SEQ ID NOs: 349 (or SEQ ID NO: 351) as CDR1; SEQ ID NO: 339 (or SEQ ID NO: 341) as CDR2; and SEQ ID NO: 301 (or SEQ ID NO: 303) as CDR3], respectively. Examples of AX132 antibody molecules include without limitation: (i) a Fab which comprises a light chain comprising SEQ ID NO: 554 and an Fd chain comprising amino acids comprising amino acids 1-221 of SEQ ID NO: 552 (or SEQ ID NO: 552); (ii) a full length antibody molecule which comprises a light chain comprising SEQ ID NO: 558 and a heavy chain comprising SEQ ID NO: 556; and (iii) an antibody produced by the expression of SEQ ID NO: 560.

In specific embodiments, AX132 variants comprise in contiguous order for one or both heavy or light chains: (a) framework 1 (FR1) sequence; (b) CDR1 sequence; (c) framework 2 (FR2) sequence; (d) CDR2 sequence; (e) framework 3 (FR3) sequence, (f) CDR3 sequence; and (g) framework 4 (FR4) sequence. In specific embodiments, the heavy chain comprises in contiguous order: (a) FR1 sequence SEQ ID NO: 583; (b) CDR1 sequence selected from the group consisting of: SEQ ID NOs: 183, 185, 187, 189, 193, and 197-294; (c) FR2 sequence SEQ ID NO: 584; (d) CDR2 sequence selected from the group consisting of: SEQ ID NOs: 64, 66, 68, 72, and 76-182; (e) FR3 sequence SEQ ID NO: 585; (f) CDR3 sequence selected from the group consisting of: SEQ ID NOs: 1, 3, 5, 9, and 13-63; and (g) FR4 sequence SEQ ID NO: 586. In specific embodiments, the light chain comprises in contiguous order: (a) FR1 sequence SEQ ID NO: 587; (b) CDR1 sequence selected from the group consisting of: SEQ ID NOs: 347, 349 and 353-359; (c) FR2 sequence SEQ ID NO: 588; (d) CDR2 sequence selected from the group consisting of: SEQ ID NOs: 335, 337, 339, and 3430-346; (e) FR3 sequence SEQ ID NO: 589; (f) CDR3 sequence selected from the group consisting of: SEQ ID NOs: 295, 297, 299, 301, and 305-334; and (g) FR4 sequence SEQ ID NO: 590. The present invention includes antibody molecules have both heavy and light chains as described above and equivalents thereof characterized as having one or more (in specific embodiments, 1-5 or 1-3) amino acid substitutions that do not reduce specificity for PCSK9 by more than 50% (in specific embodiments, by more than 60%, 70%, 80%, and 90%). The select group of AX132 antibodies exemplified demonstrate without limitation that PCSK9-specific antagonists as disclosed herein effectively inhibit human PCSK9.

One particular AX132 variant is AX213. AX213 antibody molecules are characterized as comprising a (i) heavy chain variable region ("VH") comprising SEQ ID NO: 362 or SEQ ID NO: 363; and (ii) a light chain variable region ("VL") comprising SEQ ID NO: 511. Said VH and VL regions comprise the full complement of disclosed CDRs 1, 2 and 3 for the VH [SEQ ID NO: 193 (or SEQ ID NO: 195) as CDR1; SEQ ID NO: 72 (or SEQ ID NO: 74) as CDR2; and SEQ ID NO: 9 (or SEQ ID NO: 11) as CDR3)] and VL regions [SEQ ID NO: 349 (or SEQ ID NO: 351) as CDR1; SEQ ID NO: 339 (or SEQ ID NO: 341) as CDR2; and SEQ ID NO: 301 (or SEQ ID NO: 303) as CDR3], respectively. Examples of AX213 antibody molecules include without limitation: (i) a Fab which comprises a light chain comprising SEQ ID NO: 554 and an Fd chain comprising amino acids comprising amino acids 1-221 of SEQ ID NO: 562 (or SEQ ID NO: 562); (ii) a full length antibody molecule which comprises a light chain comprising SEQ ID NO: 566 and a heavy chain comprising SEQ ID NO: 564; and (iii) an antibody produced by the expression of SEQ ID NO: 569.

The CDR definitions arrived at and disclosed herein were defined using the Abmaxis in-silico program, Luo et al., U.S. Pat. No. 7,117,096 and U.S. Patent Publication No. US2004/0010376 or WO03/099999. Applicants wish to note, however, that various other methods are also available to delineate and define the start and end points of the CDR sequences, including but not limited to Kabat, 1991 *Sequences of Proteins of Immunological Interest*, 5$^{th}$ edit., NIH Publication no. 91-3242 U.S. Department of Health and Human Services; Clothia et al., 1987 *J. Mol. Biol.* 196:901-917; Clothia et al., 1989 *Nature* 342:877-883; Lefranc, 1997 *Immunol. Today*, 18:509; and Chen et al., 1999 *J. Mol. Biol.* 293:865-881. These and other methods have been reviewed and are well within the realm of skills possessed by those in the art; see, e.g., Honegger & Plückthun, 2001 *J. Mol. Biol.* 309:657-670. While the current inventors have employed the Abmaxis program to define the CDRs, the present invention fully encompasses the different definitions around the sequences and the varying CDR delineations arrived at through use of any different analysis software or methods. For example, CDRs may also be defined as the component of the antibody molecules that binds an epitope or which is involved in binding the antigen. The CDR may comprise from 5-20 amino acids. In particular embodiments, the CDRs may further comprise from 2-6 flanking amino acids on each side of the CDR into the framework region. The above methods and resulting CDR definitions based on the presently disclosed sequences are fully within the scope of the present disclosure and anticipated herein.

PCSK9-specific molecules also have utility for various diagnostic purposes in the detection and quantification of PCSK9.

Disclosed PCSK9-specific antagonists are, furthermore, unique in that select embodiments have demonstrated a preferential recognition of processed PCSK9, the active form of PCSK9.

PCSK9-specific antagonists as disclosed herein are desirable molecules for lowering plasma LDL cholesterol levels and are of utility for any primate, mammal or vertebrate of commercial or domestic veterinary importance. PCSK9-specific antagonists are of utility as well to inhibit the activity of PCSK9 in any population of cells or tissues possessing the LDL receptor. The utility of the disclosed antagonists is directly measurable by assays readily available to the skilled artisan. Means for measuring LDL uptake are described in the literature; see, e.g., Barak & Webb, 1981 *J. Cell Biol.* 90:595-604, and Stephan & Yurachek, 1993 *J. Lipid Res.* 34:325330. In addition, means for measuring LDL cholesterol in plasma is well described in the literature; see, e.g., McNamara et al., 2006 *Clinica Chimica Acta* 369:158-167. The particular impact of the disclosed antagonists on cellular LDL uptake may also be measured through a method which comprises providing purified PCSK9 and labeled LDL particles to a cell sample; providing a PCSK9 antagonist to the cell sample; incubating said cell sample for a period of time sufficient to allow LDL particle uptake by the cells; quantifying the amount of label incorporated into the cell; and identifying those antagonists that result in an increase in the amount of quantified label taken up by the cells as compared with that observed when PCSK9 is administered alone. An additional method for measuring the impact of the disclosed antagonists comprises providing purified PCSK9 and labeled LDL particles to a cell sample; providing a PCSK9 antagonist to the cell sample; incubating said cell sample for a period of time sufficient to allow LDL particle uptake by the cells; isolating cells of the cell sample by removing the supernate; reducing non-specific association of labeled LDL particles (whether to the plate, the cells, or anything other than the LDL receptor); lysing the cells; quantifying the amount of label retained within the cell lysate; and identifying those antagonists that result in an increase in the amount of quantified label taken up by the cells as compared with that observed when PCSK9 is administered alone. Antagonists that result in an increase in the amount of quantified label are PCSK9 antagonists.

Any type of cell bearing the LDL receptor can be employed in the above methods including, but not limited to HEK cells, HepG2 cells, and CHO cells. LDL particles derived from any source are of use in the above-described assays. In particular assays, the LDL particles are fresh particles derived from blood. This can be accomplished by any method available to the skilled artisan including, but not limited to, the method of Havel et al., 1955 *J. Clin. Invest.* 34: 1345-1353. The LDL particles may be labeled with fluorescence. The labeled LDL particles may have incorporated therein visible wavelength excited fluorophore 3,3'-dioctadecylindocarbocyanine iodide (dil(3)) to form the highly fluorescent LDL derivative dil(3)-LDL. Any label which enables the skilled artisan to detect LDL in the cellular lysate may be used. An LDL analog may be used that would only become detectable (e.g., become fluorescent or fluoresce at a different wavelength, etc.) when metabolized intracellularly or, for instance, if it were to become associated with (or dissociated from) other molecules in the process of becoming internalized (e.g. a FRET assay, in which an LDL analog would become associated with a secondary fluor, or else be dissociated from a quencher). Any means available in the art for detecting internalization of labeled LDL particles can be employed. The incubation time for the LDL particles and PCSK9 with the cells is an amount of time sufficient to allow LDL particle uptake by the cells. This time may be within the range of 5 minutes to 360 minutes. The concentration of PCSK9 added to the cells may be in the range of 1 nM to 5 µM and, in specific methods, be in the range of 0.1 nM to 3 µM. One specific means by which the skilled artisan can determine a range of concentrations for a particular PCSK9 protein is to develop a dose response curve in the LDL-uptake assay. A concentration of PCSK9 can be selected that promotes close to maximal loss of LDL-uptake and is still in the linear range of the dose response curve. Typically, this concentration is ~5 times the EC-50 of the protein extracted from the dose response curve. The concentrations can vary by protein.

Broadly, PCSK9-specific antagonists as defined herein selectively recognize and specifically bind to PCSK9. An antibody is typically said to specifically bind an antigen when the dissociation constant is ≤1 µM, preferably ≤100 nM and most preferably ≤10 nM. Use of the terms "selective" or "specific" herein, further, refers to the fact that the disclosed antagonists do not show significant binding to proteins other than PCSK9, except in those specific instances where the antagonist is supplemented or designed to confer an additional, distinct specificity to the PCSK9-specific binding portion (as, for example, in bispecific or bifunctional molecules where the molecule is designed to bind two molecules or effect two functions, at least one of which is to specifically bind PCSK9). In specific embodiments, PCSK9-specific antagonists bind to human PCSK9 with a $K_D$ of $1.2 \times 10^{-6}$ M or less. In more specific embodiments, PCSK9-specific antagonists bind to human PCSK9 with a $K_D$ of $5 \times 10^{-7}$ M or less, of $2 \times 10^{-7}$ M or less, or of $1 \times 10^{-7}$ M or less. In additional embodiments, PCSK9-specific antagonists bind to human PCSK9 with a $K_D$ of $1 \times 10^{-8}$ M or less. In further embodiments, PCSK9-specific antagonists bind to human PCSK9 with a $K_D$ of $5 \times 10^{-9}$ M or less, or of $1 \times 10^{-9}$ M or less. In select embodiments, PCSK9-specific antagonists bind to human PCSK9 with a $K_D$ of $1 \times 10^{-10}$ M or less, a $K_D$ of $1 \times 10^{-11}$ M or less, or a $K_D$ of $1 \times 10^{-12}$ M or less. In specific embodiments, PCSK9-specific antagonists do not bind proteins other than PCSK9 at the above $K_D$s. $K_D$ refers to the dissociation constant obtained from the ratio of $K_d$ (the dissociation rate of a particular binding molecule-target protein interaction) to $K_a$ (the association rate of the particular binding molecule-target protein interaction), or $K_d/K_a$ which is expressed as a molar concentration (M). $K_D$ values can be determined using methods well established in the art. A preferred method for determining the $K_D$ of a binding molecule is by using surface plasmon resonance, for example employing a biosensor system such as a Biacore™ (GE Healthcare Life Sciences) system.

PCSK9-specific antagonists disclosed herein have been shown to dose-dependently inhibit human PCSK9 dependent effects on LDL uptake. Accordingly, PCSK9-specific antagonists as disclosed herein are characterized by their ability to counteract PCSK9-dependent inhibition of LDL uptake into cells. This uptake of LDL into cells by the LDL receptor is referred to herein as "cellular LDL uptake". In specific embodiments, PCSK9-specific antagonists counteract or antagonize human PCSK9-dependent inhibition of LDL uptake into cells, exhibiting an $IC_{50}$ of less than $1.0 \times 10^{-6}$ M, or, in order of preference, less than $1 \times 10^{-7}$ M, $1 \times 10^{-8}$ M, $1 \times 10^{-9}$ M, $1 \times 10^{-10}$ M, $1 \times 10^{-11}$ M and $1 \times 10^{-12}$ M. The extent of inhibition by any PCSK9-specific antagonist may be measured quantitatively in statistical comparison to a control, or via any alternative method available in the art for assessing a negative effect on, or inhibition of, PCSK9 function (i.e., any method capable of assessing antagonism of PCSK9 function). In specific embodiments, the inhibition is at least about 10% inhibition. In other embodiments, the inhibition is at least 20%, 30%, 40%, 50%, 60%, 70,%, 80%, 90%, or 95%. Accordingly, PCSK9-specific antagonists capable of effecting these levels of inhibition of PCSK9 function form particular embodiments hereof. Specific embodiments provide PCSK9 antagonists as described that, upon administration to a subject, lower LDL by at least 20%, 25%, 30%, 35%, 40%, 45%, 50%, 55%, 60%, 65% and above. In specific embodiments, the PCSK9 antagonists lower LDL by those levels for a period of at least 7 days, 10 days, 15 days, 20 days, 25 days, 30 days, 35 days, 40 days and longer. In particular embodiments, the percent lowering is greater than or equal to 10, 15, 20 and 25 for over 20, 30 or 40 days. Particular embodiments, provide lowering greater than or equal to 25% for over 40 days (see, e.g., Example 19 and FIG. 17). Specific embodiments also provide for PCSK9-specific antagonists that bind to human FcRn at approximately pH 6.0 and dissociate at approximately pH 7.3 (see, e.g., Example 17 and FIGS. 14-15). Particular embodiments are wherein the disclosed PCSK9-specific antagonists exhibit a dissociation of <5% (in specific embodiments, less than 3% or 1%) at neutral pH. Dissociation (or % bound) can be calculated as described in Example 17. Specific embodiments, also provide PCSK-9 specific antagonists as described herein that have a ½ life in mice of greater than 50, 60, 70, 80, 90 or 95 hours (see, e.g., Example 18 and FIG. 16). In particular embodiments, PCSK9-specific antagonists are provided that have a ½ life in primates of greater than 50, 60, 70, 80, 90, 100, 110, 120, 130, 140 and 145 hours (see, e.g., Example 18). The present invention also provides, in specific embodiments, PCSK9-specific antagonists that, after 1 week of stress at 45° C. (under conditions similar to that described in Example 20), in pH 5, 6, 7 or 8 buffers have essentially no increase in oligomers, higher order aggregates and exhibit no clipping (see, e.g., Example 20 and Table 13). In specific embodiments, the above effects are as seen in humans and non-human primates (or where particularly specified, mice). In specific embodiments, the above effects are seen following intravenous or subcutaneous administration.

A PCSK9-specific antagonist in accordance herewith can be any binding molecule that specifically binds human PCSK9 protein including, but not limited to, antibody molecules as defined below, any PCSK9-specific binding structure, any polypeptide or nucleic acid structure that specifically binds PCSK9, and any of the foregoing incorporated into various protein scaffolds; including but not limited to, various non-antibody-based scaffolds, and various structures capable of affording or allowing for selective binding to PCSK9 including but not limited to small modular immunopharmaceuticals (or "SMIPs"; see, Haan & Maggos, 2004 *Biocentury* January 26); Immunity proteins (see, e.g., Chak et al., 1996 *Proc. Natl. Acad. Sci. USA* 93:6437-6442); cytochrome b562 (see Ku and Schultz, 1995 *Proc. Natl. Acad. Sci. USA* 92:6552-6556); the peptide α2p8 (see Barthe et al., 2000 *Protein Sci.* 9:942-955); avimers (Avidia; see Silverman et al., 2005 *Nat. Biotechnol.* 23:1556-1561); DARPins (Molecular Partners; see Binz et al., 2003 *J. Mol. Biol.* 332:489-503; and Forrer et al., 2003 *FEBS Lett.* 539:2-6); Tetranectins (see, Kastrup et al., 1998 *Acta. Crystallogr. D. Biol. Crystallogr.* 54:757-766); Adnectins (Adnexus; see, Xu et al., 2002 *Chem. Biol.* 9:933-942), Anticalins (Pieris; see Vogt & Skerra, 2004 *Chemobiochem.* 5:191-199; Beste et al., 1999 *Proc. Natl. Acad. Sci. USA* 96:1898-1903; Lamla & Erdmann, 2003 *J. Mol. Biol.* 329:381-388; and Lamla & Erdmann, 2004 *Protein Expr. Purif.* 33:39-47); A-domain proteins (see North & Blacklow, 1999 *Biochemistry* 38:3926-3935), Lipocalins (see Schlehuber & Skerra, 2005 *Drug Discov. Today* 10:23-33); Repeat-motif proteins such as Ankyrin repeat proteins (see Sedgwick & Smerdon, 1999 *Trends Biochem. Sci.* 24:311-316; Mosavi et al., 2002 *Proc. Natl. Acad. Sci. USA* 99:16029-16034; and Binz et al., 2004 *Nat. Biotechnol.* 22:575-582); Insect Defensin A (see Zhao et al., 2004 *Peptides* 25:629-635); Kunitz domains (see Roberts et al., 1992 *Proc. Natl. Acad. Sci. USA* 89:2429-2433; Roberts et al., 1992 *Gene* 121:9-15; Dennis & Lazarus, 1994 *J. Biol. Chem.* 269:22129-22136; and Dennis & Lazarus, 1994 *J. Biol. Chem.* 269:22137-22144); PDZ-Domains (see Schneider et al., 1999 *Nat. Biotechnol.* 17:170-175); Scorpion toxins such as Charybdotoxin (see Vita et al., 1998 *Biopolymers* 47:93-100); $10^{th}$ fibronectin type III domain (or 10Fn3; see Koide et al., 1998 *J. Mol. Biol.* 284:1141-1151, and Xu et al., 2002 *Chem. Biol.* 9:933-942); CTLA-4 (extracellular domain; see Nuttall et al., 1999 *Proteins* 36:217-227; and Irving et al., 2001 *J. Immunol. Methods* 248:31-45); Knottins (see Souriau et al., 2005 *Biochemistry* 44:7143-7155 and Lehtio et al., 2000 *Proteins* 41:316-322); Neocarzinostatin (see Heyd et al. 2003 *Biochemistry* 42:5674-5683); carbohydrate binding module 4-2 (CBM4-2; see Cicortas et al., 2004 *Protein Eng. Des. Sel.* 17:213-221); Tendamistat (see McConnell & Hoess, 1995 *J. Mol. Biol.* 250:460-470, and Li et al., 2003 *Protein Eng.* 16:65-72); T cell receptor (see Holler et al., 2000 *Proc. Natl. Acad. Sci. USA* 97:5387-5392;

Shusta et al., 2000 *Nat. Biotechnol.* 18:754-759; and Li et al., 2005 *Nat. Biotechnol.* 23:349-354); Affibodies (Affibody; see Nord et al., 1995 *Protein Eng.* 8:601-608; Nord et al., 1997 *Nat. Biotechnol.* 15:772-777; Gunneriusson et al., 1999 *Protein Eng.* 12:873-878); and other selective binding proteins or scaffolds recognized in the literature; see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Antibodies and the use of antigen-binding fragments is well defined and understood in the literature. The use of alternative scaffolds for protein binding is well appreciated in the scientific literature as well, see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Accordingly, non-antibody-based scaffolds or antagonist molecules in accordance herewith exhibiting selectivity for PCSK9 that counteract PCSK9-dependent inhibition of cellular LDL-uptake form important embodiments of the present invention. Aptamers (nucleic acid or peptide molecules capable of selectively binding a target molecule) are one specific example. They can be selected from random sequence pools or identified from natural sources such as riboswitches. Peptide aptamers, nucleic acid aptamers (e.g., structured nucleic acid, including both DNA and RNA-based structures) and nucleic acid decoys can be effective for selectively binding and inhibiting proteins of interest; see, e.g., Hoppe-Seyler & Butz, 2000 *J. Mol. Med.* 78:426-430; Bock et al., 1992 *Nature* 355:564-566; Bunka & Stockley, 2006 *Nat. Rev. Microbiol.* 4:588-596; Martell et al., 2002 *Molec. Ther.* 6:30-34; Jayasena, 1999 *Clin. Chem.* 45:1628-1650; the disclosures of which are incorporated herein by reference.

The three-dimensional structure of PCSK9 in complex with the AX132 FAb, determined using x-ray crystallography, revealed that a linear sequence of the light chain of this FAb encompassing residues 26-34 with a sequence of SQYVGSYLN (SEQ ID NO: 643) makes a specific interaction with the surface of PCSK9 used to bind the EGF-A domain of LDLR. This observation suggests that peptides, heterologous proteins, or other entities that include this sequence of amino acids could be designed and used to specifically disrupt the interaction between PCSK9 and LDLR. Smaller subsets of this sequence may also be useful, and the structural studies suggest that residues 28-32 (YVGSY) (SEQ ID NO: 644) appears to be the shortest such sequence that might confer specific recognition of the PCSK9 surface. Furthermore, the crystal structure of the PCSK9:AX132 Fab complex can be used to rationally design new chemical entities that embody similar interactions as that observed in the crystal structure. Accordingly, polypeptides or peptides comprising (or consisting essentially of: SEQ ID NO: 643 or SEQ ID NO: 644 are contemplated herein.

Given AX132's significant neutralizing activity and the activity of its variants, it is clearly of interest to identify other PCSK9-specific antagonists that bind to PCSK9 in the same manner as AX132 or one of its variants. One means of identifying antagonists and particularly antibodies that bind to the same region or epitope as AX132 or its variants, or an overlapping epitope is through a competition or similar assay where the candidate antibody or binding molecule would have to out-compete AX132 (or variant) for the epitope. Competitive antagonists encompassed herein are molecules that inhibit (i.e., prevent, or interfere with, AX132 (or variant) binding in comparison to a control) or reduce AX132 (or variant) binding by at least 50%, 60%, 70%, and 80% in order of increasing preference (even more preferably, at least 90% and, most preferably, at least 95%) at 1 µM or less with AX132 (or variant) at or below its $K_D$, and in particular those molecules that antagonize (i) PCSK9 binding to the LDL receptor, (ii) PCSK9 internalization into cells, or (iii) both PCSK9 binding to the LDL receptor and PCSK9 internalization into cells. Competition between binding members may be readily assayed in vitro for example using ELISA and/or by monitoring the interaction of the antibodies with PCSK9 in solution. The exact means for conducting the analysis is not critical. PCSK9 may be immobilized to a 96-well plate or may be placed in a homogenous solution. In specific embodiments, the ability of unlabeled candidate antibody(ies) to block the binding of labeled AX132 (or variant) can be measured using radioactive, enzyme or other labels. In the reverse assay, the ability of unlabeled antibodies to interfere with the interaction of labeled AX132 (or variant) with PCSK9 wherein said AX132 (or variant) and PCSK9 are already bound is determined. In specific embodiments, (i) PCSK9 is contacted with labeled AX132 (or variant); (ii) PCSK9 is contacted with the candidate antibody or pool of antibodies; and (iii) antibodies capable of interrupting or preventing complexes between PCSK9 and AX132 (or variant) are identified. The readout in such an example is through measurement of bound label. AX132 (or variant) and the candidate antibody(ies) may be added in any order or at the same time.

Antibodies identified as AX132 (or variant) competitors in the above or other suitable assays may be tested for the ability to antagonize or neutralize (i) PCSK9 binding to the LDL receptor; and/or (ii) PCSK9 internalization into cells. These parameters may be measured through the use of assays similar to that employed or described in the current specification. In specific embodiments, the inhibition demonstrated by the competing antibody is at least about 10% inhibition. In other embodiments, the inhibition is at least 20%, 30%, 40%, 50%, 60%, 70%, 80%, 90% or 95%.

The present invention specifically encompasses PCSK9-specific antagonists and particularly monoclonal antibody molecules (and their corresponding amino acid and nucleic acid sequences) that selectively bind to the same epitope as AX132 (or variant) or an overlapping epitope interfering with AX132 (or variant)'s binding to PCSK9. Monoclonal antibodies that specifically bind to the epitope of AX132 (or variant), or an overlapping epitope antagonize or neutralize (i) PCSK9 binding to the LDL receptor; (ii) PCSK9 internalization into cells, or (iii) both. A monoclonal antibody molecule in accordance herewith may be an intact (complete or full length) antibody, a substantially intact antibody, or a portion or fragment of an antibody comprising an antigen-binding portion, e.g., a Fab fragment, Fab' fragment or F(ab')$_2$ fragment of a murine antibody or of a chimeric antibody or of a humanized antibody or of a human antibody. Monoclonal, as used herein, refers to a homogeneous or substantially homogeneous (or pure) antibody population (i.e., at least about 90%, 91%, 92%, 93%, 94%, 95%, 96%, more preferably at least about 97% or 98%, or most preferably at least 99% of the antibodies in the population are identical and would compete in an ELISA assay for the same antigen or epitope). In specific embodiments of the present invention, the present invention provides monoclonal antibodies that (i) compete for binding to PCSK9 with a AX132 (or variant) antibody molecule, reducing AX132 (or variant) binding by at least 50% at 1 μM or less with AX132 (or variant) at or below its $K_D$, (ii) block PCSK9 binding to the LDL receptor, (iii) inhibit PCSK9 internalization into the cell, and (iv) comprise a specific antigen-binding region, VH, VL, set of CDRs or heavy CDR3, heavy and/or light chain or any variant of these components as described herein.

In any of the above assays for identifying antibodies binding the same or overlapping epitope region as AX132 (or variant), binding of the known binder (i.e., AX132 (or variant) antibody molecule) as compared to the binding of the candidate binder should be distinguishable. This can (but need not) be accomplished through the use of labels on either or both molecules as will be readily appreciated by the skilled artisan. Labels, as used herein, refer to another molecule or agent incorporated into/affixed to the antibody molecule. In one embodiment, the label is a detectable marker, e.g., a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In particular embodiments, the present invention encompasses antagonists as described herein characterized as binding specifically to any epitope sequence selected from the group consisting of: SEQ ID NOs: 576, 577, 579-582 and 237-RDA, or regions therein such as 157-NL-158 or SEQ ID NO: 578. In particular embodiments, the epitope sequence is within SEQ ID NOs: 576 and/or 577, or sub-regions therein such as 157-NL-158 or SEQ ID NO: 578. In particular embodiments, the antagonists described herein bind to SEQ ID NOs: 579, 580, 581 and 582, as well as 237-RDA. These epitopes are described further in Example 8 and in FIG. 4. The numerical numbers provide the starting and/or ending position on human PCSK9.

In specific embodiments, binding of a PCSK9-specific antagonist is significantly reduced or a mutant PCSK9 protein having one or more (e.g., 1, 2, 3, 4, 5 or more) mutations at the following residue positions: 192 and 379, as compared to a wild-type PCSK9 protein (SEQ ID NO: 642). In certain embodiments, binding of a PCSK9-specific antagonist is significantly reduced for a mutant PCSK9 protein having one or more (e.g., 1, 2, 3, 4, 5 or more) of the following mutations: D192G and F379Y.

An AX132 (or variant) antibody used as the standard for the competition assays may be any antibody molecule described herein. Molecules (peptides, antagonists, antibody molecules, etc.) tested may be from any source or library. In particular embodiments, the molecules are selected from a phage display library. In specific embodiments the molecules are selected using an EGF_AB peptide (293-DKVCN-MARDCRDWSDEPIKECGTNECLDNNGGC-SHVCNDLKIGYECLCPDGFQLVAQ RRCEDIDECQDP-DTCSQLCVNLE-372; SEQ ID NO: 645) that competes with AX132 in a manner similar to that described in Example 11.

Expression and selection of any of the PCSK9-specific antagonists described in the present application may be achieved using suitable technologies including, but not limited to phage display (see, e.g., International Application Number WO 92/01047, Kay et al., 1996 *Phage Display of Peptides and Proteins: A Laboratory Manual*, San Diego: Academic Press), Wang et al., 2010 *J. Mol. Biol.* 1088-1101; Wang et al., U.S. Pat. No. 7,175,983, yeast display, bacterial display, T7 display, and ribosome display (see, e.g., Lowe & Jermutus, 2004 *Curr. Pharm. Biotech.* 517-527).

Particular PCSK9-specific antagonists forming part of the present invention are antibody molecules or antibodies. "Antibody molecule" or "Antibody" as described herein refers to an immunoglobulin-derived structure with selective binding to human PCSK9 including, but not limited to, a full length or whole antibody, an antigen binding fragment (a fragment derived, physically or conceptually, from an antibody structure), a derivative of any of the foregoing, a fusion of any of the foregoing with another polypeptide, or any alternative structure/composition which incorporates any of the foregoing for purposes of selectively binding to/inhibiting the function of PCSK9. Antibody molecules can exist, for example, as intact immunoglobulins or as a number of well characterized fragments produced by, for example, digestion with various peptidases. The recognized immunoglobulin genes include the kappa, lambda, alpha, gamma, delta, epsilon and mu constant region genes, as well as a myriad of immunoglobulin variable region genes. Light chains are classified as gamma, mu, alpha, delta, or epsilon, which in turn define the immunoglobulin classes, IgG, IgM, IgA, IgD and IgE, respectively. "Whole" antibodies or "full length" antibodies often refers to proteins that comprise two heavy (H) and two light (L) chains inter-connected by disulfide bonds which comprise: (1) in terms of the heavy chains, a variable region (abbreviated herein as "$V_H$") and a heavy chain constant region which comprises three domains, $C_{H1}$, $C_{H2}$, and $C_{H3}$; and (2) in terms of the light chains, a light chain variable region (abbreviated herein as "$V_L$") and a light chain constant region which comprises one domain, $C_L$. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region broken. While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

Antibody fragments and, more specifically, antigen binding fragments are molecules possessing an antibody variable region or segment thereof (which comprises one or more of the disclosed CDR 3 or CDR2 domains, heavy and/or light, within framework regions of heavy and/or light chains, as appropriate), which confers selective binding to PCSK9, and particularly human PCSK9. Antibody fragments containing such an antibody variable region include, but are not limited to the following antibody molecules: a Fab, a F(ab')$_2$, a Fd, a Fv, a scFv, ccFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, an isolated CDR3, a minibody, a 'scAb', a dAb fragment, a diabody, a triabody, a tetrabody, a minibody, and artificial antibodies based upon protein scaffolds, including but not limited to fibronectin type III polypeptide antibodies (see, e.g., U.S. Pat. No. 6,703,199 and International Application Numbers WO 02/32925 and WO 00/34784) or cytochrome B; see, e.g., Nygren et al., 1997 Curr. Opinion Struct. Biol. 7:463-469; the disclosures of which are incorporated herein by reference. The antibody portions or binding fragments may be natural, or partly or wholly synthetically produced. Such antibody portions can be prepared by various means known by one of skill in the art, including, but not limited to, conventional techniques, such as papain or pepsin digestion. One of skill in the art will, furthermore, appreciate that any of the above antibody molecules, including full length as well as the various antibody fragments, may be synthesized de novo either chemically or by utilizing recombinant DNA methodology. Thus, the term antibody, as used herein, also includes full length antibodies and antibody fragments either produced by the generation or modification of whole antibodies or those synthesized de novo using recombinant DNA methodologies.

The term "isolated" as used herein in reference to antibody molecules, PCSK9-specific antagonists in general, encoding nucleic acid or other describes a property as it pertains to the disclosed PCSK9-specific antagonists, nucleic acid or other that makes them different from that found in nature. The difference can be, for example, that they are of a different purity than that found in nature, or that they are of a different structure or form part of a different structure than that found in nature. A structure not found in nature, for example, includes recombinant human immunoglobulin structures including, but not limited to, recombinant human immunoglobulin structures with optimized CDRs. Other examples of structures not found in nature are PCSK9-specific antagonists or nucleic acid substantially free of other cellular material. Isolated PCSK9-specific antagonists are generally free of other protein-specific antagonists having different protein specificities (i.e., possess an affinity for other than PCSK9).

In one particular aspect, the present invention provides isolated PCSK9-specific antagonists which antagonize PCSK9 function. In particular embodiments, said PCSK9-specific antagonists inhibit human PCSK9's antagonism of cellular LDL uptake by interfering with PCSK9 binding to the LDL receptor and resultant PCSK9 cell internalization. Disclosed PCSK9-specific antagonists, thus, form desirable molecules for lowering plasma LDL-cholesterol levels; see, e.g., Cohen et al., 2005 Nat. Genet. 37:161-165 (wherein significantly lower plasma LDL cholesterol levels were noted in individuals heterozygous for a nonsense mutation in allele PCSK9); Rashid et al., 2005 Proc. Natl. Acad. Sci. USA 102:5374-5379 (wherein PCSK9-knockout mice evidenced increased numbers of LDLRs in hepatocytes, accelerated plasma LDL clearance, and significantly lower plasma cholesterol levels); and Cohen et al., 2006 N Engl. J. Med. 354: 1264-1272 (wherein humans heterozygous for mutated, loss of function, PCSK9 exhibited a significant reduction in the long-term risk of developing atherosclerotic heart disease).

Through repeat experiments, antibody molecules tested herein herein dose-dependently inhibited the effects of both human PCSK9 on LDL uptake. In specific embodiments, the present invention, thus, encompasses isolated PCSK9-specific antagonists as described herein, as well as equivalents (characterized as having one or more (in specific embodiments, 1-5 or 1-3) amino acid substitutions that do not degrade the PCSK9-selective property of the disclosed AX132 or variant antibody molecules) or homologs thereof. Particular embodiments comprise isolated PCSK9-specific antagonists that comprise the CDR domains disclosed herein or sets of heavy and/or light chain CDR domains disclosed herein, or equivalents thereof, characterized as having one or more amino acid substitutions.

Use of the terms "domain" or "region" herein simply refers to the respective portion of the antibody molecule wherein the sequence or segment at issue will reside or, in the alternative, currently resides.

In specific embodiments, the present invention provides isolated PCSK9-specific antagonists and, in more specific embodiments, antibody molecules that comprise (i) a heavy chain variable region selected from the group consisting of: SEQ ID NOs: 360-510 and/or (ii) a light chain variable region selected from the group consisting of: SEQ ID NOs: 511-549; equivalents thereof characterized as having one or more (in particular embodiments, 1-5 or 1-3) amino acid substitutions, and homologs thereof. This group also encompasses, for SEQ ID NOs: 360, 362, and 364-510, PCSK9 antibody molecules that do not have the last 3 amino acid residues in the sequence (see, e.g., SEQ ID NOs: 361 and 363); due to varying interpretations on variable region boundaries. The disclosed antagonists should counteract or inhibit human PCSK9-dependent inhibition of cellular LDL uptake. In specific embodiments, the present invention provides homologs of the disclosed antagonists characterized as comprising a heavy chain variable and/or a light chain variable region being at least 90% (or in specific embodiments, at least 95%, 97% or 99%) identical in sequence to either or both, respectively, of (i) a heavy chain variable region selected from the group consisting of: SEQ ID NOs: 360-510 and/or (ii) a light chain variable region selected from the group consisting of: SEQ ID NOs: 511-549; said antagonists which inhibit human PCSK9-dependent inhibition of cellular LDL uptake by at least 10%.

In particular embodiments, the present invention provides isolated PCSK9-specific antagonists and, in more specific embodiments, PCSK9 antibody molecules that comprise (i) variable heavy CDR3 sequence selected from the group consisting of: SEQ ID NOs: 1-5, 7, 9, 11, 13-63 and residues 4-12 of SEQ ID NOs: 1, 3, 5, 9 and 13-63 and/or (ii) variable light CDR3 sequence selected from the group consisting of: SEQ ID NOs: 295-301, 303, 305-334 and residues 4-13 of SEQ ID NOs: 295, 297, 299, 301 and 305-334; and equivalents thereof characterized as having one or more (in particular embodiments, 1-5 or 1-3) amino acid substitutions; specific embodiments of which inhibit human PCSK9-dependent inhibition of cellular LDL uptake by at least 10%. Specific embodiments provide isolated antagonists which additionally comprise in the heavy and/or light chain variable regions CDR1 and/or CDR2 sequences as described herein; or equivalents thereof characterized as having one or more (in specific embodiments, 1-5 or 1-3) amino acid substitutions in any one or more of the CDR sequences. In specific embodiments, the present invention provides homologs of the disclosed antagonists characterized as being at least 90% (in specific embodiments, 95%, 97%, or 99%) identical to the CDR3 sequences or within each of the CDR1, CDR2 and CDR3 sequences; said antagonists which inhibit human PCSK9-dependent inhibition of cellular LDL uptake by at least 10%.

In particular embodiments, the present invention provides isolated PCSK9-specific antagonists and, in more specific embodiments, PCSK9 antibody molecules that comprise (i) variable heavy CDR2 sequence selected from the group consisting of: SEQ ID NOs: 64-68, 70, 72, 74, 76-182 and residues 4-20 of SEQ ID NOs: 64, 66, 68, 72 and 76-182 and/or (ii) variable light CDR2 sequence selected from the group consisting of: SEQ ID NOs: 335-339, 341, 343-346, and residues 4-10 of SEQ ID NOs: 335, 337, 339 and 343-346; and equivalents thereof characterized as having one or more (in particular embodiments, 1-5 or 1-3) amino acid substitutions; specific embodiments of which inhibit human PCSK9-dependent inhibition of cellular LDL uptake by at least 10%. Specific embodiments provide isolated antagonists which additionally comprise heavy and/or light chain variable regions CDR1 and/or CDR3 sequences as described herein; or equivalents thereof characterized as having one or more (in specific embodiments, 1-5 or 1-3) amino acid substitutions in any one or more of the CDR sequences. In specific embodiments, the present invention provides homologs of the disclosed antagonists characterized as being at least 90% (in specific embodiments, 95%, 97%, or 99%) identical to the CDR2 sequences or within each of the CDR1, CDR2 and CDR3 sequences; said antagonists which inhibit human PCSK9-dependent inhibition of cellular LDL uptake by at least 10%.

Select variable heavy CDR1 regions comprise sequence selected from the group consisting of: SEQ ID NOs: 183-189, 191, 193, 195 197-294, and residues 4-13 of SEQ ID NOs: 183, 185, 187, 189, 193 and 197-294; and equivalents thereof characterized as having one or more (in particular embodiments, 1-5 or 1-3) amino acid substitutions.

Select variable light CDR1 regions comprise sequence selected from the group consisting of: SEQ ID NOs: 347-349, 351, 353-359, and residues 4-14 of SEQ ID NOs: 347, 349 and 353-359; and equivalents thereof characterized as having one or more (in particular embodiments, 1-5 or 1-3) amino acid substitutions.

Specific embodiments provide isolated PCSK9-specific antagonists and, in more specific embodiments, antibody molecules which comprise one or more (in particular embodiments, one of each CDR1, 2, and 3 regions) heavy chain variable region CDR1, CDR2, and CDR3 sequences and light chain variable region CDR1, CDR2, and CDR3 sequences as disclosed herein; and equivalents thereof characterized as having one or more (in particular embodiments, 1-5 or 1-3) amino acid substitutions in any one or more of the CDR sequences; specific embodiments of which inhibit human PCSK9-dependent inhibition of cellular LDL uptake by at least 10%. In specific embodiments, the present invention provides homologs of the disclosed antagonists characterized as being at least 90% (in specific embodiments, 95%, 97%, or 99%) identical over the disclosed heavy and light chain variable region CDR1, CDR2 and CDR3 sequences, respectively; said antagonists which inhibit human PCSK9-dependent inhibition of cellular LDL uptake by at least 10%.

One particular aspect of the present invention encompasses isolated PCSK9-specific antagonists and, in more specific embodiments, antibody molecules which are variants of that disclosed above which inhibit human PCSK9-dependent inhibition of cellular LDL uptake by at least 10%.

Additional distinct embodiments encompass isolated PCSK9-specific antagonists which comprise: (a) a heavy chain variable region comprising CDR1, CDR2 and CDR3 sequence, wherein (i) the CDR1 sequence is selected from the group consisting of: SEQ ID NOs: 183-189, 191, 193, 195, 197-294, and residues 4-13 of SEQ ID NOs: 183, 185, 187, 189, 193, and 197-294; (ii) the CDR2 sequence is selected from the group consisting of: SEQ ID NOs: 64-68, 70, 72, 74, 76-182 and residues 4-20 of SEQ ID NOs: 64, 66, 68, 72 and 76-182; and (iii) the CDR3 sequence is selected from the group consisting of: SEQ ID NOs: 1-5, 7, 9, 11, 13-63, and residues 4-12 of SEQ ID NOs: 1, 3, 5, 9 and 13-63 and/or (b) a light chain variable region comprising CDR1, CDR2 and CDR3 sequence, wherein (i) the CDR1 sequence is selected from the group consisting of: SEQ ID NOs: 347-349, 351, 353-359, and residues 4-14 of SEQ ID NOs: 347, 349 and 353-359; (ii) the CDR2 sequence is selected from the group consisting of: SEQ ID NOs: 335-339, 341, 343-346 and residues 4-10 of SEQ ID NOs: 335, 337, 339, and 343-346; and (iii) the CDR3 sequence is selected from the group consisting of: SEQ ID NOs: 295-301, 303, 305-334, and residues 4-13 of SEQ ID NOs: 295, 297, 299, 301 and 305-334; and equivalents thereof characterized as having one or more (in particular embodiments, 1-5 or 1-3) amino acid substitutions; specific embodiments of which inhibit human PCSK9-dependent inhibition of cellular LDL uptake by at least 10%.

In specific embodiments herein the CDRs are in place of the corresponding regions of AX132 (or disclosed variants) or alternative antagonist, antibody molecule or scaffold structure with or without amino acid substitutions (in specific embodiments, 1-5 or 1-3); specific embodiments of which inhibit human PCSK9-dependent inhibition of cellular LDL uptake by at least 10%.

Particular embodiments are isolated PCSK9-specific antagonists which comprise the above-described VH and VL regions in a full length antibody. Specific embodiments herein further comprise a series of amino acids selected from the group consisting of: SEQ ID NO: 572 (IgG1), SEQ ID NO: 573 (IgG2), SEQ ID NO: 574 (IgG4) and SEQ ID NO: 575 (IgG2 m4).

Amino acid substitutions encompassed herein may be conservative or non-conservative amino acid substitutions. Amino acid substitutions, as one of ordinary skill in the art will appreciate, are substitutions that replace an amino acid residue with one imparting similar or better (for the intended purpose) functional and/or chemical characteristics. Antagonists bearing amino acid substitutions can be tested for retained or better activity using functional assays available in the art or described herein. PCSK9-specific antagonists possessing one or more amino acid substitutions which retain the ability to selectively bind to human PCSK9 and antagonize PCSK9 functioning at a level the same or better than AX132 (or variant) antibody molecules as described herein are referred to herein as "functional equivalents" of the disclosed antagonists and form specific embodiments of the present invention. Conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Modifications as described above may or may not be designed to significantly alter the binding or functional inhibition characteristics of the PCSK9-specific antagonist, and may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis as discussed in, for example, MacLennan et al., 1998 *Acta Physiol. Scand. Suppl.* 643:55-67, and Sasaki et al., 1998 *Adv. Biophys.* 35:1-24.

In one specific embodiment of the present invention, a CDR disclosed herein is altered so as to generate a more stable variant or a variant that is recombinantly expressed at higher levels. For example, if Asn-Gly or Asp-Gly is in a CDR, the invention encompasses variants wherein the Asp or Asn is changed to Glu or Ala or wherein the Gly is changed to Ala. A benefit of such a change is removal of the potential for isoaspartate formation. Also, if a Met is in a CDR in an exposed position, the scope of the present invention includes variants wherein the Met is changed to Lys, Leu, Ala, or Phe. A benefit of such a change is removal of the potential for methionine oxidation. If an Asn is in a CDR of the invention, the scope of the present invention includes variants wherein Asn is changed to Gln or Ala. A benefit of such a change is removal of the potential for deamidation. Furthermore, if an Asn-Pro is in a CDR of the present invention, the present invention includes variants wherein Asn is changed to Gln or Ala or wherein Pro is changed to Ala. A benefit of such a change is removal of a possible scissile Asn-Pro peptide bond. The scope of the invention includes embodiments wherein the heavy or light chain CDRs of any of the disclosed antibody molecules are independently changed in one or more places as described above.

In another aspect, the present invention provides isolated PCSK9-specific antagonists and, in more specific embodiments, antibody molecules which comprise heavy and/or light chain variable regions comprising amino acid sequences that are homologous to the corresponding amino acid sequences of the disclosed antibodies, wherein the antibody molecules inhibit PCSK9-dependent inhibition of cellular LDL uptake. Specific embodiments are antagonists which comprise heavy and/or light chain variable regions which are at least 90% identical to disclosed heavy and/or light chain variable regions (or heavy and/or light chains), respectively. Reference to "at least 90% identical" includes at least 90, 91, 92, 93, 94, 95, 96, 97, 98, 99 and 100% identical sequences along the full length of the molecule disclosed herein.

PCSK9-specific antagonists with amino acid sequences homologous to the amino acid sequences of antagonists described herein are typically produced to improve one or more of the properties of the antagonist without negatively impacting its specificity for PCSK9. One method of obtaining such sequences, which is not the only method available to the skilled artisan, is to mutate sequence encoding the PCSK9-specific antagonist or specificity-determining region(s) thereof, express an antagonist comprising the mutated sequence(s), and test the encoded antagonist for retained function using available functional assays including those described herein. Mutation may be by site-directed or random mutagenesis. As one of skill in the art will appreciate, however, other methods of mutagenesis can readily bring about the same effect. For example, in certain methods, the spectrum of mutants are constrained by non-randomly targeting amino acid substitutions based on either amino acid chemical or structural characteristics, or else by protein structural considerations. In affinity maturation experiments, several such mutations may be found in a single selected molecule, whether they are randomly or non-randomly selected. There are also various structure-based approaches toward affinity maturation as demonstrated in, e.g., U.S. Pat. No. 7,117,096, PCT Pub. Nos.: WO 02/084277 and WO 03/099999; the disclosures of which are incorporated herein by reference.

As used herein, the percent homology between two amino acid or nucleic acid sequences is equivalent to the percent identity between the two sequences, and these two terms will be used interchangeably throughout. As used herein, % identity of two nucleic acid or amino acid sequences is determined using the algorithm of Karlin and Altschul (Proc. Natl. Acad. Sci. USA 90:5873-5877, 1993). Such an algorithm is incorporated into the NBLAST and XBLAST programs of Altschul et al., 1990 *J. Mol. Biol.* 215:403-410. BLAST nucleotide searches are performed with the NBLAST program, score=100, wordlength=12, to obtain nucleic acid sequences homologous to a nucleic acid molecule of the invention. BLAST protein searches are performed with the XBLAST program, score=50, wordlength=3, to obtain amino acid sequences homologous to an amino acid sequence disclosed herein. To obtain gapped alignments for comparison purposes, Gapped BLAST is utilized as described in Altschul et al., 1997 *Nucleic Acids Res.* 25:3389-3402. When utilizing BLAST and Gapped BLAST programs, the default parameters of the respective programs (e.g., XBLAST and NBLAST) are used.

Utilization of components of one or more disclosed PCSK9-specific molecules to produce other binding molecules with similar or better specificity is well within the realm of one skilled in the art. This can be accomplished, for example, using techniques of recombinant DNA technology. One specific example of this involves the introduction of DNA encoding the immunoglobulin variable region, or one or more of the CDRs, of an antibody to the variable region, constant region, or constant region plus framework regions, as appropriate, of a different immunoglobulin. Such molecules form important aspects of the present invention. Specific immunoglobulins or the corresponding sequences, into which particular disclosed sequences may be inserted or, in the alternative, form the essential part of, include but are not limited to the following antibody molecules which form particular embodiments of the present invention: a Fab (monovalent fragment with variable light (VL), variable heavy (VH), constant light (CL) and constant heavy 1 (CH1) domains), a F(ab')$_2$ (bivalent fragment comprising two Fab fragments linked by a disulfide bridge or alternative at the hinge region), a Fd (VH and CH1 domains), a Fv (VL and VH domains), a scFv (a single chain Fv where VL and VH are joined by a linker, e.g., a peptide linker, see, e.g., Bird et al., 1988 *Science* 242:423-426, Huston et al., 1988 *PNAS USA* 85:5879-5883), a bispecific antibody molecule (an antibody molecule comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer (see, e.g., PCT/US92/09965), an isolated CDR3, a minibody (single chain-CH$_3$ fusion that self assembles into a bivalent dimer of about 80 kDa), a 'scAb' (an antibody fragment containing VH and VL as well as either CL or CH$_1$), a dAb fragment (VH domain, see, e.g., Ward et al., 1989 *Nature* 341:544-546, and McCafferty et al., 1990 *Nature* 348:552-554; or VL domain; Holt et al., 2003 *Trends in Biotechnology* 21:484-489), a diabody (see, e.g., Holliger et al., 1993 *PNAS USA* 90:6444-6448 and International Application Number WO 94/13804), a triabody, a tetrabody, a minibody (a scFv joined to a CH3; see, e.g., Hu et al., 1996 *Cancer Res.* 56:3055-3061), IgG, IgG1, IgG2, IgG3, IgG4, IgM, IgD, IgA, IgE or any derivatives thereof, and artificial antibodies based upon protein scaffolds, including but not limited to fibronectin type III polypeptide antibodies (see, e.g., U.S. Pat. No. 6,703,199 and International Application Number WO 02/32925) or cytochrome B; see, e.g., Koide et al., 1998 *J. Molec. Biol.* 284:1141-1151, and Nygren et al., 1997 *Current Opinion in Structural Biology* 7:463-469; the disclosures of which are incorporated herein by reference. Certain antibody molecules including, but not limited to, Fv, scFv, diabody molecules or domain antibodies (Domantis) may be stabilized by incorporating disulfide bridges to line the VH and VL domains, see, e.g., Reiter et al., 1996 *Nature Biotech.* 14:1239-1245; the disclosure of which is incorporated herein by reference. Bispecific antibodies may be produced using conventional technologies (see, e.g., Holliger & Winter, 1993 *Current Opinion Biotechnol.* 4:446-449, specific methods of which include production chemically, or from hybrid hybridomas) and other technologies including, but not limited to, the BiTE™ technology (molecules possessing antigen binding regions of different specificity with a peptide linker) and knobs-into-holes engineering (see, e.g., Ridgeway et al., 1996 *Protein Eng.* 9:616-621; the disclosure of which is incorporated herein by reference). Bispecific diabodies may be produced in *E. coli*, and these molecules as other PCSK9-specific antagonists, as one of skill in the art will appreciate, may be selected using phage display in the appropriate libraries (see, e.g., International Application Number WO 94/13804; the disclosure of which is incorporated herein by reference).

Variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992 *Bio/Technology* 10:779-783; the disclosure of which is incorporated herein by reference. A variable heavy domain may be paired with a variable light domain to provide an antigen binding site. In addition, independent regions (e.g., a variable heavy domain alone) may be used to bind antigen. The artisan is well aware, as well, that two domains of an Fv fragment, VL and VH, while perhaps coded by separate genes, may be joined, using recombinant methods, by a synthetic linker that enables them to be made as a single protein chain in which the VL and VH regions pair to form monovalent molecules (scFvs).

Specific embodiments provide the CDR(s) in germline framework regions. Framework regions, including but not limited to human framework regions, are known to those of skill in the art (e.g., a human or non-human framework). The framework regions may be naturally occurring or consensus framework regions. In one aspect, the framework region of an antibody of the invention is human (see, e.g., Clothia et al., 1998 *J. Mol. Biol.* 278:457-479 for a listing of human framework regions; said disclosure of which is incorporated herein by reference in its entirety). Specific embodiments herein provide the disclosed heavy and/or light chain variable CDR3 sequences into VH3 or VK3, respectively, in place of the relevant CDR. Specific embodiments herein provide the disclosed heavy and/or light chain variable CDR1, CDR2 and/or CDR3 sequences into VH3 or VK3, respectively, in place of the relevant CDRs.

The present invention encompasses antibody molecules that are human, humanized, deimmunized, chimeric and primatized. The invention also encompasses antibody molecules produced by the process of veneering; see, e.g., Mark et al., 1994 Handbook of Experimental Pharmacology, vol. 113: The pharmacology of monoclonal Antibodies, Springer-Verlag, pp. 105-134; the disclosure of which is incorporated herein by reference. "Human" in reference to the disclosed antibody molecules specifically refers to antibody molecules having variable and/or constant regions derived from human germline immunoglobulin sequences, wherein said sequences may, but need not, be modified/altered to have certain amino acid substitutions or residues that are not encoded by human germline immunoglobulin sequence. Such mutations can be introduced by methods including, but not limited to, random or site-specific mutagenesis in vitro, or by somatic mutation in vivo. Specific examples of mutation techniques discussed in the literature are that disclosed in Gram et al., 1992 *PNAS USA* 89:3576-3580; Barbas et al., 1994 *PNAS USA* 91:3809-3813, and Schier et al., 1996 *J. Mol. Biol.* 263:551-567; the disclosures of which are incorporated herein by reference. These are only specific examples and do not represent the only available techniques. There are a plethora of mutation techniques in the scientific literature which are available to, and widely appreciated by, the skilled artisan. "Humanized" in reference to the disclosed antibody molecules refers specifically to antibody molecules wherein CDR sequences derived from another mammalian species, such as a mouse, are grafted onto human framework sequences. "Primatized" in reference to the disclosed antibody molecules refers to antibody molecules wherein CDR sequences of a non-primate are inserted into primate framework sequences, see, e.g., WO 93/02108 and WO 99/55369; the disclosures of which are incorporated herein by reference.

Specific antibodies of the present invention are monoclonal antibodies and, in particular embodiments, are in one of the following antibody formats: IgD, IgA, IgE, IgM, IgG1, IgG2, IgG3, IgG4 or any derivative of any of the foregoing. The language "derivatives thereof" or "derivatives" in this respect includes, inter alia, (i) antibodies and antibody molecules with amino acid modifications in one or both variable regions (i.e., VH and/or VL), (ii) antibodies and antibody molecules with manipulations in the constant regions of the heavy and/or light chains, and/or (iii) antibodies and antibody molecules that contain additional chemical moieties which are not normally a part of the immunoglobulin molecule (e.g., pegylation).

Manipulations of the variable regions can be within one or more of the VH and/or VL CDR regions. Site-directed mutagenesis, random mutagenesis or other method for generating sequence or molecule diversity can be utilized to create mutants which can subsequently be tested for a particular functional property of interest in available in vitro or in vivo assays including those described herein.

Antibodies of the present invention also include those in which modifications have been made to the framework residues within VH and/or VL to improve one or more properties of the antibody of interest. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al; the disclosure of which is incorporated herein by reference.

In addition or alternative to modifications made within the framework or CDR regions, antibodies of the invention may be engineered to include modifications within the Fc or constant regions, where present, typically to alter one or more functional properties of the antibody, such as serum half-life, complement fixation, Fc receptor binding, and/or antigen-dependent cellular cytotoxicity.

The concept of generating "hybrids" or "combinatorial" IgG forms comprising various antibody isotypes to hone in on desired effector functionality has generally been described; see, e.g., Tao et al., 1991 *J. Exp. Med.* 173:1025-1028. A specific embodiment of the present invention encompasses antibody molecules that possess specific manipulations in the Fc region which have been found to result in reduced or altered binding to FcγR receptors, C1q or FcRn on the part of the antibody. The present invention, therefore, encompasses antibodies in accordance with the present description that do not provoke (or provoke to a lesser extent) antibody-dependent cellular cytotoxicity ("ADCC"), complement-mediated cytotoxicity ("CMC"), or form immune complexes, while retaining normal pharmacokinetic ("PK") properties. Specific embodiments of the present invention provide an antibody molecule as defined in accordance with the present invention which comprises, as part of its immunoglobulin structure, SEQ ID NO: 575 and, in particular embodiments, residues 107-326 of SEQ ID NO: 575 as part of the immunoglobulin structure. The present invention encompasses antibody molecules which comprise: (i) a light chain variable region selected from the group consisting of: SEQ ID NOs: 511-549 (and in specific embodiments, selected from the group consisting of: SEQ ID NOs: 511-518, 520-524 and 526-549), and (ii) a heavy chain variable region selected from the group consisting of: SEQ ID NOs: 360-510 in sequence with (adjacent to) or followed by a series of amino acids selected from the group consisting of: SEQ ID NO: 572 (IgG1), SEQ ID NO: 573 (IgG2), SEQ ID NO: 574 (IgG4) and SEQ ID NO: 575 (IgG2 m4). In particular embodiments, the light chain and heavy chain pairings of (i) and (ii) above are (a) SEQ ID NOs: 360 and 511, and (b) SEQ ID NOs: 362 and 511.

The present invention also encompasses crystals The present invention includes crystals comprising any PCSK9-specific antagonist of the invention complexed with PCSK9 or a peptide epitope thereof.

Several crystallization methods are known in the art (Giegé, et al., (1994) Acta Crystallogr. D50: 339-350; McPherson, (1990) Eur. J. Biochem. 189: 1-23). Such methods include microbatch, hanging drop, seeding and dialysis. Preferably, hanging-drop vapor diffusion (McPherson, (1976) J. Biol. Chem. 251: 6300-6303) or microbatch methods (Chayen (1997) Structure 5: 1269-1274) are used. In each of these methods, it is important to promote continued crystal growth after nucleation by maintaining a supersaturated solution. In the microbatch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels.

Once a crystal of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of the PCSK9/PCSK9-specific antagonist complex. The present invention includes crystals which effectively diffract X-rays for the determination of the atomic coordinates of the PCSK9/PCSK9-specific antagonist complex to a resolution of greater than about 5.0 Ångströms (e.g., about 4.5 Å, about 4.0 Å, about 3 Å, about 2.5 Å, about 2 Å, about 1.95 Å, about 1 Å), preferably greater than about 4.0 Ångströms (e.g., about 3 Å, about 2.5 Å, about 2 Å, about 1.95 Å, about 1 Å), more preferably greater than about 2.8 Ångströms (e.g., about 2.5 Å, about 2 Å, about 1.95 Å, about 1 Å) and most preferably greater than about 2.0 Ångströms (e.g., about 1.95 Å, about 1.5 Å, about 1.0 Å).

The scope of the present invention also encompasses a crystalline complex between a PCSK9-specific antagonist of the present invention (e.g., a Fab comprising the heavy chain amino acid sequence set forth in SEQ ID NO: 552 and the light chain amino acid sequence set forth in SEQ ID NO: 554) and PCSK9 in space group The complex of PCSK9 and the AX132 Fab fragment crystallized in space group $P6_5$ and comprising the unit cell dimensions a=155.946 Å, b=155.946 Å, c=160.037 Å and α=90°, β=90°, γ=120°, wherein the Fab is derived from the antibody AX132 as described herein.

The present invention includes PCSK9/PCSK9-specific antagonist complex crystals whose three-dimensional structure is described by the structure coordinates set forth in Table 14. The scope of the present invention also includes crystals that possess structural coordinates which are similar to those set forth in Table 14. Structural similarity between crystals is discussed in detail below.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The present invention includes crystals exhibiting structural coordinates which are similar to those set forth in Table 14 but for crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Table 14, the resulting three-dimensional shape is considered to be the same and, accordingly, the modified crystal is considered to be within the scope of the present invention.

Various computational analyses may be used to determine whether a crystal is sufficiently similar to the crystals whose structural coordinates are set forth in Table 14 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation, and 4) analyze the results. Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as alpha carbon atoms (Cα) or all protein backbone atoms (N, Cα, C and O) for all conserved residues between the two structures being compared. When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Ångströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

The term "least squares" relates to a method based on the principle that the best estimate of a value is that in which the sum of the squares of the deviations of observed values is a minimum.

For the purpose of this invention, any crystalline molecule characterized by a set of structure coordinates that has a RMSD of conserved residue backbone atoms (N, Cα, C, O) or of alpha carbon atoms (Cα) only of less than about 1.5 Å when superimposed—using backbone atoms or alpha carbon atoms—on the relevant structure coordinates of Table 14 are considered identical and are within the scope of the present invention. In an embodiment, the root mean square deviation is about 1.5 Å or about 1.0 Å or about 0.75 Å or about 0.5 Å or about 0.25 Å or about 0.10 Å.

The present invention also encompasses any non-crystalline PCSK9-specific antagonist that, when converted to Fab format, binds to human PCSK9 in a manner characterized by a three dimensional structure which is characterized by a set of structure coordinates that has a RMSD of conserved residue backbone atoms (N, Cα, C, O) or of alpha carbon atoms (Cα) only of less than about 1.5 Å when superimposed—using backbone atoms or alpha carbon atoms—on the relevant structure coordinates of Table 14 are considered identical and are within the scope of the present invention. In an embodiment, the root mean square deviation is about 1.5 Å or about 1.0 Å or about 0.75 Å or about 0.5 Å or about 0.25 Å or about 0.10 Å.

In particular embodiments, the present invention encompasses PCSK9-specific antagonists that bind to PCSK9 within 10 Å or less from at least one (in specific embodiments, at least 2, 4, 10, 15, 20, 25, 30 or 35; or all) of the following residues on PCSK9: S153, I154, P155, W156, N157, L158, D192, H193, R194, E195, I196, E197, G198, R199, 5221, H229, G232, S235, G236, 8237, D238, A239, G240, K243, G244, D367, I368, I369, G370, A371, S372, S373, D374, C375, 5376, T377, C378, F379, V380, S381. In specific embodiments, the present invention encompasses PCSK9-specific antagonists that bind to PCSK9 within 5 Å or less from at least one (in specific embodiments, at least 2, 4 or 10; or all) of the following residues on PCSK9: S153, P155, R194, E195, R237, D238, A239, I369, D374, C375, S376, T377, C378, F379.

Specific PCSK9-specific antagonists may carry a detectable label, or may be conjugated to a toxin (e.g., a cytotoxin), a radioactive isotope, a radionuclide, a liposome, a targeting moiety, a biosensor, a cationic tail, or an enzyme (e.g., via a peptidyl bond or linker). Such PCSK9-specific antagonist compositions form an additional aspect of the present invention.

In another aspect, the present invention provides isolated nucleic acid encoding disclosed PCSK9-specific antagonists. "Isolated" as mentioned prior refers to the property of the thing referred to that makes them different from that found in nature. The difference can be, for example, that they are of a different purity than that found in nature, or that they are of a different structure or form part of a different structure than that found in nature. An example of nucleic acid not found in nature is, for example, nucleic acid substantially free of other cellular material. The nucleic acid may be present in whole cells, in a cell lysate, or in a partially purified or substantially pure form. In specific instances, a nucleic acid may be isolated when purified away from other cellular components or other contaminants, e.g., other cellular nucleic acids or proteins, for example, using standard techniques, including without limitation, alkaline/SDS treatment, CsCl banding, column chromatography, agarose gel electrophoresis and other suitable methods known in the art. The nucleic acid may include DNA (inclusive of cDNA) and/or RNA. Nucleic acids of the present invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

The present invention encompasses isolated nucleic acid encoding disclosed variable heavy and/or light chains and select components thereof, particularly the disclosed variable or respective CDR regions. In specific embodiments hereof, the CDR(s) are provided within antibody framework regions and, in particular embodiments, human framework regions. Specific embodiments provide isolated nucleic acid encoding the CDR(s) into germline framework regions including, but not limited to, human germline framework regions. Specific embodiments herein provide isolated nucleic acid encoding heavy chain CDR3 sequence selected from the group consisting of: SEQ ID NOs: 1-5, 7, 9, 11, 13-63, and residues 4-12 of SEQ ID NOs: 1, 3, 5, 9, and 13-63 (in specific embodiments, said nucleic acid of which comprises a sequence selected from the group consisting of: SEQ ID NOs: 6, 8, 10 and 12). Specific embodiments herein provide isolated nucleic acid encoding heavy chain CDR2 sequence selected from the group consisting of: SEQ ID NOs: 64-68, 70, 72, 74, 76-182, and residues 4-20 of SEQ ID NOs: 64, 66, 68, 72 and 76-182 (in specific embodiments, said nucleic acid of which comprises a sequence selected from the group consisting of: SEQ ID NOs: 69, 71, 73 and 75). Specific embodiments herein provide isolated nucleic acid encoding heavy chain CDR1 sequence selected from the group consisting of: SEQ ID NOs: 183-189, 191, 193, 195, 197-294 and residues 4-13 of SEQ ID NOs: 183, 185, 187, 189, 193 and 197-294 (in specific embodiments, said nucleic acid of which comprises a sequence selected from the group consisting of: SEQ ID NOs: 190, 192, 194 and 196). Specific embodiments herein provide nucleic acid encoding the disclosed heavy chain variable CDR1, CDR2 and/or CDR3 sequences into VH3 in place of the relevant CDRs. Specific embodiments herein provide isolated nucleic acid encoding light chain CDR3 sequence selected from the group consisting of: SEQ ID NOs: 295-301, 303, 305-334, and residues 4-13 of SEQ ID NOs: 295, 297, 299, 301 and 305-334 (in specific embodiments, said nucleic acid of which comprises a sequence selected from the group consisting of: SEQ ID NOs: 302 and 304). Specific embodiments herein provide isolated nucleic acid encoding light chain CDR2 sequence selected from the group consisting of: SEQ ID NOs: 335-339, 341, 343-346, and residues 4-10 of SEQ ID NOs: 335, 337, 339 and 343-346 (in specific embodiments, said nucleic acid of which comprises a sequence selected from the group consisting of: SEQ ID NOs: 340 and 342). Specific embodiments herein provide isolated nucleic acid encoding light chain CDR1 sequence selected from the group consisting of: SEQ ID NOs: 347-349, 351, 353-359 and residues 4-14 of SEQ ID NOs: 347, 349 and 353-359 (in specific embodiments, said nucleic acid of which comprises a sequence selected from the group consisting of: SEQ ID NOs: 350 and 352). Specific embodiments herein provide nucleic acid encoding the disclosed light chain variable CDR1, CDR2 and/or CDR3 sequences into VK3 (or VK1) in place of the relevant CDRs. Specific embodiments provide both the heavy and light chain CDRs (1, 2 and 3) or some combination of one or more thereof.

The isolated nucleic acid encoding the variable regions can be provided within any desired antibody molecule format including, but not limited to, the following: F(ab')$_2$, a Fab, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, a minibody, a dAb fragment, diabody, triabody or tetrabody, a minibody, IgG, IgG1, IgG2, IgG3, IgG4, IgM, IgD, IgA, IgE or any derivatives thereof.

Specific embodiments provide isolated nucleic acid which encodes PCSK9-specific antagonists and, in more specific embodiments, antibody molecules comprising (i) a heavy chain variable domain selected from the group consisting of: SEQ ID NOs: 360-510; specific embodiments of which comprise nucleic acid sequence SEQ ID NO: 550 or SEQ ID NO: 561; and/or (ii) a light chain variable domain selected from the group consisting of: SEQ ID NOs: 511-549; specific embodiments of which comprise nucleic acid sequence SEQ ID NO: 551. The present invention further provides in specific embodiments, homologs of the antagonists disclosed above, characterized as being at least 90% (in specific embodiments, 95%, 97% or 99%) identical through the heavy and/or light chain variable regions.

Additional embodiments provide isolated nucleic acid encoding PCSK9-specific antagonists and, in more specific embodiments, antibody molecules which comprise (i) a light chain selected from the group consisting of: SEQ ID NOs: 558, 566, and 554 (specific embodiments of which comprise nucleic acid selected from the group consisting of: SEQ ID NOs: 559, 567, 568 and 555); and/or (ii) a heavy chain or Fd chain selected from the group consisting of: SEQ ID NOs: 552, 562, 556, 564 and amino acids 1-221 of SEQ ID NOs: 562 and 552 (specific embodiments of which comprise nucleic acid selected from the group consisting of: SEQ ID NOs: 553, 563, 557, 565 and nucleotides 1-663 of SEQ ID NOs: 553 and 563. The present invention further provides in specific embodiments, homologs of the antagonists disclosed above, characterized as being at least 90% identical over the heavy and/or light chains.

Specific embodiments of the present invention encompass nucleic acid encoding antibody molecules that possess manipulations in the Fc region which result in reduced or altered binding to FcγR receptors, C1q or FcRn on the part of the antibody. One specific embodiment of the present invention is isolated nucleic acid which encodes for antibody molecules comprising as part of their immunoglobulin structure SEQ ID NO: 575 and, in particular embodiments, residues 107-326 of SEQ ID NO: 575. In specific embodiments, synthetic PCSK9-specific antagonists can be produced by expression from nucleic acid generated from oligonucleotides synthesized and assembled within suitable expression vectors; see, e.g., Knappick et al., 2000 *J. Mol. Biol.* 296:57-86, and Krebs et al., 2001 *J. Immunol. Methods* 254:67-84.

The present invention encompasses nucleic acid encoding antibody molecules which comprise: (i) the disclosed nucleic acid encoding the light chain variable region, and (ii) the disclosed nucleic acid encoding the heavy chain variable region, followed in sequence by (adjacent to) a set of nucleotides encoding for a set of amino acids selected from the group consisting of: SEQ ID NO: 572 (IgG1), SEQ ID NO: 573 (IgG2), SEQ ID NO: 574 (IgG4) and SEQ ID NO: 575 (IgG2 m4). Plasmid sequence comprising heavy and light chain AX132 anti-PCSK9 antibody molecule sequence can be found as SEQ ID NO: 560. Plasmid sequence comprising heavy and light chain AX213 anti-PCSK9 antibody molecule sequence can be found as SEQ ID NO: 569. Nucleic acid encoding such antibody molecules form important embodiments hereof. Additional plasmid sequences can be obtained by substituting the altered region for that present in the disclosed plasmid sequences.

Also included within the present invention are isolated nucleic acids comprising nucleotide sequences which are at least about 90% identical and more preferably at least about 95% identical to the full length of the nucleotide sequences described herein, and which nucleotide sequences encode PCSK9-specific antagonists which inhibit PCSK9-dependent inhibition of cellular LDL uptake by at least 10%.

Reference to "at least about 90% identical" throughout the application includes at least about 90, 91, 92, 93, 94, 95, 96, 97, 98, 99 or 100% identical.

The invention further provides isolated nucleic acid at least a portion of which hybridizes to the complement of nucleic acid encoding any one of the variable heavy, variable light, heavy chain, and light chain regions disclosed herein under stringent hybridization conditions, said nucleic acid of which confers upon antibody molecules the ability to specifically bind PCSK9 and antagonize PCSK9 function, and PCSK9-specific antagonists expressed employing said nucleic acid. Methods for hybridizing nucleic acids are well-known in the art; see, e.g., Ausubel, *Current Protocols in Molecular Biology*, John Wiley & Sons, N.Y., 6.3.1-6.3.6, 1989. Stringent hybridization conditions involve hybridizing at 68° C. in 5×SSC/5×Denhardt's solution (or equivalent)/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. The skilled artisan can manipulate various hybridization and/or washing conditions to specifically target nucleic acid in the hybridizing portion that is at least 80, 85, 90, 95, 98, or 99% identical to the variable heavy, variable light, heavy chain and/or light chain regions disclosed herein. Basic parameters affecting the choice of hybridization conditions and guidance for devising suitable conditions are set forth by Sambrook et al., *Molecular Cloning: A Laboratory Manual*, Cold Spring Harbor Laboratory Press, Cold Spring Harbor, N.Y., chapters 9 and 11, 1989 and Ausubel et al. (eds), *Current Protocols in Molecular Biology*, John Wiley & Sons, Inc., sections 2.10 and 6.3-6.4, 1995 (the disclosures of which are incorporated herein by reference), and can be readily determined by those having ordinary skill in the art. PCSK9 antagonists having one or more regions comprising nucleic acid which hybridizes to the disclosed heavy chain, light chain, variable heavy or variable light regions under stringent hybridization conditions should be effective in antagonizing one or more functions of PCSK9. Said antagonists and encoding nucleic acid, thus, form important embodiments of the present invention.

In another aspect, the present invention provides vectors comprising the nucleic acid disclosed herein. Vectors in accordance with the present invention include, but are not limited to, plasmids and other expression constructs (e.g., phage or phagemid, as appropriate) suitable for the expression of the desired antibody molecule at the appropriate level for the intended purpose; see, e.g., Sambrook & Russell, *Molecular Cloning: A Laboratory Manual: 3rd Edition*, Cold Spring Harbor Laboratory Press; the disclosure of which is incorporated herein by reference. For most cloning purposes, DNA vectors may be used. Typical vectors include plasmids, modified viruses, bacteriophage, cosmids, yeast artificial chromosomes, bacterial artificial chromosomes, and other forms of episomal or integrated DNA. It is well within the purview of the skilled artisan to determine an appropriate vector for a particular gene transfer, generation of a recombinant PCSK9-specific antagonist, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, and/or other sequences as appropriate and the potential for high copy number. Examples of expression vectors for the production of protein-specific antagonists are well known in the art; see, e.g., Persic et al., 1997 *Gene* 187:9-18; Boel et al., 2000 *J. Immunol. Methods* 239:153-166, and Liang et al., 2001 *J. Immunol. Methods* 247:119-130; the disclosures of which are incorporated herein by reference. If desired, nucleic acid encoding the antagonist may be integrated into the host chromosome using techniques well known in the art; see, e.g., Ausubel, *Current Protocols in Molecular Biology*, John Wiley & Sons, 1999, and Marks et al., International Application Number WO 95/17516. Nucleic acid may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10. Specifically with regards to antibody molecules, the antibody light chain gene and the antibody heavy chain gene can be inserted into separate vectors or, more typically, both genes may be inserted into the same expression vector. Nucleic acid encoding any PCSK9-specific antagonist or component thereof can be inserted into an expression vector using standard methods (e.g., ligation of complementary restriction sites on the nucleic acid fragment and vector, or blunt end ligation if no restriction sites are present). Another specific example of how this may be carried out is through use of recombinational methods, e.g. the Clontech "InFusion" system, or Invitrogen "TOPO" system (both in vitro), or intracellularly (e.g. the Cre-Lox system). Specifically with regards to antibody molecules, the light and heavy chain variable regions can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector comprising nucleic acid encoding a PCSK9-specific antagonist can encode a signal peptide that facilitates secretion of the antagonist from a host cell. The nucleic acid can be cloned into the vector such that the nucleic acid encoding a signal peptide is linked in-frame adjacent to the PCSK9-specific antagonist-encoding nucleic acid. The signal peptide may be an immunoglobulin or a non-immunoglobulin signal peptide. Any technique available to the skilled artisan may be employed to introduce the nucleic acid into the host cell; see, e.g., Morrison, 1985 *Science,* 229:1202. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The PCSK9-specific antagonist so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) comprising nucleic acid encoding disclosed PCSK9-specific antagonists. A variety of different cell lines are contemplated herein and can be used for the recombinant production of PCSK9-specific antagonists, including but not limited to those from prokaryotic organisms (e.g., *E. coli, Bacillus*, and *Streptomyces*) and from eukaryotic (e.g., yeast, Baculovirus, and mammalian); see, e.g., Breitling et al., Recombinant antibodies, John Wiley & Sons, Inc. and Spektrum Akademischer Verlag, 1999; the disclosure of which is incorporated herein by reference. Plant cells, including transgenic plants, and animal cells, including transgenic animals (other than humans), comprising the nucleic acid or antagonists disclosed herein are also contemplated as part of the present invention. Suitable mammalian cells or cell lines including, but not limited to, those derived from Chinese Hamster Ovary (CHO cells, including but not limited to DHFR-CHO cells (described in Urlaub and Chasin, 1980 *Proc. Natl. Acad. Sci. USA* 77:4216-4220) used, for example, with a DHFR selectable marker (e.g., as described in Kaufman and Sharp, 1982 *Mol. Biol.* 159:601-621), NS0 myeloma cells (where a GS expression system as described in WO 87/04462, WO 89/01036, and EP 338,841 may be used), COS cells, SP2 cells, HeLa cells, baby hamster kidney cells, YB2/0 rat myeloma cells, human embryonic kidney cells, human embryonic retina cells, and others comprising the nucleic acid or antagonists disclosed herein form additional embodiments of the present invention; the preceding cited disclosures of which are incorporated herein by reference. Specific embodiments of the present invention comprising nucleic acid encoding disclosed PCSK9-specific antagonists include, but are not limited to, *E. coli*; see, e.g., Plückthun, 1991 *Bio/Technology* 9:545-551, or yeast, such as *Pichia*, and recombinant derivatives thereof (see, e.g., Li et al., 2006 *Nat. Biotechnol.* 24:210-215); the preceding disclosures of which are incorporated herein by reference. Specific embodiments of the present invention relate to eukaryotic cells comprising nucleic acid encoding the disclosed PCSK9-specific antagonists, see, Chadd & Chamow, 2001 *Current Opinion in Biotechnology* 12:188-194, Andersen & Krummen, 2002 *Current Opinion in Biotechnology* 13:117, Larrick & Thomas, 2001 *Current Opinion in Biotechnology* 12:411-418; the disclosures of which are incorporated herein by reference. Specific embodiments of the present invention relate to mammalian cells comprising nucleic acid encoding the disclosed PCSK9-specific antagonists which are able to produce PCSK9-specific antagonists with proper post translational modifications. Post translational modifications include, but are by no means limited to, disulfide bond formation and glycosylation. Another type of post translational modification is signal peptide cleavage. Preferred embodiments herein have the appropriate glycosylation; see, e.g., Yoo et al., 2002 *J. Immunol. Methods* 261:1-20; the disclosure of which is incorporated herein by reference. Naturally occurring antibodies contain at least one N-linked carbohydrate attached to a heavy chain. Id. Different types of mammalian host cells can be used to provide for efficient post-translational modifications. Examples of such host cells include Chinese Hamster Ovary (CHO), HeLa, C6, PC12, and myeloma cells; see, Yoo et al., 2002 *J. Immunol. Methods* 261:1-20, and Persic et al., 1997 *Gene* 187:9-18; the disclosures of which are incorporated herein by reference.

In another aspect, the present invention provides isolated cell(s) comprising a polypeptide of the present invention.

In another aspect, the present invention provides a method of making a PCSK9-specific antagonist of the present invention, which comprises incubating a cell comprising nucleic acid encoding the PCSK9-specific antagonist, or a heavy and/or light chain or a fragment thereof (e.g., VH and/or VL, or one or more of the disclosed heavy and/or light chain variable region CDRs) of a desired PCSK9-specific antagonist (dictated by the desired antagonist) with specificity for human PCSK9 under conditions that allow the expression of the PCSK9-specific antagonist, or the expression and assembly of said heavy and/or light chains or fragment into a PCSK9-specific antagonist, and isolating said PCSK9-specific antagonist from the cell. One example by which to generate particular desired heavy and/or light chain sequence or fragment is to first amplify (and modify) the germline heavy and/or light chain variable sequences or fragment using PCR. Germline sequence for human heavy and/or light variable regions are readily available to the skilled artisan, see, e.g., the "Vbase" human germline sequence database, and Kabat, E. A. et al., 1991 *Sequences of Proteins of Immunological Interest*, Fifth Edition, U.S. Department of Health and Human Services, NIH Publication No. 91-3242; Tomlinson, I. M. et al., 1992 "The Repertoire of Human Germline VH Sequences Reveals about Fifty Groups of VH Segments with Different Hypervariable Loops" *J. Mol. Biol.* 227:776-798; and Cox, J. P. L. et al., 1994 "A Directory of Human Germ-line VK Segments Reveals a Strong Bias in their Usage" *Eur. J. Immunol.* 24:827-836; the disclosures of which are incorporated herein by reference. Mutagenesis of germline sequences may be carried out using standard methods, e.g., PCR-mediated mutagenesis where the mutations are incorporated into PCR primers, or site-directed mutagenesis. If full-length antibodies are desired, sequence is available for the human heavy chain constant region genes; see, e.g., Kabat. E. A. et al., 1991 *Sequences of Proteins of Immunological Interest*, Fifth Edition, U.S. Department of Health and Human Services, NIH Publication No. 91-3242. Fragments containing these regions may be obtained, for example, by standard PCR amplification. Alternatively, the skilled artisan can avail him/herself of vectors already encoding heavy and/or light chain constant regions.

Fab expression and purification may be achieved in a number of ways. One common way is to perform papain digestion of whole IgG1s to release two equivalents of Fab and one equivalent of Fc region. However, for phage displayed libraries, which also needs to be expressed in *E. coli*, Fab is typically displayed via covalent linkage to a protein and also to a hexahistidine tag (His-tag). In a typical fashion, induction by IPTG is followed by intracellular expression of the Fab. Subsequently, whole cells are lysed and the desired Fab is purified using a nickel affinity column. Depending on the specific case, this can yield high background in analytical SE-HPLC, presumably from misfolded, partially folded, disulfide scrambled or proteolyzed Fabs containing the His-tag since His-tag does not discriminate between these and the correctly folded Fab. Thus, in specific embodiments, expression of Fabs is carried out as follows: the periplasmic transport signal from phage, such as pIII and pVIII coat protein leader sequences, are utilized in the expression vector to localize the Fab polypeptides into the oxidizing environment of the periplasmic space. There, chaperone-like enzymes can facilitate correct Fab folding and thus allow formation of correct disulfide bonds. The initial overnight growth phase may be set at 30° C. Subsequently, the bacterial culture can be induced into Fab production, using lower concentration of IPTG (1 mM, 0.5 mM, or 0.1 mM) to induce the lac operon and start translation of the Fab genes. The temperature can be lowered to 22-23° C. Both the low IPTG and low temperature slow the *E. coli* protein synthesis in order to avoid overloading the periplasmic folding machinery. Cells may then be harvested by low speed centrifugation (~4000 g) and undergo periplasmic extraction. Periplasmic extraction is a gentle osmotic release process that primarily aims to make the outer bacterial cell wall leaky via mild osmotic shock, allowing Fabs to escape the periplasm into the surrounding media. After extraction, the cells can then be centrifuged at high speed (>15000 g) and the supernatant, containing released soluble Fab is saved for affinity chromatography.

In the specific embodiment above, affinity chromatography can be as follows: Affinity purification using protein G resin selectively binds folded constant region of the Fab at neutral pH (typically, using PBS or HBS at ~7.0-7.4). The bound Fab can be released under acidic pH (typically with glycine-HCl, pH 2.7-4.0) and eluted into a tube containing 1M Tris base at pH 9 to minimize exposure of the Fab to acidic pH. Alternatively, because the extract from the periplasmic extraction is relatively clean compared to a whole cell lysate, a nickel affinity column may be used to purify a Fab with a His-tag. In both cases, the eluted Fabs are buffer exchanged (e.g., by dialysis or centrifugal filtration using 30 kD MW cutoff filters) into the storage buffer, typically PBS or any preferred formulation buffer. The sample can be analyzed using analytical size exclusion (SE) HPLC generally show single peak consisting of >95% desired product. Additional polishing may be performed, if desired, using orthogonal methods, such as cation (CEX) or anion exchange (AEX) or hydrophobic interaction (HIC) chromatography.

Accordingly, in specific embodiments, the expression vector used for expression of the disclosed PCSK9-specific antagonists comprises sequence for phage coat protein pIII or pVIII leaders sequence or other export leader sequence to export the expressed antagonist into the bacterial periplasm. In specific embodiments, this is for the expression of Fab. In specific embodiments, the invention comprises a method for producing a PCSK9-specific antagonist which comprises: (a) inserting a vector as described herein into a cell (in particular embodiments, the vector encodes a Fab); wherein the vector comprises a phage coat protein PIII or pVIII leader sequence; (b) culturing the cell under conditions appropriate for production of the PCSK9-specific antagonist; and (c) isolating the PCSK9-specific antagonist produced by periplasmic extraction using gentle lysis conditions to disrupt primarily the outer cell wall to release periplasmic contents and minimize contamination by intracellular contents. In specific embodiments, this may further comprise purifying the PCSK9-specific antagonist by: (i) affinity of the constant domain to protein G to purify correctly folded PCSK9-specific antagonists (such as Fabs); (ii) affinity of the His-tag to a nickel affinity column; or (iii) other suitable purification technique. This may then be followed by analyzing the buffer-exchanged Fab or isolated PCSK9-specific antagonist using SDS-PAGE, analytical SE-HPLC, or mass spectrometry to QC the final product.

Available techniques exist to recombinantly produce other antibody molecules which retain the specificity of an original antibody. A specific example of this is where DNA encoding the immunoglobulin variable region or the CDRs is introduced into the constant regions, or constant regions and framework regions, or simply the framework regions, of another antibody molecule; see, e.g., EP-184,187, GB 2188638, and EP-239400; the disclosures of which are incorporated herein by reference. Cloning and expression of antibody molecules, including chimeric antibodies, are described in the literature; see, e.g., EP 0120694 and EP 0125023; the disclosures of which are incorporated herein by reference.

Antibody molecules in accordance with the present invention may, in one instance, be raised and then screened for characteristics identified herein using known techniques. Basic techniques for the preparation of monoclonal antibodies are described in the literature, see, e.g., Kohler and Milstein (1975, *Nature* 256:495-497); the disclosure of which is incorporated herein by reference. Fully human monoclonal antibodies can be produced by available methods. These methods include, but are by no means limited to, the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, full human monoclonal antibodies. This technology is well known in the art and is fully detailed in various publications, including but not limited to U.S. Pat. Nos. 5,545,806; 5,569,825; 5,625,126; 5,633,425; 5,789,650; 5,877,397; 5,661,016; 5,814,318; 5,874,299; 5,770,249 (assigned to GenPharm International and available through Medarex, under the umbrella of the "UltraMab Human Antibody Development System"); as well as U.S. Pat. Nos. 5,939, 598; 6,075,181; 6,114,598; 6,150,584 and related family members (assigned to Abgenix, disclosing their XenoMouse® technology); the disclosures of which are incorporated herein by reference. See also reviews from Kellerman and Green, 2002 *Curr. Opinion in Biotechnology* 13:593-597, and Kontermann & Stefan, 2001 *Antibody Engineering*, Springer Laboratory Manuals; the disclosures of which are incorporated herein by reference.

Alternatively, a library having potential PCSK9-specific antagonists or any library of antibody molecules may be brought into contact with PCSK9, and ones able to demonstrate specific binding selected. Functional studies can then be carried out to ensure proper functionality, e.g., inhibition of PCSK9-dependent inhibition of cellular LDL uptake. There are various techniques available to the skilled artisan for the selection of protein-specific molecules from libraries using enrichment technologies including, but not limited to, phage display (e.g., see technology from Abmaxis disclosed in U.S. Pat. Nos. 7,175,983 and 7,117,096, WO 03/099999, and Wang et al., 2010 *J. Mol. Biol.* 395:1088-1101 and Cambridge Antibody Technology ("CAT") disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or applications which rely on priority filing GB 9206318, filed May 24, 1992; see also Vaughn et al., 1996, *Nature Biotechnology* 14:309-314), ribosome display (see, e.g., Hanes and Pluckthün, 1997 *Proc. Natl. Acad. Sci.* 94:4937-4942), bacterial display (see, e.g., Georgiou, et al., 1997 *Nature Biotechnology* 15:29-34) and/or yeast display (see, e.g., Kieke, et al., 1997 *Protein Engineering* 10:1303-1310, and Wang et al., 2010 *J. Immunol. Methods* 354:11-19); the preceding disclosures of which are incorporated herein by reference. A library, for example, can be displayed on the surface of bacteriophage particles, with nucleic acid encoding the PCSK9-specific antagonist or fragment thereof expressed and displayed on its surface. Nucleic acid may then be isolated from bacteriophage particles exhibiting the desired level of activity and the nucleic acid used in the development of desired antagonist. Phage display has been thoroughly described in the literature; see, e.g., Wang et al., 2010 *J. Mol. Biol.* 395:1088-1101, Kontermann & Stefan, supra, and International Application Number WO 92/01047; the disclosures of which are incorporated herein by reference. Specifically with regard to antibody molecules, individual heavy or light chain clones in accordance with the present invention may also be used to screen for complementary heavy or light chains, respectively, capable of interaction therewith to form a molecule of the combined heavy and light chains; see, e.g., International Application Number WO 92/01047. Any method of panning which is available to the skilled artisan may be used to identify PCSK9-specific antagonists. Another specific method for accomplishing this is to pan against the target antigen in solution, e.g. biotinylated, soluble PCSK9, and then capture the PCSK9-specific antagonist-phage complexes on streptavidin-coated magnetic beads, which are then washed to remove nonspecifically-bound phage. The captured phage can then be recovered from the beads in the same way they would be recovered from the surface of a plate, as described herein.

PCSK9-specific antagonists may be purified by techniques available to one of skill in the art. Titers of the relevant antagonist preparation, ascites, hybridoma culture fluids, or relevant sample may be determined by various serological or immunological assays which include, but are not limited to, precipitation, passive agglutination, enzyme-linked immunosorbent antibody ("ELISA") techniques and radioimmunoassay ("RIA") techniques.

The present invention relates in part to methods employing PCSK9-specific antagonists described herein for antagonizing PCSK9 function; said methods of which are further described below. Use of the term "antagonizing" throughout the present application refers to the act of opposing, inhibiting, counteracting, neutralizing or curtailing one or more functions of PCSK9. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. Specific embodiments of the present invention include such methods wherein the cell is a human cell.

In another aspect, the present invention provides a method for antagonizing the activity of PCSK9 in a subject, which comprises administering to the subject a therapeutically effective amount of a PCSK9-specific antagonist of the present invention. In specific embodiments, the methods for antagonizing PCSK9 function are for the treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated for a particular subject. In select embodiments, the condition may be hypercholesterolemia, coronary heart disease, metabolic syndrome, acute coronary syndrome or related conditions.

The present invention, thus, contemplates the use of PCSK9-specific antagonists described herein in various methods of treatment where antagonizing PCSK9 function is desirable. The method of treatment can be prophylactic or therapeutic in nature. In specific embodiments, the present invention relates to a method of treatment for a condition associated with/attributed to PCSK9 activity, or a condition where the functioning of PCSK9 is contraindicated for a particular subject, which comprises administering to the subject a therapeutically effective amount of a PCSK9-specific antagonist of the present invention. In select embodiments, the condition may be hypercholesterolemia, coronary heart disease, metabolic syndrome, acute coronary syndrome or related conditions.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic/prophylactic effect for the period of time desired. The desired effect may be, for example, amelioration of at least one symptom associated with the treated condition. These amounts will vary, as the skilled artisan will appreciate, according to various factors, including but not limited to the disease state, age, sex and weight of the individual, and the ability of the PCSK9-specific antagonist to elicit the desired effect in the individual. The response may be documented by in vitro assay, in vivo non-human animal studies, and/or further supported from clinical trials.

The present invention provides methods for treating or preventing disorders of cholesterol or lipid homeostasis and disorders and complications associated therewith, e.g., hypercholesterolemia, hyperlipidemia, hypertriglyceridaemia, sitosterolemia, atherosclerosis, arteriosclerosis, coronary heart disease, metabolic syndrome, acute coronary syndrome, vascular inflammation, xanthoma and related conditions.

The present invention also provides methods for improving blood cholesterol markers associated with increased risk of heart disease. These markers include, but are not limited to, high total cholesterol, high LDL, high total cholesterol to HDL ratio and high LDL to HDL ratio.

In general, a total cholesterol of less than 200 mg/dL is considered desirable, 200-239 mg/dL is considered borderline high and 240 mg/dL and above is considered high. For example, the present invention comprises methods for reducing total cholesterol, e.g., to less than or equal to about 200 mg/dL by administering a therapeutically effective amount of a PCSK9-specific antagonist of the present invention.

In general, a blood LDL level of less than 100 mg/dL is considered optimal; 100-129 mg/dL is considered near optimal/above optimal, 130-159 mg/dL is considered borderline high, 160-189 mg/dL is considered high and 190 mg/dL and above is considered very high. For example, the present invention comprises methods for reducing LDL, e.g., to less than about 100 mg/dL by administering a therapeutically effective amount of a PCSK9-specific antagonist of the present invention.

In general, HDL levels considered normal are at least 35-40 mg/dL. For example, the present invention comprises methods for increasing HDL, e.g., to greater than or equal to about 35-40 mg/dL by administering a therapeutically effective amount of anti-PCSK9 antibody or antigen binding fragment thereof of the present invention.

Another indicator of heart disease risk is the ratio of total cholesterol to HDL. In general, a very low risk of heart disease correlates with a ratio of <3.4 (men) or <3.3 (women); a low risk is associated with a ratio of 4.0 (men) or 3.8 (women), an average risk is associated with a ratio of 5.0 (men) or 4.5 (women), a moderate risk is associated with a ratio of 9.5 (men) or 7.0 (women) and a high risk is associated with a ratio of >23 (men) or >11 (women). For example, the present invention comprises methods for reducing the ratio of total cholesterol to HDL, e.g., to less than about 4.5 or 5.0 by administering a therapeutically effective amount of a PCSK9-specific antagonist of the present invention.

A further indicator of heart disease risk is the ratio of LDL to HDL. In general, a very low risk is associated with a ratio of 1 (men) or 1.5 (women), an average risk is associated with a ratio of 3.6 (men) or 3.2 (women), a moderate risk is associated with a ratio of 6.3 (men) or 5.0 (women) and a high risk is associated with a ratio of 8 (men) or 6.1 (women). For example, the present invention comprises methods for the ratio of LDL to HDL, e.g., to less than or equal to about 3.2 or 3.6 by administering a therapeutically effective amount of a PCSK9-specific antagonist of the present invention.

The PCSK9-specific antagonist may be administered as a pharmaceutical composition. The present invention, thus, provides a pharmaceutically acceptable composition comprising a PCSK9-specific antagonist of the invention and a pharmaceutically acceptable carrier including but not limited to an excipient, diluent, stabilizer, buffer, or alternative designed to facilitate administration of the antagonist in the desired format and amount to the treated individual.

The pharmaceutical composition may be formulated by any number of strategies known in the art, see, e.g., McGoff and Scher, 2000 *Solution Formulation of Proteins/Peptides*: In—McNally, E. J., ed. Protein Formulation and Delivery. New York, N.Y.: Marcel Dekker; pp. 139-158; Akers & Defilippis, 2000, *Peptides and Proteins as Parenteral Solutions*. In—Pharmaceutical Formulation Development of Peptides and Proteins. Philadelphia, Pa.: Taylor and Francis; pp. 145-177; Akers et al., 2002, *Pharm. Biotechnol.* 14:47-127. A pharmaceutically acceptable composition suitable for patient administration will contain an effective amount of the PCSK9-specific antagonist in a formulation which both retains biological activity while also promoting maximal stability during storage within an acceptable temperature range.

The antagonist-based pharmaceutically acceptable composition may, in particular embodiments, be in liquid or solid form, or in the form of gas particles or aerosolized particles. Any technique for production of liquid or solid formulations may be utilized. Such techniques are well within the realm of the abilities of the skilled artisan. Solid formulations may be produced by any available method including, but not limited to, lyophilization, spray drying, or drying by supercritical fluid technology. Solid formulations for oral administration may be in any form rendering the antagonist accessible to the patient in the prescribed amount and within the prescribed period of time. The oral formulation can take the form of a number of solid formulations including, but not limited to, a tablet, capsule, or powder. Solid formulations may alternatively be lyophilized and brought into solution prior to administration for either single or multiple dosing according to methods well known to the skilled artisan. Antagonist compositions should generally be formulated within a biologically relevant pH range and may be buffered to maintain a proper pH range during storage. Both liquid and solid formulations generally require storage at lower temperatures (e.g., 2-8° C.) in order to retain stability for longer periods. Formulated antagonist compositions, especially liquid formulations, may contain a bacteriostat to prevent or minimize proteolysis during storage, including but not limited to effective concentrations (e.g., ≤1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antagonist formulation, including but not limited to sugars as a cryoprotectant (including but not limited to polyhydroxy hydrocarbons such as sorbitol, mannitol, glycerol, and dulcitol and/or disaccharides such as sucrose, lactose, maltose, or trehalose) and, in some instances, a relevant salt (including but not limited to NaCl, KCl, or LiCl). Such antagonist formulations, especially liquid formulations slated for long term storage, will rely on a useful range of total osmolarity to both promote long term stability at temperatures of, for example, 2-8° C. or higher, while also making the formulation useful for parenteral injection. As appropriate, preservatives, stabilizers, buffers, antioxidants and/or other additives may be included. The formulations may contain a divalent cation (including but not limited to $MgCl_2$, $CaCl_2$, and $MnCl_2$); and/or a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)). Any combination of such components form specific embodiments of the present invention.

Pharmaceutical compositions in liquid format may include a liquid carrier, e.g., water, petroleum, animal oil, vegetable oil, mineral oil, or synthetic oil. The liquid format may also include physiological saline solution, dextrose or other saccharide solution or glycols, such as ethylene glycol, propylene glycol or polyethylene glycol.

Preferably, the pharmaceutical composition may be in the form of a parenterally acceptable aqueous solution that is pyrogen-free with suitable pH, tonicity, and stability. Pharmaceutical compositions may be formulated for administration after dilution in isotonic vehicles, for example, Sodium Chloride Injection, Ringer's Injection, or Lactated Ringer's Injection.

One aspect of the present invention is a pharmaceutical composition which comprises: (i) about 50 to about 200 mg/mL of the PCSK9-specific antagonists described herein; (ii) a polyhydroxy hydrocarbon (including but not limited to sorbitol, mannitol, glycerol and dulcitol) and/or a disaccharide (including but not limited to sucrose, lactose, maltose and trehalose); the total of said polyhydroxy hydrocarbon and/or disaccharide being about 1% to about 6% weight per volume ("w/v") of the formulation; (iii) about 5 mM to about 200 mM of histidine, imidazole, phosphate or acetic acid which serves as a buffering agent to prevent pH drift over the shelf life of the pharmaceutical composition and as a tonicity modifier; (iv) about 5 mM to about 200 mM of arginine, proline, phenylalanine, alanine, glycine, lysine, glutamic acid, aspartic acid or methionine to counteract aggregation; (v) about 0.01M to about 0.1M of hydrochloric acid ("HCl") in an amount sufficient to achieve a pH in the range of about 5.5 to about 7.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.5 to about 7.5; and wherein said pharmaceutical composition optionally comprises about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

HCl may be added as free acid, Histidine-HCl or Arginine-HCl. Where supplied as Histidine-HCl or Arginine-HCl, the total amounts of Histidine or Arginine in the HCl form should be that specified above. Accordingly, some or all of the HCl depending on the amounts of Histidine and/or Arginine may be supplied as Histidine-HCl and/or Arginine-HCl; as appropriate. Use of the term "about" with respect to amounts disclosed in the specification means within 10% of the specified numbers provided. A range provided as, for example" in "about 50 to about 200" expressly includes as distinct embodiments each number within said range. As such in the above example, embodiments including but not limited to those having 50, 100, 125, 150 and 200 form specific embodiments herein. Pharmaceutical compositions as disclosed herein have general applicability despite the mode of administration. In specific embodiments, the disclosed pharmaceutical compositions are useful for subcutaneous administration as a liquid or upon reconstitution of a lyophilized form. Proteins that can be employed in the disclosed formulations include any polymeric protein or polypeptide characterized as comprising covalently linked amino acid residues delivered for purposes of effecting a therapeutic benefit. Proteins of use in the present compositions include but are not limited to any antibody molecules as defined herein or any non-antibody or non-immunoglobulin proteins, peptides, pegylated proteins and fusion proteins.

Specific aspects of the present invention relate to the above disclosed pharmaceutical compositions which comprise: (i) about 50 to about 200 mg/mL of the PCSK9-specific antagonists described herein; (ii) about 1% to about 6% (in particular embodiments from about 2% to about 6%) w/v mannitol, trehalose or sucrose; (iii) about 10 mM to about 100 mM of histidine; (iv) about 25 mM to about 100 mM of arginine or proline; (v) about 0.02 M to about 0.05M of hydrochloric acid ("HCl") in an amount sufficient to achieve a pH in the range of about 5.8 to about 7; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 7; and wherein said pharmaceutical composition optionally comprising about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

Specific embodiments provide pharmaceutical compositions which comprise: (i) 50 to 200 mg/mL of the PCSK9-specific antagonists described herein; (ii) about 1% to about 6% (in particular embodiments from about 2% to about 6%) w/v mannitol, trehalose or sucrose; (iii) about 10 mM to about 150 mM of histidine; (iv) about 10 mM to about 150 mM of arginine or proline; (v) about 0.03 M to about 0.05 M of hydrochloric acid ("HCl") in an amount sufficient to achieve a pH in the range of about 5.8 to about 6.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 6.5; and wherein said pharmaceutical composition optionally comprising about 0.01% to about 1% w/v of Polysorbate-80 (Tween 80™) or Polysorbate-20 (Tween 20™).

Specific embodiments herein provide pharmaceutical compositions which comprise: (i) 50 to 200 mg/mL of the PCSK9-specific antagonists described herein; (ii) about 1% to about 6% (in particular embodiments from about 2% to about 6%) w/v sucrose; (iii) about 25 mM to about 100 mM of histidine; (iv) about 25 mM to about 100 mM of arginine; (v) about 0.040 M to about 0.045 M of hydrochloric acid ("HCl") in an amount sufficient to achieve a pH of about 6; and (vi) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). In specific embodiments thereof, the levels of histidine and arginine are within 25 mM of each other and, in other embodiments are the same.

Specific embodiments herein provide pharmaceutical compositions which comprise (i) 50 to 200 mg/mL of the PCSK9-specific antagonists described herein; (ii) sucrose, histidine and arginine in one of the following amounts: (a) about 1% w/v sucrose, about 10 mM histidine and about 25 mM arginine; (b) about 2% w/v sucrose, about 25 mM histidine and about 25 mM arginine; (c) about 3% w/v sucrose, about 50 mM histidine and about 50 mM arginine; or (d) about 6% w/v sucrose, about 100 mM histidine and about 100 mM arginine; (iii) about 0.04 mol or, alternatively, about 1.46 g of HCl; and (iv) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). Specific embodiments herein are wherein the amounts of sucrose, histidine and arginine in (ii) above are that described in (c) or (d). Specific embodiments employing pharmaceutical formulations as described above wherein the amounts of sucrose, histidine and arginine are that specified in (ii) (c) were found to provide an osmolality similar to the physiological value of 300 mOsm and provided stability in both the liquid and lyophilized form.

Specific embodiments herein provide pharmaceutical compositions as described which comprise 50 to 200 mg/ml of any one of the various PCSK9-specific antagonists described herein. For purposes of exemplification of one distinct embodiment thereof, and not to be construed as a limitation, is the following: a pharmaceutical formulation as described above which comprises: a PCSK9-specific antagonist which comprises: (a) a light chain comprising SEQ ID NO: 558; and (b) a heavy chain comprising SEQ ID NO: 556; wherein said PCSK9-specific antagonist is an antibody molecule that antagonizes PCSK9's inhibition of cellular LDL uptake. An additional embodiment is a pharmaceutical formulation as described above which comprises: a PCSK9-specific antagonist which comprises: (a) a light chain comprising SEQ ID NO: 566; and (b) a heavy chain comprising SEQ ID NO: 564; wherein said PCSK9-specific antagonist is an antibody molecule that antagonizes PCSK9's inhibition of cellular LDL uptake.

Particular embodiments herein are pharmaceutical compositions according to the above description which are lyophilized and reconstituted. In specific embodiments, said protein concentration in said lyophilized and reconstituted solution is up to 2-fold higher than in the pre-lyophilized composition. In specific embodiments, the protein or PCSK9-specific antagonist concentration in the lyophilized and/or reconstituted pharmaceutical composition is in the range of about 50 mg/mL to about 300 mg/mL. Diluents useful for reconstituting the lyophilized pharmaceutical compositions include but are not limited to sterile water, bacteriostatic water for injection ("BWFI"), phosphate-buffered saline, a sterile saline solution, physiological saline solution, Ringer's solution or dextrose solution and may in specific embodiments contain 0.01-1% (w/v) of Polysorbate-80 (Tween 80™) or Polysorbate-20 (Tween 20™). In specific embodiments, lyophilized powder can be reconstituted with 1/60.2× original volume (or 0.167 mL) up to 1× (1 mL).

Exemplary embodiments of the present invention are pharmaceutical compositions as described herein which are stable. Other embodiments of the present invention are pharmaceutical compositions as described herein which are stable to lyophilization and reconstitution. Various methods are available to the skilled artisan to prepare lyophilized compositions; see, e.g., Martin & Mo, 2007 "Stability Considerations for Lyophilized Biologics" Amer. Pharm. Rev. "Stable" as used herein refers to the property of the protein or PCSK9-specific antagonist to retain its physical or chemical stability, conformational integrity, or its ability to exhibit less denaturation, protein clipping, aggregation, fragmentation, acidic variant formation or loss of biological activity compared with a control sample at a temperature in the range of 4-37° C. for at least about 30 days. Other embodiments remain stable for up to 3 months, 6 months, 12 months, 2 years or longer periods at the above temperatures. In specific embodiments the formulation exhibits no significant changes at 2-8° C. for at least 6 months, and preferably 12 months, 2 years or longer, in order of preference. Specific embodiments experience less than 10% or, in particular embodiments, less than 5% of denaturation, protein clipping, aggregation, fragmentation, acidic variant formation or loss of biological activity compared with a control sample at a temperature in the range of 25-45° C. (or alternatively 2-8° C.) for at least about 30 days, 3 months, 6 months, 12 months, 2 years or longer. Stability of the formulations can be tested via several means known to the skilled artisan including, but not limited to Size Exclusion Chromatography (SEC-HPLC) to measure aggregation and fragmentation, Dynamic Light Scattering (DLS) to measure particle size of concentrated samples, capillary SDS-PAGE to measure fragmentation and capillary iso-electric focusing (cIEF) or cation exchange chromatography ("CEX") to measure acidic variants formation. Techniques suitable for the analysis of protein stability are well understood by those of skill in the art: see review in *Peptide and Protein Drug Delivery*, 247-301, Vincent Lee Ed., Marcel Dekker, Inc., New York, N.Y., Pubs. (1991) and Jones, 1993 *Adv. Drug Delivery Rev.* 10:29-90.

Pharmaceutical compositions as described herein should be sterile. There are various techniques available to the skilled artisan to accomplish this including, but not limited to, filtration through sterile filtration membranes. In specific embodiments, employing lyophilized and reconstituted compositions, this may be done prior to or following lyophilization and reconstitution.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors including but not limited to the particular PCSK9-specific antagonist utilized, the patient being treated, the condition of the patient, the area being treated, the route of administration, and the treatment desired. A physician or veterinarian of ordinary skill can readily determine and prescribe the effective therapeutic amount of the antagonist. Dosage ranges may be from about 0.01 to 100 mg/kg, and more usually 0.05 to 25 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. For purposes of illustration, and not limitation, in specific embodiments, a dose of 5 mg to 2.0 g may be utilized to deliver the antagonist systemically. In specific embodiments, the concentration of the dose provided will be in the range of about 8 mg/mL to about 200 mg/mL. In other embodiments, a dose contemplated for use in the present invention is from about 50 mg/mL to about 150 mg/mL. In specific embodiments, the dose will be from about 0.1 mL to about 1.5 mL and in specific embodiments is 1 mL. Optimal precision in achieving concentrations of antagonist within a range that yields efficacy without toxicity requires a regimen based on the kinetics of the drug's availability to the target site(s). This involves a consideration of the distribution, equilibrium, and elimination of the PCSK9-specific antagonist. Antagonists described herein may be used alone at appropriate dosages. Alternatively, co-administration or sequential administration of other agents may be desirable. It will be possible to present a therapeutic dosing regime for the PCSK9-specific antagonists of the present invention in conjunction with alternative treatment regimes. For example, PCSK9-specific antagonists may be used in combination or in conjunction with other drugs (therapeutic and/or prophylactic). In specific embodiments, the PCSK9-specific antagonists are used in combination or in conjunction with cholesterol-lowering drugs, for example, cholesterol absorption inhibitors (e.g., Zetia®) and cholesterol synthesis inhibitors (e.g., Zocor® and Vytorin®). The present invention contemplates such combinations and they form an important embodiment hereof. Accordingly, the present invention relates to methods of treatment as described above where the PCSK9-specific antagonist is administered/delivered simultaneously with, following or prior to another drug or drugs (therapeutic and/or prophylactic), including but not limited to cholesterol-lowering drugs, including cholesterol absorption inhibitors.

Individuals (subjects) capable of treatment as described herein include primates, human and non-human, and include any non-human mammal or vertebrate of commercial or domestic veterinary importance.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), or administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment. Treatment may be provided on a daily, weekly, biweekly, or monthly basis, or any other regimen that delivers the appropriate amount of PCSK9-specific antagonist to the individual at the prescribed times such that the desired treatment is effected and maintained. The formulations may be administered in a single dose or in more than one dose at separate times.

Also contemplated are methods of using the disclosed antagonists in the manufacture of a medicament for treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated for a particular subject. In select embodiments, the condition may be hypercholesterolemia, coronary heart disease, metabolic syndrome, acute coronary syndrome or related conditions.

PCSK9-specific antagonists disclosed herein may also be used as a method of diagnosis of PCSK9. In select embodiments, the present invention encompasses methods of identifying or quantifying the level of PCSK9 present in a sample (including but not limited to a biological sample, e.g., serum or blood) which comprises contacting the sample with a PCSK9-specific antagonist described herein and detecting or quantifying, respectively, binding to PCSK9. The PCSK9-specific antagonist may be used in various assay formats known to the skilled artisan and may form part of a kit (the general features of a kit of which are further described below).

The present invention further provides for the administration of disclosed anti-PCSK9 antagonists for purposes of gene therapy. Through such methods, cells of a subject are transformed with nucleic acid encoding a PCSK9-specific antagonist of the invention. Subjects comprising the nucleic acids then produce the PCSK9-specific antagonists endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, supra, may be easily adapted for the introduction of nucleic acids encoding an anti-PCSK9 antibody of the invention to a subject.

Nucleic acids encoding any PCSK9-specific antagonist may be introduced to a subject.

The nucleic acids may be introduced to the cells of a subject by any means known in the art. In preferred embodiments, the nucleic acids are introduced as part of a viral vector. Examples of preferred viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). Preferably, the viral vectors are replication defective, that is, they are unable to replicate autonomously, and thus are not infectious, in the target cell. Preferably, the replication defective virus is a minimal virus, i.e., it retains only the sequences of its genome which are necessary for encapsidating the genome to produce viral particles. Defective viruses, which entirely or almost entirely lack viral genes, are preferred. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro One.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (PCT Publication Nos. WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio.* 489:45-57, 2001; PCT Publication Nos. WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.*, 62:1120, 1988; EP 453242 and EP178220. The retroviruses are integrating viruses which infect dividing cells.

Lentiviral vectors can be used as agents for the direct delivery and sustained expression of nucleic acids encoding a PCSK9-specific antagonist of the invention in several tissue types, including brain, retina, muscle, liver and blood. The vectors can efficiently transduce dividing and nondividing cells in these tissues, and maintain long-term expression of the PCSK9-specific antagonist. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.*, 58:491-562, 1994; Bredenbeek et al, *J. Virol.*, 67:6439-6446, 1993; Ijima et al, *Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in PCT Publication Nos. WO 95/18863 and WO 96/17823, and in U.S. Pat. No. 5,459,127.

It is also possible to introduce the vector in vivo as a naked DNA plasmid. Naked DNA vectors for gene therapy can be introduced into desired host cells by methods known in the art, e.g., electroporation, microinjection, cell fusion, DEAE dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Other reagents commonly used for transfection of plasmids include, but are by no means limited to, FuGene, Lipofectin, and Lipofectamine Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; PCT Publication Nos. WO 99/01157, WO 99/01158 and WO 99/01175).

Pharmaceutical compositions suitable for such gene therapy approaches and comprising nucleic acids encoding an anti-PCSK9 antagonist of the present invention are included within the scope of the present invention.

In another aspect, the present invention provides a method for identifying, isolating, quantifying or antagonizing PCSK9 in a sample of interest using a PCSK9-specific antagonist of the present invention. The PCSK9-specific antagonists may be utilized as research tools in immunochemical assays, such as Western blots, ELISAs, radioimmunoassay, immunohistochemical assays, immunoprecipitations, or other immunochemical assays known in the art (see, e.g., Immunological Techniques Laboratory Manual, ed. Goers, J. 1993, Academic Press) or various purification protocols. The antagonists may have a label incorporated therein or affixed thereto to facilitate ready identification or measurement of the activities associated therewith. One skilled in the art is readily familiar with the various types of detectable labels (e.g., enzymes, dyes, or other suitable molecules which are either readily detectable or cause some activity/result that is readily detectable) which are or may be useful in the above protocols.

An additional aspect of the present invention are kits comprising PCSK9-specific antagonists or pharmaceutical compositions disclosed herein and instructions for use. Kits typically but need not include a label indicating the intended use of the contents of the kit. The term label includes any writing, or recorded material supplied on or with the kit, or which otherwise accompanies the kit. In specific embodiments wherein the pharmaceutical composition is provided lyophilized, the kit may include sterile water or saline for reconstitution of the formulation into liquid form. In specific embodiments, the amount of water or saline is from about 0.1 ml to 1.0 ml.

The following examples are provided to illustrate the present invention without limiting the same hereto:

EXAMPLE 1

Abmaxis PDL1 Phage Library Panning Against PCSK9 Protein

A synthetic human Fab library was panned against human PCSK9. Antigen protein PCSK9 was coated on Maxisorp well stripe (Nunc-Immuno Modules) at a concentration of 1-10 µg/ml for overnight at 4° C. Multiple wells of antigen were prepared for each library. 5% milk in PBS was used to block the coated wells at room temperature for 1-2 hours. After a wash with PBS, 100 µl of phage library solution/well (usually $1\text{-}5\times10^{12}$ in 2% milk-PBS) was added into 4 parallel wells, and incubated for designed length of time (usually 1-2 hours). After several washings with PBST and PBS, the bound phages were eluted from the wells with fresh-prepared 1.4% triethylamine in ddH2O (10 minutes incubation at room temperature), followed immediately with neutralization by adding 50 µl of 1M Tris-HCl (pH 6.8).

The eluted, enriched phage pool was further amplified through the following steps: First, TG1 cells were infected with eluted phages at 37° C. for 1 hour, then plated out on 2YT agar plates with 2% glucose and 100 µg/ml carbenicillin for overnight culture. Thus TG1 cells harboring enriched phagemid library were harvested from the plates, and infected with helper phage GMCT for 1 hour. The Fab-display phages were then generated from those TG1 cells harboring both library phagemids and GMCT helper phage genome by overnight growth in 2xYT/carbenicillin/Kanamycin at 22° C. The phagemid particles were purified from overnight culture supernatants by precipitation with PEG/NaCl, and re-suspended in PBS. The PEG-precipitation was repeated once. The phage concentration was determined by $OD_{268}$ measurement.

With amplified first round phages, the panning process as described above was repeated twice for further enrichment of PCSK9-binding phages. The eluted phages from the third round panning were used to infect TG1 cells. The TG1 cells harboring phagemids from third round panning were picked from 2YT agar plates for Fab ELISA screening assay.

EXAMPLE 2

Fab ELISA Screening for PCSK9 Binders

Over 10,000 clones from third round panning were picked by MegaPix Picking Robot (Genetix), and inoculated into 384-well plates with 60 µl of 2YT/2% Glucose/carbenicillin for overnight culture at 30° C. with 450 rpm shaking. The duplicated plates were made by transferring ~1-3 µl overnight culture from each well into new plates with 50 µl/well of 2YT/0.1% Glucose/carbenicillin. The duplicated plates were incubated in a shaker at 30° C. for 6 hours, then 10 µl/well of IPTG was added for a final concentration of 1 mM. After overnight culture at 22° C., the soluble Fab in IPTG-induction plates were released by adding lysozyme into each well.

To detect the antigen binding activity of soluble Fabs generated from the above experiment, the antigen plates were generated by overnight coating of 5 µg/ml human PCSK9 antigen. After blocking with 5% milk-PBS and a wash with PBST, 15-20 µl of Fab samples from IPTG-induction plates was transferred into antigen plates for 1-2 hours incubation at room temperature. The plates were washed 5 times with PBS-T, and added with 1:2000 diluted goat anti-human Kappa- HRP (SouthernBiotech Cat. No. 2060-05) or 1:10,000 diluted goat anti-human Fab-HRP in 5% MPBS for 1 hour incubation. After washing away unbound HRP-conjugates with PBST, the substrate solution QuantaBlu WS (Pierce 15169) was then added to each well and incubated for 5-15 minutes. The relative fluorescence units (RFU) of each well was measured to determine the Fab binding activity by using excitation wavelength 330 nm and emission detection wavelength 410 nm.

The ELISA results showed 30 to 80% clones from third round panning of individual PDL1 sub-libraries bound to antigen PCSK9. The positive clones were then sent out for DNA sequencing. A total of 128 unique Fab sequences were identified from the PDL1 library.

One particular PCSK9 antagonist of interest, AX114, comprising the following variable heavy and variable light regions was identified from the PDL1-VH3/VK3 sub-library.

(AX114 VH)
SEQ 360
EVQLLESGGGLVQPGGSLRLSCKASGYTFSSYGMYWVRQAPGKGLEWIGW

IDPGSGGTKYNEKFKGKATISRDNSKNTLYLQMNSLRAEDTAVYYCARER

YGYYFDYWGQGTLVTVSSAS (AX114 VK)
SEQ 512
EIVLTQSPATLSLSPGERATITCRASQYVGTYLNWYQQKPGQAPRLLIYD

ASNRATGIPARFSGSGSGTDFTLTISSLEPEDFAVYYCQVWDSSPPVAFG

GGTKVEIK

EXAMPLE 3

Fab Protein Expression and Purification from TG1 Cells 50 ml of overnight cultures for individual clones in 2YT/2% glucose/Carbenicillin 100 µg/ml were grown in 37° C. shaker incubator. In the second day, 750 mL to 1 L of 2YT/0.1% glucose/100 µg/mL Carbenicillin was inoculated for each clone by transferring 5-10 ml of the overnight culture. The cultures were grown at 30° C. with shaking for approximately 3-4 hours until OD600~1. IPTG was added to the culture to reach the final concentration of 0.1-0.5 mM. After overnight IPTG induction at 22° C., the cells pellets were collected by centrifugation at 10,000 rpm for 10-15 minutes, to proceed for periplasmic preparation.

Soluble Fabs were extracted from cell periplasm. The periplasmic preparation was performed as follows. The TG1 pellet was re-suspended in 20 mL pre-chilled PPB buffer (20% Sucrose+2 mM EDTA+30 mM Tris, pH=8), and incubated on ice for 1 hour. The supernatant with soluble Fab was collected by centrifugation. Subsequently, the cell pellet was further re-suspended in 20 mL pre-chilled 5 mM magnesium sulfate with 1 hour incubation on ice. Two supernatants were combined for further Fab purification.

The soluble Fab from the periplasmic extraction was purified using a HiTrap Protein G HP column (GE Healthcare). The column was initially equilibrated with equilibration buffer (PBS or Tris, pH 7.3). The supernatant from periplasmic preparation was loaded onto a 1-ml or 5-mL protein-G column (HiTrap, GE healthcare). After wash with 10 column volumes (CVs) of equilibration buffer, Fab protein was eluted with 8 CVs of elution buffer (0.3 M acetic acid, pH3). The eluted fractions were collected, and neutralized with 0.5 volume of 1M Tris, pH 9 buffer. The Fab samples were buffer-exchanged into PBS using Amicon centrifugal filters with 10 kD molecular weight cutoff. The quality of purified Fab was analyzed using size exclusion HPLC (SE-HPLC). Purified Fab was also used for ELISA assay and Biacore assay (below). Overall, the summary of Fab yields is ~1-2 mg/L with high degree of variability, from less than 1 mg/L to well over 10 mg/L. All Fabs show single main peak by SE-HPLC. The ELISA assay results confirmed all Fabs isolated from PDL1 library bound to human PCSK9 antigen.

EXAMPLE 4

Biacore-Based PCSP9-LDL Receptor Interaction Assay

The LDL-Receptor (LDLR) and EGF_AB domain of LDLR (this domain involves the interaction with PCSK9) were immobilized on two different flow cells in the same CM5 chips by coupling of amine groups of LDLR or EGF_AB domain onto carboxylated surfaces of sensor chips according to the instruction of Amine Coupling Kit (GE/Biacore). Briefly, LDLR and EGF_AB were diluted to 20 µg/ml in pH 4.5 10 mM Acetate buffer and injected to two flow cells on the same CM5 chip to achieve an immobilization level of ~1500 RU. 100 nM human PCSK9 alone in running buffer (1×HBSP with 0.1 mM CaCl$_2$) was injected into the flow cells (at 20 µl/minute for 2.5 minutes) to measure the interaction of PSK9 with LDLR and EGF_AB domain. After injection, the flow cells were regenerated by 10 mM HCl.

Figure 1:
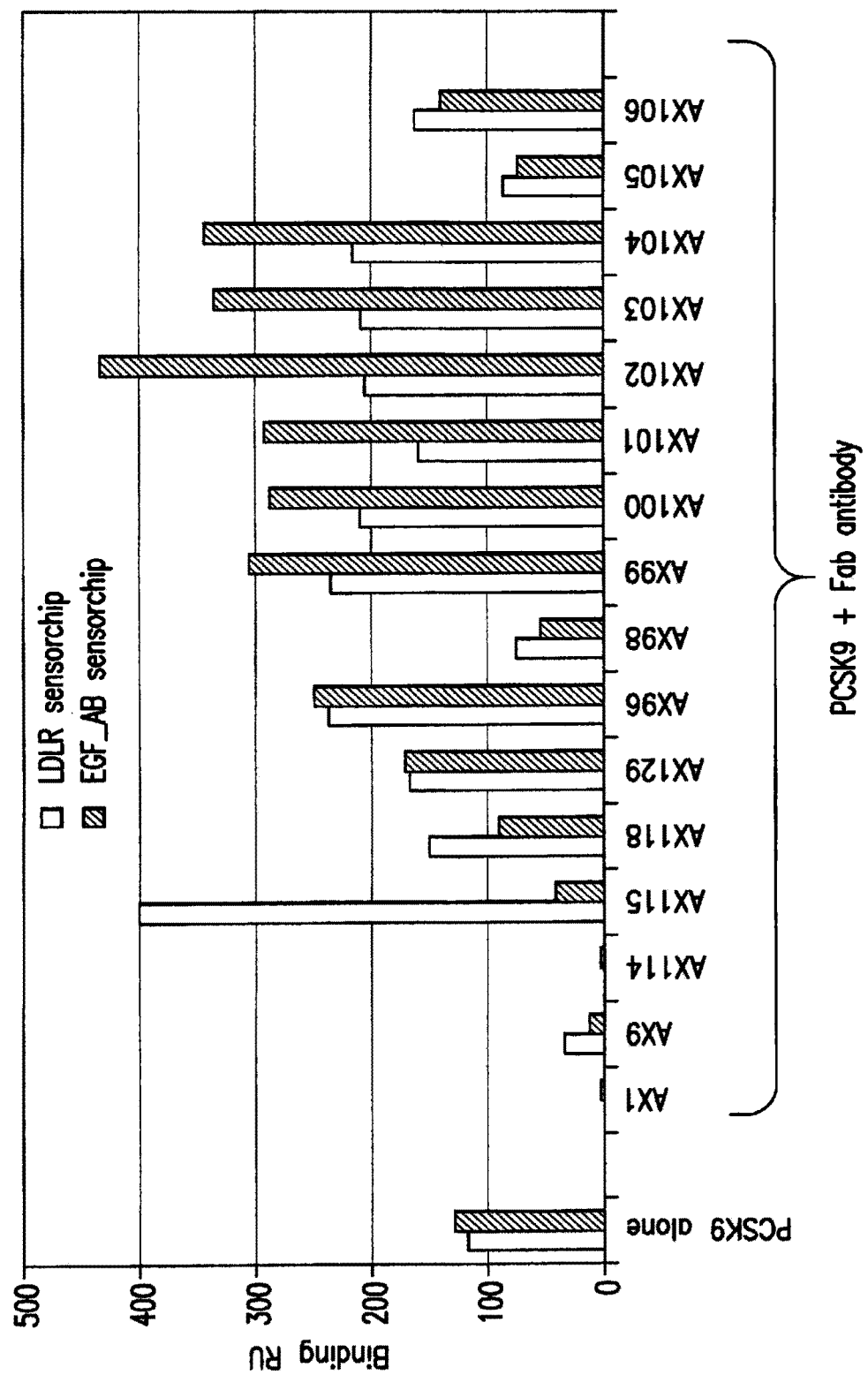
FIG. 1 illustrates the impact of PDL1 Fabs on PCSK9—LDL receptor interaction. This Biacore-based assay shows that binding of AX1, AX9, and AX114 to PCSK9 inhibits the interaction of PCSK9-LDLR and PCSK9-EGF_AB domain. EGF_AB domain in LDLR involves the interaction with PCSK9.

To determine the impact of the binding of Fab antibody to PCSK9, each purified Fab sample (1 µM in the running buffer) was incubated with human PCSK9 at the concentration of 100 nM for 30 minutes at room temperature. The prepared PCSK9/Fab samples were injected into the CM5 chip, and binding of PCSK9/Fab complex was measured. As shown in FIG. 1, human PCSK9 alone bound to both LDLR and EGF_AB domain. When the binding of Fab antibody did not inhibit the PCSK9-LDLR interaction, the binding of PCSK9/Fab complex to LDLR or EGF_AB resulted in higher binding RU then PCSK9 alone. Among the Fab antibodies tested, AX114 Fab showed significant inhibition on PCSK9 binding to LDLR or EGF_AB domain.

EXAMPLE 5

Biacore-Based Competition Assay for Binding Epitope Binning

Human PCSK9 protein was immobilized on CM5 chip by coupling primary amine groups of PCSK9 onto carboxylated surfaces of sensor chips according to the instruction of Amine Coupling Kit (GE/Biacore). Briefly, hPCSK9 protein was diluted to 50 µg/ml in pH 5.5/10 mM Acetate solution, and was injected onto the NHS/EDC activated surface to achieve an immobilization level of 1000-2000 RU, followed with surface inactivation by injection of Ethanolamine The Fab or IgG protein (1 µM in HBS-P buffer) was then injected for 3 minutes binding, followed by 5 minutes dissociation. In the binding epitope binning assay, two flow cells were immobilized with same amount of hPCSK9 protein to detect the binding competition between antibody 1 and antibody 2. On the flow cell 1, antibody 1 was injected twice to occupy its binding epitope, antibody 2 was then injected for binding. The flow cell 2 was setup as a reference, only antibody 2 was injected onto it for binding. To determine whether there was competition between antibody 1 and antibody 2, the sensorgrams of antibody 2 from both flow cells were overplayed. When two antibodies competed, pre-occupation of antibody 1 could significantly or totally inhibit the antibody 1 binding. Cross competition for 19 antibodies from PDL1 library was completed, and 3 independent epitope bins on human PCSK9 were identified, see table 2.

TABLE 2

| Bin 1 binder | Bin 2 binder | Bin 3 binder |
|---|---|---|
| AX114 | AX1 | AX116 |
| AX132 | AX9 | |
| AX139 | AX40 | |
| AX212 | AX56 | |
| AX213 | AX115 | |
| AX210 | AX118 | |
| AX211 | AX119 | |
| | AX188 | |
| | AX189 | |
| | AX191 | |

| Bin 1 Binder | VH SEQ ID NO | VL SEQ ID NO |
|---|---|---|
| AX114 | 360 | 512 |
| AX132 | 360 | 511 |
| AX137 | 360 | 517 |
| AX139 | 360 | 523 |
| AX210 | 364 | 511 |
| AX211 | 365 | 511 |
| AX212 | 366 | 511 |
| AX213 | 362 | 511 |

EXAMPLE 6

Optimization of AX114

Optimization libraries for AX114 were designed and constructed. All AX114 libraries were panned against PCSK9 antigen for 3-6 rounds as described in Example 1. The clones were picked for Fab ELISA screening as described in Example 2. The PCSK9 binding clones were expressed in TG1 cells for Fab secretion. Purified Fab proteins (Example 3) were run on Biacore for affinity measurements (see Example 14). From these libraries, a total of 135 AX114 variants (listed in table 3) that bind to human PCSK9 were identified, including AX132 (comprising VH and VL regions SEQ ID No: 360 and 511, respectively).

TABLE 3 sequence ID for AX114 and its variants

| Sequences | SEQ ID NO: |
|---|---|
| VH | 360-510 |
| VK | 511-549 |
| VH_CDR1 | 189, 191 193, 195, 197-294 |
| VH_CDR2 | 68, 70, 72, 74, 76-182 |
| VH_CDR3 | 5, 7, 9, 11, 13-63 |
| VK_CDR1 | 349, 351, 353-359 |
| VK_CDR2 | 339, 341, 343-346 |
| VK_CDR3 | 301, 303, 305-334 |

>SEQ ID NO: 360 (AX132 VH)
EVQLLESGGGLVQPGGSLRLSCKASGYTFSSYGMYWVRQAPGKGLEWI
GWIDPGSGGTKYNEKFKGKATISRDNSKNTLYLQMNSLRAEDTAVYYCA
RERYGYYFDYWGQGTLVTVSSAS [in specific embodiments,
SEQ ID NO: 361]

>SEQ ID NO: 511 (AX132 VK)
EIVLTQSPATLSLSPGERATITCRASQYVGSYLNWYQQKPGQAPRLLIY
DASNRATGIPARFSGSGSGTDFTLTISSLEPEDFAVYYCQVWDSSPP
VVFGGGTKVEIK

TABLE 3-continued

>SEQ ID NO: 362 (AX213 VH)
EVQLLESGGGLVQPGGSLRLSCKASGYTFSRYGINWVRQAPGKGLEWI
GRIDPGNGGTRYNEKFKGKATISRDNSKNTLYLQMNSLRAEDTAVYYCA
RANDGYSFDYWGQGTLVTVSSAS [in specific embodiments,
SEQ ID NO: 363]

>SEQ ID NO: 511 (AX213 VK)
EIVLTQSPATLSLSPGERATITCRASQYVGSYLNWYQQKPGQAPRLLIY
DASNRATGIPARFSGSGSGTDFTLTISSLEPEDFAVYYCQVWDSSPP
VVFGGGTKVEIK

Figure 2:
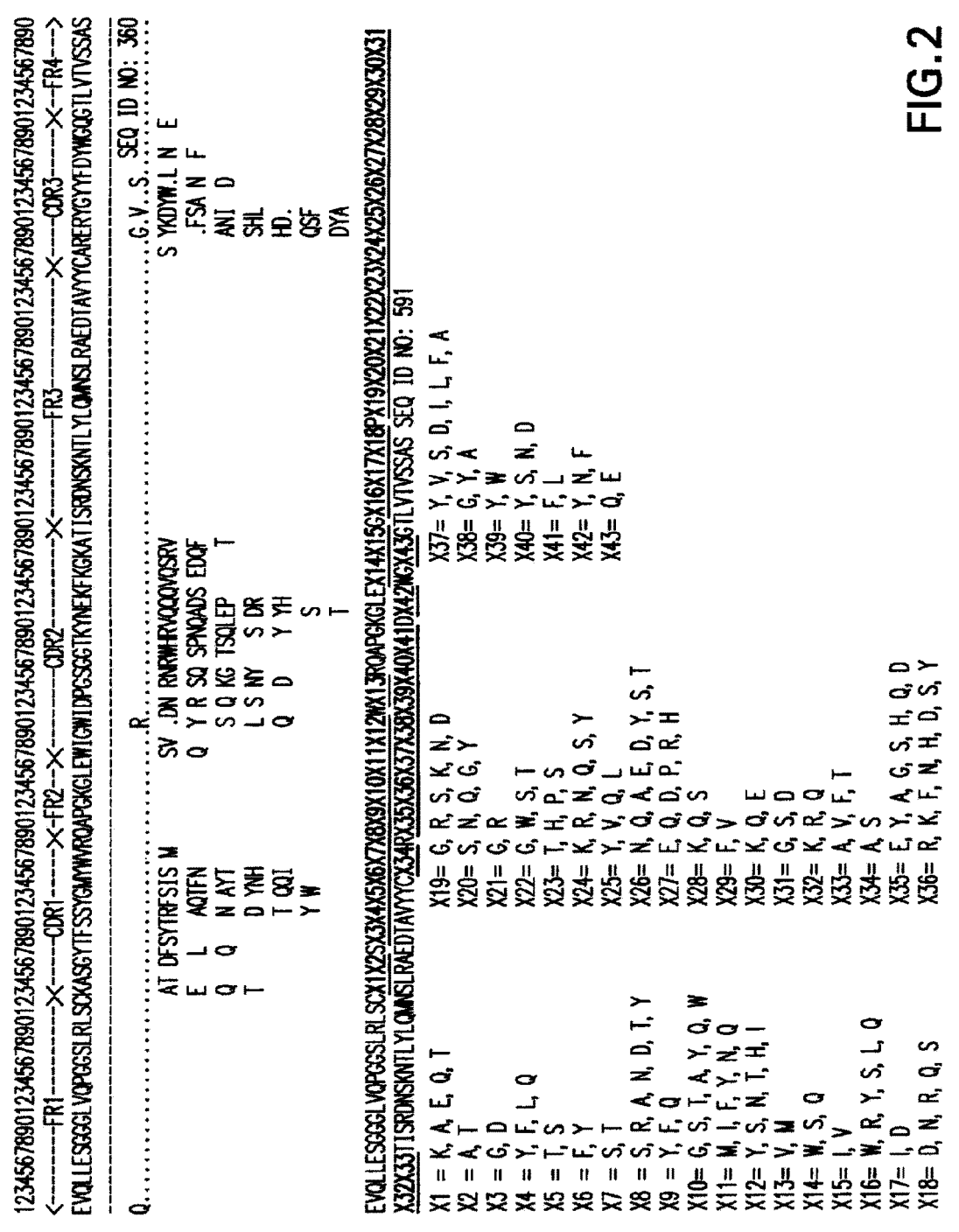

The sequence changes in the CDR regions for AX114 variants are illustrated in FIGS. 2 and 3.

EXAMPLE 7

Computational Docking and PCSK9 Mutagenesis for AX132 Epitope Mapping

Definitions: Given residue on the PCSK9 is counted as in contact with a given antibody, if Cα (see, e.g., "Introduction to Protein Structure" by Carl Branden & John Tooze, $2^{nd}$ edition, 1999 Garland publishing) atom of PCSK9 residue is within 10 Angstroms from CA of that antibody. For X-ray structure, the residues in contact define the epitope. For docking poses within a given epitope bin, the residues in the contacts with frequency higher than threshold (>50-75%) define the epitope. Two proteins (e.g. AX114 with a control Fab that competes with AX114 to bind to EGF_AB domain of LDL receptor) are defined as compete based on their structural model if the distance between any Cα atoms of these proteins is shorter than 5 Å.

Docking procedure: To determine the epitope for AX132, docking was performed with a program involving rigid-body translation/rotation of one partner with respect to the other with optimization of side-chains; see, Gray, J J et al., 2003 *J. Mol. Biol.* 331:281-299. Since AX114 and AX132 compete with the control Fab, the initial configuration was started from the X-ray structure of control Fab with antibody pulled away approximately 15 Angstroms. The low scoring poses have been clustered and analyzed for contacts to determine the epitope. The epitope for AX213 is assumed similar to AX114/AX132 based on sequence similarity and competition data.

Figures 4A, 4B:
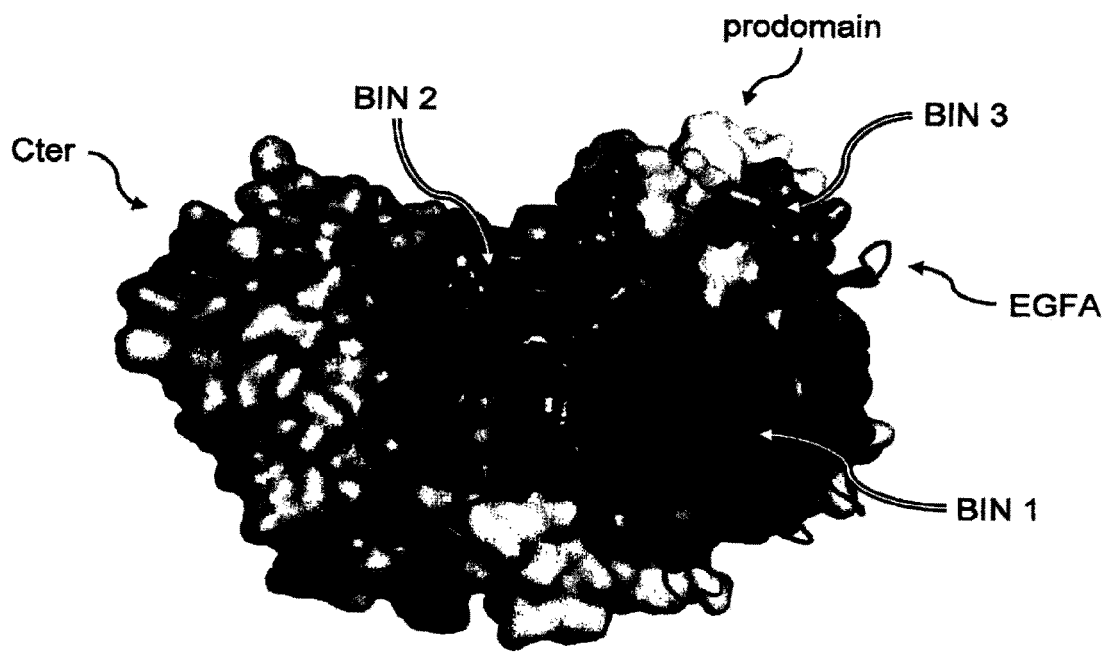
FIGS. 4A-B illustrate the three possible binding bins proposed by computational docking program for the PCSK9 antagonist antibodies isolated from PDL1 library (A). The bin #1, which involves in the binding to EGF_AB domain of LDL receptor, is predicted to be the binding region for AX132 antibody. The surface amino acid residues are provided (B).

Based on computational docking studies, three bins have been determined, as shown in FIG. 4. Based on the AX132 binding differentiation between human and rat PCSK9 (table 4), human PCSK9 chimeric mutations to rat PCSK9 residues have been selected to differentiate and test epitope bins. Total 6 chimeric mutants have been designed. Each mutant represents a patch on PCSK9, see table 5. Mutant #1 is in bin 1 and is expected to abrogate binding of AX114/AX132/AX213 based on cross-species binding data. Mutant #2 (from bin 2) or mutant 3 (from bin 3) are expected to abrogate binding of other antibodies.

TABLE 4 binding affinities of AX132 variants to human, rhesus, mouse and rat PCSK9

| Molecule | Format | Human PCSK9 $K_D$ (M) | Rhesus PCSK9 $K_D$ (M) | Mouse 9 $K_D$ (M) | rat PCSK9 $K_D$ (M) |
|---|---|---|---|---|---|
| AX114 | IgG2 | 2.40E−08 | 1.16E−08 | 1.12E−08 | N/A |
| AX132 | IgG2 | 6.16E−09 | 2.59E−09 | 2.76E−09 | E−7 |
| AX137 | IgG2 | 9.98E−09 | 1.00E−08 | no binding | N/A |
| AX210 | IgG2 | 2.64E−09 | 9.44E−10 | 3.60E−09 | N/A |

TABLE 4-continued binding affinities of AX132 variants to human, rhesus, mouse and rat PCSK9

| Molecule | Format | Human PCSK9 $K_D$ (M) | Rhesus PCSK9 $K_D$ (M) | Mouse 9 $K_D$ (M) | rat PCSK9 $K_D$ (M) |
|---|---|---|---|---|---|
| AX211 | IgG2 | 1.63E-09 | 4.93E-10 | 1.66E-09 | N/A |
| AX212 | IgG2 | 2.12E-09 | 7.74E-10 | 2.74E-09 | N/A |
| AX213 | IgG2 | 2.07E-09 | 1.89E-09 | 3.25E-09 | N/A |

TABLE 5 human PCSK9 mutants with residues of rat PCSK9

| Mutants | Residues of rat PCSK9 |
|---|---|
| Mutant #1 | 192, 379 |
| Mutant #2 | 366, 426 |
| Mutant #3 | 201, 202, 206, 207, 247, 248 |
| Mutant #4 | 245, 396, 405, 420, 440, 443 |
| Mutant #5 | 177, 179, 277, 280 |
| Mutant #6 | 162, 173 |

The human PCSK9 mutant proteins were produced from HEK293 cells. Briefly, the gene of a full-length human PCSK9 inside a mammalian expression vector with His-tag was modified by site-directed mutagenesis to induce the corresponding mutations based on table 5. Then the vectors of PCSK9 mutants were transiently transfected into human HEK293 cells for 7 to 10 days culture at 37° C. The His-tagged PCSK9 mutant proteins were purified from the culture supernatants by NTA column (GE Healthcare, Pittsburgh, Pa.). The quality of PCSK9 proteins were analyzed using 10% SDS-PAGE.

ELISA assays were performed to study the bindings of PCSK9 mutants to anti-PCSK9 antibody AX132. Briefly, the PCSK9 mutant proteins were diluted with PBS to the concentration of 5 µg/ml, and coated to a 96-well ELISA plate with 100 µl/each well for overnight at 4° C. After blocking with 5% milk-PBS, AX132 samples (in 5% milk-PBS with 1:2 serial dilution at start concentration of 4 nM) were added to the wells coated with individual PCSK9 mutants, and incubated for 1 hour at room temperature. After PBS wash, the anti-human K antibody conjugated with HRP was added and incubated for another hour. The TMB substrate solution (Thermo Scientific) was then added into PBS-washed plate for 10-20 minutes of development. After adding stop solution, the plates were measured for the absorbance at 450 nM.

Figure 5A:
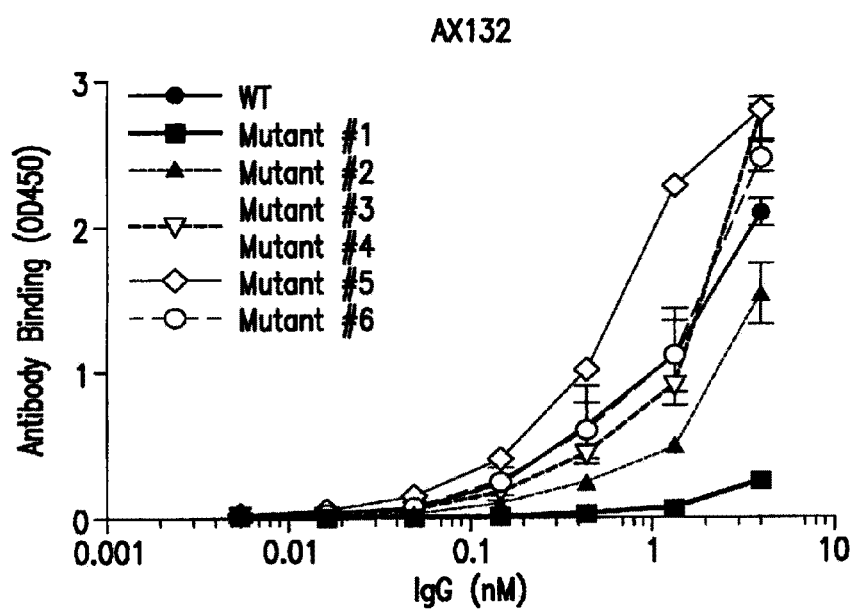
FIGS. 5A-B illustrate the structure of human PCSK9 chimeric mutant #1 with D192G and F379Y substitutions from rat PCSK9 in the Bin #1 (B). ELISA result shows that these substitutions in PCSK9 cause significant loss of binding activity to AX132 antibody (A). These data confirm the binding of AX132 to the Bin #1 as predicted.
Figure 5B:
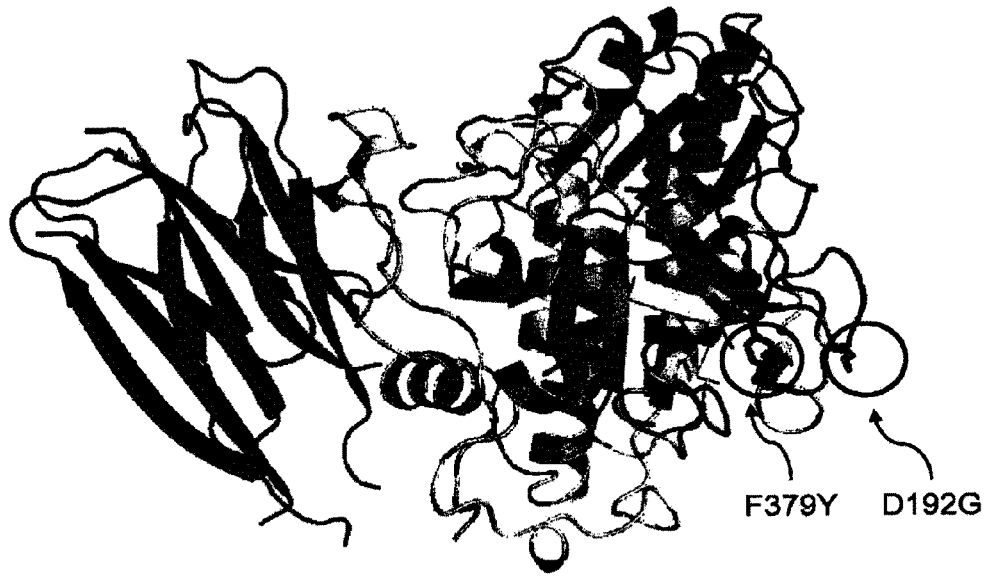

The ELISA results shown in FIG. 5A indicated a significant loss of binding of PCSK9 mutant #1 to antibody AX132. This result suggested that AX132 binds to predicted Bin I. PCSK9 mutant #1 has the amino acid substitutions of D192G and F379Y (FIG. 5B). This region is involved in the binding to EGF_AB domain of LDL receptor.

EXAMPLE 8

Epitope Mapping by Hydrogen-Deuterium Exchange Mass Spectrometry (DXMS)

In order to identify the various epitope regions of PCSK9 recognized by anti-PCSK9 antibodies, hydrogen deuterium exchange was applied to PCSK9, followed by peptide digestion and mass spectrometry based on protocol of Wood and Hamuro (2001) and further developed and automated; see Hamuro et al., 2003 *J. Biomolec. Tech.* 14:171-182; and Coales et al., 2009 *Rapid Comm. Mass Spectrom.* 23:639-647. The multi-step procedure is described in the following.

Antibody affinity column preparation: Antibody was immobilized by overnight incubation with cyanogen bromide activated Poros AL resin followed by washing with PBS using a filter funnel. The reaction was capped by resuspending the dried resin in ethanolamine solution for 2 hours and followed with washing with PBS using a filter funnel. The resin was resuspended in PBS then packed into a column. Column was equilibrated with PBS with 2 mM NaCl pH 7 in exchange buffer H at 3° C. All column injections and incubations were done using a syringe pump.

On-solution and off-column deuterium exchange: Exchange H buffer was prepared as PBS in water. Exchange D buffer was prepared as PBS in D2O. Exchange HD buffer was prepared as PBS in 50% D2O. All exchange steps were conducted at 3° C. The mAb column was cleaned with 0.8% formic acid and washed and equilibrated with exchange HD buffer. On-solution exchange of deuterons was initiated by mixing PCSK9 sample 1:1 with exchange D buffer and incubated for predetermined times. The mixture was then injected into mAb column and washed with exchange HD buffer. Off-column exchange was initiated by washing with exchange H buffer and incubating for predetermined times. Off-column exchange was quenched and PCSK9 was eluted using 0.8% formic acid. Fractions were collected and analyzed.

On- and off-column deuterium exchange: All exchange steps were conducted at 3° C. The mAb column was cleaned with 0.8% formic acid and washed and equilibrated with exchange HD buffer. PCSK9 in exchange H buffer was loaded onto the mAb column and washed with exchange H buffer. On-column exchange of deuterons was initiated by the injection of exchange HD buffer and incubating for predetermined times. Off-column exchange was performed and quenched as above. Fractions were collected and analyzed.

Full deuteration of PCSK9: PCSK9 was equilibrated in PBS prepared in D2O and incubated at 60° C. for 3 hours. This was cooled to room temperature and stored on ice. Fully deuterated PCSK9 was loaded onto an antibody affinity column in HD exchange buffer and washed in same buffer. Elution and analysis were carried out the same as above.

Peptide Analysis by Mass Spectrometry: Eluted PCSK9 was injected into an immobilized pepsin column and then onto a C18 reversed-phase LC-MS to identify fragments. PCSK9 from eluted fractions was denatured and reduced in 2M urea, 1M TCEP, pH3, 0° C. for 2 minutes. The sample was then passed over immobilized pepsin column in buffer A (0.05% TFA in water). The peptic fragments were loaded onto a reversed phase trap column and desalted in buffer A. Peptic fragments were separated by a C18 column with a linear gradient of 13-40% Buffer B (95% acetonitrile, 5% water, 0.0025% TFA) in 23 minutes. Peptides were detected by mass spectrometry.

The shift in the masses of known peptic fragments detected by MS is used to determine the HD exchange level. The percent exchange is determined from ratio HD exchange of bound vs. unbound PCSK9 and indicates degree of epitope protection by the antibody. Percent deuteration change is cutoff at 5% as threshold to remove noise.

Figure 6:
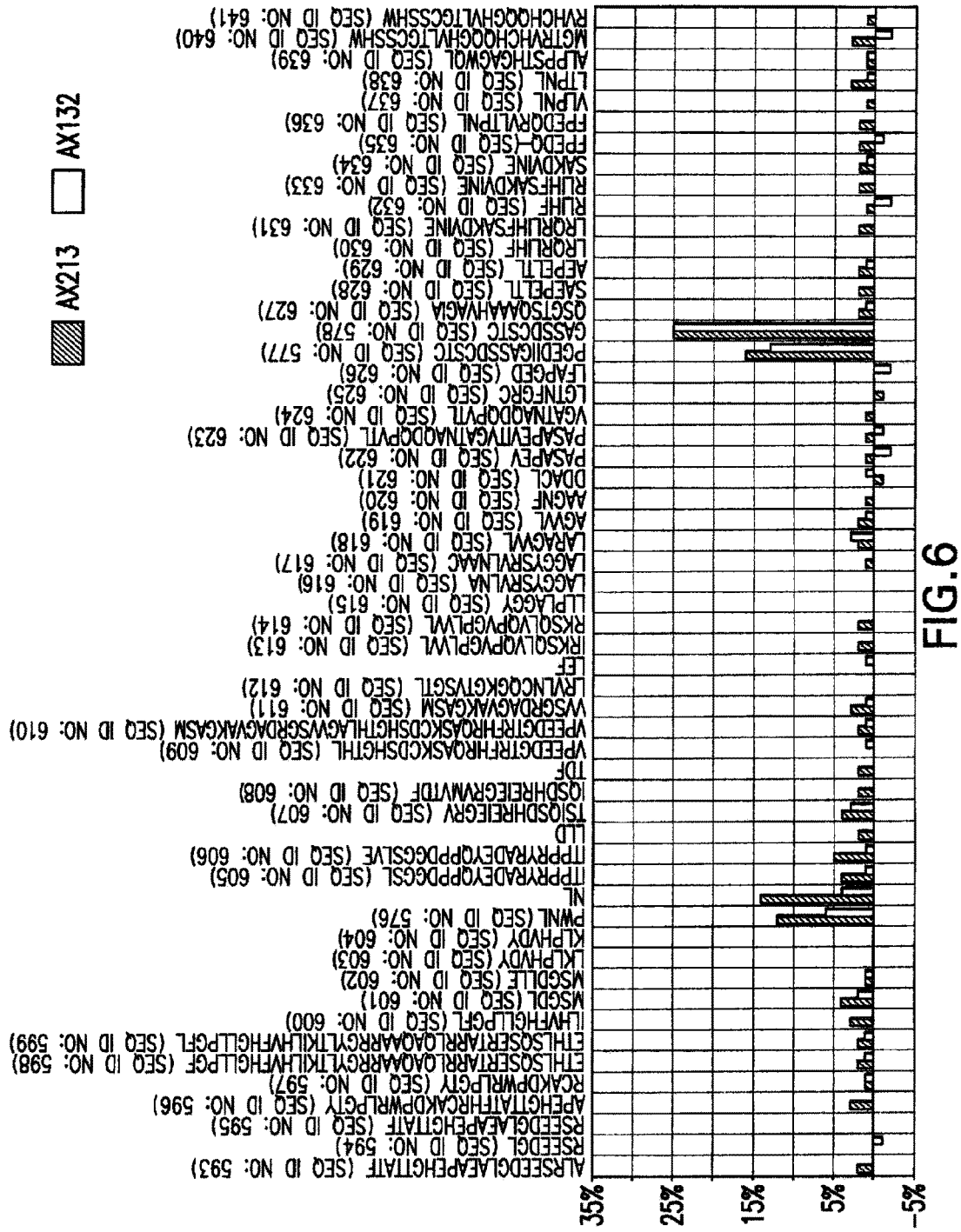

The HD exchange profiles for AX132 and AX213 antibodies are shown in FIG. 6. The PCSK9 peptic fragments that exhibit the greatest deuteration difference upon AX213 or AX132 binding are 155-PWNL-158 (SEQ ID NO: 576) and 364-PGEDIIGASSDCSTC-378 (SEQ ID NO: 577) where subfragments 157-NL-158 and 370-GASSDCSTC-378 (SEQ ID NO: 578) appear to contain the epitope. There may be other weakly interacting sites but these are below the cutoff threshold (5%) and are likely due to indirect or local structural perturbations.

Figure 7:
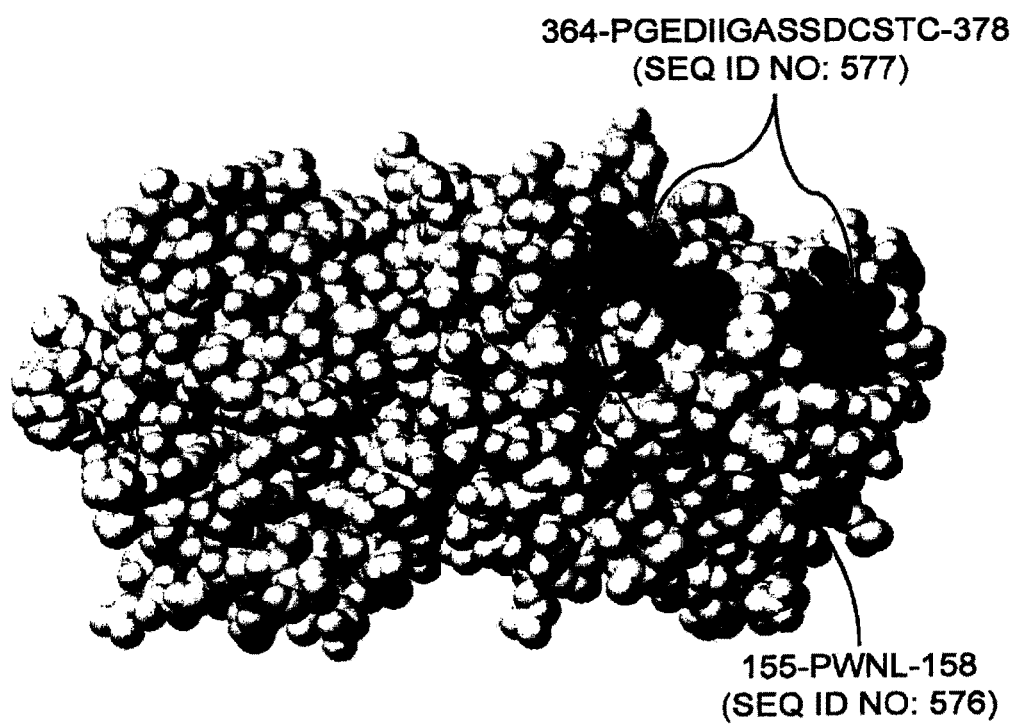

FIG. 7 shows PCSK9 (PDB: 2PMW) with the two peptic fragments containing the AX132 and AX213 epitope highlighted. Grey corresponds to 155-PWNL-158 (SEQ ID NO: 576) and dark grey corresponds to 364-PGEDIIGASSDC-STC-378 (SEQ ID NO: 577). The auto cleaved prodomain is largely hidden from this view.

The HD exchange data is consistent with the PCSK9 mutagenesis data in Example 7. Both 155- and 364-peptides are located in the epitope bin #1 as shown in FIG. 4,

EXAMPLE 9

Fab Domain Thermostability

Thermostabilities of Fabs and Fab domains were determined from DSC experiments by analysis and deconvolution of excess heat capacity function in Origin 5.0. The melting transition temperatures (Tm) for Fabs or Fab domains are indicated in Table 6. The Tm of various Fabs and Fab domains range from 72 to 78° C. for PDL1 derived antibodies, which is consistent with well folded antibody Fab region.

TABLE 6

Thermostabilities of AX114 variants

| IgG | Fab domain (Tm, ° C.) |
|---|---|
| Ax114-IgG1 | 76.7 |
| AX114-IgG2 | 76.5 |
| AX132-IgG2 | 77.4 |

EXAMPLE 10

AX132-FAB/PCS9 Crystal Structure

Expression

Nucleic acid expressing AX132 Fab was incorporated into a phage library display vector, and extraneous N- and C-terminal residues were removed from the vector prior to expression and purification of the Fab for crystallization, as follows:
1) Codons expressing 3 extra amino acids (AGS) between the p3 leader and the H chain FR1 in the vector were removed, generating an authentic heavy chain N-terminus following cleavage of the p3 signal peptide in *E. coli*.
2) In order to facilitate Fab crystallization, the GR1 adaptor domain coding region at the heavy chain C-terminus in the vector was removed prior to Fab expression and purification, and a termination codon was introduced immediately following the coding sequences of the HA and His tags. This was accomplished by subcloning the light and heavy chain Fab expression cassette (HindIII-XhoI) into plasmid pMAB9, which carries those modifications.

The final expression plasmid for purification is illustrated in FIGS. 20A-E, and the vector map is illustrated in FIG. 19. The plasmid expresses both the light and heavy chains in a bicistronic message off the lac promoter. The light chain open reading frame is expressed at the 5' end of the message following the p8 leader, and then the heavy chain follows after the p3 leader.

Purification of AX132

AX 132 was purified from *E. coli* over a nickel affinity column followed by SP Sepharose column chromatography, Purification of PCSK9:

Secreted PCSK9 was captured from HEK 293 cell over a capto Q column. The bound protein was pooled and further purified over a nickel affinity column followed by size exclusion column (S200) chromatography Complex-Generation:

Purified AX 132 was mixed with purified PCSK9 at a molar ratio of 1.5:1 and incubated for 12 hours at 4° C. The mixture was further fractionated on a 2× Superdex 200 (16-60) column to get rid of uncomplexed AX 132. The purified complex was concentrated to 10 mg/ml and crystallized without any freeze-thaws.

Crystallization

The PCSK9:AX132 complex yielded crystals in different crystallization conditions. Generally, the complex was frozen in the presence of cryoprotectant. The crystal diffracted up to 3.09 Å at synchrotron. The structure of PCSK9 bound to the AX132 Fab fragment was determined by a molecular replacement method. AX132 binds at the EGF-A binding site. The light chain of the antibody AX132 is mainly responsible for the interactions with PCSK9. Multiple hydrogen bonding and hydrophobic interactions are observed at the interface.

Figure 8:
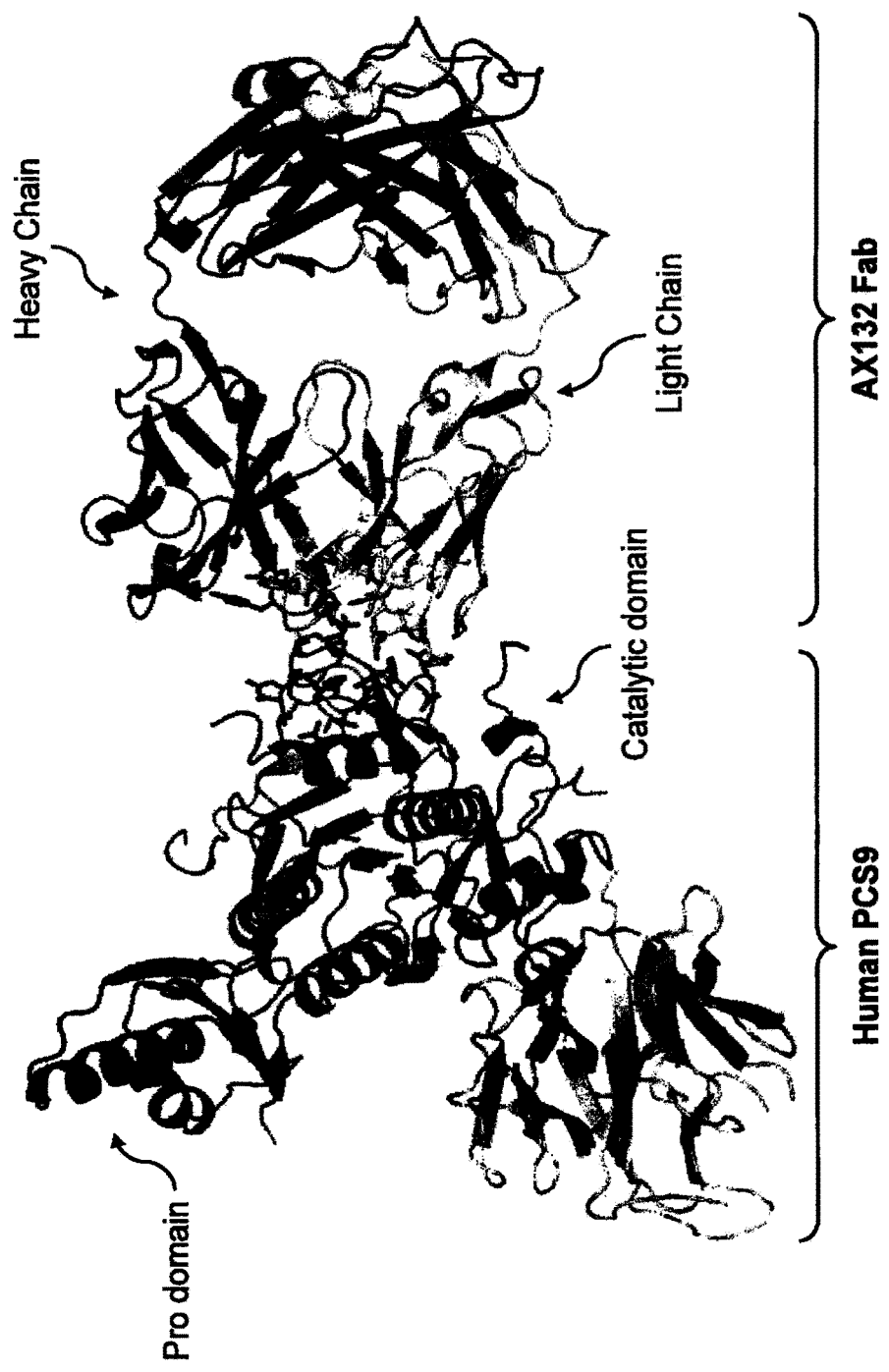

FIG. 8 depicts the crystal structure of PCSK9 bound to the AX132 antibody. FIG. 9 shows the surface area representation of PCSK9 with the AX132 epitope. The coordinates for the crystal structure discussed are presented in Table 14, Example 21.

The residues involved in the binding are identified by calculating the difference in accessible surface area between the AX132:PCSK9 crystal structure and PCSK9 structure alone. PCSK9 residues that show buried surface area upon complex formation with AX132 antibody are included as a part of the epitope. The solvent accessible surface of a protein is defined as the locus of the center of a probe sphere (representing a solvent molecule) as it rolls over the Van der Waals surface of the protein. The solvent accessible surface area was calculated by using the program AREAIMOL (see, Lee et al., 1997 *J. Mol. Biol.* 55:5-11 and Saff et al., 1997 *The Mathematical Intelligencer* 19:5-11), which generates surface points on an extended sphere about each atom (at a distance from the atom center equal to the sum of the atom and probe radii) and eliminates those that lie within equivalent spheres associated with neighboring atoms (Briggs, P. J. 2000, CCP4 Newsletter No. 38, CCLRC, Darebury).

EXAMPLE 11

Selection of Antibodies Binding to AX132 Epitope on PCSK9

The antibodies with AX132 binding epitope can also be selected out from a phage display antibody library using EGF_AB peptide that competes with AX132. After binding of phage library to human PCSK9 coated on plate, the EGF_AB protein can be added to elute the binding phages. The individual clones from the EGF_AB eluted phage pool can then be screened against human PCSK9 and PCSK9 mutant #1. As shown in FIG. 5A, AX132 bind to human PCSK9 with high affinity, but very low affinity to human PCSK9 mutant #1 (see, Example 7). The Fabs that bind to human PCSK9 can be subjected to a binding screening assay against PCSK9 mutant #1 protein, and the Fab with strong binding to human PCSK9 but weak binding to PCSK9 mutant #1 will share the AX132 binding epitope.

EXAMPLE 12

Anti-PCSK9 Monoclonal Antibody Expression and Purification From Mammalian Cells The DNA sequence encoding the Vk1 or VK3 light chain variable region was amplified by polymerase chain reaction from plasmid template. The product of this amplification was cloned into plasmid pVUNSAGS-FB-LCK that had been previously digested with Fspl and Bmtl, using the InFusion cloning system (Clontech). The resulting plasmid was verified by DNA sequencing across the variable region. Endotoxin-free plasmid preparations were made using the Qiagen Endo-Free plasmid maxiprep kit. The DNA sequence encoding the heavy chain variable region of VH3 was amplified by polymerase chain reaction, and the amplified product was cloned into plasmid pVl JNSA-BF-HCG2M4 that had been previously digested with Fspl and Bmtl. The resulting plasmid was verified by DNA sequencing across the variable region. Endotoxin-free plasmid preparations were made using the Qiagen Endo-Free plasmid maxiprep kit.

The plasmid DNA for heavy and light chain was mixed at 1:3, and co-tranfected into HEK293 cells. After 5-7 days culture, the supernatant was harvested and proceeded for Protein-A column purification. Briefly, the cell free supernatant was loaded on to protein-A column pre-equilibrated with three column volume of 20 mM Tris-HCl pH7.0 at a flow rate of 5.0 mL/min. The column was washed with three column volumes of the 20 mM Tris-HCl pH7.0 followed by a five column volume wash with 20 mM Tris-HCl pH7.0 containing 1M NaCl to remove the host cell proteins. The anti-PCSK9 antibody was eluted with five column volume of 100 mM Glycine, 100 mM Arginine pH 3.0 and immediately neutralized with 1M Tris-HCl pH8.0.

EXAMPLE 13

ANTI-PCSK9 Monoclonal Antibody Expression and Purification from Glycoengineered *Pichia pastoris*

Anti-PCSK9 IgG2 monoclonal antibodies were expressed in glyco-engineered *Pichia pastoris* GFI 5.0 host YGLY8316, which is capable of transferring terminal galactose at its complex N-linked glycan. Anti-PCSK9 heavy and light chains were codon optimized and expressed under methanol tightly inducible promoter AOX1 using *Saccharomyces cerevisiae* alpha mating factor presequence as secretion signal sequence. Anti-PCSK9 antibody from *Pichia pastoris* GFI 5.0 host YGLY8316 was captured from cell free supernatant media by affinity chromatography using MabSelect™ medium from GE Healthcare (Cat. #17-5199-01). The cell free supernatant was loaded on to Mabselect column (XK 16/20, 1.6 cm×10.0 cm) pre-equilibrated with three column volume of 20 mM Tris-HCl pH7.0 at a flow rate of 5.0 mL/min. The column was washed with three column volumes of the 20 mM Tris-HCl pH7.0 followed by a five column volume wash with 20 mM Tris-HCl pH7.0 containing 1M NaCl to remove the host cell proteins. The anti-PCSK9 antibody was eluted with five column volume of 100 mM Glycine, 100 mM Arginine pH 3.0 and immediately neutralized with 1M Tris-HCl pH8.0. AX213 antibody was well expressed in *Pichia*, yielding ca. 300-700 mg/L of protein in a small scale fermentation process. The yield for AX114 was 5 mg/L in small scale.

Strong Cation Exchange Chromatography employing Source 30S resin from GE Healthcare (Cat #17-1273-02) was used as the second step purification to remove the clipped species and aggregates. A MabSelect™ (GE Healthcare, Pittsburgh, Pa.) pool of the anti-PCSK9 antibody was 5× diluted with 25 mM Sodium acetate pH5.0 and loaded on to the Source 30S column pre-equilibrated with three column volume of 25 mM Sodium acetate pH5.0. After loading, the column was washed with three column volume of the 25 mM Sodium acetate pH5.0 and elution was performed by developing a linear gradient over ten column volume ranging from 100 mM to 150 mM Sodium chloride in 25 mM Sodium acetate pH5.0. The fractions containing good assembled anti-PCSK9 antibody was pooled together. The Source 30S pooled fractions that contained the anti-PCSK9 antibody was buffer exchanged into the formulation buffer containing 6% Sucrose, 100 mM Arginine, 100 mM Histidine pH6.0 (Hy-Clone® Cat #RR10804.02) and sterile filtered using 0.2 μm PES (PolyEtherSulfone) membrane filter and stored @4° C. until release.

EXAMPLE 14

Biacore Assay for Affinity Measurement

To determine the binding affinity of Fab to PCSK9, Fab capture-based Biacore assay was developed. First, goat anti-Fab IgGs were immobilized onto CM5 chip by amine coupling as described above. The anti-Fab IgGs were diluted to 200 μg/ml in pH 5/10 mM Acetate solution, and injected onto the NHS/EDC activated surface to achieve an immobilization level of ~10,000 RU, followed with surface inactivation by injection of Ethanolamine. Then Fab samples at concentration of 2 μg/ml in HBS-P running buffer were injected for 3 minutes at flow speed of 20 ul/min, followed with K-injection (3 minutes injection for association and 6 minutes for dissociation) of PCSK9 at concentration of 10 to 100 nM. The sensor chip surface was regenerated by 30 second injection of 100 mM phosphoric acid. The binding sensorgrams were fitted with 1:1 Langmuir binding model to determine the binding affinity. The Fab affinities of AX114, AX132 and other variants are shown in table 7.

TABLE 7

| | Fab binding affinity | | |
|---|---|---|---|
| Fabs | Binding affinity to human PCSK9 | | |
| Name | ka (1/Ms) | kd (1/s) | KD (M) |
| AX114 | 7.17E+04 | 3.48E−03 | 4.85E−08 |
| AX132 | 9.11E+04 | 1.08E−03 | 1.18E−08 |
| AX137 | 1.07E+05 | 2.08E−03 | 1.95E−08 |
| AX139 | 8.97E+04 | 1.18E−03 | 1.32E−08 |
| AX201 | 1.31E+05 | 1.02E−03 | 7.82E−09 |
| AX202 | 1.09E+05 | 1.02E−03 | 9.43E−09 |
| AX204 | 2.34E+05 | 9.87E−04 | 8.39E−09 |
| AX205 | 1.04E+05 | 9.72E−04 | 9.45E−09 |
| AX206 | 1.22E+05 | 1.03E−03 | 8.42E−09 |
| AX207 | 1.11E+05 | 1.00E−03 | 9.23E−09 |
| AX208 | 9.84E+04 | 2.59E−03 | 2.64E−08 |
| AX209 | 1.12E+05 | 1.07E−03 | 9.60E−09 |
| AX210 | 1.72E+05 | 2.87E−04 | 1.67E−09 |
| Ax211 | 1.97E+05 | 3.29E−04 | 1.67E−09 |
| AX212 | 1.59E+05 | 2.33E−04 | 1.47E−09 |
| AX213 | 2.43E+05 | 3.29E−04 | 1.37E−09 |
| AX214 | 1.92E+05 | 3.19E−04 | 1.60E−09 |
| AX215 | 1.16E+05 | 3.76E−04 | 3.47E−09 |
| AX216 | 1.15E+05 | 2.88E−04 | 2.51E−09 |
| AX217 | 1.38E+05 | 3.40E−04 | 2.52E−09 |
| AX239 | 3.03E+04 | 9.60E−04 | 3.16E−08 |
| AX240 | 1.60E+05 | 1.66E−04 | 1.04E−09 |
| AX241 | 1.97E+05 | 1.60E−04 | 8.13E−10 |
| AX242 | 1.62E+05 | 1.93E−04 | 1.19E−09 |
| AX243 | 1.31E+05 | 1.91E−04 | 1.46E−09 |
| AX244 | 1.89E+05 | 2.03E−04 | 1.07E−09 |
| AX245 | 1.12E+05 | 3.19E−04 | 2.84E−09 |
| AX246 | 2.49E+05 | 2.01E−04 | 8.06E−10 |
| AX247 | 1.86E+05 | 2.44E−04 | 1.31E−09 |
| AX248 | 1.89E+05 | 2.07E−04 | 1.09E−09 |
| AX249 | 1.90E+05 | 2.06E−04 | 1.08E−09 |

TABLE 7-continued

Fab binding affinity

| Fabs Name | Binding affinity to human PCSK9 | | |
|---|---|---|---|
| | ka (1/Ms) | kd (1/s) | KD (M) |
| AX250 | 3.07E+05 | 2.40E−04 | 7.81E−10 |
| AX251 | 2.54E+05 | 2.52E−04 | 9.93E−10 |
| AX252 | 1.37E+05 | 4.67E−04 | 3.42E−09 |
| AX253 | 1.61E+05 | 6.81E−04 | 4.23E−09 |
| AX254 | 9.24E+04 | 2.95E−04 | 3.19E−09 |
| AX255 | 9.61E+04 | 3.91E−04 | 4.07E−09 |
| AX256 | 1.26E+05 | 3.65E−04 | 2.90E−09 |
| AX257 | 2.53E+05 | 1.68E−04 | 6.64E−10 |
| AX258 | 1.12E+05 | 6.30E−04 | 5.63E−09 |
| AX259 | 6.92E+04 | 6.04E−04 | 8.73E−09 |
| AX260 | 4.19E+04 | 5.20E−04 | 1.24E−08 |
| AX260 | 2.64E+04 | 5.70E−04 | 2.16E−08 |
| AX263 | 2.78E+04 | 1.70E−04 | 6.11E−09 |
| AX267 | 1.29E+05 | 4.75E−04 | 3.70E−09 |
| AX268 | 2.77E+04 | 4.17E−04 | 1.50E−08 |
| AX269 | 1.13E+05 | 3.14E−04 | 2.77E−09 |
| AX269 | 9.49E+04 | 3.20E−04 | 3.37E−09 |
| AX299 | 1.03E+05 | 2.57E−04 | 2.51E−09 |
| AX300 | 1.15E+05 | 3.12E−04 | 2.72E−09 |
| AX301 | 1.28E+05 | 6.00E−04 | 4.67E−09 |
| AX302 | 1.14E+05 | 6.68E−04 | 5.89E−09 |
| AX303 | 7.37E+04 | 8.61E−04 | 1.17E−08 |
| AX306 | 9.04E+04 | 4.47E−04 | 4.94E−09 |
| AX307 | 8.88E+04 | 2.70E−03 | 3.03E−08 |
| AX308 | 5.23E+04 | 2.59E−03 | 4.96E−08 |
| AX310 | 1.09E+05 | 7.43E−04 | 6.79E−09 |
| AX311 | 1.47E+05 | 4.98E−04 | 3.39E−09 |
| AX312 | 1.58E+05 | 1.41E−03 | 8.94E−09 |
| AX313 | 2.13E+05 | 7.35E−04 | 3.46E−09 |
| AX314 | 1.09E+05 | 1.72E−03 | 1.58E−08 |
| AX315 | 4.65E+04 | 2.31E−04 | 4.97E−09 |
| AX316 | 1.57E+05 | 5.63E−04 | 3.59E−09 |
| AX318 | 1.67E+05 | 2.71E−05 | 1.62E−10 |
| AX319 | 2.59E+05 | 4.25E−05 | 1.64E−10 |
| AX320 | 1.51E+05 | 2.62E−05 | 1.74E−10 |
| AX322 | 1.19E+05 | 1.83E−04 | 1.54E−09 |
| AX323 | 1.79E+05 | 8.36E−05 | 4.66E−10 |
| AX325 | 1.39E+05 | 1.19E−04 | 8.53E−10 |
| AX326 | 1.68E+05 | 6.52E−05 | 3.87E−10 |
| AX329 | 1.33E+05 | 2.09E−04 | 1.57E−09 |

The Fabs which showed functional efficacy in the cell-base assays were converted into IgG molecules. The affinities of those IgG molecules were also measured by Biacore assay. Briefly, anti-human IgG monoclonal antibody form Human Antibody Capture Kit provided by Biacore was immobilized on CM5 chips at level of 8000 to 10000 RU. The IgG samples at concentration of ~0.4 μg/ml was injected onto a sensor chip for 2 minutes at a flow rate of 20 μl/min, then PCSK9 proteins at 5 concentrations (3.75 to 60 nM) were injected onto an IgG captured flow cell for binding kinetic analysis. After each round injection, the sensor chip surface was regenerated by 30 second injection of 3M Magnesium Chloride. The affinities of AX114, AX1213 and other variants are shown in table 8 and table 9.

TABLE 8

Purified IgGs against human PCSK9

| Name | ka (1/Ms) | kd (1/s) | KD (M) |
|---|---|---|---|
| AX114 | 1.51E+05 | 3.61E−03 | 2.40E−08 |
| AX132 | 2.48E+05 | 1.52E−03 | 6.16E−09 |
| AX137 | 3.33E+05 | 3.32E−03 | 9.98E−09 |
| AX210 | 2.35E+05 | 6.21E−04 | 2.64E−09 |
| AX211 | 3.61E+05 | 5.89E−04 | 1.63E−09 |
| AX212 | 1.53E+05 | 3.24E−04 | 2.12E−09 |
| AX213 | 3.53E+05 | 7.30E−04 | 2.07E−09 |

TABLE 9

Purified IgGs against rhesus PCSK9

| Name | ka (1/Ms) | kd (1/s) | KD (M) |
|---|---|---|---|
| AX240 | 1.41E+06 | 3.09E−04 | 2.20E−10 |
| AX241 | 1.56E+06 | 3.46E−04 | 2.22E−10 |
| AX242 | 1.76E+06 | 3.25E−04 | 1.85E−10 |
| AX243 | 7.71E+05 | 8.70E−04 | 1.13E−09 |
| AX245 | 8.90E+05 | 1.05E−03 | 1.18E−09 |
| AX246 | 1.48E+06 | 6.14E−04 | 4.16E−10 |
| AX248 | 1.16E+06 | 4.58E−04 | 3.96E−10 |
| AX249 | 1.22E+06 | 6.53E−04 | 5.35E−10 |
| AX250 | 2.09E+06 | 6.23E−04 | 2.98E−10 |
| AX253 | 1.62E+06 | 1.76E−03 | 1.09E−09 |
| AX267 | 1.38E+06 | 1.26E−03 | 9.13E−10 |
| AX277 | 9.99E+05 | 1.67E−03 | 1.67E−09 |
| AX369 | 9.71E+05 | 2.30E−03 | 2.37E−09 |
| AX370 | 1.01E+06 | 2.31E−03 | 2.28E−09 |
| AX402 | 1.09E+06 | 2.32E−03 | 2.12E−09 |
| AX406 | 8.86E+05 | 2.01E−03 | 2.27E−09 |
| AX408 | 7.65E+05 | 1.50E−03 | 1.96E−09 |
| AX415 | 7.50E+05 | 3.12E−03 | 4.15E−09 |
| AX417 | 1.10E+06 | 9.04E−04 | 8.22E−10 |
| AX419 | 1.25E+06 | 9.41E−04 | 7.51E−10 |
| AX426 | 6.92E+05 | 6.28E−04 | 9.08E−10 |
| AX427 | 7.45E+05 | 5.60E−04 | 7.51E−10 |
| AX428 | 6.55E+05 | 4.43E−04 | 6.76E−10 |
| AX429 | 7.25E+05 | 5.88E−04 | 8.11E−10 |
| AX430 | 9.15E+05 | 8.52E−04 | 9.31E−10 |
| AX432 | 7.39E+05 | 1.25E−03 | 1.69E−09 |
| AX436 | 4.81E+05 | 7.93E−04 | 1.65E−09 |
| AX439 | 7.40E+05 | 7.36E−04 | 9.94E−10 |
| AX441 | 7.92E+05 | 8.22E−04 | 1.04E−09 |
| AX444 | 7.08E+05 | 4.99E−04 | 7.06E−10 |

EXAMPLE 15

PCSK9-LDLR TR-FRET Assay

This assay is a variant of the one described in Fisher et al., 2007 *J. Biol. Chem.* 282:20502-20512. AlexaFluor647-labeled PCSK9 (final concentration 10 nM) was combined with varying amounts of AX132 and variants and to this was added Eu(8044)-labeled LDLR ectodomain to a final concentration of ~4 nM (sufficient to give ~20,000 counts at F1620 nM on the Rubystar) in 10 mM HEPES (pH 7.4), 150 mM NaCl, 0.1 mM $CaCl_2$, 0.05% (w/v) BSA in a total volume of 50 μL using 96 well black Dynatech U bottom plates. After at least 90 minutes of equilibration, samples were read in a Rubystar reader (BMG Corp.) using 20 flashes per well, a 50 μsec integration delay, and a 200 μsec total integration time. Data were expressed as the ratio of ($Fl_{665}/Fl_{620} \times 10000$), and $IC_{50}$s for AX132 and variants were determined from the inflection point of a sigmoidal dose-response curve using a standard four parameter fit.

FIG. 10 illustrates the activity of AX132 and its variants in the PCSK9-LDLR interaction TR-FRET assay. The IgG of AX132 and its variants are potent [with an $IC_{50}$ of 2.4 to 5.9 nM] and inhibit the PCSK9-LDLR interaction fully.

EXAMPLE 16

Exopolar Assay: Effects of Exogenous PCSK9 on Cellular LDL Uptake

On day 1, 30,000 HepG2 or HEK cells/well were plated in a 96 well polyD-lysine coated plate. On day 2, the media was switched to no-serum containing DMEM media. On day 3, the media was removed and the cells were washed with Opti-MEM. Purified PCSK9 was added in 100 μl of DMEM media containing LPDS and dI-LDL. The plates were incubated at 37° C. for 6.5 hours. The cells were washed quickly in TBS containing 2 mg/ml BSA; then washed in TBS-BSA for 2 minutes; and then washed twice (but quickly) with TBS. The cells were lysed in 100 μl RIPA buffer. Fluorescence was then measured in the plate using an Ex 520, Em 580 nm. The total cellular protein in each well was measured using a BCA Protein Assay and the fluorescence units were then normalized to total protein.

The Exopolar Assay is effective for characterizing variant effects on LDL uptake; see Table 10 below illustrating how the potencies of PCSK9 mutants correlate with plasma LDL-cholesterol in the Exopolar Assay.

TABLE 10

| Mutation | Gain/Loss | LDL-C (mg/dl) | EC-50 (nM) Exopolar |
|---|---|---|---|
| S127R | Gain | 277 | 14 |
| D374Y | Gain | 388 | 1.3 |
| Wild-type |  | 140 | 51 |
| R46L | Loss | 116 | 78 |

Results: 54 Fabs listed in table 11 inhibited the effect of human ("h"), rhesus ("rh") and murine ("m") PCSK9 on LDL uptake in a dose-dependent way, with IC50 (human PCSK9) ranging from 4~178.7 nM.

TABLE 11

Inhibition of PCSK9 on LDL uptake by Fabs

| | Fab IC50 (nM) | | |
|---|---|---|---|
| Antibody | hPCSK9 | rhPCSK9 | mPCSK9 |
| AX114 | 178.7 | 194.0 | 326.0 |
| AX132 | 62.2 | N/A | 26.9 |
| AX137 | 74.4 | N/A | 27.4 |
| AX139 | 37.7 | N/A | 22.9 |
| AX201 | 36.0 | N/A | N/A |
| AX202 | 31.2 | N/A | N/A |
| AX204 | 26.7 | N/A | N/A |
| AX205 | 26.1 | N/A | N/A |
| AX206 | 30.3 | N/A | N/A |
| AX207 | 25.6 | N/A | N/A |
| AX209 | 35.4 | N/A | N/A |
| AX210 | 26.8 | N/A | N/A |
| AX211 | 12.6 | N/A | N/A |
| AX212 | 13.8 | N/A | N/A |
| AX213 | 14.7 | N/A | N/A |
| AX214 | 15.1 | N/A | N/A |
| AX215 | 19.3 | N/A | N/A |
| AX216 | 17.1 | N/A | N/A |
| AX217 | 21.4 | N/A | N/A |
| AX240 | 65 | N/A | N/A |
| AX241 | 5 | N/A | N/A |
| AX242 | 9 | N/A | N/A |
| AX243 | 17 | N/A | N/A |
| AX244 | 13 | N/A | N/A |
| AX245 | 28 | N/A | N/A |
| AX246 | 17 | N/A | N/A |
| AX248 | 29 | N/A | N/A |
| AX249 | 25 | N/A | N/A |
| AX250 | 11 | N/A | N/A |
| AX254 | 11 | N/A | N/A |
| AX255 | 4 | N/A | N/A |
| AX256 | 18 | N/A | N/A |
| AX257 | 13 | N/A | N/A |
| AX258 | 11 | N/A | N/A |
| AX259 | 9 | N/A | N/A |
| AX267 | 11 | N/A | N/A |
| AX268 | 12 | N/A | N/A |
| AX269 | 22 | N/A | N/A |
| AX272 | 19 | N/A | N/A |

TABLE 11-continued

Inhibition of PCSK9 on LDL uptake by Fabs

| | Fab IC50 (nM) | | |
|---|---|---|---|
| Antibody | hPCSK9 | rhPCSK9 | mPCSK9 |
| AX273 | 10 | N/A | N/A |
| AX277 | 20 | N/A | N/A |
| AX302 | 20 | N/A | N/A |
| AX303 | 19 | N/A | N/A |
| AX304 | 23 | N/A | N/A |
| AX305 | 42.0 | N/A | N/A |
| AX318 | 7 | N/A | N/A |
| AX319 | 7 | N/A | N/A |
| AX320 | 9 | N/A | N/A |
| AX322 | 26 | N/A | N/A |
| AX323 | 13 | N/A | N/A |
| AX325 | 4 | N/A | N/A |
| AX326 | 11 | N/A | N/A |
| AX329 | 9 | N/A | N/A |
| AX330 | 20 | N/A | N/A |

For IgGs, 7 antibodies listed in table 12 dose-dependently inhibited the effects of both human and rhesus PCSK9 on LDL uptake (FIG. 11-13); an effect which was reproducibly observed. The amount of PCSK9 added to the cells was ~5-320 nM.

TABLE 12 inhibition of PCSK9 by IgGs

| | IgG2 IC50 (nM) | | |
|---|---|---|---|
| Antibody | hPCSK9 | rhPCSK9 | mPCSK9 |
| AX114 | 36.6 | 14.4 | 27.4 |
| AX132 | 8.9 | 11.5 | 9.4 |
| AX137 | 9.8 | 10.0 | 5.3 |
| AX210 | 6.5 | 9.7 | 15.9 |
| AX211 | 7.5 | 4.4 | 11.1 |
| AX212 | 9.5 | 4.7 | 7.3 |
| AX213 | 11.1 | 10.2 | 7.0 |

FIGS. 11A-F illustrate (i) AX114 or AX132 (IgG)'s dose-dependent inhibition of human PCSK9-dependent loss of cellular LDL-uptake (A, D); (ii) AX114 or Ax132 (IgG)'s dose-dependent inhibition of murine PCSK9-dependent loss of cellular LDL-uptake (B, E); and (iii) AX114 or AX132 (IgG)'s dose-dependent inhibition of rhesus PCSK9-dependent loss of cellular LDL-uptake (C, F).

FIGS. 12A-F illustrate (i) AX210 or AX211 (IgG)'s dose-dependent inhibition of human PCSK9-dependent loss of cellular LDL-uptake (A, D); (ii) AX210 or AX211 (IgG)'s dose-dependent inhibition of murine PCSK9-dependent loss of cellular LDL-uptake (B, E); and (iii) AX210 or AX211 (IgG)'s dose-dependent inhibition of rhesus PCSK9-dependent loss of cellular LDL-uptake (C, F).

FIGS. 13A-F illustrate (i) AX212 or AX213 (IgG)'s dose-dependent inhibition of human PCSK9-dependent loss of cellular LDL-uptake (A, D); (ii) AX212 or AX213 (IgG)'s dose-dependent inhibition of murine PCSK9-dependent loss of cellular LDL-uptake (B, E); and (iii) AX212 or AX213 (IgG)'s dose-dependent inhibition of rhesus PCSK9-dependent loss of cellular LDL-uptake (C, F).

EXAMPLE 17

In Vitro FcRn Dissociation Assay

Our internal data showed that monoclonal antibodies with identical Fc sequences but different Fab domains can bind FcRn with considerable differences. Moreover, an apparent correlation between dissociation at neutral pH and in vivo pharmacokinetics was observed: mAbs with slow dissociation (i.e. >5% "% bound" tend to show shorter terminal half life (t½) in vivo). This feature was used as an in vitro screening tool for antibody pharmacokinetics.

The neutral pH dissociation of mAbs from human FcRn was measured by SPR using a Biacore T-100 instrument. Briefly, purified FcRn protein was immobilized onto a Biacore CM5 biosensor chip and PBSP (50 mM NaPO4, 150 mM NaCl and 0.05% (v/v) Surfactant 20) pH 7.3 was used as running buffer. The mAbs were diluted with PBSP pH 6.0 to 100 nM, allowed to bind FcRn for 3 minutes to reach equilibrium and followed by 1 minute of dissociation in pH 7.3 running buffer. A report point (Stability) was inserted at 5 seconds after the end of mAb binding and the "% bound" was calculated as RUStability/RUBinding (%).

FIGS. 14-15 illustrate binding of AX114, AX132, AX210-213 to immobilized human FcRn with Biacore. The sensorgrams show both binding at pH 6.0 and dissociation at pH 7.3. A report point (Stability) was inserted at 5 seconds after then end of pH 6.0 binding and the "% bound" was calculated as $RU_{Stability}/RU_{Binding}$(%).

EXAMPLE 18

Pharmacokinetics Study in Human FcRn Mice

The interaction between IgG and FcRn is species-specific. Human FcRn mice have recently been suggested as a valuable surrogate system for evaluating mAb pharmacokinetics; Petkova et al., 2006 *Int. Immunol.* 12:1759-69. The human FcRn mice (heterozygous Tg276) used in this study were obtained from Jackson Laboratory (Bar Harbor, Me.). They are deficient in mouse FcRn-α chain and carry a human FcRn-α chain gene. Id. Our internal data showed that unlike mouse or rat FcRn, this "hybrid" FcRn had comparable human IgG binding characteristics as that of human and monkey FcRn. In addition, good terminal half life correlation between this human FcRn mice and non-human primate was observed.

For pharmacokinetics studies, each animal (2-3/group) received a single intravenous injection of mAb at 10 mg/kg via tail vein. Series of 10 µL of blood was collected at specified time points. A validated anti-human IgG immunoassay was used to determine all mAb levels.

The pharmacokinetic profile of AX114, AX132 and AX213 were determined in human FcRn mice following a single 10 mg/kg IV administration. FIG. 16 illustrates the half-life of AX114 and AX132 determined to be 79.6 and 65.5 hours, respectively. The half-life of AX213 was determined to be 97 hours.

The pharmacokinetic profile of AX132 was also determined in rhesus monkey following a single 10 mg/kg IV administration. The half-life of AX132 was determined to be 147 hours.

EXAMPLE 19

Rhesus Pharmacodynamics Study

To characterize pharmacokinetics, pharmacodynamics and target engagement of AX132, a single dose study was conducted in 6 Rhesus monkeys at 1 mg/kg with subcutaneous route of administration. All Rhesus monkeys used in the study were naive to biologies. Blood samples were collected from the saphenous/femoral vessel at designated time points post dosing and the resulting plasma/serum was stored at −70° C. until analysis.

To generate lipoprotein profiles, plasma or serum was fractionated by chromatography over Superose-6 size exclusion column (GE LifeSciences, Inc.). Total cholesterol levels in the column effluent were continuously measured via in-line mixture with a commercially available enzymatic colorimetric cholesterol detection reagent (Total Cholesterol E, Wako USA) followed by downstream spectrophotometric detection of the reaction products at 600 nm absorbance. The first peak of cholesterol eluted from the column was attributed to VLDL, the second peak to LDL and the third to HDL; the area under each peak was calculated using software provided with the HPLC. To calculate the cholesterol concentration for each lipoprotein fraction, the ratio of the corresponding peak area to total peak area was multiplied by the total cholesterol concentration measured in the sample.

The lipoprotein analysis of the serum samples were carried out as described above. An anti-human IgG ELISA using commercially available reagents was used to quantify Ax132 levels.

As shown in FIG. 17, AX132 significantly lowered LDL cholesterol following a single dose, with a maximum mean reduction of 60%, and >25% LDL-C lowering for 42 days.

EXAMPLE 20

Analytical Size Exclusion Chromatography

High Performance-Size Exclusion Chromatography (HP-SEC) is an analytical method used to separate proteins based on order of decreasing size. This method was used to quantitate the level of aggregation and/or fragmentation of proteins after process and purification (time zero) and after accelerated stability studies. Size Exclusion Chromatography was performed with a Waters 2690 Separations Module/996 Photodiode Array Detector. Material was separated using a TSK-gel G3000SW$_{XL}$ (4.6×300 mm) column with a Phenomenex pre-filter GFC 4000 (4×3 mm) The column was loaded with 10 µg of material and eluted with a 25 mM sodium phosphate 300 mM sodium chloride pH 7.0 mobile phase at a flow rate of 0.5 ml/min for 30 min. Data was acquired from 200-500 nm and 220 nm profiles were reported.

Monoclonal antibodies were formulated at 0.5 mg/ml in pH 5, 6, 7, and 8 buffers. The buffers contained 150 mM sodium chloride and 10 mM acetate, histidine, phosphate, and TRIS for pH 5, 6, 7, and 8 respectively. HP-SEC was used to characterize material purity at time zero and after one weak at 45° C. Stability results are summarized in Table 13 below. FIG. 18 shows time zero SEC profiles. The boxed labels in the figure define the approximate elution times of higher order aggregates (HOAs), oligomer, monomer, and clipped protein.

TABLE 13

Physical Stability data at time zero and after thermal stress (1 week 45 C.)

| mAb[1] | Cell line | Theoretical pI | Elution time (min) | T0 Pre Mon[2] Peak | Olig[3] | HOA[4] | Clip[5] | 1 week stress at 45 C. in pH 5, 6, 7, and 8 buffers Pre Mon[2] Peak | Inc in Olig[3] | Inc in HOA[4] | Inc in Clip[5] |
|---|---|---|---|---|---|---|---|---|---|---|---|
| AX114 | HEK293 | 7.6815 | 16.1 | no | <5% | No | no | na | no | no | no |
| AX132 | HEK293 | 7.6815 | 16.0 | no | <5% | No | no | na | no | no | 1% pH 8 |
| AX210 | HEK293 | 7.8225 | 16.1 | no | <5% | No | no | na | ≈2% | no | no |
| AX211 | HEK293 | 7.9447 | 16.1 | no | <5% | No | no | na | no | no | no |
| AX212 | HEK293 | 7.8223 | 16.2 | no | ≈25% | No | no | na | no | no | no |
| AX213 | HEK293 | 7.8231 | 16.1 | no | <5% | No | no | na | no | no | no |

[1]mAb: monoclonal antibody
[2]Mon: monomer
[3]Olig: Oligomer
[4]HOA: higher order aggregate
[5]Clip: Clipped protein

EXAMPLE 21

Crystal Coordinates

The coordinates for the crystal structures discussed in Example 10 are presented in Table 14 (full length PCSK9 and AX132 Fab).

TABLE 14

PCSK9 and AX132 Fab complex x-ray structure

| ATOM | 17 | CB | PRO | B | 155 | −82.132 | 20.346 | −24.263 | 1.00 | 87.08 | C |
|---|---|---|---|---|---|---|---|---|---|---|---|
| ATOM | 1 | N | SER | B | 153 | −87.150 | 14.839 | −25.924 | 1.00 | 107.36 | N |
| ATOM | 2 | CA | SER | B | 153 | −87.121 | 15.824 | −27.023 | 1.00 | 107.09 | C |
| ATOM | 3 | CB | SER | B | 153 | −88.455 | 16.570 | −27.109 | 1.00 | 107.02 | C |
| ATOM | 4 | OG | SER | B | 153 | −88.594 | 17.255 | −28.345 | 1.00 | 107.56 | O |
| ATOM | 5 | C | SER | B | 153 | −85.944 | 16.829 | −26.896 | 1.00 | 106.67 | C |
| ATOM | 6 | O | SER | B | 153 | −85.196 | 16.763 | −25.908 | 1.00 | 107.20 | O |
| ATOM | 7 | N | ILE | B | 154 | −85.791 | 17.752 | −27.900 | 1.00 | 98.66 | N |
| ATOM | 8 | CA | ILE | B | 154 | −84.757 | 18.804 | −27.957 | 1.00 | 97.20 | C |
| ATOM | 9 | CB | ILE | B | 154 | −84.874 | 19.708 | −29.237 | 1.00 | 97.44 | C |
| ATOM | 10 | CG1 | ILE | B | 154 | −84.778 | 18.907 | −30.560 | 1.00 | 97.90 | C |
| ATOM | 11 | CD1 | ILE | B | 154 | −83.348 | 18.623 | −31.113 | 1.00 | 99.30 | C |
| ATOM | 12 | CG2 | ILE | B | 154 | −83.924 | 20.925 | −29.210 | 1.00 | 97.05 | C |
| ATOM | 13 | C | ILE | B | 154 | −84.794 | 19.659 | −26.673 | 1.00 | 96.02 | C |
| ATOM | 14 | O | ILE | B | 154 | −85.832 | 20.274 | −26.366 | 1.00 | 96.01 | O |
| ATOM | 15 | N | PRO | B | 155 | −83.657 | 19.697 | −25.928 | 1.00 | 87.96 | N |
| ATOM | 16 | CA | PRO | B | 155 | −83.593 | 20.523 | −24.706 | 1.00 | 86.99 | C |
| ATOM | 18 | CG | PRO | B | 155 | −81.704 | 19.043 | −24.862 | 1.00 | 86.72 | C |
| ATOM | 19 | CD | PRO | B | 155 | −82.363 | 19.027 | −26.185 | 1.00 | 87.68 | C |
| ATOM | 20 | C | PRO | B | 155 | −83.939 | 22.001 | −24.985 | 1.00 | 85.91 | C |
| ATOM | 21 | O | PRO | B | 155 | −83.438 | 22.547 | −25.973 | 1.00 | 85.74 | O |
| ATOM | 22 | N | TRP | B | 156 | −84.796 | 22.642 | −24.145 | 1.00 | 79.85 | N |
| ATOM | 23 | CA | TRP | B | 156 | −85.226 | 24.051 | −24.327 | 1.00 | 79.03 | C |
| ATOM | 24 | CB | TRP | B | 156 | −85.929 | 24.634 | −23.078 | 1.00 | 78.53 | C |
| ATOM | 25 | CG | TRP | B | 156 | −85.005 | 25.173 | −22.022 | 1.00 | 77.29 | C |
| ATOM | 26 | CD1 | TRP | B | 156 | −84.573 | 24.522 | −20.904 | 1.00 | 77.25 | C |
| ATOM | 27 | NE1 | TRP | B | 156 | −83.715 | 25.325 | −20.186 | 1.00 | 76.73 | N |
| ATOM | 28 | CE2 | TRP | B | 156 | −83.578 | 26.525 | −20.835 | 1.00 | 76.79 | C |
| ATOM | 29 | CD2 | TRP | B | 156 | −84.383 | 26.469 | −21.995 | 1.00 | 77.04 | C |
| ATOM | 30 | CE3 | TRP | B | 156 | −84.414 | 27.588 | −22.849 | 1.00 | 77.32 | C |
| ATOM | 31 | CZ3 | TRP | B | 156 | −83.643 | 28.695 | −22.529 | 1.00 | 76.08 | C |
| ATOM | 32 | CH2 | TRP | B | 156 | −82.875 | 28.729 | −21.359 | 1.00 | 76.36 | C |
| ATOM | 33 | CZ2 | TRP | B | 156 | −82.833 | 27.660 | −20.494 | 1.00 | 76.64 | C |
| ATOM | 34 | C | TRP | B | 156 | −84.141 | 25.004 | −24.852 | 1.00 | 78.84 | C |
| ATOM | 35 | O | TRP | B | 156 | −84.399 | 25.797 | −25.755 | 1.00 | 78.45 | O |
| ATOM | 36 | N | ASN | B | 157 | −82.937 | 24.912 | −24.262 | 1.00 | 76.67 | N |
| ATOM | 37 | CA | ASN | B | 157 | −81.762 | 25.708 | −24.553 | 1.00 | 76.65 | C |
| ATOM | 38 | CB | ASN | B | 157 | −80.649 | 25.360 | −23.568 | 1.00 | 76.70 | C |
| ATOM | 39 | CG | ASN | B | 157 | −80.500 | 23.895 | −23.179 | 1.00 | 77.44 | C |
| ATOM | 40 | OD1 | ASN | B | 157 | −81.398 | 23.247 | −22.587 | 1.00 | 78.09 | O |

TABLE 14-continued

PCSK9 and AX132 Fab complex x-ray structure

| | | | | | | | | | | | |
|---|---|---|---|---|---|---|---|---|---|---|---|
| ATOM | 41 | ND2 | ASN | B | 157 | −79.332 | 23.336 | −23.494 | 1.00 | 78.70 | N |
| ATOM | 42 | C | ASN | B | 157 | −81.302 | 25.627 | −26.021 | 1.00 | 76.86 | C |
| ATOM | 43 | O | ASN | B | 157 | −80.858 | 26.632 | −26.591 | 1.00 | 76.92 | O |
| ATOM | 44 | N | LEU | B | 158 | −81.451 | 24.440 | −26.641 | 1.00 | 78.20 | N |
| ATOM | 45 | CA | LEU | B | 158 | −81.061 | 24.168 | −28.028 | 1.00 | 78.40 | C |
| ATOM | 46 | CB | LEU | B | 158 | −80.758 | 22.675 | −28.179 | 1.00 | 78.20 | C |
| ATOM | 47 | CG | LEU | B | 158 | −79.638 | 22.072 | −27.335 | 1.00 | 77.54 | C |
| ATOM | 48 | CD1 | LEU | B | 158 | −79.387 | 20.643 | −27.746 | 1.00 | 77.52 | C |
| ATOM | 49 | CD2 | LEU | B | 158 | −78.357 | 22.824 | −27.511 | 1.00 | 77.42 | C |
| ATOM | 50 | C | LEU | B | 158 | −82.081 | 24.636 | −29.115 | 1.00 | 78.95 | C |
| ATOM | 51 | O | LEU | B | 158 | −81.763 | 24.593 | −30.320 | 1.00 | 78.73 | O |
| ATOM | 52 | N | GLU | B | 159 | −83.291 | 25.099 | −28.677 | 1.00 | 80.20 | N |
| ATOM | 53 | CA | GLU | B | 159 | −84.392 | 25.571 | −29.528 | 1.00 | 80.74 | C |
| ATOM | 54 | CB | GLU | B | 159 | −85.654 | 25.870 | −28.689 | 1.00 | 80.85 | C |
| ATOM | 55 | CG | GLU | B | 159 | −86.337 | 24.617 | −28.128 | 1.00 | 83.98 | C |
| ATOM | 56 | CD | GLU | B | 159 | −87.623 | 24.729 | −27.301 | 1.00 | 87.83 | C |
| ATOM | 57 | OE1 | GLU | B | 159 | −88.207 | 25.840 | −27.214 | 1.00 | 89.05 | O |
| ATOM | 58 | OE2 | GLU | B | 159 | −88.049 | 23.686 | −26.740 | 1.00 | 88.45 | O |
| ATOM | 59 | C | GLU | B | 159 | −84.070 | 26.715 | −30.528 | 1.00 | 80.76 | C |
| ATOM | 60 | O | GLU | B | 159 | −84.777 | 26.852 | −31.529 | 1.00 | 80.51 | O |
| ATOM | 61 | N | ARG | B | 160 | −83.009 | 27.513 | −30.275 | 1.00 | 79.37 | N |
| ATOM | 62 | CA | ARG | B | 160 | −82.620 | 28.641 | −31.131 | 1.00 | 79.76 | C |
| ATOM | 63 | CB | ARG | B | 160 | −82.410 | 29.887 | −30.277 | 1.00 | 79.64 | C |
| ATOM | 64 | CG | ARG | B | 160 | −83.685 | 30.582 | −29.832 | 1.00 | 79.80 | C |
| ATOM | 65 | CD | ARG | B | 160 | −83.400 | 32.060 | −29.603 | 1.00 | 80.11 | C |
| ATOM | 66 | NE | ARG | B | 160 | −83.932 | 32.569 | −28.335 | 1.00 | 79.71 | N |
| ATOM | 67 | CZ | ARG | B | 160 | −85.105 | 33.176 | −28.210 | 1.00 | 79.38 | C |
| ATOM | 68 | NH1 | ARG | B | 160 | −85.894 | 33.338 | −29.269 | 1.00 | 80.19 | N |
| ATOM | 69 | NH2 | ARG | B | 160 | −85.506 | 33.617 | −27.031 | 1.00 | 78.06 | N |
| ATOM | 70 | C | ARG | B | 160 | −81.386 | 28.416 | −32.041 | 1.00 | 80.50 | C |
| ATOM | 71 | O | ARG | B | 160 | −80.926 | 29.378 | −32.691 | 1.00 | 80.44 | O |
| ATOM | 72 | N | ILE | B | 161 | −80.841 | 27.159 | −32.081 | 1.00 | 82.33 | N |
| ATOM | 73 | CA | ILE | B | 161 | −79.657 | 26.815 | −32.892 | 1.00 | 83.00 | C |
| ATOM | 74 | CB | ILE | B | 161 | −78.418 | 26.346 | −32.057 | 1.00 | 82.95 | C |
| ATOM | 75 | CG1 | ILE | B | 161 | −78.717 | 25.103 | −31.232 | 1.00 | 83.40 | C |
| ATOM | 76 | CD1 | ILE | B | 161 | −78.270 | 23.767 | −31.910 | 1.00 | 85.12 | C |
| ATOM | 77 | CG2 | ILE | B | 161 | −77.847 | 27.458 | −31.182 | 1.00 | 82.40 | C |
| ATOM | 78 | C | ILE | B | 161 | −79.984 | 25.903 | −34.106 | 1.00 | 83.49 | C |
| ATOM | 79 | O | ILE | B | 161 | −80.884 | 25.057 | −34.006 | 1.00 | 83.63 | O |
| ATOM | 80 | N | THR | B | 162 | −79.224 | 26.091 | −35.244 | 1.00 | 83.22 | N |
| ATOM | 81 | CA | THR | B | 162 | −79.316 | 25.413 | −36.559 | 1.00 | 83.35 | C |
| ATOM | 82 | CB | THR | B | 162 | −78.521 | 24.057 | −36.634 | 1.00 | 83.59 | C |
| ATOM | 83 | OG1 | THR | B | 162 | −77.332 | 24.237 | −37.432 | 1.00 | 83.88 | O |
| ATOM | 84 | CG2 | THR | B | 162 | −79.360 | 22.854 | −37.155 | 1.00 | 83.18 | C |
| ATOM | 85 | C | THR | B | 162 | −80.735 | 25.516 | −37.147 | 1.00 | 83.30 | C |
| ATOM | 86 | O | THR | B | 162 | −81.293 | 26.622 | −37.185 | 1.00 | 83.19 | O |
| ATOM | 87 | N | GLY | B | 176 | −70.723 | 20.546 | −35.205 | 1.00 | 140.14 | N |
| ATOM | 88 | CA | GLY | B | 176 | −69.466 | 20.083 | −35.782 | 1.00 | 140.14 | C |
| ATOM | 89 | C | GLY | B | 176 | −68.282 | 21.003 | −35.539 | 1.00 | 140.03 | C |
| ATOM | 90 | O | GLY | B | 176 | −68.462 | 22.201 | −35.295 | 1.00 | 140.10 | O |
| ATOM | 91 | N | GLY | B | 177 | −67.073 | 20.432 | −35.614 | 1.00 | 136.95 | N |
| ATOM | 92 | CA | GLY | B | 177 | −65.807 | 21.142 | −35.416 | 1.00 | 136.21 | C |
| ATOM | 93 | C | GLY | B | 177 | −64.711 | 20.729 | −36.389 | 1.00 | 135.59 | C |
| ATOM | 94 | O | GLY | B | 177 | −64.029 | 19.720 | −36.147 | 1.00 | 135.76 | O |
| ATOM | 95 | N | SER | B | 178 | −64.539 | 21.534 | −37.507 | 1.00 | 128.99 | N |
| ATOM | 96 | CA | SER | B | 178 | −63.569 | 21.359 | −38.622 | 1.00 | 127.64 | C |
| ATOM | 97 | CB | SER | B | 178 | −64.250 | 21.579 | −39.977 | 1.00 | 128.00 | C |
| ATOM | 98 | OG | SER | B | 178 | −64.514 | 22.945 | −40.265 | 1.00 | 128.21 | O |
| ATOM | 99 | C | SER | B | 178 | −62.324 | 22.258 | −38.493 | 1.00 | 126.31 | C |
| ATOM | 100 | O | SER | B | 178 | −62.346 | 23.420 | −38.931 | 1.00 | 126.19 | O |
| ATOM | 101 | N | LEU | B | 179 | −61.235 | 21.706 | −37.884 | 1.00 | 118.00 | N |
| ATOM | 102 | CA | LEU | B | 179 | −59.969 | 22.406 | −37.598 | 1.00 | 115.97 | C |
| ATOM | 103 | CB | LEU | B | 179 | −59.268 | 22.923 | −38.892 | 1.00 | 116.34 | C |
| ATOM | 104 | CG | LEU | B | 179 | −57.735 | 22.921 | −38.922 | 1.00 | 116.65 | C |
| ATOM | 105 | CD1 | LEU | B | 179 | −57.196 | 21.592 | −39.416 | 1.00 | 116.41 | C |
| ATOM | 106 | CD2 | LEU | B | 179 | −57.216 | 24.022 | −39.817 | 1.00 | 116.41 | C |
| ATOM | 107 | C | LEU | B | 179 | −60.259 | 23.551 | −36.573 | 1.00 | 114.12 | C |
| ATOM | 108 | O | LEU | B | 179 | −59.376 | 24.361 | −36.285 | 1.00 | 114.17 | O |
| ATOM | 109 | N | VAL | B | 180 | −61.512 | 23.591 | −36.026 | 1.00 | 105.44 | N |
| ATOM | 110 | CA | VAL | B | 180 | −61.996 | 24.548 | −35.027 | 1.00 | 102.74 | C |
| ATOM | 111 | CB | VAL | B | 180 | −63.488 | 24.952 | −35.144 | 1.00 | 102.92 | C |
| ATOM | 112 | CG1 | VAL | B | 180 | −63.808 | 26.126 | −34.229 | 1.00 | 102.10 | C |
| ATOM | 113 | CG2 | VAL | B | 180 | −63.860 | 25.286 | −36.568 | 1.00 | 103.04 | C |
| ATOM | 114 | C | VAL | B | 180 | −61.737 | 23.899 | −33.705 | 1.00 | 100.85 | C |
| ATOM | 115 | O | VAL | B | 180 | −62.422 | 22.940 | −33.302 | 1.00 | 100.51 | O |
| ATOM | 116 | N | GLU | B | 181 | −60.725 | 24.429 | −33.040 | 1.00 | 95.52 | N |
| ATOM | 117 | CA | GLU | B | 181 | −60.286 | 23.968 | −31.750 | 1.00 | 93.31 | C |
| ATOM | 118 | CB | GLU | B | 181 | −58.754 | 23.963 | −31.695 | 1.00 | 93.78 | C |

TABLE 14-continued

PCSK9 and AX132 Fab complex x-ray structure

| ATOM | 119 | CG | GLU | B | 181 | −58.163 | 22.856 | −30.839 | 1.00 | 95.42 | C |
|---|---|---|---|---|---|---|---|---|---|---|---|
| ATOM | 120 | CD | GLU | B | 181 | −58.611 | 21.438 | −31.161 | 1.00 | 97.54 | C |
| ATOM | 121 | OE1 | GLU | B | 181 | −59.571 | 20.963 | −30.510 | 1.00 | 98.37 | O |
| ATOM | 122 | OE2 | GLU | B | 181 | −58.003 | 20.801 | −32.054 | 1.00 | 98.34 | O |
| ATOM | 123 | C | GLU | B | 181 | −60.882 | 24.838 | −30.661 | 1.00 | 91.24 | C |
| ATOM | 124 | O | GLU | B | 181 | −60.742 | 26.058 | −30.691 | 1.00 | 90.90 | O |
| ATOM | 125 | N | VAL | B | 182 | −61.574 | 24.198 | −29.720 | 1.00 | 83.34 | N |
| ATOM | 126 | CA | VAL | B | 182 | −62.203 | 24.834 | −28.581 | 1.00 | 80.42 | C |
| ATOM | 127 | CB | VAL | B | 182 | −63.678 | 24.408 | −28.435 | 1.00 | 80.28 | C |
| ATOM | 128 | CG1 | VAL | B | 182 | −64.275 | 24.918 | −27.133 | 1.00 | 79.85 | C |
| ATOM | 129 | CG2 | VAL | B | 182 | −64.503 | 24.882 | −29.616 | 1.00 | 79.66 | C |
| ATOM | 130 | C | VAL | B | 182 | −61.385 | 24.448 | −27.363 | 1.00 | 78.88 | C |
| ATOM | 131 | O | VAL | B | 182 | −61.327 | 23.273 | −27.006 | 1.00 | 78.56 | O |
| ATOM | 132 | N | TYR | B | 183 | −60.732 | 25.424 | −26.744 | 1.00 | 75.90 | N |
| ATOM | 133 | CA | TYR | B | 183 | −59.945 | 25.203 | −25.541 | 1.00 | 74.25 | C |
| ATOM | 134 | CB | TYR | B | 183 | −58.703 | 26.075 | −25.548 | 1.00 | 74.20 | C |
| ATOM | 135 | CG | TYR | B | 183 | −57.561 | 25.512 | −26.366 | 1.00 | 75.11 | C |
| ATOM | 136 | CD1 | TYR | B | 183 | −56.510 | 24.831 | −25.756 | 1.00 | 75.82 | C |
| ATOM | 137 | CE1 | TYR | B | 183 | −55.436 | 24.342 | −26.501 | 1.00 | 76.26 | C |
| ATOM | 138 | CZ | TYR | B | 183 | −55.406 | 24.533 | −27.875 | 1.00 | 76.26 | C |
| ATOM | 139 | OH | TYR | B | 183 | −54.348 | 24.061 | −28.624 | 1.00 | 77.47 | O |
| ATOM | 140 | CE2 | TYR | B | 183 | −56.453 | 25.187 | −28.502 | 1.00 | 75.43 | C |
| ATOM | 141 | CD2 | TYR | B | 183 | −57.512 | 25.685 | −27.746 | 1.00 | 75.11 | C |
| ATOM | 142 | C | TYR | B | 183 | −60.805 | 25.516 | −24.330 | 1.00 | 72.94 | C |
| ATOM | 143 | O | TYR | B | 183 | −61.482 | 26.538 | −24.300 | 1.00 | 73.00 | O |
| ATOM | 144 | N | LEU | B | 184 | −60.802 | 24.650 | −23.341 | 1.00 | 68.66 | N |
| ATOM | 145 | CA | LEU | B | 184 | −61.598 | 24.882 | −22.156 | 1.00 | 67.26 | C |
| ATOM | 146 | CB | LEU | B | 184 | −62.680 | 23.801 | −22.077 | 1.00 | 67.15 | C |
| ATOM | 147 | CG | LEU | B | 184 | −63.354 | 23.530 | −20.744 | 1.00 | 67.01 | C |
| ATOM | 148 | CD1 | LEU | B | 184 | −64.242 | 24.673 | −20.322 | 1.00 | 67.88 | C |
| ATOM | 149 | CD2 | LEU | B | 184 | −64.171 | 22.290 | −20.831 | 1.00 | 66.74 | C |
| ATOM | 150 | C | LEU | B | 184 | −60.725 | 24.918 | −20.906 | 1.00 | 66.66 | C |
| ATOM | 151 | O | LEU | B | 184 | −60.114 | 23.913 | −20.563 | 1.00 | 66.73 | O |
| ATOM | 152 | N | LEU | B | 185 | −60.651 | 26.071 | −20.240 | 1.00 | 65.50 | N |
| ATOM | 153 | CA | LEU | B | 185 | −59.894 | 26.218 | −19.007 | 1.00 | 65.04 | C |
| ATOM | 154 | CB | LEU | B | 185 | −59.206 | 27.584 | −18.911 | 1.00 | 64.85 | C |
| ATOM | 155 | CG | LEU | B | 185 | −57.923 | 27.771 | −19.677 | 1.00 | 63.72 | C |
| ATOM | 156 | CD1 | LEU | B | 185 | −58.192 | 28.459 | −20.951 | 1.00 | 62.36 | C |
| ATOM | 157 | CD2 | LEU | B | 185 | −56.975 | 28.647 | −18.914 | 1.00 | 62.83 | C |
| ATOM | 158 | C | LEU | B | 185 | −60.943 | 26.118 | −17.933 | 1.00 | 65.33 | C |
| ATOM | 159 | O | LEU | B | 185 | −61.788 | 27.002 | −17.826 | 1.00 | 65.52 | O |
| ATOM | 160 | N | ASP | B | 186 | −60.923 | 25.033 | −17.162 | 1.00 | 69.66 | N |
| ATOM | 161 | CA | ASP | B | 186 | −61.877 | 24.787 | −16.096 | 1.00 | 69.85 | C |
| ATOM | 162 | CB | ASP | B | 186 | −63.224 | 24.309 | −16.694 | 1.00 | 70.50 | C |
| ATOM | 163 | CG | ASP | B | 186 | −64.456 | 24.744 | −15.888 | 1.00 | 73.29 | C |
| ATOM | 164 | OD1 | ASP | B | 186 | −65.209 | 23.853 | −15.411 | 1.00 | 74.50 | O |
| ATOM | 165 | OD2 | ASP | B | 186 | −64.666 | 25.982 | −15.722 | 1.00 | 77.37 | O |
| ATOM | 166 | C | ASP | B | 186 | −61.306 | 23.784 | −15.098 | 1.00 | 69.28 | C |
| ATOM | 167 | O | ASP | B | 186 | −60.110 | 23.791 | −14.810 | 1.00 | 68.99 | O |
| ATOM | 168 | N | THR | B | 187 | −62.175 | 22.937 | −14.559 | 1.00 | 69.19 | N |
| ATOM | 169 | CA | THR | B | 187 | −61.860 | 21.885 | −13.606 | 1.00 | 68.93 | C |
| ATOM | 170 | CB | THR | B | 187 | −63.157 | 21.450 | −12.844 | 1.00 | 68.58 | C |
| ATOM | 171 | OG1 | THR | B | 187 | −64.084 | 20.833 | −13.739 | 1.00 | 67.31 | O |
| ATOM | 172 | CG2 | THR | B | 187 | −63.827 | 22.585 | −12.090 | 1.00 | 68.14 | C |
| ATOM | 173 | C | THR | B | 187 | −61.353 | 20.698 | −14.426 | 1.00 | 69.35 | C |
| ATOM | 174 | O | THR | B | 187 | −61.200 | 20.799 | −15.658 | 1.00 | 69.24 | O |
| ATOM | 175 | N | SER | B | 188 | −61.133 | 19.564 | −13.747 | 1.00 | 72.98 | N |
| ATOM | 176 | CA | SER | B | 188 | −60.778 | 18.312 | −14.397 | 1.00 | 73.83 | C |
| ATOM | 177 | CB | SER | B | 188 | −60.395 | 17.274 | −13.348 | 1.00 | 73.82 | C |
| ATOM | 178 | OG | SER | B | 188 | −61.266 | 17.343 | −12.228 | 1.00 | 75.61 | O |
| ATOM | 179 | C | SER | B | 188 | −62.075 | 17.877 | −15.146 | 1.00 | 73.93 | C |
| ATOM | 180 | O | SER | B | 188 | −63.155 | 18.377 | −14.828 | 1.00 | 74.16 | O |
| ATOM | 181 | N | ILE | B | 189 | −61.974 | 17.023 | −16.166 | 1.00 | 75.20 | N |
| ATOM | 182 | CA | ILE | B | 189 | −63.160 | 16.595 | −16.918 | 1.00 | 75.33 | C |
| ATOM | 183 | CB | ILE | B | 189 | −63.315 | 17.325 | −18.303 | 1.00 | 75.17 | C |
| ATOM | 184 | CG1 | ILE | B | 189 | −62.291 | 16.857 | −19.328 | 1.00 | 74.91 | C |
| ATOM | 185 | CD1 | ILE | B | 189 | −62.849 | 16.079 | −20.326 | 1.00 | 74.99 | C |
| ATOM | 186 | CG2 | ILE | B | 189 | −63.244 | 18.842 | −18.208 | 1.00 | 74.89 | C |
| ATOM | 187 | C | ILE | B | 189 | −63.173 | 15.060 | −17.055 | 1.00 | 75.92 | C |
| ATOM | 188 | O | ILE | B | 189 | −62.105 | 14.431 | −17.112 | 1.00 | 76.37 | O |
| ATOM | 189 | N | GLN | B | 190 | −64.377 | 14.464 | −17.115 | 1.00 | 78.71 | N |
| ATOM | 190 | CA | GLN | B | 190 | −64.573 | 13.031 | −17.324 | 1.00 | 78.81 | C |
| ATOM | 191 | CB | GLN | B | 190 | −65.935 | 12.599 | −16.719 | 1.00 | 79.20 | C |
| ATOM | 192 | CG | GLN | B | 190 | −66.291 | 11.106 | −16.838 | 1.00 | 80.98 | C |
| ATOM | 193 | CD | GLN | B | 190 | −65.218 | 10.268 | −16.184 | 1.00 | 84.40 | C |
| ATOM | 194 | OE1 | GLN | B | 190 | −64.398 | 9.600 | −16.863 | 1.00 | 85.93 | O |
| ATOM | 195 | NE2 | GLN | B | 190 | −65.178 | 10.319 | −14.838 | 1.00 | 84.61 | N |
| ATOM | 196 | C | GLN | B | 190 | −64.528 | 12.852 | −18.868 | 1.00 | 78.44 | C |

TABLE 14-continued

PCSK9 and AX132 Fab complex x-ray structure

| ATOM | 197 | O | GLN | B | 190 | −65.557 | 12.986 | −19.530 | 1.00 | 78.67 | O |
|---|---|---|---|---|---|---|---|---|---|---|---|
| ATOM | 198 | N | SER | B | 191 | −63.335 | 12.619 | −19.437 | 1.00 | 76.26 | N |
| ATOM | 199 | CA | SER | B | 191 | −63.125 | 12.472 | −20.886 | 1.00 | 76.40 | C |
| ATOM | 200 | CB | SER | B | 191 | −61.641 | 12.584 | −21.242 | 1.00 | 76.30 | C |
| ATOM | 201 | OG | SER | B | 191 | −60.774 | 11.931 | −20.321 | 1.00 | 76.89 | O |
| ATOM | 202 | C | SER | B | 191 | −63.742 | 11.221 | −21.507 | 1.00 | 76.56 | C |
| ATOM | 203 | O | SER | B | 191 | −63.870 | 11.147 | −22.735 | 1.00 | 76.51 | O |
| ATOM | 204 | N | ASP | B | 192 | −64.123 | 10.249 | −20.657 | 1.00 | 76.51 | N |
| ATOM | 205 | CA | ASP | B | 192 | −64.731 | 8.972 | −21.021 | 1.00 | 77.11 | C |
| ATOM | 206 | CB | ASP | B | 192 | −64.437 | 7.919 | −19.946 | 1.00 | 77.96 | C |
| ATOM | 207 | CG | ASP | B | 192 | −62.956 | 7.651 | −19.710 | 1.00 | 81.51 | C |
| ATOM | 208 | OD1 | ASP | B | 192 | −62.098 | 8.236 | −20.470 | 1.00 | 85.26 | O |
| ATOM | 209 | OD2 | ASP | B | 192 | −62.633 | 6.861 | −18.764 | 1.00 | 84.42 | O |
| ATOM | 210 | C | ASP | B | 192 | −66.228 | 9.066 | −21.249 | 1.00 | 76.46 | C |
| ATOM | 211 | O | ASP | B | 192 | −66.799 | 8.171 | −21.881 | 1.00 | 76.47 | O |
| ATOM | 212 | N | HIS | B | 193 | −66.868 | 10.135 | −20.742 | 1.00 | 71.48 | N |
| ATOM | 213 | CA | HIS | B | 193 | −68.302 | 10.347 | −20.896 | 1.00 | 70.66 | C |
| ATOM | 214 | CB | HIS | B | 193 | −68.760 | 11.679 | −20.308 | 1.00 | 69.92 | C |
| ATOM | 215 | CG | HIS | B | 193 | −70.227 | 11.703 | −20.063 | 1.00 | 67.58 | C |
| ATOM | 216 | ND1 | HIS | B | 193 | −70.738 | 11.592 | −18.798 | 1.00 | 65.49 | N |
| ATOM | 217 | CE1 | HIS | B | 193 | −72.055 | 11.611 | −18.938 | 1.00 | 65.26 | C |
| ATOM | 218 | NE2 | HIS | B | 193 | −72.408 | 11.730 | −20.211 | 1.00 | 65.88 | N |
| ATOM | 219 | CD2 | HIS | B | 193 | −71.250 | 11.777 | −20.942 | 1.00 | 66.29 | C |
| ATOM | 220 | C | HIS | B | 193 | −68.702 | 10.216 | −22.354 | 1.00 | 71.00 | C |
| ATOM | 221 | O | HIS | B | 193 | −68.100 | 10.843 | −23.217 | 1.00 | 70.97 | O |
| ATOM | 222 | N | ARG | B | 194 | −69.698 | 9.364 | −22.618 | 1.00 | 72.56 | N |
| ATOM | 223 | CA | ARG | B | 194 | −70.195 | 9.035 | −23.949 | 1.00 | 72.97 | C |
| ATOM | 224 | CB | ARG | B | 194 | −71.371 | 8.065 | −23.872 | 1.00 | 73.07 | C |
| ATOM | 225 | CG | ARG | B | 194 | −71.020 | 6.680 | −23.334 | 1.00 | 71.88 | C |
| ATOM | 226 | CD | ARG | B | 194 | −70.534 | 5.692 | −24.386 | 1.00 | 70.41 | C |
| ATOM | 227 | NE | ARG | B | 194 | −71.239 | 5.796 | −25.672 | 1.00 | 69.15 | N |
| ATOM | 228 | CZ | ARG | B | 194 | −72.366 | 5.156 | −25.988 | 1.00 | 67.53 | C |
| ATOM | 229 | NH1 | ARG | B | 194 | −72.916 | 5.324 | −27.182 | 1.00 | 66.06 | N |
| ATOM | 230 | NH2 | ARG | B | 194 | −72.952 | 4.350 | −25.110 | 1.00 | 66.67 | N |
| ATOM | 231 | C | ARG | B | 194 | −70.530 | 10.244 | −24.783 | 1.00 | 73.51 | C |
| ATOM | 232 | O | ARG | B | 194 | −70.356 | 10.201 | −25.999 | 1.00 | 73.71 | O |
| ATOM | 233 | N | GLU | B | 195 | −70.984 | 11.321 | −24.140 | 1.00 | 74.05 | N |
| ATOM | 234 | CA | GLU | B | 195 | −71.321 | 12.577 | −24.796 | 1.00 | 74.65 | C |
| ATOM | 235 | CB | GLU | B | 195 | −71.857 | 13.566 | −23.770 | 1.00 | 74.69 | C |
| ATOM | 236 | CG | GLU | B | 195 | −73.312 | 13.345 | −23.447 | 1.00 | 75.96 | C |
| ATOM | 237 | CD | GLU | B | 195 | −74.199 | 14.009 | −24.471 | 1.00 | 78.05 | C |
| ATOM | 238 | OE1 | GLU | B | 195 | −74.682 | 13.293 | −25.377 | 1.00 | 78.92 | O |
| ATOM | 239 | OE2 | GLU | B | 195 | −74.397 | 15.244 | −24.381 | 1.00 | 79.60 | O |
| ATOM | 240 | C | GLU | B | 195 | −70.102 | 13.201 | −25.436 | 1.00 | 74.65 | C |
| ATOM | 241 | O | GLU | B | 195 | −70.190 | 13.725 | −26.548 | 1.00 | 74.72 | O |
| ATOM | 242 | N | ILE | B | 196 | −68.967 | 13.149 | −24.730 | 1.00 | 73.62 | N |
| ATOM | 243 | CA | ILE | B | 196 | −67.730 | 13.773 | −25.156 | 1.00 | 73.67 | C |
| ATOM | 244 | CB | ILE | B | 196 | −67.386 | 14.919 | −24.181 | 1.00 | 73.39 | C |
| ATOM | 245 | CG1 | ILE | B | 196 | −67.087 | 14.413 | −22.746 | 1.00 | 72.89 | C |
| ATOM | 246 | CD1 | ILE | B | 196 | −66.340 | 15.398 | −21.869 | 1.00 | 71.68 | C |
| ATOM | 247 | CG2 | ILE | B | 196 | −68.451 | 16.011 | −24.223 | 1.00 | 73.36 | C |
| ATOM | 248 | C | ILE | B | 196 | −66.528 | 12.877 | −25.455 | 1.00 | 74.30 | C |
| ATOM | 249 | O | ILE | B | 196 | −65.459 | 13.403 | −25.759 | 1.00 | 74.46 | O |
| ATOM | 250 | N | GLU | B | 197 | −66.671 | 11.556 | −25.367 | 1.00 | 77.64 | N |
| ATOM | 251 | CA | GLU | B | 197 | −65.571 | 10.634 | −25.623 | 1.00 | 78.11 | C |
| ATOM | 252 | CB | GLU | B | 197 | −66.039 | 9.218 | −25.284 | 1.00 | 78.29 | C |
| ATOM | 253 | CG | GLU | B | 197 | −65.094 | 8.094 | −25.675 | 1.00 | 80.67 | C |
| ATOM | 254 | CD | GLU | B | 197 | −65.213 | 7.595 | −27.109 | 1.00 | 84.14 | C |
| ATOM | 255 | OE1 | GLU | B | 197 | −64.154 | 7.241 | −27.691 | 1.00 | 85.48 | O |
| ATOM | 256 | OE2 | GLU | B | 197 | −66.352 | 7.566 | −27.652 | 1.00 | 84.38 | O |
| ATOM | 257 | C | GLU | B | 197 | −65.078 | 10.775 | −27.088 | 1.00 | 78.33 | C |
| ATOM | 258 | O | GLU | B | 197 | −65.889 | 10.888 | −28.006 | 1.00 | 77.70 | O |
| ATOM | 259 | N | GLY | B | 198 | −63.760 | 10.805 | −27.279 | 1.00 | 79.97 | N |
| ATOM | 260 | CA | GLY | B | 198 | −63.155 | 10.931 | −28.601 | 1.00 | 80.78 | C |
| ATOM | 261 | C | GLY | B | 198 | −63.125 | 12.335 | −29.184 | 1.00 | 81.70 | C |
| ATOM | 262 | O | GLY | B | 198 | −62.354 | 12.594 | −30.119 | 1.00 | 81.82 | O |
| ATOM | 263 | N | ARG | B | 199 | −63.974 | 13.254 | −28.657 | 1.00 | 82.07 | N |
| ATOM | 264 | CA | ARG | B | 199 | −64.025 | 14.643 | −29.107 | 1.00 | 82.71 | C |
| ATOM | 265 | CB | ARG | B | 199 | −65.478 | 15.135 | −29.363 | 1.00 | 83.22 | C |
| ATOM | 266 | CG | ARG | B | 199 | −66.383 | 14.288 | −30.315 | 1.00 | 85.09 | C |
| ATOM | 267 | CD | ARG | B | 199 | −65.757 | 13.859 | −31.646 | 1.00 | 88.67 | C |
| ATOM | 268 | NE | ARG | B | 199 | −65.336 | 15.001 | −32.478 | 1.00 | 93.40 | N |
| ATOM | 269 | CZ | ARG | B | 199 | −64.332 | 14.985 | −33.365 | 1.00 | 95.58 | C |
| ATOM | 270 | NH1 | ARG | B | 199 | −63.613 | 13.880 | −33.552 | 1.00 | 96.91 | N |
| ATOM | 271 | NH2 | ARG | B | 199 | −64.033 | 16.080 | −34.059 | 1.00 | 96.23 | N |
| ATOM | 272 | C | ARG | B | 199 | −63.255 | 15.546 | −28.128 | 1.00 | 82.57 | C |
| ATOM | 273 | O | ARG | B | 199 | −62.553 | 16.450 | −28.562 | 1.00 | 82.54 | O |
| ATOM | 274 | N | VAL | B | 200 | −63.346 | 15.278 | −26.823 | 1.00 | 81.88 | N |

TABLE 14-continued

PCSK9 and AX132 Fab complex x-ray structure

| ATOM | 275 | CA  | VAL | B | 200 | −62.645 | 16.074 | −25.811 | 1.00 | 82.39 | C |
| ATOM | 276 | CB  | VAL | B | 200 | −63.532 | 16.470 | −24.599 | 1.00 | 82.30 | C |
| ATOM | 277 | CG1 | VAL | B | 200 | −62.754 | 17.342 | −23.624 | 1.00 | 82.32 | C |
| ATOM | 278 | CG2 | VAL | B | 200 | −64.785 | 17.208 | −25.063 | 1.00 | 82.80 | C |
| ATOM | 279 | C   | VAL | B | 200 | −61.318 | 15.438 | −25.401 | 1.00 | 82.80 | C |
| ATOM | 280 | O   | VAL | B | 200 | −61.308 | 14.351 | −24.833 | 1.00 | 83.26 | O |
| ATOM | 281 | N   | MET | B | 201 | −60.210 | 16.138 | −25.687 | 1.00 | 81.97 | N |
| ATOM | 282 | CA  | MET | B | 201 | −58.824 | 15.754 | −25.428 | 1.00 | 82.08 | C |
| ATOM | 283 | CB  | MET | B | 201 | −57.973 | 16.215 | −26.633 | 1.00 | 82.67 | C |
| ATOM | 284 | CG  | MET | B | 201 | −56.563 | 15.650 | −26.664 | 1.00 | 86.68 | C |
| ATOM | 285 | SD  | MET | B | 201 | −55.285 | 16.848 | −26.166 | 1.00 | 94.50 | S |
| ATOM | 286 | CE  | MET | B | 201 | −53.765 | 15.772 | −26.202 | 1.00 | 93.41 | C |
| ATOM | 287 | C   | MET | B | 201 | −58.299 | 16.402 | −24.139 | 1.00 | 81.18 | C |
| ATOM | 288 | O   | MET | B | 201 | −58.375 | 17.613 | −24.004 | 1.00 | 81.66 | O |
| ATOM | 289 | N   | VAL | B | 202 | −57.742 | 15.619 | −23.207 | 1.00 | 76.40 | N |
| ATOM | 290 | CA  | VAL | B | 202 | −57.201 | 16.193 | −21.968 | 1.00 | 75.21 | C |
| ATOM | 291 | CB  | VAL | B | 202 | −57.488 | 15.305 | −20.727 | 1.00 | 74.80 | C |
| ATOM | 292 | CG1 | VAL | B | 202 | −56.634 | 15.704 | −19.538 | 1.00 | 74.05 | C |
| ATOM | 293 | CG2 | VAL | B | 202 | −58.961 | 15.338 | −20.355 | 1.00 | 74.22 | C |
| ATOM | 294 | C   | VAL | B | 202 | −55.714 | 16.527 | −22.138 | 1.00 | 74.85 | C |
| ATOM | 295 | O   | VAL | B | 202 | −54.922 | 15.636 | −22.431 | 1.00 | 74.77 | O |
| ATOM | 296 | N   | THR | B | 203 | −55.341 | 17.804 | −21.957 | 1.00 | 76.16 | N |
| ATOM | 297 | CA  | THR | B | 203 | −53.939 | 18.230 | −22.074 | 1.00 | 75.76 | C |
| ATOM | 298 | CB  | THR | B | 203 | −53.791 | 19.707 | −22.484 | 1.00 | 75.68 | C |
| ATOM | 299 | OG1 | THR | B | 203 | −54.117 | 20.556 | −21.381 | 1.00 | 75.47 | O |
| ATOM | 300 | CG2 | THR | B | 203 | −54.603 | 20.071 | −23.730 | 1.00 | 75.36 | C |
| ATOM | 301 | C   | THR | B | 203 | −53.191 | 17.904 | −20.784 | 1.00 | 75.63 | C |
| ATOM | 302 | O   | THR | B | 203 | −53.823 | 17.586 | −19.767 | 1.00 | 75.46 | O |
| ATOM | 303 | N   | ASP | B | 204 | −51.847 | 17.984 | −20.823 | 1.00 | 77.72 | N |
| ATOM | 304 | CA  | ASP | B | 204 | −51.004 | 17.699 | −19.657 | 1.00 | 77.96 | C |
| ATOM | 305 | CB  | ASP | B | 204 | −49.553 | 17.422 | −20.106 | 1.00 | 77.97 | C |
| ATOM | 306 | C   | ASP | B | 204 | −51.035 | 18.862 | −18.648 | 1.00 | 78.07 | C |
| ATOM | 307 | O   | ASP | B | 204 | −50.476 | 18.734 | −17.551 | 1.00 | 78.14 | O |
| ATOM | 308 | N   | PHE | B | 205 | −51.681 | 20.000 | −19.026 | 1.00 | 77.35 | N |
| ATOM | 309 | CA  | PHE | B | 205 | −51.773 | 21.198 | −18.201 | 1.00 | 77.05 | C |
| ATOM | 310 | CB  | PHE | B | 205 | −52.185 | 22.435 | −19.014 | 1.00 | 76.92 | C |
| ATOM | 311 | CG  | PHE | B | 205 | −52.052 | 23.686 | −18.184 | 1.00 | 76.42 | C |
| ATOM | 312 | CD1 | PHE | B | 205 | −50.846 | 24.370 | −18.120 | 1.00 | 76.04 | C |
| ATOM | 313 | CE1 | PHE | B | 205 | −50.711 | 25.509 | −17.322 | 1.00 | 76.41 | C |
| ATOM | 314 | CZ  | PHE | B | 205 | −51.770 | 25.942 | −16.555 | 1.00 | 76.80 | C |
| ATOM | 315 | CE2 | PHE | B | 205 | −52.975 | 25.265 | −16.595 | 1.00 | 76.24 | C |
| ATOM | 316 | CD2 | PHE | B | 205 | −53.117 | 24.147 | −17.414 | 1.00 | 76.25 | C |
| ATOM | 317 | C   | PHE | B | 205 | −52.658 | 21.061 | −16.999 | 1.00 | 77.20 | C |
| ATOM | 318 | O   | PHE | B | 205 | −53.790 | 20.576 | −17.103 | 1.00 | 77.05 | O |
| ATOM | 319 | N   | GLU | B | 206 | −52.138 | 21.560 | −15.861 | 1.00 | 78.14 | N |
| ATOM | 320 | CA  | GLU | B | 206 | −52.770 | 21.615 | −14.550 | 1.00 | 78.71 | C |
| ATOM | 321 | CB  | GLU | B | 206 | −52.774 | 20.246 | −13.895 | 1.00 | 78.73 | C |
| ATOM | 322 | CG  | GLU | B | 206 | −53.559 | 20.204 | −12.606 | 1.00 | 80.94 | C |
| ATOM | 323 | CD  | GLU | B | 206 | −53.553 | 18.848 | −11.930 | 1.00 | 83.15 | C |
| ATOM | 324 | OE1 | GLU | B | 206 | −54.647 | 18.256 | −11.754 | 1.00 | 83.16 | O |
| ATOM | 325 | OE2 | GLU | B | 206 | −52.446 | 18.379 | −11.573 | 1.00 | 85.09 | O |
| ATOM | 326 | C   | GLU | B | 206 | −52.023 | 22.608 | −13.673 | 1.00 | 78.91 | C |
| ATOM | 327 | O   | GLU | B | 206 | −50.796 | 22.571 | −13.591 | 1.00 | 78.97 | O |
| ATOM | 328 | N   | ASN | B | 207 | −52.771 | 23.509 | −13.038 | 1.00 | 79.45 | N |
| ATOM | 329 | CA  | ASN | B | 207 | −52.290 | 24.546 | −12.123 | 1.00 | 79.62 | C |
| ATOM | 330 | CB  | ASN | B | 207 | −51.621 | 25.721 | −12.860 | 1.00 | 79.53 | C |
| ATOM | 331 | CG  | ASN | B | 207 | −50.999 | 26.739 | −11.913 | 1.00 | 79.76 | C |
| ATOM | 332 | OD1 | ASN | B | 207 | −51.654 | 27.303 | −11.010 | 1.00 | 81.14 | O |
| ATOM | 333 | ND2 | ASN | B | 207 | −49.712 | 27.006 | −12.090 | 1.00 | 79.96 | N |
| ATOM | 334 | C   | ASN | B | 207 | −53.491 | 25.008 | −11.308 | 1.00 | 79.67 | C |
| ATOM | 335 | O   | ASN | B | 207 | −54.229 | 25.903 | −11.720 | 1.00 | 79.86 | O |
| ATOM | 336 | N   | VAL | B | 208 | −53.708 | 24.368 | −10.169 | 1.00 | 77.92 | N |
| ATOM | 337 | CA  | VAL | B | 208 | −54.844 | 24.685 | −9.309  | 1.00 | 78.49 | C |
| ATOM | 338 | CB  | VAL | B | 208 | −55.932 | 23.555 | −9.333  | 1.00 | 78.44 | C |
| ATOM | 339 | CG1 | VAL | B | 208 | −56.307 | 23.167 | −10.757 | 1.00 | 78.06 | C |
| ATOM | 340 | CG2 | VAL | B | 208 | −55.512 | 22.320 | −8.537  | 1.00 | 78.22 | C |
| ATOM | 341 | C   | VAL | B | 208 | −54.378 | 25.014 | −7.893  | 1.00 | 79.11 | C |
| ATOM | 342 | O   | VAL | B | 208 | −53.314 | 24.559 | −7.507  | 1.00 | 79.41 | O |
| ATOM | 343 | N   | PRO | B | 209 | −55.135 | 25.755 | −7.070  | 1.00 | 81.83 | N |
| ATOM | 344 | CA  | PRO | B | 209 | −54.683 | 25.979 | −5.690  | 1.00 | 82.62 | C |
| ATOM | 345 | CB  | PRO | B | 209 | −55.588 | 27.115 | −5.195  | 1.00 | 82.43 | C |
| ATOM | 346 | CG  | PRO | B | 209 | −56.400 | 27.543 | −6.378  | 1.00 | 82.07 | C |
| ATOM | 347 | CD  | PRO | B | 209 | −56.440 | 26.399 | −7.306  | 1.00 | 81.97 | C |
| ATOM | 348 | C   | PRO | B | 209 | −54.901 | 24.721 | −4.848  | 1.00 | 83.65 | C |
| ATOM | 349 | O   | PRO | B | 209 | −55.779 | 23.915 | −5.171  | 1.00 | 83.64 | O |
| ATOM | 350 | N   | GLU | B | 210 | −54.111 | 24.546 | −3.768  | 1.00 | 88.20 | N |
| ATOM | 351 | CA  | GLU | B | 210 | −54.277 | 23.383 | −2.889  | 1.00 | 89.74 | C |
| ATOM | 352 | CB  | GLU | B | 210 | −53.256 | 23.381 | −1.729  | 1.00 | 89.55 | C |

TABLE 14-continued

PCSK9 and AX132 Fab complex x-ray structure

| ATOM | 353 | C | GLU | B | 210 | −55.719 | 23.435 | −2.380 | 1.00 | 90.57 | C |
|---|---|---|---|---|---|---|---|---|---|---|---|
| ATOM | 354 | O | GLU | B | 210 | −56.228 | 24.532 | −2.087 | 1.00 | 90.41 | O |
| ATOM | 355 | N | GLU | B | 211 | −56.397 | 22.265 | −2.362 | 1.00 | 94.51 | N |
| ATOM | 356 | CA | GLU | B | 211 | −57.792 | 22.170 | −1.924 | 1.00 | 95.89 | C |
| ATOM | 357 | CB | GLU | B | 211 | −58.384 | 20.760 | −2.085 | 1.00 | 95.83 | C |
| ATOM | 358 | CG | GLU | B | 211 | −59.166 | 20.582 | −3.374 | 1.00 | 96.71 | C |
| ATOM | 359 | CD | GLU | B | 211 | −58.341 | 20.326 | −4.626 | 1.00 | 98.31 | C |
| ATOM | 360 | OE1 | GLU | B | 211 | −57.101 | 20.520 | −4.597 | 1.00 | 99.53 | O |
| ATOM | 361 | OE2 | GLU | B | 211 | −58.943 | 19.930 | −5.651 | 1.00 | 98.49 | O |
| ATOM | 362 | C | GLU | B | 211 | −57.994 | 22.716 | −0.527 | 1.00 | 96.75 | C |
| ATOM | 363 | O | GLU | B | 211 | −57.235 | 22.401 | 0.402 | 1.00 | 96.76 | O |
| ATOM | 364 | N | ASP | B | 212 | −59.002 | 23.594 | −0.403 | 1.00 | 100.07 | N |
| ATOM | 365 | CA | ASP | B | 212 | −59.353 | 24.245 | 0.855 | 1.00 | 100.92 | C |
| ATOM | 366 | CB | ASP | B | 212 | −59.966 | 25.636 | 0.574 | 1.00 | 100.87 | C |
| ATOM | 367 | C | ASP | B | 212 | −60.273 | 23.321 | 1.699 | 1.00 | 101.36 | C |
| ATOM | 368 | O | ASP | B | 212 | −59.990 | 22.121 | 1.877 | 1.00 | 101.83 | O |
| ATOM | 369 | N | ALA | B | 220 | −64.416 | 12.642 | −5.714 | 1.00 | 107.90 | N |
| ATOM | 370 | CA | ALA | B | 220 | −63.510 | 12.432 | −6.856 | 1.00 | 108.17 | C |
| ATOM | 371 | CB | ALA | B | 220 | −62.875 | 11.044 | −6.803 | 1.00 | 108.18 | C |
| ATOM | 372 | C | ALA | B | 220 | −64.175 | 12.680 | −8.228 | 1.00 | 107.99 | C |
| ATOM | 373 | O | ALA | B | 220 | −63.526 | 13.212 | −9.133 | 1.00 | 108.10 | O |
| ATOM | 374 | N | SER | B | 221 | −65.463 | 12.279 | −8.380 | 1.00 | 105.36 | N |
| ATOM | 375 | CA | SER | B | 221 | −66.286 | 12.492 | −9.588 | 1.00 | 104.82 | C |
| ATOM | 376 | CB | SER | B | 221 | −66.943 | 11.200 | −10.083 | 1.00 | 104.98 | C |
| ATOM | 377 | OG | SER | B | 221 | −66.303 | 10.735 | −11.264 | 1.00 | 106.07 | O |
| ATOM | 378 | C | SER | B | 221 | −67.299 | 13.640 | −9.308 | 1.00 | 103.94 | C |
| ATOM | 379 | O | SER | B | 221 | −68.445 | 13.644 | −9.772 | 1.00 | 104.03 | O |
| ATOM | 380 | N | LYS | B | 222 | −66.813 | 14.603 | −8.502 | 1.00 | 97.73 | N |
| ATOM | 381 | CA | LYS | B | 222 | −67.413 | 15.840 | −8.056 | 1.00 | 96.15 | C |
| ATOM | 382 | CB | LYS | B | 222 | −67.589 | 15.848 | −6.533 | 1.00 | 96.42 | C |
| ATOM | 383 | CG | LYS | B | 222 | −68.380 | 17.045 | −5.993 | 1.00 | 97.85 | C |
| ATOM | 384 | CD | LYS | B | 222 | −69.836 | 17.113 | −6.522 | 1.00 | 100.51 | C |
| ATOM | 385 | CE | LYS | B | 222 | −70.544 | 18.401 | −6.165 | 1.00 | 101.09 | C |
| ATOM | 386 | NZ | LYS | B | 222 | −71.729 | 18.637 | −7.034 | 1.00 | 101.72 | N |
| ATOM | 387 | C | LYS | B | 222 | −66.420 | 16.908 | −8.498 | 1.00 | 94.80 | C |
| ATOM | 388 | O | LYS | B | 222 | −66.796 | 18.070 | −8.600 | 1.00 | 94.92 | O |
| ATOM | 389 | N | CYS | B | 223 | −65.149 | 16.516 | −8.779 | 1.00 | 89.06 | N |
| ATOM | 390 | CA | CYS | B | 223 | −64.125 | 17.431 | −9.279 | 1.00 | 87.39 | C |
| ATOM | 391 | CB | CYS | B | 223 | −62.733 | 16.818 | −9.218 | 1.00 | 87.43 | C |
| ATOM | 392 | SG | CYS | B | 223 | −62.208 | 16.366 | −7.551 | 1.00 | 90.01 | S |
| ATOM | 393 | C | CYS | B | 223 | −64.506 | 17.717 | −10.681 | 1.00 | 85.86 | C |
| ATOM | 394 | O | CYS | B | 223 | −64.776 | 18.872 | −11.006 | 1.00 | 86.32 | O |
| ATOM | 395 | N | ASP | B | 224 | −64.594 | 16.660 | −11.508 | 1.00 | 80.28 | N |
| ATOM | 396 | CA | ASP | B | 224 | −64.974 | 16.782 | −12.908 | 1.00 | 78.53 | C |
| ATOM | 397 | CB | ASP | B | 224 | −64.517 | 15.581 | −13.764 | 1.00 | 79.51 | C |
| ATOM | 398 | CG | ASP | B | 224 | −64.381 | 14.211 | −13.116 | 1.00 | 81.45 | C |
| ATOM | 399 | OD1 | ASP | B | 224 | −65.095 | 13.951 | −12.105 | 1.00 | 83.11 | O |
| ATOM | 400 | OD2 | ASP | B | 224 | −63.569 | 13.382 | −13.636 | 1.00 | 83.60 | O |
| ATOM | 401 | C | ASP | B | 224 | −66.417 | 17.221 | −13.200 | 1.00 | 76.34 | C |
| ATOM | 402 | O | ASP | B | 224 | −66.799 | 17.373 | −14.348 | 1.00 | 75.54 | O |
| ATOM | 403 | N | SER | B | 225 | −67.176 | 17.481 | −12.146 | 1.00 | 72.60 | N |
| ATOM | 404 | CA | SER | B | 225 | −68.564 | 17.906 | −12.142 | 1.00 | 70.75 | C |
| ATOM | 405 | CB | SER | B | 225 | −68.948 | 18.338 | −10.732 | 1.00 | 70.68 | C |
| ATOM | 406 | OG | SER | B | 225 | −70.346 | 18.509 | −10.593 | 1.00 | 71.29 | O |
| ATOM | 407 | C | SER | B | 225 | −68.881 | 19.022 | −13.134 | 1.00 | 69.45 | C |
| ATOM | 408 | O | SER | B | 225 | −69.705 | 18.849 | −14.037 | 1.00 | 69.51 | O |
| ATOM | 409 | N | HIS | B | 226 | −68.213 | 20.152 | −12.959 | 1.00 | 67.18 | N |
| ATOM | 410 | CA | HIS | B | 226 | −68.384 | 21.368 | −13.731 | 1.00 | 65.54 | C |
| ATOM | 411 | CB | HIS | B | 226 | −67.775 | 22.527 | −12.943 | 1.00 | 66.03 | C |
| ATOM | 412 | CG | HIS | B | 226 | −68.050 | 23.885 | −13.494 | 1.00 | 67.26 | C |
| ATOM | 413 | ND1 | HIS | B | 226 | −67.015 | 24.731 | −13.866 | 1.00 | 68.03 | N |
| ATOM | 414 | CE1 | HIS | B | 226 | −67.596 | 25.843 | −14.284 | 1.00 | 69.18 | C |
| ATOM | 415 | NE2 | HIS | B | 226 | −68.929 | 25.764 | −14.196 | 1.00 | 68.94 | N |
| ATOM | 416 | CD2 | HIS | B | 226 | −69.229 | 24.521 | −13.682 | 1.00 | 68.58 | C |
| ATOM | 417 | C | HIS | B | 226 | −67.837 | 21.304 | −15.152 | 1.00 | 64.16 | C |
| ATOM | 418 | O | HIS | B | 226 | −68.570 | 21.600 | −16.087 | 1.00 | 64.08 | O |
| ATOM | 419 | N | GLY | B | 227 | −66.569 | 20.938 | −15.308 | 1.00 | 59.89 | N |
| ATOM | 420 | CA | GLY | B | 227 | −65.918 | 20.862 | −16.606 | 1.00 | 57.91 | C |
| ATOM | 421 | C | GLY | B | 227 | −66.559 | 19.870 | −17.542 | 1.00 | 57.07 | C |
| ATOM | 422 | O | GLY | B | 227 | −66.580 | 20.101 | −18.749 | 1.00 | 56.80 | O |
| ATOM | 423 | N | THR | B | 228 | −67.066 | 18.749 | −16.997 | 1.00 | 56.49 | N |
| ATOM | 424 | CA | THR | B | 228 | −67.718 | 17.703 | −17.779 | 1.00 | 55.25 | C |
| ATOM | 425 | CB | THR | B | 228 | −67.908 | 16.416 | −16.945 | 1.00 | 55.36 | C |
| ATOM | 426 | OG1 | THR | B | 228 | −66.617 | 15.986 | −16.499 | 1.00 | 55.00 | O |
| ATOM | 427 | CG2 | THR | B | 228 | −68.598 | 15.284 | −17.718 | 1.00 | 54.69 | C |
| ATOM | 428 | C | THR | B | 228 | −68.980 | 18.294 | −18.344 | 1.00 | 54.71 | C |
| ATOM | 429 | O | THR | B | 228 | −69.159 | 18.226 | −19.558 | 1.00 | 54.21 | O |
| ATOM | 430 | N | HIS | B | 229 | −69.822 | 18.921 | −17.478 | 1.00 | 54.98 | N |

TABLE 14-continued

PCSK9 and AX132 Fab complex x-ray structure

| ATOM | 431 | CA | HIS | B | 229 | −71.068 | 19.581 | −17.869 | 1.00 | 54.94 | C |
|---|---|---|---|---|---|---|---|---|---|---|---|
| ATOM | 432 | CB | HIS | B | 229 | −71.761 | 20.249 | −16.676 | 1.00 | 54.87 | C |
| ATOM | 433 | CG | HIS | B | 229 | −73.182 | 20.612 | −16.969 | 1.00 | 56.60 | C |
| ATOM | 434 | ND1 | HIS | B | 229 | −73.533 | 21.889 | −17.344 | 1.00 | 58.44 | N |
| ATOM | 435 | CE1 | HIS | B | 229 | −74.838 | 21.861 | −17.560 | 1.00 | 58.78 | C |
| ATOM | 436 | NE2 | HIS | B | 229 | −75.347 | 20.652 | −17.328 | 1.00 | 59.04 | N |
| ATOM | 437 | CD2 | HIS | B | 229 | −74.295 | 19.839 | −16.964 | 1.00 | 58.70 | C |
| ATOM | 438 | C | HIS | B | 229 | −70.830 | 20.596 | −18.986 | 1.00 | 54.67 | C |
| ATOM | 439 | O | HIS | B | 229 | −71.518 | 20.524 | −20.001 | 1.00 | 54.62 | O |
| ATOM | 440 | N | LEU | B | 230 | −69.850 | 21.508 | −18.831 | 1.00 | 54.53 | N |
| ATOM | 441 | CA | LEU | B | 230 | −69.571 | 22.503 | −19.852 | 1.00 | 54.58 | C |
| ATOM | 442 | CB | LEU | B | 230 | −68.631 | 23.570 | −19.340 | 1.00 | 54.42 | C |
| ATOM | 443 | CG | LEU | B | 230 | −69.134 | 24.331 | −18.137 | 1.00 | 54.76 | C |
| ATOM | 444 | CD1 | LEU | B | 230 | −68.075 | 25.189 | −17.588 | 1.00 | 53.99 | C |
| ATOM | 445 | CD2 | LEU | B | 230 | −70.327 | 25.160 | −18.468 | 1.00 | 54.36 | C |
| ATOM | 446 | C | LEU | B | 230 | −69.079 | 21.900 | −21.169 | 1.00 | 55.03 | C |
| ATOM | 447 | O | LEU | B | 230 | −69.569 | 22.309 | −22.234 | 1.00 | 55.41 | O |
| ATOM | 448 | N | ALA | B | 231 | −68.146 | 20.920 | −21.120 | 1.00 | 56.16 | N |
| ATOM | 449 | CA | ALA | B | 231 | −67.674 | 20.261 | −22.329 | 1.00 | 56.30 | C |
| ATOM | 450 | CB | ALA | B | 231 | −66.598 | 19.260 | −21.978 | 1.00 | 56.06 | C |
| ATOM | 451 | C | ALA | B | 231 | −68.909 | 19.545 | −22.980 | 1.00 | 56.96 | C |
| ATOM | 452 | O | ALA | B | 231 | −69.020 | 19.449 | −24.220 | 1.00 | 56.80 | O |
| ATOM | 453 | N | GLY | B | 232 | −69.836 | 19.095 | −22.121 | 1.00 | 59.26 | N |
| ATOM | 454 | CA | GLY | B | 232 | −71.076 | 18.461 | −22.529 | 1.00 | 59.55 | C |
| ATOM | 455 | C | GLY | B | 232 | −71.926 | 19.502 | −23.210 | 1.00 | 60.10 | C |
| ATOM | 456 | O | GLY | B | 232 | −72.435 | 19.243 | −24.292 | 1.00 | 60.36 | O |
| ATOM | 457 | N | VAL | B | 233 | −72.041 | 20.710 | −22.618 | 1.00 | 61.09 | N |
| ATOM | 458 | CA | VAL | B | 233 | −72.819 | 21.810 | −23.203 | 1.00 | 61.50 | C |
| ATOM | 459 | CB | VAL | B | 233 | −72.984 | 23.009 | −22.244 | 1.00 | 61.31 | C |
| ATOM | 460 | CG1 | VAL | B | 233 | −73.636 | 24.194 | −22.945 | 1.00 | 60.60 | C |
| ATOM | 461 | CG2 | VAL | B | 233 | −73.789 | 22.612 | −21.018 | 1.00 | 61.89 | C |
| ATOM | 462 | C | VAL | B | 233 | −72.251 | 22.248 | −24.573 | 1.00 | 61.96 | C |
| ATOM | 463 | O | VAL | B | 233 | −73.034 | 22.489 | −25.497 | 1.00 | 62.26 | O |
| ATOM | 464 | N | VAL | B | 234 | −70.922 | 22.337 | −24.714 | 1.00 | 60.75 | N |
| ATOM | 465 | CA | VAL | B | 234 | −70.352 | 22.756 | −25.989 | 1.00 | 61.40 | C |
| ATOM | 466 | CB | VAL | B | 234 | −68.872 | 23.198 | −25.877 | 1.00 | 61.51 | C |
| ATOM | 467 | CG1 | VAL | B | 234 | −68.288 | 23.565 | −27.247 | 1.00 | 59.64 | C |
| ATOM | 468 | CG2 | VAL | B | 234 | −68.713 | 24.336 | −24.879 | 1.00 | 61.44 | C |
| ATOM | 469 | C | VAL | B | 234 | −70.522 | 21.730 | −27.102 | 1.00 | 62.31 | C |
| ATOM | 470 | O | VAL | B | 234 | −71.164 | 22.032 | −28.107 | 1.00 | 62.51 | O |
| ATOM | 471 | N | SER | B | 235 | −69.936 | 20.528 | −26.924 | 1.00 | 65.08 | N |
| ATOM | 472 | CA | SER | B | 235 | −69.889 | 19.474 | −27.934 | 1.00 | 65.81 | C |
| ATOM | 473 | CB | SER | B | 235 | −68.441 | 19.226 | −28.329 | 1.00 | 65.94 | C |
| ATOM | 474 | OG | SER | B | 235 | −67.686 | 18.789 | −27.205 | 1.00 | 67.86 | O |
| ATOM | 475 | C | SER | B | 235 | −70.558 | 18.146 | −27.670 | 1.00 | 66.01 | C |
| ATOM | 476 | O | SER | B | 235 | −70.314 | 17.225 | −28.436 | 1.00 | 65.96 | O |
| ATOM | 477 | N | GLY | B | 236 | −71.380 | 18.036 | −26.636 | 1.00 | 66.49 | N |
| ATOM | 478 | CA | GLY | B | 236 | −72.083 | 16.792 | −26.322 | 1.00 | 67.15 | C |
| ATOM | 479 | C | GLY | B | 236 | −72.830 | 16.189 | −27.497 | 1.00 | 67.77 | C |
| ATOM | 480 | O | GLY | B | 236 | −73.471 | 16.909 | −28.263 | 1.00 | 67.70 | O |
| ATOM | 481 | N | ARG | B | 237 | −72.720 | 14.860 | −27.666 | 1.00 | 70.52 | N |
| ATOM | 482 | CA | ARG | B | 237 | −73.357 | 14.101 | −28.748 | 1.00 | 71.20 | C |
| ATOM | 483 | CB | ARG | B | 237 | −72.983 | 12.613 | −28.639 | 1.00 | 71.49 | C |
| ATOM | 484 | CG | ARG | B | 237 | −71.768 | 12.239 | −29.499 | 1.00 | 72.04 | C |
| ATOM | 485 | CD | ARG | B | 237 | −71.175 | 10.847 | −29.206 | 1.00 | 71.96 | C |
| ATOM | 486 | NE | ARG | B | 237 | −69.909 | 10.643 | −29.937 | 1.00 | 71.37 | N |
| ATOM | 487 | CZ | ARG | B | 237 | −68.687 | 10.761 | −29.415 | 1.00 | 71.09 | C |
| ATOM | 488 | NH1 | ARG | B | 237 | −68.531 | 11.077 | −28.132 | 1.00 | 70.70 | N |
| ATOM | 489 | NH2 | ARG | B | 237 | −67.614 | 10.563 | −30.171 | 1.00 | 71.58 | N |
| ATOM | 490 | C | ARG | B | 237 | −74.892 | 14.283 | −28.885 | 1.00 | 71.39 | C |
| ATOM | 491 | O | ARG | B | 237 | −75.409 | 14.334 | −30.007 | 1.00 | 71.19 | O |
| ATOM | 492 | N | ASP | B | 238 | −75.601 | 14.382 | −27.749 | 1.00 | 71.16 | N |
| ATOM | 493 | CA | ASP | B | 238 | −77.054 | 14.516 | −27.705 | 1.00 | 71.52 | C |
| ATOM | 494 | CB | ASP | B | 238 | −77.650 | 13.479 | −26.722 | 1.00 | 71.63 | C |
| ATOM | 495 | CG | ASP | B | 238 | −77.532 | 12.031 | −27.144 | 1.00 | 73.10 | C |
| ATOM | 496 | OD1 | ASP | B | 238 | −77.848 | 11.720 | −28.334 | 1.00 | 75.60 | O |
| ATOM | 497 | OD2 | ASP | B | 238 | −77.149 | 11.198 | −26.293 | 1.00 | 74.54 | O |
| ATOM | 498 | C | ASP | B | 238 | −77.556 | 15.870 | −27.282 | 1.00 | 71.43 | C |
| ATOM | 499 | O | ASP | B | 238 | −78.565 | 16.337 | −27.810 | 1.00 | 71.16 | O |
| ATOM | 500 | N | ALA | B | 239 | −76.906 | 16.456 | −26.268 | 1.00 | 69.73 | N |
| ATOM | 501 | CA | ALA | B | 239 | −77.309 | 17.714 | −25.671 | 1.00 | 69.78 | C |
| ATOM | 502 | CB | ALA | B | 239 | −77.607 | 17.499 | −24.192 | 1.00 | 69.61 | C |
| ATOM | 503 | C | ALA | B | 239 | −76.339 | 18.888 | −25.878 | 1.00 | 69.98 | C |
| ATOM | 504 | O | ALA | B | 239 | −76.380 | 19.860 | −25.117 | 1.00 | 70.14 | O |
| ATOM | 505 | N | GLY | B | 240 | −75.507 | 18.809 | −26.914 | 1.00 | 69.35 | N |
| ATOM | 506 | CA | GLY | B | 240 | −74.540 | 19.858 | −27.223 | 1.00 | 69.93 | C |
| ATOM | 507 | C | GLY | B | 240 | −75.059 | 20.857 | −28.230 | 1.00 | 70.35 | C |
| ATOM | 508 | O | GLY | B | 240 | −75.989 | 20.552 | −28.991 | 1.00 | 70.72 | O |

TABLE 14-continued

PCSK9 and AX132 Fab complex x-ray structure

| ATOM | 509 | N | VAL | B | 241 | −74.477 | 22.071 | −28.227 | 1.00 | 68.65 | N |
|---|---|---|---|---|---|---|---|---|---|---|---|
| ATOM | 510 | CA | VAL | B | 241 | −74.865 | 23.136 | −29.153 | 1.00 | 68.57 | C |
| ATOM | 511 | CB | VAL | B | 241 | −74.481 | 24.545 | −28.611 | 1.00 | 68.64 | C |
| ATOM | 512 | CG1 | VAL | B | 241 | −74.415 | 25.596 | −29.720 | 1.00 | 69.14 | C |
| ATOM | 513 | CG2 | VAL | B | 241 | −75.455 | 24.997 | −27.535 | 1.00 | 68.83 | C |
| ATOM | 514 | C | VAL | B | 241 | −74.203 | 22.769 | −30.469 | 1.00 | 68.68 | C |
| ATOM | 515 | O | VAL | B | 241 | −74.902 | 22.445 | −31.431 | 1.00 | 68.58 | O |
| ATOM | 516 | N | ALA | B | 242 | −72.849 | 22.751 | −30.471 | 1.00 | 67.47 | N |
| ATOM | 517 | CA | ALA | B | 242 | −71.997 | 22.391 | −31.603 | 1.00 | 67.98 | C |
| ATOM | 518 | CB | ALA | B | 242 | −70.755 | 23.270 | −31.637 | 1.00 | 67.56 | C |
| ATOM | 519 | C | ALA | B | 242 | −71.611 | 20.928 | −31.472 | 1.00 | 68.56 | C |
| ATOM | 520 | O | ALA | B | 242 | −70.426 | 20.625 | −31.362 | 1.00 | 68.61 | O |
| ATOM | 521 | N | LYS | B | 243 | −72.625 | 20.019 | −31.484 | 1.00 | 70.17 | N |
| ATOM | 522 | CA | LYS | B | 243 | −72.479 | 18.549 | −31.373 | 1.00 | 70.58 | C |
| ATOM | 523 | CB | LYS | B | 243 | −73.758 | 17.824 | −31.839 | 1.00 | 70.40 | C |
| ATOM | 524 | CG | LYS | B | 243 | −74.950 | 17.975 | −30.932 | 1.00 | 70.91 | C |
| ATOM | 525 | CD | LYS | B | 243 | −76.200 | 17.759 | −31.720 | 1.00 | 72.46 | C |
| ATOM | 526 | CE | LYS | B | 243 | −77.325 | 17.308 | −30.848 | 1.00 | 73.73 | C |
| ATOM | 527 | NZ | LYS | B | 243 | −78.202 | 18.439 | −30.481 | 1.00 | 74.94 | N |
| ATOM | 528 | C | LYS | B | 243 | −71.289 | 18.034 | −32.199 | 1.00 | 70.80 | C |
| ATOM | 529 | O | LYS | B | 243 | −71.208 | 18.312 | −33.406 | 1.00 | 70.91 | O |
| ATOM | 530 | N | GLY | B | 244 | −70.372 | 17.340 | −31.532 | 1.00 | 71.40 | N |
| ATOM | 531 | CA | GLY | B | 244 | −69.188 | 16.758 | −32.149 | 1.00 | 71.80 | C |
| ATOM | 532 | C | GLY | B | 244 | −67.989 | 17.656 | −32.409 | 1.00 | 72.07 | C |
| ATOM | 533 | O | GLY | B | 244 | −67.100 | 17.249 | −33.170 | 1.00 | 72.10 | O |
| ATOM | 534 | N | ALA | B | 245 | −67.931 | 18.881 | −31.786 | 1.00 | 74.12 | N |
| ATOM | 535 | CA | ALA | B | 245 | −66.802 | 19.826 | −31.942 | 1.00 | 73.82 | C |
| ATOM | 536 | CB | ALA | B | 245 | −67.190 | 21.205 | −31.464 | 1.00 | 73.58 | C |
| ATOM | 537 | C | ALA | B | 245 | −65.612 | 19.324 | −31.149 | 1.00 | 73.72 | C |
| ATOM | 538 | O | ALA | B | 245 | −65.804 | 18.821 | −30.056 | 1.00 | 73.86 | O |
| ATOM | 539 | N | SER | B | 246 | −64.390 | 19.405 | −31.684 | 1.00 | 76.47 | N |
| ATOM | 540 | CA | SER | B | 246 | −63.265 | 18.895 | −30.892 | 1.00 | 76.25 | C |
| ATOM | 541 | CB | SER | B | 246 | −62.144 | 18.310 | −31.755 | 1.00 | 76.56 | C |
| ATOM | 542 | OG | SER | B | 246 | −61.518 | 19.218 | −32.647 | 1.00 | 77.19 | O |
| ATOM | 543 | C | SER | B | 246 | −62.796 | 19.919 | −29.879 | 1.00 | 75.82 | C |
| ATOM | 544 | O | SER | B | 246 | −62.778 | 21.113 | −30.174 | 1.00 | 75.68 | O |
| ATOM | 545 | N | MET | B | 247 | −62.484 | 19.452 | −28.664 | 1.00 | 75.61 | N |
| ATOM | 546 | CA | MET | B | 247 | −62.064 | 20.290 | −27.540 | 1.00 | 75.40 | C |
| ATOM | 547 | CB | MET | B | 247 | −63.145 | 20.308 | −26.465 | 1.00 | 75.44 | C |
| ATOM | 548 | CG | MET | B | 247 | −64.413 | 20.931 | −26.899 | 1.00 | 76.86 | C |
| ATOM | 549 | SD | MET | B | 247 | −65.642 | 20.855 | −25.589 | 1.00 | 79.70 | S |
| ATOM | 550 | CE | MET | B | 247 | −64.971 | 22.118 | −24.482 | 1.00 | 79.04 | C |
| ATOM | 551 | C | MET | B | 247 | −60.806 | 19.822 | −26.860 | 1.00 | 74.96 | C |
| ATOM | 552 | O | MET | B | 247 | −60.548 | 18.620 | −26.791 | 1.00 | 75.05 | O |
| ATOM | 553 | N | ARG | B | 248 | −60.047 | 20.777 | −26.312 | 1.00 | 75.49 | N |
| ATOM | 554 | CA | ARG | B | 248 | −58.836 | 20.513 | −25.545 | 1.00 | 74.89 | C |
| ATOM | 555 | CB | ARG | B | 248 | −57.587 | 21.112 | −26.198 | 1.00 | 75.20 | C |
| ATOM | 556 | CG | ARG | B | 248 | −57.578 | 20.887 | −27.698 | 1.00 | 77.26 | C |
| ATOM | 557 | CD | ARG | B | 248 | −56.245 | 21.122 | −28.343 | 1.00 | 79.96 | C |
| ATOM | 558 | NE | ARG | B | 248 | −55.613 | 19.847 | −28.644 | 1.00 | 81.95 | N |
| ATOM | 559 | CZ | ARG | B | 248 | −54.391 | 19.515 | −28.244 | 1.00 | 83.83 | C |
| ATOM | 560 | NH1 | ARG | B | 248 | −53.894 | 18.316 | −28.540 | 1.00 | 84.54 | N |
| ATOM | 561 | NH2 | ARG | B | 248 | −53.653 | 20.376 | −27.541 | 1.00 | 84.67 | N |
| ATOM | 562 | C | ARG | B | 248 | −59.087 | 21.076 | −24.158 | 1.00 | 74.04 | C |
| ATOM | 563 | O | ARG | B | 248 | −59.463 | 22.232 | −24.032 | 1.00 | 73.90 | O |
| ATOM | 564 | N | SER | B | 249 | −58.950 | 20.239 | −23.128 | 1.00 | 71.20 | N |
| ATOM | 565 | CA | SER | B | 249 | −59.164 | 20.579 | −21.729 | 1.00 | 70.17 | C |
| ATOM | 566 | CB | SER | B | 249 | −59.736 | 19.366 | −20.999 | 1.00 | 69.92 | C |
| ATOM | 567 | OG | SER | B | 249 | −59.511 | 19.446 | −19.602 | 1.00 | 68.99 | O |
| ATOM | 568 | C | SER | B | 249 | −57.850 | 21.031 | −21.050 | 1.00 | 69.89 | C |
| ATOM | 569 | O | SER | B | 249 | −56.810 | 20.406 | −21.278 | 1.00 | 70.14 | O |
| ATOM | 570 | N | LEU | B | 250 | −57.916 | 22.099 | −20.203 | 1.00 | 66.61 | N |
| ATOM | 571 | CA | LEU | B | 250 | −56.812 | 22.648 | −19.391 | 1.00 | 65.82 | C |
| ATOM | 572 | CB | LEU | B | 250 | −56.351 | 23.994 | −19.919 | 1.00 | 65.38 | C |
| ATOM | 573 | CG | LEU | B | 250 | −55.208 | 23.974 | −20.898 | 1.00 | 64.50 | C |
| ATOM | 574 | CD1 | LEU | B | 250 | −55.702 | 23.663 | −22.312 | 1.00 | 64.17 | C |
| ATOM | 575 | CD2 | LEU | B | 250 | −54.523 | 25.306 | −20.908 | 1.00 | 63.05 | C |
| ATOM | 576 | C | LEU | B | 250 | −57.325 | 22.798 | −17.956 | 1.00 | 65.75 | C |
| ATOM | 577 | O | LEU | B | 250 | −58.399 | 23.350 | −17.777 | 1.00 | 66.25 | O |
| ATOM | 578 | N | ARG | B | 251 | −56.608 | 22.285 | −16.937 | 1.00 | 67.20 | N |
| ATOM | 579 | CA | ARG | B | 251 | −57.095 | 22.367 | −15.552 | 1.00 | 67.06 | C |
| ATOM | 580 | CB | ARG | B | 251 | −56.857 | 21.076 | −14.773 | 1.00 | 66.51 | C |
| ATOM | 581 | CG | ARG | B | 251 | −57.683 | 21.030 | −13.516 | 1.00 | 65.46 | C |
| ATOM | 582 | CD | ARG | B | 251 | −57.459 | 19.766 | −12.738 | 1.00 | 65.04 | C |
| ATOM | 583 | NE | ARG | B | 251 | −58.350 | 19.702 | −11.575 | 1.00 | 65.85 | N |
| ATOM | 584 | CZ | ARG | B | 251 | −57.945 | 19.431 | −10.334 | 1.00 | 65.92 | C |
| ATOM | 585 | NH1 | ARG | B | 251 | −58.822 | 19.402 | −9.332 | 1.00 | 66.09 | N |
| ATOM | 586 | NH2 | ARG | B | 251 | −56.658 | 19.186 | −10.085 | 1.00 | 66.35 | N |

TABLE 14-continued

PCSK9 and AX132 Fab complex x-ray structure

| ATOM | 587 | C | ARG | B | 251 | −56.608 | 23.553 | −14.764 | 1.00 | 67.70 | C |
|------|-----|-----|-----|---|-----|---------|--------|---------|------|-------|---|
| ATOM | 588 | O | ARG | B | 251 | −55.438 | 23.587 | −14.360 | 1.00 | 67.90 | O |
| ATOM | 589 | N | VAL | B | 252 | −57.518 | 24.528 | −14.524 | 1.00 | 67.49 | N |
| ATOM | 590 | CA | VAL | B | 252 | −57.211 | 25.746 | −13.756 | 1.00 | 67.57 | C |
| ATOM | 591 | CB | VAL | B | 252 | −57.228 | 27.057 | −14.566 | 1.00 | 67.13 | C |
| ATOM | 592 | CG1 | VAL | B | 252 | −56.161 | 27.053 | −15.656 | 1.00 | 67.37 | C |
| ATOM | 593 | CG2 | VAL | B | 252 | −58.607 | 27.350 | −15.131 | 1.00 | 66.31 | C |
| ATOM | 594 | C | VAL | B | 252 | −58.046 | 25.845 | −12.498 | 1.00 | 68.12 | C |
| ATOM | 595 | O | VAL | B | 252 | −57.782 | 26.706 | −11.650 | 1.00 | 68.43 | O |
| ATOM | 596 | N | LEU | B | 253 | −59.048 | 24.968 | −12.365 | 1.00 | 65.71 | N |
| ATOM | 597 | CA | LEU | B | 253 | −59.889 | 24.997 | −11.189 | 1.00 | 66.27 | C |
| ATOM | 598 | CB | LEU | B | 253 | −61.365 | 25.338 | −11.518 | 1.00 | 65.95 | C |
| ATOM | 599 | CG | LEU | B | 253 | −61.632 | 26.540 | −12.451 | 1.00 | 64.62 | C |
| ATOM | 600 | CD1 | LEU | B | 253 | −63.059 | 26.692 | −12.730 | 1.00 | 63.03 | C |
| ATOM | 601 | CD2 | LEU | B | 253 | −61.039 | 27.832 | −11.937 | 1.00 | 63.96 | C |
| ATOM | 602 | C | LEU | B | 253 | −59.746 | 23.712 | −10.404 | 1.00 | 67.24 | C |
| ATOM | 603 | O | LEU | B | 253 | −59.663 | 22.636 | −10.990 | 1.00 | 67.26 | O |
| ATOM | 604 | N | ASN | B | 254 | −59.679 | 23.826 | −9.070 | 1.00 | 72.03 | N |
| ATOM | 605 | CA | ASN | B | 254 | −59.555 | 22.675 | −8.196 | 1.00 | 73.18 | C |
| ATOM | 606 | CB | ASN | B | 254 | −58.866 | 23.055 | −6.882 | 1.00 | 73.11 | C |
| ATOM | 607 | CG | ASN | B | 254 | −59.635 | 23.933 | −5.921 | 1.00 | 73.35 | C |
| ATOM | 608 | OD1 | ASN | B | 254 | −60.873 | 23.945 | −5.851 | 1.00 | 73.95 | O |
| ATOM | 609 | ND2 | ASN | B | 254 | −58.895 | 24.683 | −5.117 | 1.00 | 73.40 | N |
| ATOM | 610 | C | ASN | B | 254 | −60.929 | 22.017 | −8.018 | 1.00 | 74.16 | C |
| ATOM | 611 | O | ASN | B | 254 | −61.852 | 22.372 | −8.732 | 1.00 | 74.14 | O |
| ATOM | 612 | N | CYS | B | 255 | −61.074 | 21.070 | −7.085 | 1.00 | 80.58 | N |
| ATOM | 613 | CA | CYS | B | 255 | −62.333 | 20.370 | −6.860 | 1.00 | 82.09 | C |
| ATOM | 614 | CB | CYS | B | 255 | −62.127 | 19.108 | −6.036 | 1.00 | 82.62 | C |
| ATOM | 615 | SG | CYS | B | 255 | −61.022 | 17.905 | −6.832 | 1.00 | 89.25 | S |
| ATOM | 616 | C | CYS | B | 255 | −63.427 | 21.222 | −6.329 | 1.00 | 81.75 | C |
| ATOM | 617 | O | CYS | B | 255 | −64.589 | 20.917 | −6.584 | 1.00 | 82.38 | O |
| ATOM | 618 | N | GLN | B | 256 | −63.079 | 22.314 | −5.639 | 1.00 | 77.66 | N |
| ATOM | 619 | CA | GLN | B | 256 | −64.057 | 23.252 | −5.091 | 1.00 | 77.30 | C |
| ATOM | 620 | CB | GLN | B | 256 | −63.590 | 23.807 | −3.733 | 1.00 | 77.93 | C |
| ATOM | 621 | CG | GLN | B | 256 | −63.313 | 22.757 | −2.649 | 1.00 | 81.07 | C |
| ATOM | 622 | CD | GLN | B | 256 | −61.881 | 22.827 | −2.088 | 1.00 | 87.25 | C |
| ATOM | 623 | OE1 | GLN | B | 256 | −61.041 | 23.719 | −2.429 | 1.00 | 89.83 | O |
| ATOM | 624 | NE2 | GLN | B | 256 | −61.568 | 21.877 | −1.194 | 1.00 | 88.70 | N |
| ATOM | 625 | C | GLN | B | 256 | −64.361 | 24.387 | −6.094 | 1.00 | 76.06 | C |
| ATOM | 626 | O | GLN | B | 256 | −64.995 | 25.374 | −5.747 | 1.00 | 76.16 | O |
| ATOM | 627 | N | GLY | B | 257 | −63.912 | 24.223 | −7.330 | 1.00 | 70.38 | N |
| ATOM | 628 | CA | GLY | B | 257 | −64.100 | 25.186 | −8.411 | 1.00 | 68.58 | C |
| ATOM | 629 | C | GLY | B | 257 | −63.271 | 26.444 | −8.277 | 1.00 | 67.40 | C |
| ATOM | 630 | O | GLY | B | 257 | −63.500 | 27.409 | −9.009 | 1.00 | 67.30 | O |
| ATOM | 631 | N | LYS | B | 258 | −62.297 | 26.434 | −7.349 | 1.00 | 63.96 | N |
| ATOM | 632 | CA | LYS | B | 258 | −61.401 | 27.547 | −7.062 | 1.00 | 62.84 | C |
| ATOM | 633 | CB | LYS | B | 258 | −61.073 | 27.568 | −5.566 | 1.00 | 62.59 | C |
| ATOM | 634 | CG | LYS | B | 258 | −60.889 | 28.968 | −5.004 | 1.00 | 63.89 | C |
| ATOM | 635 | CD | LYS | B | 258 | −61.172 | 29.003 | −3.504 | 1.00 | 66.19 | C |
| ATOM | 636 | CE | LYS | B | 258 | −59.925 | 29.279 | −2.696 | 1.00 | 68.11 | C |
| ATOM | 637 | NZ | LYS | B | 258 | −59.951 | 28.592 | −1.372 | 1.00 | 70.08 | N |
| ATOM | 638 | C | LYS | B | 258 | −60.123 | 27.507 | −7.911 | 1.00 | 62.15 | C |
| ATOM | 639 | O | LYS | B | 258 | −59.550 | 26.452 | −8.117 | 1.00 | 62.29 | O |
| ATOM | 640 | N | GLY | B | 259 | −59.711 | 28.661 | −8.409 | 1.00 | 62.62 | N |
| ATOM | 641 | CA | GLY | B | 259 | −58.507 | 28.810 | −9.211 | 1.00 | 61.64 | C |
| ATOM | 642 | C | GLY | B | 259 | −57.771 | 30.085 | −8.845 | 1.00 | 61.25 | C |
| ATOM | 643 | O | GLY | B | 259 | −58.114 | 30.754 | −7.853 | 1.00 | 61.08 | O |
| ATOM | 644 | N | THR | B | 260 | −56.742 | 30.431 | −9.633 | 1.00 | 60.84 | N |
| ATOM | 645 | CA | THR | B | 260 | −55.981 | 31.658 | −9.397 | 1.00 | 60.16 | C |
| ATOM | 646 | CB | THR | B | 260 | −54.619 | 31.406 | −8.736 | 1.00 | 59.90 | C |
| ATOM | 647 | OG1 | THR | B | 260 | −53.793 | 30.546 | −9.540 | 1.00 | 60.29 | O |
| ATOM | 648 | CG2 | THR | B | 260 | −54.741 | 30.915 | −7.327 | 1.00 | 58.45 | C |
| ATOM | 649 | C | THR | B | 260 | −55.826 | 32.420 | −10.684 | 1.00 | 60.24 | C |
| ATOM | 650 | O | THR | B | 260 | −55.965 | 31.834 | −11.759 | 1.00 | 60.08 | O |
| ATOM | 651 | N | VAL | B | 261 | −55.559 | 33.736 | −10.580 | 1.00 | 62.43 | N |
| ATOM | 652 | CA | VAL | B | 261 | −55.346 | 34.609 | −11.732 | 1.00 | 62.54 | C |
| ATOM | 653 | CB | VAL | B | 261 | −55.159 | 36.076 | −11.269 | 1.00 | 62.53 | C |
| ATOM | 654 | CG1 | VAL | B | 261 | −54.689 | 36.982 | −12.411 | 1.00 | 62.52 | C |
| ATOM | 655 | CG2 | VAL | B | 261 | −56.443 | 36.614 | −10.639 | 1.00 | 62.50 | C |
| ATOM | 656 | C | VAL | B | 261 | −54.105 | 34.051 | −12.435 | 1.00 | 62.77 | C |
| ATOM | 657 | O | VAL | B | 261 | −54.156 | 33.687 | −13.615 | 1.00 | 62.53 | O |
| ATOM | 658 | N | SER | B | 262 | −53.013 | 33.932 | −11.655 | 1.00 | 64.10 | N |
| ATOM | 659 | CA | SER | B | 262 | −51.694 | 33.417 | −12.028 | 1.00 | 63.98 | C |
| ATOM | 660 | CB | SER | B | 262 | −50.844 | 33.245 | −10.768 | 1.00 | 63.93 | C |
| ATOM | 661 | OG | SER | B | 262 | −51.594 | 32.577 | −9.765 | 1.00 | 63.42 | O |
| ATOM | 662 | C | SER | B | 262 | −51.805 | 32.088 | −12.800 | 1.00 | 63.70 | C |
| ATOM | 663 | O | SER | B | 262 | −51.284 | 31.978 | −13.911 | 1.00 | 63.66 | O |
| ATOM | 664 | N | GLY | B | 263 | −52.499 | 31.118 | −12.212 | 1.00 | 59.41 | N |

TABLE 14-continued

PCSK9 and AX132 Fab complex x-ray structure

| ATOM | 665 | CA | GLY | B | 263 | −52.699 | 29.818 | −12.829 | 1.00 | 59.00 | C |
|------|-----|-----|-----|---|-----|---------|--------|---------|------|-------|---|
| ATOM | 666 | C | GLY | B | 263 | −53.432 | 29.909 | −14.148 | 1.00 | 58.77 | C |
| ATOM | 667 | O | GLY | B | 263 | −53.094 | 29.199 | −15.085 | 1.00 | 58.40 | O |
| ATOM | 668 | N | THR | B | 264 | −54.435 | 30.800 | −14.230 | 1.00 | 59.19 | N |
| ATOM | 669 | CA | THR | B | 264 | −55.214 | 31.016 | −15.446 | 1.00 | 59.40 | C |
| ATOM | 670 | CB | THR | B | 264 | −56.492 | 31.846 | −15.157 | 1.00 | 59.23 | C |
| ATOM | 671 | OG1 | THR | B | 264 | −57.212 | 31.270 | −14.085 | 1.00 | 57.85 | O |
| ATOM | 672 | CG2 | THR | B | 264 | −57.407 | 31.974 | −16.359 | 1.00 | 58.64 | C |
| ATOM | 673 | C | THR | B | 264 | −54.255 | 31.654 | −16.486 | 1.00 | 60.21 | C |
| ATOM | 674 | O | THR | B | 264 | −54.314 | 31.273 | −17.654 | 1.00 | 60.35 | O |
| ATOM | 675 | N | LEU | B | 265 | −53.363 | 32.592 | −16.064 | 1.00 | 60.92 | N |
| ATOM | 676 | CA | LEU | B | 265 | −52.390 | 33.217 | −16.968 | 1.00 | 61.51 | C |
| ATOM | 677 | CB | LEU | B | 265 | −51.507 | 34.228 | −16.242 | 1.00 | 61.56 | C |
| ATOM | 678 | CG | LEU | B | 265 | −52.105 | 35.499 | −15.796 | 1.00 | 61.07 | C |
| ATOM | 679 | CD1 | LEU | B | 265 | −51.031 | 36.384 | −15.256 | 1.00 | 61.15 | C |
| ATOM | 680 | CD2 | LEU | B | 265 | −52.793 | 36.196 | −16.930 | 1.00 | 61.14 | C |
| ATOM | 681 | C | LEU | B | 265 | −51.475 | 32.148 | −17.562 | 1.00 | 62.10 | C |
| ATOM | 682 | O | LEU | B | 265 | −51.352 | 32.085 | −18.782 | 1.00 | 62.27 | O |
| ATOM | 683 | N | ILE | B | 266 | −50.845 | 31.306 | −16.699 | 1.00 | 62.02 | N |
| ATOM | 684 | CA | ILE | B | 266 | −49.958 | 30.220 | −17.110 | 1.00 | 62.61 | C |
| ATOM | 685 | CB | ILE | B | 266 | −49.356 | 29.498 | −15.889 | 1.00 | 62.34 | C |
| ATOM | 686 | CG1 | ILE | B | 266 | −48.527 | 30.489 | −15.077 | 1.00 | 61.21 | C |
| ATOM | 687 | CD1 | ILE | B | 266 | −48.121 | 30.072 | −13.744 | 1.00 | 59.56 | C |
| ATOM | 688 | CG2 | ILE | B | 266 | −48.495 | 28.315 | −16.321 | 1.00 | 62.82 | C |
| ATOM | 689 | C | ILE | B | 266 | −50.668 | 29.297 | −18.126 | 1.00 | 63.41 | C |
| ATOM | 690 | O | ILE | B | 266 | −50.049 | 28.912 | −19.122 | 1.00 | 63.60 | O |
| ATOM | 691 | N | GLY | B | 267 | −51.962 | 29.030 | −17.891 | 1.00 | 64.02 | N |
| ATOM | 692 | CA | GLY | B | 267 | −52.840 | 28.261 | −18.763 | 1.00 | 64.93 | C |
| ATOM | 693 | C | GLY | B | 267 | −53.057 | 28.971 | −20.086 | 1.00 | 66.04 | C |
| ATOM | 694 | O | GLY | B | 267 | −53.084 | 28.326 | −21.120 | 1.00 | 66.22 | O |
| ATOM | 695 | N | LEU | B | 268 | −53.191 | 30.301 | −20.091 | 1.00 | 68.50 | N |
| ATOM | 696 | CA | LEU | B | 268 | −53.379 | 31.042 | −21.340 | 1.00 | 69.85 | C |
| ATOM | 697 | CB | LEU | B | 268 | −53.910 | 32.463 | −21.083 | 1.00 | 69.65 | C |
| ATOM | 698 | CG | LEU | B | 268 | −55.356 | 32.607 | −20.643 | 1.00 | 68.47 | C |
| ATOM | 699 | CD1 | LEU | B | 268 | −55.673 | 34.048 | −20.359 | 1.00 | 67.56 | C |
| ATOM | 700 | CD2 | LEU | B | 268 | −56.322 | 32.090 | −21.679 | 1.00 | 67.17 | C |
| ATOM | 701 | C | LEU | B | 268 | −52.068 | 31.097 | −22.137 | 1.00 | 71.25 | C |
| ATOM | 702 | O | LEU | B | 268 | −52.103 | 31.106 | −23.374 | 1.00 | 71.19 | O |
| ATOM | 703 | N | GLU | B | 269 | −50.918 | 31.140 | −21.413 | 1.00 | 76.14 | N |
| ATOM | 704 | CA | GLU | B | 269 | −49.556 | 31.179 | −21.963 | 1.00 | 77.92 | C |
| ATOM | 705 | CB | GLU | B | 269 | −48.522 | 31.419 | −20.838 | 1.00 | 78.06 | C |
| ATOM | 706 | CG | GLU | B | 269 | −47.137 | 31.853 | −21.311 | 1.00 | 80.49 | C |
| ATOM | 707 | CD | GLU | B | 269 | −45.980 | 31.559 | −20.357 | 1.00 | 84.46 | C |
| ATOM | 708 | OE1 | GLU | B | 269 | −45.848 | 30.397 | −19.901 | 1.00 | 85.61 | O |
| ATOM | 709 | OE2 | GLU | B | 269 | −45.191 | 32.492 | −20.081 | 1.00 | 85.68 | O |
| ATOM | 710 | C | GLU | B | 269 | −49.311 | 29.834 | −22.667 | 1.00 | 78.53 | C |
| ATOM | 711 | O | GLU | B | 269 | −48.644 | 29.787 | −23.705 | 1.00 | 78.67 | O |
| ATOM | 712 | N | PHE | B | 270 | −49.890 | 28.756 | −22.102 | 1.00 | 77.08 | N |
| ATOM | 713 | CA | PHE | B | 270 | −49.835 | 27.406 | −22.618 | 1.00 | 77.95 | C |
| ATOM | 714 | CB | PHE | B | 270 | −50.502 | 26.457 | −21.619 | 1.00 | 77.76 | C |
| ATOM | 715 | CG | PHE | B | 270 | −50.556 | 25.010 | −22.025 | 1.00 | 77.89 | C |
| ATOM | 716 | CD1 | PHE | B | 270 | −49.751 | 24.066 | −21.401 | 1.00 | 78.17 | C |
| ATOM | 717 | CE1 | PHE | B | 270 | −49.803 | 22.720 | −21.779 | 1.00 | 78.00 | C |
| ATOM | 718 | CZ | PHE | B | 270 | −50.656 | 22.319 | −22.783 | 1.00 | 77.50 | C |
| ATOM | 719 | CE2 | PHE | B | 270 | −51.467 | 23.236 | −23.408 | 1.00 | 77.66 | C |
| ATOM | 720 | CD2 | PHE | B | 270 | −51.426 | 24.579 | −23.024 | 1.00 | 77.70 | C |
| ATOM | 721 | C | PHE | B | 270 | −50.555 | 27.378 | −23.977 | 1.00 | 78.85 | C |
| ATOM | 722 | O | PHE | B | 270 | −49.995 | 26.856 | −24.934 | 1.00 | 79.16 | O |
| ATOM | 723 | N | ILE | B | 271 | −51.781 | 27.942 | −24.067 | 1.00 | 78.91 | N |
| ATOM | 724 | CA | ILE | B | 271 | −52.584 | 28.020 | −25.297 | 1.00 | 79.98 | C |
| ATOM | 725 | CB | ILE | B | 271 | −53.980 | 28.639 | −25.023 | 1.00 | 79.66 | C |
| ATOM | 726 | CG1 | ILE | B | 271 | −54.744 | 27.834 | −23.994 | 1.00 | 79.30 | C |
| ATOM | 727 | CD1 | ILE | B | 271 | −55.932 | 28.488 | −23.539 | 1.00 | 79.71 | C |
| ATOM | 728 | CG2 | ILE | B | 271 | −54.806 | 28.767 | −26.297 | 1.00 | 79.37 | C |
| ATOM | 729 | C | ILE | B | 271 | −51.834 | 28.818 | −26.364 | 1.00 | 81.30 | C |
| ATOM | 730 | O | ILE | B | 271 | −51.953 | 28.499 | −27.540 | 1.00 | 80.98 | O |
| ATOM | 731 | N | ARG | B | 272 | −51.076 | 29.861 | −25.957 | 1.00 | 89.76 | N |
| ATOM | 732 | CA | ARG | B | 272 | −50.321 | 30.685 | −26.897 | 1.00 | 91.79 | C |
| ATOM | 733 | CB | ARG | B | 272 | −49.724 | 31.948 | −26.240 | 1.00 | 91.99 | C |
| ATOM | 734 | CG | ARG | B | 272 | −49.015 | 32.925 | −27.212 | 1.00 | 93.58 | C |
| ATOM | 735 | CD | ARG | B | 272 | −49.915 | 33.388 | −28.356 | 1.00 | 96.32 | C |
| ATOM | 736 | NE | ARG | B | 272 | −49.252 | 34.288 | −29.309 | 1.00 | 98.43 | N |
| ATOM | 737 | CZ | ARG | B | 272 | −49.192 | 34.072 | −30.623 | 1.00 | 99.37 | C |
| ATOM | 738 | NH1 | ARG | B | 272 | −49.730 | 32.977 | −31.149 | 1.00 | 99.79 | N |
| ATOM | 739 | NH2 | ARG | B | 272 | −48.586 | 34.946 | −31.419 | 1.00 | 99.85 | N |
| ATOM | 740 | C | ARG | B | 272 | −49.266 | 29.850 | −27.565 | 1.00 | 92.79 | C |
| ATOM | 741 | O | ARG | B | 272 | −49.134 | 29.938 | −28.779 | 1.00 | 93.00 | O |
| ATOM | 742 | N | LYS | B | 273 | −48.549 | 29.016 | −26.788 | 1.00 | 96.33 | N |

TABLE 14-continued

PCSK9 and AX132 Fab complex x-ray structure

| ATOM | 743 | CA | LYS | B | 273 | −47.516 | 28.113 | −27.295 | 1.00 | 97.71 | C |
|---|---|---|---|---|---|---|---|---|---|---|---|
| ATOM | 744 | CB | LYS | B | 273 | −46.703 | 27.484 | −26.153 | 1.00 | 97.59 | C |
| ATOM | 745 | CG | LYS | B | 273 | −45.899 | 28.533 | −25.361 | 1.00 | 99.09 | C |
| ATOM | 746 | CD | LYS | B | 273 | −45.328 | 27.986 | −24.044 | 1.00 | 100.65 | C |
| ATOM | 747 | CE | LYS | B | 273 | −44.717 | 29.045 | −23.148 | 1.00 | 100.83 | C |
| ATOM | 748 | NZ | LYS | B | 273 | −44.250 | 28.449 | −21.855 | 1.00 | 101.62 | N |
| ATOM | 749 | C | LYS | B | 273 | −48.172 | 27.061 | −28.176 | 1.00 | 98.53 | C |
| ATOM | 750 | O | LYS | B | 273 | −47.726 | 26.863 | −29.302 | 1.00 | 98.77 | O |
| ATOM | 751 | N | SER | B | 274 | −49.273 | 26.449 | −27.707 | 1.00 | 99.80 | N |
| ATOM | 752 | CA | SER | B | 274 | −50.037 | 25.441 | −28.450 | 1.00 | 101.05 | C |
| ATOM | 753 | CB | SER | B | 274 | −51.272 | 25.015 | −27.662 | 1.00 | 101.07 | C |
| ATOM | 754 | OG | SER | B | 274 | −50.945 | 24.670 | −26.328 | 1.00 | 102.23 | O |
| ATOM | 755 | C | SER | B | 274 | −50.486 | 25.957 | −29.809 | 1.00 | 101.70 | C |
| ATOM | 756 | O | SER | B | 274 | −50.572 | 25.180 | −30.755 | 1.00 | 101.92 | O |
| ATOM | 757 | N | GLN | B | 275 | −50.789 | 27.259 | −29.896 | 1.00 | 101.88 | N |
| ATOM | 758 | CA | GLN | B | 275 | −51.251 | 27.923 | −31.104 | 1.00 | 102.84 | C |
| ATOM | 759 | CB | GLN | B | 275 | −51.856 | 29.289 | −30.743 | 1.00 | 102.72 | C |
| ATOM | 760 | CG | GLN | B | 275 | −52.759 | 29.880 | −31.816 | 1.00 | 102.15 | C |
| ATOM | 761 | CD | GLN | B | 275 | −52.885 | 31.385 | −31.755 | 1.00 | 100.72 | C |
| ATOM | 762 | OE1 | GLN | B | 275 | −52.233 | 32.074 | −30.964 | 1.00 | 100.81 | O |
| ATOM | 763 | NE2 | GLN | B | 275 | −53.735 | 31.931 | −32.605 | 1.00 | 100.53 | N |
| ATOM | 764 | C | GLN | B | 275 | −50.100 | 28.079 | −32.082 | 1.00 | 103.88 | C |
| ATOM | 765 | O | GLN | B | 275 | −50.283 | 27.824 | −33.272 | 1.00 | 104.18 | O |
| ATOM | 766 | N | LEU | B | 276 | −48.920 | 28.490 | −31.583 | 1.00 | 107.99 | N |
| ATOM | 767 | CA | LEU | B | 276 | −47.721 | 28.700 | −32.391 | 1.00 | 109.33 | C |
| ATOM | 768 | CB | LEU | B | 276 | −46.615 | 29.395 | −31.577 | 1.00 | 109.22 | C |
| ATOM | 769 | CG | LEU | B | 276 | −46.896 | 30.833 | −31.126 | 1.00 | 109.42 | C |
| ATOM | 770 | CD1 | LEU | B | 276 | −46.028 | 31.208 | −29.954 | 1.00 | 109.47 | C |
| ATOM | 771 | CD2 | LEU | B | 276 | −46.742 | 31.838 | −32.268 | 1.00 | 109.48 | C |
| ATOM | 772 | C | LEU | B | 276 | −47.221 | 27.386 | −32.974 | 1.00 | 110.36 | C |
| ATOM | 773 | O | LEU | B | 276 | −47.159 | 27.245 | −34.202 | 1.00 | 110.44 | O |
| ATOM | 774 | N | VAL | B | 277 | −46.894 | 26.416 | −32.080 | 1.00 | 116.52 | N |
| ATOM | 775 | CA | VAL | B | 277 | −46.396 | 25.061 | −32.383 | 1.00 | 117.56 | C |
| ATOM | 776 | CB | VAL | B | 277 | −46.286 | 24.164 | −31.102 | 1.00 | 117.53 | C |
| ATOM | 777 | CG1 | VAL | B | 277 | −46.084 | 22.685 | −31.446 | 1.00 | 117.63 | C |
| ATOM | 778 | CG2 | VAL | B | 277 | −45.172 | 24.662 | −30.182 | 1.00 | 117.65 | C |
| ATOM | 779 | C | VAL | B | 277 | −47.229 | 24.437 | −33.507 | 1.00 | 118.10 | C |
| ATOM | 780 | O | VAL | B | 277 | −46.736 | 24.368 | −34.636 | 1.00 | 118.31 | O |
| ATOM | 781 | N | GLN | B | 278 | −48.489 | 24.045 | −33.207 | 1.00 | 120.99 | N |
| ATOM | 782 | CA | GLN | B | 278 | −49.422 | 23.455 | −34.161 | 1.00 | 121.66 | C |
| ATOM | 783 | CB | GLN | B | 278 | −50.691 | 22.919 | −33.450 | 1.00 | 121.92 | C |
| ATOM | 784 | CG | GLN | B | 278 | −50.444 | 21.903 | −32.324 | 1.00 | 123.58 | C |
| ATOM | 785 | CD | GLN | B | 278 | −51.715 | 21.462 | −31.608 | 1.00 | 126.12 | C |
| ATOM | 786 | OE1 | GLN | B | 278 | −52.738 | 22.166 | −31.571 | 1.00 | 127.28 | O |
| ATOM | 787 | NE2 | GLN | B | 278 | −51.677 | 20.276 | −31.009 | 1.00 | 126.75 | N |
| ATOM | 788 | C | GLN | B | 278 | −49.803 | 24.535 | −35.196 | 1.00 | 121.49 | C |
| ATOM | 789 | O | GLN | B | 278 | −50.590 | 25.429 | −34.855 | 1.00 | 121.77 | O |
| ATOM | 790 | N | PRO | B | 279 | −49.239 | 24.526 | −36.443 | 1.00 | 122.36 | N |
| ATOM | 791 | CA | PRO | B | 279 | −49.655 | 25.544 | −37.427 | 1.00 | 121.69 | C |
| ATOM | 792 | CB | PRO | B | 279 | −48.575 | 25.458 | −38.532 | 1.00 | 121.88 | C |
| ATOM | 793 | CG | PRO | B | 279 | −47.539 | 24.434 | −38.030 | 1.00 | 122.28 | C |
| ATOM | 794 | CD | PRO | B | 279 | −48.296 | 23.566 | −37.058 | 1.00 | 122.41 | C |
| ATOM | 795 | C | PRO | B | 279 | −51.051 | 25.080 | −37.864 | 1.00 | 120.73 | C |
| ATOM | 796 | O | PRO | B | 279 | −51.204 | 24.135 | −38.659 | 1.00 | 120.92 | O |
| ATOM | 797 | N | VAL | B | 280 | −52.071 | 25.680 | −37.228 | 1.00 | 115.26 | N |
| ATOM | 798 | CA | VAL | B | 280 | −53.465 | 25.315 | −37.445 | 1.00 | 113.52 | C |
| ATOM | 799 | CB | VAL | B | 280 | −54.075 | 24.563 | −36.204 | 1.00 | 113.87 | C |
| ATOM | 800 | CG1 | VAL | B | 280 | −53.477 | 23.156 | −36.042 | 1.00 | 113.62 | C |
| ATOM | 801 | CG2 | VAL | B | 280 | −53.941 | 25.378 | −34.907 | 1.00 | 113.84 | C |
| ATOM | 802 | C | VAL | B | 280 | −54.311 | 26.493 | −37.970 | 1.00 | 112.03 | C |
| ATOM | 803 | O | VAL | B | 280 | −53.749 | 27.428 | −38.557 | 1.00 | 111.92 | O |
| ATOM | 804 | N | GLY | B | 281 | −55.637 | 26.408 | −37.767 | 1.00 | 105.64 | N |
| ATOM | 805 | CA | GLY | B | 281 | −56.626 | 27.405 | −38.168 | 1.00 | 102.84 | C |
| ATOM | 806 | C | GLY | B | 281 | −57.292 | 28.151 | −37.017 | 1.00 | 100.46 | C |
| ATOM | 807 | O | GLY | B | 281 | −56.594 | 28.825 | −36.246 | 1.00 | 100.89 | O |
| ATOM | 808 | N | PRO | B | 282 | −58.652 | 28.074 | −36.883 | 1.00 | 91.19 | N |
| ATOM | 809 | CA | PRO | B | 282 | −59.336 | 28.813 | −35.810 | 1.00 | 89.14 | C |
| ATOM | 810 | CB | PRO | B | 282 | −60.793 | 28.825 | −36.263 | 1.00 | 89.19 | C |
| ATOM | 811 | CG | PRO | B | 282 | −60.943 | 27.627 | −37.050 | 1.00 | 89.93 | C |
| ATOM | 812 | CD | PRO | B | 282 | −59.628 | 27.349 | −37.717 | 1.00 | 91.00 | C |
| ATOM | 813 | C | PRO | B | 282 | −59.167 | 28.240 | −34.408 | 1.00 | 87.01 | C |
| ATOM | 814 | O | PRO | B | 282 | −58.887 | 27.050 | −34.242 | 1.00 | 86.82 | O |
| ATOM | 815 | N | LEU | B | 283 | −59.339 | 29.115 | −33.401 | 1.00 | 80.72 | N |
| ATOM | 816 | CA | LEU | B | 283 | −59.198 | 28.804 | −31.981 | 1.00 | 78.15 | C |
| ATOM | 817 | CB | LEU | B | 283 | −57.789 | 29.242 | −31.551 | 1.00 | 78.20 | C |
| ATOM | 818 | CG | LEU | B | 283 | −57.040 | 28.350 | −30.582 | 1.00 | 78.62 | C |
| ATOM | 819 | CD1 | LEU | B | 283 | −56.323 | 27.223 | −31.317 | 1.00 | 79.96 | C |
| ATOM | 820 | CD2 | LEU | B | 283 | −56.004 | 29.145 | −29.848 | 1.00 | 78.44 | C |

TABLE 14-continued

PCSK9 and AX132 Fab complex x-ray structure

| ATOM | 821 | C   | LEU | B | 283 | −60.248 | 29.532 | −31.107 | 1.00 | 76.26 | C |
| ---- | --- | --- | --- | - | --- | ------- | ------ | ------- | ---- | ----- | - |
| ATOM | 822 | O   | LEU | B | 283 | −60.404 | 30.746 | −31.215 | 1.00 | 76.25 | O |
| ATOM | 823 | N   | VAL | B | 284 | −60.948 | 28.794 | −30.240 | 1.00 | 69.65 | N |
| ATOM | 824 | CA  | VAL | B | 284 | −61.933 | 29.344 | −29.306 | 1.00 | 66.85 | C |
| ATOM | 825 | CB  | VAL | B | 284 | −63.381 | 28.841 | −29.550 | 1.00 | 66.64 | C |
| ATOM | 826 | CG1 | VAL | B | 284 | −64.343 | 29.377 | −28.497 | 1.00 | 65.54 | C |
| ATOM | 827 | CG2 | VAL | B | 284 | −63.863 | 29.209 | −30.942 | 1.00 | 65.81 | C |
| ATOM | 828 | C   | VAL | B | 284 | −61.444 | 29.024 | −27.895 | 1.00 | 65.45 | C |
| ATOM | 829 | O   | VAL | B | 284 | −61.199 | 27.872 | −27.592 | 1.00 | 65.31 | O |
| ATOM | 830 | N   | VAL | B | 285 | −61.270 | 30.022 | −27.047 | 1.00 | 64.37 | N |
| ATOM | 831 | CA  | VAL | B | 285 | −60.844 | 29.783 | −25.674 | 1.00 | 63.25 | C |
| ATOM | 832 | CB  | VAL | B | 285 | −59.605 | 30.599 | −25.256 | 1.00 | 63.09 | C |
| ATOM | 833 | CG1 | VAL | B | 285 | −59.359 | 30.481 | −23.766 | 1.00 | 62.67 | C |
| ATOM | 834 | CG2 | VAL | B | 285 | −58.371 | 30.144 | −26.020 | 1.00 | 63.08 | C |
| ATOM | 835 | C   | VAL | B | 285 | −62.045 | 30.077 | −24.809 | 1.00 | 62.71 | C |
| ATOM | 836 | O   | VAL | B | 285 | −62.540 | 31.205 | −24.818 | 1.00 | 62.92 | O |
| ATOM | 837 | N   | LEU | B | 286 | −62.545 | 29.067 | −24.097 | 1.00 | 63.34 | N |
| ATOM | 838 | CA  | LEU | B | 286 | −63.694 | 29.235 | −23.217 | 1.00 | 62.71 | C |
| ATOM | 839 | CB  | LEU | B | 286 | −64.766 | 28.183 | −23.501 | 1.00 | 62.52 | C |
| ATOM | 840 | CG  | LEU | B | 286 | −65.735 | 27.853 | −22.392 | 1.00 | 62.69 | C |
| ATOM | 841 | CD1 | LEU | B | 286 | −66.769 | 28.949 | −22.197 | 1.00 | 62.31 | C |
| ATOM | 842 | CD2 | LEU | B | 286 | −66.418 | 26.550 | −22.686 | 1.00 | 63.41 | C |
| ATOM | 843 | C   | LEU | B | 286 | −63.215 | 29.258 | −21.743 | 1.00 | 62.46 | C |
| ATOM | 844 | O   | LEU | B | 286 | −62.615 | 28.292 | −21.246 | 1.00 | 62.37 | O |
| ATOM | 845 | N   | LEU | B | 287 | −63.451 | 30.412 | −21.082 | 1.00 | 62.84 | N |
| ATOM | 846 | CA  | LEU | B | 287 | −63.089 | 30.686 | −19.698 | 1.00 | 62.24 | C |
| ATOM | 847 | CB  | LEU | B | 287 | −62.236 | 31.948 | −19.625 | 1.00 | 62.14 | C |
| ATOM | 848 | CG  | LEU | B | 287 | −60.959 | 31.917 | −20.414 | 1.00 | 61.78 | C |
| ATOM | 849 | CD1 | LEU | B | 287 | −60.962 | 33.019 | −21.408 | 1.00 | 61.94 | C |
| ATOM | 850 | CD2 | LEU | B | 287 | −59.779 | 32.050 | −19.518 | 1.00 | 60.79 | C |
| ATOM | 851 | C   | LEU | B | 287 | −64.385 | 30.871 | −18.905 | 1.00 | 62.08 | C |
| ATOM | 852 | O   | LEU | B | 287 | −64.886 | 31.998 | −18.807 | 1.00 | 62.29 | O |
| ATOM | 853 | N   | PRO | B | 288 | −64.966 | 29.773 | −18.353 | 1.00 | 63.14 | N |
| ATOM | 854 | CA  | PRO | B | 288 | −66.243 | 29.892 | −17.615 | 1.00 | 62.63 | C |
| ATOM | 855 | CB  | PRO | B | 288 | −66.932 | 28.565 | −17.937 | 1.00 | 62.45 | C |
| ATOM | 856 | CG  | PRO | B | 288 | −65.820 | 27.623 | −18.305 | 1.00 | 62.93 | C |
| ATOM | 857 | CD  | PRO | B | 288 | −64.524 | 28.370 | −18.394 | 1.00 | 63.06 | C |
| ATOM | 858 | C   | PRO | B | 288 | −66.010 | 30.119 | −16.112 | 1.00 | 62.16 | C |
| ATOM | 859 | O   | PRO | B | 288 | −66.469 | 29.365 | −15.245 | 1.00 | 62.44 | O |
| ATOM | 860 | N   | LEU | B | 289 | −65.265 | 31.183 | −15.823 | 1.00 | 62.09 | N |
| ATOM | 861 | CA  | LEU | B | 289 | −64.851 | 31.538 | −14.492 | 1.00 | 61.42 | C |
| ATOM | 862 | CB  | LEU | B | 289 | −63.469 | 30.909 | −14.214 | 1.00 | 61.52 | C |
| ATOM | 863 | CG  | LEU | B | 289 | −62.367 | 31.084 | −15.278 | 1.00 | 60.95 | C |
| ATOM | 864 | CD1 | LEU | B | 289 | −61.614 | 32.401 | −15.094 | 1.00 | 59.80 | C |
| ATOM | 865 | CD2 | LEU | B | 289 | −61.395 | 29.911 | −15.247 | 1.00 | 60.26 | C |
| ATOM | 866 | C   | LEU | B | 289 | −64.805 | 33.038 | −14.291 | 1.00 | 61.25 | C |
| ATOM | 867 | O   | LEU | B | 289 | −64.786 | 33.797 | −15.256 | 1.00 | 61.35 | O |
| ATOM | 868 | N   | ALA | B | 290 | −64.756 | 33.473 | −13.038 | 1.00 | 61.46 | N |
| ATOM | 869 | CA  | ALA | B | 290 | −64.732 | 34.884 | −12.737 | 1.00 | 61.26 | C |
| ATOM | 870 | CB  | ALA | B | 290 | −66.158 | 35.363 | −12.513 | 1.00 | 61.09 | C |
| ATOM | 871 | C   | ALA | B | 290 | −63.893 | 35.186 | −11.516 | 1.00 | 61.37 | C |
| ATOM | 872 | O   | ALA | B | 290 | −63.746 | 34.334 | −10.649 | 1.00 | 61.38 | O |
| ATOM | 873 | N   | GLY | B | 291 | −63.370 | 36.398 | −11.459 | 1.00 | 60.73 | N |
| ATOM | 874 | CA  | GLY | B | 291 | −62.595 | 36.936 | −10.351 | 1.00 | 61.16 | C |
| ATOM | 875 | C   | GLY | B | 291 | −62.833 | 38.433 | −10.364 | 1.00 | 61.50 | C |
| ATOM | 876 | O   | GLY | B | 291 | −63.539 | 38.924 | −11.244 | 1.00 | 61.91 | O |
| ATOM | 877 | N   | GLY | B | 292 | −62.253 | 39.175 | −9.432  | 1.00 | 61.91 | N |
| ATOM | 878 | CA  | GLY | B | 292 | −62.401 | 40.623 | −9.436  | 1.00 | 62.03 | C |
| ATOM | 879 | C   | GLY | B | 292 | −61.699 | 41.185 | −10.660 | 1.00 | 62.38 | C |
| ATOM | 880 | O   | GLY | B | 292 | −60.960 | 40.443 | −11.327 | 1.00 | 62.27 | O |
| ATOM | 881 | N   | TYR | B | 293 | −61.909 | 42.493 | −10.987 | 1.00 | 64.79 | N |
| ATOM | 882 | CA  | TYR | B | 293 | −61.232 | 43.050 | −12.157 | 1.00 | 64.90 | C |
| ATOM | 883 | CB  | TYR | B | 293 | −61.637 | 44.508 | −12.443 | 1.00 | 64.83 | C |
| ATOM | 884 | CG  | TYR | B | 293 | −60.623 | 45.227 | −13.312 | 1.00 | 65.53 | C |
| ATOM | 885 | CD1 | TYR | B | 293 | −60.693 | 45.163 | −14.700 | 1.00 | 66.24 | C |
| ATOM | 886 | CE1 | TYR | B | 293 | −59.739 | 45.790 | −15.502 | 1.00 | 67.57 | C |
| ATOM | 887 | CZ  | TYR | B | 293 | −58.686 | 46.482 | −14.913 | 1.00 | 68.84 | C |
| ATOM | 888 | OH  | TYR | B | 293 | −57.712 | 47.094 | −15.680 | 1.00 | 71.12 | O |
| ATOM | 889 | CE2 | TYR | B | 293 | −58.592 | 46.543 | −13.534 | 1.00 | 67.77 | C |
| ATOM | 890 | CD2 | TYR | B | 293 | −59.563 | 45.929 | −12.746 | 1.00 | 66.45 | C |
| ATOM | 891 | C   | TYR | B | 293 | −59.714 | 42.903 | −11.993 | 1.00 | 64.84 | C |
| ATOM | 892 | O   | TYR | B | 293 | −59.172 | 43.323 | −10.968 | 1.00 | 64.89 | O |
| ATOM | 893 | N   | SER | B | 294 | −59.048 | 42.287 | −12.987 | 1.00 | 64.99 | N |
| ATOM | 894 | CA  | SER | B | 294 | −57.600 | 42.074 | −13.014 | 1.00 | 65.59 | C |
| ATOM | 895 | CB  | SER | B | 294 | −57.289 | 40.586 | −13.096 | 1.00 | 65.66 | C |
| ATOM | 896 | OG  | SER | B | 294 | −55.979 | 40.351 | −13.585 | 1.00 | 65.02 | O |
| ATOM | 897 | C   | SER | B | 294 | −56.990 | 42.734 | −14.231 | 1.00 | 66.16 | C |
| ATOM | 898 | O   | SER | B | 294 | −57.414 | 42.428 | −15.345 | 1.00 | 66.20 | O |

TABLE 14-continued

PCSK9 and AX132 Fab complex x-ray structure

| | | | | | | | | | | |
|---|---|---|---|---|---|---|---|---|---|---|
| ATOM | 899 | N | ARG | B | 295 | −55.970 | 43.597 | −14.041 | 1.00 | 68.26 | N |
| ATOM | 900 | CA | ARG | B | 295 | −55.282 | 44.255 | −15.158 | 1.00 | 68.63 | C |
| ATOM | 901 | CB | ARG | B | 295 | −54.300 | 45.317 | −14.636 | 1.00 | 68.95 | C |
| ATOM | 902 | CG | ARG | B | 295 | −53.713 | 46.206 | −15.724 | 1.00 | 69.57 | C |
| ATOM | 903 | CD | ARG | B | 295 | −52.767 | 47.221 | −15.138 | 1.00 | 70.03 | C |
| ATOM | 904 | NE | ARG | B | 295 | −52.075 | 47.948 | −16.200 | 1.00 | 72.60 | N |
| ATOM | 905 | CZ | ARG | B | 295 | −51.133 | 48.873 | −16.008 | 1.00 | 73.70 | C |
| ATOM | 906 | NH1 | ARG | B | 295 | −50.745 | 49.194 | −14.778 | 1.00 | 74.10 | N |
| ATOM | 907 | NH2 | ARG | B | 295 | −50.562 | 49.472 | −17.047 | 1.00 | 74.62 | N |
| ATOM | 908 | C | ARG | B | 295 | −54.538 | 43.203 | −15.999 | 1.00 | 68.50 | C |
| ATOM | 909 | O | ARG | B | 295 | −54.693 | 43.179 | −17.217 | 1.00 | 68.72 | O |
| ATOM | 910 | N | VAL | B | 296 | −53.761 | 42.326 | −15.333 | 1.00 | 66.22 | N |
| ATOM | 911 | CA | VAL | B | 296 | −52.969 | 41.263 | −15.956 | 1.00 | 65.91 | C |
| ATOM | 912 | CB | VAL | B | 296 | −51.887 | 40.658 | −15.025 | 1.00 | 65.76 | C |
| ATOM | 913 | CG1 | VAL | B | 296 | −52.460 | 39.654 | −14.039 | 1.00 | 64.52 | C |
| ATOM | 914 | CG2 | VAL | B | 296 | −50.778 | 40.031 | −15.833 | 1.00 | 65.21 | C |
| ATOM | 915 | C | VAL | B | 296 | −53.767 | 40.230 | −16.733 | 1.00 | 66.07 | C |
| ATOM | 916 | O | VAL | B | 296 | −53.389 | 39.925 | −17.846 | 1.00 | 66.43 | O |
| ATOM | 917 | N | LEU | B | 297 | −54.848 | 39.698 | −16.172 | 1.00 | 64.68 | N |
| ATOM | 918 | CA | LEU | B | 297 | −55.660 | 38.716 | −16.865 | 1.00 | 64.85 | C |
| ATOM | 919 | CB | LEU | B | 297 | −56.741 | 38.146 | −15.935 | 1.00 | 64.83 | C |
| ATOM | 920 | CG | LEU | B | 297 | −57.642 | 37.028 | −16.456 | 1.00 | 64.77 | C |
| ATOM | 921 | CD1 | LEU | B | 297 | −56.857 | 35.817 | −16.880 | 1.00 | 64.90 | C |
| ATOM | 922 | CD2 | LEU | B | 297 | −58.574 | 36.588 | −15.382 | 1.00 | 65.00 | C |
| ATOM | 923 | C | LEU | B | 297 | −56.255 | 39.385 | −18.090 | 1.00 | 65.24 | C |
| ATOM | 924 | O | LEU | B | 297 | −56.053 | 38.885 | −19.184 | 1.00 | 65.29 | O |
| ATOM | 925 | N | ASN | B | 298 | −56.909 | 40.548 | −17.928 | 1.00 | 65.33 | N |
| ATOM | 926 | CA | ASN | B | 298 | −57.491 | 41.310 | −19.030 | 1.00 | 65.69 | C |
| ATOM | 927 | CB | ASN | B | 298 | −58.071 | 42.609 | −18.523 | 1.00 | 65.52 | C |
| ATOM | 928 | CG | ASN | B | 298 | −59.430 | 42.467 | −17.930 | 1.00 | 65.42 | C |
| ATOM | 929 | OD1 | ASN | B | 298 | −59.889 | 41.361 | −17.614 | 1.00 | 64.87 | O |
| ATOM | 930 | ND2 | ASN | B | 298 | −60.108 | 43.588 | −17.769 | 1.00 | 64.99 | N |
| ATOM | 931 | C | ASN | B | 298 | −56.485 | 41.616 | −20.137 | 1.00 | 66.28 | C |
| ATOM | 932 | O | ASN | B | 298 | −56.849 | 41.546 | −21.314 | 1.00 | 66.62 | O |
| ATOM | 933 | N | ALA | B | 299 | −55.237 | 41.965 | −19.760 | 1.00 | 64.24 | N |
| ATOM | 934 | CA | ALA | B | 299 | −54.166 | 42.287 | −20.679 | 1.00 | 64.70 | C |
| ATOM | 935 | CB | ALA | B | 299 | −52.941 | 42.711 | −19.895 | 1.00 | 64.65 | C |
| ATOM | 936 | C | ALA | B | 299 | −53.842 | 41.079 | −21.527 | 1.00 | 65.39 | C |
| ATOM | 937 | O | ALA | B | 299 | −53.663 | 41.214 | −22.735 | 1.00 | 65.12 | O |
| ATOM | 938 | N | ALA | B | 300 | −53.773 | 39.898 | −20.882 | 1.00 | 66.94 | N |
| ATOM | 939 | CA | ALA | B | 300 | −53.476 | 38.603 | −21.477 | 1.00 | 68.02 | C |
| ATOM | 940 | CB | ALA | B | 300 | −53.287 | 37.563 | −20.386 | 1.00 | 67.68 | C |
| ATOM | 941 | C | ALA | B | 300 | −54.589 | 38.172 | −22.428 | 1.00 | 68.95 | C |
| ATOM | 942 | O | ALA | B | 300 | −54.325 | 37.566 | −23.455 | 1.00 | 69.09 | O |
| ATOM | 943 | N | CYS | B | 301 | −55.824 | 38.491 | −22.105 | 1.00 | 74.05 | N |
| ATOM | 944 | CA | CYS | B | 301 | −56.923 | 38.122 | −22.970 | 1.00 | 75.78 | C |
| ATOM | 945 | CB | CYS | B | 301 | −58.244 | 38.228 | −22.222 | 1.00 | 75.64 | C |
| ATOM | 946 | SG | CYS | B | 301 | −58.381 | 37.099 | −20.810 | 1.00 | 78.21 | S |
| ATOM | 947 | C | CYS | B | 301 | −56.895 | 39.004 | −24.200 | 1.00 | 76.78 | C |
| ATOM | 948 | O | CYS | B | 301 | −57.223 | 38.542 | −25.298 | 1.00 | 77.13 | O |
| ATOM | 949 | N | GLN | B | 302 | −56.467 | 40.269 | −24.019 | 1.00 | 81.35 | N |
| ATOM | 950 | CA | GLN | B | 302 | −56.351 | 41.259 | −25.081 | 1.00 | 82.53 | C |
| ATOM | 951 | CB | GLN | B | 302 | −56.133 | 42.670 | −24.496 | 1.00 | 82.87 | C |
| ATOM | 952 | CG | GLN | B | 302 | −55.970 | 43.814 | −25.507 | 1.00 | 84.29 | C |
| ATOM | 953 | CD | GLN | B | 302 | −54.565 | 44.367 | −25.477 | 1.00 | 87.06 | C |
| ATOM | 954 | OE1 | GLN | B | 302 | −53.874 | 44.430 | −26.512 | 1.00 | 89.24 | O |
| ATOM | 955 | NE2 | GLN | B | 302 | −54.092 | 44.774 | −24.290 | 1.00 | 87.85 | N |
| ATOM | 956 | C | GLN | B | 302 | −55.236 | 40.840 | −26.022 | 1.00 | 82.94 | C |
| ATOM | 957 | O | GLN | B | 302 | −55.491 | 40.793 | −27.216 | 1.00 | 83.12 | O |
| ATOM | 958 | N | ARG | B | 303 | −54.033 | 40.495 | −25.499 | 1.00 | 83.14 | N |
| ATOM | 959 | CA | ARG | B | 303 | −52.901 | 40.065 | −26.319 | 1.00 | 83.88 | C |
| ATOM | 960 | CB | ARG | B | 303 | −51.648 | 39.825 | −25.459 | 1.00 | 84.35 | C |
| ATOM | 961 | CG | ARG | B | 303 | −50.440 | 39.294 | −26.239 | 1.00 | 87.43 | C |
| ATOM | 962 | CD | ARG | B | 303 | −49.226 | 40.219 | −26.312 | 1.00 | 92.85 | C |
| ATOM | 963 | NE | ARG | B | 303 | −48.042 | 39.479 | −26.791 | 1.00 | 96.60 | N |
| ATOM | 964 | CZ | ARG | B | 303 | −46.772 | 39.876 | −26.661 | 1.00 | 98.59 | C |
| ATOM | 965 | NH1 | ARG | B | 303 | −46.484 | 41.029 | −26.055 | 1.00 | 99.18 | N |
| ATOM | 966 | NH2 | ARG | B | 303 | −45.783 | 39.123 | −27.133 | 1.00 | 99.96 | N |
| ATOM | 967 | C | ARG | B | 303 | −53.262 | 38.840 | −27.190 | 1.00 | 83.75 | C |
| ATOM | 968 | O | ARG | B | 303 | −52.950 | 38.815 | −28.387 | 1.00 | 84.03 | O |
| ATOM | 969 | N | LEU | B | 304 | −53.945 | 37.853 | −26.592 | 1.00 | 79.66 | N |
| ATOM | 970 | CA | LEU | B | 304 | −54.403 | 36.617 | −27.227 | 1.00 | 79.27 | C |
| ATOM | 971 | CB | LEU | B | 304 | −55.014 | 35.732 | −26.133 | 1.00 | 79.28 | C |
| ATOM | 972 | CG | LEU | B | 304 | −54.840 | 34.216 | −26.188 | 1.00 | 79.49 | C |
| ATOM | 973 | CD1 | LEU | B | 304 | −53.393 | 33.793 | −26.419 | 1.00 | 79.48 | C |
| ATOM | 974 | CD2 | LEU | B | 304 | −55.271 | 33.617 | −24.883 | 1.00 | 80.20 | C |
| ATOM | 975 | C | LEU | B | 304 | −55.433 | 36.891 | −28.332 | 1.00 | 79.16 | C |
| ATOM | 976 | O | LEU | B | 304 | −55.456 | 36.190 | −29.332 | 1.00 | 78.82 | O |

TABLE 14-continued

PCSK9 and AX132 Fab complex x-ray structure

| ATOM | 977 | N | ALA | B | 305 | −56.274 | 37.915 | −28.150 | 1.00 | 78.62 | N |
|---|---|---|---|---|---|---|---|---|---|---|---|
| ATOM | 978 | CA | ALA | B | 305 | −57.295 | 38.302 | −29.116 | 1.00 | 78.76 | C |
| ATOM | 979 | CB | ALA | B | 305 | −58.250 | 39.295 | −28.483 | 1.00 | 78.61 | C |
| ATOM | 980 | C | ALA | B | 305 | −56.650 | 38.889 | −30.371 | 1.00 | 78.89 | C |
| ATOM | 981 | O | ALA | B | 305 | −57.161 | 38.683 | −31.473 | 1.00 | 78.50 | O |
| ATOM | 982 | N | ARG | B | 306 | −55.513 | 39.607 | −30.182 | 1.00 | 82.77 | N |
| ATOM | 983 | CA | ARG | B | 306 | −54.686 | 40.219 | −31.233 | 1.00 | 83.19 | C |
| ATOM | 984 | CB | ARG | B | 306 | −53.537 | 41.096 | −30.666 | 1.00 | 83.62 | C |
| ATOM | 985 | CG | ARG | B | 306 | −53.958 | 42.091 | −29.584 | 1.00 | 86.19 | C |
| ATOM | 986 | CD | ARG | B | 306 | −53.874 | 43.551 | −29.983 | 1.00 | 90.92 | C |
| ATOM | 987 | NE | ARG | B | 306 | −55.167 | 44.216 | −29.792 | 1.00 | 93.38 | N |
| ATOM | 988 | CZ | ARG | B | 306 | −55.325 | 45.431 | −29.268 | 1.00 | 94.24 | C |
| ATOM | 989 | NH1 | ARG | B | 306 | −54.266 | 46.135 | −28.868 | 1.00 | 94.00 | N |
| ATOM | 990 | NH2 | ARG | B | 306 | −56.545 | 45.950 | −29.137 | 1.00 | 94.74 | N |
| ATOM | 991 | C | ARG | B | 306 | −54.096 | 39.059 | −32.014 | 1.00 | 82.50 | C |
| ATOM | 992 | O | ARG | B | 306 | −54.136 | 39.084 | −33.241 | 1.00 | 82.73 | O |
| ATOM | 993 | N | ALA | B | 307 | −53.612 | 38.009 | −31.307 | 1.00 | 79.21 | N |
| ATOM | 994 | CA | ALA | B | 307 | −53.081 | 36.802 | −31.941 | 1.00 | 78.26 | C |
| ATOM | 995 | CB | ALA | B | 307 | −52.368 | 35.919 | −30.916 | 1.00 | 78.38 | C |
| ATOM | 996 | C | ALA | B | 307 | −54.190 | 36.012 | −32.675 | 1.00 | 77.40 | C |
| ATOM | 997 | O | ALA | B | 307 | −53.981 | 34.858 | −33.022 | 1.00 | 77.54 | O |
| ATOM | 998 | N | GLY | B | 308 | −55.342 | 36.649 | −32.902 | 1.00 | 76.27 | N |
| ATOM | 999 | CA | GLY | B | 308 | −56.490 | 36.098 | −33.620 | 1.00 | 75.00 | C |
| ATOM | 1000 | C | GLY | B | 308 | −57.519 | 35.267 | −32.875 | 1.00 | 74.15 | C |
| ATOM | 1001 | O | GLY | B | 308 | −58.621 | 35.044 | −33.392 | 1.00 | 74.25 | O |
| ATOM | 1002 | N | VAL | B | 309 | −57.170 | 34.798 | −31.665 | 1.00 | 74.16 | N |
| ATOM | 1003 | CA | VAL | B | 309 | −58.005 | 33.952 | −30.798 | 1.00 | 72.79 | C |
| ATOM | 1004 | CB | VAL | B | 309 | −57.222 | 33.470 | −29.545 | 1.00 | 72.94 | C |
| ATOM | 1005 | CG1 | VAL | B | 309 | −57.930 | 32.303 | −28.879 | 1.00 | 73.15 | C |
| ATOM | 1006 | CG2 | VAL | B | 309 | −55.775 | 33.092 | −29.876 | 1.00 | 72.80 | C |
| ATOM | 1007 | C | VAL | B | 309 | −59.361 | 34.588 | −30.403 | 1.00 | 71.77 | C |
| ATOM | 1008 | O | VAL | B | 309 | −59.451 | 35.794 | −30.139 | 1.00 | 71.89 | O |
| ATOM | 1009 | N | VAL | B | 310 | −60.404 | 33.751 | −30.354 | 1.00 | 67.70 | N |
| ATOM | 1010 | CA | VAL | B | 310 | −61.773 | 34.115 | −29.964 | 1.00 | 65.94 | C |
| ATOM | 1011 | CB | VAL | B | 310 | −62.806 | 33.548 | −30.985 | 1.00 | 66.01 | C |
| ATOM | 1012 | CG1 | VAL | B | 310 | −64.228 | 33.545 | −30.432 | 1.00 | 65.64 | C |
| ATOM | 1013 | CG2 | VAL | B | 310 | −62.732 | 34.304 | −32.304 | 1.00 | 64.95 | C |
| ATOM | 1014 | C | VAL | B | 310 | −61.973 | 33.586 | −28.526 | 1.00 | 64.79 | C |
| ATOM | 1015 | O | VAL | B | 310 | −61.924 | 32.389 | −28.309 | 1.00 | 64.43 | O |
| ATOM | 1016 | N | LEU | B | 311 | −62.136 | 34.484 | −27.548 | 1.00 | 65.24 | N |
| ATOM | 1017 | CA | LEU | B | 311 | −62.322 | 34.107 | −26.141 | 1.00 | 64.15 | C |
| ATOM | 1018 | CB | LEU | B | 311 | −61.370 | 34.859 | −25.202 | 1.00 | 63.97 | C |
| ATOM | 1019 | CG | LEU | B | 311 | −59.878 | 34.536 | −25.347 | 1.00 | 64.52 | C |
| ATOM | 1020 | CD1 | LEU | B | 311 | −59.187 | 35.472 | −26.313 | 1.00 | 65.02 | C |
| ATOM | 1021 | CD2 | LEU | B | 311 | −59.174 | 34.704 | −24.056 | 1.00 | 64.24 | C |
| ATOM | 1022 | C | LEU | B | 311 | −63.759 | 34.342 | −25.734 | 1.00 | 63.45 | C |
| ATOM | 1023 | O | LEU | B | 311 | −64.360 | 35.368 | −26.100 | 1.00 | 63.75 | O |
| ATOM | 1024 | N | VAL | B | 312 | −64.337 | 33.365 | −25.016 | 1.00 | 61.15 | N |
| ATOM | 1025 | CA | VAL | B | 312 | −65.720 | 33.450 | −24.529 | 1.00 | 59.55 | C |
| ATOM | 1026 | CB | VAL | B | 312 | −66.698 | 32.496 | −25.240 | 1.00 | 59.24 | C |
| ATOM | 1027 | CG1 | VAL | B | 312 | −68.120 | 32.761 | −24.793 | 1.00 | 58.49 | C |
| ATOM | 1028 | CG2 | VAL | B | 312 | −66.583 | 32.632 | −26.757 | 1.00 | 58.14 | C |
| ATOM | 1029 | C | VAL | B | 312 | −65.665 | 33.287 | −23.028 | 1.00 | 59.03 | C |
| ATOM | 1030 | O | VAL | B | 312 | −64.942 | 32.420 | −22.542 | 1.00 | 59.28 | O |
| ATOM | 1031 | N | THR | B | 313 | −66.364 | 34.159 | −22.298 | 1.00 | 60.50 | N |
| ATOM | 1032 | CA | THR | B | 313 | −66.337 | 34.186 | −20.834 | 1.00 | 59.73 | C |
| ATOM | 1033 | CB | THR | B | 313 | −65.370 | 35.307 | −20.388 | 1.00 | 59.82 | C |
| ATOM | 1034 | OG1 | THR | B | 313 | −65.293 | 35.342 | −18.954 | 1.00 | 61.73 | O |
| ATOM | 1035 | CG2 | THR | B | 313 | −65.781 | 36.664 | −20.889 | 1.00 | 59.54 | C |
| ATOM | 1036 | C | THR | B | 313 | −67.686 | 34.306 | −20.124 | 1.00 | 58.80 | C |
| ATOM | 1037 | O | THR | B | 313 | −68.658 | 34.806 | −20.700 | 1.00 | 58.72 | O |
| ATOM | 1038 | N | ALA | B | 314 | −67.739 | 33.872 | −18.854 | 1.00 | 56.48 | N |
| ATOM | 1039 | CA | ALA | B | 314 | −68.978 | 33.997 | −18.079 | 1.00 | 56.09 | C |
| ATOM | 1040 | CB | ALA | B | 314 | −68.988 | 33.039 | −16.893 | 1.00 | 55.49 | C |
| ATOM | 1041 | C | ALA | B | 314 | −69.050 | 35.440 | −17.593 | 1.00 | 55.97 | C |
| ATOM | 1042 | O | ALA | B | 314 | −68.021 | 36.021 | −17.215 | 1.00 | 56.24 | O |
| ATOM | 1043 | N | ALA | B | 315 | −70.247 | 36.036 | −17.626 | 1.00 | 54.10 | N |
| ATOM | 1044 | CA | ALA | B | 315 | −70.388 | 37.397 | −17.154 | 1.00 | 53.49 | C |
| ATOM | 1045 | CB | ALA | B | 315 | −71.734 | 37.952 | −17.549 | 1.00 | 53.36 | C |
| ATOM | 1046 | C | ALA | B | 315 | −70.200 | 37.440 | −15.627 | 1.00 | 53.40 | C |
| ATOM | 1047 | O | ALA | B | 315 | −69.737 | 38.460 | −15.106 | 1.00 | 53.51 | O |
| ATOM | 1048 | N | GLY | B | 316 | −70.496 | 36.326 | −14.944 | 1.00 | 50.96 | N |
| ATOM | 1049 | CA | GLY | B | 316 | −70.407 | 36.221 | −13.500 | 1.00 | 51.09 | C |
| ATOM | 1050 | C | GLY | B | 316 | −71.795 | 36.017 | −12.933 | 1.00 | 51.70 | C |
| ATOM | 1051 | O | GLY | B | 316 | −72.798 | 36.418 | −13.540 | 1.00 | 51.47 | O |
| ATOM | 1052 | N | ASN | B | 317 | −71.873 | 35.369 | −11.775 | 1.00 | 53.82 | N |
| ATOM | 1053 | CA | ASN | B | 317 | −73.149 | 35.071 | −11.126 | 1.00 | 54.21 | C |
| ATOM | 1054 | CB | ASN | B | 317 | −73.183 | 33.588 | −10.795 | 1.00 | 53.67 | C |

TABLE 14-continued

PCSK9 and AX132 Fab complex x-ray structure

| ATOM | 1055 | CG | ASN | B | 317 | −72.945 | 32.681 | −11.969 | 1.00 | 53.09 | C |
|---|---|---|---|---|---|---|---|---|---|---|---|
| ATOM | 1056 | OD1 | ASN | B | 317 | −73.258 | 32.996 | −13.112 | 1.00 | 52.07 | O |
| ATOM | 1057 | ND2 | ASN | B | 317 | −72.392 | 31.521 | −11.710 | 1.00 | 53.94 | N |
| ATOM | 1058 | C | ASN | B | 317 | −73.322 | 35.916 | −9.866 | 1.00 | 55.00 | C |
| ATOM | 1059 | O | ASN | B | 317 | −73.792 | 35.435 | −8.843 | 1.00 | 55.03 | O |
| ATOM | 1060 | N | PHE | B | 318 | −72.957 | 37.174 | −9.939 | 1.00 | 57.87 | N |
| ATOM | 1061 | CA | PHE | B | 318 | −73.018 | 38.000 | −8.759 | 1.00 | 59.18 | C |
| ATOM | 1062 | CB | PHE | B | 318 | −71.639 | 38.625 | −8.558 | 1.00 | 59.07 | C |
| ATOM | 1063 | CG | PHE | B | 318 | −70.543 | 37.591 | −8.502 | 1.00 | 60.43 | C |
| ATOM | 1064 | CD1 | PHE | B | 318 | −70.408 | 36.753 | −7.397 | 1.00 | 60.99 | C |
| ATOM | 1065 | CE1 | PHE | B | 318 | −69.408 | 35.784 | −7.353 | 1.00 | 61.38 | C |
| ATOM | 1066 | CZ | PHE | B | 318 | −68.543 | 35.638 | −8.418 | 1.00 | 62.04 | C |
| ATOM | 1067 | CE2 | PHE | B | 318 | −68.652 | 36.469 | −9.513 | 1.00 | 61.99 | C |
| ATOM | 1068 | CD2 | PHE | B | 318 | −69.664 | 37.433 | −9.562 | 1.00 | 61.64 | C |
| ATOM | 1069 | C | PHE | B | 318 | −74.093 | 39.053 | −8.750 | 1.00 | 59.93 | C |
| ATOM | 1070 | O | PHE | B | 318 | −74.101 | 39.886 | −7.840 | 1.00 | 60.27 | O |
| ATOM | 1071 | N | ARG | B | 319 | −75.009 | 39.028 | −9.748 | 1.00 | 62.41 | N |
| ATOM | 1072 | CA | ARG | B | 319 | −76.081 | 40.020 | −9.913 | 1.00 | 63.19 | C |
| ATOM | 1073 | CB | ARG | B | 319 | −77.305 | 39.725 | −9.016 | 1.00 | 63.23 | C |
| ATOM | 1074 | CG | ARG | B | 319 | −78.540 | 40.496 | −9.473 | 1.00 | 64.48 | C |
| ATOM | 1075 | CD | ARG | B | 319 | −79.855 | 39.992 | −8.921 | 1.00 | 67.70 | C |
| ATOM | 1076 | NE | ARG | B | 319 | −80.960 | 40.830 | −9.410 | 1.00 | 71.37 | N |
| ATOM | 1077 | CZ | ARG | B | 319 | −82.248 | 40.501 | −9.322 | 1.00 | 72.76 | C |
| ATOM | 1078 | NH1 | ARG | B | 319 | −82.612 | 39.345 | −8.777 | 1.00 | 73.52 | N |
| ATOM | 1079 | NH2 | ARG | B | 319 | −83.183 | 41.314 | −9.813 | 1.00 | 72.41 | N |
| ATOM | 1080 | C | ARG | B | 319 | −75.479 | 41.435 | −9.704 | 1.00 | 63.42 | C |
| ATOM | 1081 | O | ARG | B | 319 | −76.033 | 42.268 | −8.989 | 1.00 | 63.73 | O |
| ATOM | 1082 | N | ASP | B | 320 | −74.312 | 41.662 | −10.320 | 1.00 | 60.42 | N |
| ATOM | 1083 | CA | ASP | B | 320 | −73.530 | 42.873 | −10.230 | 1.00 | 60.55 | C |
| ATOM | 1084 | CB | ASP | B | 320 | −72.304 | 42.552 | −9.364 | 1.00 | 60.60 | C |
| ATOM | 1085 | CG | ASP | B | 320 | −71.544 | 43.741 | −8.807 | 1.00 | 61.89 | C |
| ATOM | 1086 | OD1 | ASP | B | 320 | −72.018 | 44.900 | −8.997 | 1.00 | 63.22 | O |
| ATOM | 1087 | OD2 | ASP | B | 320 | −70.464 | 43.523 | −8.172 | 1.00 | 63.66 | O |
| ATOM | 1088 | C | ASP | B | 320 | −73.091 | 43.307 | −11.623 | 1.00 | 60.89 | C |
| ATOM | 1089 | O | ASP | B | 320 | −73.323 | 42.608 | −12.596 | 1.00 | 60.80 | O |
| ATOM | 1090 | N | ASP | B | 321 | −72.457 | 44.456 | −11.723 | 1.00 | 62.47 | N |
| ATOM | 1091 | CA | ASP | B | 321 | −71.955 | 44.980 | −12.973 | 1.00 | 63.25 | C |
| ATOM | 1092 | CB | ASP | B | 321 | −71.748 | 46.490 | −12.827 | 1.00 | 63.52 | C |
| ATOM | 1093 | CG | ASP | B | 321 | −70.868 | 47.151 | −13.863 | 1.00 | 66.23 | C |
| ATOM | 1094 | OD1 | ASP | B | 321 | −70.991 | 46.787 | −15.099 | 1.00 | 68.25 | O |
| ATOM | 1095 | OD2 | ASP | B | 321 | −70.047 | 48.029 | −13.466 | 1.00 | 69.51 | O |
| ATOM | 1096 | C | ASP | B | 321 | −70.664 | 44.203 | −13.367 | 1.00 | 63.26 | C |
| ATOM | 1097 | O | ASP | B | 321 | −69.640 | 44.266 | −12.668 | 1.00 | 63.00 | O |
| ATOM | 1098 | N | ALA | B | 322 | −70.742 | 43.466 | −14.505 | 1.00 | 63.34 | N |
| ATOM | 1099 | CA | ALA | B | 322 | −69.678 | 42.617 | −15.058 | 1.00 | 63.47 | C |
| ATOM | 1100 | CB | ALA | B | 322 | −70.135 | 41.973 | −16.351 | 1.00 | 63.32 | C |
| ATOM | 1101 | C | ALA | B | 322 | −68.329 | 43.277 | −15.249 | 1.00 | 63.71 | C |
| ATOM | 1102 | O | ALA | B | 322 | −67.333 | 42.599 | −15.461 | 1.00 | 63.80 | O |
| ATOM | 1103 | N | CYS | B | 323 | −68.293 | 44.587 | −15.157 | 1.00 | 65.81 | N |
| ATOM | 1104 | CA | CYS | B | 323 | −67.083 | 45.376 | −15.328 | 1.00 | 66.30 | C |
| ATOM | 1105 | CB | CYS | B | 323 | −67.449 | 46.810 | −15.689 | 1.00 | 66.41 | C |
| ATOM | 1106 | SG | CYS | B | 323 | −68.421 | 46.951 | −17.215 | 1.00 | 71.16 | S |
| ATOM | 1107 | C | CYS | B | 323 | −66.222 | 45.326 | −14.114 | 1.00 | 65.76 | C |
| ATOM | 1108 | O | CYS | B | 323 | −65.083 | 45.788 | −14.154 | 1.00 | 66.03 | O |
| ATOM | 1109 | N | LEU | B | 324 | −66.755 | 44.785 | −13.022 | 1.00 | 60.42 | N |
| ATOM | 1110 | CA | LEU | B | 324 | −66.002 | 44.698 | −11.774 | 1.00 | 60.17 | C |
| ATOM | 1111 | CB | LEU | B | 324 | −66.902 | 44.989 | −10.549 | 1.00 | 59.89 | C |
| ATOM | 1112 | CG | LEU | B | 324 | −67.731 | 46.250 | −10.542 | 1.00 | 57.86 | C |
| ATOM | 1113 | CD1 | LEU | B | 324 | −68.629 | 46.254 | −9.347 | 1.00 | 56.82 | C |
| ATOM | 1114 | CD2 | LEU | B | 324 | −66.874 | 47.477 | −10.635 | 1.00 | 54.79 | C |
| ATOM | 1115 | C | LEU | B | 324 | −65.353 | 43.332 | −11.636 | 1.00 | 60.54 | C |
| ATOM | 1116 | O | LEU | B | 324 | −64.750 | 43.051 | −10.593 | 1.00 | 60.71 | O |
| ATOM | 1117 | N | TYR | B | 325 | −65.481 | 42.497 | −12.694 | 1.00 | 60.77 | N |
| ATOM | 1118 | CA | TYR | B | 325 | −64.988 | 41.133 | −12.770 | 1.00 | 61.44 | C |
| ATOM | 1119 | CB | TYR | B | 325 | −66.184 | 40.173 | −12.748 | 1.00 | 61.31 | C |
| ATOM | 1120 | CG | TYR | B | 325 | −67.056 | 40.381 | −11.534 | 1.00 | 61.96 | C |
| ATOM | 1121 | CD1 | TYR | B | 325 | −66.831 | 39.667 | −10.359 | 1.00 | 62.39 | C |
| ATOM | 1122 | CE1 | TYR | B | 325 | −67.591 | 39.901 | −9.216 | 1.00 | 63.69 | C |
| ATOM | 1123 | CZ | TYR | B | 325 | −68.614 | 40.841 | −9.250 | 1.00 | 64.04 | C |
| ATOM | 1124 | OH | TYR | B | 325 | −69.381 | 41.077 | −8.135 | 1.00 | 65.21 | O |
| ATOM | 1125 | CE2 | TYR | B | 325 | −68.855 | 41.563 | −10.408 | 1.00 | 63.14 | C |
| ATOM | 1126 | CD2 | TYR | B | 325 | −68.082 | 41.324 | −11.542 | 1.00 | 62.84 | C |
| ATOM | 1127 | C | TYR | B | 325 | −64.132 | 40.863 | −13.994 | 1.00 | 62.04 | C |
| ATOM | 1128 | O | TYR | B | 325 | −64.366 | 41.428 | −15.044 | 1.00 | 61.85 | O |
| ATOM | 1129 | N | SER | B | 326 | −63.156 | 39.989 | −13.873 | 1.00 | 62.89 | N |
| ATOM | 1130 | CA | SER | B | 326 | −62.288 | 39.610 | −14.988 | 1.00 | 63.61 | C |
| ATOM | 1131 | CB | SER | B | 326 | −60.863 | 40.095 | −14.774 | 1.00 | 63.85 | C |
| ATOM | 1132 | OG | SER | B | 326 | −60.802 | 41.499 | −14.935 | 1.00 | 64.07 | O |

TABLE 14-continued

PCSK9 and AX132 Fab complex x-ray structure

| ATOM | 1133 | C   | SER | B | 326 | −62.317 | 38.100 | −15.085 | 1.00 | 63.80 | C |
|------|------|-----|-----|---|-----|---------|--------|---------|------|-------|---|
| ATOM | 1134 | O   | SER | B | 326 | −62.452 | 37.444 | −14.051 | 1.00 | 64.86 | O |
| ATOM | 1135 | N   | PRO | B | 327 | −62.235 | 37.505 | −16.286 | 1.00 | 65.20 | N |
| ATOM | 1136 | CA  | PRO | B | 327 | −62.054 | 38.141 | −17.592 | 1.00 | 64.67 | C |
| ATOM | 1137 | CB  | PRO | B | 327 | −61.389 | 37.029 | −18.418 | 1.00 | 64.01 | C |
| ATOM | 1138 | CG  | PRO | B | 327 | −61.990 | 35.765 | −17.876 | 1.00 | 65.29 | C |
| ATOM | 1139 | CD  | PRO | B | 327 | −62.281 | 36.032 | −16.410 | 1.00 | 64.99 | C |
| ATOM | 1140 | C   | PRO | B | 327 | −63.287 | 38.808 | −18.223 | 1.00 | 64.37 | C |
| ATOM | 1141 | O   | PRO | B | 327 | −63.144 | 39.327 | −19.323 | 1.00 | 64.00 | O |
| ATOM | 1142 | N   | ALA | B | 328 | −64.462 | 38.849 | −17.542 | 1.00 | 62.54 | N |
| ATOM | 1143 | CA  | ALA | B | 328 | −65.677 | 39.500 | −18.072 | 1.00 | 62.61 | C |
| ATOM | 1144 | CB  | ALA | B | 328 | −66.788 | 39.500 | −17.029 | 1.00 | 62.46 | C |
| ATOM | 1145 | C   | ALA | B | 328 | −65.443 | 40.936 | −18.573 | 1.00 | 62.77 | C |
| ATOM | 1146 | O   | ALA | B | 328 | −65.986 | 41.317 | −19.615 | 1.00 | 62.83 | O |
| ATOM | 1147 | N   | SER | B | 329 | −64.635 | 41.719 | −17.839 | 1.00 | 62.16 | N |
| ATOM | 1148 | CA  | SER | B | 329 | −64.330 | 43.111 | −18.152 | 1.00 | 62.02 | C |
| ATOM | 1149 | CB  | SER | B | 329 | −63.787 | 43.835 | −16.930 | 1.00 | 61.96 | C |
| ATOM | 1150 | OG  | SER | B | 329 | −62.597 | 43.229 | −16.448 | 1.00 | 61.98 | O |
| ATOM | 1151 | C   | SER | B | 329 | −63.422 | 43.347 | −19.347 | 1.00 | 62.28 | C |
| ATOM | 1152 | O   | SER | B | 329 | −63.419 | 44.473 | −19.854 | 1.00 | 62.32 | O |
| ATOM | 1153 | N   | ALA | B | 330 | −62.636 | 42.327 | −19.796 | 1.00 | 65.17 | N |
| ATOM | 1154 | CA  | ALA | B | 330 | −61.765 | 42.458 | −20.969 | 1.00 | 65.63 | C |
| ATOM | 1155 | CB  | ALA | B | 330 | −60.979 | 41.177 | −21.200 | 1.00 | 65.46 | C |
| ATOM | 1156 | C   | ALA | B | 330 | −62.722 | 42.749 | −22.153 | 1.00 | 66.41 | C |
| ATOM | 1157 | O   | ALA | B | 330 | −63.680 | 41.992 | −22.382 | 1.00 | 66.58 | O |
| ATOM | 1158 | N   | PRO | B | 331 | −62.585 | 43.907 | −22.844 | 1.00 | 73.00 | N |
| ATOM | 1159 | CA  | PRO | B | 331 | −63.554 | 44.219 | −23.923 | 1.00 | 73.50 | C |
| ATOM | 1160 | CB  | PRO | B | 331 | −63.334 | 45.714 | −24.166 | 1.00 | 73.46 | C |
| ATOM | 1161 | CG  | PRO | B | 331 | −61.916 | 45.944 | −23.767 | 1.00 | 72.99 | C |
| ATOM | 1162 | CD  | PRO | B | 331 | −61.573 | 44.978 | −22.687 | 1.00 | 72.92 | C |
| ATOM | 1163 | C   | PRO | B | 331 | −63.366 | 43.369 | −25.188 | 1.00 | 73.88 | C |
| ATOM | 1164 | O   | PRO | B | 331 | −64.265 | 43.259 | −26.028 | 1.00 | 74.31 | O |
| ATOM | 1165 | N   | GLU | B | 332 | −62.191 | 42.757 | −25.294 | 1.00 | 77.27 | N |
| ATOM | 1166 | CA  | GLU | B | 332 | −61.781 | 41.912 | −26.398 | 1.00 | 77.53 | C |
| ATOM | 1167 | CB  | GLU | B | 332 | −60.258 | 41.718 | −26.367 | 1.00 | 78.10 | C |
| ATOM | 1168 | CG  | GLU | B | 332 | −59.474 | 43.022 | −26.258 | 1.00 | 81.67 | C |
| ATOM | 1169 | CD  | GLU | B | 332 | −59.396 | 43.680 | −24.879 | 1.00 | 86.35 | C |
| ATOM | 1170 | OE1 | GLU | B | 332 | −59.799 | 43.043 | −23.874 | 1.00 | 86.76 | O |
| ATOM | 1171 | OE2 | GLU | B | 332 | −58.924 | 44.841 | −24.807 | 1.00 | 88.63 | O |
| ATOM | 1172 | C   | GLU | B | 332 | −62.503 | 40.562 | −26.373 | 1.00 | 76.52 | C |
| ATOM | 1173 | O   | GLU | B | 332 | −62.771 | 39.986 | −27.436 | 1.00 | 77.06 | O |
| ATOM | 1174 | N   | VAL | B | 333 | −62.818 | 40.060 | −25.164 | 1.00 | 70.74 | N |
| ATOM | 1175 | CA  | VAL | B | 333 | −63.481 | 38.769 | −24.964 | 1.00 | 68.74 | C |
| ATOM | 1176 | CB  | VAL | B | 333 | −63.067 | 38.120 | −23.622 | 1.00 | 68.83 | C |
| ATOM | 1177 | CG1 | VAL | B | 333 | −61.556 | 38.105 | −23.460 | 1.00 | 68.45 | C |
| ATOM | 1178 | CG2 | VAL | B | 333 | −63.708 | 38.838 | −22.453 | 1.00 | 68.60 | C |
| ATOM | 1179 | C   | VAL | B | 333 | −64.993 | 38.873 | −25.115 | 1.00 | 67.53 | C |
| ATOM | 1180 | O   | VAL | B | 333 | −65.553 | 39.955 | −24.914 | 1.00 | 67.70 | O |
| ATOM | 1181 | N   | ILE | B | 334 | −65.654 | 37.763 | −25.476 | 1.00 | 62.01 | N |
| ATOM | 1182 | CA  | ILE | B | 334 | −67.101 | 37.785 | −25.621 | 1.00 | 60.41 | C |
| ATOM | 1183 | CB  | ILE | B | 334 | −67.598 | 36.945 | −26.826 | 1.00 | 60.26 | C |
| ATOM | 1184 | CG1 | ILE | B | 334 | −67.270 | 37.654 | −28.123 | 1.00 | 60.39 | C |
| ATOM | 1185 | CD1 | ILE | B | 334 | −66.925 | 36.721 | −29.207 | 1.00 | 62.55 | C |
| ATOM | 1186 | CG2 | ILE | B | 334 | −69.098 | 36.676 | −26.764 | 1.00 | 59.89 | C |
| ATOM | 1187 | C   | ILE | B | 334 | −67.676 | 37.401 | −24.267 | 1.00 | 59.53 | C |
| ATOM | 1188 | O   | ILE | B | 334 | −67.498 | 36.266 | −23.833 | 1.00 | 59.55 | O |
| ATOM | 1189 | N   | THR | B | 335 | −68.313 | 38.373 | −23.578 | 1.00 | 57.48 | N |
| ATOM | 1190 | CA  | THR | B | 335 | −68.887 | 38.225 | −22.242 | 1.00 | 56.89 | C |
| ATOM | 1191 | CB  | THR | B | 335 | −68.621 | 39.466 | −21.384 | 1.00 | 56.86 | C |
| ATOM | 1192 | OG1 | THR | B | 335 | −67.231 | 39.840 | −21.464 | 1.00 | 57.03 | O |
| ATOM | 1193 | CG2 | THR | B | 335 | −69.005 | 39.267 | −19.945 | 1.00 | 56.65 | C |
| ATOM | 1194 | C   | THR | B | 335 | −70.320 | 37.833 | −22.344 | 1.00 | 56.75 | C |
| ATOM | 1195 | O   | THR | B | 335 | −71.130 | 38.558 | −22.901 | 1.00 | 56.71 | O |
| ATOM | 1196 | N   | VAL | B | 336 | −70.640 | 36.665 | −21.808 | 1.00 | 55.91 | N |
| ATOM | 1197 | CA  | VAL | B | 336 | −71.988 | 36.106 | −21.868 | 1.00 | 55.24 | C |
| ATOM | 1198 | CB  | VAL | B | 336 | −71.927 | 34.722 | −22.551 | 1.00 | 55.29 | C |
| ATOM | 1199 | CG1 | VAL | B | 336 | −73.309 | 34.265 | −22.994 | 1.00 | 55.31 | C |
| ATOM | 1200 | CG2 | VAL | B | 336 | −70.941 | 34.717 | −23.721 | 1.00 | 55.00 | C |
| ATOM | 1201 | C   | VAL | B | 336 | −72.746 | 36.041 | −20.532 | 1.00 | 55.10 | C |
| ATOM | 1202 | O   | VAL | B | 336 | −72.345 | 35.348 | −19.588 | 1.00 | 54.55 | O |
| ATOM | 1203 | N   | GLY | B | 337 | −73.860 | 36.744 | −20.491 | 1.00 | 54.20 | N |
| ATOM | 1204 | CA  | GLY | B | 337 | −74.765 | 36.737 | −19.350 | 1.00 | 54.32 | C |
| ATOM | 1205 | C   | GLY | B | 337 | −75.665 | 35.524 | −19.514 | 1.00 | 54.86 | C |
| ATOM | 1206 | O   | GLY | B | 337 | −75.630 | 34.863 | −20.568 | 1.00 | 54.77 | O |
| ATOM | 1207 | N   | ALA | B | 338 | −76.478 | 35.199 | −18.499 | 1.00 | 55.32 | N |
| ATOM | 1208 | CA  | ALA | B | 338 | −77.341 | 34.029 | −18.609 | 1.00 | 55.65 | C |
| ATOM | 1209 | CB  | ALA | B | 338 | −76.927 | 32.989 | −17.593 | 1.00 | 55.37 | C |
| ATOM | 1210 | C   | ALA | B | 338 | −78.802 | 34.362 | −18.439 | 1.00 | 56.20 | C |

TABLE 14-continued

PCSK9 and AX132 Fab complex x-ray structure

| ATOM | 1211 | O | ALA | B | 338 | −79.153 | 35.135 | −17.537 | 1.00 | 56.29 | O |
|---|---|---|---|---|---|---|---|---|---|---|---|
| ATOM | 1212 | N | THR | B | 339 | −79.660 | 33.766 | −19.304 | 1.00 | 57.13 | N |
| ATOM | 1213 | CA | THR | B | 339 | −81.121 | 33.916 | −19.264 | 1.00 | 57.44 | C |
| ATOM | 1214 | CB | THR | B | 339 | −81.695 | 34.682 | −20.460 | 1.00 | 57.24 | C |
| ATOM | 1215 | OG1 | THR | B | 339 | −81.399 | 33.995 | −21.678 | 1.00 | 56.49 | O |
| ATOM | 1216 | CG2 | THR | B | 339 | −81.275 | 36.110 | −20.491 | 1.00 | 57.07 | C |
| ATOM | 1217 | C | THR | B | 339 | −81.804 | 32.556 | −19.161 | 1.00 | 58.11 | C |
| ATOM | 1218 | O | THR | B | 339 | −81.255 | 31.538 | −19.589 | 1.00 | 58.12 | O |
| ATOM | 1219 | N | ASN | B | 340 | −83.013 | 32.544 | −18.609 | 1.00 | 61.87 | N |
| ATOM | 1220 | CA | ASN | B | 340 | −83.762 | 31.311 | −18.486 | 1.00 | 62.65 | C |
| ATOM | 1221 | CB | ASN | B | 340 | −84.601 | 31.300 | −17.235 | 1.00 | 62.41 | C |
| ATOM | 1222 | CG | ASN | B | 340 | −85.516 | 32.464 | −17.167 | 1.00 | 62.27 | C |
| ATOM | 1223 | OD1 | ASN | B | 340 | −86.269 | 32.767 | −18.103 | 1.00 | 60.60 | O |
| ATOM | 1224 | ND2 | ASN | B | 340 | −85.447 | 33.145 | −16.043 | 1.00 | 62.99 | N |
| ATOM | 1225 | C | ASN | B | 340 | −84.609 | 31.019 | −19.714 | 1.00 | 63.43 | C |
| ATOM | 1226 | O | ASN | B | 340 | −84.453 | 31.674 | −20.758 | 1.00 | 63.12 | O |
| ATOM | 1227 | N | ALA | B | 341 | −85.494 | 29.995 | −19.584 | 1.00 | 66.06 | N |
| ATOM | 1228 | CA | ALA | B | 341 | −86.365 | 29.522 | −20.647 | 1.00 | 67.26 | C |
| ATOM | 1229 | CB | ALA | B | 341 | −87.083 | 28.264 | −20.224 | 1.00 | 66.99 | C |
| ATOM | 1230 | C | ALA | B | 341 | −87.329 | 30.561 | −21.175 | 1.00 | 68.26 | C |
| ATOM | 1231 | O | ALA | B | 341 | −87.692 | 30.499 | −22.356 | 1.00 | 68.61 | O |
| ATOM | 1232 | N | GLN | B | 342 | −87.703 | 31.537 | −20.315 | 1.00 | 69.30 | N |
| ATOM | 1233 | CA | GLN | B | 342 | −88.617 | 32.635 | −20.628 | 1.00 | 70.34 | C |
| ATOM | 1234 | CB | GLN | B | 342 | −89.531 | 32.965 | −19.440 | 1.00 | 70.57 | C |
| ATOM | 1235 | CG | GLN | B | 342 | −90.370 | 31.805 | −18.937 | 1.00 | 72.94 | C |
| ATOM | 1236 | CD | GLN | B | 342 | −89.597 | 30.971 | −17.945 | 1.00 | 76.85 | C |
| ATOM | 1237 | OE1 | GLN | B | 342 | −89.030 | 31.481 | −16.957 | 1.00 | 77.98 | O |
| ATOM | 1238 | NE2 | GLN | B | 342 | −89.547 | 29.660 | −18.195 | 1.00 | 77.87 | N |
| ATOM | 1239 | C | GLN | B | 342 | −87.824 | 33.860 | −21.006 | 1.00 | 70.57 | C |
| ATOM | 1240 | O | GLN | B | 342 | −88.361 | 34.961 | −20.998 | 1.00 | 70.82 | O |
| ATOM | 1241 | N | ASP | B | 343 | −86.543 | 33.673 | −21.330 | 1.00 | 71.09 | N |
| ATOM | 1242 | CA | ASP | B | 343 | −85.611 | 34.727 | −21.727 | 1.00 | 71.24 | C |
| ATOM | 1243 | CB | ASP | B | 343 | −85.893 | 35.218 | −23.147 | 1.00 | 71.51 | C |
| ATOM | 1244 | CG | ASP | B | 343 | −85.819 | 34.036 | −24.078 | 1.00 | 74.17 | C |
| ATOM | 1245 | OD1 | ASP | B | 343 | −84.666 | 33.581 | −24.392 | 1.00 | 76.97 | O |
| ATOM | 1246 | OD2 | ASP | B | 343 | −86.896 | 33.516 | −24.459 | 1.00 | 78.55 | O |
| ATOM | 1247 | C | ASP | B | 343 | −85.408 | 35.815 | −20.705 | 1.00 | 70.72 | C |
| ATOM | 1248 | O | ASP | B | 343 | −85.076 | 36.951 | −21.036 | 1.00 | 70.59 | O |
| ATOM | 1249 | N | GLN | B | 344 | −85.570 | 35.442 | −19.442 | 1.00 | 67.52 | N |
| ATOM | 1250 | CA | GLN | B | 344 | −85.422 | 36.350 | −18.324 | 1.00 | 67.56 | C |
| ATOM | 1251 | CB | GLN | B | 344 | −86.637 | 36.247 | −17.404 | 1.00 | 67.61 | C |
| ATOM | 1252 | CG | GLN | B | 344 | −87.911 | 36.741 | −18.088 | 1.00 | 68.31 | C |
| ATOM | 1253 | CD | GLN | B | 344 | −87.688 | 38.051 | −18.840 | 1.00 | 70.11 | C |
| ATOM | 1254 | OE1 | GLN | B | 344 | −87.908 | 38.154 | −20.067 | 1.00 | 68.92 | O |
| ATOM | 1255 | NE2 | GLN | B | 344 | −87.223 | 39.082 | −18.113 | 1.00 | 71.30 | N |
| ATOM | 1256 | C | GLN | B | 344 | −84.085 | 36.159 | −17.625 | 1.00 | 67.41 | C |
| ATOM | 1257 | O | GLN | B | 344 | −83.588 | 35.027 | −17.597 | 1.00 | 67.29 | O |
| ATOM | 1258 | N | PRO | B | 345 | −83.429 | 37.242 | −17.131 | 1.00 | 66.24 | N |
| ATOM | 1259 | CA | PRO | B | 345 | −82.117 | 37.052 | −16.496 | 1.00 | 66.31 | C |
| ATOM | 1260 | CB | PRO | B | 345 | −81.731 | 38.445 | −16.016 | 1.00 | 66.17 | C |
| ATOM | 1261 | CG | PRO | B | 345 | −82.587 | 39.369 | −16.736 | 1.00 | 66.05 | C |
| ATOM | 1262 | CD | PRO | B | 345 | −83.849 | 38.653 | −17.080 | 1.00 | 66.08 | C |
| ATOM | 1263 | C | PRO | B | 345 | −82.240 | 36.042 | −15.371 | 1.00 | 66.57 | C |
| ATOM | 1264 | O | PRO | B | 345 | −83.214 | 36.098 | −14.591 | 1.00 | 66.73 | O |
| ATOM | 1265 | N | VAL | B | 346 | −81.297 | 35.076 | −15.336 | 1.00 | 67.36 | N |
| ATOM | 1266 | CA | VAL | B | 346 | −81.278 | 33.987 | −14.364 | 1.00 | 67.43 | C |
| ATOM | 1267 | CB | VAL | B | 346 | −80.250 | 32.896 | −14.756 | 1.00 | 67.44 | C |
| ATOM | 1268 | CG1 | VAL | B | 346 | −80.161 | 31.789 | −13.712 | 1.00 | 67.51 | C |
| ATOM | 1269 | CG2 | VAL | B | 346 | −80.601 | 32.291 | −16.095 | 1.00 | 67.50 | C |
| ATOM | 1270 | C | VAL | B | 346 | −81.105 | 34.456 | −12.936 | 1.00 | 67.73 | C |
| ATOM | 1271 | O | VAL | B | 346 | −80.188 | 35.216 | −12.646 | 1.00 | 67.53 | O |
| ATOM | 1272 | N | THR | B | 347 | −81.994 | 33.994 | −12.041 | 1.00 | 73.64 | N |
| ATOM | 1273 | CA | THR | B | 347 | −81.890 | 34.274 | −10.610 | 1.00 | 74.69 | C |
| ATOM | 1274 | CB | THR | B | 347 | −83.182 | 34.813 | −10.024 | 1.00 | 74.30 | C |
| ATOM | 1275 | OG1 | THR | B | 347 | −83.446 | 36.056 | −10.662 | 1.00 | 74.34 | O |
| ATOM | 1276 | CG2 | THR | B | 347 | −83.080 | 35.038 | −8.534 | 1.00 | 74.12 | C |
| ATOM | 1277 | C | THR | B | 347 | −81.330 | 32.997 | −9.955 | 1.00 | 75.60 | C |
| ATOM | 1278 | O | THR | B | 347 | −81.999 | 31.954 | −9.960 | 1.00 | 76.22 | O |
| ATOM | 1279 | N | LEU | B | 348 | −80.064 | 33.083 | −9.471 | 1.00 | 80.17 | N |
| ATOM | 1280 | CA | LEU | B | 348 | −79.281 | 32.008 | −8.826 | 1.00 | 80.74 | C |
| ATOM | 1281 | CB | LEU | B | 348 | −77.863 | 31.912 | −9.460 | 1.00 | 80.52 | C |
| ATOM | 1282 | CG | LEU | B | 348 | −77.772 | 31.673 | −10.954 | 1.00 | 80.04 | C |
| ATOM | 1283 | CD1 | LEU | B | 348 | −76.563 | 32.385 | −11.548 | 1.00 | 78.71 | C |
| ATOM | 1284 | CD2 | LEU | B | 348 | −77.802 | 30.199 | −11.271 | 1.00 | 80.04 | C |
| ATOM | 1285 | C | LEU | B | 348 | −79.159 | 32.383 | −7.349 | 1.00 | 81.10 | C |
| ATOM | 1286 | O | LEU | B | 348 | −78.241 | 33.132 | −6.972 | 1.00 | 81.74 | O |
| ATOM | 1287 | N | GLY | B | 349 | −80.108 | 31.914 | −6.545 | 1.00 | 80.68 | N |
| ATOM | 1288 | CA | GLY | B | 349 | −80.145 | 32.243 | −5.127 | 1.00 | 80.71 | C |

TABLE 14-continued

PCSK9 and AX132 Fab complex x-ray structure

| ATOM | 1289 | C | GLY | B | 349 | −80.483 | 33.700 | −4.864 | 1.00 | 80.56 | C |
|---|---|---|---|---|---|---|---|---|---|---|---|
| ATOM | 1290 | O | GLY | B | 349 | −81.431 | 34.254 | −5.447 | 1.00 | 80.70 | O |
| ATOM | 1291 | N | THR | B | 350 | −79.697 | 34.337 | −3.978 | 1.00 | 80.62 | N |
| ATOM | 1292 | CA | THR | B | 350 | −79.888 | 35.763 | −3.619 | 1.00 | 80.69 | C |
| ATOM | 1293 | CB | THR | B | 350 | −79.344 | 36.046 | −2.201 | 1.00 | 80.96 | C |
| ATOM | 1294 | OG1 | THR | B | 350 | −77.978 | 35.604 | −2.099 | 1.00 | 82.21 | O |
| ATOM | 1295 | CG2 | THR | B | 350 | −80.205 | 35.381 | −1.117 | 1.00 | 81.74 | C |
| ATOM | 1296 | C | THR | B | 350 | −79.277 | 36.677 | −4.689 | 1.00 | 79.69 | C |
| ATOM | 1297 | O | THR | B | 350 | −79.548 | 37.877 | −4.748 | 1.00 | 79.91 | O |
| ATOM | 1298 | N | LEU | B | 351 | −78.453 | 36.061 | −5.531 | 1.00 | 74.98 | N |
| ATOM | 1299 | CA | LEU | B | 351 | −77.746 | 36.657 | −6.628 | 1.00 | 73.84 | C |
| ATOM | 1300 | CB | LEU | B | 351 | −76.284 | 36.235 | −6.512 | 1.00 | 74.24 | C |
| ATOM | 1301 | CG | LEU | B | 351 | −75.557 | 36.676 | −5.255 | 1.00 | 74.58 | C |
| ATOM | 1302 | CD1 | LEU | B | 351 | −74.238 | 36.009 | −5.168 | 1.00 | 75.49 | C |
| ATOM | 1303 | CD2 | LEU | B | 351 | −75.356 | 38.179 | −5.229 | 1.00 | 75.38 | C |
| ATOM | 1304 | C | LEU | B | 351 | −78.381 | 36.247 | −7.983 | 1.00 | 72.90 | C |
| ATOM | 1305 | O | LEU | B | 351 | −79.607 | 36.113 | −8.083 | 1.00 | 73.12 | O |
| ATOM | 1306 | N | GLY | B | 352 | −77.553 | 36.090 | −9.004 | 1.00 | 68.29 | N |
| ATOM | 1307 | CA | GLY | B | 352 | −77.976 | 35.757 | −10.354 | 1.00 | 66.37 | C |
| ATOM | 1308 | C | GLY | B | 352 | −77.007 | 36.329 | −11.365 | 1.00 | 65.12 | C |
| ATOM | 1309 | O | GLY | B | 352 | −75.901 | 36.746 | −10.992 | 1.00 | 64.78 | O |
| ATOM | 1310 | N | THR | B | 353 | −77.407 | 36.367 | −12.648 | 1.00 | 62.17 | N |
| ATOM | 1311 | CA | THR | B | 353 | −76.532 | 36.867 | −13.713 | 1.00 | 61.44 | C |
| ATOM | 1312 | CB | THR | B | 353 | −77.124 | 36.662 | −15.111 | 1.00 | 61.66 | C |
| ATOM | 1313 | OG1 | THR | B | 353 | −76.054 | 36.868 | −16.040 | 1.00 | 61.54 | O |
| ATOM | 1314 | CG2 | THR | B | 353 | −78.303 | 37.631 | −15.429 | 1.00 | 61.65 | C |
| ATOM | 1315 | C | THR | B | 353 | −76.077 | 38.298 | −13.587 | 1.00 | 61.03 | C |
| ATOM | 1316 | O | THR | B | 353 | −76.855 | 39.160 | −13.168 | 1.00 | 60.67 | O |
| ATOM | 1317 | N | ASN | B | 354 | −74.824 | 38.558 | −14.015 | 1.00 | 58.04 | N |
| ATOM | 1318 | CA | ASN | B | 354 | −74.276 | 39.903 | −14.038 | 1.00 | 57.12 | C |
| ATOM | 1319 | CB | ASN | B | 354 | −72.749 | 39.874 | −14.104 | 1.00 | 57.05 | C |
| ATOM | 1320 | CG | ASN | B | 354 | −72.064 | 39.672 | −12.776 | 1.00 | 56.66 | C |
| ATOM | 1321 | OD1 | ASN | B | 354 | −72.706 | 39.594 | −11.736 | 1.00 | 57.85 | O |
| ATOM | 1322 | ND2 | ASN | B | 354 | −70.743 | 39.579 | −12.765 | 1.00 | 55.21 | N |
| ATOM | 1323 | C | ASN | B | 354 | −74.893 | 40.594 | −15.265 | 1.00 | 57.09 | C |
| ATOM | 1324 | O | ASN | B | 354 | −75.561 | 39.948 | −16.068 | 1.00 | 56.51 | O |
| ATOM | 1325 | N | PHE | B | 355 | −74.684 | 41.902 | −15.396 | 1.00 | 58.97 | N |
| ATOM | 1326 | CA | PHE | B | 355 | −75.226 | 42.761 | −16.455 | 1.00 | 58.97 | C |
| ATOM | 1327 | CB | PHE | B | 355 | −76.600 | 43.333 | −15.984 | 1.00 | 58.89 | C |
| ATOM | 1328 | CG | PHE | B | 355 | −76.642 | 43.671 | −14.500 | 1.00 | 58.25 | C |
| ATOM | 1329 | CD1 | PHE | B | 355 | −77.335 | 42.862 | −13.605 | 1.00 | 56.71 | C |
| ATOM | 1330 | CE1 | PHE | B | 355 | −77.323 | 43.140 | −12.238 | 1.00 | 56.45 | C |
| ATOM | 1331 | CZ | PHE | B | 355 | −76.618 | 44.223 | −11.758 | 1.00 | 56.46 | C |
| ATOM | 1332 | CE2 | PHE | B | 355 | −75.933 | 45.039 | −12.626 | 1.00 | 57.61 | C |
| ATOM | 1333 | CD2 | PHE | B | 355 | −75.922 | 44.753 | −13.991 | 1.00 | 57.66 | C |
| ATOM | 1334 | C | PHE | B | 355 | −74.251 | 43.911 | −16.701 | 1.00 | 59.20 | C |
| ATOM | 1335 | O | PHE | B | 355 | −73.104 | 43.883 | −16.238 | 1.00 | 59.27 | O |
| ATOM | 1336 | N | GLY | B | 356 | −74.725 | 44.932 | −17.385 | 1.00 | 60.17 | N |
| ATOM | 1337 | CA | GLY | B | 356 | −73.904 | 46.095 | −17.649 | 1.00 | 60.92 | C |
| ATOM | 1338 | C | GLY | B | 356 | −73.343 | 46.069 | −19.034 | 1.00 | 61.66 | C |
| ATOM | 1339 | O | GLY | B | 356 | −73.620 | 45.134 | −19.790 | 1.00 | 61.68 | O |
| ATOM | 1340 | N | ARG | B | 357 | −72.579 | 47.127 | −19.367 | 1.00 | 64.73 | N |
| ATOM | 1341 | CA | ARG | B | 357 | −71.935 | 47.380 | −20.662 | 1.00 | 65.38 | C |
| ATOM | 1342 | CB | ARG | B | 357 | −71.306 | 48.777 | −20.705 | 1.00 | 65.63 | C |
| ATOM | 1343 | CG | ARG | B | 357 | −70.518 | 49.113 | −19.467 | 1.00 | 66.74 | C |
| ATOM | 1344 | CD | ARG | B | 357 | −69.864 | 50.459 | −19.552 | 1.00 | 68.76 | C |
| ATOM | 1345 | NE | ARG | B | 357 | −68.612 | 50.445 | −18.800 | 1.00 | 69.87 | N |
| ATOM | 1346 | CZ | ARG | B | 357 | −67.437 | 50.189 | −19.354 | 1.00 | 70.36 | C |
| ATOM | 1347 | NH1 | ARG | B | 357 | −67.346 | 49.960 | −20.662 | 1.00 | 70.41 | N |
| ATOM | 1348 | NH2 | ARG | B | 357 | −66.340 | 50.161 | −18.608 | 1.00 | 71.53 | N |
| ATOM | 1349 | C | ARG | B | 357 | −70.919 | 46.329 | −21.055 | 1.00 | 65.47 | C |
| ATOM | 1350 | O | ARG | B | 357 | −70.777 | 46.056 | −22.249 | 1.00 | 65.45 | O |
| ATOM | 1351 | N | CYS | B | 358 | −70.244 | 45.716 | −20.067 | 1.00 | 67.67 | N |
| ATOM | 1352 | CA | CYS | B | 358 | −69.251 | 44.680 | −20.337 | 1.00 | 68.19 | C |
| ATOM | 1353 | CB | CYS | B | 358 | −68.303 | 44.504 | −19.162 | 1.00 | 68.27 | C |
| ATOM | 1354 | SG | CYS | B | 358 | −67.381 | 46.018 | −18.746 | 1.00 | 70.93 | S |
| ATOM | 1355 | C | CYS | B | 358 | −69.827 | 43.353 | −20.848 | 1.00 | 68.00 | C |
| ATOM | 1356 | O | CYS | B | 358 | −69.128 | 42.613 | −21.543 | 1.00 | 68.04 | O |
| ATOM | 1357 | N | VAL | B | 359 | −71.118 | 43.091 | −20.558 | 1.00 | 67.04 | N |
| ATOM | 1358 | CA | VAL | B | 359 | −71.850 | 41.916 | −21.035 | 1.00 | 66.98 | C |
| ATOM | 1359 | CB | VAL | B | 359 | −73.146 | 41.644 | −20.231 | 1.00 | 66.79 | C |
| ATOM | 1360 | CG1 | VAL | B | 359 | −73.978 | 40.544 | −20.865 | 1.00 | 66.32 | C |
| ATOM | 1361 | CG2 | VAL | B | 359 | −72.828 | 41.290 | −18.800 | 1.00 | 66.58 | C |
| ATOM | 1362 | C | VAL | B | 359 | −72.156 | 42.215 | −22.506 | 1.00 | 67.34 | C |
| ATOM | 1363 | O | VAL | B | 359 | −72.738 | 43.273 | −22.817 | 1.00 | 68.24 | O |
| ATOM | 1364 | N | ASP | B | 360 | −71.728 | 41.309 | −23.407 | 1.00 | 67.45 | N |
| ATOM | 1365 | CA | ASP | B | 360 | −71.927 | 41.451 | −24.838 | 1.00 | 67.13 | C |
| ATOM | 1366 | CB | ASP | B | 360 | −70.766 | 40.803 | −25.610 | 1.00 | 67.44 | C |

TABLE 14-continued

| | | | | | | | | | | |
|---|---|---|---|---|---|---|---|---|---|---|
| ATOM | 1367 | CG | ASP | B | 360 | −69.434 | 41.534 | −25.368 | 1.00 | 70.71 C |
| ATOM | 1368 | OD1 | ASP | B | 360 | −69.374 | 42.758 | −25.618 | 1.00 | 74.94 O |
| ATOM | 1369 | OD2 | ASP | B | 360 | −68.444 | 40.878 | −24.919 | 1.00 | 73.47 O |
| ATOM | 1370 | C | ASP | B | 360 | −73.303 | 40.935 | −25.240 | 1.00 | 66.55 C |
| ATOM | 1371 | O | ASP | B | 360 | −73.968 | 41.539 | −26.091 | 1.00 | 66.82 O |
| ATOM | 1372 | N | LEU | B | 361 | −73.754 | 39.849 | −24.602 | 1.00 | 62.14 N |
| ATOM | 1373 | CA | LEU | B | 361 | −75.047 | 39.220 | −24.876 | 1.00 | 61.50 C |
| ATOM | 1374 | CB | LEU | B | 361 | −75.059 | 38.557 | −26.280 | 1.00 | 61.27 C |
| ATOM | 1375 | CG | LEU | B | 361 | −74.367 | 37.179 | −26.492 | 1.00 | 61.28 C |
| ATOM | 1376 | CD1 | LEU | B | 361 | −74.698 | 36.631 | −27.854 | 1.00 | 60.90 C |
| ATOM | 1377 | CD2 | LEU | B | 361 | −72.831 | 37.244 | −26.309 | 1.00 | 60.87 C |
| ATOM | 1378 | C | LEU | B | 361 | −75.373 | 38.192 | −23.815 | 1.00 | 61.29 C |
| ATOM | 1379 | O | LEU | B | 361 | −74.502 | 37.803 | −23.045 | 1.00 | 61.49 O |
| ATOM | 1380 | N | PHE | B | 362 | −76.611 | 37.747 | −23.789 | 1.00 | 61.00 N |
| ATOM | 1381 | CA | PHE | B | 362 | −77.075 | 36.747 | −22.863 | 1.00 | 61.06 C |
| ATOM | 1382 | CB | PHE | B | 362 | −78.384 | 37.205 | −22.234 | 1.00 | 60.86 C |
| ATOM | 1383 | CG | PHE | B | 362 | −78.173 | 38.342 | −21.274 | 1.00 | 60.86 C |
| ATOM | 1384 | CD1 | PHE | B | 362 | −78.162 | 38.120 | −19.906 | 1.00 | 59.91 C |
| ATOM | 1385 | CE1 | PHE | B | 362 | −77.950 | 39.175 | −19.018 | 1.00 | 58.68 C |
| ATOM | 1386 | CZ | PHE | B | 362 | −77.733 | 40.449 | −19.495 | 1.00 | 58.51 C |
| ATOM | 1387 | CE2 | PHE | B | 362 | −77.725 | 40.689 | −20.847 | 1.00 | 59.36 C |
| ATOM | 1388 | CD2 | PHE | B | 362 | −77.951 | 39.637 | −21.737 | 1.00 | 61.08 C |
| ATOM | 1389 | C | PHE | B | 362 | −77.261 | 35.479 | −23.667 | 1.00 | 61.49 C |
| ATOM | 1390 | O | PHE | B | 362 | −77.217 | 35.536 | −24.895 | 1.00 | 61.81 O |
| ATOM | 1391 | N | ALA | B | 363 | −77.445 | 34.343 | −23.003 | 1.00 | 62.20 N |
| ATOM | 1392 | CA | ALA | B | 363 | −77.624 | 33.047 | −23.648 | 1.00 | 62.13 C |
| ATOM | 1393 | CB | ALA | B | 363 | −76.264 | 32.485 | −24.055 | 1.00 | 62.04 C |
| ATOM | 1394 | C | ALA | B | 363 | −78.261 | 32.122 | −22.617 | 1.00 | 62.26 C |
| ATOM | 1395 | O | ALA | B | 363 | −78.217 | 32.436 | −21.416 | 1.00 | 62.48 O |
| ATOM | 1396 | N | PRO | B | 364 | −78.824 | 30.971 | −23.028 | 1.00 | 60.56 N |
| ATOM | 1397 | CA | PRO | B | 364 | −79.418 | 30.053 | −22.046 | 1.00 | 60.70 C |
| ATOM | 1398 | CB | PRO | B | 364 | −79.785 | 28.853 | −22.896 | 1.00 | 60.33 C |
| ATOM | 1399 | CG | PRO | B | 364 | −79.975 | 29.394 | −24.223 | 1.00 | 59.88 C |
| ATOM | 1400 | CD | PRO | B | 364 | −78.984 | 30.455 | −24.396 | 1.00 | 60.34 C |
| ATOM | 1401 | C | PRO | B | 364 | −78.468 | 29.647 | −20.917 | 1.00 | 61.27 C |
| ATOM | 1402 | O | PRO | B | 364 | −77.380 | 29.150 | −21.194 | 1.00 | 61.78 O |
| ATOM | 1403 | N | GLY | B | 365 | −78.885 | 29.866 | −19.666 | 1.00 | 63.45 N |
| ATOM | 1404 | CA | GLY | B | 365 | −78.091 | 29.540 | −18.481 | 1.00 | 63.91 C |
| ATOM | 1405 | C | GLY | B | 365 | −78.856 | 29.033 | −17.268 | 1.00 | 64.44 C |
| ATOM | 1406 | O | GLY | B | 365 | −78.378 | 29.171 | −16.142 | 1.00 | 64.33 O |
| ATOM | 1407 | N | GLU | B | 366 | −80.033 | 28.444 | −17.474 | 1.00 | 66.98 N |
| ATOM | 1408 | CA | GLU | B | 366 | −80.819 | 27.923 | −16.367 | 1.00 | 68.00 C |
| ATOM | 1409 | CB | GLU | B | 366 | −81.943 | 28.894 | −15.962 | 1.00 | 68.37 C |
| ATOM | 1410 | CG | GLU | B | 366 | −82.522 | 28.588 | −14.592 | 1.00 | 71.56 C |
| ATOM | 1411 | CD | GLU | B | 366 | −83.672 | 29.463 | −14.135 | 1.00 | 76.80 C |
| ATOM | 1412 | OE1 | GLU | B | 366 | −83.399 | 30.568 | −13.599 | 1.00 | 79.89 O |
| ATOM | 1413 | OE2 | GLU | B | 366 | −84.845 | 29.045 | −14.306 | 1.00 | 78.54 O |
| ATOM | 1414 | C | GLU | B | 366 | −81.388 | 26.570 | −16.715 | 1.00 | 67.88 C |
| ATOM | 1415 | O | GLU | B | 366 | −81.985 | 26.415 | −17.777 | 1.00 | 67.93 O |
| ATOM | 1416 | N | ASP | B | 367 | −81.234 | 25.598 | −15.799 | 1.00 | 68.26 N |
| ATOM | 1417 | CA | ASP | B | 367 | −81.717 | 24.241 | −15.963 | 1.00 | 68.38 C |
| ATOM | 1418 | CB | ASP | B | 367 | −83.232 | 24.160 | −15.669 | 1.00 | 69.02 C |
| ATOM | 1419 | CG | ASP | B | 367 | −84.035 | 23.000 | −16.269 | 1.00 | 72.86 C |
| ATOM | 1420 | OD1 | ASP | B | 367 | −83.614 | 21.803 | −16.083 | 1.00 | 77.07 O |
| ATOM | 1421 | OD2 | ASP | B | 367 | −85.099 | 23.275 | −16.919 | 1.00 | 76.42 O |
| ATOM | 1422 | C | ASP | B | 367 | −81.239 | 23.723 | −17.325 | 1.00 | 67.72 C |
| ATOM | 1423 | O | ASP | B | 367 | −82.011 | 23.400 | −18.220 | 1.00 | 67.13 O |
| ATOM | 1424 | N | ILE | B | 368 | −79.919 | 23.728 | −17.483 | 1.00 | 64.65 N |
| ATOM | 1425 | CA | ILE | B | 368 | −79.262 | 23.289 | −18.692 | 1.00 | 64.75 C |
| ATOM | 1426 | CB | ILE | B | 368 | −78.073 | 24.205 | −19.070 | 1.00 | 64.52 C |
| ATOM | 1427 | CG1 | ILE | B | 368 | −78.462 | 25.700 | −19.157 | 1.00 | 64.19 C |
| ATOM | 1428 | CD1 | ILE | B | 368 | −79.483 | 26.137 | −20.261 | 1.00 | 63.84 C |
| ATOM | 1429 | CG2 | ILE | B | 368 | −77.334 | 23.692 | −20.320 | 1.00 | 63.95 C |
| ATOM | 1430 | C | ILE | B | 368 | −78.851 | 21.836 | −18.541 | 1.00 | 65.40 C |
| ATOM | 1431 | O | ILE | B | 368 | −77.982 | 21.492 | −17.728 | 1.00 | 65.45 O |
| ATOM | 1432 | N | ILE | B | 369 | −79.479 | 20.983 | −19.342 | 1.00 | 68.85 N |
| ATOM | 1433 | CA | ILE | B | 369 | −79.184 | 19.564 | −19.310 | 1.00 | 69.23 C |
| ATOM | 1434 | CB | ILE | B | 369 | −80.406 | 18.721 | −19.759 | 1.00 | 69.28 C |
| ATOM | 1435 | CG1 | ILE | B | 369 | −80.376 | 17.337 | −19.141 | 1.00 | 70.78 C |
| ATOM | 1436 | CD1 | ILE | B | 369 | −80.909 | 17.246 | −17.682 | 1.00 | 73.48 C |
| ATOM | 1437 | CG2 | ILE | B | 369 | −80.594 | 18.651 | −21.256 | 1.00 | 69.21 C |
| ATOM | 1438 | C | ILE | B | 369 | −77.888 | 19.296 | −20.049 | 1.00 | 69.27 C |
| ATOM | 1439 | O | ILE | B | 369 | −77.704 | 19.817 | −21.152 | 1.00 | 69.70 O |
| ATOM | 1440 | N | GLY | B | 370 | −76.991 | 18.544 | −19.414 | 1.00 | 67.64 N |
| ATOM | 1441 | CA | GLY | B | 370 | −75.678 | 18.200 | −19.957 | 1.00 | 67.43 C |
| ATOM | 1442 | C | GLY | B | 370 | −74.966 | 17.113 | −19.179 | 1.00 | 67.40 C |
| ATOM | 1443 | O | GLY | B | 370 | −75.383 | 16.770 | −18.075 | 1.00 | 67.49 O |
| ATOM | 1444 | N | ALA | B | 371 | −73.878 | 16.575 | −19.748 | 1.00 | 67.13 N |

TABLE 14-continued

PCSK9 and AX132 Fab complex x-ray structure

| ATOM | 1445 | CA  | ALA | B | 371 | −73.044 | 15.510 | −19.191 | 1.00 | 66.88 | C |
|------|------|-----|-----|---|-----|---------|--------|---------|------|-------|---|
| ATOM | 1446 | CB  | ALA | B | 371 | −71.784 | 15.340 | −20.020 | 1.00 | 66.63 | C |
| ATOM | 1447 | C   | ALA | B | 371 | −72.685 | 15.559 | −17.699 | 1.00 | 67.05 | C |
| ATOM | 1448 | O   | ALA | B | 371 | −71.899 | 16.414 | −17.248 | 1.00 | 67.24 | O |
| ATOM | 1449 | N   | SER | B | 372 | −73.234 | 14.587 | −16.935 | 1.00 | 69.52 | N |
| ATOM | 1450 | CA  | SER | B | 372 | −72.948 | 14.425 | −15.507 | 1.00 | 69.69 | C |
| ATOM | 1451 | CB  | SER | B | 372 | −74.163 | 13.888 | −14.773 | 1.00 | 69.34 | C |
| ATOM | 1452 | OG  | SER | B | 372 | −73.778 | 13.661 | −13.432 | 1.00 | 68.66 | O |
| ATOM | 1453 | C   | SER | B | 372 | −71.789 | 13.435 | −15.337 | 1.00 | 70.18 | C |
| ATOM | 1454 | O   | SER | B | 372 | −71.873 | 12.313 | −15.834 | 1.00 | 70.36 | O |
| ATOM | 1455 | N   | SER | B | 373 | −70.712 | 13.842 | −14.640 | 1.00 | 74.56 | N |
| ATOM | 1456 | CA  | SER | B | 373 | −69.540 | 12.991 | −14.390 | 1.00 | 74.78 | C |
| ATOM | 1457 | CB  | SER | B | 373 | −68.397 | 13.804 | −13.788 | 1.00 | 74.54 | C |
| ATOM | 1458 | OG  | SER | B | 373 | −68.850 | 14.486 | −12.629 | 1.00 | 74.19 | O |
| ATOM | 1459 | C   | SER | B | 373 | −69.893 | 11.784 | −13.489 | 1.00 | 75.14 | C |
| ATOM | 1460 | O   | SER | B | 373 | −69.060 | 10.880 | −13.352 | 1.00 | 75.75 | O |
| ATOM | 1461 | N   | ASP | B | 374 | −71.121 | 11.761 | −12.898 | 1.00 | 76.21 | N |
| ATOM | 1462 | CA  | ASP | B | 374 | −71.622 | 10.677 | −12.050 | 1.00 | 76.51 | C |
| ATOM | 1463 | CB  | ASP | B | 374 | −73.078 | 10.926 | −11.658 | 1.00 | 76.87 | C |
| ATOM | 1464 | CG  | ASP | B | 374 | −73.278 | 11.831 | −10.456 | 1.00 | 77.21 | C |
| ATOM | 1465 | OD1 | ASP | B | 374 | −72.258 | 12.144 | −9.768  | 1.00 | 77.96 | O |
| ATOM | 1466 | OD2 | ASP | B | 374 | −74.471 | 12.237 | −10.193 | 1.00 | 76.93 | O |
| ATOM | 1467 | C   | ASP | B | 374 | −71.489 | 9.273  | −12.686 | 1.00 | 76.86 | C |
| ATOM | 1468 | O   | ASP | B | 374 | −71.069 | 8.341  | −11.998 | 1.00 | 77.61 | O |
| ATOM | 1469 | N   | CYS | B | 375 | −71.848 | 9.121  | −13.977 | 1.00 | 73.83 | N |
| ATOM | 1470 | CA  | CYS | B | 375 | −71.746 | 7.884  | −14.756 | 1.00 | 73.51 | C |
| ATOM | 1471 | CB  | CYS | B | 375 | −72.947 | 6.965  | −14.529 | 1.00 | 73.63 | C |
| ATOM | 1472 | SG  | CYS | B | 375 | −74.337 | 7.199  | −15.678 | 1.00 | 76.02 | S |
| ATOM | 1473 | C   | CYS | B | 375 | −71.561 | 8.290  | −16.221 | 1.00 | 73.03 | C |
| ATOM | 1474 | O   | CYS | B | 375 | −71.981 | 9.388  | −16.577 | 1.00 | 73.09 | O |
| ATOM | 1475 | N   | SER | B | 376 | −70.912 | 7.455  | −17.064 | 1.00 | 68.20 | N |
| ATOM | 1476 | CA  | SER | B | 376 | −70.627 | 7.806  | −18.467 | 1.00 | 67.70 | C |
| ATOM | 1477 | CB  | SER | B | 376 | −69.542 | 6.924  | −19.071 | 1.00 | 67.82 | C |
| ATOM | 1478 | OG  | SER | B | 376 | −70.072 | 5.678  | −19.480 | 1.00 | 68.81 | O |
| ATOM | 1479 | C   | SER | B | 376 | −71.787 | 8.094  | −19.439 | 1.00 | 67.35 | C |
| ATOM | 1480 | O   | SER | B | 376 | −71.529 | 8.558  | −20.554 | 1.00 | 66.71 | O |
| ATOM | 1481 | N   | THR | B | 377 | −73.055 | 7.869  | −19.012 | 1.00 | 66.32 | N |
| ATOM | 1482 | CA  | THR | B | 377 | −74.239 | 8.165  | −19.829 | 1.00 | 66.42 | C |
| ATOM | 1483 | CB  | THR | B | 377 | −74.876 | 6.901  | −20.383 | 1.00 | 66.19 | C |
| ATOM | 1484 | OG1 | THR | B | 377 | −75.281 | 6.064  | −19.314 | 1.00 | 65.85 | O |
| ATOM | 1485 | CG2 | THR | B | 377 | −73.982 | 6.162  | −21.326 | 1.00 | 66.15 | C |
| ATOM | 1486 | C   | THR | B | 377 | −75.243 | 9.045  | −19.074 | 1.00 | 66.82 | C |
| ATOM | 1487 | O   | THR | B | 377 | −76.346 | 9.295  | −19.570 | 1.00 | 67.04 | O |
| ATOM | 1488 | N   | CYS | B | 378 | −74.857 | 9.523  | −17.882 | 1.00 | 69.75 | N |
| ATOM | 1489 | CA  | CYS | B | 378 | −75.691 | 10.360 | −17.010 | 1.00 | 70.60 | C |
| ATOM | 1490 | CB  | CYS | B | 378 | −75.242 | 10.253 | −15.553 | 1.00 | 70.72 | C |
| ATOM | 1491 | SG  | CYS | B | 378 | −75.535 | 8.635  | −14.779 | 1.00 | 76.79 | S |
| ATOM | 1492 | C   | CYS | B | 378 | −75.737 | 11.815 | −17.436 | 1.00 | 69.95 | C |
| ATOM | 1493 | O   | CYS | B | 378 | −74.714 | 12.384 | −17.826 | 1.00 | 69.93 | O |
| ATOM | 1494 | N   | PHE | B | 379 | −76.914 | 12.435 | −17.273 | 1.00 | 68.10 | N |
| ATOM | 1495 | CA  | PHE | B | 379 | −77.121 | 13.845 | −17.529 | 1.00 | 67.31 | C |
| ATOM | 1496 | CB  | PHE | B | 379 | −78.233 | 14.050 | −18.545 | 1.00 | 67.28 | C |
| ATOM | 1497 | CG  | PHE | B | 379 | −77.766 | 13.764 | −19.933 | 1.00 | 67.51 | C |
| ATOM | 1498 | CD1 | PHE | B | 379 | −77.097 | 14.732 | −20.668 | 1.00 | 67.75 | C |
| ATOM | 1499 | CE1 | PHE | B | 379 | −76.638 | 14.459 | −21.959 | 1.00 | 67.92 | C |
| ATOM | 1500 | CZ  | PHE | B | 379 | −76.858 | 13.219 | −22.517 | 1.00 | 68.53 | C |
| ATOM | 1501 | CE2 | PHE | B | 379 | −77.516 | 12.243 | −21.796 | 1.00 | 69.39 | C |
| ATOM | 1502 | CD2 | PHE | B | 379 | −77.972 | 12.519 | −20.505 | 1.00 | 68.25 | C |
| ATOM | 1503 | C   | PHE | B | 379 | −77.485 | 14.553 | −16.242 | 1.00 | 66.84 | C |
| ATOM | 1504 | O   | PHE | B | 379 | −78.048 | 13.957 | −15.328 | 1.00 | 66.88 | O |
| ATOM | 1505 | N   | VAL | B | 380 | −77.182 | 15.831 | −16.174 | 1.00 | 66.05 | N |
| ATOM | 1506 | CA  | VAL | B | 380 | −77.512 | 16.661 | −15.029 | 1.00 | 65.75 | C |
| ATOM | 1507 | CB  | VAL | B | 380 | −76.405 | 16.742 | −13.944 | 1.00 | 65.44 | C |
| ATOM | 1508 | CG1 | VAL | B | 380 | −75.179 | 17.514 | −14.436 | 1.00 | 65.48 | C |
| ATOM | 1509 | CG2 | VAL | B | 380 | −76.945 | 17.343 | −12.653 | 1.00 | 64.28 | C |
| ATOM | 1510 | C   | VAL | B | 380 | −77.930 | 18.021 | −15.542 | 1.00 | 65.90 | C |
| ATOM | 1511 | O   | VAL | B | 380 | −77.429 | 18.493 | −16.573 | 1.00 | 66.20 | O |
| ATOM | 1512 | N   | SER | B | 381 | −78.840 | 18.649 | −14.816 | 1.00 | 65.11 | N |
| ATOM | 1513 | CA  | SER | B | 381 | −79.308 | 19.958 | −15.153 | 1.00 | 64.86 | C |
| ATOM | 1514 | CB  | SER | B | 381 | −80.818 | 20.000 | −14.994 | 1.00 | 64.84 | C |
| ATOM | 1515 | OG  | SER | B | 381 | −81.278 | 21.322 | −14.804 | 1.00 | 65.85 | O |
| ATOM | 1516 | C   | SER | B | 381 | −78.584 | 20.962 | −14.261 | 1.00 | 64.52 | C |
| ATOM | 1517 | O   | SER | B | 381 | −78.762 | 20.938 | −13.051 | 1.00 | 64.12 | O |
| ATOM | 1518 | N   | GLN | B | 382 | −77.738 | 21.818 | −14.859 | 1.00 | 65.97 | N |
| ATOM | 1519 | CA  | GLN | B | 382 | −76.989 | 22.857 | −14.125 | 1.00 | 66.38 | C |
| ATOM | 1520 | CB  | GLN | B | 382 | −75.483 | 22.638 | −14.200 | 1.00 | 66.64 | C |
| ATOM | 1521 | CG  | GLN | B | 382 | −75.010 | 21.530 | −13.285 | 1.00 | 68.46 | C |
| ATOM | 1522 | CD  | GLN | B | 382 | −73.504 | 21.374 | −13.324 | 1.00 | 71.37 | C |

TABLE 14-continued

PCSK9 and AX132 Fab complex x-ray structure

| ATOM | 1523 | OE1 | GLN | B | 382 | −72.728 | 22.346 | −13.165 | 1.00 | 73.24 | O |
|---|---|---|---|---|---|---|---|---|---|---|---|
| ATOM | 1524 | NE2 | GLN | B | 382 | −73.052 | 20.136 | −13.508 | 1.00 | 71.55 | N |
| ATOM | 1525 | C | GLN | B | 382 | −77.347 | 24.270 | −14.559 | 1.00 | 65.83 | C |
| ATOM | 1526 | O | GLN | B | 382 | −78.046 | 24.421 | −15.560 | 1.00 | 66.06 | O |
| ATOM | 1527 | N | SER | B | 383 | −76.907 | 25.303 | −13.804 | 1.00 | 64.06 | N |
| ATOM | 1528 | CA | SER | B | 383 | −77.200 | 26.709 | −14.136 | 1.00 | 63.37 | C |
| ATOM | 1529 | CB | SER | B | 383 | −78.417 | 27.208 | −13.363 | 1.00 | 63.26 | C |
| ATOM | 1530 | OG | SER | B | 383 | −79.509 | 26.312 | −13.464 | 1.00 | 63.66 | O |
| ATOM | 1531 | C | SER | B | 383 | −76.005 | 27.650 | −13.911 | 1.00 | 62.65 | C |
| ATOM | 1532 | O | SER | B | 383 | −75.120 | 27.339 | −13.109 | 1.00 | 63.21 | O |
| ATOM | 1533 | N | GLY | B | 384 | −75.972 | 28.782 | −14.610 | 1.00 | 61.71 | N |
| ATOM | 1534 | CA | GLY | B | 384 | −74.884 | 29.739 | −14.426 | 1.00 | 60.72 | C |
| ATOM | 1535 | C | GLY | B | 384 | −74.402 | 30.424 | −15.675 | 1.00 | 60.19 | C |
| ATOM | 1536 | O | GLY | B | 384 | −74.737 | 30.001 | −16.775 | 1.00 | 60.26 | O |
| ATOM | 1537 | N | THR | B | 385 | −73.606 | 31.484 | −15.527 | 1.00 | 60.84 | N |
| ATOM | 1538 | CA | THR | B | 385 | −73.095 | 32.176 | −16.696 | 1.00 | 60.30 | C |
| ATOM | 1539 | CB | THR | B | 385 | −72.612 | 33.595 | −16.392 | 1.00 | 60.29 | C |
| ATOM | 1540 | OG1 | THR | B | 385 | −71.719 | 33.599 | −15.282 | 1.00 | 60.49 | O |
| ATOM | 1541 | CG2 | THR | B | 385 | −73.734 | 34.539 | −16.152 | 1.00 | 60.32 | C |
| ATOM | 1542 | C | THR | B | 385 | −72.096 | 31.285 | −17.414 | 1.00 | 60.14 | C |
| ATOM | 1543 | O | THR | B | 385 | −71.858 | 31.498 | −18.600 | 1.00 | 60.76 | O |
| ATOM | 1544 | N | SER | B | 386 | −71.538 | 30.259 | −16.718 | 1.00 | 59.68 | N |
| ATOM | 1545 | CA | SER | B | 386 | −70.610 | 29.290 | −17.308 | 1.00 | 58.69 | C |
| ATOM | 1546 | CB | SER | B | 386 | −70.208 | 28.255 | −16.276 | 1.00 | 58.66 | C |
| ATOM | 1547 | OG | SER | B | 386 | −69.090 | 28.756 | −15.570 | 1.00 | 59.58 | O |
| ATOM | 1548 | C | SER | B | 386 | −71.328 | 28.575 | −18.415 | 1.00 | 58.08 | C |
| ATOM | 1549 | O | SER | B | 386 | −70.886 | 28.598 | −19.560 | 1.00 | 57.08 | O |
| ATOM | 1550 | N | GLN | B | 387 | −72.474 | 27.969 | −18.068 | 1.00 | 57.98 | N |
| ATOM | 1551 | CA | GLN | B | 387 | −73.350 | 27.253 | −18.974 | 1.00 | 58.10 | C |
| ATOM | 1552 | CB | GLN | B | 387 | −74.580 | 26.756 | −18.211 | 1.00 | 58.10 | C |
| ATOM | 1553 | CG | GLN | B | 387 | −74.321 | 25.450 | −17.479 | 1.00 | 59.28 | C |
| ATOM | 1554 | CD | GLN | B | 387 | −73.438 | 25.567 | −16.264 | 1.00 | 62.12 | C |
| ATOM | 1555 | OE1 | GLN | B | 387 | −73.404 | 26.591 | −15.573 | 1.00 | 64.35 | O |
| ATOM | 1556 | NE2 | GLN | B | 387 | −72.688 | 24.512 | −15.964 | 1.00 | 63.82 | N |
| ATOM | 1557 | C | GLN | B | 387 | −73.706 | 28.133 | −20.185 | 1.00 | 57.84 | C |
| ATOM | 1558 | O | GLN | B | 387 | −73.647 | 27.665 | −21.320 | 1.00 | 57.46 | O |
| ATOM | 1559 | N | ALA | B | 388 | −73.996 | 29.413 | −19.940 | 1.00 | 57.44 | N |
| ATOM | 1560 | CA | ALA | B | 388 | −74.321 | 30.379 | −20.971 | 1.00 | 57.87 | C |
| ATOM | 1561 | CB | ALA | B | 388 | −74.751 | 31.670 | −20.321 | 1.00 | 58.03 | C |
| ATOM | 1562 | C | ALA | B | 388 | −73.137 | 30.628 | −21.913 | 1.00 | 58.24 | C |
| ATOM | 1563 | O | ALA | B | 388 | −73.307 | 30.586 | −23.137 | 1.00 | 58.05 | O |
| ATOM | 1564 | N | ALA | B | 389 | −71.932 | 30.874 | −21.330 | 1.00 | 59.19 | N |
| ATOM | 1565 | CA | ALA | B | 389 | −70.680 | 31.119 | −22.054 | 1.00 | 59.09 | C |
| ATOM | 1566 | CB | ALA | B | 389 | −69.537 | 31.386 | −21.083 | 1.00 | 58.69 | C |
| ATOM | 1567 | C | ALA | B | 389 | −70.379 | 29.920 | −22.949 | 1.00 | 59.41 | C |
| ATOM | 1568 | O | ALA | B | 389 | −70.090 | 30.121 | −24.127 | 1.00 | 59.39 | O |
| ATOM | 1569 | N | ALA | B | 390 | −70.536 | 28.675 | −22.417 | 1.00 | 59.10 | N |
| ATOM | 1570 | CA | ALA | B | 390 | −70.335 | 27.416 | −23.148 | 1.00 | 59.27 | C |
| ATOM | 1571 | CB | ALA | B | 390 | −70.634 | 26.231 | −22.246 | 1.00 | 59.50 | C |
| ATOM | 1572 | C | ALA | B | 390 | −71.223 | 27.368 | −24.389 | 1.00 | 59.18 | C |
| ATOM | 1573 | O | ALA | B | 390 | −70.762 | 27.016 | −25.465 | 1.00 | 58.96 | O |
| ATOM | 1574 | N | HIS | B | 391 | −72.466 | 27.771 | −24.245 | 1.00 | 59.70 | N |
| ATOM | 1575 | CA | HIS | B | 391 | −73.437 | 27.824 | −25.327 | 1.00 | 60.45 | C |
| ATOM | 1576 | CB | HIS | B | 391 | −74.748 | 28.343 | −24.754 | 1.00 | 60.64 | C |
| ATOM | 1577 | CG | HIS | B | 391 | −75.881 | 28.349 | −25.711 | 1.00 | 61.44 | C |
| ATOM | 1578 | ND1 | HIS | B | 391 | −76.895 | 27.390 | −25.638 | 1.00 | 62.58 | N |
| ATOM | 1579 | CE1 | HIS | B | 391 | −77.758 | 27.717 | −26.591 | 1.00 | 62.78 | C |
| ATOM | 1580 | NE2 | HIS | B | 391 | −77.364 | 28.815 | −27.263 | 1.00 | 61.77 | N |
| ATOM | 1581 | CD2 | HIS | B | 391 | −76.170 | 29.229 | −26.701 | 1.00 | 60.82 | C |
| ATOM | 1582 | C | HIS | B | 391 | −72.941 | 28.752 | −26.446 | 1.00 | 60.78 | C |
| ATOM | 1583 | O | HIS | B | 391 | −73.011 | 28.394 | −27.626 | 1.00 | 60.82 | O |
| ATOM | 1584 | N | VAL | B | 392 | −72.431 | 29.940 | −26.073 | 1.00 | 60.26 | N |
| ATOM | 1585 | CA | VAL | B | 392 | −71.934 | 30.895 | −27.048 | 1.00 | 60.56 | C |
| ATOM | 1586 | CB | VAL | B | 392 | −71.837 | 32.337 | −26.501 | 1.00 | 60.49 | C |
| ATOM | 1587 | CG1 | VAL | B | 392 | −70.866 | 33.192 | −27.316 | 1.00 | 59.89 | C |
| ATOM | 1588 | CG2 | VAL | B | 392 | −73.219 | 32.987 | −26.456 | 1.00 | 60.00 | C |
| ATOM | 1589 | C | VAL | B | 392 | −70.675 | 30.361 | −27.706 | 1.00 | 60.89 | C |
| ATOM | 1590 | O | VAL | B | 392 | −70.504 | 30.544 | −28.910 | 1.00 | 61.08 | O |
| ATOM | 1591 | N | ALA | B | 393 | −69.822 | 29.658 | −26.943 | 1.00 | 60.20 | N |
| ATOM | 1592 | CA | ALA | B | 393 | −68.610 | 29.042 | −27.496 | 1.00 | 60.46 | C |
| ATOM | 1593 | CB | ALA | B | 393 | −67.728 | 28.480 | −26.381 | 1.00 | 60.29 | C |
| ATOM | 1594 | C | ALA | B | 393 | −69.051 | 27.932 | −28.506 | 1.00 | 60.76 | C |
| ATOM | 1595 | O | ALA | B | 393 | −68.423 | 27.773 | −29.542 | 1.00 | 60.67 | O |
| ATOM | 1596 | N | GLY | B | 394 | −70.158 | 27.237 | −28.218 | 1.00 | 60.47 | N |
| ATOM | 1597 | CA | GLY | B | 394 | −70.731 | 26.231 | −29.105 | 1.00 | 60.83 | C |
| ATOM | 1598 | C | GLY | B | 394 | −71.095 | 26.913 | −30.409 | 1.00 | 61.49 | C |
| ATOM | 1599 | O | GLY | B | 394 | −70.561 | 26.545 | −31.452 | 1.00 | 61.48 | O |
| ATOM | 1600 | N | ILE | B | 395 | −71.940 | 27.986 | −30.350 | 1.00 | 59.97 | N |

TABLE 14-continued

PCSK9 and AX132 Fab complex x-ray structure

| ATOM | 1601 | CA | ILE | B | 395 | −72.324 | 28.798 | −31.517 | 1.00 | 60.21 | C |
|---|---|---|---|---|---|---|---|---|---|---|---|
| ATOM | 1602 | CB | ILE | B | 395 | −73.238 | 29.997 | −31.149 | 1.00 | 59.85 | C |
| ATOM | 1603 | CG1 | ILE | B | 395 | −74.560 | 29.509 | −30.540 | 1.00 | 59.07 | C |
| ATOM | 1604 | CD1 | ILE | B | 395 | −75.597 | 30.517 | −30.318 | 1.00 | 56.08 | C |
| ATOM | 1605 | CG2 | ILE | B | 395 | −73.496 | 30.836 | −32.396 | 1.00 | 58.99 | C |
| ATOM | 1606 | C | ILE | B | 395 | −71.075 | 29.268 | −32.270 | 1.00 | 60.82 | C |
| ATOM | 1607 | O | ILE | B | 395 | −70.963 | 29.023 | −33.459 | 1.00 | 60.79 | O |
| ATOM | 1608 | N | ALA | B | 396 | −70.132 | 29.901 | −31.572 | 1.00 | 62.66 | N |
| ATOM | 1609 | CA | ALA | B | 396 | −68.893 | 30.389 | −32.166 | 1.00 | 63.99 | C |
| ATOM | 1610 | CB | ALA | B | 396 | −67.994 | 30.993 | −31.104 | 1.00 | 63.67 | C |
| ATOM | 1611 | C | ALA | B | 396 | −68.144 | 29.297 | −32.910 | 1.00 | 65.18 | C |
| ATOM | 1612 | O | ALA | B | 396 | −67.522 | 29.590 | −33.929 | 1.00 | 65.64 | O |
| ATOM | 1613 | N | ALA | B | 397 | −68.192 | 28.046 | −32.420 | 1.00 | 66.67 | N |
| ATOM | 1614 | CA | ALA | B | 397 | −67.481 | 26.966 | −33.077 | 1.00 | 67.47 | C |
| ATOM | 1615 | CB | ALA | B | 397 | −67.364 | 25.760 | −32.167 | 1.00 | 67.14 | C |
| ATOM | 1616 | C | ALA | B | 397 | −68.193 | 26.611 | −34.351 | 1.00 | 68.29 | C |
| ATOM | 1617 | O | ALA | B | 397 | −67.538 | 26.383 | −35.358 | 1.00 | 68.46 | O |
| ATOM | 1618 | N | MET | B | 398 | −69.518 | 26.615 | −34.346 | 1.00 | 70.12 | N |
| ATOM | 1619 | CA | MET | B | 398 | −70.253 | 26.291 | −35.562 | 1.00 | 71.55 | C |
| ATOM | 1620 | CB | MET | B | 398 | −71.707 | 26.108 | −35.259 | 1.00 | 71.19 | C |
| ATOM | 1621 | CG | MET | B | 398 | −72.011 | 24.717 | −34.979 | 1.00 | 71.23 | C |
| ATOM | 1622 | SD | MET | B | 398 | −73.527 | 24.713 | −34.090 | 1.00 | 72.01 | S |
| ATOM | 1623 | CE | MET | B | 398 | −74.705 | 24.947 | −35.431 | 1.00 | 72.24 | C |
| ATOM | 1624 | C | MET | B | 398 | −70.068 | 27.307 | −36.668 | 1.00 | 72.80 | C |
| ATOM | 1625 | O | MET | B | 398 | −70.022 | 26.937 | −37.845 | 1.00 | 73.11 | O |
| ATOM | 1626 | N | MET | B | 399 | −69.950 | 28.584 | −36.276 | 1.00 | 75.45 | N |
| ATOM | 1627 | CA | MET | B | 399 | −69.737 | 29.715 | −37.153 | 1.00 | 76.60 | C |
| ATOM | 1628 | CB | MET | B | 399 | −69.784 | 30.998 | −36.335 | 1.00 | 76.93 | C |
| ATOM | 1629 | CG | MET | B | 399 | −71.138 | 31.385 | −35.885 | 1.00 | 78.25 | C |
| ATOM | 1630 | SD | MET | B | 399 | −71.060 | 33.142 | −35.460 | 1.00 | 81.74 | S |
| ATOM | 1631 | CE | MET | B | 399 | −72.769 | 33.407 | −35.066 | 1.00 | 81.33 | C |
| ATOM | 1632 | C | MET | B | 399 | −68.353 | 29.584 | −37.760 | 1.00 | 77.22 | C |
| ATOM | 1633 | O | MET | B | 399 | −68.220 | 29.669 | −38.974 | 1.00 | 77.23 | O |
| ATOM | 1634 | N | LEU | B | 400 | −67.325 | 29.365 | −36.915 | 1.00 | 76.33 | N |
| ATOM | 1635 | CA | LEU | B | 400 | −65.936 | 29.226 | −37.346 | 1.00 | 77.44 | C |
| ATOM | 1636 | CB | LEU | B | 400 | −64.965 | 29.365 | −36.170 | 1.00 | 77.12 | C |
| ATOM | 1637 | CG | LEU | B | 400 | −64.811 | 30.729 | −35.539 | 1.00 | 76.49 | C |
| ATOM | 1638 | CD1 | LEU | B | 400 | −64.013 | 30.617 | −34.295 | 1.00 | 76.33 | C |
| ATOM | 1639 | CD2 | LEU | B | 400 | −64.101 | 31.702 | −36.459 | 1.00 | 75.61 | C |
| ATOM | 1640 | C | LEU | B | 400 | −65.679 | 27.928 | −38.104 | 1.00 | 78.55 | C |
| ATOM | 1641 | O | LEU | B | 400 | −64.640 | 27.811 | −38.754 | 1.00 | 78.47 | O |
| ATOM | 1642 | N | SER | B | 401 | −66.614 | 26.951 | −38.008 | 1.00 | 83.21 | N |
| ATOM | 1643 | CA | SER | B | 401 | −66.532 | 25.676 | −38.712 | 1.00 | 84.86 | C |
| ATOM | 1644 | CB | SER | B | 401 | −67.538 | 24.675 | −38.161 | 1.00 | 85.02 | C |
| ATOM | 1645 | OG | SER | B | 401 | −66.854 | 23.694 | −37.400 | 1.00 | 86.31 | O |
| ATOM | 1646 | C | SER | B | 401 | −66.806 | 25.932 | −40.171 | 1.00 | 85.71 | C |
| ATOM | 1647 | O | SER | B | 401 | −66.036 | 25.489 | −41.022 | 1.00 | 85.97 | O |
| ATOM | 1648 | N | ALA | B | 402 | −67.881 | 26.692 | −40.453 | 1.00 | 87.49 | N |
| ATOM | 1649 | CA | ALA | B | 402 | −68.301 | 27.071 | −41.792 | 1.00 | 88.50 | C |
| ATOM | 1650 | CB | ALA | B | 402 | −69.740 | 27.534 | −41.756 | 1.00 | 88.32 | C |
| ATOM | 1651 | C | ALA | B | 402 | −67.408 | 28.157 | −42.437 | 1.00 | 89.39 | C |
| ATOM | 1652 | O | ALA | B | 402 | −67.193 | 28.122 | −43.651 | 1.00 | 90.05 | O |
| ATOM | 1653 | N | GLU | B | 403 | −66.905 | 29.121 | −41.654 | 1.00 | 88.89 | N |
| ATOM | 1654 | CA | GLU | B | 403 | −66.093 | 30.194 | −42.210 | 1.00 | 89.62 | C |
| ATOM | 1655 | CB | GLU | B | 403 | −66.934 | 31.483 | −42.301 | 1.00 | 89.85 | C |
| ATOM | 1656 | CG | GLU | B | 403 | −68.060 | 31.403 | −43.317 | 1.00 | 91.79 | C |
| ATOM | 1657 | CD | GLU | B | 403 | −69.147 | 32.466 | −43.267 | 1.00 | 94.98 | C |
| ATOM | 1658 | OE1 | GLU | B | 403 | −70.339 | 32.075 | −43.285 | 1.00 | 96.52 | O |
| ATOM | 1659 | OE2 | GLU | B | 403 | −68.822 | 33.679 | −43.231 | 1.00 | 95.76 | O |
| ATOM | 1660 | C | GLU | B | 403 | −64.809 | 30.399 | −41.401 | 1.00 | 89.80 | C |
| ATOM | 1661 | O | GLU | B | 403 | −64.673 | 31.415 | −40.722 | 1.00 | 89.82 | O |
| ATOM | 1662 | N | PRO | B | 404 | −63.837 | 29.467 | −41.471 | 1.00 | 88.89 | N |
| ATOM | 1663 | CA | PRO | B | 404 | −62.587 | 29.614 | −40.692 | 1.00 | 89.06 | C |
| ATOM | 1664 | CB | PRO | B | 404 | −61.704 | 28.485 | −41.210 | 1.00 | 88.92 | C |
| ATOM | 1665 | CG | PRO | B | 404 | −62.379 | 27.990 | −42.431 | 1.00 | 89.10 | C |
| ATOM | 1666 | CD | PRO | B | 404 | −63.827 | 28.207 | −42.225 | 1.00 | 88.89 | C |
| ATOM | 1667 | C | PRO | B | 404 | −61.843 | 30.937 | −40.746 | 1.00 | 89.38 | C |
| ATOM | 1668 | O | PRO | B | 404 | −61.071 | 31.243 | −39.833 | 1.00 | 89.29 | O |
| ATOM | 1669 | N | GLU | B | 405 | −62.077 | 31.724 | −41.800 | 1.00 | 94.03 | N |
| ATOM | 1670 | CA | GLU | B | 405 | −61.424 | 33.021 | −41.962 | 1.00 | 94.48 | C |
| ATOM | 1671 | CB | GLU | B | 405 | −60.953 | 33.222 | −43.414 | 1.00 | 94.82 | C |
| ATOM | 1672 | CG | GLU | B | 405 | −59.644 | 32.488 | −43.697 | 1.00 | 97.73 | C |
| ATOM | 1673 | CD | GLU | B | 405 | −59.402 | 32.015 | −45.125 | 1.00 | 102.06 | C |
| ATOM | 1674 | OE1 | GLU | B | 405 | −59.461 | 32.859 | −46.057 | 1.00 | 103.17 | O |
| ATOM | 1675 | OE2 | GLU | B | 405 | −59.138 | 30.798 | −45.309 | 1.00 | 103.58 | O |
| ATOM | 1676 | C | GLU | B | 405 | −62.212 | 34.217 | −41.358 | 1.00 | 93.93 | C |
| ATOM | 1677 | O | GLU | B | 405 | −61.967 | 35.374 | −41.720 | 1.00 | 94.12 | O |
| ATOM | 1678 | N | LEU | B | 406 | −63.146 | 33.927 | −40.414 | 1.00 | 90.47 | N |

TABLE 14-continued

PCSK9 and AX132 Fab complex x-ray structure

| ATOM | 1679 | CA  | LEU | B | 406 | −63.928 | 34.956 | −39.725 | 1.00 | 89.50 | C |
|------|------|-----|-----|---|-----|---------|--------|---------|------|-------|---|
| ATOM | 1680 | CB  | LEU | B | 406 | −65.167 | 34.369 | −39.024 | 1.00 | 89.48 | C |
| ATOM | 1681 | CG  | LEU | B | 406 | −66.506 | 34.396 | −39.753 | 1.00 | 88.84 | C |
| ATOM | 1682 | CD1 | LEU | B | 406 | −67.483 | 33.473 | −39.089 | 1.00 | 88.84 | C |
| ATOM | 1683 | CD2 | LEU | B | 406 | −67.102 | 35.767 | −39.764 | 1.00 | 87.85 | C |
| ATOM | 1684 | C   | LEU | B | 406 | −63.031 | 35.560 | −38.669 | 1.00 | 89.00 | C |
| ATOM | 1685 | O   | LEU | B | 406 | −62.284 | 34.841 | −37.990 | 1.00 | 89.04 | O |
| ATOM | 1686 | N   | THR | B | 407 | −63.094 | 36.872 | −38.523 | 1.00 | 88.63 | N |
| ATOM | 1687 | CA  | THR | B | 407 | −62.281 | 37.526 | −37.512 | 1.00 | 87.98 | C |
| ATOM | 1688 | CB  | THR | B | 407 | −61.776 | 38.896 | −37.998 | 1.00 | 88.20 | C |
| ATOM | 1689 | OG1 | THR | B | 407 | −62.718 | 39.924 | −37.660 | 1.00 | 88.82 | O |
| ATOM | 1690 | CG2 | THR | B | 407 | −61.437 | 38.917 | −39.497 | 1.00 | 88.11 | C |
| ATOM | 1691 | C   | THR | B | 407 | −63.112 | 37.632 | −36.240 | 1.00 | 87.20 | C |
| ATOM | 1692 | O   | THR | B | 407 | −64.333 | 37.469 | −36.293 | 1.00 | 87.26 | O |
| ATOM | 1693 | N   | LEU | B | 408 | −62.461 | 37.926 | −35.104 | 1.00 | 83.82 | N |
| ATOM | 1694 | CA  | LEU | B | 408 | −63.150 | 38.086 | −33.837 | 1.00 | 82.78 | C |
| ATOM | 1695 | CB  | LEU | B | 408 | −62.143 | 38.376 | −32.722 | 1.00 | 82.53 | C |
| ATOM | 1696 | CG  | LEU | B | 408 | −62.696 | 38.851 | −31.380 | 1.00 | 82.25 | C |
| ATOM | 1697 | CD1 | LEU | B | 408 | −63.598 | 37.798 | −30.727 | 1.00 | 82.62 | C |
| ATOM | 1698 | CD2 | LEU | B | 408 | −61.576 | 39.199 | −30.436 | 1.00 | 82.94 | C |
| ATOM | 1699 | C   | LEU | B | 408 | −64.180 | 39.215 | −33.955 | 1.00 | 82.54 | C |
| ATOM | 1700 | O   | LEU | B | 408 | −65.314 | 39.051 | −33.489 | 1.00 | 82.55 | O |
| ATOM | 1701 | N   | ALA | B | 409 | −63.795 | 40.344 | −34.605 | 1.00 | 81.97 | N |
| ATOM | 1702 | CA  | ALA | B | 409 | −64.659 | 41.516 | −34.779 | 1.00 | 81.35 | C |
| ATOM | 1703 | CB  | ALA | B | 409 | −63.871 | 42.672 | −35.361 | 1.00 | 81.52 | C |
| ATOM | 1704 | C   | ALA | B | 409 | −65.874 | 41.213 | −35.633 | 1.00 | 80.96 | C |
| ATOM | 1705 | O   | ALA | B | 409 | −66.945 | 41.771 | −35.386 | 1.00 | 80.76 | O |
| ATOM | 1706 | N   | GLU | B | 410 | −65.699 | 40.309 | −36.617 | 1.00 | 80.96 | N |
| ATOM | 1707 | CA  | GLU | B | 410 | −66.710 | 39.842 | −37.567 | 1.00 | 80.62 | C |
| ATOM | 1708 | CB  | GLU | B | 410 | −66.014 | 39.093 | −38.711 | 1.00 | 80.93 | C |
| ATOM | 1709 | CG  | GLU | B | 410 | −65.963 | 39.834 | −40.033 | 1.00 | 83.23 | C |
| ATOM | 1710 | CD  | GLU | B | 410 | −64.677 | 39.602 | −40.809 | 1.00 | 87.13 | C |
| ATOM | 1711 | OE1 | GLU | B | 410 | −64.421 | 38.451 | −41.248 | 1.00 | 88.89 | O |
| ATOM | 1712 | OE2 | GLU | B | 410 | −63.915 | 40.584 | −40.969 | 1.00 | 89.23 | O |
| ATOM | 1713 | C   | GLU | B | 410 | −67.650 | 38.891 | −36.874 | 1.00 | 79.82 | C |
| ATOM | 1714 | O   | GLU | B | 410 | −68.822 | 38.779 | −37.234 | 1.00 | 79.68 | O |
| ATOM | 1715 | N   | LEU | B | 411 | −67.113 | 38.187 | −35.889 | 1.00 | 78.35 | N |
| ATOM | 1716 | CA  | LEU | B | 411 | −67.839 | 37.207 | −35.119 | 1.00 | 77.79 | C |
| ATOM | 1717 | CB  | LEU | B | 411 | −66.867 | 36.153 | −34.596 | 1.00 | 77.78 | C |
| ATOM | 1718 | CG  | LEU | B | 411 | −67.515 | 34.903 | −34.097 | 1.00 | 78.03 | C |
| ATOM | 1719 | CD1 | LEU | B | 411 | −67.345 | 33.767 | −35.086 | 1.00 | 78.21 | C |
| ATOM | 1720 | CD2 | LEU | B | 411 | −66.983 | 34.561 | −32.737 | 1.00 | 79.18 | C |
| ATOM | 1721 | C   | LEU | B | 411 | −68.681 | 37.847 | −34.001 | 1.00 | 77.24 | C |
| ATOM | 1722 | O   | LEU | B | 411 | −69.831 | 37.441 | −33.802 | 1.00 | 77.27 | O |
| ATOM | 1723 | N   | ARG | B | 412 | −68.130 | 38.849 | −33.291 | 1.00 | 76.11 | N |
| ATOM | 1724 | CA  | ARG | B | 412 | −68.868 | 39.539 | −32.231 | 1.00 | 75.55 | C |
| ATOM | 1725 | CB  | ARG | B | 412 | −68.009 | 40.629 | −31.581 | 1.00 | 75.61 | C |
| ATOM | 1726 | CG  | ARG | B | 412 | −68.578 | 41.165 | −30.270 | 1.00 | 75.68 | C |
| ATOM | 1727 | CD  | ARG | B | 412 | −67.779 | 42.318 | −29.686 | 1.00 | 76.09 | C |
| ATOM | 1728 | NE  | ARG | B | 412 | −66.410 | 41.948 | −29.333 | 1.00 | 76.59 | N |
| ATOM | 1729 | CZ  | ARG | B | 412 | −65.366 | 42.123 | −30.143 | 1.00 | 78.24 | C |
| ATOM | 1730 | NH1 | ARG | B | 412 | −65.535 | 42.649 | −31.357 | 1.00 | 78.09 | N |
| ATOM | 1731 | NH2 | ARG | B | 412 | −64.146 | 41.775 | −29.749 | 1.00 | 79.25 | N |
| ATOM | 1732 | C   | ARG | B | 412 | −70.114 | 40.149 | −32.851 | 1.00 | 75.03 | C |
| ATOM | 1733 | O   | ARG | B | 412 | −71.220 | 39.914 | −32.358 | 1.00 | 75.17 | O |
| ATOM | 1734 | N   | GLN | B | 413 | −69.921 | 40.886 | −33.966 | 1.00 | 74.22 | N |
| ATOM | 1735 | CA  | GLN | B | 413 | −70.953 | 41.540 | −34.766 | 1.00 | 73.43 | C |
| ATOM | 1736 | CB  | GLN | B | 413 | −70.301 | 42.219 | −35.965 | 1.00 | 73.44 | C |
| ATOM | 1737 | CG  | GLN | B | 413 | −69.415 | 43.393 | −35.576 | 1.00 | 73.24 | C |
| ATOM | 1738 | CD  | GLN | B | 413 | −70.167 | 44.690 | −35.561 | 1.00 | 72.45 | C |
| ATOM | 1739 | OE1 | GLN | B | 413 | −71.411 | 44.719 | −35.704 | 1.00 | 72.48 | O |
| ATOM | 1740 | NE2 | GLN | B | 413 | −69.425 | 45.783 | −35.373 | 1.00 | 70.30 | N |
| ATOM | 1741 | C   | GLN | B | 413 | −72.012 | 40.539 | −35.229 | 1.00 | 73.02 | C |
| ATOM | 1742 | O   | GLN | B | 413 | −73.201 | 40.787 | −35.048 | 1.00 | 72.86 | O |
| ATOM | 1743 | N   | ARG | B | 414 | −71.571 | 39.396 | −35.800 | 1.00 | 75.91 | N |
| ATOM | 1744 | CA  | ARG | B | 414 | −72.421 | 38.300 | −36.272 | 1.00 | 75.71 | C |
| ATOM | 1745 | CB  | ARG | B | 414 | −71.555 | 37.219 | −36.942 | 1.00 | 76.10 | C |
| ATOM | 1746 | CG  | ARG | B | 414 | −72.166 | 36.681 | −38.235 | 1.00 | 79.15 | C |
| ATOM | 1747 | CD  | ARG | B | 414 | −71.243 | 35.718 | −38.987 | 1.00 | 85.28 | C |
| ATOM | 1748 | NE  | ARG | B | 414 | −71.509 | 35.701 | −40.431 | 1.00 | 88.74 | N |
| ATOM | 1749 | CZ  | ARG | B | 414 | −71.101 | 36.643 | −41.287 | 1.00 | 91.15 | C |
| ATOM | 1750 | NH1 | ARG | B | 414 | −71.403 | 36.551 | −42.578 | 1.00 | 92.85 | N |
| ATOM | 1751 | NH2 | ARG | B | 414 | −70.399 | 37.695 | −40.851 | 1.00 | 91.02 | N |
| ATOM | 1752 | C   | ARG | B | 414 | −73.325 | 37.712 | −35.133 | 1.00 | 74.46 | C |
| ATOM | 1753 | O   | ARG | B | 414 | −74.515 | 37.478 | −35.356 | 1.00 | 74.04 | O |
| ATOM | 1754 | N   | LEU | B | 415 | −72.759 | 37.512 | −33.921 | 1.00 | 68.09 | N |
| ATOM | 1755 | CA  | LEU | B | 415 | −73.501 | 37.017 | −32.764 | 1.00 | 67.32 | C |
| ATOM | 1756 | CB  | LEU | B | 415 | −72.561 | 36.841 | −31.577 | 1.00 | 67.07 | C |

TABLE 14-continued

PCSK9 and AX132 Fab complex x-ray structure

| ATOM | 1757 | CG  | LEU | B | 415 | −71.715 | 35.604 | −31.538 | 1.00 | 66.56 | C |
|------|------|-----|-----|---|-----|---------|--------|---------|------|-------|---|
| ATOM | 1758 | CD1 | LEU | B | 415 | −70.568 | 35.777 | −30.549 | 1.00 | 66.03 | C |
| ATOM | 1759 | CD2 | LEU | B | 415 | −72.554 | 34.350 | −31.266 | 1.00 | 65.00 | C |
| ATOM | 1760 | C   | LEU | B | 415 | −74.591 | 38.032 | −32.381 | 1.00 | 67.36 | C |
| ATOM | 1761 | O   | LEU | B | 415 | −75.722 | 37.642 | −32.052 | 1.00 | 67.10 | O |
| ATOM | 1762 | N   | ILE | B | 416 | −74.234 | 39.348 | −32.425 | 1.00 | 68.45 | N |
| ATOM | 1763 | CA  | ILE | B | 416 | −75.152 | 40.442 | −32.127 | 1.00 | 68.32 | C |
| ATOM | 1764 | CB  | ILE | B | 416 | −74.435 | 41.815 | −32.035 | 1.00 | 67.86 | C |
| ATOM | 1765 | CG1 | ILE | B | 416 | −73.425 | 41.848 | −30.881 | 1.00 | 67.10 | C |
| ATOM | 1766 | CD1 | ILE | B | 416 | −72.503 | 43.080 | −30.854 | 1.00 | 65.57 | C |
| ATOM | 1767 | CG2 | ILE | B | 416 | −75.453 | 42.945 | −31.889 | 1.00 | 66.91 | C |
| ATOM | 1768 | C   | ILE | B | 416 | −76.298 | 40.439 | −33.154 | 1.00 | 68.96 | C |
| ATOM | 1769 | O   | ILE | B | 416 | −77.454 | 40.451 | −32.752 | 1.00 | 68.93 | O |
| ATOM | 1770 | N   | HIS | B | 417 | −75.975 | 40.390 | −34.462 | 1.00 | 74.14 | N |
| ATOM | 1771 | CA  | HIS | B | 417 | −76.957 | 40.405 | −35.536 | 1.00 | 75.34 | C |
| ATOM | 1772 | CB  | HIS | B | 417 | −76.288 | 40.576 | −36.912 | 1.00 | 76.00 | C |
| ATOM | 1773 | CG  | HIS | B | 417 | −77.281 | 40.887 | −37.995 | 1.00 | 79.28 | C |
| ATOM | 1774 | ND1 | HIS | B | 417 | −77.849 | 42.162 | −38.121 | 1.00 | 82.13 | N |
| ATOM | 1775 | CE1 | HIS | B | 417 | −78.699 | 42.080 | −39.137 | 1.00 | 82.76 | C |
| ATOM | 1776 | NE2 | HIS | B | 417 | −78.727 | 40.842 | −39.657 | 1.00 | 83.50 | N |
| ATOM | 1777 | CD2 | HIS | B | 417 | −77.825 | 40.071 | −38.935 | 1.00 | 81.69 | C |
| ATOM | 1778 | C   | HIS | B | 417 | −77.945 | 39.241 | −35.522 | 1.00 | 75.44 | C |
| ATOM | 1779 | O   | HIS | B | 417 | −79.073 | 39.401 | −35.971 | 1.00 | 75.49 | O |
| ATOM | 1780 | N   | PHE | B | 418 | −77.541 | 38.085 | −35.001 | 1.00 | 76.60 | N |
| ATOM | 1781 | CA  | PHE | B | 418 | −78.407 | 36.912 | −34.952 | 1.00 | 76.73 | C |
| ATOM | 1782 | CB  | PHE | B | 418 | −77.574 | 35.642 | −35.078 | 1.00 | 77.20 | C |
| ATOM | 1783 | CG  | PHE | B | 418 | −76.787 | 35.408 | −36.338 | 1.00 | 79.44 | C |
| ATOM | 1784 | CD1 | PHE | B | 418 | −76.803 | 36.338 | −37.377 | 1.00 | 81.12 | C |
| ATOM | 1785 | CE1 | PHE | B | 418 | −76.056 | 36.129 | −38.533 | 1.00 | 82.00 | C |
| ATOM | 1786 | CZ  | PHE | B | 418 | −75.304 | 34.976 | −38.667 | 1.00 | 82.73 | C |
| ATOM | 1787 | CE2 | PHE | B | 418 | −75.286 | 34.034 | −37.656 | 1.00 | 82.54 | C |
| ATOM | 1788 | CD2 | PHE | B | 418 | −76.022 | 34.254 | −36.491 | 1.00 | 81.60 | C |
| ATOM | 1789 | C   | PHE | B | 418 | −79.206 | 36.813 | −33.663 | 1.00 | 76.39 | C |
| ATOM | 1790 | O   | PHE | B | 418 | −80.242 | 36.139 | −33.646 | 1.00 | 76.28 | O |
| ATOM | 1791 | N   | SER | B | 419 | −78.701 | 37.427 | −32.578 | 1.00 | 73.74 | N |
| ATOM | 1792 | CA  | SER | B | 419 | −79.308 | 37.404 | −31.256 | 1.00 | 73.75 | C |
| ATOM | 1793 | CB  | SER | B | 419 | −78.556 | 38.338 | −30.314 | 1.00 | 73.84 | C |
| ATOM | 1794 | OG  | SER | B | 419 | −77.436 | 37.727 | −29.700 | 1.00 | 74.19 | O |
| ATOM | 1795 | C   | SER | B | 419 | −80.734 | 37.853 | −31.302 | 1.00 | 73.84 | C |
| ATOM | 1796 | O   | SER | B | 419 | −81.040 | 38.766 | −32.061 | 1.00 | 73.99 | O |
| ATOM | 1797 | N   | ALA | B | 420 | −81.605 | 37.240 | −30.484 | 1.00 | 71.93 | N |
| ATOM | 1798 | CA  | ALA | B | 420 | −83.005 | 37.625 | −30.365 | 1.00 | 72.07 | C |
| ATOM | 1799 | CB  | ALA | B | 420 | −83.745 | 36.590 | −29.542 | 1.00 | 71.93 | C |
| ATOM | 1800 | C   | ALA | B | 420 | −83.013 | 38.999 | −29.644 | 1.00 | 72.40 | C |
| ATOM | 1801 | O   | ALA | B | 420 | −82.185 | 39.205 | −28.751 | 1.00 | 72.46 | O |
| ATOM | 1802 | N   | LYS | B | 421 | −83.897 | 39.937 | −30.051 | 1.00 | 74.23 | N |
| ATOM | 1803 | CA  | LYS | B | 421 | −83.988 | 41.299 | −29.487 | 1.00 | 74.62 | C |
| ATOM | 1804 | CB  | LYS | B | 421 | −83.947 | 42.338 | −30.610 | 1.00 | 74.66 | C |
| ATOM | 1805 | CG  | LYS | B | 421 | −82.547 | 42.783 | −30.946 | 1.00 | 76.25 | C |
| ATOM | 1806 | CD  | LYS | B | 421 | −81.924 | 41.947 | −32.054 | 1.00 | 78.94 | C |
| ATOM | 1807 | CE  | LYS | B | 421 | −80.544 | 42.425 | −32.471 | 1.00 | 79.71 | C |
| ATOM | 1808 | NZ  | LYS | B | 421 | −79.899 | 41.465 | −33.406 | 1.00 | 80.33 | N |
| ATOM | 1809 | C   | LYS | B | 421 | −85.189 | 41.583 | −28.572 | 1.00 | 74.71 | C |
| ATOM | 1810 | O   | LYS | B | 421 | −86.234 | 40.961 | −28.717 | 1.00 | 74.88 | O |
| ATOM | 1811 | N   | ASP | B | 422 | −85.035 | 42.533 | −27.638 | 1.00 | 75.41 | N |
| ATOM | 1812 | CA  | ASP | B | 422 | −86.057 | 42.990 | −26.672 | 1.00 | 75.73 | C |
| ATOM | 1813 | CB  | ASP | B | 422 | −87.007 | 44.040 | −27.285 | 1.00 | 76.30 | C |
| ATOM | 1814 | CG  | ASP | B | 422 | −86.437 | 44.958 | −28.360 | 1.00 | 78.13 | C |
| ATOM | 1815 | OD1 | ASP | B | 422 | −85.237 | 45.372 | −28.230 | 1.00 | 78.71 | O |
| ATOM | 1816 | OD2 | ASP | B | 422 | −87.193 | 45.274 | −29.336 | 1.00 | 80.16 | O |
| ATOM | 1817 | C   | ASP | B | 422 | −86.846 | 41.924 | −25.868 | 1.00 | 75.29 | C |
| ATOM | 1818 | O   | ASP | B | 422 | −87.839 | 42.245 | −25.206 | 1.00 | 75.54 | O |
| ATOM | 1819 | N   | VAL | B | 423 | −86.389 | 40.677 | −25.899 | 1.00 | 72.35 | N |
| ATOM | 1820 | CA  | VAL | B | 423 | −87.045 | 39.568 | −25.209 | 1.00 | 71.53 | C |
| ATOM | 1821 | CB  | VAL | B | 423 | −86.847 | 38.225 | −25.933 | 1.00 | 71.50 | C |
| ATOM | 1822 | CG1 | VAL | B | 423 | −87.586 | 38.219 | −27.275 | 1.00 | 71.38 | C |
| ATOM | 1823 | CG2 | VAL | B | 423 | −85.370 | 37.910 | −26.124 | 1.00 | 71.72 | C |
| ATOM | 1824 | C   | VAL | B | 423 | −86.777 | 39.517 | −23.713 | 1.00 | 71.24 | C |
| ATOM | 1825 | O   | VAL | B | 423 | −87.544 | 38.891 | −22.980 | 1.00 | 71.04 | O |
| ATOM | 1826 | N   | ILE | B | 424 | −85.710 | 40.192 | −23.253 | 1.00 | 69.40 | N |
| ATOM | 1827 | CA  | ILE | B | 424 | −85.372 | 40.256 | −21.831 | 1.00 | 69.33 | C |
| ATOM | 1828 | CB  | ILE | B | 424 | −83.852 | 40.479 | −21.624 | 1.00 | 69.22 | C |
| ATOM | 1829 | CG1 | ILE | B | 424 | −82.966 | 39.459 | −22.357 | 1.00 | 68.76 | C |
| ATOM | 1830 | CD1 | ILE | B | 424 | −81.464 | 39.930 | −22.473 | 1.00 | 67.42 | C |
| ATOM | 1831 | CG2 | ILE | B | 424 | −83.513 | 40.562 | −20.155 | 1.00 | 69.12 | C |
| ATOM | 1832 | C   | ILE | B | 424 | −86.142 | 41.435 | −21.246 | 1.00 | 69.45 | C |
| ATOM | 1833 | O   | ILE | B | 424 | −86.150 | 42.493 | −21.869 | 1.00 | 69.43 | O |
| ATOM | 1834 | N   | ASN | B | 425 | −86.764 | 41.278 | −20.062 | 1.00 | 72.98 | N |

TABLE 14-continued

PCSK9 and AX132 Fab complex x-ray structure

| ATOM | 1835 | CA  | ASN | B | 425 | −87.468 | 42.374 | −19.397 | 1.00 | 73.43 | C |
| ATOM | 1836 | CB  | ASN | B | 425 | −88.543 | 41.841 | −18.432 | 1.00 | 73.75 | C |
| ATOM | 1837 | CG  | ASN | B | 425 | −89.486 | 42.891 | −17.818 | 1.00 | 75.20 | C |
| ATOM | 1838 | OD1 | ASN | B | 425 | −89.341 | 44.124 | −18.010 | 1.00 | 77.09 | O |
| ATOM | 1839 | ND2 | ASN | B | 425 | −90.491 | 42.419 | −17.056 | 1.00 | 75.14 | N |
| ATOM | 1840 | C   | ASN | B | 425 | −86.405 | 43.217 | −18.656 | 1.00 | 73.62 | C |
| ATOM | 1841 | O   | ASN | B | 425 | −85.893 | 42.785 | −17.618 | 1.00 | 73.33 | O |
| ATOM | 1842 | N   | GLU | B | 426 | −86.061 | 44.408 | −19.211 | 1.00 | 76.51 | N |
| ATOM | 1843 | CA  | GLU | B | 426 | −85.051 | 45.338 | −18.671 | 1.00 | 76.99 | C |
| ATOM | 1844 | CB  | GLU | B | 426 | −84.946 | 46.653 | −19.505 | 1.00 | 77.36 | C |
| ATOM | 1845 | CG  | GLU | B | 426 | −84.451 | 46.494 | −20.946 | 1.00 | 80.58 | C |
| ATOM | 1846 | CD  | GLU | B | 426 | −82.965 | 46.603 | −21.329 | 1.00 | 85.39 | C |
| ATOM | 1847 | OE1 | GLU | B | 426 | −82.675 | 47.253 | −22.367 | 1.00 | 86.18 | O |
| ATOM | 1848 | OE2 | GLU | B | 426 | −82.097 | 46.025 | −20.625 | 1.00 | 86.84 | O |
| ATOM | 1849 | C   | GLU | B | 426 | −85.252 | 45.650 | −17.181 | 1.00 | 76.56 | C |
| ATOM | 1850 | O   | GLU | B | 426 | −84.302 | 46.052 | −16.515 | 1.00 | 76.36 | O |
| ATOM | 1851 | N   | ALA | B | 427 | −86.480 | 45.442 | −16.667 | 1.00 | 75.86 | N |
| ATOM | 1852 | CA  | ALA | B | 427 | −86.903 | 45.679 | −15.282 | 1.00 | 75.92 | C |
| ATOM | 1853 | CB  | ALA | B | 427 | −88.383 | 45.409 | −15.137 | 1.00 | 75.89 | C |
| ATOM | 1854 | C   | ALA | B | 427 | −86.121 | 44.920 | −14.195 | 1.00 | 75.95 | C |
| ATOM | 1855 | O   | ALA | B | 427 | −85.977 | 45.442 | −13.089 | 1.00 | 76.02 | O |
| ATOM | 1856 | N   | TRP | B | 428 | −85.611 | 43.715 | −14.505 | 1.00 | 75.20 | N |
| ATOM | 1857 | CA  | TRP | B | 428 | −84.837 | 42.878 | −13.588 | 1.00 | 75.04 | C |
| ATOM | 1858 | CB  | TRP | B | 428 | −84.603 | 41.511 | −14.243 | 1.00 | 75.43 | C |
| ATOM | 1859 | CG  | TRP | B | 428 | −83.974 | 40.446 | −13.377 | 1.00 | 77.09 | C |
| ATOM | 1860 | CD1 | TRP | B | 428 | −84.627 | 39.444 | −12.722 | 1.00 | 78.40 | C |
| ATOM | 1861 | NE1 | TRP | B | 428 | −83.720 | 38.604 | −12.105 | 1.00 | 78.60 | N |
| ATOM | 1862 | CE2 | TRP | B | 428 | −82.445 | 39.035 | −12.383 | 1.00 | 77.96 | C |
| ATOM | 1863 | CD2 | TRP | B | 428 | −82.560 | 40.204 | −13.171 | 1.00 | 78.20 | C |
| ATOM | 1864 | CE3 | TRP | B | 428 | −81.382 | 40.862 | −13.572 | 1.00 | 77.89 | C |
| ATOM | 1865 | CZ3 | TRP | B | 428 | −80.160 | 40.346 | −13.171 | 1.00 | 77.32 | C |
| ATOM | 1866 | CH2 | TRP | B | 428 | −80.081 | 39.181 | −12.399 | 1.00 | 76.83 | C |
| ATOM | 1867 | CZ2 | TRP | B | 428 | −81.206 | 38.518 | −11.981 | 1.00 | 77.51 | C |
| ATOM | 1868 | C   | TRP | B | 428 | −83.502 | 43.533 | −13.263 | 1.00 | 74.49 | C |
| ATOM | 1869 | O   | TRP | B | 428 | −82.938 | 43.281 | −12.201 | 1.00 | 74.39 | O |
| ATOM | 1870 | N   | PHE | B | 429 | −82.992 | 44.352 | −14.180 | 1.00 | 71.16 | N |
| ATOM | 1871 | CA  | PHE | B | 429 | −81.722 | 45.030 | −14.002 | 1.00 | 71.13 | C |
| ATOM | 1872 | CB  | PHE | B | 429 | −81.100 | 45.403 | −15.369 | 1.00 | 70.85 | C |
| ATOM | 1873 | CG  | PHE | B | 429 | −80.897 | 44.253 | −16.314 | 1.00 | 70.76 | C |
| ATOM | 1874 | CD1 | PHE | B | 429 | −80.117 | 43.159 | −15.949 | 1.00 | 71.06 | C |
| ATOM | 1875 | CE1 | PHE | B | 429 | −79.955 | 42.075 | −16.812 | 1.00 | 70.57 | C |
| ATOM | 1876 | CZ  | PHE | B | 429 | −80.551 | 42.090 | −18.052 | 1.00 | 70.73 | C |
| ATOM | 1877 | CE2 | PHE | B | 429 | −81.311 | 43.175 | −18.440 | 1.00 | 70.60 | C |
| ATOM | 1878 | CD2 | PHE | B | 429 | −81.482 | 44.257 | −17.571 | 1.00 | 70.51 | C |
| ATOM | 1879 | C   | PHE | B | 429 | −81.861 | 46.287 | −13.170 | 1.00 | 71.33 | C |
| ATOM | 1880 | O   | PHE | B | 429 | −82.913 | 46.900 | −13.188 | 1.00 | 71.38 | O |
| ATOM | 1881 | N   | PRO | B | 430 | −80.807 | 46.735 | −12.470 | 1.00 | 73.47 | N |
| ATOM | 1882 | CA  | PRO | B | 430 | −80.905 | 48.014 | −11.761 | 1.00 | 73.85 | C |
| ATOM | 1883 | CB  | PRO | B | 430 | −79.493 | 48.199 | −11.175 | 1.00 | 73.71 | C |
| ATOM | 1884 | CG  | PRO | B | 430 | −78.873 | 46.883 | −11.199 | 1.00 | 73.53 | C |
| ATOM | 1885 | CD  | PRO | B | 430 | −79.454 | 46.157 | −12.353 | 1.00 | 73.62 | C |
| ATOM | 1886 | C   | PRO | B | 430 | −81.189 | 49.125 | −12.788 | 1.00 | 74.59 | C |
| ATOM | 1887 | O   | PRO | B | 430 | −80.551 | 49.129 | −13.836 | 1.00 | 74.54 | O |
| ATOM | 1888 | N   | GLU | B | 431 | −82.130 | 50.055 | −12.498 | 1.00 | 80.83 | N |
| ATOM | 1889 | CA  | GLU | B | 431 | −82.507 | 51.176 | −13.378 | 1.00 | 81.60 | C |
| ATOM | 1890 | CB  | GLU | B | 431 | −83.287 | 52.266 | −12.613 | 1.00 | 82.19 | C |
| ATOM | 1891 | CG  | GLU | B | 431 | −84.205 | 51.738 | −11.499 | 1.00 | 86.77 | C |
| ATOM | 1892 | CD  | GLU | B | 431 | −85.528 | 52.458 | −11.219 | 1.00 | 91.61 | C |
| ATOM | 1893 | OE1 | GLU | B | 431 | −85.495 | 53.696 | −11.002 | 1.00 | 93.91 | O |
| ATOM | 1894 | OE2 | GLU | B | 431 | −86.592 | 51.781 | −11.204 | 1.00 | 92.08 | O |
| ATOM | 1895 | C   | GLU | B | 431 | −81.322 | 51.797 | −14.118 | 1.00 | 81.10 | C |
| ATOM | 1896 | O   | GLU | B | 431 | −81.396 | 52.006 | −15.332 | 1.00 | 81.11 | O |
| ATOM | 1897 | N   | ASP | B | 432 | −80.212 | 52.054 | −13.405 | 1.00 | 79.98 | N |
| ATOM | 1898 | CA  | ASP | B | 432 | −79.032 | 52.650 | −14.039 | 1.00 | 79.83 | C |
| ATOM | 1899 | CB  | ASP | B | 432 | −78.114 | 53.367 | −13.030 | 1.00 | 80.23 | C |
| ATOM | 1900 | CG  | ASP | B | 432 | −77.464 | 52.452 | −12.013 | 1.00 | 82.98 | C |
| ATOM | 1901 | OD1 | ASP | B | 432 | −76.200 | 52.487 | −11.896 | 1.00 | 85.48 | O |
| ATOM | 1902 | OD2 | ASP | B | 432 | −78.211 | 51.687 | −11.327 | 1.00 | 85.86 | O |
| ATOM | 1903 | C   | ASP | B | 432 | −78.266 | 51.729 | −14.994 | 1.00 | 79.05 | C |
| ATOM | 1904 | O   | ASP | B | 432 | −77.451 | 52.233 | −15.759 | 1.00 | 79.13 | O |
| ATOM | 1905 | N   | GLN | B | 433 | −78.530 | 50.388 | −14.964 | 1.00 | 74.87 | N |
| ATOM | 1906 | CA  | GLN | B | 433 | −77.887 | 49.397 | −15.849 | 1.00 | 73.54 | C |
| ATOM | 1907 | CB  | GLN | B | 433 | −77.585 | 48.078 | −15.128 | 1.00 | 73.41 | C |
| ATOM | 1908 | CG  | GLN | B | 433 | −76.494 | 48.154 | −14.079 | 1.00 | 73.19 | C |
| ATOM | 1909 | CD  | GLN | B | 433 | −75.246 | 48.854 | −14.525 | 1.00 | 72.32 | C |
| ATOM | 1910 | OE1 | GLN | B | 433 | −74.502 | 48.395 | −15.396 | 1.00 | 72.62 | O |
| ATOM | 1911 | NE2 | GLN | B | 433 | −74.996 | 50.003 | −13.925 | 1.00 | 72.78 | N |
| ATOM | 1912 | C   | GLN | B | 433 | −78.673 | 49.113 | −17.124 | 1.00 | 72.69 | C |

TABLE 14-continued

PCSK9 and AX132 Fab complex x-ray structure

| ATOM | 1913 | O   | GLN | B | 433 | −78.066 | 48.758 | −18.122 | 1.00 | 72.79 | O |
|------|------|-----|-----|---|-----|---------|--------|---------|------|-------|---|
| ATOM | 1914 | N   | ARG | B | 434 | −80.001 | 49.284 | −17.096 | 1.00 | 70.39 | N |
| ATOM | 1915 | CA  | ARG | B | 434 | −80.933 | 49.043 | −18.202 | 1.00 | 69.41 | C |
| ATOM | 1916 | CB  | ARG | B | 434 | −82.350 | 49.503 | −17.846 | 1.00 | 69.21 | C |
| ATOM | 1917 | CG  | ARG | B | 434 | −82.790 | 49.107 | −16.459 | 1.00 | 69.34 | C |
| ATOM | 1918 | CD  | ARG | B | 434 | −84.272 | 48.914 | −16.404 | 1.00 | 72.35 | C |
| ATOM | 1919 | NE  | ARG | B | 434 | −84.937 | 49.688 | −15.347 | 1.00 | 74.41 | N |
| ATOM | 1920 | CZ  | ARG | B | 434 | −85.379 | 49.180 | −14.198 | 1.00 | 74.96 | C |
| ATOM | 1921 | NH1 | ARG | B | 434 | −85.209 | 47.899 | −13.924 | 1.00 | 75.62 | N |
| ATOM | 1922 | NH2 | ARG | B | 434 | −85.997 | 49.954 | −13.318 | 1.00 | 75.15 | N |
| ATOM | 1923 | C   | ARG | B | 434 | −80.487 | 49.584 | −19.565 | 1.00 | 68.75 | C |
| ATOM | 1924 | O   | ARG | B | 434 | −80.503 | 48.863 | −20.567 | 1.00 | 68.68 | O |
| ATOM | 1925 | N   | VAL | B | 435 | −80.063 | 50.824 | −19.605 | 1.00 | 69.69 | N |
| ATOM | 1926 | CA  | VAL | B | 435 | −79.630 | 51.434 | −20.859 | 1.00 | 69.16 | C |
| ATOM | 1927 | CB  | VAL | B | 435 | −79.319 | 52.950 | −20.680 | 1.00 | 69.68 | C |
| ATOM | 1928 | CG1 | VAL | B | 435 | −79.223 | 53.634 | −22.034 | 1.00 | 69.67 | C |
| ATOM | 1929 | CG2 | VAL | B | 435 | −80.336 | 53.662 | −19.758 | 1.00 | 70.48 | C |
| ATOM | 1930 | C   | VAL | B | 435 | −78.405 | 50.727 | −21.446 | 1.00 | 68.06 | C |
| ATOM | 1931 | O   | VAL | B | 435 | −78.319 | 50.560 | −22.659 | 1.00 | 68.42 | O |
| ATOM | 1932 | N   | LEU | B | 436 | −77.455 | 50.355 | −20.583 | 1.00 | 62.44 | N |
| ATOM | 1933 | CA  | LEU | B | 436 | −76.184 | 49.748 | −20.936 | 1.00 | 61.31 | C |
| ATOM | 1934 | CB  | LEU | B | 436 | −75.187 | 50.001 | −19.814 | 1.00 | 61.19 | C |
| ATOM | 1935 | CG  | LEU | B | 436 | −75.048 | 51.449 | −19.364 | 1.00 | 60.52 | C |
| ATOM | 1936 | CD1 | LEU | B | 436 | −75.019 | 51.546 | −17.855 | 1.00 | 58.88 | C |
| ATOM | 1937 | CD2 | LEU | B | 436 | −73.804 | 52.074 | −19.923 | 1.00 | 59.40 | C |
| ATOM | 1938 | C   | LEU | B | 436 | −76.227 | 48.265 | −21.243 | 1.00 | 60.83 | C |
| ATOM | 1939 | O   | LEU | B | 436 | −75.425 | 47.798 | −22.044 | 1.00 | 60.74 | O |
| ATOM | 1940 | N   | THR | B | 437 | −77.122 | 47.523 | −20.600 | 1.00 | 61.21 | N |
| ATOM | 1941 | CA  | THR | B | 437 | −77.254 | 46.086 | −20.776 | 1.00 | 60.77 | C |
| ATOM | 1942 | CB  | THR | B | 437 | −77.896 | 45.475 | −19.558 | 1.00 | 60.68 | C |
| ATOM | 1943 | OG1 | THR | B | 437 | −77.178 | 45.957 | −18.448 | 1.00 | 60.46 | O |
| ATOM | 1944 | CG2 | THR | B | 437 | −77.811 | 43.977 | −19.557 | 1.00 | 60.66 | C |
| ATOM | 1945 | C   | THR | B | 437 | −77.946 | 45.730 | −22.094 | 1.00 | 60.69 | C |
| ATOM | 1946 | O   | THR | B | 437 | −79.155 | 46.032 | −22.257 | 1.00 | 60.93 | O |
| ATOM | 1947 | N   | PRO | B | 438 | −77.186 | 45.075 | −23.030 | 1.00 | 59.45 | N |
| ATOM | 1948 | CA  | PRO | B | 438 | −77.763 | 44.714 | −24.323 | 1.00 | 59.43 | C |
| ATOM | 1949 | CB  | PRO | B | 438 | −76.575 | 44.148 | −25.106 | 1.00 | 59.07 | C |
| ATOM | 1950 | CG  | PRO | B | 438 | −75.608 | 43.738 | −24.113 | 1.00 | 59.06 | C |
| ATOM | 1951 | CD  | PRO | B | 438 | −75.772 | 44.650 | −22.948 | 1.00 | 59.53 | C |
| ATOM | 1952 | C   | PRO | B | 438 | −78.874 | 43.715 | −24.166 | 1.00 | 59.80 | C |
| ATOM | 1953 | O   | PRO | B | 438 | −78.681 | 42.690 | −23.504 | 1.00 | 59.99 | O |
| ATOM | 1954 | N   | ASN | B | 439 | −80.048 | 44.031 | −24.734 | 1.00 | 61.38 | N |
| ATOM | 1955 | CA  | ASN | B | 439 | −81.202 | 43.156 | −24.666 | 1.00 | 61.71 | C |
| ATOM | 1956 | CB  | ASN | B | 439 | −82.453 | 43.972 | −24.765 | 1.00 | 61.56 | C |
| ATOM | 1957 | CG  | ASN | B | 439 | −83.616 | 43.278 | −24.141 | 1.00 | 62.42 | C |
| ATOM | 1958 | OD1 | ASN | B | 439 | −83.963 | 42.129 | −24.488 | 1.00 | 64.09 | O |
| ATOM | 1959 | ND2 | ASN | B | 439 | −84.250 | 43.957 | −23.198 | 1.00 | 62.21 | N |
| ATOM | 1960 | C   | ASN | B | 439 | −81.103 | 42.097 | −25.788 | 1.00 | 61.96 | C |
| ATOM | 1961 | O   | ASN | B | 439 | −81.911 | 42.076 | −26.722 | 1.00 | 62.22 | O |
| ATOM | 1962 | N   | LEU | B | 440 | −80.090 | 41.216 | −25.678 | 1.00 | 61.01 | N |
| ATOM | 1963 | CA  | LEU | B | 440 | −79.773 | 40.158 | −26.642 | 1.00 | 61.13 | C |
| ATOM | 1964 | CB  | LEU | B | 440 | −78.401 | 40.491 | −27.264 | 1.00 | 61.11 | C |
| ATOM | 1965 | CG  | LEU | B | 440 | −78.293 | 41.836 | −27.960 | 1.00 | 59.46 | C |
| ATOM | 1966 | CD1 | LEU | B | 440 | −76.926 | 42.042 | −28.476 | 1.00 | 58.29 | C |
| ATOM | 1967 | CD2 | LEU | B | 440 | −79.271 | 41.930 | −29.105 | 1.00 | 58.76 | C |
| ATOM | 1968 | C   | LEU | B | 440 | −79.736 | 38.721 | −26.091 | 1.00 | 61.57 | C |
| ATOM | 1969 | O   | LEU | B | 440 | −79.230 | 38.491 | −24.994 | 1.00 | 61.27 | O |
| ATOM | 1970 | N   | VAL | B | 441 | −80.247 | 37.758 | −26.862 | 1.00 | 62.02 | N |
| ATOM | 1971 | CA  | VAL | B | 441 | −80.214 | 36.328 | −26.483 | 1.00 | 62.90 | C |
| ATOM | 1972 | CB  | VAL | B | 441 | −81.570 | 35.746 | −26.017 | 1.00 | 62.40 | C |
| ATOM | 1973 | CG1 | VAL | B | 441 | −81.444 | 34.252 | −25.761 | 1.00 | 62.92 | C |
| ATOM | 1974 | CG2 | VAL | B | 441 | −82.092 | 36.460 | −24.775 | 1.00 | 61.58 | C |
| ATOM | 1975 | C   | VAL | B | 441 | −79.655 | 35.552 | −27.680 | 1.00 | 63.94 | C |
| ATOM | 1976 | O   | VAL | B | 441 | −80.283 | 35.579 | −28.737 | 1.00 | 64.07 | O |
| ATOM | 1977 | N   | ALA | B | 442 | −78.496 | 34.882 | −27.524 | 1.00 | 63.55 | N |
| ATOM | 1978 | CA  | ALA | B | 442 | −77.838 | 34.123 | −28.593 | 1.00 | 65.18 | C |
| ATOM | 1979 | CB  | ALA | B | 442 | −76.643 | 33.361 | −28.056 | 1.00 | 64.97 | C |
| ATOM | 1980 | C   | ALA | B | 442 | −78.740 | 33.182 | −29.379 | 1.00 | 66.71 | C |
| ATOM | 1981 | O   | ALA | B | 442 | −79.629 | 32.497 | −28.839 | 1.00 | 66.50 | O |
| ATOM | 1982 | N   | ALA | B | 443 | −78.506 | 33.180 | −30.688 | 1.00 | 72.51 | N |
| ATOM | 1983 | CA  | ALA | B | 443 | −79.223 | 32.337 | −31.630 | 1.00 | 74.74 | C |
| ATOM | 1984 | CB  | ALA | B | 443 | −80.508 | 33.007 | −32.070 | 1.00 | 74.63 | C |
| ATOM | 1985 | C   | ALA | B | 443 | −78.323 | 32.072 | −32.820 | 1.00 | 76.48 | C |
| ATOM | 1986 | O   | ALA | B | 443 | −77.381 | 32.839 | −33.082 | 1.00 | 76.64 | O |
| ATOM | 1987 | N   | LEU | B | 444 | −78.576 | 30.936 | −33.489 | 1.00 | 83.55 | N |
| ATOM | 1988 | CA  | LEU | B | 444 | −77.880 | 30.481 | −34.689 | 1.00 | 85.83 | C |
| ATOM | 1989 | CB  | LEU | B | 444 | −76.964 | 29.278 | −34.398 | 1.00 | 85.77 | C |
| ATOM | 1990 | CG  | LEU | B | 444 | −75.812 | 29.013 | −35.370 | 1.00 | 85.71 | C |

TABLE 14-continued

PCSK9 and AX132 Fab complex x-ray structure

| ATOM | 1991 | CD1 | LEU | B | 444 | −76.248 | 28.122 | −36.509 | 1.00 | 85.91 | C |
|---|---|---|---|---|---|---|---|---|---|---|---|
| ATOM | 1992 | CD2 | LEU | B | 444 | −75.150 | 30.303 | −35.853 | 1.00 | 85.83 | C |
| ATOM | 1993 | C | LEU | B | 444 | −79.042 | 30.122 | −35.619 | 1.00 | 87.65 | C |
| ATOM | 1994 | O | LEU | B | 444 | −79.531 | 28.979 | −35.621 | 1.00 | 87.86 | O |
| ATOM | 1995 | N | PRO | B | 445 | −79.562 | 31.140 | −36.347 | 1.00 | 91.99 | N |
| ATOM | 1996 | CA | PRO | B | 445 | −80.728 | 30.905 | −37.201 | 1.00 | 93.36 | C |
| ATOM | 1997 | CB | PRO | B | 445 | −81.401 | 32.282 | −37.238 | 1.00 | 93.34 | C |
| ATOM | 1998 | CG | PRO | B | 445 | −80.375 | 33.270 | −36.705 | 1.00 | 92.71 | C |
| ATOM | 1999 | CD | PRO | B | 445 | −79.122 | 32.545 | −36.433 | 1.00 | 91.94 | C |
| ATOM | 2000 | C | PRO | B | 445 | −80.406 | 30.379 | −38.603 | 1.00 | 94.82 | C |
| ATOM | 2001 | O | PRO | B | 445 | −79.243 | 30.442 | −39.030 | 1.00 | 95.02 | O |
| ATOM | 2002 | N | PRO | B | 446 | −81.423 | 29.864 | −39.339 | 1.00 | 100.30 | N |
| ATOM | 2003 | CA | PRO | B | 446 | −81.172 | 29.360 | −40.707 | 1.00 | 101.67 | C |
| ATOM | 2004 | CB | PRO | B | 446 | −82.565 | 28.945 | −41.192 | 1.00 | 101.62 | C |
| ATOM | 2005 | CG | PRO | B | 446 | −83.513 | 29.671 | −40.290 | 1.00 | 100.98 | C |
| ATOM | 2006 | CD | PRO | B | 446 | −82.841 | 29.705 | −38.971 | 1.00 | 100.26 | C |
| ATOM | 2007 | C | PRO | B | 446 | −80.494 | 30.374 | −41.646 | 1.00 | 103.06 | C |
| ATOM | 2008 | O | PRO | B | 446 | −81.112 | 31.345 | −42.102 | 1.00 | 103.50 | O |
| ATOM | 2009 | N | SER | B | 447 | −79.193 | 30.120 | −41.908 | 1.00 | 108.30 | N |
| ATOM | 2010 | CA | SER | B | 447 | −78.239 | 30.894 | −42.717 | 1.00 | 109.79 | C |
| ATOM | 2011 | CB | SER | B | 447 | −77.048 | 30.038 | −43.148 | 1.00 | 109.70 | C |
| ATOM | 2012 | OG | SER | B | 447 | −77.472 | 28.871 | −43.833 | 1.00 | 110.07 | O |
| ATOM | 2013 | C | SER | B | 447 | −78.721 | 31.820 | −43.859 | 1.00 | 110.65 | C |
| ATOM | 2014 | O | SER | B | 447 | −78.629 | 33.043 | −43.691 | 1.00 | 110.94 | O |
| ATOM | 2015 | N | THR | B | 448 | −79.205 | 31.263 | −45.007 | 1.00 | 111.76 | N |
| ATOM | 2016 | CA | THR | B | 448 | −79.627 | 32.021 | −46.211 | 1.00 | 112.95 | C |
| ATOM | 2017 | CB | THR | B | 448 | −81.051 | 32.675 | −46.122 | 1.00 | 113.38 | C |
| ATOM | 2018 | OG1 | THR | B | 448 | −81.534 | 32.935 | −47.451 | 1.00 | 114.43 | O |
| ATOM | 2019 | CG2 | THR | B | 448 | −81.088 | 33.990 | −45.303 | 1.00 | 113.43 | C |
| ATOM | 2020 | C | THR | B | 448 | −78.504 | 32.906 | −46.819 | 1.00 | 113.06 | C |
| ATOM | 2021 | O | THR | B | 448 | −77.312 | 32.666 | −46.587 | 1.00 | 113.35 | O |
| ATOM | 2022 | N | GLY | B | 452 | −75.461 | 38.623 | −50.141 | 1.00 | 127.63 | N |
| ATOM | 2023 | CA | GLY | B | 452 | −74.322 | 39.520 | −50.305 | 1.00 | 127.36 | C |
| ATOM | 2024 | C | GLY | B | 452 | −73.994 | 40.335 | −49.067 | 1.00 | 127.27 | C |
| ATOM | 2025 | O | GLY | B | 452 | −74.774 | 40.335 | −48.104 | 1.00 | 127.36 | O |
| ATOM | 2026 | N | TRP | B | 453 | −72.829 | 41.046 | −49.090 | 1.00 | 122.80 | N |
| ATOM | 2027 | CA | TRP | B | 453 | −72.319 | 41.891 | −47.987 | 1.00 | 122.17 | C |
| ATOM | 2028 | CB | TRP | B | 453 | −70.949 | 42.535 | −48.332 | 1.00 | 122.48 | C |
| ATOM | 2029 | CG | TRP | B | 453 | −70.383 | 43.388 | −47.225 | 1.00 | 124.10 | C |
| ATOM | 2030 | CD1 | TRP | B | 453 | −69.563 | 42.980 | −46.214 | 1.00 | 125.45 | C |
| ATOM | 2031 | NE1 | TRP | B | 453 | −69.277 | 44.037 | −45.377 | 1.00 | 125.89 | N |
| ATOM | 2032 | CE2 | TRP | B | 453 | −69.926 | 45.156 | −45.830 | 1.00 | 126.02 | C |
| ATOM | 2033 | CD2 | TRP | B | 453 | −70.633 | 44.786 | −46.998 | 1.00 | 125.51 | C |
| ATOM | 2034 | CE3 | TRP | B | 453 | −71.391 | 45.766 | −47.669 | 1.00 | 126.21 | C |
| ATOM | 2035 | CZ3 | TRP | B | 453 | −71.418 | 47.056 | −47.160 | 1.00 | 126.79 | C |
| ATOM | 2036 | CH2 | TRP | B | 453 | −70.706 | 47.393 | −45.998 | 1.00 | 127.19 | C |
| ATOM | 2037 | CZ2 | TRP | B | 453 | −69.963 | 46.457 | −45.312 | 1.00 | 126.61 | C |
| ATOM | 2038 | C | TRP | B | 453 | −73.304 | 42.963 | −47.472 | 1.00 | 121.09 | C |
| ATOM | 2039 | O | TRP | B | 453 | −73.843 | 43.745 | −48.267 | 1.00 | 121.09 | O |
| ATOM | 2040 | N | GLN | B | 454 | −73.493 | 43.010 | −46.132 | 1.00 | 112.45 | N |
| ATOM | 2041 | CA | GLN | B | 454 | −74.348 | 43.982 | −45.450 | 1.00 | 110.83 | C |
| ATOM | 2042 | CB | GLN | B | 454 | −75.655 | 43.349 | −44.953 | 1.00 | 111.06 | C |
| ATOM | 2043 | CG | GLN | B | 454 | −76.547 | 42.747 | −46.064 | 1.00 | 112.66 | C |
| ATOM | 2044 | CD | GLN | B | 454 | −76.778 | 43.590 | −47.325 | 1.00 | 114.86 | C |
| ATOM | 2045 | OE1 | GLN | B | 454 | −77.171 | 44.775 | −47.288 | 1.00 | 116.38 | O |
| ATOM | 2046 | NE2 | GLN | B | 454 | −76.544 | 42.975 | −48.487 | 1.00 | 115.50 | N |
| ATOM | 2047 | C | GLN | B | 454 | −73.595 | 44.729 | −44.337 | 1.00 | 109.32 | C |
| ATOM | 2048 | O | GLN | B | 454 | −72.538 | 44.271 | −43.875 | 1.00 | 109.03 | O |
| ATOM | 2049 | N | LEU | B | 455 | −74.120 | 45.907 | −43.938 | 1.00 | 102.05 | N |
| ATOM | 2050 | CA | LEU | B | 455 | −73.486 | 46.731 | −42.907 | 1.00 | 100.09 | C |
| ATOM | 2051 | CB | LEU | B | 455 | −73.601 | 48.239 | −43.203 | 1.00 | 99.99 | C |
| ATOM | 2052 | CG | LEU | B | 455 | −72.755 | 49.173 | −42.336 | 1.00 | 99.59 | C |
| ATOM | 2053 | CD1 | LEU | B | 455 | −71.273 | 48.977 | −42.577 | 1.00 | 98.61 | C |
| ATOM | 2054 | CD2 | LEU | B | 455 | −73.148 | 50.606 | −42.538 | 1.00 | 99.38 | C |
| ATOM | 2055 | C | LEU | B | 455 | −73.909 | 46.390 | −41.474 | 1.00 | 98.78 | C |
| ATOM | 2056 | O | LEU | B | 455 | −75.098 | 46.445 | −41.116 | 1.00 | 98.56 | O |
| ATOM | 2057 | N | PHE | B | 456 | −72.909 | 46.036 | −40.657 | 1.00 | 93.82 | N |
| ATOM | 2058 | CA | PHE | B | 456 | −73.130 | 45.694 | −39.266 | 1.00 | 92.42 | C |
| ATOM | 2059 | CB | PHE | B | 456 | −72.575 | 44.301 | −38.925 | 1.00 | 92.95 | C |
| ATOM | 2060 | CG | PHE | B | 456 | −73.280 | 43.119 | −39.552 | 1.00 | 94.75 | C |
| ATOM | 2061 | CD1 | PHE | B | 456 | −74.642 | 43.167 | −39.835 | 1.00 | 96.82 | C |
| ATOM | 2062 | CE1 | PHE | B | 456 | −75.290 | 42.077 | −40.415 | 1.00 | 97.51 | C |
| ATOM | 2063 | CZ | PHE | B | 456 | −74.586 | 40.924 | −40.684 | 1.00 | 98.15 | C |
| ATOM | 2064 | CE2 | PHE | B | 456 | −73.240 | 40.850 | −40.395 | 1.00 | 97.34 | C |
| ATOM | 2065 | CD2 | PHE | B | 456 | −72.590 | 41.946 | −39.826 | 1.00 | 96.09 | C |
| ATOM | 2066 | C | PHE | B | 456 | −72.531 | 46.742 | −38.370 | 1.00 | 90.96 | C |
| ATOM | 2067 | O | PHE | B | 456 | −71.347 | 47.078 | −38.502 | 1.00 | 90.49 | O |
| ATOM | 2068 | N | CYS | B | 457 | −73.373 | 47.247 | −37.450 | 1.00 | 87.32 | N |

TABLE 14-continued

PCSK9 and AX132 Fab complex x-ray structure

| ATOM | 2069 | CA | CYS | B | 457 | −73.034 | 48.272 | −36.478 | 1.00 | 85.52 | C |
|---|---|---|---|---|---|---|---|---|---|---|---|
| ATOM | 2070 | CB | CYS | B | 457 | −73.687 | 49.596 | −36.852 | 1.00 | 85.99 | C |
| ATOM | 2071 | SG | CYS | B | 457 | −73.007 | 50.355 | −38.340 | 1.00 | 87.56 | S |
| ATOM | 2072 | C | CYS | B | 457 | −73.413 | 47.873 | −35.088 | 1.00 | 83.67 | C |
| ATOM | 2073 | O | CYS | B | 457 | −74.446 | 47.243 | −34.870 | 1.00 | 83.32 | O |
| ATOM | 2074 | N | ARG | B | 458 | −72.595 | 48.290 | −34.140 | 1.00 | 77.84 | N |
| ATOM | 2075 | CA | ARG | B | 458 | −72.821 | 48.044 | −32.733 | 1.00 | 76.05 | C |
| ATOM | 2076 | CB | ARG | B | 458 | −72.061 | 46.810 | −32.248 | 1.00 | 75.58 | C |
| ATOM | 2077 | CG | ARG | B | 458 | −70.567 | 46.915 | −32.358 | 1.00 | 73.81 | C |
| ATOM | 2078 | CD | ARG | B | 458 | −69.871 | 45.766 | −31.679 | 1.00 | 72.65 | C |
| ATOM | 2079 | NE | ARG | B | 458 | −68.418 | 45.964 | −31.645 | 1.00 | 71.73 | N |
| ATOM | 2080 | CZ | ARG | B | 458 | −67.708 | 46.168 | −30.542 | 1.00 | 70.47 | C |
| ATOM | 2081 | NH1 | ARG | B | 458 | −68.301 | 46.188 | −29.357 | 1.00 | 69.87 | N |
| ATOM | 2082 | NH2 | ARG | B | 458 | −66.402 | 46.355 | −30.615 | 1.00 | 71.94 | N |
| ATOM | 2083 | C | ARG | B | 458 | −72.488 | 49.289 | −31.914 | 1.00 | 75.38 | C |
| ATOM | 2084 | O | ARG | B | 458 | −71.528 | 50.012 | −32.201 | 1.00 | 75.32 | O |
| ATOM | 2085 | N | THR | B | 459 | −73.298 | 49.526 | −30.897 | 1.00 | 74.97 | N |
| ATOM | 2086 | CA | THR | B | 459 | −73.165 | 50.632 | −29.970 | 1.00 | 74.11 | C |
| ATOM | 2087 | CB | THR | B | 459 | −74.576 | 50.978 | −29.470 | 1.00 | 74.25 | C |
| ATOM | 2088 | OG1 | THR | B | 459 | −75.305 | 51.553 | −30.549 | 1.00 | 75.21 | O |
| ATOM | 2089 | CG2 | THR | B | 459 | −74.583 | 51.928 | −28.291 | 1.00 | 74.38 | C |
| ATOM | 2090 | C | THR | B | 459 | −72.233 | 50.216 | −28.829 | 1.00 | 73.34 | C |
| ATOM | 2091 | O | THR | B | 459 | −72.508 | 49.232 | −28.140 | 1.00 | 73.34 | O |
| ATOM | 2092 | N | VAL | B | 460 | −71.143 | 50.946 | −28.626 | 1.00 | 71.16 | N |
| ATOM | 2093 | CA | VAL | B | 460 | −70.229 | 50.646 | −27.524 | 1.00 | 70.53 | C |
| ATOM | 2094 | CB | VAL | B | 460 | −68.835 | 50.047 | −27.892 | 1.00 | 70.38 | C |
| ATOM | 2095 | CG1 | VAL | B | 460 | −68.605 | 50.023 | −29.385 | 1.00 | 70.18 | C |
| ATOM | 2096 | CG2 | VAL | B | 460 | −67.669 | 50.708 | −27.151 | 1.00 | 70.10 | C |
| ATOM | 2097 | C | VAL | B | 460 | −70.219 | 51.769 | −26.496 | 1.00 | 70.41 | C |
| ATOM | 2098 | O | VAL | B | 460 | −69.932 | 52.922 | −26.831 | 1.00 | 70.49 | O |
| ATOM | 2099 | N | TRP | B | 461 | −70.587 | 51.449 | −25.256 | 1.00 | 71.19 | N |
| ATOM | 2100 | CA | TRP | B | 461 | −70.600 | 52.468 | −24.220 | 1.00 | 71.20 | C |
| ATOM | 2101 | CB | TRP | B | 461 | −71.716 | 52.230 | −23.222 | 1.00 | 70.38 | C |
| ATOM | 2102 | CG | TRP | B | 461 | −73.086 | 52.530 | −23.725 | 1.00 | 68.32 | C |
| ATOM | 2103 | CD1 | TRP | B | 461 | −73.821 | 51.788 | −24.600 | 1.00 | 66.23 | C |
| ATOM | 2104 | NE1 | TRP | B | 461 | −75.082 | 52.327 | −24.739 | 1.00 | 65.16 | N |
| ATOM | 2105 | CE2 | TRP | B | 461 | −75.176 | 53.441 | −23.950 | 1.00 | 65.89 | C |
| ATOM | 2106 | CD2 | TRP | B | 461 | −73.944 | 53.582 | −23.271 | 1.00 | 67.24 | C |
| ATOM | 2107 | CE3 | TRP | B | 461 | −73.789 | 54.645 | −22.363 | 1.00 | 66.29 | C |
| ATOM | 2108 | CZ3 | TRP | B | 461 | −74.852 | 55.511 | −22.164 | 1.00 | 65.24 | C |
| ATOM | 2109 | CH2 | TRP | B | 461 | −76.054 | 55.355 | −22.858 | 1.00 | 64.31 | C |
| ATOM | 2110 | CZ2 | TRP | B | 461 | −76.233 | 54.336 | −23.768 | 1.00 | 64.76 | C |
| ATOM | 2111 | C | TRP | B | 461 | −69.271 | 52.531 | −23.493 | 1.00 | 72.30 | C |
| ATOM | 2112 | O | TRP | B | 461 | −68.647 | 51.506 | −23.189 | 1.00 | 72.67 | O |
| ATOM | 2113 | N | SER | B | 462 | −68.861 | 53.744 | −23.181 | 1.00 | 74.24 | N |
| ATOM | 2114 | CA | SER | B | 462 | −67.647 | 53.992 | −22.450 | 1.00 | 75.66 | C |
| ATOM | 2115 | CB | SER | B | 462 | −67.283 | 55.462 | −22.583 | 1.00 | 75.63 | C |
| ATOM | 2116 | OG | SER | B | 462 | −67.969 | 56.222 | −21.593 | 1.00 | 75.96 | O |
| ATOM | 2117 | C | SER | B | 462 | −67.941 | 53.748 | −20.995 | 1.00 | 76.81 | C |
| ATOM | 2118 | O | SER | B | 462 | −69.083 | 53.488 | −20.615 | 1.00 | 76.78 | O |
| ATOM | 2119 | N | ALA | B | 463 | −66.913 | 53.899 | −20.169 | 1.00 | 83.59 | N |
| ATOM | 2120 | CA | ALA | B | 463 | −67.059 | 53.845 | −18.733 | 1.00 | 85.46 | C |
| ATOM | 2121 | CB | ALA | B | 463 | −65.747 | 53.449 | −18.103 | 1.00 | 85.21 | C |
| ATOM | 2122 | C | ALA | B | 463 | −67.388 | 55.321 | −18.382 | 1.00 | 86.93 | C |
| ATOM | 2123 | O | ALA | B | 463 | −66.940 | 56.237 | −19.096 | 1.00 | 87.12 | O |
| ATOM | 2124 | N | HIS | B | 464 | −68.181 | 55.542 | −17.317 | 1.00 | 91.57 | N |
| ATOM | 2125 | CA | HIS | B | 464 | −68.569 | 56.865 | −16.837 | 1.00 | 93.29 | C |
| ATOM | 2126 | CB | HIS | B | 464 | −69.353 | 56.682 | −15.550 | 1.00 | 93.19 | C |
| ATOM | 2127 | CG | HIS | B | 464 | −70.259 | 57.811 | −15.222 | 1.00 | 94.40 | C |
| ATOM | 2128 | ND1 | HIS | B | 464 | −70.153 | 58.482 | −14.026 | 1.00 | 95.91 | N |
| ATOM | 2129 | CE1 | HIS | B | 464 | −71.114 | 59.398 | −14.042 | 1.00 | 96.37 | C |
| ATOM | 2130 | NE2 | HIS | B | 464 | −71.815 | 59.356 | −15.177 | 1.00 | 96.33 | N |
| ATOM | 2131 | CD2 | HIS | B | 464 | −71.279 | 58.342 | −15.938 | 1.00 | 95.65 | C |
| ATOM | 2132 | C | HIS | B | 464 | −67.316 | 57.718 | −16.583 | 1.00 | 94.53 | C |
| ATOM | 2133 | O | HIS | B | 464 | −66.354 | 57.220 | −16.007 | 1.00 | 94.76 | O |
| ATOM | 2134 | N | SER | B | 465 | −67.299 | 58.973 | −17.040 | 1.00 | 98.33 | N |
| ATOM | 2135 | CA | SER | B | 465 | −66.131 | 59.856 | −16.882 | 1.00 | 100.02 | C |
| ATOM | 2136 | CB | SER | B | 465 | −66.287 | 61.104 | −17.743 | 1.00 | 99.96 | C |
| ATOM | 2137 | OG | SER | B | 465 | −67.287 | 61.959 | −17.209 | 1.00 | 100.90 | O |
| ATOM | 2138 | C | SER | B | 465 | −65.818 | 60.262 | −15.426 | 1.00 | 101.11 | C |
| ATOM | 2139 | O | SER | B | 465 | −64.683 | 60.648 | −15.123 | 1.00 | 101.22 | O |
| ATOM | 2140 | N | GLY | B | 466 | −66.819 | 60.185 | −14.555 | 1.00 | 105.25 | N |
| ATOM | 2141 | CA | GLY | B | 466 | −66.659 | 60.566 | −13.161 | 1.00 | 106.92 | C |
| ATOM | 2142 | C | GLY | B | 466 | −67.039 | 62.020 | −12.944 | 1.00 | 108.18 | C |
| ATOM | 2143 | O | GLY | B | 466 | −67.212 | 62.759 | −13.923 | 1.00 | 108.28 | O |
| ATOM | 2144 | N | PRO | B | 467 | −67.153 | 62.482 | −11.672 | 1.00 | 110.29 | N |
| ATOM | 2145 | CA | PRO | B | 467 | −67.595 | 63.862 | −11.426 | 1.00 | 110.92 | C |
| ATOM | 2146 | CB | PRO | B | 467 | −68.260 | 63.783 | −10.037 | 1.00 | 110.81 | C |

TABLE 14-continued

PCSK9 and AX132 Fab complex x-ray structure

| ATOM | 2147 | CG  | PRO | B | 467 | −68.208 | 62.298 | −9.634  | 1.00 | 110.68 | C |
| ---- | ---- | --- | --- | - | --- | ------- | ------ | ------- | ---- | ------ | - |
| ATOM | 2148 | CD  | PRO | B | 467 | −67.043 | 61.752 | −10.399 | 1.00 | 110.39 | C |
| ATOM | 2149 | C   | PRO | B | 467 | −66.599 | 65.015 | −11.571 | 1.00 | 111.61 | C |
| ATOM | 2150 | O   | PRO | B | 467 | −66.978 | 66.145 | −11.229 | 1.00 | 111.89 | O |
| ATOM | 2151 | N   | THR | B | 468 | −65.366 | 64.776 | −12.095 | 1.00 | 112.93 | N |
| ATOM | 2152 | CA  | THR | B | 468 | −64.389 | 65.867 | −12.288 | 1.00 | 113.63 | C |
| ATOM | 2153 | CB  | THR | B | 468 | −63.022 | 65.346 | −12.752 | 1.00 | 113.72 | C |
| ATOM | 2154 | OG1 | THR | B | 468 | −62.623 | 64.204 | −11.980 | 1.00 | 114.00 | O |
| ATOM | 2155 | CG2 | THR | B | 468 | −61.943 | 66.443 | −12.763 | 1.00 | 113.06 | C |
| ATOM | 2156 | C   | THR | B | 468 | −64.931 | 66.818 | −13.341 | 1.00 | 114.18 | C |
| ATOM | 2157 | O   | THR | B | 468 | −65.436 | 66.351 | −14.358 | 1.00 | 114.47 | O |
| ATOM | 2158 | N   | ARG | B | 469 | −64.854 | 68.139 | −13.109 | 1.00 | 116.36 | N |
| ATOM | 2159 | CA  | ARG | B | 469 | −65.353 | 69.118 | −14.087 | 1.00 | 116.78 | C |
| ATOM | 2160 | CB  | ARG | B | 469 | −65.519 | 70.513 | −13.460 | 1.00 | 116.61 | C |
| ATOM | 2161 | C   | ARG | B | 469 | −64.473 | 69.131 | −15.377 | 1.00 | 117.02 | C |
| ATOM | 2162 | O   | ARG | B | 469 | −64.922 | 69.595 | −16.431 | 1.00 | 117.28 | O |
| ATOM | 2163 | N   | MET | B | 470 | −63.235 | 68.594 | −15.286 | 1.00 | 115.47 | N |
| ATOM | 2164 | CA  | MET | B | 470 | −62.323 | 68.485 | −16.418 | 1.00 | 115.35 | C |
| ATOM | 2165 | CB  | MET | B | 470 | −61.003 | 69.219 | −16.122 | 1.00 | 115.40 | C |
| ATOM | 2166 | C   | MET | B | 470 | −62.120 | 66.978 | −16.703 | 1.00 | 115.23 | C |
| ATOM | 2167 | O   | MET | B | 470 | −60.997 | 66.521 | −16.945 | 1.00 | 115.36 | O |
| ATOM | 2168 | N   | ALA | B | 471 | −63.240 | 66.207 | −16.656 | 1.00 | 112.94 | N |
| ATOM | 2169 | CA  | ALA | B | 471 | −63.279 | 64.754 | −16.886 | 1.00 | 112.30 | C |
| ATOM | 2170 | CB  | ALA | B | 471 | −64.280 | 64.082 | −15.953 | 1.00 | 112.14 | C |
| ATOM | 2171 | C   | ALA | B | 471 | −63.595 | 64.378 | −18.328 | 1.00 | 111.87 | C |
| ATOM | 2172 | O   | ALA | B | 471 | −64.359 | 65.075 | −19.019 | 1.00 | 111.95 | O |
| ATOM | 2173 | N   | THR | B | 472 | −63.013 | 63.245 | −18.764 | 1.00 | 108.06 | N |
| ATOM | 2174 | CA  | THR | B | 472 | −63.203 | 62.708 | −20.104 | 1.00 | 107.28 | C |
| ATOM | 2175 | CB  | THR | B | 472 | −62.134 | 63.281 | −21.061 | 1.00 | 107.44 | C |
| ATOM | 2176 | OG1 | THR | B | 472 | −62.624 | 63.256 | −22.403 | 1.00 | 107.35 | O |
| ATOM | 2177 | CG2 | THR | B | 472 | −60.753 | 62.607 | −20.918 | 1.00 | 107.39 | C |
| ATOM | 2178 | C   | THR | B | 472 | −63.468 | 61.169 | −20.148 | 1.00 | 106.42 | C |
| ATOM | 2179 | O   | THR | B | 472 | −62.699 | 60.386 | −19.579 | 1.00 | 106.26 | O |
| ATOM | 2180 | N   | ALA | B | 473 | −64.578 | 60.768 | −20.808 | 1.00 | 100.03 | N |
| ATOM | 2181 | CA  | ALA | B | 473 | −64.996 | 59.380 | −21.021 | 1.00 | 98.90  | C |
| ATOM | 2182 | CB  | ALA | B | 473 | −66.484 | 59.238 | −20.767 | 1.00 | 98.99  | C |
| ATOM | 2183 | C   | ALA | B | 473 | −64.674 | 59.012 | −22.481 | 1.00 | 98.11  | C |
| ATOM | 2184 | O   | ALA | B | 473 | −65.074 | 59.735 | −23.392 | 1.00 | 97.85  | O |
| ATOM | 2185 | N   | ILE | B | 474 | −63.934 | 57.908 | −22.701 | 1.00 | 94.49  | N |
| ATOM | 2186 | CA  | ILE | B | 474 | −63.512 | 57.467 | −24.042 | 1.00 | 93.51  | C |
| ATOM | 2187 | CB  | ILE | B | 474 | −61.943 | 57.470 | −24.185 | 1.00 | 93.53  | C |
| ATOM | 2188 | CG1 | ILE | B | 474 | −61.326 | 58.856 | −23.878 | 1.00 | 93.64  | C |
| ATOM | 2189 | CD1 | ILE | B | 474 | −60.862 | 59.102 | −22.394 | 1.00 | 94.37  | C |
| ATOM | 2190 | CG2 | ILE | B | 474 | −61.478 | 57.016 | −25.563 | 1.00 | 93.58  | C |
| ATOM | 2191 | C   | ILE | B | 474 | −64.149 | 56.122 | −24.419 | 1.00 | 92.67  | C |
| ATOM | 2192 | O   | ILE | B | 474 | −64.214 | 55.218 | −23.588 | 1.00 | 92.53  | O |
| ATOM | 2193 | N   | ALA | B | 475 | −64.619 | 56.010 | −25.670 | 1.00 | 89.81  | N |
| ATOM | 2194 | CA  | ALA | B | 475 | −65.227 | 54.810 | −26.233 | 1.00 | 89.14  | C |
| ATOM | 2195 | CB  | ALA | B | 475 | −66.705 | 55.038 | −26.489 | 1.00 | 88.89  | C |
| ATOM | 2196 | C   | ALA | B | 475 | −64.489 | 54.415 | −27.532 | 1.00 | 88.97  | C |
| ATOM | 2197 | O   | ALA | B | 475 | −64.430 | 55.202 | −28.478 | 1.00 | 88.77  | O |
| ATOM | 2198 | N   | ARG | B | 476 | −63.899 | 53.202 | −27.555 | 1.00 | 91.20  | N |
| ATOM | 2199 | CA  | ARG | B | 476 | −63.126 | 52.687 | −28.694 | 1.00 | 91.05  | C |
| ATOM | 2200 | CB  | ARG | B | 476 | −61.694 | 52.324 | −28.252 | 1.00 | 91.07  | C |
| ATOM | 2201 | CG  | ARG | B | 476 | −60.980 | 53.406 | −27.489 | 1.00 | 91.51  | C |
| ATOM | 2202 | CD  | ARG | B | 476 | −59.652 | 52.942 | −26.945 | 1.00 | 93.16  | C |
| ATOM | 2203 | NE  | ARG | B | 476 | −58.894 | 54.061 | −26.366 | 1.00 | 95.08  | N |
| ATOM | 2204 | CZ  | ARG | B | 476 | −58.959 | 54.441 | −25.086 | 1.00 | 95.78  | C |
| ATOM | 2205 | NH1 | ARG | B | 476 | −59.744 | 53.793 | −24.230 | 1.00 | 96.38  | N |
| ATOM | 2206 | NH2 | ARG | B | 476 | −58.241 | 55.476 | −24.657 | 1.00 | 95.88  | N |
| ATOM | 2207 | C   | ARG | B | 476 | −63.785 | 51.463 | −29.343 | 1.00 | 90.94  | C |
| ATOM | 2208 | O   | ARG | B | 476 | −64.694 | 50.868 | −28.758 | 1.00 | 90.98  | O |
| ATOM | 2209 | N   | CYS | B | 477 | −63.304 | 51.083 | −30.552 | 1.00 | 88.88  | N |
| ATOM | 2210 | CA  | CYS | B | 477 | −63.772 | 49.922 | −31.321 | 1.00 | 88.83  | C |
| ATOM | 2211 | CB  | CYS | B | 477 | −64.138 | 50.326 | −32.744 | 1.00 | 88.48  | C |
| ATOM | 2212 | SG  | CYS | B | 477 | −65.297 | 51.695 | −32.860 | 1.00 | 87.32  | S |
| ATOM | 2213 | C   | CYS | B | 477 | −62.704 | 48.862 | −31.359 | 1.00 | 89.31  | C |
| ATOM | 2214 | O   | CYS | B | 477 | −61.568 | 49.075 | −30.903 | 1.00 | 89.18  | O |
| ATOM | 2215 | N   | ALA | B | 478 | −63.054 | 47.733 | −31.983 | 1.00 | 94.15  | N |
| ATOM | 2216 | CA  | ALA | B | 478 | −62.116 | 46.645 | −32.192 | 1.00 | 94.86  | C |
| ATOM | 2217 | CB  | ALA | B | 478 | −62.863 | 45.389 | −32.620 | 1.00 | 95.20  | C |
| ATOM | 2218 | C   | ALA | B | 478 | −61.164 | 47.106 | −33.316 | 1.00 | 95.16  | C |
| ATOM | 2219 | O   | ALA | B | 478 | −61.631 | 47.763 | −34.248 | 1.00 | 95.16  | O |
| ATOM | 2220 | N   | PRO | B | 479 | −59.846 | 46.811 | −33.249 | 1.00 | 97.02  | N |
| ATOM | 2221 | CA  | PRO | B | 479 | −58.929 | 47.265 | −34.309 | 1.00 | 97.37  | C |
| ATOM | 2222 | CB  | PRO | B | 479 | −57.707 | 46.383 | −34.097 | 1.00 | 97.36  | C |
| ATOM | 2223 | CG  | PRO | B | 479 | −57.687 | 46.161 | −32.634 | 1.00 | 97.31  | C |
| ATOM | 2224 | CD  | PRO | B | 479 | −59.118 | 46.070 | −32.201 | 1.00 | 97.04  | C |

TABLE 14-continued

PCSK9 and AX132 Fab complex x-ray structure

| ATOM | 2225 | C | PRO | B | 479 | −59.451 | 47.186 | −35.747 | 1.00 | 97.84 | C |
| ATOM | 2226 | O | PRO | B | 479 | −59.298 | 48.148 | −36.511 | 1.00 | 98.32 | O |
| ATOM | 2227 | N | ASP | B | 480 | −60.100 | 46.072 | −36.106 | 1.00 | 98.53 | N |
| ATOM | 2228 | CA | ASP | B | 480 | −60.631 | 45.901 | −37.448 | 1.00 | 98.64 | C |
| ATOM | 2229 | CB | ASP | B | 480 | −60.437 | 44.456 | −37.960 | 1.00 | 99.11 | C |
| ATOM | 2230 | CG | ASP | B | 480 | −60.712 | 43.321 | −36.971 | 1.00 | 101.51 | C |
| ATOM | 2231 | OD1 | ASP | B | 480 | −60.634 | 43.567 | −35.723 | 1.00 | 103.08 | O |
| ATOM | 2232 | OD2 | ASP | B | 480 | −60.994 | 42.179 | −37.436 | 1.00 | 103.88 | O |
| ATOM | 2233 | C | ASP | B | 480 | −62.046 | 46.457 | −37.642 | 1.00 | 98.13 | C |
| ATOM | 2234 | O | ASP | B | 480 | −62.797 | 45.971 | −38.492 | 1.00 | 98.13 | O |
| ATOM | 2235 | N | GLU | B | 481 | −62.394 | 47.501 | −36.867 | 1.00 | 95.63 | N |
| ATOM | 2236 | CA | GLU | B | 481 | −63.689 | 48.187 | −36.919 | 1.00 | 95.12 | C |
| ATOM | 2237 | CB | GLU | B | 481 | −64.466 | 48.026 | −35.600 | 1.00 | 94.98 | C |
| ATOM | 2238 | CG | GLU | B | 481 | −65.174 | 46.694 | −35.404 | 1.00 | 93.55 | C |
| ATOM | 2239 | CD | GLU | B | 481 | −66.047 | 46.588 | −34.164 | 1.00 | 91.31 | C |
| ATOM | 2240 | OE1 | GLU | B | 481 | −65.681 | 47.169 | −33.115 | 1.00 | 89.30 | O |
| ATOM | 2241 | OE2 | GLU | B | 481 | −67.097 | 45.909 | −34.240 | 1.00 | 90.31 | O |
| ATOM | 2242 | C | GLU | B | 481 | −63.471 | 49.667 | −37.174 | 1.00 | 95.14 | C |
| ATOM | 2243 | O | GLU | B | 481 | −62.396 | 50.193 | −36.855 | 1.00 | 95.26 | O |
| ATOM | 2244 | N | GLU | B | 482 | −64.501 | 50.343 | −37.733 | 1.00 | 96.88 | N |
| ATOM | 2245 | CA | GLU | B | 482 | −64.494 | 51.782 | −38.033 | 1.00 | 96.69 | C |
| ATOM | 2246 | CB | GLU | B | 482 | −64.755 | 52.040 | −39.542 | 1.00 | 97.05 | C |
| ATOM | 2247 | CG | GLU | B | 482 | −63.538 | 51.866 | −40.458 | 1.00 | 98.77 | C |
| ATOM | 2248 | CD | GLU | B | 482 | −62.350 | 52.817 | −40.312 | 1.00 | 100.97 | C |
| ATOM | 2249 | OE1 | GLU | B | 482 | −62.551 | 54.010 | −39.973 | 1.00 | 101.66 | O |
| ATOM | 2250 | OE2 | GLU | B | 482 | −61.208 | 52.359 | −40.555 | 1.00 | 101.54 | O |
| ATOM | 2251 | C | GLU | B | 482 | −65.510 | 52.552 | −37.160 | 1.00 | 95.97 | C |
| ATOM | 2252 | O | GLU | B | 482 | −66.665 | 52.138 | −37.067 | 1.00 | 96.15 | O |
| ATOM | 2253 | N | LEU | B | 483 | −65.086 | 53.661 | −36.525 | 1.00 | 94.44 | N |
| ATOM | 2254 | CA | LEU | B | 483 | −65.987 | 54.467 | −35.695 | 1.00 | 93.65 | C |
| ATOM | 2255 | CB | LEU | B | 483 | −65.188 | 55.264 | −34.656 | 1.00 | 93.65 | C |
| ATOM | 2256 | CG | LEU | B | 483 | −65.994 | 55.805 | −33.488 | 1.00 | 92.96 | C |
| ATOM | 2257 | CD1 | LEU | B | 483 | −65.282 | 55.536 | −32.197 | 1.00 | 92.61 | C |
| ATOM | 2258 | CD2 | LEU | B | 483 | −66.223 | 57.289 | −33.628 | 1.00 | 92.74 | C |
| ATOM | 2259 | C | LEU | B | 483 | −66.763 | 55.413 | −36.611 | 1.00 | 93.20 | C |
| ATOM | 2260 | O | LEU | B | 483 | −66.282 | 56.505 | −36.919 | 1.00 | 92.99 | O |
| ATOM | 2261 | N | LEU | B | 484 | −67.948 | 54.990 | −37.057 | 1.00 | 91.03 | N |
| ATOM | 2262 | CA | LEU | B | 484 | −68.770 | 55.780 | −37.969 | 1.00 | 90.35 | C |
| ATOM | 2263 | CB | LEU | B | 484 | −69.846 | 54.914 | −38.623 | 1.00 | 90.12 | C |
| ATOM | 2264 | CG | LEU | B | 484 | −69.384 | 53.855 | −39.611 | 1.00 | 90.20 | C |
| ATOM | 2265 | CD1 | LEU | B | 484 | −70.429 | 53.636 | −40.680 | 1.00 | 89.15 | C |
| ATOM | 2266 | CD2 | LEU | B | 484 | −67.994 | 54.169 | −40.221 | 1.00 | 89.63 | C |
| ATOM | 2267 | C | LEU | B | 484 | −69.424 | 56.993 | −37.337 | 1.00 | 90.26 | C |
| ATOM | 2268 | O | LEU | B | 484 | −69.623 | 58.010 | −38.005 | 1.00 | 90.42 | O |
| ATOM | 2269 | N | SER | B | 485 | −69.800 | 56.877 | −36.073 | 1.00 | 90.25 | N |
| ATOM | 2270 | CA | SER | B | 485 | −70.469 | 57.948 | −35.371 | 1.00 | 89.82 | C |
| ATOM | 2271 | CB | SER | B | 485 | −71.974 | 57.816 | −35.544 | 1.00 | 89.68 | C |
| ATOM | 2272 | OG | SER | B | 485 | −72.718 | 57.958 | −34.345 | 1.00 | 89.43 | O |
| ATOM | 2273 | C | SER | B | 485 | −70.095 | 57.962 | −33.916 | 1.00 | 89.74 | C |
| ATOM | 2274 | O | SER | B | 485 | −69.499 | 57.017 | −33.401 | 1.00 | 89.92 | O |
| ATOM | 2275 | N | CYS | B | 486 | −70.447 | 59.055 | −33.257 | 1.00 | 89.97 | N |
| ATOM | 2276 | CA | CYS | B | 486 | −70.186 | 59.279 | −31.850 | 1.00 | 89.87 | C |
| ATOM | 2277 | CB | CYS | B | 486 | −68.778 | 59.840 | −31.644 | 1.00 | 90.20 | C |
| ATOM | 2278 | SG | CYS | B | 486 | −68.445 | 60.453 | −29.975 | 1.00 | 93.44 | S |
| ATOM | 2279 | C | CYS | B | 486 | −71.276 | 60.219 | −31.339 | 1.00 | 88.92 | C |
| ATOM | 2280 | O | CYS | B | 486 | −71.765 | 61.088 | −32.076 | 1.00 | 88.97 | O |
| ATOM | 2281 | N | SER | B | 487 | −71.697 | 59.966 | −30.095 | 1.00 | 83.57 | N |
| ATOM | 2282 | CA | SER | B | 487 | −72.712 | 60.680 | −29.337 | 1.00 | 82.49 | C |
| ATOM | 2283 | CB | SER | B | 487 | −74.099 | 60.102 | −29.605 | 1.00 | 82.58 | C |
| ATOM | 2284 | OG | SER | B | 487 | −74.369 | 58.914 | −28.880 | 1.00 | 82.74 | O |
| ATOM | 2285 | C | SER | B | 487 | −72.306 | 60.585 | −27.861 | 1.00 | 81.85 | C |
| ATOM | 2286 | O | SER | B | 487 | −71.257 | 60.001 | −27.570 | 1.00 | 81.86 | O |
| ATOM | 2287 | N | SER | B | 488 | −73.086 | 61.194 | −26.942 | 1.00 | 79.82 | N |
| ATOM | 2288 | CA | SER | B | 488 | −72.791 | 61.200 | −25.502 | 1.00 | 79.19 | C |
| ATOM | 2289 | CB | SER | B | 488 | −71.826 | 62.331 | −25.148 | 1.00 | 79.19 | C |
| ATOM | 2290 | OG | SER | B | 488 | −72.426 | 63.603 | −25.331 | 1.00 | 79.03 | O |
| ATOM | 2291 | C | SER | B | 488 | −74.054 | 61.326 | −24.675 | 1.00 | 78.79 | C |
| ATOM | 2292 | O | SER | B | 488 | −75.085 | 61.775 | −25.188 | 1.00 | 78.90 | O |
| ATOM | 2293 | N | PHE | B | 489 | −73.974 | 60.952 | −23.391 | 1.00 | 75.75 | N |
| ATOM | 2294 | CA | PHE | B | 489 | −75.117 | 61.012 | −22.485 | 1.00 | 75.43 | C |
| ATOM | 2295 | CB | PHE | B | 489 | −75.921 | 59.717 | −22.597 | 1.00 | 75.12 | C |
| ATOM | 2296 | CG | PHE | B | 489 | −77.093 | 59.529 | −21.677 | 1.00 | 73.56 | C |
| ATOM | 2297 | CD1 | PHE | B | 489 | −78.318 | 60.123 | −21.958 | 1.00 | 71.80 | C |
| ATOM | 2298 | CE1 | PHE | B | 489 | −79.419 | 59.928 | −21.123 | 1.00 | 70.76 | C |
| ATOM | 2299 | CZ | PHE | B | 489 | −79.303 | 59.114 | −20.020 | 1.00 | 70.83 | C |
| ATOM | 2300 | CE2 | PHE | B | 489 | −78.095 | 58.500 | −19.732 | 1.00 | 70.74 | C |
| ATOM | 2301 | CD2 | PHE | B | 489 | −76.993 | 58.704 | −20.563 | 1.00 | 71.60 | C |
| ATOM | 2302 | C | PHE | B | 489 | −74.686 | 61.267 | −21.056 | 1.00 | 75.85 | C |

TABLE 14-continued

PCSK9 and AX132 Fab complex x-ray structure

| ATOM | 2303 | O | PHE | B | 489 | −73.584 | 60.884 | −20.653 | 1.00 | 75.64 | O |
|---|---|---|---|---|---|---|---|---|---|---|---|
| ATOM | 2304 | N | SER | B | 490 | −75.571 | 61.918 | −20.305 | 1.00 | 79.05 | N |
| ATOM | 2305 | CA | SER | B | 490 | −75.419 | 62.298 | −18.911 | 1.00 | 79.93 | C |
| ATOM | 2306 | CB | SER | B | 490 | −74.873 | 63.722 | −18.835 | 1.00 | 80.03 | C |
| ATOM | 2307 | OG | SER | B | 490 | −75.315 | 64.449 | −17.699 | 1.00 | 81.51 | O |
| ATOM | 2308 | C | SER | B | 490 | −76.810 | 62.206 | −18.296 | 1.00 | 80.40 | C |
| ATOM | 2309 | O | SER | B | 490 | −77.742 | 62.767 | −18.856 | 1.00 | 80.25 | O |
| ATOM | 2310 | N | ARG | B | 491 | −76.964 | 61.477 | −17.170 | 1.00 | 84.03 | N |
| ATOM | 2311 | CA | ARG | B | 491 | −78.258 | 61.283 | −16.500 | 1.00 | 85.04 | C |
| ATOM | 2312 | CB | ARG | B | 491 | −78.178 | 60.137 | −15.482 | 1.00 | 84.72 | C |
| ATOM | 2313 | C | ARG | B | 491 | −78.840 | 62.573 | −15.886 | 1.00 | 86.05 | C |
| ATOM | 2314 | O | ARG | B | 491 | −80.022 | 62.591 | −15.560 | 1.00 | 86.32 | O |
| ATOM | 2315 | N | SER | B | 492 | −78.013 | 63.650 | −15.761 | 1.00 | 91.60 | N |
| ATOM | 2316 | CA | SER | B | 492 | −78.324 | 64.991 | −15.218 | 1.00 | 92.72 | C |
| ATOM | 2317 | CB | SER | B | 492 | −77.248 | 65.420 | −14.212 | 1.00 | 92.72 | C |
| ATOM | 2318 | OG | SER | B | 492 | −76.036 | 65.860 | −14.812 | 1.00 | 92.51 | O |
| ATOM | 2319 | C | SER | B | 492 | −78.477 | 66.092 | −16.313 | 1.00 | 93.57 | C |
| ATOM | 2320 | O | SER | B | 492 | −78.938 | 67.198 | −16.019 | 1.00 | 94.01 | O |
| ATOM | 2321 | N | GLY | B | 493 | −78.053 | 65.788 | −17.540 | 1.00 | 96.27 | N |
| ATOM | 2322 | CA | GLY | B | 493 | −78.109 | 66.709 | −18.671 | 1.00 | 96.99 | C |
| ATOM | 2323 | C | GLY | B | 493 | −76.892 | 67.606 | −18.788 | 1.00 | 97.51 | C |
| ATOM | 2324 | O | GLY | B | 493 | −76.600 | 68.118 | −19.876 | 1.00 | 97.74 | O |
| ATOM | 2325 | N | LYS | B | 494 | −76.173 | 67.795 | −17.661 | 1.00 | 98.26 | N |
| ATOM | 2326 | CA | LYS | B | 494 | −74.973 | 68.633 | −17.543 | 1.00 | 98.74 | C |
| ATOM | 2327 | CB | LYS | B | 494 | −74.570 | 68.799 | −16.055 | 1.00 | 98.94 | C |
| ATOM | 2328 | CG | LYS | B | 494 | −75.584 | 69.547 | −15.192 | 1.00 | 100.15 | C |
| ATOM | 2329 | CD | LYS | B | 494 | −75.531 | 69.091 | −13.731 | 1.00 | 102.35 | C |
| ATOM | 2330 | CE | LYS | B | 494 | −76.668 | 69.652 | −12.887 | 1.00 | 103.47 | C |
| ATOM | 2331 | NZ | LYS | B | 494 | −78.005 | 69.083 | −13.257 | 1.00 | 103.97 | N |
| ATOM | 2332 | C | LYS | B | 494 | −73.784 | 68.125 | −18.385 | 1.00 | 98.61 | C |
| ATOM | 2333 | O | LYS | B | 494 | −72.873 | 67.487 | −17.851 | 1.00 | 98.84 | O |
| ATOM | 2334 | N | ARG | B | 495 | −73.792 | 68.407 | −19.695 | 1.00 | 96.50 | N |
| ATOM | 2335 | CA | ARG | B | 495 | −72.702 | 67.973 | −20.574 | 1.00 | 96.64 | C |
| ATOM | 2336 | CB | ARG | B | 495 | −73.033 | 66.666 | −21.333 | 1.00 | 96.79 | C |
| ATOM | 2337 | CG | ARG | B | 495 | −74.345 | 66.675 | −22.085 | 1.00 | 96.15 | C |
| ATOM | 2338 | CD | ARG | B | 495 | −74.561 | 65.412 | −22.880 | 1.00 | 95.77 | C |
| ATOM | 2339 | NE | ARG | B | 495 | −75.702 | 65.601 | −23.773 | 1.00 | 96.50 | N |
| ATOM | 2340 | CZ | ARG | B | 495 | −75.601 | 65.836 | −25.078 | 1.00 | 96.55 | C |
| ATOM | 2341 | NH1 | ARG | B | 495 | −76.692 | 66.036 | −25.808 | 1.00 | 96.40 | N |
| ATOM | 2342 | NH2 | ARG | B | 495 | −74.410 | 65.868 | −25.666 | 1.00 | 96.96 | N |
| ATOM | 2343 | C | ARG | B | 495 | −72.171 | 69.040 | −21.503 | 1.00 | 96.85 | C |
| ATOM | 2344 | O | ARG | B | 495 | −72.881 | 69.988 | −21.831 | 1.00 | 96.81 | O |
| ATOM | 2345 | N | ARG | B | 496 | −70.912 | 68.882 | −21.915 | 1.00 | 96.61 | N |
| ATOM | 2346 | CA | ARG | B | 496 | −70.236 | 69.795 | −22.829 | 1.00 | 97.36 | C |
| ATOM | 2347 | CB | ARG | B | 496 | −68.947 | 70.374 | −22.207 | 1.00 | 97.76 | C |
| ATOM | 2348 | CG | ARG | B | 496 | −69.188 | 71.646 | −21.366 | 1.00 | 99.31 | C |
| ATOM | 2349 | CD | ARG | B | 496 | −67.969 | 72.560 | −21.228 | 1.00 | 101.85 | C |
| ATOM | 2350 | NE | ARG | B | 496 | −66.832 | 71.927 | −20.546 | 1.00 | 104.10 | N |
| ATOM | 2351 | CZ | ARG | B | 496 | −65.770 | 71.399 | −21.157 | 1.00 | 104.55 | C |
| ATOM | 2352 | NH1 | ARG | B | 496 | −65.676 | 71.420 | −22.485 | 1.00 | 104.86 | N |
| ATOM | 2353 | NH2 | ARG | B | 496 | −64.797 | 70.845 | −20.446 | 1.00 | 104.83 | N |
| ATOM | 2354 | C | ARG | B | 496 | −69.997 | 69.133 | −24.191 | 1.00 | 97.42 | C |
| ATOM | 2355 | O | ARG | B | 496 | −69.019 | 69.439 | −24.880 | 1.00 | 97.20 | O |
| ATOM | 2356 | N | GLY | B | 497 | −70.911 | 68.232 | −24.552 | 1.00 | 97.26 | N |
| ATOM | 2357 | CA | GLY | B | 497 | −70.893 | 67.497 | −25.810 | 1.00 | 97.69 | C |
| ATOM | 2358 | C | GLY | B | 497 | −69.932 | 66.331 | −25.891 | 1.00 | 98.14 | C |
| ATOM | 2359 | O | GLY | B | 497 | −69.592 | 65.716 | −24.876 | 1.00 | 98.09 | O |
| ATOM | 2360 | N | GLU | B | 498 | −69.501 | 66.026 | −27.130 | 1.00 | 99.98 | N |
| ATOM | 2361 | CA | GLU | B | 498 | −68.601 | 64.928 | −27.490 | 1.00 | 100.60 | C |
| ATOM | 2362 | CB | GLU | B | 498 | −69.422 | 63.637 | −27.690 | 1.00 | 100.54 | C |
| ATOM | 2363 | CG | GLU | B | 498 | −70.232 | 63.578 | −28.982 | 1.00 | 99.77 | C |
| ATOM | 2364 | CD | GLU | B | 498 | −71.598 | 64.247 | −29.036 | 1.00 | 99.78 | C |
| ATOM | 2365 | OE1 | GLU | B | 498 | −72.349 | 64.209 | −28.031 | 1.00 | 99.38 | O |
| ATOM | 2366 | OE2 | GLU | B | 498 | −71.933 | 64.781 | −30.118 | 1.00 | 99.93 | O |
| ATOM | 2367 | C | GLU | B | 498 | −67.810 | 65.231 | −28.770 | 1.00 | 101.27 | C |
| ATOM | 2368 | O | GLU | B | 498 | −68.208 | 66.105 | −29.542 | 1.00 | 101.37 | O |
| ATOM | 2369 | N | ARG | B | 499 | −66.720 | 64.488 | −29.015 | 1.00 | 102.02 | N |
| ATOM | 2370 | CA | ARG | B | 499 | −65.915 | 64.670 | −30.220 | 1.00 | 103.16 | C |
| ATOM | 2371 | CB | ARG | B | 499 | −64.914 | 65.838 | −30.075 | 1.00 | 103.36 | C |
| ATOM | 2372 | CG | ARG | B | 499 | −63.771 | 65.661 | −29.066 | 1.00 | 104.82 | C |
| ATOM | 2373 | CD | ARG | B | 499 | −63.010 | 66.968 | −28.889 | 1.00 | 107.27 | C |
| ATOM | 2374 | NE | ARG | B | 499 | −61.560 | 66.786 | −28.803 | 1.00 | 108.74 | N |
| ATOM | 2375 | CZ | ARG | B | 499 | −60.748 | 66.743 | −29.859 | 1.00 | 110.20 | C |
| ATOM | 2376 | NH1 | ARG | B | 499 | −61.237 | 66.848 | −31.091 | 1.00 | 110.76 | N |
| ATOM | 2377 | NH2 | ARG | B | 499 | −59.440 | 66.584 | −29.690 | 1.00 | 110.74 | N |
| ATOM | 2378 | C | ARG | B | 499 | −65.212 | 63.403 | −30.683 | 1.00 | 103.63 | C |
| ATOM | 2379 | O | ARG | B | 499 | −64.716 | 62.654 | −29.843 | 1.00 | 103.79 | O |
| ATOM | 2380 | N | MET | B | 500 | −65.166 | 63.166 | −32.016 | 1.00 | 104.97 | N |

TABLE 14-continued

PCSK9 and AX132 Fab complex x-ray structure

| ATOM | 2381 | CA  | MET | B | 500 | −64.464 | 62.024 | −32.618 | 1.00 | 105.67 | C |
|------|------|-----|-----|---|-----|---------|--------|---------|------|--------|---|
| ATOM | 2382 | CB  | MET | B | 500 | −65.081 | 61.555 | −33.951 | 1.00 | 105.49 | C |
| ATOM | 2383 | CG  | MET | B | 500 | −66.574 | 61.518 | −33.996 | 1.00 | 105.68 | C |
| ATOM | 2384 | SD  | MET | B | 500 | −67.135 | 61.048 | −35.655 | 1.00 | 106.00 | S |
| ATOM | 2385 | CE  | MET | B | 500 | −68.702 | 61.924 | −35.734 | 1.00 | 106.42 | C |
| ATOM | 2386 | C   | MET | B | 500 | −63.063 | 62.545 | −32.907 | 1.00 | 106.25 | C |
| ATOM | 2387 | O   | MET | B | 500 | −62.922 | 63.593 | −33.548 | 1.00 | 106.65 | O |
| ATOM | 2388 | N   | GLU | B | 501 | −62.032 | 61.841 | −32.436 | 1.00 | 108.32 | N |
| ATOM | 2389 | CA  | GLU | B | 501 | −60.643 | 62.261 | −32.642 | 1.00 | 108.99 | C |
| ATOM | 2390 | CB  | GLU | B | 501 | −60.233 | 63.351 | −31.631 | 1.00 | 109.08 | C |
| ATOM | 2391 | CG  | GLU | B | 501 | −60.598 | 63.038 | −30.191 | 1.00 | 109.68 | C |
| ATOM | 2392 | CD  | GLU | B | 501 | −59.428 | 63.072 | −29.234 | 1.00 | 111.33 | C |
| ATOM | 2393 | OE1 | GLU | B | 501 | −58.397 | 62.407 | −29.499 | 1.00 | 112.50 | O |
| ATOM | 2394 | OE2 | GLU | B | 501 | −59.550 | 63.768 | −28.203 | 1.00 | 111.64 | O |
| ATOM | 2395 | C   | GLU | B | 501 | −59.677 | 61.091 | −32.599 | 1.00 | 109.25 | C |
| ATOM | 2396 | O   | GLU | B | 501 | −59.884 | 60.161 | −31.813 | 1.00 | 109.40 | O |
| ATOM | 2397 | N   | ALA | B | 502 | −58.619 | 61.134 | −33.439 | 1.00 | 110.32 | N |
| ATOM | 2398 | CA  | ALA | B | 502 | −57.623 | 60.066 | −33.487 | 1.00 | 110.50 | C |
| ATOM | 2399 | CB  | ALA | B | 502 | −56.732 | 60.212 | −34.706 | 1.00 | 110.43 | C |
| ATOM | 2400 | C   | ALA | B | 502 | −56.799 | 60.056 | −32.206 | 1.00 | 110.60 | C |
| ATOM | 2401 | O   | ALA | B | 502 | −56.305 | 61.106 | −31.785 | 1.00 | 110.53 | O |
| ATOM | 2402 | N   | GLN | B | 503 | −56.705 | 58.877 | −31.556 | 1.00 | 111.55 | N |
| ATOM | 2403 | CA  | GLN | B | 503 | −55.966 | 58.704 | −30.301 | 1.00 | 111.77 | C |
| ATOM | 2404 | CB  | GLN | B | 503 | −56.926 | 58.536 | −29.112 | 1.00 | 111.82 | C |
| ATOM | 2405 | CG  | GLN | B | 503 | −56.555 | 59.397 | −27.905 | 1.00 | 112.75 | C |
| ATOM | 2406 | CD  | GLN | B | 503 | −56.913 | 58.792 | −26.555 | 1.00 | 113.67 | C |
| ATOM | 2407 | OE1 | GLN | B | 503 | −57.487 | 59.470 | −25.683 | 1.00 | 113.67 | O |
| ATOM | 2408 | NE2 | GLN | B | 503 | −56.572 | 57.514 | −26.337 | 1.00 | 113.24 | N |
| ATOM | 2409 | C   | GLN | B | 503 | −54.970 | 57.548 | −30.402 | 1.00 | 111.66 | C |
| ATOM | 2410 | O   | GLN | B | 503 | −54.878 | 56.702 | −29.506 | 1.00 | 111.55 | O |
| ATOM | 2411 | N   | GLY | B | 504 | −54.226 | 57.547 | −31.504 | 1.00 | 110.07 | N |
| ATOM | 2412 | CA  | GLY | B | 504 | −53.219 | 56.544 | −31.810 | 1.00 | 109.96 | C |
| ATOM | 2413 | C   | GLY | B | 504 | −53.490 | 55.899 | −33.147 | 1.00 | 109.86 | C |
| ATOM | 2414 | O   | GLY | B | 504 | −53.667 | 54.682 | −33.219 | 1.00 | 110.09 | O |
| ATOM | 2415 | N   | GLY | B | 505 | −53.547 | 56.727 | −34.193 | 1.00 | 107.76 | N |
| ATOM | 2416 | CA  | GLY | B | 505 | −53.794 | 56.312 | −35.574 | 1.00 | 107.17 | C |
| ATOM | 2417 | C   | GLY | B | 505 | −55.244 | 55.983 | −35.853 | 1.00 | 106.75 | C |
| ATOM | 2418 | O   | GLY | B | 505 | −55.739 | 56.207 | −36.966 | 1.00 | 106.70 | O |
| ATOM | 2419 | N   | LYS | B | 506 | −55.921 | 55.438 | −34.817 | 1.00 | 103.97 | N |
| ATOM | 2420 | CA  | LYS | B | 506 | −57.319 | 55.021 | −34.795 | 1.00 | 103.43 | C |
| ATOM | 2421 | CB  | LYS | B | 506 | −57.475 | 53.707 | −34.009 | 1.00 | 103.22 | C |
| ATOM | 2422 | C   | LYS | B | 506 | −58.195 | 56.119 | −34.201 | 1.00 | 102.98 | C |
| ATOM | 2423 | O   | LYS | B | 506 | −57.736 | 56.916 | −33.374 | 1.00 | 102.94 | O |
| ATOM | 2424 | N   | LEU | B | 507 | −59.462 | 56.138 | −34.640 | 1.00 | 100.19 | N |
| ATOM | 2425 | CA  | LEU | B | 507 | −60.488 | 57.086 | −34.243 | 1.00 | 99.60  | C |
| ATOM | 2426 | CB  | LEU | B | 507 | −61.489 | 57.283 | −35.389 | 1.00 | 99.62  | C |
| ATOM | 2427 | CG  | LEU | B | 507 | −61.238 | 58.461 | −36.300 | 1.00 | 99.92  | C |
| ATOM | 2428 | CD1 | LEU | B | 507 | −62.162 | 58.412 | −37.512 | 1.00 | 99.81  | C |
| ATOM | 2429 | CD2 | LEU | B | 507 | −61.374 | 59.779 | −35.541 | 1.00 | 100.26 | C |
| ATOM | 2430 | C   | LEU | B | 507 | −61.244 | 56.677 | −33.010 | 1.00 | 99.14  | C |
| ATOM | 2431 | O   | LEU | B | 507 | −62.007 | 55.710 | −33.045 | 1.00 | 99.30  | O |
| ATOM | 2432 | N   | VAL | B | 508 | −61.059 | 57.418 | −31.926 | 1.00 | 97.74  | N |
| ATOM | 2433 | CA  | VAL | B | 508 | −61.807 | 57.153 | −30.702 | 1.00 | 97.21  | C |
| ATOM | 2434 | CB  | VAL | B | 508 | −60.965 | 57.106 | −29.391 | 1.00 | 97.40  | C |
| ATOM | 2435 | CG1 | VAL | B | 508 | −59.822 | 56.097 | −29.491 | 1.00 | 97.46  | C |
| ATOM | 2436 | CG2 | VAL | B | 508 | −60.459 | 58.492 | −28.979 | 1.00 | 97.58  | C |
| ATOM | 2437 | C   | VAL | B | 508 | −62.985 | 58.151 | −30.656 | 1.00 | 96.62  | C |
| ATOM | 2438 | O   | VAL | B | 508 | −63.221 | 58.856 | −31.633 | 1.00 | 96.62  | O |
| ATOM | 2439 | N   | CYS | B | 509 | −63.723 | 58.190 | −29.551 | 1.00 | 95.28  | N |
| ATOM | 2440 | CA  | CYS | B | 509 | −64.854 | 59.076 | −29.355 | 1.00 | 94.70  | C |
| ATOM | 2441 | CB  | CYS | B | 509 | −66.158 | 58.379 | −29.765 | 1.00 | 94.39  | C |
| ATOM | 2442 | SG  | CYS | B | 509 | −67.660 | 58.918 | −28.888 | 1.00 | 93.73  | S |
| ATOM | 2443 | C   | CYS | B | 509 | −64.799 | 59.439 | −27.882 | 1.00 | 94.85  | C |
| ATOM | 2444 | O   | CYS | B | 509 | −64.850 | 58.556 | −27.023 | 1.00 | 94.75  | O |
| ATOM | 2445 | N   | ARG | B | 510 | −64.580 | 60.734 | −27.590 | 1.00 | 98.66  | N |
| ATOM | 2446 | CA  | ARG | B | 510 | −64.523 | 61.210 | −26.214 | 1.00 | 98.77  | C |
| ATOM | 2447 | CB  | ARG | B | 510 | −63.126 | 61.622 | −25.716 | 1.00 | 98.96  | C |
| ATOM | 2448 | CG  | ARG | B | 510 | −62.429 | 62.761 | −26.441 | 1.00 | 99.61  | C |
| ATOM | 2449 | CD  | ARG | B | 510 | −61.444 | 63.535 | −25.547 | 1.00 | 101.26 | C |
| ATOM | 2450 | NE  | ARG | B | 510 | −60.647 | 62.705 | −24.625 | 1.00 | 101.83 | N |
| ATOM | 2451 | CZ  | ARG | B | 510 | −59.442 | 62.197 | −24.891 | 1.00 | 102.45 | C |
| ATOM | 2452 | NH1 | ARG | B | 510 | −58.866 | 62.412 | −26.068 | 1.00 | 102.46 | N |
| ATOM | 2453 | NH2 | ARG | B | 510 | −58.806 | 61.463 | −23.979 | 1.00 | 102.87 | N |
| ATOM | 2454 | C   | ARG | B | 510 | −65.574 | 62.221 | −25.907 | 1.00 | 98.65  | C |
| ATOM | 2455 | O   | ARG | B | 510 | −65.911 | 63.044 | −26.755 | 1.00 | 98.46  | O |
| ATOM | 2456 | N   | ALA | B | 511 | −66.129 | 62.119 | −24.704 | 1.00 | 99.45  | N |
| ATOM | 2457 | CA  | ALA | B | 511 | −67.163 | 63.007 | −24.210 | 1.00 | 99.87  | C |
| ATOM | 2458 | CB  | ALA | B | 511 | −68.338 | 62.210 | −23.677 | 1.00 | 99.79  | C |

TABLE 14-continued

PCSK9 and AX132 Fab complex x-ray structure

| ATOM | 2459 | C | ALA | B | 511 | −66.569 | 63.865 | −23.118 | 1.00 | 100.26 | C |
|------|------|------|-----|---|-----|---------|--------|---------|------|--------|---|
| ATOM | 2460 | O | ALA | B | 511 | −65.663 | 63.428 | −22.394 | 1.00 | 100.16 | O |
| ATOM | 2461 | N | HIS | B | 512 | −67.062 | 65.104 | −23.017 | 1.00 | 103.56 | N |
| ATOM | 2462 | CA | HIS | B | 512 | −66.572 | 66.038 | −22.022 | 1.00 | 103.97 | C |
| ATOM | 2463 | CB | HIS | B | 512 | −66.059 | 67.328 | −22.680 | 1.00 | 104.15 | C |
| ATOM | 2464 | CG | HIS | B | 512 | −65.158 | 67.086 | −23.851 | 1.00 | 104.58 | C |
| ATOM | 2465 | ND1 | HIS | B | 512 | −63.836 | 66.696 | −23.679 | 1.00 | 104.80 | N |
| ATOM | 2466 | CE1 | HIS | B | 512 | −63.344 | 66.555 | −24.901 | 1.00 | 105.05 | C |
| ATOM | 2467 | NE2 | HIS | B | 512 | −64.263 | 66.828 | −25.833 | 1.00 | 104.85 | N |
| ATOM | 2468 | CD2 | HIS | B | 512 | −65.424 | 67.166 | −25.176 | 1.00 | 104.75 | C |
| ATOM | 2469 | C | HIS | B | 512 | −67.647 | 66.339 | −21.017 | 1.00 | 104.07 | C |
| ATOM | 2470 | O | HIS | B | 512 | −68.814 | 66.544 | −21.377 | 1.00 | 103.94 | O |
| ATOM | 2471 | N | ASN | B | 513 | −67.249 | 66.344 | −19.745 | 1.00 | 108.70 | N |
| ATOM | 2472 | CA | ASN | B | 513 | −68.135 | 66.661 | −18.637 | 1.00 | 109.06 | C |
| ATOM | 2473 | CB | ASN | B | 513 | −67.662 | 65.942 | −17.371 | 1.00 | 108.93 | C |
| ATOM | 2474 | CG | ASN | B | 513 | −68.626 | 66.037 | −16.216 | 1.00 | 109.02 | C |
| ATOM | 2475 | OD1 | ASN | B | 513 | −69.822 | 65.727 | −16.324 | 1.00 | 108.87 | O |
| ATOM | 2476 | ND2 | ASN | B | 513 | −68.118 | 66.469 | −15.077 | 1.00 | 109.30 | N |
| ATOM | 2477 | C | ASN | B | 513 | −68.090 | 68.195 | −18.458 | 1.00 | 109.45 | C |
| ATOM | 2478 | O | ASN | B | 513 | −67.032 | 68.806 | −18.668 | 1.00 | 109.67 | O |
| ATOM | 2479 | N | ALA | B | 514 | −69.225 | 68.822 | −18.102 | 1.00 | 112.49 | N |
| ATOM | 2480 | CA | ALA | B | 514 | −69.271 | 70.277 | −17.905 | 1.00 | 112.56 | C |
| ATOM | 2481 | CB | ALA | B | 514 | −70.691 | 70.785 | −18.130 | 1.00 | 112.61 | C |
| ATOM | 2482 | C | ALA | B | 514 | −68.781 | 70.659 | −16.492 | 1.00 | 112.54 | C |
| ATOM | 2483 | O | ALA | B | 514 | −68.324 | 69.783 | −15.741 | 1.00 | 112.68 | O |
| ATOM | 2484 | N | PHE | B | 515 | −68.862 | 71.962 | −16.126 | 1.00 | 112.66 | N |
| ATOM | 2485 | CA | PHE | B | 515 | −68.475 | 72.372 | −14.779 | 1.00 | 112.19 | C |
| ATOM | 2486 | CB | PHE | B | 515 | −68.331 | 73.903 | −14.673 | 1.00 | 112.23 | C |
| ATOM | 2487 | C | PHE | B | 515 | −69.586 | 71.830 | −13.844 | 1.00 | 111.78 | C |
| ATOM | 2488 | O | PHE | B | 515 | −70.780 | 72.017 | −14.123 | 1.00 | 111.67 | O |
| ATOM | 2489 | N | GLY | B | 516 | −69.175 | 71.100 | −12.804 | 1.00 | 110.55 | N |
| ATOM | 2490 | CA | GLY | B | 516 | −70.078 | 70.509 | −11.817 | 1.00 | 109.70 | C |
| ATOM | 2491 | C | GLY | B | 516 | −71.000 | 69.405 | −12.305 | 1.00 | 109.14 | C |
| ATOM | 2492 | O | GLY | B | 516 | −71.985 | 69.068 | −11.632 | 1.00 | 109.15 | O |
| ATOM | 2493 | N | GLY | B | 517 | −70.672 | 68.842 | −13.468 | 1.00 | 107.91 | N |
| ATOM | 2494 | CA | GLY | B | 517 | −71.421 | 67.753 | −14.079 | 1.00 | 106.83 | C |
| ATOM | 2495 | C | GLY | B | 517 | −71.141 | 66.421 | −13.414 | 1.00 | 106.05 | C |
| ATOM | 2496 | O | GLY | B | 517 | −69.981 | 66.074 | −13.178 | 1.00 | 105.89 | O |
| ATOM | 2497 | N | GLU | B | 518 | −72.218 | 65.673 | −13.112 | 1.00 | 104.44 | N |
| ATOM | 2498 | CA | GLU | B | 518 | −72.240 | 64.353 | −12.468 | 1.00 | 103.79 | C |
| ATOM | 2499 | CB | GLU | B | 518 | −73.714 | 63.883 | −12.390 | 1.00 | 104.31 | C |
| ATOM | 2500 | CG | GLU | B | 518 | −73.988 | 62.379 | −12.342 | 1.00 | 107.59 | C |
| ATOM | 2501 | CD | GLU | B | 518 | −74.554 | 61.735 | −13.604 | 1.00 | 111.39 | C |
| ATOM | 2502 | OE1 | GLU | B | 518 | −74.894 | 62.473 | −14.563 | 1.00 | 112.80 | O |
| ATOM | 2503 | OE2 | GLU | B | 518 | −74.652 | 60.483 | −13.630 | 1.00 | 112.20 | O |
| ATOM | 2504 | C | GLU | B | 518 | −71.289 | 63.314 | −13.137 | 1.00 | 102.42 | C |
| ATOM | 2505 | O | GLU | B | 518 | −70.720 | 62.456 | −12.452 | 1.00 | 102.42 | O |
| ATOM | 2506 | N | GLY | B | 519 | −71.128 | 63.434 | −14.456 | 1.00 | 95.77 | N |
| ATOM | 2507 | CA | GLY | B | 519 | −70.298 | 62.569 | −15.288 | 1.00 | 93.38 | C |
| ATOM | 2508 | C | GLY | B | 519 | −70.952 | 62.276 | −16.624 | 1.00 | 91.71 | C |
| ATOM | 2509 | O | GLY | B | 519 | −72.173 | 62.415 | −16.775 | 1.00 | 91.45 | O |
| ATOM | 2510 | N | VAL | B | 520 | −70.136 | 61.873 | −17.604 | 1.00 | 85.33 | N |
| ATOM | 2511 | CA | VAL | B | 520 | −70.610 | 61.549 | −18.953 | 1.00 | 83.96 | C |
| ATOM | 2512 | CB | VAL | B | 520 | −70.257 | 62.615 | −20.026 | 1.00 | 83.84 | C |
| ATOM | 2513 | CG1 | VAL | B | 520 | −71.053 | 63.895 | −19.825 | 1.00 | 84.23 | C |
| ATOM | 2514 | CG2 | VAL | B | 520 | −68.762 | 62.878 | −20.107 | 1.00 | 82.88 | C |
| ATOM | 2515 | C | VAL | B | 520 | −70.246 | 60.147 | −19.455 | 1.00 | 83.10 | C |
| ATOM | 2516 | O | VAL | B | 520 | −69.364 | 59.482 | −18.903 | 1.00 | 82.93 | O |
| ATOM | 2517 | N | TYR | B | 521 | −70.927 | 59.734 | −20.542 | 1.00 | 77.36 | N |
| ATOM | 2518 | CA | TYR | B | 521 | −70.719 | 58.483 | −21.248 | 1.00 | 76.11 | C |
| ATOM | 2519 | CB | TYR | B | 521 | −72.014 | 57.659 | −21.271 | 1.00 | 75.84 | C |
| ATOM | 2520 | CG | TYR | B | 521 | −72.279 | 56.875 | −20.014 | 1.00 | 74.40 | C |
| ATOM | 2521 | CD1 | TYR | B | 521 | −71.496 | 55.778 | −19.678 | 1.00 | 73.61 | C |
| ATOM | 2522 | CE1 | TYR | B | 521 | −71.726 | 55.057 | −18.514 | 1.00 | 73.69 | C |
| ATOM | 2523 | CZ | TYR | B | 521 | −72.783 | 55.405 | −17.690 | 1.00 | 73.71 | C |
| ATOM | 2524 | OH | TYR | B | 521 | −73.029 | 54.664 | −16.560 | 1.00 | 75.02 | O |
| ATOM | 2525 | CE2 | TYR | B | 521 | −73.591 | 56.480 | −18.016 | 1.00 | 73.04 | C |
| ATOM | 2526 | CD2 | TYR | B | 521 | −73.333 | 57.208 | −19.172 | 1.00 | 73.38 | C |
| ATOM | 2527 | C | TYR | B | 521 | −70.376 | 58.817 | −22.676 | 1.00 | 75.67 | C |
| ATOM | 2528 | O | TYR | B | 521 | −71.056 | 59.644 | −23.272 | 1.00 | 75.79 | O |
| ATOM | 2529 | N | ALA | B | 522 | −69.352 | 58.187 | −23.236 | 1.00 | 75.50 | N |
| ATOM | 2530 | CA | ALA | B | 522 | −69.011 | 58.380 | −24.644 | 1.00 | 75.36 | C |
| ATOM | 2531 | CB | ALA | B | 522 | −67.509 | 58.343 | −24.849 | 1.00 | 75.31 | C |
| ATOM | 2532 | C | ALA | B | 522 | −69.682 | 57.201 | −25.354 | 1.00 | 75.24 | C |
| ATOM | 2533 | O | ALA | B | 522 | −69.425 | 56.045 | −25.017 | 1.00 | 75.54 | O |
| ATOM | 2534 | N | ILE | B | 523 | −70.584 | 57.471 | −26.280 | 1.00 | 75.34 | N |
| ATOM | 2535 | CA | ILE | B | 523 | −71.266 | 56.367 | −26.911 | 1.00 | 75.13 | C |
| ATOM | 2536 | CB | ILE | B | 523 | −72.780 | 56.459 | −26.667 | 1.00 | 74.87 | C |

TABLE 14-continued

PCSK9 and AX132 Fab complex x-ray structure

| ATOM | 2537 | CG1 | ILE | B | 523 | −73.084 | 56.834 | −25.200 | 1.00 | 74.58 | C |
|---|---|---|---|---|---|---|---|---|---|---|---|
| ATOM | 2538 | CD1 | ILE | B | 523 | −74.213 | 57.663 | −25.036 | 1.00 | 74.23 | C |
| ATOM | 2539 | CG2 | ILE | B | 523 | −73.447 | 55.142 | −27.051 | 1.00 | 74.99 | C |
| ATOM | 2540 | C | ILE | B | 523 | −70.871 | 56.188 | −28.372 | 1.00 | 75.66 | C |
| ATOM | 2541 | O | ILE | B | 523 | −71.472 | 56.794 | −29.261 | 1.00 | 75.68 | O |
| ATOM | 2542 | N | ALA | B | 524 | −69.855 | 55.338 | −28.624 | 1.00 | 77.17 | N |
| ATOM | 2543 | CA | ALA | B | 524 | −69.367 | 55.050 | −29.976 | 1.00 | 77.63 | C |
| ATOM | 2544 | CB | ALA | B | 524 | −67.969 | 54.457 | −29.905 | 1.00 | 77.24 | C |
| ATOM | 2545 | C | ALA | B | 524 | −70.312 | 54.102 | −30.761 | 1.00 | 78.11 | C |
| ATOM | 2546 | O | ALA | B | 524 | −70.984 | 53.267 | −30.151 | 1.00 | 78.12 | O |
| ATOM | 2547 | N | ARG | B | 525 | −70.370 | 54.249 | −32.104 | 1.00 | 78.26 | N |
| ATOM | 2548 | CA | ARG | B | 525 | −71.152 | 53.387 | −32.983 | 1.00 | 79.17 | C |
| ATOM | 2549 | CB | ARG | B | 525 | −72.256 | 54.140 | −33.724 | 1.00 | 78.49 | C |
| ATOM | 2550 | CG | ARG | B | 525 | −73.134 | 53.238 | −34.584 | 1.00 | 77.19 | C |
| ATOM | 2551 | CD | ARG | B | 525 | −74.204 | 52.490 | −33.806 | 1.00 | 74.80 | C |
| ATOM | 2552 | NE | ARG | B | 525 | −75.051 | 51.713 | −34.710 | 1.00 | 71.66 | N |
| ATOM | 2553 | CZ | ARG | B | 525 | −76.000 | 50.870 | −34.324 | 1.00 | 69.01 | C |
| ATOM | 2554 | NH1 | ARG | B | 525 | −76.228 | 50.663 | −33.034 | 1.00 | 68.93 | N |
| ATOM | 2555 | NH2 | ARG | B | 525 | −76.730 | 50.224 | −35.224 | 1.00 | 67.79 | N |
| ATOM | 2556 | C | ARG | B | 525 | −70.131 | 52.755 | −33.927 | 1.00 | 80.77 | C |
| ATOM | 2557 | O | ARG | B | 525 | −69.737 | 53.366 | −34.930 | 1.00 | 81.03 | O |
| ATOM | 2558 | N | CYS | B | 526 | −69.661 | 51.534 | −33.550 | 1.00 | 84.10 | N |
| ATOM | 2559 | CA | CYS | B | 526 | −68.646 | 50.752 | −34.245 | 1.00 | 85.63 | C |
| ATOM | 2560 | CB | CYS | B | 526 | −67.808 | 49.986 | −33.240 | 1.00 | 85.67 | C |
| ATOM | 2561 | SG | CYS | B | 526 | −67.028 | 51.045 | −32.001 | 1.00 | 86.73 | S |
| ATOM | 2562 | C | CYS | B | 526 | −69.216 | 49.854 | −35.307 | 1.00 | 86.72 | C |
| ATOM | 2563 | O | CYS | B | 526 | −70.177 | 49.127 | −35.059 | 1.00 | 86.85 | O |
| ATOM | 2564 | N | CYS | B | 527 | −68.638 | 49.930 | −36.517 | 1.00 | 86.58 | N |
| ATOM | 2565 | CA | CYS | B | 527 | −69.110 | 49.182 | −37.679 | 1.00 | 88.11 | C |
| ATOM | 2566 | CB | CYS | B | 527 | −69.933 | 50.094 | −38.590 | 1.00 | 87.81 | C |
| ATOM | 2567 | SG | CYS | B | 527 | −71.199 | 51.072 | −37.722 | 1.00 | 87.72 | S |
| ATOM | 2568 | C | CYS | B | 527 | −68.031 | 48.439 | −38.457 | 1.00 | 89.37 | C |
| ATOM | 2569 | O | CYS | B | 527 | −66.840 | 48.717 | −38.310 | 1.00 | 89.09 | O |
| ATOM | 2570 | N | LEU | B | 528 | −68.464 | 47.481 | −39.284 | 1.00 | 91.74 | N |
| ATOM | 2571 | CA | LEU | B | 528 | −67.579 | 46.684 | −40.136 | 1.00 | 94.12 | C |
| ATOM | 2572 | CB | LEU | B | 528 | −67.845 | 45.175 | −39.990 | 1.00 | 93.84 | C |
| ATOM | 2573 | CG | LEU | B | 528 | −67.467 | 44.499 | −38.679 | 1.00 | 93.16 | C |
| ATOM | 2574 | CD1 | LEU | B | 528 | −67.902 | 43.074 | −38.710 | 1.00 | 92.63 | C |
| ATOM | 2575 | CD2 | LEU | B | 528 | −65.968 | 44.576 | −38.403 | 1.00 | 92.08 | C |
| ATOM | 2576 | C | LEU | B | 528 | −67.726 | 47.142 | −41.604 | 1.00 | 96.20 | C |
| ATOM | 2577 | O | LEU | B | 528 | −68.639 | 46.703 | −42.330 | 1.00 | 96.27 | O |
| ATOM | 2578 | N | LEU | B | 529 | −66.826 | 48.060 | −42.013 | 1.00 | 101.19 | N |
| ATOM | 2579 | CA | LEU | B | 529 | −66.801 | 48.654 | −43.341 | 1.00 | 103.82 | C |
| ATOM | 2580 | CB | LEU | B | 529 | −67.066 | 50.162 | −43.241 | 1.00 | 103.71 | C |
| ATOM | 2581 | CG | LEU | B | 529 | −67.526 | 50.876 | −44.500 | 1.00 | 103.99 | C |
| ATOM | 2582 | CD1 | LEU | B | 529 | −68.929 | 50.463 | −44.903 | 1.00 | 103.65 | C |
| ATOM | 2583 | CD2 | LEU | B | 529 | −67.502 | 52.368 | −44.292 | 1.00 | 104.17 | C |
| ATOM | 2584 | C | LEU | B | 529 | −65.463 | 48.354 | −43.998 | 1.00 | 105.85 | C |
| ATOM | 2585 | O | LEU | B | 529 | −64.440 | 48.938 | −43.629 | 1.00 | 105.85 | O |
| ATOM | 2586 | N | PRO | B | 530 | −65.462 | 47.394 | −44.950 | 1.00 | 113.01 | N |
| ATOM | 2587 | CA | PRO | B | 530 | −64.207 | 47.020 | −45.619 | 1.00 | 114.85 | C |
| ATOM | 2588 | CB | PRO | B | 530 | −64.560 | 45.707 | −46.324 | 1.00 | 114.74 | C |
| ATOM | 2589 | CG | PRO | B | 530 | −66.027 | 45.796 | −46.581 | 1.00 | 114.03 | C |
| ATOM | 2590 | CD | PRO | B | 530 | −66.609 | 46.618 | −45.471 | 1.00 | 113.18 | C |
| ATOM | 2591 | C | PRO | B | 530 | −63.733 | 48.104 | −46.587 | 1.00 | 116.79 | C |
| ATOM | 2592 | O | PRO | B | 530 | −64.550 | 48.652 | −47.352 | 1.00 | 117.04 | O |
| ATOM | 2593 | N | GLN | B | 531 | −62.405 | 48.413 | −46.538 | 1.00 | 120.37 | N |
| ATOM | 2594 | CA | GLN | B | 531 | −61.736 | 49.449 | −47.339 | 1.00 | 122.30 | C |
| ATOM | 2595 | CB | GLN | B | 531 | −61.674 | 49.073 | −48.844 | 1.00 | 122.37 | C |
| ATOM | 2596 | CG | GLN | B | 531 | −60.765 | 47.872 | −49.170 | 1.00 | 123.50 | C |
| ATOM | 2597 | CD | GLN | B | 531 | −61.035 | 47.202 | −50.518 | 1.00 | 125.13 | C |
| ATOM | 2598 | OE1 | GLN | B | 531 | −61.895 | 47.613 | −51.314 | 1.00 | 125.49 | O |
| ATOM | 2599 | NE2 | GLN | B | 531 | −60.297 | 46.132 | −50.803 | 1.00 | 125.67 | N |
| ATOM | 2600 | C | GLN | B | 531 | −62.456 | 50.797 | −47.061 | 1.00 | 123.38 | C |
| ATOM | 2601 | O | GLN | B | 531 | −63.323 | 51.236 | −47.832 | 1.00 | 123.60 | O |
| ATOM | 2602 | N | ALA | B | 532 | −62.136 | 51.406 | −45.908 | 1.00 | 124.93 | N |
| ATOM | 2603 | CA | ALA | B | 532 | −62.755 | 52.653 | −45.485 | 1.00 | 126.34 | C |
| ATOM | 2604 | CB | ALA | B | 532 | −63.765 | 52.379 | −44.380 | 1.00 | 126.15 | C |
| ATOM | 2605 | C | ALA | B | 532 | −61.735 | 53.690 | −45.027 | 1.00 | 127.47 | C |
| ATOM | 2606 | O | ALA | B | 532 | −60.935 | 53.423 | −44.123 | 1.00 | 127.79 | O |
| ATOM | 2607 | N | ASN | B | 533 | −61.760 | 54.874 | −45.667 | 1.00 | 129.58 | N |
| ATOM | 2608 | CA | ASN | B | 533 | −60.896 | 56.006 | −45.335 | 1.00 | 130.77 | C |
| ATOM | 2609 | CB | ASN | B | 533 | −60.371 | 56.707 | −46.611 | 1.00 | 130.82 | C |
| ATOM | 2610 | CG | ASN | B | 533 | −59.372 | 55.919 | −47.435 | 1.00 | 131.44 | C |
| ATOM | 2611 | OD1 | ASN | B | 533 | −58.173 | 55.852 | −47.120 | 1.00 | 132.13 | O |
| ATOM | 2612 | ND2 | ASN | B | 533 | −59.841 | 55.321 | −48.530 | 1.00 | 131.80 | N |
| ATOM | 2613 | C | ASN | B | 533 | −61.818 | 56.929 | −44.539 | 1.00 | 131.52 | C |
| ATOM | 2614 | O | ASN | B | 533 | −62.575 | 57.704 | −45.132 | 1.00 | 131.65 | O |

TABLE 14-continued

| | | | | | | | | | | |
|---|---|---|---|---|---|---|---|---|---|---|
| ATOM | 2615 | N | CYS | B | 534 | −61.818 | 56.803 | −43.207 | 1.00 | 132.79 N |
| ATOM | 2616 | CA | CYS | B | 534 | −62.710 | 57.648 | −42.419 | 1.00 | 133.86 C |
| ATOM | 2617 | CB | CYS | B | 534 | −63.591 | 56.830 | −41.481 | 1.00 | 133.93 C |
| ATOM | 2618 | SG | CYS | B | 534 | −64.768 | 55.741 | −42.336 | 1.00 | 135.03 S |
| ATOM | 2619 | C | CYS | B | 534 | −62.004 | 58.801 | −41.720 | 1.00 | 134.34 C |
| ATOM | 2620 | O | CYS | B | 534 | −60.982 | 58.585 | −41.062 | 1.00 | 134.48 O |
| ATOM | 2621 | N | SER | B | 535 | −62.545 | 60.034 | −41.898 | 1.00 | 133.21 N |
| ATOM | 2622 | CA | SER | B | 535 | −61.988 | 61.287 | −41.371 | 1.00 | 133.80 C |
| ATOM | 2623 | CB | SER | B | 535 | −61.343 | 62.075 | −42.512 | 1.00 | 133.78 C |
| ATOM | 2624 | OG | SER | B | 535 | −62.285 | 62.439 | −43.512 | 1.00 | 134.38 O |
| ATOM | 2625 | C | SER | B | 535 | −62.971 | 62.205 | −40.630 | 1.00 | 134.13 C |
| ATOM | 2626 | O | SER | B | 535 | −64.168 | 62.208 | −40.920 | 1.00 | 133.92 O |
| ATOM | 2627 | N | VAL | B | 536 | −62.436 | 63.018 | −39.704 | 1.00 | 133.66 N |
| ATOM | 2628 | CA | VAL | B | 536 | −63.204 | 63.990 | −38.926 | 1.00 | 134.48 C |
| ATOM | 2629 | CB | VAL | B | 536 | −62.823 | 64.004 | −37.423 | 1.00 | 134.45 C |
| ATOM | 2630 | CG1 | VAL | B | 536 | −63.703 | 64.970 | −36.626 | 1.00 | 134.41 C |
| ATOM | 2631 | CG2 | VAL | B | 536 | −62.907 | 62.610 | −36.834 | 1.00 | 134.51 C |
| ATOM | 2632 | C | VAL | B | 536 | −63.047 | 65.372 | −39.554 | 1.00 | 135.15 C |
| ATOM | 2633 | O | VAL | B | 536 | −61.924 | 65.824 | −39.800 | 1.00 | 135.25 O |
| ATOM | 2634 | N | HIS | B | 537 | −64.176 | 66.039 | −39.809 | 1.00 | 136.24 N |
| ATOM | 2635 | CA | HIS | B | 537 | −64.192 | 67.375 | −40.380 | 1.00 | 137.05 C |
| ATOM | 2636 | CB | HIS | B | 537 | −65.002 | 67.415 | −41.688 | 1.00 | 137.20 C |
| ATOM | 2637 | CG | HIS | B | 537 | −64.287 | 66.848 | −42.883 | 1.00 | 138.47 C |
| ATOM | 2638 | ND1 | HIS | B | 537 | −64.571 | 67.293 | −44.171 | 1.00 | 139.63 N |
| ATOM | 2639 | CE1 | HIS | B | 537 | −63.786 | 66.590 | −44.974 | 1.00 | 139.83 C |
| ATOM | 2640 | NE2 | HIS | B | 537 | −63.020 | 65.733 | −44.288 | 1.00 | 139.91 N |
| ATOM | 2641 | CD2 | HIS | B | 537 | −63.331 | 65.887 | −42.955 | 1.00 | 139.28 C |
| ATOM | 2642 | C | HIS | B | 537 | −64.690 | 68.370 | −39.330 | 1.00 | 137.40 C |
| ATOM | 2643 | O | HIS | B | 537 | −65.864 | 68.736 | −39.305 | 1.00 | 137.42 O |
| ATOM | 2644 | N | THR | B | 538 | −63.777 | 68.780 | −38.441 | 1.00 | 136.73 N |
| ATOM | 2645 | CA | THR | B | 538 | −64.031 | 69.734 | −37.362 | 1.00 | 137.31 C |
| ATOM | 2646 | CB | THR | B | 538 | −62.838 | 69.736 | −36.391 | 1.00 | 137.31 C |
| ATOM | 2647 | OG1 | THR | B | 538 | −62.335 | 68.410 | −36.237 | 1.00 | 137.37 O |
| ATOM | 2648 | CG2 | THR | B | 538 | −63.182 | 70.320 | −35.032 | 1.00 | 137.41 C |
| ATOM | 2649 | C | THR | B | 538 | −64.244 | 71.142 | −37.951 | 1.00 | 137.73 C |
| ATOM | 2650 | O | THR | B | 538 | −63.608 | 71.494 | −38.949 | 1.00 | 137.83 O |
| ATOM | 2651 | N | ALA | B | 539 | −65.130 | 71.940 | −37.328 | 1.00 | 137.80 N |
| ATOM | 2652 | CA | ALA | B | 539 | −65.430 | 73.316 | −37.741 | 1.00 | 138.09 C |
| ATOM | 2653 | CB | ALA | B | 539 | −66.688 | 73.353 | −38.607 | 1.00 | 137.95 C |
| ATOM | 2654 | C | ALA | B | 539 | −65.597 | 74.208 | −36.488 | 1.00 | 138.39 C |
| ATOM | 2655 | O | ALA | B | 539 | −66.600 | 74.053 | −35.789 | 1.00 | 138.43 O |
| ATOM | 2656 | N | PRO | B | 540 | −64.639 | 75.124 | −36.163 | 1.00 | 137.90 N |
| ATOM | 2657 | CA | PRO | B | 540 | −64.789 | 75.965 | −34.955 | 1.00 | 138.18 C |
| ATOM | 2658 | CB | PRO | B | 540 | −63.554 | 76.868 | −35.000 | 1.00 | 138.11 C |
| ATOM | 2659 | CG | PRO | B | 540 | −62.563 | 76.098 | −35.784 | 1.00 | 138.04 C |
| ATOM | 2660 | CD | PRO | B | 540 | −63.372 | 75.428 | −36.854 | 1.00 | 137.89 C |
| ATOM | 2661 | C | PRO | B | 540 | −66.092 | 76.771 | −34.890 | 1.00 | 138.52 C |
| ATOM | 2662 | O | PRO | B | 540 | −66.703 | 77.001 | −35.937 | 1.00 | 138.52 O |
| ATOM | 2663 | N | PRO | B | 541 | −66.550 | 77.190 | −33.683 | 1.00 | 140.26 N |
| ATOM | 2664 | CA | PRO | B | 541 | −67.822 | 77.938 | −33.594 | 1.00 | 140.69 C |
| ATOM | 2665 | CB | PRO | B | 541 | −67.994 | 78.175 | −32.090 | 1.00 | 140.62 C |
| ATOM | 2666 | CG | PRO | B | 541 | −67.103 | 77.184 | −31.430 | 1.00 | 140.29 C |
| ATOM | 2667 | CD | PRO | B | 541 | −65.952 | 76.993 | −32.347 | 1.00 | 140.16 C |
| ATOM | 2668 | C | PRO | B | 541 | −67.874 | 79.243 | −34.397 | 1.00 | 141.21 C |
| ATOM | 2669 | O | PRO | B | 541 | −66.997 | 80.103 | −34.245 | 1.00 | 141.24 O |
| ATOM | 2670 | N | ALA | B | 542 | −68.902 | 79.372 | −35.269 | 1.00 | 143.91 N |
| ATOM | 2671 | CA | ALA | B | 542 | −69.118 | 80.543 | −36.131 | 1.00 | 144.42 C |
| ATOM | 2672 | CB | ALA | B | 542 | −69.882 | 80.143 | −37.381 | 1.00 | 144.31 C |
| ATOM | 2673 | C | ALA | B | 542 | −69.822 | 81.712 | −35.419 | 1.00 | 144.79 C |
| ATOM | 2674 | O | ALA | B | 542 | −69.664 | 82.863 | −35.843 | 1.00 | 144.89 O |
| ATOM | 2675 | N | GLU | B | 543 | −70.603 | 81.409 | −34.344 | 1.00 | 146.53 N |
| ATOM | 2676 | CA | GLU | B | 543 | −71.364 | 82.347 | −33.488 | 1.00 | 146.91 C |
| ATOM | 2677 | CB | GLU | B | 543 | −70.434 | 83.292 | −32.689 | 1.00 | 146.88 C |
| ATOM | 2678 | CG | GLU | B | 543 | −69.338 | 82.595 | −31.894 | 1.00 | 147.35 C |
| ATOM | 2679 | CD | GLU | B | 543 | −67.935 | 83.145 | −32.090 | 1.00 | 147.98 C |
| ATOM | 2680 | OE1 | GLU | B | 543 | −67.271 | 83.452 | −31.072 | 1.00 | 148.23 O |
| ATOM | 2681 | OE2 | GLU | B | 543 | −67.497 | 83.270 | −33.258 | 1.00 | 148.17 O |
| ATOM | 2682 | C | GLU | B | 543 | −72.480 | 83.137 | −34.206 | 1.00 | 147.16 C |
| ATOM | 2683 | O | GLU | B | 543 | −73.279 | 83.804 | −33.539 | 1.00 | 147.21 O |
| ATOM | 2684 | N | ALA | B | 544 | −72.538 | 83.042 | −35.553 | 1.00 | 149.04 N |
| ATOM | 2685 | CA | ALA | B | 544 | −73.493 | 83.719 | −36.434 | 1.00 | 149.34 C |
| ATOM | 2686 | CB | ALA | B | 544 | −72.873 | 83.882 | −37.817 | 1.00 | 149.30 C |
| ATOM | 2687 | C | ALA | B | 544 | −74.877 | 83.025 | −36.540 | 1.00 | 149.62 C |
| ATOM | 2688 | O | ALA | B | 544 | −75.082 | 81.958 | −35.948 | 1.00 | 149.52 O |
| ATOM | 2689 | N | SER | B | 545 | −75.827 | 83.658 | −37.299 | 1.00 | 151.45 N |
| ATOM | 2690 | CA | SER | B | 545 | −77.200 | 83.181 | −37.566 | 1.00 | 151.69 C |
| ATOM | 2691 | CB | SER | B | 545 | −78.032 | 84.266 | −38.246 | 1.00 | 151.68 C |
| ATOM | 2692 | OG | SER | B | 545 | −78.545 | 85.206 | −37.317 | 1.00 | 151.78 O |

TABLE 14-continued

PCSK9 and AX132 Fab complex x-ray structure

| ATOM | 2693 | C | SER | B | 545 | −77.176 | 81.923 | −38.437 | 1.00 | 151.85 | C |
|---|---|---|---|---|---|---|---|---|---|---|---|
| ATOM | 2694 | O | SER | B | 545 | −78.085 | 81.092 | −38.348 | 1.00 | 151.87 | O |
| ATOM | 2695 | N | MET | B | 546 | −76.114 | 81.791 | −39.272 | 1.00 | 153.34 | N |
| ATOM | 2696 | CA | MET | B | 546 | −75.849 | 80.651 | −40.155 | 1.00 | 153.39 | C |
| ATOM | 2697 | CB | MET | B | 546 | −74.703 | 80.994 | −41.125 | 1.00 | 153.18 | C |
| ATOM | 2698 | C | MET | B | 546 | −75.479 | 79.409 | −39.301 | 1.00 | 153.47 | C |
| ATOM | 2699 | O | MET | B | 546 | −75.531 | 78.278 | −39.800 | 1.00 | 153.61 | O |
| ATOM | 2700 | N | GLY | B | 547 | −75.123 | 79.654 | −38.028 | 1.00 | 153.18 | N |
| ATOM | 2701 | CA | GLY | B | 547 | −74.730 | 78.652 | −37.042 | 1.00 | 152.83 | C |
| ATOM | 2702 | C | GLY | B | 547 | −73.400 | 78.010 | −37.378 | 1.00 | 152.65 | C |
| ATOM | 2703 | O | GLY | B | 547 | −72.613 | 78.582 | −38.144 | 1.00 | 152.76 | O |
| ATOM | 2704 | N | THR | B | 548 | −73.138 | 76.812 | −36.812 | 1.00 | 150.47 | N |
| ATOM | 2705 | CA | THR | B | 548 | −71.906 | 76.068 | −37.091 | 1.00 | 149.88 | C |
| ATOM | 2706 | CB | THR | B | 548 | −71.132 | 75.686 | −35.821 | 1.00 | 149.84 | C |
| ATOM | 2707 | OG1 | THR | B | 548 | −71.382 | 76.632 | −34.786 | 1.00 | 149.65 | O |
| ATOM | 2708 | CG2 | THR | B | 548 | −69.648 | 75.634 | −36.061 | 1.00 | 149.67 | C |
| ATOM | 2709 | C | THR | B | 548 | −72.256 | 74.903 | −38.018 | 1.00 | 149.55 | C |
| ATOM | 2710 | O | THR | B | 548 | −73.048 | 74.028 | −37.651 | 1.00 | 149.53 | O |
| ATOM | 2711 | N | ARG | B | 549 | −71.690 | 74.925 | −39.238 | 1.00 | 147.12 | N |
| ATOM | 2712 | CA | ARG | B | 549 | −71.929 | 73.922 | −40.278 | 1.00 | 146.62 | C |
| ATOM | 2713 | CB | ARG | B | 549 | −72.792 | 74.529 | −41.403 | 1.00 | 146.51 | C |
| ATOM | 2714 | CG | ARG | B | 549 | −74.211 | 74.886 | −40.969 | 1.00 | 146.04 | C |
| ATOM | 2715 | CD | ARG | B | 549 | −74.934 | 75.740 | −41.987 | 1.00 | 145.51 | C |
| ATOM | 2716 | NE | ARG | B | 549 | −76.346 | 75.935 | −41.643 | 1.00 | 144.95 | N |
| ATOM | 2717 | CZ | ARG | B | 549 | −77.362 | 75.291 | −42.217 | 1.00 | 144.63 | C |
| ATOM | 2718 | NH1 | ARG | B | 549 | −77.136 | 74.398 | −43.175 | 1.00 | 144.47 | N |
| ATOM | 2719 | NH2 | ARG | B | 549 | −78.611 | 75.536 | −41.840 | 1.00 | 144.53 | N |
| ATOM | 2720 | C | ARG | B | 549 | −70.622 | 73.340 | −40.844 | 1.00 | 146.42 | C |
| ATOM | 2721 | O | ARG | B | 549 | −69.584 | 74.009 | −40.816 | 1.00 | 146.41 | O |
| ATOM | 2722 | N | VAL | B | 550 | −70.684 | 72.080 | −41.337 | 1.00 | 145.57 | N |
| ATOM | 2723 | CA | VAL | B | 550 | −69.584 | 71.312 | −41.954 | 1.00 | 145.24 | C |
| ATOM | 2724 | CB | VAL | B | 550 | −68.425 | 70.923 | −40.987 | 1.00 | 145.19 | C |
| ATOM | 2725 | CG1 | VAL | B | 550 | −68.861 | 69.903 | −39.940 | 1.00 | 145.05 | C |
| ATOM | 2726 | CG2 | VAL | B | 550 | −67.199 | 70.440 | −41.753 | 1.00 | 145.00 | C |
| ATOM | 2727 | C | VAL | B | 550 | −70.151 | 70.126 | −42.755 | 1.00 | 145.09 | C |
| ATOM | 2728 | O | VAL | B | 550 | −71.102 | 69.486 | −42.295 | 1.00 | 145.05 | O |
| ATOM | 2729 | N | HIS | B | 551 | −69.587 | 69.850 | −43.956 | 1.00 | 145.41 | N |
| ATOM | 2730 | CA | HIS | B | 551 | −70.079 | 68.758 | −44.798 | 1.00 | 145.22 | C |
| ATOM | 2731 | CB | HIS | B | 551 | −71.275 | 69.187 | −45.673 | 1.00 | 145.55 | C |
| ATOM | 2732 | CG | HIS | B | 551 | −70.979 | 70.102 | −46.819 | 1.00 | 146.57 | C |
| ATOM | 2733 | ND1 | HIS | B | 551 | −70.529 | 71.399 | −46.618 | 1.00 | 147.29 | N |
| ATOM | 2734 | CE1 | HIS | B | 551 | −70.406 | 71.925 | −47.826 | 1.00 | 147.67 | C |
| ATOM | 2735 | NE2 | HIS | B | 551 | −70.775 | 71.061 | −48.778 | 1.00 | 147.78 | N |
| ATOM | 2736 | CD2 | HIS | B | 551 | −71.158 | 69.900 | −48.147 | 1.00 | 147.30 | C |
| ATOM | 2737 | C | HIS | B | 551 | −69.075 | 67.895 | −45.558 | 1.00 | 144.66 | C |
| ATOM | 2738 | O | HIS | B | 551 | −67.962 | 68.337 | −45.874 | 1.00 | 144.55 | O |
| ATOM | 2739 | N | CYS | B | 552 | −69.501 | 66.638 | −45.833 | 1.00 | 142.01 | N |
| ATOM | 2740 | CA | CYS | B | 552 | −68.746 | 65.621 | −46.566 | 1.00 | 141.40 | C |
| ATOM | 2741 | CB | CYS | B | 552 | −69.012 | 64.216 | −46.023 | 1.00 | 141.22 | C |
| ATOM | 2742 | SG | CYS | B | 552 | −68.536 | 63.969 | −44.292 | 1.00 | 139.76 | S |
| ATOM | 2743 | C | CYS | B | 552 | −69.128 | 65.732 | −48.037 | 1.00 | 141.30 | C |
| ATOM | 2744 | O | CYS | B | 552 | −70.177 | 65.231 | −48.462 | 1.00 | 141.33 | O |
| ATOM | 2745 | N | HIS | B | 553 | −68.278 | 66.420 | −48.799 | 1.00 | 140.49 | N |
| ATOM | 2746 | CA | HIS | B | 553 | −68.472 | 66.649 | −50.224 | 1.00 | 140.01 | C |
| ATOM | 2747 | CB | HIS | B | 553 | −68.969 | 68.077 | −50.447 | 1.00 | 140.00 | C |
| ATOM | 2748 | C | HIS | B | 553 | −67.175 | 66.373 | −50.985 | 1.00 | 139.66 | C |
| ATOM | 2749 | O | HIS | B | 553 | −66.997 | 66.840 | −52.114 | 1.00 | 139.69 | O |
| ATOM | 2750 | N | GLN | B | 554 | −66.277 | 65.584 | −50.354 | 1.00 | 137.93 | N |
| ATOM | 2751 | CA | GLN | B | 554 | −64.980 | 65.160 | −50.881 | 1.00 | 137.37 | C |
| ATOM | 2752 | CB | GLN | B | 554 | −64.135 | 64.574 | −49.728 | 1.00 | 137.42 | C |
| ATOM | 2753 | CG | GLN | B | 554 | −62.657 | 64.982 | −49.707 | 1.00 | 137.46 | C |
| ATOM | 2754 | CD | GLN | B | 554 | −61.878 | 64.336 | −48.570 | 1.00 | 137.87 | C |
| ATOM | 2755 | OE1 | GLN | B | 554 | −62.354 | 64.218 | −47.431 | 1.00 | 138.13 | O |
| ATOM | 2756 | NE2 | GLN | B | 554 | −60.652 | 63.905 | −48.848 | 1.00 | 137.66 | N |
| ATOM | 2757 | C | GLN | B | 554 | −65.214 | 64.123 | −52.013 | 1.00 | 136.96 | C |
| ATOM | 2758 | O | GLN | B | 554 | −66.355 | 63.942 | −52.465 | 1.00 | 136.89 | O |
| ATOM | 2759 | N | GLN | B | 555 | −64.140 | 63.455 | −52.472 | 1.00 | 136.84 | N |
| ATOM | 2760 | CA | GLN | B | 555 | −64.193 | 62.457 | −53.544 | 1.00 | 136.32 | C |
| ATOM | 2761 | CB | GLN | B | 555 | −62.766 | 62.050 | −53.968 | 1.00 | 136.30 | C |
| ATOM | 2762 | C | GLN | B | 555 | −65.084 | 61.219 | −53.223 | 1.00 | 135.91 | C |
| ATOM | 2763 | O | GLN | B | 555 | −64.559 | 60.153 | −52.872 | 1.00 | 136.01 | O |
| ATOM | 2764 | N | GLY | B | 556 | −66.413 | 61.384 | −53.354 | 1.00 | 133.72 | N |
| ATOM | 2765 | CA | GLY | B | 556 | −67.408 | 60.339 | −53.098 | 1.00 | 132.66 | C |
| ATOM | 2766 | C | GLY | B | 556 | −67.532 | 59.892 | −51.649 | 1.00 | 131.92 | C |
| ATOM | 2767 | O | GLY | B | 556 | −68.062 | 58.806 | −51.374 | 1.00 | 131.89 | O |
| ATOM | 2768 | N | HIS | B | 557 | −67.022 | 60.734 | −50.718 | 1.00 | 130.00 | N |
| ATOM | 2769 | CA | HIS | B | 557 | −67.022 | 60.539 | −49.268 | 1.00 | 129.20 | C |
| ATOM | 2770 | CB | HIS | B | 557 | −66.075 | 61.560 | −48.601 | 1.00 | 129.39 | C |

TABLE 14-continued

| PCSK9 and AX132 Fab complex x-ray structure | | | | | | | | | | |
|---|---|---|---|---|---|---|---|---|---|---|
| ATOM | 2771 | CG | HIS | B | 557 | −64.616 | 61.179 | −48.582 | 1.00 | 130.76 C |
| ATOM | 2772 | ND1 | HIS | B | 557 | −63.909 | 60.921 | −49.757 | 1.00 | 131.87 N |
| ATOM | 2773 | CE1 | HIS | B | 557 | −62.667 | 60.645 | −49.378 | 1.00 | 131.98 C |
| ATOM | 2774 | NE2 | HIS | B | 557 | −62.530 | 60.719 | −48.050 | 1.00 | 132.18 N |
| ATOM | 2775 | CD2 | HIS | B | 557 | −63.762 | 61.075 | −47.531 | 1.00 | 131.65 C |
| ATOM | 2776 | C | HIS | B | 557 | −68.452 | 60.738 | −48.744 | 1.00 | 128.37 C |
| ATOM | 2777 | O | HIS | B | 557 | −69.127 | 61.687 | −49.166 | 1.00 | 128.41 O |
| ATOM | 2778 | N | VAL | B | 558 | −68.922 | 59.845 | −47.833 | 1.00 | 123.42 N |
| ATOM | 2779 | CA | VAL | B | 558 | −70.278 | 59.929 | −47.252 | 1.00 | 122.31 C |
| ATOM | 2780 | CB | VAL | B | 558 | −71.199 | 58.691 | −47.485 | 1.00 | 122.30 C |
| ATOM | 2781 | CG1 | VAL | B | 558 | −72.624 | 59.133 | −47.810 | 1.00 | 122.05 C |
| ATOM | 2782 | CG2 | VAL | B | 558 | −70.663 | 57.762 | −48.573 | 1.00 | 122.17 C |
| ATOM | 2783 | C | VAL | B | 558 | −70.256 | 60.358 | −45.777 | 1.00 | 121.63 C |
| ATOM | 2784 | O | VAL | B | 558 | −69.283 | 60.081 | −45.068 | 1.00 | 121.34 O |
| ATOM | 2785 | N | LEU | B | 559 | −71.327 | 61.051 | −45.332 | 1.00 | 117.23 N |
| ATOM | 2786 | CA | LEU | B | 559 | −71.486 | 61.517 | −43.958 | 1.00 | 116.45 C |
| ATOM | 2787 | CB | LEU | B | 559 | −72.326 | 62.806 | −43.897 | 1.00 | 116.37 C |
| ATOM | 2788 | CG | LEU | B | 559 | −72.570 | 63.383 | −42.503 | 1.00 | 115.80 C |
| ATOM | 2789 | CD1 | LEU | B | 559 | −71.488 | 64.347 | −42.122 | 1.00 | 115.41 C |
| ATOM | 2790 | CD2 | LEU | B | 559 | −73.930 | 64.037 | −42.415 | 1.00 | 115.21 C |
| ATOM | 2791 | C | LEU | B | 559 | −72.162 | 60.397 | −43.186 | 1.00 | 116.11 C |
| ATOM | 2792 | O | LEU | B | 559 | −73.250 | 59.945 | −43.567 | 1.00 | 115.98 O |
| ATOM | 2793 | N | THR | B | 560 | −71.501 | 59.946 | −42.109 | 1.00 | 114.52 N |
| ATOM | 2794 | CA | THR | B | 560 | −71.975 | 58.856 | −41.261 | 1.00 | 114.17 C |
| ATOM | 2795 | CB | THR | B | 560 | −70.936 | 57.742 | −41.193 | 1.00 | 114.04 C |
| ATOM | 2796 | OG1 | THR | B | 560 | −69.707 | 58.299 | −40.747 | 1.00 | 113.63 O |
| ATOM | 2797 | CG2 | THR | B | 560 | −70.738 | 57.039 | −42.529 | 1.00 | 113.63 C |
| ATOM | 2798 | C | THR | B | 560 | −72.408 | 59.303 | −39.877 | 1.00 | 114.27 C |
| ATOM | 2799 | O | THR | B | 560 | −73.401 | 58.785 | −39.366 | 1.00 | 114.13 O |
| ATOM | 2800 | N | GLY | B | 561 | −71.673 | 60.243 | −39.282 | 1.00 | 117.40 N |
| ATOM | 2801 | CA | GLY | B | 561 | −71.985 | 60.734 | −37.945 | 1.00 | 117.64 C |
| ATOM | 2802 | C | GLY | B | 561 | −71.793 | 62.211 | −37.677 | 1.00 | 117.75 C |
| ATOM | 2803 | O | GLY | B | 561 | −70.841 | 62.828 | −38.169 | 1.00 | 117.59 O |
| ATOM | 2804 | N | CYS | B | 562 | −72.706 | 62.763 | −36.849 | 1.00 | 121.48 N |
| ATOM | 2805 | CA | CYS | B | 562 | −72.740 | 64.161 | −36.417 | 1.00 | 121.78 C |
| ATOM | 2806 | CB | CYS | B | 562 | −74.093 | 64.807 | −36.735 | 1.00 | 122.20 C |
| ATOM | 2807 | SG | CYS | B | 562 | −74.284 | 65.432 | −38.438 | 1.00 | 124.74 S |
| ATOM | 2808 | C | CYS | B | 562 | −72.408 | 64.282 | −34.924 | 1.00 | 121.24 C |
| ATOM | 2809 | O | CYS | B | 562 | −73.171 | 63.821 | −34.071 | 1.00 | 121.19 O |
| ATOM | 2810 | N | SER | B | 563 | −71.279 | 64.913 | −34.617 | 1.00 | 117.71 N |
| ATOM | 2811 | CA | SER | B | 563 | −70.834 | 65.153 | −33.246 | 1.00 | 117.39 C |
| ATOM | 2812 | CB | SER | B | 563 | −69.533 | 64.413 | −32.958 | 1.00 | 117.54 C |
| ATOM | 2813 | OG | SER | B | 563 | −69.786 | 63.090 | −32.517 | 1.00 | 117.97 O |
| ATOM | 2814 | C | SER | B | 563 | −70.649 | 66.651 | −33.033 | 1.00 | 116.99 C |
| ATOM | 2815 | O | SER | B | 563 | −70.457 | 67.375 | −34.006 | 1.00 | 116.83 O |
| ATOM | 2816 | N | SER | B | 564 | −70.711 | 67.120 | −31.773 | 1.00 | 114.82 N |
| ATOM | 2817 | CA | SER | B | 564 | −70.551 | 68.535 | −31.436 | 1.00 | 114.48 C |
| ATOM | 2818 | CB | SER | B | 564 | −71.828 | 69.317 | −31.734 | 1.00 | 114.59 C |
| ATOM | 2819 | OG | SER | B | 564 | −71.646 | 70.710 | −31.531 | 1.00 | 114.76 O |
| ATOM | 2820 | C | SER | B | 564 | −70.180 | 68.741 | −29.992 | 1.00 | 114.22 C |
| ATOM | 2821 | O | SER | B | 564 | −70.838 | 68.191 | −29.107 | 1.00 | 114.08 O |
| ATOM | 2822 | N | HIS | B | 565 | −69.151 | 69.574 | −29.749 | 1.00 | 113.98 N |
| ATOM | 2823 | CA | HIS | B | 565 | −68.708 | 69.894 | −28.392 | 1.00 | 113.78 C |
| ATOM | 2824 | CB | HIS | B | 565 | −67.494 | 69.057 | −27.985 | 1.00 | 113.77 C |
| ATOM | 2825 | CG | HIS | B | 565 | −66.183 | 69.733 | −28.190 | 1.00 | 113.56 C |
| ATOM | 2826 | ND1 | HIS | B | 565 | −65.582 | 69.762 | −29.427 | 1.00 | 113.36 N |
| ATOM | 2827 | CE1 | HIS | B | 565 | −64.445 | 70.415 | −29.253 | 1.00 | 113.77 C |
| ATOM | 2828 | NE2 | HIS | B | 565 | −64.295 | 70.814 | −27.985 | 1.00 | 113.71 N |
| ATOM | 2829 | CD2 | HIS | B | 565 | −65.397 | 70.382 | −27.297 | 1.00 | 113.47 C |
| ATOM | 2830 | C | HIS | B | 565 | −68.514 | 71.397 | −28.124 | 1.00 | 113.61 C |
| ATOM | 2831 | O | HIS | B | 565 | −68.098 | 72.138 | −29.014 | 1.00 | 113.77 O |
| ATOM | 2832 | N | TRP | B | 566 | −68.811 | 71.832 | −26.887 | 1.00 | 111.53 N |
| ATOM | 2833 | CA | TRP | B | 566 | −68.699 | 73.226 | −26.459 | 1.00 | 111.30 C |
| ATOM | 2834 | CB | TRP | B | 566 | −70.073 | 73.892 | −26.382 | 1.00 | 110.76 C |
| ATOM | 2835 | CG | TRP | B | 566 | −71.099 | 73.138 | −25.594 | 1.00 | 108.53 C |
| ATOM | 2836 | CD1 | TRP | B | 566 | −71.464 | 73.367 | −24.303 | 1.00 | 107.11 C |
| ATOM | 2837 | NE1 | TRP | B | 566 | −72.470 | 72.505 | −23.934 | 1.00 | 106.14 N |
| ATOM | 2838 | CE2 | TRP | B | 566 | −72.776 | 71.694 | −24.996 | 1.00 | 105.83 C |
| ATOM | 2839 | CD2 | TRP | B | 566 | −71.936 | 72.070 | −26.065 | 1.00 | 106.56 C |
| ATOM | 2840 | CE3 | TRP | B | 566 | −72.043 | 71.377 | −27.284 | 1.00 | 105.74 C |
| ATOM | 2841 | CZ3 | TRP | B | 566 | −72.978 | 70.362 | −27.399 | 1.00 | 104.64 C |
| ATOM | 2842 | CH2 | TRP | B | 566 | −73.805 | 70.015 | −26.323 | 1.00 | 104.70 C |
| ATOM | 2843 | CZ2 | TRP | B | 566 | −73.721 | 70.664 | −25.111 | 1.00 | 105.03 C |
| ATOM | 2844 | C | TRP | B | 566 | −67.886 | 73.431 | −25.176 | 1.00 | 111.98 C |
| ATOM | 2845 | O | TRP | B | 566 | −67.531 | 72.456 | −24.509 | 1.00 | 111.85 O |
| ATOM | 2846 | N | GLU | B | 567 | −67.561 | 74.707 | −24.858 | 1.00 | 114.23 N |
| ATOM | 2847 | CA | GLU | B | 567 | −66.761 | 75.104 | −23.688 | 1.00 | 115.12 C |
| ATOM | 2848 | CB | GLU | B | 567 | −65.441 | 75.762 | −24.139 | 1.00 | 115.08 C |

TABLE 14-continued

PCSK9 and AX132 Fab complex x-ray structure

| ATOM | 2849 | CG  | GLU | B | 567 | −64.472 | 74.828 | −24.866 | 1.00 | 115.87 | C |
|------|------|-----|-----|---|-----|---------|--------|---------|------|--------|---|
| ATOM | 2850 | CD  | GLU | B | 567 | −64.594 | 74.654 | −26.379 | 1.00 | 117.42 | C |
| ATOM | 2851 | OE1 | GLU | B | 567 | −63.621 | 74.151 | −26.991 | 1.00 | 118.08 | O |
| ATOM | 2852 | OE2 | GLU | B | 567 | −65.652 | 75.009 | −26.953 | 1.00 | 117.83 | O |
| ATOM | 2853 | C   | GLU | B | 567 | −67.542 | 75.993 | −22.684 | 1.00 | 115.59 | C |
| ATOM | 2854 | O   | GLU | B | 567 | −67.103 | 76.191 | −21.549 | 1.00 | 115.56 | O |
| ATOM | 2855 | N   | VAL | B | 568 | −68.716 | 76.482 | −23.111 | 1.00 | 117.31 | N |
| ATOM | 2856 | CA  | VAL | B | 568 | −69.635 | 77.344 | −22.368 | 1.00 | 118.32 | C |
| ATOM | 2857 | CB  | VAL | B | 568 | −70.463 | 78.177 | −23.408 | 1.00 | 118.29 | C |
| ATOM | 2858 | CG1 | VAL | B | 568 | −71.539 | 77.344 | −24.110 | 1.00 | 118.30 | C |
| ATOM | 2859 | CG2 | VAL | B | 568 | −71.051 | 79.447 | −22.803 | 1.00 | 118.56 | C |
| ATOM | 2860 | C   | VAL | B | 568 | −70.501 | 76.567 | −21.313 | 1.00 | 119.01 | C |
| ATOM | 2861 | O   | VAL | B | 568 | −70.265 | 75.385 | −21.061 | 1.00 | 119.09 | O |
| ATOM | 2862 | N   | GLU | B | 569 | −71.477 | 77.251 | −20.693 | 1.00 | 122.68 | N |
| ATOM | 2863 | CA  | GLU | B | 569 | −72.409 | 76.693 | −19.717 | 1.00 | 123.60 | C |
| ATOM | 2864 | CB  | GLU | B | 569 | −72.467 | 77.576 | −18.453 | 1.00 | 123.70 | C |
| ATOM | 2865 | CG  | GLU | B | 569 | −73.180 | 76.948 | −17.254 | 1.00 | 124.32 | C |
| ATOM | 2866 | CD  | GLU | B | 569 | −74.701 | 77.019 | −17.209 | 1.00 | 125.29 | C |
| ATOM | 2867 | OE1 | GLU | B | 569 | −75.277 | 78.004 | −17.728 | 1.00 | 125.60 | O |
| ATOM | 2868 | OE2 | GLU | B | 569 | −75.319 | 76.086 | −16.644 | 1.00 | 125.58 | O |
| ATOM | 2869 | C   | GLU | B | 569 | −73.802 | 76.581 | −20.364 | 1.00 | 124.11 | C |
| ATOM | 2870 | O   | GLU | B | 569 | −74.515 | 75.611 | −20.085 | 1.00 | 124.23 | O |
| ATOM | 2871 | N   | ASP | B | 570 | −74.194 | 77.564 | −21.219 | 1.00 | 125.99 | N |
| ATOM | 2872 | CA  | ASP | B | 570 | −75.518 | 77.548 | −21.864 | 1.00 | 126.58 | C |
| ATOM | 2873 | CB  | ASP | B | 570 | −76.498 | 78.498 | −21.136 | 1.00 | 126.73 | C |
| ATOM | 2874 | CG  | ASP | B | 570 | −77.684 | 77.795 | −20.486 | 1.00 | 127.25 | C |
| ATOM | 2875 | OD1 | ASP | B | 570 | −77.472 | 77.067 | −19.479 | 1.00 | 127.50 | O |
| ATOM | 2876 | OD2 | ASP | B | 570 | −78.825 | 77.974 | −20.980 | 1.00 | 127.65 | O |
| ATOM | 2877 | C   | ASP | B | 570 | −75.590 | 77.646 | −23.424 | 1.00 | 126.73 | C |
| ATOM | 2878 | O   | ASP | B | 570 | −74.856 | 76.924 | −24.118 | 1.00 | 126.77 | O |
| ATOM | 2879 | N   | LEU | B | 571 | −76.516 | 78.506 | −23.954 | 1.00 | 124.61 | N |
| ATOM | 2880 | CA  | LEU | B | 571 | −76.769 | 78.734 | −25.387 | 1.00 | 124.78 | C |
| ATOM | 2881 | CB  | LEU | B | 571 | −77.398 | 77.485 | −26.034 | 1.00 | 124.75 | C |
| ATOM | 2882 | C   | LEU | B | 571 | −77.608 | 80.015 | −25.697 | 1.00 | 124.83 | C |
| ATOM | 2883 | O   | LEU | B | 571 | −77.023 | 81.037 | −26.069 | 1.00 | 125.00 | O |
| ATOM | 2884 | N   | GLY | B | 572 | −78.945 | 79.933 | −25.562 | 1.00 | 119.93 | N |
| ATOM | 2885 | CA  | GLY | B | 572 | −79.876 | 81.033 | −25.819 | 1.00 | 119.70 | C |
| ATOM | 2886 | C   | GLY | B | 572 | −80.172 | 81.292 | −27.285 | 1.00 | 119.66 | C |
| ATOM | 2887 | O   | GLY | B | 572 | −81.252 | 81.776 | −27.636 | 1.00 | 119.48 | O |
| ATOM | 2888 | N   | GLN | B | 584 | −78.485 | 72.651 | −48.615 | 1.00 | 150.06 | N |
| ATOM | 2889 | CA  | GLN | B | 584 | −77.758 | 72.137 | −47.448 | 1.00 | 150.10 | C |
| ATOM | 2890 | CB  | GLN | B | 584 | −78.497 | 72.514 | −46.135 | 1.00 | 150.24 | C |
| ATOM | 2891 | CG  | GLN | B | 584 | −79.016 | 73.963 | −46.047 | 1.00 | 150.44 | C |
| ATOM | 2892 | CD  | GLN | B | 584 | −80.441 | 74.074 | −45.527 | 1.00 | 150.94 | C |
| ATOM | 2893 | OE1 | GLN | B | 584 | −80.989 | 73.160 | −44.898 | 1.00 | 151.33 | O |
| ATOM | 2894 | NE2 | GLN | B | 584 | −81.078 | 75.207 | −45.777 | 1.00 | 150.78 | N |
| ATOM | 2895 | C   | GLN | B | 584 | −77.532 | 70.583 | −47.559 | 1.00 | 149.91 | C |
| ATOM | 2896 | O   | GLN | B | 584 | −78.009 | 69.837 | −46.690 | 1.00 | 149.95 | O |
| ATOM | 2897 | N   | PRO | B | 585 | −76.804 | 70.067 | −48.596 | 1.00 | 147.52 | N |
| ATOM | 2898 | CA  | PRO | B | 585 | −76.641 | 68.600 | −48.725 | 1.00 | 147.11 | C |
| ATOM | 2899 | CB  | PRO | B | 585 | −76.683 | 68.379 | −50.247 | 1.00 | 147.20 | C |
| ATOM | 2900 | CG  | PRO | B | 585 | −76.395 | 69.773 | −50.875 | 1.00 | 147.42 | C |
| ATOM | 2901 | CD  | PRO | B | 585 | −76.181 | 70.757 | −49.746 | 1.00 | 147.59 | C |
| ATOM | 2902 | C   | PRO | B | 585 | −75.394 | 67.962 | −48.090 | 1.00 | 146.51 | C |
| ATOM | 2903 | O   | PRO | B | 585 | −74.286 | 68.507 | −48.215 | 1.00 | 146.59 | O |
| ATOM | 2904 | N   | ASN | B | 586 | −75.584 | 66.773 | −47.437 | 1.00 | 140.53 | N |
| ATOM | 2905 | CA  | ASN | B | 586 | −74.557 | 65.960 | −46.745 | 1.00 | 139.64 | C |
| ATOM | 2906 | CB  | ASN | B | 586 | −73.540 | 65.361 | −47.762 | 1.00 | 139.67 | C |
| ATOM | 2907 | CG  | ASN | B | 586 | −73.382 | 63.848 | −47.758 | 1.00 | 139.54 | C |
| ATOM | 2908 | OD1 | ASN | B | 586 | −72.264 | 63.324 | −47.760 | 1.00 | 139.19 | O |
| ATOM | 2909 | ND2 | ASN | B | 586 | −74.483 | 63.103 | −47.775 | 1.00 | 139.50 | N |
| ATOM | 2910 | C   | ASN | B | 586 | −73.854 | 66.757 | −45.611 | 1.00 | 139.03 | C |
| ATOM | 2911 | O   | ASN | B | 586 | −72.642 | 66.614 | −45.420 | 1.00 | 138.94 | O |
| ATOM | 2912 | N   | GLN | B | 587 | −74.640 | 67.573 | −44.850 | 1.00 | 133.89 | N |
| ATOM | 2913 | CA  | GLN | B | 587 | −74.172 | 68.457 | −43.772 | 1.00 | 133.19 | C |
| ATOM | 2914 | CB  | GLN | B | 587 | −74.544 | 69.920 | −44.107 | 1.00 | 133.41 | C |
| ATOM | 2915 | CG  | GLN | B | 587 | −73.611 | 70.981 | −43.503 | 1.00 | 134.10 | C |
| ATOM | 2916 | CD  | GLN | B | 587 | −73.858 | 72.385 | −44.004 | 1.00 | 135.07 | C |
| ATOM | 2917 | OE1 | GLN | B | 587 | −74.969 | 72.928 | −43.898 | 1.00 | 135.42 | O |
| ATOM | 2918 | NE2 | GLN | B | 587 | −72.812 | 73.011 | −44.542 | 1.00 | 135.30 | N |
| ATOM | 2919 | C   | GLN | B | 587 | −74.564 | 68.125 | −42.319 | 1.00 | 132.46 | C |
| ATOM | 2920 | O   | GLN | B | 587 | −75.651 | 67.611 | −42.038 | 1.00 | 132.24 | O |
| ATOM | 2921 | N   | CYS | B | 588 | −73.642 | 68.469 | −41.404 | 1.00 | 127.56 | N |
| ATOM | 2922 | CA  | CYS | B | 588 | −73.739 | 68.333 | −39.955 | 1.00 | 126.80 | C |
| ATOM | 2923 | CB  | CYS | B | 588 | −72.441 | 67.765 | −39.381 | 1.00 | 126.59 | C |
| ATOM | 2924 | SG  | CYS | B | 588 | −72.434 | 65.971 | −39.116 | 1.00 | 125.32 | S |
| ATOM | 2925 | C   | CYS | B | 588 | −73.998 | 69.737 | −39.413 | 1.00 | 126.66 | C |
| ATOM | 2926 | O   | CYS | B | 588 | −73.106 | 70.597 | −39.478 | 1.00 | 126.58 | O |

TABLE 14-continued

PCSK9 and AX132 Fab complex x-ray structure

| ATOM | 2927 | N | VAL | B | 589 | −75.203 | 69.979 | −38.882 | 1.00 | 125.88 | N |
|---|---|---|---|---|---|---|---|---|---|---|---|
| ATOM | 2928 | CA | VAL | B | 589 | −75.524 | 71.301 | −38.350 | 1.00 | 125.64 | C |
| ATOM | 2929 | CB | VAL | B | 589 | −76.688 | 71.994 | −39.099 | 1.00 | 125.70 | C |
| ATOM | 2930 | CG1 | VAL | B | 589 | −76.844 | 73.445 | −38.646 | 1.00 | 125.90 | C |
| ATOM | 2931 | CG2 | VAL | B | 589 | −76.497 | 71.921 | −40.615 | 1.00 | 125.82 | C |
| ATOM | 2932 | C | VAL | B | 589 | −75.699 | 71.334 | −36.832 | 1.00 | 125.41 | C |
| ATOM | 2933 | O | VAL | B | 589 | −76.718 | 70.880 | −36.312 | 1.00 | 125.19 | O |
| ATOM | 2934 | N | GLY | B | 590 | −74.703 | 71.898 | −36.154 | 1.00 | 127.02 | N |
| ATOM | 2935 | CA | GLY | B | 590 | −74.688 | 72.066 | −34.705 | 1.00 | 126.97 | C |
| ATOM | 2936 | C | GLY | B | 590 | −74.906 | 73.513 | −34.301 | 1.00 | 126.94 | C |
| ATOM | 2937 | O | GLY | B | 590 | −74.917 | 74.401 | −35.162 | 1.00 | 126.90 | O |
| ATOM | 2938 | N | HIS | B | 591 | −75.077 | 73.763 | −32.980 | 1.00 | 128.31 | N |
| ATOM | 2939 | CA | HIS | B | 591 | −75.290 | 75.093 | −32.382 | 1.00 | 128.33 | C |
| ATOM | 2940 | CB | HIS | B | 591 | −75.465 | 74.964 | −30.851 | 1.00 | 128.36 | C |
| ATOM | 2941 | CG | HIS | B | 591 | −75.848 | 76.229 | −30.138 | 1.00 | 128.50 | C |
| ATOM | 2942 | ND1 | HIS | B | 591 | −74.894 | 77.149 | −29.728 | 1.00 | 128.48 | N |
| ATOM | 2943 | CE1 | HIS | B | 591 | −75.564 | 78.124 | −29.135 | 1.00 | 128.57 | C |
| ATOM | 2944 | NE2 | HIS | B | 591 | −76.874 | 77.883 | −29.131 | 1.00 | 128.60 | N |
| ATOM | 2945 | CD2 | HIS | B | 591 | −77.068 | 76.670 | −29.754 | 1.00 | 128.45 | C |
| ATOM | 2946 | C | HIS | B | 591 | −74.140 | 76.070 | −32.735 | 1.00 | 128.35 | C |
| ATOM | 2947 | O | HIS | B | 591 | −72.996 | 75.638 | −32.916 | 1.00 | 128.27 | O |
| ATOM | 2948 | N | ARG | B | 592 | −74.464 | 77.382 | −32.845 | 1.00 | 130.35 | N |
| ATOM | 2949 | CA | ARG | B | 592 | −73.526 | 78.465 | −33.174 | 1.00 | 130.16 | C |
| ATOM | 2950 | CB | ARG | B | 592 | −74.251 | 79.820 | −33.346 | 1.00 | 130.23 | C |
| ATOM | 2951 | CG | ARG | B | 592 | −75.283 | 80.125 | −32.268 | 1.00 | 130.52 | C |
| ATOM | 2952 | CD | ARG | B | 592 | −75.698 | 81.590 | −32.219 | 1.00 | 131.28 | C |
| ATOM | 2953 | NE | ARG | B | 592 | −76.802 | 81.788 | −31.269 | 1.00 | 131.92 | N |
| ATOM | 2954 | CZ | ARG | B | 592 | −76.657 | 82.148 | −29.993 | 1.00 | 131.97 | C |
| ATOM | 2955 | NH1 | ARG | B | 592 | −75.446 | 82.385 | −29.494 | 1.00 | 131.94 | N |
| ATOM | 2956 | NH2 | ARG | B | 592 | −77.723 | 82.283 | −29.209 | 1.00 | 131.77 | N |
| ATOM | 2957 | C | ARG | B | 592 | −72.293 | 78.564 | −32.238 | 1.00 | 129.90 | C |
| ATOM | 2958 | O | ARG | B | 592 | −71.166 | 78.662 | −32.736 | 1.00 | 129.80 | O |
| ATOM | 2959 | N | GLU | B | 593 | −72.513 | 78.509 | −30.898 | 1.00 | 127.81 | N |
| ATOM | 2960 | CA | GLU | B | 593 | −71.474 | 78.591 | −29.854 | 1.00 | 127.53 | C |
| ATOM | 2961 | CB | GLU | B | 593 | −72.107 | 78.883 | −28.475 | 1.00 | 127.55 | C |
| ATOM | 2962 | CG | GLU | B | 593 | −72.567 | 80.316 | −28.243 | 1.00 | 127.44 | C |
| ATOM | 2963 | CD | GLU | B | 593 | −72.865 | 80.663 | −26.791 | 1.00 | 127.43 | C |
| ATOM | 2964 | OE1 | GLU | B | 593 | −74.035 | 80.521 | −26.362 | 1.00 | 127.08 | O |
| ATOM | 2965 | OE2 | GLU | B | 593 | −71.921 | 81.080 | −26.081 | 1.00 | 127.50 | O |
| ATOM | 2966 | C | GLU | B | 593 | −70.550 | 77.346 | −29.750 | 1.00 | 127.34 | C |
| ATOM | 2967 | O | GLU | B | 593 | −69.465 | 77.438 | −29.160 | 1.00 | 127.36 | O |
| ATOM | 2968 | N | ALA | B | 594 | −70.987 | 76.191 | −30.309 | 1.00 | 125.85 | N |
| ATOM | 2969 | CA | ALA | B | 594 | −70.270 | 74.904 | −30.279 | 1.00 | 125.30 | C |
| ATOM | 2970 | CB | ALA | B | 594 | −71.239 | 73.797 | −29.915 | 1.00 | 125.28 | C |
| ATOM | 2971 | C | ALA | B | 594 | −69.558 | 74.534 | −31.580 | 1.00 | 124.94 | C |
| ATOM | 2972 | O | ALA | B | 594 | −70.001 | 74.939 | −32.656 | 1.00 | 124.87 | O |
| ATOM | 2973 | N | SER | B | 595 | −68.465 | 73.739 | −31.475 | 1.00 | 122.91 | N |
| ATOM | 2974 | CA | SER | B | 595 | −67.691 | 73.248 | −32.625 | 1.00 | 122.59 | C |
| ATOM | 2975 | CB | SER | B | 595 | −66.283 | 72.828 | −32.211 | 1.00 | 122.36 | C |
| ATOM | 2976 | OG | SER | B | 595 | −65.804 | 73.570 | −31.103 | 1.00 | 122.18 | O |
| ATOM | 2977 | C | SER | B | 595 | −68.431 | 72.034 | −33.200 | 1.00 | 122.55 | C |
| ATOM | 2978 | O | SER | B | 595 | −68.960 | 71.224 | −32.432 | 1.00 | 122.50 | O |
| ATOM | 2979 | N | ILE | B | 596 | −68.489 | 71.920 | −34.541 | 1.00 | 122.51 | N |
| ATOM | 2980 | CA | ILE | B | 596 | −69.152 | 70.812 | −35.234 | 1.00 | 122.52 | C |
| ATOM | 2981 | CB | ILE | B | 596 | −70.392 | 71.213 | −36.108 | 1.00 | 122.49 | C |
| ATOM | 2982 | CG1 | ILE | B | 596 | −71.112 | 69.996 | −36.722 | 1.00 | 122.49 | C |
| ATOM | 2983 | CD1 | ILE | B | 596 | −72.218 | 69.408 | −35.909 | 1.00 | 122.57 | C |
| ATOM | 2984 | CG2 | ILE | B | 596 | −70.043 | 72.208 | −37.194 | 1.00 | 122.93 | C |
| ATOM | 2985 | C | ILE | B | 596 | −68.140 | 69.889 | −35.916 | 1.00 | 122.55 | C |
| ATOM | 2986 | O | ILE | B | 596 | −67.267 | 70.340 | −36.662 | 1.00 | 122.43 | O |
| ATOM | 2987 | N | HIS | B | 597 | −68.254 | 68.592 | −35.601 | 1.00 | 123.80 | N |
| ATOM | 2988 | CA | HIS | B | 597 | −67.429 | 67.504 | −36.118 | 1.00 | 123.82 | C |
| ATOM | 2989 | CB | HIS | B | 597 | −66.876 | 66.643 | −34.975 | 1.00 | 123.73 | C |
| ATOM | 2990 | CG | HIS | B | 597 | −66.178 | 67.399 | −33.892 | 1.00 | 123.54 | C |
| ATOM | 2991 | ND1 | HIS | B | 597 | −64.810 | 67.319 | −33.731 | 1.00 | 123.54 | N |
| ATOM | 2992 | CE1 | HIS | B | 597 | −64.529 | 68.074 | −32.682 | 1.00 | 123.72 | C |
| ATOM | 2993 | NE2 | HIS | B | 597 | −65.631 | 68.621 | −32.165 | 1.00 | 123.77 | N |
| ATOM | 2994 | CD2 | HIS | B | 597 | −66.689 | 68.189 | −32.919 | 1.00 | 123.49 | C |
| ATOM | 2995 | C | HIS | B | 597 | −68.322 | 66.643 | −37.008 | 1.00 | 123.91 | C |
| ATOM | 2996 | O | HIS | B | 597 | −69.529 | 66.534 | −36.760 | 1.00 | 123.96 | O |
| ATOM | 2997 | N | ALA | B | 598 | −67.737 | 66.040 | −38.043 | 1.00 | 126.34 | N |
| ATOM | 2998 | CA | ALA | B | 598 | −68.474 | 65.191 | −38.969 | 1.00 | 126.61 | C |
| ATOM | 2999 | CB | ALA | B | 598 | −68.871 | 65.991 | −40.196 | 1.00 | 126.45 | C |
| ATOM | 3000 | C | ALA | B | 598 | −67.612 | 64.022 | −39.379 | 1.00 | 126.91 | C |
| ATOM | 3001 | O | ALA | B | 598 | −66.396 | 64.193 | −39.509 | 1.00 | 126.98 | O |
| ATOM | 3002 | N | SER | B | 599 | −68.216 | 62.835 | −39.584 | 1.00 | 130.56 | N |
| ATOM | 3003 | CA | SER | B | 599 | −67.431 | 61.686 | −40.022 | 1.00 | 130.97 | C |
| ATOM | 3004 | CB | SER | B | 599 | −67.738 | 60.438 | −39.210 | 1.00 | 131.14 | C |

TABLE 14-continued

PCSK9 and AX132 Fab complex x-ray structure

| ATOM | 3005 | OG | SER | B | 599 | −66.822 | 59.400 | −39.528 | 1.00 | 132.04 | O |
|------|------|------|-----|---|-----|---------|--------|---------|------|--------|---|
| ATOM | 3006 | C | SER | B | 599 | −67.633 | 61.448 | −41.505 | 1.00 | 131.08 | C |
| ATOM | 3007 | O | SER | B | 599 | −68.756 | 61.189 | −41.947 | 1.00 | 130.93 | O |
| ATOM | 3008 | N | CYS | B | 600 | −66.536 | 61.585 | −42.275 | 1.00 | 136.15 | N |
| ATOM | 3009 | CA | CYS | B | 600 | −66.507 | 61.421 | −43.728 | 1.00 | 136.70 | C |
| ATOM | 3010 | CB | CYS | B | 600 | −65.754 | 62.571 | −44.403 | 1.00 | 137.12 | C |
| ATOM | 3011 | SG | CYS | B | 600 | −66.513 | 64.211 | −44.198 | 1.00 | 139.29 | S |
| ATOM | 3012 | C | CYS | B | 600 | −65.893 | 60.079 | −44.067 | 1.00 | 136.36 | C |
| ATOM | 3013 | O | CYS | B | 600 | −64.730 | 59.836 | −43.734 | 1.00 | 136.42 | O |
| ATOM | 3014 | N | CYS | B | 601 | −66.665 | 59.207 | −44.720 | 1.00 | 136.31 | N |
| ATOM | 3015 | CA | CYS | B | 601 | −66.163 | 57.888 | −45.071 | 1.00 | 136.05 | C |
| ATOM | 3016 | CB | CYS | B | 601 | −66.877 | 56.799 | −44.274 | 1.00 | 135.96 | C |
| ATOM | 3017 | SG | CYS | B | 601 | −66.493 | 56.808 | −42.505 | 1.00 | 135.19 | S |
| ATOM | 3018 | C | CYS | B | 601 | −66.175 | 57.599 | −46.557 | 1.00 | 136.06 | C |
| ATOM | 3019 | O | CYS | B | 601 | −67.227 | 57.682 | −47.201 | 1.00 | 136.04 | O |
| ATOM | 3020 | N | HIS | B | 602 | −64.999 | 57.250 | −47.104 | 1.00 | 139.94 | N |
| ATOM | 3021 | CA | HIS | B | 602 | −64.915 | 56.900 | −48.510 | 1.00 | 139.95 | C |
| ATOM | 3022 | CB | HIS | B | 602 | −63.577 | 57.301 | −49.168 | 1.00 | 140.20 | C |
| ATOM | 3023 | CG | HIS | B | 602 | −63.501 | 56.998 | −50.648 | 1.00 | 141.34 | C |
| ATOM | 3024 | ND1 | HIS | B | 602 | −64.637 | 57.006 | −51.463 | 1.00 | 142.03 | N |
| ATOM | 3025 | CE1 | HIS | B | 602 | −64.212 | 56.698 | −52.679 | 1.00 | 142.05 | C |
| ATOM | 3026 | NE2 | HIS | B | 602 | −62.890 | 56.501 | −52.703 | 1.00 | 142.35 | N |
| ATOM | 3027 | CD2 | HIS | B | 602 | −62.425 | 56.689 | −51.413 | 1.00 | 142.20 | C |
| ATOM | 3028 | C | HIS | B | 602 | −65.202 | 55.412 | −48.652 | 1.00 | 139.62 | C |
| ATOM | 3029 | O | HIS | B | 602 | −64.468 | 54.562 | −48.125 | 1.00 | 139.50 | O |
| ATOM | 3030 | N | ALA | B | 603 | −66.317 | 55.124 | −49.341 | 1.00 | 139.92 | N |
| ATOM | 3031 | CA | ALA | B | 603 | −66.846 | 53.804 | −49.666 | 1.00 | 139.45 | C |
| ATOM | 3032 | CB | ALA | B | 603 | −67.448 | 53.142 | −48.433 | 1.00 | 139.37 | C |
| ATOM | 3033 | C | ALA | B | 603 | −67.911 | 54.017 | −50.764 | 1.00 | 139.05 | C |
| ATOM | 3034 | O | ALA | B | 603 | −69.043 | 54.427 | −50.468 | 1.00 | 139.15 | O |
| ATOM | 3035 | N | PRO | B | 604 | −67.543 | 53.796 | −52.055 | 1.00 | 138.26 | N |
| ATOM | 3036 | CA | PRO | B | 604 | −68.514 | 54.008 | −53.149 | 1.00 | 137.56 | C |
| ATOM | 3037 | CB | PRO | B | 604 | −67.654 | 53.930 | −54.425 | 1.00 | 137.66 | C |
| ATOM | 3038 | CG | PRO | B | 604 | −66.209 | 53.965 | −53.954 | 1.00 | 137.98 | C |
| ATOM | 3039 | CD | PRO | B | 604 | −66.241 | 53.345 | −52.586 | 1.00 | 138.32 | C |
| ATOM | 3040 | C | PRO | B | 604 | −69.671 | 53.007 | −53.167 | 1.00 | 136.75 | C |
| ATOM | 3041 | O | PRO | B | 604 | −70.647 | 53.224 | −53.896 | 1.00 | 136.87 | O |
| ATOM | 3042 | N | GLY | B | 605 | −69.552 | 51.938 | −52.370 | 1.00 | 132.29 | N |
| ATOM | 3043 | CA | GLY | B | 605 | −70.575 | 50.907 | −52.240 | 1.00 | 130.75 | C |
| ATOM | 3044 | C | GLY | B | 605 | −71.601 | 51.257 | −51.180 | 1.00 | 129.57 | C |
| ATOM | 3045 | O | GLY | B | 605 | −72.657 | 50.619 | −51.101 | 1.00 | 129.70 | O |
| ATOM | 3046 | N | LEU | B | 606 | −71.288 | 52.296 | −50.365 | 1.00 | 124.93 | N |
| ATOM | 3047 | CA | LEU | B | 606 | −72.087 | 52.803 | −49.246 | 1.00 | 123.32 | C |
| ATOM | 3048 | CB | LEU | B | 606 | −71.135 | 53.282 | −48.127 | 1.00 | 123.34 | C |
| ATOM | 3049 | CG | LEU | B | 606 | −71.403 | 52.923 | −46.648 | 1.00 | 123.22 | C |
| ATOM | 3050 | CD1 | LEU | B | 606 | −71.064 | 54.097 | −45.742 | 1.00 | 122.43 | C |
| ATOM | 3051 | CD2 | LEU | B | 606 | −72.825 | 52.421 | −46.395 | 1.00 | 123.19 | C |
| ATOM | 3052 | C | LEU | B | 606 | −72.996 | 53.963 | −49.617 | 1.00 | 122.22 | C |
| ATOM | 3053 | O | LEU | B | 606 | −72.507 | 54.983 | −50.120 | 1.00 | 122.10 | O |
| ATOM | 3054 | N | GLU | B | 607 | −74.310 | 53.820 | −49.322 | 1.00 | 118.39 | N |
| ATOM | 3055 | CA | GLU | B | 607 | −75.315 | 54.853 | −49.553 | 1.00 | 116.97 | C |
| ATOM | 3056 | CB | GLU | B | 607 | −76.260 | 54.530 | −50.732 | 1.00 | 116.99 | C |
| ATOM | 3057 | CG | GLU | B | 607 | −77.272 | 53.410 | −50.532 | 1.00 | 117.68 | C |
| ATOM | 3058 | CD | GLU | B | 607 | −78.624 | 53.643 | −51.193 | 1.00 | 118.47 | C |
| ATOM | 3059 | OE1 | GLU | B | 607 | −79.321 | 52.643 | −51.483 | 1.00 | 118.49 | O |
| ATOM | 3060 | OE2 | GLU | B | 607 | −78.992 | 54.821 | −51.417 | 1.00 | 118.52 | O |
| ATOM | 3061 | C | GLU | B | 607 | −76.030 | 55.270 | −48.246 | 1.00 | 115.91 | C |
| ATOM | 3062 | O | GLU | B | 607 | −76.739 | 54.465 | −47.637 | 1.00 | 116.06 | O |
| ATOM | 3063 | N | CYS | B | 608 | −75.802 | 56.530 | −47.807 | 1.00 | 112.37 | N |
| ATOM | 3064 | CA | CYS | B | 608 | −76.366 | 57.102 | −46.574 | 1.00 | 110.58 | C |
| ATOM | 3065 | CB | CYS | B | 608 | −75.259 | 57.654 | −45.681 | 1.00 | 110.79 | C |
| ATOM | 3066 | SG | CYS | B | 608 | −74.059 | 56.409 | −45.131 | 1.00 | 112.17 | S |
| ATOM | 3067 | C | CYS | B | 608 | −77.498 | 58.127 | −46.762 | 1.00 | 108.94 | C |
| ATOM | 3068 | O | CYS | B | 608 | −77.508 | 58.886 | −47.732 | 1.00 | 108.93 | O |
| ATOM | 3069 | N | LYS | B | 609 | −78.442 | 58.147 | −45.816 | 1.00 | 100.85 | N |
| ATOM | 3070 | CA | LYS | B | 609 | −79.581 | 59.057 | −45.811 | 1.00 | 98.69 | C |
| ATOM | 3071 | CB | LYS | B | 609 | −80.818 | 58.412 | −46.448 | 1.00 | 98.51 | C |
| ATOM | 3072 | CG | LYS | B | 609 | −81.449 | 57.310 | −45.646 | 1.00 | 97.62 | C |
| ATOM | 3073 | CD | LYS | B | 609 | −82.927 | 57.350 | −45.822 | 1.00 | 97.09 | C |
| ATOM | 3074 | CE | LYS | B | 609 | −83.510 | 55.972 | −45.802 | 1.00 | 97.54 | C |
| ATOM | 3075 | NZ | LYS | B | 609 | −84.954 | 56.009 | −46.121 | 1.00 | 98.08 | N |
| ATOM | 3076 | C | LYS | B | 609 | −79.857 | 59.592 | −44.402 | 1.00 | 97.61 | C |
| ATOM | 3077 | O | LYS | B | 609 | −79.117 | 59.264 | −43.477 | 1.00 | 97.62 | O |
| ATOM | 3078 | N | VAL | B | 610 | −80.895 | 60.441 | −44.239 | 1.00 | 95.01 | N |
| ATOM | 3079 | CA | VAL | B | 610 | −81.250 | 61.021 | −42.937 | 1.00 | 93.13 | C |
| ATOM | 3080 | CB | VAL | B | 610 | −80.857 | 62.524 | −42.796 | 1.00 | 92.98 | C |
| ATOM | 3081 | CG1 | VAL | B | 610 | −81.313 | 63.089 | −41.457 | 1.00 | 92.75 | C |
| ATOM | 3082 | CG2 | VAL | B | 610 | −79.350 | 62.739 | −42.970 | 1.00 | 92.08 | C |

TABLE 14-continued

PCSK9 and AX132 Fab complex x-ray structure

| ATOM | 3083 | C | VAL | B | 610 | −82.722 | 60.786 | −42.671 | 1.00 | 92.11 | C |
|---|---|---|---|---|---|---|---|---|---|---|---|
| ATOM | 3084 | O | VAL | B | 610 | −83.506 | 60.775 | −43.609 | 1.00 | 92.08 | O |
| ATOM | 3085 | N | LYS | B | 611 | −83.083 | 60.557 | −41.404 | 1.00 | 91.38 | N |
| ATOM | 3086 | CA | LYS | B | 611 | −84.454 | 60.370 | −40.941 | 1.00 | 90.39 | C |
| ATOM | 3087 | CB | LYS | B | 611 | −84.782 | 58.907 | −40.668 | 1.00 | 90.56 | C |
| ATOM | 3088 | CG | LYS | B | 611 | −86.289 | 58.613 | −40.749 | 1.00 | 91.05 | C |
| ATOM | 3089 | CD | LYS | B | 611 | −86.626 | 57.145 | −41.098 | 1.00 | 92.07 | C |
| ATOM | 3090 | CE | LYS | B | 611 | −86.088 | 56.691 | −42.456 | 1.00 | 92.88 | C |
| ATOM | 3091 | NZ | LYS | B | 611 | −86.867 | 57.237 | −43.622 | 1.00 | 93.51 | N |
| ATOM | 3092 | C | LYS | B | 611 | −84.597 | 61.214 | −39.687 | 1.00 | 89.60 | C |
| ATOM | 3093 | O | LYS | B | 611 | −83.626 | 61.343 | −38.933 | 1.00 | 89.74 | O |
| ATOM | 3094 | N | GLU | B | 612 | −85.772 | 61.833 | −39.483 | 1.00 | 87.15 | N |
| ATOM | 3095 | CA | GLU | B | 612 | −86.002 | 62.705 | −38.337 | 1.00 | 86.15 | C |
| ATOM | 3096 | CB | GLU | B | 612 | −85.823 | 64.171 | −38.749 | 1.00 | 86.59 | C |
| ATOM | 3097 | CG | GLU | B | 612 | −84.395 | 64.674 | −38.837 | 1.00 | 88.33 | C |
| ATOM | 3098 | CD | GLU | B | 612 | −84.229 | 66.187 | −38.948 | 1.00 | 90.95 | C |
| ATOM | 3099 | OE1 | GLU | B | 612 | −85.200 | 66.927 | −38.645 | 1.00 | 91.46 | O |
| ATOM | 3100 | OE2 | GLU | B | 612 | −83.120 | 66.633 | −39.340 | 1.00 | 92.27 | O |
| ATOM | 3101 | C | GLU | B | 612 | −87.386 | 62.586 | −37.773 | 1.00 | 84.94 | C |
| ATOM | 3102 | O | GLU | B | 612 | −88.346 | 62.351 | −38.505 | 1.00 | 85.08 | O |
| ATOM | 3103 | N | HIS | B | 613 | −87.510 | 62.805 | −36.478 | 1.00 | 80.41 | N |
| ATOM | 3104 | CA | HIS | B | 613 | −88.797 | 62.818 | −35.798 | 1.00 | 79.40 | C |
| ATOM | 3105 | CB | HIS | B | 613 | −89.366 | 61.441 | −35.482 | 1.00 | 78.55 | C |
| ATOM | 3106 | CG | HIS | B | 613 | −90.704 | 61.500 | −34.811 | 1.00 | 76.10 | C |
| ATOM | 3107 | ND1 | HIS | B | 613 | −90.843 | 61.259 | −33.460 | 1.00 | 74.15 | N |
| ATOM | 3108 | CE1 | HIS | B | 613 | −92.141 | 61.369 | −33.200 | 1.00 | 72.72 | C |
| ATOM | 3109 | NE2 | HIS | B | 613 | −92.832 | 61.678 | −34.297 | 1.00 | 72.67 | N |
| ATOM | 3110 | CD2 | HIS | B | 613 | −91.926 | 61.770 | −35.332 | 1.00 | 73.99 | C |
| ATOM | 3111 | C | HIS | B | 613 | −88.613 | 63.585 | −34.552 | 1.00 | 79.83 | C |
| ATOM | 3112 | O | HIS | B | 613 | −87.692 | 63.295 | −33.791 | 1.00 | 80.05 | O |
| ATOM | 3113 | N | GLY | B | 614 | −89.459 | 64.585 | −34.375 | 1.00 | 82.49 | N |
| ATOM | 3114 | CA | GLY | B | 614 | −89.444 | 65.441 | −33.208 | 1.00 | 82.79 | C |
| ATOM | 3115 | C | GLY | B | 614 | −90.823 | 65.612 | −32.638 | 1.00 | 83.07 | C |
| ATOM | 3116 | O | GLY | B | 614 | −91.803 | 65.424 | −33.362 | 1.00 | 82.78 | O |
| ATOM | 3117 | N | ILE | B | 615 | −90.911 | 65.966 | −31.346 | 1.00 | 88.23 | N |
| ATOM | 3118 | CA | ILE | B | 615 | −92.196 | 66.213 | −30.683 | 1.00 | 89.18 | C |
| ATOM | 3119 | CB | ILE | B | 615 | −93.076 | 64.985 | −30.329 | 1.00 | 89.23 | C |
| ATOM | 3120 | CG1 | ILE | B | 615 | −92.261 | 63.813 | −29.798 | 1.00 | 88.59 | C |
| ATOM | 3121 | CD1 | ILE | B | 615 | −92.242 | 63.843 | −28.398 | 1.00 | 88.33 | C |
| ATOM | 3122 | CG2 | ILE | B | 615 | −94.050 | 64.602 | −31.489 | 1.00 | 89.10 | C |
| ATOM | 3123 | C | ILE | B | 615 | −92.141 | 67.291 | −29.596 | 1.00 | 89.92 | C |
| ATOM | 3124 | O | ILE | B | 615 | −91.193 | 67.289 | −28.815 | 1.00 | 90.14 | O |
| ATOM | 3125 | N | PRO | B | 616 | −93.132 | 68.230 | −29.591 | 1.00 | 92.46 | N |
| ATOM | 3126 | CA | PRO | B | 616 | −93.155 | 69.352 | −28.639 | 1.00 | 92.93 | C |
| ATOM | 3127 | CB | PRO | B | 616 | −94.598 | 69.867 | −28.758 | 1.00 | 92.90 | C |
| ATOM | 3128 | CG | PRO | B | 616 | −95.310 | 68.911 | −29.645 | 1.00 | 92.45 | C |
| ATOM | 3129 | CD | PRO | B | 616 | −94.277 | 68.348 | −30.508 | 1.00 | 92.34 | C |
| ATOM | 3130 | C | PRO | B | 616 | −92.673 | 69.260 | −27.175 | 1.00 | 93.54 | C |
| ATOM | 3131 | O | PRO | B | 616 | −91.577 | 69.768 | −26.866 | 1.00 | 93.58 | O |
| ATOM | 3132 | N | ALA | B | 617 | −93.519 | 68.703 | −26.269 | 1.00 | 96.94 | N |
| ATOM | 3133 | CA | ALA | B | 617 | −93.242 | 68.553 | −24.839 | 1.00 | 97.57 | C |
| ATOM | 3134 | CB | ALA | B | 617 | −94.431 | 69.057 | −24.028 | 1.00 | 97.36 | C |
| ATOM | 3135 | C | ALA | B | 617 | −93.013 | 67.053 | −24.597 | 1.00 | 97.97 | C |
| ATOM | 3136 | O | ALA | B | 617 | −93.990 | 66.330 | −24.307 | 1.00 | 98.46 | O |
| ATOM | 3137 | N | PRO | B | 618 | −91.751 | 66.545 | −24.766 | 1.00 | 98.47 | N |
| ATOM | 3138 | CA | PRO | B | 618 | −91.525 | 65.101 | −24.623 | 1.00 | 98.62 | C |
| ATOM | 3139 | CB | PRO | B | 618 | −90.209 | 64.854 | −25.377 | 1.00 | 98.31 | C |
| ATOM | 3140 | CG | PRO | B | 618 | −89.803 | 66.158 | −25.913 | 1.00 | 98.18 | C |
| ATOM | 3141 | CD | PRO | B | 618 | −90.498 | 67.217 | −25.140 | 1.00 | 98.25 | C |
| ATOM | 3142 | C | PRO | B | 618 | −91.446 | 64.630 | −23.191 | 1.00 | 98.94 | C |
| ATOM | 3143 | O | PRO | B | 618 | −90.715 | 65.232 | −22.386 | 1.00 | 99.07 | O |
| ATOM | 3144 | N | GLN | B | 619 | −92.203 | 63.530 | −22.893 | 1.00 | 100.32 | N |
| ATOM | 3145 | CA | GLN | B | 619 | −92.267 | 62.858 | −21.590 | 1.00 | 100.41 | C |
| ATOM | 3146 | CB | GLN | B | 619 | −93.209 | 61.620 | −21.646 | 1.00 | 100.77 | C |
| ATOM | 3147 | CG | GLN | B | 619 | −94.720 | 61.924 | −21.757 | 1.00 | 102.64 | C |
| ATOM | 3148 | CD | GLN | B | 619 | −95.221 | 62.146 | −23.187 | 1.00 | 105.52 | C |
| ATOM | 3149 | OE1 | GLN | B | 619 | −95.170 | 61.245 | −24.049 | 1.00 | 106.91 | O |
| ATOM | 3150 | NE2 | GLN | B | 619 | −95.732 | 63.351 | −23.468 | 1.00 | 105.63 | N |
| ATOM | 3151 | C | GLN | B | 619 | −90.813 | 62.447 | −21.227 | 1.00 | 99.99 | C |
| ATOM | 3152 | O | GLN | B | 619 | −90.130 | 63.183 | −20.494 | 1.00 | 100.29 | O |
| ATOM | 3153 | N | GLU | B | 620 | −90.318 | 61.323 | −21.796 | 1.00 | 94.10 | N |
| ATOM | 3154 | CA | GLU | B | 620 | −88.954 | 60.893 | −21.519 | 1.00 | 92.71 | C |
| ATOM | 3155 | CB | GLU | B | 620 | −88.935 | 59.482 | −20.901 | 1.00 | 92.50 | C |
| ATOM | 3156 | C | GLU | B | 620 | −88.053 | 60.992 | −22.752 | 1.00 | 91.86 | C |
| ATOM | 3157 | O | GLU | B | 620 | −86.984 | 61.626 | −22.694 | 1.00 | 91.83 | O |
| ATOM | 3158 | N | GLN | B | 621 | −88.487 | 60.374 | −23.872 | 1.00 | 85.55 | N |
| ATOM | 3159 | CA | GLN | B | 621 | −87.670 | 60.349 | −25.080 | 1.00 | 84.47 | C |
| ATOM | 3160 | CB | GLN | B | 621 | −86.844 | 59.042 | −25.162 | 1.00 | 84.60 | C |

TABLE 14-continued

PCSK9 and AX132 Fab complex x-ray structure

| ATOM | 3161 | CG  | GLN | B | 621 | −87.462 | 57.832 | −24.461 | 1.00 | 84.63  | C |
| ATOM | 3162 | CD  | GLN | B | 621 | −87.643 | 56.685 | −25.402 | 1.00 | 84.43  | C |
| ATOM | 3163 | OE1 | GLN | B | 621 | −86.689 | 55.973 | −25.708 | 1.00 | 85.62  | O |
| ATOM | 3164 | NE2 | GLN | B | 621 | −88.871 | 56.482 | −25.882 | 1.00 | 84.34  | N |
| ATOM | 3165 | C   | GLN | B | 621 | −88.374 | 60.638 | −26.386 | 1.00 | 83.76  | C |
| ATOM | 3166 | O   | GLN | B | 621 | −89.598 | 60.733 | −26.423 | 1.00 | 83.59  | O |
| ATOM | 3167 | N   | VAL | B | 622 | −87.563 | 60.800 | −27.458 | 1.00 | 79.91  | N |
| ATOM | 3168 | CA  | VAL | B | 622 | −87.932 | 61.064 | −28.848 | 1.00 | 79.67  | C |
| ATOM | 3169 | CB  | VAL | B | 622 | −87.664 | 62.526 | −29.281 | 1.00 | 79.63  | C |
| ATOM | 3170 | CG1 | VAL | B | 622 | −87.873 | 62.702 | −30.771 | 1.00 | 79.21  | C |
| ATOM | 3171 | CG2 | VAL | B | 622 | −88.559 | 63.495 | −28.516 | 1.00 | 79.49  | C |
| ATOM | 3172 | C   | VAL | B | 622 | −87.170 | 60.043 | −29.682 | 1.00 | 79.82  | C |
| ATOM | 3173 | O   | VAL | B | 622 | −85.939 | 59.991 | −29.653 | 1.00 | 79.77  | O |
| ATOM | 3174 | N   | THR | B | 623 | −87.927 | 59.218 | −30.410 | 1.00 | 82.55  | N |
| ATOM | 3175 | CA  | THR | B | 623 | −87.419 | 58.107 | −31.207 | 1.00 | 82.68  | C |
| ATOM | 3176 | CB  | THR | B | 623 | −87.976 | 56.814 | −30.555 | 1.00 | 82.61  | C |
| ATOM | 3177 | OG1 | THR | B | 623 | −87.045 | 56.385 | −29.562 | 1.00 | 82.15  | O |
| ATOM | 3178 | CG2 | THR | B | 623 | −88.326 | 55.694 | −31.553 | 1.00 | 82.02  | C |
| ATOM | 3179 | C   | THR | B | 623 | −87.629 | 58.197 | −32.723 | 1.00 | 83.06  | C |
| ATOM | 3180 | O   | THR | B | 623 | −88.686 | 58.617 | −33.191 | 1.00 | 83.23  | O |
| ATOM | 3181 | N   | VAL | B | 624 | −86.622 | 57.744 | −33.474 | 1.00 | 85.14  | N |
| ATOM | 3182 | CA  | VAL | B | 624 | −86.620 | 57.659 | −34.935 | 1.00 | 85.55  | C |
| ATOM | 3183 | CB  | VAL | B | 624 | −86.190 | 58.982 | −35.648 | 1.00 | 85.38  | C |
| ATOM | 3184 | CG1 | VAL | B | 624 | −84.702 | 59.294 | −35.472 | 1.00 | 85.50  | C |
| ATOM | 3185 | CG2 | VAL | B | 624 | −86.563 | 58.962 | −37.122 | 1.00 | 85.18  | C |
| ATOM | 3186 | C   | VAL | B | 624 | −85.823 | 56.397 | −35.353 | 1.00 | 86.01  | C |
| ATOM | 3187 | O   | VAL | B | 624 | −84.642 | 56.262 | −35.013 | 1.00 | 85.58  | O |
| ATOM | 3188 | N   | ALA | B | 625 | −86.483 | 55.463 | −36.046 | 1.00 | 89.04  | N |
| ATOM | 3189 | CA  | ALA | B | 625 | −85.810 | 54.229 | −36.462 | 1.00 | 90.03  | C |
| ATOM | 3190 | CB  | ALA | B | 625 | −86.573 | 53.019 | −35.942 | 1.00 | 89.71  | C |
| ATOM | 3191 | C   | ALA | B | 625 | −85.616 | 54.118 | −37.974 | 1.00 | 90.84  | C |
| ATOM | 3192 | O   | ALA | B | 625 | −86.465 | 54.600 | −38.730 | 1.00 | 91.18  | O |
| ATOM | 3193 | N   | CYS | B | 626 | −84.519 | 53.467 | −38.416 | 1.00 | 92.62  | N |
| ATOM | 3194 | CA  | CYS | B | 626 | −84.249 | 53.242 | −39.833 | 1.00 | 93.74  | C |
| ATOM | 3195 | CB  | CYS | B | 626 | −82.845 | 52.686 | −40.028 | 1.00 | 93.68  | C |
| ATOM | 3196 | SG  | CYS | B | 626 | −81.521 | 53.825 | −39.563 | 1.00 | 96.55  | S |
| ATOM | 3197 | C   | CYS | B | 626 | −85.294 | 52.278 | −40.417 | 1.00 | 94.25  | C |
| ATOM | 3198 | O   | CYS | B | 626 | −85.991 | 51.581 | −39.670 | 1.00 | 94.23  | O |
| ATOM | 3199 | N   | GLU | B | 627 | −85.397 | 52.224 | −41.750 | 1.00 | 99.01  | N |
| ATOM | 3200 | CA  | GLU | B | 627 | −86.313 | 51.280 | −42.372 | 1.00 | 99.57  | C |
| ATOM | 3201 | CB  | GLU | B | 627 | −86.699 | 51.724 | −43.779 | 1.00 | 99.82  | C |
| ATOM | 3202 | CG  | GLU | B | 627 | −87.846 | 52.708 | −43.822 | 1.00 | 101.35 | C |
| ATOM | 3203 | CD  | GLU | B | 627 | −87.453 | 54.073 | −44.351 | 1.00 | 103.72 | C |
| ATOM | 3204 | OE1 | GLU | B | 627 | −86.269 | 54.258 | −44.725 | 1.00 | 104.08 | O |
| ATOM | 3205 | OE2 | GLU | B | 627 | −88.334 | 54.965 | −44.379 | 1.00 | 105.10 | O |
| ATOM | 3206 | C   | GLU | B | 627 | −85.575 | 49.950 | −42.474 | 1.00 | 99.72  | C |
| ATOM | 3207 | O   | GLU | B | 627 | −84.331 | 49.916 | −42.454 | 1.00 | 99.64  | O |
| ATOM | 3208 | N   | GLU | B | 628 | −86.347 | 48.852 | −42.602 | 1.00 | 99.87  | N |
| ATOM | 3209 | CA  | GLU | B | 628 | −85.806 | 47.503 | −42.759 | 1.00 | 99.87  | C |
| ATOM | 3210 | CB  | GLU | B | 628 | −86.981 | 46.504 | −42.940 | 1.00 | 100.27 | C |
| ATOM | 3211 | CG  | GLU | B | 628 | −86.774 | 45.326 | −43.885 | 1.00 | 102.66 | C |
| ATOM | 3212 | CD  | GLU | B | 628 | −85.816 | 44.225 | −43.459 | 1.00 | 105.44 | C |
| ATOM | 3213 | OE1 | GLU | B | 628 | −85.760 | 43.908 | −42.246 | 1.00 | 106.67 | O |
| ATOM | 3214 | OE2 | GLU | B | 628 | −85.130 | 43.664 | −44.348 | 1.00 | 106.45 | O |
| ATOM | 3215 | C   | GLU | B | 628 | −84.797 | 47.549 | −43.934 | 1.00 | 99.03  | C |
| ATOM | 3216 | O   | GLU | B | 628 | −85.098 | 48.102 | −44.990 | 1.00 | 98.78  | O |
| ATOM | 3217 | N   | GLY | B | 629 | −83.593 | 47.065 | −43.694 | 1.00 | 97.03  | N |
| ATOM | 3218 | CA  | GLY | B | 629 | −82.544 | 47.072 | −44.706 | 1.00 | 96.58  | C |
| ATOM | 3219 | C   | GLY | B | 629 | −81.530 | 48.174 | −44.506 | 1.00 | 96.44  | C |
| ATOM | 3220 | O   | GLY | B | 629 | −80.403 | 48.111 | −45.014 | 1.00 | 96.39  | O |
| ATOM | 3221 | N   | TRP | B | 630 | −81.928 | 49.190 | −43.757 | 1.00 | 99.26  | N |
| ATOM | 3222 | CA  | TRP | B | 630 | −81.056 | 50.308 | −43.456 | 1.00 | 99.05  | C |
| ATOM | 3223 | CB  | TRP | B | 630 | −81.851 | 51.611 | −43.533 | 1.00 | 99.48  | C |
| ATOM | 3224 | CG  | TRP | B | 630 | −82.241 | 51.986 | −44.934 | 1.00 | 100.47 | C |
| ATOM | 3225 | CD1 | TRP | B | 630 | −83.413 | 51.692 | −45.576 | 1.00 | 100.68 | C |
| ATOM | 3226 | NE1 | TRP | B | 630 | −83.394 | 52.210 | −46.852 | 1.00 | 100.42 | N |
| ATOM | 3227 | CE2 | TRP | B | 630 | −82.198 | 52.855 | −47.054 | 1.00 | 100.71 | C |
| ATOM | 3228 | CD2 | TRP | B | 630 | −81.443 | 52.723 | −45.868 | 1.00 | 100.98 | C |
| ATOM | 3229 | CE3 | TRP | B | 630 | −80.163 | 53.307 | −45.809 | 1.00 | 101.56 | C |
| ATOM | 3230 | CZ3 | TRP | B | 630 | −79.684 | 53.996 | −46.915 | 1.00 | 101.51 | C |
| ATOM | 3231 | CH2 | TRP | B | 630 | −80.444 | 54.095 | −48.085 | 1.00 | 101.62 | C |
| ATOM | 3232 | CZ2 | TRP | B | 630 | −81.710 | 53.541 | −48.175 | 1.00 | 101.13 | C |
| ATOM | 3233 | C   | TRP | B | 630 | −80.456 | 50.094 | −42.074 | 1.00 | 98.40  | C |
| ATOM | 3234 | O   | TRP | B | 630 | −81.127 | 49.576 | −41.181 | 1.00 | 98.36  | O |
| ATOM | 3235 | N   | THR | B | 631 | −79.197 | 50.479 | −41.910 | 1.00 | 95.20  | N |
| ATOM | 3236 | CA  | THR | B | 631 | −78.443 | 50.347 | −40.667 | 1.00 | 94.44  | C |
| ATOM | 3237 | CB  | THR | B | 631 | −77.185 | 49.515 | −40.966 | 1.00 | 94.47  | C |
| ATOM | 3238 | OG1 | THR | B | 631 | −77.579 | 48.155 | −41.135 | 1.00 | 94.93  | O |

TABLE 14-continued

PCSK9 and AX132 Fab complex x-ray structure

| ATOM | 3239 | CG2 | THR | B | 631 | −76.114 | 49.624 | −39.898 | 1.00 | 94.21 | C |
|------|------|-----|-----|---|-----|---------|--------|---------|------|-------|---|
| ATOM | 3240 | C   | THR | B | 631 | −78.164 | 51.727 | −40.033 | 1.00 | 93.85 | C |
| ATOM | 3241 | O   | THR | B | 631 | −77.579 | 52.598 | −40.681 | 1.00 | 93.88 | O |
| ATOM | 3242 | N   | LEU | B | 632 | −78.569 | 51.919 | −38.772 | 1.00 | 91.41 | N |
| ATOM | 3243 | CA  | LEU | B | 632 | −78.332 | 53.177 | −38.074 | 1.00 | 90.60 | C |
| ATOM | 3244 | CB  | LEU | B | 632 | −79.138 | 53.227 | −36.766 | 1.00 | 90.50 | C |
| ATOM | 3245 | CG  | LEU | B | 632 | −78.971 | 54.451 | −35.885 | 1.00 | 89.65 | C |
| ATOM | 3246 | CD1 | LEU | B | 632 | −79.409 | 55.660 | −36.593 | 1.00 | 89.50 | C |
| ATOM | 3247 | CD2 | LEU | B | 632 | −79.817 | 54.334 | −34.678 | 1.00 | 89.05 | C |
| ATOM | 3248 | C   | LEU | B | 632 | −76.849 | 53.315 | −37.798 | 1.00 | 90.39 | C |
| ATOM | 3249 | O   | LEU | B | 632 | −76.288 | 52.506 | −37.062 | 1.00 | 90.51 | O |
| ATOM | 3250 | N   | THR | B | 633 | −76.208 | 54.313 | −38.411 | 1.00 | 90.81 | N |
| ATOM | 3251 | CA  | THR | B | 633 | −74.772 | 54.565 | −38.232 | 1.00 | 90.43 | C |
| ATOM | 3252 | CB  | THR | B | 633 | −74.066 | 54.794 | −39.567 | 1.00 | 90.45 | C |
| ATOM | 3253 | OG1 | THR | B | 633 | −74.591 | 55.988 | −40.166 | 1.00 | 91.14 | O |
| ATOM | 3254 | CG2 | THR | B | 633 | −74.184 | 53.604 | −40.500 | 1.00 | 90.51 | C |
| ATOM | 3255 | C   | THR | B | 633 | −74.524 | 55.759 | −37.317 | 1.00 | 90.16 | C |
| ATOM | 3256 | O   | THR | B | 633 | −73.538 | 55.764 | −36.582 | 1.00 | 90.12 | O |
| ATOM | 3257 | N   | GLY | B | 634 | −75.394 | 56.763 | −37.396 | 1.00 | 87.09 | N |
| ATOM | 3258 | CA  | GLY | B | 634 | −75.267 | 57.961 | −36.581 | 1.00 | 86.65 | C |
| ATOM | 3259 | C   | GLY | B | 634 | −76.542 | 58.364 | −35.880 | 1.00 | 86.41 | C |
| ATOM | 3260 | O   | GLY | B | 634 | −77.612 | 58.389 | −36.502 | 1.00 | 86.54 | O |
| ATOM | 3261 | N   | CYS | B | 635 | −76.438 | 58.699 | −34.585 | 1.00 | 82.25 | N |
| ATOM | 3262 | CA  | CYS | B | 635 | −77.609 | 59.131 | −33.820 | 1.00 | 82.04 | C |
| ATOM | 3263 | CB  | CYS | B | 635 | −78.076 | 58.027 | −32.879 | 1.00 | 81.41 | C |
| ATOM | 3264 | SG  | CYS | B | 635 | −79.434 | 58.486 | −31.778 | 1.00 | 79.97 | S |
| ATOM | 3265 | C   | CYS | B | 635 | −77.254 | 60.442 | −33.099 | 1.00 | 82.61 | C |
| ATOM | 3266 | O   | CYS | B | 635 | −76.128 | 60.590 | −32.595 | 1.00 | 82.41 | O |
| ATOM | 3267 | N   | SER | B | 636 | −78.190 | 61.428 | −33.153 | 1.00 | 83.71 | N |
| ATOM | 3268 | CA  | SER | B | 636 | −78.043 | 62.796 | −32.610 | 1.00 | 84.47 | C |
| ATOM | 3269 | CB  | SER | B | 636 | −77.178 | 63.631 | −33.551 | 1.00 | 84.28 | C |
| ATOM | 3270 | OG  | SER | B | 636 | −77.693 | 63.523 | −34.868 | 1.00 | 84.69 | O |
| ATOM | 3271 | C   | SER | B | 636 | −79.369 | 63.520 | −32.421 | 1.00 | 84.91 | C |
| ATOM | 3272 | O   | SER | B | 636 | −80.422 | 62.986 | −32.751 | 1.00 | 84.87 | O |
| ATOM | 3273 | N   | ALA | B | 637 | −79.306 | 64.751 | −31.900 | 1.00 | 87.69 | N |
| ATOM | 3274 | CA  | ALA | B | 637 | −80.478 | 65.601 | −31.676 | 1.00 | 88.87 | C |
| ATOM | 3275 | CB  | ALA | B | 637 | −80.790 | 65.706 | −30.192 | 1.00 | 88.44 | C |
| ATOM | 3276 | C   | ALA | B | 637 | −80.287 | 66.994 | −32.279 | 1.00 | 89.84 | C |
| ATOM | 3277 | O   | ALA | B | 637 | −79.159 | 67.500 | −32.334 | 1.00 | 90.01 | O |
| ATOM | 3278 | N   | LEU | B | 638 | −81.395 | 67.603 | −32.745 | 1.00 | 95.18 | N |
| ATOM | 3279 | CA  | LEU | B | 638 | −81.383 | 68.934 | −33.337 | 1.00 | 96.41 | C |
| ATOM | 3280 | CB  | LEU | B | 638 | −82.722 | 69.272 | −34.006 | 1.00 | 96.25 | C |
| ATOM | 3281 | CG  | LEU | B | 638 | −82.911 | 68.746 | −35.428 | 1.00 | 95.86 | C |
| ATOM | 3282 | CD1 | LEU | B | 638 | −84.116 | 69.356 | −36.057 | 1.00 | 95.51 | C |
| ATOM | 3283 | CD2 | LEU | B | 638 | −81.710 | 69.046 | −36.310 | 1.00 | 94.65 | C |
| ATOM | 3284 | C   | LEU | B | 638 | −80.990 | 69.951 | −32.267 | 1.00 | 97.73 | C |
| ATOM | 3285 | O   | LEU | B | 638 | −81.656 | 70.016 | −31.223 | 1.00 | 97.77 | O |
| ATOM | 3286 | N   | PRO | B | 639 | −79.864 | 70.688 | −32.494 | 1.00 | 105.30 | N |
| ATOM | 3287 | CA  | PRO | B | 639 | −79.352 | 71.634 | −31.482 | 1.00 | 106.33 | C |
| ATOM | 3288 | CB  | PRO | B | 639 | −78.161 | 72.308 | −32.178 | 1.00 | 106.24 | C |
| ATOM | 3289 | CG  | PRO | B | 639 | −78.327 | 72.005 | −33.615 | 1.00 | 105.87 | C |
| ATOM | 3290 | CD  | PRO | B | 639 | −78.974 | 70.662 | −33.669 | 1.00 | 105.46 | C |
| ATOM | 3291 | C   | PRO | B | 639 | −80.325 | 72.645 | −30.907 | 1.00 | 107.40 | C |
| ATOM | 3292 | O   | PRO | B | 639 | −80.205 | 73.000 | −29.722 | 1.00 | 107.75 | O |
| ATOM | 3293 | N   | GLY | B | 640 | −81.274 | 73.081 | −31.741 | 1.00 | 113.40 | N |
| ATOM | 3294 | CA  | GLY | B | 640 | −82.310 | 74.042 | −31.372 | 1.00 | 114.55 | C |
| ATOM | 3295 | C   | GLY | B | 640 | −83.280 | 73.426 | −30.393 | 1.00 | 115.12 | C |
| ATOM | 3296 | O   | GLY | B | 640 | −84.423 | 73.114 | −30.755 | 1.00 | 115.42 | O |
| ATOM | 3297 | N   | THR | B | 641 | −82.800 | 73.215 | −29.150 | 1.00 | 117.71 | N |
| ATOM | 3298 | CA  | THR | B | 641 | −83.559 | 72.584 | −28.075 | 1.00 | 118.36 | C |
| ATOM | 3299 | CB  | THR | B | 641 | −83.562 | 71.037 | −28.234 | 1.00 | 118.30 | C |
| ATOM | 3300 | OG1 | THR | B | 641 | −84.491 | 70.483 | −27.300 | 1.00 | 118.10 | O |
| ATOM | 3301 | CG2 | THR | B | 641 | −82.167 | 70.408 | −28.050 | 1.00 | 118.37 | C |
| ATOM | 3302 | C   | THR | B | 641 | −83.112 | 73.048 | −26.691 | 1.00 | 118.77 | C |
| ATOM | 3303 | O   | THR | B | 641 | −82.100 | 73.750 | −26.555 | 1.00 | 119.16 | O |
| ATOM | 3304 | N   | SER | B | 642 | −83.885 | 72.626 | −25.671 | 1.00 | 118.42 | N |
| ATOM | 3305 | CA  | SER | B | 642 | −83.692 | 72.923 | −24.260 | 1.00 | 118.43 | C |
| ATOM | 3306 | CB  | SER | B | 642 | −85.050 | 73.128 | −23.585 | 1.00 | 118.78 | C |
| ATOM | 3307 | OG  | SER | B | 642 | −85.914 | 73.957 | −24.352 | 1.00 | 119.68 | O |
| ATOM | 3308 | C   | SER | B | 642 | −82.882 | 71.797 | −23.600 | 1.00 | 117.89 | C |
| ATOM | 3309 | O   | SER | B | 642 | −81.844 | 71.394 | −24.144 | 1.00 | 117.93 | O |
| ATOM | 3310 | N   | HIS | B | 643 | −83.345 | 71.289 | −22.444 | 1.00 | 114.82 | N |
| ATOM | 3311 | CA  | HIS | B | 643 | −82.631 | 70.240 | −21.720 | 1.00 | 114.07 | C |
| ATOM | 3312 | CB  | HIS | B | 643 | −82.906 | 70.289 | −20.189 | 1.00 | 114.71 | C |
| ATOM | 3313 | CG  | HIS | B | 643 | −81.719 | 69.984 | −19.295 | 1.00 | 116.80 | C |
| ATOM | 3314 | ND1 | HIS | B | 643 | −80.426 | 70.430 | −19.601 | 1.00 | 118.25 | N |
| ATOM | 3315 | CE1 | HIS | B | 643 | −79.653 | 70.006 | −18.607 | 1.00 | 118.56 | C |
| ATOM | 3316 | NE2 | HIS | B | 643 | −80.355 | 69.336 | −17.686 | 1.00 | 118.87 | N |

TABLE 14-continued

PCSK9 and AX132 Fab complex x-ray structure

| ATOM | 3317 | CD2 | HIS | B | 643 | −81.677 | 69.321 | −18.109 | 1.00 | 118.39 | C |
|------|------|-----|-----|---|-----|---------|--------|---------|------|--------|---|
| ATOM | 3318 | C   | HIS | B | 643 | −82.757 | 68.829 | −22.313 | 1.00 | 112.56 | C |
| ATOM | 3319 | O   | HIS | B | 643 | −83.777 | 68.140 | −22.151 | 1.00 | 112.68 | O |
| ATOM | 3320 | N   | VAL | B | 644 | −81.695 | 68.422 | −23.023 | 1.00 | 102.35 | N |
| ATOM | 3321 | CA  | VAL | B | 644 | −81.587 | 67.090 | −23.585 | 1.00 | 100.09 | C |
| ATOM | 3322 | CB  | VAL | B | 644 | −81.702 | 66.933 | −25.117 | 1.00 | 100.10 | C |
| ATOM | 3323 | CG1 | VAL | B | 644 | −82.987 | 67.561 | −25.623 | 1.00 | 99.99  | C |
| ATOM | 3324 | CG2 | VAL | B | 644 | −80.491 | 67.488 | −25.854 | 1.00 | 99.85  | C |
| ATOM | 3325 | C   | VAL | B | 644 | −80.366 | 66.454 | −22.963 | 1.00 | 98.62  | C |
| ATOM | 3326 | O   | VAL | B | 644 | −79.243 | 66.985 | −23.051 | 1.00 | 98.76  | O |
| ATOM | 3327 | N   | LEU | B | 645 | −80.619 | 65.347 | −22.262 | 1.00 | 90.02  | N |
| ATOM | 3328 | CA  | LEU | B | 645 | −79.643 | 64.550 | −21.532 | 1.00 | 87.53  | C |
| ATOM | 3329 | CB  | LEU | B | 645 | −80.385 | 63.455 | −20.757 | 1.00 | 87.46  | C |
| ATOM | 3330 | CG  | LEU | B | 645 | −81.162 | 63.901 | −19.502 | 1.00 | 86.73  | C |
| ATOM | 3331 | CD1 | LEU | B | 645 | −82.312 | 64.792 | −19.839 | 1.00 | 86.67  | C |
| ATOM | 3332 | CD2 | LEU | B | 645 | −81.741 | 62.719 | −18.779 | 1.00 | 86.22  | C |
| ATOM | 3333 | C   | LEU | B | 645 | −78.572 | 63.976 | −22.465 | 1.00 | 85.94  | C |
| ATOM | 3334 | O   | LEU | B | 645 | −77.389 | 64.002 | −22.136 | 1.00 | 85.72  | O |
| ATOM | 3335 | N   | GLY | B | 646 | −78.999 | 63.512 | −23.633 | 1.00 | 81.27  | N |
| ATOM | 3336 | CA  | GLY | B | 646 | −78.124 | 62.949 | −24.655 | 1.00 | 78.79  | C |
| ATOM | 3337 | C   | GLY | B | 646 | −78.847 | 62.091 | −25.670 | 1.00 | 77.11  | C |
| ATOM | 3338 | O   | GLY | B | 646 | −80.079 | 62.007 | −25.682 | 1.00 | 76.86  | O |
| ATOM | 3339 | N   | ALA | B | 647 | −78.075 | 61.445 | −26.532 | 1.00 | 74.90  | N |
| ATOM | 3340 | CA  | ALA | B | 647 | −78.608 | 60.554 | −27.563 | 1.00 | 73.60  | C |
| ATOM | 3341 | CB  | ALA | B | 647 | −78.740 | 61.280 | −28.888 | 1.00 | 73.68  | C |
| ATOM | 3342 | C   | ALA | B | 647 | −77.744 | 59.328 | −27.734 | 1.00 | 72.61  | C |
| ATOM | 3343 | O   | ALA | B | 647 | −76.515 | 59.395 | −27.653 | 1.00 | 72.32  | O |
| ATOM | 3344 | N   | TYR | B | 648 | −78.402 | 58.202 | −27.970 | 1.00 | 71.64  | N |
| ATOM | 3345 | CA  | TYR | B | 648 | −77.731 | 56.920 | −28.182 | 1.00 | 70.40  | C |
| ATOM | 3346 | CB  | TYR | B | 648 | −77.415 | 56.200 | −26.842 | 1.00 | 69.77  | C |
| ATOM | 3347 | CG  | TYR | B | 648 | −78.580 | 56.130 | −25.876 | 1.00 | 67.74  | C |
| ATOM | 3348 | CD1 | TYR | B | 648 | −78.712 | 57.058 | −24.843 | 1.00 | 66.20  | C |
| ATOM | 3349 | CE1 | TYR | B | 648 | −79.797 | 57.015 | −23.964 | 1.00 | 64.71  | C |
| ATOM | 3350 | CZ  | TYR | B | 648 | −80.767 | 56.030 | −24.113 | 1.00 | 64.68  | C |
| ATOM | 3351 | OH  | TYR | B | 648 | −81.835 | 55.960 | −23.239 | 1.00 | 63.83  | O |
| ATOM | 3352 | CE2 | TYR | B | 648 | −80.647 | 55.092 | −25.132 | 1.00 | 64.61  | C |
| ATOM | 3353 | CD2 | TYR | B | 648 | −79.555 | 55.145 | −26.000 | 1.00 | 65.13  | C |
| ATOM | 3354 | C   | TYR | B | 648 | −78.543 | 56.035 | −29.123 | 1.00 | 70.18  | C |
| ATOM | 3355 | O   | TYR | B | 648 | −79.767 | 56.174 | −29.210 | 1.00 | 70.19  | O |
| ATOM | 3356 | N   | ALA | B | 649 | −77.859 | 55.118 | −29.813 | 1.00 | 71.65  | N |
| ATOM | 3357 | CA  | ALA | B | 649 | −78.512 | 54.174 | −30.718 | 1.00 | 71.10  | C |
| ATOM | 3358 | CB  | ALA | B | 649 | −77.614 | 53.899 | −31.910 | 1.00 | 71.27  | C |
| ATOM | 3359 | C   | ALA | B | 649 | −78.831 | 52.869 | −30.005 | 1.00 | 70.52  | C |
| ATOM | 3360 | O   | ALA | B | 649 | −78.006 | 52.355 | −29.249 | 1.00 | 70.51  | O |
| ATOM | 3361 | N   | VAL | B | 650 | −80.019 | 52.347 | −30.226 | 1.00 | 70.69  | N |
| ATOM | 3362 | CA  | VAL | B | 650 | −80.446 | 51.073 | −29.657 | 1.00 | 70.72  | C |
| ATOM | 3363 | CB  | VAL | B | 650 | −81.517 | 51.182 | −28.569 | 1.00 | 70.58  | C |
| ATOM | 3364 | CG1 | VAL | B | 650 | −81.723 | 49.839 | −27.885 | 1.00 | 70.02  | C |
| ATOM | 3365 | CG2 | VAL | B | 650 | −81.146 | 52.245 | −27.549 | 1.00 | 70.80  | C |
| ATOM | 3366 | C   | VAL | B | 650 | −80.897 | 50.209 | −30.814 | 1.00 | 71.06  | C |
| ATOM | 3367 | O   | VAL | B | 650 | −82.092 | 50.194 | −31.175 | 1.00 | 70.88  | O |
| ATOM | 3368 | N   | ASP | B | 651 | −79.911 | 49.492 | −31.401 | 1.00 | 74.95  | N |
| ATOM | 3369 | CA  | ASP | B | 651 | −80.052 | 48.625 | −32.559 | 1.00 | 75.66  | C |
| ATOM | 3370 | CB  | ASP | B | 651 | −81.277 | 47.685 | −32.445 | 1.00 | 76.16  | C |
| ATOM | 3371 | CG  | ASP | B | 651 | −81.529 | 46.758 | −33.626 | 1.00 | 78.41  | C |
| ATOM | 3372 | OD1 | ASP | B | 651 | −80.530 | 46.195 | −34.180 | 1.00 | 80.78  | O |
| ATOM | 3373 | OD2 | ASP | B | 651 | −82.727 | 46.584 | −34.003 | 1.00 | 80.71  | O |
| ATOM | 3374 | C   | ASP | B | 651 | −80.132 | 49.596 | −33.710 | 1.00 | 75.69  | C |
| ATOM | 3375 | O   | ASP | B | 651 | −79.143 | 50.298 | −33.950 | 1.00 | 75.69  | O |
| ATOM | 3376 | N   | ASN | B | 652 | −81.294 | 49.702 | −34.387 | 1.00 | 77.61  | N |
| ATOM | 3377 | CA  | ASN | B | 652 | −81.461 | 50.629 | −35.493 | 1.00 | 77.68  | C |
| ATOM | 3378 | CB  | ASN | B | 652 | −81.874 | 49.898 | −36.775 | 1.00 | 77.48  | C |
| ATOM | 3379 | CG  | ASN | B | 652 | −80.748 | 49.236 | −37.560 | 1.00 | 77.93  | C |
| ATOM | 3380 | OD1 | ASN | B | 652 | −79.540 | 49.314 | −37.242 | 1.00 | 78.69  | O |
| ATOM | 3381 | ND2 | ASN | B | 652 | −81.135 | 48.552 | −38.626 | 1.00 | 78.67  | N |
| ATOM | 3382 | C   | ASN | B | 652 | −82.435 | 51.728 | −35.091 | 1.00 | 77.91  | C |
| ATOM | 3383 | O   | ASN | B | 652 | −83.069 | 52.348 | −35.940 | 1.00 | 78.35  | O |
| ATOM | 3384 | N   | THR | B | 653 | −82.551 | 51.977 | −33.791 | 1.00 | 75.16  | N |
| ATOM | 3385 | CA  | THR | B | 653 | −83.417 | 53.015 | −33.281 | 1.00 | 75.21  | C |
| ATOM | 3386 | CB  | THR | B | 653 | −84.473 | 52.452 | −32.330 | 1.00 | 75.26  | C |
| ATOM | 3387 | OG1 | THR | B | 653 | −85.255 | 51.464 | −33.006 | 1.00 | 75.72  | O |
| ATOM | 3388 | CG2 | THR | B | 653 | −85.399 | 53.526 | −31.794 | 1.00 | 74.72  | C |
| ATOM | 3389 | C   | THR | B | 653 | −82.546 | 54.045 | −32.635 | 1.00 | 75.52  | C |
| ATOM | 3390 | O   | THR | B | 653 | −81.665 | 53.697 | −31.861 | 1.00 | 75.87  | O |
| ATOM | 3391 | N   | CYS | B | 654 | −82.767 | 55.319 | −32.972 | 1.00 | 76.26  | N |
| ATOM | 3392 | CA  | CYS | B | 654 | −82.038 | 56.437 | −32.405 | 1.00 | 76.22  | C |
| ATOM | 3393 | CB  | CYS | B | 654 | −81.803 | 57.509 | −33.454 | 1.00 | 76.68  | C |
| ATOM | 3394 | SG  | CYS | B | 654 | −81.111 | 59.037 | −32.794 | 1.00 | 79.21  | S |

TABLE 14-continued

PCSK9 and AX132 Fab complex x-ray structure

| ATOM | 3395 | C | CYS | B | 654 | −82.871 | 56.956 | −31.255 | 1.00 | 75.66 | C |
|---|---|---|---|---|---|---|---|---|---|---|---|
| ATOM | 3396 | O | CYS | B | 654 | −84.076 | 57.208 | −31.421 | 1.00 | 75.66 | O |
| ATOM | 3397 | N | VAL | B | 655 | −82.248 | 57.048 | −30.064 | 1.00 | 70.52 | N |
| ATOM | 3398 | CA | VAL | B | 655 | −82.914 | 57.520 | −28.847 | 1.00 | 69.96 | C |
| ATOM | 3399 | CB | VAL | B | 655 | −82.983 | 56.490 | −27.703 | 1.00 | 69.62 | C |
| ATOM | 3400 | CG1 | VAL | B | 655 | −83.639 | 57.095 | −26.464 | 1.00 | 68.37 | C |
| ATOM | 3401 | CG2 | VAL | B | 655 | −83.715 | 55.226 | −28.147 | 1.00 | 69.18 | C |
| ATOM | 3402 | C | VAL | B | 655 | −82.292 | 58.801 | −28.392 | 1.00 | 70.24 | C |
| ATOM | 3403 | O | VAL | B | 655 | −81.069 | 58.871 | −28.242 | 1.00 | 69.75 | O |
| ATOM | 3404 | N | VAL | B | 656 | −83.151 | 59.819 | −28.201 | 1.00 | 71.61 | N |
| ATOM | 3405 | CA | VAL | B | 656 | −82.816 | 61.150 | −27.714 | 1.00 | 72.11 | C |
| ATOM | 3406 | CB | VAL | B | 656 | −83.183 | 62.263 | −28.729 | 1.00 | 72.14 | C |
| ATOM | 3407 | CG1 | VAL | B | 656 | −83.344 | 63.625 | −28.055 | 1.00 | 72.22 | C |
| ATOM | 3408 | CG2 | VAL | B | 656 | −82.148 | 62.334 | −29.843 | 1.00 | 71.57 | C |
| ATOM | 3409 | C | VAL | B | 656 | −83.560 | 61.248 | −26.401 | 1.00 | 72.63 | C |
| ATOM | 3410 | O | VAL | B | 656 | −84.772 | 61.054 | −26.372 | 1.00 | 72.38 | O |
| ATOM | 3411 | N | ARG | B | 657 | −82.825 | 61.480 | −25.304 | 1.00 | 78.59 | N |
| ATOM | 3412 | CA | ARG | B | 657 | −83.387 | 61.567 | −23.953 | 1.00 | 79.74 | C |
| ATOM | 3413 | CB | ARG | B | 657 | −82.539 | 60.731 | −22.976 | 1.00 | 79.78 | C |
| ATOM | 3414 | CG | ARG | B | 657 | −82.737 | 59.207 | −23.123 | 1.00 | 80.65 | C |
| ATOM | 3415 | CD | ARG | B | 657 | −83.820 | 58.623 | −22.204 | 1.00 | 82.56 | C |
| ATOM | 3416 | NE | ARG | B | 657 | −83.525 | 58.905 | −20.795 | 1.00 | 85.35 | N |
| ATOM | 3417 | CZ | ARG | B | 657 | −82.733 | 58.168 | −20.003 | 1.00 | 87.81 | C |
| ATOM | 3418 | NH1 | ARG | B | 657 | −82.173 | 57.043 | −20.459 | 1.00 | 88.85 | N |
| ATOM | 3419 | NH2 | ARG | B | 657 | −82.504 | 58.544 | −18.748 | 1.00 | 88.39 | N |
| ATOM | 3420 | C | ARG | B | 657 | −83.533 | 63.037 | −23.534 | 1.00 | 80.41 | C |
| ATOM | 3421 | O | ARG | B | 657 | −82.609 | 63.828 | −23.747 | 1.00 | 80.41 | O |
| ATOM | 3422 | N | SER | B | 658 | −84.706 | 63.407 | −22.982 | 1.00 | 83.27 | N |
| ATOM | 3423 | CA | SER | B | 658 | −85.011 | 64.791 | −22.589 | 1.00 | 84.33 | C |
| ATOM | 3424 | CB | SER | B | 658 | −85.972 | 65.406 | −23.597 | 1.00 | 84.44 | C |
| ATOM | 3425 | OG | SER | B | 658 | −87.160 | 64.623 | −23.627 | 1.00 | 85.47 | O |
| ATOM | 3426 | C | SER | B | 658 | −85.614 | 64.919 | −21.181 | 1.00 | 84.82 | C |
| ATOM | 3427 | O | SER | B | 658 | −86.333 | 64.018 | −20.728 | 1.00 | 85.31 | O |
| ATOM | 3428 | N | ARG | B | 659 | −85.349 | 66.076 | −20.511 | 1.00 | 83.80 | N |
| ATOM | 3429 | CA | ARG | B | 659 | −85.794 | 66.403 | −19.147 | 1.00 | 83.94 | C |
| ATOM | 3430 | CB | ARG | B | 659 | −84.813 | 67.394 | −18.504 | 1.00 | 83.98 | C |
| ATOM | 3431 | C | ARG | B | 659 | −87.216 | 66.937 | −19.109 | 1.00 | 83.92 | C |
| ATOM | 3432 | O | ARG | B | 659 | −88.139 | 66.240 | −19.535 | 1.00 | 84.37 | O |
| ATOM | 3433 | N | GLU | B | 670 | −90.617 | 74.494 | −28.169 | 1.00 | 107.03 | N |
| ATOM | 3434 | CA | GLU | B | 670 | −90.150 | 73.859 | −29.399 | 1.00 | 107.20 | C |
| ATOM | 3435 | CB | GLU | B | 670 | −88.867 | 74.517 | −29.912 | 1.00 | 107.28 | C |
| ATOM | 3436 | CG | GLU | B | 670 | −88.726 | 74.422 | −31.425 | 1.00 | 108.21 | C |
| ATOM | 3437 | CD | GLU | B | 670 | −87.325 | 74.535 | −31.995 | 1.00 | 109.40 | C |
| ATOM | 3438 | OE1 | GLU | B | 670 | −86.487 | 75.246 | −31.390 | 1.00 | 109.72 | O |
| ATOM | 3439 | OE2 | GLU | B | 670 | −87.068 | 73.917 | −33.056 | 1.00 | 109.72 | O |
| ATOM | 3440 | C | GLU | B | 670 | −89.976 | 72.318 | −29.299 | 1.00 | 107.16 | C |
| ATOM | 3441 | O | GLU | B | 670 | −89.705 | 71.776 | −28.212 | 1.00 | 107.43 | O |
| ATOM | 3442 | N | ALA | B | 671 | −90.138 | 71.624 | −30.458 | 1.00 | 103.50 | N |
| ATOM | 3443 | CA | ALA | B | 671 | −90.045 | 70.172 | −30.584 | 1.00 | 102.63 | C |
| ATOM | 3444 | CB | ALA | B | 671 | −90.734 | 69.700 | −31.852 | 1.00 | 102.68 | C |
| ATOM | 3445 | C | ALA | B | 671 | −88.626 | 69.671 | −30.551 | 1.00 | 102.05 | C |
| ATOM | 3446 | O | ALA | B | 671 | −87.751 | 70.194 | −31.255 | 1.00 | 101.78 | O |
| ATOM | 3447 | N | VAL | B | 672 | −88.409 | 68.639 | −29.715 | 1.00 | 98.57 | N |
| ATOM | 3448 | CA | VAL | B | 672 | −87.128 | 67.956 | −29.538 | 1.00 | 97.51 | C |
| ATOM | 3449 | CB | VAL | B | 672 | −87.063 | 67.254 | −28.166 | 1.00 | 97.29 | C |
| ATOM | 3450 | CG1 | VAL | B | 672 | −85.709 | 66.595 | −27.963 | 1.00 | 97.24 | C |
| ATOM | 3451 | CG2 | VAL | B | 672 | −87.360 | 68.223 | −27.039 | 1.00 | 96.37 | C |
| ATOM | 3452 | C | VAL | B | 672 | −87.071 | 66.945 | −30.680 | 1.00 | 97.19 | C |
| ATOM | 3453 | O | VAL | B | 672 | −87.936 | 66.062 | −30.741 | 1.00 | 97.15 | O |
| ATOM | 3454 | N | THR | B | 673 | −86.084 | 67.082 | −31.590 | 1.00 | 93.85 | N |
| ATOM | 3455 | CA | THR | B | 673 | −86.007 | 66.179 | −32.738 | 1.00 | 93.22 | C |
| ATOM | 3456 | CB | THR | B | 673 | −86.082 | 66.971 | −34.055 | 1.00 | 93.20 | C |
| ATOM | 3457 | OG1 | THR | B | 673 | −87.252 | 67.789 | −34.046 | 1.00 | 93.18 | O |
| ATOM | 3458 | CG2 | THR | B | 673 | −86.115 | 66.071 | −35.288 | 1.00 | 93.30 | C |
| ATOM | 3459 | C | THR | B | 673 | −84.862 | 65.181 | −32.725 | 1.00 | 92.78 | C |
| ATOM | 3460 | O | THR | B | 673 | −83.703 | 65.600 | −32.638 | 1.00 | 92.70 | O |
| ATOM | 3461 | N | ALA | B | 674 | −85.193 | 63.863 | −32.857 | 1.00 | 85.71 | N |
| ATOM | 3462 | CA | ALA | B | 674 | −84.223 | 62.776 | −32.942 | 1.00 | 85.33 | C |
| ATOM | 3463 | CB | ALA | B | 674 | −84.859 | 61.471 | −32.509 | 1.00 | 85.28 | C |
| ATOM | 3464 | C | ALA | B | 674 | −83.760 | 62.709 | −34.412 | 1.00 | 85.29 | C |
| ATOM | 3465 | O | ALA | B | 674 | −84.589 | 62.797 | −35.317 | 1.00 | 85.26 | O |
| ATOM | 3466 | N | VAL | B | 675 | −82.442 | 62.626 | −34.650 | 1.00 | 81.79 | N |
| ATOM | 3467 | CA | VAL | B | 675 | −81.863 | 62.631 | −35.999 | 1.00 | 82.25 | C |
| ATOM | 3468 | CB | VAL | B | 675 | −81.074 | 63.949 | −36.260 | 1.00 | 82.10 | C |
| ATOM | 3469 | CG1 | VAL | B | 675 | −80.323 | 63.902 | −37.582 | 1.00 | 81.84 | C |
| ATOM | 3470 | CG2 | VAL | B | 675 | −81.986 | 65.173 | −36.207 | 1.00 | 81.53 | C |
| ATOM | 3471 | C | VAL | B | 675 | −81.012 | 61.389 | −36.259 | 1.00 | 82.96 | C |
| ATOM | 3472 | O | VAL | B | 675 | −79.932 | 61.222 | −35.671 | 1.00 | 82.87 | O |

TABLE 14-continued

PCSK9 and AX132 Fab complex x-ray structure

| | | | | | | | | | | |
|---|---|---|---|---|---|---|---|---|---|---|
| ATOM | 3473 | N | ALA | B | 676 | −81.483 | 60.541 | −37.182 | 1.00 | 83.86 N |
| ATOM | 3474 | CA | ALA | B | 676 | −80.804 | 59.298 | −37.538 | 1.00 | 84.66 C |
| ATOM | 3475 | CB | ALA | B | 676 | −81.787 | 58.148 | −37.422 | 1.00 | 84.58 C |
| ATOM | 3476 | C | ALA | B | 676 | −80.159 | 59.282 | −38.926 | 1.00 | 85.33 C |
| ATOM | 3477 | O | ALA | B | 676 | −80.844 | 59.573 | −39.898 | 1.00 | 85.57 O |
| ATOM | 3478 | N | ILE | B | 677 | −78.866 | 58.922 | −39.027 | 1.00 | 85.93 N |
| ATOM | 3479 | CA | ILE | B | 677 | −78.177 | 58.793 | −40.309 | 1.00 | 87.29 C |
| ATOM | 3480 | CB | ILE | B | 677 | −76.731 | 59.365 | −40.279 | 1.00 | 87.10 C |
| ATOM | 3481 | CG1 | ILE | B | 677 | −76.739 | 60.894 | −40.163 | 1.00 | 86.31 C |
| ATOM | 3482 | CD1 | ILE | B | 677 | −75.397 | 61.517 | −39.806 | 1.00 | 85.43 C |
| ATOM | 3483 | CG2 | ILE | B | 677 | −75.901 | 58.886 | −41.506 | 1.00 | 87.10 C |
| ATOM | 3484 | C | ILE | B | 677 | −78.200 | 57.285 | −40.643 | 1.00 | 88.69 C |
| ATOM | 3485 | O | ILE | B | 677 | −77.514 | 56.508 | −39.976 | 1.00 | 88.82 O |
| ATOM | 3486 | N | CYS | B | 678 | −78.983 | 56.879 | −41.662 | 1.00 | 95.76 N |
| ATOM | 3487 | CA | CYS | B | 678 | −79.116 | 55.479 | −42.075 | 1.00 | 97.30 C |
| ATOM | 3488 | CB | CYS | B | 678 | −80.583 | 55.115 | −42.238 | 1.00 | 96.90 C |
| ATOM | 3489 | SG | CYS | B | 678 | −81.590 | 55.474 | −40.783 | 1.00 | 96.44 S |
| ATOM | 3490 | C | CYS | B | 678 | −78.311 | 55.090 | −43.309 | 1.00 | 98.81 C |
| ATOM | 3491 | O | CYS | B | 678 | −78.330 | 55.806 | −44.300 | 1.00 | 98.90 O |
| ATOM | 3492 | N | CYS | B | 679 | −77.630 | 53.935 | −43.265 | 1.00 | 107.42 N |
| ATOM | 3493 | CA | CYS | B | 679 | −76.839 | 53.458 | −44.401 | 1.00 | 109.62 C |
| ATOM | 3494 | CB | CYS | B | 679 | −75.362 | 53.759 | −44.203 | 1.00 | 109.63 C |
| ATOM | 3495 | SG | CYS | B | 679 | −75.035 | 55.440 | −43.622 | 1.00 | 112.09 S |
| ATOM | 3496 | C | CYS | B | 679 | −77.080 | 51.998 | −44.779 | 1.00 | 110.70 C |
| ATOM | 3497 | O | CYS | B | 679 | −77.664 | 51.247 | −43.996 | 1.00 | 110.76 O |
| ATOM | 3498 | N | ARG | B | 680 | −76.668 | 51.620 | −46.014 | 1.00 | 115.73 N |
| ATOM | 3499 | CA | ARG | B | 680 | −76.780 | 50.274 | −46.602 | 1.00 | 117.24 C |
| ATOM | 3500 | CB | ARG | B | 680 | −78.259 | 49.884 | −46.889 | 1.00 | 117.32 C |
| ATOM | 3501 | CG | ARG | B | 680 | −78.910 | 50.627 | −48.051 | 1.00 | 118.28 C |
| ATOM | 3502 | CD | ARG | B | 680 | −80.001 | 49.809 | −48.728 | 1.00 | 120.20 C |
| ATOM | 3503 | NE | ARG | B | 680 | −80.512 | 50.497 | −49.921 | 1.00 | 121.55 N |
| ATOM | 3504 | CZ | ARG | B | 680 | −81.798 | 50.736 | −50.181 | 1.00 | 121.99 C |
| ATOM | 3505 | NH1 | ARG | B | 680 | −82.742 | 50.334 | −49.335 | 1.00 | 122.32 N |
| ATOM | 3506 | NH2 | ARG | B | 680 | −82.148 | 51.381 | −51.288 | 1.00 | 122.33 N |
| ATOM | 3507 | C | ARG | B | 680 | −75.906 | 50.131 | −47.873 | 1.00 | 118.03 C |
| ATOM | 3508 | O | ARG | B | 680 | −75.131 | 51.036 | −48.200 | 1.00 | 117.95 O |
| ATOM | 3509 | N | SER | B | 681 | −76.034 | 48.972 | −48.568 | 1.00 | 120.44 N |
| ATOM | 3510 | CA | SER | B | 681 | −75.376 | 48.656 | −49.838 | 1.00 | 121.18 C |
| ATOM | 3511 | CB | SER | B | 681 | −74.457 | 47.442 | −49.711 | 1.00 | 121.11 C |
| ATOM | 3512 | OG | SER | B | 681 | −73.359 | 47.574 | −50.602 | 1.00 | 121.38 O |
| ATOM | 3513 | C | SER | B | 681 | −76.549 | 48.417 | −50.821 | 1.00 | 121.58 C |
| ATOM | 3514 | O | SER | B | 681 | −77.264 | 47.411 | −50.695 | 1.00 | 121.71 O |
| ATOM | 3515 | N | ARG | B | 682 | −76.777 | 49.412 | −51.737 | 1.00 | 120.01 N |
| ATOM | 3516 | CA | ARG | B | 682 | −77.837 | 49.537 | −52.769 | 1.00 | 120.22 C |
| ATOM | 3517 | CB | ARG | B | 682 | −77.387 | 50.442 | −53.933 | 1.00 | 120.08 C |
| ATOM | 3518 | C | ARG | B | 682 | −78.603 | 48.269 | −53.249 | 1.00 | 120.27 C |
| ATOM | 3519 | O | ARG | B | 682 | −78.104 | 47.460 | −54.034 | 1.00 | 120.40 O |
| TER | 3520 | | ARG | B | 682 | | | | | |
| ATOM | 3521 | N | THR | A | 61 | −42.992 | 55.146 | −11.374 | 1.00 | 94.08 N |
| ATOM | 3522 | CA | THR | A | 61 | −43.825 | 54.985 | −12.583 | 1.00 | 94.03 C |
| ATOM | 3523 | CB | THR | A | 61 | −43.011 | 55.185 | −13.899 | 1.00 | 94.36 C |
| ATOM | 3524 | OG1 | THR | A | 61 | −41.662 | 55.588 | −13.626 | 1.00 | 95.12 O |
| ATOM | 3525 | CG2 | THR | A | 61 | −43.697 | 56.150 | −14.889 | 1.00 | 94.34 C |
| ATOM | 3526 | C | THR | A | 61 | −44.554 | 53.625 | −12.600 | 1.00 | 93.40 C |
| ATOM | 3527 | O | THR | A | 61 | −45.562 | 53.477 | −13.300 | 1.00 | 93.63 O |
| ATOM | 3528 | N | ALA | A | 62 | −44.025 | 52.632 | −11.841 | 1.00 | 86.60 N |
| ATOM | 3529 | CA | ALA | A | 62 | −44.604 | 51.293 | −11.751 | 1.00 | 85.19 C |
| ATOM | 3530 | CB | ALA | A | 62 | −43.541 | 50.270 | −11.387 | 1.00 | 85.12 C |
| ATOM | 3531 | C | ALA | A | 62 | −45.728 | 51.292 | −10.735 | 1.00 | 84.17 C |
| ATOM | 3532 | O | ALA | A | 62 | −45.572 | 51.771 | −9.607 | 1.00 | 84.03 O |
| ATOM | 3533 | N | THR | A | 63 | −46.872 | 50.770 | −11.152 | 1.00 | 78.31 N |
| ATOM | 3534 | CA | THR | A | 63 | −48.064 | 50.711 | −10.314 | 1.00 | 77.03 C |
| ATOM | 3535 | CB | THR | A | 63 | −49.247 | 51.320 | −11.047 | 1.00 | 77.14 C |
| ATOM | 3536 | OG1 | THR | A | 63 | −49.183 | 50.975 | −12.444 | 1.00 | 77.22 O |
| ATOM | 3537 | CG2 | THR | A | 63 | −49.309 | 52.826 | −10.855 | 1.00 | 77.10 C |
| ATOM | 3538 | C | THR | A | 63 | −48.358 | 49.331 | −9.758 | 1.00 | 75.91 C |
| ATOM | 3539 | O | THR | A | 63 | −47.909 | 48.323 | −10.298 | 1.00 | 75.80 O |
| ATOM | 3540 | N | PHE | A | 64 | −49.094 | 49.294 | −8.667 | 1.00 | 69.45 N |
| ATOM | 3541 | CA | PHE | A | 64 | −49.457 | 48.047 | −8.055 | 1.00 | 68.44 C |
| ATOM | 3542 | CB | PHE | A | 64 | −48.972 | 47.998 | −6.617 | 1.00 | 68.44 C |
| ATOM | 3543 | CG | PHE | A | 64 | −49.525 | 46.873 | −5.781 | 1.00 | 68.49 C |
| ATOM | 3544 | CD1 | PHE | A | 64 | −48.948 | 45.612 | −5.815 | 1.00 | 68.43 C |
| ATOM | 3545 | CE1 | PHE | A | 64 | −49.459 | 44.576 | −5.029 | 1.00 | 68.32 C |
| ATOM | 3546 | CZ | PHE | A | 64 | −50.539 | 44.802 | −4.201 | 1.00 | 68.09 C |
| ATOM | 3547 | CE2 | PHE | A | 64 | −51.113 | 46.050 | −4.146 | 1.00 | 67.74 C |
| ATOM | 3548 | CD2 | PHE | A | 64 | −50.610 | 47.083 | −4.936 | 1.00 | 67.80 C |
| ATOM | 3549 | C | PHE | A | 64 | −50.961 | 47.864 | −8.183 | 1.00 | 67.94 C |
| ATOM | 3550 | O | PHE | A | 64 | −51.731 | 48.822 | −8.140 | 1.00 | 67.79 O |

TABLE 14-continued

PCSK9 and AX132 Fab complex x-ray structure

| ATOM | 3551 | N | HIS | A | 65 | −51.371 | 46.616 | −8.385 | 1.00 | 70.21 | N |
|---|---|---|---|---|---|---|---|---|---|---|---|
| ATOM | 3552 | CA | HIS | A | 65 | −52.759 | 46.236 | −8.570 | 1.00 | 69.19 | C |
| ATOM | 3553 | CB | HIS | A | 65 | −53.006 | 45.898 | −10.048 | 1.00 | 69.21 | C |
| ATOM | 3554 | CG | HIS | A | 65 | −52.742 | 47.070 | −10.939 | 1.00 | 70.70 | C |
| ATOM | 3555 | ND1 | HIS | A | 65 | −51.443 | 47.456 | −11.268 | 1.00 | 72.28 | N |
| ATOM | 3556 | CE1 | HIS | A | 65 | −51.562 | 48.539 | −12.014 | 1.00 | 71.06 | C |
| ATOM | 3557 | NE2 | HIS | A | 65 | −52.840 | 48.865 | −12.190 | 1.00 | 71.69 | N |
| ATOM | 3558 | CD2 | HIS | A | 65 | −53.606 | 47.942 | −11.501 | 1.00 | 71.22 | C |
| ATOM | 3559 | C | HIS | A | 65 | −53.114 | 45.081 | −7.683 | 1.00 | 68.59 | C |
| ATOM | 3560 | O | HIS | A | 65 | −52.321 | 44.163 | −7.508 | 1.00 | 68.49 | O |
| ATOM | 3561 | N | ARG | A | 66 | −54.295 | 45.143 | −7.099 | 1.00 | 67.78 | N |
| ATOM | 3562 | CA | ARG | A | 66 | −54.830 | 44.100 | −6.240 | 1.00 | 67.53 | C |
| ATOM | 3563 | CB | ARG | A | 66 | −54.410 | 44.260 | −4.762 | 1.00 | 67.50 | C |
| ATOM | 3564 | CG | ARG | A | 66 | −54.777 | 45.560 | −4.108 | 1.00 | 68.39 | C |
| ATOM | 3565 | CD | ARG | A | 66 | −55.971 | 45.345 | −3.237 | 1.00 | 70.95 | C |
| ATOM | 3566 | NE | ARG | A | 66 | −56.472 | 46.607 | −2.707 | 1.00 | 72.19 | N |
| ATOM | 3567 | CZ | ARG | A | 66 | −57.602 | 46.744 | −2.019 | 1.00 | 72.89 | C |
| ATOM | 3568 | NH1 | ARG | A | 66 | −58.362 | 45.682 | −1.752 | 1.00 | 73.37 | N |
| ATOM | 3569 | NH2 | ARG | A | 66 | −57.984 | 47.942 | −1.595 | 1.00 | 74.64 | N |
| ATOM | 3570 | C | ARG | A | 66 | −56.332 | 43.981 | −6.436 | 1.00 | 67.14 | C |
| ATOM | 3571 | O | ARG | A | 66 | −56.961 | 44.864 | −7.024 | 1.00 | 67.05 | O |
| ATOM | 3572 | N | CYS | A | 67 | −56.902 | 42.877 | −5.981 | 1.00 | 67.36 | N |
| ATOM | 3573 | CA | CYS | A | 67 | −58.323 | 42.631 | −6.127 | 1.00 | 66.60 | C |
| ATOM | 3574 | CB | CYS | A | 67 | −58.642 | 41.169 | −5.830 | 1.00 | 66.74 | C |
| ATOM | 3575 | SG | CYS | A | 67 | −60.357 | 40.701 | −6.178 | 1.00 | 67.75 | S |
| ATOM | 3576 | C | CYS | A | 67 | −59.103 | 43.565 | −5.237 | 1.00 | 65.89 | C |
| ATOM | 3577 | O | CYS | A | 67 | −58.732 | 43.748 | −4.081 | 1.00 | 65.55 | O |
| ATOM | 3578 | N | ALA | A | 68 | −60.173 | 44.168 | −5.780 | 1.00 | 65.52 | N |
| ATOM | 3579 | CA | ALA | A | 68 | −61.061 | 45.076 | −5.044 | 1.00 | 64.94 | C |
| ATOM | 3580 | CB | ALA | A | 68 | −61.968 | 45.802 | −6.008 | 1.00 | 64.52 | C |
| ATOM | 3581 | C | ALA | A | 68 | −61.884 | 44.292 | −3.995 | 1.00 | 64.88 | C |
| ATOM | 3582 | O | ALA | A | 68 | −62.169 | 44.823 | −2.928 | 1.00 | 64.74 | O |
| ATOM | 3583 | N | LYS | A | 69 | −62.228 | 43.024 | −4.286 | 1.00 | 67.62 | N |
| ATOM | 3584 | CA | LYS | A | 69 | −62.968 | 42.154 | −3.366 | 1.00 | 68.11 | C |
| ATOM | 3585 | CB | LYS | A | 69 | −63.802 | 41.076 | −4.116 | 1.00 | 68.34 | C |
| ATOM | 3586 | CG | LYS | A | 69 | −64.420 | 41.527 | −5.465 | 1.00 | 70.40 | C |
| ATOM | 3587 | CD | LYS | A | 69 | −65.785 | 42.295 | −5.349 | 1.00 | 73.07 | C |
| ATOM | 3588 | CE | LYS | A | 69 | −66.163 | 43.111 | −6.579 | 1.00 | 73.40 | C |
| ATOM | 3589 | NZ | LYS | A | 69 | −67.238 | 44.114 | −6.294 | 1.00 | 73.28 | N |
| ATOM | 3590 | C | LYS | A | 69 | −61.946 | 41.533 | −2.403 | 1.00 | 68.01 | C |
| ATOM | 3591 | O | LYS | A | 69 | −61.297 | 40.544 | −2.732 | 1.00 | 67.83 | O |
| ATOM | 3592 | N | ASP | A | 70 | −61.781 | 42.142 | −1.225 | 1.00 | 72.25 | N |
| ATOM | 3593 | CA | ASP | A | 70 | −60.823 | 41.685 | −0.221 | 1.00 | 72.93 | C |
| ATOM | 3594 | CB | ASP | A | 70 | −60.900 | 42.495 | 1.069 | 1.00 | 73.96 | C |
| ATOM | 3595 | CG | ASP | A | 70 | −60.314 | 43.895 | 0.917 | 1.00 | 78.57 | C |
| ATOM | 3596 | OD1 | ASP | A | 70 | −59.122 | 44.095 | 1.329 | 1.00 | 82.61 | O |
| ATOM | 3597 | OD2 | ASP | A | 70 | −61.038 | 44.802 | 0.379 | 1.00 | 81.92 | O |
| ATOM | 3598 | C | ASP | A | 70 | −60.733 | 40.191 | 0.053 | 1.00 | 72.06 | C |
| ATOM | 3599 | O | ASP | A | 70 | −59.614 | 39.696 | 0.074 | 1.00 | 72.62 | O |
| ATOM | 3600 | N | PRO | A | 71 | −61.835 | 39.425 | 0.219 | 1.00 | 65.61 | N |
| ATOM | 3601 | CA | PRO | A | 71 | −61.692 | 37.979 | 0.491 | 1.00 | 64.69 | C |
| ATOM | 3602 | CB | PRO | A | 71 | −63.120 | 37.531 | 0.763 | 1.00 | 64.75 | C |
| ATOM | 3603 | CG | PRO | A | 71 | −63.888 | 38.762 | 1.004 | 1.00 | 65.16 | C |
| ATOM | 3604 | CD | PRO | A | 71 | −63.251 | 39.825 | 0.221 | 1.00 | 65.34 | C |
| ATOM | 3605 | C | PRO | A | 71 | −61.110 | 37.126 | −0.629 | 1.00 | 64.06 | C |
| ATOM | 3606 | O | PRO | A | 71 | −60.814 | 35.951 | −0.395 | 1.00 | 64.26 | O |
| ATOM | 3607 | N | TRP | A | 72 | −60.970 | 37.698 | −1.847 | 1.00 | 62.84 | N |
| ATOM | 3608 | CA | TRP | A | 72 | −60.442 | 37.025 | −3.029 | 1.00 | 61.80 | C |
| ATOM | 3609 | CB | TRP | A | 72 | −61.200 | 37.473 | −4.272 | 1.00 | 61.49 | C |
| ATOM | 3610 | CG | TRP | A | 72 | −62.596 | 36.957 | −4.323 | 1.00 | 60.52 | C |
| ATOM | 3611 | CD1 | TRP | A | 72 | −63.195 | 36.113 | −3.434 | 1.00 | 60.19 | C |
| ATOM | 3612 | NE1 | TRP | A | 72 | −64.489 | 35.863 | −3.815 | 1.00 | 59.75 | N |
| ATOM | 3613 | CE2 | TRP | A | 72 | −64.758 | 36.559 | −4.967 | 1.00 | 59.41 | C |
| ATOM | 3614 | CD2 | TRP | A | 72 | −63.577 | 37.249 | −5.323 | 1.00 | 59.63 | C |
| ATOM | 3615 | CE3 | TRP | A | 72 | −63.583 | 38.042 | −6.481 | 1.00 | 59.30 | C |
| ATOM | 3616 | CZ3 | TRP | A | 72 | −64.748 | 38.123 | −7.226 | 1.00 | 58.49 | C |
| ATOM | 3617 | CH2 | TRP | A | 72 | −65.891 | 37.403 | −6.863 | 1.00 | 57.68 | C |
| ATOM | 3618 | CZ2 | TRP | A | 72 | −65.922 | 36.618 | −5.741 | 1.00 | 57.93 | C |
| ATOM | 3619 | C | TRP | A | 72 | −58.977 | 37.271 | −3.205 | 1.00 | 61.81 | C |
| ATOM | 3620 | O | TRP | A | 72 | −58.348 | 36.600 | −4.020 | 1.00 | 61.74 | O |
| ATOM | 3621 | N | ARG | A | 73 | −58.419 | 38.234 | −2.453 | 1.00 | 63.78 | N |
| ATOM | 3622 | CA | ARG | A | 73 | −56.999 | 38.583 | −2.518 | 1.00 | 63.69 | C |
| ATOM | 3623 | CB | ARG | A | 73 | −56.719 | 39.805 | −1.667 | 1.00 | 63.71 | C |
| ATOM | 3624 | CG | ARG | A | 73 | −57.297 | 41.081 | −2.210 | 1.00 | 64.55 | C |
| ATOM | 3625 | CD | ARG | A | 73 | −57.007 | 42.217 | −1.260 | 1.00 | 66.07 | C |
| ATOM | 3626 | NE | ARG | A | 73 | −55.585 | 42.541 | −1.253 | 1.00 | 67.02 | N |
| ATOM | 3627 | CZ | ARG | A | 73 | −55.066 | 43.593 | −0.634 | 1.00 | 67.26 | C |
| ATOM | 3628 | NH1 | ARG | A | 73 | −53.756 | 43.823 | −0.688 | 1.00 | 67.03 | N |

TABLE 14-continued

| | | | | | PCSK9 and AX132 Fab complex x-ray structure | | | | | |
|---|---|---|---|---|---|---|---|---|---|---|
| ATOM | 3629 | NH2 | ARG | A | 73 | −55.856 | 44.444 | 0.021 | 1.00 | 68.05 N |
| ATOM | 3630 | C | ARG | A | 73 | −56.125 | 37.442 | −2.039 | 1.00 | 63.44 C |
| ATOM | 3631 | O | ARG | A | 73 | −56.520 | 36.701 | −1.125 | 1.00 | 63.26 O |
| ATOM | 3632 | N | LEU | A | 74 | −54.938 | 37.299 | −2.660 | 1.00 | 62.91 N |
| ATOM | 3633 | CA | LEU | A | 74 | −53.974 | 36.250 | −2.301 | 1.00 | 63.06 C |
| ATOM | 3634 | CB | LEU | A | 74 | −53.932 | 35.125 | −3.349 | 1.00 | 62.90 C |
| ATOM | 3635 | CG | LEU | A | 74 | −55.224 | 34.373 | −3.584 | 1.00 | 61.25 C |
| ATOM | 3636 | CD1 | LEU | A | 74 | −55.053 | 33.386 | −4.668 | 1.00 | 59.62 C |
| ATOM | 3637 | CD2 | LEU | A | 74 | −55.713 | 33.711 | −2.332 | 1.00 | 59.04 C |
| ATOM | 3638 | C | LEU | A | 74 | −52.586 | 36.842 | −2.076 | 1.00 | 63.27 C |
| ATOM | 3639 | O | LEU | A | 74 | −51.678 | 36.573 | −2.875 | 1.00 | 63.60 O |
| ATOM | 3640 | N | PRO | A | 75 | −52.399 | 37.647 | −0.988 | 1.00 | 64.69 N |
| ATOM | 3641 | CA | PRO | A | 75 | −51.076 | 38.265 | −0.739 | 1.00 | 64.81 C |
| ATOM | 3642 | CB | PRO | A | 75 | −51.294 | 39.086 | 0.528 | 1.00 | 64.47 C |
| ATOM | 3643 | CG | PRO | A | 75 | −52.506 | 38.486 | 1.148 | 1.00 | 64.57 C |
| ATOM | 3644 | CD | PRO | A | 75 | −53.370 | 38.037 | 0.053 | 1.00 | 64.42 C |
| ATOM | 3645 | C | PRO | A | 75 | −49.965 | 37.240 | −0.582 | 1.00 | 64.82 C |
| ATOM | 3646 | O | PRO | A | 75 | −50.240 | 36.119 | −0.168 | 1.00 | 65.20 O |
| ATOM | 3647 | N | GLY | A | 76 | −48.747 | 37.611 | −0.953 | 1.00 | 65.10 N |
| ATOM | 3648 | CA | GLY | A | 76 | −47.627 | 36.689 | −0.893 | 1.00 | 65.15 C |
| ATOM | 3649 | C | GLY | A | 76 | −47.257 | 36.182 | −2.270 | 1.00 | 65.43 C |
| ATOM | 3650 | O | GLY | A | 76 | −46.132 | 35.730 | −2.481 | 1.00 | 65.75 O |
| ATOM | 3651 | N | THR | A | 77 | −48.185 | 36.258 | −3.225 | 1.00 | 66.14 N |
| ATOM | 3652 | CA | THR | A | 77 | −47.894 | 35.832 | −4.588 | 1.00 | 66.17 C |
| ATOM | 3653 | CB | THR | A | 77 | −48.593 | 34.534 | −4.943 | 1.00 | 66.36 C |
| ATOM | 3654 | OG1 | THR | A | 77 | −48.498 | 33.644 | −3.813 | 1.00 | 67.43 O |
| ATOM | 3655 | CG2 | THR | A | 77 | −47.989 | 33.881 | −6.188 | 1.00 | 65.71 C |
| ATOM | 3656 | C | THR | A | 77 | −48.193 | 36.989 | −5.481 | 1.00 | 66.17 C |
| ATOM | 3657 | O | THR | A | 77 | −49.247 | 37.602 | −5.356 | 1.00 | 66.06 O |
| ATOM | 3658 | N | TYR | A | 78 | −47.234 | 37.335 | −6.338 | 1.00 | 65.71 N |
| ATOM | 3659 | CA | TYR | A | 78 | −47.327 | 38.487 | −7.228 | 1.00 | 66.03 C |
| ATOM | 3660 | CB | TYR | A | 78 | −46.449 | 39.646 | −6.681 | 1.00 | 65.51 C |
| ATOM | 3661 | CG | TYR | A | 78 | −46.823 | 40.011 | −5.260 | 1.00 | 64.46 C |
| ATOM | 3662 | CD1 | TYR | A | 78 | −47.766 | 41.000 | −5.000 | 1.00 | 62.96 C |
| ATOM | 3663 | CE1 | TYR | A | 78 | −48.169 | 41.290 | −3.702 | 1.00 | 61.90 C |
| ATOM | 3664 | CZ | TYR | A | 78 | −47.643 | 40.571 | −2.642 | 1.00 | 62.48 C |
| ATOM | 3665 | OH | TYR | A | 78 | −48.064 | 40.836 | −1.367 | 1.00 | 62.90 O |
| ATOM | 3666 | CE2 | TYR | A | 78 | −46.707 | 39.580 | −2.871 | 1.00 | 63.20 C |
| ATOM | 3667 | CD2 | TYR | A | 78 | −46.294 | 39.311 | −4.175 | 1.00 | 63.76 C |
| ATOM | 3668 | C | TYR | A | 78 | −46.927 | 38.144 | −8.640 | 1.00 | 67.03 C |
| ATOM | 3669 | O | TYR | A | 78 | −46.096 | 37.260 | −8.858 | 1.00 | 67.43 O |
| ATOM | 3670 | N | VAL | A | 79 | −47.515 | 38.844 | −9.603 | 1.00 | 66.76 N |
| ATOM | 3671 | CA | VAL | A | 79 | −47.203 | 38.667 | −11.018 | 1.00 | 67.72 C |
| ATOM | 3672 | CB | VAL | A | 79 | −48.450 | 38.357 | −11.887 | 1.00 | 67.49 C |
| ATOM | 3673 | CG1 | VAL | A | 79 | −48.165 | 38.537 | −13.373 | 1.00 | 66.92 C |
| ATOM | 3674 | CG2 | VAL | A | 79 | −48.959 | 36.957 | −11.613 | 1.00 | 67.53 C |
| ATOM | 3675 | C | VAL | A | 79 | −46.494 | 39.959 | −11.411 | 1.00 | 68.95 C |
| ATOM | 3676 | O | VAL | A | 79 | −47.116 | 41.031 | −11.473 | 1.00 | 69.13 O |
| ATOM | 3677 | N | VAL | A | 80 | −45.173 | 39.860 | −11.623 | 1.00 | 68.33 N |
| ATOM | 3678 | CA | VAL | A | 80 | −44.388 | 41.016 | −12.002 | 1.00 | 69.38 C |
| ATOM | 3679 | CB | VAL | A | 80 | −42.947 | 40.931 | −11.485 | 1.00 | 69.16 C |
| ATOM | 3680 | CG1 | VAL | A | 80 | −42.137 | 42.144 | −11.942 | 1.00 | 69.16 C |
| ATOM | 3681 | CG2 | VAL | A | 80 | −42.934 | 40.808 | −9.964 | 1.00 | 69.15 C |
| ATOM | 3682 | C | VAL | A | 80 | −44.485 | 41.158 | −13.504 | 1.00 | 70.51 C |
| ATOM | 3683 | O | VAL | A | 80 | −44.064 | 40.271 | −14.242 | 1.00 | 70.63 O |
| ATOM | 3684 | N | VAL | A | 81 | −45.088 | 42.250 | −13.943 | 1.00 | 71.08 N |
| ATOM | 3685 | CA | VAL | A | 81 | −45.278 | 42.520 | −15.352 | 1.00 | 72.85 C |
| ATOM | 3686 | CB | VAL | A | 81 | −46.738 | 42.913 | −15.672 | 1.00 | 72.46 C |
| ATOM | 3687 | CG1 | VAL | A | 81 | −46.901 | 43.266 | −17.136 | 1.00 | 71.97 C |
| ATOM | 3688 | CG2 | VAL | A | 81 | −47.690 | 41.790 | −15.294 | 1.00 | 72.64 C |
| ATOM | 3689 | C | VAL | A | 81 | −44.264 | 43.564 | −15.788 | 1.00 | 74.56 C |
| ATOM | 3690 | O | VAL | A | 81 | −44.175 | 44.653 | −15.203 | 1.00 | 74.54 O |
| ATOM | 3691 | N | LEU | A | 82 | −43.489 | 43.207 | −16.818 | 1.00 | 80.31 N |
| ATOM | 3692 | CA | LEU | A | 82 | −42.454 | 44.045 | −17.403 | 1.00 | 82.53 C |
| ATOM | 3693 | CB | LEU | A | 82 | −41.202 | 43.217 | −17.733 | 1.00 | 82.15 C |
| ATOM | 3694 | CG | LEU | A | 82 | −40.653 | 42.348 | −16.593 | 1.00 | 82.16 C |
| ATOM | 3695 | CD1 | LEU | A | 82 | −39.625 | 41.406 | −17.092 | 1.00 | 81.74 C |
| ATOM | 3696 | CD2 | LEU | A | 82 | −40.070 | 43.178 | −15.458 | 1.00 | 81.41 C |
| ATOM | 3697 | C | LEU | A | 82 | −42.980 | 44.810 | −18.618 | 1.00 | 84.46 C |
| ATOM | 3698 | O | LEU | A | 82 | −43.996 | 44.420 | −19.204 | 1.00 | 84.83 O |
| ATOM | 3699 | N | LYS | A | 83 | −42.301 | 45.919 | −18.974 | 1.00 | 91.85 N |
| ATOM | 3700 | CA | LYS | A | 83 | −42.649 | 46.806 | −20.083 | 1.00 | 94.25 C |
| ATOM | 3701 | CB | LYS | A | 83 | −41.678 | 47.993 | −20.147 | 1.00 | 94.21 C |
| ATOM | 3702 | CG | LYS | A | 83 | −41.986 | 49.105 | −19.144 | 1.00 | 95.08 C |
| ATOM | 3703 | CD | LYS | A | 83 | −40.695 | 49.669 | −18.537 | 1.00 | 97.23 C |
| ATOM | 3704 | CE | LYS | A | 83 | −40.735 | 51.157 | −18.255 | 1.00 | 97.94 C |
| ATOM | 3705 | NZ | LYS | A | 83 | −40.546 | 51.984 | −19.491 | 1.00 | 98.59 N |
| ATOM | 3706 | C | LYS | A | 83 | −42.769 | 46.063 | −21.424 | 1.00 | 95.90 C |

TABLE 14-continued

PCSK9 and AX132 Fab complex x-ray structure

| ATOM | 3707 | O | LYS | A | 83 | −42.054 | 45.079 | −21.642 | 1.00 | 95.76 | O |
|---|---|---|---|---|---|---|---|---|---|---|---|
| ATOM | 3708 | N | GLU | A | 84 | −43.701 | 46.526 | −22.296 | 1.00 | 102.18 | N |
| ATOM | 3709 | CA | GLU | A | 84 | −44.037 | 45.957 | −23.611 | 1.00 | 104.41 | C |
| ATOM | 3710 | CB | GLU | A | 84 | −44.691 | 47.000 | −24.543 | 1.00 | 104.70 | C |
| ATOM | 3711 | CG | GLU | A | 84 | −46.054 | 46.597 | −25.108 | 1.00 | 106.90 | C |
| ATOM | 3712 | CD | GLU | A | 84 | −46.181 | 45.235 | −25.779 | 1.00 | 109.87 | C |
| ATOM | 3713 | OE1 | GLU | A | 84 | −45.523 | 45.012 | −26.824 | 1.00 | 111.52 | O |
| ATOM | 3714 | OE2 | GLU | A | 84 | −46.950 | 44.392 | −25.259 | 1.00 | 110.62 | O |
| ATOM | 3715 | C | GLU | A | 84 | −42.984 | 45.117 | −24.364 | 1.00 | 105.41 | C |
| ATOM | 3716 | O | GLU | A | 84 | −43.124 | 43.886 | −24.441 | 1.00 | 105.62 | O |
| ATOM | 3717 | N | GLU | A | 85 | −41.941 | 45.786 | −24.914 | 1.00 | 107.79 | N |
| ATOM | 3718 | CA | GLU | A | 85 | −40.879 | 45.175 | −25.728 | 1.00 | 108.91 | C |
| ATOM | 3719 | CB | GLU | A | 85 | −40.238 | 46.222 | −26.663 | 1.00 | 109.11 | C |
| ATOM | 3720 | CG | GLU | A | 85 | −41.150 | 46.605 | −27.827 | 1.00 | 111.00 | C |
| ATOM | 3721 | CD | GLU | A | 85 | −40.772 | 47.798 | −28.696 | 1.00 | 113.16 | C |
| ATOM | 3722 | OE1 | GLU | A | 85 | −40.359 | 48.847 | −28.145 | 1.00 | 114.02 | O |
| ATOM | 3723 | OE2 | GLU | A | 85 | −40.916 | 47.685 | −29.938 | 1.00 | 113.67 | O |
| ATOM | 3724 | C | GLU | A | 85 | −39.828 | 44.309 | −25.030 | 1.00 | 109.16 | C |
| ATOM | 3725 | O | GLU | A | 85 | −38.950 | 43.780 | −25.710 | 1.00 | 109.04 | O |
| ATOM | 3726 | N | THR | A | 86 | −39.924 | 44.140 | −23.697 | 1.00 | 109.04 | N |
| ATOM | 3727 | CA | THR | A | 86 | −38.972 | 43.356 | −22.899 | 1.00 | 109.80 | C |
| ATOM | 3728 | CB | THR | A | 86 | −39.355 | 43.350 | −21.403 | 1.00 | 109.80 | C |
| ATOM | 3729 | OG1 | THR | A | 86 | −39.577 | 44.693 | −20.962 | 1.00 | 110.29 | O |
| ATOM | 3730 | CG2 | THR | A | 86 | −38.298 | 42.692 | −20.513 | 1.00 | 109.32 | C |
| ATOM | 3731 | C | THR | A | 86 | −38.697 | 41.965 | −23.462 | 1.00 | 110.40 | C |
| ATOM | 3732 | O | THR | A | 86 | −39.616 | 41.260 | −23.882 | 1.00 | 110.56 | O |
| ATOM | 3733 | N | HIS | A | 87 | −37.417 | 41.600 | −23.490 | 1.00 | 111.60 | N |
| ATOM | 3734 | CA | HIS | A | 87 | −36.944 | 40.308 | −23.955 | 1.00 | 112.22 | C |
| ATOM | 3735 | CB | HIS | A | 87 | −35.651 | 40.479 | −24.764 | 1.00 | 112.64 | C |
| ATOM | 3736 | CG | HIS | A | 87 | −35.087 | 39.185 | −25.249 | 1.00 | 115.04 | C |
| ATOM | 3737 | ND1 | HIS | A | 87 | −34.097 | 38.517 | −24.538 | 1.00 | 116.61 | N |
| ATOM | 3738 | CE1 | HIS | A | 87 | −33.845 | 37.413 | −25.224 | 1.00 | 116.85 | C |
| ATOM | 3739 | NE2 | HIS | A | 87 | −34.616 | 37.325 | −26.312 | 1.00 | 117.28 | N |
| ATOM | 3740 | CD2 | HIS | A | 87 | −35.421 | 38.447 | −26.334 | 1.00 | 116.55 | C |
| ATOM | 3741 | C | HIS | A | 87 | −36.743 | 39.422 | −22.712 | 1.00 | 111.92 | C |
| ATOM | 3742 | O | HIS | A | 87 | −36.530 | 39.955 | −21.617 | 1.00 | 111.91 | O |
| ATOM | 3743 | N | LEU | A | 88 | −36.834 | 38.083 | −22.879 | 1.00 | 108.74 | N |
| ATOM | 3744 | CA | LEU | A | 88 | −36.707 | 37.080 | −21.815 | 1.00 | 108.42 | C |
| ATOM | 3745 | CB | LEU | A | 88 | −36.914 | 35.664 | −22.370 | 1.00 | 108.37 | C |
| ATOM | 3746 | CG | LEU | A | 88 | −36.940 | 34.493 | −21.376 | 1.00 | 108.37 | C |
| ATOM | 3747 | CD1 | LEU | A | 88 | −37.980 | 34.690 | −20.308 | 1.00 | 108.28 | C |
| ATOM | 3748 | CD2 | LEU | A | 88 | −37.214 | 33.194 | −22.089 | 1.00 | 108.49 | C |
| ATOM | 3749 | C | LEU | A | 88 | −35.449 | 37.179 | −20.951 | 1.00 | 108.39 | C |
| ATOM | 3750 | O | LEU | A | 88 | −35.524 | 36.925 | −19.745 | 1.00 | 108.36 | O |
| ATOM | 3751 | N | SER | A | 89 | −34.306 | 37.554 | −21.554 | 1.00 | 107.40 | N |
| ATOM | 3752 | CA | SER | A | 89 | −33.040 | 37.724 | −20.841 | 1.00 | 107.18 | C |
| ATOM | 3753 | CB | SER | A | 89 | −31.958 | 38.227 | −21.791 | 1.00 | 107.30 | C |
| ATOM | 3754 | OG | SER | A | 89 | −32.389 | 39.349 | −22.545 | 1.00 | 107.73 | O |
| ATOM | 3755 | C | SER | A | 89 | −33.226 | 38.702 | −19.669 | 1.00 | 106.89 | C |
| ATOM | 3756 | O | SER | A | 89 | −32.757 | 38.414 | −18.572 | 1.00 | 106.96 | O |
| ATOM | 3757 | N | GLN | A | 90 | −33.954 | 39.828 | −19.900 | 1.00 | 105.98 | N |
| ATOM | 3758 | CA | GLN | A | 90 | −34.269 | 40.851 | −18.899 | 1.00 | 105.55 | C |
| ATOM | 3759 | CB | GLN | A | 90 | −34.803 | 42.130 | −19.540 | 1.00 | 105.69 | C |
| ATOM | 3760 | CG | GLN | A | 90 | −33.738 | 42.972 | −20.218 | 1.00 | 106.15 | C |
| ATOM | 3761 | CD | GLN | A | 90 | −34.174 | 43.457 | −21.582 | 1.00 | 106.52 | C |
| ATOM | 3762 | OE1 | GLN | A | 90 | −34.701 | 42.699 | −22.415 | 1.00 | 106.51 | O |
| ATOM | 3763 | NE2 | GLN | A | 90 | −33.953 | 44.737 | −21.845 | 1.00 | 106.74 | N |
| ATOM | 3764 | C | GLN | A | 90 | −35.279 | 40.333 | −17.894 | 1.00 | 105.10 | C |
| ATOM | 3765 | O | GLN | A | 90 | −35.180 | 40.702 | −16.723 | 1.00 | 105.02 | O |
| ATOM | 3766 | N | SER | A | 91 | −36.256 | 39.491 | −18.343 | 1.00 | 102.39 | N |
| ATOM | 3767 | CA | SER | A | 91 | −37.274 | 38.889 | −17.470 | 1.00 | 101.79 | C |
| ATOM | 3768 | CB | SER | A | 91 | −38.193 | 37.948 | −18.249 | 1.00 | 101.84 | C |
| ATOM | 3769 | OG | SER | A | 91 | −39.238 | 38.596 | −18.954 | 1.00 | 102.28 | O |
| ATOM | 3770 | C | SER | A | 91 | −36.561 | 38.108 | −16.373 | 1.00 | 101.27 | C |
| ATOM | 3771 | O | SER | A | 91 | −36.857 | 38.277 | −15.189 | 1.00 | 101.03 | O |
| ATOM | 3772 | N | GLU | A | 92 | −35.586 | 37.287 | −16.783 | 1.00 | 100.39 | N |
| ATOM | 3773 | CA | GLU | A | 92 | −34.776 | 36.464 | −15.894 | 1.00 | 100.06 | C |
| ATOM | 3774 | CB | GLU | A | 92 | −34.044 | 35.389 | −16.698 | 1.00 | 100.14 | C |
| ATOM | 3775 | CG | GLU | A | 92 | −34.964 | 34.502 | −17.515 | 1.00 | 101.12 | C |
| ATOM | 3776 | CD | GLU | A | 92 | −34.249 | 33.372 | −18.225 | 1.00 | 102.83 | C |
| ATOM | 3777 | OE1 | GLU | A | 92 | −33.476 | 33.651 | −19.174 | 1.00 | 103.80 | O |
| ATOM | 3778 | OE2 | GLU | A | 92 | −34.457 | 32.204 | −17.823 | 1.00 | 103.76 | O |
| ATOM | 3779 | C | GLU | A | 92 | −33.796 | 37.332 | −15.093 | 1.00 | 99.64 | C |
| ATOM | 3780 | O | GLU | A | 92 | −33.559 | 37.054 | −13.917 | 1.00 | 99.53 | O |
| ATOM | 3781 | N | ARG | A | 93 | −33.252 | 38.391 | −15.728 | 1.00 | 98.20 | N |
| ATOM | 3782 | CA | ARG | A | 93 | −32.324 | 39.345 | −15.129 | 1.00 | 97.82 | C |
| ATOM | 3783 | CB | ARG | A | 93 | −31.948 | 40.416 | −16.180 | 1.00 | 98.13 | C |
| ATOM | 3784 | CG | ARG | A | 93 | −30.644 | 41.194 | −15.937 | 1.00 | 99.80 | C |

TABLE 14-continued

| | | | | | | | | | | |
|---|---|---|---|---|---|---|---|---|---|---|
| | PCSK9 and AX132 Fab complex x-ray structure |

| | | | | | | | | | | |
|---|---|---|---|---|---|---|---|---|---|---|
| ATOM | 3785 | CD | ARG | A | 93 | −30.129 | 41.910 | −17.197 | 1.00 | 101.97 C |
| ATOM | 3786 | NE | ARG | A | 93 | −29.467 | 40.988 | −18.135 | 1.00 | 103.42 N |
| ATOM | 3787 | CZ | ARG | A | 93 | −29.900 | 40.713 | −19.368 | 1.00 | 104.31 C |
| ATOM | 3788 | NH1 | ARG | A | 93 | −30.993 | 41.300 | −19.844 | 1.00 | 104.87 N |
| ATOM | 3789 | NH2 | ARG | A | 93 | −29.237 | 39.857 | −20.137 | 1.00 | 104.19 N |
| ATOM | 3790 | C | ARG | A | 93 | −33.000 | 39.981 | −13.894 | 1.00 | 97.21 C |
| ATOM | 3791 | O | ARG | A | 93 | −32.505 | 39.807 | −12.772 | 1.00 | 96.98 O |
| ATOM | 3792 | N | THR | A | 94 | −34.167 | 40.664 | −14.112 | 1.00 | 93.34 N |
| ATOM | 3793 | CA | THR | A | 94 | −34.986 | 41.337 | −13.089 | 1.00 | 92.40 C |
| ATOM | 3794 | CB | THR | A | 94 | −36.149 | 42.137 | −13.722 | 1.00 | 92.32 C |
| ATOM | 3795 | OG1 | THR | A | 94 | −35.743 | 42.711 | −14.963 | 1.00 | 91.98 O |
| ATOM | 3796 | CG2 | THR | A | 94 | −36.642 | 43.246 | −12.826 | 1.00 | 92.59 C |
| ATOM | 3797 | C | THR | A | 94 | −35.426 | 40.359 | −11.987 | 1.00 | 91.90 C |
| ATOM | 3798 | O | THR | A | 94 | −35.417 | 40.728 | −10.813 | 1.00 | 91.73 O |
| ATOM | 3799 | N | ALA | A | 95 | −35.776 | 39.111 | −12.367 | 1.00 | 90.39 N |
| ATOM | 3800 | CA | ALA | A | 95 | −36.178 | 38.065 | −11.428 | 1.00 | 89.91 C |
| ATOM | 3801 | CB | ALA | A | 95 | −36.591 | 36.809 | −12.176 | 1.00 | 89.80 C |
| ATOM | 3802 | C | ALA | A | 95 | −35.030 | 37.763 | −10.478 | 1.00 | 89.75 C |
| ATOM | 3803 | O | ALA | A | 95 | −35.226 | 37.805 | −9.263 | 1.00 | 89.56 O |
| ATOM | 3804 | N | ARG | A | 96 | −33.819 | 37.503 | −11.036 | 1.00 | 91.58 N |
| ATOM | 3805 | CA | ARG | A | 96 | −32.603 | 37.207 | −10.270 | 1.00 | 91.34 C |
| ATOM | 3806 | CB | ARG | A | 96 | −31.462 | 36.736 | −11.179 | 1.00 | 91.22 C |
| ATOM | 3807 | C | ARG | A | 96 | −32.214 | 38.424 | −9.448 | 1.00 | 91.23 C |
| ATOM | 3808 | O | ARG | A | 96 | −31.926 | 38.264 | −8.264 | 1.00 | 91.23 O |
| ATOM | 3809 | N | ARG | A | 97 | −32.279 | 39.640 | −10.048 | 1.00 | 92.37 N |
| ATOM | 3810 | CA | ARG | A | 97 | −31.984 | 40.908 | −9.365 | 1.00 | 92.44 C |
| ATOM | 3811 | CB | ARG | A | 97 | −32.107 | 42.115 | −10.334 | 1.00 | 92.70 C |
| ATOM | 3812 | CG | ARG | A | 97 | −31.829 | 43.487 | −9.690 | 1.00 | 94.77 C |
| ATOM | 3813 | CD | ARG | A | 97 | −31.046 | 44.479 | −10.557 | 1.00 | 99.05 C |
| ATOM | 3814 | NE | ARG | A | 97 | −30.156 | 45.347 | −9.762 | 1.00 | 102.58 N |
| ATOM | 3815 | CZ | ARG | A | 97 | −28.901 | 45.033 | −9.409 | 1.00 | 104.00 C |
| ATOM | 3816 | NH1 | ARG | A | 97 | −28.367 | 43.869 | −9.779 | 1.00 | 104.30 N |
| ATOM | 3817 | NH2 | ARG | A | 97 | −28.174 | 45.881 | −8.685 | 1.00 | 104.49 N |
| ATOM | 3818 | C | ARG | A | 97 | −32.900 | 41.071 | −8.132 | 1.00 | 92.06 C |
| ATOM | 3819 | O | ARG | A | 97 | −32.456 | 41.576 | −7.090 | 1.00 | 91.94 O |
| ATOM | 3820 | N | LEU | A | 98 | −34.168 | 40.614 | −8.249 | 1.00 | 89.01 N |
| ATOM | 3821 | CA | LEU | A | 98 | −35.133 | 40.692 | −7.161 | 1.00 | 88.35 C |
| ATOM | 3822 | CB | LEU | A | 98 | −36.565 | 40.441 | −7.675 | 1.00 | 88.23 C |
| ATOM | 3823 | CG | LEU | A | 98 | −37.717 | 40.358 | −6.657 | 1.00 | 86.92 C |
| ATOM | 3824 | CD1 | LEU | A | 98 | −37.893 | 41.650 | −5.897 | 1.00 | 85.51 C |
| ATOM | 3825 | CD2 | LEU | A | 98 | −38.990 | 39.987 | −7.346 | 1.00 | 85.38 C |
| ATOM | 3826 | C | LEU | A | 98 | −34.767 | 39.743 | −6.033 | 1.00 | 88.29 C |
| ATOM | 3827 | O | LEU | A | 98 | −34.586 | 40.197 | −4.903 | 1.00 | 88.02 O |
| ATOM | 3828 | N | GLN | A | 99 | −34.634 | 38.440 | −6.343 | 1.00 | 89.27 N |
| ATOM | 3829 | CA | GLN | A | 99 | −34.303 | 37.381 | −5.382 | 1.00 | 89.54 C |
| ATOM | 3830 | CB | GLN | A | 99 | −33.991 | 36.078 | −6.121 | 1.00 | 89.39 C |
| ATOM | 3831 | CG | GLN | A | 99 | −35.159 | 35.469 | −6.851 | 1.00 | 89.38 C |
| ATOM | 3832 | CD | GLN | A | 99 | −35.074 | 33.967 | −6.829 | 1.00 | 89.63 C |
| ATOM | 3833 | OE1 | GLN | A | 99 | −34.580 | 33.333 | −7.783 | 1.00 | 89.30 O |
| ATOM | 3834 | NE2 | GLN | A | 99 | −35.562 | 33.360 | −5.734 | 1.00 | 88.93 N |
| ATOM | 3835 | C | GLN | A | 99 | −33.104 | 37.765 | −4.510 | 1.00 | 89.87 C |
| ATOM | 3836 | O | GLN | A | 99 | −33.076 | 37.461 | −3.305 | 1.00 | 89.84 O |
| ATOM | 3837 | N | ALA | A | 100 | −32.126 | 38.454 | −5.158 | 1.00 | 92.62 N |
| ATOM | 3838 | CA | ALA | A | 100 | −30.861 | 38.948 | −4.632 | 1.00 | 92.57 C |
| ATOM | 3839 | CB | ALA | A | 100 | −29.977 | 39.414 | −5.779 | 1.00 | 92.48 C |
| ATOM | 3840 | C | ALA | A | 100 | −31.049 | 40.073 | −3.639 | 1.00 | 92.61 C |
| ATOM | 3841 | O | ALA | A | 100 | −30.585 | 39.950 | −2.501 | 1.00 | 92.73 O |
| ATOM | 3842 | N | GLN | A | 101 | −31.713 | 41.170 | −4.062 | 1.00 | 91.54 N |
| ATOM | 3843 | CA | GLN | A | 101 | −31.960 | 42.316 | −3.201 | 1.00 | 91.53 C |
| ATOM | 3844 | CB | GLN | A | 101 | −32.680 | 43.415 | −3.967 | 1.00 | 91.53 C |
| ATOM | 3845 | CG | GLN | A | 101 | −31.748 | 44.103 | −4.951 | 1.00 | 92.66 C |
| ATOM | 3846 | CD | GLN | A | 101 | −32.418 | 45.048 | −5.921 | 1.00 | 93.49 C |
| ATOM | 3847 | OE1 | GLN | A | 101 | −33.454 | 45.666 | −5.642 | 1.00 | 94.00 O |
| ATOM | 3848 | NE2 | GLN | A | 101 | −31.820 | 45.198 | −7.088 | 1.00 | 93.98 N |
| ATOM | 3849 | C | GLN | A | 101 | −32.727 | 41.902 | −1.947 | 1.00 | 91.42 C |
| ATOM | 3850 | O | GLN | A | 101 | −32.433 | 42.403 | −0.864 | 1.00 | 91.36 O |
| ATOM | 3851 | N | ALA | A | 102 | −33.656 | 40.943 | −2.095 | 1.00 | 89.40 N |
| ATOM | 3852 | CA | ALA | A | 102 | −34.489 | 40.393 | −1.032 | 1.00 | 89.26 C |
| ATOM | 3853 | CB | ALA | A | 102 | −35.525 | 39.462 | −1.639 | 1.00 | 89.34 C |
| ATOM | 3854 | C | ALA | A | 102 | −33.670 | 39.643 | 0.016 | 1.00 | 89.33 C |
| ATOM | 3855 | O | ALA | A | 102 | −33.893 | 39.807 | 1.226 | 1.00 | 88.78 O |
| ATOM | 3856 | N | ALA | A | 103 | −32.726 | 38.810 | −0.471 | 1.00 | 91.22 N |
| ATOM | 3857 | CA | ALA | A | 103 | −31.824 | 37.998 | 0.339 | 1.00 | 91.41 C |
| ATOM | 3858 | CB | ALA | A | 103 | −30.920 | 37.189 | −0.559 | 1.00 | 91.23 C |
| ATOM | 3859 | C | ALA | A | 103 | −30.993 | 38.867 | 1.290 | 1.00 | 91.64 C |
| ATOM | 3860 | O | ALA | A | 103 | −30.890 | 38.530 | 2.476 | 1.00 | 91.67 O |
| ATOM | 3861 | N | ARG | A | 104 | −30.449 | 40.012 | 0.799 | 1.00 | 94.32 N |
| ATOM | 3862 | CA | ARG | A | 104 | −29.663 | 40.899 | 1.654 | 1.00 | 94.63 C |

TABLE 14-continued

PCSK9 and AX132 Fab complex x-ray structure

| ATOM | 3863 | CB | ARG | A | 104 | −28.583 | 41.665 | 0.885 | 1.00 | 94.83 | C |
|---|---|---|---|---|---|---|---|---|---|---|---|
| ATOM | 3864 | CG | ARG | A | 104 | −29.067 | 42.802 | 0.027 | 1.00 | 96.25 | C |
| ATOM | 3865 | CD | ARG | A | 104 | −27.874 | 43.433 | −0.654 | 1.00 | 99.40 | C |
| ATOM | 3866 | NE | ARG | A | 104 | −27.452 | 42.662 | −1.828 | 1.00 | 101.85 | N |
| ATOM | 3867 | CZ | ARG | A | 104 | −27.671 | 43.032 | −3.088 | 1.00 | 103.05 | C |
| ATOM | 3868 | NH1 | ARG | A | 104 | −28.292 | 44.181 | −3.356 | 1.00 | 103.65 | N |
| ATOM | 3869 | NH2 | ARG | A | 104 | −27.261 | 42.264 | −4.092 | 1.00 | 103.39 | N |
| ATOM | 3870 | C | ARG | A | 104 | −30.469 | 41.734 | 2.686 | 1.00 | 94.43 | C |
| ATOM | 3871 | O | ARG | A | 104 | −30.007 | 42.773 | 3.178 | 1.00 | 94.68 | O |
| ATOM | 3872 | N | ARG | A | 105 | −31.691 | 41.250 | 3.002 | 1.00 | 92.86 | N |
| ATOM | 3873 | CA | ARG | A | 105 | −32.636 | 41.790 | 3.982 | 1.00 | 92.14 | C |
| ATOM | 3874 | CB | ARG | A | 105 | −33.644 | 42.787 | 3.381 | 1.00 | 91.95 | C |
| ATOM | 3875 | CG | ARG | A | 105 | −33.428 | 43.105 | 1.915 | 1.00 | 92.08 | C |
| ATOM | 3876 | CD | ARG | A | 105 | −33.438 | 44.586 | 1.583 | 1.00 | 92.24 | C |
| ATOM | 3877 | NE | ARG | A | 105 | −32.759 | 44.822 | 0.305 | 1.00 | 93.09 | N |
| ATOM | 3878 | CZ | ARG | A | 105 | −32.665 | 46.001 | −0.304 | 1.00 | 93.45 | C |
| ATOM | 3879 | NH1 | ARG | A | 105 | −32.019 | 46.108 | −1.462 | 1.00 | 93.87 | N |
| ATOM | 3880 | NH2 | ARG | A | 105 | −33.218 | 47.084 | 0.239 | 1.00 | 92.83 | N |
| ATOM | 3881 | C | ARG | A | 105 | −33.305 | 40.591 | 4.655 | 1.00 | 91.76 | C |
| ATOM | 3882 | O | ARG | A | 105 | −34.331 | 40.718 | 5.320 | 1.00 | 91.78 | O |
| ATOM | 3883 | N | GLY | A | 106 | −32.669 | 39.435 | 4.481 | 1.00 | 92.07 | N |
| ATOM | 3884 | CA | GLY | A | 106 | −33.080 | 38.152 | 5.033 | 1.00 | 91.54 | C |
| ATOM | 3885 | C | GLY | A | 106 | −34.368 | 37.585 | 4.478 | 1.00 | 91.23 | C |
| ATOM | 3886 | O | GLY | A | 106 | −35.000 | 36.770 | 5.159 | 1.00 | 91.33 | O |
| ATOM | 3887 | N | TYR | A | 107 | −34.772 | 37.993 | 3.236 | 1.00 | 91.05 | N |
| ATOM | 3888 | CA | TYR | A | 107 | −36.023 | 37.498 | 2.641 | 1.00 | 90.30 | C |
| ATOM | 3889 | CB | TYR | A | 107 | −36.851 | 38.620 | 1.995 | 1.00 | 90.38 | C |
| ATOM | 3890 | CG | TYR | A | 107 | −37.421 | 39.660 | 2.931 | 1.00 | 90.13 | C |
| ATOM | 3891 | CD1 | TYR | A | 107 | −38.543 | 39.389 | 3.706 | 1.00 | 90.22 | C |
| ATOM | 3892 | CE1 | TYR | A | 107 | −39.084 | 40.353 | 4.552 | 1.00 | 90.37 | C |
| ATOM | 3893 | CZ | TYR | A | 107 | −38.527 | 41.620 | 4.595 | 1.00 | 90.32 | C |
| ATOM | 3894 | OH | TYR | A | 107 | −39.056 | 42.597 | 5.402 | 1.00 | 90.92 | O |
| ATOM | 3895 | CE2 | TYR | A | 107 | −37.433 | 41.920 | 3.808 | 1.00 | 90.06 | C |
| ATOM | 3896 | CD2 | TYR | A | 107 | −36.888 | 40.942 | 2.984 | 1.00 | 90.34 | C |
| ATOM | 3897 | C | TYR | A | 107 | −35.904 | 36.341 | 1.654 | 1.00 | 89.73 | C |
| ATOM | 3898 | O | TYR | A | 107 | −35.287 | 36.483 | 0.584 | 1.00 | 89.59 | O |
| ATOM | 3899 | N | LEU | A | 108 | −36.553 | 35.210 | 2.000 | 1.00 | 89.78 | N |
| ATOM | 3900 | CA | LEU | A | 108 | −36.596 | 34.024 | 1.147 | 1.00 | 89.15 | C |
| ATOM | 3901 | CB | LEU | A | 108 | −37.005 | 32.768 | 1.945 | 1.00 | 89.21 | C |
| ATOM | 3902 | C | LEU | A | 108 | −37.615 | 34.303 | 0.044 | 1.00 | 88.57 | C |
| ATOM | 3903 | O | LEU | A | 108 | −38.684 | 34.859 | 0.306 | 1.00 | 88.75 | O |
| ATOM | 3904 | N | THR | A | 109 | −37.271 | 33.969 | −1.194 | 1.00 | 88.76 | N |
| ATOM | 3905 | CA | THR | A | 109 | −38.167 | 34.182 | −2.334 | 1.00 | 87.99 | C |
| ATOM | 3906 | CB | THR | A | 109 | −37.788 | 35.446 | −3.139 | 1.00 | 87.90 | C |
| ATOM | 3907 | OG1 | THR | A | 109 | −36.479 | 35.304 | −3.706 | 1.00 | 88.28 | O |
| ATOM | 3908 | CG2 | THR | A | 109 | −37.888 | 36.713 | −2.328 | 1.00 | 87.68 | C |
| ATOM | 3909 | C | THR | A | 109 | −38.200 | 32.924 | −3.208 | 1.00 | 87.61 | C |
| ATOM | 3910 | O | THR | A | 109 | −37.363 | 32.029 | −3.042 | 1.00 | 87.87 | O |
| ATOM | 3911 | N | LYS | A | 110 | −39.173 | 32.852 | −4.121 | 1.00 | 84.64 | N |
| ATOM | 3912 | CA | LYS | A | 110 | −39.291 | 31.738 | −5.026 | 1.00 | 83.87 | C |
| ATOM | 3913 | CB | LYS | A | 110 | −40.053 | 30.557 | −4.399 | 1.00 | 84.18 | C |
| ATOM | 3914 | CG | LYS | A | 110 | −39.846 | 29.262 | −5.196 | 1.00 | 86.24 | C |
| ATOM | 3915 | CD | LYS | A | 110 | −40.683 | 28.061 | −4.705 | 1.00 | 88.77 | C |
| ATOM | 3916 | CE | LYS | A | 110 | −40.382 | 26.772 | −5.466 | 1.00 | 90.05 | C |
| ATOM | 3917 | NZ | LYS | A | 110 | −40.771 | 26.822 | −6.914 | 1.00 | 91.41 | N |
| ATOM | 3918 | C | LYS | A | 110 | −39.923 | 32.192 | −6.318 | 1.00 | 82.95 | C |
| ATOM | 3919 | O | LYS | A | 110 | −41.078 | 32.611 | −6.311 | 1.00 | 83.40 | O |
| ATOM | 3920 | N | ILE | A | 111 | −39.167 | 32.133 | −7.434 | 1.00 | 78.43 | N |
| ATOM | 3921 | CA | ILE | A | 111 | −39.712 | 32.489 | −8.736 | 1.00 | 77.08 | C |
| ATOM | 3922 | CB | ILE | A | 111 | −38.652 | 32.868 | −9.795 | 1.00 | 76.80 | C |
| ATOM | 3923 | CG1 | ILE | A | 111 | −37.712 | 33.990 | −9.317 | 1.00 | 76.57 | C |
| ATOM | 3924 | CD1 | ILE | A | 111 | −38.290 | 35.430 | −9.093 | 1.00 | 77.16 | C |
| ATOM | 3925 | CG2 | ILE | A | 111 | −39.300 | 33.187 | −11.155 | 1.00 | 76.13 | C |
| ATOM | 3926 | C | ILE | A | 111 | −40.459 | 31.232 | −9.106 | 1.00 | 76.77 | C |
| ATOM | 3927 | O | ILE | A | 111 | −39.839 | 30.180 | −9.312 | 1.00 | 77.12 | O |
| ATOM | 3928 | N | LEU | A | 112 | −41.787 | 31.319 | −9.123 | 1.00 | 75.11 | N |
| ATOM | 3929 | CA | LEU | A | 112 | −42.641 | 30.175 | −9.424 | 1.00 | 74.58 | C |
| ATOM | 3930 | CB | LEU | A | 112 | −44.014 | 30.333 | −8.758 | 1.00 | 74.58 | C |
| ATOM | 3931 | CG | LEU | A | 112 | −44.028 | 30.542 | −7.254 | 1.00 | 74.49 | C |
| ATOM | 3932 | CD1 | LEU | A | 112 | −45.400 | 30.996 | −6.785 | 1.00 | 74.48 | C |
| ATOM | 3933 | CD2 | LEU | A | 112 | −43.653 | 29.296 | −6.541 | 1.00 | 74.31 | C |
| ATOM | 3934 | C | LEU | A | 112 | −42.795 | 29.870 | −10.921 | 1.00 | 74.27 | C |
| ATOM | 3935 | O | LEU | A | 112 | −43.036 | 28.704 | −11.278 | 1.00 | 74.36 | O |
| ATOM | 3936 | N | HIS | A | 113 | −42.668 | 30.895 | −11.787 | 1.00 | 70.23 | N |
| ATOM | 3937 | CA | HIS | A | 113 | −42.822 | 30.737 | −13.228 | 1.00 | 70.12 | C |
| ATOM | 3938 | CB | HIS | A | 113 | −44.303 | 30.468 | −13.557 | 1.00 | 69.91 | C |
| ATOM | 3939 | CG | HIS | A | 113 | −44.636 | 30.283 | −15.001 | 1.00 | 69.54 | C |
| ATOM | 3940 | ND1 | HIS | A | 113 | −44.687 | 31.363 | −15.878 | 1.00 | 68.93 | N |

TABLE 14-continued

| | | | | | | | | | | |
|---|---|---|---|---|---|---|---|---|---|---|
| ATOM | 3941 | CE1 | HIS | A | 113 | −45.038 | 30.863 | −17.050 | 1.00 | 68.78 C |
| ATOM | 3942 | NE2 | HIS | A | 113 | −45.249 | 29.546 | −16.975 | 1.00 | 69.46 N |
| ATOM | 3943 | CD2 | HIS | A | 113 | −45.012 | 29.165 | −15.663 | 1.00 | 69.45 C |
| ATOM | 3944 | C | HIS | A | 113 | −42.332 | 31.997 | −13.912 | 1.00 | 70.51 C |
| ATOM | 3945 | O | HIS | A | 113 | −42.406 | 33.083 | −13.331 | 1.00 | 70.03 O |
| ATOM | 3946 | N | VAL | A | 114 | −41.808 | 31.843 | −15.152 | 1.00 | 73.95 N |
| ATOM | 3947 | CA | VAL | A | 114 | −41.298 | 32.949 | −15.962 | 1.00 | 74.60 C |
| ATOM | 3948 | CB | VAL | A | 114 | −39.759 | 32.926 | −16.188 | 1.00 | 74.41 C |
| ATOM | 3949 | CG1 | VAL | A | 114 | −39.344 | 33.815 | −17.351 | 1.00 | 74.28 C |
| ATOM | 3950 | CG2 | VAL | A | 114 | −39.009 | 33.334 | −14.922 | 1.00 | 74.15 C |
| ATOM | 3951 | C | VAL | A | 114 | −42.111 | 33.067 | −17.228 | 1.00 | 75.54 C |
| ATOM | 3952 | O | VAL | A | 114 | −42.191 | 32.135 | −18.031 | 1.00 | 75.89 O |
| ATOM | 3953 | N | PHE | A | 115 | −42.731 | 34.227 | −17.376 | 1.00 | 80.92 N |
| ATOM | 3954 | CA | PHE | A | 115 | −43.586 | 34.562 | −18.486 | 1.00 | 81.92 C |
| ATOM | 3955 | CB | PHE | A | 115 | −44.639 | 35.607 | −18.064 | 1.00 | 81.57 C |
| ATOM | 3956 | CG | PHE | A | 115 | −45.657 | 35.047 | −17.087 | 1.00 | 80.39 C |
| ATOM | 3957 | CD1 | PHE | A | 115 | −46.708 | 34.249 | −17.530 | 1.00 | 79.09 C |
| ATOM | 3958 | CE1 | PHE | A | 115 | −47.632 | 33.719 | −16.628 | 1.00 | 78.02 C |
| ATOM | 3959 | CZ | PHE | A | 115 | −47.499 | 33.970 | −15.279 | 1.00 | 77.62 C |
| ATOM | 3960 | CE2 | PHE | A | 115 | −46.454 | 34.737 | −14.818 | 1.00 | 78.07 C |
| ATOM | 3961 | CD2 | PHE | A | 115 | −45.540 | 35.285 | −15.722 | 1.00 | 78.92 C |
| ATOM | 3962 | C | PHE | A | 115 | −42.843 | 34.933 | −19.751 | 1.00 | 83.07 C |
| ATOM | 3963 | O | PHE | A | 115 | −41.997 | 35.835 | −19.758 | 1.00 | 83.24 O |
| ATOM | 3964 | N | HIS | A | 116 | −43.160 | 34.207 | −20.824 | 1.00 | 90.64 N |
| ATOM | 3965 | CA | HIS | A | 116 | −42.624 | 34.381 | −22.174 | 1.00 | 92.40 C |
| ATOM | 3966 | CB | HIS | A | 116 | −41.201 | 33.785 | −22.337 | 1.00 | 93.28 C |
| ATOM | 3967 | CG | HIS | A | 116 | −41.077 | 32.299 | −22.140 | 1.00 | 97.26 C |
| ATOM | 3968 | ND1 | HIS | A | 116 | −41.478 | 31.674 | −20.953 | 1.00 | 100.73 N |
| ATOM | 3969 | CE1 | HIS | A | 116 | −41.215 | 30.384 | −21.115 | 1.00 | 101.46 C |
| ATOM | 3970 | NE2 | HIS | A | 116 | −40.660 | 30.144 | −22.310 | 1.00 | 102.09 N |
| ATOM | 3971 | CD2 | HIS | A | 116 | −40.558 | 31.361 | −22.969 | 1.00 | 100.23 C |
| ATOM | 3972 | C | HIS | A | 116 | −43.634 | 33.829 | −23.188 | 1.00 | 92.48 C |
| ATOM | 3973 | O | HIS | A | 116 | −44.050 | 32.662 | −23.105 | 1.00 | 92.81 O |
| ATOM | 3974 | N | GLY | A | 117 | −44.051 | 34.691 | −24.102 | 1.00 | 90.93 N |
| ATOM | 3975 | CA | GLY | A | 117 | −45.027 | 34.327 | −25.113 | 1.00 | 90.80 C |
| ATOM | 3976 | C | GLY | A | 117 | −46.240 | 35.218 | −25.019 | 1.00 | 91.00 C |
| ATOM | 3977 | O | GLY | A | 117 | −46.557 | 35.937 | −25.982 | 1.00 | 91.62 O |
| ATOM | 3978 | N | LEU | A | 118 | −46.927 | 35.201 | −23.852 | 1.00 | 87.58 N |
| ATOM | 3979 | CA | LEU | A | 118 | −48.088 | 36.078 | −23.718 | 1.00 | 87.01 C |
| ATOM | 3980 | CB | LEU | A | 118 | −49.182 | 35.470 | −22.839 | 1.00 | 87.19 C |
| ATOM | 3981 | CG | LEU | A | 118 | −50.491 | 35.037 | −23.510 | 1.00 | 87.82 C |
| ATOM | 3982 | CD1 | LEU | A | 118 | −51.568 | 34.849 | −22.472 | 1.00 | 87.94 C |
| ATOM | 3983 | CD2 | LEU | A | 118 | −50.967 | 36.030 | −24.575 | 1.00 | 87.14 C |
| ATOM | 3984 | C | LEU | A | 118 | −47.705 | 37.470 | −23.214 | 1.00 | 86.38 C |
| ATOM | 3985 | O | LEU | A | 118 | −47.981 | 38.459 | −23.880 | 1.00 | 86.36 O |
| ATOM | 3986 | N | LEU | A | 119 | −47.074 | 37.540 | −22.041 | 1.00 | 83.97 N |
| ATOM | 3987 | CA | LEU | A | 119 | −46.673 | 38.791 | −21.420 | 1.00 | 83.10 C |
| ATOM | 3988 | CB | LEU | A | 119 | −47.568 | 39.056 | −20.183 | 1.00 | 83.27 C |
| ATOM | 3989 | CG | LEU | A | 119 | −49.077 | 39.314 | −20.409 | 1.00 | 84.36 C |
| ATOM | 3990 | CD1 | LEU | A | 119 | −49.871 | 39.090 | −19.137 | 1.00 | 84.64 C |
| ATOM | 3991 | CD2 | LEU | A | 119 | −49.371 | 40.720 | −21.008 | 1.00 | 85.48 C |
| ATOM | 3992 | C | LEU | A | 119 | −45.229 | 38.688 | −20.952 | 1.00 | 82.38 C |
| ATOM | 3993 | O | LEU | A | 119 | −44.767 | 37.580 | −20.689 | 1.00 | 82.51 O |
| ATOM | 3994 | N | PRO | A | 120 | −44.499 | 39.813 | −20.789 | 1.00 | 79.41 N |
| ATOM | 3995 | CA | PRO | A | 120 | −43.127 | 39.709 | −20.275 | 1.00 | 78.62 C |
| ATOM | 3996 | CB | PRO | A | 120 | −42.417 | 40.903 | −20.935 | 1.00 | 78.79 C |
| ATOM | 3997 | CG | PRO | A | 120 | −43.545 | 41.870 | −21.375 | 1.00 | 79.03 C |
| ATOM | 3998 | CD | PRO | A | 120 | −44.864 | 41.224 | −21.052 | 1.00 | 79.38 C |
| ATOM | 3999 | C | PRO | A | 120 | −43.121 | 39.827 | −18.745 | 1.00 | 77.86 C |
| ATOM | 4000 | O | PRO | A | 120 | −43.469 | 40.869 | −18.194 | 1.00 | 77.99 O |
| ATOM | 4001 | N | GLY | A | 121 | −42.747 | 38.776 | −18.051 | 1.00 | 74.71 N |
| ATOM | 4002 | CA | GLY | A | 121 | −42.714 | 38.879 | −16.603 | 1.00 | 73.64 C |
| ATOM | 4003 | C | GLY | A | 121 | −42.383 | 37.594 | −15.901 | 1.00 | 73.19 C |
| ATOM | 4004 | O | GLY | A | 121 | −41.774 | 36.705 | −16.493 | 1.00 | 73.07 O |
| ATOM | 4005 | N | PHE | A | 122 | −42.783 | 37.497 | −14.629 | 1.00 | 72.55 N |
| ATOM | 4006 | CA | PHE | A | 122 | −42.575 | 36.315 | −13.794 | 1.00 | 72.16 C |
| ATOM | 4007 | CB | PHE | A | 122 | −41.104 | 36.163 | −13.373 | 1.00 | 71.78 C |
| ATOM | 4008 | CG | PHE | A | 122 | −40.538 | 37.359 | −12.656 | 1.00 | 70.60 C |
| ATOM | 4009 | CD1 | PHE | A | 122 | −39.948 | 38.400 | −13.367 | 1.00 | 69.65 C |
| ATOM | 4010 | CE1 | PHE | A | 122 | −39.431 | 39.512 | −12.706 | 1.00 | 69.74 C |
| ATOM | 4011 | CZ | PHE | A | 122 | −39.504 | 39.590 | −11.329 | 1.00 | 69.97 C |
| ATOM | 4012 | CE2 | PHE | A | 122 | −40.080 | 38.561 | −10.605 | 1.00 | 69.86 C |
| ATOM | 4013 | CD2 | PHE | A | 122 | −40.589 | 37.446 | −11.268 | 1.00 | 70.03 C |
| ATOM | 4014 | C | PHE | A | 122 | −43.485 | 36.339 | −12.575 | 1.00 | 72.41 C |
| ATOM | 4015 | O | PHE | A | 122 | −43.845 | 37.417 | −12.079 | 1.00 | 72.62 O |
| ATOM | 4016 | N | LEU | A | 123 | −43.850 | 35.146 | −12.102 | 1.00 | 71.35 N |
| ATOM | 4017 | CA | LEU | A | 123 | −44.689 | 34.938 | −10.928 | 1.00 | 71.32 C |
| ATOM | 4018 | CB | LEU | A | 123 | −45.588 | 33.706 | −11.156 | 1.00 | 71.45 C |

TABLE 14-continued

PCSK9 and AX132 Fab complex x-ray structure

| ATOM | 4019 | CG  | LEU | A | 123 | −46.407 | 33.184 | −9.985  | 1.00 | 71.79 | C |
|------|------|-----|-----|---|-----|---------|--------|---------|------|-------|---|
| ATOM | 4020 | CD1 | LEU | A | 123 | −47.567 | 34.116 | −9.673  | 1.00 | 72.22 | C |
| ATOM | 4021 | CD2 | LEU | A | 123 | −46.943 | 31.817 | −10.296 | 1.00 | 71.36 | C |
| ATOM | 4022 | C   | LEU | A | 123 | −43.749 | 34.746 | −9.743  | 1.00 | 71.15 | C |
| ATOM | 4023 | O   | LEU | A | 123 | −42.853 | 33.910 | −9.801  | 1.00 | 71.24 | O |
| ATOM | 4024 | N   | VAL | A | 124 | −43.921 | 35.526 | −8.684  | 1.00 | 71.84 | N |
| ATOM | 4025 | CA  | VAL | A | 124 | −43.021 | 35.422 | −7.534  | 1.00 | 71.78 | C |
| ATOM | 4026 | CB  | VAL | A | 124 | −41.969 | 36.576 | −7.520  | 1.00 | 71.84 | C |
| ATOM | 4027 | CG1 | VAL | A | 124 | −42.624 | 37.963 | −7.403  | 1.00 | 71.15 | C |
| ATOM | 4028 | CG2 | VAL | A | 124 | −40.911 | 36.361 | −6.441  | 1.00 | 71.27 | C |
| ATOM | 4029 | C   | VAL | A | 124 | −43.701 | 35.243 | −6.192  | 1.00 | 71.82 | C |
| ATOM | 4030 | O   | VAL | A | 124 | −44.545 | 36.053 | −5.816  | 1.00 | 71.98 | O |
| ATOM | 4031 | N   | LYS | A | 125 | −43.316 | 34.205 | −5.462  | 1.00 | 73.15 | N |
| ATOM | 4032 | CA  | LYS | A | 125 | −43.822 | 33.981 | −4.117  | 1.00 | 73.52 | C |
| ATOM | 4033 | CB  | LYS | A | 125 | −43.860 | 32.480 | −3.785  | 1.00 | 73.77 | C |
| ATOM | 4034 | CG  | LYS | A | 125 | −44.453 | 32.158 | −2.419  | 1.00 | 75.03 | C |
| ATOM | 4035 | CD  | LYS | A | 125 | −44.431 | 30.659 | −2.133  | 1.00 | 77.65 | C |
| ATOM | 4036 | CE  | LYS | A | 125 | −45.562 | 30.252 | −1.220  | 1.00 | 78.44 | C |
| ATOM | 4037 | NZ  | LYS | A | 125 | −46.906 | 30.461 | −1.868  | 1.00 | 80.43 | N |
| ATOM | 4038 | C   | LYS | A | 125 | −42.824 | 34.738 | −3.213  | 1.00 | 73.44 | C |
| ATOM | 4039 | O   | LYS | A | 125 | −41.657 | 34.367 | −3.168  | 1.00 | 73.50 | O |
| ATOM | 4040 | N   | MET | A | 126 | −43.263 | 35.815 | −2.547  | 1.00 | 74.18 | N |
| ATOM | 4041 | CA  | MET | A | 126 | −42.411 | 36.649 | −1.681  | 1.00 | 74.20 | C |
| ATOM | 4042 | CB  | MET | A | 126 | −41.531 | 37.602 | −2.516  | 1.00 | 74.36 | C |
| ATOM | 4043 | CG  | MET | A | 126 | −42.316 | 38.391 | −3.520  | 1.00 | 75.18 | C |
| ATOM | 4044 | SD  | MET | A | 126 | −41.581 | 39.962 | −3.943  | 1.00 | 78.44 | S |
| ATOM | 4045 | CE  | MET | A | 126 | −42.995 | 41.032 | −3.741  | 1.00 | 77.19 | C |
| ATOM | 4046 | C   | MET | A | 126 | −43.241 | 37.473 | −0.711  | 1.00 | 74.00 | C |
| ATOM | 4047 | O   | MET | A | 126 | −44.452 | 37.577 | −0.868  | 1.00 | 74.18 | O |
| ATOM | 4048 | N   | SER | A | 127 | −42.586 | 38.085 | 0.273   | 1.00 | 74.27 | N |
| ATOM | 4049 | CA  | SER | A | 127 | −43.271 | 38.900 | 1.260   | 1.00 | 74.17 | C |
| ATOM | 4050 | CB  | SER | A | 127 | −42.361 | 39.142 | 2.454   | 1.00 | 74.01 | C |
| ATOM | 4051 | OG  | SER | A | 127 | −42.917 | 40.117 | 3.314   | 1.00 | 73.62 | O |
| ATOM | 4052 | C   | SER | A | 127 | −43.756 | 40.228 | 0.663   | 1.00 | 74.70 | C |
| ATOM | 4053 | O   | SER | A | 127 | −43.087 | 40.813 | −0.197  | 1.00 | 75.08 | O |
| ATOM | 4054 | N   | GLY | A | 128 | −44.916 | 40.688 | 1.132   | 1.00 | 76.07 | N |
| ATOM | 4055 | CA  | GLY | A | 128 | −45.507 | 41.948 | 0.709   | 1.00 | 75.96 | C |
| ATOM | 4056 | C   | GLY | A | 128 | −44.600 | 43.117 | 1.025   | 1.00 | 76.12 | C |
| ATOM | 4057 | O   | GLY | A | 128 | −44.691 | 44.161 | 0.382   | 1.00 | 76.50 | O |
| ATOM | 4058 | N   | ASP | A | 129 | −43.679 | 42.932 | 1.994   | 1.00 | 75.99 | N |
| ATOM | 4059 | CA  | ASP | A | 129 | −42.690 | 43.931 | 2.407   | 1.00 | 75.71 | C |
| ATOM | 4060 | CB  | ASP | A | 129 | −41.849 | 43.373 | 3.561   | 1.00 | 75.74 | C |
| ATOM | 4061 | CG  | ASP | A | 129 | −42.588 | 43.212 | 4.879   | 1.00 | 76.66 | C |
| ATOM | 4062 | OD1 | ASP | A | 129 | −43.780 | 43.637 | 4.959   | 1.00 | 77.70 | O |
| ATOM | 4063 | OD2 | ASP | A | 129 | −41.978 | 42.661 | 5.843   | 1.00 | 77.23 | O |
| ATOM | 4064 | C   | ASP | A | 129 | −41.756 | 44.310 | 1.262   | 1.00 | 75.35 | C |
| ATOM | 4065 | O   | ASP | A | 129 | −41.245 | 45.427 | 1.225   | 1.00 | 75.27 | O |
| ATOM | 4066 | N   | LEU | A | 130 | −41.532 | 43.372 | 0.334   | 1.00 | 72.31 | N |
| ATOM | 4067 | CA  | LEU | A | 130 | −40.650 | 43.577 | −0.796  | 1.00 | 72.16 | C |
| ATOM | 4068 | CB  | LEU | A | 130 | −40.086 | 42.234 | −1.248  | 1.00 | 72.44 | C |
| ATOM | 4069 | CG  | LEU | A | 130 | −39.214 | 41.518 | −0.227  | 1.00 | 73.24 | C |
| ATOM | 4070 | CD1 | LEU | A | 130 | −39.243 | 39.998 | −0.443  | 1.00 | 74.34 | C |
| ATOM | 4071 | CD2 | LEU | A | 130 | −37.794 | 42.090 | −0.214  | 1.00 | 73.18 | C |
| ATOM | 4072 | C   | LEU | A | 130 | −41.283 | 44.327 | −1.957  | 1.00 | 71.98 | C |
| ATOM | 4073 | O   | LEU | A | 130 | −40.645 | 44.495 | −2.997  | 1.00 | 71.98 | O |
| ATOM | 4074 | N   | LEU | A | 131 | −42.515 | 44.805 | −1.782  | 1.00 | 72.28 | N |
| ATOM | 4075 | CA  | LEU | A | 131 | −43.224 | 45.519 | −2.841  | 1.00 | 72.36 | C |
| ATOM | 4076 | CB  | LEU | A | 131 | −44.713 | 45.607 | −2.556  | 1.00 | 72.27 | C |
| ATOM | 4077 | CG  | LEU | A | 131 | −45.490 | 44.354 | −2.851  | 1.00 | 72.00 | C |
| ATOM | 4078 | CD1 | LEU | A | 131 | −46.830 | 44.400 | −2.152  | 1.00 | 72.02 | C |
| ATOM | 4079 | CD2 | LEU | A | 131 | −45.624 | 44.126 | −4.382  | 1.00 | 71.72 | C |
| ATOM | 4080 | C   | LEU | A | 131 | −42.669 | 46.861 | −3.291  | 1.00 | 72.59 | C |
| ATOM | 4081 | O   | LEU | A | 131 | −42.585 | 47.090 | −4.495  | 1.00 | 72.42 | O |
| ATOM | 4082 | N   | GLU | A | 132 | −42.300 | 47.743 | −2.345  | 1.00 | 74.85 | N |
| ATOM | 4083 | CA  | GLU | A | 132 | −41.749 | 49.072 | −2.623  | 1.00 | 75.47 | C |
| ATOM | 4084 | CB  | GLU | A | 132 | −41.481 | 49.822 | −1.313  | 1.00 | 75.52 | C |
| ATOM | 4085 | CG  | GLU | A | 132 | −40.977 | 51.238 | −1.542  | 1.00 | 75.63 | C |
| ATOM | 4086 | CD  | GLU | A | 132 | −40.813 | 52.067 | −0.286  | 1.00 | 76.52 | C |
| ATOM | 4087 | OE1 | GLU | A | 132 | −40.124 | 51.581 | 0.643   | 1.00 | 76.99 | O |
| ATOM | 4088 | OE2 | GLU | A | 132 | −41.367 | 53.195 | −0.226  | 1.00 | 76.49 | O |
| ATOM | 4089 | C   | GLU | A | 132 | −40.461 | 48.935 | −3.416  | 1.00 | 75.73 | C |
| ATOM | 4090 | O   | GLU | A | 132 | −40.226 | 49.689 | −4.372  | 1.00 | 75.85 | O |
| ATOM | 4091 | N   | LEU | A | 133 | −39.651 | 47.942 | −3.003  | 1.00 | 75.20 | N |
| ATOM | 4092 | CA  | LEU | A | 133 | −38.358 | 47.552 | −3.558  | 1.00 | 75.36 | C |
| ATOM | 4093 | CB  | LEU | A | 133 | −37.824 | 46.454 | −2.620  | 1.00 | 75.46 | C |
| ATOM | 4094 | CG  | LEU | A | 133 | −36.419 | 45.899 | −2.779  | 1.00 | 75.90 | C |
| ATOM | 4095 | CD1 | LEU | A | 133 | −36.028 | 45.162 | −1.510  | 1.00 | 76.47 | C |
| ATOM | 4096 | CD2 | LEU | A | 133 | −36.344 | 44.882 | −3.913  | 1.00 | 76.30 | C |

TABLE 14-continued

PCSK9 and AX132 Fab complex x-ray structure

| ATOM | 4097 | C | LEU | A | 133 | −38.510 | 47.025 | −5.002 | 1.00 | 75.29 | C |
|---|---|---|---|---|---|---|---|---|---|---|---|
| ATOM | 4098 | O | LEU | A | 133 | −37.793 | 47.484 | −5.891 | 1.00 | 75.23 | O |
| ATOM | 4099 | N | ALA | A | 134 | −39.425 | 46.041 | −5.205 | 1.00 | 73.18 | N |
| ATOM | 4100 | CA | ALA | A | 134 | −39.725 | 45.403 | −6.480 | 1.00 | 73.41 | C |
| ATOM | 4101 | CB | ALA | A | 134 | −40.666 | 44.241 | −6.271 | 1.00 | 73.33 | C |
| ATOM | 4102 | C | ALA | A | 134 | −40.315 | 46.385 | −7.497 | 1.00 | 73.84 | C |
| ATOM | 4103 | O | ALA | A | 134 | −39.999 | 46.301 | −8.690 | 1.00 | 73.72 | O |
| ATOM | 4104 | N | LEU | A | 135 | −41.153 | 47.329 | −7.043 | 1.00 | 74.72 | N |
| ATOM | 4105 | CA | LEU | A | 135 | −41.733 | 48.309 | −7.956 | 1.00 | 75.35 | C |
| ATOM | 4106 | CB | LEU | A | 135 | −42.880 | 49.050 | −7.283 | 1.00 | 75.03 | C |
| ATOM | 4107 | CG | LEU | A | 135 | −44.174 | 48.289 | −7.229 | 1.00 | 74.09 | C |
| ATOM | 4108 | CD1 | LEU | A | 135 | −44.935 | 48.673 | −6.047 | 1.00 | 74.22 | C |
| ATOM | 4109 | CD2 | LEU | A | 135 | −45.020 | 48.559 | −8.423 | 1.00 | 73.06 | C |
| ATOM | 4110 | C | LEU | A | 135 | −40.663 | 49.285 | −8.486 | 1.00 | 76.31 | C |
| ATOM | 4111 | O | LEU | A | 135 | −40.848 | 49.909 | −9.546 | 1.00 | 76.40 | O |
| ATOM | 4112 | N | LYS | A | 136 | −39.530 | 49.390 | −7.735 | 1.00 | 78.69 | N |
| ATOM | 4113 | CA | LYS | A | 136 | −38.383 | 50.232 | −8.049 | 1.00 | 79.02 | C |
| ATOM | 4114 | CB | LYS | A | 136 | −37.654 | 50.652 | −6.763 | 1.00 | 78.89 | C |
| ATOM | 4115 | CG | LYS | A | 136 | −38.294 | 51.859 | −6.084 | 1.00 | 79.70 | C |
| ATOM | 4116 | CD | LYS | A | 136 | −37.604 | 52.235 | −4.755 | 1.00 | 80.63 | C |
| ATOM | 4117 | CE | LYS | A | 136 | −38.268 | 53.405 | −4.035 | 1.00 | 81.81 | C |
| ATOM | 4118 | NZ | LYS | A | 136 | −37.773 | 53.576 | −2.632 | 1.00 | 81.67 | N |
| ATOM | 4119 | C | LYS | A | 136 | −37.440 | 49.570 | −9.071 | 1.00 | 79.35 | C |
| ATOM | 4120 | O | LYS | A | 136 | −36.595 | 50.260 | −9.640 | 1.00 | 79.86 | O |
| ATOM | 4121 | N | LEU | A | 137 | −37.598 | 48.261 | −9.335 | 1.00 | 78.98 | N |
| ATOM | 4122 | CA | LEU | A | 137 | −36.766 | 47.543 | −10.309 | 1.00 | 79.57 | C |
| ATOM | 4123 | CB | LEU | A | 137 | −36.973 | 46.013 | −10.249 | 1.00 | 79.67 | C |
| ATOM | 4124 | CG | LEU | A | 137 | −36.719 | 45.300 | −8.926 | 1.00 | 80.16 | C |
| ATOM | 4125 | CD1 | LEU | A | 137 | −37.285 | 43.908 | −8.960 | 1.00 | 79.93 | C |
| ATOM | 4126 | CD2 | LEU | A | 137 | −35.244 | 45.291 | −8.560 | 1.00 | 80.74 | C |
| ATOM | 4127 | C | LEU | A | 137 | −36.988 | 48.020 | −11.752 | 1.00 | 79.92 | C |
| ATOM | 4128 | O | LEU | A | 137 | −38.106 | 48.396 | −12.132 | 1.00 | 79.79 | O |
| ATOM | 4129 | N | PRO | A | 138 | −35.927 | 47.997 | −12.583 | 1.00 | 85.61 | N |
| ATOM | 4130 | CA | PRO | A | 138 | −36.094 | 48.415 | −13.981 | 1.00 | 85.93 | C |
| ATOM | 4131 | CB | PRO | A | 138 | −34.656 | 48.580 | −14.466 | 1.00 | 85.97 | C |
| ATOM | 4132 | CG | PRO | A | 138 | −33.896 | 47.564 | −13.677 | 1.00 | 86.02 | C |
| ATOM | 4133 | CD | PRO | A | 138 | −34.531 | 47.583 | −12.315 | 1.00 | 85.82 | C |
| ATOM | 4134 | C | PRO | A | 138 | −36.835 | 47.367 | −14.807 | 1.00 | 85.94 | C |
| ATOM | 4135 | O | PRO | A | 138 | −36.753 | 46.152 | −14.541 | 1.00 | 85.89 | O |
| ATOM | 4136 | N | HIS | A | 139 | −37.530 | 47.868 | −15.838 | 1.00 | 87.14 | N |
| ATOM | 4137 | CA | HIS | A | 139 | −38.343 | 47.136 | −16.809 | 1.00 | 87.20 | C |
| ATOM | 4138 | CB | HIS | A | 139 | −37.661 | 45.869 | −17.395 | 1.00 | 87.77 | C |
| ATOM | 4139 | CG | HIS | A | 139 | −36.221 | 46.038 | −17.807 | 1.00 | 90.16 | C |
| ATOM | 4140 | ND1 | HIS | A | 139 | −35.740 | 47.238 | −18.334 | 1.00 | 91.35 | N |
| ATOM | 4141 | CE1 | HIS | A | 139 | −34.455 | 47.029 | −18.573 | 1.00 | 92.08 | C |
| ATOM | 4142 | NE2 | HIS | A | 139 | −34.091 | 45.780 | −18.259 | 1.00 | 92.76 | N |
| ATOM | 4143 | CD2 | HIS | A | 139 | −35.206 | 45.140 | −17.768 | 1.00 | 91.72 | C |
| ATOM | 4144 | C | HIS | A | 139 | −39.743 | 46.848 | −16.295 | 1.00 | 86.36 | C |
| ATOM | 4145 | O | HIS | A | 139 | −40.634 | 46.652 | −17.113 | 1.00 | 86.53 | O |
| ATOM | 4146 | N | VAL | A | 140 | −39.952 | 46.860 | −14.964 | 1.00 | 82.97 | N |
| ATOM | 4147 | CA | VAL | A | 140 | −41.242 | 46.617 | −14.312 | 1.00 | 81.89 | C |
| ATOM | 4148 | CB | VAL | A | 140 | −41.074 | 46.509 | −12.780 | 1.00 | 81.92 | C |
| ATOM | 4149 | CG1 | VAL | A | 140 | −42.392 | 46.161 | −12.109 | 1.00 | 81.92 | C |
| ATOM | 4150 | CG2 | VAL | A | 140 | −39.993 | 45.497 | −12.411 | 1.00 | 81.73 | C |
| ATOM | 4151 | C | VAL | A | 140 | −42.304 | 47.673 | −14.712 | 1.00 | 81.26 | C |
| ATOM | 4152 | O | VAL | A | 140 | −42.130 | 48.869 | −14.454 | 1.00 | 81.13 | O |
| ATOM | 4153 | N | ASP | A | 141 | −43.395 | 47.212 | −15.357 | 1.00 | 80.40 | N |
| ATOM | 4154 | CA | ASP | A | 141 | −44.498 | 48.058 | −15.821 | 1.00 | 79.27 | C |
| ATOM | 4155 | CB | ASP | A | 141 | −45.162 | 47.427 | −17.057 | 1.00 | 79.20 | C |
| ATOM | 4156 | CG | ASP | A | 141 | −46.093 | 48.336 | −17.844 | 1.00 | 79.58 | C |
| ATOM | 4157 | OD1 | ASP | A | 141 | −46.144 | 49.555 | −17.541 | 1.00 | 80.20 | O |
| ATOM | 4158 | OD2 | ASP | A | 141 | −46.766 | 47.834 | −18.766 | 1.00 | 81.10 | O |
| ATOM | 4159 | C | ASP | A | 141 | −45.503 | 48.266 | −14.682 | 1.00 | 78.54 | C |
| ATOM | 4160 | O | ASP | A | 141 | −45.864 | 49.411 | −14.374 | 1.00 | 78.85 | O |
| ATOM | 4161 | N | TYR | A | 142 | −45.948 | 47.135 | −14.067 | 1.00 | 74.15 | N |
| ATOM | 4162 | CA | TYR | A | 142 | −46.852 | 47.015 | −12.924 | 1.00 | 72.68 | C |
| ATOM | 4163 | CB | TYR | A | 142 | −48.324 | 47.248 | −13.287 | 1.00 | 72.37 | C |
| ATOM | 4164 | CG | TYR | A | 142 | −48.906 | 46.336 | −14.344 | 1.00 | 71.40 | C |
| ATOM | 4165 | CD1 | TYR | A | 142 | −48.805 | 46.654 | −15.697 | 1.00 | 70.30 | C |
| ATOM | 4166 | CE1 | TYR | A | 142 | −49.380 | 45.843 | −16.681 | 1.00 | 70.62 | C |
| ATOM | 4167 | CZ | TYR | A | 142 | −50.076 | 44.695 | −16.316 | 1.00 | 70.61 | C |
| ATOM | 4168 | OH | TYR | A | 142 | −50.623 | 43.913 | −17.321 | 1.00 | 68.55 | O |
| ATOM | 4169 | CE2 | TYR | A | 142 | −50.212 | 44.369 | −14.967 | 1.00 | 70.46 | C |
| ATOM | 4170 | CD2 | TYR | A | 142 | −49.636 | 45.196 | −13.991 | 1.00 | 70.99 | C |
| ATOM | 4171 | C | TYR | A | 142 | −46.641 | 45.671 | −12.245 | 1.00 | 72.14 | C |
| ATOM | 4172 | O | TYR | A | 142 | −46.001 | 44.789 | −12.813 | 1.00 | 71.87 | O |
| ATOM | 4173 | N | ILE | A | 143 | −47.138 | 45.537 | −11.013 | 1.00 | 69.96 | N |
| ATOM | 4174 | CA | ILE | A | 143 | −47.067 | 44.325 | −10.193 | 1.00 | 69.49 | C |

TABLE 14-continued

PCSK9 and AX132 Fab complex x-ray structure

| ATOM | 4175 | CB  | ILE | A | 143 | −46.063 | 44.457 | −9.008  | 1.00 | 69.68 | C |
|------|------|-----|-----|---|-----|---------|--------|---------|------|-------|---|
| ATOM | 4176 | CG1 | ILE | A | 143 | −44.666 | 44.972 | −9.483  | 1.00 | 69.49 | C |
| ATOM | 4177 | CD1 | ILE | A | 143 | −43.375 | 44.443 | −8.782  | 1.00 | 68.82 | C |
| ATOM | 4178 | CG2 | ILE | A | 143 | −46.013 | 43.161 | −8.154  | 1.00 | 68.95 | C |
| ATOM | 4179 | C   | ILE | A | 143 | −48.482 | 44.029 | −9.699  | 1.00 | 69.45 | C |
| ATOM | 4180 | O   | ILE | A | 143 | −49.113 | 44.897 | −9.098  | 1.00 | 69.21 | O |
| ATOM | 4181 | N   | GLU | A | 144 | −48.979 | 42.807 | −9.956  | 1.00 | 71.72 | N |
| ATOM | 4182 | CA  | GLU | A | 144 | −50.317 | 42.405 | −9.528  | 1.00 | 71.53 | C |
| ATOM | 4183 | CB  | GLU | A | 144 | −51.202 | 41.960 | −10.708 | 1.00 | 71.48 | C |
| ATOM | 4184 | CG  | GLU | A | 144 | −52.658 | 42.320 | −10.459 | 1.00 | 73.34 | C |
| ATOM | 4185 | CD  | GLU | A | 144 | −53.734 | 41.708 | −11.339 | 1.00 | 75.76 | C |
| ATOM | 4186 | OE1 | GLU | A | 144 | −53.849 | 42.145 | −12.509 | 1.00 | 75.42 | O |
| ATOM | 4187 | OE2 | GLU | A | 144 | −54.475 | 40.812 | −10.852 | 1.00 | 76.83 | O |
| ATOM | 4188 | C   | GLU | A | 144 | −50.307 | 41.347 | −8.449  | 1.00 | 70.91 | C |
| ATOM | 4189 | O   | GLU | A | 144 | −49.687 | 40.305 | −8.615  | 1.00 | 71.23 | O |
| ATOM | 4190 | N   | GLU | A | 145 | −50.998 | 41.610 | −7.348  | 1.00 | 69.74 | N |
| ATOM | 4191 | CA  | GLU | A | 145 | −51.142 | 40.646 | −6.271  | 1.00 | 69.59 | C |
| ATOM | 4192 | CB  | GLU | A | 145 | −51.809 | 41.320 | −5.059  | 1.00 | 69.65 | C |
| ATOM | 4193 | CG  | GLU | A | 145 | −52.061 | 40.413 | −3.866  | 1.00 | 71.57 | C |
| ATOM | 4194 | CD  | GLU | A | 145 | −52.590 | 41.153 | −2.648  | 1.00 | 74.80 | C |
| ATOM | 4195 | OE1 | GLU | A | 145 | −53.829 | 41.212 | −2.480  | 1.00 | 77.48 | O |
| ATOM | 4196 | OE2 | GLU | A | 145 | −51.765 | 41.678 | −1.863  | 1.00 | 74.22 | O |
| ATOM | 4197 | C   | GLU | A | 145 | −52.051 | 39.535 | −6.823  | 1.00 | 69.32 | C |
| ATOM | 4198 | O   | GLU | A | 145 | −53.051 | 39.824 | −7.485  | 1.00 | 69.54 | O |
| ATOM | 4199 | N   | ASP | A | 146 | −51.707 | 38.277 | −6.574  | 1.00 | 69.08 | N |
| ATOM | 4200 | CA  | ASP | A | 146 | −52.530 | 37.166 | −7.028  | 1.00 | 68.70 | C |
| ATOM | 4201 | CB  | ASP | A | 146 | −51.882 | 35.831 | −6.636  | 1.00 | 69.08 | C |
| ATOM | 4202 | CG  | ASP | A | 146 | −52.124 | 34.665 | −7.594  | 1.00 | 70.22 | C |
| ATOM | 4203 | OD1 | ASP | A | 146 | −52.938 | 34.827 | −8.551  | 1.00 | 70.06 | O |
| ATOM | 4204 | OD2 | ASP | A | 146 | −51.496 | 33.578 | −7.388  | 1.00 | 71.69 | O |
| ATOM | 4205 | C   | ASP | A | 146 | −53.926 | 37.280 | −6.397  | 1.00 | 68.15 | C |
| ATOM | 4206 | O   | ASP | A | 146 | −54.077 | 37.892 | −5.329  | 1.00 | 68.20 | O |
| ATOM | 4207 | N   | SER | A | 147 | −54.946 | 36.735 | −7.080  | 1.00 | 66.95 | N |
| ATOM | 4208 | CA  | SER | A | 147 | −56.331 | 36.746 | −6.607  | 1.00 | 66.13 | C |
| ATOM | 4209 | CB  | SER | A | 147 | −57.129 | 37.895 | −7.208  | 1.00 | 65.93 | C |
| ATOM | 4210 | OG  | SER | A | 147 | −56.293 | 38.909 | −7.736  | 1.00 | 66.81 | O |
| ATOM | 4211 | C   | SER | A | 147 | −56.976 | 35.441 | −6.993  | 1.00 | 65.51 | C |
| ATOM | 4212 | O   | SER | A | 147 | −56.466 | 34.728 | −7.864  | 1.00 | 65.59 | O |
| ATOM | 4213 | N   | SER | A | 148 | −58.094 | 35.123 | −6.349  | 1.00 | 62.34 | N |
| ATOM | 4214 | CA  | SER | A | 148 | −58.833 | 33.915 | −6.614  | 1.00 | 61.23 | C |
| ATOM | 4215 | CB  | SER | A | 148 | −59.607 | 33.509 | −5.369  | 1.00 | 61.20 | C |
| ATOM | 4216 | OG  | SER | A | 148 | −58.747 | 32.994 | −4.365  | 1.00 | 61.41 | O |
| ATOM | 4217 | C   | SER | A | 148 | −59.803 | 34.109 | −7.767  | 1.00 | 60.82 | C |
| ATOM | 4218 | O   | SER | A | 148 | −60.365 | 35.198 | −7.938  | 1.00 | 61.26 | O |
| ATOM | 4219 | N   | VAL | A | 149 | −59.990 | 33.049 | −8.563  | 1.00 | 58.81 | N |
| ATOM | 4220 | CA  | VAL | A | 149 | −60.944 | 32.967 | −9.672  | 1.00 | 58.28 | C |
| ATOM | 4221 | CB  | VAL | A | 149 | −60.356 | 32.896 | −11.110 | 1.00 | 58.18 | C |
| ATOM | 4222 | CG1 | VAL | A | 149 | −59.501 | 34.111 | −11.425 | 1.00 | 57.52 | C |
| ATOM | 4223 | CG2 | VAL | A | 149 | −59.594 | 31.603 | −11.364 | 1.00 | 58.33 | C |
| ATOM | 4224 | C   | VAL | A | 149 | −61.855 | 31.779 | −9.329  | 1.00 | 58.22 | C |
| ATOM | 4225 | O   | VAL | A | 149 | −61.413 | 30.884 | −8.601  | 1.00 | 58.28 | O |
| ATOM | 4226 | N   | PHE | A | 150 | −63.110 | 31.768 | −9.804  | 1.00 | 57.53 | N |
| ATOM | 4227 | CA  | PHE | A | 150 | −64.024 | 30.697 | −9.449  | 1.00 | 57.21 | C |
| ATOM | 4228 | CB  | PHE | A | 150 | −64.996 | 31.178 | −8.378  | 1.00 | 56.45 | C |
| ATOM | 4229 | CG  | PHE | A | 150 | −64.355 | 31.762 | −7.158  | 1.00 | 55.56 | C |
| ATOM | 4230 | CD1 | PHE | A | 150 | −63.975 | 30.952 | −6.100  | 1.00 | 54.34 | C |
| ATOM | 4231 | CE1 | PHE | A | 150 | −63.397 | 31.504 | −4.956  | 1.00 | 54.41 | C |
| ATOM | 4232 | CZ  | PHE | A | 150 | −63.176 | 32.864 | −4.878  | 1.00 | 54.23 | C |
| ATOM | 4233 | CE2 | PHE | A | 150 | −63.537 | 33.677 | −5.921  | 1.00 | 54.50 | C |
| ATOM | 4234 | CD2 | PHE | A | 150 | −64.146 | 33.132 | −7.053  | 1.00 | 55.55 | C |
| ATOM | 4235 | C   | PHE | A | 150 | −64.878 | 30.262 | −10.570 | 1.00 | 57.91 | C |
| ATOM | 4236 | O   | PHE | A | 150 | −65.321 | 31.089 | −11.351 | 1.00 | 58.22 | O |
| ATOM | 4237 | N   | ALA | A | 151 | −65.213 | 28.966 | −10.586 | 1.00 | 59.21 | N |
| ATOM | 4238 | CA  | ALA | A | 151 | −66.127 | 28.355 | −11.532 | 1.00 | 59.60 | C |
| ATOM | 4239 | CB  | ALA | A | 151 | −66.339 | 26.901 | −11.148 | 1.00 | 59.54 | C |
| ATOM | 4240 | C   | ALA | A | 151 | −67.445 | 29.108 | −11.409 | 1.00 | 60.14 | C |
| ATOM | 4241 | O   | ALA | A | 151 | −67.848 | 29.444 | −10.283 | 1.00 | 60.22 | O |
| ATOM | 4242 | N   | GLN | A | 152 | −68.099 | 29.394 | −12.558 | 1.00 | 61.34 | N |
| ATOM | 4243 | CA  | GLN | A | 152 | −69.375 | 30.113 | −12.638 | 1.00 | 61.85 | C |
| ATOM | 4244 | CB  | GLN | A | 152 | −69.204 | 31.376 | −13.490 | 1.00 | 61.59 | C |
| ATOM | 4245 | CG  | GLN | A | 152 | −68.267 | 32.380 | −12.889 | 1.00 | 61.62 | C |
| ATOM | 4246 | CD  | GLN | A | 152 | −68.775 | 32.876 | −11.557 | 1.00 | 62.64 | C |
| ATOM | 4247 | OE1 | GLN | A | 152 | −69.726 | 33.667 | −11.461 | 1.00 | 63.19 | O |
| ATOM | 4248 | NE2 | GLN | A | 152 | −68.163 | 32.412 | −10.476 | 1.00 | 64.63 | N |
| ATOM | 4249 | C   | GLN | A | 152 | −70.545 | 29.222 | −13.155 | 1.00 | 62.70 | C |
| ATOM | 4250 | O   | GLN | A | 152 | −71.461 | 29.742 | −13.838 | 1.00 | 63.04 | O |
| ATOM | 4251 | OXT | GLN | A | 152 | −70.552 | 27.993 | −12.901 | 1.00 | 90.28 | O |
| TER  | 4252 |     | GLN | A | 152 |         |        |         |      |       |   |

TABLE 14-continued

PCSK9 and AX132 Fab complex x-ray structure

| ATOM | 4253 | N | GLU | H | 1 | −66.128 | −17.371 | −29.550 | 1.00 | 84.16 | N |
|------|------|-----|-----|---|---|---------|---------|---------|------|-------|---|
| ATOM | 4254 | CA | GLU | H | 1 | −67.436 | −17.005 | −29.032 | 1.00 | 84.28 | C |
| ATOM | 4255 | CB | GLU | H | 1 | −68.491 | −18.106 | −29.309 | 1.00 | 84.57 | C |
| ATOM | 4256 | CG | GLU | H | 1 | −68.364 | −19.339 | −28.418 | 1.00 | 86.38 | C |
| ATOM | 4257 | CD | GLU | H | 1 | −69.088 | −20.603 | −28.841 | 1.00 | 88.58 | C |
| ATOM | 4258 | OE1 | GLU | H | 1 | −68.431 | −21.670 | −28.871 | 1.00 | 88.46 | O |
| ATOM | 4259 | OE2 | GLU | H | 1 | −70.308 | −20.532 | −29.125 | 1.00 | 89.92 | O |
| ATOM | 4260 | C | GLU | H | 1 | −67.333 | −16.729 | −27.549 | 1.00 | 83.78 | C |
| ATOM | 4261 | O | GLU | H | 1 | −66.461 | −17.307 | −26.870 | 1.00 | 83.95 | O |
| ATOM | 4262 | N | VAL | H | 2 | −68.228 | −15.850 | −27.047 | 1.00 | 78.94 | N |
| ATOM | 4263 | CA | VAL | H | 2 | −68.256 | −15.530 | −25.632 | 1.00 | 78.30 | C |
| ATOM | 4264 | CB | VAL | H | 2 | −68.442 | −14.028 | −25.340 | 1.00 | 78.19 | C |
| ATOM | 4265 | CG1 | VAL | H | 2 | −68.813 | −13.772 | −23.882 | 1.00 | 78.05 | C |
| ATOM | 4266 | CG2 | VAL | H | 2 | −67.170 | −13.270 | −25.684 | 1.00 | 77.93 | C |
| ATOM | 4267 | C | VAL | H | 2 | −69.246 | −16.451 | −24.938 | 1.00 | 78.07 | C |
| ATOM | 4268 | O | VAL | H | 2 | −70.267 | −16.801 | −25.524 | 1.00 | 78.24 | O |
| ATOM | 4269 | N | GLN | H | 3 | −68.914 | −16.889 | −23.708 | 1.00 | 77.82 | N |
| ATOM | 4270 | CA | GLN | H | 3 | −69.763 | −17.773 | −22.925 | 1.00 | 77.65 | C |
| ATOM | 4271 | CB | GLN | H | 3 | −69.436 | −19.213 | −23.262 | 1.00 | 78.12 | C |
| ATOM | 4272 | CG | GLN | H | 3 | −70.619 | −19.947 | −23.853 | 1.00 | 80.90 | C |
| ATOM | 4273 | CD | GLN | H | 3 | −70.144 | −20.979 | −24.833 | 1.00 | 84.72 | C |
| ATOM | 4274 | OE1 | GLN | H | 3 | −70.363 | −20.839 | −26.047 | 1.00 | 86.45 | O |
| ATOM | 4275 | NE2 | GLN | H | 3 | −69.473 | −22.032 | −24.330 | 1.00 | 85.45 | N |
| ATOM | 4276 | C | GLN | H | 3 | −69.640 | −17.567 | −21.436 | 1.00 | 76.67 | C |
| ATOM | 4277 | O | GLN | H | 3 | −68.525 | −17.477 | −20.924 | 1.00 | 76.75 | O |
| ATOM | 4278 | N | LEU | H | 4 | −70.787 | −17.506 | −20.739 | 1.00 | 72.16 | N |
| ATOM | 4279 | CA | LEU | H | 4 | −70.837 | −17.368 | −19.280 | 1.00 | 71.64 | C |
| ATOM | 4280 | CB | LEU | H | 4 | −71.524 | −16.069 | −18.818 | 1.00 | 71.33 | C |
| ATOM | 4281 | CG | LEU | H | 4 | −71.195 | −14.757 | −19.523 | 1.00 | 70.60 | C |
| ATOM | 4282 | CD1 | LEU | H | 4 | −71.913 | −13.625 | −18.864 | 1.00 | 70.01 | C |
| ATOM | 4283 | CD2 | LEU | H | 4 | −69.718 | −14.463 | −19.528 | 1.00 | 69.61 | C |
| ATOM | 4284 | C | LEU | H | 4 | −71.535 | −18.618 | −18.675 | 1.00 | 71.52 | C |
| ATOM | 4285 | O | LEU | H | 4 | −72.709 | −18.888 | −18.974 | 1.00 | 71.75 | O |
| ATOM | 4286 | N | LEU | H | 5 | −70.803 | −19.384 | −17.846 | 1.00 | 69.57 | N |
| ATOM | 4287 | CA | LEU | H | 5 | −71.323 | −20.591 | −17.235 | 1.00 | 69.42 | C |
| ATOM | 4288 | CB | LEU | H | 5 | −70.438 | −21.787 | −17.545 | 1.00 | 69.66 | C |
| ATOM | 4289 | CG | LEU | H | 5 | −70.935 | −22.587 | −18.733 | 1.00 | 70.41 | C |
| ATOM | 4290 | CD1 | LEU | H | 5 | −69.780 | −22.973 | −19.690 | 1.00 | 70.09 | C |
| ATOM | 4291 | CD2 | LEU | H | 5 | −71.834 | −23.750 | −18.291 | 1.00 | 70.19 | C |
| ATOM | 4292 | C | LEU | H | 5 | −71.668 | −20.530 | −15.770 | 1.00 | 69.40 | C |
| ATOM | 4293 | O | LEU | H | 5 | −70.805 | −20.593 | −14.907 | 1.00 | 69.27 | O |
| ATOM | 4294 | N | GLU | H | 6 | −72.943 | −20.461 | −15.482 | 1.00 | 71.71 | N |
| ATOM | 4295 | CA | GLU | H | 6 | −73.380 | −20.435 | −14.106 | 1.00 | 72.24 | C |
| ATOM | 4296 | CB | GLU | H | 6 | −74.742 | −19.783 | −14.004 | 1.00 | 72.34 | C |
| ATOM | 4297 | CG | GLU | H | 6 | −74.678 | −18.300 | −14.254 | 1.00 | 74.24 | C |
| ATOM | 4298 | CD | GLU | H | 6 | −75.966 | −17.699 | −14.760 | 1.00 | 76.78 | C |
| ATOM | 4299 | OE1 | GLU | H | 6 | −76.028 | −16.458 | −14.856 | 1.00 | 78.16 | O |
| ATOM | 4300 | OE2 | GLU | H | 6 | −76.912 | −18.459 | −15.059 | 1.00 | 78.55 | O |
| ATOM | 4301 | C | GLU | H | 6 | −73.445 | −21.839 | −13.519 | 1.00 | 72.29 | C |
| ATOM | 4302 | O | GLU | H | 6 | −73.777 | −22.802 | −14.225 | 1.00 | 72.74 | O |
| ATOM | 4303 | N | SER | H | 7 | −73.152 | −21.946 | −12.218 | 1.00 | 69.48 | N |
| ATOM | 4304 | CA | SER | H | 7 | −73.205 | −23.184 | −11.462 | 1.00 | 69.09 | C |
| ATOM | 4305 | CB | SER | H | 7 | −71.933 | −23.982 | −11.661 | 1.00 | 68.95 | C |
| ATOM | 4306 | OG | SER | H | 7 | −70.817 | −23.156 | −11.416 | 1.00 | 69.86 | O |
| ATOM | 4307 | C | SER | H | 7 | −73.429 | −22.835 | −10.005 | 1.00 | 68.98 | C |
| ATOM | 4308 | O | SER | H | 7 | −73.028 | −21.760 | −9.569 | 1.00 | 69.18 | O |
| ATOM | 4309 | N | GLY | H | 8 | −74.130 | −23.692 | −9.279 | 1.00 | 69.93 | N |
| ATOM | 4310 | CA | GLY | H | 8 | −74.400 | −23.446 | −7.871 | 1.00 | 69.86 | C |
| ATOM | 4311 | C | GLY | H | 8 | −75.861 | −23.338 | −7.508 | 1.00 | 69.99 | C |
| ATOM | 4312 | O | GLY | H | 8 | −76.206 | −23.020 | −6.357 | 1.00 | 70.57 | O |
| ATOM | 4313 | N | GLY | H | 9 | −76.723 | −23.574 | −8.483 | 1.00 | 70.65 | N |
| ATOM | 4314 | CA | GLY | H | 9 | −78.159 | −23.495 | −8.255 | 1.00 | 70.59 | C |
| ATOM | 4315 | C | GLY | H | 9 | −78.664 | −24.743 | −7.563 | 1.00 | 70.37 | C |
| ATOM | 4316 | O | GLY | H | 9 | −78.070 | −25.815 | −7.714 | 1.00 | 70.41 | O |
| ATOM | 4317 | N | GLY | H | 10 | −79.748 | −24.604 | −6.812 | 1.00 | 67.78 | N |
| ATOM | 4318 | CA | GLY | H | 10 | −80.338 | −25.717 | −6.099 | 1.00 | 67.44 | C |
| ATOM | 4319 | C | GLY | H | 10 | −81.143 | −25.309 | −4.900 | 1.00 | 67.59 | C |
| ATOM | 4320 | O | GLY | H | 10 | −81.720 | −24.214 | −4.870 | 1.00 | 67.31 | O |
| ATOM | 4321 | N | LEU | H | 11 | −81.196 | −26.202 | −3.904 | 1.00 | 69.83 | N |
| ATOM | 4322 | CA | LEU | H | 11 | −81.963 | −25.902 | −2.713 | 1.00 | 70.67 | C |
| ATOM | 4323 | CB | LEU | H | 11 | −82.755 | −27.099 | −2.219 | 1.00 | 70.63 | C |
| ATOM | 4324 | CG | LEU | H | 11 | −84.051 | −27.363 | −2.918 | 1.00 | 70.82 | C |
| ATOM | 4325 | CD1 | LEU | H | 11 | −84.469 | −28.777 | −2.695 | 1.00 | 71.32 | C |
| ATOM | 4326 | CD2 | LEU | H | 11 | −85.144 | −26.348 | −2.511 | 1.00 | 71.57 | C |
| ATOM | 4327 | C | LEU | H | 11 | −81.134 | −25.361 | −1.602 | 1.00 | 71.27 | C |
| ATOM | 4328 | O | LEU | H | 11 | −80.059 | −25.887 | −1.300 | 1.00 | 71.33 | O |
| ATOM | 4329 | N | VAL | H | 12 | −81.636 | −24.293 | −0.985 | 1.00 | 77.04 | N |
| ATOM | 4330 | CA | VAL | H | 12 | −80.974 | −23.659 | 0.152 | 1.00 | 77.83 | C |

TABLE 14-continued

PCSK9 and AX132 Fab complex x-ray structure

| ATOM | 4331 | CB | VAL | H | 12 | −80.394 | −22.247 | −0.154 | 1.00 | 77.74 | C |
|---|---|---|---|---|---|---|---|---|---|---|---|
| ATOM | 4332 | CG1 | VAL | H | 12 | −79.444 | −21.815 | 0.949 | 1.00 | 77.50 | C |
| ATOM | 4333 | CG2 | VAL | H | 12 | −79.676 | −22.202 | −1.502 | 1.00 | 76.57 | C |
| ATOM | 4334 | C | VAL | H | 12 | −82.020 | −23.624 | 1.262 | 1.00 | 78.58 | C |
| ATOM | 4335 | O | VAL | H | 12 | −83.201 | −23.385 | 0.982 | 1.00 | 78.68 | O |
| ATOM | 4336 | N | GLN | H | 13 | −81.603 | −23.892 | 2.508 | 1.00 | 82.84 | N |
| ATOM | 4337 | CA | GLN | H | 13 | −82.524 | −23.873 | 3.644 | 1.00 | 83.70 | C |
| ATOM | 4338 | CB | GLN | H | 13 | −81.931 | −24.645 | 4.835 | 1.00 | 83.95 | C |
| ATOM | 4339 | CG | GLN | H | 13 | −81.539 | −26.106 | 4.538 | 1.00 | 86.04 | C |
| ATOM | 4340 | CD | GLN | H | 13 | −82.707 | −26.981 | 4.115 | 1.00 | 88.73 | C |
| ATOM | 4341 | OE1 | GLN | H | 13 | −82.682 | −27.649 | 3.048 | 1.00 | 89.35 | O |
| ATOM | 4342 | NE2 | GLN | H | 13 | −83.766 | −26.985 | 4.935 | 1.00 | 89.33 | N |
| ATOM | 4343 | C | GLN | H | 13 | −82.738 | −22.430 | 4.052 | 1.00 | 83.88 | C |
| ATOM | 4344 | O | GLN | H | 13 | −81.774 | −21.673 | 3.978 | 1.00 | 83.93 | O |
| ATOM | 4345 | N | PRO | H | 14 | −83.946 | −21.995 | 4.478 | 1.00 | 84.30 | N |
| ATOM | 4346 | CA | PRO | H | 14 | −84.102 | −20.599 | 4.921 | 1.00 | 84.50 | C |
| ATOM | 4347 | CB | PRO | H | 14 | −85.560 | −20.519 | 5.377 | 1.00 | 84.18 | C |
| ATOM | 4348 | CG | PRO | H | 14 | −85.967 | −21.904 | 5.600 | 1.00 | 84.55 | C |
| ATOM | 4349 | CD | PRO | H | 14 | −85.207 | −22.732 | 4.625 | 1.00 | 84.42 | C |
| ATOM | 4350 | C | PRO | H | 14 | −83.101 | −20.312 | 6.049 | 1.00 | 84.71 | C |
| ATOM | 4351 | O | PRO | H | 14 | −82.966 | −21.105 | 6.995 | 1.00 | 85.21 | O |
| ATOM | 4352 | N | GLY | H | 15 | −82.351 | −19.227 | 5.880 | 1.00 | 84.98 | N |
| ATOM | 4353 | CA | GLY | H | 15 | −81.285 | −18.815 | 6.782 | 1.00 | 84.47 | C |
| ATOM | 4354 | C | GLY | H | 15 | −79.928 | −19.168 | 6.199 | 1.00 | 84.16 | C |
| ATOM | 4355 | O | GLY | H | 15 | −78.915 | −18.539 | 6.533 | 1.00 | 84.38 | O |
| ATOM | 4356 | N | GLY | H | 16 | −79.916 | −20.164 | 5.311 | 1.00 | 82.42 | N |
| ATOM | 4357 | CA | GLY | H | 16 | −78.720 | −20.637 | 4.622 | 1.00 | 82.29 | C |
| ATOM | 4358 | C | GLY | H | 16 | −78.183 | −19.668 | 3.589 | 1.00 | 82.05 | C |
| ATOM | 4359 | O | GLY | H | 16 | −78.700 | −18.556 | 3.439 | 1.00 | 82.21 | O |
| ATOM | 4360 | N | SER | H | 17 | −77.142 | −20.072 | 2.863 | 1.00 | 80.66 | N |
| ATOM | 4361 | CA | SER | H | 17 | −76.571 | −19.159 | 1.888 | 1.00 | 80.48 | C |
| ATOM | 4362 | CB | SER | H | 17 | −75.275 | −18.544 | 2.425 | 1.00 | 80.55 | C |
| ATOM | 4363 | OG | SER | H | 17 | −74.139 | −19.386 | 2.286 | 1.00 | 80.34 | O |
| ATOM | 4364 | C | SER | H | 17 | −76.367 | −19.745 | 0.497 | 1.00 | 80.27 | C |
| ATOM | 4365 | O | SER | H | 17 | −75.852 | −20.859 | 0.369 | 1.00 | 80.77 | O |
| ATOM | 4366 | N | LEU | H | 18 | −76.747 | −18.988 | −0.550 | 1.00 | 76.11 | N |
| ATOM | 4367 | CA | LEU | H | 18 | −76.545 | −19.440 | −1.921 | 1.00 | 75.09 | C |
| ATOM | 4368 | CB | LEU | H | 18 | −77.591 | −18.880 | −2.916 | 1.00 | 75.04 | C |
| ATOM | 4369 | CG | LEU | H | 18 | −77.659 | −17.363 | −3.144 | 1.00 | 75.02 | C |
| ATOM | 4370 | CD1 | LEU | H | 18 | −76.848 | −16.963 | −4.328 | 1.00 | 75.68 | C |
| ATOM | 4371 | CD2 | LEU | H | 18 | −79.075 | −16.892 | −3.389 | 1.00 | 74.44 | C |
| ATOM | 4372 | C | LEU | H | 18 | −75.139 | −19.051 | −2.317 | 1.00 | 74.76 | C |
| ATOM | 4373 | O | LEU | H | 18 | −74.662 | −17.972 | −1.969 | 1.00 | 74.41 | O |
| ATOM | 4374 | N | ARG | H | 19 | −74.469 | −19.938 | −3.019 | 1.00 | 74.61 | N |
| ATOM | 4375 | CA | ARG | H | 19 | −73.126 | −19.699 | −3.480 | 1.00 | 74.54 | C |
| ATOM | 4376 | CB | ARG | H | 19 | −72.095 | −20.339 | −2.549 | 1.00 | 74.56 | C |
| ATOM | 4377 | CG | ARG | H | 19 | −72.184 | −19.622 | −1.214 | 1.00 | 77.55 | C |
| ATOM | 4378 | CD | ARG | H | 19 | −71.373 | −20.123 | −0.058 | 1.00 | 83.29 | C |
| ATOM | 4379 | NE | ARG | H | 19 | −69.959 | −20.310 | −0.377 | 1.00 | 88.54 | N |
| ATOM | 4380 | CZ | ARG | H | 19 | −69.093 | −19.351 | −0.709 | 1.00 | 90.54 | C |
| ATOM | 4381 | NH1 | ARG | H | 19 | −69.494 | −18.085 | −0.809 | 1.00 | 88.60 | N |
| ATOM | 4382 | NH2 | ARG | H | 19 | −67.824 | −19.655 | −0.965 | 1.00 | 92.32 | N |
| ATOM | 4383 | C | ARG | H | 19 | −73.095 | −20.139 | −4.912 | 1.00 | 74.06 | C |
| ATOM | 4384 | O | ARG | H | 19 | −73.229 | −21.330 | −5.216 | 1.00 | 74.25 | O |
| ATOM | 4385 | N | LEU | H | 20 | −73.043 | −19.123 | −5.804 | 1.00 | 72.96 | N |
| ATOM | 4386 | CA | LEU | H | 20 | −73.058 | −19.247 | −7.263 | 1.00 | 72.22 | C |
| ATOM | 4387 | CB | LEU | H | 20 | −74.155 | −18.353 | −7.833 | 1.00 | 71.98 | C |
| ATOM | 4388 | CG | LEU | H | 20 | −75.551 | −18.561 | −7.313 | 1.00 | 72.09 | C |
| ATOM | 4389 | CD1 | LEU | H | 20 | −76.477 | −17.556 | −7.895 | 1.00 | 72.12 | C |
| ATOM | 4390 | CD2 | LEU | H | 20 | −76.073 | −19.910 | −7.662 | 1.00 | 73.03 | C |
| ATOM | 4391 | C | LEU | H | 20 | −71.739 | −18.889 | −7.927 | 1.00 | 71.91 | C |
| ATOM | 4392 | O | LEU | H | 20 | −70.989 | −18.053 | −7.424 | 1.00 | 72.10 | O |
| ATOM | 4393 | N | SER | H | 21 | −71.471 | −19.504 | −9.064 | 1.00 | 70.87 | N |
| ATOM | 4394 | CA | SER | H | 21 | −70.270 | −19.236 | −9.818 | 1.00 | 70.98 | C |
| ATOM | 4395 | CB | SER | H | 21 | −69.358 | −20.450 | −9.838 | 1.00 | 70.95 | C |
| ATOM | 4396 | OG | SER | H | 21 | −68.806 | −20.617 | −8.545 | 1.00 | 72.22 | O |
| ATOM | 4397 | C | SER | H | 21 | −70.667 | −18.909 | −11.205 | 1.00 | 71.06 | C |
| ATOM | 4398 | O | SER | H | 21 | −71.741 | −19.314 | −11.637 | 1.00 | 71.48 | O |
| ATOM | 4399 | N | CYS | H | 22 | −69.800 | −18.180 | −11.917 | 1.00 | 72.15 | N |
| ATOM | 4400 | CA | CYS | H | 22 | −70.004 | −17.784 | −13.300 | 1.00 | 71.80 | C |
| ATOM | 4401 | CB | CYS | H | 22 | −70.666 | −16.416 | −13.379 | 1.00 | 71.77 | C |
| ATOM | 4402 | SG | CYS | H | 22 | −70.891 | −15.818 | −15.071 | 1.00 | 73.52 | S |
| ATOM | 4403 | C | CYS | H | 22 | −68.658 | −17.809 | −13.994 | 1.00 | 71.24 | C |
| ATOM | 4404 | O | CYS | H | 22 | −67.748 | −17.129 | −13.552 | 1.00 | 71.34 | O |
| ATOM | 4405 | N | LYS | H | 23 | −68.516 | −18.612 | −15.042 | 1.00 | 70.46 | N |
| ATOM | 4406 | CA | LYS | H | 23 | −67.258 | −18.740 | −15.754 | 1.00 | 70.46 | C |
| ATOM | 4407 | CB | LYS | H | 23 | −66.749 | −20.185 | −15.748 | 1.00 | 70.57 | C |
| ATOM | 4408 | CG | LYS | H | 23 | −65.377 | −20.323 | −16.393 | 1.00 | 71.74 | C |

TABLE 14-continued

PCSK9 and AX132 Fab complex x-ray structure

| ATOM | 4409 | CD | LYS | H | 23 | −64.644 | −21.565 | −15.971 | 1.00 | 73.39 | C |
|------|------|-----|-----|---|----|---------|---------|---------|------|-------|---|
| ATOM | 4410 | CE | LYS | H | 23 | −63.311 | −21.675 | −16.687 | 1.00 | 74.92 | C |
| ATOM | 4411 | NZ | LYS | H | 23 | −62.357 | −20.557 | −16.371 | 1.00 | 76.84 | N |
| ATOM | 4412 | C | LYS | H | 23 | −67.265 | −18.169 | −17.158 | 1.00 | 70.28 | C |
| ATOM | 4413 | O | LYS | H | 23 | −67.860 | −18.748 | −18.079 | 1.00 | 70.43 | O |
| ATOM | 4414 | N | ALA | H | 24 | −66.532 | −17.064 | −17.331 | 1.00 | 68.97 | N |
| ATOM | 4415 | CA | ALA | H | 24 | −66.411 | −16.386 | −18.606 | 1.00 | 68.52 | C |
| ATOM | 4416 | CB | ALA | H | 24 | −66.065 | −14.937 | −18.374 | 1.00 | 68.52 | C |
| ATOM | 4417 | C | ALA | H | 24 | −65.376 | −17.041 | −19.532 | 1.00 | 68.37 | C |
| ATOM | 4418 | O | ALA | H | 24 | −64.365 | −17.608 | −19.075 | 1.00 | 68.38 | O |
| ATOM | 4419 | N | SER | H | 25 | −65.639 | −16.951 | −20.850 | 1.00 | 67.81 | N |
| ATOM | 4420 | CA | SER | H | 25 | −64.741 | −17.502 | −21.852 | 1.00 | 67.76 | C |
| ATOM | 4421 | CB | SER | H | 25 | −65.021 | −18.992 | −22.075 | 1.00 | 67.84 | C |
| ATOM | 4422 | OG | SER | H | 25 | −66.129 | −19.288 | −22.919 | 1.00 | 68.84 | O |
| ATOM | 4423 | C | SER | H | 25 | −64.789 | −16.748 | −23.172 | 1.00 | 67.61 | C |
| ATOM | 4424 | O | SER | H | 25 | −65.830 | −16.243 | −23.557 | 1.00 | 67.59 | O |
| ATOM | 4425 | N | GLY | H | 26 | −63.665 | −16.714 | −23.862 | 1.00 | 69.08 | N |
| ATOM | 4426 | CA | GLY | H | 26 | −63.575 | −16.119 | −25.181 | 1.00 | 69.03 | C |
| ATOM | 4427 | C | GLY | H | 26 | −63.341 | −14.638 | −25.287 | 1.00 | 69.20 | C |
| ATOM | 4428 | O | GLY | H | 26 | −63.493 | −14.092 | −26.386 | 1.00 | 69.36 | O |
| ATOM | 4429 | N | TYR | H | 27 | −62.995 | −13.970 | −24.164 | 1.00 | 69.63 | N |
| ATOM | 4430 | CA | TYR | H | 27 | −62.726 | −12.530 | −24.121 | 1.00 | 69.19 | C |
| ATOM | 4431 | CB | TYR | H | 27 | −64.031 | −11.724 | −23.993 | 1.00 | 69.19 | C |
| ATOM | 4432 | CG | TYR | H | 27 | −64.705 | −11.748 | −22.638 | 1.00 | 68.24 | C |
| ATOM | 4433 | CD1 | TYR | H | 27 | −64.480 | −10.736 | −21.708 | 1.00 | 68.05 | C |
| ATOM | 4434 | CE1 | TYR | H | 27 | −65.106 | −10.744 | −20.461 | 1.00 | 68.69 | C |
| ATOM | 4435 | CZ | TYR | H | 27 | −66.016 | −11.747 | −20.153 | 1.00 | 68.90 | C |
| ATOM | 4436 | OH | TYR | H | 27 | −66.662 | −11.746 | −18.934 | 1.00 | 68.89 | O |
| ATOM | 4437 | CE2 | TYR | H | 27 | −66.286 | −12.739 | −21.084 | 1.00 | 68.63 | C |
| ATOM | 4438 | CD2 | TYR | H | 27 | −65.633 | −12.730 | −22.318 | 1.00 | 68.29 | C |
| ATOM | 4439 | C | TYR | H | 27 | −61.719 | −12.216 | −23.023 | 1.00 | 69.14 | C |
| ATOM | 4440 | O | TYR | H | 27 | −61.306 | −13.141 | −22.321 | 1.00 | 69.30 | O |
| ATOM | 4441 | N | THR | H | 28 | −61.305 | −10.937 | −22.865 | 1.00 | 69.86 | N |
| ATOM | 4442 | CA | THR | H | 28 | −60.364 | −10.551 | −21.809 | 1.00 | 69.57 | C |
| ATOM | 4443 | CB | THR | H | 28 | −59.416 | −9.454 | −22.290 | 1.00 | 69.64 | C |
| ATOM | 4444 | OG1 | THR | H | 28 | −58.599 | −10.020 | −23.328 | 1.00 | 70.12 | O |
| ATOM | 4445 | CG2 | THR | H | 28 | −58.490 | −8.947 | −21.164 | 1.00 | 70.18 | C |
| ATOM | 4446 | C | THR | H | 28 | −61.190 | −10.249 | −20.594 | 1.00 | 69.14 | C |
| ATOM | 4447 | O | THR | H | 28 | −61.860 | −9.228 | −20.548 | 1.00 | 69.14 | O |
| ATOM | 4448 | N | PHE | H | 29 | −61.191 | −11.175 | −19.641 | 1.00 | 66.46 | N |
| ATOM | 4449 | CA | PHE | H | 29 | −61.992 | −11.133 | −18.418 | 1.00 | 66.27 | C |
| ATOM | 4450 | CB | PHE | H | 29 | −61.609 | −12.272 | −17.465 | 1.00 | 65.85 | C |
| ATOM | 4451 | CG | PHE | H | 29 | −62.516 | −12.405 | −16.266 | 1.00 | 64.34 | C |
| ATOM | 4452 | CD1 | PHE | H | 29 | −63.828 | −12.828 | −16.411 | 1.00 | 62.78 | C |
| ATOM | 4453 | CE1 | PHE | H | 29 | −64.669 | −12.936 | −15.307 | 1.00 | 62.24 | C |
| ATOM | 4454 | CZ | PHE | H | 29 | −64.202 | −12.634 | −14.053 | 1.00 | 62.61 | C |
| ATOM | 4455 | CE2 | PHE | H | 29 | −62.901 | −12.214 | −13.883 | 1.00 | 63.53 | C |
| ATOM | 4456 | CD2 | PHE | H | 29 | −62.058 | −12.100 | −14.991 | 1.00 | 64.31 | C |
| ATOM | 4457 | C | PHE | H | 29 | −62.113 | −9.794 | −17.703 | 1.00 | 66.91 | C |
| ATOM | 4458 | O | PHE | H | 29 | −63.226 | −9.389 | −17.324 | 1.00 | 67.42 | O |
| ATOM | 4459 | N | SER | H | 30 | −60.974 | −9.101 | −17.559 | 1.00 | 70.34 | N |
| ATOM | 4460 | CA | SER | H | 30 | −60.817 | −7.798 | −16.892 | 1.00 | 70.63 | C |
| ATOM | 4461 | CB | SER | H | 30 | −59.363 | −7.584 | −16.504 | 1.00 | 70.51 | C |
| ATOM | 4462 | OG | SER | H | 30 | −58.532 | −8.272 | −17.429 | 1.00 | 71.36 | O |
| ATOM | 4463 | C | SER | H | 30 | −61.348 | −6.570 | −17.645 | 1.00 | 70.64 | C |
| ATOM | 4464 | O | SER | H | 30 | −61.698 | −5.591 | −16.981 | 1.00 | 71.00 | O |
| ATOM | 4465 | N | SER | H | 31 | −61.415 | −6.611 | −18.999 | 1.00 | 70.40 | N |
| ATOM | 4466 | CA | SER | H | 31 | −61.896 | −5.500 | −19.836 | 1.00 | 70.53 | C |
| ATOM | 4467 | CB | SER | H | 31 | −61.750 | −5.815 | −21.322 | 1.00 | 70.69 | C |
| ATOM | 4468 | OG | SER | H | 31 | −60.508 | −6.406 | −21.666 | 1.00 | 73.12 | O |
| ATOM | 4469 | C | SER | H | 31 | −63.350 | −5.120 | −19.587 | 1.00 | 70.40 | C |
| ATOM | 4470 | O | SER | H | 31 | −63.729 | −3.961 | −19.838 | 1.00 | 71.01 | O |
| ATOM | 4471 | N | TYR | H | 32 | −64.174 | −6.086 | −19.129 | 1.00 | 68.08 | N |
| ATOM | 4472 | CA | TYR | H | 32 | −65.602 | −5.849 | −18.906 | 1.00 | 67.28 | C |
| ATOM | 4473 | CB | TYR | H | 32 | −66.415 | −6.861 | −19.719 | 1.00 | 66.88 | C |
| ATOM | 4474 | CG | TYR | H | 32 | −66.227 | −6.729 | −21.207 | 1.00 | 65.13 | C |
| ATOM | 4475 | CD1 | TYR | H | 32 | −65.053 | −7.163 | −21.824 | 1.00 | 64.22 | C |
| ATOM | 4476 | CE1 | TYR | H | 32 | −64.867 | −7.035 | −23.201 | 1.00 | 63.90 | C |
| ATOM | 4477 | CZ | TYR | H | 32 | −65.885 | −6.510 | −23.985 | 1.00 | 64.65 | C |
| ATOM | 4478 | OH | TYR | H | 32 | −65.720 | −6.373 | −25.344 | 1.00 | 64.76 | O |
| ATOM | 4479 | CE2 | TYR | H | 32 | −67.076 | −6.102 | −23.394 | 1.00 | 65.21 | C |
| ATOM | 4480 | CD2 | TYR | H | 32 | −67.233 | −6.204 | −22.010 | 1.00 | 65.21 | C |
| ATOM | 4481 | C | TYR | H | 32 | −65.999 | −5.939 | −17.443 | 1.00 | 67.37 | C |
| ATOM | 4482 | O | TYR | H | 32 | −65.254 | −6.497 | −16.667 | 1.00 | 67.35 | O |
| ATOM | 4483 | N | GLY | H | 33 | −67.157 | −5.396 | −17.092 | 1.00 | 65.63 | N |
| ATOM | 4484 | CA | GLY | H | 33 | −67.692 | −5.452 | −15.746 | 1.00 | 66.06 | C |
| ATOM | 4485 | C | GLY | H | 33 | −68.749 | −6.530 | −15.700 | 1.00 | 66.58 | C |
| ATOM | 4486 | O | GLY | H | 33 | −69.274 | −6.910 | −16.749 | 1.00 | 66.80 | O |

TABLE 14-continued

PCSK9 and AX132 Fab complex x-ray structure

| ATOM | 4487 | N | MET | H | 34 | −69.065 | −7.046 | −14.499 | 1.00 | 66.52 | N |
|---|---|---|---|---|---|---|---|---|---|---|---|
| ATOM | 4488 | CA | MET | H | 34 | −70.046 | −8.104 | −14.319 | 1.00 | 66.65 | C |
| ATOM | 4489 | CB | MET | H | 34 | −69.394 | −9.345 | −13.737 | 1.00 | 67.09 | C |
| ATOM | 4490 | CG | MET | H | 34 | −68.225 | −9.905 | −14.497 | 1.00 | 69.58 | C |
| ATOM | 4491 | SD | MET | H | 34 | −68.573 | −10.522 | −16.142 | 1.00 | 75.28 | S |
| ATOM | 4492 | CE | MET | H | 34 | −70.078 | −11.560 | −15.865 | 1.00 | 73.82 | C |
| ATOM | 4493 | C | MET | H | 34 | −71.076 | −7.717 | −13.313 | 1.00 | 66.50 | C |
| ATOM | 4494 | O | MET | H | 34 | −70.731 | −7.254 | −12.228 | 1.00 | 66.14 | O |
| ATOM | 4495 | N | TYR | H | 35 | −72.347 | −7.964 | −13.641 | 1.00 | 64.67 | N |
| ATOM | 4496 | CA | TYR | H | 35 | −73.482 | −7.743 | −12.760 | 1.00 | 64.82 | C |
| ATOM | 4497 | CB | TYR | H | 35 | −74.594 | −6.958 | −13.494 | 1.00 | 65.00 | C |
| ATOM | 4498 | CG | TYR | H | 35 | −74.530 | −5.446 | −13.399 | 1.00 | 65.80 | C |
| ATOM | 4499 | CD1 | TYR | H | 35 | −75.447 | −4.732 | −12.621 | 1.00 | 66.36 | C |
| ATOM | 4500 | CE1 | TYR | H | 35 | −75.405 | −3.339 | −12.546 | 1.00 | 66.85 | C |
| ATOM | 4501 | CZ | TYR | H | 35 | −74.443 | −2.644 | −13.266 | 1.00 | 68.42 | C |
| ATOM | 4502 | OH | TYR | H | 35 | −74.340 | −1.268 | −13.236 | 1.00 | 67.78 | O |
| ATOM | 4503 | CE2 | TYR | H | 35 | −73.537 | −3.337 | −14.058 | 1.00 | 68.00 | C |
| ATOM | 4504 | CD2 | TYR | H | 35 | −73.595 | −4.725 | −14.130 | 1.00 | 66.03 | C |
| ATOM | 4505 | C | TYR | H | 35 | −74.038 | −9.135 | −12.369 | 1.00 | 64.88 | C |
| ATOM | 4506 | O | TYR | H | 35 | −73.866 | −10.119 | −13.088 | 1.00 | 64.57 | O |
| ATOM | 4507 | N | TRP | H | 36 | −74.697 | −9.208 | −11.227 | 1.00 | 65.02 | N |
| ATOM | 4508 | CA | TRP | H | 36 | −75.374 | −10.413 | −10.792 | 1.00 | 65.39 | C |
| ATOM | 4509 | CB | TRP | H | 36 | −74.875 | −10.937 | −9.433 | 1.00 | 65.09 | C |
| ATOM | 4510 | CG | TRP | H | 36 | −73.758 | −11.924 | −9.543 | 1.00 | 64.98 | C |
| ATOM | 4511 | CD1 | TRP | H | 36 | −72.449 | −11.700 | −9.255 | 1.00 | 65.63 | C |
| ATOM | 4512 | NE1 | TRP | H | 36 | −71.710 | −12.843 | −9.467 | 1.00 | 65.37 | N |
| ATOM | 4513 | CE2 | TRP | H | 36 | −72.537 | −13.828 | −9.937 | 1.00 | 65.27 | C |
| ATOM | 4514 | CD2 | TRP | H | 36 | −73.844 | −13.292 | −9.976 | 1.00 | 65.14 | C |
| ATOM | 4515 | CE3 | TRP | H | 36 | −74.891 | −14.110 | −10.421 | 1.00 | 64.75 | C |
| ATOM | 4516 | CZ3 | TRP | H | 36 | −74.605 | −15.413 | −10.800 | 1.00 | 64.19 | C |
| ATOM | 4517 | CH2 | TRP | H | 36 | −73.296 | −15.915 | −10.750 | 1.00 | 63.74 | C |
| ATOM | 4518 | CZ2 | TRP | H | 36 | −72.250 | −15.143 | −10.321 | 1.00 | 64.26 | C |
| ATOM | 4519 | C | TRP | H | 36 | −76.798 | −9.886 | −10.721 | 1.00 | 65.98 | C |
| ATOM | 4520 | O | TRP | H | 36 | −77.055 | −8.937 | −9.981 | 1.00 | 66.19 | O |
| ATOM | 4521 | N | VAL | H | 37 | −77.686 | −10.396 | −11.569 | 1.00 | 69.64 | N |
| ATOM | 4522 | CA | VAL | H | 37 | −79.080 | −9.940 | −11.610 | 1.00 | 70.22 | C |
| ATOM | 4523 | CB | VAL | H | 37 | −79.428 | −9.296 | −12.987 | 1.00 | 70.35 | C |
| ATOM | 4524 | CG1 | VAL | H | 37 | −80.856 | −8.750 | −13.008 | 1.00 | 70.21 | C |
| ATOM | 4525 | CG2 | VAL | H | 37 | −78.425 | −8.208 | −13.382 | 1.00 | 70.26 | C |
| ATOM | 4526 | C | VAL | H | 37 | −79.956 | −11.161 | −11.350 | 1.00 | 70.46 | C |
| ATOM | 4527 | O | VAL | H | 37 | −79.578 | −12.261 | −11.754 | 1.00 | 70.87 | O |
| ATOM | 4528 | N | ARG | H | 38 | −81.112 | −10.980 | −10.694 | 1.00 | 71.70 | N |
| ATOM | 4529 | CA | ARG | H | 38 | −82.038 | −12.072 | −10.437 | 1.00 | 71.83 | C |
| ATOM | 4530 | CB | ARG | H | 38 | −82.063 | −12.479 | −8.962 | 1.00 | 71.52 | C |
| ATOM | 4531 | CG | ARG | H | 38 | −82.784 | −11.516 | −8.019 | 1.00 | 70.95 | C |
| ATOM | 4532 | CD | ARG | H | 38 | −82.776 | −12.049 | −6.600 | 1.00 | 70.37 | C |
| ATOM | 4533 | NE | ARG | H | 38 | −83.622 | −11.259 | −5.700 | 1.00 | 69.30 | N |
| ATOM | 4534 | CZ | ARG | H | 38 | −83.680 | −11.458 | −4.385 | 1.00 | 69.01 | C |
| ATOM | 4535 | NH1 | ARG | H | 38 | −82.938 | −12.401 | −3.815 | 1.00 | 69.40 | N |
| ATOM | 4536 | NH2 | ARG | H | 38 | −84.473 | −10.703 | −3.626 | 1.00 | 68.45 | N |
| ATOM | 4537 | C | ARG | H | 38 | −83.424 | −11.737 | −10.958 | 1.00 | 72.40 | C |
| ATOM | 4538 | O | ARG | H | 38 | −83.737 | −10.563 | −11.168 | 1.00 | 72.42 | O |
| ATOM | 4539 | N | GLN | H | 39 | −84.261 | −12.761 | −11.175 | 1.00 | 74.58 | N |
| ATOM | 4540 | CA | GLN | H | 39 | −85.621 | −12.539 | −11.653 | 1.00 | 75.17 | C |
| ATOM | 4541 | CB | GLN | H | 39 | −85.635 | −12.551 | −13.173 | 1.00 | 74.95 | C |
| ATOM | 4542 | CG | GLN | H | 39 | −86.998 | −12.352 | −13.788 | 1.00 | 73.81 | C |
| ATOM | 4543 | CD | GLN | H | 39 | −86.864 | −12.405 | −15.275 | 1.00 | 72.62 | C |
| ATOM | 4544 | OE1 | GLN | H | 39 | −86.133 | −13.251 | −15.833 | 1.00 | 72.71 | O |
| ATOM | 4545 | NE2 | GLN | H | 39 | −87.566 | −11.505 | −15.945 | 1.00 | 71.94 | N |
| ATOM | 4546 | C | GLN | H | 39 | −86.554 | −13.585 | −11.070 | 1.00 | 75.87 | C |
| ATOM | 4547 | O | GLN | H | 39 | −86.428 | −14.765 | −11.400 | 1.00 | 76.00 | O |
| ATOM | 4548 | N | ALA | H | 40 | −87.468 | −13.157 | −10.179 | 1.00 | 79.68 | N |
| ATOM | 4549 | CA | ALA | H | 40 | −88.437 | −14.055 | −9.557 | 1.00 | 80.51 | C |
| ATOM | 4550 | CB | ALA | H | 40 | −89.123 | −13.369 | −8.400 | 1.00 | 80.27 | C |
| ATOM | 4551 | C | ALA | H | 40 | −89.450 | −14.438 | −10.628 | 1.00 | 81.37 | C |
| ATOM | 4552 | O | ALA | H | 40 | −89.762 | −13.580 | −11.452 | 1.00 | 81.84 | O |
| ATOM | 4553 | N | PRO | H | 41 | −89.930 | −15.711 | −10.671 | 1.00 | 85.05 | N |
| ATOM | 4554 | CA | PRO | H | 41 | −90.859 | −16.153 | −11.737 | 1.00 | 85.30 | C |
| ATOM | 4555 | CB | PRO | H | 41 | −91.486 | −17.431 | −11.164 | 1.00 | 85.19 | C |
| ATOM | 4556 | CG | PRO | H | 41 | −90.921 | −17.572 | −9.757 | 1.00 | 85.38 | C |
| ATOM | 4557 | CD | PRO | H | 41 | −89.629 | −16.838 | −9.771 | 1.00 | 85.27 | C |
| ATOM | 4558 | C | PRO | H | 41 | −91.864 | −15.170 | −12.361 | 1.00 | 85.47 | C |
| ATOM | 4559 | O | PRO | H | 41 | −91.797 | −14.903 | −13.573 | 1.00 | 85.58 | O |
| ATOM | 4560 | N | GLY | H | 42 | −92.765 | −14.631 | −11.549 | 1.00 | 86.15 | N |
| ATOM | 4561 | CA | GLY | H | 42 | −93.730 | −13.665 | −12.056 | 1.00 | 86.25 | C |
| ATOM | 4562 | C | GLY | H | 42 | −93.048 | −12.352 | −12.411 | 1.00 | 86.19 | C |
| ATOM | 4563 | O | GLY | H | 42 | −93.180 | −11.852 | −13.535 | 1.00 | 86.40 | O |
| ATOM | 4564 | N | LYS | H | 43 | −92.278 | −11.819 | −11.440 | 1.00 | 82.73 | N |

TABLE 14-continued

PCSK9 and AX132 Fab complex x-ray structure

| ATOM | 4565 | CA | LYS | H | 43 | −91.509 | −10.583 | −11.480 | 1.00 | 81.98 | C |
|---|---|---|---|---|---|---|---|---|---|---|---|
| ATOM | 4566 | CB | LYS | H | 43 | −90.766 | −10.431 | −10.140 | 1.00 | 82.07 | C |
| ATOM | 4567 | C | LYS | H | 43 | −90.538 | −10.346 | −12.691 | 1.00 | 81.47 | C |
| ATOM | 4568 | O | LYS | H | 43 | −90.332 | −11.213 | −13.556 | 1.00 | 81.20 | O |
| ATOM | 4569 | N | GLY | H | 44 | −89.976 | −9.138 | −12.705 | 1.00 | 76.91 | N |
| ATOM | 4570 | CA | GLY | H | 44 | −89.006 | −8.663 | −13.671 | 1.00 | 76.29 | C |
| ATOM | 4571 | C | GLY | H | 44 | −87.603 | −8.677 | −13.092 | 1.00 | 75.96 | C |
| ATOM | 4572 | O | GLY | H | 44 | −87.377 | −9.231 | −12.008 | 1.00 | 76.24 | O |
| ATOM | 4573 | N | LEU | H | 45 | −86.651 | −8.057 | −13.813 | 1.00 | 71.99 | N |
| ATOM | 4574 | CA | LEU | H | 45 | −85.230 | −7.989 | −13.471 | 1.00 | 71.27 | C |
| ATOM | 4575 | CB | LEU | H | 45 | −84.412 | −7.534 | −14.691 | 1.00 | 70.96 | C |
| ATOM | 4576 | CG | LEU | H | 45 | −84.619 | −8.373 | −15.941 | 1.00 | 70.10 | C |
| ATOM | 4577 | CD1 | LEU | H | 45 | −84.088 | −7.696 | −17.142 | 1.00 | 69.71 | C |
| ATOM | 4578 | CD2 | LEU | H | 45 | −83.974 | −9.728 | −15.812 | 1.00 | 69.93 | C |
| ATOM | 4579 | C | LEU | H | 45 | −84.886 | −7.181 | −12.223 | 1.00 | 71.13 | C |
| ATOM | 4580 | O | LEU | H | 45 | −85.286 | −6.030 | −12.107 | 1.00 | 71.44 | O |
| ATOM | 4581 | N | GLU | H | 46 | −84.145 | −7.788 | −11.286 | 1.00 | 73.29 | N |
| ATOM | 4582 | CA | GLU | H | 46 | −83.716 | −7.147 | −10.043 | 1.00 | 73.28 | C |
| ATOM | 4583 | CB | GLU | H | 46 | −84.414 | −7.770 | −8.821 | 1.00 | 73.31 | C |
| ATOM | 4584 | CG | GLU | H | 46 | −83.727 | −7.488 | −7.486 | 1.00 | 75.03 | C |
| ATOM | 4585 | CD | GLU | H | 46 | −84.613 | −7.644 | −6.265 | 1.00 | 77.42 | C |
| ATOM | 4586 | OE1 | GLU | H | 46 | −84.689 | −6.677 | −5.471 | 1.00 | 78.48 | O |
| ATOM | 4587 | OE2 | GLU | H | 46 | −85.241 | −8.720 | −6.107 | 1.00 | 79.58 | O |
| ATOM | 4588 | C | GLU | H | 46 | −82.200 | −7.225 | −9.934 | 1.00 | 72.99 | C |
| ATOM | 4589 | O | GLU | H | 46 | −81.642 | −8.316 | −9.826 | 1.00 | 73.27 | O |
| ATOM | 4590 | N | TRP | H | 47 | −81.522 | −6.072 | −9.987 | 1.00 | 71.13 | N |
| ATOM | 4591 | CA | TRP | H | 47 | −80.064 | −6.082 | −9.906 | 1.00 | 70.33 | C |
| ATOM | 4592 | CB | TRP | H | 47 | −79.464 | −4.756 | −10.410 | 1.00 | 70.46 | C |
| ATOM | 4593 | CG | TRP | H | 47 | −79.220 | −3.703 | −9.368 | 1.00 | 70.46 | C |
| ATOM | 4594 | CD1 | TRP | H | 47 | −80.151 | −2.919 | −8.759 | 1.00 | 70.13 | C |
| ATOM | 4595 | NE1 | TRP | H | 47 | −79.540 | −2.068 | −7.863 | 1.00 | 70.12 | N |
| ATOM | 4596 | CE2 | TRP | H | 47 | −78.188 | −2.281 | −7.895 | 1.00 | 69.84 | C |
| ATOM | 4597 | CD2 | TRP | H | 47 | −77.948 | −3.305 | −8.834 | 1.00 | 70.37 | C |
| ATOM | 4598 | CE3 | TRP | H | 47 | −76.626 | −3.732 | −9.042 | 1.00 | 70.17 | C |
| ATOM | 4599 | CZ3 | TRP | H | 47 | −75.611 | −3.129 | −8.320 | 1.00 | 69.26 | C |
| ATOM | 4600 | CH2 | TRP | H | 47 | −75.884 | −2.125 | −7.388 | 1.00 | 67.91 | C |
| ATOM | 4601 | CZ2 | TRP | H | 47 | −77.162 | −1.681 | −7.167 | 1.00 | 69.50 | C |
| ATOM | 4602 | C | TRP | H | 47 | −79.628 | −6.443 | −8.497 | 1.00 | 69.74 | C |
| ATOM | 4603 | O | TRP | H | 47 | −80.275 | −6.030 | −7.534 | 1.00 | 69.62 | O |
| ATOM | 4604 | N | ILE | H | 48 | −78.575 | −7.253 | −8.373 | 1.00 | 67.17 | N |
| ATOM | 4605 | CA | ILE | H | 48 | −78.067 | −7.669 | −7.064 | 1.00 | 66.52 | C |
| ATOM | 4606 | CB | ILE | H | 48 | −77.870 | −9.212 | −6.979 | 1.00 | 66.45 | C |
| ATOM | 4607 | CG1 | ILE | H | 48 | −79.214 | −9.941 | −7.101 | 1.00 | 66.20 | C |
| ATOM | 4608 | CD1 | ILE | H | 48 | −79.091 | −11.089 | −7.877 | 1.00 | 66.59 | C |
| ATOM | 4609 | CG2 | ILE | H | 48 | −77.080 | −9.657 | −5.735 | 1.00 | 66.23 | C |
| ATOM | 4610 | C | ILE | H | 48 | −76.832 | −6.845 | −6.727 | 1.00 | 66.16 | C |
| ATOM | 4611 | O | ILE | H | 48 | −76.856 | −6.080 | −5.767 | 1.00 | 65.97 | O |
| ATOM | 4612 | N | GLY | H | 49 | −75.792 | −6.990 | −7.535 | 1.00 | 65.65 | N |
| ATOM | 4613 | CA | GLY | H | 49 | −74.543 | −6.282 | −7.350 | 1.00 | 65.29 | C |
| ATOM | 4614 | C | GLY | H | 49 | −73.689 | −6.230 | −8.598 | 1.00 | 65.45 | C |
| ATOM | 4615 | O | GLY | H | 49 | −73.948 | −6.930 | −9.586 | 1.00 | 65.27 | O |
| ATOM | 4616 | N | TRP | H | 50 | −72.642 | −5.399 | −8.540 | 1.00 | 66.73 | N |
| ATOM | 4617 | CA | TRP | H | 50 | −71.678 | −5.202 | −9.622 | 1.00 | 66.82 | C |
| ATOM | 4618 | CB | TRP | H | 50 | −71.910 | −3.831 | −10.298 | 1.00 | 66.43 | C |
| ATOM | 4619 | CG | TRP | H | 50 | −70.814 | −3.413 | −11.230 | 1.00 | 63.90 | C |
| ATOM | 4620 | CD1 | TRP | H | 50 | −70.646 | −3.800 | −12.527 | 1.00 | 62.55 | C |
| ATOM | 4621 | NE1 | TRP | H | 50 | −69.511 | −3.235 | −13.050 | 1.00 | 61.58 | N |
| ATOM | 4622 | CE2 | TRP | H | 50 | −68.897 | −2.487 | −12.073 | 1.00 | 62.09 | C |
| ATOM | 4623 | CD2 | TRP | H | 50 | −69.698 | −2.580 | −10.909 | 1.00 | 62.02 | C |
| ATOM | 4624 | CE3 | TRP | H | 50 | −69.267 | −1.930 | −9.734 | 1.00 | 61.51 | C |
| ATOM | 4625 | CZ3 | TRP | H | 50 | −68.091 | −1.193 | −9.768 | 1.00 | 59.88 | C |
| ATOM | 4626 | CH2 | TRP | H | 50 | −67.316 | −1.118 | −10.934 | 1.00 | 60.16 | C |
| ATOM | 4627 | CZ2 | TRP | H | 50 | −67.695 | −1.755 | −12.100 | 1.00 | 60.79 | C |
| ATOM | 4628 | C | TRP | H | 50 | −70.229 | −5.335 | −9.111 | 1.00 | 67.37 | C |
| ATOM | 4629 | O | TRP | H | 50 | −69.966 | −5.052 | −7.941 | 1.00 | 67.16 | O |
| ATOM | 4630 | N | ILE | H | 51 | −69.307 | −5.748 | −9.997 | 1.00 | 65.38 | N |
| ATOM | 4631 | CA | ILE | H | 51 | −67.901 | −5.890 | −9.687 | 1.00 | 66.71 | C |
| ATOM | 4632 | CB | ILE | H | 51 | −67.561 | −7.267 | −9.077 | 1.00 | 66.78 | C |
| ATOM | 4633 | CG1 | ILE | H | 51 | −66.179 | −7.234 | −8.328 | 1.00 | 66.43 | C |
| ATOM | 4634 | CD1 | ILE | H | 51 | −65.274 | −8.456 | −8.481 | 1.00 | 64.32 | C |
| ATOM | 4635 | CG2 | ILE | H | 51 | −67.671 | −8.400 | −10.138 | 1.00 | 66.18 | C |
| ATOM | 4636 | C | ILE | H | 51 | −67.044 | −5.617 | −10.913 | 1.00 | 67.98 | C |
| ATOM | 4637 | O | ILE | H | 51 | −67.364 | −6.085 | −12.009 | 1.00 | 68.13 | O |
| ATOM | 4638 | N | ASP | H | 52 | −65.936 | −4.884 | −10.726 | 1.00 | 73.76 | N |
| ATOM | 4639 | CA | ASP | H | 52 | −65.022 | −4.621 | −11.812 | 1.00 | 75.48 | C |
| ATOM | 4640 | CB | ASP | H | 52 | −64.515 | −3.183 | −11.781 | 1.00 | 75.68 | C |
| ATOM | 4641 | CG | ASP | H | 52 | −63.282 | −2.949 | −12.637 | 1.00 | 77.20 | C |
| ATOM | 4642 | OD1 | ASP | H | 52 | −62.384 | −2.192 | −12.178 | 1.00 | 78.73 | O |

TABLE 14-continued

PCSK9 and AX132 Fab complex x-ray structure

| ATOM | 4643 | OD2 | ASP | H | 52 | −63.202 | −3.543 | −13.781 | 1.00 | 76.29 | O |
|---|---|---|---|---|---|---|---|---|---|---|---|
| ATOM | 4644 | C | ASP | H | 52 | −63.879 | −5.644 | −11.705 | 1.00 | 76.31 | C |
| ATOM | 4645 | O | ASP | H | 52 | −63.042 | −5.534 | −10.801 | 1.00 | 76.43 | O |
| ATOM | 4646 | N | PRO | H | 53 | −63.823 | −6.653 | −12.614 | 1.00 | 78.05 | N |
| ATOM | 4647 | CA | PRO | H | 53 | −62.752 | −7.660 | −12.543 | 1.00 | 78.76 | C |
| ATOM | 4648 | CB | PRO | H | 53 | −63.074 | −8.626 | −13.689 | 1.00 | 78.77 | C |
| ATOM | 4649 | CG | PRO | H | 53 | −64.483 | −8.421 | −13.982 | 1.00 | 78.29 | C |
| ATOM | 4650 | CD | PRO | H | 53 | −64.746 | −6.957 | −13.720 | 1.00 | 78.12 | C |
| ATOM | 4651 | C | PRO | H | 53 | −61.357 | −7.071 | −12.678 | 1.00 | 79.46 | C |
| ATOM | 4652 | O | PRO | H | 53 | −60.378 | −7.777 | −12.418 | 1.00 | 80.25 | O |
| ATOM | 4653 | N | GLY | H | 54 | −61.281 | −5.799 | −13.079 | 1.00 | 78.39 | N |
| ATOM | 4654 | CA | GLY | H | 54 | −60.023 | −5.083 | −13.210 | 1.00 | 78.15 | C |
| ATOM | 4655 | C | GLY | H | 54 | −59.461 | −4.803 | −11.832 | 1.00 | 77.68 | C |
| ATOM | 4656 | O | GLY | H | 54 | −58.483 | −5.434 | −11.420 | 1.00 | 77.62 | O |
| ATOM | 4657 | N | SER | H | 55 | −60.121 | −3.897 | −11.099 | 1.00 | 77.03 | N |
| ATOM | 4658 | CA | SER | H | 55 | −59.740 | −3.476 | −9.757 | 1.00 | 76.83 | C |
| ATOM | 4659 | CB | SER | H | 55 | −60.242 | −2.065 | −9.479 | 1.00 | 76.80 | C |
| ATOM | 4660 | OG | SER | H | 55 | −61.658 | −1.999 | −9.501 | 1.00 | 77.10 | O |
| ATOM | 4661 | C | SER | H | 55 | −60.208 | −4.397 | −8.646 | 1.00 | 76.83 | C |
| ATOM | 4662 | O | SER | H | 55 | −59.390 | −4.929 | −7.895 | 1.00 | 77.56 | O |
| ATOM | 4663 | N | GLY | H | 56 | −61.515 | −4.563 | −8.547 | 1.00 | 75.37 | N |
| ATOM | 4664 | CA | GLY | H | 56 | −62.203 | −5.325 | −7.517 | 1.00 | 74.42 | C |
| ATOM | 4665 | C | GLY | H | 56 | −63.294 | −4.422 | −6.966 | 1.00 | 74.06 | C |
| ATOM | 4666 | O | GLY | H | 56 | −63.938 | −4.746 | −5.961 | 1.00 | 73.96 | O |
| ATOM | 4667 | N | GLY | H | 57 | −63.480 | −3.279 | −7.643 | 1.00 | 70.98 | N |
| ATOM | 4668 | CA | GLY | H | 57 | −64.487 | −2.277 | −7.332 | 1.00 | 70.53 | C |
| ATOM | 4669 | C | GLY | H | 57 | −65.847 | −2.934 | −7.303 | 1.00 | 70.34 | C |
| ATOM | 4670 | O | GLY | H | 57 | −66.218 | −3.660 | −8.226 | 1.00 | 70.61 | O |
| ATOM | 4671 | N | THR | H | 58 | −66.588 | −2.704 | −6.243 | 1.00 | 68.48 | N |
| ATOM | 4672 | CA | THR | H | 58 | −67.841 | −3.386 | −6.090 | 1.00 | 67.80 | C |
| ATOM | 4673 | CB | THR | H | 58 | −67.484 | −4.512 | −5.112 | 1.00 | 67.50 | C |
| ATOM | 4674 | OG1 | THR | H | 58 | −67.790 | −5.788 | −5.635 | 1.00 | 68.57 | O |
| ATOM | 4675 | CG2 | THR | H | 58 | −67.909 | −4.281 | −3.694 | 1.00 | 67.36 | C |
| ATOM | 4676 | C | THR | H | 58 | −69.012 | −2.480 | −5.715 | 1.00 | 67.57 | C |
| ATOM | 4677 | O | THR | H | 58 | −68.824 | −1.568 | −4.922 | 1.00 | 67.91 | O |
| ATOM | 4678 | N | LYS | H | 59 | −70.215 | −2.712 | −6.273 | 1.00 | 66.54 | N |
| ATOM | 4679 | CA | LYS | H | 59 | −71.445 | −1.942 | −5.922 | 1.00 | 66.37 | C |
| ATOM | 4680 | CB | LYS | H | 59 | −71.880 | −0.954 | −7.023 | 1.00 | 65.94 | C |
| ATOM | 4681 | CG | LYS | H | 59 | −70.839 | 0.083 | −7.387 | 1.00 | 65.87 | C |
| ATOM | 4682 | CD | LYS | H | 59 | −71.473 | 1.258 | −8.101 | 1.00 | 65.73 | C |
| ATOM | 4683 | CE | LYS | H | 59 | −70.641 | 1.831 | −9.224 | 1.00 | 63.88 | C |
| ATOM | 4684 | NZ | LYS | H | 59 | −71.283 | 1.617 | −10.566 | 1.00 | 63.65 | N |
| ATOM | 4685 | C | LYS | H | 59 | −72.578 | −2.953 | −5.633 | 1.00 | 66.37 | C |
| ATOM | 4686 | O | LYS | H | 59 | −72.665 | −3.953 | −6.343 | 1.00 | 66.46 | O |
| ATOM | 4687 | N | TYR | H | 60 | −73.409 | −2.725 | −4.601 | 1.00 | 65.94 | N |
| ATOM | 4688 | CA | TYR | H | 60 | −74.512 | −3.641 | −4.260 | 1.00 | 66.27 | C |
| ATOM | 4689 | CB | TYR | H | 60 | −74.252 | −4.386 | −2.949 | 1.00 | 65.68 | C |
| ATOM | 4690 | CG | TYR | H | 60 | −72.987 | −5.203 | −2.907 | 1.00 | 65.72 | C |
| ATOM | 4691 | CD1 | TYR | H | 60 | −73.000 | −6.567 | −3.200 | 1.00 | 66.37 | C |
| ATOM | 4692 | CE1 | TYR | H | 60 | −71.828 | −7.332 | −3.145 | 1.00 | 66.03 | C |
| ATOM | 4693 | CZ | TYR | H | 60 | −70.635 | −6.732 | −2.776 | 1.00 | 65.40 | C |
| ATOM | 4694 | OH | TYR | H | 60 | −69.455 | −7.428 | −2.716 | 1.00 | 65.30 | O |
| ATOM | 4695 | CE2 | TYR | H | 60 | −70.618 | −5.390 | −2.444 | 1.00 | 65.92 | C |
| ATOM | 4696 | CD2 | TYR | H | 60 | −71.786 | −4.635 | −2.514 | 1.00 | 65.58 | C |
| ATOM | 4697 | C | TYR | H | 60 | −75.861 | −2.946 | −4.124 | 1.00 | 66.96 | C |
| ATOM | 4698 | O | TYR | H | 60 | −75.927 | −1.776 | −3.747 | 1.00 | 66.93 | O |
| ATOM | 4699 | N | ASN | H | 61 | −76.945 | −3.676 | −4.408 | 1.00 | 74.07 | N |
| ATOM | 4700 | CA | ASN | H | 61 | −78.296 | −3.147 | −4.254 | 1.00 | 75.29 | C |
| ATOM | 4701 | CB | ASN | H | 61 | −79.308 | −4.131 | −4.838 | 1.00 | 75.03 | C |
| ATOM | 4702 | CG | ASN | H | 61 | −80.745 | −3.687 | −4.798 | 1.00 | 75.28 | C |
| ATOM | 4703 | OD1 | ASN | H | 61 | −81.168 | −2.881 | −3.969 | 1.00 | 76.17 | O |
| ATOM | 4704 | ND2 | ASN | H | 61 | −81.556 | −4.221 | −5.695 | 1.00 | 75.49 | N |
| ATOM | 4705 | C | ASN | H | 61 | −78.496 | −2.964 | −2.728 | 1.00 | 76.55 | C |
| ATOM | 4706 | O | ASN | H | 61 | −78.137 | −3.869 | −1.957 | 1.00 | 76.87 | O |
| ATOM | 4707 | N | GLU | H | 62 | −79.025 | −1.791 | −2.287 | 1.00 | 79.72 | N |
| ATOM | 4708 | CA | GLU | H | 62 | −79.246 | −1.525 | −0.867 | 1.00 | 80.72 | C |
| ATOM | 4709 | CB | GLU | H | 62 | −79.777 | −0.116 | −0.635 | 1.00 | 80.60 | C |
| ATOM | 4710 | C | GLU | H | 62 | −80.103 | −2.614 | −0.172 | 1.00 | 81.74 | C |
| ATOM | 4711 | O | GLU | H | 62 | −79.878 | −2.866 | 1.017 | 1.00 | 82.04 | O |
| ATOM | 4712 | N | LYS | H | 63 | −81.036 | −3.298 | −0.914 | 1.00 | 83.34 | N |
| ATOM | 4713 | CA | LYS | H | 63 | −81.869 | −4.389 | −0.382 | 1.00 | 84.18 | C |
| ATOM | 4714 | CB | LYS | H | 63 | −82.757 | −5.008 | −1.483 | 1.00 | 83.83 | C |
| ATOM | 4715 | C | LYS | H | 63 | −80.984 | −5.473 | 0.302 | 1.00 | 85.07 | C |
| ATOM | 4716 | O | LYS | H | 63 | −81.297 | −5.897 | 1.409 | 1.00 | 85.46 | O |
| ATOM | 4717 | N | PHE | H | 64 | −79.859 | −5.868 | −0.328 | 1.00 | 87.41 | N |
| ATOM | 4718 | CA | PHE | H | 64 | −78.931 | −6.878 | 0.200 | 1.00 | 88.13 | C |
| ATOM | 4719 | CB | PHE | H | 64 | −78.508 | −7.839 | −0.932 | 1.00 | 87.91 | C |
| ATOM | 4720 | CG | PHE | H | 64 | −79.520 | −8.037 | −2.037 | 1.00 | 87.18 | C |

TABLE 14-continued

PCSK9 and AX132 Fab complex x-ray structure

| ATOM | 4721 | CD1 | PHE | H | 64 | −79.311 | −7.497 | −3.295 | 1.00 | 86.67 | C |
|---|---|---|---|---|---|---|---|---|---|---|---|
| ATOM | 4722 | CE1 | PHE | H | 64 | −80.249 | −7.678 | −4.311 | 1.00 | 85.39 | C |
| ATOM | 4723 | CZ | PHE | H | 64 | −81.392 | −8.399 | −4.074 | 1.00 | 84.32 | C |
| ATOM | 4724 | CE2 | PHE | H | 64 | −81.614 | −8.940 | −2.836 | 1.00 | 84.40 | C |
| ATOM | 4725 | CD2 | PHE | H | 64 | −80.684 | −8.757 | −1.817 | 1.00 | 85.74 | C |
| ATOM | 4726 | C | PHE | H | 64 | −77.685 | −6.241 | 0.902 | 1.00 | 89.03 | C |
| ATOM | 4727 | O | PHE | H | 64 | −76.527 | −6.644 | 0.650 | 1.00 | 89.44 | O |
| ATOM | 4728 | N | LYS | H | 65 | −77.934 | −5.234 | 1.784 | 1.00 | 91.91 | N |
| ATOM | 4729 | CA | LYS | H | 65 | −76.890 | −4.511 | 2.534 | 1.00 | 91.95 | C |
| ATOM | 4730 | CB | LYS | H | 65 | −77.490 | −3.335 | 3.342 | 1.00 | 92.18 | C |
| ATOM | 4731 | C | LYS | H | 65 | −76.126 | −5.469 | 3.448 | 1.00 | 91.81 | C |
| ATOM | 4732 | O | LYS | H | 65 | −76.642 | −5.894 | 4.490 | 1.00 | 91.86 | O |
| ATOM | 4733 | N | GLY | H | 66 | −74.923 | −5.832 | 3.012 | 1.00 | 91.10 | N |
| ATOM | 4734 | CA | GLY | H | 66 | −74.065 | −6.752 | 3.746 | 1.00 | 90.88 | C |
| ATOM | 4735 | C | GLY | H | 66 | −74.492 | −8.201 | 3.618 | 1.00 | 90.89 | C |
| ATOM | 4736 | O | GLY | H | 66 | −73.743 | −9.096 | 4.020 | 1.00 | 91.20 | O |
| ATOM | 4737 | N | LYS | H | 67 | −75.705 | −8.450 | 3.056 | 1.00 | 90.67 | N |
| ATOM | 4738 | CA | LYS | H | 67 | −76.247 | −9.793 | 2.832 | 1.00 | 90.02 | C |
| ATOM | 4739 | CB | LYS | H | 67 | −77.753 | −9.724 | 2.558 | 1.00 | 89.88 | C |
| ATOM | 4740 | C | LYS | H | 67 | −75.497 | −10.467 | 1.667 | 1.00 | 89.63 | C |
| ATOM | 4741 | O | LYS | H | 67 | −75.191 | −11.654 | 1.742 | 1.00 | 89.64 | O |
| ATOM | 4742 | N | ALA | H | 68 | −75.170 | −9.683 | 0.615 | 1.00 | 88.82 | N |
| ATOM | 4743 | CA | ALA | H | 68 | −74.462 | −10.118 | −0.595 | 1.00 | 88.21 | C |
| ATOM | 4744 | CB | ALA | H | 68 | −75.108 | −9.486 | −1.819 | 1.00 | 88.14 | C |
| ATOM | 4745 | C | ALA | H | 68 | −72.935 | −9.842 | −0.588 | 1.00 | 87.72 | C |
| ATOM | 4746 | O | ALA | H | 68 | −72.471 | −8.920 | 0.093 | 1.00 | 88.14 | O |
| ATOM | 4747 | N | THR | H | 69 | −72.163 | −10.654 | −1.350 | 1.00 | 84.50 | N |
| ATOM | 4748 | CA | THR | H | 69 | −70.708 | −10.544 | −1.477 | 1.00 | 83.53 | C |
| ATOM | 4749 | CB | THR | H | 69 | −69.985 | −11.394 | −0.401 | 1.00 | 83.59 | C |
| ATOM | 4750 | OG1 | THR | H | 69 | −70.545 | −11.172 | 0.899 | 1.00 | 83.87 | O |
| ATOM | 4751 | CG2 | THR | H | 69 | −68.457 | −11.205 | −0.407 | 1.00 | 82.58 | C |
| ATOM | 4752 | C | THR | H | 69 | −70.303 | −11.027 | −2.862 | 1.00 | 83.16 | C |
| ATOM | 4753 | O | THR | H | 69 | −70.386 | −12.231 | −3.146 | 1.00 | 83.89 | O |
| ATOM | 4754 | N | ILE | H | 70 | −69.850 | −10.106 | −3.719 | 1.00 | 77.88 | N |
| ATOM | 4755 | CA | ILE | H | 70 | −69.410 | −10.456 | −5.071 | 1.00 | 76.85 | C |
| ATOM | 4756 | CB | ILE | H | 70 | −70.094 | −9.611 | −6.180 | 1.00 | 76.87 | C |
| ATOM | 4757 | CG1 | ILE | H | 70 | −71.608 | −9.667 | −6.025 | 1.00 | 76.68 | C |
| ATOM | 4758 | CD1 | ILE | H | 70 | −72.269 | −8.566 | −6.573 | 1.00 | 76.66 | C |
| ATOM | 4759 | CG2 | ILE | H | 70 | −69.696 | −10.099 | −7.589 | 1.00 | 76.64 | C |
| ATOM | 4760 | C | ILE | H | 70 | −67.894 | −10.426 | −5.147 | 1.00 | 76.29 | C |
| ATOM | 4761 | O | ILE | H | 70 | −67.276 | −9.485 | −4.649 | 1.00 | 76.21 | O |
| ATOM | 4762 | N | SER | H | 71 | −67.303 | −11.463 | −5.768 | 1.00 | 73.60 | N |
| ATOM | 4763 | CA | SER | H | 71 | −65.858 | −11.583 | −5.946 | 1.00 | 73.32 | C |
| ATOM | 4764 | CB | SER | H | 71 | −65.213 | −12.345 | −4.791 | 1.00 | 73.02 | C |
| ATOM | 4765 | OG | SER | H | 71 | −65.483 | −13.734 | −4.787 | 1.00 | 72.63 | O |
| ATOM | 4766 | C | SER | H | 71 | −65.472 | −12.142 | −7.311 | 1.00 | 73.44 | C |
| ATOM | 4767 | O | SER | H | 71 | −66.354 | −12.477 | −8.098 | 1.00 | 73.35 | O |
| ATOM | 4768 | N | ARG | H | 72 | −64.170 | −12.201 | −7.605 | 1.00 | 75.48 | N |
| ATOM | 4769 | CA | ARG | H | 72 | −63.661 | −12.700 | −8.875 | 1.00 | 76.24 | C |
| ATOM | 4770 | CB | ARG | H | 72 | −63.371 | −11.515 | −9.819 | 1.00 | 76.60 | C |
| ATOM | 4771 | CG | ARG | H | 72 | −61.963 | −10.932 | −9.644 | 1.00 | 78.47 | C |
| ATOM | 4772 | CD | ARG | H | 72 | −61.921 | −9.442 | −9.758 | 1.00 | 82.25 | C |
| ATOM | 4773 | NE | ARG | H | 72 | −61.252 | −8.815 | −8.620 | 1.00 | 83.67 | N |
| ATOM | 4774 | CZ | ARG | H | 72 | −60.030 | −8.300 | −8.661 | 1.00 | 84.64 | C |
| ATOM | 4775 | NH1 | ARG | H | 72 | −59.317 | −8.353 | −9.783 | 1.00 | 85.32 | N |
| ATOM | 4776 | NH2 | ARG | H | 72 | −59.506 | −7.731 | −7.582 | 1.00 | 85.79 | N |
| ATOM | 4777 | C | ARG | H | 72 | −62.388 | −13.538 | −8.670 | 1.00 | 76.09 | C |
| ATOM | 4778 | O | ARG | H | 72 | −61.857 | −13.605 | −7.562 | 1.00 | 76.37 | O |
| ATOM | 4779 | N | ASP | H | 73 | −61.883 | −14.140 | −9.747 | 1.00 | 77.73 | N |
| ATOM | 4780 | CA | ASP | H | 73 | −60.662 | −14.929 | −9.737 | 1.00 | 77.99 | C |
| ATOM | 4781 | CB | ASP | H | 73 | −60.971 | −16.362 | −9.276 | 1.00 | 78.21 | C |
| ATOM | 4782 | CG | ASP | H | 73 | −59.812 | −17.175 | −8.705 | 1.00 | 78.48 | C |
| ATOM | 4783 | OD1 | ASP | H | 73 | −58.651 | −16.988 | −9.181 | 1.00 | 76.53 | O |
| ATOM | 4784 | OD2 | ASP | H | 73 | −60.075 | −18.043 | −7.806 | 1.00 | 80.10 | O |
| ATOM | 4785 | C | ASP | H | 73 | −60.098 | −14.881 | −11.160 | 1.00 | 78.17 | C |
| ATOM | 4786 | O | ASP | H | 73 | −60.113 | −15.882 | −11.877 | 1.00 | 77.98 | O |
| ATOM | 4787 | N | ASN | H | 74 | −59.616 | −13.692 | −11.568 | 1.00 | 77.75 | N |
| ATOM | 4788 | CA | ASN | H | 74 | −59.066 | −13.424 | −12.893 | 1.00 | 77.93 | C |
| ATOM | 4789 | CB | ASN | H | 74 | −58.226 | −12.155 | −12.872 | 1.00 | 78.15 | C |
| ATOM | 4790 | CG | ASN | H | 74 | −59.031 | −10.887 | −12.827 | 1.00 | 79.65 | C |
| ATOM | 4791 | OD1 | ASN | H | 74 | −59.705 | −10.592 | −11.843 | 1.00 | 81.86 | O |
| ATOM | 4792 | ND2 | ASN | H | 74 | −58.965 | −10.105 | −13.894 | 1.00 | 80.65 | N |
| ATOM | 4793 | C | ASN | H | 74 | −58.281 | −14.578 | −13.525 | 1.00 | 77.75 | C |
| ATOM | 4794 | O | ASN | H | 74 | −58.295 | −14.729 | −14.753 | 1.00 | 77.58 | O |
| ATOM | 4795 | N | SER | H | 75 | −57.597 | −15.383 | −12.681 | 1.00 | 77.01 | N |
| ATOM | 4796 | CA | SER | H | 75 | −56.783 | −16.530 | −13.091 | 1.00 | 76.66 | C |
| ATOM | 4797 | CB | SER | H | 75 | −55.966 | −17.040 | −11.919 | 1.00 | 76.52 | C |
| ATOM | 4798 | OG | SER | H | 75 | −56.841 | −17.302 | −10.835 | 1.00 | 77.70 | O |

TABLE 14-continued

PCSK9 and AX132 Fab complex x-ray structure

| ATOM | 4799 | C   | SER | H | 75 | −57.635 | −17.658 | −13.638 | 1.00 | 76.26 | C |
|------|------|-----|-----|---|----|---------|---------|---------|------|-------|---|
| ATOM | 4800 | O   | SER | H | 75 | −57.148 | −18.418 | −14.476 | 1.00 | 76.65 | O |
| ATOM | 4801 | N   | LYS | H | 76 | −58.892 | −17.778 | −13.161 | 1.00 | 73.56 | N |
| ATOM | 4802 | CA  | LYS | H | 76 | −59.837 | −18.808 | −13.593 | 1.00 | 72.90 | C |
| ATOM | 4803 | CB  | LYS | H | 76 | −60.073 | −19.891 | −12.521 | 1.00 | 72.97 | C |
| ATOM | 4804 | CG  | LYS | H | 76 | −60.109 | −19.394 | −11.094 | 1.00 | 73.34 | C |
| ATOM | 4805 | CD  | LYS | H | 76 | −60.812 | −20.371 | −10.118 | 1.00 | 74.83 | C |
| ATOM | 4806 | CE  | LYS | H | 76 | −59.884 | −21.119 | −9.187  | 1.00 | 75.51 | C |
| ATOM | 4807 | NZ  | LYS | H | 76 | −59.171 | −22.235 | −9.885  | 1.00 | 76.07 | N |
| ATOM | 4808 | C   | LYS | H | 76 | −61.131 | −18.218 | −14.154 | 1.00 | 72.42 | C |
| ATOM | 4809 | O   | LYS | H | 76 | −62.174 | −18.882 | −14.187 | 1.00 | 72.36 | O |
| ATOM | 4810 | N   | ASN | H | 77 | −61.053 | −16.942 | −14.599 | 1.00 | 72.21 | N |
| ATOM | 4811 | CA  | ASN | H | 77 | −62.142 | −16.171 | −15.213 | 1.00 | 71.28 | C |
| ATOM | 4812 | CB  | ASN | H | 77 | −62.280 | −16.601 | −16.669 | 1.00 | 70.88 | C |
| ATOM | 4813 | CG  | ASN | H | 77 | −61.140 | −16.232 | −17.561 | 1.00 | 70.31 | C |
| ATOM | 4814 | OD1 | ASN | H | 77 | −61.354 | −15.894 | −18.724 | 1.00 | 70.39 | O |
| ATOM | 4815 | ND2 | ASN | H | 77 | −59.916 | −16.293 | −17.071 | 1.00 | 70.87 | N |
| ATOM | 4816 | C   | ASN | H | 77 | −63.491 | −16.338 | −14.497 | 1.00 | 71.06 | C |
| ATOM | 4817 | O   | ASN | H | 77 | −64.552 | −16.213 | −15.119 | 1.00 | 71.17 | O |
| ATOM | 4818 | N   | THR | H | 78 | −63.457 | −16.641 | −13.209 | 1.00 | 67.84 | N |
| ATOM | 4819 | CA  | THR | H | 78 | −64.706 | −16.851 | −12.516 | 1.00 | 67.61 | C |
| ATOM | 4820 | CB  | THR | H | 78 | −64.782 | −18.234 | −11.818 | 1.00 | 67.66 | C |
| ATOM | 4821 | OG1 | THR | H | 78 | −63.489 | −18.573 | −11.370 | 1.00 | 68.59 | O |
| ATOM | 4822 | CG2 | THR | H | 78 | −65.170 | −19.328 | −12.744 | 1.00 | 67.39 | C |
| ATOM | 4823 | C   | THR | H | 78 | −65.160 | −15.666 | −11.724 | 1.00 | 67.05 | C |
| ATOM | 4824 | O   | THR | H | 78 | −64.359 | −14.867 | −11.264 | 1.00 | 66.86 | O |
| ATOM | 4825 | N   | LEU | H | 79 | −66.455 | −15.564 | −11.581 | 1.00 | 65.03 | N |
| ATOM | 4826 | CA  | LEU | H | 79 | −67.135 | −14.527 | −10.853 | 1.00 | 64.84 | C |
| ATOM | 4827 | CB  | LEU | H | 79 | −68.018 | −13.799 | −11.856 | 1.00 | 64.81 | C |
| ATOM | 4828 | CG  | LEU | H | 79 | −68.966 | −12.782 | −11.324 | 1.00 | 65.04 | C |
| ATOM | 4829 | CD1 | LEU | H | 79 | −68.254 | −11.520 | −11.026 | 1.00 | 66.20 | C |
| ATOM | 4830 | CD2 | LEU | H | 79 | −70.119 | −12.567 | −12.297 | 1.00 | 64.91 | C |
| ATOM | 4831 | C   | LEU | H | 79 | −67.964 | −15.271 | −9.823  | 1.00 | 65.02 | C |
| ATOM | 4832 | O   | LEU | H | 79 | −68.577 | −16.281 | −10.162 | 1.00 | 65.22 | O |
| ATOM | 4833 | N   | TYR | H | 80 | −67.953 | −14.829 | −8.568  | 1.00 | 64.32 | N |
| ATOM | 4834 | CA  | TYR | H | 80 | −68.694 | −15.535 | −7.532  | 1.00 | 64.62 | C |
| ATOM | 4835 | CB  | TYR | H | 80 | −67.752 | −16.122 | −6.458  | 1.00 | 64.08 | C |
| ATOM | 4836 | CG  | TYR | H | 80 | −66.626 | −17.007 | −6.950  | 1.00 | 64.44 | C |
| ATOM | 4837 | CD1 | TYR | H | 80 | −65.364 | −16.481 | −7.220  | 1.00 | 64.70 | C |
| ATOM | 4838 | CE1 | TYR | H | 80 | −64.320 | −17.289 | −7.668  | 1.00 | 64.48 | C |
| ATOM | 4839 | CZ  | TYR | H | 80 | −64.520 | −18.650 | −7.812  | 1.00 | 65.60 | C |
| ATOM | 4840 | OH  | TYR | H | 80 | −63.491 | −19.448 | −8.253  | 1.00 | 66.92 | O |
| ATOM | 4841 | CE2 | TYR | H | 80 | −65.758 | −19.203 | −7.516  | 1.00 | 65.49 | C |
| ATOM | 4842 | CD2 | TYR | H | 80 | −66.802 | −18.380 | −7.093  | 1.00 | 64.95 | C |
| ATOM | 4843 | C   | TYR | H | 80 | −69.660 | −14.609 | −6.841  | 1.00 | 65.53 | C |
| ATOM | 4844 | O   | TYR | H | 80 | −69.348 | −13.437 | −6.613  | 1.00 | 65.93 | O |
| ATOM | 4845 | N   | LEU | H | 81 | −70.823 | −15.144 | −6.473  | 1.00 | 68.48 | N |
| ATOM | 4846 | CA  | LEU | H | 81 | −71.832 | −14.431 | −5.709  | 1.00 | 69.08 | C |
| ATOM | 4847 | CB  | LEU | H | 81 | −73.130 | −14.187 | −6.522  | 1.00 | 68.98 | C |
| ATOM | 4848 | CG  | LEU | H | 81 | −74.458 | −13.954 | −5.745  | 1.00 | 68.46 | C |
| ATOM | 4849 | CD1 | LEU | H | 81 | −74.497 | −12.601 | −5.103  | 1.00 | 67.63 | C |
| ATOM | 4850 | CD2 | LEU | H | 81 | −75.635 | −14.096 | −6.645  | 1.00 | 68.63 | C |
| ATOM | 4851 | C   | LEU | H | 81 | −72.114 | −15.283 | −4.473  | 1.00 | 69.89 | C |
| ATOM | 4852 | O   | LEU | H | 81 | −72.090 | −16.521 | −4.544  | 1.00 | 69.50 | O |
| ATOM | 4853 | N   | GLN | H | 82 | −72.370 | −14.604 | −3.347  | 1.00 | 77.02 | N |
| ATOM | 4854 | CA  | GLN | H | 82 | −72.741 | −15.211 | −2.086  | 1.00 | 78.47 | C |
| ATOM | 4855 | CB  | GLN | H | 82 | −71.554 | −15.328 | −1.145  | 1.00 | 78.56 | C |
| ATOM | 4856 | CG  | GLN | H | 82 | −71.958 | −16.041 |  0.147  | 1.00 | 81.03 | C |
| ATOM | 4857 | CD  | GLN | H | 82 | −70.901 | −16.019 |  1.216  | 1.00 | 83.34 | C |
| ATOM | 4858 | OE1 | GLN | H | 82 | −70.408 | −17.081 |  1.631  | 1.00 | 84.08 | O |
| ATOM | 4859 | NE2 | GLN | H | 82 | −70.538 | −14.812 |  1.684  | 1.00 | 84.60 | N |
| ATOM | 4860 | C   | GLN | H | 82 | −73.840 | −14.384 | −1.440  | 1.00 | 79.23 | C |
| ATOM | 4861 | O   | GLN | H | 82 | −73.697 | −13.170 | −1.306  | 1.00 | 79.44 | O |
| ATOM | 4862 | N   | MET | H | 83 | −74.924 | −15.037 | −1.039  | 1.00 | 79.50 | N |
| ATOM | 4863 | CA  | MET | H | 83 | −76.023 | −14.364 | −0.377  | 1.00 | 80.56 | C |
| ATOM | 4864 | CB  | MET | H | 83 | −77.223 | −14.186 | −1.301  | 1.00 | 80.59 | C |
| ATOM | 4865 | CG  | MET | H | 83 | −77.063 | −13.048 | −2.260  | 1.00 | 81.48 | C |
| ATOM | 4866 | SD  | MET | H | 83 | −78.606 | −12.506 | −3.041  | 1.00 | 83.98 | S |
| ATOM | 4867 | CE  | MET | H | 83 | −79.683 | −12.206 | −1.544  | 1.00 | 82.79 | C |
| ATOM | 4868 | C   | MET | H | 83 | −76.373 | −15.165 |  0.842  | 1.00 | 81.17 | C |
| ATOM | 4869 | O   | MET | H | 83 | −76.792 | −16.308 |  0.725  | 1.00 | 81.21 | O |
| ATOM | 4870 | N   | ASN | H | 84 | −76.171 | −14.561 |  2.014  | 1.00 | 83.17 | N |
| ATOM | 4871 | CA  | ASN | H | 84 | −76.391 | −15.144 |  3.332  | 1.00 | 84.11 | C |
| ATOM | 4872 | CB  | ASN | H | 84 | −75.286 | −14.659 |  4.258  | 1.00 | 84.31 | C |
| ATOM | 4873 | CG  | ASN | H | 84 | −73.927 | −14.697 |  3.596  | 1.00 | 85.99 | C |
| ATOM | 4874 | OD1 | ASN | H | 84 | −73.459 | −15.742 |  3.103  | 1.00 | 87.19 | O |
| ATOM | 4875 | ND2 | ASN | H | 84 | −73.261 | −13.545 |  3.552  | 1.00 | 88.48 | N |
| ATOM | 4876 | C   | ASN | H | 84 | −77.774 | −14.819 |  3.899  | 1.00 | 84.38 | C |

TABLE 14-continued

PCSK9 and AX132 Fab complex x-ray structure

| ATOM | 4877 | O | ASN | H | 84 | −78.430 | −13.895 | 3.412 | 1.00 | 84.40 | O |
|---|---|---|---|---|---|---|---|---|---|---|---|
| ATOM | 4878 | N | SER | H | 85 | −78.219 | −15.591 | 4.922 | 1.00 | 86.21 | N |
| ATOM | 4879 | CA | SER | H | 85 | −79.510 | −15.426 | 5.625 | 1.00 | 86.62 | C |
| ATOM | 4880 | CB | SER | H | 85 | −79.454 | −14.250 | 6.608 | 1.00 | 86.59 | C |
| ATOM | 4881 | OG | SER | H | 85 | −78.255 | −14.235 | 7.371 | 1.00 | 87.47 | O |
| ATOM | 4882 | C | SER | H | 85 | −80.736 | −15.325 | 4.686 | 1.00 | 86.64 | C |
| ATOM | 4883 | O | SER | H | 85 | −81.513 | −14.367 | 4.769 | 1.00 | 86.92 | O |
| ATOM | 4884 | N | LEU | H | 86 | −80.904 | −16.326 | 3.804 | 1.00 | 83.88 | N |
| ATOM | 4885 | CA | LEU | H | 86 | −81.992 | −16.360 | 2.828 | 1.00 | 83.85 | C |
| ATOM | 4886 | CB | LEU | H | 86 | −81.655 | −17.283 | 1.646 | 1.00 | 83.52 | C |
| ATOM | 4887 | CG | LEU | H | 86 | −80.321 | −17.018 | 0.942 | 1.00 | 82.64 | C |
| ATOM | 4888 | CD1 | LEU | H | 86 | −79.953 | −18.143 | 0.069 | 1.00 | 80.79 | C |
| ATOM | 4889 | CD2 | LEU | H | 86 | −80.341 | −15.740 | 0.154 | 1.00 | 82.74 | C |
| ATOM | 4890 | C | LEU | H | 86 | −83.391 | −16.631 | 3.388 | 1.00 | 84.25 | C |
| ATOM | 4891 | O | LEU | H | 86 | −83.540 | −17.250 | 4.432 | 1.00 | 84.08 | O |
| ATOM | 4892 | N | ARG | H | 87 | −84.408 | −16.117 | 2.692 | 1.00 | 87.49 | N |
| ATOM | 4893 | CA | ARG | H | 87 | −85.833 | −16.239 | 2.996 | 1.00 | 87.95 | C |
| ATOM | 4894 | CB | ARG | H | 87 | −86.424 | −14.875 | 3.359 | 1.00 | 88.25 | C |
| ATOM | 4895 | CG | ARG | H | 87 | −85.590 | −14.081 | 4.356 | 1.00 | 90.00 | C |
| ATOM | 4896 | CD | ARG | H | 87 | −86.349 | −12.904 | 4.913 | 1.00 | 93.13 | C |
| ATOM | 4897 | NE | ARG | H | 87 | −86.517 | −11.838 | 3.924 | 1.00 | 95.49 | N |
| ATOM | 4898 | CZ | ARG | H | 87 | −86.363 | −10.540 | 4.182 | 1.00 | 97.17 | C |
| ATOM | 4899 | NH1 | ARG | H | 87 | −86.542 | −9.639 | 3.220 | 1.00 | 97.17 | N |
| ATOM | 4900 | NH2 | ARG | H | 87 | −86.028 | −10.132 | 5.406 | 1.00 | 98.62 | N |
| ATOM | 4901 | C | ARG | H | 87 | −86.476 | −16.753 | 1.724 | 1.00 | 87.88 | C |
| ATOM | 4902 | O | ARG | H | 87 | −85.829 | −16.724 | 0.680 | 1.00 | 88.02 | O |
| ATOM | 4903 | N | ALA | H | 88 | −87.727 | −17.223 | 1.777 | 1.00 | 89.65 | N |
| ATOM | 4904 | CA | ALA | H | 88 | −88.388 | −17.752 | 0.580 | 1.00 | 89.55 | C |
| ATOM | 4905 | CB | ALA | H | 88 | −89.723 | −18.371 | 0.940 | 1.00 | 89.60 | C |
| ATOM | 4906 | C | ALA | H | 88 | −88.531 | −16.737 | −0.573 | 1.00 | 89.59 | C |
| ATOM | 4907 | O | ALA | H | 88 | −88.712 | −17.146 | −1.719 | 1.00 | 89.56 | O |
| ATOM | 4908 | N | GLU | H | 89 | −88.407 | −15.422 | −0.274 | 1.00 | 92.07 | N |
| ATOM | 4909 | CA | GLU | H | 89 | −88.474 | −14.325 | −1.253 | 1.00 | 91.99 | C |
| ATOM | 4910 | CB | GLU | H | 89 | −88.520 | −12.960 | −0.564 | 1.00 | 92.37 | C |
| ATOM | 4911 | CG | GLU | H | 89 | −89.657 | −12.783 | 0.418 | 1.00 | 95.67 | C |
| ATOM | 4912 | CD | GLU | H | 89 | −89.184 | −12.521 | 1.834 | 1.00 | 100.06 | C |
| ATOM | 4913 | OE1 | GLU | H | 89 | −89.344 | −13.430 | 2.688 | 1.00 | 101.77 | O |
| ATOM | 4914 | OE2 | GLU | H | 89 | −88.648 | −11.411 | 2.085 | 1.00 | 101.51 | O |
| ATOM | 4915 | C | GLU | H | 89 | −87.246 | −14.337 | −2.146 | 1.00 | 91.13 | C |
| ATOM | 4916 | O | GLU | H | 89 | −87.320 | −13.892 | −3.296 | 1.00 | 91.47 | O |
| ATOM | 4917 | N | ASP | H | 90 | −86.105 | −14.827 | −1.614 | 1.00 | 88.34 | N |
| ATOM | 4918 | CA | ASP | H | 90 | −84.853 | −14.908 | −2.353 | 1.00 | 86.96 | C |
| ATOM | 4919 | CB | ASP | H | 90 | −83.650 | −14.902 | −1.408 | 1.00 | 87.15 | C |
| ATOM | 4920 | CG | ASP | H | 90 | −83.592 | −13.651 | −0.532 | 1.00 | 88.39 | C |
| ATOM | 4921 | OD1 | ASP | H | 90 | −83.867 | −12.532 | −1.056 | 1.00 | 89.29 | O |
| ATOM | 4922 | OD2 | ASP | H | 90 | −83.279 | −13.783 | 0.679 | 1.00 | 90.20 | O |
| ATOM | 4923 | C | ASP | H | 90 | −84.831 | −16.019 | −3.410 | 1.00 | 85.83 | C |
| ATOM | 4924 | O | ASP | H | 90 | −83.819 | −16.208 | −4.082 | 1.00 | 85.71 | O |
| ATOM | 4925 | N | THR | H | 91 | −85.976 | −16.717 | −3.596 | 1.00 | 81.43 | N |
| ATOM | 4926 | CA | THR | H | 91 | −86.138 | −17.750 | −4.618 | 1.00 | 79.99 | C |
| ATOM | 4927 | CB | THR | H | 91 | −87.349 | −18.647 | −4.339 | 1.00 | 80.13 | C |
| ATOM | 4928 | OG1 | THR | H | 91 | −87.316 | −19.113 | −2.991 | 1.00 | 80.98 | O |
| ATOM | 4929 | CG2 | THR | H | 91 | −87.457 | −19.804 | −5.322 | 1.00 | 78.80 | C |
| ATOM | 4930 | C | THR | H | 91 | −86.352 | −17.032 | −5.938 | 1.00 | 78.71 | C |
| ATOM | 4931 | O | THR | H | 91 | −87.298 | −16.237 | −6.059 | 1.00 | 78.84 | O |
| ATOM | 4932 | N | ALA | H | 92 | −85.475 | −17.309 | −6.914 | 1.00 | 73.98 | N |
| ATOM | 4933 | CA | ALA | H | 92 | −85.505 | −16.731 | −8.254 | 1.00 | 72.60 | C |
| ATOM | 4934 | CB | ALA | H | 92 | −85.247 | −15.231 | −8.182 | 1.00 | 72.66 | C |
| ATOM | 4935 | C | ALA | H | 92 | −84.441 | −17.367 | −9.120 | 1.00 | 71.70 | C |
| ATOM | 4936 | O | ALA | H | 92 | −83.702 | −18.250 | −8.682 | 1.00 | 72.05 | O |
| ATOM | 4937 | N | VAL | H | 93 | −84.360 | −16.903 | −10.361 | 1.00 | 68.26 | N |
| ATOM | 4938 | CA | VAL | H | 93 | −83.351 | −17.341 | −11.306 | 1.00 | 66.99 | C |
| ATOM | 4939 | CB | VAL | H | 93 | −83.925 | −17.581 | −12.704 | 1.00 | 66.60 | C |
| ATOM | 4940 | CG1 | VAL | H | 93 | −82.815 | −17.806 | −13.705 | 1.00 | 66.29 | C |
| ATOM | 4941 | CG2 | VAL | H | 93 | −84.839 | −18.779 | −12.672 | 1.00 | 65.83 | C |
| ATOM | 4942 | C | VAL | H | 93 | −82.247 | −16.264 | −11.243 | 1.00 | 66.74 | C |
| ATOM | 4943 | O | VAL | H | 93 | −82.529 | −15.062 | −11.295 | 1.00 | 66.88 | O |
| ATOM | 4944 | N | TYR | H | 94 | −81.015 | −16.707 | −11.080 | 1.00 | 65.99 | N |
| ATOM | 4945 | CA | TYR | H | 94 | −79.873 | −15.853 | −10.929 | 1.00 | 64.93 | C |
| ATOM | 4946 | CB | TYR | H | 94 | −79.072 | −16.318 | −9.710 | 1.00 | 65.01 | C |
| ATOM | 4947 | CG | TYR | H | 94 | −79.755 | −15.960 | −8.407 | 1.00 | 65.23 | C |
| ATOM | 4948 | CD1 | TYR | H | 94 | −79.333 | −14.870 | −7.655 | 1.00 | 64.68 | C |
| ATOM | 4949 | CE1 | TYR | H | 94 | −79.985 | −14.506 | −6.480 | 1.00 | 64.28 | C |
| ATOM | 4950 | CZ | TYR | H | 94 | −81.081 | −15.233 | −6.046 | 1.00 | 64.51 | C |
| ATOM | 4951 | OH | TYR | H | 94 | −81.723 | −14.863 | −4.893 | 1.00 | 65.03 | O |
| ATOM | 4952 | CE2 | TYR | H | 94 | −81.526 | −16.321 | −6.779 | 1.00 | 64.86 | C |
| ATOM | 4953 | CD2 | TYR | H | 94 | −80.859 | −16.683 | −7.948 | 1.00 | 65.33 | C |
| ATOM | 4954 | C | TYR | H | 94 | −79.051 | −15.838 | −12.178 | 1.00 | 64.74 | C |

TABLE 14-continued

PCSK9 and AX132 Fab complex x-ray structure

| ATOM | 4955 | O | TYR | H | 94 | −78.686 | −16.889 | −12.708 | 1.00 | 64.40 | O |
|---|---|---|---|---|---|---|---|---|---|---|---|
| ATOM | 4956 | N | TYR | H | 95 | −78.764 | −14.622 | −12.658 | 1.00 | 63.64 | N |
| ATOM | 4957 | CA | TYR | H | 95 | −77.994 | −14.382 | −13.859 | 1.00 | 63.12 | C |
| ATOM | 4958 | CB | TYR | H | 95 | −78.812 | −13.503 | −14.829 | 1.00 | 62.92 | C |
| ATOM | 4959 | CG | TYR | H | 95 | −80.064 | −14.156 | −15.365 | 1.00 | 61.93 | C |
| ATOM | 4960 | CD1 | TYR | H | 95 | −80.006 | −15.057 | −16.429 | 1.00 | 61.03 | C |
| ATOM | 4961 | CE1 | TYR | H | 95 | −81.152 | −15.685 | −16.905 | 1.00 | 61.11 | C |
| ATOM | 4962 | CZ | TYR | H | 95 | −82.384 | −15.383 | −16.346 | 1.00 | 61.42 | C |
| ATOM | 4963 | OH | TYR | H | 95 | −83.528 | −15.996 | −16.814 | 1.00 | 61.35 | O |
| ATOM | 4964 | CE2 | TYR | H | 95 | −82.467 | −14.466 | −15.309 | 1.00 | 60.44 | C |
| ATOM | 4965 | CD2 | TYR | H | 95 | −81.309 | −13.863 | −14.824 | 1.00 | 60.20 | C |
| ATOM | 4966 | C | TYR | H | 95 | −76.738 | −13.643 | −13.582 | 1.00 | 63.30 | C |
| ATOM | 4967 | O | TYR | H | 95 | −76.719 | −12.802 | −12.701 | 1.00 | 63.44 | O |
| ATOM | 4968 | N | CYS | H | 96 | −75.701 | −13.910 | −14.359 | 1.00 | 67.44 | N |
| ATOM | 4969 | CA | CYS | H | 96 | −74.483 | −13.120 | −14.364 | 1.00 | 68.48 | C |
| ATOM | 4970 | CB | CYS | H | 96 | −73.190 | −13.894 | −14.097 | 1.00 | 68.59 | C |
| ATOM | 4971 | SG | CYS | H | 96 | −72.852 | −15.230 | −15.268 | 1.00 | 73.30 | S |
| ATOM | 4972 | C | CYS | H | 96 | −74.556 | −12.530 | −15.791 | 1.00 | 68.14 | C |
| ATOM | 4973 | O | CYS | H | 96 | −75.032 | −13.201 | −16.720 | 1.00 | 68.02 | O |
| ATOM | 4974 | N | ALA | H | 97 | −74.221 | −11.241 | −15.927 | 1.00 | 67.03 | N |
| ATOM | 4975 | CA | ALA | H | 97 | −74.282 | −10.541 | −17.191 | 1.00 | 66.44 | C |
| ATOM | 4976 | CB | ALA | H | 97 | −75.520 | −9.668 | −17.251 | 1.00 | 66.41 | C |
| ATOM | 4977 | C | ALA | H | 97 | −73.063 | −9.706 | −17.338 | 1.00 | 66.28 | C |
| ATOM | 4978 | O | ALA | H | 97 | −72.676 | −8.995 | −16.413 | 1.00 | 66.42 | O |
| ATOM | 4979 | N | ARG | H | 98 | −72.447 | −9.788 | −18.500 | 1.00 | 65.71 | N |
| ATOM | 4980 | CA | ARG | H | 98 | −71.268 | −9.014 | −18.822 | 1.00 | 65.78 | C |
| ATOM | 4981 | CB | ARG | H | 98 | −70.573 | −9.689 | −19.983 | 1.00 | 65.49 | C |
| ATOM | 4982 | CG | ARG | H | 98 | −69.167 | −9.269 | −20.286 | 1.00 | 62.95 | C |
| ATOM | 4983 | CD | ARG | H | 98 | −69.244 | −9.112 | −21.758 | 1.00 | 60.25 | C |
| ATOM | 4984 | NE | ARG | H | 98 | −68.042 | −9.526 | −22.443 | 1.00 | 59.34 | N |
| ATOM | 4985 | CZ | ARG | H | 98 | −67.847 | −9.378 | −23.752 | 1.00 | 59.47 | C |
| ATOM | 4986 | NH1 | ARG | H | 98 | −68.779 | −8.817 | −24.511 | 1.00 | 57.40 | N |
| ATOM | 4987 | NH2 | ARG | H | 98 | −66.713 | −9.776 | −24.306 | 1.00 | 59.29 | N |
| ATOM | 4988 | C | ARG | H | 98 | −71.754 | −7.628 | −19.209 | 1.00 | 66.54 | C |
| ATOM | 4989 | O | ARG | H | 98 | −72.796 | −7.506 | −19.850 | 1.00 | 66.86 | O |
| ATOM | 4990 | N | GLU | H | 99 | −71.022 | −6.582 | −18.789 | 1.00 | 70.53 | N |
| ATOM | 4991 | CA | GLU | H | 99 | −71.356 | −5.177 | −19.043 | 1.00 | 71.00 | C |
| ATOM | 4992 | CB | GLU | H | 99 | −71.418 | −4.405 | −17.703 | 1.00 | 70.96 | C |
| ATOM | 4993 | CG | GLU | H | 99 | −71.527 | −2.885 | −17.795 | 1.00 | 72.27 | C |
| ATOM | 4994 | CD | GLU | H | 99 | −71.137 | −2.115 | −16.540 | 1.00 | 74.67 | C |
| ATOM | 4995 | OE1 | GLU | H | 99 | −71.774 | −1.072 | −16.248 | 1.00 | 75.05 | O |
| ATOM | 4996 | OE2 | GLU | H | 99 | −70.195 | −2.560 | −15.841 | 1.00 | 75.63 | O |
| ATOM | 4997 | C | GLU | H | 99 | −70.333 | −4.548 | −19.946 | 1.00 | 71.25 | C |
| ATOM | 4998 | O | GLU | H | 99 | −69.143 | −4.641 | −19.659 | 1.00 | 71.38 | O |
| ATOM | 4999 | N | ARG | H | 100 | −70.792 | −3.911 | −21.039 | 1.00 | 72.41 | N |
| ATOM | 5000 | CA | ARG | H | 100 | −69.919 | −3.163 | −21.943 | 1.00 | 72.84 | C |
| ATOM | 5001 | CB | ARG | H | 100 | −70.354 | −3.224 | −23.414 | 1.00 | 72.83 | C |
| ATOM | 5002 | CG | ARG | H | 100 | −69.329 | −2.517 | −24.278 | 1.00 | 72.50 | C |
| ATOM | 5003 | CD | ARG | H | 100 | −69.664 | −2.380 | −25.740 | 1.00 | 72.55 | C |
| ATOM | 5004 | NE | ARG | H | 100 | −68.761 | −1.403 | −26.352 | 1.00 | 73.88 | N |
| ATOM | 5005 | CZ | ARG | H | 100 | −68.848 | −0.952 | −27.601 | 1.00 | 74.27 | C |
| ATOM | 5006 | NH1 | ARG | H | 100 | −69.805 | −1.397 | −28.413 | 1.00 | 73.63 | N |
| ATOM | 5007 | NH2 | ARG | H | 100 | −67.977 | −0.057 | −28.049 | 1.00 | 74.01 | N |
| ATOM | 5008 | C | ARG | H | 100 | −70.093 | −1.768 | −21.397 | 1.00 | 73.26 | C |
| ATOM | 5009 | O | ARG | H | 100 | −71.149 | −1.165 | −21.573 | 1.00 | 73.35 | O |
| ATOM | 5010 | N | TYR | H | 101 | −69.107 | −1.285 | −20.662 | 1.00 | 75.23 | N |
| ATOM | 5011 | CA | TYR | H | 101 | −69.181 | 0.023 | −20.022 | 1.00 | 75.75 | C |
| ATOM | 5012 | CB | TYR | H | 101 | −67.837 | 0.402 | −19.426 | 1.00 | 76.28 | C |
| ATOM | 5013 | CG | TYR | H | 101 | −67.339 | −0.535 | −18.344 | 1.00 | 79.85 | C |
| ATOM | 5014 | CD1 | TYR | H | 101 | −66.172 | −1.282 | −18.522 | 1.00 | 82.83 | C |
| ATOM | 5015 | CE1 | TYR | H | 101 | −65.661 | −2.084 | −17.502 | 1.00 | 84.43 | C |
| ATOM | 5016 | CZ | TYR | H | 101 | −66.329 | −2.162 | −16.288 | 1.00 | 85.43 | C |
| ATOM | 5017 | OH | TYR | H | 101 | −65.820 | −2.948 | −15.284 | 1.00 | 86.44 | O |
| ATOM | 5018 | CE2 | TYR | H | 101 | −67.496 | −1.437 | −16.089 | 1.00 | 84.58 | C |
| ATOM | 5019 | CD2 | TYR | H | 101 | −67.992 | −0.626 | −17.113 | 1.00 | 82.47 | C |
| ATOM | 5020 | C | TYR | H | 101 | −69.764 | 1.160 | −20.866 | 1.00 | 74.82 | C |
| ATOM | 5021 | O | TYR | H | 101 | −69.277 | 1.443 | −21.961 | 1.00 | 74.74 | O |
| ATOM | 5022 | N | GLY | H | 102 | −70.823 | 1.772 | −20.346 | 1.00 | 71.45 | N |
| ATOM | 5023 | CA | GLY | H | 102 | −71.510 | 2.890 | −20.985 | 1.00 | 70.66 | C |
| ATOM | 5024 | C | GLY | H | 102 | −72.424 | 2.481 | −22.117 | 1.00 | 70.17 | C |
| ATOM | 5025 | O | GLY | H | 102 | −73.112 | 3.327 | −22.700 | 1.00 | 70.31 | O |
| ATOM | 5026 | N | TYR | H | 103 | −72.451 | 1.166 | −22.417 | 1.00 | 67.53 | N |
| ATOM | 5027 | CA | TYR | H | 103 | −73.238 | 0.609 | −23.497 | 1.00 | 66.65 | C |
| ATOM | 5028 | CB | TYR | H | 103 | −72.334 | −0.117 | −24.495 | 1.00 | 66.73 | C |
| ATOM | 5029 | CG | TYR | H | 103 | −71.616 | 0.826 | −25.428 | 1.00 | 67.87 | C |
| ATOM | 5030 | CD1 | TYR | H | 103 | −72.107 | 1.082 | −26.705 | 1.00 | 68.67 | C |
| ATOM | 5031 | CE1 | TYR | H | 103 | −71.450 | 1.956 | −27.571 | 1.00 | 67.79 | C |
| ATOM | 5032 | CZ | TYR | H | 103 | −70.303 | 2.604 | −27.151 | 1.00 | 67.83 | C |

TABLE 14-continued

PCSK9 and AX132 Fab complex x-ray structure

| ATOM | 5033 | OH | TYR | H | 103 | −69.666 | 3.479 | −27.994 | 1.00 | 69.69 | O |
|------|------|-----|-----|---|-----|---------|--------|---------|------|-------|---|
| ATOM | 5034 | CE2 | TYR | H | 103 | −69.808 | 2.381 | −25.877 | 1.00 | 67.02 | C |
| ATOM | 5035 | CD2 | TYR | H | 103 | −70.454 | 1.481 | −25.032 | 1.00 | 67.47 | C |
| ATOM | 5036 | C | TYR | H | 103 | −74.426 | −0.225 | −23.116 | 1.00 | 65.83 | C |
| ATOM | 5037 | O | TYR | H | 103 | −75.530 | 0.291 | −23.102 | 1.00 | 65.67 | O |
| ATOM | 5038 | N | TYR | H | 104 | −74.219 | −1.512 | −22.833 | 1.00 | 63.53 | N |
| ATOM | 5039 | CA | TYR | H | 104 | −75.274 | −2.500 | −22.568 | 1.00 | 62.64 | C |
| ATOM | 5040 | CB | TYR | H | 104 | −75.902 | −2.908 | −23.950 | 1.00 | 62.17 | C |
| ATOM | 5041 | CG | TYR | H | 104 | −74.866 | −3.054 | −25.055 | 1.00 | 61.14 | C |
| ATOM | 5042 | CD1 | TYR | H | 104 | −73.904 | −4.065 | −25.013 | 1.00 | 61.33 | C |
| ATOM | 5043 | CE1 | TYR | H | 104 | −72.921 | −4.175 | −25.999 | 1.00 | 60.48 | C |
| ATOM | 5044 | CZ | TYR | H | 104 | −72.888 | −3.265 | −27.041 | 1.00 | 58.82 | C |
| ATOM | 5045 | OH | TYR | H | 104 | −71.911 | −3.370 | −28.007 | 1.00 | 56.93 | O |
| ATOM | 5046 | CE2 | TYR | H | 104 | −73.833 | −2.249 | −27.097 | 1.00 | 59.35 | C |
| ATOM | 5047 | CD2 | TYR | H | 104 | −74.813 | −2.153 | −26.109 | 1.00 | 60.02 | C |
| ATOM | 5048 | C | TYR | H | 104 | −74.712 | −3.786 | −21.964 | 1.00 | 62.35 | C |
| ATOM | 5049 | O | TYR | H | 104 | −73.491 | −3.944 | −21.821 | 1.00 | 62.32 | O |
| ATOM | 5050 | N | PHE | H | 105 | −75.626 | −4.738 | −21.697 | 1.00 | 60.95 | N |
| ATOM | 5051 | CA | PHE | H | 105 | −75.321 | −6.081 | −21.233 | 1.00 | 60.08 | C |
| ATOM | 5052 | CB | PHE | H | 105 | −76.422 | −6.581 | −20.308 | 1.00 | 59.40 | C |
| ATOM | 5053 | CG | PHE | H | 105 | −76.500 | −5.899 | −18.968 | 1.00 | 58.42 | C |
| ATOM | 5054 | CD1 | PHE | H | 105 | −77.665 | −5.252 | −18.564 | 1.00 | 56.91 | C |
| ATOM | 5055 | CE1 | PHE | H | 105 | −77.752 | −4.655 | −17.301 | 1.00 | 56.33 | C |
| ATOM | 5056 | CZ | PHE | H | 105 | −76.677 | −4.698 | −16.441 | 1.00 | 56.75 | C |
| ATOM | 5057 | CE2 | PHE | H | 105 | −75.519 | −5.337 | −16.822 | 1.00 | 57.86 | C |
| ATOM | 5058 | CD2 | PHE | H | 105 | −75.432 | −5.951 | −18.079 | 1.00 | 57.85 | C |
| ATOM | 5059 | C | PHE | H | 105 | −75.312 | −6.912 | −22.504 | 1.00 | 60.10 | C |
| ATOM | 5060 | O | PHE | H | 105 | −76.378 | −7.137 | −23.084 | 1.00 | 60.18 | O |
| ATOM | 5061 | N | ASP | H | 106 | −74.139 | −7.310 | −22.982 | 1.00 | 62.16 | N |
| ATOM | 5062 | CA | ASP | H | 106 | −74.102 | −8.089 | −24.215 | 1.00 | 63.03 | C |
| ATOM | 5063 | CB | ASP | H | 106 | −72.863 | −7.804 | −25.072 | 1.00 | 63.28 | C |
| ATOM | 5064 | CG | ASP | H | 106 | −71.598 | −7.570 | −24.296 | 1.00 | 65.40 | C |
| ATOM | 5065 | OD1 | ASP | H | 106 | −71.564 | −7.925 | −23.086 | 1.00 | 67.53 | O |
| ATOM | 5066 | OD2 | ASP | H | 106 | −70.634 | −7.024 | −24.887 | 1.00 | 66.52 | O |
| ATOM | 5067 | C | ASP | H | 106 | −74.312 | −9.586 | −24.020 | 1.00 | 63.00 | C |
| ATOM | 5068 | O | ASP | H | 106 | −75.097 | −10.196 | −24.752 | 1.00 | 63.66 | O |
| ATOM | 5069 | N | TYR | H | 107 | −73.647 | −10.168 | −23.027 | 1.00 | 62.37 | N |
| ATOM | 5070 | CA | TYR | H | 107 | −73.737 | −11.583 | −22.724 | 1.00 | 62.23 | C |
| ATOM | 5071 | CB | TYR | H | 107 | −72.371 | −12.194 | −22.904 | 1.00 | 62.04 | C |
| ATOM | 5072 | CG | TYR | H | 107 | −71.963 | −12.148 | −24.360 | 1.00 | 61.88 | C |
| ATOM | 5073 | CD1 | TYR | H | 107 | −72.543 | −13.003 | −25.290 | 1.00 | 61.17 | C |
| ATOM | 5074 | CE1 | TYR | H | 107 | −72.181 | −12.969 | −26.629 | 1.00 | 61.06 | C |
| ATOM | 5075 | CZ | TYR | H | 107 | −71.227 | −12.071 | −27.061 | 1.00 | 61.23 | C |
| ATOM | 5076 | OH | TYR | H | 107 | −70.917 | −12.079 | −28.399 | 1.00 | 61.91 | O |
| ATOM | 5077 | CE2 | TYR | H | 107 | −70.647 | −11.186 | −26.160 | 1.00 | 61.81 | C |
| ATOM | 5078 | CD2 | TYR | H | 107 | −71.025 | −11.223 | −24.818 | 1.00 | 62.31 | C |
| ATOM | 5079 | C | TYR | H | 107 | −74.322 | −11.875 | −21.359 | 1.00 | 62.66 | C |
| ATOM | 5080 | O | TYR | H | 107 | −74.063 | −11.130 | −20.410 | 1.00 | 62.89 | O |
| ATOM | 5081 | N | TRP | H | 108 | −75.144 | −12.946 | −21.268 | 1.00 | 63.37 | N |
| ATOM | 5082 | CA | TRP | H | 108 | −75.808 | −13.377 | −20.032 | 1.00 | 63.55 | C |
| ATOM | 5083 | CB | TRP | H | 108 | −77.321 | −13.169 | −20.130 | 1.00 | 63.40 | C |
| ATOM | 5084 | CG | TRP | H | 108 | −77.792 | −11.753 | −20.274 | 1.00 | 63.22 | C |
| ATOM | 5085 | CD1 | TRP | H | 108 | −77.723 | −10.970 | −21.390 | 1.00 | 63.42 | C |
| ATOM | 5086 | NE1 | TRP | H | 108 | −78.324 | −9.757 | −21.155 | 1.00 | 63.16 | N |
| ATOM | 5087 | CE2 | TRP | H | 108 | −78.811 | −9.742 | −19.873 | 1.00 | 61.71 | C |
| ATOM | 5088 | CD2 | TRP | H | 108 | −78.521 | −10.999 | −19.298 | 1.00 | 62.25 | C |
| ATOM | 5089 | CE3 | TRP | H | 108 | −78.912 | −11.245 | −17.974 | 1.00 | 61.41 | C |
| ATOM | 5090 | CZ3 | TRP | H | 108 | −79.556 | −10.244 | −17.279 | 1.00 | 62.45 | C |
| ATOM | 5091 | CH2 | TRP | H | 108 | −79.838 | −9.007 | −17.880 | 1.00 | 61.71 | C |
| ATOM | 5092 | CZ2 | TRP | H | 108 | −79.478 | −8.738 | −19.173 | 1.00 | 60.73 | C |
| ATOM | 5093 | C | TRP | H | 108 | −75.560 | −14.857 | −19.782 | 1.00 | 64.14 | C |
| ATOM | 5094 | O | TRP | H | 108 | −75.353 | −15.610 | −20.730 | 1.00 | 64.01 | O |
| ATOM | 5095 | N | GLY | H | 109 | −75.600 | −15.271 | −18.519 | 1.00 | 66.93 | N |
| ATOM | 5096 | CA | GLY | H | 109 | −75.436 | −16.674 | −18.144 | 1.00 | 67.80 | C |
| ATOM | 5097 | C | GLY | H | 109 | −76.725 | −17.385 | −18.497 | 1.00 | 68.72 | C |
| ATOM | 5098 | O | GLY | H | 109 | −77.722 | −16.721 | −18.806 | 1.00 | 68.99 | O |
| ATOM | 5099 | N | GLN | H | 110 | −76.726 | −18.726 | −18.483 | 1.00 | 71.11 | N |
| ATOM | 5100 | CA | GLN | H | 110 | −77.903 | −19.541 | −18.838 | 1.00 | 71.79 | C |
| ATOM | 5101 | CB | GLN | H | 110 | −77.539 | −21.035 | −18.947 | 1.00 | 72.34 | C |
| ATOM | 5102 | CG | GLN | H | 110 | −77.089 | −21.720 | −17.625 | 1.00 | 75.60 | C |
| ATOM | 5103 | CD | GLN | H | 110 | −75.597 | −21.586 | −17.254 | 1.00 | 80.03 | C |
| ATOM | 5104 | OE1 | GLN | H | 110 | −74.927 | −20.544 | −17.468 | 1.00 | 81.28 | O |
| ATOM | 5105 | NE2 | GLN | H | 110 | −75.050 | −22.650 | −16.662 | 1.00 | 80.71 | N |
| ATOM | 5106 | C | GLN | H | 110 | −79.129 | −19.331 | −17.951 | 1.00 | 71.61 | C |
| ATOM | 5107 | O | GLN | H | 110 | −80.256 | −19.487 | −18.415 | 1.00 | 71.64 | O |
| ATOM | 5108 | N | GLY | H | 111 | −78.888 | −18.964 | −16.700 | 1.00 | 69.26 | N |
| ATOM | 5109 | CA | GLY | H | 111 | −79.910 | −18.755 | −15.687 | 1.00 | 69.55 | C |
| ATOM | 5110 | C | GLY | H | 111 | −79.862 | −19.902 | −14.703 | 1.00 | 69.85 | C |

TABLE 14-continued

PCSK9 and AX132 Fab complex x-ray structure

| ATOM | 5111 | O   | GLY | H | 111 | −80.013 | −21.050 | −15.114 | 1.00 | 70.20 | O |
|------|------|-----|-----|---|-----|---------|---------|---------|------|-------|---|
| ATOM | 5112 | N   | THR | H | 112 | −79.605 | −19.619 | −13.410 | 1.00 | 67.06 | N |
| ATOM | 5113 | CA  | THR | H | 112 | −79.543 | −20.649 | −12.355 | 1.00 | 66.93 | C |
| ATOM | 5114 | CB  | THR | H | 112 | −78.146 | −20.856 | −11.717 | 1.00 | 66.96 | C |
| ATOM | 5115 | OG1 | THR | H | 112 | −77.302 | −19.782 | −12.092 | 1.00 | 68.20 | O |
| ATOM | 5116 | CG2 | THR | H | 112 | −77.479 | −22.189 | −12.133 | 1.00 | 67.65 | C |
| ATOM | 5117 | C   | THR | H | 112 | −80.638 | −20.458 | −11.341 | 1.00 | 66.57 | C |
| ATOM | 5118 | O   | THR | H | 112 | −80.784 | −19.391 | −10.759 | 1.00 | 66.47 | O |
| ATOM | 5119 | N   | LEU | H | 113 | −81.422 | −21.502 | −11.140 | 1.00 | 66.57 | N |
| ATOM | 5120 | CA  | LEU | H | 113 | −82.509 | −21.442 | −10.191 | 1.00 | 66.09 | C |
| ATOM | 5121 | CB  | LEU | H | 113 | −83.640 | −22.395 | −10.589 | 1.00 | 65.95 | C |
| ATOM | 5122 | CG  | LEU | H | 113 | −84.753 | −22.495 | −9.569  | 1.00 | 66.57 | C |
| ATOM | 5123 | CD1 | LEU | H | 113 | −85.585 | −21.204 | −9.506  | 1.00 | 65.93 | C |
| ATOM | 5124 | CD2 | LEU | H | 113 | −85.578 | −23.706 | −9.806  | 1.00 | 67.95 | C |
| ATOM | 5125 | C   | LEU | H | 113 | −82.033 | −21.766 | −8.794  | 1.00 | 65.67 | C |
| ATOM | 5126 | O   | LEU | H | 113 | −81.336 | −22.771 | −8.593  | 1.00 | 65.82 | O |
| ATOM | 5127 | N   | VAL | H | 114 | −82.422 | −20.921 | −7.836  | 1.00 | 62.65 | N |
| ATOM | 5128 | CA  | VAL | H | 114 | −82.107 | −21.118 | −6.438  | 1.00 | 62.66 | C |
| ATOM | 5129 | CB  | VAL | H | 114 | −81.151 | −20.031 | −5.865  | 1.00 | 62.38 | C |
| ATOM | 5130 | CG1 | VAL | H | 114 | −81.011 | −20.153 | −4.352  | 1.00 | 61.88 | C |
| ATOM | 5131 | CG2 | VAL | H | 114 | −79.779 | −20.090 | −6.514  | 1.00 | 62.63 | C |
| ATOM | 5132 | C   | VAL | H | 114 | −83.477 | −21.141 | −5.743  | 1.00 | 63.09 | C |
| ATOM | 5133 | O   | VAL | H | 114 | −84.211 | −20.145 | −5.793  | 1.00 | 62.87 | O |
| ATOM | 5134 | N   | THR | H | 115 | −83.835 | −22.298 | −5.138  | 1.00 | 66.30 | N |
| ATOM | 5135 | CA  | THR | H | 115 | −85.096 | −22.454 | −4.406  | 1.00 | 66.71 | C |
| ATOM | 5136 | CB  | THR | H | 115 | −86.002 | −23.586 | −4.957  | 1.00 | 66.71 | C |
| ATOM | 5137 | OG1 | THR | H | 115 | −86.136 | −23.455 | −6.375  | 1.00 | 65.99 | O |
| ATOM | 5138 | CG2 | THR | H | 115 | −87.399 | −23.542 | −4.358  | 1.00 | 66.36 | C |
| ATOM | 5139 | C   | THR | H | 115 | −84.799 | −22.474 | −2.911  | 1.00 | 67.37 | C |
| ATOM | 5140 | O   | THR | H | 115 | −83.917 | −23.222 | −2.441  | 1.00 | 67.19 | O |
| ATOM | 5141 | N   | VAL | H | 116 | −85.518 | −21.615 | −2.178  | 1.00 | 70.14 | N |
| ATOM | 5142 | CA  | VAL | H | 116 | −85.344 | −21.459 | −0.735  | 1.00 | 71.22 | C |
| ATOM | 5143 | CB  | VAL | H | 116 | −85.010 | −19.986 | −0.351  | 1.00 | 71.13 | C |
| ATOM | 5144 | CG1 | VAL | H | 116 | −83.751 | −19.498 | −1.085  | 1.00 | 71.19 | C |
| ATOM | 5145 | CG2 | VAL | H | 116 | −84.834 | −19.835 | 1.150   | 1.00 | 71.12 | C |
| ATOM | 5146 | C   | VAL | H | 116 | −86.503 | −22.093 | 0.058   | 1.00 | 71.93 | C |
| ATOM | 5147 | O   | VAL | H | 116 | −87.568 | −21.501 | 0.188   | 1.00 | 72.15 | O |
| ATOM | 5148 | N   | SER | H | 117 | −86.281 | −23.311 | 0.571   | 1.00 | 75.85 | N |
| ATOM | 5149 | CA  | SER | H | 117 | −87.269 | −24.072 | 1.325   | 1.00 | 76.81 | C |
| ATOM | 5150 | CB  | SER | H | 117 | −88.179 | −24.851 | 0.378   | 1.00 | 76.95 | C |
| ATOM | 5151 | OG  | SER | H | 117 | −89.002 | −25.799 | 1.043   | 1.00 | 77.25 | O |
| ATOM | 5152 | C   | SER | H | 117 | −86.648 | −25.048 | 2.307   | 1.00 | 77.41 | C |
| ATOM | 5153 | O   | SER | H | 117 | −85.645 | −25.715 | 2.005   | 1.00 | 77.73 | O |
| ATOM | 5154 | N   | SER | H | 118 | −87.311 | −25.159 | 3.476   | 1.00 | 79.00 | N |
| ATOM | 5155 | CA  | SER | H | 118 | −86.988 | −26.050 | 4.599   | 1.00 | 79.39 | C |
| ATOM | 5156 | CB  | SER | H | 118 | −87.461 | −25.432 | 5.911   | 1.00 | 79.16 | C |
| ATOM | 5157 | OG  | SER | H | 118 | −88.754 | −24.877 | 5.731   | 1.00 | 80.04 | O |
| ATOM | 5158 | C   | SER | H | 118 | −87.660 | −27.426 | 4.387   | 1.00 | 79.64 | C |
| ATOM | 5159 | O   | SER | H | 118 | −87.480 | −28.330 | 5.218   | 1.00 | 80.15 | O |
| ATOM | 5160 | N   | ALA | H | 119 | −88.417 | −27.587 | 3.266   | 1.00 | 73.07 | N |
| ATOM | 5161 | CA  | ALA | H | 119 | −89.074 | −28.836 | 2.926   | 1.00 | 72.98 | C |
| ATOM | 5162 | CB  | ALA | H | 119 | −90.050 | −28.632 | 1.784   | 1.00 | 73.09 | C |
| ATOM | 5163 | C   | ALA | H | 119 | −88.066 | −29.956 | 2.607   | 1.00 | 73.10 | C |
| ATOM | 5164 | O   | ALA | H | 119 | −86.893 | −29.696 | 2.305   | 1.00 | 72.72 | O |
| ATOM | 5165 | N   | SER | H | 120 | −88.550 | −31.209 | 2.716   | 1.00 | 72.01 | N |
| ATOM | 5166 | CA  | SER | H | 120 | −87.807 | −32.453 | 2.522   | 1.00 | 72.04 | C |
| ATOM | 5167 | CB  | SER | H | 120 | −87.893 | −33.299 | 3.782   | 1.00 | 71.83 | C |
| ATOM | 5168 | OG  | SER | H | 120 | −87.997 | −32.449 | 4.913   | 1.00 | 72.64 | O |
| ATOM | 5169 | C   | SER | H | 120 | −88.343 | −33.239 | 1.343   | 1.00 | 72.00 | C |
| ATOM | 5170 | O   | SER | H | 120 | −89.547 | −33.176 | 1.060   | 1.00 | 71.77 | O |
| ATOM | 5171 | N   | THR | H | 121 | −87.434 | −33.976 | 0.654   | 1.00 | 70.38 | N |
| ATOM | 5172 | CA  | THR | H | 121 | −87.764 | −34.779 | −0.515  | 1.00 | 70.68 | C |
| ATOM | 5173 | CB  | THR | H | 121 | −86.523 | −35.458 | −1.138  | 1.00 | 70.30 | C |
| ATOM | 5174 | OG1 | THR | H | 121 | −85.504 | −34.491 | −1.375  | 1.00 | 69.93 | O |
| ATOM | 5175 | CG2 | THR | H | 121 | −86.829 | −36.146 | −2.451  | 1.00 | 69.49 | C |
| ATOM | 5176 | C   | THR | H | 121 | −88.901 | −35.717 | −0.151  | 1.00 | 71.62 | C |
| ATOM | 5177 | O   | THR | H | 121 | −88.827 | −36.431 | 0.851   | 1.00 | 72.00 | O |
| ATOM | 5178 | N   | LYS | H | 122 | −89.972 | −35.653 | −0.936  | 1.00 | 72.71 | N |
| ATOM | 5179 | CA  | LYS | H | 122 | −91.168 | −36.441 | −0.774  | 1.00 | 73.30 | C |
| ATOM | 5180 | CB  | LYS | H | 122 | −92.131 | −35.708 | 0.189   | 1.00 | 73.06 | C |
| ATOM | 5181 | CG  | LYS | H | 122 | −93.643 | −35.827 | −0.089  | 1.00 | 73.63 | C |
| ATOM | 5182 | CD  | LYS | H | 122 | −94.355 | −36.996 | 0.603   | 1.00 | 73.39 | C |
| ATOM | 5183 | CE  | LYS | H | 122 | −95.860 | −36.793 | 0.652   | 1.00 | 73.30 | C |
| ATOM | 5184 | NZ  | LYS | H | 122 | −96.591 | −37.550 | −0.418  | 1.00 | 74.03 | N |
| ATOM | 5185 | C   | LYS | H | 122 | −91.754 | −36.731 | −2.177  | 1.00 | 74.13 | C |
| ATOM | 5186 | O   | LYS | H | 122 | −91.985 | −35.802 | −2.956  | 1.00 | 74.29 | O |
| ATOM | 5187 | N   | GLY | H | 123 | −91.933 | −38.022 | −2.490  | 1.00 | 76.46 | N |
| ATOM | 5188 | CA  | GLY | H | 123 | −92.503 | −38.498 | −3.745  | 1.00 | 77.46 | C |

TABLE 14-continued

| | | | | | | | | | | |
|---|---|---|---|---|---|---|---|---|---|---|
| ATOM | 5189 | C | GLY | H | 123 | −93.959 | −38.081 | −3.787 | 1.00 | 78.54 | C |
| ATOM | 5190 | O | GLY | H | 123 | −94.538 | −37.830 | −2.723 | 1.00 | 78.57 | O |
| ATOM | 5191 | N | PRO | H | 124 | −94.605 | −37.960 | −4.972 | 1.00 | 80.93 | N |
| ATOM | 5192 | CA | PRO | H | 124 | −96.000 | −37.518 | −4.987 | 1.00 | 81.90 | C |
| ATOM | 5193 | CB | PRO | H | 124 | −96.172 | −37.027 | −6.418 | 1.00 | 81.54 | C |
| ATOM | 5194 | CG | PRO | H | 124 | −95.326 | −37.916 | −7.208 | 1.00 | 80.73 | C |
| ATOM | 5195 | CD | PRO | H | 124 | −94.124 | −38.210 | −6.346 | 1.00 | 80.84 | C |
| ATOM | 5196 | C | PRO | H | 124 | −97.007 | −38.620 | −4.701 | 1.00 | 83.35 | C |
| ATOM | 5197 | O | PRO | H | 124 | −96.687 | −39.819 | −4.762 | 1.00 | 83.63 | O |
| ATOM | 5198 | N | SER | H | 125 | −98.240 | −38.183 | −4.426 | 1.00 | 86.85 | N |
| ATOM | 5199 | CA | SER | H | 125 | −99.417 | −39.010 | −4.201 | 1.00 | 88.24 | C |
| ATOM | 5200 | CB | SER | H | 125 | −100.136 | −38.587 | −2.915 | 1.00 | 88.05 | C |
| ATOM | 5201 | OG | SER | H | 125 | −99.245 | −38.444 | −1.816 | 1.00 | 88.30 | O |
| ATOM | 5202 | C | SER | H | 125 | −100.277 | −38.707 | −5.446 | 1.00 | 89.31 | C |
| ATOM | 5203 | O | SER | H | 125 | −100.723 | −37.571 | −5.615 | 1.00 | 89.76 | O |
| ATOM | 5204 | N | VAL | H | 126 | −100.456 | −39.694 | −6.343 | 1.00 | 90.66 | N |
| ATOM | 5205 | CA | VAL | H | 126 | −101.241 | −39.522 | −7.578 | 1.00 | 91.88 | C |
| ATOM | 5206 | CB | VAL | H | 126 | −100.536 | −40.090 | −8.832 | 1.00 | 91.55 | C |
| ATOM | 5207 | CG1 | VAL | H | 126 | −101.344 | −39.818 | −10.089 | 1.00 | 91.30 | C |
| ATOM | 5208 | CG2 | VAL | H | 126 | −99.146 | −39.507 | −8.971 | 1.00 | 91.37 | C |
| ATOM | 5209 | C | VAL | H | 126 | −102.703 | −39.986 | −7.448 | 1.00 | 93.21 | C |
| ATOM | 5210 | O | VAL | H | 126 | −102.989 | −41.177 | −7.310 | 1.00 | 93.26 | O |
| ATOM | 5211 | N | PHE | H | 127 | −103.619 | −39.023 | −7.514 | 1.00 | 97.08 | N |
| ATOM | 5212 | CA | PHE | H | 127 | −105.053 | −39.266 | −7.430 | 1.00 | 98.63 | C |
| ATOM | 5213 | CB | PHE | H | 127 | −105.664 | −38.352 | −6.381 | 1.00 | 98.32 | C |
| ATOM | 5214 | CG | PHE | H | 127 | −105.044 | −38.479 | −5.018 | 1.00 | 98.24 | C |
| ATOM | 5215 | CD1 | PHE | H | 127 | −104.950 | −39.715 | −4.392 | 1.00 | 97.94 | C |
| ATOM | 5216 | CE1 | PHE | H | 127 | −104.411 | −39.829 | −3.112 | 1.00 | 98.10 | C |
| ATOM | 5217 | CZ | PHE | H | 127 | −103.972 | −38.708 | −2.451 | 1.00 | 98.37 | C |
| ATOM | 5218 | CE2 | PHE | H | 127 | −104.059 | −37.473 | −3.056 | 1.00 | 98.37 | C |
| ATOM | 5219 | CD2 | PHE | H | 127 | −104.590 | −37.361 | −4.340 | 1.00 | 97.97 | C |
| ATOM | 5220 | C | PHE | H | 127 | −105.733 | −39.022 | −8.783 | 1.00 | 100.17 | C |
| ATOM | 5221 | O | PHE | H | 127 | −105.388 | −38.041 | −9.446 | 1.00 | 100.19 | O |
| ATOM | 5222 | N | PRO | H | 128 | −106.701 | −39.871 | −9.224 | 1.00 | 105.15 | N |
| ATOM | 5223 | CA | PRO | H | 128 | −107.348 | −39.619 | −10.525 | 1.00 | 106.35 | C |
| ATOM | 5224 | CB | PRO | H | 128 | −108.033 | −40.949 | −10.828 | 1.00 | 106.09 | C |
| ATOM | 5225 | CG | PRO | H | 128 | −108.388 | −41.479 | −9.482 | 1.00 | 105.49 | C |
| ATOM | 5226 | CD | PRO | H | 128 | −107.246 | −41.088 | −8.584 | 1.00 | 105.11 | C |
| ATOM | 5227 | C | PRO | H | 128 | −108.372 | −38.485 | −10.473 | 1.00 | 107.79 | C |
| ATOM | 5228 | O | PRO | H | 128 | −108.853 | −38.108 | −9.396 | 1.00 | 108.04 | O |
| ATOM | 5229 | N | LEU | H | 129 | −108.703 | −37.948 | −11.649 | 1.00 | 110.12 | N |
| ATOM | 5230 | CA | LEU | H | 129 | −109.708 | −36.904 | −11.827 | 1.00 | 111.66 | C |
| ATOM | 5231 | CB | LEU | H | 129 | −109.089 | −35.597 | −12.368 | 1.00 | 111.44 | C |
| ATOM | 5232 | CG | LEU | H | 129 | −108.038 | −34.916 | −11.497 | 1.00 | 110.89 | C |
| ATOM | 5233 | CD1 | LEU | H | 129 | −107.266 | −33.891 | −12.296 | 1.00 | 110.21 | C |
| ATOM | 5234 | CD2 | LEU | H | 129 | −108.651 | −34.321 | −10.217 | 1.00 | 109.59 | C |
| ATOM | 5235 | C | LEU | H | 129 | −110.686 | −37.551 | −12.809 | 1.00 | 112.94 | C |
| ATOM | 5236 | O | LEU | H | 129 | −110.593 | −37.359 | −14.028 | 1.00 | 113.16 | O |
| ATOM | 5237 | N | ALA | H | 130 | −111.573 | −38.399 | −12.242 | 1.00 | 116.25 | N |
| ATOM | 5238 | CA | ALA | H | 130 | −112.592 | −39.223 | −12.898 | 1.00 | 117.58 | C |
| ATOM | 5239 | CB | ALA | H | 130 | −113.404 | −39.975 | −11.851 | 1.00 | 117.55 | C |
| ATOM | 5240 | C | ALA | H | 130 | −113.530 | −38.511 | −13.889 | 1.00 | 118.57 | C |
| ATOM | 5241 | O | ALA | H | 130 | −114.213 | −37.554 | −13.498 | 1.00 | 118.42 | O |
| ATOM | 5242 | N | PRO | H | 131 | −113.593 | −38.985 | −15.168 | 1.00 | 122.13 | N |
| ATOM | 5243 | CA | PRO | H | 131 | −114.505 | −38.351 | −16.137 | 1.00 | 123.31 | C |
| ATOM | 5244 | CB | PRO | H | 131 | −114.164 | −39.038 | −17.468 | 1.00 | 123.07 | C |
| ATOM | 5245 | CG | PRO | H | 131 | −113.532 | −40.323 | −17.098 | 1.00 | 122.46 | C |
| ATOM | 5246 | CD | PRO | H | 131 | −112.864 | −40.124 | −15.769 | 1.00 | 122.18 | C |
| ATOM | 5247 | C | PRO | H | 131 | −115.957 | −38.570 | −15.707 | 1.00 | 124.68 | C |
| ATOM | 5248 | O | PRO | H | 131 | −116.427 | −39.716 | −15.642 | 1.00 | 125.03 | O |
| ATOM | 5249 | N | SER | H | 132 | −116.648 | −37.466 | −15.356 | 1.00 | 128.46 | N |
| ATOM | 5250 | CA | SER | H | 132 | −118.036 | −37.475 | −14.896 | 1.00 | 129.79 | C |
| ATOM | 5251 | CB | SER | H | 132 | −118.581 | −36.055 | −14.767 | 1.00 | 129.75 | C |
| ATOM | 5252 | OG | SER | H | 132 | −118.974 | −35.502 | −16.015 | 1.00 | 129.83 | O |
| ATOM | 5253 | C | SER | H | 132 | −118.948 | −38.294 | −15.792 | 1.00 | 130.80 | C |
| ATOM | 5254 | O | SER | H | 132 | −118.817 | −38.263 | −17.026 | 1.00 | 130.81 | O |
| ATOM | 5255 | N | SER | H | 133 | −119.871 | −39.028 | −15.145 | 1.00 | 135.47 | N |
| ATOM | 5256 | CA | SER | H | 133 | −120.893 | −39.875 | −15.765 | 1.00 | 136.57 | C |
| ATOM | 5257 | CB | SER | H | 133 | −121.600 | −40.707 | −14.693 | 1.00 | 136.61 | C |
| ATOM | 5258 | OG | SER | H | 133 | −120.690 | −41.259 | −13.752 | 1.00 | 136.55 | O |
| ATOM | 5259 | C | SER | H | 133 | −121.896 | −38.958 | −16.527 | 1.00 | 137.33 | C |
| ATOM | 5260 | O | SER | H | 133 | −122.243 | −39.245 | −17.680 | 1.00 | 137.30 | O |
| ATOM | 5261 | N | ALA | H | 134 | −122.313 | −37.834 | −15.873 | 1.00 | 140.39 | N |
| ATOM | 5262 | CA | ALA | H | 134 | −123.211 | −36.795 | −16.395 | 1.00 | 141.31 | C |
| ATOM | 5263 | CB | ALA | H | 134 | −123.830 | −36.020 | −15.237 | 1.00 | 141.10 | C |
| ATOM | 5264 | C | ALA | H | 134 | −122.409 | −35.838 | −17.305 | 1.00 | 142.01 | C |
| ATOM | 5265 | O | ALA | H | 134 | −121.176 | −35.913 | −17.327 | 1.00 | 142.33 | O |
| ATOM | 5266 | N | SER | H | 135 | −123.104 | −34.956 | −18.069 | 1.00 | 145.31 | N |

TABLE 14-continued

PCSK9 and AX132 Fab complex x-ray structure

| ATOM | 5267 | CA | SER | H | 135 | −122.515 | −33.965 | −18.999 | 1.00 | 145.93 | C |
|---|---|---|---|---|---|---|---|---|---|---|---|
| ATOM | 5268 | CB | SER | H | 135 | −121.745 | −32.877 | −18.238 | 1.00 | 145.96 | C |
| ATOM | 5269 | OG | SER | H | 135 | −121.187 | −31.874 | −19.076 | 1.00 | 146.36 | O |
| ATOM | 5270 | C | SER | H | 135 | −121.673 | −34.557 | −20.168 | 1.00 | 146.25 | C |
| ATOM | 5271 | O | SER | H | 135 | −121.344 | −33.818 | −21.109 | 1.00 | 146.30 | O |
| ATOM | 5272 | N | THR | H | 136 | −121.350 | −35.883 | −20.106 | 1.00 | 147.23 | N |
| ATOM | 5273 | CA | THR | H | 136 | −120.552 | −36.654 | −21.078 | 1.00 | 147.51 | C |
| ATOM | 5274 | CB | THR | H | 136 | −120.503 | −38.158 | −20.698 | 1.00 | 147.62 | C |
| ATOM | 5275 | OG1 | THR | H | 136 | −119.503 | −38.812 | −21.484 | 1.00 | 147.69 | O |
| ATOM | 5276 | CG2 | THR | H | 136 | −121.855 | −38.872 | −20.851 | 1.00 | 147.57 | C |
| ATOM | 5277 | C | THR | H | 136 | −120.818 | −36.342 | −22.577 | 1.00 | 147.51 | C |
| ATOM | 5278 | O | THR | H | 136 | −119.865 | −36.256 | −23.367 | 1.00 | 147.44 | O |
| ATOM | 5279 | N | SER | H | 137 | −122.115 | −36.144 | −22.939 | 1.00 | 146.29 | N |
| ATOM | 5280 | CA | SER | H | 137 | −122.646 | −35.828 | −24.276 | 1.00 | 146.19 | C |
| ATOM | 5281 | CB | SER | H | 137 | −122.269 | −34.406 | −24.720 | 1.00 | 146.28 | C |
| ATOM | 5282 | OG | SER | H | 137 | −120.871 | −34.156 | −24.769 | 1.00 | 146.61 | O |
| ATOM | 5283 | C | SER | H | 137 | −122.398 | −36.918 | −25.353 | 1.00 | 145.85 | C |
| ATOM | 5284 | O | SER | H | 137 | −122.723 | −38.090 | −25.127 | 1.00 | 145.77 | O |
| ATOM | 5285 | N | GLY | H | 138 | −121.852 | −36.505 | −26.498 | 1.00 | 144.07 | N |
| ATOM | 5286 | CA | GLY | H | 138 | −121.516 | −37.350 | −27.641 | 1.00 | 143.40 | C |
| ATOM | 5287 | C | GLY | H | 138 | −120.173 | −36.970 | −28.240 | 1.00 | 142.93 | C |
| ATOM | 5288 | O | GLY | H | 138 | −119.533 | −37.782 | −28.923 | 1.00 | 142.93 | O |
| ATOM | 5289 | N | GLY | H | 139 | −119.759 | −35.729 | −27.966 | 1.00 | 140.56 | N |
| ATOM | 5290 | CA | GLY | H | 139 | −118.500 | −35.162 | −28.426 | 1.00 | 139.72 | C |
| ATOM | 5291 | C | GLY | H | 139 | −117.340 | −35.626 | −27.576 | 1.00 | 139.13 | C |
| ATOM | 5292 | O | GLY | H | 139 | −117.018 | −36.819 | −27.566 | 1.00 | 139.16 | O |
| ATOM | 5293 | N | THR | H | 140 | −116.719 | −34.680 | −26.844 | 1.00 | 135.91 | N |
| ATOM | 5294 | CA | THR | H | 140 | −115.571 | −34.936 | −25.964 | 1.00 | 134.98 | C |
| ATOM | 5295 | CB | THR | H | 140 | −114.324 | −34.106 | −26.390 | 1.00 | 135.14 | C |
| ATOM | 5296 | OG1 | THR | H | 140 | −114.688 | −32.735 | −26.576 | 1.00 | 134.94 | O |
| ATOM | 5297 | CG2 | THR | H | 140 | −113.635 | −34.656 | −27.649 | 1.00 | 134.96 | C |
| ATOM | 5298 | C | THR | H | 140 | −115.892 | −34.858 | −24.455 | 1.00 | 134.14 | C |
| ATOM | 5299 | O | THR | H | 140 | −116.939 | −34.337 | −24.050 | 1.00 | 134.03 | O |
| ATOM | 5300 | N | ALA | H | 141 | −114.969 | −35.393 | −23.638 | 1.00 | 130.14 | N |
| ATOM | 5301 | CA | ALA | H | 141 | −115.025 | −35.437 | −22.178 | 1.00 | 128.96 | C |
| ATOM | 5302 | CB | ALA | H | 141 | −115.462 | −36.821 | −21.724 | 1.00 | 129.08 | C |
| ATOM | 5303 | C | ALA | H | 141 | −113.639 | −35.110 | −21.603 | 1.00 | 128.00 | C |
| ATOM | 5304 | O | ALA | H | 141 | −112.625 | −35.341 | −22.273 | 1.00 | 127.86 | O |
| ATOM | 5305 | N | ALA | H | 142 | −113.592 | −34.570 | −20.370 | 1.00 | 124.07 | N |
| ATOM | 5306 | CA | ALA | H | 142 | −112.317 | −34.238 | −19.735 | 1.00 | 122.79 | C |
| ATOM | 5307 | CB | ALA | H | 142 | −112.213 | −32.751 | −19.459 | 1.00 | 122.91 | C |
| ATOM | 5308 | C | ALA | H | 142 | −112.031 | −35.037 | −18.471 | 1.00 | 121.84 | C |
| ATOM | 5309 | O | ALA | H | 142 | −112.859 | −35.113 | −17.563 | 1.00 | 121.72 | O |
| ATOM | 5310 | N | LEU | H | 143 | −110.845 | −35.643 | −18.440 | 1.00 | 118.17 | N |
| ATOM | 5311 | CA | LEU | H | 143 | −110.325 | −36.452 | −17.342 | 1.00 | 116.96 | C |
| ATOM | 5312 | CB | LEU | H | 143 | −110.519 | −37.958 | −17.618 | 1.00 | 116.97 | C |
| ATOM | 5313 | CG | LEU | H | 143 | −109.759 | −38.579 | −18.793 | 1.00 | 117.14 | C |
| ATOM | 5314 | CD1 | LEU | H | 143 | −108.530 | −39.301 | −18.321 | 1.00 | 117.80 | C |
| ATOM | 5315 | CD2 | LEU | H | 143 | −110.608 | −39.563 | −19.497 | 1.00 | 117.95 | C |
| ATOM | 5316 | C | LEU | H | 143 | −108.845 | −36.130 | −17.138 | 1.00 | 115.95 | C |
| ATOM | 5317 | O | LEU | H | 143 | −108.161 | −35.694 | −18.073 | 1.00 | 115.91 | O |
| ATOM | 5318 | N | GLY | H | 144 | −108.362 | −36.374 | −15.933 | 1.00 | 112.56 | N |
| ATOM | 5319 | CA | GLY | H | 144 | −106.967 | −36.137 | −15.605 | 1.00 | 110.59 | C |
| ATOM | 5320 | C | GLY | H | 144 | −106.543 | −36.856 | −14.352 | 1.00 | 109.20 | C |
| ATOM | 5321 | O | GLY | H | 144 | −107.200 | −37.808 | −13.928 | 1.00 | 109.35 | O |
| ATOM | 5322 | N | CYS | H | 145 | −105.433 | −36.418 | −13.762 | 1.00 | 104.64 | N |
| ATOM | 5323 | CA | CYS | H | 145 | −104.937 | −36.963 | −12.503 | 1.00 | 102.92 | C |
| ATOM | 5324 | CB | CYS | H | 145 | −104.190 | −38.296 | −12.643 | 1.00 | 102.96 | C |
| ATOM | 5325 | SG | CYS | H | 145 | −102.651 | −38.216 | −13.596 | 1.00 | 103.88 | S |
| ATOM | 5326 | C | CYS | H | 145 | −104.155 | −35.917 | −11.747 | 1.00 | 101.35 | C |
| ATOM | 5327 | O | CYS | H | 145 | −103.278 | −35.281 | −12.320 | 1.00 | 100.90 | O |
| ATOM | 5328 | N | LEU | H | 146 | −104.545 | −35.685 | −10.484 | 1.00 | 97.25 | N |
| ATOM | 5329 | CA | LEU | H | 146 | −103.920 | −34.733 | −9.570 | 1.00 | 95.86 | C |
| ATOM | 5330 | CB | LEU | H | 146 | −104.934 | −34.217 | −8.530 | 1.00 | 95.89 | C |
| ATOM | 5331 | CG | LEU | H | 146 | −104.393 | −33.386 | −7.349 | 1.00 | 96.05 | C |
| ATOM | 5332 | CD1 | LEU | H | 146 | −103.887 | −32.001 | −7.806 | 1.00 | 97.22 | C |
| ATOM | 5333 | CD2 | LEU | H | 146 | −105.440 | −33.233 | −6.263 | 1.00 | 95.05 | C |
| ATOM | 5334 | C | LEU | H | 146 | −102.705 | −35.392 | −8.879 | 1.00 | 94.95 | C |
| ATOM | 5335 | O | LEU | H | 146 | −102.849 | −36.416 | −8.189 | 1.00 | 94.83 | O |
| ATOM | 5336 | N | VAL | H | 147 | −101.509 | −34.790 | −9.092 | 1.00 | 91.45 | N |
| ATOM | 5337 | CA | VAL | H | 147 | −100.210 | −35.192 | −8.550 | 1.00 | 89.84 | C |
| ATOM | 5338 | CB | VAL | H | 147 | −99.138 | −35.042 | −9.638 | 1.00 | 89.60 | C |
| ATOM | 5339 | CG1 | VAL | H | 147 | −97.805 | −35.572 | −9.154 | 1.00 | 90.04 | C |
| ATOM | 5340 | CG2 | VAL | H | 147 | −99.556 | −35.762 | −10.904 | 1.00 | 88.81 | C |
| ATOM | 5341 | C | VAL | H | 147 | −100.003 | −34.275 | −7.337 | 1.00 | 89.01 | C |
| ATOM | 5342 | O | VAL | H | 147 | −99.572 | −33.133 | −7.472 | 1.00 | 88.83 | O |
| ATOM | 5343 | N | LYS | H | 148 | −100.400 | −34.759 | −6.162 | 1.00 | 88.49 | N |
| ATOM | 5344 | CA | LYS | H | 148 | −100.378 | −33.988 | −4.925 | 1.00 | 87.97 | C |

TABLE 14-continued

PCSK9 and AX132 Fab complex x-ray structure

| ATOM | 5345 | CB | LYS | H | 148 | −101.753 | −34.128 | −4.213 | 1.00 | 87.92 | C |
|---|---|---|---|---|---|---|---|---|---|---|---|
| ATOM | 5346 | CG | LYS | H | 148 | −102.260 | −32.874 | −3.503 | 1.00 | 87.57 | C |
| ATOM | 5347 | CD | LYS | H | 148 | −102.671 | −33.147 | −2.062 | 1.00 | 87.09 | C |
| ATOM | 5348 | CE | LYS | H | 148 | −103.187 | −31.899 | −1.371 | 1.00 | 87.40 | C |
| ATOM | 5349 | NZ | LYS | H | 148 | −103.089 | −31.965 | 0.119 | 1.00 | 87.10 | N |
| ATOM | 5350 | C | LYS | H | 148 | −99.254 | −34.345 | −3.964 | 1.00 | 87.69 | C |
| ATOM | 5351 | O | LYS | H | 148 | −98.770 | −35.482 | −3.947 | 1.00 | 87.61 | O |
| ATOM | 5352 | N | ASP | H | 149 | −98.870 | −33.353 | −3.140 | 1.00 | 87.66 | N |
| ATOM | 5353 | CA | ASP | H | 149 | −97.877 | −33.460 | −2.087 | 1.00 | 87.23 | C |
| ATOM | 5354 | CB | ASP | H | 149 | −98.495 | −34.184 | −0.875 | 1.00 | 87.43 | C |
| ATOM | 5355 | CG | ASP | H | 149 | −99.611 | −33.408 | −0.191 | 1.00 | 88.64 | C |
| ATOM | 5356 | OD1 | ASP | H | 149 | −99.662 | −32.147 | −0.356 | 1.00 | 89.99 | O |
| ATOM | 5357 | OD2 | ASP | H | 149 | −100.428 | −34.047 | 0.524 | 1.00 | 89.69 | O |
| ATOM | 5358 | C | ASP | H | 149 | −96.559 | −34.084 | −2.510 | 1.00 | 86.55 | C |
| ATOM | 5359 | O | ASP | H | 149 | −96.368 | −35.292 | −2.350 | 1.00 | 86.72 | O |
| ATOM | 5360 | N | TYR | H | 150 | −95.665 | −33.256 | −3.087 | 1.00 | 82.33 | N |
| ATOM | 5361 | CA | TYR | H | 150 | −94.323 | −33.634 | −3.552 | 1.00 | 81.28 | C |
| ATOM | 5362 | CB | TYR | H | 150 | −94.313 | −34.227 | −4.996 | 1.00 | 80.95 | C |
| ATOM | 5363 | CG | TYR | H | 150 | −94.522 | −33.233 | −6.118 | 1.00 | 79.79 | C |
| ATOM | 5364 | CD1 | TYR | H | 150 | −93.468 | −32.449 | −6.590 | 1.00 | 79.35 | C |
| ATOM | 5365 | CE1 | TYR | H | 150 | −93.659 | −31.499 | −7.595 | 1.00 | 78.26 | C |
| ATOM | 5366 | CZ | TYR | H | 150 | −94.914 | −31.342 | −8.160 | 1.00 | 77.80 | C |
| ATOM | 5367 | OH | TYR | H | 150 | −95.084 | −30.431 | −9.178 | 1.00 | 76.14 | O |
| ATOM | 5368 | CE2 | TYR | H | 150 | −95.971 | −32.137 | −7.729 | 1.00 | 78.33 | C |
| ATOM | 5369 | CD2 | TYR | H | 150 | −95.768 | −33.077 | −6.714 | 1.00 | 78.62 | C |
| ATOM | 5370 | C | TYR | H | 150 | −93.338 | −32.481 | −3.397 | 1.00 | 81.02 | C |
| ATOM | 5371 | O | TYR | H | 150 | −93.745 | −31.318 | −3.379 | 1.00 | 80.65 | O |
| ATOM | 5372 | N | PHE | H | 151 | −92.041 | −32.808 | −3.298 | 1.00 | 80.24 | N |
| ATOM | 5373 | CA | PHE | H | 151 | −90.930 | −31.858 | −3.173 | 1.00 | 80.24 | C |
| ATOM | 5374 | CB | PHE | H | 151 | −90.891 | −31.234 | −1.772 | 1.00 | 80.03 | C |
| ATOM | 5375 | CG | PHE | H | 151 | −89.858 | −30.152 | −1.607 | 1.00 | 79.36 | C |
| ATOM | 5376 | CD1 | PHE | H | 151 | −88.574 | −30.455 | −1.154 | 1.00 | 78.48 | C |
| ATOM | 5377 | CE1 | PHE | H | 151 | −87.613 | −29.455 | −1.002 | 1.00 | 77.04 | C |
| ATOM | 5378 | CZ | PHE | H | 151 | −87.935 | −28.147 | −1.286 | 1.00 | 76.80 | C |
| ATOM | 5379 | CE2 | PHE | H | 151 | −89.205 | −27.825 | −1.724 | 1.00 | 77.16 | C |
| ATOM | 5380 | CD2 | PHE | H | 151 | −90.163 | −28.830 | −1.896 | 1.00 | 77.48 | C |
| ATOM | 5381 | C | PHE | H | 151 | −89.630 | −32.607 | −3.477 | 1.00 | 80.47 | C |
| ATOM | 5382 | O | PHE | H | 151 | −89.544 | −33.745 | −3.037 | 1.00 | 80.63 | O |
| ATOM | 5383 | N | PRO | H | 152 | −88.606 | −32.081 | −4.209 | 1.00 | 83.43 | N |
| ATOM | 5384 | CA | PRO | H | 152 | −88.427 | −30.756 | −4.834 | 1.00 | 83.19 | C |
| ATOM | 5385 | CB | PRO | H | 152 | −86.933 | −30.718 | −5.186 | 1.00 | 83.10 | C |
| ATOM | 5386 | CG | PRO | H | 152 | −86.322 | −31.871 | −4.473 | 1.00 | 83.56 | C |
| ATOM | 5387 | CD | PRO | H | 152 | −87.398 | −32.888 | −4.413 | 1.00 | 83.45 | C |
| ATOM | 5388 | C | PRO | H | 152 | −89.355 | −30.408 | −5.988 | 1.00 | 83.21 | C |
| ATOM | 5389 | O | PRO | H | 152 | −90.542 | −30.634 | −5.855 | 1.00 | 83.44 | O |
| ATOM | 5390 | N | GLU | H | 153 | −88.869 | −29.838 | −7.092 | 1.00 | 85.80 | N |
| ATOM | 5391 | CA | GLU | H | 153 | −89.855 | −29.416 | −8.056 | 1.00 | 85.87 | C |
| ATOM | 5392 | CB | GLU | H | 153 | −89.952 | −27.900 | −8.138 | 1.00 | 85.58 | C |
| ATOM | 5393 | CG | GLU | H | 153 | −91.374 | −27.408 | −7.948 | 1.00 | 85.41 | C |
| ATOM | 5394 | CD | GLU | H | 153 | −92.111 | −26.963 | −9.195 | 1.00 | 85.00 | C |
| ATOM | 5395 | OE1 | GLU | H | 153 | −92.597 | −27.837 | −9.955 | 1.00 | 84.39 | O |
| ATOM | 5396 | OE2 | GLU | H | 153 | −92.222 | −25.729 | −9.398 | 1.00 | 84.81 | O |
| ATOM | 5397 | C | GLU | H | 153 | −90.029 | −30.019 | −9.406 | 1.00 | 86.38 | C |
| ATOM | 5398 | O | GLU | H | 153 | −91.154 | −29.908 | −9.891 | 1.00 | 87.16 | O |
| ATOM | 5399 | N | PRO | H | 154 | −89.067 | −30.641 | −10.075 | 1.00 | 82.97 | N |
| ATOM | 5400 | CA | PRO | H | 154 | −89.363 | −31.178 | −11.422 | 1.00 | 82.81 | C |
| ATOM | 5401 | CB | PRO | H | 154 | −88.144 | −31.998 | −11.761 | 1.00 | 82.87 | C |
| ATOM | 5402 | CG | PRO | H | 154 | −87.059 | −31.343 | −10.977 | 1.00 | 83.12 | C |
| ATOM | 5403 | CD | PRO | H | 154 | −87.664 | −30.849 | −9.699 | 1.00 | 82.87 | C |
| ATOM | 5404 | C | PRO | H | 154 | −90.708 | −31.866 | −11.752 | 1.00 | 82.98 | C |
| ATOM | 5405 | O | PRO | H | 154 | −91.522 | −31.184 | −12.391 | 1.00 | 83.54 | O |
| ATOM | 5406 | N | VAL | H | 155 | −90.973 | −33.154 | −11.339 | 1.00 | 80.51 | N |
| ATOM | 5407 | CA | VAL | H | 155 | −92.198 | −33.952 | −11.670 | 1.00 | 80.32 | C |
| ATOM | 5408 | CB | VAL | H | 155 | −93.380 | −33.981 | −10.663 | 1.00 | 80.32 | C |
| ATOM | 5409 | CG1 | VAL | H | 155 | −94.519 | −33.072 | −11.087 | 1.00 | 80.02 | C |
| ATOM | 5410 | CG2 | VAL | H | 155 | −93.909 | −35.403 | −10.518 | 1.00 | 81.10 | C |
| ATOM | 5411 | C | VAL | H | 155 | −92.678 | −33.935 | −13.151 | 1.00 | 80.22 | C |
| ATOM | 5412 | O | VAL | H | 155 | −93.103 | −32.900 | −13.645 | 1.00 | 80.15 | O |
| ATOM | 5413 | N | THR | H | 156 | −92.635 | −35.088 | −13.837 | 1.00 | 82.36 | N |
| ATOM | 5414 | CA | THR | H | 156 | −93.051 | −35.181 | −15.241 | 1.00 | 82.95 | C |
| ATOM | 5415 | CB | THR | H | 156 | −91.871 | −35.400 | −16.183 | 1.00 | 82.72 | C |
| ATOM | 5416 | OG1 | THR | H | 156 | −91.085 | −36.512 | −15.749 | 1.00 | 83.41 | O |
| ATOM | 5417 | CG2 | THR | H | 156 | −91.007 | −34.163 | −16.312 | 1.00 | 83.21 | C |
| ATOM | 5418 | C | THR | H | 156 | −94.217 | −36.094 | −15.553 | 1.00 | 83.35 | C |
| ATOM | 5419 | O | THR | H | 156 | −94.100 | −37.315 | −15.448 | 1.00 | 83.44 | O |
| ATOM | 5420 | N | VAL | H | 157 | −95.335 | −35.494 | −15.987 | 1.00 | 84.88 | N |
| ATOM | 5421 | CA | VAL | H | 157 | −96.543 | −36.220 | −16.367 | 1.00 | 85.29 | C |
| ATOM | 5422 | CB | VAL | H | 157 | −97.852 | −35.527 | −15.929 | 1.00 | 85.05 | C |

TABLE 14-continued

PCSK9 and AX132 Fab complex x-ray structure

| ATOM | 5423 | CG1 | VAL | H | 157 | −99.047 | −36.460 | −16.116 | 1.00 | 85.24 | C |
|---|---|---|---|---|---|---|---|---|---|---|---|
| ATOM | 5424 | CG2 | VAL | H | 157 | −97.766 | −35.038 | −14.485 | 1.00 | 85.07 | C |
| ATOM | 5425 | C | VAL | H | 157 | −96.560 | −36.494 | −17.862 | 1.00 | 85.97 | C |
| ATOM | 5426 | O | VAL | H | 157 | −96.249 | −35.624 | −18.682 | 1.00 | 86.10 | O |
| ATOM | 5427 | N | SER | H | 158 | −96.942 | −37.713 | −18.198 | 1.00 | 88.64 | N |
| ATOM | 5428 | CA | SER | H | 158 | −97.084 | −38.197 | −19.559 | 1.00 | 89.64 | C |
| ATOM | 5429 | CB | SER | H | 158 | −95.836 | −38.971 | −19.993 | 1.00 | 89.51 | C |
| ATOM | 5430 | OG | SER | H | 158 | −96.025 | −40.372 | −20.126 | 1.00 | 88.95 | O |
| ATOM | 5431 | C | SER | H | 158 | −98.323 | −39.091 | −19.553 | 1.00 | 90.56 | C |
| ATOM | 5432 | O | SER | H | 158 | −98.538 | −39.794 | −18.561 | 1.00 | 90.78 | O |
| ATOM | 5433 | N | TRP | H | 159 | −99.144 | −39.060 | −20.633 | 1.00 | 92.59 | N |
| ATOM | 5434 | CA | TRP | H | 159 | −100.333 | −39.907 | −20.723 | 1.00 | 92.98 | C |
| ATOM | 5435 | CB | TRP | H | 159 | −101.561 | −39.104 | −21.090 | 1.00 | 92.58 | C |
| ATOM | 5436 | CG | TRP | H | 159 | −102.045 | −38.260 | −19.953 | 1.00 | 91.88 | C |
| ATOM | 5437 | CD1 | TRP | H | 159 | −101.611 | −37.013 | −19.616 | 1.00 | 91.55 | C |
| ATOM | 5438 | NE1 | TRP | H | 159 | −102.312 | −36.542 | −18.527 | 1.00 | 91.01 | N |
| ATOM | 5439 | CE2 | TRP | H | 159 | −103.198 | −37.503 | −18.119 | 1.00 | 90.69 | C |
| ATOM | 5440 | CD2 | TRP | H | 159 | −103.060 | −38.602 | −18.998 | 1.00 | 91.08 | C |
| ATOM | 5441 | CE3 | TRP | H | 159 | −103.876 | −39.729 | −18.805 | 1.00 | 90.75 | C |
| ATOM | 5442 | CZ3 | TRP | H | 159 | −104.781 | −39.726 | −17.754 | 1.00 | 91.05 | C |
| ATOM | 5443 | CH2 | TRP | H | 159 | −104.885 | −38.627 | −16.889 | 1.00 | 91.05 | C |
| ATOM | 5444 | CZ2 | TRP | H | 159 | −104.101 | −37.505 | −17.052 | 1.00 | 90.75 | C |
| ATOM | 5445 | C | TRP | H | 159 | −100.114 | −41.115 | −21.635 | 1.00 | 93.84 | C |
| ATOM | 5446 | O | TRP | H | 159 | −99.360 | −41.028 | −22.620 | 1.00 | 93.86 | O |
| ATOM | 5447 | N | ASN | H | 160 | −100.749 | −42.254 | −21.261 | 1.00 | 97.57 | N |
| ATOM | 5448 | CA | ASN | H | 160 | −100.698 | −43.567 | −21.922 | 1.00 | 98.31 | C |
| ATOM | 5449 | CB | ASN | H | 160 | −101.820 | −43.740 | −22.950 | 1.00 | 98.36 | C |
| ATOM | 5450 | CG | ASN | H | 160 | −103.205 | −43.845 | −22.348 | 1.00 | 99.33 | C |
| ATOM | 5451 | OD1 | ASN | H | 160 | −103.408 | −44.390 | −21.255 | 1.00 | 100.83 | O |
| ATOM | 5452 | ND2 | ASN | H | 160 | −104.203 | −43.325 | −23.048 | 1.00 | 100.10 | N |
| ATOM | 5453 | C | ASN | H | 160 | −99.332 | −43.897 | −22.492 | 1.00 | 98.70 | C |
| ATOM | 5454 | O | ASN | H | 160 | −99.196 | −44.110 | −23.694 | 1.00 | 98.51 | O |
| ATOM | 5455 | N | SER | H | 161 | −98.311 | −43.901 | −21.613 | 1.00 | 100.95 | N |
| ATOM | 5456 | CA | SER | H | 161 | −96.899 | −44.191 | −21.914 | 1.00 | 101.67 | C |
| ATOM | 5457 | CB | SER | H | 161 | −96.663 | −45.691 | −22.072 | 1.00 | 101.66 | C |
| ATOM | 5458 | OG | SER | H | 161 | −97.176 | −46.390 | −20.948 | 1.00 | 102.13 | O |
| ATOM | 5459 | C | SER | H | 161 | −96.307 | −43.382 | −23.078 | 1.00 | 102.05 | C |
| ATOM | 5460 | O | SER | H | 161 | −95.469 | −43.878 | −23.843 | 1.00 | 102.08 | O |
| ATOM | 5461 | N | GLY | H | 162 | −96.748 | −42.131 | −23.177 | 1.00 | 103.84 | N |
| ATOM | 5462 | CA | GLY | H | 162 | −96.291 | −41.207 | −24.204 | 1.00 | 104.22 | C |
| ATOM | 5463 | C | GLY | H | 162 | −96.960 | −41.387 | −25.546 | 1.00 | 104.40 | C |
| ATOM | 5464 | O | GLY | H | 162 | −96.344 | −41.119 | −26.583 | 1.00 | 104.66 | O |
| ATOM | 5465 | N | ALA | H | 163 | −98.223 | −41.842 | −25.536 | 1.00 | 105.13 | N |
| ATOM | 5466 | CA | ALA | H | 163 | −99.000 | −42.038 | −26.755 | 1.00 | 105.10 | C |
| ATOM | 5467 | CB | ALA | H | 163 | −99.670 | −43.401 | −26.755 | 1.00 | 105.12 | C |
| ATOM | 5468 | C | ALA | H | 163 | −100.036 | −40.918 | −26.873 | 1.00 | 104.95 | C |
| ATOM | 5469 | O | ALA | H | 163 | −100.053 | −40.227 | −27.897 | 1.00 | 105.29 | O |
| ATOM | 5470 | N | LEU | H | 164 | −100.872 | −40.717 | −25.829 | 1.00 | 102.14 | N |
| ATOM | 5471 | CA | LEU | H | 164 | −101.883 | −39.664 | −25.819 | 1.00 | 101.80 | C |
| ATOM | 5472 | CB | LEU | H | 164 | −103.008 | −40.001 | −24.814 | 1.00 | 101.61 | C |
| ATOM | 5473 | CG | LEU | H | 164 | −103.991 | −38.899 | −24.407 | 1.00 | 101.38 | C |
| ATOM | 5474 | CD1 | LEU | H | 164 | −104.862 | −38.446 | −25.572 | 1.00 | 101.25 | C |
| ATOM | 5475 | CD2 | LEU | H | 164 | −104.847 | −39.360 | −23.263 | 1.00 | 100.62 | C |
| ATOM | 5476 | C | LEU | H | 164 | −101.200 | −38.296 | −25.553 | 1.00 | 101.92 | C |
| ATOM | 5477 | O | LEU | H | 164 | −100.692 | −38.055 | −24.450 | 1.00 | 102.13 | O |
| ATOM | 5478 | N | THR | H | 165 | −101.171 | −37.427 | −26.599 | 1.00 | 102.51 | N |
| ATOM | 5479 | CA | THR | H | 165 | −100.559 | −36.088 | −26.619 | 1.00 | 102.09 | C |
| ATOM | 5480 | CB | THR | H | 165 | −99.382 | −36.040 | −27.600 | 1.00 | 102.06 | C |
| ATOM | 5481 | OG1 | THR | H | 165 | −99.135 | −34.668 | −27.916 | 1.00 | 102.39 | O |
| ATOM | 5482 | CG2 | THR | H | 165 | −99.656 | −36.816 | −28.901 | 1.00 | 102.11 | C |
| ATOM | 5483 | C | THR | H | 165 | −101.542 | −34.931 | −26.897 | 1.00 | 101.78 | C |
| ATOM | 5484 | O | THR | H | 165 | −101.409 | −33.860 | −26.296 | 1.00 | 101.69 | O |
| ATOM | 5485 | N | SER | H | 166 | −102.483 | −35.126 | −27.834 | 1.00 | 100.47 | N |
| ATOM | 5486 | CA | SER | H | 166 | −103.452 | −34.095 | −28.178 | 1.00 | 99.92 | C |
| ATOM | 5487 | CB | SER | H | 166 | −104.168 | −34.428 | −29.484 | 1.00 | 99.96 | C |
| ATOM | 5488 | OG | SER | H | 166 | −103.821 | −33.519 | −30.519 | 1.00 | 100.95 | O |
| ATOM | 5489 | C | SER | H | 166 | −104.447 | −33.894 | −27.055 | 1.00 | 99.35 | C |
| ATOM | 5490 | O | SER | H | 166 | −104.954 | −34.865 | −26.485 | 1.00 | 99.39 | O |
| ATOM | 5491 | N | GLY | H | 167 | −104.692 | −32.625 | −26.739 | 1.00 | 98.50 | N |
| ATOM | 5492 | CA | GLY | H | 167 | −105.620 | −32.206 | −25.695 | 1.00 | 97.67 | C |
| ATOM | 5493 | C | GLY | H | 167 | −105.093 | −32.351 | −24.284 | 1.00 | 97.17 | C |
| ATOM | 5494 | O | GLY | H | 167 | −105.836 | −32.081 | −23.340 | 1.00 | 97.21 | O |
| ATOM | 5495 | N | VAL | H | 168 | −103.801 | −32.767 | −24.126 | 1.00 | 95.72 | N |
| ATOM | 5496 | CA | VAL | H | 168 | −103.112 | −32.965 | −22.840 | 1.00 | 94.89 | C |
| ATOM | 5497 | CB | VAL | H | 168 | −101.922 | −33.953 | −22.958 | 1.00 | 94.85 | C |
| ATOM | 5498 | CG1 | VAL | H | 168 | −101.187 | −34.094 | −21.632 | 1.00 | 94.65 | C |
| ATOM | 5499 | CG2 | VAL | H | 168 | −102.370 | −35.317 | −23.462 | 1.00 | 95.14 | C |
| ATOM | 5500 | C | VAL | H | 168 | −102.645 | −31.616 | −22.294 | 1.00 | 94.37 | C |

TABLE 14-continued

PCSK9 and AX132 Fab complex x-ray structure

| ATOM | 5501 | O   | VAL | H | 168 | -101.856 | -30.933 | -22.952 | 1.00 | 94.37 | O |
|------|------|-----|-----|---|-----|----------|---------|---------|------|-------|---|
| ATOM | 5502 | N   | HIS | H | 169 | -103.114 | -31.250 | -21.089 | 1.00 | 91.67 | N |
| ATOM | 5503 | CA  | HIS | H | 169 | -102.761 | -29.997 | -20.436 | 1.00 | 91.22 | C |
| ATOM | 5504 | CB  | HIS | H | 169 | -103.975 | -29.060 | -20.360 | 1.00 | 91.22 | C |
| ATOM | 5505 | CG  | HIS | H | 169 | -104.261 | -28.301 | -21.616 | 1.00 | 91.46 | C |
| ATOM | 5506 | ND1 | HIS | H | 169 | -103.604 | -28.577 | -22.806 | 1.00 | 91.91 | N |
| ATOM | 5507 | CE1 | HIS | H | 169 | -104.112 | -27.742 | -23.700 | 1.00 | 91.47 | C |
| ATOM | 5508 | NE2 | HIS | H | 169 | -105.044 | -26.954 | -23.158 | 1.00 | 91.76 | N |
| ATOM | 5509 | CD2 | HIS | H | 169 | -105.152 | -27.306 | -21.831 | 1.00 | 91.43 | C |
| ATOM | 5510 | C   | HIS | H | 169 | -102.183 | -30.178 | -19.056 | 1.00 | 91.04 | C |
| ATOM | 5511 | O   | HIS | H | 169 | -102.940 | -30.139 | -18.074 | 1.00 | 90.98 | O |
| ATOM | 5512 | N   | THR | H | 170 | -100.839 | -30.341 | -18.963 | 1.00 | 89.21 | N |
| ATOM | 5513 | CA  | THR | H | 170 | -100.155 | -30.465 | -17.665 | 1.00 | 88.80 | C |
| ATOM | 5514 | CB  | THR | H | 170 | -98.889  | -31.300 | -17.749 | 1.00 | 88.65 | C |
| ATOM | 5515 | OG1 | THR | H | 170 | -99.131  | -32.484 | -18.516 | 1.00 | 88.62 | O |
| ATOM | 5516 | CG2 | THR | H | 170 | -98.359  | -31.656 | -16.376 | 1.00 | 88.55 | C |
| ATOM | 5517 | C   | THR | H | 170 | -99.927  | -29.048 | -17.116 | 1.00 | 88.66 | C |
| ATOM | 5518 | O   | THR | H | 170 | -99.163  | -28.267 | -17.694 | 1.00 | 88.44 | O |
| ATOM | 5519 | N   | PHE | H | 171 | -100.631 | -28.712 | -16.028 | 1.00 | 89.66 | N |
| ATOM | 5520 | CA  | PHE | H | 171 | -100.588 | -27.393 | -15.418 | 1.00 | 89.85 | C |
| ATOM | 5521 | CB  | PHE | H | 171 | -101.810 | -27.185 | -14.518 | 1.00 | 90.12 | C |
| ATOM | 5522 | CG  | PHE | H | 171 | -103.058 | -26.965 | -15.322 | 1.00 | 91.71 | C |
| ATOM | 5523 | CD1 | PHE | H | 171 | -103.897 | -28.028 | -15.638 | 1.00 | 92.97 | C |
| ATOM | 5524 | CE1 | PHE | H | 171 | -105.041 | -27.833 | -16.406 | 1.00 | 93.11 | C |
| ATOM | 5525 | CZ  | PHE | H | 171 | -105.350 | -26.577 | -16.863 | 1.00 | 93.49 | C |
| ATOM | 5526 | CE2 | PHE | H | 171 | -104.526 | -25.512 | -16.568 | 1.00 | 93.17 | C |
| ATOM | 5527 | CD2 | PHE | H | 171 | -103.377 | -25.706 | -15.806 | 1.00 | 92.71 | C |
| ATOM | 5528 | C   | PHE | H | 171 | -99.363  | -27.130 | -14.609 | 1.00 | 89.75 | C |
| ATOM | 5529 | O   | PHE | H | 171 | -98.851  | -28.065 | -13.978 | 1.00 | 90.18 | O |
| ATOM | 5530 | N   | PRO | H | 172 | -98.904  | -25.849 | -14.542 | 1.00 | 87.98 | N |
| ATOM | 5531 | CA  | PRO | H | 172 | -97.760  | -25.525 | -13.674 | 1.00 | 87.45 | C |
| ATOM | 5532 | CB  | PRO | H | 172 | -97.648  | -24.001 | -13.796 | 1.00 | 87.33 | C |
| ATOM | 5533 | CG  | PRO | H | 172 | -98.322  | -23.665 | -15.037 | 1.00 | 87.68 | C |
| ATOM | 5534 | CD  | PRO | H | 172 | -99.420  | -24.639 | -15.210 | 1.00 | 87.92 | C |
| ATOM | 5535 | C   | PRO | H | 172 | -98.071  | -25.903 | -12.220 | 1.00 | 86.77 | C |
| ATOM | 5536 | O   | PRO | H | 172 | -99.229  | -25.810 | -11.797 | 1.00 | 86.77 | O |
| ATOM | 5537 | N   | ALA | H | 173 | -97.053  | -26.340 | -11.457 | 1.00 | 83.63 | N |
| ATOM | 5538 | CA  | ALA | H | 173 | -97.233  | -26.716 | -10.051 | 1.00 | 83.04 | C |
| ATOM | 5539 | CB  | ALA | H | 173 | -95.950  | -27.329 | -9.510  | 1.00 | 82.99 | C |
| ATOM | 5540 | C   | ALA | H | 173 | -97.657  | -25.522 | -9.184  | 1.00 | 82.58 | C |
| ATOM | 5541 | O   | ALA | H | 173 | -97.655  | -24.373 | -9.636  | 1.00 | 82.40 | O |
| ATOM | 5542 | N   | VAL | H | 174 | -98.029  | -25.797 | -7.948  | 1.00 | 82.52 | N |
| ATOM | 5543 | CA  | VAL | H | 174 | -98.410  | -24.751 | -7.019  | 1.00 | 82.63 | C |
| ATOM | 5544 | CB  | VAL | H | 174 | -99.915  | -24.380 | -7.047  | 1.00 | 82.71 | C |
| ATOM | 5545 | CG1 | VAL | H | 174 | -100.815 | -25.563 | -6.700  | 1.00 | 83.00 | C |
| ATOM | 5546 | CG2 | VAL | H | 174 | -100.205 | -23.192 | -6.140  | 1.00 | 83.07 | C |
| ATOM | 5547 | C   | VAL | H | 174 | -97.897  | -25.120 | -5.657  | 1.00 | 82.53 | C |
| ATOM | 5548 | O   | VAL | H | 174 | -98.127  | -26.240 | -5.209  | 1.00 | 82.89 | O |
| ATOM | 5549 | N   | LEU | H | 175 | -97.177  | -24.202 | -5.010  | 1.00 | 81.53 | N |
| ATOM | 5550 | CA  | LEU | H | 175 | -96.615  | -24.424 | -3.680  | 1.00 | 81.33 | C |
| ATOM | 5551 | CB  | LEU | H | 175 | -95.444  | -23.472 | -3.417  | 1.00 | 80.93 | C |
| ATOM | 5552 | CG  | LEU | H | 175 | -94.733  | -23.605 | -2.103  | 1.00 | 80.42 | C |
| ATOM | 5553 | CD1 | LEU | H | 175 | -94.223  | -25.004 | -1.892  | 1.00 | 81.14 | C |
| ATOM | 5554 | CD2 | LEU | H | 175 | -93.606  | -22.641 | -2.031  | 1.00 | 79.66 | C |
| ATOM | 5555 | C   | LEU | H | 175 | -97.701  | -24.258 | -2.644  | 1.00 | 81.61 | C |
| ATOM | 5556 | O   | LEU | H | 175 | -98.313  | -23.193 | -2.550  | 1.00 | 81.55 | O |
| ATOM | 5557 | N   | GLN | H | 176 | -97.954  | -25.321 | -1.883  | 1.00 | 85.15 | N |
| ATOM | 5558 | CA  | GLN | H | 176 | -98.989  | -25.317 | -0.856  | 1.00 | 85.67 | C |
| ATOM | 5559 | CB  | GLN | H | 176 | -99.579  | -26.711 | -0.689  | 1.00 | 85.64 | C |
| ATOM | 5560 | CG  | GLN | H | 176 | -100.237 | -27.269 | -1.931  | 1.00 | 85.96 | C |
| ATOM | 5561 | CD  | GLN | H | 176 | -100.703 | -28.657 | -1.616  | 1.00 | 87.03 | C |
| ATOM | 5562 | OE1 | GLN | H | 176 | -101.887 | -28.871 | -1.313  | 1.00 | 88.32 | O |
| ATOM | 5563 | NE2 | GLN | H | 176 | -99.783  | -29.632 | -1.655  | 1.00 | 86.68 | N |
| ATOM | 5564 | C   | GLN | H | 176 | -98.428  | -24.839 | 0.469   | 1.00 | 86.04 | C |
| ATOM | 5565 | O   | GLN | H | 176 | -97.205  | -24.852 | 0.652   | 1.00 | 86.10 | O |
| ATOM | 5566 | N   | SER | H | 177 | -99.324  | -24.426 | 1.399   | 1.00 | 88.86 | N |
| ATOM | 5567 | CA  | SER | H | 177 | -98.974  | -23.948 | 2.742   | 1.00 | 89.53 | C |
| ATOM | 5568 | CB  | SER | H | 177 | -100.230 | -23.631 | 3.542   | 1.00 | 89.52 | C |
| ATOM | 5569 | OG  | SER | H | 177 | -101.138 | -24.715 | 3.455   | 1.00 | 90.38 | O |
| ATOM | 5570 | C   | SER | H | 177 | -98.094  | -24.979 | 3.474   | 1.00 | 89.80 | C |
| ATOM | 5571 | O   | SER | H | 177 | -97.163  | -24.593 | 4.193   | 1.00 | 89.96 | O |
| ATOM | 5572 | N   | SER | H | 178 | -98.353  | -26.292 | 3.237   | 1.00 | 90.01 | N |
| ATOM | 5573 | CA  | SER | H | 178 | -97.573  | -27.400 | 3.799   | 1.00 | 90.10 | C |
| ATOM | 5574 | CB  | SER | H | 178 | -98.120  | -28.740 | 3.311   | 1.00 | 90.17 | C |
| ATOM | 5575 | OG  | SER | H | 178 | -98.173  | -28.854 | 1.897   | 1.00 | 90.19 | O |
| ATOM | 5576 | C   | SER | H | 178 | -96.093  | -27.261 | 3.414   | 1.00 | 90.15 | C |
| ATOM | 5577 | O   | SER | H | 178 | -95.216  | -27.536 | 4.228   | 1.00 | 90.30 | O |
| ATOM | 5578 | N   | GLY | H | 179 | -95.847  | -26.795 | 2.190   | 1.00 | 89.38 | N |

TABLE 14-continued

PCSK9 and AX132 Fab complex x-ray structure

| ATOM | 5579 | CA | GLY | H | 179 | −94.520 | −26.586 | 1.624 | 1.00 | 89.50 | C |
|---|---|---|---|---|---|---|---|---|---|---|---|
| ATOM | 5580 | C | GLY | H | 179 | −94.222 | −27.558 | 0.504 | 1.00 | 89.56 | C |
| ATOM | 5581 | O | GLY | H | 179 | −93.095 | −27.588 | −0.006 | 1.00 | 89.51 | O |
| ATOM | 5582 | N | LEU | H | 180 | −95.249 | −28.353 | 0.120 | 1.00 | 86.59 | N |
| ATOM | 5583 | CA | LEU | H | 180 | −95.204 | −29.364 | −0.934 | 1.00 | 86.55 | C |
| ATOM | 5584 | CB | LEU | H | 180 | −95.808 | −30.690 | −0.432 | 1.00 | 86.49 | C |
| ATOM | 5585 | CG | LEU | H | 180 | −95.213 | −31.355 | 0.829 | 1.00 | 85.74 | C |
| ATOM | 5586 | CD1 | LEU | H | 180 | −95.895 | −32.655 | 1.095 | 1.00 | 84.95 | C |
| ATOM | 5587 | CD2 | LEU | H | 180 | −93.741 | −31.644 | 0.678 | 1.00 | 85.10 | C |
| ATOM | 5588 | C | LEU | H | 180 | −95.961 | −28.891 | −2.171 | 1.00 | 86.73 | C |
| ATOM | 5589 | O | LEU | H | 180 | −97.032 | −28.322 | −2.045 | 1.00 | 86.85 | O |
| ATOM | 5590 | N | TYR | H | 181 | −95.415 | −29.126 | −3.358 | 1.00 | 87.14 | N |
| ATOM | 5591 | CA | TYR | H | 181 | −96.052 | −28.716 | −4.603 | 1.00 | 87.59 | C |
| ATOM | 5592 | CB | TYR | H | 181 | −95.016 | −28.595 | −5.735 | 1.00 | 87.56 | C |
| ATOM | 5593 | CG | TYR | H | 181 | −93.948 | −27.568 | −5.454 | 1.00 | 87.55 | C |
| ATOM | 5594 | CD1 | TYR | H | 181 | −94.132 | −26.235 | −5.796 | 1.00 | 87.69 | C |
| ATOM | 5595 | CE1 | TYR | H | 181 | −93.161 | −25.278 | −5.515 | 1.00 | 87.87 | C |
| ATOM | 5596 | CZ | TYR | H | 181 | −91.992 | −25.651 | −4.873 | 1.00 | 87.74 | C |
| ATOM | 5597 | OH | TYR | H | 181 | −91.035 | −24.707 | −4.584 | 1.00 | 88.45 | O |
| ATOM | 5598 | CE2 | TYR | H | 181 | −91.790 | −26.973 | −4.522 | 1.00 | 87.55 | C |
| ATOM | 5599 | CD2 | TYR | H | 181 | −92.767 | −27.920 | −4.810 | 1.00 | 87.68 | C |
| ATOM | 5600 | C | TYR | H | 181 | −97.149 | −29.678 | −5.018 | 1.00 | 88.10 | C |
| ATOM | 5601 | O | TYR | H | 181 | −97.100 | −30.866 | −4.684 | 1.00 | 88.23 | O |
| ATOM | 5602 | N | SER | H | 182 | −98.136 | −29.166 | −5.767 | 1.00 | 91.91 | N |
| ATOM | 5603 | CA | SER | H | 182 | −99.248 | −29.952 | −6.308 | 1.00 | 92.59 | C |
| ATOM | 5604 | CB | SER | H | 182 | −100.509 | −29.785 | −5.470 | 1.00 | 92.69 | C |
| ATOM | 5605 | OG | SER | H | 182 | −100.330 | −30.303 | −4.164 | 1.00 | 93.52 | O |
| ATOM | 5606 | C | SER | H | 182 | −99.541 | −29.520 | −7.717 | 1.00 | 92.83 | C |
| ATOM | 5607 | O | SER | H | 182 | −99.540 | −28.324 | −8.016 | 1.00 | 92.92 | O |
| ATOM | 5608 | N | LEU | H | 183 | −99.775 | −30.479 | −8.591 | 1.00 | 94.42 | N |
| ATOM | 5609 | CA | LEU | H | 183 | −100.126 | −30.156 | −9.964 | 1.00 | 95.22 | C |
| ATOM | 5610 | CB | LEU | H | 183 | −98.948 | −29.977 | −10.943 | 1.00 | 95.09 | C |
| ATOM | 5611 | CG | LEU | H | 183 | −98.157 | −31.170 | −11.505 | 1.00 | 94.86 | C |
| ATOM | 5612 | CD1 | LEU | H | 183 | −98.956 | −31.979 | −12.521 | 1.00 | 95.07 | C |
| ATOM | 5613 | CD2 | LEU | H | 183 | −96.968 | −30.650 | −12.264 | 1.00 | 95.32 | C |
| ATOM | 5614 | C | LEU | H | 183 | −101.162 | −31.078 | −10.497 | 1.00 | 95.90 | C |
| ATOM | 5615 | O | LEU | H | 183 | −101.322 | −32.196 | −10.002 | 1.00 | 96.13 | O |
| ATOM | 5616 | N | SER | H | 184 | −101.854 | −30.623 | −11.521 | 1.00 | 95.87 | N |
| ATOM | 5617 | CA | SER | H | 184 | −102.879 | −31.424 | −12.135 | 1.00 | 96.50 | C |
| ATOM | 5618 | CB | SER | H | 184 | −104.260 | −30.840 | −11.836 | 1.00 | 96.55 | C |
| ATOM | 5619 | OG | SER | H | 184 | −104.294 | −29.427 | −11.978 | 1.00 | 96.78 | O |
| ATOM | 5620 | C | SER | H | 184 | −102.628 | −31.509 | −13.615 | 1.00 | 96.87 | C |
| ATOM | 5621 | O | SER | H | 184 | −102.418 | −30.487 | −14.271 | 1.00 | 96.82 | O |
| ATOM | 5622 | N | SER | H | 185 | −102.604 | −32.728 | −14.140 | 1.00 | 96.92 | N |
| ATOM | 5623 | CA | SER | H | 185 | −102.465 | −32.910 | −15.572 | 1.00 | 97.63 | C |
| ATOM | 5624 | CB | SER | H | 185 | −101.491 | −34.018 | −15.925 | 1.00 | 97.50 | C |
| ATOM | 5625 | OG | SER | H | 185 | −101.281 | −34.000 | −17.329 | 1.00 | 97.39 | O |
| ATOM | 5626 | C | SER | H | 185 | −103.862 | −33.263 | −16.038 | 1.00 | 98.29 | C |
| ATOM | 5627 | O | SER | H | 185 | −104.576 | −34.020 | −15.365 | 1.00 | 98.57 | O |
| ATOM | 5628 | N | VAL | H | 186 | −104.272 | −32.687 | −17.159 | 1.00 | 98.00 | N |
| ATOM | 5629 | CA | VAL | H | 186 | −105.602 | −32.908 | −17.690 | 1.00 | 98.39 | C |
| ATOM | 5630 | CB | VAL | H | 186 | −106.449 | −31.646 | −17.393 | 1.00 | 98.15 | C |
| ATOM | 5631 | CG1 | VAL | H | 186 | −106.939 | −30.947 | −18.653 | 1.00 | 98.29 | C |
| ATOM | 5632 | CG2 | VAL | H | 186 | −107.579 | −31.941 | −16.419 | 1.00 | 97.38 | C |
| ATOM | 5633 | C | VAL | H | 186 | −105.545 | −33.335 | −19.166 | 1.00 | 99.17 | C |
| ATOM | 5634 | O | VAL | H | 186 | −104.532 | −33.123 | −19.843 | 1.00 | 99.02 | O |
| ATOM | 5635 | N | VAL | H | 187 | −106.617 | −33.988 | −19.637 | 1.00 | 101.68 | N |
| ATOM | 5636 | CA | VAL | H | 187 | −106.742 | −34.433 | −21.023 | 1.00 | 102.74 | C |
| ATOM | 5637 | CB | VAL | H | 187 | −106.004 | −35.767 | −21.355 | 1.00 | 102.60 | C |
| ATOM | 5638 | CG1 | VAL | H | 187 | −106.720 | −36.984 | −20.774 | 1.00 | 102.47 | C |
| ATOM | 5639 | CG2 | VAL | H | 187 | −105.770 | −35.918 | −22.853 | 1.00 | 102.04 | C |
| ATOM | 5640 | C | VAL | H | 187 | −108.192 | −34.310 | −21.543 | 1.00 | 103.69 | C |
| ATOM | 5641 | O | VAL | H | 187 | −109.132 | −34.245 | −20.745 | 1.00 | 103.73 | O |
| ATOM | 5642 | N | THR | H | 188 | −108.344 | −34.211 | −22.880 | 1.00 | 107.37 | N |
| ATOM | 5643 | CA | THR | H | 188 | −109.603 | −34.099 | −23.613 | 1.00 | 108.41 | C |
| ATOM | 5644 | CB | THR | H | 188 | −109.767 | −32.673 | −24.199 | 1.00 | 108.35 | C |
| ATOM | 5645 | OG1 | THR | H | 188 | −110.529 | −31.892 | −23.270 | 1.00 | 107.92 | O |
| ATOM | 5646 | CG2 | THR | H | 188 | −110.414 | −32.645 | −25.597 | 1.00 | 108.00 | C |
| ATOM | 5647 | C | THR | H | 188 | −109.659 | −35.281 | −24.573 | 1.00 | 109.45 | C |
| ATOM | 5648 | O | THR | H | 188 | −108.768 | −35.458 | −25.419 | 1.00 | 109.44 | O |
| ATOM | 5649 | N | VAL | H | 189 | −110.685 | −36.121 | −24.383 | 1.00 | 114.13 | N |
| ATOM | 5650 | CA | VAL | H | 189 | −110.934 | −37.340 | −25.162 | 1.00 | 115.59 | C |
| ATOM | 5651 | CB | VAL | H | 189 | −110.343 | −38.638 | −24.522 | 1.00 | 115.62 | C |
| ATOM | 5652 | CG1 | VAL | H | 189 | −108.822 | −38.708 | −24.677 | 1.00 | 115.89 | C |
| ATOM | 5653 | CG2 | VAL | H | 189 | −110.773 | −38.810 | −23.066 | 1.00 | 115.45 | C |
| ATOM | 5654 | C | VAL | H | 189 | −112.427 | −37.499 | −25.477 | 1.00 | 116.45 | C |
| ATOM | 5655 | O | VAL | H | 189 | −113.262 | −37.061 | −24.681 | 1.00 | 116.41 | O |
| ATOM | 5656 | N | PRO | H | 190 | −112.796 | −38.137 | −26.609 | 1.00 | 120.19 | N |

TABLE 14-continued

PCSK9 and AX132 Fab complex x-ray structure

| ATOM | 5657 | CA  | PRO | H | 190 | −114.227 | −38.305 | −26.893 | 1.00 | 120.99 | C |
| ATOM | 5658 | CB  | PRO | H | 190 | −114.267 | −38.550 | −28.402 | 1.00 | 121.02 | C |
| ATOM | 5659 | CG  | PRO | H | 190 | −112.925 | −39.111 | −28.741 | 1.00 | 120.60 | C |
| ATOM | 5660 | CD  | PRO | H | 190 | −111.951 | −38.732 | −27.671 | 1.00 | 120.17 | C |
| ATOM | 5661 | C   | PRO | H | 190 | −114.908 | −39.418 | −26.090 | 1.00 | 121.84 | C |
| ATOM | 5662 | O   | PRO | H | 190 | −114.259 | −40.397 | −25.691 | 1.00 | 121.99 | O |
| ATOM | 5663 | N   | SER | H | 191 | −116.237 | −39.263 | −25.865 | 1.00 | 123.47 | N |
| ATOM | 5664 | CA  | SER | H | 191 | −117.101 | −40.221 | −25.153 | 1.00 | 124.15 | C |
| ATOM | 5665 | CB  | SER | H | 191 | −118.450 | −39.576 | −24.858 | 1.00 | 124.20 | C |
| ATOM | 5666 | OG  | SER | H | 191 | −118.261 | −38.280 | −24.310 | 1.00 | 124.30 | O |
| ATOM | 5667 | C   | SER | H | 191 | −117.282 | −41.493 | −26.014 | 1.00 | 124.53 | C |
| ATOM | 5668 | O   | SER | H | 191 | −117.612 | −42.568 | −25.506 | 1.00 | 124.41 | O |
| ATOM | 5669 | N   | SER | H | 192 | −117.017 | −41.336 | −27.329 | 1.00 | 126.09 | N |
| ATOM | 5670 | CA  | SER | H | 192 | −117.054 | −42.319 | −28.417 | 1.00 | 126.73 | C |
| ATOM | 5671 | CB  | SER | H | 192 | −117.251 | −41.599 | −29.757 | 1.00 | 126.76 | C |
| ATOM | 5672 | OG  | SER | H | 192 | −116.846 | −40.236 | −29.760 | 1.00 | 127.04 | O |
| ATOM | 5673 | C   | SER | H | 192 | −115.799 | −43.260 | −28.454 | 1.00 | 127.12 | C |
| ATOM | 5674 | O   | SER | H | 192 | −115.557 | −43.952 | −29.454 | 1.00 | 127.14 | O |
| ATOM | 5675 | N   | SER | H | 193 | −115.018 | −43.279 | −27.349 | 1.00 | 127.68 | N |
| ATOM | 5676 | CA  | SER | H | 193 | −113.805 | −44.088 | −27.149 | 1.00 | 127.78 | C |
| ATOM | 5677 | CB  | SER | H | 193 | −112.610 | −43.461 | −27.873 | 1.00 | 127.70 | C |
| ATOM | 5678 | OG  | SER | H | 193 | −112.345 | −42.148 | −27.408 | 1.00 | 127.41 | O |
| ATOM | 5679 | C   | SER | H | 193 | −113.513 | −44.240 | −25.639 | 1.00 | 127.76 | C |
| ATOM | 5680 | O   | SER | H | 193 | −112.439 | −44.720 | −25.261 | 1.00 | 127.76 | O |
| ATOM | 5681 | N   | LEU | H | 194 | −114.488 | −43.838 | −24.794 | 1.00 | 126.91 | N |
| ATOM | 5682 | CA  | LEU | H | 194 | −114.439 | −43.864 | −23.333 | 1.00 | 126.94 | C |
| ATOM | 5683 | CB  | LEU | H | 194 | −115.735 | −43.260 | −22.749 | 1.00 | 126.93 | C |
| ATOM | 5684 | CG  | LEU | H | 194 | −115.625 | −42.156 | −21.690 | 1.00 | 126.77 | C |
| ATOM | 5685 | CD1 | LEU | H | 194 | −114.795 | −40.978 | −22.167 | 1.00 | 126.96 | C |
| ATOM | 5686 | CD2 | LEU | H | 194 | −115.156 | −42.691 | −20.368 | 1.00 | 126.40 | C |
| ATOM | 5687 | C   | LEU | H | 194 | −114.115 | −45.241 | −22.725 | 1.00 | 127.07 | C |
| ATOM | 5688 | O   | LEU | H | 194 | −112.938 | −45.531 | −22.502 | 1.00 | 127.06 | O |
| ATOM | 5689 | N   | GLY | H | 195 | −115.138 | −46.067 | −22.483 | 1.00 | 129.35 | N |
| ATOM | 5690 | CA  | GLY | H | 195 | −114.991 | −47.405 | −21.910 | 1.00 | 129.33 | C |
| ATOM | 5691 | C   | GLY | H | 195 | −114.124 | −48.369 | −22.705 | 1.00 | 129.46 | C |
| ATOM | 5692 | O   | GLY | H | 195 | −113.689 | −49.391 | −22.166 | 1.00 | 129.50 | O |
| ATOM | 5693 | N   | THR | H | 196 | −113.858 | −48.040 | −23.993 | 1.00 | 132.04 | N |
| ATOM | 5694 | CA  | THR | H | 196 | −113.058 | −48.820 | −24.960 | 1.00 | 131.92 | C |
| ATOM | 5695 | CB  | THR | H | 196 | −113.477 | −48.498 | −26.438 | 1.00 | 132.08 | C |
| ATOM | 5696 | OG1 | THR | H | 196 | −112.751 | −47.369 | −26.949 | 1.00 | 132.25 | O |
| ATOM | 5697 | CG2 | THR | H | 196 | −114.999 | −48.281 | −26.613 | 1.00 | 132.06 | C |
| ATOM | 5698 | C   | THR | H | 196 | −111.518 | −48.784 | −24.700 | 1.00 | 131.67 | C |
| ATOM | 5699 | O   | THR | H | 196 | −110.919 | −49.843 | −24.463 | 1.00 | 131.82 | O |
| ATOM | 5700 | N   | GLN | H | 197 | −110.895 | −47.565 | −24.756 | 1.00 | 129.94 | N |
| ATOM | 5701 | CA  | GLN | H | 197 | −109.460 | −47.311 | −24.533 | 1.00 | 129.20 | C |
| ATOM | 5702 | CB  | GLN | H | 197 | −108.927 | −46.224 | −25.488 | 1.00 | 129.35 | C |
| ATOM | 5703 | CG  | GLN | H | 197 | −108.355 | −46.753 | −26.805 | 1.00 | 130.14 | C |
| ATOM | 5704 | CD  | GLN | H | 197 | −109.414 | −47.071 | −27.848 | 1.00 | 131.31 | C |
| ATOM | 5705 | OE1 | GLN | H | 197 | −109.587 | −48.228 | −28.262 | 1.00 | 131.48 | O |
| ATOM | 5706 | NE2 | GLN | H | 197 | −110.143 | −46.051 | −28.303 | 1.00 | 131.48 | N |
| ATOM | 5707 | C   | GLN | H | 197 | −109.207 | −46.879 | −23.097 | 1.00 | 128.43 | C |
| ATOM | 5708 | O   | GLN | H | 197 | −109.925 | −46.022 | −22.565 | 1.00 | 128.38 | O |
| ATOM | 5709 | N   | THR | H | 198 | −108.180 | −47.470 | −22.474 | 1.00 | 125.73 | N |
| ATOM | 5710 | CA  | THR | H | 198 | −107.796 | −47.158 | −21.094 | 1.00 | 124.61 | C |
| ATOM | 5711 | CB  | THR | H | 198 | −107.122 | −48.363 | −20.388 | 1.00 | 124.84 | C |
| ATOM | 5712 | OG1 | THR | H | 198 | −106.301 | −49.105 | −21.306 | 1.00 | 124.99 | O |
| ATOM | 5713 | CG2 | THR | H | 198 | −108.135 | −49.283 | −19.708 | 1.00 | 124.58 | C |
| ATOM | 5714 | C   | THR | H | 198 | −106.987 | −45.857 | −20.999 | 1.00 | 123.61 | C |
| ATOM | 5715 | O   | THR | H | 198 | −106.191 | −45.551 | −21.896 | 1.00 | 123.40 | O |
| ATOM | 5716 | N   | TYR | H | 199 | −107.204 | −45.094 | −19.909 | 1.00 | 120.57 | N |
| ATOM | 5717 | CA  | TYR | H | 199 | −106.506 | −43.832 | −19.665 | 1.00 | 119.19 | C |
| ATOM | 5718 | CB  | TYR | H | 199 | −107.477 | −42.643 | −19.713 | 1.00 | 119.46 | C |
| ATOM | 5719 | CG  | TYR | H | 199 | −108.092 | −42.453 | −21.085 | 1.00 | 120.39 | C |
| ATOM | 5720 | CD1 | TYR | H | 199 | −109.468 | −42.546 | −21.275 | 1.00 | 120.86 | C |
| ATOM | 5721 | CE1 | TYR | H | 199 | −110.036 | −42.391 | −22.539 | 1.00 | 120.91 | C |
| ATOM | 5722 | CZ  | TYR | H | 199 | −109.221 | −42.155 | −23.635 | 1.00 | 121.46 | C |
| ATOM | 5723 | OH  | TYR | H | 199 | −109.762 | −41.999 | −24.888 | 1.00 | 122.60 | O |
| ATOM | 5724 | CE2 | TYR | H | 199 | −107.849 | −42.073 | −23.473 | 1.00 | 121.10 | C |
| ATOM | 5725 | CD2 | TYR | H | 199 | −107.293 | −42.222 | −22.204 | 1.00 | 120.87 | C |
| ATOM | 5726 | C   | TYR | H | 199 | −105.636 | −43.860 | −18.403 | 1.00 | 117.92 | C |
| ATOM | 5727 | O   | TYR | H | 199 | −106.150 | −43.787 | −17.280 | 1.00 | 117.83 | O |
| ATOM | 5728 | N   | ILE | H | 200 | −104.307 | −44.000 | −18.607 | 1.00 | 112.18 | N |
| ATOM | 5729 | CA  | ILE | H | 200 | −103.305 | −44.070 | −17.537 | 1.00 | 110.28 | C |
| ATOM | 5730 | CB  | ILE | H | 200 | −102.635 | −45.478 | −17.422 | 1.00 | 110.33 | C |
| ATOM | 5731 | CG1 | ILE | H | 200 | −101.813 | −45.869 | −18.686 | 1.00 | 110.02 | C |
| ATOM | 5732 | CD1 | ILE | H | 200 | −100.273 | −45.895 | −18.502 | 1.00 | 109.68 | C |
| ATOM | 5733 | CG2 | ILE | H | 200 | −103.663 | −46.562 | −17.076 | 1.00 | 109.77 | C |
| ATOM | 5734 | C   | ILE | H | 200 | −102.294 | −42.915 | −17.595 | 1.00 | 108.97 | C |

TABLE 14-continued

PCSK9 and AX132 Fab complex x-ray structure

| ATOM | 5735 | O | ILE | H | 200 | −101.857 | −42.550 | −18.690 | 1.00 | 108.81 | O |
|---|---|---|---|---|---|---|---|---|---|---|---|
| ATOM | 5736 | N | CYS | H | 201 | −101.938 | −42.331 | −16.422 | 1.00 | 104.63 | N |
| ATOM | 5737 | CA | CYS | H | 201 | −100.972 | −41.234 | −16.360 | 1.00 | 102.83 | C |
| ATOM | 5738 | CB | CYS | H | 201 | −101.548 | −39.967 | −15.742 | 1.00 | 103.00 | C |
| ATOM | 5739 | SG | CYS | H | 201 | −102.047 | −40.124 | −14.011 | 1.00 | 103.57 | S |
| ATOM | 5740 | C | CYS | H | 201 | −99.664 | −41.619 | −15.735 | 1.00 | 101.34 | C |
| ATOM | 5741 | O | CYS | H | 201 | −99.620 | −42.123 | −14.623 | 1.00 | 101.22 | O |
| ATOM | 5742 | N | ASN | H | 202 | −98.597 | −41.387 | −16.472 | 1.00 | 97.30 | N |
| ATOM | 5743 | CA | ASN | H | 202 | −97.247 | −41.704 | −16.069 | 1.00 | 95.57 | C |
| ATOM | 5744 | CB | ASN | H | 202 | −96.462 | −42.241 | −17.251 | 1.00 | 95.80 | C |
| ATOM | 5745 | CG | ASN | H | 202 | −97.176 | −43.346 | −17.972 | 1.00 | 96.46 | C |
| ATOM | 5746 | OD1 | ASN | H | 202 | −98.343 | −43.214 | −18.378 | 1.00 | 96.34 | O |
| ATOM | 5747 | ND2 | ASN | H | 202 | −96.477 | −44.464 | −18.152 | 1.00 | 98.40 | N |
| ATOM | 5748 | C | ASN | H | 202 | −96.563 | −40.507 | −15.428 | 1.00 | 94.12 | C |
| ATOM | 5749 | O | ASN | H | 202 | −96.055 | −39.600 | −16.099 | 1.00 | 93.94 | O |
| ATOM | 5750 | N | VAL | H | 203 | −96.574 | −40.524 | −14.105 | 1.00 | 87.41 | N |
| ATOM | 5751 | CA | VAL | H | 203 | −95.967 | −39.525 | −13.258 | 1.00 | 85.59 | C |
| ATOM | 5752 | CB | VAL | H | 203 | −96.882 | −39.258 | −12.061 | 1.00 | 85.50 | C |
| ATOM | 5753 | CG1 | VAL | H | 203 | −96.265 | −38.251 | −11.108 | 1.00 | 85.70 | C |
| ATOM | 5754 | CG2 | VAL | H | 203 | −98.249 | −38.784 | −12.539 | 1.00 | 84.95 | C |
| ATOM | 5755 | C | VAL | H | 203 | −94.577 | −40.030 | −12.858 | 1.00 | 84.64 | C |
| ATOM | 5756 | O | VAL | H | 203 | −94.391 | −41.218 | −12.574 | 1.00 | 84.45 | O |
| ATOM | 5757 | N | ASN | H | 204 | −93.588 | −39.138 | −12.902 | 1.00 | 83.70 | N |
| ATOM | 5758 | CA | ASN | H | 204 | −92.224 | −39.481 | −12.540 | 1.00 | 82.43 | C |
| ATOM | 5759 | CB | ASN | H | 204 | −91.418 | −40.035 | −13.723 | 1.00 | 82.54 | C |
| ATOM | 5760 | CG | ASN | H | 204 | −89.922 | −40.165 | −13.482 | 1.00 | 83.30 | C |
| ATOM | 5761 | OD1 | ASN | H | 204 | −89.441 | −40.517 | −12.383 | 1.00 | 85.27 | O |
| ATOM | 5762 | ND2 | ASN | H | 204 | −89.140 | −39.879 | −14.517 | 1.00 | 83.81 | N |
| ATOM | 5763 | C | ASN | H | 204 | −91.565 | −38.291 | −11.889 | 1.00 | 81.30 | C |
| ATOM | 5764 | O | ASN | H | 204 | −91.286 | −37.288 | −12.550 | 1.00 | 81.32 | O |
| ATOM | 5765 | N | HIS | H | 205 | −91.337 | −38.414 | −10.574 | 1.00 | 77.58 | N |
| ATOM | 5766 | CA | HIS | H | 205 | −90.685 | −37.427 | −9.744 | 1.00 | 76.14 | C |
| ATOM | 5767 | CB | HIS | H | 205 | −91.454 | −37.230 | −8.442 | 1.00 | 76.06 | C |
| ATOM | 5768 | CG | HIS | H | 205 | −90.857 | −36.229 | −7.503 | 1.00 | 75.64 | C |
| ATOM | 5769 | ND1 | HIS | H | 205 | −90.239 | −36.625 | −6.336 | 1.00 | 76.03 | N |
| ATOM | 5770 | CE1 | HIS | H | 205 | −89.849 | −35.513 | −5.734 | 1.00 | 76.64 | C |
| ATOM | 5771 | NE2 | HIS | H | 205 | −90.180 | −34.432 | −6.441 | 1.00 | 77.05 | N |
| ATOM | 5772 | CD2 | HIS | H | 205 | −90.829 | −34.877 | −7.573 | 1.00 | 76.21 | C |
| ATOM | 5773 | C | HIS | H | 205 | −89.299 | −37.980 | −9.517 | 1.00 | 75.44 | C |
| ATOM | 5774 | O | HIS | H | 205 | −89.065 | −38.743 | −8.589 | 1.00 | 75.18 | O |
| ATOM | 5775 | N | LYS | H | 206 | −88.385 | −37.600 | −10.417 | 1.00 | 73.96 | N |
| ATOM | 5776 | CA | LYS | H | 206 | −86.979 | −37.986 | −10.447 | 1.00 | 73.15 | C |
| ATOM | 5777 | CB | LYS | H | 206 | −86.281 | −37.363 | −11.656 | 1.00 | 73.27 | C |
| ATOM | 5778 | CG | LYS | H | 206 | −86.794 | −37.835 | −13.003 | 1.00 | 74.94 | C |
| ATOM | 5779 | CD | LYS | H | 206 | −87.115 | −36.632 | −13.910 | 1.00 | 78.37 | C |
| ATOM | 5780 | CE | LYS | H | 206 | −87.147 | −36.984 | −15.395 | 1.00 | 79.68 | C |
| ATOM | 5781 | NZ | LYS | H | 206 | −85.794 | −37.337 | −15.949 | 1.00 | 80.06 | N |
| ATOM | 5782 | C | LYS | H | 206 | −86.209 | −37.648 | −9.163 | 1.00 | 72.47 | C |
| ATOM | 5783 | O | LYS | H | 206 | −85.353 | −38.461 | −8.802 | 1.00 | 72.50 | O |
| ATOM | 5784 | N | PRO | H | 207 | −86.462 | −36.491 | −8.455 | 1.00 | 70.56 | N |
| ATOM | 5785 | CA | PRO | H | 207 | −85.697 | −36.185 | −7.225 | 1.00 | 70.13 | C |
| ATOM | 5786 | CB | PRO | H | 207 | −86.322 | −34.879 | −6.743 | 1.00 | 69.80 | C |
| ATOM | 5787 | CG | PRO | H | 207 | −86.924 | −34.278 | −7.905 | 1.00 | 70.09 | C |
| ATOM | 5788 | CD | PRO | H | 207 | −87.425 | −35.399 | −8.735 | 1.00 | 70.58 | C |
| ATOM | 5789 | C | PRO | H | 207 | −85.773 | −37.227 | −6.108 | 1.00 | 70.07 | C |
| ATOM | 5790 | O | PRO | H | 207 | −84.820 | −37.356 | −5.335 | 1.00 | 69.87 | O |
| ATOM | 5791 | N | SER | H | 208 | −86.916 | −37.935 | −6.018 | 1.00 | 68.21 | N |
| ATOM | 5792 | CA | SER | H | 208 | −87.194 | −38.973 | −5.046 | 1.00 | 67.94 | C |
| ATOM | 5793 | CB | SER | H | 208 | −88.539 | −38.716 | −4.385 | 1.00 | 67.92 | C |
| ATOM | 5794 | OG | SER | H | 208 | −89.602 | −38.909 | −5.302 | 1.00 | 67.48 | O |
| ATOM | 5795 | C | SER | H | 208 | −87.246 | −40.314 | −5.716 | 1.00 | 68.07 | C |
| ATOM | 5796 | O | SER | H | 208 | −87.561 | −41.284 | −5.045 | 1.00 | 68.37 | O |
| ATOM | 5797 | N | ASN | H | 209 | −86.987 | −40.383 | −7.039 | 1.00 | 68.59 | N |
| ATOM | 5798 | CA | ASN | H | 209 | −87.007 | −41.608 | −7.863 | 1.00 | 69.03 | C |
| ATOM | 5799 | CB | ASN | H | 209 | −85.849 | −42.531 | −7.490 | 1.00 | 68.43 | C |
| ATOM | 5800 | CG | ASN | H | 209 | −85.528 | −43.582 | −8.510 | 1.00 | 67.30 | C |
| ATOM | 5801 | OD1 | ASN | H | 209 | −84.818 | −44.533 | −8.219 | 1.00 | 66.47 | O |
| ATOM | 5802 | ND2 | ASN | H | 209 | −86.032 | −43.453 | −9.735 | 1.00 | 66.92 | N |
| ATOM | 5803 | C | ASN | H | 209 | −88.377 | −42.353 | −7.902 | 1.00 | 69.99 | C |
| ATOM | 5804 | O | ASN | H | 209 | −88.433 | −43.554 | −8.197 | 1.00 | 70.02 | O |
| ATOM | 5805 | N | THR | H | 210 | −89.471 | −41.613 | −7.631 | 1.00 | 72.45 | N |
| ATOM | 5806 | CA | THR | H | 210 | −90.855 | −42.086 | −7.590 | 1.00 | 73.73 | C |
| ATOM | 5807 | CB | THR | H | 210 | −91.646 | −41.269 | −6.551 | 1.00 | 73.38 | C |
| ATOM | 5808 | OG1 | THR | H | 210 | −91.020 | −41.436 | −5.287 | 1.00 | 73.71 | O |
| ATOM | 5809 | CG2 | THR | H | 210 | −93.102 | −41.676 | −6.445 | 1.00 | 73.49 | C |
| ATOM | 5810 | C | THR | H | 210 | −91.535 | −42.071 | −8.946 | 1.00 | 74.90 | C |
| ATOM | 5811 | O | THR | H | 210 | −92.022 | −41.024 | −9.360 | 1.00 | 75.20 | O |
| ATOM | 5812 | N | LYS | H | 211 | −91.585 | −43.231 | −9.620 | 1.00 | 77.05 | N |

TABLE 14-continued

PCSK9 and AX132 Fab complex x-ray structure

| ATOM | 5813 | CA | LYS | H | 211 | −92.263 | −43.437 | −10.906 | 1.00 | 78.60 | C |
|---|---|---|---|---|---|---|---|---|---|---|---|
| ATOM | 5814 | CB | LYS | H | 211 | −91.466 | −44.407 | −11.799 | 1.00 | 78.20 | C |
| ATOM | 5815 | CG | LYS | H | 211 | −90.121 | −43.868 | −12.276 | 1.00 | 78.47 | C |
| ATOM | 5816 | CD | LYS | H | 211 | −89.225 | −44.961 | −12.861 | 1.00 | 79.14 | C |
| ATOM | 5817 | CE | LYS | H | 211 | −87.899 | −45.180 | −12.118 | 1.00 | 79.84 | C |
| ATOM | 5818 | NZ | LYS | H | 211 | −88.045 | −45.808 | −10.756 | 1.00 | 79.07 | N |
| ATOM | 5819 | C | LYS | H | 211 | −93.626 | −44.036 | −10.514 | 1.00 | 79.91 | C |
| ATOM | 5820 | O | LYS | H | 211 | −93.659 | −45.045 | −9.812 | 1.00 | 80.45 | O |
| ATOM | 5821 | N | VAL | H | 212 | −94.737 | −43.412 | −10.906 | 1.00 | 82.17 | N |
| ATOM | 5822 | CA | VAL | H | 212 | −96.090 | −43.875 | −10.541 | 1.00 | 83.80 | C |
| ATOM | 5823 | CB | VAL | H | 212 | −96.641 | −42.980 | −9.387 | 1.00 | 83.43 | C |
| ATOM | 5824 | CG1 | VAL | H | 212 | −98.161 | −42.945 | −9.333 | 1.00 | 82.71 | C |
| ATOM | 5825 | CG2 | VAL | H | 212 | −96.056 | −43.399 | −8.048 | 1.00 | 83.07 | C |
| ATOM | 5826 | C | VAL | H | 212 | −97.043 | −43.973 | −11.768 | 1.00 | 85.51 | C |
| ATOM | 5827 | O | VAL | H | 212 | −96.916 | −43.183 | −12.705 | 1.00 | 85.62 | O |
| ATOM | 5828 | N | ASP | H | 213 | −97.978 | −44.954 | −11.767 | 1.00 | 91.75 | N |
| ATOM | 5829 | CA | ASP | H | 213 | −98.956 | −45.139 | −12.847 | 1.00 | 93.82 | C |
| ATOM | 5830 | CB | ASP | H | 213 | −98.589 | −46.341 | −13.728 | 1.00 | 93.63 | C |
| ATOM | 5831 | CG | ASP | H | 213 | −97.548 | −46.026 | −14.798 | 1.00 | 94.16 | C |
| ATOM | 5832 | OD1 | ASP | H | 213 | −96.407 | −45.655 | −14.433 | 1.00 | 93.97 | O |
| ATOM | 5833 | OD2 | ASP | H | 213 | −97.872 | −46.152 | −15.999 | 1.00 | 95.62 | O |
| ATOM | 5834 | C | ASP | H | 213 | −100.383 | −45.216 | −12.285 | 1.00 | 95.40 | C |
| ATOM | 5835 | O | ASP | H | 213 | −100.652 | −46.061 | −11.428 | 1.00 | 95.72 | O |
| ATOM | 5836 | N | LYS | H | 214 | −101.282 | −44.302 | −12.722 | 1.00 | 100.62 | N |
| ATOM | 5837 | CA | LYS | H | 214 | −102.669 | −44.262 | −12.237 | 1.00 | 102.69 | C |
| ATOM | 5838 | CB | LYS | H | 214 | −102.927 | −43.032 | −11.344 | 1.00 | 102.71 | C |
| ATOM | 5839 | CG | LYS | H | 214 | −103.874 | −43.291 | −10.173 | 1.00 | 103.55 | C |
| ATOM | 5840 | CD | LYS | H | 214 | −103.192 | −44.189 | −9.125 | 1.00 | 105.57 | C |
| ATOM | 5841 | CE | LYS | H | 214 | −104.059 | −44.491 | −7.930 | 1.00 | 106.85 | C |
| ATOM | 5842 | NZ | LYS | H | 214 | −103.355 | −45.388 | −6.978 | 1.00 | 107.17 | N |
| ATOM | 5843 | C | LYS | H | 214 | −103.738 | −44.391 | −13.331 | 1.00 | 104.02 | C |
| ATOM | 5844 | O | LYS | H | 214 | −103.780 | −43.579 | −14.257 | 1.00 | 104.21 | O |
| ATOM | 5845 | N | LYS | H | 215 | −104.602 | −45.424 | −13.210 | 1.00 | 107.40 | N |
| ATOM | 5846 | CA | LYS | H | 215 | −105.688 | −45.687 | −14.146 | 1.00 | 108.78 | C |
| ATOM | 5847 | CB | LYS | H | 215 | −106.100 | −47.176 | −14.114 | 1.00 | 108.88 | C |
| ATOM | 5848 | CG | LYS | H | 215 | −107.148 | −47.597 | −15.157 | 1.00 | 109.42 | C |
| ATOM | 5849 | CD | LYS | H | 215 | −107.634 | −49.047 | −14.925 | 1.00 | 109.90 | C |
| ATOM | 5850 | CE | LYS | H | 215 | −108.585 | −49.581 | −15.984 | 1.00 | 109.81 | C |
| ATOM | 5851 | NZ | LYS | H | 215 | −109.153 | −50.911 | −15.614 | 1.00 | 109.19 | N |
| ATOM | 5852 | C | LYS | H | 215 | −106.856 | −44.787 | −13.794 | 1.00 | 109.66 | C |
| ATOM | 5853 | O | LYS | H | 215 | −107.389 | −44.852 | −12.682 | 1.00 | 109.51 | O |
| ATOM | 5854 | N | VAL | H | 216 | −107.230 | −43.924 | −14.746 | 1.00 | 113.78 | N |
| ATOM | 5855 | CA | VAL | H | 216 | −108.363 | −43.014 | −14.588 | 1.00 | 115.02 | C |
| ATOM | 5856 | CB | VAL | H | 216 | −108.107 | −41.543 | −15.014 | 1.00 | 114.92 | C |
| ATOM | 5857 | CG1 | VAL | H | 216 | −109.154 | −40.613 | −14.400 | 1.00 | 115.00 | C |
| ATOM | 5858 | CG2 | VAL | H | 216 | −106.699 | −41.087 | −14.631 | 1.00 | 115.30 | C |
| ATOM | 5859 | C | VAL | H | 216 | −109.536 | −43.669 | −15.330 | 1.00 | 115.97 | C |
| ATOM | 5860 | O | VAL | H | 216 | −109.489 | −43.867 | −16.557 | 1.00 | 116.09 | O |
| ATOM | 5861 | N | GLU | H | 217 | −110.555 | −44.058 | −14.540 | 1.00 | 117.62 | N |
| ATOM | 5862 | CA | GLU | H | 217 | −111.782 | −44.729 | −14.961 | 1.00 | 118.53 | C |
| ATOM | 5863 | CB | GLU | H | 217 | −111.995 | −45.986 | −14.109 | 1.00 | 118.74 | C |
| ATOM | 5864 | CG | GLU | H | 217 | −111.067 | −47.138 | −14.433 | 1.00 | 119.59 | C |
| ATOM | 5865 | CD | GLU | H | 217 | −111.166 | −48.270 | −13.432 | 1.00 | 120.38 | C |
| ATOM | 5866 | OE1 | GLU | H | 217 | −111.208 | −49.441 | −13.875 | 1.00 | 121.05 | O |
| ATOM | 5867 | OE2 | GLU | H | 217 | −111.207 | −47.989 | −12.209 | 1.00 | 119.83 | O |
| ATOM | 5868 | C | GLU | H | 217 | −112.953 | −43.808 | −14.703 | 1.00 | 118.88 | C |
| ATOM | 5869 | O | GLU | H | 217 | −112.821 | −42.934 | −13.834 | 1.00 | 118.97 | O |
| ATOM | 5870 | N | PRO | H | 218 | −114.122 | −44.009 | −15.386 | 1.00 | 116.71 | N |
| ATOM | 5871 | CA | PRO | H | 218 | −115.287 | −43.133 | −15.123 | 1.00 | 116.74 | C |
| ATOM | 5872 | CB | PRO | H | 218 | −116.291 | −43.519 | −16.221 | 1.00 | 116.73 | C |
| ATOM | 5873 | CG | PRO | H | 218 | −115.502 | −44.323 | −17.225 | 1.00 | 116.66 | C |
| ATOM | 5874 | CD | PRO | H | 218 | −114.436 | −45.003 | −16.436 | 1.00 | 116.64 | C |
| ATOM | 5875 | C | PRO | H | 218 | −115.854 | −43.290 | −13.704 | 1.00 | 116.70 | C |
| ATOM | 5876 | O | PRO | H | 218 | −115.904 | −44.408 | −13.181 | 1.00 | 116.58 | O |
| ATOM | 5877 | N | LYS | H | 219 | −116.237 | −42.143 | −13.088 | 1.00 | 113.24 | N |
| ATOM | 5878 | CA | LYS | H | 219 | −116.788 | −41.948 | −11.735 | 1.00 | 113.26 | C |
| ATOM | 5879 | CB | LYS | H | 219 | −117.941 | −40.927 | −11.762 | 1.00 | 113.15 | C |
| ATOM | 5880 | C | LYS | H | 219 | −117.177 | −43.217 | −10.958 | 1.00 | 113.17 | C |
| ATOM | 5881 | O | LYS | H | 219 | −116.309 | −43.911 | −10.428 | 1.00 | 113.03 | O |
| TER | 5882 | | LYS | H | 219 | | | | | | |
| ATOM | 5883 | N | GLU | L | 1 | −83.598 | 9.104 | −8.215 | 1.00 | 89.00 | N |
| ATOM | 5884 | CA | GLU | L | 1 | −83.105 | 8.099 | −9.150 | 1.00 | 88.92 | C |
| ATOM | 5885 | CB | GLU | L | 1 | −82.880 | 6.751 | −8.461 | 1.00 | 89.36 | C |
| ATOM | 5886 | CG | GLU | L | 1 | −84.070 | 6.181 | −7.715 | 1.00 | 91.53 | C |
| ATOM | 5887 | CD | GLU | L | 1 | −83.726 | 4.828 | −7.121 | 1.00 | 95.85 | C |
| ATOM | 5888 | OE1 | GLU | L | 1 | −84.033 | 3.797 | −7.766 | 1.00 | 97.73 | O |
| ATOM | 5889 | OE2 | GLU | L | 1 | −83.125 | 4.799 | −6.020 | 1.00 | 97.18 | O |
| ATOM | 5890 | C | GLU | L | 1 | −84.004 | 7.949 | −10.356 | 1.00 | 88.12 | C |

TABLE 14-continued

PCSK9 and AX132 Fab complex x-ray structure

| ATOM | 5891 | O   | GLU | L | 1  | −85.216  | 8.101  | −10.217 | 1.00 | 88.16 | O |
|------|------|-----|-----|---|----|----------|--------|---------|------|-------|---|
| ATOM | 5892 | N   | ILE | L | 2  | −83.411  | 7.657  | −11.540 | 1.00 | 80.34 | N |
| ATOM | 5893 | CA  | ILE | L | 2  | −84.157  | 7.483  | −12.793 | 1.00 | 79.70 | C |
| ATOM | 5894 | CB  | ILE | L | 2  | −83.280  | 7.451  | −14.089 | 1.00 | 79.60 | C |
| ATOM | 5895 | CG1 | ILE | L | 2  | −82.210  | 8.557  | −14.067 | 1.00 | 79.33 | C |
| ATOM | 5896 | CD1 | ILE | L | 2  | −81.071  | 8.384  | −15.048 | 1.00 | 79.74 | C |
| ATOM | 5897 | CG2 | ILE | L | 2  | −84.147  | 7.542  | −15.369 | 1.00 | 78.97 | C |
| ATOM | 5898 | C   | ILE | L | 2  | −85.116  | 6.292  | −12.684 | 1.00 | 79.51 | C |
| ATOM | 5899 | O   | ILE | L | 2  | −84.774  | 5.260  | −12.087 | 1.00 | 79.69 | O |
| ATOM | 5900 | N   | VAL | L | 3  | −86.336  | 6.475  | −13.222 | 1.00 | 75.05 | N |
| ATOM | 5901 | CA  | VAL | L | 3  | −87.387  | 5.480  | −13.213 | 1.00 | 74.49 | C |
| ATOM | 5902 | CB  | VAL | L | 3  | −88.466  | 5.847  | −12.180 | 1.00 | 74.17 | C |
| ATOM | 5903 | CG1 | VAL | L | 3  | −89.738  | 5.038  | −12.386 | 1.00 | 73.26 | C |
| ATOM | 5904 | CG2 | VAL | L | 3  | −87.938  | 5.678  | −10.762 | 1.00 | 73.55 | C |
| ATOM | 5905 | C   | VAL | L | 3  | −87.930  | 5.343  | −14.619 | 1.00 | 74.81 | C |
| ATOM | 5906 | O   | VAL | L | 3  | −88.324  | 6.345  | −15.213 | 1.00 | 75.07 | O |
| ATOM | 5907 | N   | LEU | L | 4  | −87.943  | 4.102  | −15.150 | 1.00 | 76.54 | N |
| ATOM | 5908 | CA  | LEU | L | 4  | −88.444  | 3.802  | −16.494 | 1.00 | 76.82 | C |
| ATOM | 5909 | CB  | LEU | L | 4  | −87.469  | 2.927  | −17.283 | 1.00 | 76.43 | C |
| ATOM | 5910 | CG  | LEU | L | 4  | −86.023  | 3.376  | −17.305 | 1.00 | 75.61 | C |
| ATOM | 5911 | CD1 | LEU | L | 4  | −85.152  | 2.333  | −17.948 | 1.00 | 75.85 | C |
| ATOM | 5912 | CD2 | LEU | L | 4  | −85.867  | 4.665  | −18.035 | 1.00 | 75.72 | C |
| ATOM | 5913 | C   | LEU | L | 4  | −89.832  | 3.173  | −16.430 | 1.00 | 77.41 | C |
| ATOM | 5914 | O   | LEU | L | 4  | −90.056  | 2.200  | −15.694 | 1.00 | 77.43 | O |
| ATOM | 5915 | N   | THR | L | 5  | −90.771  | 3.759  | −17.190 | 1.00 | 81.19 | N |
| ATOM | 5916 | CA  | THR | L | 5  | −92.164  | 3.318  | −17.228 | 1.00 | 81.79 | C |
| ATOM | 5917 | CB  | THR | L | 5  | −93.081  | 4.395  | −16.653 | 1.00 | 81.50 | C |
| ATOM | 5918 | OG1 | THR | L | 5  | −92.466  | 4.961  | −15.492 | 1.00 | 81.23 | O |
| ATOM | 5919 | CG2 | THR | L | 5  | −94.456  | 3.864  | −16.325 | 1.00 | 81.01 | C |
| ATOM | 5920 | C   | THR | L | 5  | −92.589  | 2.850  | −18.609 | 1.00 | 82.60 | C |
| ATOM | 5921 | O   | THR | L | 5  | −92.693  | 3.655  | −19.545 | 1.00 | 82.60 | O |
| ATOM | 5922 | N   | GLN | L | 6  | −92.844  | 1.542  | −18.718 | 1.00 | 86.45 | N |
| ATOM | 5923 | CA  | GLN | L | 6  | −93.272  | 0.915  | −19.961 | 1.00 | 87.55 | C |
| ATOM | 5924 | CB  | GLN | L | 6  | −92.783  | −0.532 | −20.062 | 1.00 | 87.69 | C |
| ATOM | 5925 | CG  | GLN | L | 6  | −91.335  | −0.717 | −19.614 | 1.00 | 88.23 | C |
| ATOM | 5926 | CD  | GLN | L | 6  | −90.571  | −1.688 | −20.464 | 1.00 | 88.69 | C |
| ATOM | 5927 | OE1 | GLN | L | 6  | −90.813  | −1.842 | −21.674 | 1.00 | 89.57 | O |
| ATOM | 5928 | NE2 | GLN | L | 6  | −89.610  | −2.339 | −19.849 | 1.00 | 88.76 | N |
| ATOM | 5929 | C   | GLN | L | 6  | −94.794  | 1.027  | −20.150 | 1.00 | 88.17 | C |
| ATOM | 5930 | O   | GLN | L | 6  | −95.549  | 0.843  | −19.186 | 1.00 | 88.08 | O |
| ATOM | 5931 | N   | SER | L | 7  | −95.210  | 1.356  | −21.406 | 1.00 | 92.93 | N |
| ATOM | 5932 | CA  | SER | L | 7  | −96.564  | 1.589  | −21.944 | 1.00 | 93.33 | C |
| ATOM | 5933 | CB  | SER | L | 7  | −96.506  | 1.734  | −23.455 | 1.00 | 93.66 | C |
| ATOM | 5934 | OG  | SER | L | 7  | −95.744  | 0.662  | −24.002 | 1.00 | 94.08 | O |
| ATOM | 5935 | C   | SER | L | 7  | −97.621  | 0.545  | −21.540 | 1.00 | 93.56 | C |
| ATOM | 5936 | O   | SER | L | 7  | −98.173  | 0.714  | −20.438 | 1.00 | 94.05 | O |
| ATOM | 5937 | N   | PRO | L | 8  | −98.002  | −0.509 | −22.328 | 1.00 | 89.31 | N |
| ATOM | 5938 | CA  | PRO | L | 8  | −98.988  | −1.432 | −21.786 | 1.00 | 89.18 | C |
| ATOM | 5939 | CB  | PRO | L | 8  | −99.665  | −1.986 | −23.045 | 1.00 | 88.74 | C |
| ATOM | 5940 | CG  | PRO | L | 8  | −98.757  | −1.659 | −24.189 | 1.00 | 88.87 | C |
| ATOM | 5941 | CD  | PRO | L | 8  | −97.560  | −0.968 | −23.664 | 1.00 | 89.25 | C |
| ATOM | 5942 | C   | PRO | L | 8  | −98.220  | −2.509 | −21.001 | 1.00 | 89.49 | C |
| ATOM | 5943 | O   | PRO | L | 8  | −97.120  | −2.908 | −21.409 | 1.00 | 90.02 | O |
| ATOM | 5944 | N   | ALA | L | 9  | −98.759  | −2.985 | −19.873 | 1.00 | 88.96 | N |
| ATOM | 5945 | CA  | ALA | L | 9  | −98.053  | −4.053 | −19.169 | 1.00 | 88.68 | C |
| ATOM | 5946 | CB  | ALA | L | 9  | −98.765  | −4.391 | −17.872 | 1.00 | 88.39 | C |
| ATOM | 5947 | C   | ALA | L | 9  | −98.084  | −5.251 | −20.134 | 1.00 | 88.68 | C |
| ATOM | 5948 | O   | ALA | L | 9  | −97.112  | −6.002 | −20.221 | 1.00 | 89.05 | O |
| ATOM | 5949 | N   | THR | L | 10 | −99.207  | −5.369 | −20.898 | 1.00 | 87.79 | N |
| ATOM | 5950 | CA  | THR | L | 10 | −99.482  | −6.385 | −21.913 | 1.00 | 87.63 | C |
| ATOM | 5951 | CB  | THR | L | 10 | −100.425 | −7.495 | −21.408 | 1.00 | 87.57 | C |
| ATOM | 5952 | OG1 | THR | L | 10 | −100.164 | −7.809 | −20.032 | 1.00 | 87.90 | O |
| ATOM | 5953 | CG2 | THR | L | 10 | −100.347 | −8.760 | −22.273 | 1.00 | 87.29 | C |
| ATOM | 5954 | C   | THR | L | 10 | −100.075 | −5.713 | −23.137 | 1.00 | 87.50 | C |
| ATOM | 5955 | O   | THR | L | 10 | −100.917 | −4.820 | −23.010 | 1.00 | 87.67 | O |
| ATOM | 5956 | N   | LEU | L | 11 | −99.629  | −6.162 | −24.311 | 1.00 | 85.14 | N |
| ATOM | 5957 | CA  | LEU | L | 11 | −100.052 | −5.694 | −25.610 | 1.00 | 85.16 | C |
| ATOM | 5958 | CB  | LEU | L | 11 | −98.939  | −4.864 | −26.272 | 1.00 | 84.97 | C |
| ATOM | 5959 | CG  | LEU | L | 11 | −99.099  | −4.581 | −27.782 | 1.00 | 85.13 | C |
| ATOM | 5960 | CD1 | LEU | L | 11 | −100.036 | −3.397 | −28.052 | 1.00 | 84.72 | C |
| ATOM | 5961 | CD2 | LEU | L | 11 | −97.749  | −4.410 | −28.473 | 1.00 | 84.38 | C |
| ATOM | 5962 | C   | LEU | L | 11 | −100.430 | −6.921 | −26.449 | 1.00 | 85.59 | C |
| ATOM | 5963 | O   | LEU | L | 11 | −99.553  | −7.668 | −26.915 | 1.00 | 85.35 | O |
| ATOM | 5964 | N   | SER | L | 12 | −101.755 | −7.126 | −26.629 | 1.00 | 87.35 | N |
| ATOM | 5965 | CA  | SER | L | 12 | −102.331 | −8.240 | −27.392 | 1.00 | 87.63 | C |
| ATOM | 5966 | CB  | SER | L | 12 | −103.635 | −8.699 | −26.760 | 1.00 | 87.50 | C |
| ATOM | 5967 | OG  | SER | L | 12 | −103.508 | −8.769 | −25.348 | 1.00 | 87.38 | O |
| ATOM | 5968 | C   | SER | L | 12 | −102.526 | −7.861 | −28.853 | 1.00 | 88.07 | C |

TABLE 14-continued

PCSK9 and AX132 Fab complex x-ray structure

| ATOM | 5969 | O   | SER | L | 12 | −103.264 | −6.922  | −29.161 | 1.00 | 87.95  | O |
|------|------|-----|-----|---|----|----------|---------|---------|------|--------|---|
| ATOM | 5970 | N   | LEU | L | 13 | −101.813 | −8.565  | −29.745 | 1.00 | 90.88  | N |
| ATOM | 5971 | CA  | LEU | L | 13 | −101.831 | −8.335  | −31.192 | 1.00 | 91.71  | C |
| ATOM | 5972 | CB  | LEU | L | 13 | −100.701 | −7.378  | −31.623 | 1.00 | 91.67  | C |
| ATOM | 5973 | CG  | LEU | L | 13 | −100.791 | −5.903  | −31.217 | 1.00 | 91.61  | C |
| ATOM | 5974 | CD1 | LEU | L | 13 | −102.052 | −5.231  | −31.759 | 1.00 | 91.18  | C |
| ATOM | 5975 | CD2 | LEU | L | 13 | −99.596  | −5.163  | −31.719 | 1.00 | 91.99  | C |
| ATOM | 5976 | C   | LEU | L | 13 | −101.728 | −9.624  | −31.998 | 1.00 | 92.38  | C |
| ATOM | 5977 | O   | LEU | L | 13 | −101.018 | −10.548 | −31.621 | 1.00 | 92.53  | O |
| ATOM | 5978 | N   | SER | L | 14 | −102.430 | −9.669  | −33.122 | 1.00 | 94.83  | N |
| ATOM | 5979 | CA  | SER | L | 14 | −102.440 | −10.820 | −34.029 | 1.00 | 95.63  | C |
| ATOM | 5980 | CB  | SER | L | 14 | −103.631 | −10.708 | −34.985 | 1.00 | 95.73  | C |
| ATOM | 5981 | OG  | SER | L | 14 | −104.781 | −10.186 | −34.330 | 1.00 | 96.70  | O |
| ATOM | 5982 | C   | SER | L | 14 | −101.129 | −10.844 | −34.826 | 1.00 | 95.79  | C |
| ATOM | 5983 | O   | SER | L | 14 | −100.555 | −9.778  | −35.019 | 1.00 | 95.83  | O |
| ATOM | 5984 | N   | PRO | L | 15 | −100.625 | −11.998 | −35.321 | 1.00 | 95.86  | N |
| ATOM | 5985 | CA  | PRO | L | 15 | −99.367  | −11.968 | −36.100 | 1.00 | 96.06  | C |
| ATOM | 5986 | CB  | PRO | L | 15 | −99.108  | −13.443 | −36.424 | 1.00 | 95.91  | C |
| ATOM | 5987 | CG  | PRO | L | 15 | −99.911  | −14.201 | −35.411 | 1.00 | 95.88  | C |
| ATOM | 5988 | CD  | PRO | L | 15 | −101.133 | −13.376 | −35.187 | 1.00 | 95.86  | C |
| ATOM | 5989 | C   | PRO | L | 15 | −99.449  | −11.099 | −37.359 | 1.00 | 96.26  | C |
| ATOM | 5990 | O   | PRO | L | 15 | −100.544 | −10.705 | −37.754 | 1.00 | 96.51  | O |
| ATOM | 5991 | N   | GLY | L | 16 | −98.295  | −10.773 | −37.943 | 1.00 | 98.11  | N |
| ATOM | 5992 | CA  | GLY | L | 16 | −98.181  | −9.941  | −39.143 | 1.00 | 98.33  | C |
| ATOM | 5993 | C   | GLY | L | 16 | −98.383  | −8.449  | −38.937 | 1.00 | 98.54  | C |
| ATOM | 5994 | O   | GLY | L | 16 | −97.993  | −7.651  | −39.799 | 1.00 | 98.67  | O |
| ATOM | 5995 | N   | GLU | L | 17 | −98.983  | −8.062  | −37.787 | 1.00 | 99.90  | N |
| ATOM | 5996 | CA  | GLU | L | 17 | −99.288  | −6.683  | −37.389 | 1.00 | 100.20 | C |
| ATOM | 5997 | CB  | GLU | L | 17 | −100.384 | −6.688  | −36.311 | 1.00 | 100.28 | C |
| ATOM | 5998 | CG  | GLU | L | 17 | −101.685 | −7.324  | −36.768 | 1.00 | 101.97 | C |
| ATOM | 5999 | CD  | GLU | L | 17 | −102.932 | −6.814  | −36.069 | 1.00 | 104.11 | C |
| ATOM | 6000 | OE1 | GLU | L | 17 | −103.215 | −7.262  | −34.930 | 1.00 | 104.25 | O |
| ATOM | 6001 | OE2 | GLU | L | 17 | −103.634 | −5.966  | −36.673 | 1.00 | 105.22 | O |
| ATOM | 6002 | C   | GLU | L | 17 | −98.093  | −5.813  | −36.901 | 1.00 | 100.05 | C |
| ATOM | 6003 | O   | GLU | L | 17 | −97.050  | −6.343  | −36.489 | 1.00 | 100.22 | O |
| ATOM | 6004 | N   | ARG | L | 18 | −98.274  | −4.462  | −36.940 | 1.00 | 98.61  | N |
| ATOM | 6005 | CA  | ARG | L | 18 | −97.294  | −3.490  | −36.448 | 1.00 | 97.96  | C |
| ATOM | 6006 | CB  | ARG | L | 18 | −97.411  | −2.125  | −37.150 | 1.00 | 98.00  | C |
| ATOM | 6007 | C   | ARG | L | 18 | −97.512  | −3.364  | −34.938 | 1.00 | 97.49  | C |
| ATOM | 6008 | O   | ARG | L | 18 | −98.662  | −3.277  | −34.478 | 1.00 | 97.17  | O |
| ATOM | 6009 | N   | ALA | L | 19 | −96.403  | −3.387  | −34.168 | 1.00 | 96.77  | N |
| ATOM | 6010 | CA  | ALA | L | 19 | −96.424  | −3.329  | −32.702 | 1.00 | 96.23  | C |
| ATOM | 6011 | CB  | ALA | L | 19 | −95.987  | −4.681  | −32.146 | 1.00 | 96.39  | C |
| ATOM | 6012 | C   | ALA | L | 19 | −95.547  | −2.230  | −32.103 | 1.00 | 95.76  | C |
| ATOM | 6013 | O   | ALA | L | 19 | −94.357  | −2.166  | −32.434 | 1.00 | 95.97  | O |
| ATOM | 6014 | N   | THR | L | 20 | −96.110  | −1.376  | −31.214 | 1.00 | 91.20  | N |
| ATOM | 6015 | CA  | THR | L | 20 | −95.293  | −0.340  | −30.572 | 1.00 | 90.40  | C |
| ATOM | 6016 | CB  | THR | L | 20 | −95.325  | 1.056   | −31.230 | 1.00 | 90.54  | C |
| ATOM | 6017 | OG1 | THR | L | 20 | −96.588  | 1.682   | −31.029 | 1.00 | 90.68  | O |
| ATOM | 6018 | CG2 | THR | L | 20 | −94.868  | 1.074   | −32.696 | 1.00 | 89.99  | C |
| ATOM | 6019 | C   | THR | L | 20 | −95.401  | −0.299  | −29.058 | 1.00 | 89.89  | C |
| ATOM | 6020 | O   | THR | L | 20 | −96.507  | −0.211  | −28.515 | 1.00 | 89.67  | O |
| ATOM | 6021 | N   | ILE | L | 21 | −94.216  | −0.348  | −28.391 | 1.00 | 89.06  | N |
| ATOM | 6022 | CA  | ILE | L | 21 | −93.995  | −0.313  | −26.942 | 1.00 | 88.32  | C |
| ATOM | 6023 | CB  | ILE | L | 21 | −93.116  | −1.528  | −26.499 | 1.00 | 88.77  | C |
| ATOM | 6024 | CG1 | ILE | L | 21 | −93.768  | −2.851  | −26.920 | 1.00 | 88.67  | C |
| ATOM | 6025 | CD1 | ILE | L | 21 | −92.833  | −3.954  | −27.076 | 1.00 | 89.74  | C |
| ATOM | 6026 | CG2 | ILE | L | 21 | −92.802  | −1.523  | −24.965 | 1.00 | 89.13  | C |
| ATOM | 6027 | C   | ILE | L | 21 | −93.336  | 1.017   | −26.593 | 1.00 | 87.50  | C |
| ATOM | 6028 | O   | ILE | L | 21 | −92.492  | 1.502   | −27.343 | 1.00 | 87.42  | O |
| ATOM | 6029 | N   | THR | L | 22 | −93.711  | 1.580   | −25.442 | 1.00 | 86.61  | N |
| ATOM | 6030 | CA  | THR | L | 22 | −93.228  | 2.852   | −24.892 | 1.00 | 85.95  | C |
| ATOM | 6031 | CB  | THR | L | 22 | −94.429  | 3.829   | −24.756 | 1.00 | 85.95  | C |
| ATOM | 6032 | OG1 | THR | L | 22 | −94.598  | 4.524   | −25.986 | 1.00 | 85.76  | O |
| ATOM | 6033 | CG2 | THR | L | 22 | −94.339  | 4.803   | −23.539 | 1.00 | 85.55  | C |
| ATOM | 6034 | C   | THR | L | 22 | −92.460  | 2.679   | −23.572 | 1.00 | 85.64  | C |
| ATOM | 6035 | O   | THR | L | 22 | −92.794  | 1.806   | −22.769 | 1.00 | 85.64  | O |
| ATOM | 6036 | N   | CYS | L | 23 | −91.430  | 3.531   | −23.376 | 1.00 | 84.41  | N |
| ATOM | 6037 | CA  | CYS | L | 23 | −90.581  | 3.635   | −22.193 | 1.00 | 83.87  | C |
| ATOM | 6038 | CB  | CYS | L | 23 | −89.210  | 2.993   | −22.411 | 1.00 | 83.55  | C |
| ATOM | 6039 | SG  | CYS | L | 23 | −88.246  | 2.756   | −20.884 | 1.00 | 83.84  | S |
| ATOM | 6040 | C   | CYS | L | 23 | −90.476  | 5.130   | −21.926 | 1.00 | 83.58  | C |
| ATOM | 6041 | O   | CYS | L | 23 | −90.122  | 5.901   | −22.825 | 1.00 | 83.61  | O |
| ATOM | 6042 | N   | ARG | L | 24 | −90.854  | 5.547   | −20.722 | 1.00 | 86.10  | N |
| ATOM | 6043 | CA  | ARG | L | 24 | −90.808  | 6.952   | −20.364 | 1.00 | 85.89  | C |
| ATOM | 6044 | CB  | ARG | L | 24 | −92.213  | 7.501   | −20.108 | 1.00 | 86.58  | C |
| ATOM | 6045 | CG  | ARG | L | 24 | −92.329  | 9.003   | −20.355 | 1.00 | 89.45  | C |
| ATOM | 6046 | CD  | ARG | L | 24 | −93.738  | 9.387   | −20.754 | 1.00 | 93.99  | C |

TABLE 14-continued

PCSK9 and AX132 Fab complex x-ray structure

| ATOM | 6047 | NE  | ARG | L | 24 | -94.140 | 8.740  | -22.011 | 1.00 | 97.92  | N |
|------|------|-----|-----|---|----|---------|--------|---------|------|--------|---|
| ATOM | 6048 | CZ  | ARG | L | 24 | -95.395 | 8.676  | -22.464 | 1.00 | 99.98  | C |
| ATOM | 6049 | NH1 | ARG | L | 24 | -96.391 | 9.220  | -21.767 | 1.00 | 100.74 | N |
| ATOM | 6050 | NH2 | ARG | L | 24 | -95.661 | 8.067  | -23.617 | 1.00 | 100.60 | N |
| ATOM | 6051 | C   | ARG | L | 24 | -89.905 | 7.151  | -19.167 | 1.00 | 84.88  | C |
| ATOM | 6052 | O   | ARG | L | 24 | -90.261 | 6.760  | -18.045 | 1.00 | 84.96  | O |
| ATOM | 6053 | N   | ALA | L | 25 | -88.724 | 7.744  | -19.412 | 1.00 | 81.15  | N |
| ATOM | 6054 | CA  | ALA | L | 25 | -87.731 | 8.027  | -18.382 | 1.00 | 79.72  | C |
| ATOM | 6055 | CB  | ALA | L | 25 | -86.380 | 8.312  | -19.017 | 1.00 | 79.78  | C |
| ATOM | 6056 | C   | ALA | L | 25 | -88.200 | 9.231  | -17.572 | 1.00 | 78.88  | C |
| ATOM | 6057 | O   | ALA | L | 25 | -88.784 | 10.167 | -18.138 | 1.00 | 78.99  | O |
| ATOM | 6058 | N   | SER | L | 26 | -87.966 | 9.206  | -16.247 | 1.00 | 76.82  | N |
| ATOM | 6059 | CA  | SER | L | 26 | -88.358 | 10.287 | -15.348 | 1.00 | 75.42  | C |
| ATOM | 6060 | CB  | SER | L | 26 | -88.450 | 9.772  | -13.915 | 1.00 | 75.49  | C |
| ATOM | 6061 | OG  | SER | L | 26 | -87.222 | 9.221  | -13.472 | 1.00 | 75.52  | O |
| ATOM | 6062 | C   | SER | L | 26 | -87.406 | 11.488 | -15.437 | 1.00 | 74.61  | C |
| ATOM | 6063 | O   | SER | L | 26 | -87.717 | 12.544 | -14.900 | 1.00 | 74.72  | O |
| ATOM | 6064 | N   | GLN | L | 27 | -86.253 | 11.323 | -16.107 | 1.00 | 72.38  | N |
| ATOM | 6065 | CA  | GLN | L | 27 | -85.220 | 12.338 | -16.288 | 1.00 | 70.85  | C |
| ATOM | 6066 | CB  | GLN | L | 27 | -84.048 | 12.033 | -15.370 | 1.00 | 71.05  | C |
| ATOM | 6067 | CG  | GLN | L | 27 | -84.312 | 12.084 | -13.891 | 1.00 | 72.55  | C |
| ATOM | 6068 | CD  | GLN | L | 27 | -83.007 | 11.927 | -13.147 | 1.00 | 75.22  | C |
| ATOM | 6069 | OE1 | GLN | L | 27 | -82.991 | 11.733 | -11.922 | 1.00 | 77.67  | O |
| ATOM | 6070 | NE2 | GLN | L | 27 | -81.878 | 12.001 | -13.860 | 1.00 | 74.71  | N |
| ATOM | 6071 | C   | GLN | L | 27 | -84.659 | 12.234 | -17.689 | 1.00 | 69.65  | C |
| ATOM | 6072 | O   | GLN | L | 27 | -84.826 | 11.201 | -18.338 | 1.00 | 69.54  | O |
| ATOM | 6073 | N   | TYR | L | 28 | -83.938 | 13.270 | -18.144 | 1.00 | 67.82  | N |
| ATOM | 6074 | CA  | TYR | L | 28 | -83.315 | 13.256 | -19.469 | 1.00 | 66.27  | C |
| ATOM | 6075 | CB  | TYR | L | 28 | -82.720 | 14.647 | -19.814 | 1.00 | 65.44  | C |
| ATOM | 6076 | CG  | TYR | L | 28 | -82.242 | 14.748 | -21.246 | 1.00 | 62.81  | C |
| ATOM | 6077 | CD1 | TYR | L | 28 | -83.140 | 14.945 | -22.287 | 1.00 | 60.19  | C |
| ATOM | 6078 | CE1 | TYR | L | 28 | -82.712 | 15.014 | -23.616 | 1.00 | 60.09  | C |
| ATOM | 6079 | CZ  | TYR | L | 28 | -81.367 | 14.853 | -23.920 | 1.00 | 59.59  | C |
| ATOM | 6080 | OH  | TYR | L | 28 | -80.976 | 14.901 | -25.241 | 1.00 | 59.93  | O |
| ATOM | 6081 | CE2 | TYR | L | 28 | -80.448 | 14.675 | -22.895 | 1.00 | 59.81  | C |
| ATOM | 6082 | CD2 | TYR | L | 28 | -80.891 | 14.616 | -21.566 | 1.00 | 61.47  | C |
| ATOM | 6083 | C   | TYR | L | 28 | -82.227 | 12.130 | -19.499 | 1.00 | 65.99  | C |
| ATOM | 6084 | O   | TYR | L | 28 | -81.359 | 12.080 | -18.619 | 1.00 | 65.99  | O |
| ATOM | 6085 | N   | VAL | L | 29 | -82.307 | 11.221 | -20.474 | 1.00 | 63.65  | N |
| ATOM | 6086 | CA  | VAL | L | 29 | -81.330 | 10.143 | -20.565 | 1.00 | 63.33  | C |
| ATOM | 6087 | CB  | VAL | L | 29 | -81.883 | 8.722  | -20.249 | 1.00 | 63.11  | C |
| ATOM | 6088 | CG1 | VAL | L | 29 | -82.900 | 8.275  | -21.283 | 1.00 | 62.31  | C |
| ATOM | 6089 | CG2 | VAL | L | 29 | -82.446 | 8.626  | -18.831 | 1.00 | 62.70  | C |
| ATOM | 6090 | C   | VAL | L | 29 | -80.584 | 10.181 | -21.876 | 1.00 | 63.57  | C |
| ATOM | 6091 | O   | VAL | L | 29 | -79.775 | 9.281  | -22.153 | 1.00 | 63.59  | O |
| ATOM | 6092 | N   | GLY | L | 30 | -80.845 | 11.218 | -22.662 | 1.00 | 64.62  | N |
| ATOM | 6093 | CA  | GLY | L | 30 | -80.229 | 11.366 | -23.972 | 1.00 | 64.86  | C |
| ATOM | 6094 | C   | GLY | L | 30 | -80.687 | 10.222 | -24.847 | 1.00 | 64.90  | C |
| ATOM | 6095 | O   | GLY | L | 30 | -81.855 | 9.848  | -24.790 | 1.00 | 64.96  | O |
| ATOM | 6096 | N   | SER | L | 31 | -79.789 | 9.641  | -25.626 | 1.00 | 66.85  | N |
| ATOM | 6097 | CA  | SER | L | 31 | -80.160 | 8.525  | -26.486 | 1.00 | 67.60  | C |
| ATOM | 6098 | CB  | SER | L | 31 | -79.676 | 8.789  | -27.908 | 1.00 | 67.46  | C |
| ATOM | 6099 | OG  | SER | L | 31 | -78.259 | 8.838  | -27.958 | 1.00 | 68.34  | O |
| ATOM | 6100 | C   | SER | L | 31 | -79.553 | 7.209  | -25.949 | 1.00 | 68.05  | C |
| ATOM | 6101 | O   | SER | L | 31 | -79.537 | 6.187  | -26.654 | 1.00 | 68.16  | O |
| ATOM | 6102 | N   | TYR | L | 32 | -79.038 | 7.245  | -24.705 | 1.00 | 68.98  | N |
| ATOM | 6103 | CA  | TYR | L | 32 | -78.390 | 6.098  | -24.101 | 1.00 | 68.93  | C |
| ATOM | 6104 | CB  | TYR | L | 32 | -77.203 | 6.540  | -23.233 | 1.00 | 68.85  | C |
| ATOM | 6105 | CG  | TYR | L | 32 | -76.275 | 7.517  | -23.913 | 1.00 | 68.85  | C |
| ATOM | 6106 | CD1 | TYR | L | 32 | -75.477 | 7.123  | -24.981 | 1.00 | 68.62  | C |
| ATOM | 6107 | CE1 | TYR | L | 32 | -74.636 | 8.030  | -25.628 | 1.00 | 69.48  | C |
| ATOM | 6108 | CZ  | TYR | L | 32 | -74.565 | 9.342  | -25.188 | 1.00 | 68.65  | C |
| ATOM | 6109 | OH  | TYR | L | 32 | -73.723 | 10.220 | -25.823 | 1.00 | 68.17  | O |
| ATOM | 6110 | CE2 | TYR | L | 32 | -75.337 | 9.752  | -24.114 | 1.00 | 69.22  | C |
| ATOM | 6111 | CD2 | TYR | L | 32 | -76.191 | 8.842  | -23.487 | 1.00 | 69.84  | C |
| ATOM | 6112 | C   | TYR | L | 32 | -79.343 | 5.149  | -23.374 | 1.00 | 69.13  | C |
| ATOM | 6113 | O   | TYR | L | 32 | -79.173 | 4.893  | -22.172 | 1.00 | 69.45  | O |
| ATOM | 6114 | N   | LEU | L | 33 | -80.338 | 4.620  | -24.111 | 1.00 | 69.39  | N |
| ATOM | 6115 | CA  | LEU | L | 33 | -81.322 | 3.663  | -23.592 | 1.00 | 69.21  | C |
| ATOM | 6116 | CB  | LEU | L | 33 | -82.734 | 4.277  | -23.585 | 1.00 | 68.46  | C |
| ATOM | 6117 | CG  | LEU | L | 33 | -83.871 | 3.332  | -23.289 | 1.00 | 67.58  | C |
| ATOM | 6118 | CD1 | LEU | L | 33 | -84.932 | 3.981  | -22.450 | 1.00 | 66.45  | C |
| ATOM | 6119 | CD2 | LEU | L | 33 | -84.435 | 2.734  | -24.551 | 1.00 | 66.54  | C |
| ATOM | 6120 | C   | LEU | L | 33 | -81.253 | 2.322  | -24.409 | 1.00 | 69.54  | C |
| ATOM | 6121 | O   | LEU | L | 33 | -81.075 | 2.353  | -25.634 | 1.00 | 69.48  | O |
| ATOM | 6122 | N   | ASN | L | 34 | -81.395 | 1.160  | -23.726 | 1.00 | 69.21  | N |
| ATOM | 6123 | CA  | ASN | L | 34 | -81.354 | -0.137 | -24.394 | 1.00 | 69.16  | C |
| ATOM | 6124 | CB  | ASN | L | 34 | -80.198 | -0.975 | -23.892 | 1.00 | 69.25  | C |

TABLE 14-continued

PCSK9 and AX132 Fab complex x-ray structure

| ATOM | 6125 | CG | ASN | L | 34 | −78.849 | −0.323 | −24.010 | 1.00 | 68.89 | C |
|---|---|---|---|---|---|---|---|---|---|---|---|
| ATOM | 6126 | OD1 | ASN | L | 34 | −78.531 | 0.370 | −24.980 | 1.00 | 69.33 | O |
| ATOM | 6127 | ND2 | ASN | L | 34 | −78.024 | −0.530 | −23.008 | 1.00 | 67.82 | N |
| ATOM | 6128 | C | ASN | L | 34 | −82.650 | −0.889 | −24.231 | 1.00 | 69.14 | C |
| ATOM | 6129 | O | ASN | L | 34 | −83.387 | −0.656 | −23.268 | 1.00 | 69.19 | O |
| ATOM | 6130 | N | TRP | L | 35 | −82.925 | −1.789 | −25.199 | 1.00 | 67.73 | N |
| ATOM | 6131 | CA | TRP | L | 35 | −84.099 | −2.654 | −25.283 | 1.00 | 67.27 | C |
| ATOM | 6132 | CB | TRP | L | 35 | −84.932 | −2.329 | −26.539 | 1.00 | 67.21 | C |
| ATOM | 6133 | CG | TRP | L | 35 | −85.741 | −1.060 | −26.474 | 1.00 | 66.74 | C |
| ATOM | 6134 | CD1 | TRP | L | 35 | −85.421 | 0.143 | −27.035 | 1.00 | 66.52 | C |
| ATOM | 6135 | NE1 | TRP | L | 35 | −86.415 | 1.068 | −26.782 | 1.00 | 65.54 | N |
| ATOM | 6136 | CE2 | TRP | L | 35 | −87.413 | 0.463 | −26.069 | 1.00 | 64.58 | C |
| ATOM | 6137 | CD2 | TRP | L | 35 | −87.026 | −0.884 | −25.859 | 1.00 | 64.96 | C |
| ATOM | 6138 | CE3 | TRP | L | 35 | −87.877 | −1.723 | −25.131 | 1.00 | 64.93 | C |
| ATOM | 6139 | CZ3 | TRP | L | 35 | −89.082 | −1.206 | −24.654 | 1.00 | 66.19 | C |
| ATOM | 6140 | CH2 | TRP | L | 35 | −89.442 | 0.131 | −24.882 | 1.00 | 65.61 | C |
| ATOM | 6141 | CZ2 | TRP | L | 35 | −88.623 | 0.983 | −25.590 | 1.00 | 64.83 | C |
| ATOM | 6142 | C | TRP | L | 35 | −83.669 | −4.127 | −25.304 | 1.00 | 67.29 | C |
| ATOM | 6143 | O | TRP | L | 35 | −82.820 | −4.533 | −26.114 | 1.00 | 67.16 | O |
| ATOM | 6144 | N | TYR | L | 36 | −84.255 | −4.924 | −24.404 | 1.00 | 67.91 | N |
| ATOM | 6145 | CA | TYR | L | 36 | −83.976 | −6.350 | −24.282 | 1.00 | 68.00 | C |
| ATOM | 6146 | CB | TYR | L | 36 | −83.469 | −6.681 | −22.860 | 1.00 | 67.89 | C |
| ATOM | 6147 | CG | TYR | L | 36 | −82.120 | −6.066 | −22.548 | 1.00 | 68.25 | C |
| ATOM | 6148 | CD1 | TYR | L | 36 | −82.022 | −4.778 | −22.030 | 1.00 | 67.50 | C |
| ATOM | 6149 | CE1 | TYR | L | 36 | −80.786 | −4.178 | −21.813 | 1.00 | 67.54 | C |
| ATOM | 6150 | CZ | TYR | L | 36 | −79.624 | −4.878 | −22.084 | 1.00 | 67.87 | C |
| ATOM | 6151 | OH | TYR | L | 36 | −78.406 | −4.290 | −21.837 | 1.00 | 68.43 | O |
| ATOM | 6152 | CE2 | TYR | L | 36 | −79.693 | −6.165 | −22.593 | 1.00 | 68.13 | C |
| ATOM | 6153 | CD2 | TYR | L | 36 | −80.938 | −6.750 | −22.825 | 1.00 | 68.33 | C |
| ATOM | 6154 | C | TYR | L | 36 | −85.218 | −7.145 | −24.578 | 1.00 | 68.21 | C |
| ATOM | 6155 | O | TYR | L | 36 | −86.330 | −6.679 | −24.296 | 1.00 | 68.38 | O |
| ATOM | 6156 | N | GLN | L | 37 | −85.047 | −8.355 | −25.124 | 1.00 | 70.41 | N |
| ATOM | 6157 | CA | GLN | L | 37 | −86.171 | −9.249 | −25.404 | 1.00 | 70.69 | C |
| ATOM | 6158 | CB | GLN | L | 37 | −86.217 | −9.637 | −26.884 | 1.00 | 70.79 | C |
| ATOM | 6159 | CG | GLN | L | 37 | −87.418 | −10.520 | −27.247 | 1.00 | 71.62 | C |
| ATOM | 6160 | CD | GLN | L | 37 | −87.155 | −11.323 | −28.493 | 1.00 | 72.47 | C |
| ATOM | 6161 | OE1 | GLN | L | 37 | −86.164 | −12.081 | −28.566 | 1.00 | 72.90 | O |
| ATOM | 6162 | NE2 | GLN | L | 37 | −88.040 | −11.177 | −29.500 | 1.00 | 71.79 | N |
| ATOM | 6163 | C | GLN | L | 37 | −86.013 | −10.494 | −24.545 | 1.00 | 70.52 | C |
| ATOM | 6164 | O | GLN | L | 37 | −84.967 | −11.132 | −24.592 | 1.00 | 70.54 | O |
| ATOM | 6165 | N | GLN | L | 38 | −87.038 | −10.860 | −23.775 | 1.00 | 70.53 | N |
| ATOM | 6166 | CA | GLN | L | 38 | −86.931 | −12.057 | −22.949 | 1.00 | 70.45 | C |
| ATOM | 6167 | CB | GLN | L | 38 | −86.840 | −11.705 | −21.480 | 1.00 | 69.65 | C |
| ATOM | 6168 | CG | GLN | L | 38 | −86.360 | −12.875 | −20.682 | 1.00 | 67.53 | C |
| ATOM | 6169 | CD | GLN | L | 38 | −86.403 | −12.621 | −19.208 | 1.00 | 65.49 | C |
| ATOM | 6170 | OE1 | GLN | L | 38 | −87.137 | −11.746 | −18.711 | 1.00 | 64.80 | O |
| ATOM | 6171 | NE2 | GLN | L | 38 | −85.617 | −13.401 | −18.475 | 1.00 | 64.47 | N |
| ATOM | 6172 | C | GLN | L | 38 | −87.991 | −13.132 | −23.217 | 1.00 | 71.40 | C |
| ATOM | 6173 | O | GLN | L | 38 | −89.150 | −13.018 | −22.787 | 1.00 | 71.38 | O |
| ATOM | 6174 | N | LYS | L | 39 | −87.566 | −14.201 | −23.925 | 1.00 | 74.27 | N |
| ATOM | 6175 | CA | LYS | L | 39 | −88.414 | −15.349 | −24.242 | 1.00 | 75.11 | C |
| ATOM | 6176 | CB | LYS | L | 39 | −87.917 | −16.069 | −25.506 | 1.00 | 75.03 | C |
| ATOM | 6177 | CG | LYS | L | 39 | −88.706 | −15.584 | −26.739 | 1.00 | 76.39 | C |
| ATOM | 6178 | CD | LYS | L | 39 | −88.360 | −16.236 | −28.081 | 1.00 | 77.40 | C |
| ATOM | 6179 | CE | LYS | L | 39 | −87.221 | −15.555 | −28.788 | 1.00 | 78.26 | C |
| ATOM | 6180 | NZ | LYS | L | 39 | −85.899 | −16.095 | −28.348 | 1.00 | 80.80 | N |
| ATOM | 6181 | C | LYS | L | 39 | −88.491 | −16.269 | −23.017 | 1.00 | 75.58 | C |
| ATOM | 6182 | O | LYS | L | 39 | −87.502 | −16.370 | −22.291 | 1.00 | 75.90 | O |
| ATOM | 6183 | N | PRO | L | 40 | −89.644 | −16.914 | −22.719 | 1.00 | 76.29 | N |
| ATOM | 6184 | CA | PRO | L | 40 | −89.708 | −17.786 | −21.518 | 1.00 | 76.35 | C |
| ATOM | 6185 | CB | PRO | L | 40 | −91.147 | −18.292 | −21.501 | 1.00 | 76.20 | C |
| ATOM | 6186 | CG | PRO | L | 40 | −91.894 | −17.355 | −22.405 | 1.00 | 76.93 | C |
| ATOM | 6187 | CD | PRO | L | 40 | −90.925 | −16.909 | −23.450 | 1.00 | 76.38 | C |
| ATOM | 6188 | C | PRO | L | 40 | −88.664 | −18.916 | −21.460 | 1.00 | 76.28 | C |
| ATOM | 6189 | O | PRO | L | 40 | −88.345 | −19.556 | −22.485 | 1.00 | 75.89 | O |
| ATOM | 6190 | N | GLY | L | 41 | −88.107 | −19.098 | −20.254 | 1.00 | 75.59 | N |
| ATOM | 6191 | CA | GLY | L | 41 | −87.064 | −20.078 | −19.974 | 1.00 | 75.41 | C |
| ATOM | 6192 | C | GLY | L | 41 | −85.731 | −19.660 | −20.566 | 1.00 | 75.49 | C |
| ATOM | 6193 | O | GLY | L | 41 | −84.851 | −20.497 | −20.835 | 1.00 | 75.64 | O |
| ATOM | 6194 | N | GLN | L | 42 | −85.586 | −18.334 | −20.781 | 1.00 | 74.30 | N |
| ATOM | 6195 | CA | GLN | L | 42 | −84.397 | −17.742 | −21.368 | 1.00 | 73.61 | C |
| ATOM | 6196 | CB | GLN | L | 42 | −84.606 | −17.525 | −22.862 | 1.00 | 73.45 | C |
| ATOM | 6197 | CG | GLN | L | 42 | −84.387 | −18.753 | −23.706 | 1.00 | 74.36 | C |
| ATOM | 6198 | CD | GLN | L | 42 | −84.748 | −18.410 | −25.116 | 1.00 | 77.03 | C |
| ATOM | 6199 | OE1 | GLN | L | 42 | −84.038 | −17.674 | −25.821 | 1.00 | 77.97 | O |
| ATOM | 6200 | NE2 | GLN | L | 42 | −85.886 | −18.913 | −25.555 | 1.00 | 79.35 | N |
| ATOM | 6201 | C | GLN | L | 42 | −84.012 | −16.443 | −20.711 | 1.00 | 73.06 | C |
| ATOM | 6202 | O | GLN | L | 42 | −84.839 | −15.780 | −20.086 | 1.00 | 73.00 | O |

TABLE 14-continued

PCSK9 and AX132 Fab complex x-ray structure

| ATOM | 6203 | N   | ALA | L | 43 | −82.740 | −16.086 | −20.869 | 1.00 | 70.82 | N |
| ATOM | 6204 | CA  | ALA | L | 43 | −82.159 | −14.862 | −20.351 | 1.00 | 70.31 | C |
| ATOM | 6205 | CB  | ALA | L | 43 | −80.642 | −15.010 | −20.300 | 1.00 | 70.14 | C |
| ATOM | 6206 | C   | ALA | L | 43 | −82.520 | −13.713 | −21.290 | 1.00 | 70.06 | C |
| ATOM | 6207 | O   | ALA | L | 43 | −82.668 | −13.970 | −22.495 | 1.00 | 70.12 | O |
| ATOM | 6208 | N   | PRO | L | 44 | −82.621 | −12.445 | −20.795 | 1.00 | 68.44 | N |
| ATOM | 6209 | CA  | PRO | L | 44 | −82.891 | −11.307 | −21.703 | 1.00 | 68.13 | C |
| ATOM | 6210 | CB  | PRO | L | 44 | −82.750 | −10.099 | −20.791 | 1.00 | 68.16 | C |
| ATOM | 6211 | CG  | PRO | L | 44 | −83.034 | −10.619 | −19.432 | 1.00 | 68.17 | C |
| ATOM | 6212 | CD  | PRO | L | 44 | −82.459 | −11.985 | −19.402 | 1.00 | 68.24 | C |
| ATOM | 6213 | C   | PRO | L | 44 | −81.876 | −11.226 | −22.844 | 1.00 | 68.23 | C |
| ATOM | 6214 | O   | PRO | L | 44 | −80.758 | −11.726 | −22.700 | 1.00 | 68.47 | O |
| ATOM | 6215 | N   | ARG | L | 45 | −82.266 | −10.642 | −23.989 | 1.00 | 70.66 | N |
| ATOM | 6216 | CA  | ARG | L | 45 | −81.416 | −10.533 | −25.184 | 1.00 | 71.08 | C |
| ATOM | 6217 | CB  | ARG | L | 45 | −81.934 | −11.471 | −26.279 | 1.00 | 71.21 | C |
| ATOM | 6218 | CG  | ARG | L | 45 | −81.142 | −11.415 | −27.568 | 1.00 | 73.90 | C |
| ATOM | 6219 | CD  | ARG | L | 45 | −81.430 | −12.596 | −28.471 | 1.00 | 79.03 | C |
| ATOM | 6220 | NE  | ARG | L | 45 | −80.438 | −12.683 | −29.554 | 1.00 | 84.54 | N |
| ATOM | 6221 | CZ  | ARG | L | 45 | −80.690 | −12.402 | −30.835 | 1.00 | 87.00 | C |
| ATOM | 6222 | NH1 | ARG | L | 45 | −81.918 | −12.030 | −31.216 | 1.00 | 87.47 | N |
| ATOM | 6223 | NH2 | ARG | L | 45 | −79.723 | −12.505 | −31.749 | 1.00 | 86.89 | N |
| ATOM | 6224 | C   | ARG | L | 45 | −81.367 | −9.117  | −25.714 | 1.00 | 70.91 | C |
| ATOM | 6225 | O   | ARG | L | 45 | −82.420 | −8.556  | −26.019 | 1.00 | 71.15 | O |
| ATOM | 6226 | N   | LEU | L | 46 | −80.163 | −8.546  | −25.857 | 1.00 | 67.97 | N |
| ATOM | 6227 | CA  | LEU | L | 46 | −80.068 | −7.188  | −26.379 | 1.00 | 67.99 | C |
| ATOM | 6228 | CB  | LEU | L | 46 | −78.637 | −6.625  | −26.287 | 1.00 | 67.90 | C |
| ATOM | 6229 | CG  | LEU | L | 46 | −78.428 | −5.211  | −26.816 | 1.00 | 66.29 | C |
| ATOM | 6230 | CD1 | LEU | L | 46 | −78.915 | −4.190  | −25.840 | 1.00 | 65.28 | C |
| ATOM | 6231 | CD2 | LEU | L | 46 | −77.002 | −4.987  | −27.135 | 1.00 | 65.27 | C |
| ATOM | 6232 | C   | LEU | L | 46 | −80.601 | −7.154  | −27.807 | 1.00 | 68.29 | C |
| ATOM | 6233 | O   | LEU | L | 46 | −80.152 | −7.933  | −28.653 | 1.00 | 68.46 | O |
| ATOM | 6234 | N   | LEU | L | 47 | −81.579 | −6.270  | −28.044 | 1.00 | 68.06 | N |
| ATOM | 6235 | CA  | LEU | L | 47 | −82.283 | −6.067  | −29.308 | 1.00 | 68.32 | C |
| ATOM | 6236 | CB  | LEU | L | 47 | −83.743 | −5.852  | −28.923 | 1.00 | 68.34 | C |
| ATOM | 6237 | CG  | LEU | L | 47 | −84.817 | −6.605  | −29.597 | 1.00 | 68.82 | C |
| ATOM | 6238 | CD1 | LEU | L | 47 | −84.498 | −8.086  | −29.676 | 1.00 | 69.06 | C |
| ATOM | 6239 | CD2 | LEU | L | 47 | −86.095 | −6.363  | −28.862 | 1.00 | 69.14 | C |
| ATOM | 6240 | C   | LEU | L | 47 | −81.796 | −4.780  | −29.959 | 1.00 | 68.67 | C |
| ATOM | 6241 | O   | LEU | L | 47 | −81.148 | −4.803  | −31.017 | 1.00 | 68.41 | O |
| ATOM | 6242 | N   | ILE | L | 48 | −82.145 | −3.649  | −29.306 | 1.00 | 69.72 | N |
| ATOM | 6243 | CA  | ILE | L | 48 | −81.815 | −2.284  | −29.689 | 1.00 | 70.11 | C |
| ATOM | 6244 | CB  | ILE | L | 48 | −83.112 | −1.431  | −29.887 | 1.00 | 70.29 | C |
| ATOM | 6245 | CG1 | ILE | L | 48 | −84.065 | −2.014  | −30.955 | 1.00 | 70.86 | C |
| ATOM | 6246 | CD1 | ILE | L | 48 | −83.492 | −2.138  | −32.379 | 1.00 | 71.97 | C |
| ATOM | 6247 | CG2 | ILE | L | 48 | −82.829 | 0.066   | −30.109 | 1.00 | 70.03 | C |
| ATOM | 6248 | C   | ILE | L | 48 | −80.942 | −1.687  | −28.602 | 1.00 | 70.39 | C |
| ATOM | 6249 | O   | ILE | L | 48 | −81.302 | −1.745  | −27.420 | 1.00 | 70.31 | O |
| ATOM | 6250 | N   | TYR | L | 49 | −79.810 | −1.099  | −28.989 | 1.00 | 70.70 | N |
| ATOM | 6251 | CA  | TYR | L | 49 | −78.968 | −0.435  | −28.010 | 1.00 | 71.20 | C |
| ATOM | 6252 | CB  | TYR | L | 49 | −77.590 | −1.069  | −27.911 | 1.00 | 70.96 | C |
| ATOM | 6253 | CG  | TYR | L | 49 | −76.714 | −0.865  | −29.117 | 1.00 | 71.03 | C |
| ATOM | 6254 | CD1 | TYR | L | 49 | −75.752 | 0.141   | −29.142 | 1.00 | 70.52 | C |
| ATOM | 6255 | CE1 | TYR | L | 49 | −74.926 | 0.328   | −30.249 | 1.00 | 70.02 | C |
| ATOM | 6256 | CZ  | TYR | L | 49 | −75.042 | −0.514  | −31.342 | 1.00 | 71.17 | C |
| ATOM | 6257 | OH  | TYR | L | 49 | −74.224 | −0.342  | −32.434 | 1.00 | 73.08 | O |
| ATOM | 6258 | CE2 | TYR | L | 49 | −75.972 | −1.545  | −31.326 | 1.00 | 71.85 | C |
| ATOM | 6259 | CD2 | TYR | L | 49 | −76.808 | −1.707  | −30.220 | 1.00 | 71.13 | C |
| ATOM | 6260 | C   | TYR | L | 49 | −78.919 | 1.044   | −28.346 | 1.00 | 71.57 | C |
| ATOM | 6261 | O   | TYR | L | 49 | −79.238 | 1.408   | −29.469 | 1.00 | 71.66 | O |
| ATOM | 6262 | N   | ASP | L | 50 | −78.564 | 1.905   | −27.395 | 1.00 | 74.27 | N |
| ATOM | 6263 | CA  | ASP | L | 50 | −78.497 | 3.349   | −27.653 | 1.00 | 75.00 | C |
| ATOM | 6264 | CB  | ASP | L | 50 | −77.139 | 3.735   | −28.250 | 1.00 | 74.83 | C |
| ATOM | 6265 | CG  | ASP | L | 50 | −75.967 | 3.734   | −27.284 | 1.00 | 75.63 | C |
| ATOM | 6266 | OD1 | ASP | L | 50 | −76.147 | 3.291   | −26.100 | 1.00 | 75.34 | O |
| ATOM | 6267 | OD2 | ASP | L | 50 | −74.876 | 4.166   | −27.694 | 1.00 | 77.19 | O |
| ATOM | 6268 | C   | ASP | L | 50 | −79.668 | 3.901   | −28.491 | 1.00 | 75.23 | C |
| ATOM | 6269 | O   | ASP | L | 50 | −79.471 | 4.380   | −29.597 | 1.00 | 75.08 | O |
| ATOM | 6270 | N   | ALA | L | 51 | −80.886 | 3.792   | −27.941 | 1.00 | 77.17 | N |
| ATOM | 6271 | CA  | ALA | L | 51 | −82.191 | 4.225   | −28.464 | 1.00 | 77.67 | C |
| ATOM | 6272 | CB  | ALA | L | 51 | −82.332 | 5.731   | −28.423 | 1.00 | 77.83 | C |
| ATOM | 6273 | C   | ALA | L | 51 | −82.707 | 3.685   | −29.785 | 1.00 | 78.01 | C |
| ATOM | 6274 | O   | ALA | L | 51 | −83.899 | 3.370   | −29.859 | 1.00 | 78.23 | O |
| ATOM | 6275 | N   | SER | L | 52 | −81.851 | 3.588   | −30.815 | 1.00 | 79.08 | N |
| ATOM | 6276 | CA  | SER | L | 52 | −82.236 | 3.167   | −32.165 | 1.00 | 79.89 | C |
| ATOM | 6277 | CB  | SER | L | 52 | −82.583 | 4.422   | −32.960 | 1.00 | 79.80 | C |
| ATOM | 6278 | OG  | SER | L | 52 | −81.464 | 5.303   | −32.972 | 1.00 | 80.89 | O |
| ATOM | 6279 | C   | SER | L | 52 | −81.107 | 2.426   | −32.902 | 1.00 | 80.36 | C |
| ATOM | 6280 | O   | SER | L | 52 | −80.630 | 2.898   | −33.927 | 1.00 | 80.53 | O |

TABLE 14-continued

PCSK9 and AX132 Fab complex x-ray structure

| ATOM | 6281 | N | ASN | L | 53 | −80.655 | 1.307 | −32.399 | 1.00 | 79.99 | N |
|---|---|---|---|---|---|---|---|---|---|---|---|
| ATOM | 6282 | CA | ASN | L | 53 | −79.569 | 0.605 | −33.068 | 1.00 | 81.01 | C |
| ATOM | 6283 | CB | ASN | L | 53 | −78.217 | 0.976 | −32.453 | 1.00 | 81.07 | C |
| ATOM | 6284 | CG | ASN | L | 53 | −77.521 | 2.098 | −33.126 | 1.00 | 81.94 | C |
| ATOM | 6285 | OD1 | ASN | L | 53 | −77.719 | 3.262 | −32.801 | 1.00 | 83.25 | O |
| ATOM | 6286 | ND2 | ASN | L | 53 | −76.688 | 1.768 | −34.084 | 1.00 | 83.66 | N |
| ATOM | 6287 | C | ASN | L | 53 | −79.799 | −0.856 | −32.911 | 1.00 | 81.48 | C |
| ATOM | 6288 | O | ASN | L | 53 | −79.855 | −1.332 | −31.775 | 1.00 | 81.69 | O |
| ATOM | 6289 | N | ARG | L | 54 | −79.942 | −1.578 | −34.030 | 1.00 | 83.24 | N |
| ATOM | 6290 | CA | ARG | L | 54 | −80.161 | −3.016 | −33.967 | 1.00 | 83.75 | C |
| ATOM | 6291 | CB | ARG | L | 54 | −80.652 | −3.569 | −35.300 | 1.00 | 83.62 | C |
| ATOM | 6292 | CG | ARG | L | 54 | −82.146 | −3.516 | −35.411 | 1.00 | 84.05 | C |
| ATOM | 6293 | CD | ARG | L | 54 | −82.627 | −4.184 | −36.662 | 1.00 | 85.38 | C |
| ATOM | 6294 | NE | ARG | L | 54 | −82.768 | −3.201 | −37.726 | 1.00 | 86.77 | N |
| ATOM | 6295 | CZ | ARG | L | 54 | −82.077 | −3.221 | −38.862 | 1.00 | 87.66 | C |
| ATOM | 6296 | NH1 | ARG | L | 54 | −82.265 | −2.273 | −39.774 | 1.00 | 88.38 | N |
| ATOM | 6297 | NH2 | ARG | L | 54 | −81.202 | −4.198 | −39.103 | 1.00 | 86.69 | N |
| ATOM | 6298 | C | ARG | L | 54 | −78.886 | −3.698 | −33.520 | 1.00 | 84.05 | C |
| ATOM | 6299 | O | ARG | L | 54 | −77.815 | −3.445 | −34.090 | 1.00 | 83.98 | O |
| ATOM | 6300 | N | ALA | L | 55 | −78.992 | −4.530 | −32.472 | 1.00 | 84.40 | N |
| ATOM | 6301 | CA | ALA | L | 55 | −77.839 | −5.247 | −31.952 | 1.00 | 85.14 | C |
| ATOM | 6302 | CB | ALA | L | 55 | −78.179 | −5.893 | −30.624 | 1.00 | 85.11 | C |
| ATOM | 6303 | C | ALA | L | 55 | −77.477 | −6.305 | −32.968 | 1.00 | 85.71 | C |
| ATOM | 6304 | O | ALA | L | 55 | −78.351 | −6.712 | −33.745 | 1.00 | 85.99 | O |
| ATOM | 6305 | N | THR | L | 56 | −76.206 | −6.751 | −32.979 | 1.00 | 86.17 | N |
| ATOM | 6306 | CA | THR | L | 56 | −75.759 | −7.777 | −33.927 | 1.00 | 86.69 | C |
| ATOM | 6307 | CB | THR | L | 56 | −74.278 | −8.136 | −33.741 | 1.00 | 86.68 | C |
| ATOM | 6308 | OG1 | THR | L | 56 | −73.521 | −6.939 | −33.546 | 1.00 | 87.91 | O |
| ATOM | 6309 | CG2 | THR | L | 56 | −73.711 | −8.891 | −34.927 | 1.00 | 86.39 | C |
| ATOM | 6310 | C | THR | L | 56 | −76.706 | −8.988 | −33.974 | 1.00 | 86.77 | C |
| ATOM | 6311 | O | THR | L | 56 | −77.074 | −9.564 | −32.935 | 1.00 | 86.59 | O |
| ATOM | 6312 | N | GLY | L | 57 | −77.126 | −9.299 | −35.192 | 1.00 | 87.23 | N |
| ATOM | 6313 | CA | GLY | L | 57 | −77.993 | −10.423 | −35.490 | 1.00 | 87.57 | C |
| ATOM | 6314 | C | GLY | L | 57 | −79.441 | −10.290 | −35.096 | 1.00 | 87.78 | C |
| ATOM | 6315 | O | GLY | L | 57 | −80.049 | −11.273 | −34.658 | 1.00 | 88.10 | O |
| ATOM | 6316 | N | ILE | L | 58 | −80.016 | −9.101 | −35.244 | 1.00 | 87.20 | N |
| ATOM | 6317 | CA | ILE | L | 58 | −81.425 | −8.978 | −34.934 | 1.00 | 87.35 | C |
| ATOM | 6318 | CB | ILE | L | 58 | −81.811 | −8.327 | −33.570 | 1.00 | 87.35 | C |
| ATOM | 6319 | CG1 | ILE | L | 58 | −81.827 | −6.826 | −33.620 | 1.00 | 88.03 | C |
| ATOM | 6320 | CD1 | ILE | L | 58 | −83.170 | −6.347 | −33.346 | 1.00 | 88.97 | C |
| ATOM | 6321 | CG2 | ILE | L | 58 | −81.034 | −8.853 | −32.365 | 1.00 | 86.77 | C |
| ATOM | 6322 | C | ILE | L | 58 | −82.207 | −8.508 | −36.187 | 1.00 | 87.67 | C |
| ATOM | 6323 | O | ILE | L | 58 | −81.730 | −7.605 | −36.890 | 1.00 | 87.84 | O |
| ATOM | 6324 | N | PRO | L | 59 | −83.368 | −9.149 | −36.519 | 1.00 | 89.23 | N |
| ATOM | 6325 | CA | PRO | L | 59 | −84.122 | −8.763 | −37.733 | 1.00 | 88.93 | C |
| ATOM | 6326 | CB | PRO | L | 59 | −85.388 | −9.623 | −37.657 | 1.00 | 89.01 | C |
| ATOM | 6327 | CG | PRO | L | 59 | −85.468 | −10.082 | −36.245 | 1.00 | 89.16 | C |
| ATOM | 6328 | CD | PRO | L | 59 | −84.048 | −10.261 | −35.824 | 1.00 | 89.32 | C |
| ATOM | 6329 | C | PRO | L | 59 | −84.504 | −7.301 | −37.868 | 1.00 | 88.54 | C |
| ATOM | 6330 | O | PRO | L | 59 | −84.854 | −6.653 | −36.870 | 1.00 | 88.42 | O |
| ATOM | 6331 | N | ALA | L | 60 | −84.477 | −6.816 | −39.137 | 1.00 | 83.84 | N |
| ATOM | 6332 | CA | ALA | L | 60 | −84.799 | −5.458 | −39.570 | 1.00 | 82.93 | C |
| ATOM | 6333 | CB | ALA | L | 60 | −84.606 | −5.330 | −41.062 | 1.00 | 82.66 | C |
| ATOM | 6334 | C | ALA | L | 60 | −86.193 | −5.018 | −39.187 | 1.00 | 82.59 | C |
| ATOM | 6335 | O | ALA | L | 60 | −86.461 | −3.816 | −39.182 | 1.00 | 82.81 | O |
| ATOM | 6336 | N | ARG | L | 61 | −87.084 | −5.969 | −38.843 | 1.00 | 82.13 | N |
| ATOM | 6337 | CA | ARG | L | 61 | −88.445 | −5.623 | −38.435 | 1.00 | 81.73 | C |
| ATOM | 6338 | CB | ARG | L | 61 | −89.354 | −6.847 | −38.462 | 1.00 | 81.85 | C |
| ATOM | 6339 | CG | ARG | L | 61 | −89.359 | −7.659 | −37.194 | 1.00 | 81.26 | C |
| ATOM | 6340 | CD | ARG | L | 61 | −90.278 | −8.822 | −37.413 | 1.00 | 80.17 | C |
| ATOM | 6341 | NE | ARG | L | 61 | −89.937 | −9.963 | −36.570 | 1.00 | 78.82 | N |
| ATOM | 6342 | CZ | ARG | L | 61 | −89.029 | −10.886 | −36.873 | 1.00 | 76.91 | C |
| ATOM | 6343 | NH1 | ARG | L | 61 | −88.341 | −10.807 | −38.009 | 1.00 | 76.02 | N |
| ATOM | 6344 | NH2 | ARG | L | 61 | −88.809 | −11.902 | −36.046 | 1.00 | 75.12 | N |
| ATOM | 6345 | C | ARG | L | 61 | −88.481 | −4.876 | −37.082 | 1.00 | 81.60 | C |
| ATOM | 6346 | O | ARG | L | 61 | −89.505 | −4.278 | −36.719 | 1.00 | 81.34 | O |
| ATOM | 6347 | N | PHE | L | 62 | −87.340 | −4.909 | −36.361 | 1.00 | 80.86 | N |
| ATOM | 6348 | CA | PHE | L | 62 | −87.142 | −4.233 | −35.085 | 1.00 | 80.77 | C |
| ATOM | 6349 | CB | PHE | L | 62 | −86.330 | −5.095 | −34.126 | 1.00 | 80.82 | C |
| ATOM | 6350 | CG | PHE | L | 62 | −87.051 | −6.304 | −33.582 | 1.00 | 80.99 | C |
| ATOM | 6351 | CD1 | PHE | L | 62 | −87.891 | −6.194 | −32.474 | 1.00 | 80.48 | C |
| ATOM | 6352 | CE1 | PHE | L | 62 | −88.549 | −7.317 | −31.961 | 1.00 | 80.37 | C |
| ATOM | 6353 | CZ | PHE | L | 62 | −88.358 | −8.552 | −32.544 | 1.00 | 80.39 | C |
| ATOM | 6354 | CE2 | PHE | L | 62 | −87.521 | −8.680 | −33.637 | 1.00 | 80.11 | C |
| ATOM | 6355 | CD2 | PHE | L | 62 | −86.869 | −7.558 | −34.156 | 1.00 | 80.48 | C |
| ATOM | 6356 | C | PHE | L | 62 | −86.454 | −2.885 | −35.304 | 1.00 | 80.72 | C |
| ATOM | 6357 | O | PHE | L | 62 | −85.473 | −2.781 | −36.065 | 1.00 | 80.48 | O |
| ATOM | 6358 | N | SER | L | 63 | −86.988 | −1.842 | −34.650 | 1.00 | 80.01 | N |

TABLE 14-continued

PCSK9 and AX132 Fab complex x-ray structure

| ATOM | 6359 | CA  | SER | L | 63 | −86.451 | −0.496 | −34.796 | 1.00 | 79.87 | C |
| ---- | ---- | --- | --- | - | -- | ------- | ------ | ------- | ---- | ----- | - |
| ATOM | 6360 | CB  | SER | L | 63 | −87.097 | 0.188  | −35.998 | 1.00 | 79.76 | C |
| ATOM | 6361 | OG  | SER | L | 63 | −88.492 | 0.346  | −35.794 | 1.00 | 79.38 | O |
| ATOM | 6362 | C   | SER | L | 63 | −86.716 | 0.313  | −33.545 | 1.00 | 79.80 | C |
| ATOM | 6363 | O   | SER | L | 63 | −87.756 | 0.134  | −32.899 | 1.00 | 80.10 | O |
| ATOM | 6364 | N   | GLY | L | 64 | −85.796 | 1.216  | −33.233 | 1.00 | 78.03 | N |
| ATOM | 6365 | CA  | GLY | L | 64 | −85.932 | 2.069  | −32.064 | 1.00 | 77.81 | C |
| ATOM | 6366 | C   | GLY | L | 64 | −85.979 | 3.545  | −32.369 | 1.00 | 77.75 | C |
| ATOM | 6367 | O   | GLY | L | 64 | −85.410 | 4.015  | −33.362 | 1.00 | 77.54 | O |
| ATOM | 6368 | N   | SER | L | 65 | −86.648 | 4.286  | −31.498 | 1.00 | 79.48 | N |
| ATOM | 6369 | CA  | SER | L | 65 | −86.786 | 5.725  | −31.645 | 1.00 | 79.85 | C |
| ATOM | 6370 | CB  | SER | L | 65 | −88.071 | 6.061  | −32.395 | 1.00 | 80.07 | C |
| ATOM | 6371 | OG  | SER | L | 65 | −88.936 | 6.916  | −31.658 | 1.00 | 81.22 | O |
| ATOM | 6372 | C   | SER | L | 65 | −86.802 | 6.406  | −30.303 | 1.00 | 79.90 | C |
| ATOM | 6373 | O   | SER | L | 65 | −87.218 | 5.810  | −29.299 | 1.00 | 80.21 | O |
| ATOM | 6374 | N   | GLY | L | 66 | −86.396 | 7.669  | −30.313 | 1.00 | 80.25 | N |
| ATOM | 6375 | CA  | GLY | L | 66 | −86.375 | 8.510  | −29.129 | 1.00 | 80.40 | C |
| ATOM | 6376 | C   | GLY | L | 66 | −85.013 | 9.072  | −28.796 | 1.00 | 80.53 | C |
| ATOM | 6377 | O   | GLY | L | 66 | −83.974 | 8.600  | −29.272 | 1.00 | 80.70 | O |
| ATOM | 6378 | N   | SER | L | 67 | −85.042 | 10.114 | −27.981 | 1.00 | 81.13 | N |
| ATOM | 6379 | CA  | SER | L | 67 | −83.919 | 10.852 | −27.414 | 1.00 | 80.80 | C |
| ATOM | 6380 | CB  | SER | L | 67 | −83.189 | 11.697 | −28.461 | 1.00 | 80.91 | C |
| ATOM | 6381 | OG  | SER | L | 67 | −81.853 | 12.039 | −28.110 | 1.00 | 80.63 | O |
| ATOM | 6382 | C   | SER | L | 67 | −84.608 | 11.712 | −26.369 | 1.00 | 80.78 | C |
| ATOM | 6383 | O   | SER | L | 67 | −85.638 | 12.359 | −26.648 | 1.00 | 80.82 | O |
| ATOM | 6384 | N   | GLY | L | 68 | −84.106 | 11.629 | −25.152 | 1.00 | 80.25 | N |
| ATOM | 6385 | CA  | GLY | L | 68 | −84.685 | 12.411 | −24.086 | 1.00 | 80.31 | C |
| ATOM | 6386 | C   | GLY | L | 68 | −85.363 | 11.660 | −22.985 | 1.00 | 80.31 | C |
| ATOM | 6387 | O   | GLY | L | 68 | −84.718 | 11.273 | −22.015 | 1.00 | 80.51 | O |
| ATOM | 6388 | N   | THR | L | 69 | −86.675 | 11.515 | −23.100 | 1.00 | 82.51 | N |
| ATOM | 6389 | CA  | THR | L | 69 | −87.485 | 10.843 | −22.083 | 1.00 | 82.90 | C |
| ATOM | 6390 | CB  | THR | L | 69 | −88.233 | 11.868 | −21.213 | 1.00 | 82.86 | C |
| ATOM | 6391 | OG1 | THR | L | 69 | −88.760 | 12.908 | −22.052 | 1.00 | 83.26 | O |
| ATOM | 6392 | CG2 | THR | L | 69 | −87.358 | 12.459 | −20.113 | 1.00 | 82.48 | C |
| ATOM | 6393 | C   | THR | L | 69 | −88.458 | 9.850  | −22.679 | 1.00 | 83.07 | C |
| ATOM | 6394 | O   | THR | L | 69 | −88.748 | 8.848  | −22.029 | 1.00 | 83.38 | O |
| ATOM | 6395 | N   | ASP | L | 70 | −88.978 | 10.129 | −23.894 | 1.00 | 81.27 | N |
| ATOM | 6396 | CA  | ASP | L | 70 | −89.936 | 9.260  | −24.569 | 1.00 | 81.42 | C |
| ATOM | 6397 | CB  | ASP | L | 70 | −91.097 | 10.072 | −25.179 | 1.00 | 81.76 | C |
| ATOM | 6398 | CG  | ASP | L | 70 | −92.078 | 10.729 | −24.185 | 1.00 | 83.01 | C |
| ATOM | 6399 | OD1 | ASP | L | 70 | −91.678 | 10.988 | −23.004 | 1.00 | 84.07 | O |
| ATOM | 6400 | OD2 | ASP | L | 70 | −93.239 | 11.000 | −24.587 | 1.00 | 84.40 | O |
| ATOM | 6401 | C   | ASP | L | 70 | −89.221 | 8.380  | −25.574 | 1.00 | 81.29 | C |
| ATOM | 6402 | O   | ASP | L | 70 | −88.591 | 8.878  | −26.524 | 1.00 | 81.22 | O |
| ATOM | 6403 | N   | PHE | L | 71 | −89.282 | 7.055  | −25.315 | 1.00 | 79.43 | N |
| ATOM | 6404 | CA  | PHE | L | 71 | −88.621 | 6.023  | −26.116 | 1.00 | 79.47 | C |
| ATOM | 6405 | CB  | PHE | L | 71 | −87.491 | 5.341  | −25.318 | 1.00 | 79.30 | C |
| ATOM | 6406 | CG  | PHE | L | 71 | −86.342 | 6.288  | −25.047 | 1.00 | 79.06 | C |
| ATOM | 6407 | CD1 | PHE | L | 71 | −85.296 | 6.423  | −25.959 | 1.00 | 78.12 | C |
| ATOM | 6408 | CE1 | PHE | L | 71 | −84.259 | 7.324  | −25.724 | 1.00 | 77.00 | C |
| ATOM | 6409 | CZ  | PHE | L | 71 | −84.270 | 8.099  | −24.591 | 1.00 | 77.40 | C |
| ATOM | 6410 | CE2 | PHE | L | 71 | −85.299 | 7.997  | −23.685 | 1.00 | 77.46 | C |
| ATOM | 6411 | CD2 | PHE | L | 71 | −86.331 | 7.089  | −23.906 | 1.00 | 78.77 | C |
| ATOM | 6412 | C   | PHE | L | 71 | −89.580 | 5.022  | −26.738 | 1.00 | 79.78 | C |
| ATOM | 6413 | O   | PHE | L | 71 | −90.625 | 4.711  | −26.151 | 1.00 | 79.63 | O |
| ATOM | 6414 | N   | THR | L | 72 | −89.225 | 4.525  | −27.942 | 1.00 | 81.31 | N |
| ATOM | 6415 | CA  | THR | L | 72 | −90.081 | 3.603  | −28.663 | 1.00 | 81.88 | C |
| ATOM | 6416 | CB  | THR | L | 72 | −91.065 | 4.427  | −29.511 | 1.00 | 81.84 | C |
| ATOM | 6417 | OG1 | THR | L | 72 | −92.207 | 4.693  | −28.695 | 1.00 | 81.96 | O |
| ATOM | 6418 | CG2 | THR | L | 72 | −91.477 | 3.749  | −30.838 | 1.00 | 81.93 | C |
| ATOM | 6419 | C   | THR | L | 72 | −89.439 | 2.388  | −29.356 | 1.00 | 82.43 | C |
| ATOM | 6420 | O   | THR | L | 72 | −88.468 | 2.512  | −30.116 | 1.00 | 82.66 | O |
| ATOM | 6421 | N   | LEU | L | 73 | −90.034 | 1.210  | −29.100 | 1.00 | 83.21 | N |
| ATOM | 6422 | CA  | LEU | L | 73 | −89.652 | −0.054 | −29.719 | 1.00 | 83.49 | C |
| ATOM | 6423 | CB  | LEU | L | 73 | −89.457 | −1.179 | −28.699 | 1.00 | 83.62 | C |
| ATOM | 6424 | CG  | LEU | L | 73 | −89.058 | −2.517 | −29.301 | 1.00 | 82.79 | C |
| ATOM | 6425 | CD1 | LEU | L | 73 | −87.582 | −2.573 | −29.584 | 1.00 | 82.29 | C |
| ATOM | 6426 | CD2 | LEU | L | 73 | −89.460 | −3.618 | −28.413 | 1.00 | 82.50 | C |
| ATOM | 6427 | C   | LEU | L | 73 | −90.770 | −0.407 | −30.711 | 1.00 | 83.73 | C |
| ATOM | 6428 | O   | LEU | L | 73 | −91.959 | −0.372 | −30.355 | 1.00 | 83.42 | O |
| ATOM | 6429 | N   | THR | L | 74 | −90.369 | −0.732 | −31.956 | 1.00 | 86.82 | N |
| ATOM | 6430 | CA  | THR | L | 74 | −91.277 | −1.021 | −33.053 | 1.00 | 87.24 | C |
| ATOM | 6431 | CB  | THR | L | 74 | −91.296 | 0.199  | −34.006 | 1.00 | 87.18 | C |
| ATOM | 6432 | OG1 | THR | L | 74 | −91.718 | 1.370  | −33.299 | 1.00 | 87.71 | O |
| ATOM | 6433 | CG2 | THR | L | 74 | −92.148 | −0.020 | −35.242 | 1.00 | 87.14 | C |
| ATOM | 6434 | C   | THR | L | 74 | −90.953 | −2.305 | −33.805 | 1.00 | 87.64 | C |
| ATOM | 6435 | O   | THR | L | 74 | −89.853 | −2.457 | −34.353 | 1.00 | 87.70 | O |
| ATOM | 6436 | N   | ILE | L | 75 | −91.949 | −3.209 | −33.850 | 1.00 | 89.18 | N |

TABLE 14-continued

PCSK9 and AX132 Fab complex x-ray structure

| ATOM | 6437 | CA | ILE | L | 75 | -91.918 | -4.473 | -34.589 | 1.00 | 89.53 | C |
|---|---|---|---|---|---|---|---|---|---|---|---|
| ATOM | 6438 | CB | ILE | L | 75 | -92.331 | -5.734 | -33.753 | 1.00 | 89.53 | C |
| ATOM | 6439 | CG1 | ILE | L | 75 | -91.573 | -5.839 | -32.405 | 1.00 | 89.06 | C |
| ATOM | 6440 | CD1 | ILE | L | 75 | -92.289 | -5.229 | -31.167 | 1.00 | 89.50 | C |
| ATOM | 6441 | CG2 | ILE | L | 75 | -92.117 | -7.001 | -34.571 | 1.00 | 89.83 | C |
| ATOM | 6442 | C | ILE | L | 75 | -92.877 | -4.185 | -35.761 | 1.00 | 89.77 | C |
| ATOM | 6443 | O | ILE | L | 75 | -94.087 | -4.009 | -35.537 | 1.00 | 89.63 | O |
| ATOM | 6444 | N | SER | L | 76 | -92.317 | -4.061 | -36.993 | 1.00 | 91.77 | N |
| ATOM | 6445 | CA | SER | L | 76 | -93.070 | -3.740 | -38.216 | 1.00 | 92.22 | C |
| ATOM | 6446 | CB | SER | L | 76 | -92.136 | -3.517 | -39.405 | 1.00 | 92.21 | C |
| ATOM | 6447 | OG | SER | L | 76 | -91.592 | -4.712 | -39.940 | 1.00 | 92.40 | O |
| ATOM | 6448 | C | SER | L | 76 | -94.186 | -4.736 | -38.535 | 1.00 | 92.44 | C |
| ATOM | 6449 | O | SER | L | 76 | -95.344 | -4.330 | -38.640 | 1.00 | 92.48 | O |
| ATOM | 6450 | N | SER | L | 77 | -93.837 | -6.033 | -38.661 | 1.00 | 93.86 | N |
| ATOM | 6451 | CA | SER | L | 77 | -94.764 | -7.135 | -38.930 | 1.00 | 94.04 | C |
| ATOM | 6452 | CB | SER | L | 77 | -94.588 | -7.661 | -40.356 | 1.00 | 94.11 | C |
| ATOM | 6453 | OG | SER | L | 77 | -93.307 | -8.246 | -40.564 | 1.00 | 94.95 | O |
| ATOM | 6454 | C | SER | L | 77 | -94.478 | -8.241 | -37.914 | 1.00 | 93.95 | C |
| ATOM | 6455 | O | SER | L | 77 | -93.479 | -8.965 | -38.057 | 1.00 | 94.05 | O |
| ATOM | 6456 | N | LEU | L | 78 | -95.325 | -8.358 | -36.873 | 1.00 | 91.52 | N |
| ATOM | 6457 | CA | LEU | L | 78 | -95.143 | -9.379 | -35.846 | 1.00 | 91.26 | C |
| ATOM | 6458 | CB | LEU | L | 78 | -96.280 | -9.355 | -34.816 | 1.00 | 90.85 | C |
| ATOM | 6459 | CG | LEU | L | 78 | -96.090 | -8.432 | -33.626 | 1.00 | 91.04 | C |
| ATOM | 6460 | CD1 | LEU | L | 78 | -97.403 | -8.180 | -32.922 | 1.00 | 90.49 | C |
| ATOM | 6461 | CD2 | LEU | L | 78 | -95.079 | -8.997 | -32.635 | 1.00 | 90.90 | C |
| ATOM | 6462 | C | LEU | L | 78 | -94.984 | -10.795 | -36.418 | 1.00 | 91.43 | C |
| ATOM | 6463 | O | LEU | L | 78 | -95.784 | -11.244 | -37.252 | 1.00 | 91.64 | O |
| ATOM | 6464 | N | GLU | L | 79 | -93.919 | -11.477 | -35.993 | 1.00 | 91.30 | N |
| ATOM | 6465 | CA | GLU | L | 79 | -93.657 | -12.867 | -36.364 | 1.00 | 91.18 | C |
| ATOM | 6466 | CB | GLU | L | 79 | -92.191 | -13.076 | -36.792 | 1.00 | 91.43 | C |
| ATOM | 6467 | CG | GLU | L | 79 | -91.819 | -12.376 | -38.093 | 1.00 | 92.72 | C |
| ATOM | 6468 | CD | GLU | L | 79 | -92.563 | -12.807 | -39.343 | 1.00 | 95.02 | C |
| ATOM | 6469 | OE1 | GLU | L | 79 | -92.181 | -13.849 | -39.923 | 1.00 | 96.62 | O |
| ATOM | 6470 | OE2 | GLU | L | 79 | -93.520 | -12.106 | -39.747 | 1.00 | 95.71 | O |
| ATOM | 6471 | C | GLU | L | 79 | -94.037 | -13.648 | -35.090 | 1.00 | 90.77 | C |
| ATOM | 6472 | O | GLU | L | 79 | -94.210 | -13.018 | -34.051 | 1.00 | 90.66 | O |
| ATOM | 6473 | N | PRO | L | 80 | -94.246 | -14.970 | -35.092 | 1.00 | 91.38 | N |
| ATOM | 6474 | CA | PRO | L | 80 | -94.642 | -15.622 | -33.827 | 1.00 | 91.17 | C |
| ATOM | 6475 | CB | PRO | L | 80 | -95.162 | -16.983 | -34.277 | 1.00 | 90.98 | C |
| ATOM | 6476 | CG | PRO | L | 80 | -94.416 | -17.259 | -35.530 | 1.00 | 91.14 | C |
| ATOM | 6477 | CD | PRO | L | 80 | -94.137 | -15.944 | -36.197 | 1.00 | 91.24 | C |
| ATOM | 6478 | C | PRO | L | 80 | -93.529 | -15.710 | -32.776 | 1.00 | 90.98 | C |
| ATOM | 6479 | O | PRO | L | 80 | -93.824 | -15.728 | -31.579 | 1.00 | 90.95 | O |
| ATOM | 6480 | N | GLU | L | 81 | -92.252 | -15.738 | -33.220 | 1.00 | 92.87 | N |
| ATOM | 6481 | CA | GLU | L | 81 | -91.086 | -15.803 | -32.334 | 1.00 | 92.64 | C |
| ATOM | 6482 | CB | GLU | L | 81 | -89.820 | -16.179 | -33.114 | 1.00 | 92.93 | C |
| ATOM | 6483 | CG | GLU | L | 81 | -89.377 | -15.155 | -34.143 | 1.00 | 94.89 | C |
| ATOM | 6484 | CD | GLU | L | 81 | -89.752 | -15.458 | -35.582 | 1.00 | 98.75 | C |
| ATOM | 6485 | OE1 | GLU | L | 81 | -88.963 | -15.078 | -36.483 | 1.00 | 100.80 | O |
| ATOM | 6486 | OE2 | GLU | L | 81 | -90.828 | -16.065 | -35.812 | 1.00 | 99.87 | O |
| ATOM | 6487 | C | GLU | L | 81 | -90.882 | -14.511 | -31.519 | 1.00 | 91.98 | C |
| ATOM | 6488 | O | GLU | L | 81 | -90.150 | -14.520 | -30.521 | 1.00 | 92.22 | O |
| ATOM | 6489 | N | ASP | L | 82 | -91.546 | -13.415 | -31.959 | 1.00 | 89.40 | N |
| ATOM | 6490 | CA | ASP | L | 82 | -91.539 | -12.075 | -31.379 | 1.00 | 87.95 | C |
| ATOM | 6491 | CB | ASP | L | 82 | -91.895 | -11.046 | -32.449 | 1.00 | 87.98 | C |
| ATOM | 6492 | CG | ASP | L | 82 | -90.926 | -10.958 | -33.602 | 1.00 | 88.45 | C |
| ATOM | 6493 | OD1 | ASP | L | 82 | -89.798 | -11.506 | -33.485 | 1.00 | 88.93 | O |
| ATOM | 6494 | OD2 | ASP | L | 82 | -91.284 | -10.338 | -34.620 | 1.00 | 88.57 | O |
| ATOM | 6495 | C | ASP | L | 82 | -92.511 | -11.901 | -30.230 | 1.00 | 87.09 | C |
| ATOM | 6496 | O | ASP | L | 82 | -92.614 | -10.788 | -29.709 | 1.00 | 87.36 | O |
| ATOM | 6497 | N | PHE | L | 83 | -93.237 | -12.953 | -29.829 | 1.00 | 83.84 | N |
| ATOM | 6498 | CA | PHE | L | 83 | -94.176 | -12.805 | -28.726 | 1.00 | 82.86 | C |
| ATOM | 6499 | CB | PHE | L | 83 | -95.420 | -13.661 | -28.959 | 1.00 | 83.10 | C |
| ATOM | 6500 | CG | PHE | L | 83 | -96.319 | -13.096 | -30.029 | 1.00 | 83.64 | C |
| ATOM | 6501 | CD1 | PHE | L | 83 | -97.359 | -12.230 | -29.701 | 1.00 | 83.50 | C |
| ATOM | 6502 | CE1 | PHE | L | 83 | -98.177 | -11.689 | -30.693 | 1.00 | 83.49 | C |
| ATOM | 6503 | CZ | PHE | L | 83 | -97.966 | -12.014 | -32.016 | 1.00 | 84.02 | C |
| ATOM | 6504 | CE2 | PHE | L | 83 | -96.938 | -12.869 | -32.365 | 1.00 | 83.78 | C |
| ATOM | 6505 | CD2 | PHE | L | 83 | -96.117 | -13.413 | -31.369 | 1.00 | 83.83 | C |
| ATOM | 6506 | C | PHE | L | 83 | -93.453 | -13.101 | -27.412 | 1.00 | 82.13 | C |
| ATOM | 6507 | O | PHE | L | 83 | -93.299 | -14.268 | -27.028 | 1.00 | 82.31 | O |
| ATOM | 6508 | N | ALA | L | 84 | -92.949 | -12.033 | -26.751 | 1.00 | 76.94 | N |
| ATOM | 6509 | CA | ALA | L | 84 | -92.164 | -12.159 | -25.522 | 1.00 | 75.79 | C |
| ATOM | 6510 | CB | ALA | L | 84 | -90.682 | -12.323 | -25.879 | 1.00 | 75.58 | C |
| ATOM | 6511 | C | ALA | L | 84 | -92.334 | -10.966 | -24.594 | 1.00 | 75.01 | C |
| ATOM | 6512 | O | ALA | L | 84 | -93.255 | -10.160 | -24.765 | 1.00 | 75.03 | O |
| ATOM | 6513 | N | VAL | L | 85 | -91.438 | -10.861 | -23.600 | 1.00 | 71.29 | N |
| ATOM | 6514 | CA | VAL | L | 85 | -91.432 | -9.745 | -22.678 | 1.00 | 70.32 | C |

TABLE 14-continued

PCSK9 and AX132 Fab complex x-ray structure

| ATOM | 6515 | CB  | VAL | L | 85 | −91.437 | −10.138 | −21.183 | 1.00 | 70.16 | C |
| ---- | ---- | --- | --- | - | -- | ------- | ------- | ------- | ---- | ----- | - |
| ATOM | 6516 | CG1 | VAL | L | 85 | −91.439 | −8.908  | −20.288 | 1.00 | 69.53 | C |
| ATOM | 6517 | CG2 | VAL | L | 85 | −92.651 | −10.994 | −20.866 | 1.00 | 69.88 | C |
| ATOM | 6518 | C   | VAL | L | 85 | −90.304 | −8.797  | −23.120 | 1.00 | 70.01 | C |
| ATOM | 6519 | O   | VAL | L | 85 | −89.175 | −9.222  | −23.397 | 1.00 | 69.49 | O |
| ATOM | 6520 | N   | TYR | L | 86 | −90.654 | −7.517  | −23.255 | 1.00 | 71.60 | N |
| ATOM | 6521 | CA  | TYR | L | 86 | −89.729 | −6.496  | −23.705 | 1.00 | 71.23 | C |
| ATOM | 6522 | CB  | TYR | L | 86 | −90.308 | −5.790  | −24.934 | 1.00 | 71.07 | C |
| ATOM | 6523 | CG  | TYR | L | 86 | −90.265 | −6.692  | −26.152 | 1.00 | 71.27 | C |
| ATOM | 6524 | CD1 | TYR | L | 86 | −91.321 | −7.560  | −26.446 | 1.00 | 71.96 | C |
| ATOM | 6525 | CE1 | TYR | L | 86 | −91.269 | −8.413  | −27.552 | 1.00 | 72.18 | C |
| ATOM | 6526 | CZ  | TYR | L | 86 | −90.142 | −8.412  | −28.365 | 1.00 | 72.28 | C |
| ATOM | 6527 | OH  | TYR | L | 86 | −90.035 | −9.235  | −29.460 | 1.00 | 72.35 | O |
| ATOM | 6528 | CE2 | TYR | L | 86 | −89.084 | −7.566  | −28.083 | 1.00 | 71.38 | C |
| ATOM | 6529 | CD2 | TYR | L | 86 | −89.139 | −6.736  | −26.969 | 1.00 | 71.38 | C |
| ATOM | 6530 | C   | TYR | L | 86 | −89.346 | −5.577  | −22.575 | 1.00 | 71.10 | C |
| ATOM | 6531 | O   | TYR | L | 86 | −90.215 | −5.087  | −21.856 | 1.00 | 70.74 | O |
| ATOM | 6532 | N   | TYR | L | 87 | −88.031 | −5.404  | −22.384 | 1.00 | 72.64 | N |
| ATOM | 6533 | CA  | TYR | L | 87 | −87.469 | −4.603  | −21.302 | 1.00 | 72.75 | C |
| ATOM | 6534 | CB  | TYR | L | 87 | −86.618 | −5.511  | −20.388 | 1.00 | 72.34 | C |
| ATOM | 6535 | CG  | TYR | L | 87 | −87.400 | −6.389  | −19.435 | 1.00 | 71.58 | C |
| ATOM | 6536 | CD1 | TYR | L | 87 | −87.502 | −7.761  | −19.645 | 1.00 | 70.97 | C |
| ATOM | 6537 | CE1 | TYR | L | 87 | −88.202 | −8.579  | −18.759 | 1.00 | 70.24 | C |
| ATOM | 6538 | CZ  | TYR | L | 87 | −88.801 | −8.023  | −17.642 | 1.00 | 71.79 | C |
| ATOM | 6539 | OH  | TYR | L | 87 | −89.522 | −8.801  | −16.773 | 1.00 | 73.47 | O |
| ATOM | 6540 | CE2 | TYR | L | 87 | −88.691 | −6.665  | −17.400 | 1.00 | 72.08 | C |
| ATOM | 6541 | CD2 | TYR | L | 87 | −87.982 | −5.860  | −18.289 | 1.00 | 72.03 | C |
| ATOM | 6542 | C   | TYR | L | 87 | −86.616 | −3.414  | −21.770 | 1.00 | 73.36 | C |
| ATOM | 6543 | O   | TYR | L | 87 | −85.750 | −3.591  | −22.628 | 1.00 | 73.54 | O |
| ATOM | 6544 | N   | CYS | L | 88 | −86.835 | −2.217  | −21.188 | 1.00 | 77.68 | N |
| ATOM | 6545 | CA  | CYS | L | 88 | −86.028 | −1.041  | −21.514 | 1.00 | 78.32 | C |
| ATOM | 6546 | CB  | CYS | L | 88 | −86.872 | 0.181   | −21.865 | 1.00 | 78.96 | C |
| ATOM | 6547 | SG  | CYS | L | 88 | −88.008 | 0.730   | −20.559 | 1.00 | 82.86 | S |
| ATOM | 6548 | C   | CYS | L | 88 | −85.079 | −0.775  | −20.355 | 1.00 | 77.79 | C |
| ATOM | 6549 | O   | CYS | L | 88 | −85.490 | −0.841  | −19.189 | 1.00 | 78.19 | O |
| ATOM | 6550 | N   | GLN | L | 89 | −83.803 | −0.530  | −20.661 | 1.00 | 70.42 | N |
| ATOM | 6551 | CA  | GLN | L | 89 | −82.794 | −0.329  | −19.635 | 1.00 | 69.48 | C |
| ATOM | 6552 | CB  | GLN | L | 89 | −81.862 | −1.567  | −19.598 | 1.00 | 69.41 | C |
| ATOM | 6553 | CG  | GLN | L | 89 | −80.596 | −1.517  | −18.716 | 1.00 | 68.63 | C |
| ATOM | 6554 | CD  | GLN | L | 89 | −79.316 | −1.228  | −19.493 | 1.00 | 68.91 | C |
| ATOM | 6555 | OE1 | GLN | L | 89 | −78.460 | −0.440  | −19.069 | 1.00 | 70.17 | O |
| ATOM | 6556 | NE2 | GLN | L | 89 | −79.141 | −1.849  | −20.646 | 1.00 | 66.41 | N |
| ATOM | 6557 | C   | GLN | L | 89 | −82.029 | 0.950   | −19.865 | 1.00 | 69.23 | C |
| ATOM | 6558 | O   | GLN | L | 89 | −81.925 | 1.426   | −20.997 | 1.00 | 69.03 | O |
| ATOM | 6559 | N   | VAL | L | 90 | −81.461 | 1.492   | −18.775 | 1.00 | 68.06 | N |
| ATOM | 6560 | CA  | VAL | L | 90 | −80.656 | 2.706   | −18.760 | 1.00 | 67.45 | C |
| ATOM | 6561 | CB  | VAL | L | 90 | −81.630 | 3.921   | −18.668 | 1.00 | 67.12 | C |
| ATOM | 6562 | CG1 | VAL | L | 90 | −81.574 | 4.653   | −17.333 | 1.00 | 65.60 | C |
| ATOM | 6563 | CG2 | VAL | L | 90 | −81.443 | 4.859   | −19.837 | 1.00 | 66.82 | C |
| ATOM | 6564 | C   | VAL | L | 90 | −79.600 | 2.620   | −17.618 | 1.00 | 67.58 | C |
| ATOM | 6565 | O   | VAL | L | 90 | −79.731 | 1.769   | −16.729 | 1.00 | 67.28 | O |
| ATOM | 6566 | N   | TRP | L | 91 | −78.554 | 3.479   | −17.661 | 1.00 | 68.82 | N |
| ATOM | 6567 | CA  | TRP | L | 91 | −77.536 | 3.549   | −16.616 | 1.00 | 68.81 | C |
| ATOM | 6568 | CB  | TRP | L | 91 | −76.122 | 3.592   | −17.187 | 1.00 | 68.19 | C |
| ATOM | 6569 | CG  | TRP | L | 91 | −75.783 | 2.532   | −18.187 | 1.00 | 66.71 | C |
| ATOM | 6570 | CD1 | TRP | L | 91 | −75.505 | 2.718   | −19.507 | 1.00 | 66.34 | C |
| ATOM | 6571 | NE1 | TRP | L | 91 | −75.241 | 1.517   | −20.112 | 1.00 | 64.66 | N |
| ATOM | 6572 | CE2 | TRP | L | 91 | −75.303 | 0.524   | −19.173 | 1.00 | 65.19 | C |
| ATOM | 6573 | CD2 | TRP | L | 91 | −75.648 | 1.130   | −17.944 | 1.00 | 65.02 | C |
| ATOM | 6574 | CE3 | TRP | L | 91 | −75.782 | 0.317   | −16.803 | 1.00 | 63.85 | C |
| ATOM | 6575 | CZ3 | TRP | L | 91 | −75.544 | −1.041  | −16.918 | 1.00 | 63.53 | C |
| ATOM | 6576 | CH2 | TRP | L | 91 | −75.188 | −1.613  | −18.147 | 1.00 | 64.30 | C |
| ATOM | 6577 | CZ2 | TRP | L | 91 | −75.069 | −0.853  | −19.289 | 1.00 | 65.06 | C |
| ATOM | 6578 | C   | TRP | L | 91 | −77.833 | 4.838   | −15.823 | 1.00 | 69.85 | C |
| ATOM | 6579 | O   | TRP | L | 91 | −78.470 | 5.746   | −16.355 | 1.00 | 70.18 | O |
| ATOM | 6580 | N   | ASP | L | 92 | −77.387 | 4.921   | −14.559 | 1.00 | 75.57 | N |
| ATOM | 6581 | CA  | ASP | L | 92 | −77.627 | 6.045   | −13.651 | 1.00 | 76.89 | C |
| ATOM | 6582 | CB  | ASP | L | 92 | −79.015 | 5.835   | −12.988 | 1.00 | 77.25 | C |
| ATOM | 6583 | CG  | ASP | L | 92 | −79.606 | 6.941   | −12.110 | 1.00 | 79.26 | C |
| ATOM | 6584 | OD1 | ASP | L | 92 | −80.722 | 6.727   | −11.559 | 1.00 | 80.34 | O |
| ATOM | 6585 | OD2 | ASP | L | 92 | −78.948 | 8.033   | −11.967 | 1.00 | 81.56 | O |
| ATOM | 6586 | C   | ASP | L | 92 | −76.487 | 6.084   | −12.615 | 1.00 | 77.32 | C |
| ATOM | 6587 | O   | ASP | L | 92 | −75.542 | 5.313   | −12.746 | 1.00 | 77.83 | O |
| ATOM | 6588 | N   | SER | L | 93 | −76.544 | 6.982   | −11.610 | 1.00 | 79.15 | N |
| ATOM | 6589 | CA  | SER | L | 93 | −75.499 | 7.077   | −10.590 | 1.00 | 79.73 | C |
| ATOM | 6590 | CB  | SER | L | 93 | −75.288 | 8.516   | −10.152 | 1.00 | 79.60 | C |
| ATOM | 6591 | OG  | SER | L | 93 | −76.511 | 9.086   | −9.725  | 1.00 | 79.94 | O |
| ATOM | 6592 | C   | SER | L | 93 | −75.697 | 6.163   | −9.379  | 1.00 | 80.03 | C |

TABLE 14-continued

PCSK9 and AX132 Fab complex x-ray structure

| ATOM | 6593 | O   | SER | L | 93  | −74.897 | 5.233   | −9.249  | 1.00 | 80.11 | O |
|------|------|-----|-----|---|-----|---------|---------|---------|------|-------|---|
| ATOM | 6594 | N   | SER | L | 94  | −76.748 | 6.441   | −8.493  | 1.00 | 84.21 | N |
| ATOM | 6595 | CA  | SER | L | 94  | −77.148 | 5.744   | −7.232  | 1.00 | 84.27 | C |
| ATOM | 6596 | CB  | SER | L | 94  | −78.393 | 6.365   | −6.597  | 1.00 | 84.59 | C |
| ATOM | 6597 | OG  | SER | L | 94  | −79.012 | 5.503   | −5.650  | 1.00 | 85.72 | O |
| ATOM | 6598 | C   | SER | L | 94  | −77.349 | 4.300   | −7.562  | 1.00 | 84.06 | C |
| ATOM | 6599 | O   | SER | L | 94  | −76.424 | 3.532   | −7.245  | 1.00 | 85.11 | O |
| ATOM | 6600 | N   | PRO | L | 95  | −78.446 | 3.857   | −8.247  | 1.00 | 79.86 | N |
| ATOM | 6601 | CA  | PRO | L | 95  | −78.457 | 2.457   | −8.692  | 1.00 | 78.96 | C |
| ATOM | 6602 | CB  | PRO | L | 95  | −79.941 | 2.139   | −8.851  | 1.00 | 79.07 | C |
| ATOM | 6603 | CG  | PRO | L | 95  | −80.647 | 3.510   | −9.000  | 1.00 | 80.00 | C |
| ATOM | 6604 | CD  | PRO | L | 95  | −79.618 | 4.596   | −8.780  | 1.00 | 79.83 | C |
| ATOM | 6605 | C   | PRO | L | 95  | −77.667 | 2.548   | −10.032 | 1.00 | 77.85 | C |
| ATOM | 6606 | O   | PRO | L | 95  | −77.942 | 3.448   | −10.846 | 1.00 | 78.00 | O |
| ATOM | 6607 | N   | PRO | L | 96  | −76.603 | 1.761   | −10.262 | 1.00 | 70.15 | N |
| ATOM | 6608 | CA  | PRO | L | 96  | −75.851 | 1.923   | −11.509 | 1.00 | 69.43 | C |
| ATOM | 6609 | CB  | PRO | L | 96  | −74.619 | 1.023   | −11.313 | 1.00 | 69.39 | C |
| ATOM | 6610 | CG  | PRO | L | 96  | −74.644 | 0.592   | −9.927  | 1.00 | 69.41 | C |
| ATOM | 6611 | CD  | PRO | L | 96  | −76.042 | 0.682   | −9.445  | 1.00 | 70.05 | C |
| ATOM | 6612 | C   | PRO | L | 96  | −76.651 | 1.573   | −12.768 | 1.00 | 68.90 | C |
| ATOM | 6613 | O   | PRO | L | 96  | −76.341 | 2.061   | −13.862 | 1.00 | 68.98 | O |
| ATOM | 6614 | N   | VAL | L | 97  | −77.686 | 0.745   | −12.598 | 1.00 | 66.11 | N |
| ATOM | 6615 | CA  | VAL | L | 97  | −78.557 | 0.277   | −13.659 | 1.00 | 65.48 | C |
| ATOM | 6616 | CB  | VAL | L | 97  | −78.293 | −1.226  | −13.890 | 1.00 | 65.27 | C |
| ATOM | 6617 | CG1 | VAL | L | 97  | −78.875 | −2.070  | −12.764 | 1.00 | 64.59 | C |
| ATOM | 6618 | CG2 | VAL | L | 97  | −78.798 | −1.693  | −15.259 | 1.00 | 65.12 | C |
| ATOM | 6619 | C   | VAL | L | 97  | −80.005 | 0.547   | −13.304 | 1.00 | 65.49 | C |
| ATOM | 6620 | O   | VAL | L | 97  | −80.340 | 0.630   | −12.131 | 1.00 | 65.64 | O |
| ATOM | 6621 | N   | VAL | L | 98  | −80.859 | 0.719   | −14.312 | 1.00 | 67.13 | N |
| ATOM | 6622 | CA  | VAL | L | 98  | −82.298 | 0.927   | −14.142 | 1.00 | 67.28 | C |
| ATOM | 6623 | CB  | VAL | L | 98  | −82.792 | 2.409   | −14.141 | 1.00 | 67.09 | C |
| ATOM | 6624 | CG1 | VAL | L | 98  | −84.293 | 2.487   | −13.853 | 1.00 | 66.37 | C |
| ATOM | 6625 | CG2 | VAL | L | 98  | −82.029 | 3.259   | −13.133 | 1.00 | 67.24 | C |
| ATOM | 6626 | C   | VAL | L | 98  | −82.954 | 0.110   | −15.239 | 1.00 | 67.85 | C |
| ATOM | 6627 | O   | VAL | L | 98  | −82.553 | 0.205   | −16.409 | 1.00 | 67.78 | O |
| ATOM | 6628 | N   | PHE | L | 99  | −83.944 | −0.706  | −14.863 | 1.00 | 70.44 | N |
| ATOM | 6629 | CA  | PHE | L | 99  | −84.703 | −1.527  | −15.806 | 1.00 | 70.85 | C |
| ATOM | 6630 | CB  | PHE | L | 99  | −84.611 | −3.026  | −15.427 | 1.00 | 70.67 | C |
| ATOM | 6631 | CG  | PHE | L | 99  | −83.397 | −3.764  | −15.931 | 1.00 | 69.18 | C |
| ATOM | 6632 | CD1 | PHE | L | 99  | −82.386 | −4.146  | −15.060 | 1.00 | 68.29 | C |
| ATOM | 6633 | CE1 | PHE | L | 99  | −81.243 | −4.810  | −15.532 | 1.00 | 68.03 | C |
| ATOM | 6634 | CZ  | PHE | L | 99  | −81.128 | −5.108  | −16.874 | 1.00 | 67.77 | C |
| ATOM | 6635 | CE2 | PHE | L | 99  | −82.132 | −4.742  | −17.750 | 1.00 | 67.63 | C |
| ATOM | 6636 | CD2 | PHE | L | 99  | −83.266 | −4.080  | −17.278 | 1.00 | 67.90 | C |
| ATOM | 6637 | C   | PHE | L | 99  | −86.164 | −1.108  | −15.758 | 1.00 | 71.49 | C |
| ATOM | 6638 | O   | PHE | L | 99  | −86.664 | −0.705  | −14.712 | 1.00 | 71.24 | O |
| ATOM | 6639 | N   | GLY | L | 100 | −86.847 | −1.233  | −16.875 | 1.00 | 73.30 | N |
| ATOM | 6640 | CA  | GLY | L | 100 | −88.275 | −0.956  | −16.922 | 1.00 | 74.74 | C |
| ATOM | 6641 | C   | GLY | L | 100 | −89.021 | −2.176  | −16.395 | 1.00 | 75.62 | C |
| ATOM | 6642 | O   | GLY | L | 100 | −88.418 | −3.247  | −16.191 | 1.00 | 75.82 | O |
| ATOM | 6643 | N   | GLY | L | 101 | −90.325 | −2.017  | −16.173 | 1.00 | 77.20 | N |
| ATOM | 6644 | CA  | GLY | L | 101 | −91.194 | −3.082  | −15.670 | 1.00 | 78.41 | C |
| ATOM | 6645 | C   | GLY | L | 101 | −91.351 | −4.249  | −16.630 | 1.00 | 79.36 | C |
| ATOM | 6646 | O   | GLY | L | 101 | −91.566 | −5.391  | −16.204 | 1.00 | 79.33 | O |
| ATOM | 6647 | N   | GLY | L | 102 | −91.211 | −3.952  | −17.923 | 1.00 | 79.85 | N |
| ATOM | 6648 | CA  | GLY | L | 102 | −91.351 | −4.918  | −18.998 | 1.00 | 80.96 | C |
| ATOM | 6649 | C   | GLY | L | 102 | −92.736 | −4.862  | −19.597 | 1.00 | 81.95 | C |
| ATOM | 6650 | O   | GLY | L | 102 | −93.700 | −4.480  | −18.921 | 1.00 | 82.12 | O |
| ATOM | 6651 | N   | THR | L | 103 | −92.842 | −5.243  | −20.873 | 1.00 | 82.02 | N |
| ATOM | 6652 | CA  | THR | L | 103 | −94.110 | −5.263  | −21.594 | 1.00 | 82.88 | C |
| ATOM | 6653 | CB  | THR | L | 103 | −94.169 | −4.102  | −22.607 | 1.00 | 82.67 | C |
| ATOM | 6654 | OG1 | THR | L | 103 | −94.459 | −2.902  | −21.906 | 1.00 | 82.87 | O |
| ATOM | 6655 | CG2 | THR | L | 103 | −95.193 | −4.313  | −23.719 | 1.00 | 82.37 | C |
| ATOM | 6656 | C   | THR | L | 103 | −94.255 | −6.640  | −22.208 | 1.00 | 83.86 | C |
| ATOM | 6657 | O   | THR | L | 103 | −93.358 | −7.072  | −22.945 | 1.00 | 83.91 | O |
| ATOM | 6658 | N   | LYS | L | 104 | −95.367 | −7.334  | −21.899 | 1.00 | 84.99 | N |
| ATOM | 6659 | CA  | LYS | L | 104 | −95.620 | −8.650  | −22.460 | 1.00 | 86.22 | C |
| ATOM | 6660 | CB  | LYS | L | 104 | −96.429 | −9.521  | −21.486 | 1.00 | 86.41 | C |
| ATOM | 6661 | CG  | LYS | L | 104 | −96.530 | −10.982 | −21.928 | 1.00 | 87.85 | C |
| ATOM | 6662 | CD  | LYS | L | 104 | −97.400 | −11.773 | −20.983 | 1.00 | 90.43 | C |
| ATOM | 6663 | CE  | LYS | L | 104 | −98.252 | −12.784 | −21.725 | 1.00 | 92.63 | C |
| ATOM | 6664 | NZ  | LYS | L | 104 | −99.625 | −12.928 | −21.124 | 1.00 | 94.80 | N |
| ATOM | 6665 | C   | LYS | L | 104 | −96.359 | −8.467  | −23.780 | 1.00 | 86.73 | C |
| ATOM | 6666 | O   | LYS | L | 104 | −97.348 | −7.744  | −23.820 | 1.00 | 87.11 | O |
| ATOM | 6667 | N   | VAL | L | 105 | −95.869 | −9.096  | −24.858 | 1.00 | 87.60 | N |
| ATOM | 6668 | CA  | VAL | L | 105 | −96.499 | −9.049  | −26.181 | 1.00 | 88.62 | C |
| ATOM | 6669 | CB  | VAL | L | 105 | −95.529 | −8.643  | −27.320 | 1.00 | 88.32 | C |
| ATOM | 6670 | CG1 | VAL | L | 105 | −96.210 | −8.683  | −28.680 | 1.00 | 87.75 | C |

TABLE 14-continued

PCSK9 and AX132 Fab complex x-ray structure

| ATOM | 6671 | CG2 | VAL | L | 105 | −94.934 | −7.267 | −27.067 | 1.00 | 88.51 | C |
|---|---|---|---|---|---|---|---|---|---|---|---|
| ATOM | 6672 | C | VAL | L | 105 | −97.097 | −10.445 | −26.370 | 1.00 | 89.97 | C |
| ATOM | 6673 | O | VAL | L | 105 | −96.359 | −11.421 | −26.588 | 1.00 | 90.13 | O |
| ATOM | 6674 | N | GLU | L | 106 | −98.437 | −10.530 | −26.218 | 1.00 | 92.87 | N |
| ATOM | 6675 | CA | GLU | L | 106 | −99.263 | −11.740 | −26.323 | 1.00 | 94.05 | C |
| ATOM | 6676 | CB | GLU | L | 106 | −100.269 | −11.748 | −25.136 | 1.00 | 93.91 | C |
| ATOM | 6677 | CG | GLU | L | 106 | −101.676 | −12.282 | −25.390 | 1.00 | 95.35 | C |
| ATOM | 6678 | CD | GLU | L | 106 | −102.706 | −12.100 | −24.284 | 1.00 | 97.66 | C |
| ATOM | 6679 | OE1 | GLU | L | 106 | −103.918 | −12.230 | −24.581 | 1.00 | 98.65 | O |
| ATOM | 6680 | OE2 | GLU | L | 106 | −102.309 | −11.837 | −23.123 | 1.00 | 98.64 | O |
| ATOM | 6681 | C | GLU | L | 106 | −99.950 | −11.798 | −27.714 | 1.00 | 94.62 | C |
| ATOM | 6682 | O | GLU | L | 106 | −100.023 | −10.774 | −28.395 | 1.00 | 94.58 | O |
| ATOM | 6683 | N | ILE | L | 107 | −100.419 | −12.986 | −28.144 | 1.00 | 95.83 | N |
| ATOM | 6684 | CA | ILE | L | 107 | −101.120 | −13.133 | −29.426 | 1.00 | 96.60 | C |
| ATOM | 6685 | CB | ILE | L | 107 | −100.935 | −14.524 | −30.095 | 1.00 | 96.59 | C |
| ATOM | 6686 | CG1 | ILE | L | 107 | −99.502 | −15.040 | −29.959 | 1.00 | 97.14 | C |
| ATOM | 6687 | CD1 | ILE | L | 107 | −99.405 | −16.507 | −29.631 | 1.00 | 99.25 | C |
| ATOM | 6688 | CG2 | ILE | L | 107 | −101.348 | −14.475 | −31.577 | 1.00 | 96.87 | C |
| ATOM | 6689 | C | ILE | L | 107 | −102.607 | −12.810 | −29.244 | 1.00 | 96.95 | C |
| ATOM | 6690 | O | ILE | L | 107 | −103.225 | −13.346 | −28.328 | 1.00 | 96.97 | O |
| ATOM | 6691 | N | LYS | L | 108 | −103.176 | −11.938 | −30.108 | 1.00 | 96.98 | N |
| ATOM | 6692 | CA | LYS | L | 108 | −104.599 | −11.607 | −30.058 | 1.00 | 97.38 | C |
| ATOM | 6693 | CB | LYS | L | 108 | −104.900 | −10.160 | −30.481 | 1.00 | 97.23 | C |
| ATOM | 6694 | C | LYS | L | 108 | −105.325 | −12.611 | −30.945 | 1.00 | 97.70 | C |
| ATOM | 6695 | O | LYS | L | 108 | −104.957 | −12.802 | −32.106 | 1.00 | 97.86 | O |
| ATOM | 6696 | N | ARG | L | 109 | −106.320 | −13.293 | −30.379 | 1.00 | 97.85 | N |
| ATOM | 6697 | CA | ARG | L | 109 | −107.120 | −14.292 | −31.082 | 1.00 | 98.21 | C |
| ATOM | 6698 | CB | ARG | L | 109 | −106.779 | −15.722 | −30.606 | 1.00 | 98.23 | C |
| ATOM | 6699 | C | ARG | L | 109 | −108.608 | −14.008 | −30.891 | 1.00 | 98.48 | C |
| ATOM | 6700 | O | ARG | L | 109 | −109.004 | −13.183 | −30.048 | 1.00 | 98.46 | O |
| ATOM | 6701 | N | THR | L | 110 | −109.425 | −14.704 | −31.702 | 1.00 | 97.91 | N |
| ATOM | 6702 | CA | THR | L | 110 | −110.881 | −14.658 | −31.715 | 1.00 | 98.06 | C |
| ATOM | 6703 | CB | THR | L | 110 | −111.405 | −15.547 | −32.862 | 1.00 | 98.16 | C |
| ATOM | 6704 | OG1 | THR | L | 110 | −112.496 | −16.344 | −32.388 | 1.00 | 99.22 | O |
| ATOM | 6705 | CG2 | THR | L | 110 | −110.303 | −16.459 | −33.489 | 1.00 | 98.04 | C |
| ATOM | 6706 | C | THR | L | 110 | −111.359 | −15.063 | −30.318 | 1.00 | 98.03 | C |
| ATOM | 6707 | O | THR | L | 110 | −110.979 | −16.131 | −29.828 | 1.00 | 98.07 | O |
| ATOM | 6708 | N | VAL | L | 111 | −112.132 | −14.190 | −29.665 | 1.00 | 96.70 | N |
| ATOM | 6709 | CA | VAL | L | 111 | −112.642 | −14.402 | −28.307 | 1.00 | 97.03 | C |
| ATOM | 6710 | CB | VAL | L | 111 | −113.562 | −13.244 | −27.827 | 1.00 | 97.09 | C |
| ATOM | 6711 | CG1 | VAL | L | 111 | −113.975 | −13.413 | −26.361 | 1.00 | 96.68 | C |
| ATOM | 6712 | CG2 | VAL | L | 111 | −112.899 | −11.889 | −28.048 | 1.00 | 97.07 | C |
| ATOM | 6713 | C | VAL | L | 111 | −113.266 | −15.799 | −28.123 | 1.00 | 97.35 | C |
| ATOM | 6714 | O | VAL | L | 111 | −114.399 | −16.045 | −28.535 | 1.00 | 97.33 | O |
| ATOM | 6715 | N | ALA | L | 112 | −112.487 | −16.715 | −27.528 | 1.00 | 98.73 | N |
| ATOM | 6716 | CA | ALA | L | 112 | −112.891 | −18.095 | −27.255 | 1.00 | 98.93 | C |
| ATOM | 6717 | CB | ALA | L | 112 | −111.740 | −19.049 | −27.531 | 1.00 | 98.76 | C |
| ATOM | 6718 | C | ALA | L | 112 | −113.411 | −18.247 | −25.814 | 1.00 | 99.15 | C |
| ATOM | 6719 | O | ALA | L | 112 | −113.018 | −17.496 | −24.916 | 1.00 | 99.01 | O |
| ATOM | 6720 | N | ALA | L | 113 | −114.331 | −19.202 | −25.620 | 1.00 | 101.81 | N |
| ATOM | 6721 | CA | ALA | L | 113 | −114.977 | −19.468 | −24.336 | 1.00 | 102.10 | C |
| ATOM | 6722 | CB | ALA | L | 113 | −116.492 | −19.449 | −24.498 | 1.00 | 102.05 | C |
| ATOM | 6723 | C | ALA | L | 113 | −114.502 | −20.788 | −23.690 | 1.00 | 102.28 | C |
| ATOM | 6724 | O | ALA | L | 113 | −114.144 | −21.749 | −24.405 | 1.00 | 102.06 | O |
| ATOM | 6725 | N | PRO | L | 114 | −114.478 | −20.839 | −22.331 | 1.00 | 103.19 | N |
| ATOM | 6726 | CA | PRO | L | 114 | −113.984 | −22.049 | −21.663 | 1.00 | 103.27 | C |
| ATOM | 6727 | CB | PRO | L | 114 | −113.447 | −21.511 | −20.332 | 1.00 | 103.29 | C |
| ATOM | 6728 | CG | PRO | L | 114 | −114.314 | −20.314 | −20.022 | 1.00 | 103.13 | C |
| ATOM | 6729 | CD | PRO | L | 114 | −114.848 | −19.793 | −21.346 | 1.00 | 103.11 | C |
| ATOM | 6730 | C | PRO | L | 114 | −114.993 | −23.176 | −21.451 | 1.00 | 103.39 | C |
| ATOM | 6731 | O | PRO | L | 114 | −116.121 | −22.949 | −20.990 | 1.00 | 103.53 | O |
| ATOM | 6732 | N | SER | L | 115 | −114.560 | −24.407 | −21.775 | 1.00 | 102.39 | N |
| ATOM | 6733 | CA | SER | L | 115 | −115.326 | −25.629 | −21.582 | 1.00 | 102.50 | C |
| ATOM | 6734 | CB | SER | L | 115 | −114.770 | −26.762 | −22.451 | 1.00 | 102.27 | C |
| ATOM | 6735 | OG | SER | L | 115 | −114.168 | −26.312 | −23.655 | 1.00 | 102.46 | O |
| ATOM | 6736 | C | SER | L | 115 | −115.063 | −25.913 | −20.101 | 1.00 | 102.76 | C |
| ATOM | 6737 | O | SER | L | 115 | −113.972 | −26.357 | −19.774 | 1.00 | 103.38 | O |
| ATOM | 6738 | N | VAL | L | 116 | −116.005 | −25.584 | −19.202 | 1.00 | 103.10 | N |
| ATOM | 6739 | CA | VAL | L | 116 | −115.844 | −25.775 | −17.746 | 1.00 | 103.42 | C |
| ATOM | 6740 | CB | VAL | L | 116 | −116.618 | −24.694 | −16.929 | 1.00 | 103.37 | C |
| ATOM | 6741 | CG1 | VAL | L | 116 | −116.510 | −24.909 | −15.417 | 1.00 | 103.06 | C |
| ATOM | 6742 | CG2 | VAL | L | 116 | −116.146 | −23.289 | −17.306 | 1.00 | 102.93 | C |
| ATOM | 6743 | C | VAL | L | 116 | −116.082 | −27.243 | −17.276 | 1.00 | 103.88 | C |
| ATOM | 6744 | O | VAL | L | 116 | −116.879 | −27.965 | −17.875 | 1.00 | 103.91 | O |
| ATOM | 6745 | N | PHE | L | 117 | −115.334 | −27.686 | −16.243 | 1.00 | 103.74 | N |
| ATOM | 6746 | CA | PHE | L | 117 | −115.403 | −29.026 | −15.653 | 1.00 | 104.14 | C |
| ATOM | 6747 | CB | PHE | L | 117 | −114.356 | −29.950 | −16.276 | 1.00 | 103.83 | C |
| ATOM | 6748 | CG | PHE | L | 117 | −114.546 | −30.170 | −17.752 | 1.00 | 103.51 | C |

TABLE 14-continued

PCSK9 and AX132 Fab complex x-ray structure

| ATOM | 6749 | CD1 | PHE | L | 117 | −115.308 | −31.228 | −18.220 | 1.00 | 103.82 | C |
|---|---|---|---|---|---|---|---|---|---|---|---|
| ATOM | 6750 | CE1 | PHE | L | 117 | −115.481 | −31.431 | −19.594 | 1.00 | 103.88 | C |
| ATOM | 6751 | CZ | PHE | L | 117 | −114.894 | −30.572 | −20.500 | 1.00 | 102.95 | C |
| ATOM | 6752 | CE2 | PHE | L | 117 | −114.135 | −29.520 | −20.049 | 1.00 | 102.47 | C |
| ATOM | 6753 | CD2 | PHE | L | 117 | −113.957 | −29.322 | −18.679 | 1.00 | 102.84 | C |
| ATOM | 6754 | C | PHE | L | 117 | −115.221 | −28.963 | −14.135 | 1.00 | 104.79 | C |
| ATOM | 6755 | O | PHE | L | 117 | −114.699 | −27.976 | −13.608 | 1.00 | 104.81 | O |
| ATOM | 6756 | N | ILE | L | 118 | −115.689 | −29.999 | −13.429 | 1.00 | 105.72 | N |
| ATOM | 6757 | CA | ILE | L | 118 | −115.570 | −30.083 | −11.973 | 1.00 | 106.31 | C |
| ATOM | 6758 | CB | ILE | L | 118 | −116.703 | −29.392 | −11.157 | 1.00 | 106.17 | C |
| ATOM | 6759 | CG1 | ILE | L | 118 | −116.318 | −29.259 | −9.671 | 1.00 | 106.10 | C |
| ATOM | 6760 | CD1 | ILE | L | 118 | −116.971 | −28.104 | −8.948 | 1.00 | 105.90 | C |
| ATOM | 6761 | CG2 | ILE | L | 118 | −118.068 | −30.061 | −11.350 | 1.00 | 106.16 | C |
| ATOM | 6762 | C | ILE | L | 118 | −115.273 | −31.515 | −11.585 | 1.00 | 106.81 | C |
| ATOM | 6763 | O | ILE | L | 118 | −115.994 | −32.425 | −12.004 | 1.00 | 106.98 | O |
| ATOM | 6764 | N | PHE | L | 119 | −114.173 | −31.715 | −10.838 | 1.00 | 107.59 | N |
| ATOM | 6765 | CA | PHE | L | 119 | −113.720 | −33.030 | −10.400 | 1.00 | 107.97 | C |
| ATOM | 6766 | CB | PHE | L | 119 | −112.327 | −33.337 | −10.936 | 1.00 | 107.73 | C |
| ATOM | 6767 | CG | PHE | L | 119 | −112.211 | −33.252 | −12.437 | 1.00 | 107.44 | C |
| ATOM | 6768 | CD1 | PHE | L | 119 | −111.963 | −32.035 | −13.065 | 1.00 | 107.12 | C |
| ATOM | 6769 | CE1 | PHE | L | 119 | −111.832 | −31.959 | −14.454 | 1.00 | 107.46 | C |
| ATOM | 6770 | CZ | PHE | L | 119 | −111.941 | −33.100 | −15.220 | 1.00 | 107.76 | C |
| ATOM | 6771 | CE2 | PHE | L | 119 | −112.180 | −34.317 | −14.613 | 1.00 | 107.82 | C |
| ATOM | 6772 | CD2 | PHE | L | 119 | −112.321 | −34.390 | −13.223 | 1.00 | 107.63 | C |
| ATOM | 6773 | C | PHE | L | 119 | −113.773 | −33.107 | −8.885 | 1.00 | 108.58 | C |
| ATOM | 6774 | O | PHE | L | 119 | −113.236 | −32.223 | −8.204 | 1.00 | 108.62 | O |
| ATOM | 6775 | N | PRO | L | 120 | −114.453 | −34.144 | −8.342 | 1.00 | 109.75 | N |
| ATOM | 6776 | CA | PRO | L | 120 | −114.597 | −34.244 | −6.882 | 1.00 | 110.10 | C |
| ATOM | 6777 | CB | PRO | L | 120 | −115.986 | −34.865 | −6.729 | 1.00 | 110.03 | C |
| ATOM | 6778 | CG | PRO | L | 120 | −116.210 | −35.651 | −8.017 | 1.00 | 109.68 | C |
| ATOM | 6779 | CD | PRO | L | 120 | −115.169 | −35.245 | −9.024 | 1.00 | 109.58 | C |
| ATOM | 6780 | C | PRO | L | 120 | −113.509 | −35.063 | −6.169 | 1.00 | 110.63 | C |
| ATOM | 6781 | O | PRO | L | 120 | −112.884 | −35.921 | −6.813 | 1.00 | 110.39 | O |
| ATOM | 6782 | N | PRO | L | 121 | −113.284 | −34.826 | −4.839 | 1.00 | 112.38 | N |
| ATOM | 6783 | CA | PRO | L | 121 | −112.258 | −35.591 | −4.101 | 1.00 | 112.95 | C |
| ATOM | 6784 | CB | PRO | L | 121 | −112.477 | −35.183 | −2.645 | 1.00 | 112.85 | C |
| ATOM | 6785 | CG | PRO | L | 121 | −113.056 | −33.833 | −2.741 | 1.00 | 112.82 | C |
| ATOM | 6786 | CD | PRO | L | 121 | −113.936 | −33.839 | −3.955 | 1.00 | 112.45 | C |
| ATOM | 6787 | C | PRO | L | 121 | −112.342 | −37.096 | −4.304 | 1.00 | 113.61 | C |
| ATOM | 6788 | O | PRO | L | 121 | −113.373 | −37.733 | −4.076 | 1.00 | 113.95 | O |
| ATOM | 6789 | N | SER | L | 122 | −111.224 | −37.636 | −4.780 | 1.00 | 115.25 | N |
| ATOM | 6790 | CA | SER | L | 122 | −110.957 | −39.021 | −5.134 | 1.00 | 115.76 | C |
| ATOM | 6791 | CB | SER | L | 122 | −109.538 | −39.115 | −5.709 | 1.00 | 115.91 | C |
| ATOM | 6792 | OG | SER | L | 122 | −109.262 | −40.311 | −6.419 | 1.00 | 116.00 | O |
| ATOM | 6793 | C | SER | L | 122 | −111.161 | −40.037 | −3.991 | 1.00 | 116.05 | C |
| ATOM | 6794 | O | SER | L | 122 | −111.533 | −39.700 | −2.859 | 1.00 | 115.84 | O |
| ATOM | 6795 | N | ASP | L | 123 | −110.912 | −41.303 | −4.349 | 1.00 | 116.73 | N |
| ATOM | 6796 | CA | ASP | L | 123 | −110.946 | −42.528 | −3.559 | 1.00 | 117.16 | C |
| ATOM | 6797 | CB | ASP | L | 123 | −110.564 | −43.724 | −4.488 | 1.00 | 117.21 | C |
| ATOM | 6798 | CG | ASP | L | 123 | −109.458 | −43.456 | −5.531 | 1.00 | 117.36 | C |
| ATOM | 6799 | OD1 | ASP | L | 123 | −108.256 | −43.470 | −5.152 | 1.00 | 117.15 | O |
| ATOM | 6800 | OD2 | ASP | L | 123 | −109.799 | −43.244 | −6.721 | 1.00 | 117.04 | O |
| ATOM | 6801 | C | ASP | L | 123 | −109.973 | −42.424 | −2.361 | 1.00 | 117.43 | C |
| ATOM | 6802 | O | ASP | L | 123 | −110.401 | −42.159 | −1.226 | 1.00 | 117.38 | O |
| ATOM | 6803 | N | GLU | L | 124 | −108.659 | −42.605 | −2.650 | 1.00 | 115.50 | N |
| ATOM | 6804 | CA | GLU | L | 124 | −107.540 | −42.560 | −1.721 | 1.00 | 115.75 | C |
| ATOM | 6805 | CB | GLU | L | 124 | −106.249 | −43.030 | −2.405 | 1.00 | 115.57 | C |
| ATOM | 6806 | C | GLU | L | 124 | −107.375 | −41.165 | −1.165 | 1.00 | 116.01 | C |
| ATOM | 6807 | O | GLU | L | 124 | −106.902 | −41.025 | −0.037 | 1.00 | 116.10 | O |
| ATOM | 6808 | N | GLN | L | 125 | −107.782 | −40.132 | −1.944 | 1.00 | 114.68 | N |
| ATOM | 6809 | CA | GLN | L | 125 | −107.713 | −38.721 | −1.544 | 1.00 | 114.99 | C |
| ATOM | 6810 | CB | GLN | L | 125 | −108.446 | −37.837 | −2.570 | 1.00 | 114.92 | C |
| ATOM | 6811 | CG | GLN | L | 125 | −107.624 | −36.687 | −3.144 | 1.00 | 114.27 | C |
| ATOM | 6812 | CD | GLN | L | 125 | −107.616 | −35.471 | −2.268 | 1.00 | 113.67 | C |
| ATOM | 6813 | OE1 | GLN | L | 125 | −108.568 | −34.712 | −2.245 | 1.00 | 113.40 | O |
| ATOM | 6814 | NE2 | GLN | L | 125 | −106.543 | −35.261 | −1.535 | 1.00 | 113.42 | N |
| ATOM | 6815 | C | GLN | L | 125 | −108.358 | −38.560 | −0.166 | 1.00 | 115.37 | C |
| ATOM | 6816 | O | GLN | L | 125 | −107.775 | −37.929 | 0.721 | 1.00 | 115.33 | O |
| ATOM | 6817 | N | LEU | L | 126 | −109.542 | −39.176 | 0.015 | 1.00 | 116.16 | N |
| ATOM | 6818 | CA | LEU | L | 126 | −110.274 | −39.125 | 1.268 | 1.00 | 116.50 | C |
| ATOM | 6819 | CB | LEU | L | 126 | −111.768 | −39.246 | 1.028 | 1.00 | 116.54 | C |
| ATOM | 6820 | CG | LEU | L | 126 | −112.405 | −37.947 | 0.560 | 1.00 | 117.03 | C |
| ATOM | 6821 | CD1 | LEU | L | 126 | −113.452 | −38.207 | −0.498 | 1.00 | 117.40 | C |
| ATOM | 6822 | CD2 | LEU | L | 126 | −112.930 | −37.122 | 1.734 | 1.00 | 116.35 | C |
| ATOM | 6823 | C | LEU | L | 126 | −109.768 | −40.117 | 2.295 | 1.00 | 116.62 | C |
| ATOM | 6824 | O | LEU | L | 126 | −109.705 | −39.763 | 3.478 | 1.00 | 116.58 | O |
| ATOM | 6825 | N | LYS | L | 127 | −109.360 | −41.341 | 1.848 | 1.00 | 116.04 | N |
| ATOM | 6826 | CA | LYS | L | 127 | −108.796 | −42.389 | 2.722 | 1.00 | 116.17 | C |

TABLE 14-continued

PCSK9 and AX132 Fab complex x-ray structure

| ATOM | 6827 | CB | LYS | L | 127 | −108.491 | −43.676 | 1.930 | 1.00 | 115.92 | C |
|------|------|-----|-----|---|-----|----------|---------|-------|------|--------|---|
| ATOM | 6828 | C | LYS | L | 127 | −107.530 | −41.864 | 3.449 | 1.00 | 116.32 | C |
| ATOM | 6829 | O | LYS | L | 127 | −107.066 | −42.491 | 4.403 | 1.00 | 116.50 | O |
| ATOM | 6830 | N | SER | L | 128 | −107.004 | −40.693 | 2.994 | 1.00 | 115.89 | N |
| ATOM | 6831 | CA | SER | L | 128 | −105.839 | −39.983 | 3.526 | 1.00 | 115.99 | C |
| ATOM | 6832 | CB | SER | L | 128 | −104.979 | −39.431 | 2.391 | 1.00 | 115.95 | C |
| ATOM | 6833 | OG | SER | L | 128 | −105.498 | −38.222 | 1.860 | 1.00 | 116.15 | O |
| ATOM | 6834 | C | SER | L | 128 | −106.254 | −38.851 | 4.489 | 1.00 | 116.09 | C |
| ATOM | 6835 | O | SER | L | 128 | −105.440 | −38.405 | 5.302 | 1.00 | 116.17 | O |
| ATOM | 6836 | N | GLY | L | 129 | −107.498 | −38.394 | 4.378 | 1.00 | 115.76 | N |
| ATOM | 6837 | CA | GLY | L | 129 | −108.029 | −37.348 | 5.242 | 1.00 | 115.83 | C |
| ATOM | 6838 | C | GLY | L | 129 | −107.873 | −35.923 | 4.756 | 1.00 | 115.89 | C |
| ATOM | 6839 | O | GLY | L | 129 | −107.638 | −35.014 | 5.560 | 1.00 | 115.86 | O |
| ATOM | 6840 | N | THR | L | 130 | −108.023 | −35.717 | 3.440 | 1.00 | 116.18 | N |
| ATOM | 6841 | CA | THR | L | 130 | −107.929 | −34.404 | 2.804 | 1.00 | 116.14 | C |
| ATOM | 6842 | CB | THR | L | 130 | −106.470 | −33.935 | 2.694 | 1.00 | 116.00 | C |
| ATOM | 6843 | OG1 | THR | L | 130 | −106.445 | −32.519 | 2.542 | 1.00 | 115.74 | O |
| ATOM | 6844 | CG2 | THR | L | 130 | −105.685 | −34.641 | 1.590 | 1.00 | 115.70 | C |
| ATOM | 6845 | C | THR | L | 130 | −108.774 | −34.374 | 1.530 | 1.00 | 116.34 | C |
| ATOM | 6846 | O | THR | L | 130 | −108.796 | −35.354 | 0.790 | 1.00 | 116.29 | O |
| ATOM | 6847 | N | ALA | L | 131 | −109.493 | −33.274 | 1.289 | 1.00 | 117.60 | N |
| ATOM | 6848 | CA | ALA | L | 131 | −110.354 | −33.187 | 0.112 | 1.00 | 117.89 | C |
| ATOM | 6849 | CB | ALA | L | 131 | −111.803 | −33.060 | 0.539 | 1.00 | 117.93 | C |
| ATOM | 6850 | C | ALA | L | 131 | −109.974 | −32.076 | −0.872 | 1.00 | 118.00 | C |
| ATOM | 6851 | O | ALA | L | 131 | −110.061 | −30.888 | −0.541 | 1.00 | 117.96 | O |
| ATOM | 6852 | N | SER | L | 132 | −109.554 | −32.479 | −2.088 | 1.00 | 118.64 | N |
| ATOM | 6853 | CA | SER | L | 132 | −109.147 | −31.585 | −3.170 | 1.00 | 118.99 | C |
| ATOM | 6854 | CB | SER | L | 132 | −107.705 | −31.864 | −3.607 | 1.00 | 119.09 | C |
| ATOM | 6855 | OG | SER | L | 132 | −106.716 | −31.360 | −2.719 | 1.00 | 119.55 | O |
| ATOM | 6856 | C | SER | L | 132 | −110.126 | −31.669 | −4.353 | 1.00 | 119.16 | C |
| ATOM | 6857 | O | SER | L | 132 | −110.204 | −32.688 | −5.058 | 1.00 | 119.13 | O |
| ATOM | 6858 | N | VAL | L | 133 | −110.883 | −30.575 | −4.546 | 1.00 | 121.01 | N |
| ATOM | 6859 | CA | VAL | L | 133 | −111.888 | −30.410 | −5.601 | 1.00 | 121.04 | C |
| ATOM | 6860 | CB | VAL | L | 133 | −113.241 | −29.885 | −5.055 | 1.00 | 121.01 | C |
| ATOM | 6861 | CG1 | VAL | L | 133 | −114.409 | −30.512 | −5.805 | 1.00 | 120.93 | C |
| ATOM | 6862 | CG2 | VAL | L | 133 | −113.379 | −30.109 | −3.550 | 1.00 | 120.63 | C |
| ATOM | 6863 | C | VAL | L | 133 | −111.316 | −29.472 | −6.662 | 1.00 | 121.16 | C |
| ATOM | 6864 | O | VAL | L | 133 | −110.865 | −28.368 | −6.330 | 1.00 | 121.07 | O |
| ATOM | 6865 | N | VAL | L | 134 | −111.306 | −29.913 | −7.929 | 1.00 | 123.41 | N |
| ATOM | 6866 | CA | VAL | L | 134 | −110.745 | −29.089 | −9.000 | 1.00 | 123.87 | C |
| ATOM | 6867 | CB | VAL | L | 134 | −109.389 | −29.596 | −9.575 | 1.00 | 123.85 | C |
| ATOM | 6868 | CG1 | VAL | L | 134 | −108.399 | −29.935 | −8.468 | 1.00 | 124.11 | C |
| ATOM | 6869 | CG2 | VAL | L | 134 | −109.573 | −30.782 | −10.510 | 1.00 | 124.19 | C |
| ATOM | 6870 | C | VAL | L | 134 | −111.715 | −28.622 | −10.084 | 1.00 | 124.09 | C |
| ATOM | 6871 | O | VAL | L | 134 | −112.620 | −29.356 | −10.470 | 1.00 | 124.11 | O |
| ATOM | 6872 | N | CYS | L | 135 | −111.492 | −27.394 | −10.580 | 1.00 | 126.57 | N |
| ATOM | 6873 | CA | CYS | L | 135 | −112.270 | −26.746 | −11.628 | 1.00 | 126.85 | C |
| ATOM | 6874 | CB | CYS | L | 135 | −112.871 | −25.443 | −11.105 | 1.00 | 127.54 | C |
| ATOM | 6875 | SG | CYS | L | 135 | −114.387 | −24.909 | −11.952 | 1.00 | 131.74 | S |
| ATOM | 6876 | C | CYS | L | 135 | −111.368 | −26.496 | −12.838 | 1.00 | 125.82 | C |
| ATOM | 6877 | O | CYS | L | 135 | −110.424 | −25.711 | −12.749 | 1.00 | 125.75 | O |
| ATOM | 6878 | N | LEU | L | 136 | −111.645 | −27.170 | −13.952 | 1.00 | 118.46 | N |
| ATOM | 6879 | CA | LEU | L | 136 | −110.892 | −27.007 | −15.186 | 1.00 | 117.54 | C |
| ATOM | 6880 | CB | LEU | L | 136 | −110.699 | −28.362 | −15.885 | 1.00 | 117.36 | C |
| ATOM | 6881 | CG | LEU | L | 136 | −110.258 | −28.353 | −17.364 | 1.00 | 117.14 | C |
| ATOM | 6882 | CD1 | LEU | L | 136 | −108.845 | −27.832 | −17.534 | 1.00 | 117.06 | C |
| ATOM | 6883 | CD2 | LEU | L | 136 | −110.347 | −29.727 | −17.963 | 1.00 | 116.88 | C |
| ATOM | 6884 | C | LEU | L | 136 | −111.616 | −26.017 | −16.100 | 1.00 | 117.22 | C |
| ATOM | 6885 | O | LEU | L | 136 | −112.834 | −26.070 | −16.223 | 1.00 | 117.23 | O |
| ATOM | 6886 | N | LEU | L | 137 | −110.862 | −25.113 | −16.732 | 1.00 | 113.80 | N |
| ATOM | 6887 | CA | LEU | L | 137 | −111.347 | −24.097 | −17.663 | 1.00 | 113.18 | C |
| ATOM | 6888 | CB | LEU | L | 137 | −111.033 | −22.697 | −17.099 | 1.00 | 113.02 | C |
| ATOM | 6889 | CG | LEU | L | 137 | −112.020 | −22.035 | −16.120 | 1.00 | 112.83 | C |
| ATOM | 6890 | CD1 | LEU | L | 137 | −112.092 | −22.756 | −14.777 | 1.00 | 112.58 | C |
| ATOM | 6891 | CD2 | LEU | L | 137 | −111.601 | −20.602 | −15.845 | 1.00 | 112.49 | C |
| ATOM | 6892 | C | LEU | L | 137 | −110.550 | −24.361 | −18.944 | 1.00 | 113.02 | C |
| ATOM | 6893 | O | LEU | L | 137 | −109.562 | −23.679 | −19.214 | 1.00 | 113.12 | O |
| ATOM | 6894 | N | ASN | L | 138 | −110.943 | −25.399 | −19.700 | 1.00 | 111.77 | N |
| ATOM | 6895 | CA | ASN | L | 138 | −110.253 | −25.808 | −20.920 | 1.00 | 111.61 | C |
| ATOM | 6896 | CB | ASN | L | 138 | −110.601 | −27.233 | −21.292 | 1.00 | 111.47 | C |
| ATOM | 6897 | CG | ASN | L | 138 | −109.505 | −27.894 | −22.084 | 1.00 | 111.38 | C |
| ATOM | 6898 | OD1 | ASN | L | 138 | −109.548 | −27.949 | −23.314 | 1.00 | 111.97 | O |
| ATOM | 6899 | ND2 | ASN | L | 138 | −108.488 | −28.400 | −21.401 | 1.00 | 110.73 | N |
| ATOM | 6900 | C | ASN | L | 138 | −110.408 | −24.870 | −22.109 | 1.00 | 111.70 | C |
| ATOM | 6901 | O | ASN | L | 138 | −111.489 | −24.343 | −22.331 | 1.00 | 111.74 | O |
| ATOM | 6902 | N | ASN | L | 139 | −109.310 | −24.671 | −22.862 | 1.00 | 112.71 | N |
| ATOM | 6903 | CA | ASN | L | 139 | −109.150 | −23.835 | −24.063 | 1.00 | 113.10 | C |
| ATOM | 6904 | CB | ASN | L | 139 | −109.074 | −24.695 | −25.321 | 1.00 | 112.89 | C |

TABLE 14-continued

PCSK9 and AX132 Fab complex x-ray structure

| ATOM | 6905 | CG  | ASN | L | 139 | −107.809 | −25.512 | −25.418 | 1.00 | 112.69 | C |
| ATOM | 6906 | OD1 | ASN | L | 139 | −106.698 | −24.985 | −25.592 | 1.00 | 113.25 | O |
| ATOM | 6907 | ND2 | ASN | L | 139 | −107.952 | −26.824 | −25.323 | 1.00 | 112.42 | N |
| ATOM | 6908 | C   | ASN | L | 139 | −110.022 | −22.557 | −24.256 | 1.00 | 113.51 | C |
| ATOM | 6909 | O   | ASN | L | 139 | −111.145 | −22.634 | −24.764 | 1.00 | 113.56 | O |
| ATOM | 6910 | N   | PHE | L | 140 | −109.474 | −21.388 | −23.869 | 1.00 | 114.58 | N |
| ATOM | 6911 | CA  | PHE | L | 140 | −110.117 | −20.073 | −23.982 | 1.00 | 115.21 | C |
| ATOM | 6912 | CB  | PHE | L | 140 | −110.910 | −19.733 | −22.710 | 1.00 | 114.98 | C |
| ATOM | 6913 | CG  | PHE | L | 140 | −110.131 | −19.560 | −21.427 | 1.00 | 114.30 | C |
| ATOM | 6914 | CD1 | PHE | L | 140 | −109.951 | −18.301 | −20.871 | 1.00 | 113.56 | C |
| ATOM | 6915 | CE1 | PHE | L | 140 | −109.252 | −18.145 | −19.665 | 1.00 | 113.30 | C |
| ATOM | 6916 | CZ  | PHE | L | 140 | −108.742 | −19.248 | −19.012 | 1.00 | 112.97 | C |
| ATOM | 6917 | CE2 | PHE | L | 140 | −108.925 | −20.503 | −19.544 | 1.00 | 113.00 | C |
| ATOM | 6918 | CD2 | PHE | L | 140 | −109.630 | −20.662 | −20.742 | 1.00 | 113.60 | C |
| ATOM | 6919 | C   | PHE | L | 140 | −109.093 | −18.977 | −24.336 | 1.00 | 115.99 | C |
| ATOM | 6920 | O   | PHE | L | 140 | −107.912 | −19.174 | −24.052 | 1.00 | 116.10 | O |
| ATOM | 6921 | N   | TYR | L | 141 | −109.521 | −17.845 | −24.979 | 1.00 | 120.17 | N |
| ATOM | 6922 | CA  | TYR | L | 141 | −108.566 | −16.788 | −25.348 | 1.00 | 121.05 | C |
| ATOM | 6923 | CB  | TYR | L | 141 | −108.589 | −16.291 | −26.823 | 1.00 | 120.82 | C |
| ATOM | 6924 | CG  | TYR | L | 141 | −107.750 | −15.032 | −26.958 | 1.00 | 120.68 | C |
| ATOM | 6925 | CD1 | TYR | L | 141 | −106.363 | −15.080 | −26.839 | 1.00 | 120.23 | C |
| ATOM | 6926 | CE1 | TYR | L | 141 | −105.598 | −13.920 | −26.835 | 1.00 | 119.92 | C |
| ATOM | 6927 | CZ  | TYR | L | 141 | −106.211 | −12.689 | −26.980 | 1.00 | 119.83 | C |
| ATOM | 6928 | OH  | TYR | L | 141 | −105.449 | −11.549 | −27.013 | 1.00 | 119.70 | O |
| ATOM | 6929 | CE2 | TYR | L | 141 | −107.589 | −12.612 | −27.082 | 1.00 | 120.07 | C |
| ATOM | 6930 | CD2 | TYR | L | 141 | −108.350 | −13.779 | −27.060 | 1.00 | 120.62 | C |
| ATOM | 6931 | C   | TYR | L | 141 | −108.327 | −15.636 | −24.355 | 1.00 | 121.93 | C |
| ATOM | 6932 | O   | TYR | L | 141 | −107.188 | −15.543 | −23.901 | 1.00 | 122.12 | O |
| ATOM | 6933 | N   | PRO | L | 142 | −109.244 | −14.684 | −24.062 | 1.00 | 123.73 | N |
| ATOM | 6934 | CA  | PRO | L | 142 | −108.861 | −13.603 | −23.124 | 1.00 | 124.38 | C |
| ATOM | 6935 | CB  | PRO | L | 142 | −110.113 | −12.728 | −23.040 | 1.00 | 124.21 | C |
| ATOM | 6936 | CG  | PRO | L | 142 | −110.923 | −13.107 | −24.228 | 1.00 | 124.05 | C |
| ATOM | 6937 | CD  | PRO | L | 142 | −110.642 | −14.545 | −24.504 | 1.00 | 123.75 | C |
| ATOM | 6938 | C   | PRO | L | 142 | −108.418 | −14.197 | −21.774 | 1.00 | 125.09 | C |
| ATOM | 6939 | O   | PRO | L | 142 | −109.144 | −15.019 | −21.200 | 1.00 | 125.32 | O |
| ATOM | 6940 | N   | ARG | L | 143 | −107.192 | −13.856 | −21.311 | 1.00 | 124.90 | N |
| ATOM | 6941 | CA  | ARG | L | 143 | −106.641 | −14.409 | −20.070 | 1.00 | 125.50 | C |
| ATOM | 6942 | CB  | ARG | L | 143 | −105.176 | −14.017 | −19.884 | 1.00 | 125.50 | C |
| ATOM | 6943 | CG  | ARG | L | 143 | −104.366 | −15.117 | −19.235 | 1.00 | 125.34 | C |
| ATOM | 6944 | CD  | ARG | L | 143 | −103.690 | −14.659 | −17.962 | 1.00 | 125.22 | C |
| ATOM | 6945 | NE  | ARG | L | 143 | −102.648 | −15.606 | −17.567 | 1.00 | 125.08 | N |
| ATOM | 6946 | CZ  | ARG | L | 143 | −101.400 | −15.591 | −18.034 | 1.00 | 125.16 | C |
| ATOM | 6947 | NH1 | ARG | L | 143 | −101.021 | −14.666 | −18.911 | 1.00 | 124.93 | N |
| ATOM | 6948 | NH2 | ARG | L | 143 | −100.524 | −16.506 | −17.634 | 1.00 | 124.72 | N |
| ATOM | 6949 | C   | ARG | L | 143 | −107.452 | −14.106 | −18.824 | 1.00 | 125.98 | C |
| ATOM | 6950 | O   | ARG | L | 143 | −107.460 | −14.920 | −17.901 | 1.00 | 125.95 | O |
| ATOM | 6951 | N   | GLU | L | 144 | −108.136 | −12.949 | −18.798 | 1.00 | 128.30 | N |
| ATOM | 6952 | CA  | GLU | L | 144 | −108.959 | −12.548 | −17.665 | 1.00 | 129.21 | C |
| ATOM | 6953 | CB  | GLU | L | 144 | −109.478 | −11.103 | −17.821 | 1.00 | 129.25 | C |
| ATOM | 6954 | CG  | GLU | L | 144 | −109.909 | −10.468 | −16.501 | 1.00 | 130.44 | C |
| ATOM | 6955 | CD  | GLU | L | 144 | −111.255 | −9.759  | −16.456 | 1.00 | 132.01 | C |
| ATOM | 6956 | OE1 | GLU | L | 144 | −111.271 | −8.538  | −16.169 | 1.00 | 132.64 | O |
| ATOM | 6957 | OE2 | GLU | L | 144 | −112.294 | −10.425 | −16.687 | 1.00 | 132.51 | O |
| ATOM | 6958 | C   | GLU | L | 144 | −110.108 | −13.544 | −17.456 | 1.00 | 129.64 | C |
| ATOM | 6959 | O   | GLU | L | 144 | −110.948 | −13.736 | −18.341 | 1.00 | 129.70 | O |
| ATOM | 6960 | N   | ALA | L | 145 | −110.107 | −14.200 | −16.290 | 1.00 | 131.03 | N |
| ATOM | 6961 | CA  | ALA | L | 145 | −111.117 | −15.180 | −15.884 | 1.00 | 131.73 | C |
| ATOM | 6962 | CB  | ALA | L | 145 | −110.778 | −16.562 | −16.436 | 1.00 | 131.51 | C |
| ATOM | 6963 | C   | ALA | L | 145 | −111.214 | −15.215 | −14.350 | 1.00 | 132.29 | C |
| ATOM | 6964 | O   | ALA | L | 145 | −110.184 | −15.248 | −13.663 | 1.00 | 132.37 | O |
| ATOM | 6965 | N   | LYS | L | 146 | −112.449 | −15.182 | −13.817 | 1.00 | 132.82 | N |
| ATOM | 6966 | CA  | LYS | L | 146 | −112.696 | −15.209 | −12.374 | 1.00 | 133.49 | C |
| ATOM | 6967 | CB  | LYS | L | 146 | −113.637 | −14.067 | −11.965 | 1.00 | 133.42 | C |
| ATOM | 6968 | C   | LYS | L | 146 | −113.287 | −16.547 | −11.963 | 1.00 | 133.99 | C |
| ATOM | 6969 | O   | LYS | L | 146 | −114.152 | −17.070 | −12.668 | 1.00 | 134.05 | O |
| ATOM | 6970 | N   | VAL | L | 147 | −112.806 | −17.113 | −10.839 | 1.00 | 133.98 | N |
| ATOM | 6971 | CA  | VAL | L | 147 | −113.292 | −18.390 | −10.304 | 1.00 | 134.69 | C |
| ATOM | 6972 | CB  | VAL | L | 147 | −112.411 | −19.629 | −10.661 | 1.00 | 134.54 | C |
| ATOM | 6973 | CG1 | VAL | L | 147 | −112.819 | −20.859 | −9.854  | 1.00 | 134.55 | C |
| ATOM | 6974 | CG2 | VAL | L | 147 | −112.471 | −19.944 | −12.152 | 1.00 | 134.47 | C |
| ATOM | 6975 | C   | VAL | L | 147 | −113.592 | −18.267 | −8.801  | 1.00 | 135.34 | C |
| ATOM | 6976 | O   | VAL | L | 147 | −112.688 | −17.986 | −8.011  | 1.00 | 135.35 | O |
| ATOM | 6977 | N   | GLN | L | 148 | −114.876 | −18.465 | −8.429  | 1.00 | 137.17 | N |
| ATOM | 6978 | CA  | GLN | L | 148 | −115.370 | −18.427 | −7.052  | 1.00 | 137.96 | C |
| ATOM | 6979 | CB  | GLN | L | 148 | −116.388 | −17.291 | −6.837  | 1.00 | 137.70 | C |
| ATOM | 6980 | C   | GLN | L | 148 | −115.979 | −19.790 | −6.736  | 1.00 | 138.61 | C |
| ATOM | 6981 | O   | GLN | L | 148 | −116.844 | −20.271 | −7.470  | 1.00 | 138.56 | O |
| ATOM | 6982 | N   | TRP | L | 149 | −115.491 | −20.421 | −5.660  | 1.00 | 141.36 | N |

TABLE 14-continued

PCSK9 and AX132 Fab complex x-ray structure

| ATOM | 6983 | CA | TRP | L | 149 | −115.938 | −21.733 | −5.203 | 1.00 | 142.14 | C |
|------|------|------|-----|---|-----|----------|---------|--------|------|--------|---|
| ATOM | 6984 | CB | TRP | L | 149 | −114.788 | −22.495 | −4.521 | 1.00 | 142.24 | C |
| ATOM | 6985 | CG | TRP | L | 149 | −113.731 | −23.024 | −5.447 | 1.00 | 142.43 | C |
| ATOM | 6986 | CD1 | TRP | L | 149 | −112.536 | −22.439 | −5.742 | 1.00 | 142.44 | C |
| ATOM | 6987 | NE1 | TRP | L | 149 | −111.814 | −23.239 | −6.596 | 1.00 | 142.71 | N |
| ATOM | 6988 | CE2 | TRP | L | 149 | −112.534 | −24.376 | −6.862 | 1.00 | 142.61 | C |
| ATOM | 6989 | CD2 | TRP | L | 149 | −113.748 | −24.278 | −6.148 | 1.00 | 142.57 | C |
| ATOM | 6990 | CE3 | TRP | L | 149 | −114.676 | −25.329 | −6.246 | 1.00 | 142.51 | C |
| ATOM | 6991 | CZ3 | TRP | L | 149 | −114.365 | −26.424 | −7.041 | 1.00 | 142.73 | C |
| ATOM | 6992 | CH2 | TRP | L | 149 | −113.153 | −26.494 | −7.739 | 1.00 | 142.48 | C |
| ATOM | 6993 | CZ2 | TRP | L | 149 | −112.221 | −25.486 | −7.661 | 1.00 | 142.42 | C |
| ATOM | 6994 | C | TRP | L | 149 | −117.120 | −21.591 | −4.247 | 1.00 | 142.57 | C |
| ATOM | 6995 | O | TRP | L | 149 | −117.033 | −20.863 | −3.249 | 1.00 | 142.67 | O |
| ATOM | 6996 | N | LYS | L | 150 | −118.226 | −22.295 | −4.569 | 1.00 | 144.16 | N |
| ATOM | 6997 | CA | LYS | L | 150 | −119.468 | −22.302 | −3.801 | 1.00 | 144.48 | C |
| ATOM | 6998 | CB | LYS | L | 150 | −120.683 | −22.049 | −4.710 | 1.00 | 144.30 | C |
| ATOM | 6999 | C | LYS | L | 150 | −119.632 | −23.585 | −2.988 | 1.00 | 144.77 | C |
| ATOM | 7000 | O | LYS | L | 150 | −120.027 | −24.625 | −3.528 | 1.00 | 144.70 | O |
| ATOM | 7001 | N | VAL | L | 151 | −119.311 | −23.497 | −1.679 | 1.00 | 146.31 | N |
| ATOM | 7002 | CA | VAL | L | 151 | −119.412 | −24.586 | −0.692 | 1.00 | 146.66 | C |
| ATOM | 7003 | CB | VAL | L | 151 | −118.294 | −24.522 | 0.403 | 1.00 | 146.70 | C |
| ATOM | 7004 | CG1 | VAL | L | 151 | −116.953 | −24.974 | −0.164 | 1.00 | 146.41 | C |
| ATOM | 7005 | CG2 | VAL | L | 151 | −118.160 | −23.130 | 1.029 | 1.00 | 146.67 | C |
| ATOM | 7006 | C | VAL | L | 151 | −120.871 | −24.606 | −0.156 | 1.00 | 146.88 | C |
| ATOM | 7007 | O | VAL | L | 151 | −121.145 | −24.253 | 1.003 | 1.00 | 147.08 | O |
| ATOM | 7008 | N | ASP | L | 152 | −121.801 | −25.021 | −1.065 | 1.00 | 146.82 | N |
| ATOM | 7009 | CA | ASP | L | 152 | −123.271 | −25.064 | −0.959 | 1.00 | 146.80 | C |
| ATOM | 7010 | CB | ASP | L | 152 | −123.897 | −26.226 | −0.126 | 1.00 | 146.83 | C |
| ATOM | 7011 | CG | ASP | L | 152 | −123.537 | −26.390 | 1.350 | 1.00 | 147.22 | C |
| ATOM | 7012 | OD1 | ASP | L | 152 | −123.286 | −27.540 | 1.772 | 1.00 | 147.06 | O |
| ATOM | 7013 | OD2 | ASP | L | 152 | −123.542 | −25.373 | 2.091 | 1.00 | 147.71 | O |
| ATOM | 7014 | C | ASP | L | 152 | −123.869 | −23.668 | −0.765 | 1.00 | 146.65 | C |
| ATOM | 7015 | O | ASP | L | 152 | −124.196 | −23.261 | 0.357 | 1.00 | 146.71 | O |
| ATOM | 7016 | N | ASN | L | 153 | −123.943 | −22.914 | −1.897 | 1.00 | 144.71 | N |
| ATOM | 7017 | CA | ASN | L | 153 | −124.425 | −21.528 | −2.001 | 1.00 | 144.46 | C |
| ATOM | 7018 | CB | ASN | L | 153 | −125.953 | −21.439 | −1.869 | 1.00 | 144.46 | C |
| ATOM | 7019 | C | ASN | L | 153 | −123.674 | −20.586 | −1.028 | 1.00 | 144.28 | C |
| ATOM | 7020 | O | ASN | L | 153 | −124.248 | −19.633 | −0.488 | 1.00 | 144.25 | O |
| ATOM | 7021 | N | ALA | L | 154 | −122.372 | −20.880 | −0.818 | 1.00 | 143.01 | N |
| ATOM | 7022 | CA | ALA | L | 154 | −121.464 | −20.135 | 0.053 | 1.00 | 142.71 | C |
| ATOM | 7023 | CB | ALA | L | 154 | −121.086 | −20.977 | 1.267 | 1.00 | 142.72 | C |
| ATOM | 7024 | C | ALA | L | 154 | −120.210 | −19.610 | −0.706 | 1.00 | 142.37 | C |
| ATOM | 7025 | O | ALA | L | 154 | −120.130 | −19.742 | −1.932 | 1.00 | 142.19 | O |
| ATOM | 7026 | N | LEU | L | 155 | −119.257 | −18.993 | 0.023 | 1.00 | 140.88 | N |
| ATOM | 7027 | CA | LEU | L | 155 | −118.050 | −18.380 | −0.536 | 1.00 | 140.44 | C |
| ATOM | 7028 | CB | LEU | L | 155 | −117.823 | −16.932 | 0.015 | 1.00 | 140.45 | C |
| ATOM | 7029 | CG | LEU | L | 155 | −117.618 | −16.618 | 1.545 | 1.00 | 140.69 | C |
| ATOM | 7030 | CD1 | LEU | L | 155 | −116.331 | −17.180 | 2.121 | 1.00 | 140.65 | C |
| ATOM | 7031 | CD2 | LEU | L | 155 | −118.850 | −16.895 | 2.408 | 1.00 | 140.93 | C |
| ATOM | 7032 | C | LEU | L | 155 | −116.732 | −19.183 | −0.610 | 1.00 | 140.07 | C |
| ATOM | 7033 | O | LEU | L | 155 | −116.588 | −20.271 | −0.034 | 1.00 | 140.03 | O |
| ATOM | 7034 | N | GLN | L | 156 | −115.773 | −18.599 | −1.355 | 1.00 | 139.27 | N |
| ATOM | 7035 | CA | GLN | L | 156 | −114.412 | −19.065 | −1.560 | 1.00 | 138.38 | C |
| ATOM | 7036 | CB | GLN | L | 156 | −114.000 | −18.872 | −3.028 | 1.00 | 138.41 | C |
| ATOM | 7037 | C | GLN | L | 156 | −113.579 | −18.175 | −0.623 | 1.00 | 137.73 | C |
| ATOM | 7038 | O | GLN | L | 156 | −113.130 | −17.093 | −1.018 | 1.00 | 137.58 | O |
| ATOM | 7039 | N | SER | L | 157 | −113.446 | −18.616 | 0.646 | 1.00 | 136.55 | N |
| ATOM | 7040 | CA | SER | L | 157 | −112.721 | −17.929 | 1.721 | 1.00 | 135.68 | C |
| ATOM | 7041 | CB | SER | L | 157 | −112.829 | −18.725 | 3.024 | 1.00 | 135.72 | C |
| ATOM | 7042 | OG | SER | L | 157 | −112.063 | −18.164 | 4.078 | 1.00 | 135.84 | O |
| ATOM | 7043 | C | SER | L | 157 | −111.255 | −17.640 | 1.348 | 1.00 | 134.91 | C |
| ATOM | 7044 | O | SER | L | 157 | −110.917 | −16.495 | 1.039 | 1.00 | 134.84 | O |
| ATOM | 7045 | N | GLY | L | 158 | −110.430 | −18.685 | 1.368 | 1.00 | 133.80 | N |
| ATOM | 7046 | CA | GLY | L | 158 | −109.008 | −18.642 | 1.050 | 1.00 | 132.49 | C |
| ATOM | 7047 | C | GLY | L | 158 | −108.431 | −20.040 | 0.993 | 1.00 | 131.57 | C |
| ATOM | 7048 | O | GLY | L | 158 | −107.393 | −20.317 | 1.605 | 1.00 | 131.46 | O |
| ATOM | 7049 | N | ASN | L | 159 | −109.134 | −20.930 | 0.262 | 1.00 | 131.76 | N |
| ATOM | 7050 | CA | ASN | L | 159 | −108.811 | −22.342 | 0.056 | 1.00 | 130.80 | C |
| ATOM | 7051 | CB | ASN | L | 159 | −109.929 | −23.221 | 0.638 | 1.00 | 131.25 | C |
| ATOM | 7052 | CG | ASN | L | 159 | −109.880 | −23.451 | 2.142 | 1.00 | 132.31 | C |
| ATOM | 7053 | OD1 | ASN | L | 159 | −109.971 | −24.598 | 2.618 | 1.00 | 133.26 | O |
| ATOM | 7054 | ND2 | ASN | L | 159 | −109.757 | −22.379 | 2.935 | 1.00 | 132.94 | N |
| ATOM | 7055 | C | ASN | L | 159 | −108.624 | −22.653 | −1.431 | 1.00 | 129.73 | C |
| ATOM | 7056 | O | ASN | L | 159 | −108.505 | −23.822 | −1.804 | 1.00 | 129.65 | O |
| ATOM | 7057 | N | SER | L | 160 | −108.591 | −21.603 | −2.274 | 1.00 | 127.52 | N |
| ATOM | 7058 | CA | SER | L | 160 | −108.425 | −21.704 | −3.725 | 1.00 | 126.23 | C |
| ATOM | 7059 | CB | SER | L | 160 | −109.469 | −20.846 | −4.446 | 1.00 | 126.30 | C |
| ATOM | 7060 | OG | SER | L | 160 | −109.200 | −20.655 | −5.828 | 1.00 | 126.45 | O |

TABLE 14-continued

PCSK9 and AX132 Fab complex x-ray structure

| ATOM | 7061 | C | SER | L | 160 | −106.999 | −21.339 | −4.185 | 1.00 | 125.19 | C |
|---|---|---|---|---|---|---|---|---|---|---|---|
| ATOM | 7062 | O | SER | L | 160 | −106.455 | −20.296 | −3.786 | 1.00 | 125.17 | O |
| ATOM | 7063 | N | GLN | L | 161 | −106.411 | −22.217 | −5.030 | 1.00 | 121.47 | N |
| ATOM | 7064 | CA | GLN | L | 161 | −105.083 | −22.072 | −5.635 | 1.00 | 119.85 | C |
| ATOM | 7065 | CB | GLN | L | 161 | −104.056 | −23.039 | −5.005 | 1.00 | 119.86 | C |
| ATOM | 7066 | CG | GLN | L | 161 | −103.506 | −22.571 | −3.653 | 1.00 | 118.84 | C |
| ATOM | 7067 | CD | GLN | L | 161 | −102.328 | −23.378 | −3.158 | 1.00 | 117.16 | C |
| ATOM | 7068 | OE1 | GLN | L | 161 | −102.397 | −24.603 | −2.963 | 1.00 | 116.92 | O |
| ATOM | 7069 | NE2 | GLN | L | 161 | −101.222 | −22.698 | −2.921 | 1.00 | 116.03 | N |
| ATOM | 7070 | C | GLN | L | 161 | −105.242 | −22.319 | −7.133 | 1.00 | 118.95 | C |
| ATOM | 7071 | O | GLN | L | 161 | −105.766 | −23.363 | −7.528 | 1.00 | 118.82 | O |
| ATOM | 7072 | N | GLU | L | 162 | −104.825 | −21.345 | −7.963 | 1.00 | 118.33 | N |
| ATOM | 7073 | CA | GLU | L | 162 | −104.962 | −21.418 | −9.426 | 1.00 | 117.09 | C |
| ATOM | 7074 | CB | GLU | L | 162 | −105.833 | −20.264 | −9.963 | 1.00 | 117.33 | C |
| ATOM | 7075 | CG | GLU | L | 162 | −107.230 | −20.213 | −9.365 | 1.00 | 118.23 | C |
| ATOM | 7076 | CD | GLU | L | 162 | −108.093 | −19.008 | −9.697 | 1.00 | 119.60 | C |
| ATOM | 7077 | OE1 | GLU | L | 162 | −108.981 | −18.686 | −8.871 | 1.00 | 120.56 | O |
| ATOM | 7078 | OE2 | GLU | L | 162 | −107.893 | −18.394 | −10.774 | 1.00 | 119.76 | O |
| ATOM | 7079 | C | GLU | L | 162 | −103.644 | −21.459 | −10.184 | 1.00 | 115.93 | C |
| ATOM | 7080 | O | GLU | L | 162 | −102.662 | −20.845 | −9.766 | 1.00 | 115.86 | O |
| ATOM | 7081 | N | SER | L | 163 | −103.647 | −22.165 | −11.322 | 1.00 | 111.07 | N |
| ATOM | 7082 | CA | SER | L | 163 | −102.489 | −22.316 | −12.191 | 1.00 | 109.71 | C |
| ATOM | 7083 | CB | SER | L | 163 | −101.877 | −23.692 | −11.995 | 1.00 | 109.62 | C |
| ATOM | 7084 | OG | SER | L | 163 | −100.544 | −23.673 | −12.462 | 1.00 | 109.51 | O |
| ATOM | 7085 | C | SER | L | 163 | −102.920 | −22.133 | −13.642 | 1.00 | 108.94 | C |
| ATOM | 7086 | O | SER | L | 163 | −103.903 | −22.743 | −14.060 | 1.00 | 108.88 | O |
| ATOM | 7087 | N | VAL | L | 164 | −102.201 | −21.295 | −14.405 | 1.00 | 105.03 | N |
| ATOM | 7088 | CA | VAL | L | 164 | −102.542 | −21.022 | −15.802 | 1.00 | 103.99 | C |
| ATOM | 7089 | CB | VAL | L | 164 | −102.773 | −19.514 | −16.036 | 1.00 | 103.97 | C |
| ATOM | 7090 | CG1 | VAL | L | 164 | −103.039 | −19.200 | −17.514 | 1.00 | 103.77 | C |
| ATOM | 7091 | CG2 | VAL | L | 164 | −103.910 | −18.992 | −15.150 | 1.00 | 103.63 | C |
| ATOM | 7092 | C | VAL | L | 164 | −101.564 | −21.644 | −16.792 | 1.00 | 103.53 | C |
| ATOM | 7093 | O | VAL | L | 164 | −100.362 | −21.538 | −16.601 | 1.00 | 103.39 | O |
| ATOM | 7094 | N | THR | L | 165 | −102.091 | −22.274 | −17.853 | 1.00 | 101.85 | N |
| ATOM | 7095 | CA | THR | L | 165 | −101.325 | −22.954 | −18.890 | 1.00 | 101.44 | C |
| ATOM | 7096 | CB | THR | L | 165 | −102.216 | −23.832 | −19.797 | 1.00 | 101.33 | C |
| ATOM | 7097 | OG1 | THR | L | 165 | −101.518 | −25.050 | −20.047 | 1.00 | 101.63 | O |
| ATOM | 7098 | CG2 | THR | L | 165 | −102.564 | −23.174 | −21.154 | 1.00 | 101.27 | C |
| ATOM | 7099 | C | THR | L | 165 | −100.281 | −22.150 | −19.652 | 1.00 | 101.38 | C |
| ATOM | 7100 | O | THR | L | 165 | −99.298 | −22.756 | −20.095 | 1.00 | 101.70 | O |
| ATOM | 7101 | N | GLU | L | 166 | −100.472 | −20.818 | −19.816 | 1.00 | 99.24 | N |
| ATOM | 7102 | CA | GLU | L | 166 | −99.572 | −19.945 | −20.587 | 1.00 | 98.97 | C |
| ATOM | 7103 | CB | GLU | L | 166 | −98.098 | −19.974 | −20.102 | 1.00 | 98.88 | C |
| ATOM | 7104 | C | GLU | L | 166 | −99.697 | −20.306 | −22.078 | 1.00 | 98.77 | C |
| ATOM | 7105 | O | GLU | L | 166 | −99.142 | −21.307 | −22.528 | 1.00 | 98.60 | O |
| ATOM | 7106 | N | GLN | L | 167 | −100.477 | −19.476 | −22.806 | 1.00 | 98.98 | N |
| ATOM | 7107 | CA | GLN | L | 167 | −100.866 | −19.465 | −24.226 | 1.00 | 98.76 | C |
| ATOM | 7108 | CB | GLN | L | 167 | −100.619 | −18.080 | −24.829 | 1.00 | 98.72 | C |
| ATOM | 7109 | CG | GLN | L | 167 | −101.771 | −17.617 | −25.680 | 1.00 | 99.11 | C |
| ATOM | 7110 | CD | GLN | L | 167 | −101.652 | −16.212 | −26.210 | 1.00 | 98.86 | C |
| ATOM | 7111 | OE1 | GLN | L | 167 | −100.585 | −15.749 | −26.632 | 1.00 | 97.98 | O |
| ATOM | 7112 | NE2 | GLN | L | 167 | −102.774 | −15.509 | −26.232 | 1.00 | 98.96 | N |
| ATOM | 7113 | C | GLN | L | 167 | −100.379 | −20.583 | −25.164 | 1.00 | 98.55 | C |
| ATOM | 7114 | O | GLN | L | 167 | −99.184 | −20.661 | −25.437 | 1.00 | 98.71 | O |
| ATOM | 7115 | N | ASP | L | 168 | −101.315 | −21.413 | −25.685 | 1.00 | 99.05 | N |
| ATOM | 7116 | CA | ASP | L | 168 | −101.028 | −22.523 | −26.606 | 1.00 | 99.09 | C |
| ATOM | 7117 | CB | ASP | L | 168 | −102.317 | −23.274 | −26.979 | 1.00 | 99.32 | C |
| ATOM | 7118 | CG | ASP | L | 168 | −102.104 | −24.674 | −27.550 | 1.00 | 99.97 | C |
| ATOM | 7119 | OD1 | ASP | L | 168 | −102.562 | −25.653 | −26.910 | 1.00 | 100.99 | O |
| ATOM | 7120 | OD2 | ASP | L | 168 | −101.493 | −24.792 | −28.649 | 1.00 | 100.34 | O |
| ATOM | 7121 | C | ASP | L | 168 | −100.314 | −22.062 | −27.873 | 1.00 | 98.85 | C |
| ATOM | 7122 | O | ASP | L | 168 | −100.550 | −20.955 | −28.348 | 1.00 | 98.71 | O |
| ATOM | 7123 | N | SER | L | 169 | −99.438 | −22.909 | −28.415 | 1.00 | 100.81 | N |
| ATOM | 7124 | CA | SER | L | 169 | −98.685 | −22.582 | −29.627 | 1.00 | 101.16 | C |
| ATOM | 7125 | CB | SER | L | 169 | −97.451 | −23.472 | −29.760 | 1.00 | 101.15 | C |
| ATOM | 7126 | OG | SER | L | 169 | −97.761 | −24.820 | −29.446 | 1.00 | 101.65 | O |
| ATOM | 7127 | C | SER | L | 169 | −99.575 | −22.679 | −30.869 | 1.00 | 101.31 | C |
| ATOM | 7128 | O | SER | L | 169 | −99.754 | −21.678 | −31.580 | 1.00 | 101.38 | O |
| ATOM | 7129 | N | LYS | L | 170 | −100.153 | −23.883 | −31.102 | 1.00 | 102.36 | N |
| ATOM | 7130 | CA | LYS | L | 170 | −101.038 | −24.200 | −32.217 | 1.00 | 102.39 | C |
| ATOM | 7131 | CB | LYS | L | 170 | −101.379 | −25.698 | −32.216 | 1.00 | 102.24 | C |
| ATOM | 7132 | C | LYS | L | 170 | −102.314 | −23.331 | −32.252 | 1.00 | 102.58 | C |
| ATOM | 7133 | O | LYS | L | 170 | −102.579 | −22.700 | −33.279 | 1.00 | 102.74 | O |
| ATOM | 7134 | N | ASP | L | 171 | −103.082 | −23.269 | −31.147 | 1.00 | 102.64 | N |
| ATOM | 7135 | CA | ASP | L | 171 | −104.324 | −22.495 | −31.140 | 1.00 | 102.90 | C |
| ATOM | 7136 | CB | ASP | L | 171 | −105.526 | −23.442 | −31.106 | 1.00 | 103.27 | C |
| ATOM | 7137 | CG | ASP | L | 171 | −105.506 | −24.392 | −29.928 | 1.00 | 104.57 | C |
| ATOM | 7138 | OD1 | ASP | L | 171 | −105.745 | −23.923 | −28.777 | 1.00 | 104.99 | O |

TABLE 14-continued

PCSK9 and AX132 Fab complex x-ray structure

| ATOM | 7139 | OD2 | ASP | L | 171 | −105.253 | −25.610 | −30.149 | 1.00 | 106.77 | O |
| ATOM | 7140 | C | ASP | L | 171 | −104.471 | −21.335 | −30.135 | 1.00 | 102.74 | C |
| ATOM | 7141 | O | ASP | L | 171 | −105.576 | −21.073 | −29.646 | 1.00 | 102.59 | O |
| ATOM | 7142 | N | SER | L | 172 | −103.359 | −20.635 | −29.852 | 1.00 | 100.89 | N |
| ATOM | 7143 | CA | SER | L | 172 | −103.227 | −19.472 | −28.961 | 1.00 | 100.63 | C |
| ATOM | 7144 | CB | SER | L | 172 | −103.082 | −18.200 | −29.785 | 1.00 | 100.55 | C |
| ATOM | 7145 | OG | SER | L | 172 | −101.988 | −18.375 | −30.673 | 1.00 | 100.64 | O |
| ATOM | 7146 | C | SER | L | 172 | −104.216 | −19.316 | −27.790 | 1.00 | 100.63 | C |
| ATOM | 7147 | O | SER | L | 172 | −104.704 | −18.214 | −27.521 | 1.00 | 100.47 | O |
| ATOM | 7148 | N | THR | L | 173 | −104.472 | −20.427 | −27.075 | 1.00 | 101.55 | N |
| ATOM | 7149 | CA | THR | L | 173 | −105.404 | −20.472 | −25.947 | 1.00 | 101.94 | C |
| ATOM | 7150 | CB | THR | L | 173 | −106.570 | −21.451 | −26.219 | 1.00 | 102.01 | C |
| ATOM | 7151 | OG1 | THR | L | 173 | −106.081 | −22.676 | −26.772 | 1.00 | 101.82 | O |
| ATOM | 7152 | CG2 | THR | L | 173 | −107.633 | −20.855 | −27.104 | 1.00 | 101.98 | C |
| ATOM | 7153 | C | THR | L | 173 | −104.772 | −20.776 | −24.598 | 1.00 | 102.15 | C |
| ATOM | 7154 | O | THR | L | 173 | −103.765 | −21.484 | −24.518 | 1.00 | 102.13 | O |
| ATOM | 7155 | N | TYR | L | 174 | −105.412 | −20.244 | −23.535 | 1.00 | 103.33 | N |
| ATOM | 7156 | CA | TYR | L | 174 | −105.056 | −20.408 | −22.127 | 1.00 | 103.64 | C |
| ATOM | 7157 | CB | TYR | L | 174 | −105.206 | −19.082 | −21.362 | 1.00 | 103.64 | C |
| ATOM | 7158 | CG | TYR | L | 174 | −104.277 | −17.986 | −21.829 | 1.00 | 104.23 | C |
| ATOM | 7159 | CD1 | TYR | L | 174 | −104.687 | −17.055 | −22.777 | 1.00 | 104.83 | C |
| ATOM | 7160 | CE1 | TYR | L | 174 | −103.842 | −16.032 | −23.202 | 1.00 | 104.70 | C |
| ATOM | 7161 | CZ | TYR | L | 174 | −102.566 | −15.937 | −22.680 | 1.00 | 104.23 | C |
| ATOM | 7162 | OH | TYR | L | 174 | −101.722 | −14.944 | −23.097 | 1.00 | 104.02 | O |
| ATOM | 7163 | CE2 | TYR | L | 174 | −102.141 | −16.844 | −21.726 | 1.00 | 104.62 | C |
| ATOM | 7164 | CD2 | TYR | L | 174 | −102.998 | −17.860 | −21.304 | 1.00 | 104.52 | C |
| ATOM | 7165 | C | TYR | L | 174 | −105.997 | −21.431 | −21.504 | 1.00 | 103.87 | C |
| ATOM | 7166 | O | TYR | L | 174 | −107.064 | −21.700 | −22.057 | 1.00 | 104.08 | O |
| ATOM | 7167 | N | SER | L | 175 | −105.595 | −21.995 | −20.347 | 1.00 | 102.93 | N |
| ATOM | 7168 | CA | SER | L | 175 | −106.332 | −22.973 | −19.539 | 1.00 | 103.00 | C |
| ATOM | 7169 | CB | SER | L | 175 | −106.041 | −24.403 | −19.985 | 1.00 | 102.80 | C |
| ATOM | 7170 | OG | SER | L | 175 | −106.359 | −24.591 | −21.356 | 1.00 | 102.75 | O |
| ATOM | 7171 | C | SER | L | 175 | −105.962 | −22.755 | −18.072 | 1.00 | 103.21 | C |
| ATOM | 7172 | O | SER | L | 175 | −104.783 | −22.635 | −17.747 | 1.00 | 103.20 | O |
| ATOM | 7173 | N | LEU | L | 176 | −106.977 | −22.654 | −17.203 | 1.00 | 103.24 | N |
| ATOM | 7174 | CA | LEU | L | 176 | −106.843 | −22.420 | −15.768 | 1.00 | 103.52 | C |
| ATOM | 7175 | CB | LEU | L | 176 | −107.739 | −21.236 | −15.365 | 1.00 | 103.27 | C |
| ATOM | 7176 | CG | LEU | L | 176 | −107.431 | −20.545 | −14.039 | 1.00 | 103.20 | C |
| ATOM | 7177 | CD1 | LEU | L | 176 | −107.592 | −19.051 | −14.163 | 1.00 | 103.38 | C |
| ATOM | 7178 | CD2 | LEU | L | 176 | −108.324 | −21.057 | −12.919 | 1.00 | 102.64 | C |
| ATOM | 7179 | C | LEU | L | 176 | −107.242 | −23.673 | −14.992 | 1.00 | 104.05 | C |
| ATOM | 7180 | O | LEU | L | 176 | −108.113 | −24.416 | −15.435 | 1.00 | 104.03 | O |
| ATOM | 7181 | N | SER | L | 177 | −106.604 | −23.901 | −13.838 | 1.00 | 106.42 | N |
| ATOM | 7182 | CA | SER | L | 177 | −106.865 | −25.033 | −12.954 | 1.00 | 107.19 | C |
| ATOM | 7183 | CB | SER | L | 177 | −105.776 | −26.103 | −13.103 | 1.00 | 107.15 | C |
| ATOM | 7184 | OG | SER | L | 177 | −105.396 | −26.726 | −11.883 | 1.00 | 107.51 | O |
| ATOM | 7185 | C | SER | L | 177 | −106.960 | −24.511 | −11.525 | 1.00 | 107.81 | C |
| ATOM | 7186 | O | SER | L | 177 | −105.938 | −24.183 | −10.913 | 1.00 | 107.98 | O |
| ATOM | 7187 | N | SER | L | 178 | −108.187 | −24.401 | −11.006 | 1.00 | 109.82 | N |
| ATOM | 7188 | CA | SER | L | 178 | −108.404 | −23.923 | −9.640 | 1.00 | 110.68 | C |
| ATOM | 7189 | CB | SER | L | 178 | −109.637 | −23.037 | −9.550 | 1.00 | 110.59 | C |
| ATOM | 7190 | OG | SER | L | 178 | −109.580 | −22.260 | −8.365 | 1.00 | 110.61 | O |
| ATOM | 7191 | C | SER | L | 178 | −108.545 | −25.119 | −8.723 | 1.00 | 111.35 | C |
| ATOM | 7192 | O | SER | L | 178 | −109.106 | −26.138 | −9.138 | 1.00 | 111.31 | O |
| ATOM | 7193 | N | THR | L | 179 | −108.013 | −25.016 | −7.490 | 1.00 | 112.95 | N |
| ATOM | 7194 | CA | THR | L | 179 | −108.073 | −26.125 | −6.548 | 1.00 | 113.88 | C |
| ATOM | 7195 | CB | THR | L | 179 | −106.758 | −26.909 | −6.514 | 1.00 | 113.79 | C |
| ATOM | 7196 | OG1 | THR | L | 179 | −106.386 | −27.280 | −7.847 | 1.00 | 113.74 | O |
| ATOM | 7197 | CG2 | THR | L | 179 | −106.834 | −28.145 | −5.611 | 1.00 | 113.77 | C |
| ATOM | 7198 | C | THR | L | 179 | −108.553 | −25.724 | −5.182 | 1.00 | 114.71 | C |
| ATOM | 7199 | O | THR | L | 179 | −107.882 | −24.962 | −4.474 | 1.00 | 114.65 | O |
| ATOM | 7200 | N | LEU | L | 180 | −109.722 | −26.275 | −4.812 | 1.00 | 118.09 | N |
| ATOM | 7201 | CA | LEU | L | 180 | −110.357 | −26.055 | −3.520 | 1.00 | 119.20 | C |
| ATOM | 7202 | CB | LEU | L | 180 | −111.889 | −26.053 | −3.651 | 1.00 | 119.25 | C |
| ATOM | 7203 | CG | LEU | L | 180 | −112.697 | −25.644 | −2.407 | 1.00 | 119.28 | C |
| ATOM | 7204 | CD1 | LEU | L | 180 | −114.165 | −25.928 | −2.615 | 1.00 | 119.03 | C |
| ATOM | 7205 | CD2 | LEU | L | 180 | −112.461 | −24.166 | −2.009 | 1.00 | 119.13 | C |
| ATOM | 7206 | C | LEU | L | 180 | −109.866 | −27.159 | −2.606 | 1.00 | 119.92 | C |
| ATOM | 7207 | O | LEU | L | 180 | −110.065 | −28.345 | −2.899 | 1.00 | 119.94 | O |
| ATOM | 7208 | N | THR | L | 181 | −109.184 | −26.772 | −1.521 | 1.00 | 122.06 | N |
| ATOM | 7209 | CA | THR | L | 181 | −108.604 | −27.754 | −0.616 | 1.00 | 123.16 | C |
| ATOM | 7210 | CB | THR | L | 181 | −107.127 | −28.063 | −1.014 | 1.00 | 123.08 | C |
| ATOM | 7211 | OG1 | THR | L | 181 | −106.567 | −29.038 | −0.136 | 1.00 | 123.12 | O |
| ATOM | 7212 | CG2 | THR | L | 181 | −106.238 | −26.818 | −1.078 | 1.00 | 123.36 | C |
| ATOM | 7213 | C | THR | L | 181 | −108.908 | −27.572 | 0.878 | 1.00 | 123.93 | C |
| ATOM | 7214 | O | THR | L | 181 | −108.302 | −26.732 | 1.551 | 1.00 | 123.89 | O |
| ATOM | 7215 | N | LEU | L | 182 | −109.843 | −28.402 | 1.387 | 1.00 | 125.26 | N |
| ATOM | 7216 | CA | LEU | L | 182 | −110.268 | −28.455 | 2.796 | 1.00 | 126.41 | C |

TABLE 14-continued

| PCSK9 and AX132 Fab complex x-ray structure | | | | | | | | | | |
|---|---|---|---|---|---|---|---|---|---|---|
| ATOM | 7217 | CB | LEU | L | 182 | −111.637 | −27.786 | 3.030 | 1.00 | 126.34 C |
| ATOM | 7218 | CG | LEU | L | 182 | −112.719 | −28.101 | 2.014 | 1.00 | 126.48 C |
| ATOM | 7219 | CD1 | LEU | L | 182 | −113.984 | −28.549 | 2.693 | 1.00 | 126.44 C |
| ATOM | 7220 | CD2 | LEU | L | 182 | −112.970 | −26.921 | 1.120 | 1.00 | 126.14 C |
| ATOM | 7221 | C | LEU | L | 182 | −110.209 | −29.909 | 3.360 | 1.00 | 127.14 C |
| ATOM | 7222 | O | LEU | L | 182 | −110.020 | −30.857 | 2.582 | 1.00 | 127.07 O |
| ATOM | 7223 | N | SER | L | 183 | −110.342 | −30.071 | 4.710 | 1.00 | 128.51 N |
| ATOM | 7224 | CA | SER | L | 183 | −110.276 | −31.365 | 5.420 | 1.00 | 129.50 C |
| ATOM | 7225 | CB | SER | L | 183 | −110.270 | −31.151 | 6.933 | 1.00 | 129.46 C |
| ATOM | 7226 | OG | SER | L | 183 | −111.490 | −30.598 | 7.401 | 1.00 | 129.48 O |
| ATOM | 7227 | C | SER | L | 183 | −111.373 | −32.372 | 5.024 | 1.00 | 130.09 C |
| ATOM | 7228 | O | SER | L | 183 | −112.396 | −31.961 | 4.470 | 1.00 | 130.38 O |
| ATOM | 7229 | N | LYS | L | 184 | −111.155 | −33.690 | 5.317 | 1.00 | 129.50 N |
| ATOM | 7230 | CA | LYS | L | 184 | −112.095 | −34.801 | 5.041 | 1.00 | 129.96 C |
| ATOM | 7231 | CB | LYS | L | 184 | −111.467 | −36.149 | 5.457 | 1.00 | 129.94 C |
| ATOM | 7232 | CG | LYS | L | 184 | −112.371 | −37.378 | 5.337 | 1.00 | 130.00 C |
| ATOM | 7233 | CD | LYS | L | 184 | −111.722 | −38.645 | 5.899 | 1.00 | 130.26 C |
| ATOM | 7234 | CE | LYS | L | 184 | −111.877 | −38.816 | 7.398 | 1.00 | 130.53 C |
| ATOM | 7235 | NZ | LYS | L | 184 | −111.238 | −40.069 | 7.891 | 1.00 | 130.87 N |
| ATOM | 7236 | C | LYS | L | 184 | −113.443 | −34.572 | 5.767 | 1.00 | 130.23 C |
| ATOM | 7237 | O | LYS | L | 184 | −114.502 | −34.925 | 5.229 | 1.00 | 130.35 O |
| ATOM | 7238 | N | ALA | L | 185 | −113.383 | −33.962 | 6.979 | 1.00 | 128.95 N |
| ATOM | 7239 | CA | ALA | L | 185 | −114.520 | −33.631 | 7.835 | 1.00 | 129.05 C |
| ATOM | 7240 | CB | ALA | L | 185 | −114.017 | −33.124 | 9.179 | 1.00 | 128.94 C |
| ATOM | 7241 | C | ALA | L | 185 | −115.462 | −32.597 | 7.185 | 1.00 | 129.19 C |
| ATOM | 7242 | O | ALA | L | 185 | −116.605 | −32.936 | 6.863 | 1.00 | 129.18 O |
| ATOM | 7243 | N | ASP | L | 186 | −114.966 | −31.354 | 6.971 | 1.00 | 128.16 N |
| ATOM | 7244 | CA | ASP | L | 186 | −115.687 | −30.221 | 6.376 | 1.00 | 128.35 C |
| ATOM | 7245 | CB | ASP | L | 186 | −114.806 | −28.953 | 6.347 | 1.00 | 128.45 C |
| ATOM | 7246 | CG | ASP | L | 186 | −114.168 | −28.529 | 7.673 | 1.00 | 129.00 C |
| ATOM | 7247 | OD1 | ASP | L | 186 | −114.007 | −29.394 | 8.569 | 1.00 | 129.87 O |
| ATOM | 7248 | OD2 | ASP | L | 186 | −113.810 | −27.337 | 7.806 | 1.00 | 129.15 O |
| ATOM | 7249 | C | ASP | L | 186 | −116.305 | −30.524 | 4.993 | 1.00 | 128.32 C |
| ATOM | 7250 | O | ASP | L | 186 | −117.296 | −29.897 | 4.615 | 1.00 | 128.32 O |
| ATOM | 7251 | N | TYR | L | 187 | −115.733 | −31.497 | 4.259 | 1.00 | 127.00 N |
| ATOM | 7252 | CA | TYR | L | 187 | −116.209 | −31.924 | 2.945 | 1.00 | 127.07 C |
| ATOM | 7253 | CB | TYR | L | 187 | −115.100 | −32.670 | 2.180 | 1.00 | 126.77 C |
| ATOM | 7254 | CG | TYR | L | 187 | −115.569 | −33.414 | 0.944 | 1.00 | 125.78 C |
| ATOM | 7255 | CD1 | TYR | L | 187 | −115.946 | −32.728 | −0.206 | 1.00 | 124.72 C |
| ATOM | 7256 | CE1 | TYR | L | 187 | −116.374 | −33.406 | −1.348 | 1.00 | 124.08 C |
| ATOM | 7257 | CZ | TYR | L | 187 | −116.404 | −34.790 | −1.356 | 1.00 | 123.97 C |
| ATOM | 7258 | OH | TYR | L | 187 | −116.821 | −35.459 | −2.483 | 1.00 | 123.19 O |
| ATOM | 7259 | CE2 | TYR | L | 187 | −116.021 | −35.494 | −0.225 | 1.00 | 124.41 C |
| ATOM | 7260 | CD2 | TYR | L | 187 | −115.610 | −34.804 | 0.916 | 1.00 | 125.07 C |
| ATOM | 7261 | C | TYR | L | 187 | −117.468 | −32.791 | 3.070 | 1.00 | 127.53 C |
| ATOM | 7262 | O | TYR | L | 187 | −118.479 | −32.485 | 2.430 | 1.00 | 127.68 O |
| ATOM | 7263 | N | GLU | L | 188 | −117.399 | −33.880 | 3.883 | 1.00 | 129.18 N |
| ATOM | 7264 | CA | GLU | L | 188 | −118.501 | −34.818 | 4.128 | 1.00 | 129.38 C |
| ATOM | 7265 | CB | GLU | L | 188 | −118.018 | −36.009 | 4.966 | 1.00 | 129.23 C |
| ATOM | 7266 | C | GLU | L | 188 | −119.720 | −34.118 | 4.776 | 1.00 | 129.63 C |
| ATOM | 7267 | O | GLU | L | 188 | −120.858 | −34.507 | 4.509 | 1.00 | 129.72 O |
| ATOM | 7268 | N | LYS | L | 189 | −119.473 | −33.061 | 5.588 | 1.00 | 129.95 N |
| ATOM | 7269 | CA | LYS | L | 189 | −120.511 | −32.273 | 6.264 | 1.00 | 130.00 C |
| ATOM | 7270 | CB | LYS | L | 189 | −120.039 | −31.825 | 7.670 | 1.00 | 129.92 C |
| ATOM | 7271 | CG | LYS | L | 189 | −118.929 | −30.782 | 7.664 | 1.00 | 129.43 C |
| ATOM | 7272 | CD | LYS | L | 189 | −118.905 | −29.927 | 8.907 | 1.00 | 128.46 C |
| ATOM | 7273 | CE | LYS | L | 189 | −118.314 | −28.582 | 8.591 | 1.00 | 127.90 C |
| ATOM | 7274 | NZ | LYS | L | 189 | −118.087 | −27.786 | 9.815 | 1.00 | 127.98 N |
| ATOM | 7275 | C | LYS | L | 189 | −121.069 | −31.088 | 5.414 | 1.00 | 130.15 C |
| ATOM | 7276 | O | LYS | L | 189 | −121.505 | −30.081 | 5.980 | 1.00 | 130.07 O |
| ATOM | 7277 | N | HIS | L | 190 | −121.065 | −31.213 | 4.066 | 1.00 | 131.73 N |
| ATOM | 7278 | CA | HIS | L | 190 | −121.571 | −30.175 | 3.149 | 1.00 | 131.90 C |
| ATOM | 7279 | CB | HIS | L | 190 | −120.507 | −29.099 | 2.854 | 1.00 | 131.89 C |
| ATOM | 7280 | CG | HIS | L | 190 | −120.453 | −27.999 | 3.875 | 1.00 | 132.02 C |
| ATOM | 7281 | ND1 | HIS | L | 190 | −119.727 | −28.135 | 5.050 | 1.00 | 132.00 N |
| ATOM | 7282 | CE1 | HIS | L | 190 | −119.891 | −26.999 | 5.709 | 1.00 | 131.80 C |
| ATOM | 7283 | NE2 | HIS | L | 190 | −120.668 | −26.149 | 5.035 | 1.00 | 131.85 N |
| ATOM | 7284 | CD2 | HIS | L | 190 | −121.033 | −26.774 | 3.863 | 1.00 | 132.09 C |
| ATOM | 7285 | C | HIS | L | 190 | −122.174 | −30.772 | 1.865 | 1.00 | 132.01 C |
| ATOM | 7286 | O | HIS | L | 190 | −121.590 | −31.676 | 1.268 | 1.00 | 131.94 O |
| ATOM | 7287 | N | LYS | L | 191 | −123.346 | −30.255 | 1.450 | 1.00 | 133.19 N |
| ATOM | 7288 | CA | LYS | L | 191 | −124.125 | −30.712 | 0.292 | 1.00 | 133.24 C |
| ATOM | 7289 | CB | LYS | L | 191 | −125.583 | −30.226 | 0.390 | 1.00 | 133.19 C |
| ATOM | 7290 | C | LYS | L | 191 | −123.561 | −30.517 | −1.125 | 1.00 | 133.24 C |
| ATOM | 7291 | O | LYS | L | 191 | −122.976 | −31.456 | −1.677 | 1.00 | 133.17 O |
| ATOM | 7292 | N | VAL | L | 192 | −123.773 | −29.304 | −1.709 | 1.00 | 134.37 N |
| ATOM | 7293 | CA | VAL | L | 192 | −123.399 | −28.887 | −3.077 | 1.00 | 134.31 C |
| ATOM | 7294 | CB | VAL | L | 192 | −124.535 | −28.062 | −3.783 | 1.00 | 134.37 C |

TABLE 14-continued

| | | | | | | | | | | |
|---|---|---|---|---|---|---|---|---|---|---|
| ATOM | 7295 | CG1 | VAL | L | 192 | −125.918 | −28.395 | −3.228 | 1.00 | 134.20 C |
| ATOM | 7296 | CG2 | VAL | L | 192 | −124.511 | −28.243 | −5.303 | 1.00 | 134.07 C |
| ATOM | 7297 | C | VAL | L | 192 | −122.028 | −28.179 | −3.199 | 1.00 | 134.22 C |
| ATOM | 7298 | O | VAL | L | 192 | −121.539 | −27.580 | −2.235 | 1.00 | 134.12 O |
| ATOM | 7299 | N | TYR | L | 193 | −121.430 | −28.253 | −4.417 | 1.00 | 133.81 N |
| ATOM | 7300 | CA | TYR | L | 193 | −120.149 | −27.659 | −4.813 | 1.00 | 133.58 C |
| ATOM | 7301 | CB | TYR | L | 193 | −119.001 | −28.671 | −4.620 | 1.00 | 133.46 C |
| ATOM | 7302 | CG | TYR | L | 193 | −118.739 | −29.051 | −3.181 | 1.00 | 133.01 C |
| ATOM | 7303 | CD1 | TYR | L | 193 | −118.875 | −30.366 | −2.752 | 1.00 | 132.19 C |
| ATOM | 7304 | CE1 | TYR | L | 193 | −118.643 | −30.720 | −1.424 | 1.00 | 131.86 C |
| ATOM | 7305 | CZ | TYR | L | 193 | −118.251 | −29.752 | −0.512 | 1.00 | 131.88 C |
| ATOM | 7306 | OH | TYR | L | 193 | −118.014 | −30.081 | 0.802 | 1.00 | 131.77 O |
| ATOM | 7307 | CE2 | TYR | L | 193 | −118.107 | −28.437 | −0.920 | 1.00 | 132.04 C |
| ATOM | 7308 | CD2 | TYR | L | 193 | −118.345 | −28.096 | −2.248 | 1.00 | 132.53 C |
| ATOM | 7309 | C | TYR | L | 193 | −120.174 | −27.183 | −6.281 | 1.00 | 133.60 C |
| ATOM | 7310 | O | TYR | L | 193 | −120.575 | −27.945 | −7.169 | 1.00 | 133.62 O |
| ATOM | 7311 | N | ALA | L | 194 | −119.740 | −25.930 | −6.530 | 1.00 | 133.66 N |
| ATOM | 7312 | CA | ALA | L | 194 | −119.665 | −25.342 | −7.876 | 1.00 | 133.63 C |
| ATOM | 7313 | CB | ALA | L | 194 | −121.049 | −24.958 | −8.382 | 1.00 | 133.53 C |
| ATOM | 7314 | C | ALA | L | 194 | −118.735 | −24.126 | −7.930 | 1.00 | 133.57 C |
| ATOM | 7315 | O | ALA | L | 194 | −118.548 | −23.429 | −6.929 | 1.00 | 133.52 O |
| ATOM | 7316 | N | CYS | L | 195 | −118.161 | −23.874 | −9.113 | 1.00 | 133.43 N |
| ATOM | 7317 | CA | CYS | L | 195 | −117.267 | −22.740 | −9.350 | 1.00 | 133.34 C |
| ATOM | 7318 | CB | CYS | L | 195 | −115.877 | −23.185 | −9.815 | 1.00 | 133.14 C |
| ATOM | 7319 | SG | CYS | L | 195 | −115.801 | −24.879 | −10.473 | 1.00 | 132.53 S |
| ATOM | 7320 | C | CYS | L | 195 | −117.914 | −21.755 | −10.331 | 1.00 | 133.40 C |
| ATOM | 7321 | O | CYS | L | 195 | −118.453 | −22.174 | −11.358 | 1.00 | 133.32 O |
| ATOM | 7322 | N | GLU | L | 196 | −117.874 | −20.455 | −10.011 | 1.00 | 134.32 N |
| ATOM | 7323 | CA | GLU | L | 196 | −118.465 | −19.444 | −10.880 | 1.00 | 134.46 C |
| ATOM | 7324 | CB | GLU | L | 196 | −119.065 | −18.302 | −10.040 | 1.00 | 134.58 C |
| ATOM | 7325 | CG | GLU | L | 196 | −120.267 | −17.617 | −10.681 | 1.00 | 135.04 C |
| ATOM | 7326 | CD | GLU | L | 196 | −121.579 | −18.381 | −10.662 | 1.00 | 135.55 C |
| ATOM | 7327 | OE1 | GLU | L | 196 | −121.760 | −19.254 | −9.778 | 1.00 | 135.81 O |
| ATOM | 7328 | OE2 | GLU | L | 196 | −122.434 | −18.093 | −11.532 | 1.00 | 135.51 O |
| ATOM | 7329 | C | GLU | L | 196 | −117.416 | −18.934 | −11.879 | 1.00 | 134.37 C |
| ATOM | 7330 | O | GLU | L | 196 | −116.423 | −18.340 | −11.458 | 1.00 | 134.31 O |
| ATOM | 7331 | N | VAL | L | 197 | −117.636 | −19.176 | −13.196 | 1.00 | 133.36 N |
| ATOM | 7332 | CA | VAL | L | 197 | −116.719 | −18.778 | −14.283 | 1.00 | 133.27 C |
| ATOM | 7333 | CB | VAL | L | 197 | −116.337 | −19.982 | −15.188 | 1.00 | 133.17 C |
| ATOM | 7334 | CG1 | VAL | L | 197 | −115.194 | −19.624 | −16.131 | 1.00 | 132.97 C |
| ATOM | 7335 | CG2 | VAL | L | 197 | −115.984 | −21.209 | −14.357 | 1.00 | 133.07 C |
| ATOM | 7336 | C | VAL | L | 197 | −117.217 | −17.552 | −15.101 | 1.00 | 133.31 C |
| ATOM | 7337 | O | VAL | L | 197 | −118.137 | −17.677 | −15.917 | 1.00 | 133.28 O |
| ATOM | 7338 | N | THR | L | 198 | −116.575 | −16.382 | −14.887 | 1.00 | 133.26 N |
| ATOM | 7339 | CA | THR | L | 198 | −116.887 | −15.099 | −15.541 | 1.00 | 133.21 C |
| ATOM | 7340 | CB | THR | L | 198 | −116.962 | −13.990 | −14.468 | 1.00 | 133.25 C |
| ATOM | 7341 | OG1 | THR | L | 198 | −117.383 | −14.550 | −13.215 | 1.00 | 133.25 O |
| ATOM | 7342 | CG2 | THR | L | 198 | −117.879 | −12.849 | −14.872 | 1.00 | 133.03 C |
| ATOM | 7343 | C | THR | L | 198 | −115.863 | −14.812 | −16.668 | 1.00 | 133.19 C |
| ATOM | 7344 | O | THR | L | 198 | −114.677 | −14.630 | −16.373 | 1.00 | 133.08 O |
| ATOM | 7345 | N | HIS | L | 199 | −116.314 | −14.791 | −17.952 | 1.00 | 132.62 N |
| ATOM | 7346 | CA | HIS | L | 199 | −115.419 | −14.594 | −19.104 | 1.00 | 132.74 C |
| ATOM | 7347 | CB | HIS | L | 199 | −114.732 | −15.945 | −19.441 | 1.00 | 132.53 C |
| ATOM | 7348 | CG | HIS | L | 199 | −113.816 | −15.924 | −20.625 | 1.00 | 132.36 C |
| ATOM | 7349 | ND1 | HIS | L | 199 | −112.592 | −15.293 | −20.576 | 1.00 | 132.07 N |
| ATOM | 7350 | CE1 | HIS | L | 199 | −112.048 | −15.482 | −21.764 | 1.00 | 131.86 C |
| ATOM | 7351 | NE2 | HIS | L | 199 | −112.843 | −16.186 | −22.565 | 1.00 | 132.18 N |
| ATOM | 7352 | CD2 | HIS | L | 199 | −113.974 | −16.479 | −21.850 | 1.00 | 132.26 C |
| ATOM | 7353 | C | HIS | L | 199 | −116.057 | −13.921 | −20.361 | 1.00 | 133.02 C |
| ATOM | 7354 | O | HIS | L | 199 | −116.002 | −12.693 | −20.484 | 1.00 | 133.04 O |
| ATOM | 7355 | N | GLN | L | 200 | −116.617 | −14.739 | −21.297 | 1.00 | 135.50 N |
| ATOM | 7356 | CA | GLN | L | 200 | −117.267 | −14.333 | −22.548 | 1.00 | 135.70 C |
| ATOM | 7357 | CB | GLN | L | 200 | −116.849 | −15.247 | −23.719 | 1.00 | 135.56 C |
| ATOM | 7358 | C | GLN | L | 200 | −118.801 | −14.300 | −22.335 | 1.00 | 135.94 C |
| ATOM | 7359 | O | GLN | L | 200 | −119.373 | −13.205 | −22.296 | 1.00 | 135.79 O |
| ATOM | 7360 | N | GLY | L | 201 | −119.440 | −15.467 | −22.161 | 1.00 | 136.37 N |
| ATOM | 7361 | CA | GLY | L | 201 | −120.882 | −15.553 | −21.905 | 1.00 | 136.75 C |
| ATOM | 7362 | C | GLY | L | 201 | −121.202 | −15.288 | −20.440 | 1.00 | 136.97 C |
| ATOM | 7363 | O | GLY | L | 201 | −120.302 | −15.402 | −19.596 | 1.00 | 137.00 O |
| ATOM | 7364 | N | LEU | L | 202 | −122.472 | −14.930 | −20.109 | 1.00 | 134.74 N |
| ATOM | 7365 | CA | LEU | L | 202 | −122.867 | −14.645 | −18.717 | 1.00 | 134.75 C |
| ATOM | 7366 | CB | LEU | L | 202 | −124.283 | −14.035 | −18.632 | 1.00 | 134.74 C |
| ATOM | 7367 | CG | LEU | L | 202 | −124.427 | −12.560 | −18.170 | 1.00 | 134.94 C |
| ATOM | 7368 | CD1 | LEU | L | 202 | −123.963 | −12.347 | −16.720 | 1.00 | 134.59 C |
| ATOM | 7369 | CD2 | LEU | L | 202 | −123.779 | −11.579 | −19.147 | 1.00 | 134.83 C |
| ATOM | 7370 | C | LEU | L | 202 | −122.724 | −15.854 | −17.774 | 1.00 | 134.70 C |
| ATOM | 7371 | O | LEU | L | 202 | −123.054 | −16.975 | −18.176 | 1.00 | 134.76 O |
| ATOM | 7372 | N | SER | L | 203 | −122.207 | −15.602 | −16.531 | 1.00 | 132.85 N |

TABLE 14-continued

PCSK9 and AX132 Fab complex x-ray structure

| ATOM | 7373 | CA  | SER | L | 203 | −121.939 | −16.541 | −15.416 | 1.00 | 132.69 | C |
|------|------|-----|-----|---|-----|----------|---------|---------|------|--------|---|
| ATOM | 7374 | CB  | SER | L | 203 | −122.407 | −15.956 | −14.084 | 1.00 | 132.67 | C |
| ATOM | 7375 | OG  | SER | L | 203 | −121.456 | −15.053 | −13.544 | 1.00 | 132.56 | O |
| ATOM | 7376 | C   | SER | L | 203 | −122.401 | −18.015 | −15.589 | 1.00 | 132.56 | C |
| ATOM | 7377 | O   | SER | L | 203 | −123.604 | −18.287 | −15.636 | 1.00 | 132.54 | O |
| ATOM | 7378 | N   | SER | L | 204 | −121.425 | −18.953 | −15.678 | 1.00 | 131.25 | N |
| ATOM | 7379 | CA  | SER | L | 204 | −121.638 | −20.395 | −15.878 | 1.00 | 130.96 | C |
| ATOM | 7380 | CB  | SER | L | 204 | −121.054 | −20.820 | −17.229 | 1.00 | 130.82 | C |
| ATOM | 7381 | OG  | SER | L | 204 | −120.861 | −22.219 | −17.363 | 1.00 | 130.49 | O |
| ATOM | 7382 | C   | SER | L | 204 | −121.140 | −21.326 | −14.709 | 1.00 | 130.87 | C |
| ATOM | 7383 | O   | SER | L | 204 | −119.996 | −21.801 | −14.776 | 1.00 | 130.88 | O |
| ATOM | 7384 | N   | PRO | L | 205 | −121.976 | −21.642 | −13.662 | 1.00 | 129.59 | N |
| ATOM | 7385 | CA  | PRO | L | 205 | −121.498 | −22.529 | −12.582 | 1.00 | 129.34 | C |
| ATOM | 7386 | CB  | PRO | L | 205 | −122.188 | −21.966 | −11.329 | 1.00 | 129.18 | C |
| ATOM | 7387 | CG  | PRO | L | 205 | −123.445 | −21.284 | −11.852 | 1.00 | 129.34 | C |
| ATOM | 7388 | CD  | PRO | L | 205 | −123.354 | −21.187 | −13.377 | 1.00 | 129.61 | C |
| ATOM | 7389 | C   | PRO | L | 205 | −121.783 | −24.031 | −12.775 | 1.00 | 129.05 | C |
| ATOM | 7390 | O   | PRO | L | 205 | −122.934 | −24.470 | −12.651 | 1.00 | 129.03 | O |
| ATOM | 7391 | N   | VAL | L | 206 | −120.725 | −24.823 | −13.066 | 1.00 | 126.14 | N |
| ATOM | 7392 | CA  | VAL | L | 206 | −120.845 | −26.276 | −13.214 | 1.00 | 125.92 | C |
| ATOM | 7393 | CB  | VAL | L | 206 | −119.918 | −26.893 | −14.300 | 1.00 | 125.90 | C |
| ATOM | 7394 | CG1 | VAL | L | 206 | −119.966 | −28.417 | −14.279 | 1.00 | 125.78 | C |
| ATOM | 7395 | CG2 | VAL | L | 206 | −120.302 | −26.382 | −15.685 | 1.00 | 125.56 | C |
| ATOM | 7396 | C   | VAL | L | 206 | −120.724 | −26.885 | −11.794 | 1.00 | 125.88 | C |
| ATOM | 7397 | O   | VAL | L | 206 | −119.719 | −26.691 | −11.099 | 1.00 | 125.71 | O |
| ATOM | 7398 | N   | THR | L | 207 | −121.805 | −27.568 | −11.367 | 1.00 | 124.30 | N |
| ATOM | 7399 | CA  | THR | L | 207 | −121.986 | −28.167 | −10.047 | 1.00 | 124.17 | C |
| ATOM | 7400 | CB  | THR | L | 207 | −123.337 | −27.725 | −9.471  | 1.00 | 124.15 | C |
| ATOM | 7401 | C   | THR | L | 207 | −121.831 | −29.677 | −9.931  | 1.00 | 124.10 | C |
| ATOM | 7402 | O   | THR | L | 207 | −121.768 | −30.406 | −10.930 | 1.00 | 123.98 | O |
| ATOM | 7403 | N   | LYS | L | 208 | −121.783 | −30.124 | −8.660  | 1.00 | 122.52 | N |
| ATOM | 7404 | CA  | LYS | L | 208 | −121.667 | −31.498 | −8.184  | 1.00 | 122.52 | C |
| ATOM | 7405 | CB  | LYS | L | 208 | −120.276 | −32.080 | −8.506  | 1.00 | 122.45 | C |
| ATOM | 7406 | C   | LYS | L | 208 | −121.901 | −31.530 | −6.663  | 1.00 | 122.58 | C |
| ATOM | 7407 | O   | LYS | L | 208 | −121.475 | −30.621 | −5.947  | 1.00 | 122.64 | O |
| ATOM | 7408 | N   | SER | L | 209 | −122.584 | −32.578 | −6.183  | 1.00 | 120.30 | N |
| ATOM | 7409 | CA  | SER | L | 209 | −122.872 | −32.856 | −4.770  | 1.00 | 120.25 | C |
| ATOM | 7410 | CB  | SER | L | 209 | −124.216 | −32.272 | −4.345  | 1.00 | 120.16 | C |
| ATOM | 7411 | OG  | SER | L | 209 | −125.283 | −32.698 | −5.173  | 1.00 | 120.24 | O |
| ATOM | 7412 | C   | SER | L | 209 | −122.830 | −34.387 | −4.659  | 1.00 | 120.28 | C |
| ATOM | 7413 | O   | SER | L | 209 | −123.482 | −35.073 | −5.458  | 1.00 | 120.26 | O |
| ATOM | 7414 | N   | PHE | L | 210 | −122.005 | −34.914 | −3.725  | 1.00 | 117.17 | N |
| ATOM | 7415 | CA  | PHE | L | 210 | −121.750 | −36.351 | −3.506  | 1.00 | 117.28 | C |
| ATOM | 7416 | CB  | PHE | L | 210 | −120.883 | −36.611 | −2.253  | 1.00 | 117.33 | C |
| ATOM | 7417 | CG  | PHE | L | 210 | −121.132 | −35.842 | −0.967  | 1.00 | 117.55 | C |
| ATOM | 7418 | CD1 | PHE | L | 210 | −120.074 | −35.499 | −0.128  | 1.00 | 117.54 | C |
| ATOM | 7419 | CE1 | PHE | L | 210 | −120.300 | −34.825 | 1.076   | 1.00 | 117.48 | C |
| ATOM | 7420 | CZ  | PHE | L | 210 | −121.585 | −34.509 | 1.459   | 1.00 | 117.93 | C |
| ATOM | 7421 | CE2 | PHE | L | 210 | −122.650 | −34.837 | 0.646   | 1.00 | 118.09 | C |
| ATOM | 7422 | CD2 | PHE | L | 210 | −122.427 | −35.521 | −0.560  | 1.00 | 117.92 | C |
| ATOM | 7423 | C   | PHE | L | 210 | −122.906 | −37.373 | −3.653  | 1.00 | 117.31 | C |
| ATOM | 7424 | O   | PHE | L | 210 | −122.822 | −38.309 | −4.460  | 1.00 | 117.16 | O |
| TER  | 7425 |     | PHE | L | 210 |          |         |         |      |        |   |
| END  |      |     |     |   |     |          |         |         |      |        |   |

SEQUENCES

LIST OF VH SEQUENCES

SEQ ID NO: 360
EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARER
YGYYFDYWGQGTLVTVSSAS

SEQ ID NO: 361 (=360-AS)
EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARER
YGYYFDYWGQGTLVTVSS

SEQ ID NO: 550 AX132_VH DNA SEQUENCE
GAAGTGCAGCTGCTGGAATCTGGTGGTGGTCTGGTGCAGCCAGGTGGTTCTCTGCGTCTGTCTTGCAAGGCCTCTGGTTACACCTTCTCTTCTTACGGGA
TGTACTGGGTGCGTCAGGCACCAGGTAAGGGTCTGGAATGGATCGGTTGGATCGACCCAGGCAGCGGTGGCACCAAGTACAACGAAAAGTTCAAGGGTAA
GGCCACCATCTCTAGAGACAACTCTAAGAACACCCTGTACTTGCAGATGAACTCTCTGCGTGCCGAGGACACTGCAGTGTACTACTGCGCCCGTGAACGT
TACGGTTACTACTTCGACTACTGGGGTCAGGGTACGCTGGTGACTGTCTCGAGC

| SEQUENCES |
|---|
| SEQ ID NO: 362<br>EVQLLESGGGLVQPGGSLRLSCKASGYTFSRYGINWVRQAPGKGLEWIGRIDPGNGGTRYNEKFKGKATISRDNSKNTLYLQMNSLRAEDTAVYYCARAN<br>DGYSFDYWGQGTLVTVSSAS |
| SEQ ID NO: 363 (=362-AS)<br>EVQLLESGGGLVQPGGSLRLSCKASGYTFSRYGINWVRQAPGKGLEWIGRIDPGNGGTRYNEKFKGKATISRDNSKNTLYLQMNSLRAEDTAVYYCARAN<br>DGYSFDYWGQGTLVTVSS |
| SEQ ID NO: 561 >AX213-VH [SEQ ID NO: 12]<br>CAGGTGCAATTGCTGGAATCTGGTGGTGGTCTGGTGCAGCCAGGTGGTTCTCTGCGTCTGTCTTGCAAGGCTAGCGGTTACACCTTCTCTCGCTACGGTATCA<br>ACTGGGTGCGTCAGGCACCAGGTAAGGGTCTGAATGGATCGGTCGGATCGACCCAGGTAACGGTGGTACTAGGTACAACGAAAAGTTCAAGGGTAAGGCCACC<br>ATCTCTAGAGACAACTCTAAGAACACCCTGTACTTGCAGATGAACTCTCTGCGTGCCGAGGACACTGCAGTGTACTACTGCGCCCGTGCAAATGACGGTTACT<br>CCTTCGACTACTGGGGTCAGGGTACGCTGGTGACTGTCTCGAGC |
| SEQ ID NO: 364<br>QVQLLESGGGLVQPGGSLRLSCKASGYTFSSYSIYWVRQAPGKGLEWIGWIDPGNGGTRYNQKFQSKATISRDNSKNTLYLQMNSLRAEDTAVYYCARAR<br>VGYSLDYWGQGTLVTVSSAS |
| SEQ ID NO: 365<br>QVQLLESGGGLVQPGGSLRLSCKASGYTFSRQGFTWVRQAPGKGLEWIGWIDPGNGGTRYNEKFKGKATISRDNSKNTLYLQMNSLRAEDTAVYYCARYR<br>VGYSLDYWGQGTLVTVSSAS |
| SEQ ID NO: 366<br>QVQLLESGGGLVQPGGSLRLSCKASGYTFSSYSFSWVRQAPGKGLEWIGYIDPGSGGTKYNQKFQGKATISRDNSKNTLYLQMNSLRAEDTAVYYCARQR<br>VGYSLDYWGQGTLVTVSSAS |
| SEQ ID NO: 367<br>QVQLLESGGGLVQPGGSLRLSCKASGYTFSRYGINWVRQAPGKGLEWIGRIDPGNGGTRYNEKFKGKATISRDNSKNTLYLQMNSLRAEDTAVYYCARAN<br>DGYSFDYWGQGTLVTVSSAS |
| SEQ ID NO: 368<br>QVQLLESGGGLVQPGGSLRLSCKASGYTFSRYGISWVRQAPGKGLEQIGWIDPGSGGTRYNQKFKSKATISRDNSKNTLYLQMNSLRAEDTAVYYCARAR<br>VGYSFDYWGQGTLVTVSSAS |
| SEQ ID NO: 369<br>QVQLLESGGGLVQPGGSLRLSCKASGYTFSSYTNYWVRQAPGKGLEWIGYIDPGSGGTRYNQKFQGKATISRDNSKNTLYLQMNSLRAEDTAVYYCARSR<br>VGYSFDYWGQGTLVTVSSAS |
| SEQ ID NO: 370<br>QVQLLESGGGLVQPGGSLRLSCKASGYTFSRYSYYWVRQAPGKGLEWIGYIDPGSGGTKYNQKFQSKATISRDNSKNTLYLQMNSLRAEDTAVYYCARAR<br>VGYSLDYWGQGTLVTVSSAS |
| SEQ ID NO: 371<br>QVQLLESGGGLVQPGGSLRLSCKASGYTFSSYANTWVRQAPGKGLEWIGWIDPGNGGTSYNQKFKSKATISRDNSKNTLYLQMNSLRAEDTAVYYCARYR<br>SGYSLDYWGQGTLVTVSSAS |
| SEQ ID NO: 372<br>QVQLLESGGGLVQPGGSLRLSCKASGYTFSSYGYYWVRQAPGKGLEWIGWIDPGSGGTRYNQKFKGKATISRDNSKNTLYLQMNSLRAEDTAVYYCARER<br>VGYSLDYWGQGTLVTVSSAS |
| SEQ ID NO: 373<br>QVQLLESGGGLVQPGGSLRLSCKASGYTFSRYAINWVRQAPGKGLEWIGWIDPGSGGTRYNEKFKGQATISRDNSKNTLYLQMNSLRAEDTAVYYCARHR<br>VGYSLDFWGQGTLVTVSSAS |
| SEQ ID NO: 374<br>QVQLLESGGGLVQPGGSLRLSCKASGYTFSRYGIYWVRQAPGKGLEWIGYIDPGSGGTRYNEKFKGKATISRDNSKNTLYLQMNSLRAEDTAVYYCARYH<br>YGYSFDYWGQGTLVTVSSAS |
| SEQ ID NO: 375<br>QVQLLESGGGLVQPGGSLRLSCKASGYTFSRYGYYWVRQVPGKGLEWIGYIDPGNGGTSYNEKFKGKATISRDNSKNTLYLQMNSLRAEDTAVYYCARYH<br>DGYSFDYWGQGTLVTVSSAS |
| SEQ ID NO: 376<br>QVQLLESGGGLVQPGGSLRLSCKASGYTFSRYAYNWVRQAPGKGLEWIGWIDPGSGGTRYNQKFKGKATISRDNSKNTLYLQMNSLRAEDTAVYYCARER<br>FAYYLDYWGQGTLVTVSSAS |
| SEQ ID NO: 377<br>QVQLLESGGGLVQPGGSLRLSCKASGYTFSRYGFSWVRQAPGKGLEWIGRIDPGSGGTRYNQQFQGKATISRDNSKNTLYLQMNSLRAEDTAVYYCARSR<br>DGYYFDYWGQGTLVTVSSAS |
| SEQ ID NO: 378<br>QVQLLESGGGLVQPGGSLRLSCKASGYTFSRYAFNWVRQAPGKGLEWIGYIDPGSGGTRYNEKFQGKATISRDNSKNTLYLQMNSLRAEDTAVYYCARAR<br>DGYSFDYWGQGTLVTVSSAS |
| SEQ ID NO: 379<br>QVQLLESGGGLVQPGGSLRLSCKASGYTFSSYGIYWVRQAPGKGLEWIGWIDPGSGGTRYNEKFQSKATISRDNSKNTLYLQMNSLRAEDTAVYYCARER<br>AGYYLDYWGQGTLVTVSSAS |

| SEQUENCES |
|---|
| SEQ ID NO: 380<br>QVQLLESGGGLVQPGGSLRLSCKASGYTFSRYTITWVRQAPGKGLEWIGYIDPGSGGTKYNEKFQGKATISRDNSKNTLYLQMNSLRAEDTAVYYCARHR<br>VGYYFDYWGQGTLVTVSSAS |
| SEQ ID NO: 381<br>QVQLLESGGGLVQPGGSLRLSCKASGYTFSRYSFIWVRQAPGKGLEWIGYIDPGSGGTKYNQKFKGKATISRDNSKNTLYLQMNSLRTEDTAVYYCARYR<br>SGYSLDYWGQGTLVTVSSAS |
| SEQ ID NO: 382<br>QVQLLESGGGLVQPGGSLRLSCKASGYTFSRYTFYWVRQAPGKGLEWIGYIDPGSGGTRYNQKFKGKATISRDNSKNTLYLQMNSLRAEDTAVYYCARAR<br>VGYSFDYWGQGTLVTVSSAS |
| SEQ ID NO: 383<br>QVQLLESGGGLVQPGGSLRLSCKASGQTFSSYGFNWVRQAPGKGLEWIGWIDPGSGGTRYNQKFKSKATISRDNSKNTLYLQMNSLRAEDTAVYYCARAN<br>VGYSFDYWGQGTLVTVSSAS |
| SEQ ID NO: 384<br>QVQLLESGGGLVQPGGSLRLSCKASGYTFSRYGYYWVRQAPGKGLEWIGRIDPGSGGTSYNEKFQSKATISRDNSKNTLYLQMNSLRAEDTAVYYCARAR<br>VG?SFDYWGQGTLVTVSSAS |
| SEQ ID NO: 385<br>QVQLLESGGGLVQPGGSLRLSCKASGYTFSRYGIYWVRQAPGKGLEWIGRIDPGNGGTRYNQKFQSKATISRDNSKNTLYLQMNSLRAEDTAVYYCARSR<br>VGYSFDYWGQGTLVTVSSAS |
| SEQ ID NO: 386<br>QVQLLESGGGLVQPGGSLRLSCKASGYTFSRYANYWVRQAPGKGLEWIGYIDPGSGGTKYNEKFKGKATISRDNSKNTLYLQMNSLRAEDTAVYYCARSH<br>VGYYFDYWGQGTLVTVSSAS |
| SEQ ID NO: 387<br>QVQLLESGGGLVQPGGSLRLSCKASGYTFSRYSNWVRQAPGKGLEWIGWIDPGNGGTRYNQKFQSKATISRDNSKNTLYLQMNSLRAEDTAVYYCARAR<br>VGYSFDYWGQGTLVTVSSAS |
| SEQ ID NO: 388<br>QVQLLESGGGLVQPGGSLRLSCKASGYTFSSYSITWVRQAPGKGLEWIGWIDPGSGGTRYNEKFKSKATISRDNSKNTLYLQMNSLRAEDTAVYYCARHR<br>VGYSLDYWGQGTLVTVSSAS |
| SEQ ID NO: 389<br>QVQLLESGGGLVQPGGSLRLSCKASGYTFSRYGFSWVRQAPGKGLEWIGWIDPGNGGTRYNQQFKGKATISRDNSKNTLYLQMNSLRAEDTAVYYCARSR<br>VGYSLDYWGQGTLVTVSSAS |
| SEQ ID NO: 390<br>QVQLLESGGGLVQPGGSLRLSCKASGYTFSSYTYTWVRQAPGKGLEWIGWIDPGSGGTRYNEKFEGKATISRDNSKNTLYLQMNSLRAEDTAVYYCARSR<br>VGYSLDYWGQGTLVTVSSAS |
| SEQ ID NO: 391<br>QVQLLESGGGLVQPGGSLRLSCKASGYTFSSYSYYWVRQAPGKGLEWIGRIDPGSGGTRYNQKFQGKATISRDNSKNTLYLQMNSLRAEDTAVYYCARYR<br>DGYSFDYWGQGTLVTVSSAS |
| SEQ ID NO: 392<br>QVQLLESGGGLVQPGGSLRLSCKASGYTFSSYGYSWVRQAPGKGLEWIGRIDPGSGGTKYNEKFKGKATISRDNSKNTLYLQMNSLRAEDTAVYYCARDR<br>VGYSLDYWGQGTLVTVSSAS |
| SEQ ID NO: 393<br>QVQLLESGGGLVQPGGSLRLSCKASGYTFSRYTFSWVRQAPGKGLEWIGYIDPGNGGTRYNEQFKGKATISRDNSKNTLYLQMNSLRAEDTAVYYCARQR<br>VGYNLDYWGQGTLVTVSSAS |
| SEQ ID NO: 394<br>QVQLLESGGGLVQPGGSLRLSCKASGYTFSSYGFSWVRQAPGKGLEWIGWIDPGNGGTRYNEQFQGKATISRDNSKNTLYLQMNSLRAEDTAVYYCARQR<br>VGYSLDYWGEGTLVTVSSAS |
| SEQ ID NO: 395<br>QVQLLESGGGLVQPGGSLRLSCKASGYTFSRYSNWVRQAPGKGLEWIGWIDPGNGGTRYNEQFQGKATISRDNSKNTLYLQMNSLRAEDTAVYYCARQR<br>VGYSLDYWGQGTLVTVSSAS |
| SEQ ID NO: 396<br>QVQLLESGGGLVQPGGSLRLSCKASGYTFSSYGQSWVRQAPGKGLEWIGRIDPGSGGTRYNEKFQGKATISRDNSKNTLYLQMNSLRAEDTAVYYCARSR<br>DGYSLDYWGQGTLVTVSSAS |
| SEQ ID NO: 397<br>QVQLLESGGGLVQPGGSLRLSCKASGYTFSSYAISWVRQAPGKGLEWIGRIDPGSGGTRYNEKFQSKATISRDNSKNTLYLQMNSLRAEDTAVYYCARSR<br>DGYSLDYWGQGTLVTVSSAS |
| SEQ ID NO: 398<br>QVQLLESGGGLVQPGGSLRLSCKASGYTFSRYSYYWVRQAPGKGLEWIGYIDPGSGGTKYNQKFKGKATISRDNSKNTLYLQMNSLRAEDTAVYYCARYR<br>DGYSFDYWGQGTLVTVSSAS |

| SEQUENCES |
|---|
| SEQ ID NO: 399<br>QVQLLESGGGLVQPGGSLRLSCKASGYTFSSYTYNWVRQAPGKGLEWIGYIDPGNGGTNYNQKFQSKATISRDNSKNTLYLQMNSLRAEDTAVYYCARSR<br>VGYSLDYWGQGTLVTVSSAS |
| SEQ ID NO: 400<br>QVQLLESGGGLVQPGGSLRLSCKASGYTFSSYTISWVRQAPGKGLEWIGYIDPGNGGTRYNQQFQGKATISRDNSKNTLYLQMNSLRVEDTAVYYCARSR<br>VGYSFDYWGQGTLVTVSSAS |
| SEQ ID NO: 401<br>QVQLLESGGGLLQPGGSLRLSCKASGYTFSRYTFNWVRQAPGKGLEWIGWIDPGSGGTRYNQKFQSKATISRDNSKNTLYLQMNSLRAEDTAVYYCARAR<br>VGYSFDYWGQGTLVTVSSAS |
| SEQ ID NO: 402<br>QVQLLESGGGLVQPGGSLRLSCKGQRLPPRYGYYWVRQAPGKGLEWIGYIDPGNGGTRYNEKFQSKATISRDNSKNTLYLQMNSLRAEDTAVYYCARYRS<br>GYYLDYWGQGTLVTVSSAS |
| SEQ ID NO: 403<br>QVQLLESGGGLVQPGGSLRLSCKASGYTYSRYTFSWVRQAPGKGLEWIGYIDPGSGGTKYNQKFKGKATISRDNSKNTLYLQMNSLRAEDTAVYYCARAR<br>VGYSFDYWGQGTLVTVSSAS |
| SEQ ID NO: 404<br>QVQLLESGGGLVQPGGSLRLSCKASGYTFSSYGYYWVRQAPGKGLEWIGYIDPGSGGTRYNQKFKSKATISRDNSKNTLYLQMNSLRAEDTAVYYCARYR<br>VGYSFDYWGQGTLVTVSSAS |
| SEQ ID NO: 405<br>QVQLLESGGGLVQPGGSLRLSCKASGYTFSRYGFSWVRQAPGKGLEWIGRIDPGSGGTRYNEKFQSKATISWDNSKNTLYLQMNSLRAEDTAVYYCARSR<br>DGYSFDYWGQGTLVTVSSAS |
| SEQ ID NO: 406<br>QVQLLESGGGLVQPGGSLRLSCKASDYTFSSYGNNWVRQAPGKGLEWIGRIDPGNGGTRYNEKFQGKATISRDNSKNTLYLQMNSLRAEDTAVYYCARAR<br>DGYSLDYWGQGTLVTVSSAS |
| SEQ ID NO: 407<br>QVQLLESGGGLVQPGGSLRLSCKASGYTFSSYGISWVRQAPGKGLEWIGWIDPGNGGTKYNQKFQSKATISRDNSKNTLYLQMNSLRAEDTAVYYCARSR<br>VGYSLDYWGQGTLVTVSSAS |
| SEQ ID NO: 408<br>QVQLLESGGGLVQPGGSLRLSCKASGYTFSSYTINWVRQAPGKGLEWIGWIDPGSGGTRYNEKFQGKATISRDNSKNTLYLQMNSLRAEDTAVYYCARHR<br>VGYSFDYWGQGTLVTVSSAS |
| SEQ ID NO: 409<br>QVQLLESGGGLVQPGGSLRLSCKASGYTFSRYGISWVRQAPGKGLEWIGRIDPGSGGTRYNEKFQSKATISRDNSKNTLYLQMNSLRAQDTAVYYCARAN<br>DGYSFDYWGQGTLVTVSSAS |
| SEQ ID NO: 410<br>QVQLLESGGGLVQPGGSLRLSCKASGYTFSRYGINWVRQAPGKGLEWIGRIDPGNGGTRYNEKFKGKATISRDNSKNTLYLQMNSLRAEDTAVYYCARAD<br>VGYSFDYWGQGTLVTVSSAS |
| SEQ ID NO: 411<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGF<br>VYYSFDYWGQGTLVTVSSAS |
| SEQ ID NO: 412<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGF<br>IYYSFDYWGQGTLVTVSSAS |
| SEQ ID NO: 413<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGF<br>LYYSFDYWGQGTLVTVSSAS |
| SEQ ID NO: 414<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGR<br>IYYSFDYWGQGTLVTVSSAS |
| SEQ ID NO: 415<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGR<br>FYYSFDYWGQGTLVTVSSAS |
| SEQ ID NO: 416<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGR<br>LYYSLDYWGQGTLVTVSSAS |
| SEQ ID NO: 417<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGF<br>IYYDFDYWGQGTLVTVSSAS |

| SEQUENCES |
| --- |
| SEQ ID NO: 418<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGK<br>IYYSFDYWGQGTLVTVSSAS |
| SEQ ID NO: 419<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGY<br>LYYSFDYWGQGTLVTVSSAS |
| SEQ ID NO: 420<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGF<br>IYYSLDYWGQGTLVTVSSAS |
| SEQ ID NO: 421<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGN<br>LYYSLDYWGQGTLVTVSSAS |
| SEQ ID NO: 422<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCSRGK<br>VGYSLDYWGQGTLVTVSSAS |
| SEQ ID NO: 423<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGS<br>IGYNLDYWGQGTLVTVSSAS |
| SEQ ID NO: 424<br>EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARGR<br>DGYSLDYWGQGTLVTVSSAS |
| SEQ ID NO: 425<br>EVQLLESGGGLVQPGGSLRLSCKASGFTFSAYGMYWVRQAPGKGLEWIGRIDPSNGGTKYNQKFKGKATISRDNSKNTLYLQMNSLRAEDAAVYYCARER<br>YGYYFDYWGQGTLVTVSSAS |
| SEQ ID NO: 426<br>EVQLLESGGGLVQPGGSLRLSCKASGFTFSDYGMYWVRQAPGKGLEWIGRINPNSGGTKYNEKFKGKATISRDNSKNTLYLQMNSLRAEDTAVYYCARER<br>YGYYFDYWGQGTLVTVSSAS |
| SEQ ID NO: 427<br>EVQLLESGGGLVQPGGSLRLSCKASGFTFSSYQMSWVRQAPGKGLEWIGRIDPGSGGTKYNQKFKGKATISRDNSKNTLYLQMNSLRAEDTAVYYCARER<br>YGYYFDYWGQGTLVTVSSAS |
| SEQ ID NO: 428<br>EVQLLESGGGLVQPGGSLRLSCKASGFTFSYYYMYWVRQAPGKGLEWVGRISPSGGSTYYADSVKGRFTISRDNSKNTLYLQMNSLRAEDTAVYYCARER<br>YGYYFDYWGQGTLVTVSSAS |
| SEQ ID NO: 429<br>EVQLLESGGGLVQPGGSLRLSCKASGFTFTAYGMYWVRQAPGKGLEWIGRIDPGSGGTKYNQKFKGKATISRDNSKNTLYLQMNSLRAEDTAVYYCARER<br>YGYYFDYWGQGTLVTVSSAS |
| SEQ ID NO: 430<br>EVQLLESGGGLVQPGGSLRLSCKASGFTFTSYQMSWVRQAPGKGLEWIGRINPGSGGTKYDEKFKGRATISRDNSKNTLYLQMNSLRAEDTAVYYCARER<br>YGYYFDYWGQGTLVTVSSAS |
| SEQ ID NO: 431<br>EVQLLESGGGLVQPGGSLRLSCKASGFTFTSYWMSWVRQAPGKGLEWIGRINPGSGGTKYDEKFKGRATISRDNSKNTLYLQMNSLRAEDTAVYYCARER<br>YGYYFDYWGQGTLVTVSSAS |
| SEQ ID NO: 432<br>EVQLLESGGGLVQPGGSLRLSCKASGLTFTDYGMYWVRQAPGKGLEWIGWINPDSGSTKYAEKFKGRATISRDNSKNTLYLQMNSLRAEDTAVYYCARER<br>YGYYFDYWGQGTLVTVSSAS |
| SEQ ID NO: 433<br>EVQLLESGGGLVQPGGSLRLSCKASGYTFSYYGMYWVRQAPGKGLEWIGRIDPGSGGTKYNEKFKGKATISRDNSKNTLYLQMNSLRAEDTAVYYCARER<br>YGYYFDYWGQGTLVTVSSAS |
| SEQ ID NO: 434<br>EVQLLESGGGLVQPGGSLRLSCKASGYTFTDYGMYWVRQAPGKGLEWIGWIDPGSGGTKYNEKFKGKATISRDNSKNTLYLQMNSLRAEDTAVYYCARER<br>YGYYFDYWGQGTLVTVSSAS |
| SEQ ID NO: 435<br>EVQLLESGGGLVQPGGSLRLSCKASGYTFTNYGMNWVRQAPGKGLEWIGRIDPSSGGTKYNQKFKGKATISRDNSKNTLYLQMNSLRAEDTAVYYCARER<br>YGYYFDYWGQGTLVTVSSAS |
| SEQ ID NO: 436<br>EVQLLESGGGLVQPGGSLRLSCKASGYTFTSYGMYWVRQAPGKGLEWIGRIDPSSGGTKYNQKFKGKATISRDNSKNTLYLQMNSLRAEDTAVYYCARER<br>YGYYFDYWGQGTLVTVSSAS |

| SEQUENCES |
|---|
| SEQ ID NO: 437<br>EVQLLESGGGLVQPGGSLRLSCKASGYTFTSYWMSWVRQAPGKGLEWVGRISPGGGTTYYADSVKGRFTISRDNSKNTLYLQMNSLRAEDTAVYYCARER<br>YGYYFDYWGQGTLVTVSSAS |
| SEQ ID NO: 438<br>EVQLLESGGGLVQPGGSLRLSCQASGYTFSSYGMYWVRQAPGKGLEWIGRINPGSGGTNYDEKFKGRATISRDNSKNTLYLQMNSLRAEDTAVYYCARER<br>YGYYFDYWGQGTLVTVSSAS |
| SEQ ID NO: 439<br>EVQLLESGGGLVQPGGSLRLSCEASGFTFSSYGMYWVRQAPGKGLEWIGRINPKQRWHKYNQKFKGKVTISRDNSKNTLYLQMNSLRAEDTAVYYCARER<br>YGYYFDYWGQGTLVTVSSAS |
| SEQ ID NO: 440<br>EVQLLESGGGLVQPGGSLRLSCEASGFSFSNYGMYWVRQAPGKGLEWIGLDRPRQRWHQLNEKFQGRATISRDNSKNTLYLQMNSLRAEDTAVYYCARER<br>YGYYFDYWGQGTLVTVSSAS |
| SEQ ID NO: 441<br>EVQLLESGGGLVQPGGSLRLSCAASGYSFSAYYIHWVRQAPGKGLESIGRIDPGSGGTKYNEKFQGRATISRDNSKNTLYLQMNSLRAEDTAVYYCARER<br>YGYYFDYWGQGTLVTVSSAS |
| SEQ ID NO: 442<br>EVQLLESGGGLVQPGGSLRLSCKASGFSFSSYGIYWVRQAPGKGLEWIGLDRPKQRVGTKYNQKFQGRVTISRDNSKNTLYLQMNSLRAEDTAVYYCARE<br>RYGYYFDYWGQGTLVTVSSAS |
| SEQ ID NO: 443<br>EVQLLESGGGLVQPGDSLRLSCAASGYSFSTFGIYWVRQAPGKGLEWIGLDRPRQRWPKYNEKFKGRATISRDNSKNTLYLQMNSLRAEDTAVYYCARER<br>YGYYFDYWGQGTLVTVSSAS |
| SEQ ID NO: 444<br>EVQLLESGGGLVQPGGSLRLSCEASGFTFSDYGIHWVRQAPGKGLEWIGLDRPKQRWHQYNEKFQGRATISRDNSKNTLYLQMNSLRAEDTAVYYCARER<br>YGYYFDYWGQGTLVTVSSAS |
| SEQ ID NO: 445<br>EVQLLESGGGLVQPGGSLRLSCAASGYTFSDFGIYWVRQAPGKGLEWIGSDRPRQRVAPKYNQKFKGRATISRDNSKNTLYLQMNSLRAEDTAVYYCARE<br>RYGYYFDYWGQGTLVTVSSAS |
| SEQ ID NO: 446<br>EVQLLESGGGLVQPGGSLRLSCQASGYSFTTYGMYWVRQAPGKGLEWIGRIDPSSGGTKYNQKFQGRVTISRDNSKNTLYLQMNSLRAEDTAVYYCARER<br>YGYYFDYWGQGTLVTVSSAS |
| SEQ ID NO: 447<br>EVQLLESGGGLVQPGGSLRLSCAASGFTFTNYGMYWVRQAPGKGLEWIGLDRPKQRGTKYNQKFQGRATISRDNSKNTLYLQMNSLRAEDTAVYYCARER<br>YGYYFDYWGQGTLVTVSSAS |
| SEQ ID NO: 448<br>EVQLLESGGGLVQPGGSLRLSCKASGYTFSYFGIYWVRQAPGKGLEWIGSDRPRQRWHQVQRKFKGRATISRDNSKNTLYLQMNSLRAEDTAVYYCARER<br>YGYYFDYWGQGTLVTVSSAS |
| SEQ ID NO: 449<br>EVQLLESGGGLVQPGGSLRLSCTASGFTFSNYGMYWVRQAPGKGLEWIGRIDPNSGGTKYNEKFQGRATISRDNSKNTLYLQMNSLRAEDTAVYYCARER<br>YGYYFDYWGQGTLVTVSSAS |
| SEQ ID NO: 450<br>EVQLLESGGGLVQPGGSLRLSCTASGYSFTAFGMYWVRQAPGKGLEWIGRINPSSGGTNYNEQFQGRATISRDNSKNTLYLQMNSLRAEDTAVYYCARER<br>YGYYFDYWGQGTLVTVSSAS |
| SEQ ID NO: 451<br>EVQLLESGGGLVQPGGSLRLSCKASGFTFSSYGMYWVRQAPGKGLEWIGSDRPRQRWHQVQPKVQGRATISRDNSKNTLYLQMNSLRAEDTAVYYCARER<br>YGYYFDYWGQGTLVTVSSAS |
| SEQ ID NO: 452<br>EVQLLESGGGLVQPGGSLRLSCKASGYSFSAYGMYWVRQAPGKGLEWIGRIDPNSGGTKQNEKFQGRATISRDNSKNTLYLQMNSLRAEDTAVYYCARER<br>YGYYFDYWGQGTLVTVSSAS |
| SEQ ID NO: 453<br>EVQLLESGGGLVQPGGSLRLSCEASGYTFTSFQMHWVRQAPGKGLESIGRIDPGSGGTKYNQKFQGRATISRDNSKNTLYLQMNSLRAEDTAVYYCARER<br>YGYYFDYWGQGTLVTVSSAS |
| SEQ ID NO: 454<br>EVQLLESGGGLVQPGGSLRLSCAASGYTFSSFSMYWVRQAPGKGLEWIGLDRPRQRWHQVNEKFQGRATISRDNSKNTLYLQMNSLRAEDTAVYYCARER<br>YGYYFDYWGQGTLVTVSSAS |
| SEQ ID NO: 455<br>EVQLLESGGGLVQPGGSLRLSCQASGYTFTNYGMYWVRQAPGKGLEWIGRIDPGNGGTKYNEKFKGKVTISRDNSKNTLYLQMNSLRAEDTAVYYCARER<br>YGYYFDYWGQGTLVTVSSAS |

| SEQUENCES |
|---|
| SEQ ID NO: 456<br>EVQLLESGGGLVQPGGSLRLSCQASGYTFTAFGMYWVRQAPGKGLEWIGRIDPGSGGTKYNEKFQGKVTISRDNSKNTLYLQMNSLRAEDTAVYYCARER<br>YGYYFDYWGQGTLVTVSSAS |
| SEQ ID NO: 457<br>EVQLLESGGGLVQPGGSLRLSCKASGFSFTSYGMYWVRQAPGKGLEWIGQDRPKYGGTKYNEKFKGRVTISRDNSKNTLYLQMNSLRAEDTAVYYCARER<br>YGYYFDYWGQGTLVTVSSAS |
| SEQ ID NO: 458<br>EVQLLESGGGLVQPGGSLRLSCQASGFTFSTYGIYWVRQAPGKGLEWIGRINPSNGGTKYNEKFKGRATISRDNSKNTLYLQMNSLRAEDTAVYYCARER<br>YGYYFDYWGQGTLVTVSSAS |
| SEQ ID NO: 459<br>EVQLLESGGGLVQPGGSLRLSCKASGFSFSSYGMYWVRQAPGKGLEWIGSDRPRQRWGTKYNEKFQGRVTISRDNSKNTLYLQMNSLRAEDTAVYYCARE<br>RYGYYFDYWGQGTLVTVSSAS |
| SEQ ID NO: 460<br>EVQLLESGGGLVQPGGSLRLSCEASGYSFSNFGMYWVRQAPGKGLEWIGWINPSNGGTKYNEKFKGRATISRDNSKNTLYLQMNSLRAEDTAVYYCARER<br>GYYYFDYWGQGTLVTVSSAS |
| SEQ ID NO: 461<br>EVQLLESGGGLVQPGGSLRLSCTASDFSFSTFSMYWVRQAPGKGLEWIGSDQPRQGGTKYNEKFKGRATISRDNSKNTLYLQMNSLRAEDTAVYYCARER<br>YGYYFDYWGQGTLVTVSSAS |
| SEQ ID NO: 462<br>EVQLLESGGGLVQPGGSLRLSCAASGYTFSDFGIYWVRQAPGKGLEWIGSDRPRQGGTKYNEKFKDRVTISRDNSKNTLYLQMNSLRAEDTAVYYCARER<br>YGYYFDYWGQGTLVTVSSAS |
| SEQ ID NO: 463<br>EVQLLESGGGLVQPGGSLRLSCAASGYSFTSFGIYWVRQAPGKGLEWIGSDRPKQRGTKYNEKFKGKVTISRDNSKNTLYLQMNSLRAEDTAVYYCARER<br>YGYYFDYWGQGTLVTVSSAS |
| SEQ ID NO: 464<br>EVQLLESGGGLVQPGGSLRLSCQASGFSFSDYYMSWVRQAPGKGLESIGRINPGSGGTKYNEKFQGRATISRDNSKNTLYLQMNSLRAEDTAVYYCARER<br>YGYYFDYWGQGTLVTVSSAS |
| SEQ ID NO: 465<br>EVQLLESGGGLVQPGGSLRLSCAASGYSFSDYGIYWVRQAPGKGLEWIGSDRPKQRWHQVNEKFQGKVTISRDNSKNTLYLQMNSLRAEDTAVYYCARER<br>YGYYFDYWGQGTLVTVSSAS |
| SEQ ID NO: 466<br>EVQLLESGGGLVQPGGSLRLSCKASGYSFSTYYMYWVRQAPGKGLEWIGRIDPDSGGTKYNEKFQGRATISRDNSKNTLYLQMNSLRAEDTAVYYCARER<br>YGYYFDYWGQGTLVTVSSAS |
| SEQ ID NO: 467<br>EVQLLESGGGLVQPGGSLRLSCEASGYTFSAFQIYWVRQAPGKGLEWIGRIDPGNGGTKYNEKFKGKATISRDNSKNTLYLQMNSLRAEDTAVYYCARER<br>YGYYFDYWGQGTLVTVSSAS |
| SEQ ID NO: 468<br>EVQLLESGGGLVQPGGSLRLSCQASGFSFSNFYMYWVRQAPGKGLEWIGRIDPGSGGTKYNEKFQGRATISRDNSKNTLYLQMNSLRAEDTAVYYCARER<br>YGYYFDYWGQGTLVTVSSAS |
| SEQ ID NO: 469<br>EVQLLESGGGLVQPGGSLRLSCKASGFTFSAFGIYWVRQAPGKGLEWIGRINPDNGGTKYNEKFQGRVTISRDNSKNTLYLQMNSLRAEDTAVYYCARER<br>YGYYFDYWGQGTLVTVSSAS |
| SEQ ID NO: 470<br>EVQLLESGGGLVQPGGSLRLSCKASGYTFSTYGMYWVRQAPGKGLEWIGRDQPRQGGTNYNEKFQGRATISRDNSKNTLYLQMNSLRAEDTAVYYCARER<br>YGYYFDYWGQGTLVTVSSAS |
| SEQ ID NO: 471<br>EVQLLESGGGLVQPGGSLRLSCAASGYSFSTYGIYWVRQAPGKGLEWIGRINPNNGGTKYNEKFQGKATISRDNSKNTLYLQMNSLRAEDTAVYYCARER<br>YGYYFDYWGQGTLVTVSSAS |
| SEQ ID NO: 472<br>EVQLLESGGGLVQPGGSLRLSCTASGFSFSAYGMYWVRQAPGKGLEWIGSDRPRQGGTKYNEKFKGRVTISRDNSKNTLYLQMNSLRAEDTAVYYCARER<br>YGYYFDYWGQGTLVTVSSAS |
| SEQ ID NO: 473<br>EVQLLESGGGLVQPGGSLRLSCAASGFSFSNYMYWVRQAPGKGLEWIGRIDPGSGGTKYNEKFQGRATISRDNSKNTLYLQMNSLRAEDTAVYYCARER<br>YGYYFDYWGQGTLVTVSSAS |
| SEQ ID NO: 474<br>EVQLLESGGGLVQPGGSLRLSCEASGYTFTSYGMYWMRQAPGKGLEWIGRIDPGSGGTKYNEKFQGRVTISRDNSKNTLYLQMNSLRAEDTAVYYCARER<br>YGYYFDYWGQGTLVTVSSAS |

| SEQUENCES |
| --- |

SEQ ID NO: 475
EVQLLESGGGLVQPGGSLRLSCAASGFTFTNYGMYWVRQAPGKGLEWIGSDRPKQRWAPKYNEKFKGRATISRDNSKNTLYLQMNSLRAEDTAVYYCARE
RYGYYFDYWGQGTLVTVSSAS

SEQ ID NO: 476
EVQLLESGGGLVQPGGSLRLSCKASGYTFSDFAMYWVRQAPGKGLEWIGSDQPRQRWHQVQPKVQGRVTISRDNSKNTLYLQMNSLRAEDTAVYYCARER
YGYYFDYWGQGTLVTVSSAS

SEQ ID NO: 477
EVQLLESGGGLVQPGGSLRLSCKASGYSFTNFGMYWVRQAPGKGLEWIGRINPGNGGTKQNEKFKGRATISRDNSKNTLYLQMNSLRAEDTAVYYCARER
YGYYFDYWGQGTLVTVSSAS

SEQ ID NO: 478
EVQLLESGGGLVQPGGSLRLSCAASGYSFSYYGMYWVRQAPGKGLEWIGRINPSSGGTKYNEKFKGRATISRDNSKNTLYLQMNSLRAEDTAVYYCARER
YGYYFDYWGQGTLVTVSSAS

SEQ ID NO: 479
EVQLLESGGGLVQPGGSLRLSCEASGYSFSAFGIYWVRQAPGKGLEWIGRINPNSGGTKYNEKFKGRVTISRDNSKNTLYLQMNSLRAEDTAVYYCARER
YGYYFDYWGQGTLVTVSSAS

SEQ ID NO: 480
EVQLLESGGGLVQPGGSLRLSCKTSGYTFSAFQIYWVRQAPGKGLEWIGRIDPGSGGTKYNQKFKGRTTISRDNSKNTLYLQMNSLRAEDTAVYYCARER
YGYYFDYWGQGTLVTVSSAS

SEQ ID NO: 481
EVQLLESGGGLVQPGGSLRLSCKASGYTFSSYGMYWVRQAPGKGLEWIGWIDPGSGGTKYQDKFKGKATISRDNSKNTLYLQMNSLRAEDTAVYYCAREK
YGYYFDYWGQGTLVTVSSAS

SEQ ID NO: 482
EVQLLESGGGLVQPGGSLRLSCKASGYTFSSYGMYWVRQAPGKGLEWIGWIDPGSGGTKYQEKFKGKVTISRDNSKNTLYLQMNSLRAEDTAVYYCAREK
YGYYFDYWGQGTLVTVSSAS

SEQ ID NO: 483
EVQLLESGGGLVQPGGSLRLSCKASGYTFSSYGMYWVRQAPGKGLEWIGWIDPGSGGTKYQEKFKGKATISRDNSKNTLYLQMNSLRAEDTAVYYCARYK
SGWYFDYWGQGTLVTVSSAS

SEQ ID NO: 484
EVQLLESGGGLVQPGGSLRLSCKASGYTFSSYGMYWVRQAPGKGLEWIGWIDPGSGGTKYQEKFKGKATISRDNSKNTLYLQMNSLRAEDTALYYCAREK
YGYYFDYWGQGMLVTVSSAS

SEQ ID NO: 485
EVQLLESGGGLVQPGGSLRLSCKASGYTFSSYGMYWVRQAPGKGLEWIGWIDPGSGGTNYQEKFKGKATISRDNSKNTLYLQMNSLRAEDTAVYYCARYR
SGYYFDYWGQGTLVTVSSAS

SEQ ID NO: 486
EVQLLESGGGLVQPGGSLRLSCKASGYTFSSYGMYWVRQAPGKGLEWIGWIDPGSGGTKYQEKFKGKATISRDNSKNTLYLQMNSLRAEDTAVYYCARYR
SGYYFDYWGQGTLVTVSSAS

SEQ ID NO: 487
EVQLLESGGGLVQPGGSLRLSCKASGYTFSSYGMYWVRQAPGKGLEWIGWIDPGSGGTNYQQKFKGKATISRDNSKNTLYLQMNSLRAEDTAVYYCARYK
SGYYFDYWGQGTLVTVSSAS

SEQ ID NO: 488
EVQLLESGGGLVQPGGSLRLSCKASGYTFSSYGMYWVRQAPGKGLEWIGWIDPGSGGTKYADKFKGKATISRDNSKNTLYLQMNSLRAEDTAVYYCARYR
SGYYFDYWGQGTLVTVSSAS

SEQ ID NO: 489
EVQLLESGGGLVQPGGSLRLSCKASGYTFSSYGMYWVRQAPGKGLEWIGWIDPGSGGTKYEEKFKGKATISRDNSKNTLYLQMNSLRAEDTAVYYCARER
YGYYFDYWGQGTLVTVSSAS

SEQ ID NO: 490
EVQLLESGGGLVQPGGSLRLSCKASGYTFSSYGMYWVRQAPGKGLEWIGWIDPGSGGTKYQDKFKGKATISRDNSKNTLYLQMNSLRAEDTAVYYCAREK
SGYYFDYWGQGTLVTVSSAS

SEQ ID NO: 491
EVQLLESGGGLVQPGGSLRLSCKASGYTFSSYGMYWVRQAPGKGLEWIGWIDPGSGGTKYQEKFKGKATISRDNSKNTLYLQMNSLRAEDTAVYYCAREK
YGYYFDYWGQGTLVTVSSAS

SEQ ID NO: 492
EVQLLESGGGLVQPGGSLRLSCKASGYTFSSYGMYWVRQAPGKGLEWIGWIDPGSGGTKYNDKFKGKATISRDNSKNTLYLQMNSLRAEDTAVYYCARYR
SGYYFDYWGQGTLVTVSSAS

SEQ ID NO: 493
EVQLLESGGGLVQPGGSVRLSCKASGYTFSSYGMYWVRQAPGKGLEWIGWIDPGSGGTKYYEKFKGKATISRDNSKNTLYLQMNSLRAEDTAVYYCARYK
SGYYFDYWGQGTLVTVSSAS

| SEQUENCES |
| --- |

SEQ ID NO: 494
EVQLLESGGGLVQPGGSLRLSCKASGYTFSSYGMYWVRQAPGKGLEWIGWIDPGSGGTKYEEKFKGKATISRDNSKNTLYLQMNSLRAEDTAVYYCARYK
SGYYFDYWGQGTLVTVSSAS

SEQ ID NO: 495
EVQLLESGGGLVQPGGSLRLSCKASGYTFSSYGMYWMRQAPGKGLEWIGWIDPGSGGTKYEDKFEGKATISRDNSKNTLYLQMNSLRAEDTAVYYCARER
SGYYFDYWGQGTLVTVSSAS

SEQ ID NO: 496
EVQLLESGGGLVQPGGSLRLSCKASGYTFSSYGMYWVRQAPGKGLEWIGWIDPGSGGTNYTQKFKGKATISRDNSKNTLYLQMNSLRAEDTAVYYCARYR
SGYYFDYWGQGTLVTVSSAS

SEQ ID NO: 497
EVQLLESGGGLVQPGGSLRLSCKASGYTFSSYGMYWVRQAPGKGLEWIGWIDPGSGGTKYSHKFKGKATISRDNSKNTLYLQMNSLRAEDTAVYYCARER
YGYYFDYWGQGTLVTVSSAS

SEQ ID NO: 498
EVQLLESGGGLVQPGGSLRLSCAASGYSFSAYYIHWVRQAPGKGLEWIGRIDPGSGGTKYNEKFQGRATISRDNSKNTLYLQMNSLRAEDTAVYYCARER
YGYYFDYWGQGTLVTVSSAS

SEQ ID NO: 499
EVQLLESGGGLVQPGGSLRLSCAASGYSFSAYYIHWVRQAPGKGLEWIGRIDPGSGGTKYNEKFQGRATISRDNSKNTLYLQMNSLRAEDTAVYYCARGF
LYYSFDYWGQGTLVTVSSAS

SEQ ID NO: 500
EVQLLESGGGLVQPGGSLRLSCKASGYTFSRYGINWVRQAPGKGLEWIGRIDPGNGGTRYNEKFKGKATISRDNSKNTLYLQMNSLRAEDTAVYYCARGF
LYYSFDYWGQGTLVTVSSAS

SEQ ID NO: 501
EVQLLESGGGLVQPGGSLRLSCKASGYTFSSYTINWVRQAPGKGLEWIGYIDPGSGGTRYNEKFQSKATISRDNSKNTLYLQMNSLRAEDTAVYYCARAR
VGYSFDYWGQGTLVTVSSAS

SEQ ID NO: 502
EVQLLESGGGLVQPGGSLRLSCKASGYTFSRYTISWVRQAPGKGLEWIGYIDPGNGGTRYNQKFKSKATISRDNSKNTLYLQMNSLRAEDTAVYYCARAR
VGYSLDYWGQGTLVTVSSAS

SEQ ID NO: 503
EVQLLESGGGLVQPGGSLRLSCKASGYTFSRYTINWVRQAPGKGLEWIGWIDPGSGGTRYNEKFQSKATISRDNSKNTLYLQMNSLRAEDTAVYYCARAR
VGYSFDYWGQGTLVTVSSAS

SEQ ID NO: 504
EVQLLESGGGLVQPGGSLRLSCKASGYTFSRYTINWVRQAPGKGLEWIGWIDPGNGGSRYNQKFKGKATISRDNSKNTLYLQMNSLRAEDTAVYYCARSR
VGYSFDYWGQGTLVTVSSAS

SEQ ID NO: 505
EVQLLESGGGLVQPGGSLRLSCKASGYTFSRYTINWVRQAPGKGLEWIGYIDPGSGGTRYNQKFKSKATISRDNSKNTLYLQMNSLRAEDTAVYYCARSR
VGYSFDNWGQGTLVTVSSAS

SEQ ID NO: 506
EVQLLESGGGLVQPGGSLRLSCKASGYTFSRYSINWVRQAPGKGLEWIGYIDPGNGGTRYNEKFQGKATISRDNSKNTLYLQMNSLRAEDTAVYYCARAR
VGYSLDYWGQGTLVTVSSAS

SEQ ID NO: 507
EVQLLESGGGLVQPGGSLRLSCKASGYTFSSYTINWVRQAPGKGLEWIGWIDPGSGGTRYNEKFQSKATISRDNSKNTLYLQMNSLRAEDTAVYYCARAR
VGYSFDYWGQGTLVTVSSAS

SEQ ID NO: 508
EVQLLESGGGLVQPGGSLRLSCKASGYTFSSYSINWVRQAPGKGLEWIGYIDPGNGGTKYNQKFQGKATISRDNSKNTLYLQMNSLRAEDTAVYYCARAR
VGYSLDYWGQGTLVTVSSAS

SEQ ID NO: 509
EVQLLESGGGLVQPGGSLRLSCKASGYTFSSYAINWVRQAPGKGLEWIGYIDPGSGGTKYNEKFKGKATISRDNSKNTLYLQMNSLRAEDTAVYYCARAR
VGYSLDYWGQGTLVTVSSAS

SEQ ID NO: 510
EVQLLESGGGLVQPGGSLRLSCKASGYTFSRYSISWVRQAPGKGLEWIGYIDPGSGGTRYNQKFKSKATISRDNSKNTLYLQMNSLRAEDTAVYYCARQR
VGYSLDYWGQGTLVTVSSAS

| LIST OF VK SEQUENCES |
| --- |

SEQ ID NO: 512
EIVLTQSPATLSLSPGERATITCRASQYVGTYLNWYQQKPGQAPRLLIYDASNRATGIPARFSGSGSGTDFTLTISSLEPEDFAVYYCQVWDSSPPVAFG
GGTKVEIK

SEQ ID NO: 511
EIVLTQSPATLSLSPGERATITCRASQYVGSYLNWYQQKPGQAPRLLIYDASNRATGIPARFSGSGSGTDFTLTISSLEPEDFAVYYCQVWDSSPPVVFG
GGTKVEIK

| SEQUENCES |
| --- |
| SEQ ID NO: 551 AX132_VK DNA SEQUENCE<br>GAAATCGTGCTGACCCAGTCTCCAGCCACCCTGTCTCTGTCTCCCGGGGAACGTGCCACCATCACCTGCCGTGCCTCTCAGTATGTCGGCAGCTACCTGA<br>ACTGGTATCAGCAGAAGCCAGGTCAGGCGCCACGTCTGCTGATCTACGACGCCTCTAACCGTGCCACCGGTATCCCAGCCCGTTTCTCTGGTTCTGGTTC<br>TGGCACCGACTTCACCCTGACCATCTCTTCTCTGGAACCAGAAGACTTCGCCGTGTACTACTGCCAGGTATGGGACAGCTCTCCTCCTGTGGTGTTCGGT<br>GGTGGTACCAAAGTGGAGATCAAA |
| SEQ ID NO: 513<br>EIVLTQSPATLSLSPGERATITCRASQYVGTYLNWYQQKPGQAPRLLIYDASNRATGIPARFSGSGSGTDFTLTISSLEPEDFAVYYCQVWDSSPPVVFG<br>GGTKVEIK |
| SEQ ID NO: 514<br>EIVLTQSPATLSLSPGERATITCRASQYVGSYLNWYQQKPGQAPRLLIYDASNRATGIPARFSGSGSGTDFTLTISSLEPEDFAVYYCQVWDSSPPVAFG<br>GGTKVEIK |
| SEQ ID NO: 515<br>EIVLTQSPATLSLSPGERATITCRASQYVGSYLNWYQQKPGQAPRLLIYDASNRATGIPARFSGSGSGTDFTLTISSLEPEDFAVYYCQVWDSSPPLVFG<br>GGTKVEIK |
| SEQ ID NO: 516<br>EIVLTQSPATLSLSPGERATITCRASQYVGSYLNWYQQKPGQAPRLLIYDASNRATGIPARFSGSGSGTDFTLTISSLEPEDFAVYYCQVWDSSPPLAFG<br>GGTKVEIK |
| SEQ ID NO: 517<br>EIVLTQSPATLSLSPGERATITCRASQYIGSYLNWYQQKPGQAPRLLIYDASNRATGIPARFSGSGSGTDFTLTISSLEPEDFAVYYCQAWDSSPPVVFG<br>GGTKVEIK |
| SEQ ID NO: 518<br>EIVLTQSPATLSLSPGERATITCRASQYVGSYLNWYQQKPGQAPRLLIYDASNRATGIPARFSGSGSGTDFTLTISSLEPEDFAVYYCQVWDSSPPVMFG<br>GGTKVEIK |
| SEQ ID NO: 519<br>DIQMTQSPSSLSASVGDRVTITCRASQAISNYLTWYQQKPGKAPKLLIYAASSLQSGVPSRFSGSGSGTDFTLTISSLQPEDFATYYCQGWDSSPTFGGG<br>TKVEIK |
| SEQ ID NO: 520<br>EIVLTQSPATLSLSPGERATITCRASQYVGTYLNWYQQKPGQAPRLLIYDASNRATGIPARFSGSGSGTDFTLTISSLEPEDFAVYYCQVWDSSPPLVFG<br>GGTKVEIK |
| SEQ ID NO: 521<br>EIVLTQSPATLSLSPGERATITCRASQYVGSYLTWYQQKPGQAPRLLIYDASNRATGIPARFSGSGSGTDFTLTISSLEPEDFAVYYCQVWDSSPPVVFG<br>GGTKVEIK |
| SEQ ID NO: 522<br>EIVLTQSPATLSLSPGERATITCRASQYVGTYLNWYQQKPGQAPRLLIYDASNRATGIPARFSGSGSGTDFTLTISSLEPEDFAVYYCQVWDNSPPVVFG<br>GGTKVEIK |
| SEQ ID NO: 523<br>EIVLTQSPATLSLSPGERATITCRASQYVGSYLNWYQQKPGQAPRLLIYDAANRATGIPARFSGSGSGTDFTLTISSLEPEDFAVYYCQVWDSSPPVVFG<br>GGTKVEIK |
| SEQ ID NO: 524<br>EIVLTQSPATLSLSPGERATITCRASQYIGSYLNWYQQKPGQAPRLLIYDASNRATGIPARFSGSGSGTDFTLTISSLEPEDFAVYYCQAWDSSPPVTFG<br>DGTKVEIK |
| SEQ ID NO: 525<br>DIQMTQSPSSLSASVGDRVTITCRASQDVSNYLNWYQQKPGKAPKLLIYAASSLQSGVPSRFSGSGSGTDFTLTISSLQPEDFATYYCQQSGSYLTFGGG<br>TKVEIK |
| SEQ ID NO: 526<br>EIVLTQSPATLSLSPGERATITCQASQYVGSYLSWYQQKPGQAPRLLIYDASNRATGIPARFSGSGSGTDFTLTISSLEPEDFAVYYCQVWDSYHAVVFG<br>GGTKVEIK |
| SEQ ID NO: 527<br>EIVLTQSPATLSLSPGERATITCQASQYVGSYLSWYQQKPGQAPRLLIYDASNRAAGIPARFSGSGSGTDFTLTISSLEPEDFAVYYCQVWGSYHAVMFG<br>GGTKVEIK |
| SEQ ID NO: 528<br>EIVLTQSPATLSLSPGERATITCRASQYVGSYLSWYQQKPGQAPRLLIYDASNRAAGIPARFSGSGSGTDFTLNISSLEPEDFAVYYCQVWGSYHSVMFG<br>GGTKVEIK |
| SEQ ID NO: 529<br>EIVLTQSPATLSLSPGERATITCQASQYVGSYLSWYQQKPGQAPRLLIYDASNRAAGIPARFSGSGSGTDFTLTISSLEPEDFAVYYCQVWDTDHSVVFG<br>GGTKVEIK |
| SEQ ID NO: 530<br>EIVLTQSPATLSLSPGERATITCQASQYVGSYLSWYQQKPGQAPRLLIYDASNRATGIPARFSGSGSGTDFTLTISSLEPEDFAVYYCQVWDTDHAVAFG<br>GGTKVEIK |

| SEQUENCES |
| --- |
| SEQ ID NO: 531<br>EIVLTQSPATLSLSPGERATITCRASQYVGSYLSWYQQKPGQAPRLLIYDASNRASGIPARFSGSGSGTDFTLTISSLEPEDFAVYYCQVWDSSHSVIFG<br>GGTKVEIK |
| SEQ ID NO: 532<br>EIVLTQSPATLSLSPGERATITCRASQYVGSYLSWYQQKPGQAPRLLIYDASNRATGIPARFSGSGSGTDFTLTISSLEPEDFAVYYCQVWDSYPPVVFG<br>GGTKVEIK |
| SEQ ID NO: 533<br>EIVLTQSPATLSLSPGERATITCRASQYVGSYLSWYQQKPGQAPRLLIYDASNRATGIPARFSGSGSGTDFTLTISSLEPEDFAVYYCQVWDSYHAVVFG<br>GGTKVEIK |
| SEQ ID NO: 534<br>EIVLTQSPATLSLSPGERATITCRASQYVGSYLSWYQQKPGQAPRLLIYDASNRASGIPARFSGSGSGTDFTLTISSLEPEDFAVYYCQVWDSDHAVVFG<br>GGTKVEIK |
| SEQ ID NO: 535<br>EIVLTQSPATLSLSPGERATITCRASQYVGSYLNWYQQKPGQAPRLLIYDAANRATGIPARFSGSGSGTDFTLTISSLEPEDFAVYYCQVWGSNHASLFG<br>GGTKVEIK |
| SEQ ID NO: 536<br>EIVLTQSPATLSLSPGERATITCRASQYVGSYLNWYQQKPGQAPRLLIYDAANRATGIPARFSGSGSGTDFTLTISSLEPEDFAVYYCQVWGSTARVAFG<br>GGTKVEIK |
| SEQ ID NO: 537<br>EIVLTQSPATLSLSPGERATITCRASQYVGSYLNWYQQKPGQAPRLLIYDAANRATGIPARFSGSGSGTDFTLTISSLEPEDFAVYYCQVWNSTPPVVFG<br>GGTKVEIK |
| SEQ ID NO: 538<br>EIVLTQSPATLSLSPGERATITCRASQYVGSYLNWYQQKPGQAPRLLIYDAANRATGIPARFSGSGSGTDFTLTISSLEPEDFAVYYCQVWSSSPPVIFG<br>GGTKVEIK |
| SEQ ID NO: 539<br>EIVLTQSPATLSLSPGERATITCRASQYVGSYLNWYQQKPGQAPRLLIYDAANRATGIPARFSGSGSGTDFTLTISSLEPEDFAVYYCQVWSSSPPVVFG<br>GGTKVEIK |
| SEQ ID NO: 540<br>EIVLTQSPATLSLSPGERATITCRASQYVGSYLNWYQQKPGQAPRLLIYDAANRATGIPARFSGSGSGTDFTLTISSLEPEDFAVYYCQVWSSNHAVVFG<br>GGTKVEIK |
| SEQ ID NO: 541<br>EIVLTQSPATLSLSPGERATITCRASQYVGSYLNWYQQKPGQAPRLLIYDAANRATGIPARFSGSGSGTDFTLTISSLEPEDFAVYYCQVWGSNPPVAFG<br>GGTKVEIK |
| SEQ ID NO: 542<br>EIVLTQSPATLSLSPGERATITCRASQYVGSYLNWYQQKPGQAPRLLIYDAANRATGIPARFSGSGSGTDFTLTISSLEPEDFAVYYCQVWDSTPPVVFG<br>GGTKVEIK |
| SEQ ID NO: 543<br>EIVLTQSPATLSLSPGERATITCRASQYVGSYLNWYQQKPGQAPRLLIYDAANRATGIPARFSGSGSGTDFTLTISSLEPEDFAVYYCQVWDSNPPVVFG<br>GGTKVEIK |
| SEQ ID NO: 544<br>EIVLTQSPATLSLSPGERATITCRASQYVGSYLNWYQQKPGQAPRLLIYDAANRATGIPARFSGSGSGTDFTLTISSLEPEDFAVYYCQGYSSNDGVIFG<br>GGTKVEIK |
| SEQ ID NO: 545<br>EIVLTQSPATLSLSPGERATITCRASQYVGSYLNWYQQKPGQAPRLLIYDAANRATGIPARFSGSGSGTDFTLTISSLEPEDFAVYYCQVWGSNHSVVFG<br>GGTKVEIK |
| SEQ ID NO: 546<br>EIVLTQSPATLSLSPGERATITCRASQYVGSYLNWYQQKPGQAPRLLIYDAANRATGIPARFSGSGSGTDFTLTISSLEPEDFAVYYCQVWDSNHSVVFG<br>GGTKVEIK |
| SEQ ID NO: 547<br>EIVLTQSPATLSLSPGERATITCRASQYVGSYLNWYQQKPGQAPRLLIYDASNRAAGIPARFSGSGSGTDFTLTISSLEPEDFAVYYCQVWDSSPPVVFG<br>GGTKVEIK |
| SEQ ID NO: 548<br>EIVLTQSPATLSLSPGERATITCRASQYVGSYLNWYQQKPGQAPRLLIYDASNRATGIPARFSGSGSGTDFTLTISSLEPEDFAVYYCQVWDSSSAVVFG<br>GGTKVEIK |
| SEQ ID NO: 549<br>EIVLTQSPATLSLSPGERATITCRASQYVGSYLNWYQQKPGQAPRLLIYDASNRATGIPARFSGSGSGTDLTLTISSLEPEDFAVYYCQVWDSSPPVVFG<br>GGTKVEIK |

SEQUENCES

LIST OF VH-CDR1 SEQUENCES

SEQ ID NO: 183
Consensus sequence for Variant Heavy Chain CDR1 Sequence
XXSXXXXXXXXXXWXR
Wherein X at position 1 is K, A, E, Q or T; X at position 2 is A or T; X at position 4 is G or D; X at position 5 is Y, F, L or Q; X at position 6 is T or S; X at position 7 is F or Y; X at position 8 is S or T; X at position 9 is S, R, A, N, D, T or Y; X at position 10 is Y, F or Q; X at position 11 is G, S, T, A, Y, Q or W; X at position 12 is M, I, F, Y, N or Q; X at position 13 is Y, S, N, T, H or I; and X at position 15 is V or M.

SEQ ID NO: 184
Consensus sequence for Variant Heavy Chain CDR1 Sequence
XXXXXXXXXX
Wherein X at position 1 is G or D; X at position 2 is Y, F, L or Q; X at position 3 is T or S; X at position 4 is F or Y; X at position 5 is S or T; X at position 6 is S, R, A, N, D, T or Y; X at position 7 is Y, F or Q; X at position 8 is G, S, T, A, Y, Q or W; X at position 9 is M, I, F, Y, N or Q; and X at position 10 is Y, S, N, T, H or I.

SEQ ID NO: 185
Consensus sequence for Variant Heavy Chain CDR1 Sequence
XASXXXFXXXXXXWXR
Wherein X at position 1 is K, A, E, Q or T; X at position 4 is G or D; X at position 5 is Y, F, L or Q; X at position 6 is T or S; X at position 8 is S or T; X at position 9 is S, R, A, N, D, T or Y; X at position 10 is Y, F or Q; X at position 11 is G, S, T, A, Y, Q or W; X at position 12 is M, I, F, Y, N or Q; X at position 13 is Y, S, N, T, H or I; and X at position 15 is V or M SEQ ID NO: 186
Consensus sequence for Variant Heavy Chain CDR1 Sequence
XXXFXXXXXX
Wherein X at position 1 is G or D; X at position 2 is Y, F, L or Q; X at position 3 is T or S; X at position 5 is S or T; X at position 6 is S, R, A, N, D, T or Y; X at position 7 is Y, F or Q; X at position 8 is G, S, T, A, Y, Q or W; X at position 9 is M, I, F, Y, N or Q; and X at position 10 is Y, S, N, T, H or I.

SEQ ID NO: 187
Consensus sequence for Variant Heavy Chain CDR1 Sequence
XASXXXFXXXXXXWVR
Wherein X at position 1 is K, A, E, Q or T; X at position 4 is G or D; X at position 5 is Y, F, L or Q; X at position 6 is T or S; X at position 8 is S or T; X at position 9 is S, R, A, N, D, T or Y; X at position 10 is Y, F or Q; X at position 11 is G, S, T, A, Y, Q or W; X at position 12 is M, I, F, Y, N or Q; and X at position 13 is Y, S, N, T, H or I.

SEQ ID NO: 188
Consensus sequence for Variant Heavy Chain CDR1 Sequence
XXXFXXXXXX
Wherein X at position 1 is G or D; X at position 2 is Y, F, L or Q; X at position 3 is T or S; X at position 5 is S or T; X at position 6 is S, R, A, N, D, T or Y; X at position 7 is Y, F or Q; X at position 8 is G, S, T, A, Y, Q or W; X at position 9 is M, I, F, Y, N or Q; and X at position 10 is Y, S, N, T, H or I.

SEQ ID NO: 189
KASGYTFSSYGMYWVR

SEQ ID NO: 190 132 CDR1SEQUENCE
AAGGCCTCTGGTTACACCTTCTCTTCTTACGGGATGTACTGGGTGCGT

SEQ ID NO: 191 132 CDR1 SEQUENCE (SHORTENED)
GYTFSSYGMY

SEQ ID NO: 192 132 CDR1 SEQUENCE (SHORTENED)
GGTTACACCTTCTCTTCTTACGGGATGTAC

SEQ ID NO: 197
KASGYTFSSYSIYWVR

SEQ ID NO: 198
KASGYTFSRQGFTWVR

SEQ ID NO: 199
KASGYTFSSYSFSWVR

SEQ ID NO: 193
KASGYTFSRYGINWVR

SEQ ID NO: 194 213 CDR1 SEQUENCE
AAGGCTAGCGGTTACACCTTCTCTCGCTACGGTATCAACTGGGTGCGT

| SEQUENCES |
|---|
| SEQ ID NO: 195 213 CDR1 SEQUENCE<br>GYTFSRYGIN |
| SEQ ID NO: 196 213 CDR1 SEQUENCE<br>GGTTACACCTTCTCTCGCTACGGTATCAAC |
| SEQ ID NO: 200<br>KASGYTFSRYGISWVR |
| SEQ ID NO: 201<br>KASGYTFSSYTNYWVR |
| SEQ ID NO: 202<br>KASGYTFSRYSYYWVR |
| SEQ ID NO: 203<br>KASGYTFSSYANTWVR |
| SEQ ID NO: 204<br>KASGYTFSSYGYYWVR |
| SEQ ID NO: 205<br>KASGYTFSRYAINWVR |
| SEQ ID NO: 206<br>KASGYTFSRYGIYWVR |
| SEQ ID NO: 207<br>KASGYTFSRYGYYWVR |
| SEQ ID NO: 208<br>KASGYTFSRYAYNWVR |
| SEQ ID NO: 209<br>KASGYTFSRYGFSWVR |
| SEQ ID NO: 210<br>KASGYTFSRYAFNWVR |
| SEQ ID NO: 211<br>KASGYTFSSYGIYWVR |
| SEQ ID NO: 212<br>KASGYTFSRYTITWVR |
| SEQ ID NO: 213<br>KASGYTFSRYSFIWVR |
| SEQ ID NO: 214<br>KASGYTFSRYTFYWVR |
| SEQ ID NO: 215<br>KASGQTFSSYGFNWVR |
| SEQ ID NO: 216<br>KASGYTFSRYANYWVR |
| SEQ ID NO: 217<br>KASGYTFSRYSNSWVR |
| SEQ ID NO: 218<br>KASGYTFSSYSITWVR |
| SEQ ID NO: 219<br>KASGYTFSSYTYTWVR |
| SEQ ID NO: 220<br>KASGYTFSSYSYYWVR |
| SEQ ID NO: 221<br>KASGYTFSSYGYSWVR |
| SEQ ID NO: 222<br>KASGYTFSRYTFSWVR |
| SEQ ID NO: 223<br>KASGYTFSSYGFSWVR |

-continued

| SEQUENCES |
|---|
| SEQ ID NO: 224<br>KASGYTFSSYGQSWVR |
| SEQ ID NO: 225<br>KASGYTFSSYAISWVR |
| SEQ ID NO: 226<br>KASGYTFSSYTNWVR |
| SEQ ID NO: 227<br>KASGYTFSSYTISWVR |
| SEQ ID NO: 228<br>KASGYTFSRYTFNWVR |
| SEQ ID NO: 229<br>KGQRLPPRYGYYWVR |
| SEQ ID NO: 230<br>KASGYTYSRYTFSWVR |
| SEQ ID NO: 231<br>KASDYTFSSYGNNWVR |
| SEQ ID NO: 232<br>KASGYTFSSYGISWVR |
| SEQ ID NO: 233<br>KASGYTFSSYTINWVR |
| SEQ ID NO: 234<br>KASGFTFSAYGMYWVR |
| SEQ ID NO: 235<br>KASGFTFSDYGMYWVR |
| SEQ ID NO: 236<br>KASGFTFSSYQMSWVR |
| SEQ ID NO: 237<br>KASGFTFSYYYMYWVR |
| SEQ ID NO: 238<br>KASGFTFTAYGMYWVR |
| SEQ ID NO: 239<br>KASGFTFTSYQMSWVR |
| SEQ ID NO: 240<br>KASGFTFTSYWMSWVR |
| SEQ ID NO: 241<br>KASGLTFTDYGMYWVR |
| SEQ ID NO: 242<br>KASGYTFSYYGMYWVR |
| SEQ ID NO: 243<br>KASGYTFTDYGMYWVR |
| SEQ ID NO: 244<br>KASGYTFTNYGMNWVR |
| SEQ ID NO: 245<br>KASGYTFTSYGMYWVR |
| SEQ ID NO: 246<br>KASGYTFTSYWMSWVR |
| SEQ ID NO: 247<br>QASGYTFSSYGMYWVR |
| SEQ ID NO: 248<br>EASGFTFSSYGMYWVR |
| SEQ ID NO: 249<br>EASGFSFSNYGMYWVR |

| SEQUENCES |
|---|
| SEQ ID NO: 250<br>AASGYSFSAYYIHWVR |
| SEQ ID NO: 251<br>KASGFSFSSYGIYWVR |
| SEQ ID NO: 252<br>AASGYSFSTFGIYWVR |
| SEQ ID NO: 253<br>EASGFTFSDYGIHWVR |
| SEQ ID NO: 254<br>AASGYTFSDFGIYWVR |
| SEQ ID NO: 255<br>QASGYSFTTYGMYWVR |
| SEQ ID NO: 256<br>AASGFTFTNYGMYWVR |
| SEQ ID NO: 257<br>KASGYTFSYFGIYWVR |
| SEQ ID NO: 258<br>TASGFTFSNYGMYWVR |
| SEQ ID NO: 259<br>TASGYSFTAFGMYWVR |
| SEQ ID NO: 260<br>KASGFTFSSYGMYWVR |
| SEQ ID NO: 261<br>KASGYSFSAYGMYWVR |
| SEQ ID NO: 262<br>EASGYTFTSFQMHWVR |
| SEQ ID NO: 263<br>AASGYTFSSFSMYWVR |
| SEQ ID NO: 264<br>QASGYTFTNYGMYWVR |
| SEQ ID NO: 265<br>QASGYTFTAFGMYWVR |
| SEQ ID NO: 266<br>KASGFSFTSYGMYWVR |
| SEQ ID NO: 267<br>QASGFTFSTYGIYWVR |
| SEQ ID NO: 268<br>KASGFSFSSYGMYWVR |
| SEQ ID NO: 269<br>EASGYSFSNFGMYWVR |
| SEQ ID NO: 270<br>TASDFSFSTFSMYWVR |
| SEQ ID NO: 271<br>AASGYSFTSFGIYWVR |
| SEQ ID NO: 272<br>QASGFSFSDYYMSWVR |
| SEQ ID NO: 273<br>AASGYSFSDYGIYWVR |
| SEQ ID NO: 274<br>KASGYSFSTYYMYWVR |
| SEQ ID NO: 275<br>EASGYTFSAFQIYWVR |

| SEQUENCES |
|---|
| SEQ ID NO: 276<br>QASGFSFSNFYMYWVR |
| SEQ ID NO: 277<br>KASGFTFSAFGIYWVR |
| SEQ ID NO: 278<br>KASGYTFSTYGMYWVR |
| SEQ ID NO: 279<br>AASGYSFSTYGIYWVR |
| SEQ ID NO: 280<br>TASGFSFSAYGMYWVR |
| SEQ ID NO: 281<br>AASGFSFSNYYMYWVR |
| SEQ ID NO: 282<br>EASGYTFTSYGMYWMR |
| SEQ ID NO: 283<br>KASGYTFSDFAMYWVR |
| SEQ ID NO: 284<br>KASGYSFTNFGMYWVR |
| SEQ ID NO: 285<br>AASGYSFSYYGMYWVR |
| SEQ ID NO: 286<br>EASGYSFSAFGIYWVR |
| SEQ ID NO: 287<br>KTSGYTFSAFQIYWVR |
| SEQ ID NO: 288<br>KASGYTFSSYGMYWMR |
| SEQ ID NO: 289<br>KASGYTFSRYTISWVR |
| SEQ ID NO: 290<br>KASGYTFSRYTINWVR |
| SEQ ID NO: 291<br>KASGYTFSRYSINWVR |
| SEQ ID NO: 292<br>KASGYTFSSYSINWVR |
| SEQ ID NO: 293<br>KASGYTFSSYAINWVR |
| SEQ ID NO: 294<br>KASGYTFSRYSISWVR |

| LIST OF VH-CDR2 SEQUENCES |
|---|

SEQ ID NO: 64
Consensus sequence for Variant Heavy Chain CDR2 Sequence
XXGXXXPXXXXXXXXXXXXXXXT
Wherein X at position 1 is W, S or Q; X at position 2 is I or V; X at position 4 is W, R, Y, S, L or Q; X at position 5 is I or D; X at position 6 is D, N, R, Q or S; X at position 8 is G, R, S, K, N or D; X at position 9 is S, N, Q, G or Y; X at position 10 is G or R; X at position 11 is G, W, S or T; X at position 12 is T, H, P or S; X at position 13 is K, R, N, Q, S or Y; X at position 14 is Y, V, Q or L; X at position 15 is N, Q, A, E, D, Y, S or T; X at position 16 is E, Q, D, P, R or H; X at position 17 is K, Q or S; X at position 18 is F or V; X at position 19 is K, Q or E; X at position 20 is S, or D; Xat position 21 is K, R or Q; and X at position 22 is A, V, F or T.

SEQ ID NO: 65
Consensus sequence for Variant Heavy Chain CDR2 Sequence
XXXPXXXXXXXXXXXXX
Wherein X at position 1 is R, Y, S, L or Q; X at position 2 is I or D; X at position 3 is D, N, R, Q or S; X at position 5 is G, R, S, K, N or D; X at position 6 is S, N, Q, G or Y; X at position 7 is G or R; X at position 8 is G, W, S or T; X at position 9 is T, H, P or S; X at position 10 is K, R, N, Q, S or Y; X at position 11 is Y, V, Q or L; X at position 12 is N, Q, A, E, D, Y, S or T; X at

| SEQUENCES |
| --- |
| position 13 is E, Q, D, P, R or H; X at position 14 is K, Q or S; X at position 15 is F or V; X at position 16 is K, Q or E; and X at position 17 is G, S or D.

SEQ ID NO: 66
Consensus sequence for Variant Heavy Chain CDR2 Sequence
XXGXXXPXXXXXXXYXXXXXXXT
Wherein X at position 1 is W, S or Q; X at position 2 is I or V; X at position 4 is W, R, Y, S, L or Q; X at position 5 is I or D; X at position 6 is D, N, R, Q or S; X at position 8 is G, R, S, K, N or D; X at position 9 is S, N, Q, G or Y; X at position 10 is G or R; X at position 11 is G, W, S or T; X at position 12 is T, H, P or S; X at position 13 is K, R, N, Q, S or Y; X at position 15 is N, Q, A, E, D, Y, S or T; X at position 16 is E, Q, D, P, R or H; X at position 17 is K, Q or S; X at position 18 is F or V; X at position 19 is K, Q or E; X at position 20 is G, S or D; X at position 21 is K, R or Q; and X at position 22 is A, V, F or T.

SEQ ID NO: 67
Consensus sequence for Variant Heavy Chain CDR2 Sequence
XXXPXXXXXXXYXXXXX
Wherein X at position 1 is W, R, Y, S, L or Q; X at position 2 is I or D; X at position 3 is D, N, R, Q or S; X at position 5 is G, R, S, K, N or D; X at position 6 is S, N, Q, G or Y; X at position 7 is G or R; X at position 8 is G, W, S or T; X at position 9 is T, H, P or S; X at position 10 is K, R, N, Q, S or Y; X at positino 12 is N, Q, A, E, D, Y, S or T; X at position 13 is E, Q, D, P, R or H; X at position 14 is K, Q or S; X at position 15 is F or V; X at position 16 is K, Q or E; and X at position 17 is G, S or D.

SEQ ID NO: 68
WIGWIDPGSGGTKYNEKFKGKAT

SEQ ID NO: 69 132 CDR2 SEQUENCE
TGGATCGGTTGGATCGACCCAGGCAGCGGTGGCACCAAGTACAACGAAAAGTTCAAGGGTAAGGCCACC

SEQ ID NO: 70 132 CDR2 SEQUENCE (SHORTENED)
WIDPGSGGTKYNEKFKG

SEQ ID NO: 71 132 CDR2 SEQUENCE (SHORTENED)
TGGATCGACCCAGGCAGCGGTGGCACCAAGTACAACGAAAAGTTCAAGGGT

SEQ ID NO: 76
WIGWIDPGNGGTRYNQKFQSKAT

SEQ ID NO: 77
WIGWIDPGNGGTRYNEKFKGKAT

SEQ ID NO: 78
WIGYIDPGSGGTKYNQKFQGKAT

SEQ ID NO: 72
WIGRIDPGNGGTRYNEKFKGKAT

SEQ ID NO: 73 213 CDR2 SEQUENCE
TGGATCGGTCGGATCGACCCAGGTAACGGTGGTACTAGGTACAACGAAAAGTTCAAGGGTAAGGCCACC

SEQ ID NO: 74 213 CDR2 SEQUENCE
RIDPGNGGTRYNEKFKG

SEQ ID NO: 75 213 CDR2 SEQUENCE
CGGATCGACCCAGGTAACGGTGGTACTAGGTACAACGAAAAGTTCAAGGGT

SEQ ID NO: 79
QIGWIDPGSGGTRYNQKFKSKAT

SEQ ID NO: 80
WIGYIDPGSGGTRYNQKFQGKAT

SEQ ID NO: 81
WIGYIDPGSGGTKYNQKFQSKAT

SEQ ID NO: 82
WIGWIDPGNGGTSYNQKFKSKAT

SEQ ID NO: 83
WIGWIDPGSGGTRYNQKFKGKAT

SEQ ID NO: 84
WIGWIDPGSGGTRYNEKFKGQAT

SEQ ID NO: 85
WIGYIDPGSGGTRYNEKFKGKAT |

| SEQUENCES |
|---|
| SEQ ID NO: 86<br>WIGYIDPGNGGTSYNEKFKGKAT |
| SEQ ID NO: 87<br>WIGRIDPGSGGTRYNQQFQGKAT |
| SEQ ID NO: 88<br>WIGYIDPGSGGTRYNEKFQGKAT |
| SEQ ID NO: 89<br>WIGWIDPGSGGTRYNEKFQSKAT |
| SEQ ID NO: 90<br>WIGYIDPGSGGTKYNEKFQGKAT |
| SEQ ID NO: 91<br>WIGYIDPGSGGTKYNQKFKGKAT |
| SEQ ID NO: 92<br>WIGYIDPGSGGTRYNQKFKGKAT |
| SEQ ID NO: 93<br>WIGWIDPGSGGTRYNQKFKSKAT |
| SEQ ID NO: 94<br>WIGRIDPGSGGTSYNEKFQSKAT |
| SEQ ID NO: 95<br>WIGRIDPGNGGTRYNQKFQSKAT |
| SEQ ID NO: 96<br>WIGYIDPGSGGTKYNEKFKGKAT |
| SEQ ID NO: 97<br>WIGWIDPGSGGTRYNEKFKSKAT |
| SEQ ID NO: 98<br>WIGWIDPGNGGTRYNQQFKGKAT |
| SEQ ID NO: 99<br>WIGWIDPGSGGTRYNEKFEGKAT |
| SEQ ID NO: 100<br>WIGRIDPGSGGTRYNQKFQGKAT |
| SEQ ID NO: 101<br>WIGRIDPGSGGTKYNEKFKGKAT |
| SEQ ID NO: 102<br>WIGYIDPGNGGTRYNEQFKGKAT |
| SEQ ID NO: 103<br>WIGWIDPGNGGTRYNEQFQGKAT |
| SEQ ID NO: 104<br>WIGRIDPGSGGTRYNEKFQGKAT |
| SEQ ID NO: 105<br>WIGRIDPGSGGTRYNEKFQSKAT |
| SEQ ID NO: 106<br>WIGYIDPGNGGTNYNQKFQSKAT |
| SEQ ID NO: 107<br>WIGYIDPGNGGTRYNQQFQGKAT |
| SEQ ID NO: 108<br>WIGWIDPGSGGTRYNQKFQSKAT |
| SEQ ID NO: 109<br>WIGYIDPGNGGTRYNEKFQSKAT |
| SEQ ID NO: 110<br>WIGYIDPGSGGTRYNQKFKSKAT |
| SEQ ID NO: 111<br>WIGRIDPGNGGTRYNEKFQGKAT |

| SEQUENCES |
|---|
| SEQ ID NO: 112<br>WIGWIDPGNGGTKYNQKFQSKAT |
| SEQ ID NO: 113<br>WIGWIDPGSGGTRYNEKFQGKAT |
| SEQ ID NO: 114<br>WIGRIDPSNGGTKYNQKFKGKAT |
| SEQ ID NO: 115<br>WIGRINPNSGGTKYNEKFKGKAT |
| SEQ ID NO: 116<br>WIGRIDPGSGGTKYNQKFKGKAT |
| SEQ ID NO: 117<br>WVGRISPSGGSTYYADSVKGRFT |
| SEQ ID NO: 118<br>WIGRINPGSGGTKYDEKFKGRAT |
| SEQ ID NO: 119<br>WIGWINPDSGSTKYAEKFKGRAT |
| SEQ ID NO: 120<br>WIGRIDPSSGGTKYNQKFKGKAT |
| SEQ ID NO: 121<br>WVGRISPGGGTTYYADSVKGRFT |
| SEQ ID NO: 122<br>WIGRINPGSGGTNYDEKFKGRAT |
| SEQ ID NO: 123<br>WIGRINPKQRWHKYNQKFKGKVT |
| SEQ ID NO: 124<br>WIGLDRPRQRWHQLNEKFQGRAT |
| SEQ ID NO: 125<br>SIGRIDPGSGGTKYNEKFQGRAT |
| SEQ ID NO: 126<br>WIGLDRPKQRVGTKYNQKFQGRVT |
| SEQ ID NO: 127<br>WIGLDRPRQRWPKYNEKFKGRAT |
| SEQ ID NO: 128<br>WIGLDRPKQRWHQYNEKFQGRAT |
| SEQ ID NO: 129<br>WIGSDRPRQRVAPKYNQKFKGRAT |
| SEQ ID NO: 130<br>WIGRIDPSSGGTKYNQKFQGRVT |
| SEQ ID NO: 131<br>WIGLDRPKQRGTKYNQKFQGRAT |
| SEQ ID NO: 132<br>WIGSDRPRQRWHQVQRKFKGRAT |
| SEQ ID NO: 133<br>WIGRIDPNSGGTKYNEKFQGRAT |
| SEQ ID NO: 134<br>WIGRINPSSGGTNYNEQFQGRAT |
| SEQ ID NO: 135<br>WIGSDRPRQRWHQVQPKVQGRAT |
| SEQ ID NO: 136<br>WIGRIDPNSGGTKQNEKFQGRAT |
| SEQ ID NO: 137<br>SIGRIDPGSGGTKYNQKFQGRAT |

| SEQUENCES |
|---|
| SEQ ID NO: 138<br>WIGLDRPRQRWHQVNEKFQGRAT |
| SEQ ID NO: 139<br>WIGRIDPGNGGTKYNEKFKGKVT |
| SEQ ID NO: 140<br>WIGRIDPGSGGTKYNEKFQGKVT |
| SEQ ID NO: 141<br>WIGQDRPKYGGTKYNEKFKGRVT |
| SEQ ID NO: 142<br>WIGRINPSNGGTKYNEKFKGRAT |
| SEQ ID NO: 143<br>WIGSDRPRQRWGTKYNEKFQGRVT |
| SEQ ID NO: 144<br>WIGWINPSNGGTKYNEKFKGRAT |
| SEQ ID NO: 145<br>WIGSDQPRQGGTKYNEKFKGRAT |
| SEQ ID NO: 146<br>WIGSDRPRQGGTKYNEKFKDRVT |
| SEQ ID NO: 147<br>WIGSDRPKQRGTKYNEKFKGKVT |
| SEQ ID NO: 148<br>SIGRINPGSGGTKYNEKFQGRAT |
| SEQ ID NO: 149<br>WIGSDRPKQRWHQVNEKFQGKVT |
| SEQ ID NO: 150<br>WIGRIDPDSGGTKYNEKFQGRAT |
| SEQ ID NO: 151<br>WIGRIDPGNGGTKYNEKFKGKAT |
| SEQ ID NO: 152<br>WIGRIDPGSGGTKYNEKFQGRAT |
| SEQ ID NO: 153<br>WIGRINPDNGGTKYNEKFQGRVT |
| SEQ ID NO: 154<br>WIGRDQPRQGGTNYNEKFQGRAT |
| SEQ ID NO: 155<br>WIGRINPNNGGTKYNEKFQGKAT |
| SEQ ID NO: 156<br>WIGSDRPRQGGTKYNEKFKGRVT |
| SEQ ID NO: 157<br>WIGRIDPGSGGTKYNEKFQGRVT |
| SEQ ID NO: 158<br>WIGSDRPKQRWAPKYNEKFKGRAT |
| SEQ ID NO: 159<br>WIGSDQPRQRWHQVQPKVQGRVT |
| SEQ ID NO: 160<br>WIGRINPGNGGTKQNEKFKGRAT |
| SEQ ID NO: 161<br>WIGRINPSSGGTKYNEKFKGRAT |
| SEQ ID NO: 162<br>WIGRINPNSGGTKYNEKFKGRVT |
| SEQ ID NO: 163<br>WIGRIDPGSGGTKYNQKFKGRTT |

| SEQUENCES |
| --- |

SEQ ID NO: 164
WIGWIDPGSGGTKYQDKFKGKAT

SEQ ID NO: 165
WIGWIDPGSGGTKYQEKFKGKVT

SEQ ID NO: 166
WIGWIDPGSGGTKYQEKFKGKAT

SEQ ID NO: 167
WIGWIDPGSGGTNYQEKFKGKAT

SEQ ID NO: 168
WIGWIDPGSGGTNYQQKFKGKAT

SEQ ID NO: 169
WIGWIDPGSGGTKYADKFKGKAT

SEQ ID NO: 170
WIGWIDPGSGGTKYEEKFKGKAT

SEQ ID NO: 171
WIGWIDPGSGGTKYNDKFKGKAT

SEQ ID NO: 172
WIGWIDPGSGGTKYYEKFKGKAT

SEQ ID NO: 173
WIGWIDPGSGGTKYEDKFEGKAT

SEQ ID NO: 174
WIGWIDPGSGGTNYTQKFKGKAT

SEQ ID NO: 175
WIGWIDPGSGGTKYSHKFKGKAT

SEQ ID NO: 176
WIGYIDPGSGGTRYNEKFQSKAT

SEQ ID NO: 177
WIGYIDPGNGGTRYNQKFKSKAT

SEQ ID NO: 178
WIGWIDPGSGGTRYNEKFQSKAT

SEQ ID NO: 179
WIGWIDPGNGGSRYNQKFKGKAT

SEQ ID NO: 180
WIGYIDPGNGGTRYNEKFQGKAT

SEQ ID NO: 181
WIGYIDPGNGGTKYNQKFQGKAT

SEQ ID NO: 182
WIGYIDPGSGGTKYNEKFKGKAT

| LIST OF VH-CDR3 SEQUENCES |
| --- |

SEQ ID NO: 1
Consensus sequence for Variant Heavy Chain CDR3 Sequence
CXRXXXXXXXDXWGX
Wherein X at position 2 is A or S; X at position 4 is E, Y, A, G, S. H, Q or D; X at position 5 is
R, K, F, N, H, D, S or Y; X at position 6 is Y, V, S. D, I, L. F or A; X at position 7 is G, Y or A;
X at position 8 is Y or W; X at position 9 is Y, S, N or D; X at position 10 is F or L; X at
position 12 is Y, N or F; and X at position 15 is Q or E.

SEQ ID NO: 2
Consensus sequence for Variant Heavy Chain CDR3 Sequence
XXXXXXXDX
Wherein X at position 1 is E, Y, A, G, S, H, Q or D; X at position 2 is R, K, F, N, H, D, S or Y;
X at position 3 is Y, V, S, D, I, L, F or A; X at position 4 is G, Y or A; X at position 5 is Y or W;
X at position 6 is Y, S, N or D; X at position 7 is F or L; and X at position 9 is Y, N or F.

| SEQUENCES |
|---|

SEQ ID NO: 3
Consensus sequence for Variant Heavy Chain CDR3 Sequence
CARXXXXYXXDYWGX
Wherein X at position 4 is E, Y, A, G, S, H, Q or D; X at position 5 is R, K, F, N, H, D, S or Y;
X at position 6 is Y, V, S, D, I, L, F or A; X at position 7 is G, Y or A; X at position 9 is Y, S, N
or D; X at position 10 is F or L; and X at position 15 is Q or E.

SEQ ID NO: 4
Consensus sequence for Variant Heavy Chain CDR3 Sequence
XXXXYXXDY
Wherein X at position 1 is E, Y, A, G, S, H, Q or D; X at position 2 is R, K, F, N, H, D, S or Y;
X at position 3 is Y, V, S, D, I, L, F or A; X at position 4 is G, Y or A; X at position 6 is Y, S, N
or D; and X at position 7 is F or L.

SEQ ID NO: 5
CARERYGYYFDYWGQ

SEQ ID NO: 6 132 CDR3 SEQUENCE
TGCGCCCGTGAACGTTACGGTTACTACTTCGACTACTGGGGTCAG

SEQ ID NO: 7 132 CDR3 SEQUENCE (SHORTENED)
ERYGYYFDY

SEQ ID NO: 8 132 CDR3 SEQUENCE (SHORTENED)
GAACGTTACGGTTACTACTTCGACTAC

SEQ ID NO: 13
CARARVGYSLDYWGQ

SEQ ID NO: 14
CARYRVGYSLDYWGQ

SEQ ID NO: 15
CARQRVGYSLDYWGQ

SEQ ID NO: 9
CARANDGYSFDYWGQ

SEQ ID NO: 10 213 CDR3 SEQUENCE
TGCGCCCGTGCAAATGACGGTTACTCCTTCGACTACTGGGGTCAG

SEQ ID NO: 11 213 CDR3 SEQUENCE
ANDGYSFDY

SEQ ID NO: 12 213 CDR3 SEQUENCE
GCAAATGACGGTTACTCCTTCGACTAC

SEQ ID NO: 16
CARARVGYSFDYWGQ

SEQ ID NO: 17
CARSRVGYSFDYWGQ

SEQ ID NO: 18
CARYRSGYSLDYWGQ

SEQ ID NO: 19
CARERVGYSLDYWGQ

SEQ ID NO: 20
CARHRVGYSLDFWGQ

SEQ ID NO: 21
CARYHGYSFDYWGQ

SEQ ID NO: 22
CARYHDGYSFDYWGQ

SEQ ID NO: 23
CARERFAYYLDYWGQ

SEQ ID NO: 24
CARSRDGYYFDYWGQ

SEQ ID NO: 25
CARARDGYSFDYWGQ

| SEQUENCES |
|---|
| SEQ ID NO: 26<br>CARERAGYYLDYWGQ |
| SEQ ID NO: 27<br>CARHRVGYYFDYWGQ |
| SEQ ID NO: 28<br>CARANVGYSFDYWGQ |
| SEQ ID NO: 29<br>CARSHVGYYFDYWGQ |
| SEQ ID NO: 30<br>CARHRVGYSLDYWGQ |
| SEQ ID NO: 31<br>CARSRVGYSLDYWGQ |
| SEQ ID NO: 32<br>CARYRDGYSFDYWGQ |
| SEQ ID NO: 33<br>CARDRVGYSLDYWGQ |
| SEQ ID NO: 34<br>CARQRVGYNLDYWGQ |
| SEQ ID NO: 35<br>CARQRVGYSLDYWGE |
| SEQ ID NO: 36<br>CARSRDGYSLDYWGQ |
| SEQ ID NO: 37<br>CARYRSGYYLDYWGQ |
| SEQ ID NO: 38<br>CARYRVGYSFDYWGQ |
| SEQ ID NO: 39<br>CARSRDGYSFDYWGQ |
| SEQ ID NO: 40<br>CARARDGYSLDYWGQ |
| SEQ ID NO: 41<br>CARHRVGYSFDYWGQ |
| SEQ ID NO: 42<br>CARADVGYSFDYWGQ |
| SEQ ID NO: 43<br>CARGFV |
| NO: 44<br>CARGFIYYSFDYWGQ |
| SEQ ID NO: 45<br>CARGFLYYSFDYWGQ |
| SEQ ID NO: 46<br>CARGRIYYSFDYWGQ |
| SEQ ID NO: 47<br>CARGRFYYSFDYWGQ |
| SEQ ID NO: 48<br>CARGRLYYSLDYWGQ |
| SEQ ID NO: 49<br>CARGFIYYDFDYWGQ |
| SEQ ID NO: 50<br>CARGKIYYSFDYWGQ |
| SEQ ID NO: 51<br>CARGYLYYSFDYWGQ |

-continued

| SEQUENCES |
|---|

SEQ ID NO: 52
CARGFIYYSLDYWGQ

SEQ ID NO: 53
CARGNLYYSLDYWGQ

SEQ ID NO: 54
CSRGKVGYSLDYWGQ

SEQ ID NO: 55
CARGSIGYNLDYWGQ

SEQ ID NO: 56
CARGRDGYSLDYWGQ

SEQ ID NO: 57
CAREKYGYYFDYWGQ

SEQ ID NO: 58
CARYKSGWYFDYWGQ

SEQ ID NO: 59
CARYRSGYYFDYWGQ

SEQ ID NO: 60
CARYKSGYYFDYWGQ

SEQ ID NO: 61
CAREKSGYYFDYWGQ

SEQ ID NO: 62
CARERSGYYFDYWGQ

SEQ ID NO: 63
CARSRVGYSFDNWGQ

| LIST OF VK_CDR1 |
|---|

SEQ ID NO: 347
Consensus sequence for Variant Light Chain CDR1 sequence
ITCXASQYXGXYLXWYQ
Wherein X at position 4 is R or Q; X at position 9 is V or I; X at position 11 is T or S; and X at position 14 is N, S or T.

SEQ ID NO: 348
Consensus sequence for Variant Light Chain CDR1 sequence
XASQYXGXYLX
Wherein X at position 1 is R or Q; X at position 6 is V or I; X at position 8 is T or S; and X at position 11 is S or T.

SEQ ID NO: 353
ITCRASQYVGTYLNWYQ

SEQ ID NO: 349
ITCRASQYVGSYLNWYQ

SEQ ID NO: 350  132 & 189 CDR1 SEQUENCE
ATCACCTGCCGTGCCTCTCAGTATGTCGGCAGCTACCTGAACTGGTATCAG

SEQ ID NO: 351  132 & 189 CDR1 SEQUENCE (SHORTENED)
RASQYVGSYLN

SEQ ID NO: 352  132 & 189 CDR1 SEQUENCE (SHORTENED)
CGTGCCTCTCAGTATGTCGGCAGCTACCTGAAC

SEQ ID NO: 354
ITCRASQYIGSYLNWYQ

SEQ ID NO: 355
ITCRASQAISNYLTWYQ

SEQ ID NO: 356
ITCRASQYVGSYLTWYQ

SEQ ID NO: 357
ITCRASQDVSNYLNWYQ

| SEQUENCES |
| --- |

SEQ ID NO: 358
ITCQASQYVGSYLSWYQ

SEQ ID NO: 359
ITCRASQYVGSYLSWYQ

| LIST OF VK_CDR2 |
| --- |

SEQ ID NO: 335
Consensus sequence for Variant Light Chain CDR2 sequence
LIYDXSNRAXGIP
Wherein X at position 5 is S or A; and X at position 10 is T, A or S.

SEQ ID NO: 336
Consensus sequence for Variant Light Chain CDR2 sequence
DXSNRAX
Wherein X at position 2 is S or A; and X at position 7 is T, A or S.

SEQ ID NO: 337
Consensus sequence for Variant Light Chain CDR2 sequence
LIYDAXNRAXGIP
Wherein X at position 6 is S or A; and X at position 10 is T, A or S.

SEQ ID NO: 338
Consensus sequence for Variant Light Chain CDR2 sequence
DAXNRAX
Wherein X at position 3 is S or A; and X at position 7 is T, A or S.

SEQ ID NO: 339
LIYDASNRATGIP

SEQ ID NO: 340  132 & 189 CDR2 SEQUENCE
CTGATCTACGACGCCTCTAACCGTGCCACCGGTATCCCA

SEQ ID NO: 341  132 & 189 CDR2 SEQUENCE (SHORTENED)
DASNRAT

SEQ ID NO: 342  132 & 189 CDR2 SEQUENCE (SHORTENED)
GACGCCTCTAACCGTGCCACC

SEQ ID NO: 343
LIYAASSLQSGVP

SEQ ID NO: 344
LIYDAANRATGIP

SEQ ID NO: 345
LIYDASNRAAGIP

SEQ ID NO: 346
LIYDASNRASGIP

| LIST OF VK_CDR3 |
| --- |

SEQ ID NO: 295
Consensus sequence for Variant Light Chain CDR3 Sequence
YYCQXXXXXXXXXFGX
Wherein X at position 5 is V, A or G; X at position 6 is W or Y; X at position 7 is D, G, S or N; X at position 8 is S, T or N; X at position 9 is S, N, Y, D or T; X at position 10 is P, H, A, D or S; X at position 11 is P, A, S, R or G; X at position 12 is V, L or S; X at position 13 is A, V, M, I, L or T; and X at position 16 is G or D.

SEQ ID NO: 296
Consensus sequence for Variant Light Chain CDR3 Sequence
QXXXXXXXXX
Wherein X at position 2 is V, A or G; X at position 3 is W or Y; X at position 4 is D, G, S or N; X at position 5 is S, T or N; X at position 6 is S, N, Y, D or T; X at position 7 is P, H, A, D or S; X at position 8 is P, A, S, R or G; X at position 9 is V, L or S; and X at position 10 is A, V, M, I, L or T.

SEQ ID NO: 297
Consensus sequence for Variant Light Chain CDR3 Sequence
YYCQXXXXXXXXVXFGX
Wherein X at position 5 is V, A or G; X at position 6 is W or Y; X at position 7 is D, G, S or N; X at position 8 is S, T or N; X at position 9 is S, N, Y, D or T; X at position 10 is P, H, A, D or S; X at position 11 is P, A, S, R or G; and X at position 13 is A, C, M, I, L or T.

| SEQUENCES |
| --- |
| SEQ ID NO: 298<br>Consensus sequence for Variant Light Chain CDR3 Sequence<br>QXXXXXXXVX<br>Wherein X at position 2 is V, A or G; X at position 3 is W or Y; X at position 4 is D, G, S or N; X at position 5 is S, T or N; X at position 6 is S, N, Y, D or T; X at position 7 is P, H, A, D or S; X at position 8 is P, A, S, R or G; and X at position 10 is A, V, M, I, L or T.<br><br>SEQ ID NO: 299<br>Consensus sequence for Variant Light Chain CDR3 Sequence<br>YYCQXXXXXXXVXFGG<br>Wherein X at position 5 is V, A or G; X at position 7 is D, G, S or N; X at position 8 is S, T or N; X at position 9 is S, N, Y, D or T; X at position 10 is P, H, A, D or S; X at position 11 is P, A, S, R or G; and X at position 13 is A, V, M, I, L or T.<br><br>SEQ ID NO: 300<br>Consensus sequence for Variant Light Chain CDR3 Sequence<br>QXXXXXXXVX<br>Wherein X at position 2 is V, A or G; X at position 4 is D, G, S or N; X at position 5 is S, T or N; X at position 6 is S, N, Y, D or T; X at position 7 is P, H, A, D or S; X at position 8 is P, A, S, R or G; and X at position 10 is A, V, M, I, L or T.<br><br>SEQ ID NO: 305<br>YYCQVWDSSPPVAFGG<br><br>SEQ ID NO: 301<br>YYCQVWDSSPPVVFGG<br><br>SEQ ID NO: 302 132 & 189 CDR3 SEQUENCE<br>TACTACTGCCAGGTATGGGACAGCTCTCCTCCTGTGGTGTTCGGTGGT<br><br>SEQ ID NO: 303 132 & 189 CDR3 SEQUENCE (SHORTENED)<br>QVWDSSPPVV<br><br>SEQ ID NO: 304 132 & 189 CDR3SEQUENCE (SHORTENED)<br>CAGGTATGGGACAGCTCTCCTCCTGTGGTG<br><br>SEQ ID NO: 306<br>YYCQVWDSSPPLVFGG<br><br>SEQ ID NO: 307<br>YYCQVWDSSPPLAFGG<br><br>SEQ ID NO: 308<br>YYCQAWDSSPPVVFGG<br><br>SEQ ID NO: 309<br>YYCQVWDSSPPVMFGG<br><br>SEQ ID NO: 310<br>YYCQGWDSSPTFGG<br><br>SEQ ID NO: 311<br>YYCQVWDNSPPVVFGG<br><br>SEQ ID NO: 312<br>YYCQAWDSSPPVTFGD<br><br>SEQ ID NO: 313<br>YYCQQSGSYLTFGG<br><br>SEQ ID NO: 314<br>YYCQVWDSYHAVVFGG<br><br>SEQ ID NO: 315<br>YYCQVWGSYHAVMFGG<br><br>SEQ ID NO: 316<br>YYCQVWGSYHSVMFGG<br><br>SEQ ID NO: 317<br>YYCQVWDTDHSVVFGG<br><br>SEQ ID NO: 318<br>YYCQVWDTDHAVAFGG<br><br>SEQ ID NO: 319<br>YYCQVWDSSHSVIFGG |

| SEQUENCES |
| --- |

SEQ ID NO: 320
YYCQVWDSYPPVVFGG

SEQ ID NO: 321
YYCQVWDSDHAVVFGG

SEQ ID NO: 322
YYCQVWGSNHASLFGG

SEQ ID NO: 323
YYCQVWGSTARVAFGG

SEQ ID NO: 324
YYCQVWNSTPPVVFGG

SEQ ID NO: 325
YYCQVWSSSPPVIFGG

SEQ ID NO: 326
YYCQVWSSSPPVVFGG

SEQ ID NO: 327
YYCQVWSSNHAVVFGG

SEQ ID NO: 328
YYCQVWGSNPPVAFGG

SEQ ID NO: 329
YYCQVWDSTPPVVFGG

SEQ ID NO: 330
YYCQVWDSNPPVVFGG

SEQ ID NO: 331
YYCQGYSSNDGVIFGG

SEQ ID NO: 332
YYCQVWGSNHSVVFGG

SEQ ID NO: 333
YYCQVWDSNHSVVFGG

SEQ ID NO: 334
YYCQVWDSSSAVVFGG

SEQ ID NO: 552 AX132_VH-CH1 (FAB) AMINO ACID SEQUENCE
EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARERYGY
YFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHK
PSNTKVDKKVEPKSCDKTHT

SEQ ID NO: 553 AX132_VH-CH1 (FAB) DNA SEQUENCE
GAAGTGCAGCTGCTGGAATCTGGTGGTGGTCTGGTGCAGCCAGGTGGTTCTCTGCGTCTGTCTTGCAAGGCCTCTGGTTACACCTTCTCTTCTTACGGGATGT
ACTGGGTGCGTCAGGCACCAGGTAAGGGTCTGGAATGGATCGGTTGGATCGACCCAGGCAGCGGTGGCACCAAGTACAACGAAAAGTTCAAGGGTAAGGCCAC
CATCTCTAGAGACAACTCTAAGAACACCCTGTACTTGCAGATGAACTCTCTGCGTGCCGAGGACACTGCAGTGTACTACTGCGCCCGTGAACGTTACGGTTAC
TACTTCGACTACTGGGGTCAGGGTACGCTGGTGACTGTCTCGAGCGCAAGCACCAAAGGCCCATCGGTATTCCCCTGGCACCCTCCTCCAAGAGCACCTCTG
GGGGCACAGCGGCCCTGGGCTGCCTGGTCAAGGACTACTTCCCCGAGCCGGTGACGGTGTCGTGGAACTCAGGCGCTCTGACCAGCGGCGTGCACACCTTCCC
GGCTGTCCTACAGTCCTCAGGACTCTACTCCCTCAGCAGCGTGGTGACTGTGCCCTCCAGCAGCTTGGGCACCCAGACCTACATCTGCAACGTGAATCACAAG
CCCAGCAACACTAAGGTGGACAAGAAAGTTGAGCCCAAATCTTGTGACAAAACTCACACA

SEQ ID NO: 554 AX132_VK-CK (FAB) AMINO ACID SEQUENCE
EIVLTQSPATLSLSPGERATITCRASQYVGSYLNWYQQKPGQAPRLLIYDASNRATGIPARFSGSGSGTDFTLTISSLEPEDFAVYYCQVWDSSPPVVFGGGT
KVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPV
TKSFNRGEC

SEQ ID NO: 555 AX132_VK-CK (FAB) DNA SEQUENCE
GAAATCGTGCTGACCCAGTCTCCAGCCACCCTGTCTCTGTCTCCCGGGGAACGTGCCACCATCACCTGCCGTGCCTCTCAGTATGTCGGCAGCTACCTGAACT
GGTATCAGCAGAAGCCAGGTCAGGCGCCACGTCTGCTGATCTACGACGCCTCTAACCGTGCCACCGGTATCCCAGCCCGTTTCTCTGGTTCTGGTTCTGGCAC
CGACTTCACCCTGACCATCTCTTCTCTGGAACCAGAAGACTTCGCCGTGTACTACTGCCAGGTATGGGACAGCTCTCCTCCTGTGGTGTTCGGTGGTGGTACC
AAAGTGGAGATCAAACGTACGGTGGCTGCACCATCTGTCTTCATCTTCCCGCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTC
ACAAAGAGCTTCAACAGGGGAGAGTGT

SEQUENCES

SEQ ID NO: 556 AX132 FULL HEAVY CHAIN (IGG2) AMINO ACID SEQUENCE
EVQLLESGGGLVQPGGSLRLSCKASGYTFSSYGMYWVRQAPGKGLEWIGWIDPGSGGTKYNEKFKGKATISRDNSKNTLYLQMNSLRAEDTAVYYCARERYGY
YFDYWGQGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHK
PSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKS
RWQQGNVFSCSVMHEALHNHYTQKSLSLSPGK

SEQ ID NO: 557 AX132 FULL HEAVY CHAIN (IGG2) DNA SEQUENCE
GAAGTGCAGCTGCTGGAATCTGGTGGTGGTCTGGTGCAGCCAGGTGGTTCTCTGCGTCTGTCTTGCAAGGCCTCTGGTTACACCTTCTCTTCTTACGGGATGT
ACTGGGTGCGTCAGGCACCAGGTAAGGGTCTGGAATGGATCGGTTGGATCGACCCAGGCAGCGGTGGCACCAAGTACAACGAAAAGTTCAAGGGTAAGGCCAC
CATCTCTAGAGACAACTCTAAGAACACCCTGTACTTGCAGATGAACTCTCTGCGTGCCGAGGACACTGCAGTGTACTACTGCGCCCGTGAACGTTACGGTTAC
TACTTCGACTACTGGGGTCAGGGTACGCTGGTGACTGTCTCGAGCGCTAGCACCAAGGGCCCATCGGTCTTCCCCCTGGCGCCCTGCTCCAGGAGCACCTCCG
AGAGCACAGCGGCCCTGGGCTGCCTGGTCAAGGACTACTTCCCCGAACCGGTGACGGTGTCGTGGAACTCAGGCGCTCTGACCAGCGGCGTGCACACCTTCCC
GGCTGTCCTACAGTCCTCAGGACTCTACTCCCTCAGCAGCGTGGTGACCGTGCCCTCCAGCAACTTCGGCACCCAGACCTACACCTGCAACGTAGATCACAAG
CCCAGCAACACCAAGGTGGACAAGACAGTTGAGCGCAAATGTTGTGTCGAGTGCCCACCGTGCCCAGCACCACCTGTGGCAGGACCGTCAGTCTTCCTCTTCC
CCCCAAAACCCAAGGACACCCTCATGATCTCCCGGACCCCTGAGGTCACGTGCGTGGTGGTGGACGTGAGCCACGAAGACCCCGAGGTCCAGTTCAACTGGTA
CGTGGACGGCGTGGAGGTGCATAATGCCAAGACAAAGCCACGGGAGGAGCAGTTCAACAGCACGTTCCGTGTGGTCAGCGTCCTCACCGTCGTGCACCAGGAC
TGGCTGAACGGCAAGGAGTACAAGTGCAAGGTCTCCAACAAAGGCCTCCCAGCCCCCATCGAGAAAACCATCTCCAAAACCAAAGGGCAGCCCCGAGAACCAC
AGGTGTACACCCTGCCCCCATCCCGGGAGGAGATGACCAAGAACCAGGTCAGCCTGACCTGCCTGGTCAAAGGCTTCTACCCCAGCGACATCGCCGTGGAGTG
GGAGAGCAATGGGCAGCCGGAGAACAACTACAAGACCACACCTCCCATGCTGGACTCCGACGGCTCCTTCTTCCTCTACAGCAAGCTCACCGTGGACAAGAGC
AGGTGGCAGCAGGGGAACGTCTTCTCATGCTCCGTGATGCATGAGGCTCTGCACAACCACTACACACAGAAGAGCCTCTCCCTGTCTCCGGGTAAA

SEQ ID NO: 558 AX132 FULL LIGHT CHAIN AMINO ACID SEQUENCE
EIVLTQSPATLSLSPGERATITCRASQYVGTYLNWYQQKPGQAPRLLIYDASNRATGIPARFSGSGSGTDFTLTISSLEPEDFAVYYCQVWDSSPPVAFGGGT
KVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPV
TKSFNRGEC

SEQ ID NO: 559 AX132 FULL LIGHT CHAIN DNA SEQUENCE
GAGATTGTGCTGACCCAGAGCCCTGCCACCCTGTCCCTGAGCCCTGGAGAGAGGGCTACCATCACTTGTAGGGCAAGCCAATATGTGGGCACCTACCTGAACT
GGTATCAACAGAAGCCTGGACAAGCCCCAAGACTGCTGATTTATGATGCCAGCAACAGGGCTACAGGCATCCCTGCCAGGTTCTCTGGCTCTGGCTCTGGCAC
AGACTTCACCCTGACCATCTCCTCCTTGGAACCTGAGGACTTTGCTGTCTACTACTGTCAGGTGTGGGACTCCAGCCCTCCTGTGGCATTTGGAGGAGGCACC
AAGGTGGAGATTAAGCGTACGGTGGCTGCACCATCTGTCTTCATCTTCCCGCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTC
ACAAAGAGCTTCAACAGGGGAGAGTGT

SEQ ID NO: 560 AX132 DISPLAY VECTOR SEQUENCE
GCGCAACGCAATTAATGTGAGTTAGCTCACTCATTAGGCACCCCAGGCTTTACACTTTATGCTTCCGGCTCGTATGTTGTGTGGAATTGTGAGCGGATAACAA
TTTACCGGTTCTTGTAAGGAGGAATTAAAAAATGAAAAAGTCTTTAGTCCTCAAAGCCTCCGTAGCCGTTGCTACCCTCGTTCCGATGCTAAGCTTCGCTGAA
ATCGTGCTGACCCAGTCTCCAGCCACCCTGTCTCTGTCTCCCGGGGAACGTGCCACCATCACCTGCCGTGCCTCTCAGTATGTCGGCAGCTACCTGAACTGGT
ATCAGCAGAAGCCAGGTCAGGCGCCACGTCTGCTGATCTACGACGCCTCTAACCGTGCCACCGGTATCCCAGCCCGTTTCTCTGGTTCTGGTTCTGGCACCGA
CTTCACCCTGACCATCTCTTCTCTGGAACCAGAAGATTCGCCGTGTACTACTGCCAGGTATGGGACAGCTCTCCTCCTGTGGTGTTCGGTGGTGGTACCAAA
GTGGAGATCAAACGTACGGTGGCTGCACCATCTGTCTTCATCTTCCCGCCATCTGATGAGCAGTTGAAATCTGGAACTGCCTCTGTTGTGTGCCTGCTGAATA
ACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCAC
CTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACA
AAGAGCTTCAACAGGGGAGAGTGTTGATAAGGCGCGCCACAATTTCACAGTAAGGAGGTTTAACTTATGAAAAAATTATTATTCGCAATTCCTTTAGTTGTTC
CTTTCTATTCTCACTCCGCTGGATCCGAAGTGCAGCTGCTGGAATCTGGTGGTGGTCTGGTGCAGCCAGGTGGTTCTCTGCGTCTGTCTTGCAAGGCCTCTGG
TTACACCTTCTCTTCTTACGGGATGTACTGGGTGCGTCAGGCACCAGGTAAGGGTCTGGAATGGATCGGTTGGATCGACCCAGGCAGCGGTGGCACCAAGTAC
AACGAAAAGTTCAAGGGTAAGGCCACCATCTCTAGAGACAACTCTAAGAACACCCTGTACTTGCAGATGAACTCTCTGCGTGCCGAGGACACTGCAGTGTACT
ACTGCGCCCGTGAACGTTACGGTTACTACTTCGACTACTGGGGTCAGGGTACGCTGGTGACTGTCTCGAGCGCAAGCACCAAGGGCACCAGCGGTATTCCCCT
GGCACCCTCCTCCAAGAGCACCTCTGGGGGCACAGCGGCCCTGGGCTGCCTGGTCAAGGACTACTTCCCCGAGCCGGTGACGGTGTCGTGGAACTCAGGCGCC
CTGACCAGCGGCGTGCACACCTTCCCGGCTGTCCTACAGTCCTCAGGACTCTACTCCCTCAGCAGCGTGGTGACTGTGCCCTCCAGCAGCTTGGGCACCCAGA
CCTACATCTGCAACGTGAATCACAAGCCCAGCAACACTAAGGTGGACAAGAAAGTTGAGCCCAAATCTTGTGACAAAACTCACACAGCGGCCGCTTATCCATA
CGACGTACCAGACTACGCAGGAGGTCATCACCATCATCACCATTAGAGATCTGGAGGAGGTGAGGAGAAGTCCCGGCTGTTGGAAGGAGAACCGTGAACTG
GAAAAGATCATTGCTGAGAAAGAGGAGCGTGTCTCTGAACTGCGCCATCAACTCCAGTCTGTAGGAGGTTGTTAATAAGTCGACCTCGACCAATTCGCCCTAT
AGTGAGTCGTATTACGCGCGCTCACTGGCCGTCGTTTTACAACGTCGTGACTGGGAAAACCCTGGCGTTACCCAACTTAATCGCCTTGCAGCACATCCCCCTT
TCGCCAGCTGGCGTAATAGCGAAGAGGCCCGCACCGATCGCCCTTCCCAACAGTTGCGCAGCCTGAATGGCGAATGGGACGCGCCCTGTAGCGGCGCATTAAG
CGCGGCGGGTGTGGTGGTTACGCGCAGCGTGACCGCTACACTTGCCAGCGCCCTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCTTTACGGCACCTCGACCCCAAAAAACTTGATTAGGGTGATGGTTCAC
GTAGTGGGCCATCGCCCTGATAGACGGTTTTTCGCCCTTTGACGTTGGAGTCCACGTTCTTTAATAGTGGACTCTTGTTCCAAACTGGAACAACACTCAACCC
TATCTCGGTCTATTCTTTTGATTTATAAGGGATTTTGCCGATTTCGGCCTATTGGTTAAAAAATGAGCTGATTTAACAAAAATTTAACGCGAATTTTAACAAA
ATATTAACGCTTACAATTTAGGTGGCACTTTTCGGGGAAATGTGCGCGGAACCCCTATTTGTTTATTTTTCTAAATACATTCAAATATGTATCCGCTCATGAG
ACAATAACCCTGATAAATGCTTCAATAATATTGAAAAAGGAAGAGTATGAGTATTCAACATTTCCGTGTCGCCCTTATTCCCTTTTTTGCGGCATTTTGCCTT
CCTGTTTTTGCTCACCCAGAAACGCTGGTGAAAGTAAAAGATGCTGAAGATCAGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTAAAGTTCTGCTATGTGGCGCGGTATTATCCCGTATTGACGCCGGGCAAGAGCA
ACTCGGTCGCCGCATACACTATTCTCAGAATGACTTGGTTGAGTACTCACCAGTCACAGAAAAGCATCTTACGGATGGCATGACAGTAAGAGAATTATGCAGT
GCTGCCATAACCATGAGTGATAACACTGCGGCCAACTTACTTCTGACAACGATCGGAGGACCGAAGGAGCTAACCGCTTTTTTGCACAACATGGGGGATCATG
TAACTCGCCTTGATCGTTGGGAACCGGAGCTGAATGAAGCCATACCAAACGACGAGCGTGACACCACGATGCCTGTAGCAATGGCAACAACGTTGCGCAAACT
ATTAACTGGCGAACTACTTACTCTAGCTTCCCGGCAACAATTAATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCAGCACTGGGGCCAGATGGTAAGCCCTCCCGTATCGTAGTTATCT
ACACGACGGGGAGTCAGGCAACTATGGATGAACGAAATAGACAGATCGCTGAGATAGGTGCCTCACTGATTAAGCATTGGTAACTGTCAGACCAAGTTTACTC
ATATATACTTTAGATTGATTTAAAACTTCATTTTTAATTTAAAAGGATCTAGGTGAAGATCCTTTTTGATAATCTCATGACCAAAATCCCTTAACGTGAGTTT
TCGTTCCACTGAGCGTCAGACCCCGTAGAAAAGATCAAAGGATCTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTGGCTTCAGCAGAGCGCAGATACCAAATACTGTCCTTCTAGTGTA
GCCGTAGTTAGGCCACCACTTCAAGAACTCTGTAGCACCGCCTACATACCTCGCTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTCGGGCTGAACGGGGGGTTCGTGCACACAGCCCAGCTTGGAGCGAACGACCTACA

SEQUENCES

```
CCGAACTGAGATACCTACAGCGTGAGCTATGAGAAAGCGCCACGCTTCCCGAAGGGAGAAAGGCGGACAGGTATCCGGTAAGCGGCAGGGTCGGAACAGGAGA
GCGCACGAGGGAGCTTCCAGGGGAAACGCCTGGTATCTTTATAGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGCTGGCCTTTTGCTCACATGTTCTTTCCTGCGTTATCCCCTGATT
CTGTGGATAACCGTATTACCGCCTTTGAGTGAGCTGATACCGCTCGCCGCAGCCGAACGACCGAGCGCAGCGAGTCAGTGAGCGAGGAAGCGGAAGAGCGCCC
AATACGCAAACCGCCTCTCCCCGCGCGTTGGCCGATTCATTAATGCAGCTGGCACGACAGGTTTCCCGCTGGAAAGCGGGCAGTGAA

SEQ ID NO: 572 SEQUENCE CONTAINING FC DOMAIN OF IGG1
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKAEPKSC
DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCS
VMHEALHNHYTQKSLSLSPGK

SEQ ID NO: 573 SEQUENCE CONTAINING FC DOMAIN OF IGG2
ASTKGPSVFPLAPCSRSTSESTAALGCLVKDYFPEPVTVSWNSGALTSGVHTFPAVLQSSGLYSLSSVVTVTSSNFGTQTYTCNVDHKPSNTKVDKTVERKCC
VECPIPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKG
LPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHE
ALHNHYTQKSLSLSPGK

SEQ ID NO: 574 SEQUENCE CONTAINING FC DOMAIN OF IGG4
ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYG
PPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMH
EALHNHYTQKSLSLSLGK

SEQ ID NO: 575 SEQUENCE CONTAINING FC DOMAIN OF IGG4
ASTKGPSVFPLAPCSRSTSESTAALGCLVKDYFPEPVTVSWNSGALTSGVHTFPAVLQSSGLYSLSSVVTVTSSNFGTQTYTCNVDHKPSNTKVDKTVERKCC
VECPPCPAPPVAGPSVFLFPPKPKDTLMISRTPEVTCVVVDVSQEDPEVQFNWYVDGVEVHNAKTKPREEQFNSTFRVVSVLTVLHQDWLNGKEYKCKVSNKG
LPSSIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHE
ALHNHYTQKSLSLSPGK
```

What is claimed is:

1. An isolated PCSK9-specific antagonist which comprises:
  (a) heavy chain variable region comprising CDR1, CDR2 and CDR3 sequence, wherein
    (i) the CDR1 sequence is selected from the group consisting of: SEQ ID NO: 189 and residues 4-13 of SEQ ID NO: 183;
    (ii) the CDR2 sequence is selected from the group consisting of: SEQ ID NO: 68 and residues 4-20 of SEQ ID NO: 68; and
    (iii) the CDR3 sequence is selected from the group consisting of: SEQ ID NO: 5 and residues 4-12 of SEQ ID NO: 5 and
  (b) a light chain variable region comprising CDR1, CDR2 and CDR3 sequence, wherein
    (i) the CDR1 sequence is selected from the group consisting of: SEQ ID NO: 349 and residues 4-14 of SEQ ID NO: 349;
    (ii) the CDR2 sequence is selected from the group consisting of: SEQ ID NO: 339 and residues 4-10 of SEQ ID NO: 335; and (iii) the CDR3 sequence is selected from the group consisting of: SEQ ID NO: 301 and residues 4-13 of SEQ ID NO: 301;
said antagonist which inhibits human PCSK9-dependent inhibition of cellular LDL uptake by at least 10%.

2. The PCSK9-specific antagonist of claim 1 which comprises heavy and light chain regions having, in contiguous order, sequences for framework (FR) 1, CDR1, FR2, CDR2, FR3, CDR3, FR4 comprising:
   (a) heavy chain framework (FR) sequences 1, 2, 3 and 4 of SEQ ID NOs: 583, 584, 585 and 586, respectively; and
   (b) light chain FR sequences 1, 2, 3 and 4 of SEQ ID NOs: 587, 588, 589 and 590, respectively.

3. The PCSK9-specific antagonist of claim 1 which comprises:
   (a) a heavy chain variable region comprising sequence selected from the group consisting of: SEQ ID NOs: 360-361 and
   (b) a light chain variable region comprising SEQ ID NO: 511.

4. The PCSK9-specific antagonist of claim 1 which comprises:
   (a) a heavy chain comprising SEQ ID NO: 556; and
   (b) a light chain comprising SEQ ID NO: 558.

5. The PCSK9-specific antagonist of claim 1 that binds to human PCSK9 with a $K_D$ of less than 5 nM.

6. The PCSK9-specific antagonist of claim 1 that antagonizes PCSK9's inhibition of cellular LDL uptake at an $IC_{50}$ of less than 100 nM.

7. The PCSK9-specific antagonist of claim 1 that antagonizes PCSK9's inhibition of cellular uptake by at least 50%.

8. The PCSK9-specific antagonist of claim 1 which is an antibody molecule.

9. A composition comprising the PCSK9-specific antagonist of claim 1 and a pharmaceutically acceptable carrier.

* * * * *

SEQUENCE LISTING

```
<160> NUMBER OF SEQ ID NOS: 647

<210> SEQ ID NO 1
<211> LENGTH: 15
<212> TYPE: PRT
<213> ORGANISM: Artificial Sequence
<220> FEATURE:
<223> OTHER INFORMATION: consensus sequence for AX213 and AX132 Heavy
      Chain CDR3 Antibody Region
<221> NAME/KEY: VARIANT
<222> LOCATION: (2)...(2)
<223> OTHER INFORMATION: Xaa = A or S
<221> NAME/KEY: VARIANT
<222> LOCATION: (4)...(4)
<223> OTHER INFORMATION: Xaa = E, Y, A, G, S. H, Q or D
<221> NAME/KEY: VARIANT
<222> LOCATION: (5)...(5)
<223> OTHER INFORMATION: Xaa = R, K, F, N, H, D, S or Y
<221> NAME/KEY: VARIANT
<222> LOCATION: (6)...(6)
<223> OTHER INFORMATION: Xaa = Y, V, S. D, I, L. F or A
<221> NAME/KEY: VARIANT
<222> LOCATION: (7)...(7)
<223> OTHER INFORMATION: Xaa = G, Y or A
<221> NAME/KEY: VARIANT
<222> LOCATION: (8)...(8)
<223> OTHER INFORMATION: Xaa = Y or W
<221> NAME/KEY: VARIANT
<222> LOCATION: (9)...(9)
<223> OTHER INFORMATION: Xaa = Y, S, N or D
<221> NAME/KEY: VARIANT
<222> LOCATION: (10)...(10)
<223> OTHER INFORMATION: Xaa = F or L
<221> NAME/KEY: VARIANT
<222> LOCATION: (12)...(12)
<223> OTHER INFORMATION: Xaa = Y, N or F
<221> NAME/KEY: VARIANT
<222> LOCATION: (15)...(15)
<223> OTHER INFORMATION: Xaa = Q or E
```

```
<400> SEQUENCE: 1

Cys Xaa Arg Xaa Xaa Xaa Xaa Xaa Xaa Asp Xaa Trp Gly Xaa
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Consensus sequence for AX213 and AX132 Heavy
      Chain shorter CDR3 Antibody Region
<221> NAME/KEY: VARIANT
<222> LOCATION: (1)...(1)
<223> OTHER INFORMATION: Xaa = E, Y, A, G, S, H, Q or D
<221> NAME/KEY: VARIANT
<222> LOCATION: (2)...(2)
<223> OTHER INFORMATION: Xaa = R, K, F, N, H, D, S or Y
<221> NAME/KEY: VARIANT
<222> LOCATION: (3)...(3)
<223> OTHER INFORMATION: Xaa = Y, V, S, D, I, L, F or A
<221> NAME/KEY: VARIANT
<222> LOCATION: (4)...(4)
<223> OTHER INFORMATION: Xaa = G, Y or A
<221> NAME/KEY: VARIANT
<222> LOCATION: (5)...(5)
<223> OTHER INFORMATION: Xaa = Y or W
<221> NAME/KEY: VARIANT
<222> LOCATION: (6)...(6)
<223> OTHER INFORMATION: Xaa = Y, S, N or D
<221> NAME/KEY: VARIANT
<222> LOCATION: (7)...(7)
<223> OTHER INFORMATION: Xaa = F or L
<221> NAME/KEY: VARIANT
<222> LOCATION: (9)...(9)
<223> OTHER INFORMATION: Xaa = Y, N or F

<400> SEQUENCE: 2

Xaa Xaa Xaa Xaa Xaa Xaa Xaa Asp Xaa
1               5

<210> SEQ ID NO 3
<211> LENGTH: 15
<212> TYPE: PRT
<213> ORGANISM: Artificial Sequence
<220> FEATURE:
<223> OTHER INFORMATION: Consensus sequence for AX213 and AX132 Heavy
      Chain CDR3 Antibody Region
<221> NAME/KEY: VARIANT
<222> LOCATION: (4)...(4)
<223> OTHER INFORMATION: Xaa = E, Y, A, G, S, H, Q or D
<221> NAME/KEY: VARIANT
<222> LOCATION: (5)...(5)
<223> OTHER INFORMATION: Xaa = R, K, F, N, H, D, S or Y
<221> NAME/KEY: VARIANT
<222> LOCATION: (6)...(6)
<223> OTHER INFORMATION: Xaa = Y, V, S, D, I, L, F or A
<221> NAME/KEY: VARIANT
<222> LOCATION: (7)...(7)
<223> OTHER INFORMATION: Xaa = G, Y or A
<221> NAME/KEY: VARIANT
<222> LOCATION: (9)...(9)
<223> OTHER INFORMATION: Xaa = Y, S, N or D
<221> NAME/KEY: VARIANT
<222> LOCATION: (10)...(10)
<223> OTHER INFORMATION: Xaa = F or L
<221> NAME/KEY: VARIANT
<222> LOCATION: (15)...(15)
<223> OTHER INFORMATION: Xaa = Q or E

<400> SEQUENCE: 3

Cys Ala Arg Xaa Xaa Xaa Xaa Tyr Xaa Xaa Asp Tyr Trp Gly Xaa
1               5                   10                  15
```

```
<210> SEQ ID NO 4
<211> LENGTH: 9
<212> TYPE: PRT
<213> ORGANISM: Artificial Sequence
<220> FEATURE:
<223> OTHER INFORMATION: Consensus sequence for AX213 and AX132 Heavy
      Chain shorter CDR3 Antibody Region
<221> NAME/KEY: VARIANT
<222> LOCATION: (1)...(1)
<223> OTHER INFORMATION: Xaa = E, Y, A, G, S, H, Q or D
<221> NAME/KEY: VARIANT
<222> LOCATION: (2)...(2)
<223> OTHER INFORMATION: Xaa = R, K, F, N, H, D, S or Y
<221> NAME/KEY: VARIANT
<222> LOCATION: (3)...(3)
<223> OTHER INFORMATION: Xaa = Y, V, S, D, I, L, F or A
<221> NAME/KEY: VARIANT
<222> LOCATION: (4)...(4)
<223> OTHER INFORMATION: Xaa = G, Y or A
<221> NAME/KEY: VARIANT
<222> LOCATION: (6)...(6)
<223> OTHER INFORMATION: Xaa = Y, S, N or D
<221> NAME/KEY: VARIANT
<222> LOCATION: (7)...(7)
<223> OTHER INFORMATION: Xaa = F or L

<400> SEQUENCE: 4

Xaa Xaa Xaa Xaa Tyr Xaa Xaa Asp Tyr
1               5

<210> SEQ ID NO 5
<211> LENGTH: 15
<212> TYPE: PRT
<213> ORGANISM: Artificial Sequence
<220> FEATURE:
<223> OTHER INFORMATION: AX132 Heavy Chain CDR3 Antibody Region

<400> SEQUENCE: 5

Cys Ala Arg Glu Arg Tyr Gly Tyr Tyr Phe Asp Tyr Trp Gly Gln
1               5                   10                  15

<210> SEQ ID NO 6
<211> LENGTH: 45
<212> TYPE: DNA
<213> ORGANISM: Artificial Sequence
<220> FEATURE:
<223> OTHER INFORMATION: AX132 Heavy Chain CDR3 Antibody Region

<400> SEQUENCE: 6
tgcgcccgtg aacgttacgg ttactacttc gactactggg gtcag                    45

<210> SEQ ID NO 7
<211> LENGTH: 9
<212> TYPE: PRT
<213> ORGANISM: Artificial Sequence
<220> FEATURE:
<223> OTHER INFORMATION: AX132 Heavy Chain shorter CDR3 Antibody Region

<400> SEQUENCE: 7

Glu Arg Tyr Gly Tyr Tyr Phe Asp Tyr
1               5

<210> SEQ ID NO 8
<211> LENGTH: 27
<212> TYPE: DNA
<213> ORGANISM: Artificial Sequence
<220> FEATURE:
<223> OTHER INFORMATION: AX132 Heavy Chain shorter CDR3 Antibody Region
```

```
<400> SEQUENCE: 8
gaacgttacg gttactactt cgactac                                          27

<210> SEQ ID NO 9
<211> LENGTH: 15
<212> TYPE: PRT
<213> ORGANISM: Artificial Sequence
<220> FEATURE:
<223> OTHER INFORMATION: AX213 Heavy Chain CDR3 Antibody Region

<400> SEQUENCE: 9

Cys Ala Arg Ala Asn Asp Gly Tyr Ser Phe Asp Tyr Trp Gly Gln
1               5                   10                  15

<210> SEQ ID NO 10
<211> LENGTH: 45
<212> TYPE: DNA
<213> ORGANISM: Artificial Sequence
<220> FEATURE:
<223> OTHER INFORMATION: AX213 Heavy Chain CDR3 Antibody Region

<400> SEQUENCE: 10
tgcgcccgtg caaatgacgg ttactccttc gactactggg gtcag                      45

<210> SEQ ID NO 11
<211> LENGTH: 9
<212> TYPE: PRT
<213> ORGANISM: Artificial Sequence
<220> FEATURE:
<223> OTHER INFORMATION: AX213 Heavy Chain shorter CDR3 Antibody Region

<400> SEQUENCE: 11

Ala Asn Asp Gly Tyr Ser Phe Asp Tyr
1               5

<210> SEQ ID NO 12
<211> LENGTH: 27
<212> TYPE: DNA
<213> ORGANISM: Artificial Sequence
<220> FEATURE:
<223> OTHER INFORMATION: AX213 Heavy Chain shorter CDR3 Antibody Region

<400> SEQUENCE: 12
gcaaatgacg gttactcctt cgactac                                          27

<210> SEQ ID NO 13
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 13

Cys Ala Arg Ala Arg Val Gly Tyr Ser Leu Asp Tyr Trp Gly Gln
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 14

Cys Ala Arg Tyr Arg Val Gly Tyr Ser Leu Asp Tyr Trp Gly Gln
1               5                   10                  15
```

<210> SEQ ID NO 15
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 15

Cys Ala Arg Gln Arg Val Gly Tyr Ser Leu Asp Tyr Trp Gly Gln
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 16

Cys Ala Arg Ala Arg Val Gly Tyr Ser Phe Asp Tyr Trp Gly Gln
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 17

Cys Ala Arg Ser Arg Val Gly Tyr Ser Phe Asp Tyr Trp Gly Gln
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 18

Cys Ala Arg Tyr Arg Ser Gly Tyr Ser Leu Asp Tyr Trp Gly Gln
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 19

Cys Ala Arg Glu Arg Val Gly Tyr Ser Leu Asp Tyr Trp Gly Gln
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 20

Cys Ala Arg His Arg Val Gly Tyr Ser Leu Asp Phe Trp Gly Gln
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 21

Cys Ala Arg Tyr His Tyr Gly Tyr Ser Phe Asp Tyr Trp Gly Gln
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 22

Cys Ala Arg Tyr His Asp Gly Tyr Ser Phe Asp Tyr Trp Gly Gln
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 23

Cys Ala Arg Glu Arg Phe Ala Tyr Tyr Leu Asp Tyr Trp Gly Gln
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 24

Cys Ala Arg Ser Arg Asp Gly Tyr Tyr Phe Asp Tyr Trp Gly Gln
 1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 25

Cys Ala Arg Ala Arg Asp Gly Tyr Ser Phe Asp Tyr Trp Gly Gln
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 26

Cys Ala Arg Glu Arg Ala Gly Tyr Tyr Leu Asp Tyr Trp Gly Gln
 1               5                  10                  15

```
<210> SEQ ID NO 27
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 27

Cys Ala Arg His Arg Val Gly Tyr Tyr Phe Asp Tyr Trp Gly Gln
 1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 28

Cys Ala Arg Ala Asn Val Gly Tyr Ser Phe Asp Tyr Trp Gly Gln
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 29

Cys Ala Arg Ser His Val Gly Tyr Tyr Phe Asp Tyr Trp Gly Gln
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 30

Cys Ala Arg His Arg Val Gly Tyr Ser Leu Asp Tyr Trp Gly Gln
 1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 31

Cys Ala Arg Ser Arg Val Gly Tyr Ser Leu Asp Tyr Trp Gly Gln
 1               5                  10                  15

<210> SEQ ID NO 32
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 32

Cys Ala Arg Tyr Arg Asp Gly Tyr Ser Phe Asp Tyr Trp Gly Gln
 1               5                  10                  15

<210> SEQ ID NO 33
```

```
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 33

Cys Ala Arg Asp Arg Val Gly Tyr Ser Leu Asp Tyr Trp Gly Gln
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 34

Cys Ala Arg Gln Arg Val Gly Tyr Asn Leu Asp Tyr Trp Gly Gln
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 35

Cys Ala Arg Gln Arg Val Gly Tyr Ser Leu Asp Tyr Trp Gly Glu
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 36

Cys Ala Arg Ser Arg Asp Gly Tyr Ser Leu Asp Tyr Trp Gly Gln
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 37

Cys Ala Arg Tyr Arg Ser Gly Tyr Tyr Leu Asp Tyr Trp Gly Gln
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 38

Cys Ala Arg Tyr Arg Val Gly Tyr Ser Phe Asp Tyr Trp Gly Gln
1               5                   10                  15

<210> SEQ ID NO 39
<211> LENGTH: 15
```

<212> TYPE: PRT
<213> ORGANISM: Artificial Sequence
<220> FEATURE:
<223> OTHER INFORMATION: Heavy Chain CDR3 Antibody Region

<400> SEQUENCE: 39

Cys Ala Arg Ser Arg Asp Gly Tyr Ser Phe Asp Tyr Trp Gly Gln
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 40

Cys Ala Arg Ala Arg Asp Gly Tyr Ser Leu Asp Tyr Trp Gly Gln
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 41

Cys Ala Arg His Arg Val Gly Tyr Ser Phe Asp Tyr Trp Gly Gln
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 42

Cys Ala Arg Ala Asp Val Gly Tyr Ser Phe Asp Tyr Trp Gly Gln
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 43

Cys Ala Arg Gly Phe Val Tyr Tyr Ser Phe Asp Tyr Trp Gly Gln
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 44

Cys Ala Arg Gly Phe Ile Tyr Tyr Ser Phe Asp Tyr Trp Gly Gln
1               5                   10                  15

<210> SEQ ID NO 45
<211> LENGTH: 15
<212> TYPE: PRT

```
<213> ORGANISM: Artificial Sequence
<220> FEATURE:
<223> OTHER INFORMATION: Heavy Chain CDR3 Antibody Region

<400> SEQUENCE: 45

Cys Ala Arg Gly Phe Leu Tyr Tyr Ser Phe Asp Tyr Trp Gly Gln
 1               5                  10                  15

<210> SEQ ID NO 46
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 46

Cys Ala Arg Gly Arg Ile Tyr Tyr Ser Phe Asp Tyr Trp Gly Gln
 1               5                  10                  15

<210> SEQ ID NO 47
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 47

Cys Ala Arg Gly Arg Phe Tyr Tyr Ser Phe Asp Tyr Trp Gly Gln
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 48

Cys Ala Arg Gly Arg Leu Tyr Tyr Ser Leu Asp Tyr Trp Gly Gln
 1               5                  10                  15

<210> SEQ ID NO 49
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 49

Cys Ala Arg Gly Phe Ile Tyr Tyr Asp Phe Asp Tyr Trp Gly Gln
 1               5                  10                  15

<210> SEQ ID NO 50
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 50

Cys Ala Arg Gly Lys Ile Tyr Tyr Ser Phe Asp Tyr Trp Gly Gln
 1               5                  10                  15

<210> SEQ ID NO 51
<211> LENGTH: 15
<212> TYPE: PRT
<213> ORGANISM: Artificial Sequence
```

```
<220> FEATURE:
<223> OTHER INFORMATION: Heavy Chain CDR3 Antibody Region

<400> SEQUENCE: 51

Cys Ala Arg Gly Tyr Leu Tyr Tyr Ser Phe Asp Tyr Trp Gly Gln
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 52

Cys Ala Arg Gly Phe Ile Tyr Tyr Ser Leu Asp Tyr Trp Gly Gln
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 53

Cys Ala Arg Gly Asn Leu Tyr Tyr Ser Leu Asp Tyr Trp Gly Gln
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 54

Cys Ser Arg Gly Lys Val Gly Tyr Ser Leu Asp Tyr Trp Gly Gln
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 55

Cys Ala Arg Gly Ser Ile Gly Tyr Asn Leu Asp Tyr Trp Gly Gln
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 56

Cys Ala Arg Gly Arg Asp Gly Tyr Ser Leu Asp Tyr Trp Gly Gln
1               5                   10                  15

<210> SEQ ID NO 57
<211> LENGTH: 15
<212> TYPE: PRT
<213> ORGANISM: Artificial Sequence
<220> FEATURE:
```

```
<223> OTHER INFORMATION: Heavy Chain CDR3 Antibody Region

<400> SEQUENCE: 57

Cys Ala Arg Glu Lys Tyr Gly Tyr Tyr Phe Asp Tyr Trp Gly Gln
 1               5                  10                  15

<210> SEQ ID NO 58
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 58

Cys Ala Arg Tyr Lys Ser Gly Trp Tyr Phe Asp Tyr Trp Gly Gln
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 59

Cys Ala Arg Tyr Arg Ser Gly Tyr Tyr Phe Asp Tyr Trp Gly Gln
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 60

Cys Ala Arg Tyr Lys Ser Gly Tyr Tyr Phe Asp Tyr Trp Gly Gln
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 61

Cys Ala Arg Glu Lys Ser Gly Tyr Tyr Phe Asp Tyr Trp Gly Gln
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: Heavy Chain CDR3 Antibody Region

<400> SEQUENCE: 62

Cys Ala Arg Glu Arg Ser Gly Tyr Tyr Phe Asp Tyr Trp Gly Gln
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Heavy Chain CDR3 Antibody Region
```

<400> SEQUENCE: 63

Cys Ala Arg Ser Arg Val Gly Tyr Ser Phe Asp Asn Trp Gly Gln
1               5                   10                  15

<210> SEQ ID NO 64
<211> LENGTH: 23
<212> TYPE: PRT
<213> ORGANISM: Artificial Sequence
<220> FEATURE:
<223> OTHER INFORMATION: Consensus sequence for AX213 and AX132 Heavy
      Chain CDR2 Antibody Region
<221> NAME/KEY: VARIANT
<222> LOCATION: (1)...(1)
<223> OTHER INFORMATION: Xaa = W, S or Q
<221> NAME/KEY: VARIANT
<222> LOCATION: (2)...(2)
<223> OTHER INFORMATION: Xaa = I or V
<221> NAME/KEY: VARIANT
<222> LOCATION: (4)...(4)
<223> OTHER INFORMATION: Xaa = W, R, Y, S, L or Q
<221> NAME/KEY: VARIANT
<222> LOCATION: (5)...(5)
<223> OTHER INFORMATION: Xaa = I or D
<221> NAME/KEY: VARIANT
<222> LOCATION: (6)...(6)
<223> OTHER INFORMATION: Xaa = D, N, R, Q or S
<221> NAME/KEY: VARIANT
<222> LOCATION: (8)...(8)
<223> OTHER INFORMATION: Xaa = G, R, S, K, N or D
<221> NAME/KEY: VARIANT
<222> LOCATION: (9)...(9)
<223> OTHER INFORMATION: Xaa = S, N, Q, G or Y
<221> NAME/KEY: VARIANT
<222> LOCATION: (10)...(10)
<223> OTHER INFORMATION: Xaa = G or R
<221> NAME/KEY: VARIANT
<222> LOCATION: (11)...(11)
<223> OTHER INFORMATION: Xaa = G, W, S or T
<221> NAME/KEY: VARIANT
<222> LOCATION: (12)...(12)
<223> OTHER INFORMATION: Xaa = T, H, P or S
<221> NAME/KEY: VARIANT
<222> LOCATION: (13)...(13)
<223> OTHER INFORMATION: Xaa = K, R, N, Q, S or Y
<221> NAME/KEY: VARIANT
<222> LOCATION: (14)...(14)
<223> OTHER INFORMATION: Xaa = Y, V, Q or L
<221> NAME/KEY: VARIANT
<222> LOCATION: (15)...(15)
<223> OTHER INFORMATION: Xaa = N, Q, A, E, D, Y, S or T
<221> NAME/KEY: VARIANT
<222> LOCATION: (16)...(16)
<223> OTHER INFORMATION: Xaa = E, Q, D, P, R or H
<221> NAME/KEY: VARIANT
<222> LOCATION: (17)...(17)
<223> OTHER INFORMATION: Xaa = K, Q or S
<221> NAME/KEY: VARIANT
<222> LOCATION: (18)...(18)
<223> OTHER INFORMATION: Xaa = F or V
<221> NAME/KEY: VARIANT
<222> LOCATION: (19)...(22)
<223> OTHER INFORMATION: Xaa = at position 19 K, Q or E; at position 20,
      S, or D; at postion 21 K, R or Q; at position 22
      A, V, F or T

<400> SEQUENCE: 64

Xaa Xaa Gly Xaa Xaa Xaa Pro Xaa Xaa Xaa Xaa Xaa Xaa Xaa Xaa Xaa
1               5                   10                  15

Xaa Xaa Xaa Xaa Xaa Xaa Thr
                20

<210> SEQ ID NO 65
<211> LENGTH: 17

```
<212> TYPE: PRT
<213> ORGANISM: Artificial Sequence
<220> FEATURE:
<223> OTHER INFORMATION: Consensus sequence for AX213 and AX132 Heavy
      Chain Shorter CDR2 Antibody Region
<221> NAME/KEY: VARIANT
<222> LOCATION: (1)...(1)
<223> OTHER INFORMATION: Xaa =  R, Y, S, L or Q
<221> NAME/KEY: VARIANT
<222> LOCATION: (2)...(2)
<223> OTHER INFORMATION: Xaa = I or D
<221> NAME/KEY: VARIANT
<222> LOCATION: (3)...(3)
<223> OTHER INFORMATION: Xaa = D, N, R, Q or S
<221> NAME/KEY: VARIANT
<222> LOCATION: (5)...(5)
<223> OTHER INFORMATION: Xaa = G, R, S, K, N or D
<221> NAME/KEY: VARIANT
<222> LOCATION: (6)...(6)
<223> OTHER INFORMATION: Xaa = S, N, Q, G or Y
<221> NAME/KEY: VARIANT
<222> LOCATION: (7)...(7)
<223> OTHER INFORMATION: Xaa = G or R
<221> NAME/KEY: VARIANT
<222> LOCATION: (8)...(8)
<223> OTHER INFORMATION: Xaa = G, W, S or T
<221> NAME/KEY: VARIANT
<222> LOCATION: (9)...(9)
<223> OTHER INFORMATION: Xaa = T, H, P or S
<221> NAME/KEY: VARIANT
<222> LOCATION: (10)...(10)
<223> OTHER INFORMATION: Xaa = K, R, N, Q, S or Y
<221> NAME/KEY: VARIANT
<222> LOCATION: (11)...(11)
<223> OTHER INFORMATION: Xaa = Y, V, Q or L
<221> NAME/KEY: VARIANT
<222> LOCATION: (12)...(12)
<223> OTHER INFORMATION: Xaa = N, Q, A, E, D, Y, S or T
<221> NAME/KEY: VARIANT
<222> LOCATION: (13)...(13)
<223> OTHER INFORMATION: Xaa = E, Q, D, P, R or H
<221> NAME/KEY: VARIANT
<222> LOCATION: (14)...(14)
<223> OTHER INFORMATION: Xaa = K, Q or S
<221> NAME/KEY: VARIANT
<222> LOCATION: (15)...(15)
<223> OTHER INFORMATION: Xaa = F or V
<221> NAME/KEY: VARIANT
<222> LOCATION: (16)...(16)
<223> OTHER INFORMATION: Xaa = K, Q or E
<221> NAME/KEY: VARIANT
<222> LOCATION: (17)...(17)
<223> OTHER INFORMATION: Xaa = G, S or D

<400> SEQUENCE: 65

Xaa Xaa Xaa Pro Xaa Xaa Xaa Xaa Xaa Xaa Xaa Xaa Xaa Xaa Xaa
1               5                   10                  15

Xaa

<210> SEQ ID NO 66
<211> LENGTH: 23
<212> TYPE: PRT
<213> ORGANISM: Artificial Sequence
<220> FEATURE:
<223> OTHER INFORMATION: Consensus sequence for AX213 and AX132 Heavy
      Chain CDR2 Antibody Region
<221> NAME/KEY: VARIANT
<222> LOCATION: (1)...(1)
<223> OTHER INFORMATION: Xaa = W, S or Q
<221> NAME/KEY: VARIANT
<222> LOCATION: (2)...(2)
<223> OTHER INFORMATION: XAA at position 2 = I or V
<221> NAME/KEY: VARIANT
<222> LOCATION: (4)...(4)
<223> OTHER INFORMATION: Xaa = W, R, Y, S, L or Q
<221> NAME/KEY: VARIANT
```

```
<222> LOCATION: (5)...(5)
<223> OTHER INFORMATION: Xaa = I or D
<221> NAME/KEY: VARIANT
<222> LOCATION: (6)...(6)
<223> OTHER INFORMATION: Xaa = D, N, R, Q or S
<221> NAME/KEY: VARIANT
<222> LOCATION: (8)...(8)
<223> OTHER INFORMATION: Xaa = G, R, S, K, N or D
<221> NAME/KEY: VARIANT
<222> LOCATION: (9)...(9)
<223> OTHER INFORMATION: Xaa = S, N, Q, G or Y
<221> NAME/KEY: VARIANT
<222> LOCATION: (10)...(10)
<223> OTHER INFORMATION: Xaa = G or R
<221> NAME/KEY: VARIANT
<222> LOCATION: (11)...(11)
<223> OTHER INFORMATION: Xaa = G, W, S or T
<221> NAME/KEY: VARIANT
<222> LOCATION: (12)...(12)
<223> OTHER INFORMATION: Xaa = T, H, P or S
<221> NAME/KEY: VARIANT
<222> LOCATION: (13)...(13)
<223> OTHER INFORMATION: Xaa = K, R, N, Q, S or Y
<221> NAME/KEY: VARIANT
<222> LOCATION: (15)...(15)
<223> OTHER INFORMATION: Xaa = N, Q, A, E, D, Y, S or T
<221> NAME/KEY: VARIANT
<222> LOCATION: (16)...(16)
<223> OTHER INFORMATION: Xaa = E, Q, D, P, R or H
<221> NAME/KEY: VARIANT
<222> LOCATION: (17)...(17)
<223> OTHER INFORMATION: Xaa = K, Q or S
<221> NAME/KEY: VARIANT
<222> LOCATION: (18)...(18)
<223> OTHER INFORMATION: Xaa = F or V
<221> NAME/KEY: VARIANT
<222> LOCATION: (19)...(19)
<223> OTHER INFORMATION: Xaa = K, Q or E
<221> NAME/KEY: VARIANT
<222> LOCATION: (20)...(22)
<223> OTHER INFORMATION: Xaa = at position 20 G, S or D; at position 21
      K, R or Q; Xaa at position 22 A, V, F or T

<400> SEQUENCE: 66

Xaa Xaa Gly Xaa Xaa Xaa Pro Xaa Xaa Xaa Xaa Xaa Xaa Tyr Xaa Xaa
1               5                   10                  15

Xaa Xaa Xaa Xaa Xaa Xaa Thr
            20

<210> SEQ ID NO 67
<211> LENGTH: 17
<212> TYPE: PRT
<213> ORGANISM: Artificial Sequence
<220> FEATURE:
<223> OTHER INFORMATION: Consensus sequence for AX213 and AX132 Heavy
      Chain shorter CDR2 Antibody Region
<221> NAME/KEY: VARIANT
<222> LOCATION: (1)...(1)
<223> OTHER INFORMATION: Xaa = W, R, Y, S, L or Q
<221> NAME/KEY: VARIANT
<222> LOCATION: (2)...(2)
<223> OTHER INFORMATION: Xaa = I or D
<221> NAME/KEY: VARIANT
<222> LOCATION: (3)...(3)
<223> OTHER INFORMATION: Xaa = D, N, R, Q or S
<221> NAME/KEY: VARIANT
<222> LOCATION: (5)...(5)
<223> OTHER INFORMATION: Xaa = G, R, S, K, N or D
<221> NAME/KEY: VARIANT
<222> LOCATION: (6)...(6)
<223> OTHER INFORMATION: Xaa = S, N, Q, G or Y
<221> NAME/KEY: VARIANT
<222> LOCATION: (7)...(7)
<223> OTHER INFORMATION: Xaa = G or R
<221> NAME/KEY: VARIANT
<222> LOCATION: (8)...(8)
```

<223> OTHER INFORMATION: Xaa = G, W, S or T
<221> NAME/KEY: VARIANT
<222> LOCATION: (9)...(9)
<223> OTHER INFORMATION: Xaa = T, H, P or S
<221> NAME/KEY: VARIANT
<222> LOCATION: (10)...(10)
<223> OTHER INFORMATION: Xaa = K, R, N, Q, S or Y
<221> NAME/KEY: VARIANT
<222> LOCATION: (12)...(12)
<223> OTHER INFORMATION: Xaa = N, Q, A, E, D, Y, S or T
<221> NAME/KEY: VARIANT
<222> LOCATION: (13)...(13)
<223> OTHER INFORMATION: Xaa = E, Q, D, P, R or H
<221> NAME/KEY: VARIANT
<222> LOCATION: (14)...(14)
<223> OTHER INFORMATION: Xaa = K, Q or S
<221> NAME/KEY: VARIANT
<222> LOCATION: (15)...(15)
<223> OTHER INFORMATION: Xaa = F or V
<221> NAME/KEY: VARIANT
<222> LOCATION: (16)...(16)
<223> OTHER INFORMATION: Xaa = K, Q or E
<221> NAME/KEY: VARIANT
<222> LOCATION: (17)...(17)
<223> OTHER INFORMATION: Xaa = G, S or D

<400> SEQUENCE: 67

Xaa Xaa Xaa Pro Xaa Xaa Xaa Xaa Xaa Tyr Xaa Xaa Xaa Xaa Xaa
1               5                   10                  15

Xaa

<210> SEQ ID NO 68
<211> LENGTH: 23
<212> TYPE: PRT
<213> ORGANISM: Artificial Sequence
<220> FEATURE:
<223> OTHER INFORMATION: AX132 Heavy Chain CDR2 Antibody Region

<400> SEQUENCE: 68

Trp Ile Gly Trp Ile Asp Pro Gly Ser Gly Gly Thr Lys Tyr Asn Glu
1               5                   10                  15

Lys Phe Lys Gly Lys Ala Thr
            20

<210> SEQ ID NO 69
<211> LENGTH: 69
<212> TYPE: DNA
<213> ORGANISM: Artificial Sequence
<220> FEATURE:
<223> OTHER INFORMATION: AX132 Heavy Chain CDR2 Antibody Region

<400> SEQUENCE: 69
tggatcggtt ggatcgaccc aggcagcggt ggcaccaagt acaacgaaaa gttcaagggt    60
aaggccacc                                                           69

<210> SEQ ID NO 70
<211> LENGTH: 17
<212> TYPE: PRT
<213> ORGANISM: Artificial Sequence
<220> FEATURE:
<223> OTHER INFORMATION: AX132 Heavy Chain shorter CDR2 Antibody Region

<400> SEQUENCE: 70

Trp Ile Asp Pro Gly Ser Gly Gly Thr Lys Tyr Asn Glu Lys Phe Lys
1               5                   10                  15

Gly

<210> SEQ ID NO 71
<211> LENGTH: 51
<212> TYPE: DNA
<213> ORGANISM: Artificial Sequence
<220> FEATURE:
<223> OTHER INFORMATION: AX132 Heavy Chain shorter CDR2 Antibody Region

<400> SEQUENCE: 71
tggatcgacc caggcagcgg tggcaccaag tacaacgaaa agttcaaggg t          51

<210> SEQ ID NO 72
<211> LENGTH: 23
<212> TYPE: PRT
<213> ORGANISM: Artificial Sequence
<220> FEATURE:
<223> OTHER INFORMATION: AX213 Heavy Chain CDR2 Antibody Region

<400> SEQUENCE: 72

Trp Ile Gly Arg Ile Asp Pro Gly Asn Gly Gly Thr Arg Tyr Asn Glu
1               5                   10                  15

Lys Phe Lys Gly Lys Ala Thr
            20

<210> SEQ ID NO 73
<211> LENGTH: 69
<212> TYPE: DNA
<213> ORGANISM: Artificial Sequence
<220> FEATURE:
<223> OTHER INFORMATION: AX213 Heavy Chain CDR2 Antibody Region

<400> SEQUENCE: 73
tggatcggtc ggatcgaccc aggtaacggt ggtactaggt acaacgaaaa gttcaagggt      60
aaggccacc                                                             69

<210> SEQ ID NO 74
<211> LENGTH: 17
<212> TYPE: PRT
<213> ORGANISM: Artificial Sequence
<220> FEATURE:
<223> OTHER INFORMATION: AX213 Heavy Chain shorter CDR2 Antibody Region

<400> SEQUENCE: 74

Arg Ile Asp Pro Gly Asn Gly Gly Thr Arg Tyr Asn Glu Lys Phe Lys
1               5                   10                  15

Gly

<210> SEQ ID NO 75
<211> LENGTH: 51
<212> TYPE: DNA
<213> ORGANISM: Artificial Sequence
<220> FEATURE:
<223> OTHER INFORMATION: AX213 Heavy Chain shorter CDR2 Antibody Region

<400> SEQUENCE: 75
cggatcgacc caggtaacgg tggtactagg tacaacgaaa agttcaaggg t           51

<210> SEQ ID NO 76
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 76

Trp Ile Gly Trp Ile Asp Pro Gly Asn Gly Gly Thr Arg Tyr Asn Gln

Lys Phe Gln Ser Lys Ala Thr
            20

<210> SEQ ID NO 77
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 77

Trp Ile Gly Trp Ile Asp Pro Gly Asn Gly Gly Thr Arg Tyr Asn Glu
1               5                   10                  15

Lys Phe Lys Gly Lys Ala Thr
            20

<210> SEQ ID NO 78
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 78

Trp Ile Gly Tyr Ile Asp Pro Gly Ser Gly Gly Thr Lys Tyr Asn Gln
1               5                   10                  15

Lys Phe Gln Gly Lys Ala Thr
            20

<210> SEQ ID NO 79
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 79

Gln Ile Gly Trp Ile Asp Pro Gly Ser Gly Gly Thr Arg Tyr Asn Gln
1               5                   10                  15

Lys Phe Lys Ser Lys Ala Thr
            20

<210> SEQ ID NO 80
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 80

Trp Ile Gly Tyr Ile Asp Pro Gly Ser Gly Gly Thr Arg Tyr Asn Gln
1               5                   10                  15

Lys Phe Gln Gly Lys Ala Thr
            20

<210> SEQ ID NO 81
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 81

Trp Ile Gly Tyr Ile Asp Pro Gly Ser Gly Thr Lys Tyr Asn Gln
1               5                   10                  15

Lys Phe Gln Ser Lys Ala Thr
            20

<210> SEQ ID NO 82
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 82

Trp Ile Gly Trp Ile Asp Pro Gly Asn Gly Thr Ser Tyr Asn Gln
1               5                   10                  15

Lys Phe Lys Ser Lys Ala Thr
            20

<210> SEQ ID NO 83
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 83

Trp Ile Gly Trp Ile Asp Pro Gly Ser Gly Thr Arg Tyr Asn Gln
1               5                   10                  15

Lys Phe Lys Gly Lys Ala Thr
            20

<210> SEQ ID NO 84
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 84

Trp Ile Gly Trp Ile Asp Pro Gly Ser Gly Thr Arg Tyr Asn Glu
1               5                   10                  15

Lys Phe Lys Gly Gln Ala Thr
            20

<210> SEQ ID NO 85
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 85

Trp Ile Gly Tyr Ile Asp Pro Gly Ser Gly Thr Arg Tyr Asn Glu
1               5                   10                  15

Lys Phe Lys Gly Lys Ala Thr
            20

<210> SEQ ID NO 86
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 86

Trp Ile Gly Tyr Ile Asp Pro Gly Asn Gly Gly Thr Ser Tyr Asn Glu
1               5                   10                  15

Lys Phe Lys Gly Lys Ala Thr
            20

<210> SEQ ID NO 87
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 87

Trp Ile Gly Arg Ile Asp Pro Gly Ser Gly Gly Thr Arg Tyr Asn Gln
1               5                   10                  15

Gln Phe Gln Gly Lys Ala Thr
            20

<210> SEQ ID NO 88
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 88

Trp Ile Gly Tyr Ile Asp Pro Gly Ser Gly Gly Thr Arg Tyr Asn Glu
1               5                   10                  15

Lys Phe Gln Gly Lys Ala Thr
            20

<210> SEQ ID NO 89
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 89

Trp Ile Gly Trp Ile Asp Pro Gly Ser Gly Gly Thr Arg Tyr Asn Glu
1               5                   10                  15

Lys Phe Gln Ser Lys Ala Thr
            20

<210> SEQ ID NO 90
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 90

Trp Ile Gly Tyr Ile Asp Pro Gly Ser Gly Gly Thr Lys Tyr Asn Glu
1               5                   10                  15

Lys Phe Gln Gly Lys Ala Thr
            20

<210> SEQ ID NO 91
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 91

Trp Ile Gly Tyr Ile Asp Pro Gly Ser Gly Gly Thr Lys Tyr Asn Gln
1               5                   10                  15

Lys Phe Lys Gly Lys Ala Thr
            20

<210> SEQ ID NO 92
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 92

Trp Ile Gly Tyr Ile Asp Pro Gly Ser Gly Gly Thr Arg Tyr Asn Gln
1               5                   10                  15

Lys Phe Lys Gly Lys Ala Thr
            20

<210> SEQ ID NO 93
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 93

Trp Ile Gly Trp Ile Asp Pro Gly Ser Gly Gly Thr Arg Tyr Asn Gln
1               5                   10                  15

Lys Phe Lys Ser Lys Ala Thr
            20

<210> SEQ ID NO 94
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 94

Trp Ile Gly Arg Ile Asp Pro Gly Ser Gly Gly Thr Ser Tyr Asn Glu
1               5                   10                  15

Lys Phe Gln Ser Lys Ala Thr
            20

<210> SEQ ID NO 95
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 95

Trp Ile Gly Arg Ile Asp Pro Gly Asn Gly Gly Thr Arg Tyr Asn Gln
1               5                   10                  15

Lys Phe Gln Ser Lys Ala Thr
            20

<210> SEQ ID NO 96
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 96

Trp Ile Gly Tyr Ile Asp Pro Gly Ser Gly Gly Thr Lys Tyr Asn Glu
1               5                   10                  15

Lys Phe Lys Gly Lys Ala Thr
            20

<210> SEQ ID NO 97
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 97

Trp Ile Gly Trp Ile Asp Pro Gly Ser Gly Gly Thr Arg Tyr Asn Glu
1               5                   10                  15

Lys Phe Lys Ser Lys Ala Thr
            20

<210> SEQ ID NO 98
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 98

Trp Ile Gly Trp Ile Asp Pro Gly Asn Gly Gly Thr Arg Tyr Asn Gln
1               5                   10                  15

Gln Phe Lys Gly Lys Ala Thr
            20

<210> SEQ ID NO 99
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 99

Trp Ile Gly Trp Ile Asp Pro Gly Ser Gly Gly Thr Arg Tyr Asn Glu
1               5                   10                  15

Lys Phe Glu Gly Lys Ala Thr
            20

<210> SEQ ID NO 100
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 100

Trp Ile Gly Arg Ile Asp Pro Gly Ser Gly Gly Thr Arg Tyr Asn Gln
1               5                   10                  15

Lys Phe Gln Gly Lys Ala Thr
            20

<210> SEQ ID NO 101
<211> LENGTH: 23
<212> TYPE: PRT
<213> ORGANISM: Artificial Sequence
<220> FEATURE:

<223> OTHER INFORMATION: Heavy Chain CDR2 Antibody Region

<400> SEQUENCE: 101

Trp Ile Gly Arg Ile Asp Pro Gly Ser Gly Gly Thr Lys Tyr Asn Glu
1               5                   10                  15

Lys Phe Lys Gly Lys Ala Thr
            20

<210> SEQ ID NO 102
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 102

Trp Ile Gly Tyr Ile Asp Pro Gly Asn Gly Gly Thr Arg Tyr Asn Glu
1               5                   10                  15

Gln Phe Lys Gly Lys Ala Thr
            20

<210> SEQ ID NO 103
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 103

Trp Ile Gly Trp Ile Asp Pro Gly Asn Gly Gly Thr Arg Tyr Asn Glu
1               5                   10                  15

Gln Phe Gln Gly Lys Ala Thr
            20

<210> SEQ ID NO 104
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 104

Trp Ile Gly Arg Ile Asp Pro Gly Ser Gly Gly Thr Arg Tyr Asn Glu
1               5                   10                  15

Lys Phe Gln Gly Lys Ala Thr
            20

<210> SEQ ID NO 105
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 105

Trp Ile Gly Arg Ile Asp Pro Gly Ser Gly Gly Thr Arg Tyr Asn Glu
1               5                   10                  15

Lys Phe Gln Ser Lys Ala Thr
            20

<210> SEQ ID NO 106
<211> LENGTH: 23
<212> TYPE: PRT
<213> ORGANISM: Artificial Sequence

```
<220> FEATURE:
<223> OTHER INFORMATION: Heavy Chain CDR2 Antibody Region

<400> SEQUENCE: 106

Trp Ile Gly Tyr Ile Asp Pro Gly Asn Gly Gly Thr Asn Tyr Asn Gln
1               5                   10                  15

Lys Phe Gln Ser Lys Ala Thr
            20

<210> SEQ ID NO 107
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 107

Trp Ile Gly Tyr Ile Asp Pro Gly Asn Gly Gly Thr Arg Tyr Asn Gln
1               5                   10                  15

Gln Phe Gln Gly Lys Ala Thr
            20

<210> SEQ ID NO 108
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 108

Trp Ile Gly Trp Ile Asp Pro Gly Ser Gly Gly Thr Arg Tyr Asn Gln
1               5                   10                  15

Lys Phe Gln Ser Lys Ala Thr
            20

<210> SEQ ID NO 109
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 109

Trp Ile Gly Tyr Ile Asp Pro Gly Asn Gly Gly Thr Arg Tyr Asn Glu
1               5                   10                  15

Lys Phe Gln Ser Lys Ala Thr
            20

<210> SEQ ID NO 110
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 110

Trp Ile Gly Tyr Ile Asp Pro Gly Ser Gly Gly Thr Arg Tyr Asn Gln
1               5                   10                  15

Lys Phe Lys Ser Lys Ala Thr
            20

<210> SEQ ID NO 111
<211> LENGTH: 23
<212> TYPE: PRT
```

```
<213> ORGANISM: Artificial Sequence
<220> FEATURE:
<223> OTHER INFORMATION: Heavy Chain CDR2 Antibody Region

<400> SEQUENCE: 111

Trp Ile Gly Arg Ile Asp Pro Gly Asn Gly Gly Thr Arg Tyr Asn Glu
1               5                   10                  15

Lys Phe Gln Gly Lys Ala Thr
            20

<210> SEQ ID NO 112
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 112

Trp Ile Gly Trp Ile Asp Pro Gly Asn Gly Gly Thr Lys Tyr Asn Gln
1               5                   10                  15

Lys Phe Gln Ser Lys Ala Thr
            20

<210> SEQ ID NO 113
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 113

Trp Ile Gly Trp Ile Asp Pro Gly Ser Gly Gly Thr Arg Tyr Asn Glu
1               5                   10                  15

Lys Phe Gln Gly Lys Ala Thr
            20

<210> SEQ ID NO 114
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 114

Trp Ile Gly Arg Ile Asp Pro Ser Asn Gly Gly Thr Lys Tyr Asn Gln
1               5                   10                  15

Lys Phe Lys Gly Lys Ala Thr
            20

<210> SEQ ID NO 115
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 115

Trp Ile Gly Arg Ile Asn Pro Asn Ser Gly Gly Thr Lys Tyr Asn Glu
1               5                   10                  15

Lys Phe Lys Gly Lys Ala Thr
            20

<210> SEQ ID NO 116
<211> LENGTH: 23
```

<212> TYPE: PRT
<213> ORGANISM: Artificial Sequence
<220> FEATURE:
<223> OTHER INFORMATION: Heavy Chain CDR2 Antibody Region

<400> SEQUENCE: 116

Trp Ile Gly Arg Ile Asp Pro Gly Ser Gly Gly Thr Lys Tyr Asn Gln
1               5                   10                  15
Lys Phe Lys Gly Lys Ala Thr
            20

<210> SEQ ID NO 117
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 117

Trp Val Gly Arg Ile Ser Pro Ser Gly Gly Ser Thr Tyr Tyr Ala Asp
1               5                   10                  15
Ser Val Lys Gly Arg Phe Thr
            20

<210> SEQ ID NO 118
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 118

Trp Ile Gly Arg Ile Asn Pro Gly Ser Gly Gly Thr Lys Tyr Asp Glu
1               5                   10                  15
Lys Phe Lys Gly Arg Ala Thr
            20

<210> SEQ ID NO 119
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 119

Trp Ile Gly Trp Ile Asn Pro Asp Ser Gly Ser Thr Lys Tyr Ala Glu
1               5                   10                  15
Lys Phe Lys Gly Arg Ala Thr
            20

<210> SEQ ID NO 120
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 120

Trp Ile Gly Arg Ile Asp Pro Ser Ser Gly Gly Thr Lys Tyr Asn Gln
1               5                   10                  15
Lys Phe Lys Gly Lys Ala Thr
            20

<210> SEQ ID NO 121

```
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 121

Trp Val Gly Arg Ile Ser Pro Gly Gly Gly Thr Thr Tyr Tyr Ala Asp
 1               5                  10                  15

Ser Val Lys Gly Arg Phe Thr
            20

<210> SEQ ID NO 122
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 122

Trp Ile Gly Arg Ile Asn Pro Gly Ser Gly Gly Thr Asn Tyr Asp Glu
 1               5                  10                  15

Lys Phe Lys Gly Arg Ala Thr
            20

<210> SEQ ID NO 123
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 123

Trp Ile Gly Arg Ile Asn Pro Lys Gln Arg Trp His Lys Tyr Asn Gln
 1               5                  10                  15

Lys Phe Lys Gly Lys Val Thr
            20

<210> SEQ ID NO 124
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 124

Trp Ile Gly Leu Asp Arg Pro Arg Gln Arg Trp His Gln Leu Asn Glu
 1               5                  10                  15

Lys Phe Gln Gly Arg Ala Thr
            20

<210> SEQ ID NO 125
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 125

Ser Ile Gly Arg Ile Asp Pro Gly Ser Gly Gly Thr Lys Tyr Asn Glu
 1               5                  10                  15

Lys Phe Gln Gly Arg Ala Thr
            20
```

```
<210> SEQ ID NO 126
<211> LENGTH: 24
<212> TYPE: PRT
<213> ORGANISM: Artificial Sequence
<220> FEATURE:
<223> OTHER INFORMATION: Heavy Chain CDR2 Antibody Region

<400> SEQUENCE: 126

Trp Ile Gly Leu Asp Arg Pro Lys Gln Arg Val Gly Thr Lys Tyr Asn
1               5                   10                  15

Gln Lys Phe Gln Gly Arg Val Thr
            20

<210> SEQ ID NO 127
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 127

Trp Ile Gly Leu Asp Arg Pro Arg Gln Arg Trp Pro Lys Tyr Asn Glu
1               5                   10                  15

Lys Phe Lys Gly Arg Ala Thr
            20

<210> SEQ ID NO 128
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 128

Trp Ile Gly Leu Asp Arg Pro Lys Gln Arg Trp His Gln Tyr Asn Glu
1               5                   10                  15

Lys Phe Gln Gly Arg Ala Thr
            20

<210> SEQ ID NO 129
<211> LENGTH: 24
<212> TYPE: PRT
<213> ORGANISM: Artificial Sequence
<220> FEATURE:
<223> OTHER INFORMATION: Heavy Chain CDR2 Antibody Region

<400> SEQUENCE: 129

Trp Ile Gly Ser Asp Arg Pro Arg Gln Arg Val Ala Pro Lys Tyr Asn
1               5                   10                  15

Gln Lys Phe Lys Gly Arg Ala Thr
            20

<210> SEQ ID NO 130
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 130

Trp Ile Gly Arg Ile Asp Pro Ser Ser Gly Gly Thr Lys Tyr Asn Gln
1               5                   10                  15

Lys Phe Gln Gly Arg Val Thr
            20
```

<210> SEQ ID NO 131
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 131

Trp Ile Gly Leu Asp Arg Pro Lys Gln Arg Gly Thr Lys Tyr Asn Gln
1               5                   10                  15

Lys Phe Gln Gly Arg Ala Thr
            20

<210> SEQ ID NO 132
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 132

Trp Ile Gly Ser Asp Arg Pro Arg Gln Arg Trp His Gln Val Gln Arg
1               5                   10                  15

Lys Phe Lys Gly Arg Ala Thr
            20

<210> SEQ ID NO 133
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 133

Trp Ile Gly Arg Ile Asp Pro Asn Ser Gly Gly Thr Lys Tyr Asn Glu
1               5                   10                  15

Lys Phe Gln Gly Arg Ala Thr
            20

<210> SEQ ID NO 134
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 134

Trp Ile Gly Arg Ile Asn Pro Ser Ser Gly Gly Thr Asn Tyr Asn Glu
1               5                   10                  15

Gln Phe Gln Gly Arg Ala Thr
            20

<210> SEQ ID NO 135
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 135

Trp Ile Gly Ser Asp Arg Pro Arg Gln Arg Trp His Gln Val Gln Pro
1               5                   10                  15

Lys Val Gln Gly Arg Ala Thr
            20

<210> SEQ ID NO 136
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 136

Trp Ile Gly Arg Ile Asp Pro Asn Ser Gly Gly Thr Lys Gln Asn Glu
1               5                   10                  15

Lys Phe Gln Gly Arg Ala Thr
            20

<210> SEQ ID NO 137
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 137

Ser Ile Gly Arg Ile Asp Pro Gly Ser Gly Gly Thr Lys Tyr Asn Gln
1               5                   10                  15

Lys Phe Gln Gly Arg Ala Thr
            20

<210> SEQ ID NO 138
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 138

Trp Ile Gly Leu Asp Arg Pro Arg Gln Arg Trp His Gln Val Asn Glu
1               5                   10                  15

Lys Phe Gln Gly Arg Ala Thr
            20

<210> SEQ ID NO 139
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 139

Trp Ile Gly Arg Ile Asp Pro Gly Asn Gly Gly Thr Lys Tyr Asn Glu
1               5                   10                  15

Lys Phe Lys Gly Lys Val Thr
            20

<210> SEQ ID NO 140
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 140

Trp Ile Gly Arg Ile Asp Pro Gly Ser Gly Gly Thr Lys Tyr Asn Glu
1               5                   10                  15

Lys Phe Gln Gly Lys Val Thr

<210> SEQ ID NO 141
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 141

Trp Ile Gly Gln Asp Arg Pro Lys Tyr Gly Thr Lys Tyr Asn Glu
1               5                   10                  15

Lys Phe Lys Gly Arg Val Thr
            20

<210> SEQ ID NO 142
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 142

Trp Ile Gly Arg Ile Asn Pro Ser Asn Gly Gly Thr Lys Tyr Asn Glu
1               5                   10                  15

Lys Phe Lys Gly Arg Ala Thr
            20

<210> SEQ ID NO 143
<211> LENGTH: 24
<212> TYPE: PRT
<213> ORGANISM: Artificial Sequence
<220> FEATURE:
<223> OTHER INFORMATION: Heavy Chain CDR2 Antibody Region

<400> SEQUENCE: 143

Trp Ile Gly Ser Asp Arg Pro Arg Gln Arg Trp Gly Thr Lys Tyr Asn
1               5                   10                  15

Glu Lys Phe Gln Gly Arg Val Thr
            20

<210> SEQ ID NO 144
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 144

Trp Ile Gly Trp Ile Asn Pro Ser Asn Gly Gly Thr Lys Tyr Asn Glu
1               5                   10                  15

Lys Phe Lys Gly Arg Ala Thr
            20

<210> SEQ ID NO 145
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 145

Trp Ile Gly Ser Asp Gln Pro Arg Gln Gly Gly Thr Lys Tyr Asn Glu
1               5                   10                  15

Lys Phe Lys Gly Arg Ala Thr
            20

<210> SEQ ID NO 146
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 146

Trp Ile Gly Ser Asp Arg Pro Arg Gln Gly Gly Thr Lys Tyr Asn Glu
1               5                   10                  15

Lys Phe Lys Asp Arg Val Thr
            20

<210> SEQ ID NO 147
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 147

Trp Ile Gly Ser Asp Arg Pro Lys Gln Arg Gly Thr Lys Tyr Asn Glu
1               5                   10                  15

Lys Phe Lys Gly Lys Val Thr
            20

<210> SEQ ID NO 148
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 148

Ser Ile Gly Arg Ile Asn Pro Gly Ser Gly Gly Thr Lys Tyr Asn Glu
1               5                   10                  15

Lys Phe Gln Gly Arg Ala Thr
            20

<210> SEQ ID NO 149
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 149

Trp Ile Gly Ser Asp Arg Pro Lys Gln Arg Trp His Gln Val Asn Glu
1               5                   10                  15

Lys Phe Gln Gly Lys Val Thr
            20

<210> SEQ ID NO 150
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 150

Trp Ile Gly Arg Ile Asp Pro Asp Ser Gly Gly Thr Lys Tyr Asn Glu
1               5                   10                  15

Lys Phe Gln Gly Arg Ala Thr
            20

<210> SEQ ID NO 151
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 151

Trp Ile Gly Arg Ile Asp Pro Gly Asn Gly Gly Thr Lys Tyr Asn Glu
1               5                   10                  15

Lys Phe Lys Gly Lys Ala Thr
            20

<210> SEQ ID NO 152
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 152

Trp Ile Gly Arg Ile Asp Pro Gly Ser Gly Gly Thr Lys Tyr Asn Glu
1               5                   10                  15

Lys Phe Gln Gly Arg Ala Thr
            20

<210> SEQ ID NO 153
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 153

Trp Ile Gly Arg Ile Asn Pro Asp Asn Gly Gly Thr Lys Tyr Asn Glu
1               5                   10                  15

Lys Phe Gln Gly Arg Val Thr
            20

<210> SEQ ID NO 154
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 154

Trp Ile Gly Arg Asp Gln Pro Arg Gln Gly Gly Thr Asn Tyr Asn Glu
1               5                   10                  15

Lys Phe Gln Gly Arg Ala Thr
            20

<210> SEQ ID NO 155
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 155

Trp Ile Gly Arg Ile Asn Pro Asn Asn Gly Gly Thr Lys Tyr Asn Glu

```
1               5                   10                  15
Lys Phe Gln Gly Lys Ala Thr
            20

<210> SEQ ID NO 156
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 156

Trp Ile Gly Ser Asp Arg Pro Arg Gln Gly Gly Thr Lys Tyr Asn Glu
1               5                   10                  15

Lys Phe Lys Gly Arg Val Thr
            20

<210> SEQ ID NO 157
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 157

Trp Ile Gly Arg Ile Asp Pro Gly Ser Gly Gly Thr Lys Tyr Asn Glu
1               5                   10                  15

Lys Phe Gln Gly Arg Val Thr
            20

<210> SEQ ID NO 158
<211> LENGTH: 24
<212> TYPE: PRT
<213> ORGANISM: Artificial Sequence
<220> FEATURE:
<223> OTHER INFORMATION: Heavy Chain CDR2 Antibody Region

<400> SEQUENCE: 158

Trp Ile Gly Ser Asp Arg Pro Lys Gln Arg Trp Ala Pro Lys Tyr Asn
1               5                   10                  15

Glu Lys Phe Lys Gly Arg Ala Thr
            20

<210> SEQ ID NO 159
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 159

Trp Ile Gly Ser Asp Gln Pro Arg Gln Arg Trp His Gln Val Gln Pro
1               5                   10                  15

Lys Val Gln Gly Arg Val Thr
            20

<210> SEQ ID NO 160
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 160
```

```
Trp Ile Gly Arg Ile Asn Pro Gly Asn Gly Gly Thr Lys Gln Asn Glu
 1               5                  10                  15

Lys Phe Lys Gly Arg Ala Thr
            20
```

<210> SEQ ID NO 161
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 161

```
Trp Ile Gly Arg Ile Asn Pro Ser Ser Gly Gly Thr Lys Tyr Asn Glu
 1               5                  10                  15

Lys Phe Lys Gly Arg Ala Thr
            20
```

<210> SEQ ID NO 162
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 162

```
Trp Ile Gly Arg Ile Asn Pro Asn Ser Gly Gly Thr Lys Tyr Asn Glu
 1               5                  10                  15

Lys Phe Lys Gly Arg Val Thr
            20
```

<210> SEQ ID NO 163
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 163

```
Trp Ile Gly Arg Ile Asp Pro Gly Ser Gly Gly Thr Lys Tyr Asn Gln
 1               5                  10                  15

Lys Phe Lys Gly Arg Thr Thr
            20
```

<210> SEQ ID NO 164
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 164

```
Trp Ile Gly Trp Ile Asp Pro Gly Ser Gly Gly Thr Lys Tyr Gln Asp
 1               5                  10                  15

Lys Phe Lys Gly Lys Ala Thr
            20
```

<210> SEQ ID NO 165
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 165

```
Trp Ile Gly Trp Ile Asp Pro Gly Ser Gly Gly Thr Lys Tyr Gln Glu
 1               5                  10                  15

Lys Phe Lys Gly Lys Val Thr
             20

<210> SEQ ID NO 166
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 166

Trp Ile Gly Trp Ile Asp Pro Gly Ser Gly Gly Thr Lys Tyr Gln Glu
 1               5                  10                  15

Lys Phe Lys Gly Lys Ala Thr
             20

<210> SEQ ID NO 167
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 167

Trp Ile Gly Trp Ile Asp Pro Gly Ser Gly Gly Thr Asn Tyr Gln Glu
 1               5                  10                  15

Lys Phe Lys Gly Lys Ala Thr
             20

<210> SEQ ID NO 168
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 168

Trp Ile Gly Trp Ile Asp Pro Gly Ser Gly Gly Thr Asn Tyr Gln Gln
 1               5                  10                  15

Lys Phe Lys Gly Lys Ala Thr
             20

<210> SEQ ID NO 169
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 169

Trp Ile Gly Trp Ile Asp Pro Gly Ser Gly Gly Thr Lys Tyr Ala Asp
 1               5                  10                  15

Lys Phe Lys Gly Lys Ala Thr
             20

<210> SEQ ID NO 170
<211> LENGTH: 23
<212> TYPE: PRT
<213> ORGANISM: Artificial Sequence
<220> FEATURE:
<223> OTHER INFORMATION: Heavy Chain CDR2 Antibody Region
```

```
<400> SEQUENCE: 170

Trp Ile Gly Trp Ile Asp Pro Gly Ser Gly Gly Thr Lys Tyr Glu Glu
1               5                   10                  15

Lys Phe Lys Gly Lys Ala Thr
            20

<210> SEQ ID NO 171
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 171

Trp Ile Gly Trp Ile Asp Pro Gly Ser Gly Gly Thr Lys Tyr Asn Asp
1               5                   10                  15

Lys Phe Lys Gly Lys Ala Thr
            20

<210> SEQ ID NO 172
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 172

Trp Ile Gly Trp Ile Asp Pro Gly Ser Gly Gly Thr Lys Tyr Tyr Glu
1               5                   10                  15

Lys Phe Lys Gly Lys Ala Thr
            20

<210> SEQ ID NO 173
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 173

Trp Ile Gly Trp Ile Asp Pro Gly Ser Gly Gly Thr Lys Tyr Glu Asp
1               5                   10                  15

Lys Phe Glu Gly Lys Ala Thr
            20

<210> SEQ ID NO 174
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 174

Trp Ile Gly Trp Ile Asp Pro Gly Ser Gly Gly Thr Asn Tyr Thr Gln
1               5                   10                  15

Lys Phe Lys Gly Lys Ala Thr
            20

<210> SEQ ID NO 175
<211> LENGTH: 23
<212> TYPE: PRT
<213> ORGANISM: Artificial Sequence
<220> FEATURE:
<223> OTHER INFORMATION: Heavy Chain CDR2 Antibody Region
```

```
<400> SEQUENCE: 175

Trp Ile Gly Trp Ile Asp Pro Gly Ser Gly Gly Thr Lys Tyr Ser His
1               5                   10                  15

Lys Phe Lys Gly Lys Ala Thr
            20

<210> SEQ ID NO 176
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 176

Trp Ile Gly Tyr Ile Asp Pro Gly Ser Gly Gly Thr Arg Tyr Asn Glu
1               5                   10                  15

Lys Phe Gln Ser Lys Ala Thr
            20

<210> SEQ ID NO 177
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 177

Trp Ile Gly Tyr Ile Asp Pro Gly Asn Gly Gly Thr Arg Tyr Asn Gln
1               5                   10                  15

Lys Phe Lys Ser Lys Ala Thr
            20

<210> SEQ ID NO 178
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 178

Trp Ile Gly Trp Ile Asp Pro Gly Ser Gly Gly Thr Arg Tyr Asn Glu
1               5                   10                  15

Lys Phe Gln Ser Lys Ala Thr
            20

<210> SEQ ID NO 179
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 179

Trp Ile Gly Trp Ile Asp Pro Gly Asn Gly Gly Ser Arg Tyr Asn Gln
1               5                   10                  15

Lys Phe Lys Gly Lys Ala Thr
            20

<210> SEQ ID NO 180
<211> LENGTH: 23
<212> TYPE: PRT
<213> ORGANISM: Artificial Sequence
<220> FEATURE:
```

<223> OTHER INFORMATION: Heavy Chain CDR2 Antibody Region

<400> SEQUENCE: 180

Trp Ile Gly Tyr Ile Asp Pro Gly Asn Gly Gly Thr Arg Tyr Asn Glu
 1               5                  10                  15

Lys Phe Gln Gly Lys Ala Thr
            20

<210> SEQ ID NO 181
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 181

Trp Ile Gly Tyr Ile Asp Pro Gly Asn Gly Gly Thr Lys Tyr Asn Gln
 1               5                  10                  15

Lys Phe Gln Gly Lys Ala Thr
            20

<210> SEQ ID NO 182
<211> LENGTH: 23
<212> TYPE: PRT
<213> ORGANISM: Artificial Sequence
<220> FEATURE:
<223> OTHER INFORMATION: Heavy Chain CDR2 Antibody Region

<400> SEQUENCE: 182

Trp Ile Gly Tyr Ile Asp Pro Gly Ser Gly Gly Thr Lys Tyr Asn Glu
 1               5                  10                  15

Lys Phe Lys Gly Lys Ala Thr
            20

<210> SEQ ID NO 183
<211> LENGTH: 16
<212> TYPE: PRT
<213> ORGANISM: Artificial Sequence
<220> FEATURE:
<223> OTHER INFORMATION: Consensus sequence for AX213 and AX132 Heavy
      Chain CDR1 Antibody Region
<221> NAME/KEY: VARIANT
<222> LOCATION: (1)...(1)
<223> OTHER INFORMATION: Xaa = K, A, E, Q or T
<221> NAME/KEY: VARIANT
<222> LOCATION: (2)...(2)
<223> OTHER INFORMATION: Xaa = A or T
<221> NAME/KEY: VARIANT
<222> LOCATION: (4)...(4)
<223> OTHER INFORMATION: Xaa = G or D
<221> NAME/KEY: VARIANT
<222> LOCATION: (5)...(5)
<223> OTHER INFORMATION: Xaa = Y, F, L or Q
<221> NAME/KEY: VARIANT
<222> LOCATION: (6)...(6)
<223> OTHER INFORMATION: Xaa = T or S
<221> NAME/KEY: VARIANT
<222> LOCATION: (7)...(7)
<223> OTHER INFORMATION: Xaa = F or Y
<221> NAME/KEY: VARIANT
<222> LOCATION: (8)...(8)
<223> OTHER INFORMATION: Xaa = S or T
<221> NAME/KEY: VARIANT
<222> LOCATION: (9)...(9)
<223> OTHER INFORMATION: Xaa = S, R, A, N, D, T or Y
<221> NAME/KEY: VARIANT
<222> LOCATION: (10)...(10)
<223> OTHER INFORMATION: Xaa = Y, F or Q
<221> NAME/KEY: VARIANT
<222> LOCATION: (11)...(11)

<223> OTHER INFORMATION: Xaa = G, S, T, A, Y, Q or W
<221> NAME/KEY: VARIANT
<222> LOCATION: (12)...(12)
<223> OTHER INFORMATION: Xaa = M, I, F, Y, N or Q
<221> NAME/KEY: VARIANT
<222> LOCATION: (13)...(13)
<223> OTHER INFORMATION: Xaa = Y, S, N, T, H or I
<221> NAME/KEY: VARIANT
<222> LOCATION: (15)...(15)
<223> OTHER INFORMATION: Xaa = V or M

<400> SEQUENCE: 183

Xaa Xaa Ser Xaa Xaa Xaa Xaa Xaa Xaa Xaa Xaa Xaa Trp Xaa Arg
 1               5                  10                  15

<210> SEQ ID NO 184
<211> LENGTH: 10
<212> TYPE: PRT
<213> ORGANISM: Artificial Sequence
<220> FEATURE:
<223> OTHER INFORMATION: Consensus sequence for AX213 and AX132 Heavy
      Chain shorter CDR1 Antibody Region
<221> NAME/KEY: VARIANT
<222> LOCATION: (1)...(1)
<223> OTHER INFORMATION: Xaa = G or D
<221> NAME/KEY: VARIANT
<222> LOCATION: (2)...(2)
<223> OTHER INFORMATION: Xaa = Y, F, L or Q
<221> NAME/KEY: VARIANT
<222> LOCATION: (3)...(3)
<223> OTHER INFORMATION: Xaa = T or S
<221> NAME/KEY: VARIANT
<222> LOCATION: (4)...(4)
<223> OTHER INFORMATION: Xaa = F or Y
<221> NAME/KEY: VARIANT
<222> LOCATION: (5)...(5)
<223> OTHER INFORMATION: Xaa = S or T
<221> NAME/KEY: VARIANT
<222> LOCATION: (6)...(6)
<223> OTHER INFORMATION: Xaa = S, R, A, N, D, T or Y
<221> NAME/KEY: VARIANT
<222> LOCATION: (7)...(7)
<223> OTHER INFORMATION: Xaa = Y, F or Q
<221> NAME/KEY: VARIANT
<222> LOCATION: (8)...(8)
<223> OTHER INFORMATION: Xaa = G, S, T, A, Y, Q or W
<221> NAME/KEY: VARIANT
<222> LOCATION: (9)...(9)
<223> OTHER INFORMATION: Xaa = M, I, F, Y, N or Q
<221> NAME/KEY: VARIANT
<222> LOCATION: (10)...(10)
<223> OTHER INFORMATION: Xaa = Y, S, N, T, H or I

<400> SEQUENCE: 184

Xaa Xaa Xaa Xaa Xaa Xaa Xaa Xaa Xaa Xaa
 1               5                  10

<210> SEQ ID NO 185
<211> LENGTH: 16
<212> TYPE: PRT
<213> ORGANISM: Artificial Sequence
<220> FEATURE:
<223> OTHER INFORMATION: Consensus sequence for AX213 and AX132 Heavy
      Chain CDR1 Antibody Region
<221> NAME/KEY: VARIANT
<222> LOCATION: (1)...(1)
<223> OTHER INFORMATION: Xaa = K, A, E, Q or T
<221> NAME/KEY: VARIANT
<222> LOCATION: (4)...(4)
<223> OTHER INFORMATION: Xaa = G or D
<221> NAME/KEY: VARIANT
<222> LOCATION: (5)...(5)
<223> OTHER INFORMATION: Xaa = Y, F, L or Q
<221> NAME/KEY: VARIANT
<222> LOCATION: (6)...(6)

```
<223> OTHER INFORMATION: Xaa = T or S
<221> NAME/KEY: VARIANT
<222> LOCATION: (8)...(8)
<223> OTHER INFORMATION: Xaa = S or T
<221> NAME/KEY: VARIANT
<222> LOCATION: (9)...(9)
<223> OTHER INFORMATION: Xaa = S, R, A, N, D, T or Y
<221> NAME/KEY: VARIANT
<222> LOCATION: (10)...(10)
<223> OTHER INFORMATION: Xaa = Y, F or Q
<221> NAME/KEY: VARIANT
<222> LOCATION: (11)...(11)
<223> OTHER INFORMATION: Xaa = G, S, T, A, Y, Q or W
<221> NAME/KEY: VARIANT
<222> LOCATION: (12)...(12)
<223> OTHER INFORMATION: Xaa = M, I, F, Y, N or Q
<221> NAME/KEY: VARIANT
<222> LOCATION: (13)...(13)
<223> OTHER INFORMATION: Xaa = Y, S, N, T, H or I
<221> NAME/KEY: VARIANT
<222> LOCATION: (15)...(15)
<223> OTHER INFORMATION: Xaa = V or M

<400> SEQUENCE: 185

Xaa Ala Ser Xaa Xaa Xaa Phe Xaa Xaa Xaa Xaa Xaa Xaa Trp Xaa Arg
 1               5                  10                  15

<210> SEQ ID NO 186
<211> LENGTH: 10
<212> TYPE: PRT
<213> ORGANISM: Artificial Sequence
<220> FEATURE:
<223> OTHER INFORMATION: Consensus sequence for AX213 and AX132 Heavy
      Chain shorter CDR1 Antibody Region
<221> NAME/KEY: VARIANT
<222> LOCATION: (1)...(1)
<223> OTHER INFORMATION: Xaa = G or D
<221> NAME/KEY: VARIANT
<222> LOCATION: (2)...(2)
<223> OTHER INFORMATION: Xaa = Y, F, L or Q
<221> NAME/KEY: VARIANT
<222> LOCATION: (3)...(3)
<223> OTHER INFORMATION: Xaa = T or S
<221> NAME/KEY: VARIANT
<222> LOCATION: (5)...(5)
<223> OTHER INFORMATION: Xaa = S or T
<221> NAME/KEY: VARIANT
<222> LOCATION: (6)...(6)
<223> OTHER INFORMATION: Xaa = S, R, A, N, D, T or Y
<221> NAME/KEY: VARIANT
<222> LOCATION: (7)...(7)
<223> OTHER INFORMATION: Xaa = Y, F or Q
<221> NAME/KEY: VARIANT
<222> LOCATION: (8)...(8)
<223> OTHER INFORMATION: Xaa = G, S, T, A, Y, Q or W
<221> NAME/KEY: VARIANT
<222> LOCATION: (9)...(9)
<223> OTHER INFORMATION: Xaa = M, I, F, Y, N or Q
<221> NAME/KEY: VARIANT
<222> LOCATION: (10)...(10)
<223> OTHER INFORMATION: Xaa = Y, S, N, T, H or I

<400> SEQUENCE: 186

Xaa Xaa Xaa Phe Xaa Xaa Xaa Xaa Xaa Xaa
 1               5                  10

<210> SEQ ID NO 187
<211> LENGTH: 16
<212> TYPE: PRT
<213> ORGANISM: Artificial Sequence
<220> FEATURE:
<223> OTHER INFORMATION: Consensus sequence for AX213 and AX132 Heavy
      Chain CDR1 Antibody Region
<221> NAME/KEY: VARIANT
<222> LOCATION: (1)...(1)
```

```
<223> OTHER INFORMATION: Xaa = K, A, E, Q or T
<221> NAME/KEY: VARIANT
<222> LOCATION: (4)...(4)
<223> OTHER INFORMATION: Xaa = G or D
<221> NAME/KEY: VARIANT
<222> LOCATION: (5)...(5)
<223> OTHER INFORMATION: Xaa = Y, F, L or Q
<221> NAME/KEY: VARIANT
<222> LOCATION: (6)...(6)
<223> OTHER INFORMATION: Xaa = T or S
<221> NAME/KEY: VARIANT
<222> LOCATION: (8)...(8)
<223> OTHER INFORMATION: Xaa = S or T
<221> NAME/KEY: VARIANT
<222> LOCATION: (9)...(9)
<223> OTHER INFORMATION: Xaa = S, R, A, N, D, T or Y
<221> NAME/KEY: VARIANT
<222> LOCATION: (10)...(10)
<223> OTHER INFORMATION: Xaa = Y, F or Q
<221> NAME/KEY: VARIANT
<222> LOCATION: (11)...(11)
<223> OTHER INFORMATION: Xaa = G, S, T, A, Y, Q or W
<221> NAME/KEY: VARIANT
<222> LOCATION: (12)...(12)
<223> OTHER INFORMATION: Xaa = M, I, F, Y, N or Q
<221> NAME/KEY: VARIANT
<222> LOCATION: (13)...(13)
<223> OTHER INFORMATION: Xaa = Y, S, N, T, H or I

<400> SEQUENCE: 187

Xaa Ala Ser Xaa Xaa Xaa Phe Xaa Xaa Xaa Xaa Xaa Xaa Trp Val Arg
 1               5                  10                  15

<210> SEQ ID NO 188
<211> LENGTH: 10
<212> TYPE: PRT
<213> ORGANISM: Artificial Sequence
<220> FEATURE:
<223> OTHER INFORMATION: Consensus sequence for AX213 and AX132 Heavy
      Chain shorter CDR1 Antibody Region
<221> NAME/KEY: VARIANT
<222> LOCATION: (1)...(1)
<223> OTHER INFORMATION: Xaa = G or D
<221> NAME/KEY: VARIANT
<222> LOCATION: (2)...(2)
<223> OTHER INFORMATION: Xaa = Y, F, L or Q
<221> NAME/KEY: VARIANT
<222> LOCATION: (3)...(3)
<223> OTHER INFORMATION: Xaa = T or S
<221> NAME/KEY: VARIANT
<222> LOCATION: (5)...(5)
<223> OTHER INFORMATION: Xaa = S or T
<221> NAME/KEY: VARIANT
<222> LOCATION: (6)...(6)
<223> OTHER INFORMATION: Xaa = S, R, A, N, D, T or Y
<221> NAME/KEY: VARIANT
<222> LOCATION: (7)...(7)
<223> OTHER INFORMATION: Xaa = Y, F or Q
<221> NAME/KEY: VARIANT
<222> LOCATION: (8)...(8)
<223> OTHER INFORMATION: Xaa = G, S, T, A, Y, Q or W
<221> NAME/KEY: VARIANT
<222> LOCATION: (9)...(9)
<223> OTHER INFORMATION: Xaa = M, I, F, Y, N or Q
<221> NAME/KEY: VARIANT
<222> LOCATION: (10)...(10)
<223> OTHER INFORMATION: Xaa = Y, S, N, T, H or I

<400> SEQUENCE: 188

Xaa Xaa Xaa Phe Xaa Xaa Xaa Xaa Xaa Xaa
 1               5                  10

<210> SEQ ID NO 189
<211> LENGTH: 16
<212> TYPE: PRT
```

<213> ORGANISM: Artificial Sequence
<220> FEATURE:
<223> OTHER INFORMATION: AX132 Heavy Chain CDR1 Antibody Region

<400> SEQUENCE: 189

Lys Ala Ser Gly Tyr Thr Phe Ser Ser Tyr Gly Met Tyr Trp Val Arg
1               5                   10                  15

<210> SEQ ID NO 190
<211> LENGTH: 48
<212> TYPE: DNA
<213> ORGANISM: Artificial Sequence
<220> FEATURE:
<223> OTHER INFORMATION: AX132 Heavy Chain CDR1 Antibody Region

<400> SEQUENCE: 190
aaggcctctg gttacacctt ctcttcttac gggatgtact gggtgcgt                48

<210> SEQ ID NO 191
<211> LENGTH: 10
<212> TYPE: PRT
<213> ORGANISM: Artificial Sequence
<220> FEATURE:
<223> OTHER INFORMATION: AX132 Heavy Chain shorter CDR1 Antibody Region

<400> SEQUENCE: 191

Gly Tyr Thr Phe Ser Ser Tyr Gly Met Tyr
1               5                   10

<210> SEQ ID NO 192
<211> LENGTH: 30
<212> TYPE: DNA
<213> ORGANISM: Artificial Sequence
<220> FEATURE:
<223> OTHER INFORMATION: AX132 Heavy Chain shorter CDR1 Antibody Region

<400> SEQUENCE: 192 ggttacaccct tctcttctta cgggatgtac                                   30

<210> SEQ ID NO 193
<211> LENGTH: 16
<212> TYPE: PRT
<213> ORGANISM: Artificial Sequence
<220> FEATURE:
<223> OTHER INFORMATION: AX213 Heavy Chain CDR1 Antibody Region

<400> SEQUENCE: 193

Lys Ala Ser Gly Tyr Thr Phe Ser Arg Tyr Gly Ile Asn Trp Val Arg
1               5                   10                  15

<210> SEQ ID NO 194
<211> LENGTH: 48
<212> TYPE: DNA
<213> ORGANISM: Artificial Sequence
<220> FEATURE:
<223> OTHER INFORMATION: AX213 Heavy Chain CDR1 Antibody Region

<400> SEQUENCE: 194
aaggctagcg gttacacctt ctctcgctac ggtatcaact gggtgcgt                48

<210> SEQ ID NO 195
<211> LENGTH: 10
<212> TYPE: PRT
<213> ORGANISM: Artificial Sequence
<220> FEATURE:
<223> OTHER INFORMATION: AX213 Heavy Chain shorter CDR1 Antibody Region

<400> SEQUENCE: 195

Gly Tyr Thr Phe Ser Arg Tyr Gly Ile Asn
1               5                   10

<210> SEQ ID NO 196
<211> LENGTH: 30
<212> TYPE: DNA
<213> ORGANISM: Artificial Sequence
<220> FEATURE:
<223> OTHER INFORMATION: AX213 Heavy Chain shorter CDR1 Antibody Region

<400> SEQUENCE: 196
ggttacacct tctctcgcta cggtatcaac                                      30

<210> SEQ ID NO 197
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 197

Lys Ala Ser Gly Tyr Thr Phe Ser Ser Tyr Ser Ile Tyr Trp Val Arg
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 198

Lys Ala Ser Gly Tyr Thr Phe Ser Arg Gln Gly Phe Thr Trp Val Arg
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 199

Lys Ala Ser Gly Tyr Thr Phe Ser Ser Tyr Ser Phe Ser Trp Val Arg
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 200

Lys Ala Ser Gly Tyr Thr Phe Ser Arg Tyr Gly Ile Ser Trp Val Arg
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 201

Lys Ala Ser Gly Tyr Thr Phe Ser Ser Tyr Thr Asn Tyr Trp Val Arg
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 202

Lys Ala Ser Gly Tyr Thr Phe Ser Arg Tyr Ser Tyr Tyr Trp Val Arg
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 203

Lys Ala Ser Gly Tyr Thr Phe Ser Ser Tyr Ala Asn Thr Trp Val Arg
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 204

Lys Ala Ser Gly Tyr Thr Phe Ser Ser Tyr Gly Tyr Tyr Trp Val Arg
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 205

Lys Ala Ser Gly Tyr Thr Phe Ser Arg Tyr Ala Ile Asn Trp Val Arg
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 206

Lys Ala Ser Gly Tyr Thr Phe Ser Arg Tyr Gly Ile Tyr Trp Val Arg
1               5                   10                  15

<210> SEQ ID NO 207
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 207

Lys Ala Ser Gly Tyr Thr Phe Ser Arg Tyr Gly Tyr Tyr Trp Val Arg
1               5                   10                  15

```
<210> SEQ ID NO 208
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 208

Lys Ala Ser Gly Tyr Thr Phe Ser Arg Tyr Ala Tyr Asn Trp Val Arg
 1               5                  10                  15

<210> SEQ ID NO 209
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 209

Lys Ala Ser Gly Tyr Thr Phe Ser Arg Tyr Gly Phe Ser Trp Val Arg
 1               5                  10                  15

<210> SEQ ID NO 210
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 210

Lys Ala Ser Gly Tyr Thr Phe Ser Arg Tyr Ala Phe Asn Trp Val Arg
 1               5                  10                  15

<210> SEQ ID NO 211
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 211

Lys Ala Ser Gly Tyr Thr Phe Ser Ser Tyr Gly Ile Tyr Trp Val Arg
 1               5                  10                  15

<210> SEQ ID NO 212
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 212

Lys Ala Ser Gly Tyr Thr Phe Ser Arg Tyr Thr Ile Thr Trp Val Arg
 1               5                  10                  15

<210> SEQ ID NO 213
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 213

Lys Ala Ser Gly Tyr Thr Phe Ser Arg Tyr Ser Phe Ile Trp Val Arg
 1               5                  10                  15
```

```
<210> SEQ ID NO 214
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 214

Lys Ala Ser Gly Tyr Thr Phe Ser Arg Tyr Thr Phe Tyr Trp Val Arg
 1               5                  10                  15

<210> SEQ ID NO 215
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 215

Lys Ala Ser Gly Gln Thr Phe Ser Ser Tyr Gly Phe Asn Trp Val Arg
 1               5                  10                  15

<210> SEQ ID NO 216
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 216

Lys Ala Ser Gly Tyr Thr Phe Ser Arg Tyr Ala Asn Tyr Trp Val Arg
 1               5                  10                  15

<210> SEQ ID NO 217
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 217

Lys Ala Ser Gly Tyr Thr Phe Ser Arg Tyr Ser Asn Ser Trp Val Arg
 1               5                  10                  15

<210> SEQ ID NO 218
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 218

Lys Ala Ser Gly Tyr Thr Phe Ser Ser Tyr Ser Ile Thr Trp Val Arg
 1               5                  10                  15

<210> SEQ ID NO 219
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 219

Lys Ala Ser Gly Tyr Thr Phe Ser Ser Tyr Thr Tyr Thr Trp Val Arg
 1               5                  10                  15
```

<210> SEQ ID NO 220
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 220

Lys Ala Ser Gly Tyr Thr Phe Ser Ser Tyr Ser Tyr Tyr Trp Val Arg
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 221

Lys Ala Ser Gly Tyr Thr Phe Ser Ser Tyr Gly Tyr Ser Trp Val Arg
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 222

Lys Ala Ser Gly Tyr Thr Phe Ser Arg Tyr Thr Phe Ser Trp Val Arg
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 223

Lys Ala Ser Gly Tyr Thr Phe Ser Ser Tyr Gly Phe Ser Trp Val Arg
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 224

Lys Ala Ser Gly Tyr Thr Phe Ser Ser Tyr Gly Gln Ser Trp Val Arg
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 225

Lys Ala Ser Gly Tyr Thr Phe Ser Ser Tyr Ala Ile Ser Trp Val Arg
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 226

Lys Ala Ser Gly Tyr Thr Phe Ser Ser Tyr Thr Tyr Asn Trp Val Arg
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 227

Lys Ala Ser Gly Tyr Thr Phe Ser Ser Tyr Thr Ile Ser Trp Val Arg
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 228

Lys Ala Ser Gly Tyr Thr Phe Ser Arg Tyr Thr Phe Asn Trp Val Arg
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Heavy Chain CDR1 Antibody Region

<400> SEQUENCE: 229

Lys Gly Gln Arg Leu Pro Pro Arg Tyr Gly Tyr Tyr Trp Val Arg
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 230

Lys Ala Ser Gly Tyr Thr Tyr Ser Arg Tyr Thr Phe Ser Trp Val Arg
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 231

Lys Ala Ser Asp Tyr Thr Phe Ser Ser Tyr Gly Asn Asn Trp Val Arg
1               5                   10                  15

<210> SEQ ID NO 232

```
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 232

Lys Ala Ser Gly Tyr Thr Phe Ser Ser Tyr Gly Ile Ser Trp Val Arg
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 233

Lys Ala Ser Gly Tyr Thr Phe Ser Ser Tyr Thr Ile Asn Trp Val Arg
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 234

Lys Ala Ser Gly Phe Thr Phe Ser Ala Tyr Gly Met Tyr Trp Val Arg
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 235

Lys Ala Ser Gly Phe Thr Phe Ser Asp Tyr Gly Met Tyr Trp Val Arg
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 236

Lys Ala Ser Gly Phe Thr Phe Ser Ser Tyr Gln Met Ser Trp Val Arg
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 237

Lys Ala Ser Gly Phe Thr Phe Ser Tyr Tyr Tyr Met Tyr Trp Val Arg
1               5                   10                  15

<210> SEQ ID NO 238
<211> LENGTH: 16
```

<212> TYPE: PRT
<213> ORGANISM: Artificial Sequence
<220> FEATURE:
<223> OTHER INFORMATION: Heavy Chain CDR1 Antibody Region

<400> SEQUENCE: 238

Lys Ala Ser Gly Phe Thr Phe Thr Ala Tyr Gly Met Tyr Trp Val Arg
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 239

Lys Ala Ser Gly Phe Thr Phe Thr Ser Tyr Gln Met Ser Trp Val Arg
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 240

Lys Ala Ser Gly Phe Thr Phe Thr Ser Tyr Trp Met Ser Trp Val Arg
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 241

Lys Ala Ser Gly Leu Thr Phe Thr Asp Tyr Gly Met Tyr Trp Val Arg
1               5                   10                  15

<210> SEQ ID NO 242
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 242

Lys Ala Ser Gly Tyr Thr Phe Ser Tyr Tyr Gly Met Tyr Trp Val Arg
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 243

Lys Ala Ser Gly Tyr Thr Phe Thr Asp Tyr Gly Met Tyr Trp Val Arg
1               5                   10                  15

<210> SEQ ID NO 244
<211> LENGTH: 16
<212> TYPE: PRT

<213> ORGANISM: Artificial Sequence
<220> FEATURE:
<223> OTHER INFORMATION: Heavy Chain CDR1 Antibody Region

<400> SEQUENCE: 244

Lys Ala Ser Gly Tyr Thr Phe Thr Asn Tyr Gly Met Asn Trp Val Arg
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 245

Lys Ala Ser Gly Tyr Thr Phe Thr Ser Tyr Gly Met Tyr Trp Val Arg
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 246

Lys Ala Ser Gly Tyr Thr Phe Thr Ser Tyr Trp Met Ser Trp Val Arg
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 247

Gln Ala Ser Gly Tyr Thr Phe Ser Ser Tyr Gly Met Tyr Trp Val Arg
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 248

Glu Ala Ser Gly Phe Thr Phe Ser Ser Tyr Gly Met Tyr Trp Val Arg
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 249

Glu Ala Ser Gly Phe Ser Phe Ser Asn Tyr Gly Met Tyr Trp Val Arg
1               5                   10                  15

<210> SEQ ID NO 250
<211> LENGTH: 16
<212> TYPE: PRT
<213> ORGANISM: Artificial Sequence

```
<220> FEATURE:
<223> OTHER INFORMATION: Heavy Chain CDR1 Antibody Region

<400> SEQUENCE: 250

Ala Ala Ser Gly Tyr Ser Phe Ser Ala Tyr Tyr Ile His Trp Val Arg
 1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 251

Lys Ala Ser Gly Phe Ser Phe Ser Ser Tyr Gly Ile Tyr Trp Val Arg
 1               5                   10                  15

<210> SEQ ID NO 252
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 252

Ala Ala Ser Gly Tyr Ser Phe Ser Thr Phe Gly Ile Tyr Trp Val Arg
 1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 253

Glu Ala Ser Gly Phe Thr Phe Ser Asp Tyr Gly Ile His Trp Val Arg
 1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 254

Ala Ala Ser Gly Tyr Thr Phe Ser Asp Phe Gly Ile Tyr Trp Val Arg
 1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 255

Gln Ala Ser Gly Tyr Ser Phe Thr Thr Tyr Gly Met Tyr Trp Val Arg
 1               5                   10                  15

<210> SEQ ID NO 256
<211> LENGTH: 16
<212> TYPE: PRT
<213> ORGANISM: Artificial Sequence
<220> FEATURE:
```

-continued

```
<223> OTHER INFORMATION: Heavy Chain CDR1 Antibody Region

<400> SEQUENCE: 256

Ala Ala Ser Gly Phe Thr Phe Thr Asn Tyr Gly Met Tyr Trp Val Arg
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 257

Lys Ala Ser Gly Tyr Thr Phe Ser Tyr Phe Gly Ile Tyr Trp Val Arg
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 258

Thr Ala Ser Gly Phe Thr Phe Ser Asn Tyr Gly Met Tyr Trp Val Arg
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 259

Thr Ala Ser Gly Tyr Ser Phe Thr Ala Phe Gly Met Tyr Trp Val Arg
1               5                   10                  15

<210> SEQ ID NO 260
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 260

Lys Ala Ser Gly Phe Thr Phe Ser Ser Tyr Gly Met Tyr Trp Val Arg
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 261

Lys Ala Ser Gly Tyr Ser Phe Ser Ala Tyr Gly Met Tyr Trp Val Arg
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Heavy Chain CDR1 Antibody Region
```

<400> SEQUENCE: 262

Glu Ala Ser Gly Tyr Thr Phe Thr Ser Phe Gln Met His Trp Val Arg
1               5                   10                  15

<210> SEQ ID NO 263
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 263

Ala Ala Ser Gly Tyr Thr Phe Ser Ser Phe Ser Met Tyr Trp Val Arg
1               5                   10                  15

<210> SEQ ID NO 264
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 264

Gln Ala Ser Gly Tyr Thr Phe Thr Asn Tyr Gly Met Tyr Trp Val Arg
1               5                   10                  15

<210> SEQ ID NO 265
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 265

Gln Ala Ser Gly Tyr Thr Phe Thr Ala Phe Gly Met Tyr Trp Val Arg
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 266

Lys Ala Ser Gly Phe Ser Phe Thr Ser Tyr Gly Met Tyr Trp Val Arg
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 267

Gln Ala Ser Gly Phe Thr Phe Ser Thr Tyr Gly Ile Tyr Trp Val Arg
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: Heavy Chain CDR1 Antibody Region

```
<400> SEQUENCE: 268

Lys Ala Ser Gly Phe Ser Phe Ser Ser Tyr Gly Met Tyr Trp Val Arg
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 269

Glu Ala Ser Gly Tyr Ser Phe Ser Asn Phe Gly Met Tyr Trp Val Arg
1               5                   10                  15

<210> SEQ ID NO 270
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 270

Thr Ala Ser Asp Phe Ser Phe Ser Thr Phe Ser Met Tyr Trp Val Arg
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 271

Ala Ala Ser Gly Tyr Ser Phe Thr Ser Phe Gly Ile Tyr Trp Val Arg
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 272

Gln Ala Ser Gly Phe Ser Phe Ser Asp Tyr Tyr Met Ser Trp Val Arg
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 273

Ala Ala Ser Gly Tyr Ser Phe Ser Asp Tyr Gly Ile Tyr Trp Val Arg
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 274
```

Lys Ala Ser Gly Tyr Ser Phe Ser Thr Tyr Tyr Met Tyr Trp Val Arg
1               5                   10                  15

<210> SEQ ID NO 275
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 275

Glu Ala Ser Gly Tyr Thr Phe Ser Ala Phe Gln Ile Tyr Trp Val Arg
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 276

Gln Ala Ser Gly Phe Ser Phe Ser Asn Phe Tyr Met Tyr Trp Val Arg
1               5                   10                  15

<210> SEQ ID NO 277
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 277

Lys Ala Ser Gly Phe Thr Phe Ser Ala Phe Gly Ile Tyr Trp Val Arg
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 278

Lys Ala Ser Gly Tyr Thr Phe Ser Thr Tyr Gly Met Tyr Trp Val Arg
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 279

Ala Ala Ser Gly Tyr Ser Phe Ser Thr Tyr Gly Ile Tyr Trp Val Arg
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 280

```
Thr Ala Ser Gly Phe Ser Phe Ser Ala Tyr Gly Met Tyr Trp Val Arg
  1               5                  10                  15
```

<210> SEQ ID NO 281
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 281

```
Ala Ala Ser Gly Phe Ser Phe Ser Asn Tyr Tyr Met Tyr Trp Val Arg
  1               5                  10                  15
```

<210> SEQ ID NO 282
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 282

```
Glu Ala Ser Gly Tyr Thr Phe Thr Ser Tyr Gly Met Tyr Trp Met Arg
  1               5                  10                  15
```

<210> SEQ ID NO 283
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 283

```
Lys Ala Ser Gly Tyr Thr Phe Ser Asp Phe Ala Met Tyr Trp Val Arg
  1               5                  10                  15
```

<210> SEQ ID NO 284
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 284

```
Lys Ala Ser Gly Tyr Ser Phe Thr Asn Phe Gly Met Tyr Trp Val Arg
  1               5                  10                  15
```

<210> SEQ ID NO 285
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 285

```
Ala Ala Ser Gly Tyr Ser Phe Ser Tyr Tyr Gly Met Tyr Trp Val Arg
  1               5                  10                  15
```

<210> SEQ ID NO 286
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 286

```
Glu Ala Ser Gly Tyr Ser Phe Ser Ala Phe Gly Ile Tyr Trp Val Arg
```

```
                1               5                  10                 15
```

<210> SEQ ID NO 287
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 287

```
Lys Thr Ser Gly Tyr Thr Phe Ser Ala Phe Gln Ile Tyr Trp Val Arg
1               5                  10                  15
```

<210> SEQ ID NO 288
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 288

```
Lys Ala Ser Gly Tyr Thr Phe Ser Ser Tyr Gly Met Tyr Trp Met Arg
1               5                  10                  15
```

<210> SEQ ID NO 289
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 289

```
Lys Ala Ser Gly Tyr Thr Phe Ser Arg Tyr Thr Ile Ser Trp Val Arg
1               5                  10                  15
```

<210> SEQ ID NO 290
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 290

```
Lys Ala Ser Gly Tyr Thr Phe Ser Arg Tyr Thr Ile Asn Trp Val Arg
1               5                  10                  15
```

<210> SEQ ID NO 291
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 291

```
Lys Ala Ser Gly Tyr Thr Phe Ser Arg Tyr Ser Ile Asn Trp Val Arg
1               5                  10                  15
```

<210> SEQ ID NO 292
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 292

```
Lys Ala Ser Gly Tyr Thr Phe Ser Ser Tyr Ser Ile Asn Trp Val Arg
1               5                  10                  15
```

```
<210> SEQ ID NO 293
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 293

Lys Ala Ser Gly Tyr Thr Phe Ser Ser Tyr Ala Ile Asn Trp Val Arg
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Heavy Chain CDR1 Antibody Region

<400> SEQUENCE: 294

Lys Ala Ser Gly Tyr Thr Phe Ser Arg Tyr Ser Ile Ser Trp Val Arg
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Consensus sequence for AX213 and AX132 Light
      Chain CDR3 Antibody Region
<221> NAME/KEY: VARIANT
<222> LOCATION: (5)...(5)
<223> OTHER INFORMATION: Xaa = V, A or G
<221> NAME/KEY: VARIANT
<222> LOCATION: (6)...(6)
<223> OTHER INFORMATION: Xaa = W or Y
<221> NAME/KEY: VARIANT
<222> LOCATION: (7)...(7)
<223> OTHER INFORMATION: Xaa = D, G, S or N
<221> NAME/KEY: VARIANT
<222> LOCATION: (8)...(8)
<223> OTHER INFORMATION: Xaa = S, T or N
<221> NAME/KEY: VARIANT
<222> LOCATION: (9)...(9)
<223> OTHER INFORMATION: Xaa = S, N, Y, D or T
<221> NAME/KEY: VARIANT
<222> LOCATION: (10)...(10)
<223> OTHER INFORMATION: Xaa = P, H, A, D or S
<221> NAME/KEY: VARIANT
<222> LOCATION: (11)...(11)
<223> OTHER INFORMATION: Xaa = P, A, S, R or G
<221> NAME/KEY: VARIANT
<222> LOCATION: (12)...(12)
<223> OTHER INFORMATION: Xaa = V, L or S
<221> NAME/KEY: VARIANT
<222> LOCATION: (13)...(13)
<223> OTHER INFORMATION: Xaa = A, V, M, I, L or T
<221> NAME/KEY: VARIANT
<222> LOCATION: (16)...(16)
<223> OTHER INFORMATION: Xaa = G or D

<400> SEQUENCE: 295

Tyr Tyr Cys Gln Xaa Xaa Xaa Xaa Xaa Xaa Xaa Xaa Phe Gly Xaa
1               5                   10                  15

<210> SEQ ID NO 296
<211> LENGTH: 10
<212> TYPE: PRT
<213> ORGANISM: Artificial Sequence
<220> FEATURE:
<223> OTHER INFORMATION: Consensus sequence for AX213 and AX132 Light
      Chain shorter CDR3 Antibody Region
```

```
<221> NAME/KEY: VARIANT
<222> LOCATION: (2)...(2)
<223> OTHER INFORMATION: Xaa = V, A or G
<221> NAME/KEY: VARIANT
<222> LOCATION: (3)...(3)
<223> OTHER INFORMATION: Xaa = W or Y
<221> NAME/KEY: VARIANT
<222> LOCATION: (4)...(4)
<223> OTHER INFORMATION: Xaa = D, G, S or N
<221> NAME/KEY: VARIANT
<222> LOCATION: (5)...(5)
<223> OTHER INFORMATION: Xaa = S, T or N
<221> NAME/KEY: VARIANT
<222> LOCATION: (6)...(6)
<223> OTHER INFORMATION: Xaa = S, N, Y, D or T
<221> NAME/KEY: VARIANT
<222> LOCATION: (7)...(7)
<223> OTHER INFORMATION: Xaa = P, H, A, D or S
<221> NAME/KEY: VARIANT
<222> LOCATION: (8)...(8)
<223> OTHER INFORMATION: Xaa = P, A, S, R or G
<221> NAME/KEY: VARIANT
<222> LOCATION: (9)...(9)
<223> OTHER INFORMATION: Xaa = V, L or S
<221> NAME/KEY: VARIANT
<222> LOCATION: (10)...(10)
<223> OTHER INFORMATION: Xaa = A, V, M, I, L or T

<400> SEQUENCE: 296

Gln Xaa Xaa Xaa Xaa Xaa Xaa Xaa Xaa Xaa
 1               5                  10

<210> SEQ ID NO 297
<211> LENGTH: 16
<212> TYPE: PRT
<213> ORGANISM: Artificial Sequence
<220> FEATURE:
<223> OTHER INFORMATION: Consensus sequence for AX213 and AX132 Light
      Chain CDR3 Antibody Region
<221> NAME/KEY: VARIANT
<222> LOCATION: (5)...(5)
<223> OTHER INFORMATION: Xaa = V, A or G
<221> NAME/KEY: VARIANT
<222> LOCATION: (6)...(6)
<223> OTHER INFORMATION: Xaa = W or Y
<221> NAME/KEY: VARIANT
<222> LOCATION: (7)...(7)
<223> OTHER INFORMATION: Xaa = D, G, S or N
<221> NAME/KEY: VARIANT
<222> LOCATION: (8)...(8)
<223> OTHER INFORMATION: Xaa = S, T or N
<221> NAME/KEY: VARIANT
<222> LOCATION: (9)...(9)
<223> OTHER INFORMATION: Xaa = S, N, Y, D or T
<221> NAME/KEY: VARIANT
<222> LOCATION: (10)...(10)
<223> OTHER INFORMATION: Xaa = P, H, A, D or S
<221> NAME/KEY: VARIANT
<222> LOCATION: (11)...(11)
<223> OTHER INFORMATION: Xaa = P, A, S, R or G
<221> NAME/KEY: VARIANT
<222> LOCATION: (13)...(13)
<223> OTHER INFORMATION: Xaa = A, V, M, I, L or T
<221> NAME/KEY: VARIANT
<222> LOCATION: (16)...(16)
<223> OTHER INFORMATION: Xaa = G or D

<400> SEQUENCE: 297

Tyr Tyr Cys Gln Xaa Xaa Xaa Xaa Xaa Xaa Xaa Val Xaa Phe Gly Xaa
 1               5                  10                  15

<210> SEQ ID NO 298
<211> LENGTH: 10
<212> TYPE: PRT
<213> ORGANISM: Artificial Sequence
```

```
<220> FEATURE:
<223> OTHER INFORMATION: Consensus sequence for AX213 and AX132 Light
      Chain shorter CDR3 Antibody Region
<221> NAME/KEY: VARIANT
<222> LOCATION: (2)...(2)
<223> OTHER INFORMATION: Xaa = V, A or G
<221> NAME/KEY: VARIANT
<222> LOCATION: (3)...(3)
<223> OTHER INFORMATION: Xaa = W or Y
<221> NAME/KEY: VARIANT
<222> LOCATION: (4)...(4)
<223> OTHER INFORMATION: Xaa = D, G, S or N
<221> NAME/KEY: VARIANT
<222> LOCATION: (5)...(5)
<223> OTHER INFORMATION: Xaa = S, T or N
<221> NAME/KEY: VARIANT
<222> LOCATION: (6)...(6)
<223> OTHER INFORMATION: Xaa = S, N, Y, D or T
<221> NAME/KEY: VARIANT
<222> LOCATION: (7)...(7)
<223> OTHER INFORMATION: Xaa = P, H, A, D or S
<221> NAME/KEY: VARIANT
<222> LOCATION: (8)...(8)
<223> OTHER INFORMATION: Xaa = P, A, S, R or G
<221> NAME/KEY: VARIANT
<222> LOCATION: (10)...(10)
<223> OTHER INFORMATION: Xaa = A, V, M, I, L or T

<400> SEQUENCE: 298

Gln Xaa Xaa Xaa Xaa Xaa Xaa Xaa Val Xaa
 1               5                  10

<210> SEQ ID NO 299
<211> LENGTH: 16
<212> TYPE: PRT
<213> ORGANISM: Artificial Sequence
<220> FEATURE:
<223> OTHER INFORMATION: Consensus sequence for AX213 and AX132 Light
      Chain CDR3 Antibody Region
<221> NAME/KEY: VARIANT
<222> LOCATION: (5)...(5)
<223> OTHER INFORMATION: Xaa = V, A or G
<221> NAME/KEY: VARIANT
<222> LOCATION: (6)...(6)
<223> OTHER INFORMATION: Xaa = W or Y
<221> NAME/KEY: VARIANT
<222> LOCATION: (7)...(7)
<223> OTHER INFORMATION: Xaa = D, G, S or N
<221> NAME/KEY: VARIANT
<222> LOCATION: (8)...(8)
<223> OTHER INFORMATION: Xaa = S, T or N
<221> NAME/KEY: VARIANT
<222> LOCATION: (9)...(9)
<223> OTHER INFORMATION: Xaa = S, N, Y, D or T
<221> NAME/KEY: VARIANT
<222> LOCATION: (10)...(10)
<223> OTHER INFORMATION: Xaa = P, H, A, D or S
<221> NAME/KEY: VARIANT
<222> LOCATION: (11)...(11)
<223> OTHER INFORMATION: Xaa = P, A, S, R or G
<221> NAME/KEY: VARIANT
<222> LOCATION: (13)...(13)
<223> OTHER INFORMATION: Xaa = A, V, M, I, L or T

<400> SEQUENCE: 299

Tyr Tyr Cys Gln Xaa Xaa Xaa Xaa Xaa Xaa Xaa Val Xaa Phe Gly Gly
 1               5                  10                  15

<210> SEQ ID NO 300
<211> LENGTH: 10
<212> TYPE: PRT
<213> ORGANISM: Artificial Sequence
<220> FEATURE:
<223> OTHER INFORMATION: Consensus sequence for AX213 and AX132 Light
      Chain shorter CDR3 Antibody Region
```

-continued

```
<221> NAME/KEY: VARIANT
<222> LOCATION: (2)...(2)
<223> OTHER INFORMATION: Xaa = V, A or G
<221> NAME/KEY: VARIANT
<222> LOCATION: (3)...(3)
<223> OTHER INFORMATION: Xaa = W or Y
<221> NAME/KEY: VARIANT
<222> LOCATION: (4)...(4)
<223> OTHER INFORMATION: Xaa = D, G, S or N
<221> NAME/KEY: VARIANT
<222> LOCATION: (5)...(5)
<223> OTHER INFORMATION: Xaa = S, T or N
<221> NAME/KEY: VARIANT
<222> LOCATION: (6)...(6)
<223> OTHER INFORMATION: Xaa = S, N, Y, D or T
<221> NAME/KEY: VARIANT
<222> LOCATION: (7)...(7)
<223> OTHER INFORMATION: Xaa = P, H, A, D or S
<221> NAME/KEY: VARIANT
<222> LOCATION: (8)...(8)
<223> OTHER INFORMATION: Xaa = P, A, S, R or G
<221> NAME/KEY: VARIANT
<222> LOCATION: (10)...(10)
<223> OTHER INFORMATION: Xaa = A, V, M, I, L or T

<400> SEQUENCE: 300

Gln Xaa Xaa Xaa Xaa Xaa Xaa Val Xaa
1               5

<210> SEQ ID NO 301
<211> LENGTH: 16
<212> TYPE: PRT
<213> ORGANISM: Artificial Sequence
<220> FEATURE:
<223> OTHER INFORMATION: AX132 & AX213 Light Chain CDR3 Antibody Region

<400> SEQUENCE: 301

Tyr Tyr Cys Gln Val Trp Asp Ser Ser Pro Pro Val Val Phe Gly Gly
1               5                   10                  15

<210> SEQ ID NO 302
<211> LENGTH: 48
<212> TYPE: DNA
<213> ORGANISM: Artificial Sequence
<220> FEATURE:
<223> OTHER INFORMATION: AX132 & AX213 Light Chain CDR3 Antibody Region

<400> SEQUENCE: 302
tactactgcc aggtatggga cagctctcct cctgtggtgt tcggtggt                 48

<210> SEQ ID NO 303
<211> LENGTH: 10
<212> TYPE: PRT
<213> ORGANISM: Artificial Sequence
<220> FEATURE:
<223> OTHER INFORMATION: AX132 & AX213 Light Chain shorter CDR3 Antibody
      Region

<400> SEQUENCE: 303

Gln Val Trp Asp Ser Ser Pro Pro Val Val
1               5                   10

<210> SEQ ID NO 304
<211> LENGTH: 30
<212> TYPE: DNA
<213> ORGANISM: Artificial Sequence
<220> FEATURE:
<223> OTHER INFORMATION: AX132 & AX213 Light Chain shorter CDR3 Antibody
      Region

<400> SEQUENCE: 304
```
caggtatggg acagctctcc tcctgtggtg         30

<210> SEQ ID NO 305
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 305

Tyr Tyr Cys Gln Val Trp Asp Ser Ser Pro Pro Val Ala Phe Gly Gly
 1               5                  10                  15

<210> SEQ ID NO 306
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 306

Tyr Tyr Cys Gln Val Trp Asp Ser Ser Pro Pro Leu Val Phe Gly Gly
 1               5                  10                  15

<210> SEQ ID NO 307
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 307

Tyr Tyr Cys Gln Val Trp Asp Ser Ser Pro Pro Leu Ala Phe Gly Gly
 1               5                  10                  15

<210> SEQ ID NO 308
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 308

Tyr Tyr Cys Gln Ala Trp Asp Ser Ser Pro Pro Val Val Phe Gly Gly
 1               5                  10                  15

<210> SEQ ID NO 309
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 309

Tyr Tyr Cys Gln Val Trp Asp Ser Ser Pro Pro Val Met Phe Gly Gly
 1               5                  10                  15

<210> SEQ ID NO 310
<211> LENGTH: 14
<212> TYPE: PRT
<213> ORGANISM: Artificial Sequence
<220> FEATURE:
<223> OTHER INFORMATION: Light Chain CDR3 Antibody Region

<400> SEQUENCE: 310

Tyr Tyr Cys Gln Gly Trp Asp Ser Ser Pro Thr Phe Gly Gly

```
1               5                   10
```

<210> SEQ ID NO 311
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 311

```
Tyr Tyr Cys Gln Val Trp Asp Asn Ser Pro Pro Val Val Phe Gly Gly
 1               5                   10                  15
```

<210> SEQ ID NO 312
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 312

```
Tyr Tyr Cys Gln Ala Trp Asp Ser Ser Pro Pro Val Thr Phe Gly Asp
 1               5                   10                  15
```

<210> SEQ ID NO 313
<211> LENGTH: 14
<212> TYPE: PRT
<213> ORGANISM: Artificial Sequence
<220> FEATURE:
<223> OTHER INFORMATION: Light Chain CDR3 Antibody Region

<400> SEQUENCE: 313

```
Tyr Tyr Cys Gln Gln Ser Gly Ser Tyr Leu Thr Phe Gly Gly
 1               5                   10
```

<210> SEQ ID NO 314
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 314

```
Tyr Tyr Cys Gln Val Trp Asp Ser Tyr His Ala Val Val Phe Gly Gly
 1               5                   10                  15
```

<210> SEQ ID NO 315
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 315

```
Tyr Tyr Cys Gln Val Trp Gly Ser Tyr His Ala Val Met Phe Gly Gly
 1               5                   10                  15
```

<210> SEQ ID NO 316
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 316

```
Tyr Tyr Cys Gln Val Trp Gly Ser Tyr His Ser Val Met Phe Gly Gly
 1               5                   10                  15
```

<210> SEQ ID NO 317
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 317

Tyr Tyr Cys Gln Val Trp Asp Thr Asp His Ser Val Val Phe Gly Gly
 1               5                  10                  15

<210> SEQ ID NO 318
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 318

Tyr Tyr Cys Gln Val Trp Asp Thr Asp His Ala Val Ala Phe Gly Gly
 1               5                  10                  15

<210> SEQ ID NO 319
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 319

Tyr Tyr Cys Gln Val Trp Asp Ser Ser His Ser Val Ile Phe Gly Gly
 1               5                  10                  15

<210> SEQ ID NO 320
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 320

Tyr Tyr Cys Gln Val Trp Asp Ser Tyr Pro Pro Val Val Phe Gly Gly
 1               5                  10                  15

<210> SEQ ID NO 321
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 321

Tyr Tyr Cys Gln Val Trp Asp Ser Asp His Ala Val Val Phe Gly Gly
 1               5                  10                  15

<210> SEQ ID NO 322
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 322

Tyr Tyr Cys Gln Val Trp Gly Ser Asn His Ala Ser Leu Phe Gly Gly
 1               5                  10                  15

<210> SEQ ID NO 323
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 323

Tyr Tyr Cys Gln Val Trp Gly Ser Thr Ala Arg Val Ala Phe Gly Gly
1               5                   10                  15

<210> SEQ ID NO 324
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 324

Tyr Tyr Cys Gln Val Trp Asn Ser Thr Pro Pro Val Val Phe Gly Gly
1               5                   10                  15

<210> SEQ ID NO 325
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 325

Tyr Tyr Cys Gln Val Trp Ser Ser Ser Pro Pro Val Ile Phe Gly Gly
1               5                   10                  15

<210> SEQ ID NO 326
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 326

Tyr Tyr Cys Gln Val Trp Ser Ser Ser Pro Pro Val Val Phe Gly Gly
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 327

Tyr Tyr Cys Gln Val Trp Ser Ser Asn His Ala Val Val Phe Gly Gly
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 328

Tyr Tyr Cys Gln Val Trp Gly Ser Asn Pro Pro Val Ala Phe Gly Gly
1               5                   10                  15

```
<210> SEQ ID NO 329
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 329

Tyr Tyr Cys Gln Val Trp Asp Ser Thr Pro Pro Val Val Phe Gly Gly
 1               5                  10                  15

<210> SEQ ID NO 330
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 330

Tyr Tyr Cys Gln Val Trp Asp Ser Asn Pro Pro Val Val Phe Gly Gly
 1               5                  10                  15

<210> SEQ ID NO 331
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 331

Tyr Tyr Cys Gln Gly Tyr Ser Ser Asn Asp Gly Val Ile Phe Gly Gly
 1               5                  10                  15

<210> SEQ ID NO 332
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 332

Tyr Tyr Cys Gln Val Trp Gly Ser Asn His Ser Val Val Phe Gly Gly
 1               5                  10                  15

<210> SEQ ID NO 333
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 333

Tyr Tyr Cys Gln Val Trp Asp Ser Asn His Ser Val Val Phe Gly Gly
 1               5                  10                  15

<210> SEQ ID NO 334
<211> LENGTH: 16
<212> TYPE: PRT
<213> ORGANISM: Artificial Sequence
<220> FEATURE:
<223> OTHER INFORMATION: Light Chain CDR3 Antibody Region

<400> SEQUENCE: 334

Tyr Tyr Cys Gln Val Trp Asp Ser Ser Ser Ala Val Val Phe Gly Gly
 1               5                  10                  15

<210> SEQ ID NO 335
```

```
<211> LENGTH: 13
<212> TYPE: PRT
<213> ORGANISM: Artificial Sequence
<220> FEATURE:
<223> OTHER INFORMATION: Consensus sequence for AX213 and AX132 Light
      Chain CDR2 Antibody Region
<221> NAME/KEY: VARIANT
<222> LOCATION: (5)...(5)
<223> OTHER INFORMATION: Xaa = S or A
<221> NAME/KEY: VARIANT
<222> LOCATION: (10)...(10)
<223> OTHER INFORMATION: Xaa = T, A or S

<400> SEQUENCE: 335

Leu Ile Tyr Asp Xaa Ser Asn Arg Ala Xaa Gly Ile Pro
1               5                   10

<210> SEQ ID NO 336
<211> LENGTH: 7
<212> TYPE: PRT
<213> ORGANISM: Artificial Sequence
<220> FEATURE:
<223> OTHER INFORMATION: Consensus sequence for AX213 and AX132 Light
      Chain shorter CDR2 Antibody Region
<221> NAME/KEY: VARIANT
<222> LOCATION: (2)...(2)
<223> OTHER INFORMATION: Xaa = S or A
<221> NAME/KEY: VARIANT
<222> LOCATION: (7)...(7)
<223> OTHER INFORMATION: Xaa = T, A or S

<400> SEQUENCE: 336

Asp Xaa Ser Asn Arg Ala Xaa
1               5

<210> SEQ ID NO 337
<211> LENGTH: 13
<212> TYPE: PRT
<213> ORGANISM: Artificial Sequence
<220> FEATURE:
<223> OTHER INFORMATION: Consensus sequence for AX213 and AX132 Light
      Chain CDR2 Antibody Region
<221> NAME/KEY: VARIANT
<222> LOCATION: (6)...(6)
<223> OTHER INFORMATION: Xaa = S or A
<221> NAME/KEY: VARIANT
<222> LOCATION: (10)...(10)
<223> OTHER INFORMATION: Xaa = T, A or S

<400> SEQUENCE: 337

Leu Ile Tyr Asp Ala Xaa Asn Arg Ala Xaa Gly Ile Pro
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Consensus sequence for AX213 and AX132 Light
      Chain shorter CDR2 Antibody Region
<221> NAME/KEY: VARIANT
<222> LOCATION: (3)...(3)
<223> OTHER INFORMATION: Xaa = S or A
<221> NAME/KEY: VARIANT
<222> LOCATION: (7)...(7)
<223> OTHER INFORMATION: Xaa = T, A or S

<400> SEQUENCE: 338

Asp Ala Xaa Asn Arg Ala Xaa
1               5
```

```
<210> SEQ ID NO 339
<211> LENGTH: 13
<212> TYPE: PRT
<213> ORGANISM: Artificial Sequence
<220> FEATURE:
<223> OTHER INFORMATION: AX213 and AX132 Light Chain CDR2 Antibody
      Region

<400> SEQUENCE: 339

Leu Ile Tyr Asp Ala Ser Asn Arg Ala Thr Gly Ile Pro
 1               5                  10

<210> SEQ ID NO 340
<211> LENGTH: 39
<212> TYPE: DNA
<213> ORGANISM: Artificial Sequence
<220> FEATURE:
<223> OTHER INFORMATION: AX213 and AX132 Light Chain CDR2 Antibody Region

<400> SEQUENCE: 340
ctgatctacg acgcctctaa ccgtgccacc ggtatccca                              39

<210> SEQ ID NO 341
<211> LENGTH: 7
<212> TYPE: PRT
<213> ORGANISM: Artificial Sequence
<220> FEATURE:
<223> OTHER INFORMATION: AX213 and AX132 Light Chain shorter CDR2
      Antibody Region

<400> SEQUENCE: 341

Asp Ala Ser Asn Arg Ala Thr
 1               5

<210> SEQ ID NO 342
<211> LENGTH: 21
<212> TYPE: DNA
<213> ORGANISM: Artificial Sequence
<220> FEATURE:
<223> OTHER INFORMATION: AX213 and AX132 Light Chain shorter CDR2
      Antibody Region

<400> SEQUENCE: 342
gacgcctcta accgtgccac c                                                 21

<210> SEQ ID NO 343
<211> LENGTH: 13
<212> TYPE: PRT
<213> ORGANISM: Artificial Sequence
<220> FEATURE:
<223> OTHER INFORMATION: Light Chain CDR2 Antibody Region

<400> SEQUENCE: 343

Leu Ile Tyr Ala Ala Ser Ser Leu Gln Ser Gly Val Pro
 1               5                  10

<210> SEQ ID NO 344
<211> LENGTH: 13
<212> TYPE: PRT
<213> ORGANISM: Artificial Sequence
<220> FEATURE:
<223> OTHER INFORMATION: Light Chain CDR2 Antibody Region

<400> SEQUENCE: 344

Leu Ile Tyr Asp Ala Ala Asn Arg Ala Thr Gly Ile Pro
 1               5                  10
```

```
<210> SEQ ID NO 345
<211> LENGTH: 13
<212> TYPE: PRT
<213> ORGANISM: Artificial Sequence
<220> FEATURE:
<223> OTHER INFORMATION: Light Chain CDR2 Antibody Region

<400> SEQUENCE: 345

Leu Ile Tyr Asp Ala Ser Asn Arg Ala Ala Gly Ile Pro
1               5                   10

<210> SEQ ID NO 346
<211> LENGTH: 13
<212> TYPE: PRT
<213> ORGANISM: Artificial Sequence
<220> FEATURE:
<223> OTHER INFORMATION: Light Chain CDR2 Antibody Region

<400> SEQUENCE: 346

Leu Ile Tyr Asp Ala Ser Asn Arg Ala Ser Gly Ile Pro
1               5                   10

<210> SEQ ID NO 347
<211> LENGTH: 17
<212> TYPE: PRT
<213> ORGANISM: Artificial Sequence
<220> FEATURE:
<223> OTHER INFORMATION: Consensus sequence for AX213 and AX132 Light
      Chain CDR1 Antibody Region
<221> NAME/KEY: VARIANT
<222> LOCATION: (4)...(4)
<223> OTHER INFORMATION: Xaa = R or Q
<221> NAME/KEY: VARIANT
<222> LOCATION: (9)...(9)
<223> OTHER INFORMATION: Xaa = V or I
<221> NAME/KEY: VARIANT
<222> LOCATION: (11)...(11)
<223> OTHER INFORMATION: Xaa = T or S
<221> NAME/KEY: VARIANT
<222> LOCATION: (14)...(14)
<223> OTHER INFORMATION: Xaa = N, S or T

<400> SEQUENCE: 347

Ile Thr Cys Xaa Ala Ser Gln Tyr Xaa Gly Xaa Tyr Leu Xaa Trp Tyr
1               5                   10                  15

Gln

<210> SEQ ID NO 348
<211> LENGTH: 11
<212> TYPE: PRT
<213> ORGANISM: Artificial Sequence
<220> FEATURE:
<223> OTHER INFORMATION: Consensus sequence for AX213 and AX132 Light
      Chain shorter CDR1 Antibody Region
<221> NAME/KEY: VARIANT
<222> LOCATION: (1)...(1)
<223> OTHER INFORMATION: Xaa = R or Q
<221> NAME/KEY: VARIANT
<222> LOCATION: (6)...(6)
<223> OTHER INFORMATION: Xaa = V or I
<221> NAME/KEY: VARIANT
<222> LOCATION: (8)...(8)
<223> OTHER INFORMATION: Xaa = T or S
<221> NAME/KEY: VARIANT
<222> LOCATION: (11)...(11)
<223> OTHER INFORMATION: Xaa = S or T

<400> SEQUENCE: 348

Xaa Ala Ser Gln Tyr Xaa Gly Xaa Tyr Leu Xaa
1               5                   10
```

<210> SEQ ID NO 349
<211> LENGTH: 17
<212> TYPE: PRT
<213> ORGANISM: Artificial Sequence
<220> FEATURE:
<223> OTHER INFORMATION: AX213 and AX132 Light Chain CDR1 Antibody
      Region

<400> SEQUENCE: 349

Ile Thr Cys Arg Ala Ser Gln Tyr Val Gly Ser Tyr Leu Asn Trp Tyr
1               5                   10                  15

Gln

<210> SEQ ID NO 350
<211> LENGTH: 51
<212> TYPE: DNA
<213> ORGANISM: Artificial Sequence
<220> FEATURE:
<223> OTHER INFORMATION: AX213 and AX132 Light Chain CDR1 Antibody
      Region

<400> SEQUENCE: 350
atcacctgcc gtgcctctca gtatgtcggc agctacctga actggtatca g          51

<210> SEQ ID NO 351
<211> LENGTH: 11
<212> TYPE: PRT
<213> ORGANISM: Artificial Sequence
<220> FEATURE:
<223> OTHER INFORMATION: AX213 and AX132 Light Chain shorter CDR1
      Antibody Region

<400> SEQUENCE: 351

Arg Ala Ser Gln Tyr Val Gly Ser Tyr Leu Asn
1               5                   10

<210> SEQ ID NO 352
<211> LENGTH: 33
<212> TYPE: DNA
<213> ORGANISM: Artificial Sequence
<220> FEATURE:
<223> OTHER INFORMATION: AX213 and AX132 Light Chain shorter CDR1
      Antibody Region

<400> SEQUENCE: 352
cgtgcctctc agtatgtcgg cagctacctg aac                              33

<210> SEQ ID NO 353
<211> LENGTH: 17
<212> TYPE: PRT
<213> ORGANISM: Artificial Sequence
<220> FEATURE:
<223> OTHER INFORMATION: Light Chain CDR1 Antibody Region

<400> SEQUENCE: 353

Ile Thr Cys Arg Ala Ser Gln Tyr Val Gly Thr Tyr Leu Asn Trp Tyr
1               5                   10                  15

Gln

<210> SEQ ID NO 354
<211> LENGTH: 17
<212> TYPE: PRT
<213> ORGANISM: Artificial Sequence
<220> FEATURE:
<223> OTHER INFORMATION: Light Chain CDR1 Antibody Region

```
<400> SEQUENCE: 354

Ile Thr Cys Arg Ala Ser Gln Tyr Ile Gly Ser Tyr Leu Asn Trp Tyr
1               5                   10                  15

Gln

<210> SEQ ID NO 355
<211> LENGTH: 17
<212> TYPE: PRT
<213> ORGANISM: Artificial Sequence
<220> FEATURE:
<223> OTHER INFORMATION: Light Chain CDR1 Antibody Region

<400> SEQUENCE: 355

Ile Thr Cys Arg Ala Ser Gln Ala Ile Ser Asn Tyr Leu Thr Trp Tyr
1               5                   10                  15

Gln

<210> SEQ ID NO 356
<211> LENGTH: 17
<212> TYPE: PRT
<213> ORGANISM: Artificial Sequence
<220> FEATURE:
<223> OTHER INFORMATION: Light Chain CDR1 Antibody Region

<400> SEQUENCE: 356

Ile Thr Cys Arg Ala Ser Gln Tyr Val Gly Ser Tyr Leu Thr Trp Tyr
1               5                   10                  15

Gln

<210> SEQ ID NO 357
<211> LENGTH: 17
<212> TYPE: PRT
<213> ORGANISM: Artificial Sequence
<220> FEATURE:
<223> OTHER INFORMATION: Light Chain CDR1 Antibody Region

<400> SEQUENCE: 357

Ile Thr Cys Arg Ala Ser Gln Asp Val Ser Asn Tyr Leu Asn Trp Tyr
1               5                   10                  15

Gln

<210> SEQ ID NO 358
<211> LENGTH: 17
<212> TYPE: PRT
<213> ORGANISM: Artificial Sequence
<220> FEATURE:
<223> OTHER INFORMATION: Light Chain CDR1 Antibody Region

<400> SEQUENCE: 358

Ile Thr Cys Gln Ala Ser Gln Tyr Val Gly Ser Tyr Leu Ser Trp Tyr
1               5                   10                  15

Gln

<210> SEQ ID NO 359
<211> LENGTH: 17
<212> TYPE: PRT
<213> ORGANISM: Artificial Sequence
<220> FEATURE:
<223> OTHER INFORMATION: Light Chain CDR1 Antibody Region

<400> SEQUENCE: 359

Ile Thr Cys Arg Ala Ser Gln Tyr Val Gly Ser Tyr Leu Ser Trp Tyr
1               5                   10                  15
```

Gln

<210> SEQ ID NO 360
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 360

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 361
<211> LENGTH: 118
<212> TYPE: PRT
<213> ORGANISM: Artificial Sequence
<220> FEATURE:
<223> OTHER INFORMATION: Variable Heavy Antibody Region

<400> SEQUENCE: 361

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser
        115

<210> SEQ ID NO 362
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 362

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Ile Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser
            115                 120

<210> SEQ ID NO 363
<211> LENGTH: 118
<212> TYPE: PRT
<213> ORGANISM: Artificial Sequence
<220> FEATURE:
<223> OTHER INFORMATION: Variable Heavy Antibody Region

<400> SEQUENCE: 363

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Ile Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser
            115

<210> SEQ ID NO 364
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 364

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Ser Ile Tyr Trp Val Arg Gln Ala Pro Gly Lys Gly Leu Glu Trp Ile
        35                  40                  45

```
Gly Trp Ile Asp Pro Gly Asn Gly Gly Thr Arg Tyr Asn Gln Lys Phe
         50                  55                  60

Gln Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Arg Val Gly Tyr Ser Leu Asp Tyr Trp Gly Gln Gly Thr
                100                 105                 110

Leu Val Thr Val Ser Ser Ala Ser
        115                 120

<210> SEQ ID NO 365
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 365

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Gln
                20                  25                  30

Gly Phe Thr Trp Val Arg Gln Ala Pro Gly Lys Gly Leu Glu Trp Ile
            35                  40                  45

Gly Trp Ile Asp Pro Gly Asn Gly Gly Thr Arg Tyr Asn Glu Lys Phe
         50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Arg Val Gly Tyr Ser Leu Asp Tyr Trp Gly Gln Gly Thr
                100                 105                 110

Leu Val Thr Val Ser Ser Ala Ser
        115                 120

<210> SEQ ID NO 366
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 366

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
                20                  25                  30

Ser Phe Ser Trp Val Arg Gln Ala Pro Gly Lys Gly Leu Glu Trp Ile
            35                  40                  45

Gly Tyr Ile Asp Pro Gly Ser Gly Gly Thr Lys Tyr Asn Gln Lys Phe
         50                  55                  60

Gln Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Arg Val Gly Tyr Ser Leu Asp Tyr Trp Gly Gln Gly Thr
                100                 105                 110
```

Leu Val Thr Val Ser Ser Ala Ser
        115                 120

<210> SEQ ID NO 367
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 367

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Gly Ile Asn Trp Val Arg Gln Ala Pro Gly Lys Gly Leu Glu Trp Ile
         35                  40                  45

Gly Arg Ile Asp Pro Gly Asn Gly Gly Thr Arg Tyr Asn Glu Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser
        115                 120

<210> SEQ ID NO 368
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 368

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Gly Ile Ser Trp Val Arg Gln Ala Pro Gly Lys Gly Leu Glu Gln Ile
         35                  40                  45

Gly Trp Ile Asp Pro Gly Ser Gly Gly Thr Arg Tyr Asn Gln Lys Phe
     50                  55                  60

Lys Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
        115                 120

<210> SEQ ID NO 369
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 369

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Thr Asn Tyr Trp Val Arg Gln Ala Pro Gly Lys Gly Leu Glu Trp Ile
        35                  40                  45

Gly Tyr Ile Asp Pro Gly Ser Gly Gly Thr Arg Tyr Asn Gln Lys Phe
50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Val Gly Tyr Ser Phe Asp Tyr Trp Gly Gln Gly Thr
            100                 105                 110

Leu Val Thr Val Ser Ser Ala Ser
            115                 120

<210> SEQ ID NO 370
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 370

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Ser Tyr Tyr Trp Val Arg Gln Ala Pro Gly Lys Gly Leu Glu Trp Ile
        35                  40                  45

Gly Tyr Ile Asp Pro Gly Ser Gly Gly Thr Lys Tyr Asn Gln Lys Phe
50                  55                  60

Gln Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
            115                 120

<210> SEQ ID NO 371
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 371

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Ala Asn Thr Trp Val Arg Gln Ala Pro Gly Lys Gly Leu Glu Trp Ile
        35                  40                  45

Gly Trp Ile Asp Pro Gly Asn Gly Gly Thr Ser Tyr Asn Gln Lys Phe
            50                  55                  60

Lys Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Arg Ser Gly Tyr Ser Leu Asp Tyr Trp Gly Gln Gly Thr
            100                 105                 110

Leu Val Thr Val Ser Ser Ala Ser
        115                 120

<210> SEQ ID NO 372
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 372

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30

Gly Tyr Tyr Trp Val Arg Gln Ala Pro Gly Lys Gly Leu Glu Trp Ile
         35                  40                  45

Gly Trp Ile Asp Pro Gly Ser Gly Gly Thr Arg Tyr Asn Gln Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Val Gly Tyr Ser Leu Asp Tyr Trp Gly Gln Gly Thr
            100                 105                 110

Leu Val Thr Val Ser Ser Ala Ser
        115                 120

<210> SEQ ID NO 373
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 373

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Tyr
            20                  25                  30

Ala Ile Asn Trp Val Arg Gln Ala Pro Gly Lys Gly Leu Glu Trp Ile
         35                  40                  45

Gly Trp Ile Asp Pro Gly Ser Gly Gly Thr Arg Tyr Asn Glu Lys Phe
     50                  55                  60

Lys Gly Gln Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Arg Val Gly Tyr Ser Leu Asp Phe Trp Gly Gln Gly Thr

Leu Val Thr Val Ser Ser Ala Ser
        115                 120

<210> SEQ ID NO 374
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 374

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Tyr
            20                  25                  30

Gly Ile Tyr Trp Val Arg Gln Ala Pro Gly Lys Gly Leu Glu Trp Ile
        35                  40                  45

Gly Tyr Ile Asp Pro Gly Ser Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr His Tyr Gly Tyr Ser Phe Asp Tyr Trp Gly Gln Gly Thr
            100                 105                 110

Leu Val Thr Val Ser Ser Ala Ser
        115                 120

<210> SEQ ID NO 375
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 375

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Tyr
            20                  25                  30

Gly Tyr Tyr Trp Val Arg Gln Val Pro Gly Lys Gly Leu Glu Trp Ile
        35                  40                  45

Gly Tyr Ile Asp Pro Gly Asn Gly Thr Ser Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr His Asp Gly Tyr Ser Phe Asp Tyr Trp Gly Gln Gly Thr
            100                 105                 110

Leu Val Thr Val Ser Ser Ala Ser
        115                 120

<210> SEQ ID NO 376
<211> LENGTH: 120
<212> TYPE: PRT
<213> ORGANISM: Artificial Sequence
<220> FEATURE:

<223> OTHER INFORMATION: Variable Heavy Antibody Region

<400> SEQUENCE: 376

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Ala Tyr Asn Trp Val Arg Gln Ala Pro Gly Lys Gly Leu Glu Trp Ile
        35                  40                  45

Gly Trp Ile Asp Pro Gly Ser Gly Gly Thr Arg Tyr Asn Gln Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Phe Ala Tyr Tyr Leu Asp Tyr Trp Gly Gln Gly Thr
            100                 105                 110

Leu Val Thr Val Ser Ser Ala Ser
        115                 120

<210> SEQ ID NO 377
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 377

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Phe Ser Trp Val Arg Gln Ala Pro Gly Lys Gly Leu Glu Trp Ile
        35                  40                  45

Gly Arg Ile Asp Pro Gly Ser Gly Gly Thr Arg Tyr Asn Gln Gln Phe
    50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Asp Gly Tyr Tyr Phe Asp Tyr Trp Gly Gln Gly Thr
            100                 105                 110

Leu Val Thr Val Ser Ser Ala Ser
        115                 120

<210> SEQ ID NO 378
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 378

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Ala Phe Asn Trp Val Arg Gln Ala Pro Gly Lys Gly Leu Glu Trp Ile

```
                35                  40                  45
Gly Tyr Ile Asp Pro Gly Ser Gly Gly Thr Arg Tyr Asn Glu Lys Phe
        50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Asp Gly Tyr Ser Phe Asp Tyr Trp Gly Gln Gly Thr
            100                 105                 110

Leu Val Thr Val Ser Ser Ala Ser
            115                 120

<210> SEQ ID NO 379
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 379

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Ile Tyr Trp Val Arg Gln Ala Pro Gly Lys Gly Leu Glu Trp Ile
        35                  40                  45

Gly Trp Ile Asp Pro Gly Ser Gly Gly Thr Arg Tyr Asn Glu Lys Phe
        50                  55                  60

Gln Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ala Gly Tyr Tyr Leu Asp Tyr Trp Gly Gln Gly Thr
            100                 105                 110

Leu Val Thr Val Ser Ser Ala Ser
            115                 120

<210> SEQ ID NO 380
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 380

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Thr Ile Thr Trp Val Arg Gln Ala Pro Gly Lys Gly Leu Glu Trp Ile
        35                  40                  45

Gly Tyr Ile Asp Pro Gly Ser Gly Gly Thr Lys Tyr Asn Glu Lys Phe
        50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg His Arg Val Gly Tyr Tyr Phe Asp Tyr Trp Gly Gln Gly Thr
            100                 105                 110

Leu Val Thr Val Ser Ser Ala Ser
        115                 120

<210> SEQ ID NO 381
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 381

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Ser Phe Ile Trp Val Arg Gln Ala Pro Gly Lys Gly Leu Glu Trp Ile
         35                  40                  45

Gly Tyr Ile Asp Pro Gly Ser Gly Gly Thr Lys Tyr Asn Gln Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Tyr Arg Ser Gly Tyr Ser Leu Asp Tyr Trp Gly Gln Gly Thr
            100                 105                 110

Leu Val Thr Val Ser Ser Ala Ser
        115                 120

<210> SEQ ID NO 382
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 382

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Thr Phe Tyr Trp Val Arg Gln Ala Pro Gly Lys Gly Leu Glu Trp Ile
         35                  40                  45

Gly Tyr Ile Asp Pro Gly Ser Gly Gly Thr Arg Tyr Asn Gln Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
        115                 120

<210> SEQ ID NO 383
<211> LENGTH: 120
<212> TYPE: PRT
<213> ORGANISM: Artificial Sequence
```

```
<220> FEATURE:
<223> OTHER INFORMATION: Variable Heavy Antibody Region

<400> SEQUENCE: 383

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Gln Thr Phe Ser Ser Tyr
             20                  25                  30

Gly Phe Asn Trp Val Arg Gln Ala Pro Gly Lys Gly Leu Glu Trp Ile
         35                  40                  45

Gly Trp Ile Asp Pro Gly Ser Gly Thr Arg Tyr Asn Gln Lys Phe
     50                  55                  60

Lys Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Asn Val Gly Tyr Ser Phe Asp Tyr Trp Gly Gln Gly Thr
             100                 105                 110

Leu Val Thr Val Ser Ser Ala Ser
         115                 120

<210> SEQ ID NO 384
<211> LENGTH: 119
<212> TYPE: PRT
<213> ORGANISM: Artificial Sequence
<220> FEATURE:
<223> OTHER INFORMATION: Variable Heavy Antibody Region

<400> SEQUENCE: 384

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Gly Tyr Tyr Trp Val Arg Gln Ala Pro Gly Lys Gly Leu Glu Trp Ile
         35                  40                  45

Gly Arg Ile Asp Pro Gly Ser Gly Thr Ser Tyr Asn Glu Lys Phe
     50                  55                  60

Gln Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Arg Val Gly Ser Phe Asp Tyr Trp Gly Gln Gly Thr Leu
             100                 105                 110

Val Thr Val Ser Ser Ala Ser
         115

<210> SEQ ID NO 385
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 385

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30
```

```
Gly Ile Tyr Trp Val Arg Gln Ala Pro Gly Lys Gly Leu Glu Trp Ile
        35                  40                  45

Gly Arg Ile Asp Pro Gly Asn Gly Gly Thr Arg Tyr Asn Gln Lys Phe
 50                      55                  60

Gln Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Arg Val Gly Tyr Ser Phe Asp Tyr Trp Gly Gln Gly Thr
             100                 105                 110

Leu Val Thr Val Ser Ser Ala Ser
         115                 120
```

<210> SEQ ID NO 386
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 386

```
Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Tyr
             20                  25                  30

Ala Asn Tyr Trp Val Arg Gln Ala Pro Gly Lys Gly Leu Glu Trp Ile
         35                  40                  45

Gly Tyr Ile Asp Pro Gly Ser Gly Gly Thr Lys Tyr Asn Glu Lys Phe
 50                  55                      60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser His Val Gly Tyr Tyr Phe Asp Tyr Trp Gly Gln Gly Thr
             100                 105                 110

Leu Val Thr Val Ser Ser Ala Ser
         115                 120
```

<210> SEQ ID NO 387
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 387

```
Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Tyr
             20                  25                  30

Ser Asn Ser Trp Val Arg Gln Ala Pro Gly Lys Gly Leu Glu Trp Ile
         35                  40                  45

Gly Trp Ile Asp Pro Gly Asn Gly Gly Thr Arg Tyr Asn Gln Lys Phe
 50                  55                      60

Gln Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Arg Ala Arg Val Gly Tyr Ser Phe Asp Tyr Trp Gly Gln Gly Thr
            100                 105                 110

Leu Val Thr Val Ser Ser Ala Ser
        115                 120

<210> SEQ ID NO 388
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 388

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Ser Ile Thr Trp Val Arg Gln Ala Pro Gly Lys Gly Leu Glu Trp Ile
         35                  40                  45

Gly Trp Ile Asp Pro Gly Ser Gly Gly Thr Arg Tyr Asn Glu Lys Phe
     50                  55                  60

Lys Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Arg Val Gly Tyr Ser Leu Asp Tyr Trp Gly Gln Gly Thr
            100                 105                 110

Leu Val Thr Val Ser Ser Ala Ser
        115                 120

<210> SEQ ID NO 389
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 389

Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Gly Phe Ser Trp Val Arg Gln Ala Pro Gly Lys Gly Leu Glu Trp Ile
         35                  40                  45

Gly Trp Ile Asp Pro Gly Asn Gly Gly Thr Arg Tyr Asn Gln Gln Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Arg Val Gly Tyr Ser Leu Asp Tyr Trp Gly Gln Gly Thr
            100                 105                 110

Leu Val Thr Val Ser Ser Ala Ser
        115                 120

<210> SEQ ID NO 390
<211> LENGTH: 120
<212> TYPE: PRT

```
<213> ORGANISM: Artificial Sequence
<220> FEATURE:
<223> OTHER INFORMATION: Variable Heavy Antibody Region

<400> SEQUENCE: 390

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30

Thr Tyr Thr Trp Val Arg Gln Ala Pro Gly Lys Gly Leu Glu Trp Ile
        35                  40                  45

Gly Trp Ile Asp Pro Gly Ser Gly Gly Thr Arg Tyr Asn Glu Lys Phe
    50                  55                  60

Glu Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Val Gly Tyr Ser Leu Asp Tyr Trp Gly Gln Gly Thr
            100                 105                 110

Leu Val Thr Val Ser Ser Ala Ser
        115                 120

<210> SEQ ID NO 391
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 391

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30

Ser Tyr Tyr Trp Val Arg Gln Ala Pro Gly Lys Gly Leu Glu Trp Ile
        35                  40                  45

Gly Arg Ile Asp Pro Gly Ser Gly Gly Thr Arg Tyr Asn Gln Lys Phe
    50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Asp Gly Tyr Ser Phe Asp Tyr Trp Gly Gln Gly Thr
            100                 105                 110

Leu Val Thr Val Ser Ser Ala Ser
        115                 120

<210> SEQ ID NO 392
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 392

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30
```

```
Gly Tyr Ser Trp Val Arg Gln Ala Pro Gly Lys Gly Leu Glu Trp Ile
            35                  40                  45

Gly Arg Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Tyr Ser Leu Asp Tyr Trp Gly Gln Gly Thr
                100                 105                 110

Leu Val Thr Val Ser Ser Ala Ser
            115                 120

<210> SEQ ID NO 393
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 393

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Thr Phe Ser Trp Val Arg Gln Ala Pro Gly Lys Gly Leu Glu Trp Ile
            35                  40                  45

Gly Tyr Ile Asp Pro Gly Asn Gly Gly Thr Arg Tyr Asn Glu Gln Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Val Gly Tyr Asn Leu Asp Tyr Trp Gly Gln Gly Thr
                100                 105                 110

Leu Val Thr Val Ser Ser Ala Ser
            115                 120

<210> SEQ ID NO 394
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 394

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Phe Ser Trp Val Arg Gln Ala Pro Gly Lys Gly Leu Glu Trp Ile
            35                  40                  45

Gly Trp Ile Asp Pro Gly Asn Gly Gly Thr Arg Tyr Asn Glu Gln Phe
    50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Arg Gln Arg Val Gly Tyr Ser Leu Asp Tyr Trp Gly Glu Gly Thr
                100                 105                 110
Leu Val Thr Val Ser Ser Ala Ser
        115                 120

<210> SEQ ID NO 395
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 395

Gln Val Gln Leu Leu Glu Ser Gly Gly Gly Leu Val Gln Pro Gly Gly
1               5                   10                  15
Ser Leu Arg Leu Ser Cys Lys Ala Ser Gly Tyr Thr Phe Ser Arg Tyr
            20                  25                  30
Ser Asn Ser Trp Val Arg Gln Ala Pro Gly Lys Gly Leu Glu Trp Ile
        35                  40                  45
Gly Trp Ile Asp Pro Gly Asn Gly Gly Thr Arg Tyr Asn Glu Gln Phe
    50                  55                  60
Gln Gly Lys Ala Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gln Arg Val Gly Tyr Ser Leu Asp Tyr Trp Gly Gln Gly Thr
                100                 105                 110
Leu Val Thr Val Ser Ser Ala Ser
        115                 120

<210> SEQ ID NO 396
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 396

Gln Val Gln Leu Leu Glu Ser Gly Gly Gly Leu Val Gln Pro Gly Gly
1               5                   10                  15
Ser Leu Arg Leu Ser Cys Lys Ala Ser Gly Tyr Thr Phe Ser Ser Tyr
            20                  25                  30
Gly Gln Ser Trp Val Arg Gln Ala Pro Gly Lys Gly Leu Glu Trp Ile
        35                  40                  45
Gly Arg Ile Asp Pro Gly Ser Gly Gly Thr Arg Tyr Asn Glu Lys Phe
    50                  55                  60
Gln Gly Lys Ala Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Arg Asp Gly Tyr Ser Leu Asp Tyr Trp Gly Gln Gly Thr
                100                 105                 110
Leu Val Thr Val Ser Ser Ala Ser
        115                 120

<210> SEQ ID NO 397
<211> LENGTH: 120
```

<212> TYPE: PRT
<213> ORGANISM: Artificial Sequence
<220> FEATURE:
<223> OTHER INFORMATION: Variable Heavy Antibody Region

<400> SEQUENCE: 397

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Ala Ile Ser Trp Val Arg Gln Ala Pro Gly Lys Gly Leu Glu Trp Ile
        35                  40                  45

Gly Arg Ile Asp Pro Gly Ser Gly Thr Arg Tyr Asn Glu Lys Phe
    50                  55                  60

Gln Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Asp Gly Tyr Ser Leu Asp Tyr Trp Gly Gln Gly Thr
            100                 105                 110

Leu Val Thr Val Ser Ser Ala Ser
        115                 120

<210> SEQ ID NO 398
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 398

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Ser Tyr Tyr Trp Val Arg Gln Ala Pro Gly Lys Gly Leu Glu Trp Ile
        35                  40                  45

Gly Tyr Ile Asp Pro Gly Ser Gly Thr Lys Tyr Asn Gln Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Asp Gly Tyr Ser Phe Asp Tyr Trp Gly Gln Gly Thr
            100                 105                 110

Leu Val Thr Val Ser Ser Ala Ser
        115                 120

<210> SEQ ID NO 399
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 399

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr

```
                20                  25                  30

Thr Tyr Asn Trp Val Arg Gln Ala Pro Gly Lys Gly Leu Glu Trp Ile
                35                  40                  45

Gly Tyr Ile Asp Pro Gly Asn Gly Gly Thr Tyr Asn Gln Lys Phe
        50                  55                  60

Gln Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ser Arg Val Gly Tyr Ser Leu Asp Tyr Trp Gly Gln Gly Thr
                100                 105                 110

Leu Val Thr Val Ser Ser Ala Ser
        115                 120

<210> SEQ ID NO 400
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 400

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
                20                  25                  30

Thr Ile Ser Trp Val Arg Gln Ala Pro Gly Lys Gly Leu Glu Trp Ile
                35                  40                  45

Gly Tyr Ile Asp Pro Gly Asn Gly Gly Thr Arg Tyr Asn Gln Phe
        50                  55                  60

Gln Gly Lys Ala Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                85                  90                  95

Ala Arg Ser Arg Val Gly Tyr Ser Phe Asp Tyr Trp Gly Gln Gly Thr
                100                 105                 110

Leu Val Thr Val Ser Ser Ala Ser
        115                 120

<210> SEQ ID NO 401
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 401

Gln Val Gln Leu Leu Glu Ser Gly Gly Gly Leu Leu Gln Pro Gly Gly
 1               5                  10                  15

Ser Leu Arg Leu Ser Cys Lys Ala Ser Gly Tyr Thr Phe Ser Arg Tyr
                20                  25                  30

Thr Phe Asn Trp Val Arg Gln Ala Pro Gly Lys Gly Leu Glu Trp Ile
                35                  40                  45

Gly Trp Ile Asp Pro Gly Ser Gly Gly Thr Arg Tyr Asn Gln Lys Phe
        50                  55                  60

Gln Ser Lys Ala Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
        115                 120

<210> SEQ ID NO 402
<211> LENGTH: 119
<212> TYPE: PRT
<213> ORGANISM: Artificial Sequence
<220> FEATURE:
<223> OTHER INFORMATION: Variable Heavy Antibody Region

<400> SEQUENCE: 402

Gln Val Gln Leu Leu Glu Ser Gly Gly Gly Leu Val Gln Pro Gly Gly
 1               5                  10                  15

Ser Leu Arg Leu Ser Cys Lys Gly Gln Arg Leu Pro Pro Arg Tyr Gly
            20                  25                  30

Tyr Tyr Trp Val Arg Gln Ala Pro Gly Lys Gly Leu Glu Trp Ile Gly
        35                  40                  45

Tyr Ile Asp Pro Gly Asn Gly Thr Arg Tyr Asn Glu Lys Phe Gln
    50                  55                  60

Ser Lys Ala Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Arg Ser Gly Tyr Tyr Leu Asp Tyr Trp Gly Gln Gly Thr Leu
            100                 105                 110

Val Thr Val Ser Ser Ala Ser
        115

<210> SEQ ID NO 403
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 403

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Tyr Ser Arg Tyr
            20                  25                  30

Thr Phe Ser Trp Val Arg Gln Ala Pro Gly Lys Gly Leu Glu Trp Ile
        35                  40                  45

Gly Tyr Ile Asp Pro Gly Ser Gly Thr Lys Tyr Asn Gln Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
        115                 120

<210> SEQ ID NO 404
```

```
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 404
```

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Tyr Tyr Trp Val Arg Gln Ala Pro Gly Lys Gly Leu Glu Trp Ile
        35                  40                  45

Gly Tyr Ile Asp Pro Gly Ser Gly Thr Arg Tyr Asn Gln Lys Phe
    50                  55                  60

Lys Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Val Gly Tyr Ser Phe Asp Tyr Trp Gly Gln Gly Thr
                100                 105                 110

Leu Val Thr Val Ser Ser Ala Ser
            115                 120

```
<210> SEQ ID NO 405
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 405
```

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Phe Ser Trp Val Arg Gln Ala Pro Gly Lys Gly Leu Glu Trp Ile
        35                  40                  45

Gly Arg Ile Asp Pro Gly Ser Gly Thr Arg Tyr Asn Glu Lys Phe
    50                  55                  60

Gln Ser Lys Ala Thr Ile Ser Trp Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Asp Gly Tyr Ser Phe Asp Tyr Trp Gly Gln Gly Thr
                100                 105                 110

Leu Val Thr Val Ser Ser Ala Ser
            115                 120

```
<210> SEQ ID NO 406
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 406
```

Gln Val Gln Leu Leu Glu Ser Gly Gly Gly Leu Val Gln Pro Gly Gly
1               5                   10                  15

```
Ser Leu Arg Leu Ser Cys Lys Ala Ser Asp Tyr Thr Phe Ser Ser Tyr
            20                  25                  30

Gly Asn Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Asp Gly Tyr Ser Leu Asp Tyr Trp Gly Gln Gly Thr
            100                 105                 110

Leu Val Thr Val Ser Ser Ala Ser
        115                 120

<210> SEQ ID NO 407
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 407

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Ile Ser Trp Val Arg Gln Ala Pro Gly Lys Gly Leu Glu Trp Ile
        35                  40                  45

Gly Trp Ile Asp Pro Gly Asn Gly Gly Thr Lys Tyr Asn Gln Lys Phe
    50                  55                  60

Gln Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Val Gly Tyr Ser Leu Asp Tyr Trp Gly Gln Gly Thr
            100                 105                 110

Leu Val Thr Val Ser Ser Ala Ser
        115                 120

<210> SEQ ID NO 408
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 408

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Thr Ile Asn Trp Val Arg Gln Ala Pro Gly Lys Gly Leu Glu Trp Ile
        35                  40                  45

Gly Trp Ile Asp Pro Gly Ser Gly Gly Thr Arg Tyr Asn Glu Lys Phe
    50                  55                  60

Gln Gly Lys Ala Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg His Arg Val Gly Tyr Ser Phe Asp Tyr Trp Gly Gln Gly Thr
            100                 105                 110

Leu Val Thr Val Ser Ser Ala Ser
        115                 120

<210> SEQ ID NO 409
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 409

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Tyr
            20                  25                  30

Gly Ile Ser Trp Val Arg Gln Ala Pro Gly Lys Gly Leu Glu Trp Ile
        35                  40                  45

Gly Arg Ile Asp Pro Gly Ser Gly Gly Thr Arg Tyr Asn Glu Lys Phe
    50                  55                  60

Gln Ser Lys Ala Thr Ile Ser Arg Asp Asn Ser Lys Asn Thr Leu Tyr
65                  70                  75                  80

Leu Gln Met Asn Ser Leu Arg Ala Gln Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser
        115                 120

<210> SEQ ID NO 410
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 410

Gln Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Arg Tyr
            20                  25                  30

Gly Ile Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Val Gly Tyr Ser Phe Asp Tyr Trp Gly Gln Gly Thr
            100                 105                 110

Leu Val Thr Val Ser Ser Ala Ser
        115                 120
```

```
<210> SEQ ID NO 411
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 411

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Val Tyr Tyr Ser Phe Asp Tyr Trp Gly Gln Gly Thr
            100                 105                 110

Leu Val Thr Val Ser Ser Ala Ser
        115                 120

<210> SEQ ID NO 412
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 412

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Ile Tyr Tyr Ser Phe Asp Tyr Trp Gly Gln Gly Thr
            100                 105                 110

Leu Val Thr Val Ser Ser Ala Ser
        115                 120

<210> SEQ ID NO 413
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 413

Glu Val Gln Leu Leu Glu Ser Gly Gly Gly Leu Val Gln Pro Gly Gly
 1               5                  10                  15
```

-continued

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
            35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Phe Leu Tyr Tyr Ser Phe Asp Tyr Trp Gly Gln Gly Thr
            100                 105                 110

Leu Val Thr Val Ser Ser Ala Ser
            115                 120

<210> SEQ ID NO 414
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 414

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
            35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Arg Ile Tyr Tyr Ser Phe Asp Tyr Trp Gly Gln Gly Thr
            100                 105                 110

Leu Val Thr Val Ser Ser Ala Ser
            115                 120

<210> SEQ ID NO 415
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 415

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
            35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                    85                  90                  95

Ala Arg Gly Arg Phe Tyr Tyr Ser Phe Asp Tyr Trp Gly Gln Gly Thr
                100                 105                 110

Leu Val Thr Val Ser Ser Ala Ser
            115                 120

<210> SEQ ID NO 416
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 416

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
                 20                  25                  30

Gly Met Tyr Trp Val Arg Gln Ala Pro Gly Lys Gly Leu Glu Trp Ile
             35                  40                  45

Gly Trp Ile Asp Pro Gly Ser Gly Thr Lys Tyr Asn Glu Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Gly Arg Leu Tyr Tyr Ser Leu Asp Tyr Trp Gly Gln Gly Thr
                100                 105                 110

Leu Val Thr Val Ser Ser Ala Ser
            115                 120

<210> SEQ ID NO 417
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 417

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
                 20                  25                  30

Gly Met Tyr Trp Val Arg Gln Ala Pro Gly Lys Gly Leu Glu Trp Ile
             35                  40                  45

Gly Trp Ile Asp Pro Gly Ser Gly Thr Lys Tyr Asn Glu Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Gly Phe Ile Tyr Tyr Asp Phe Asp Tyr Trp Gly Gln Gly Thr
                100                 105                 110

Leu Val Thr Val Ser Ser Ala Ser
            115                 120
```

<210> SEQ ID NO 418
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 418

```
Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Lys Ile Tyr Tyr Ser Phe Asp Tyr Trp Gly Gln Gly Thr
            100                 105                 110

Leu Val Thr Val Ser Ser Ala Ser
        115                 120
```

<210> SEQ ID NO 419
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 419

```
Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Tyr Leu Tyr Tyr Ser Phe Asp Tyr Trp Gly Gln Gly Thr
            100                 105                 110

Leu Val Thr Val Ser Ser Ala Ser
        115                 120
```

<210> SEQ ID NO 420
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 420

```
Glu Val Gln Leu Leu Glu Ser Gly Gly Gly Leu Val Gln Pro Gly Gly
```

```
                1               5                  10                  15
Ser Leu Arg Leu Ser Cys Lys Ala Ser Gly Tyr Thr Phe Ser Ser Tyr
                20                      25                  30

Gly Met Tyr Trp Val Arg Gln Ala Pro Gly Lys Gly Leu Glu Trp Ile
            35                      40                  45

Gly Trp Ile Asp Pro Gly Ser Gly Thr Lys Tyr Asn Glu Lys Phe
        50                      55                  60

Lys Gly Lys Ala Thr Ile Ser Arg Asp Asn Ser Lys Asn Thr Leu Tyr
65                      70                  75                      80

Leu Gln Met Asn Ser Leu Arg Ala Glu Asp Thr Ala Val Tyr Tyr Cys
                85                      90                  95

Ala Arg Gly Phe Ile Tyr Tyr Ser Leu Asp Tyr Trp Gly Gln Gly Thr
                    100                 105                 110

Leu Val Thr Val Ser Ser Ala Ser
                115                 120
```

<210> SEQ ID NO 421
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 421

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
                20                      25                  30

Gly Met Tyr Trp Val Arg Gln Ala Pro Gly Lys Gly Leu Glu Trp Ile
            35                      40                  45

Gly Trp Ile Asp Pro Gly Ser Gly Thr Lys Tyr Asn Glu Lys Phe
        50                      55                  60

Lys Gly Lys Ala Thr Ile Ser Arg Asp Asn Ser Lys Asn Thr Leu Tyr
65                      70                  75                      80

Leu Gln Met Asn Ser Leu Arg Ala Glu Asp Thr Ala Val Tyr Tyr Cys
                85                      90                  95

Ala Arg Gly Asn Leu Tyr Tyr Ser Leu Asp Tyr Trp Gly Gln Gly Thr
                    100                 105                 110

Leu Val Thr Val Ser Ser Ala Ser
                115                 120
```

<210> SEQ ID NO 422
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 422

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
                20                      25                  30

Gly Met Tyr Trp Val Arg Gln Ala Pro Gly Lys Gly Leu Glu Trp Ile
            35                      40                  45

Gly Trp Ile Asp Pro Gly Ser Gly Thr Lys Tyr Asn Glu Lys Phe
        50                      55                  60
```

```
Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ser Arg Gly Lys Val Gly Tyr Ser Leu Asp Tyr Trp Gly Gln Gly Thr
            100                 105                 110

Leu Val Thr Val Ser Ser Ala Ser
            115                 120
```

<210> SEQ ID NO 423
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 423

```
Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
             35                  40                  45

Gly Trp Ile Asp Pro Gly Ser Gly Gly Thr Lys Tyr Asn Glu Lys Phe
         50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Ile Gly Tyr Asn Leu Asp Tyr Trp Gly Gln Gly Thr
            100                 105                 110

Leu Val Thr Val Ser Ser Ala Ser
            115                 120
```

<210> SEQ ID NO 424
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 424

```
Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
             35                  40                  45

Gly Trp Ile Asp Pro Gly Ser Gly Gly Thr Lys Tyr Asn Glu Lys Phe
         50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Asp Gly Tyr Ser Leu Asp Tyr Trp Gly Gln Gly Thr
            100                 105                 110

Leu Val Thr Val Ser Ser Ala Ser
            115                 120
```

<210> SEQ ID NO 425
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 425

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ala Tyr
            20                  25                  30

Gly Met Tyr Trp Val Arg Gln Ala Pro Gly Lys Gly Leu Glu Trp Ile
        35                  40                  45

Gly Arg Ile Asp Pro Ser Asn Gly Gly Thr Lys Tyr Asn Gln Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 426
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 426

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Asp Tyr
            20                  25                  30

Gly Met Tyr Trp Val Arg Gln Ala Pro Gly Lys Gly Leu Glu Trp Ile
        35                  40                  45

Gly Arg Ile Asn Pro Asn Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 427
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 427

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Gln Met Ser Trp Val Arg Gln Ala Pro Gly Lys Gly Leu Glu Trp Ile
        35                  40                  45

Gly Arg Ile Asp Pro Gly Ser Gly Thr Lys Tyr Asn Gln Lys Phe
50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120
```

<210> SEQ ID NO 428
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 428

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Tyr Tyr
            20                  25                  30

Tyr Met Tyr Trp Val Arg Gln Ala Pro Gly Lys Gly Leu Glu Trp Val
        35                  40                  45

Gly Arg Ile Ser Pro Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120
```

<210> SEQ ID NO 429
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 429

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ala Tyr
            20                  25                  30

Gly Met Tyr Trp Val Arg Gln Ala Pro Gly Lys Gly Leu Glu Trp Ile
        35                  40                  45

Gly Arg Ile Asp Pro Gly Ser Gly Gly Thr Lys Tyr Asn Gln Lys Phe
50                  55                  60
```

```
Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 430
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 430

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Phe Thr Phe Thr Ser Tyr
                20                  25                  30

Gln Met Ser Trp Val Arg Gln Ala Pro Gly Lys Gly Leu Glu Trp Ile
            35                  40                  45

Gly Arg Ile Asn Pro Gly Ser Gly Thr Lys Tyr Asp Glu Lys Phe
     50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 431
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 431

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Phe Thr Phe Thr Ser Tyr
                20                  25                  30

Trp Met Ser Trp Val Arg Gln Ala Pro Gly Lys Gly Leu Glu Trp Ile
            35                  40                  45

Gly Arg Ile Asn Pro Gly Ser Gly Thr Lys Tyr Asp Glu Lys Phe
     50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
```

115                 120

<210> SEQ ID NO 432
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 432

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Leu Thr Phe Thr Asp Tyr
            20                  25                  30

Gly Met Tyr Trp Val Arg Gln Ala Pro Gly Lys Gly Leu Glu Trp Ile
        35                  40                  45

Gly Trp Ile Asn Pro Asp Ser Gly Ser Thr Lys Tyr Ala Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 433
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 433

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Tyr Tyr
            20                  25                  30

Gly Met Tyr Trp Val Arg Gln Ala Pro Gly Lys Gly Leu Glu Trp Ile
        35                  40                  45

Gly Arg Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 434
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 434

-continued

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Thr Asp Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120
```

<210> SEQ ID NO 435
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 435

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Thr Asn Tyr
            20                  25                  30

Gly Met Asn Trp Val Arg Gln Ala Pro Gly Lys Gly Leu Glu Trp Ile
        35                  40                  45

Gly Arg Ile Asp Pro Ser Ser Gly Gly Thr Lys Tyr Asn Gln Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120
```

<210> SEQ ID NO 436
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 436

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Thr Ser Tyr
            20                  25                  30

Gly Met Tyr Trp Val Arg Gln Ala Pro Gly Lys Gly Leu Glu Trp Ile
        35                  40                  45

Gly Arg Ile Asp Pro Ser Ser Gly Gly Thr Lys Tyr Asn Gln Lys Phe
```

```
            50                  55                  60
Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
            115                 120

<210> SEQ ID NO 437
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 437

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Thr Ser Tyr
                 20                  25                  30

Trp Met Ser Trp Val Arg Gln Ala Pro Gly Lys Gly Leu Glu Trp Val
             35                  40                  45

Gly Arg Ile Ser Pro Gly Gly Thr Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
            115                 120

<210> SEQ ID NO 438
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 438

Glu Val Gln Leu Leu Glu Ser Gly Gly Gly Leu Val Gln Pro Gly Gly
  1               5                  10                  15

Ser Leu Arg Leu Ser Cys Gln Ala Ser Gly Tyr Thr Phe Ser Ser Tyr
                 20                  25                  30

Gly Met Tyr Trp Val Arg Gln Ala Pro Gly Lys Gly Leu Glu Trp Ile
             35                  40                  45

Gly Arg Ile Asn Pro Gly Ser Gly Thr Asn Tyr Asp Glu Lys Phe
         50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
                100                 105                 110
```

```
Leu Val Thr Val Ser Ser Ala Ser
        115                 120

<210> SEQ ID NO 439
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 439

Glu Val Gln Leu Leu Glu Ser Gly Gly Gly Leu Val Gln Pro Gly Gly
  1               5                  10                  15

Ser Leu Arg Leu Ser Cys Glu Ala Ser Gly Phe Thr Phe Ser Ser Tyr
             20                  25                  30

Gly Met Tyr Trp Val Arg Gln Ala Pro Gly Lys Gly Leu Glu Trp Ile
         35                  40                  45

Gly Arg Ile Asn Pro Lys Gln Arg Trp His Lys Tyr Asn Gln Lys Phe
     50                  55                  60

Lys Gly Lys Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 440
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 440

Glu Val Gln Leu Leu Glu Ser Gly Gly Gly Leu Val Gln Pro Gly Gly
  1               5                  10                  15

Ser Leu Arg Leu Ser Cys Glu Ala Ser Gly Phe Ser Phe Ser Asn Tyr
             20                  25                  30

Gly Met Tyr Trp Val Arg Gln Ala Pro Gly Lys Gly Leu Glu Trp Ile
         35                  40                  45

Gly Leu Asp Arg Pro Arg Gln Arg Trp His Gln Leu Asn Glu Lys Phe
     50                  55                  60

Gln Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 441
<211> LENGTH: 120
<212> TYPE: PRT
<213> ORGANISM: Artificial Sequence
<220> FEATURE:
<223> OTHER INFORMATION: Variable Heavy Antibody Region
```

<400> SEQUENCE: 441

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Ser Ala Tyr
            20                  25                  30

Tyr Ile His Trp Val Arg Gln Ala Pro Gly Lys Gly Leu Glu Ser Ile
        35                  40                  45

Gly Arg Ile Asp Pro Gly Ser Gly Gly Thr Lys Tyr Asn Glu Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 442
<211> LENGTH: 121
<212> TYPE: PRT
<213> ORGANISM: Artificial Sequence
<220> FEATURE:
<223> OTHER INFORMATION: Variable Heavy Antibody Region

<400> SEQUENCE: 442

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Ser Phe Ser Ser Tyr
            20                  25                  30

Gly Ile Tyr Trp Val Arg Gln Ala Pro Gly Lys Gly Leu Glu Trp Ile
        35                  40                  45

Gly Leu Asp Arg Pro Lys Gln Arg Val Gly Thr Lys Tyr Asn Gln Lys
    50                  55                  60

Phe Gln Gly Arg Val Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Arg Tyr Gly Tyr Tyr Phe Asp Tyr Trp Gly Gln Gly
            100                 105                 110

Thr Leu Val Thr Val Ser Ser Ala Ser
        115                 120

<210> SEQ ID NO 443
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 443

Glu Val Gln Leu Leu Glu Ser Gly Gly Gly Leu Val Gln Pro Gly Asp
1               5                   10                  15

Ser Leu Arg Leu Ser Cys Ala Ala Ser Gly Tyr Ser Phe Ser Thr Phe
            20                  25                  30

Gly Ile Tyr Trp Val Arg Gln Ala Pro Gly Lys Gly Leu Glu Trp Ile
        35                  40                  45

-continued

Gly Leu Asp Arg Pro Arg Gln Arg Trp Pro Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 444
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 444

Glu Val Gln Leu Leu Glu Ser Gly Gly Gly Leu Val Gln Pro Gly Gly
1               5                   10                  15

Ser Leu Arg Leu Ser Cys Glu Ala Ser Gly Phe Thr Phe Ser Asp Tyr
            20                  25                  30

Gly Ile His Trp Val Arg Gln Ala Pro Gly Lys Gly Leu Glu Trp Ile
        35                  40                  45

Gly Leu Asp Arg Pro Lys Gln Arg Trp His Gln Tyr Asn Glu Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 445
<211> LENGTH: 121
<212> TYPE: PRT
<213> ORGANISM: Artificial Sequence
<220> FEATURE:
<223> OTHER INFORMATION: Variable Heavy Antibody Region

<400> SEQUENCE: 445

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Ser Asp Phe
            20                  25                  30

Gly Ile Tyr Trp Val Arg Gln Ala Pro Gly Lys Gly Leu Glu Trp Ile
        35                  40                  45

Gly Ser Asp Arg Pro Arg Gln Arg Val Ala Pro Lys Tyr Asn Gln Lys
    50                  55                  60

Phe Lys Gly Arg Ala Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Arg Tyr Gly Tyr Tyr Phe Asp Tyr Trp Gly Gln Gly
            100                 105                 110

Thr Leu Val Thr Val Ser Ser Ala Ser
        115                 120

<210> SEQ ID NO 446
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 446

Glu Val Gln Leu Leu Glu Ser Gly Gly Gly Leu Val Gln Pro Gly Gly
 1               5                  10                  15

Ser Leu Arg Leu Ser Cys Gln Ala Ser Gly Tyr Ser Phe Thr Thr Tyr
            20                  25                  30

Gly Met Tyr Trp Val Arg Gln Ala Pro Gly Lys Gly Leu Glu Trp Ile
        35                  40                  45

Gly Arg Ile Asp Pro Ser Ser Gly Gly Thr Lys Tyr Asn Gln Lys Phe
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 447
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 447

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
            20                  25                  30

Gly Met Tyr Trp Val Arg Gln Ala Pro Gly Lys Gly Leu Glu Trp Ile
        35                  40                  45

Gly Leu Asp Arg Pro Lys Gln Arg Gly Thr Lys Tyr Asn Gln Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 448
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 448

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Tyr Phe
            20                  25                  30

Gly Ile Tyr Trp Val Arg Gln Ala Pro Gly Lys Gly Leu Glu Trp Ile
        35                  40                  45

Gly Ser Asp Arg Pro Arg Gln Arg Trp His Gln Val Gln Arg Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 449
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 449

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Gly Met Tyr Trp Val Arg Gln Ala Pro Gly Lys Gly Leu Glu Trp Ile
        35                  40                  45

Gly Arg Ile Asp Pro Asn Ser Gly Gly Thr Lys Tyr Asn Glu Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 450
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 450

Glu Val Gln Leu Leu Glu Ser Gly Gly Gly Leu Val Gln Pro Gly Gly
1               5                   10                  15

Ser Leu Arg Leu Ser Cys Thr Ala Ser Gly Tyr Ser Phe Thr Ala Phe
            20                  25                  30

Gly Met Tyr Trp Val Arg Gln Ala Pro Gly Lys Gly Leu Glu Trp Ile
        35                  40                  45

Gly Arg Ile Asn Pro Ser Ser Gly Gly Thr Asn Tyr Asn Glu Gln Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 451
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 451

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Gly Met Tyr Trp Val Arg Gln Ala Pro Gly Lys Gly Leu Glu Trp Ile
        35                  40                  45

Gly Ser Asp Arg Pro Arg Gln Arg Trp His Gln Val Gln Pro Lys Val
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
            115                 120

<210> SEQ ID NO 452
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 452

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Ser Phe Ser Ala Tyr
            20                  25                  30

Gly Met Tyr Trp Val Arg Gln Ala Pro Gly Lys Gly Leu Glu Trp Ile
        35                  40                  45

Gly Arg Ile Asp Pro Asn Ser Gly Thr Lys Gln Asn Glu Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr

Leu Val Thr Val Ser Ser Ala Ser
        115                 120

<210> SEQ ID NO 453
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 453

Glu Val Gln Leu Leu Glu Ser Gly Gly Gly Leu Val Gln Pro Gly Gly
 1               5                  10                  15

Ser Leu Arg Leu Ser Cys Glu Ala Ser Gly Tyr Thr Phe Thr Ser Phe
            20                  25                  30

Gln Met His Trp Val Arg Gln Ala Pro Gly Lys Gly Leu Glu Ser Ile
        35                  40                  45

Gly Arg Ile Asp Pro Gly Ser Gly Thr Lys Tyr Asn Gln Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 454
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 454

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Phe Ser Ser Phe
            20                  25                  30

Ser Met Tyr Trp Val Arg Gln Ala Pro Gly Lys Gly Leu Glu Trp Ile
        35                  40                  45

Gly Leu Asp Arg Pro Arg Gln Arg Trp His Gln Val Asn Glu Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 455
<211> LENGTH: 120
<212> TYPE: PRT
<213> ORGANISM: Artificial Sequence
<220> FEATURE:

<223> OTHER INFORMATION: Variable Heavy Antibody Region

<400> SEQUENCE: 455

```
Glu Val Gln Leu Leu Glu Ser Gly Gly Gly Leu Val Gln Pro Gly Gly
1               5                  10                  15

Ser Leu Arg Leu Ser Cys Gln Ala Ser Gly Tyr Thr Phe Thr Asn Tyr
            20                  25                  30

Gly Met Tyr Trp Val Arg Gln Ala Pro Gly Lys Gly Leu Glu Trp Ile
        35                  40                  45

Gly Arg Ile Asp Pro Gly Asn Gly Thr Lys Tyr Asn Glu Lys Phe
    50                  55                  60

Lys Gly Lys Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120
```

<210> SEQ ID NO 456
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 456

```
Glu Val Gln Leu Leu Glu Ser Gly Gly Gly Leu Val Gln Pro Gly Gly
1               5                  10                  15

Ser Leu Arg Leu Ser Cys Gln Ala Ser Gly Tyr Thr Phe Thr Ala Phe
            20                  25                  30

Gly Met Tyr Trp Val Arg Gln Ala Pro Gly Lys Gly Leu Glu Trp Ile
        35                  40                  45

Gly Arg Ile Asp Pro Gly Ser Gly Thr Lys Tyr Asn Glu Lys Phe
    50                  55                  60

Gln Gly Lys Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120
```

<210> SEQ ID NO 457
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 457

```
Glu Val Gln Leu Leu Glu Ser Gly Gly Gly Leu Val Gln Pro Gly Gly
1               5                  10                  15

Ser Leu Arg Leu Ser Cys Lys Ala Ser Gly Phe Ser Phe Thr Ser Tyr
            20                  25                  30

Gly Met Tyr Trp Val Arg Gln Ala Pro Gly Lys Gly Leu Glu Trp Ile
```

```
                    35                   40                    45
Gly Gln Asp Arg Pro Lys Tyr Gly Gly Thr Lys Tyr Asn Glu Lys Phe
             50                  55                  60

Lys Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
             100                 105                 110

Leu Val Thr Val Ser Ser Ala Ser
            115                 120

<210> SEQ ID NO 458
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 458

Glu Val Gln Leu Leu Glu Ser Gly Gly Gly Leu Val Gln Pro Gly Gly
 1               5                  10                  15

Ser Leu Arg Leu Ser Cys Gln Ala Ser Gly Phe Thr Phe Ser Thr Tyr
             20                  25                  30

Gly Ile Tyr Trp Val Arg Gln Ala Pro Gly Lys Gly Leu Glu Trp Ile
         35                  40                  45

Gly Arg Ile Asn Pro Ser Asn Gly Gly Thr Lys Tyr Asn Glu Lys Phe
 50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
             100                 105                 110

Leu Val Thr Val Ser Ser Ala Ser
            115                 120

<210> SEQ ID NO 459
<211> LENGTH: 121
<212> TYPE: PRT
<213> ORGANISM: Artificial Sequence
<220> FEATURE:
<223> OTHER INFORMATION: Variable Heavy Antibody Region

<400> SEQUENCE: 459

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Phe Ser Phe Ser Ser Tyr
             20                  25                  30

Gly Met Tyr Trp Val Arg Gln Ala Pro Gly Lys Gly Leu Glu Trp Ile
         35                  40                  45

Gly Ser Asp Arg Pro Arg Gln Arg Trp Gly Thr Lys Tyr Asn Glu Lys
 50                  55                  60

Phe Gln Gly Arg Val Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95
```

```
Cys Ala Arg Glu Arg Tyr Gly Tyr Tyr Phe Asp Tyr Trp Gly Gln Gly
            100                 105                 110

Thr Leu Val Thr Val Ser Ser Ala Ser
        115                 120

<210> SEQ ID NO 460
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 460

Glu Val Gln Leu Leu Glu Ser Gly Gly Gly Leu Val Gln Pro Gly Gly
 1               5                  10                  15

Ser Leu Arg Leu Ser Cys Glu Ala Ser Gly Tyr Ser Phe Ser Asn Phe
            20                  25                  30

Gly Met Tyr Trp Val Arg Gln Ala Pro Gly Lys Gly Leu Glu Trp Ile
        35                  40                  45

Gly Trp Ile Asn Pro Ser Asn Gly Gly Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 461
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 461

Glu Val Gln Leu Leu Glu Ser Gly Gly Gly Leu Val Gln Pro Gly Gly
 1               5                  10                  15

Ser Leu Arg Leu Ser Cys Thr Ala Ser Asp Phe Ser Phe Ser Thr Phe
            20                  25                  30

Ser Met Tyr Trp Val Arg Gln Ala Pro Gly Lys Gly Leu Glu Trp Ile
        35                  40                  45

Gly Ser Asp Gln Pro Arg Gln Gly Gly Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 462
<211> LENGTH: 120
<212> TYPE: PRT
<213> ORGANISM: Artificial Sequence
```

<220> FEATURE:
<223> OTHER INFORMATION: Variable Heavy Antibody Region

<400> SEQUENCE: 462

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Phe Ser Asp Phe
            20                  25                  30

Gly Ile Tyr Trp Val Arg Gln Ala Pro Gly Lys Gly Leu Glu Trp Ile
        35                  40                  45

Gly Ser Asp Arg Pro Arg Gln Gly Thr Lys Tyr Asn Glu Lys Phe
    50                  55                  60

Lys Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120
```

<210> SEQ ID NO 463
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 463

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Ser Phe Thr Ser Phe
            20                  25                  30

Gly Ile Tyr Trp Val Arg Gln Ala Pro Gly Lys Gly Leu Glu Trp Ile
        35                  40                  45

Gly Ser Asp Arg Pro Lys Gln Arg Gly Thr Lys Tyr Asn Glu Lys Phe
    50                  55                  60

Lys Gly Lys Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120
```

<210> SEQ ID NO 464
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 464

```
Glu Val Gln Leu Leu Glu Ser Gly Gly Gly Leu Val Gln Pro Gly Gly
 1               5                  10                  15

Ser Leu Arg Leu Ser Cys Gln Ala Ser Gly Phe Ser Phe Ser Asp Tyr
            20                  25                  30
```

```
Tyr Met Ser Trp Val Arg Gln Ala Pro Gly Lys Gly Leu Glu Ser Ile
        35                  40                  45

Gly Arg Ile Asn Pro Gly Ser Gly Gly Thr Lys Tyr Asn Glu Lys Phe
 50                  55                  60

Gln Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
        115                 120
```

<210> SEQ ID NO 465
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 465

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Tyr Ser Phe Ser Asp Tyr
                20                  25                  30

Gly Ile Tyr Trp Val Arg Gln Ala Pro Gly Lys Gly Leu Glu Trp Ile
        35                  40                  45

Gly Ser Asp Arg Pro Lys Gln Arg Trp His Gln Val Asn Glu Lys Phe
 50                  55                  60

Gln Gly Lys Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
        115                 120
```

<210> SEQ ID NO 466
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 466

```
Glu Val Gln Leu Leu Glu Ser Gly Gly Gly Leu Val Gln Pro Gly Gly
 1               5                   10                  15

Ser Leu Arg Leu Ser Cys Lys Ala Ser Gly Tyr Ser Phe Ser Thr Tyr
                20                  25                  30

Tyr Met Tyr Trp Val Arg Gln Ala Pro Gly Lys Gly Leu Glu Trp Ile
        35                  40                  45

Gly Arg Ile Asp Pro Asp Ser Gly Gly Thr Lys Tyr Asn Glu Lys Phe
 50                  55                  60

Gln Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 467
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 467

Glu Val Gln Leu Leu Glu Ser Gly Gly Gly Leu Val Gln Pro Gly Gly
 1               5                  10                  15

Ser Leu Arg Leu Ser Cys Glu Ala Ser Gly Tyr Thr Phe Ser Ala Phe
            20                  25                  30

Gln Ile Tyr Trp Val Arg Gln Ala Pro Gly Lys Gly Leu Glu Trp Ile
        35                  40                  45

Gly Arg Ile Asp Pro Gly Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 468
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 468

Glu Val Gln Leu Leu Glu Ser Gly Gly Gly Leu Val Gln Pro Gly Gly
 1               5                  10                  15

Ser Leu Arg Leu Ser Cys Gln Ala Ser Gly Phe Ser Phe Ser Asn Phe
            20                  25                  30

Tyr Met Tyr Trp Val Arg Gln Ala Pro Gly Lys Gly Leu Glu Trp Ile
        35                  40                  45

Gly Arg Ile Asp Pro Gly Ser Gly Gly Thr Lys Tyr Asn Glu Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 469
<211> LENGTH: 120
<212> TYPE: PRT

```
<213> ORGANISM: Artificial Sequence
<220> FEATURE:
<223> OTHER INFORMATION: Variable Heavy Antibody Region

<400> SEQUENCE: 469

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Phe Thr Phe Ser Ala Phe
            20                  25                  30

Gly Ile Tyr Trp Val Arg Gln Ala Pro Gly Lys Gly Leu Glu Trp Ile
        35                  40                  45

Gly Arg Ile Asn Pro Asp Asn Gly Gly Thr Lys Tyr Asn Glu Lys Phe
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 470
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 470

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Thr Tyr
            20                  25                  30

Gly Met Tyr Trp Val Arg Gln Ala Pro Gly Lys Gly Leu Glu Trp Ile
        35                  40                  45

Gly Arg Asp Gln Pro Arg Gln Gly Gly Thr Asn Tyr Asn Glu Lys Phe
    50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 471
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 471

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Ser Phe Ser Thr Tyr
            20                  25                  30
```

```
Gly Ile Tyr Trp Val Arg Gln Ala Pro Gly Lys Gly Leu Glu Trp Ile
        35                  40                  45

Gly Arg Ile Asn Pro Asn Asn Gly Gly Thr Lys Tyr Asn Glu Lys Phe
50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
        115                 120

<210> SEQ ID NO 472
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 472

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Ser Phe Ser Ala Tyr
                20                  25                  30

Gly Met Tyr Trp Val Arg Gln Ala Pro Gly Lys Gly Leu Glu Trp Ile
        35                  40                  45

Gly Ser Asp Arg Pro Arg Gln Gly Gly Thr Lys Tyr Asn Glu Lys Phe
50                  55                  60

Lys Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
        115                 120

<210> SEQ ID NO 473
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 473

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Asn Tyr
                20                  25                  30

Tyr Met Tyr Trp Val Arg Gln Ala Pro Gly Lys Gly Leu Glu Trp Ile
        35                  40                  45

Gly Arg Ile Asp Pro Gly Ser Gly Gly Thr Lys Tyr Asn Glu Lys Phe
50                  55                  60

Gln Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 474
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 474

Glu Val Gln Leu Leu Glu Ser Gly Gly Gly Leu Val Gln Pro Gly Gly
  1               5                  10                  15

Ser Leu Arg Leu Ser Cys Glu Ala Ser Gly Tyr Thr Phe Thr Ser Tyr
             20                  25                  30

Gly Met Tyr Trp Met Arg Gln Ala Pro Gly Lys Gly Leu Glu Trp Ile
         35                  40                  45

Gly Arg Ile Asp Pro Gly Ser Gly Thr Lys Tyr Asn Glu Lys Phe
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 475
<211> LENGTH: 121
<212> TYPE: PRT
<213> ORGANISM: Artificial Sequence
<220> FEATURE:
<223> OTHER INFORMATION: Variable Heavy Antibody Region

<400> SEQUENCE: 475

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Asn Tyr
             20                  25                  30

Gly Met Tyr Trp Val Arg Gln Ala Pro Gly Lys Gly Leu Glu Trp Ile
         35                  40                  45

Gly Ser Asp Arg Pro Lys Gln Arg Trp Ala Pro Lys Tyr Asn Glu Lys
 50                  55                  60

Phe Lys Gly Arg Ala Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Glu Arg Tyr Gly Tyr Tyr Phe Asp Tyr Trp Gly Gln Gly
            100                 105                 110

Thr Leu Val Thr Val Ser Ser Ala Ser
        115                 120

<210> SEQ ID NO 476
<211> LENGTH: 120
```

```
<212> TYPE: PRT
<213> ORGANISM: Artificial Sequence
<220> FEATURE:
<223> OTHER INFORMATION: Variable Heavy Antibody Region

<400> SEQUENCE: 476
```

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Asp Phe
            20                  25                  30

Ala Met Tyr Trp Val Arg Gln Ala Pro Gly Lys Gly Leu Glu Trp Ile
        35                  40                  45

Gly Ser Asp Gln Pro Arg Gln Arg Trp His Gln Val Gln Pro Lys Val
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Arg Tyr Gly Tyr Tyr Phe Asp Tyr Trp Gly Gln Gly Thr
        100                 105                 110

Leu Val Thr Val Ser Ser Ala Ser
    115                 120

```
<210> SEQ ID NO 477
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 477
```

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Ser Phe Thr Asn Phe
            20                  25                  30

Gly Met Tyr Trp Val Arg Gln Ala Pro Gly Lys Gly Leu Glu Trp Ile
        35                  40                  45

Gly Arg Ile Asn Pro Gly Asn Gly Thr Lys Gln Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Arg Tyr Gly Tyr Tyr Phe Asp Tyr Trp Gly Gln Gly Thr
        100                 105                 110

Leu Val Thr Val Ser Ser Ala Ser
    115                 120

```
<210> SEQ ID NO 478
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 478
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Ser Phe Ser Tyr Tyr

-continued

```
                20                  25                  30
Gly Met Tyr Trp Val Arg Gln Ala Pro Gly Lys Gly Leu Glu Trp Ile
                35                  40                  45
Gly Arg Ile Asn Pro Ser Ser Gly Gly Thr Lys Tyr Asn Glu Lys Phe
         50                  55                  60
Lys Gly Arg Ala Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Arg Tyr Gly Tyr Tyr Phe Asp Tyr Trp Gly Gln Gly Thr
                100                 105                 110
Leu Val Thr Val Ser Ser Ala Ser
            115                 120
```

<210> SEQ ID NO 479
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 479

```
Glu Val Gln Leu Leu Glu Ser Gly Gly Gly Leu Val Gln Pro Gly Gly
 1               5                  10                  15
Ser Leu Arg Leu Ser Cys Glu Ala Ser Gly Tyr Ser Phe Ser Ala Phe
                20                  25                  30
Gly Ile Tyr Trp Val Arg Gln Ala Pro Gly Lys Gly Leu Glu Trp Ile
                35                  40                  45
Gly Arg Ile Asn Pro Asn Ser Gly Gly Thr Lys Tyr Asn Glu Lys Phe
         50                  55                  60
Lys Gly Arg Val Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Arg Tyr Gly Tyr Tyr Phe Asp Tyr Trp Gly Gln Gly Thr
                100                 105                 110
Leu Val Thr Val Ser Ser Ala Ser
            115                 120
```

<210> SEQ ID NO 480
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 480

```
Glu Val Gln Leu Leu Glu Ser Gly Gly Gly Leu Val Gln Pro Gly Gly
 1               5                  10                  15
Ser Leu Arg Leu Ser Cys Lys Thr Ser Gly Tyr Thr Phe Ser Ala Phe
                20                  25                  30
Gln Ile Tyr Trp Val Arg Gln Ala Pro Gly Lys Gly Leu Glu Trp Ile
                35                  40                  45
Gly Arg Ile Asp Pro Gly Ser Gly Thr Lys Tyr Asn Gln Lys Phe
         50                  55                  60
Lys Gly Arg Thr Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 481
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 481

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
         35                  40                  45

Gly Trp Ile Asp Pro Gly Ser Gly Gly Thr Lys Tyr Gln Asp Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Lys Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 482
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 482

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
         35                  40                  45

Gly Trp Ile Asp Pro Gly Ser Gly Gly Thr Lys Tyr Gln Glu Lys Phe
     50                  55                  60

Lys Gly Lys Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Lys Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 483
```

```
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 483

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Gln Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Lys Ser Gly Trp Tyr Phe Asp Tyr Trp Gly Gln Gly Thr
            100                 105                 110

Leu Val Thr Val Ser Ser Ala Ser
        115                 120

<210> SEQ ID NO 484
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 484

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Gln Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Glu Lys Tyr Gly Tyr Tyr Phe Asp Tyr Trp Gly Gln Gly Met
            100                 105                 110

Leu Val Thr Val Ser Ser Ala Ser
        115                 120

<210> SEQ ID NO 485
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 485

Glu Val Gln Leu Leu Glu Ser Gly Gly Gly Leu Val Gln Pro Gly Gly
1               5                   10                  15
```

```
Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Asn Tyr Gln Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Ser Gly Tyr Tyr Phe Asp Tyr Trp Gly Gln Gly Thr
            100                 105                 110

Leu Val Thr Val Ser Ser Ala Ser
        115                 120

<210> SEQ ID NO 486
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 486

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Gln Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Ser Gly Tyr Tyr Phe Asp Tyr Trp Gly Gln Gly Thr
            100                 105                 110

Leu Val Thr Val Ser Ser Ala Ser
        115                 120

<210> SEQ ID NO 487
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 487

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Asn Tyr Gln Gln Lys Phe
    50                  55                  60

Lys Gly Lys Ala Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Tyr Lys Ser Gly Tyr Tyr Phe Asp Tyr Trp Gly Gln Gly Thr
            100                 105                 110

Leu Val Thr Val Ser Ser Ala Ser
        115                 120

<210> SEQ ID NO 488
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 488

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
         35                  40                  45

Gly Trp Ile Asp Pro Gly Ser Gly Gly Thr Lys Tyr Ala Asp Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Arg Ser Gly Tyr Tyr Phe Asp Tyr Trp Gly Gln Gly Thr
            100                 105                 110

Leu Val Thr Val Ser Ser Ala Ser
        115                 120

<210> SEQ ID NO 489
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 489

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
         35                  40                  45

Gly Trp Ile Asp Pro Gly Ser Gly Gly Thr Lys Tyr Glu Glu Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120
```

-continued

```
<210> SEQ ID NO 490
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 490

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
         35                  40                  45

Gly Trp Ile Asp Pro Gly Ser Gly Thr Lys Tyr Gln Asp Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Lys Ser Gly Tyr Tyr Phe Asp Tyr Trp Gly Gln Gly Thr
            100                 105                 110

Leu Val Thr Val Ser Ser Ala Ser
        115                 120

<210> SEQ ID NO 491
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 491

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
         35                  40                  45

Gly Trp Ile Asp Pro Gly Ser Gly Thr Lys Tyr Gln Glu Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Lys Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 492
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 492

Glu Val Gln Leu Leu Glu Ser Gly Gly Gly Leu Val Gln Pro Gly Gly
 1               5                  10                  15
```

```
Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Asp Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Ser Gly Tyr Tyr Phe Asp Tyr Trp Gly Gln Gly Thr
            100                 105                 110

Leu Val Thr Val Ser Ser Ala Ser
            115                 120

<210> SEQ ID NO 493
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 493

Glu Val Gln Leu Leu Glu Ser Gly Gly Gly Leu Val Gln Pro Gly Gly
1               5                   10                  15

Ser Val Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Tyr Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Lys Ser Gly Tyr Tyr Phe Asp Tyr Trp Gly Gln Gly Thr
            100                 105                 110

Leu Val Thr Val Ser Ser Ala Ser
            115                 120

<210> SEQ ID NO 494
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 494

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Glu Glu Lys Phe
    50                  55                  60

Lys Gly Lys Ala Thr Ile Ser Arg Asp Asn Ser Lys Asn Thr Leu Tyr
```

```
                    65                  70                  75                  80
Leu Gln Met Asn Ser Leu Arg Ala Glu Asp Thr Ala Val Tyr Tyr Cys
                    85                  90                  95

Ala Arg Tyr Lys Ser Gly Tyr Tyr Phe Asp Tyr Trp Gly Gln Gly Thr
                100                 105                 110

Leu Val Thr Val Ser Ser Ala Ser
                115                 120

<210> SEQ ID NO 495
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 495

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
                20                  25                  30

Gly Met Tyr Trp Met Arg Gln Ala Pro Gly Lys Gly Leu Glu Trp Ile
            35                  40                  45

Gly Trp Ile Asp Pro Gly Ser Gly Thr Lys Tyr Glu Asp Lys Phe
 50                  55                  60

Glu Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Glu Arg Ser Gly Tyr Tyr Phe Asp Tyr Trp Gly Gln Gly Thr
                100                 105                 110

Leu Val Thr Val Ser Ser Ala Ser
                115                 120

<210> SEQ ID NO 496
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 496

Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
                20                  25                  30

Gly Met Tyr Trp Val Arg Gln Ala Pro Gly Lys Gly Leu Glu Trp Ile
            35                  40                  45

Gly Trp Ile Asp Pro Gly Ser Gly Thr Asn Tyr Thr Gln Lys Phe
 50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Tyr Arg Ser Gly Tyr Tyr Phe Asp Tyr Trp Gly Gln Gly Thr
                100                 105                 110

Leu Val Thr Val Ser Ser Ala Ser
                115                 120
```

<210> SEQ ID NO 497
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 497

```
Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Ser Tyr
             20                  25                  30

Gly Met Tyr Trp Val Arg Gln Ala Pro Gly Lys Gly Leu Glu Trp Ile
         35                  40                  45

Gly Trp Ile Asp Pro Gly Ser Gly Thr Lys Tyr Ser His Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
            115                 120
```

<210> SEQ ID NO 498
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 498

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Tyr Ser Phe Ser Ala Tyr
             20                  25                  30

Tyr Ile His Trp Val Arg Gln Ala Pro Gly Lys Gly Leu Glu Trp Ile
         35                  40                  45

Gly Arg Ile Asp Pro Gly Ser Gly Thr Lys Tyr Asn Glu Lys Phe
     50                  55                  60

Gln Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Gly Tyr Tyr Phe Asp Tyr Trp Gly Gln Gly Thr
                100                 105                 110

Leu Val Thr Val Ser Ser Ala Ser
            115                 120
```

<210> SEQ ID NO 499
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 499

```
Glu Val Gln Leu Leu Glu Ser Gly Gly Gly Leu Val Gln Pro Gly Gly
```

```
                1               5                  10                 15
            Ser Leu Arg Leu Ser Cys Ala Ala Ser Gly Tyr Ser Phe Ser Ala Tyr
                        20                  25                 30

Tyr Ile His Trp Val Arg Gln Ala Pro Gly Lys Gly Leu Glu Trp Ile
                        35                  40                 45

Gly Arg Ile Asp Pro Gly Ser Gly Gly Thr Lys Tyr Asn Glu Lys Phe
                        50                  55                 60

Gln Gly Arg Ala Thr Ile Ser Arg Asp Asn Ser Lys Asn Thr Leu Tyr
             65                 70                  75                 80

Leu Gln Met Asn Ser Leu Arg Ala Glu Asp Thr Ala Val Tyr Tyr Cys
                        85                  90                 95

Ala Arg Gly Phe Leu Tyr Tyr Ser Phe Asp Tyr Trp Gly Gln Gly Thr
                        100                 105                110

Leu Val Thr Val Ser Ser Ala Ser
                        115                 120

<210> SEQ ID NO 500
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 500

Glu Val Gln Leu Leu Glu Ser Gly Gly Gly Leu Val Gln Pro Gly Gly
             1                 5                  10                 15

Ser Leu Arg Leu Ser Cys Lys Ala Ser Gly Tyr Thr Phe Ser Arg Tyr
                        20                  25                 30

Gly Ile Asn Trp Val Arg Gln Ala Pro Gly Lys Gly Leu Glu Trp Ile
                        35                  40                 45

Gly Arg Ile Asp Pro Gly Asn Gly Gly Thr Arg Tyr Asn Glu Lys Phe
                        50                  55                 60

Lys Gly Lys Ala Thr Ile Ser Arg Asp Asn Ser Lys Asn Thr Leu Tyr
             65                 70                  75                 80

Leu Gln Met Asn Ser Leu Arg Ala Glu Asp Thr Ala Val Tyr Tyr Cys
                        85                  90                 95

Ala Arg Gly Phe Leu Tyr Tyr Ser Phe Asp Tyr Trp Gly Gln Gly Thr
                        100                 105                110

Leu Val Thr Val Ser Ser Ala Ser
                        115                 120

<210> SEQ ID NO 501
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 501

Glu Val Gln Leu Leu Glu Ser Gly Gly Gly Leu Val Gln Pro Gly Gly
             1                 5                  10                 15

Ser Leu Arg Leu Ser Cys Lys Ala Ser Gly Tyr Thr Phe Ser Ser Tyr
                        20                  25                 30

Thr Ile Asn Trp Val Arg Gln Ala Pro Gly Lys Gly Leu Glu Trp Ile
                        35                  40                 45

Gly Tyr Ile Asp Pro Gly Ser Gly Gly Thr Arg Tyr Asn Glu Lys Phe
                        50                  55                 60
```

-continued

```
Gln Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
            115                 120

<210> SEQ ID NO 502
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 502

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Thr Ile Ser Trp Val Arg Gln Ala Pro Gly Lys Gly Leu Glu Trp Ile
         35                  40                  45

Gly Tyr Ile Asp Pro Gly Asn Gly Gly Thr Arg Tyr Asn Gln Lys Phe
 50                  55                  60

Lys Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Arg Val Gly Tyr Ser Leu Asp Tyr Trp Gly Gln Gly Thr
            100                 105                 110

Leu Val Thr Val Ser Ser Ala Ser
            115                 120

<210> SEQ ID NO 503
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 503

Glu Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Thr Ile Asn Trp Val Arg Gln Ala Pro Gly Lys Gly Leu Glu Trp Ile
         35                  40                  45

Gly Trp Ile Asp Pro Gly Ser Gly Gly Thr Arg Tyr Asn Glu Lys Phe
 50                  55                  60

Gln Ser Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
            115                 120
```

<210> SEQ ID NO 504
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 504

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Thr Ile Asn Trp Val Arg Gln Ala Pro Gly Lys Gly Leu Glu Trp Ile
        35                  40                  45

Gly Trp Ile Asp Pro Gly Asn Gly Gly Ser Arg Tyr Asn Gln Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Val Gly Tyr Ser Phe Asp Tyr Trp Gly Gln Gly Thr
            100                 105                 110

Leu Val Thr Val Ser Ser Ala Ser
        115                 120

<210> SEQ ID NO 505
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 505

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Thr Ile Asn Trp Val Arg Gln Ala Pro Gly Lys Gly Leu Glu Trp Ile
        35                  40                  45

Gly Tyr Ile Asp Pro Gly Ser Gly Gly Thr Arg Tyr Asn Gln Lys Phe
    50                  55                  60

Lys Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Val Gly Tyr Ser Phe Asp Asn Trp Gly Gln Gly Thr
            100                 105                 110

Leu Val Thr Val Ser Ser Ala Ser
        115                 120

<210> SEQ ID NO 506
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 506

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Ser Ile Asn Trp Val Arg Gln Ala Pro Gly Lys Gly Leu Glu Trp Ile
        35                  40                  45

Gly Tyr Ile Asp Pro Gly Asn Gly Gly Thr Arg Tyr Asn Glu Lys Phe
    50                  55                  60

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Gly Tyr Ser Leu Asp Tyr Trp Gly Gln Gly Thr
            100                 105                 110

Leu Val Thr Val Ser Ser Ala Ser
            115                 120

<210> SEQ ID NO 507
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 507

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Thr Ile Asn Trp Val Arg Gln Ala Pro Gly Lys Gly Leu Glu Trp Ile
        35                  40                  45

Gly Trp Ile Asp Pro Gly Ser Gly Gly Thr Arg Tyr Asn Glu Lys Phe
    50                  55                  60

Gln Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Gly Tyr Ser Phe Asp Tyr Trp Gly Gln Gly Thr
            100                 105                 110

Leu Val Thr Val Ser Ser Ala Ser
            115                 120

<210> SEQ ID NO 508
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 508

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Ser Ile Asn Trp Val Arg Gln Ala Pro Gly Lys Gly Leu Glu Trp Ile
        35                  40                  45

Gly Tyr Ile Asp Pro Gly Asn Gly Gly Thr Lys Tyr Asn Gln Lys Phe
    50                  55                  60
```

Gln Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Gly Tyr Ser Leu Asp Tyr Trp Gly Gln Gly Thr
            100                 105                 110

Leu Val Thr Val Ser Ser Ala Ser
        115                 120

<210> SEQ ID NO 509
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 509

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Ala Ile Asn Trp Val Arg Gln Ala Pro Gly Lys Gly Leu Glu Trp Ile
        35                  40                  45

Gly Tyr Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Gly Tyr Ser Leu Asp Tyr Trp Gly Gln Gly Thr
            100                 105                 110

Leu Val Thr Val Ser Ser Ala Ser
        115                 120

<210> SEQ ID NO 510
<211> LENGTH: 120
<212> TYPE: PRT
<213> ORGANISM: Artificial Sequence
<220> FEATURE:
<223> OTHER INFORMATION: Variable Heavy Antibody Region

<400> SEQUENCE: 510

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Ser Ile Ser Trp Val Arg Gln Ala Pro Gly Lys Gly Leu Glu Trp Ile
        35                  40                  45

Gly Tyr Ile Asp Pro Gly Ser Gly Gly Thr Arg Tyr Asn Gln Lys Phe
    50                  55                  60

Lys Ser Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Arg Val Gly Tyr Ser Leu Asp Tyr Trp Gly Gln Gly Thr
            100                 105                 110

Leu Val Thr Val Ser Ser Ala Ser

```
            115                 120

<210> SEQ ID NO 511
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 511

Glu Ile Val Leu Thr Gln Ser Pro Ala Thr Leu Ser Leu Ser Pro Gly
  1               5                  10                  15

Glu Arg Ala Thr Ile Thr Cys Arg Ala Ser Gln Tyr Val Gly Ser Tyr
             20                  25                  30

Leu Asn Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                 70                  75                  80

Glu Asp Phe Ala Val Tyr Tyr Cys Gln Val Trp Asp Ser Ser Pro Pro
                 85                  90                  95

Val Val Phe Gly Gly Gly Thr Lys Val Glu Ile Lys
                100                 105

<210> SEQ ID NO 512
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 512

Glu Ile Val Leu Thr Gln Ser Pro Ala Thr Leu Ser Leu Ser Pro Gly
  1               5                  10                  15

Glu Arg Ala Thr Ile Thr Cys Arg Ala Ser Gln Tyr Val Gly Thr Tyr
             20                  25                  30

Leu Asn Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                 70                  75                  80

Glu Asp Phe Ala Val Tyr Tyr Cys Gln Val Trp Asp Ser Ser Pro Pro
                 85                  90                  95

Val Ala Phe Gly Gly Gly Thr Lys Val Glu Ile Lys
                100                 105

<210> SEQ ID NO 513
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 513

Glu Ile Val Leu Thr Gln Ser Pro Ala Thr Leu Ser Leu Ser Pro Gly
  1               5                  10                  15

Glu Arg Ala Thr Ile Thr Cys Arg Ala Ser Gln Tyr Val Gly Thr Tyr
             20                  25                  30
```

```
Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 514
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 514

Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Ala Phe Gly Gly Gly Thr Lys Val Glu Ile Lys
            100                 105

<210> SEQ ID NO 515
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 515

Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Leu Val Phe Gly Gly Gly Thr Lys Val Glu Ile Lys
            100                 105
```

-continued

<210> SEQ ID NO 516
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 516

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Leu Ala Phe Gly Gly Gly Thr Lys Val Glu Ile Lys
            100                 105

<210> SEQ ID NO 517
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 517

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Ile Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Ala Trp Asp Ser Ser Pro Pro
                85                  90                  95

Val Val Phe Gly Gly Gly Thr Lys Val Glu Ile Lys
            100                 105

<210> SEQ ID NO 518
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 518

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

```
Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Met Phe Gly Gly Gly Thr Lys Val Glu Ile Lys
            100                 105

<210> SEQ ID NO 519
<211> LENGTH: 106
<212> TYPE: PRT
<213> ORGANISM: Artificial Sequence
<220> FEATURE:
<223> OTHER INFORMATION: Variable Light Antibody Region

<400> SEQUENCE: 519

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Asn Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Trp Asp Ser Ser Pro Thr
                85                  90                  95

Phe Gly Gly Gly Thr Lys Val Glu Ile Lys
            100                 105

<210> SEQ ID NO 520
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 520

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Thr Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Leu Val Phe Gly Gly Gly Thr Lys Val Glu Ile Lys
            100                 105

<210> SEQ ID NO 521
<211> LENGTH: 108
<212> TYPE: PRT
```

-continued

```
<213> ORGANISM: Artificial Sequence
<220> FEATURE:
<223> OTHER INFORMATION: Variable Light Antibody Region

<400> SEQUENCE: 521

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Thr Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 522
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 522

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Thr Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Asn Ser Pro Pro
                85                  90                  95

Val Val Phe Gly Gly Gly Thr Lys Val Glu Ile Lys
            100                 105

<210> SEQ ID NO 523
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 523

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105
```

<210> SEQ ID NO 524
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 524

```
Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Ile Gly Ser Tyr
                20                  25                  30

Leu Asn Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Ala Trp Asp Ser Ser Pro Pro
                85                  90                  95

Val Thr Phe Gly Asp Gly Thr Lys Val Glu Ile Lys
            100                 105
```

<210> SEQ ID NO 525
<211> LENGTH: 106
<212> TYPE: PRT
<213> ORGANISM: Artificial Sequence
<220> FEATURE:
<223> OTHER INFORMATION: Variable Light Antibody Region

<400> SEQUENCE: 525

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser Tyr Leu Thr
                85                  90                  95

Phe Gly Gly Gly Thr Lys Val Glu Ile Lys
            100                 105
```

<210> SEQ ID NO 526
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 526

Glu Ile Val Leu Thr Gln Ser Pro Ala Thr Leu Ser Leu Ser Pro Gly
1               5                   10                  15

Glu Arg Ala Thr Ile Thr Cys Gln Ala Ser Gln Tyr Val Gly Ser Tyr
            20                  25                  30

Leu Ser Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Tyr His Ala
                85                  90                  95

Val Val Phe Gly Gly Gly Thr Lys Val Glu Ile Lys
            100                 105

<210> SEQ ID NO 527
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 527

Glu Ile Val Leu Thr Gln Ser Pro Ala Thr Leu Ser Leu Ser Pro Gly
1               5                   10                  15

Glu Arg Ala Thr Ile Thr Cys Gln Ala Ser Gln Tyr Val Gly Ser Tyr
            20                  25                  30

Leu Ser Trp Tyr Gln Gln Lys Pro Gly Gln Ala Pro Arg Leu Leu Ile
        35                  40                  45

Tyr Asp Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Gly Ser Tyr His Ala
                85                  90                  95

Val Met Phe Gly Gly Gly Thr Lys Val Glu Ile Lys
            100                 105

<210> SEQ ID NO 528
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 528

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Ser Trp Tyr Gln Gln Lys Pro Gly Gln Ala Pro Arg Leu Leu Ile
        35                  40                  45

Tyr Asp Ala Ser Asn Arg Ala Ala Gly Ile Pro Ala Arg Phe Ser Gly
    50                  55                  60

Ser Gly Ser Gly Thr Asp Phe Thr Leu Asn Ile Ser Ser Leu Glu Pro
65                  70                  75                  80

```
Glu Asp Phe Ala Val Tyr Tyr Cys Gln Val Trp Gly Ser Tyr His Ser
                85                  90                  95

Val Met Phe Gly Gly Gly Thr Lys Val Glu Ile Lys
            100                 105
```

<210> SEQ ID NO 529
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 529

```
Glu Ile Val Leu Thr Gln Ser Pro Ala Thr Leu Ser Leu Ser Pro Gly
  1               5                  10                  15

Glu Arg Ala Thr Ile Thr Cys Gln Ala Ser Gln Tyr Val Gly Ser Tyr
                20                  25                  30

Leu Ser Trp Tyr Gln Gln Lys Pro Gly Gln Ala Pro Arg Leu Leu Ile
            35                  40                  45

Tyr Asp Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
 65                 70                  75                  80

Glu Asp Phe Ala Val Tyr Tyr Cys Gln Val Trp Asp Thr Asp His Ser
                85                  90                  95

Val Val Phe Gly Gly Gly Thr Lys Val Glu Ile Lys
            100                 105
```

<210> SEQ ID NO 530
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 530

```
Glu Ile Val Leu Thr Gln Ser Pro Ala Thr Leu Ser Leu Ser Pro Gly
  1               5                  10                  15

Glu Arg Ala Thr Ile Thr Cys Gln Ala Ser Gln Tyr Val Gly Ser Tyr
                20                  25                  30

Leu Ser Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
 65                 70                  75                  80

Glu Asp Phe Ala Val Tyr Tyr Cys Gln Val Trp Asp Thr Asp His Ala
                85                  90                  95

Val Ala Phe Gly Gly Gly Thr Lys Val Glu Ile Lys
            100                 105
```

<210> SEQ ID NO 531
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 531

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
                20                  25                  30

Leu Ser Trp Tyr Gln Gln Lys Pro Gly Gln Ala Pro Arg Leu Leu Ile
            35                  40                  45

Tyr Asp Ala Ser Asn Arg Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser His Ser
                85                  90                  95

Val Ile Phe Gly Gly Gly Thr Lys Val Glu Ile Lys
                100                 105

<210> SEQ ID NO 532
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 532

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
                20                  25                  30

Leu Ser Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Tyr Pro Pro
                85                  90                  95

Val Val Phe Gly Gly Gly Thr Lys Val Glu Ile Lys
                100                 105

<210> SEQ ID NO 533
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 533

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
                20                  25                  30

Leu Ser Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Tyr His Ala
                85                  90                  95

```
Val Val Phe Gly Gly Gly Thr Lys Val Glu Ile Lys
            100                 105

<210> SEQ ID NO 534
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 534

Glu Ile Val Leu Thr Gln Ser Pro Ala Thr Leu Ser Leu Ser Pro Gly
 1               5                   10                  15

Glu Arg Ala Thr Ile Thr Cys Arg Ala Ser Gln Tyr Val Gly Ser Tyr
            20                  25                  30

Leu Ser Trp Tyr Gln Gln Lys Pro Gly Gln Ala Pro Arg Leu Leu Ile
        35                  40                  45

Tyr Asp Ala Ser Asn Arg Ala Ser Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Asp His Ala
                85                  90                  95

Val Val Phe Gly Gly Gly Thr Lys Val Glu Ile Lys
            100                 105

<210> SEQ ID NO 535
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 535

Glu Ile Val Leu Thr Gln Ser Pro Ala Thr Leu Ser Leu Ser Pro Gly
 1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Gly Ser Asn His Ala
                85                  90                  95

Ser Leu Phe Gly Gly Gly Thr Lys Val Glu Ile Lys
            100                 105

<210> SEQ ID NO 536
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 536

Glu Ile Val Leu Thr Gln Ser Pro Ala Thr Leu Ser Leu Ser Pro Gly
 1               5                   10                  15
```

```
Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Gly Ser Thr Ala Arg
                85                  90                  95

Val Ala Phe Gly Gly Gly Thr Lys Val Glu Ile Lys
            100                 105
```

<210> SEQ ID NO 537
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 537

```
Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asn Ser Thr Pro Pro
                85                  90                  95

Val Val Phe Gly Gly Gly Thr Lys Val Glu Ile Lys
            100                 105
```

<210> SEQ ID NO 538
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 538

```
Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Ser Ser Ser Pro Pro
                85                  90                  95

Val Ile Phe Gly Gly Gly Thr Lys Val Glu Ile Lys
            100                 105
```

<210> SEQ ID NO 539
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 539

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Ser Ser Pro Pro
                85                  90                  95

Val Val Phe Gly Gly Gly Thr Lys Val Glu Ile Lys
            100                 105

<210> SEQ ID NO 540
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 540

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Ser Ser Asn His Ala
                85                  90                  95

Val Val Phe Gly Gly Gly Thr Lys Val Glu Ile Lys
            100                 105

<210> SEQ ID NO 541
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 541

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

```
Leu Asn Trp Tyr Gln Gln Lys Pro Gly Gln Ala Pro Arg Leu Leu Ile
         35                  40                  45

Tyr Asp Ala Ala Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Val Trp Gly Ser Asn Pro Pro
                 85                  90                  95

Val Ala Phe Gly Gly Gly Thr Lys Val Glu Ile Lys
            100                 105
```

<210> SEQ ID NO 542
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 542

```
Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
             20                  25                  30

Leu Asn Trp Tyr Gln Gln Lys Pro Gly Gln Ala Pro Arg Leu Leu Ile
         35                  40                  45

Tyr Asp Ala Ala Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Val Trp Asp Ser Thr Pro Pro
                 85                  90                  95

Val Val Phe Gly Gly Gly Thr Lys Val Glu Ile Lys
            100                 105
```

<210> SEQ ID NO 543
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 543

```
Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
             20                  25                  30

Leu Asn Trp Tyr Gln Gln Lys Pro Gly Gln Ala Pro Arg Leu Leu Ile
         35                  40                  45

Tyr Asp Ala Ala Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Val Trp Asp Ser Asn Pro Pro
                 85                  90                  95

Val Val Phe Gly Gly Gly Thr Lys Val Glu Ile Lys
            100                 105
```

<210> SEQ ID NO 544

<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 544

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gly Tyr Ser Ser Asn Asp Gly
                85                  90                  95

Val Ile Phe Gly Gly Gly Thr Lys Val Glu Ile Lys
            100                 105

<210> SEQ ID NO 545
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 545

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Gly Ser Asn His Ser
                85                  90                  95

Val Val Phe Gly Gly Gly Thr Lys Val Glu Ile Lys
            100                 105

<210> SEQ ID NO 546
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 546

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

```
Tyr Asp Ala Ala Asn Arg Ala Thr Gly Ile Pro Ala Arg Phe Ser Gly
        50                   55                    60

Ser Gly Ser Gly Thr Asp Phe Thr Leu Thr Ile Ser Ser Leu Glu Pro
 65                  70                    75                  80

Glu Asp Phe Ala Val Tyr Tyr Cys Gln Val Trp Asp Ser Asn His Ser
                 85                   90                   95

Val Val Phe Gly Gly Gly Thr Lys Val Glu Ile Lys
                100                 105
```

<210> SEQ ID NO 547
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 547

```
Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
                20                  25                  30

Leu Asn Trp Tyr Gln Gln Lys Pro Gly Gln Ala Pro Arg Leu Leu Ile
            35                  40                  45

Tyr Asp Ala Ser Asn Arg Ala Ala Gly Ile Pro Ala Arg Phe Ser Gly
        50                  55                   60

Ser Gly Ser Gly Thr Asp Phe Thr Leu Thr Ile Ser Ser Leu Glu Pro
 65                  70                  75                   80

Glu Asp Phe Ala Val Tyr Tyr Cys Gln Val Trp Asp Ser Ser Pro Pro
                 85                  90                  95

Val Val Phe Gly Gly Gly Thr Lys Val Glu Ile Lys
                100                 105
```

<210> SEQ ID NO 548
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 548

```
Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
                20                  25                  30

Leu Asn Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Val Trp Asp Ser Ser Ser Ala
                 85                  90                  95

Val Val Phe Gly Gly Gly Thr Lys Val Glu Ile Lys
                100                 105
```

<210> SEQ ID NO 549
<211> LENGTH: 108
<212> TYPE: PRT
<213> ORGANISM: Artificial Sequence
<220> FEATURE:
<223> OTHER INFORMATION: Variable Light Antibody Region

<400> SEQUENCE: 549

Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Leu Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 550
<211> LENGTH: 354
<212> TYPE: DNA
<213> ORGANISM: Artificial Sequence
<220> FEATURE:
<223> OTHER INFORMATION: AX132 VARIABLE HEAVY ANTIBODY REGION

<400> SEQUENCE: 550
gaagtgcagc tgctggaatc tggtggtggt ctggtgcagc caggtggttc tctgcgtctg    60
tcttgcaagg cctctggtta caccttctct tcttacggga tgtactgggt gcgtcaggca   120
ccaggtaagg gtctggaatg gatcggttgg atcgacccag cagcggtgg caccaagtac    180 aacgaaaagt tcaagggtaa ggccaccatc tctagagaca actctaagaa caccctgtac   240
ttgcagatga actctctgcg tgccgaggac actgcagtgt actactgcgc ccgtgaacgt   300
tacggttact acttcgacta ctggggtcag ggtacgctgg tgactgtctc gagc        354

<210> SEQ ID NO 551
<211> LENGTH: 324
<212> TYPE: DNA
<213> ORGANISM: Artificial Sequence
<220> FEATURE:
<223> OTHER INFORMATION: AX132 VARIABLE HEAVY ANTIBODY REGION

<400> SEQUENCE: 551
gaaatcgtgc tgacccagtc tccagccacc ctgtctctgt ctcccgggga acgtgccacc    60
atcacctgcc gtgcctctca gtatgtcggc agctacctga ctggtatca gcagaagcca   120 ggtcaggcgc cacgtctgct gatctacgac gcctctaacc gtgccaccgg tatcccagcc   180
cgtttctctg gttctggttc tggcaccgac ttcaccctga ccatctcttc tctggaacca   240
gaagacttcg ccgtgtacta ctgccaggta tgggacagct tcctcctgt ggtgttcggt    300 ggtggtacca agtggagat caaa                                           324

<210> SEQ ID NO 552
<211> LENGTH: 226
<212> TYPE: PRT
<213> ORGANISM: Artificial Sequence
<220> FEATURE:
<223> OTHER INFORMATION: AX132 FAB VHCH1 ANTIBODY REGION

<400> SEQUENCE: 552

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr
225

<210> SEQ ID NO 553
<211> LENGTH: 678
<212> TYPE: DNA
<213> ORGANISM: Artificial Sequence
<220> FEATURE:
<223> OTHER INFORMATION: AX132 FAB VHCH1 ANTIBODY REGION

<400> SEQUENCE: 553
gaagtgcagc tgctggaatc tggtggtggt ctggtgcagc caggtggttc tctgcgtctg     60
tcttgcaagg cctctggtta caccttctct tcttacggga tgtactgggt gcgtcaggca    120
ccaggtaagg gtctggaatg gatcggttgg atcgacccag gcagcggtgg caccaagtac    180
aacgaaaagt tcaagggtaa ggccaccatc tctagagaca actctaagaa caccctgtac    240
ttgcagatga actctctgcg tgccgaggac actgcagtgt actactgcgc ccgtgaacgt    300
tacggttact acttcgacta ctggggtcag ggtacgctgg tgactgtctc gagcgcaagc    360
accaaaggcc catcggtatt ccccctggca ccctcctcca agagcacctc tgggggcaca    420
gcggccctgg gctgcctggt caaggactac ttccccgagc cggtgacggt gtcgtggaac    480
tcaggcgctc tgaccagcgg cgtgcacacc ttcccggctg tcctacagtc ctcaggactc    540
tactccctca gcagcgtggt gactgtgccc tccagcagct tgggcaccca gacctacatc    600
tgcaacgtga atcacaagcc cagcaacact aaggtggaca gaaagttga gcccaaatct    660 tgtgacaaaa ctcacaca                                                 678

<210> SEQ ID NO 554
<211> LENGTH: 215
<212> TYPE: PRT
<213> ORGANISM: Artificial Sequence
<220> FEATURE:
<223> OTHER INFORMATION: AX132 FAB VHCK ANTIBODY REGION

<400> SEQUENCE: 554

Glu Ile Val Leu Thr Gln Ser Pro Ala Thr Leu Ser Leu Ser Pro Gly
 1               5                  10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 555
<211> LENGTH: 645
<212> TYPE: DNA
<213> ORGANISM: Artificial Sequence
<220> FEATURE:
<223> OTHER INFORMATION: AX132 FAB VHCK ANTIBODY REGION

<400> SEQUENCE: 555
gaaatcgtgc tgacccagtc tccagccacc ctgtctctgt ctcccgggga acgtgccacc      60
atcacctgcc gtgcctctca gtatgtcggc agctacctga actggtatca gcagaagcca     120
ggtcaggcgc acgtctgct gatctacgac gcctctaacc gtgccaccgg tatcccagcc      180
cgtttctctg gttctggttc tggcaccgac ttcaccctga ccatctcttc tctggaacca     240
gaagacttcg ccgtgtacta ctgccaggta tgggacagct ctcctcctgt ggtgttcggt     300
ggtggtacca agtggagat caaacgtacg gtggctgcac catctgtctt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480

-continued

```
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                   645
```

<210> SEQ ID NO 556
<211> LENGTH: 444
<212> TYPE: PRT
<213> ORGANISM: Artificial Sequence
<220> FEATURE:
<223> OTHER INFORMATION: AX132 IGG2 HEAVY CHAIN ANTIBODY REGION

<400> SEQUENCE: 556

```
Glu Val Gln Leu Leu Glu Ser Gly Gly Gly Leu Val Gln Pro Gly Gly
 1               5                  10                  15

Ser Leu Arg Leu Ser Cys Lys Ala Ser Gly Tyr Thr Phe Ser Ser Tyr
                20                  25                  30

Gly Met Tyr Trp Val Arg Gln Ala Pro Gly Lys Gly Leu Glu Trp Ile
            35                  40                  45

Gly Trp Ile Asp Pro Gly Ser Gly Gly Thr Lys Tyr Asn Glu Lys Phe
        50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335
```

```
Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 557
<211> LENGTH: 1332
<212> TYPE: DNA
<213> ORGANISM: Artificial Sequence
<220> FEATURE:
<223> OTHER INFORMATION: AX132 IGG2 HEAVY CHAIN ANTIBODY REGION

<400> SEQUENCE: 557
gaagtgcagc tgctggaatc tggtggtggt ctggtgcagc caggtggttc tctgcgtctg      60
tcttgcaagg cctctggtta caccttctct tcttacggga tgtactgggt gcgtcaggca     120
ccaggtaagg gtctggaatg gatcggttgg atcgacccag gcagcggtgg caccaagtac     180
aacgaaaagt tcaagggtaa ggccaccatc tctagagaca actctaagaa caccctgtac     240
ttgcagatga ctctctgcg tgccgaggac actgcagtgt actactgcgc ccgtgaacgt     300
tacggttact acttcgacta ctggggtcag ggtacgctgg tgactgtctc gagcgctagc     360
accaagggcc catcggtctt ccccctggcg ccctgctcca ggagcacctc cgagagcaca     420
gcggccctgg gctgcctggt caaggactac ttccccgaac cggtgacggt gtcgtggaac     480
tcaggcgctc tgaccagcgg cgtgcacacc ttcccggctg tcctacagtc ctcaggactc     540
tactccctca gcagcgtggt gaccgtgccc tccagcaact tcggcaccca gacctacacc     600
tgcaacgtag atcacaagcc cagcaacacc aaggtggaca agacagttga gcgcaaatgt     660
tgtgtcgagt gcccaccgtg cccagcacca cctgtggcag gaccgtcagt cttcctcttc     720
cccccaaaac ccaaggacac cctcatgatc tcccggaccc ctgaggtcac gtgcgtggtg     780
gtggacgtga gccacgaaga ccccgaggtc cagttcaact ggtacgtgga cggcgtggag     840
gtgcataatg ccaagacaaa gccacgggag gagcagttca acagcacgtt ccgtgtggtc     900
agcgtcctca ccgtcgtgca ccaggactgg ctgaacggca aggagtacaa gtgcaaggtc     960
tccaacaaag gcctcccagc ccccatcgag aaaaccatct ccaaaccaa agggcagccc    1020 cgagaaccac aggtgtacac cctgcccca tccgggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acacctccca tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cacagaagag cctctccctg    1320
tctccgggta aa                                                        1332

<210> SEQ ID NO 558
```

<211> LENGTH: 215
<212> TYPE: PRT
<213> ORGANISM: Artificial Sequence
<220> FEATURE:
<223> OTHER INFORMATION: AX132 IGG2 LIGHT CHAIN ANTIBODY REGION

<400> SEQUENCE: 558

| Glu | Ile | Val | Leu | Thr | Gln | Ser | Pro | Ala | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Ile | Thr | Cys | Arg | Ala | Ser | Gln | Tyr | Val | Gly | Thr | Tyr |
|---|---|---|---|---|---|---|---|---|---|---|---|---|---|---|---|
| | | | 20 | | | | | 25 | | | | | 30 | | |

| Leu | Asn | Trp | Tyr | Gln | Gln | Lys | Pro | Gly | Gln | Ala | Pro | Arg | Leu | Leu | Ile |
|---|---|---|---|---|---|---|---|---|---|---|---|---|---|---|---|
| | | 35 | | | | | 40 | | | | | 45 | | | |

| Tyr | Asp | Ala | Ser | Asn | Arg | Ala | Thr | Gly | Ile | Pro | Ala | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Glu | Pro |
|---|---|---|---|---|---|---|---|---|---|---|---|---|---|---|---|
| 65 | | | | | 70 | | | | | 75 | | | | | 80 |

| Glu | Asp | Phe | Ala | Val | Tyr | Tyr | Cys | Gln | Val | Trp | Asp | Ser | Ser | Pro | Pro |
|---|---|---|---|---|---|---|---|---|---|---|---|---|---|---|---|
| | | | | 85 | | | | | 90 | | | | | 95 | |

| Val | Ala | Phe | Gly | Gly | Gly | Thr | Lys | Val | Glu | Ile | Lys | Arg | Thr | Val | Ala |
|---|---|---|---|---|---|---|---|---|---|---|---|---|---|---|---|
| | | | 100 | | | | | 105 | | | | | 110 | | |

| Ala | Pro | Ser | Val | Phe | Ile | Phe | Pro | Pro | Ser | Asp | Glu | Gln | Leu | Lys | Ser |
|---|---|---|---|---|---|---|---|---|---|---|---|---|---|---|---|
| | | 115 | | | | | 120 | | | | | 125 | | | |

| Gly | Thr | Ala | Ser | Val | Val | Cys | Leu | Leu | Asn | Asn | Phe | Tyr | Pro | Arg | Glu |
|---|---|---|---|---|---|---|---|---|---|---|---|---|---|---|---|
| | 130 | | | | | 135 | | | | | 140 | | | | |

| Ala | Lys | Val | Gln | Trp | Lys | Val | Asp | Asn | Ala | Leu | Gln | Ser | Gly | Asn | Ser |
|---|---|---|---|---|---|---|---|---|---|---|---|---|---|---|---|
| 145 | | | | | 150 | | | | | 155 | | | | | 160 |

| Gln | Glu | Ser | Val | Thr | Glu | Gln | Asp | Ser | Lys | Asp | Ser | Thr | Tyr | Ser | Leu |
|---|---|---|---|---|---|---|---|---|---|---|---|---|---|---|---|
| | | | | 165 | | | | | 170 | | | | | 175 | |

| Ser | Ser | Thr | Leu | Thr | Leu | Ser | Lys | Ala | Asp | Tyr | Glu | Lys | His | Lys | Val |
|---|---|---|---|---|---|---|---|---|---|---|---|---|---|---|---|
| | | | 180 | | | | | 185 | | | | | 190 | | |

| Tyr | Ala | Cys | Glu | Val | Thr | His | Gln | Gly | Leu | Ser | Ser | Pro | Val | Thr | Lys |
|---|---|---|---|---|---|---|---|---|---|---|---|---|---|---|---|
| | | 195 | | | | | 200 | | | | | 205 | | | |

| Ser | Phe | Asn | Arg | Gly | Glu | Cys |
|---|---|---|---|---|---|---|
| 210 | | | | | 215 | |

<210> SEQ ID NO 559
<211> LENGTH: 645
<212> TYPE: DNA
<213> ORGANISM: Artificial Sequence
<220> FEATURE:
<223> OTHER INFORMATION: AX132 IGG2 LIGHT CHAIN ANTIBODY REGION

<400> SEQUENCE: 559

```
gagattgtgc tgacccagag ccctgccacc ctgtccctga gccctggaga gagggctacc    60
atcacttgta gggcaagcca atatgtgggc acctacctga actggtatca acagaagcct   120
ggacaagccc caagactgct gatttatgat gccagcaaca gggctacagg catccctgcc   180
aggttctctg gctctggctc tggcacagac ttcaccctga ccatctcctc cttggaacct   240
gaggactttg ctgtctacta ctgtcaggtg tgggactcca gccctcctgt ggcatttgga   300
ggaggcacca aggtggagat taagcgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
```

<210> SEQ ID NO 560
<211> LENGTH: 4516
<212> TYPE: DNA
<213> ORGANISM: Artificial Sequence
<220> FEATURE:
<223> OTHER INFORMATION: AX132 VECTOR

<400> SEQUENCE: 560

```
gcgcaacgca attaatgtga gttagctcac tcattaggca ccccaggctt tacactttat      60
gcttccggct cgtatgttgt gtggaattgt gagcggataa caatttaccg gttcttgtaa     120
ggaggaatta aaaatgaaa aagtctttag tcctcaaagc ctccgtagcc gttgctaccc      180
tcgttccgat gctaagcttc gctgaaatcg tgctgaccca gtctccagcc accctgtctc    240
tgtctcccgg ggaacgtgcc accatcacct gccgtgcctc tcagtatgtc ggcagctacc    300
tgaactggta tcagcagaag ccaggtcagg cgccacgtct gctgatctac gacgcctcta    360
accgtgccac cggtatccca gcccgtttct ctggttctgg ttctggcacc gacttcaccc    420
tgaccatctc ttctctggaa ccagaagact cgccgtgta ctactgccag gtatgggaca    480
gctctcctcc tgtggtgttc ggtggtggta ccaaagtgga gatcaaacgt acggtggctg    540
caccatctgt cttcatcttc ccgccatctg atgagcagtt gaaatctgga actgcctctg    600
ttgtgtgcct gctgaataac ttctatccca gagaggccaa agtacagtgg aaggtggata    660
acgccctcca atcgggtaac tcccaggaga gtgtcacaga gcaggacagc aaggacagca    720
cctacagcct cagcagcacc ctgacgctga gcaaagcaga ctacgagaaa cacaaagtct    780
acgcctgcga agtcacccat cagggcctga gctcgcccgt cacaaagagc ttcaacaggg    840
gagagtgttg ataaggcgcg ccacaatttc acagtaagga ggtttaactt atgaaaaaat    900
tattattcgc aattccttta gttgttcctt tctattctca ctccgctgga tccgaagtgc    960
agctgctgga atctggtggt ggtctggtgc agccaggtgg ttctctgcgt ctgtcttgca   1020
aggcctctgg ttacaccttc tcttcttacg ggatgtactg ggtgcgtcag gcaccaggta   1080
agggtctgga atggatcggt tggatcgacc caggcagcgg tggcaccaag tacaacgaaa   1140
agttcaaggg taaggccacc atctctagag acaactctaa gaacaccctg tacttgcaga   1200
tgaactctct gcgtgccgag gacactgcag tgtactactg cgcccgtgaa cgttacggtt   1260
actacttcga ctactggggt cagggtacgc tggtgactgt ctcgagcgca agcaccaaag   1320
gcccatcggt attccccctg gcaccctcct ccaagagcac ctctggggc acagcggccc    1380
tgggctgcct ggtcaaggac tacttccccg agccggtgac ggtgtcgtgg aactcaggcg   1440
ctctgaccag cggcgtgcac accttccggg ctgtcctaca gtcctcagga ctctactccc   1500
tcagcagcgt ggtgactgtg ccctccagca gcttgggcac ccagacctac atctgcaacg   1560
tgaatcacaa gcccagcaac actaaggtgg acaagaaagt tgagcccaaa tcttgtgaca   1620
aaactcacac agcggccgct tatccatacg acgtaccaga ctacgcagga ggtcatcacc   1680
atcatcacca ttagagatct ggaggaggtg aggagaagtc ccggctgttg gagaaggaga   1740
accgtgaact ggaaaagatc attgctgaga agaggagcg tgtctctgaa ctgcgccatc   1800
aactccagtc tgtaggaggt tgttaataag tcgacctcga ccaattcgcc ctatagtgag   1860
tcgtattacg cgcgctcact ggccgtcgtt ttacaacgtc gtgactggga aaaccctggc   1920
gttacccaac ttaatcgcct tgcagcacat ccccctttcg ccagctggcg taatagcgaa   1980
```

```
gaggcccgca ccgatcgccc ttcccaacag ttgcgcagcc tgaatggcga atgggacgcg    2040
ccctgtagcg gcgcattaag cgcggcgggt gtggtggtta cgcgcagcgt gaccgctaca    2100
cttgccagcg ccctagcgcc cgctcctttc gctttcttcc cttcctttct cgccacgttc    2160
gccggctttc cccgtcaagc tctaaatcgg ggctcccttt agggttccg  atttagtgct    2220 ttacggcacc tcgaccccaa aaacttgat  agggtgatg  gttcacgtag tgggccatcg    2280
ccctgataga cggttttcg  ccctttgacg ttggagtcca cgttctttaa tagtggactc    2340
ttgttccaaa ctggaacaac actcaaccct atctcggtct attcttttga tttataaggg    2400
attttgccga tttcggccta ttggttaaaa aatgagctga tttaacaaaa atttaacgcg    2460
aattttaaca aaatattaac gcttacaatt taggtggcac ttttcgggga aatgtgcgcg    2520 gaaccccttat ttgtttattt ttctaaatac attcaaatat gtatccgctc atgagacaat    2580
aaccctgata aatgcttcaa taatattgaa aaggaagag  tatgagtatt caacatttcc    2640
gtgtcgccct tattcccttt tttgcggcat tttgccttcc tgttttttgct cacccagaaa    2700 cgctggtgaa agtaaaagat gctgaagatc agttgggtgc acgagtgggt tacatcgaac    2760
tggatctcaa cagcggtaag atccttgaga gttttcgccc cgaagaacgt tttccaatga    2820
tgagcacttt taaagttctg ctatgtggcg cggtattatc ccgtattgac gccgggcaag    2880
agcaactcgg tcgccgcata cactattctc agaatgactt ggttgagtac tcaccagtca    2940
cagaaaagca tcttacggat ggcatgacag taagagaatt atgcagtgct gccataacca    3000
tgagtgataa cactgcggcc aacttacttc tgacaacgat cggaggaccg aaggagctaa    3060 ccgcttttt  gcacaacatg ggggatcatg taactcgcct tgatcgttgg gaaccggagc    3120
tgaatgaagc cataccaaac gacgagcgtg acaccacgat gcctgtagca atggcaacaa    3180
cgttgcgcaa actattaact ggcgaactac ttactctagc ttcccggcaa caattaatag    3240
actggatgga ggcggataaa gttgcaggac cacttctgcg ctcggccctt ccggctggct    3300
ggtttattgc tgataaatct ggagccggtg agcgtgggtc tcgcggtatc attgcagcac    3360
tggggccaga tggtaagccc tcccgtatcg tagttatcta cacgacgggg agtcaggcaa    3420
ctatggatga acgaaataga cagatcgctg agataggtgc ctcactgatt aagcattggt    3480
aactgtcaga ccaagtttac tcatatatac tttagattga tttaaaactt catttttaat    3540
ttaaaaggat ctaggtgaag atcctttttg ataatctcat gaccaaaatc ccttaacgtg    3600
agttttcgtt ccactgagcg tcagaccccg tagaaaagat caaaggatct tcttgagatc    3660
ctttttttct gcgcgtaatc tgctgcttgc aaacaaaaaa accaccgcta ccagcggtgg    3720
tttgtttgcc ggatcaagag ctaccaactc tttttccgaa ggtaactggc ttcagcagag    3780
cgcagatacc aaatactgtc cttctagtgt agccgtagtt aggccaccac ttcaagaact    3840
ctgtagcacc gcctacatac ctcgctctgc taatcctgtt accagtggct gctgccagtg    3900
gcgataagtc gtgtcttacc gggttggact caagacgata gttaccggat aaggcgcagc    3960
ggtcgggctg aacggggggt tcgtgcacac agcccagctt ggagcgaacg acctacaccg    4020
aactgagata cctacagcgt gagctatgag aaagcgccac gcttcccgaa gggagaaagg    4080
cggacaggta tccggtaagc ggcagggtcg aacaggagag cgcacgagg  gagcttccag    4140 ggggaaacgc ctggtatctt tatagtcctg tcgggtttcg ccacctctga cttgagcgtc    4200
gatttttgtg atgctcgtca ggggggcgga gcctatggaa aaacgccagc aacgcggcct    4260
ttttacggtt cctggccttt tgctggcctt ttgctcacat gttctttcct gcgttatccc    4320
ctgattctgt ggataaccgt attaccgcct ttgagtgagc tgataccgct cgccgcagcc    4380
```

```
gaacgaccga gcgcagcgag tcagtgagcg aggaagcgga agagcgccca atacgcaaac    4440
cgcctctccc cgcgcgttgg ccgattcatt aatgcagctg gcacgacagg tttcccgact    4500
ggaaagcggg cagtga                                                     4516
```

<210> SEQ ID NO 561
<211> LENGTH: 354
<212> TYPE: DNA
<213> ORGANISM: Artificial Sequence
<220> FEATURE:
<223> OTHER INFORMATION: AX213 VARIABLE HEAVY ANTIBODY REGION

<400> SEQUENCE: 561

```
caggtgcaat tgctggaatc tggtggtggt ctggtgcagc caggtggttc tctgcgtctg     60
tcttgcaagg ctagcggtta caccttctct cgctacggta tcaactgggt gcgtcaggca    120
ccaggtaagg gtctggaatg gatcggtcgg atcgacccag gtaacggtgg tactaggtac    180
aacgaaaagt tcaagggtaa ggccaccatc tctagagaca actctaagaa caccctgtac    240
ttgcagatga actctctgcg tgccgaggac actgcagtgt actactgcgc ccgtgcaaat    300
gacggttact ccttcgacta ctggggtcag ggtacgctgg tgactgtctc gagc          354
```

<210> SEQ ID NO 562
<211> LENGTH: 226
<212> TYPE: PRT
<213> ORGANISM: Artificial Sequence
<220> FEATURE:
<223> OTHER INFORMATION: AX213 FAB VHCH1 ANTIBODY REGION

<400> SEQUENCE: 562

```
Gln Val Gln Leu Leu Glu Ser Gly Gly Gly Leu Val Gln Pro Gly Gly
  1               5                  10                  15

Ser Leu Arg Leu Ser Cys Lys Ala Ser Gly Tyr Thr Phe Ser Arg Tyr
             20                  25                  30

Gly Ile Asn Trp Val Arg Gln Ala Pro Gly Lys Gly Leu Glu Trp Ile
         35                  40                  45

Gly Arg Ile Asp Pro Gly Asn Gly Gly Thr Arg Tyr Asn Glu Lys Phe
     50                  55                  60

Lys Gly Lys Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

His Thr
225

<210> SEQ ID NO 563
<211> LENGTH: 678
<212> TYPE: DNA
<213> ORGANISM: Artificial Sequence
<220> FEATURE:
<223> OTHER INFORMATION: AX213 FAB VHCH1 ANTIBODY REGION

<400> SEQUENCE: 563

```
caggtgcaat tgctggaatc tggtggtggt ctggtgcagc caggtggttc tctgcgtctg      60
tcttgcaagg ctagcggtta caccttctct cgctacggta tcaactgggt gcgtcaggca     120
ccaggtaagg gtctggaatg gatcggtcgg atcgacccag gtaacggtgg tactaggtac     180
aacgaaaagt tcaagggtaa ggccaccatc tctagagaca actctaagaa caccctgtac     240
ttgcagatga actctctgcg tgccgaggac actgcagtgt actactgcgc cgtgcaaat      300
gacggttact ccttcgacta ctggggtcag ggtacgctgg tgactgtctc gagcgcaagc     360
accaaaggcc catcggtatt ccccctggca cctcctcca agagcaccte tgggggcaca      420
gcggccctgg gctgcctggt caaggactac ttccccgagc cggtgacggt gtcgtggaac     480
tcaggcgctc tgaccagcgg cgtgcacacc ttcccggctg tcctacagtc ctcaggactc     540
tactccctca gcagcgtggt gactgtgccc tccagcagct gggcacccca gacctacatc     600
tgcaacgtga atcacaagcc cagcaacact aaggtggaca gaaagttga gcccaaatct     660
tgtgacaaaa ctcacaca                                                  678
```

<210> SEQ ID NO 564
<211> LENGTH: 444
<212> TYPE: PRT
<213> ORGANISM: Artificial Sequence
<220> FEATURE:
<223> OTHER INFORMATION: AX213 IGG2 HEAVY CHAIN ANTIBODY REGION

<400> SEQUENCE: 564

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Ile Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
        180                 185                 190
Asn Phe Gly Thr Gln Thr Tyr Thr Cys Asn Val Asp His Lys Pro Ser
        195                 200                 205
Asn Thr Lys Val Asp Lys Thr Val Glu Arg Lys Cys Cys Val Glu Cys
210                 215                 220
Pro Pro Cys Pro Ala Pro Val Ala Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Phe Arg Val Val Ser Val Leu Thr
        290                 295                 300
Val Val His Gln Asp Trp Leu Asn Gly Lys Glu Tyr Lys Cys Lys Val
305                 310                 315                 320
Ser Asn Lys Gly Leu Pro Ala Pro Ile Glu Lys Thr Ile Ser Lys Thr
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
        370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
        435                 440

<210> SEQ ID NO 565
<211> LENGTH: 1332
<212> TYPE: DNA
<213> ORGANISM: Artificial Sequence
<220> FEATURE:
<223> OTHER INFORMATION: AX213 IGG2 HEAVY CHAIN ANTIBODY REGION

<400> SEQUENCE: 565
gaggtccaac ttttggagtc tggaggagga ctggtccaac ctggaggctc cctgagactg      60
tcctgtaagg catctggcta caccttcagc agatatggca tcaactgggt gagacaggct     120
cctggcaagg gattggagtg gattggcagg attgaccctg caatggagg caccagatac     180 aatgagaagt tcaagggcaa ggctaccatc agcagggaca cagcaagaa cacccctctac    240 ctccaaatga actccctgag gctgaggac acagcagtct actactgtgc cagggctaat      300
gatggctact cctttgacta ctggggacaa ggcaccctgg tgacagtgtc ctctgctagc     360
accaagggcc catcggtctt ccccctggcg ccctgctcca ggagcacctc cgagagcaca     420
gcggccctgg gctgcctggt caaggactac ttccccgaac cggtgacggt gtcgtggaac     480

```
tcaggcgctc tgaccagcgg cgtgcacacc ttcccggctg tcctacagtc ctcaggactc    540
tactccctca gcagcgtggt gaccgtgccc tccagcaact cggcaccca gacctacacc    600 tgcaacgtag atcacaagcc cagcaacacc aaggtggaca agacagttga gcgcaaatgt    660
tgtgtcgagt gcccaccgtg cccagcacca cctgtggcag gaccgtcagt cttcctcttc    720
cccccaaaac ccaaggacac cctcatgatc tcccggaccc ctgaggtcac gtgcgtggtg    780
gtggacgtga gccacgaaga ccccgaggtc cagttcaact ggtacgtgga cggcgtggag    840
gtgcataatg ccaagacaaa gccacgggag gagcagttca acagcacgtt ccgtgtggtc    900
agcgtcctca ccgtcgtgca ccaggactgg ctgaacggca aggagtacaa gtgcaaggtc    960
tccaacaaag gcctcccagc ccccatcgag aaaaccatct ccaaaaccaa agggcagccc   1020
cgagaaccac aggtgtacac cctgccccca tcccgggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acacctccca tgctggactc cgacggctcc   1200
ttcttcctct acagcaagct caccgtggac aagagcaggt ggcagcaggg gaacgtcttc   1260
tcatgctccg tgatgcatga ggctctgcac aaccactaca cacagaagag cctctccctg   1320
tctccgggta aa                                                       1332
```

<210> SEQ ID NO 566
<211> LENGTH: 215
<212> TYPE: PRT
<213> ORGANISM: Artificial Sequence
<220> FEATURE:
<223> OTHER INFORMATION: AX213 IGG2 LIGHT CHAIN ANTIBODY REGION

<400> SEQUENCE: 566

```
Glu Ile Val Leu Thr Gln Ser Pro Ala Thr Leu Ser Leu Ser Pro Gly
  1               5                  10                  15

Glu Arg Ala Thr Ile Thr Cys Arg Ala Ser Gln Tyr Val Gly Ser Tyr
             20                  25                  30

Leu Asn Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Val Trp Asp Ser Ser Pro Pro
                 85                  90                  95

Val Val Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
   210                 215

<210> SEQ ID NO 567
<211> LENGTH: 645
<212> TYPE: DNA
<213> ORGANISM: Artificial Sequence
<220> FEATURE:
<223> OTHER INFORMATION: AX213 IGG2 LIGHT CHAIN ANTIBODY REGION

<400> SEQUENCE: 567
gaaatcgtgc tgacccagtc tccagccacc ctgtctctgt ctcccgggga acgtgccacc      60
atcacctgcc gtgcctctca gtatgtcggc agctacctga actggtatca gcagaagcca     120
ggtcaggcgc cacgtctgct gatctacgac gcctctaacc gtgccaccgg tatcccagcc     180
cgtttctctg gttctggttc tggcaccgac ttcaccctga ccatctcttc tctggaacca     240
gaagacttcg ccgtgtacta ctgccaggta tgggacagct ctcctcctgt ggtgttcggt     300
ggtggtacca agtggaaat caagcgtacg gtggctgcac catctgtatt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag      600
ggcctgagct cgcccgtcac aaagagcttc aacaggggag agtgt                     645

<210> SEQ ID NO 568
<211> LENGTH: 645
<212> TYPE: DNA
<213> ORGANISM: Artificial Sequence
<220> FEATURE:
<223> OTHER INFORMATION: AX213 IGG2 LIGHT CHAIN ANTIBODY REGION

<400> SEQUENCE: 568
gagattgtgc tgacccagag ccctgccacc ctgtccctga gccctggaga gagggctacc      60
atcacttgta gggcaagcca atatgtgggc tcctacctga ctggtatca acagaagcct      120
ggacaagccc caagactgct gatttatgat gccagcaaca gggctacagg catccctgcc     180
aggttctctg gctctggctc tggcacagac ttcaccctga ccatctcctc cttgaacct     240
gaggactttg ctgtctacta ctgtcaggtg tgggactcca gccctcctgt ggtgtttgga     300
ggaggcacca aggtggagat taagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag      600
ggcctgagct cgcccgtcac aaagagcttc aacaggggag agtgt                     645

<210> SEQ ID NO 569
<211> LENGTH: 4507
<212> TYPE: DNA
<213> ORGANISM: Artificial Sequence
<220> FEATURE:
<223> OTHER INFORMATION: AX213 VECTOR

<400> SEQUENCE: 569
gcgcaacgca attaatgtga gttagctcac tcattaggca ccccaggctt tacactttat      60

```
gcttccggct cgtatgttgt gtggaattgt gagcggataa caatttaccg gttcttgtaa      120
ggaggaatta aaaaatgaaa aagtctttag tcctcaaagc ctccgtagcc gttgctaccc      180
tcgttccgat gctaagcttc gctgaaatcg tgctgaccca gtctccagcc accctgtctc      240
tgtctcccgg ggaacgtgcc accatcacct gccgtgcctc tcagtatgtc ggcagctacc      300
tgaactggta tcagcagaag ccaggtcagg cgccacgtct gctgatctac gacgcctcta      360
accgtgccac cggtatccca gcccgtttct ctggttctgg ttctggcacc gacttcaccc      420
tgaccatctc ttctctggaa ccagaagact cgccgtgta ctactgccag gtatgggaca      480
gctctcctcc tgtggtgttc ggtggtggta ccaaagtgga gatcaaacgt acggtggctg      540
caccatctgt cttcatcttc ccgccatctg atgagcagtt gaaatctgga actgcctctg      600
ttgtgtgcct gctgaataac ttctatccca gagaggccaa agtacagtgg aaggtggata      660
acgccctcca atcgggtaac tcccaggaga gtgtcacaga gcaggacagc aaggacagca      720
cctacagcct cagcagcacc ctgacgctga gcaaagcaga ctacgagaaa cacaaagtct      780
acgcctgcga agtcacccat cagggcctga gctcgcccgt cacaaagagc ttcaacaggg      840
gagagtgttg ataaggcgcg ccacaatttc acagtaagga gtttaacttt atgaaaaaat      900
tattattcgc aattccttta gttgttcctt tctattctca ctcccaggtg caattgctgg      960
aatctggtgg tggtctggtg cagccaggtg gttctctgcg tctgtcttgc aaggctagcg     1020
gttacacctt ctctcgctac ggtatcaact gggtgcgtca ggcaccaggt aagggtctgg     1080
aatggatcgg tcggatcgac ccaggtaacg gtggtactag gtacaacgaa aagttcaagg     1140
gtaaggccac catctctaga gacaactcta agaacaccct gtacttgcag atgaactctc     1200
tgcgtgccga ggacactgca gtgtactact gcgcccgtgc aaatgacggt tactccttcg     1260
actactgggg tcagggtacg ctggtgactg tctcgagcgc aagcaccaaa ggcccatcgg     1320
tattccccct ggcaccctcc tccaagagca cctctggggg cacagcggcc ctgggctgcc     1380
tggtcaagga ctacttcccc gagccggtga cggtgtcgtg gaactcaggc gctctgacca     1440
gcggcgtgca caccttcccg gctgtcctac agtcctcagg actctactcc ctcagcagcg     1500
tggtgactgt gccctccagc agcttgggca cccagaccta catctgcaac gtgaatcaca     1560
agcccagcaa cactaaggtg gacaagaaag ttgagcccaa atcttgtgac aaaactcaca     1620
cagcggccgc ttatccatac gacgtaccag actacgcagg aggtcatcac catcatcacc     1680
attagagatc tggaggaggt gaggagaagt cccggctgtt ggagaaggag aaccgtgaac     1740
tggaaaagat cattgctgag aaagaggagc gtgtctctga actgcgccat caactccagt     1800
ctgtaggagg ttgttaataa gtcgacctcg accaattcgc cctatagtga gtcgtattac     1860
gcgcgctcac tggccgtcgt tttacaacgt cgtgactggg aaaaccctgg cgttacccaa     1920
cttaatcgcc ttgcagcaca tccccctttc gccagctggc gtaatagcga agaggcccgc     1980
accgatcgcc cttcccaaca gttgcgcagc ctgaatggcg aatgggacgc gccctgtagc     2040
ggcgcattaa gcgcggcggg tgtggtggtt acgcgcagcg tgaccgctac acttgccagc     2100
gccctagcgc ccgctccttt cgctttcttc ccttcctttc tcgccacgtt cgccggcttt     2160
ccccgtcaag ctctaaatcg ggggctccct ttagggttcc gatttagtgc tttacggcac     2220
ctcgacccca aaaaacttga ttagggtgat ggttcacgta gtgggccatc gccctgatag     2280
acggtttttc gccctttgac gttggagtcc acgttcttta atagtggact cttgttccaa     2340
actggaacaa cactcaaccc tatctcggtc tattcttttg atttataagg gattttgccg     2400
```

-continued

```
atttcggcct attggttaaa aaatgagctg atttaacaaa aatttaacgc gaattttaac    2460
aaaatattaa cgcttacaat ttaggtggca cttttcgggg aaatgtgcgc ggaacccta    2520 tttgtttatt tttctaaata cattcaaata tgtatccgct catgagacaa taaccctgat    2580
aaatgcttca ataatattga aaaggaaga gtatgagtat tcaacatttc cgtgtcgccc    2640
ttattccctt ttttgcggca ttttgccttc ctgttttgc tcacccagaa acgctggtga    2700
aagtaaaaga tgctgaagat cagttgggtg cacgagtggg ttacatcgaa ctggatctca    2760
acagcggtaa gatccttgag agttttcgcc ccgaagaacg ttttccaatg atgagcactt    2820
ttaaagttct gctatgtggc gcggtattat cccgtattga cgccgggcaa gagcaactcg    2880
gtcgccgcat acactattct cagaatgact tggttgagta ctcaccagtc acagaaaagc    2940
atcttacgga tggcatgaca gtaagagaat tatgcagtgc tgccataacc atgagtgata    3000
acactgcggc caacttactt ctgacaacga tcggaggacc gaaggagcta accgcttttt    3060
tgcacaacat gggggatcat gtaactcgcc ttgatcgttg gaaccggag ctgaatgaag    3120 ccataccaaa cgacgagcgt gacaccacga tgcctgtagc aatggcaaca acgttgcgca    3180
aactattaac tggcgaacta cttactctag cttcccggca acaattaata gactggatgg    3240
aggcggataa agttgcagga ccacttctgc gctcggccct tccggctggc tggtttattg    3300
ctgataaatc tggagccggt gagcgtgggt ctcgcggtat cattgcagca ctggggccag    3360
atggtaagcc ctcccgtatc gtagttatct acacgacggg gagtcaggca actatggatg    3420
aacgaaatag acagatcgct gagataggtg cctcactgat taagcattgg taactgtcag    3480
accaagttta ctcatatata ctttagattg atttaaaact tcatttttaa tttaaaagga    3540
tctaggtgaa gatcctttt gataatctca tgaccaaaat cccttaacgt gagttttcgt    3600
tccactgagc gtcagacccc gtagaaaaga tcaaaggatc ttcttgagat ccttttttc    3660 tgcgcgtaat ctgctgcttg caaacaaaaa aaccaccgct accagcggtg gtttgtttgc    3720
cggatcaaga gctaccaact ctttttccga aggtaactgg cttcagcaga gcgcagatac    3780
caaatactgt ccttctagtg tagccgtagt taggccacca cttcaagaac tctgtagcac    3840
cgcctacata cctcgctctg ctaatcctgt taccagtggc tgctgccagt ggcgataagt    3900
cgtgtcttac cgggttggac tcaagacgat agttaccgga taaggcgcag cggtcgggct    3960 gaacggggg ttcgtgcaca cagcccagct tggagcgaac gacctacacc gaactgagat    4020
acctacagcg tgagctatga gaaagcgcca cgcttcccga agggagaaag cggacaggt    4080 atccggtaag cggcagggtc ggaacaggag agcgcacgag ggagcttcca gggggaaacg    4140
cctggtatct ttatagtcct gtcgggtttc gccacctctg acttgagcgt cgatttttgt    4200
gatgctcgtc agggggggcgg agcctatgga aaaacgccag caacgcggcc ttttacggt    4260 tcctggcctt ttgctggcct tttgctcaca tgttcttcc tgcgttatcc cctgattctg    4320
tggataaccg tattaccgcc tttgagtgag ctgataccgc tcgccgcagc cgaacgaccg    4380
agcgcagcga gtcagtgagc gaggaagcgg aagagcgccc aatacgcaaa ccgcctctcc    4440
ccgcgcgttg gccgattcat taatgcagct ggcacgacag gtttcccgac tggaaagcgg    4500
gcagtga                                                            4507
```

<210> SEQ ID NO 570
<211> LENGTH: 6
<212> TYPE: PRT
<213> ORGANISM: Artificial Sequence
<220> FEATURE:
<223> OTHER INFORMATION: PCKS9 Internal Processing Site

```
<400> SEQUENCE: 570

Ser Ser Val Phe Ala Gln
 1               5

<210> SEQ ID NO 571
<211> LENGTH: 6
<212> TYPE: PRT
<213> ORGANISM: Artificial Sequence
<220> FEATURE:
<223> OTHER INFORMATION: PCKS9 Internal Processing Site

<400> SEQUENCE: 571

Ser Ile Pro Trp Asn Leu
 1               5

<210> SEQ ID NO 572
<211> LENGTH: 330
<212> TYPE: PRT
<213> ORGANISM: Artificial Sequence
<220> FEATURE:
<223> OTHER INFORMATION: Sequence containing Fc domain of IgG1

<400> SEQUENCE: 572

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 573
<211> LENGTH: 326
<212> TYPE: PRT
<213> ORGANISM: Artificial Sequence
<220> FEATURE:
<223> OTHER INFORMATION: Sequence containing Fc domain of IgG2

<400> SEQUENCE: 573

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Thr Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Gly Lys
                325

<210> SEQ ID NO 574
<211> LENGTH: 327
<212> TYPE: PRT
<213> ORGANISM: Artificial Sequence
<220> FEATURE:
<223> OTHER INFORMATION: Sequence containing Fc domain of IgG4

<400> SEQUENCE: 574

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 575
<211> LENGTH: 326
<212> TYPE: PRT
<213> ORGANISM: Artificial Sequence
<220> FEATURE:
<223> OTHER INFORMATION: Sequence containing Fc domain of IgG2m4

<400> SEQUENCE: 575

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 576
<211> LENGTH: 4
<212> TYPE: PRT
<213> ORGANISM: Artificial Sequence

```
<220> FEATURE:
<223> OTHER INFORMATION: AX132 ANTIBODY EPITOPE

<400> SEQUENCE: 576

Pro Trp Asn Leu
  1

<210> SEQ ID NO 577
<211> LENGTH: 15
<212> TYPE: PRT
<213> ORGANISM: Artificial Sequence
<220> FEATURE:
<223> OTHER INFORMATION: AX132 ANTIBODY EPITOPE

<400> SEQUENCE: 577

Pro Gly Glu Asp Ile Ile Gly Ala Ser Ser Asp Cys Ser Thr Cys
  1               5                  10                  15

<210> SEQ ID NO 578
<211> LENGTH: 9
<212> TYPE: PRT
<213> ORGANISM: Artificial Sequence
<220> FEATURE:
<223> OTHER INFORMATION: AX132 ANTIBODY EPITOPE

<400> SEQUENCE: 578

Gly Ala Ser Ser Asp Cys Ser Thr Cys
  1               5

<210> SEQ ID NO 579
<211> LENGTH: 4
<212> TYPE: PRT
<213> ORGANISM: Artificial Sequence
<220> FEATURE:
<223> OTHER INFORMATION: AX132 ANTIBODY EPITOPE

<400> SEQUENCE: 579

Ser Ile Pro Trp
  1

<210> SEQ ID NO 580
<211> LENGTH: 4
<212> TYPE: PRT
<213> ORGANISM: Artificial Sequence
<220> FEATURE:
<223> OTHER INFORMATION: AX132 ANTIBODY EPITOPE

<400> SEQUENCE: 580

Asp His Arg Glu
  1

<210> SEQ ID NO 581
<211> LENGTH: 5
<212> TYPE: PRT
<213> ORGANISM: Artificial Sequence
<220> FEATURE:
<223> OTHER INFORMATION: AX132 ANTIBODY EPITOPE

<400> SEQUENCE: 581

His Arg Gln Ala Ser
  1               5

<210> SEQ ID NO 582
<211> LENGTH: 15
<212> TYPE: PRT
<213> ORGANISM: Artificial Sequence
<220> FEATURE:
```

<223> OTHER INFORMATION: AX132 ANTIBODY EPITOPE

<400> SEQUENCE: 582

Asp Ile Ile Gly Ala Ser Ser Asp Cys Ser Thr Cys Phe Val Ser
1               5                   10                  15

<210> SEQ ID NO 583
<211> LENGTH: 22
<212> TYPE: PRT
<213> ORGANISM: Artificial Sequence
<220> FEATURE:
<223> OTHER INFORMATION: AX132 AND VARIANT ANTIBODY HEAVY CHAIN
      FRAMEWORK 1 REGION
<221> NAME/KEY: VARIANT
<222> LOCATION: (1)...(1)
<223> OTHER INFORMATION: Xaa = E or Q

<400> SEQUENCE: 583

Xaa Val Gln Leu Leu Glu Ser Gly Gly Gly Leu Val Gln Pro Gly Gly
1               5                   10                  15

Ser Leu Arg Leu Ser Cys
            20

<210> SEQ ID NO 584
<211> LENGTH: 8
<212> TYPE: PRT
<213> ORGANISM: Artificial Sequence
<220> FEATURE:
<223> OTHER INFORMATION: AX132 AND VARIANT ANTIBODY HEAVY CHAIN
      FRAMEWORK 2 REGION

<400> SEQUENCE: 584

Gln Ala Pro Gly Lys Gly Leu Glu
1               5

<210> SEQ ID NO 585
<211> LENGTH: 26
<212> TYPE: PRT
<213> ORGANISM: Artificial Sequence
<220> FEATURE:
<223> OTHER INFORMATION: AX132 AND VARIANT ANTIBODY HEAVY CHAIN
      FRAMEWORK 3 REGION

<400> SEQUENCE: 585

Ile Ser Arg Asp Asn Ser Lys Asn Thr Leu Tyr Leu Gln Met Asn Ser
1               5                   10                  15

Leu Arg Ala Glu Asp Thr Ala Val Tyr Tyr
            20                  25

<210> SEQ ID NO 586
<211> LENGTH: 10
<212> TYPE: PRT
<213> ORGANISM: Artificial Sequence
<220> FEATURE:
<223> OTHER INFORMATION: AX132 AND VARIANT ANTIBODY HEAVY CHAIN
      FRAMEWORK 4 REGION

<400> SEQUENCE: 586

Gly Thr Leu Val Thr Val Ser Ser Ala Ser
1               5                   10

<210> SEQ ID NO 587
<211> LENGTH: 20
<212> TYPE: PRT
<213> ORGANISM: Artificial Sequence
<220> FEATURE:
<223> OTHER INFORMATION: AX132 AND VARIANT ANTIBODY LIGHT CHAIN

FRAMEWORK 1 REGION

<400> SEQUENCE: 587

Glu Ile Val Leu Thr Gln Ser Pro Ala Thr Leu Ser Leu Ser Pro Gly
1               5                   10                  15

Glu Arg Ala Thr
            20

<210> SEQ ID NO 588
<211> LENGTH: 9
<212> TYPE: PRT
<213> ORGANISM: Artificial Sequence
<220> FEATURE:
<223> OTHER INFORMATION: AX132 AND VARIANT ANTIBODY LIGHT CHAIN
      FRAMEWORK 2 REGION

<400> SEQUENCE: 588

Gln Lys Pro Gly Gln Ala Pro Arg Leu
1               5

<210> SEQ ID NO 589
<211> LENGTH: 26
<212> TYPE: PRT
<213> ORGANISM: Artificial Sequence
<220> FEATURE:
<223> OTHER INFORMATION: AX132 AND VARIANT ANTIBODY LIGHT CHAIN
      FRAMEWORK 3 REGION

<400> SEQUENCE: 589

Ala Arg Phe Ser Gly Ser Gly Ser Gly Thr Asp Phe Thr Leu Thr Ile
1               5                   10                  15

Ser Ser Leu Glu Pro Glu Asp Phe Ala Val
            20                  25

<210> SEQ ID NO 590
<211> LENGTH: 7
<212> TYPE: PRT
<213> ORGANISM: Artificial Sequence
<220> FEATURE:
<223> OTHER INFORMATION: AX132 AND VARIANT ANTIBODY LIGHT CHAIN
      FRAMEWORK 4 REGION

<400> SEQUENCE: 590

Gly Thr Lys Val Glu Ile Lys
1               5

<210> SEQ ID NO 591
<211> LENGTH: 120
<212> TYPE: PRT
<213> ORGANISM: Artificial Sequence
<220> FEATURE:
<223> OTHER INFORMATION: Consensus Antibody Variable Heavy Sequence
<221> NAME/KEY: VARIANT
<222> LOCATION: (23)...(24)
<223> OTHER INFORMATION: Xaa = K, A, E, Q or T at 23; A or T at 24
<221> NAME/KEY: VARIANT
<222> LOCATION: (26)...(35)
<223> OTHER INFORMATION: Xaa = G or D at 26; Y, F, L or Q at 27; T or S
      at 28; F or Y at 29; S or T at 30; S, R, A, N, D, T
      or Y at 31; Y, F or Q at 32; G, S, T, A, Y, Q or W
      at 33; M, I, F, Y, N or Q at 34; Y, S, N, T, H or
      I at 35
<221> NAME/KEY: VARIANT
<222> LOCATION: (37)...(37)
<223> OTHER INFORMATION: Xaa = V or M
<221> NAME/KEY: VARIANT
<222> LOCATION: (47)...(48)
<223> OTHER INFORMATION: Xaa = W, S or Q at 47; I or V at 48
<221> NAME/KEY: VARIANT

```
<222> LOCATION: (50)...(52)
<223> OTHER INFORMATION: Xaa = W, R, Y, S, L or Q at 50; I or D at 51;
      D, N, R, Q or S at 52
<221> NAME/KEY: VARIANT
<222> LOCATION: (54)...(68)
<223> OTHER INFORMATION: Xaa = G, R, S, K, N or D at 54; S, N, Q, G or Y
      at 55; G or R at 56; G, W, S or T at 57; T, H, P or S
      at 58; K, R, N, Q, S or Y at 59; Y, V, Q or L at
      60; N, Q, A, E, D, Y, S or T at 61; E, Q, D, P, R
      or H at 62; K, Q or S at 63; F or V at 64; K, Q or
      E at 65; G, S or D at 66; K, R or Q at 67; A, V, F
      or T at 68
<221> NAME/KEY: VARIANT
<222> LOCATION: (97)...(97)
<223> OTHER INFORMATION: Xaa = A or S
<221> NAME/KEY: VARIANT
<222> LOCATION: (99)...(105)
<223> OTHER INFORMATION: Xaa = E, Y, A, G, S, H, Q or D at 99; R, K, F,
      N, H, D, S or Y at 100; Y, V, S, D, I, L, F or A at
      101; G, Y or A at 102; Y or W at 103; Y, S, N or D
      at 104; F or L at 105
<221> NAME/KEY: VARIANT
<222> LOCATION: (107)...(107)
<223> OTHER INFORMATION: Xaa = Y, N or F
<221> NAME/KEY: VARIANT
<222> LOCATION: (110)...(110)
<223> OTHER INFORMATION: Xaa = Q or E

<400> SEQUENCE: 591

Glu Val Gln Leu Leu Glu Ser Gly Gly Gly Leu Val Gln Pro Gly Gly
 1               5                  10                  15

Ser Leu Arg Leu Ser Cys Xaa Xaa Ser Xaa Xaa Xaa Xaa Xaa Xaa Xaa
            20                  25                  30

Xaa Xaa Xaa Trp Xaa Arg Gln Ala Pro Gly Lys Gly Leu Glu Xaa Xaa
        35                  40                  45

Gly Xaa Xaa Xaa Pro Xaa Xaa Xaa Xaa Xaa Xaa Xaa Xaa Xaa Xaa Xaa
    50                  55                  60

Xaa Xaa Xaa Xaa Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Xaa Arg Xaa Xaa Xaa Xaa Xaa Xaa Xaa Asp Xaa Trp Gly Xaa Gly Thr
            100                 105                 110

Leu Val Thr Val Ser Ser Ala Ser
        115                 120

<210> SEQ ID NO 592
<211> LENGTH: 108
<212> TYPE: PRT
<213> ORGANISM: Artificial Sequence
<220> FEATURE:
<223> OTHER INFORMATION: Consensus Antibody Variable Light Sequence
<221> NAME/KEY: VARIANT
<222> LOCATION: (24)...(24)
<223> OTHER INFORMATION: Xaa = R or Q
<221> NAME/KEY: VARIANT
<222> LOCATION: (29)...(29)
<223> OTHER INFORMATION: Xaa = V or I
<221> NAME/KEY: VARIANT
<222> LOCATION: (31)...(31)
<223> OTHER INFORMATION: Xaa = T or S
<221> NAME/KEY: VARIANT
<222> LOCATION: (34)...(34)
<223> OTHER INFORMATION: Xaa = N, S or T
<221> NAME/KEY: VARIANT
<222> LOCATION: (51)...(51)
<223> OTHER INFORMATION: Xaa = S or A
<221> NAME/KEY: VARIANT
<222> LOCATION: (56)...(56)
<223> OTHER INFORMATION: Xaa = T, A or S
```

```
<221> NAME/KEY: VARIANT
<222> LOCATION: (90)...(98)
<223> OTHER INFORMATION: Xaa = V, A, or G at 90; W or Y at 91; D, G, S
      or N at 92; S, T or N at 93; S, N, Y, D or T at 94; P,
      H, A, D or S at 95; P, A, S, R or G at 96; V, L or
      S at 97; A, V, M, I, L or T at 98
<221> NAME/KEY: VARIANT
<222> LOCATION: (101)...(101)
<223> OTHER INFORMATION: Xaa = G or D

<400> SEQUENCE: 592

Glu Ile Val Leu Thr Gln Ser Pro Ala Thr Leu Ser Leu Ser Pro Gly
 1               5                  10                  15

Glu Arg Ala Thr Ile Thr Cys Xaa Ala Ser Gln Tyr Xaa Gly Xaa Tyr
             20                  25                  30

Leu Xaa Trp Tyr Gln Gln Lys Pro Gly Gln Ala Pro Arg Leu Leu Ile
         35                  40                  45

Tyr Asp Xaa Ser Asn Arg Ala Xaa Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Xaa Xaa Xaa Xaa Xaa Xaa Xaa
                 85                  90                  95

Xaa Xaa Phe Gly Xaa Gly Thr Lys Val Glu Ile Lys
            100                 105

<210> SEQ ID NO 593
<211> LENGTH: 21
<212> TYPE: PRT
<213> ORGANISM: Artificial Sequence
<220> FEATURE:
<223> OTHER INFORMATION: PCSK9 Fragment

<400> SEQUENCE: 593

Ala Leu Arg Ser Glu Glu Asp Gly Leu Ala Glu Ala Pro Glu His Gly
 1               5                  10                  15

Thr Thr Ala Thr Phe
            20

<210> SEQ ID NO 594
<211> LENGTH: 7
<212> TYPE: PRT
<213> ORGANISM: Artificial Sequence
<220> FEATURE:
<223> OTHER INFORMATION: PCSK9 Fragment

<400> SEQUENCE: 594

Arg Ser Glu Glu Asp Gly Leu
 1               5

<210> SEQ ID NO 595
<211> LENGTH: 19
<212> TYPE: PRT
<213> ORGANISM: Artificial Sequence
<220> FEATURE:
<223> OTHER INFORMATION: PCSK9 Fragment

<400> SEQUENCE: 595

Arg Ser Glu Glu Asp Gly Leu Ala Glu Ala Pro Glu His Gly Thr Thr
 1               5                  10                  15

Ala Thr Phe

<210> SEQ ID NO 596
```

```
<211> LENGTH: 24
<212> TYPE: PRT
<213> ORGANISM: Artificial Sequence
<220> FEATURE:
<223> OTHER INFORMATION: PCSK9 Fragment

<400> SEQUENCE: 596

Ala Pro Glu His Gly Thr Thr Ala Thr Phe His Arg Cys Ala Lys Asp
 1               5                  10                  15

Pro Trp Arg Leu Pro Gly Thr Tyr
            20

<210> SEQ ID NO 597
<211> LENGTH: 13
<212> TYPE: PRT
<213> ORGANISM: Artificial Sequence
<220> FEATURE:
<223> OTHER INFORMATION: PCSK9 Fragment

<400> SEQUENCE: 597

Arg Cys Ala Lys Asp Pro Trp Arg Leu Pro Gly Thr Tyr
 1               5                  10

<210> SEQ ID NO 598
<211> LENGTH: 38
<212> TYPE: PRT
<213> ORGANISM: Artificial Sequence
<220> FEATURE:
<223> OTHER INFORMATION: PCSK9 Fragment

<400> SEQUENCE: 598

Glu Thr His Leu Ser Gln Ser Glu Arg Thr Ala Arg Arg Leu Gln Ala
 1               5                  10                  15

Gln Ala Ala Arg Arg Gly Tyr Leu Thr Lys Ile Leu His Val Phe His
            20                  25                  30

Gly Leu Leu Pro Gly Phe
        35

<210> SEQ ID NO 599
<211> LENGTH: 39
<212> TYPE: PRT
<213> ORGANISM: Artificial Sequence
<220> FEATURE:
<223> OTHER INFORMATION: PCSK9 Fragment

<400> SEQUENCE: 599

Glu Thr His Leu Ser Gln Ser Glu Arg Thr Ala Arg Arg Leu Gln Ala
 1               5                  10                  15

Gln Ala Ala Arg Arg Gly Tyr Leu Thr Lys Ile Leu His Val Phe His
            20                  25                  30

Gly Leu Leu Pro Gly Phe Leu
        35

<210> SEQ ID NO 600
<211> LENGTH: 13
<212> TYPE: PRT
<213> ORGANISM: Artificial Sequence
<220> FEATURE:
<223> OTHER INFORMATION: PCSK9 Fragment

<400> SEQUENCE: 600

Ile Leu His Val Phe His Gly Leu Leu Pro Gly Phe Leu
 1               5                  10
```

```
<210> SEQ ID NO 601
<211> LENGTH: 5
<212> TYPE: PRT
<213> ORGANISM: Artificial Sequence
<220> FEATURE:
<223> OTHER INFORMATION: PCSK9 Fragment

<400> SEQUENCE: 601

Met Ser Gly Asp Leu
 1               5

<210> SEQ ID NO 602
<211> LENGTH: 7
<212> TYPE: PRT
<213> ORGANISM: Artificial Sequence
<220> FEATURE:
<223> OTHER INFORMATION: PCSK9 Fragment

<400> SEQUENCE: 602

Met Ser Gly Asp Leu Leu Glu
 1               5

<210> SEQ ID NO 603
<211> LENGTH: 8
<212> TYPE: PRT
<213> ORGANISM: Artificial Sequence
<220> FEATURE:
<223> OTHER INFORMATION: PCSK9 Fragment

<400> SEQUENCE: 603

Leu Lys Leu Pro His Val Asp Tyr
 1               5

<210> SEQ ID NO 604
<211> LENGTH: 7
<212> TYPE: PRT
<213> ORGANISM: Artificial Sequence
<220> FEATURE:
<223> OTHER INFORMATION: PCSK9 Fragment

<400> SEQUENCE: 604

Lys Leu Pro His Val Asp Tyr
 1               5

<210> SEQ ID NO 605
<211> LENGTH: 19
<212> TYPE: PRT
<213> ORGANISM: Artificial Sequence
<220> FEATURE:
<223> OTHER INFORMATION: PCSK9 Fragment

<400> SEQUENCE: 605

Ile Thr Pro Pro Arg Tyr Arg Ala Asp Glu Tyr Gln Pro Pro Asp Gly
 1               5                  10                  15

Gly Ser Leu

<210> SEQ ID NO 606
<211> LENGTH: 21
<212> TYPE: PRT
<213> ORGANISM: Artificial Sequence
<220> FEATURE:
<223> OTHER INFORMATION: PCSK9 Fragment

<400> SEQUENCE: 606

Ile Thr Pro Pro Arg Tyr Arg Ala Asp Glu Tyr Gln Pro Pro Asp Gly
 1               5                  10                  15
```

```
Gly Ser Leu Val Glu
            20

<210> SEQ ID NO 607
<211> LENGTH: 14
<212> TYPE: PRT
<213> ORGANISM: Artificial Sequence
<220> FEATURE:
<223> OTHER INFORMATION: PCSK9 Fragment

<400> SEQUENCE: 607

Thr Ser Ile Gln Ser Asp His Arg Glu Ile Glu Gly Arg Val
1               5                   10

<210> SEQ ID NO 608
<211> LENGTH: 17
<212> TYPE: PRT
<213> ORGANISM: Artificial Sequence
<220> FEATURE:
<223> OTHER INFORMATION: PCSK9 Fragment

<400> SEQUENCE: 608

Ile Gln Ser Asp His Arg Glu Ile Glu Gly Arg Val Met Val Thr Asp
1               5                   10                  15

Phe

<210> SEQ ID NO 609
<211> LENGTH: 23
<212> TYPE: PRT
<213> ORGANISM: Artificial Sequence
<220> FEATURE:
<223> OTHER INFORMATION: PCSK9 Fragment

<400> SEQUENCE: 609

Val Pro Glu Glu Asp Gly Thr Arg Phe His Arg Gln Ala Ser Lys Cys
1               5                   10                  15

Asp Ser His Gly Thr His Leu
            20

<210> SEQ ID NO 610
<211> LENGTH: 40
<212> TYPE: PRT
<213> ORGANISM: Artificial Sequence
<220> FEATURE:
<223> OTHER INFORMATION: PCSK9 Fragment

<400> SEQUENCE: 610

Val Pro Glu Glu Asp Gly Thr Arg Phe His Arg Gln Ala Ser Lys Cys
1               5                   10                  15

Asp Ser His Gly Thr His Leu Ala Gly Val Val Ser Gly Arg Asp Ala
            20                  25                  30

Gly Val Ala Lys Gly Ala Ser Met
        35                  40

<210> SEQ ID NO 611
<211> LENGTH: 15
<212> TYPE: PRT
<213> ORGANISM: Artificial Sequence
<220> FEATURE:
<223> OTHER INFORMATION: PCSK9 Fragment

<400> SEQUENCE: 611

Val Val Ser Gly Arg Asp Ala Gly Val Ala Lys Gly Ala Ser Met
1               5                   10                  15
```

```
<210> SEQ ID NO 612
<211> LENGTH: 16
<212> TYPE: PRT
<213> ORGANISM: Artificial Sequence
<220> FEATURE:
<223> OTHER INFORMATION: PCSK9 Fragment

<400> SEQUENCE: 612

Leu Arg Val Leu Asn Cys Gln Gly Lys Gly Thr Val Ser Gly Thr Leu
 1               5                  10                  15

<210> SEQ ID NO 613
<211> LENGTH: 16
<212> TYPE: PRT
<213> ORGANISM: Artificial Sequence
<220> FEATURE:
<223> OTHER INFORMATION: PCSK9 Fragment

<400> SEQUENCE: 613

Ile Arg Lys Ser Gln Leu Val Gln Pro Val Gly Pro Leu Val Val Leu
 1               5                  10                  15

<210> SEQ ID NO 614
<211> LENGTH: 15
<212> TYPE: PRT
<213> ORGANISM: Artificial Sequence
<220> FEATURE:
<223> OTHER INFORMATION: PCSK9 Fragment

<400> SEQUENCE: 614

Arg Lys Ser Gln Leu Val Gln Pro Val Gly Pro Leu Val Val Leu
 1               5                  10                  15

<210> SEQ ID NO 615
<211> LENGTH: 8
<212> TYPE: PRT
<213> ORGANISM: Artificial Sequence
<220> FEATURE:
<223> OTHER INFORMATION: PCSK9 Fragment

<400> SEQUENCE: 615

Leu Leu Pro Leu Ala Gly Gly Tyr
 1               5

<210> SEQ ID NO 616
<211> LENGTH: 11
<212> TYPE: PRT
<213> ORGANISM: Artificial Sequence
<220> FEATURE:
<223> OTHER INFORMATION: PCSK9 Fragment

<400> SEQUENCE: 616

Leu Ala Gly Gly Tyr Ser Arg Val Leu Asn Ala
 1               5                  10

<210> SEQ ID NO 617
<211> LENGTH: 13
<212> TYPE: PRT
<213> ORGANISM: Artificial Sequence
<220> FEATURE:
<223> OTHER INFORMATION: PCSK9 Fragment

<400> SEQUENCE: 617

Leu Ala Gly Gly Tyr Ser Arg Val Leu Asn Ala Ala Cys
 1               5                  10
```

-continued

```
<210> SEQ ID NO 618
<211> LENGTH: 8
<212> TYPE: PRT
<213> ORGANISM: Artificial Sequence
<220> FEATURE:
<223> OTHER INFORMATION: PCSK9 Fragment

<400> SEQUENCE: 618

Leu Ala Arg Ala Gly Val Val Leu
 1               5

<210> SEQ ID NO 619
<211> LENGTH: 5
<212> TYPE: PRT
<213> ORGANISM: Artificial Sequence
<220> FEATURE:
<223> OTHER INFORMATION: PCSK9 Fragment

<400> SEQUENCE: 619

Ala Gly Val Val Leu
 1               5

<210> SEQ ID NO 620
<211> LENGTH: 5
<212> TYPE: PRT
<213> ORGANISM: Artificial Sequence
<220> FEATURE:
<223> OTHER INFORMATION: PCSK9 Fragment

<400> SEQUENCE: 620

Ala Ala Gly Asn Phe
 1               5

<210> SEQ ID NO 621
<211> LENGTH: 5
<212> TYPE: PRT
<213> ORGANISM: Artificial Sequence
<220> FEATURE:
<223> OTHER INFORMATION: PCSK9 Fragment

<400> SEQUENCE: 621

Asp Asp Ala Cys Leu
 1               5

<210> SEQ ID NO 622
<211> LENGTH: 7
<212> TYPE: PRT
<213> ORGANISM: Artificial Sequence
<220> FEATURE:
<223> OTHER INFORMATION: PCSK9 Fragment

<400> SEQUENCE: 622

Pro Ala Ser Ala Pro Glu Val
 1               5

<210> SEQ ID NO 623
<211> LENGTH: 22
<212> TYPE: PRT
<213> ORGANISM: Artificial Sequence
<220> FEATURE:
<223> OTHER INFORMATION: PCSK9 Fragment

<400> SEQUENCE: 623

Pro Ala Ser Ala Pro Glu Val Ile Thr Val Gly Ala Thr Asn Ala Gln
 1               5                  10                  15

Asp Gln Pro Val Thr Leu
            20
```

<210> SEQ ID NO 624
<211> LENGTH: 13
<212> TYPE: PRT
<213> ORGANISM: Artificial Sequence
<220> FEATURE:
<223> OTHER INFORMATION: PCSK9 Fragment

<400> SEQUENCE: 624

Val Gly Ala Thr Asn Ala Gln Asp Gln Pro Val Thr Leu
 1               5                  10

<210> SEQ ID NO 625
<211> LENGTH: 8
<212> TYPE: PRT
<213> ORGANISM: Artificial Sequence
<220> FEATURE:
<223> OTHER INFORMATION: PCSK9 Fragment

<400> SEQUENCE: 625

Leu Gly Thr Asn Phe Gly Arg Cys
 1               5

<210> SEQ ID NO 626
<211> LENGTH: 7
<212> TYPE: PRT
<213> ORGANISM: Artificial Sequence
<220> FEATURE:
<223> OTHER INFORMATION: PCSK9 Fragment

<400> SEQUENCE: 626

Leu Phe Ala Pro Gly Glu Asp
 1               5

<210> SEQ ID NO 627
<211> LENGTH: 15
<212> TYPE: PRT
<213> ORGANISM: Artificial Sequence
<220> FEATURE:
<223> OTHER INFORMATION: PCSK9 Fragment

<400> SEQUENCE: 627

Gln Ser Gly Thr Ser Gln Ala Ala Ala His Val Ala Gly Ile Ala
 1               5                  10                  15

<210> SEQ ID NO 628
<211> LENGTH: 8
<212> TYPE: PRT
<213> ORGANISM: Artificial Sequence
<220> FEATURE:
<223> OTHER INFORMATION: PCSK9 Fragment

<400> SEQUENCE: 628

Ser Ala Glu Pro Glu Leu Thr Leu
 1               5

<210> SEQ ID NO 629
<211> LENGTH: 7
<212> TYPE: PRT
<213> ORGANISM: Artificial Sequence
<220> FEATURE:
<223> OTHER INFORMATION: PCSK9 Fragment

<400> SEQUENCE: 629

Ala Glu Pro Glu Leu Thr Leu
 1               5

```
<210> SEQ ID NO 630
<211> LENGTH: 8
<212> TYPE: PRT
<213> ORGANISM: Artificial Sequence
<220> FEATURE:
<223> OTHER INFORMATION: PCSK9 Fragment

<400> SEQUENCE: 630

Leu Arg Gln Arg Leu Ile His Phe
 1               5

<210> SEQ ID NO 631
<211> LENGTH: 16
<212> TYPE: PRT
<213> ORGANISM: Artificial Sequence
<220> FEATURE:
<223> OTHER INFORMATION: PCSK9 Fragment

<400> SEQUENCE: 631

Leu Arg Gln Arg Leu Ile His Phe Ser Ala Lys Asp Val Ile Asn Glu
 1               5                  10                  15

<210> SEQ ID NO 632
<211> LENGTH: 5
<212> TYPE: PRT
<213> ORGANISM: Artificial Sequence
<220> FEATURE:
<223> OTHER INFORMATION: PCSK9 Fragment

<400> SEQUENCE: 632

Arg Leu Ile His Phe
 1               5

<210> SEQ ID NO 633
<211> LENGTH: 13
<212> TYPE: PRT
<213> ORGANISM: Artificial Sequence
<220> FEATURE:
<223> OTHER INFORMATION: PCSK9 Fragment

<400> SEQUENCE: 633

Arg Leu Ile His Phe Ser Ala Lys Asp Val Ile Asn Glu
 1               5                  10

<210> SEQ ID NO 634
<211> LENGTH: 8
<212> TYPE: PRT
<213> ORGANISM: Artificial Sequence
<220> FEATURE:
<223> OTHER INFORMATION: PCSK9 Fragment

<400> SEQUENCE: 634

Ser Ala Lys Asp Val Ile Asn Glu
 1               5

<210> SEQ ID NO 635
<211> LENGTH: 5
<212> TYPE: PRT
<213> ORGANISM: Artificial Sequence
<220> FEATURE:
<223> OTHER INFORMATION: PCSK9 Fragment

<400> SEQUENCE: 635

Phe Pro Glu Asp Gln
 1               5
```

```
<210> SEQ ID NO 636
<211> LENGTH: 12
<212> TYPE: PRT
<213> ORGANISM: Artificial Sequence
<220> FEATURE:
<223> OTHER INFORMATION: PCSK9 Fragment

<400> SEQUENCE: 636

Phe Pro Glu Asp Gln Arg Val Leu Thr Pro Asn Leu
 1               5                  10

<210> SEQ ID NO 637
<211> LENGTH: 6
<212> TYPE: PRT
<213> ORGANISM: Artificial Sequence
<220> FEATURE:
<223> OTHER INFORMATION: PCSK9 Fragment

<400> SEQUENCE: 637

Val Leu Thr Pro Asn Leu
 1               5

<210> SEQ ID NO 638
<211> LENGTH: 5
<212> TYPE: PRT
<213> ORGANISM: Artificial Sequence
<220> FEATURE:
<223> OTHER INFORMATION: PCSK9 Fragment

<400> SEQUENCE: 638

Leu Thr Pro Asn Leu
 1               5

<210> SEQ ID NO 639
<211> LENGTH: 13
<212> TYPE: PRT
<213> ORGANISM: Artificial Sequence
<220> FEATURE:
<223> OTHER INFORMATION: PCSK9 Fragment

<400> SEQUENCE: 639

Ala Leu Pro Pro Ser Thr His Gly Ala Gly Trp Gln Leu
 1               5                  10

<210> SEQ ID NO 640
<211> LENGTH: 21
<212> TYPE: PRT
<213> ORGANISM: Artificial Sequence
<220> FEATURE:
<223> OTHER INFORMATION: PCSK9 Fragment

<400> SEQUENCE: 640

Met Gly Thr Arg Val His Cys His Gln Gln Gly His Val Leu Thr Gly
 1               5                  10                  15

Cys Ser Ser His Trp
                20

<210> SEQ ID NO 641
<211> LENGTH: 18
<212> TYPE: PRT
<213> ORGANISM: Artificial Sequence
<220> FEATURE:
<223> OTHER INFORMATION: PCSK9 Fragment

<400> SEQUENCE: 641

Arg Val His Cys His Gln Gln Gly His Val Leu Thr Gly Cys Ser Ser
 1               5                  10                  15
```

His Trp

<210> SEQ ID NO 642
<211> LENGTH: 692
<212> TYPE: PRT
<213> ORGANISM: Artificial Sequence
<220> FEATURE:
<223> OTHER INFORMATION: Human PCSK9

<400> SEQUENCE: 642

```
Met Gly Thr Val Ser Ser Arg Arg Ser Trp Trp Pro Leu Pro Leu Leu
  1               5                  10                  15

Leu Leu Leu Leu Leu Leu Leu Gly Pro Ala Gly Ala Arg Ala Gln Glu
             20                  25                  30

Asp Glu Asp Gly Asp Tyr Glu Glu Leu Val Leu Ala Leu Arg Ser Glu
         35                  40                  45

Glu Asp Gly Leu Ala Glu Ala Pro Glu His Gly Thr Thr Ala Thr Phe
 50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350
```

```
Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445

His Gly Ala Gly Trp Gln Leu Phe Cys Arg Thr Val Trp Ser Ala His
                450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
                515                 520                 525

Leu Pro Gln Ala Asn Cys Ser Val His Thr Ala Pro Pro Ala Glu Ala
                530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
                595                 600                 605

Lys Val Lys Glu His Gly Ile Pro Ala Pro Gln Glu Gln Val Thr Val
                610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
                660                 665                 670

Thr Ala Val Ala Ile Cys Cys Arg Ser Arg His Leu Ala Gln Ala Ser
                675                 680                 685

Gln Glu Leu Gln
            690

<210> SEQ ID NO 643
<211> LENGTH: 9
<212> TYPE: PRT
<213> ORGANISM: Artificial Sequence
<220> FEATURE:
<223> OTHER INFORMATION: Contact residues of AX132 FAb with PCSK9

<400> SEQUENCE: 643

Ser Gln Tyr Val Gly Ser Tyr Leu Asn
 1               5
```

-continued

```
<210> SEQ ID NO 644
<211> LENGTH: 5
<212> TYPE: PRT
<213> ORGANISM: Artificial Sequence
<220> FEATURE:
<223> OTHER INFORMATION: Contact residues of AX132 FAb with PCSK9

<400> SEQUENCE: 644

Tyr Val Gly Ser Tyr
 1               5

<210> SEQ ID NO 645
<211> LENGTH: 80
<212> TYPE: PRT
<213> ORGANISM: Artificial Sequence
<220> FEATURE:
<223> OTHER INFORMATION: EGF_AB peptide

<400> SEQUENCE: 645

Asp Lys Val Cys Asn Met Ala Arg Asp Cys Arg Asp Trp Ser Asp Glu
 1               5                  10                  15

Pro Ile Lys Glu Cys Gly Thr Asn Glu Cys Leu Asp Asn Asn Gly Gly
             20                  25                  30

Cys Ser His Val Cys Asn Asp Leu Lys Ile Gly Tyr Glu Cys Leu Cys
         35                  40                  45

Pro Asp Gly Phe Gln Leu Val Ala Gln Arg Arg Cys Glu Asp Ile Asp
     50                  55                  60

Glu Cys Gln Asp Pro Asp Thr Cys Ser Gln Leu Cys Val Asn Leu Glu
 65                  70                  75                  80

<210> SEQ ID NO 646
<211> LENGTH: 6065
<212> TYPE: DNA
<213> ORGANISM: Artificial Sequence
<220> FEATURE:
<223> OTHER INFORMATION: pMAB9-AX132 Antibody Expression Vector

<400> SEQUENCE: 646
gcgcaacgca attaatgtga gttagctcac tcattaggca ccccaggctt tacactttat      60
gcttccggct cgtatgttgt gtggaattgt gagcggataa caatttaccg gttctttaag     120
gaggaattaa aaaatgaaaa agtctttagt cctcaaagcc tccgtagccg ttgctaccct     180
cgttccgatg ctaagcttcg ctgaaatcgt gctgacccag tctccagcca ccctgtctct     240
gtctcccggg gaacgtgcca ccatcacctg ccgtgcctct cagtatgtcg gcagctacct     300
gaactggtat cagcagaagc caggtcaggc gccacgtctg ctgatctacg acgcctctaa     360
ccgtgccacc ggtatcccag cccgtttctc tggttctggt tctggcaccg acttcacct     420 gaccatctct tctctggaac agaagacttt cgccgtgtac tactgccagg tatgggacag     480
ctctcctcct gtggtgttcg gtggtggtac caaagtggag atcaaacgta cggtggctgc     540
accatctgtc ttcatcttcc cgccatctga tgagcagttg aaatctggaa ctgcctctgt     600
tgtgtgcctg ctgaataact tctatcccag agaggccaaa gtacagtgga aggtggataa     660
cgccctccaa tcgggtaact cccaggagag tgtcacagag caggacagca aggacagcac     720
ctacagcctc agcagcaccc tgacgctgag caaagcagac tacgagaaac acaaagtcta     780
cgcctgcgaa gtcacccatc agggcctgag ctcgcccgtc acaaagagct tcaacagggg     840
agagtgttga taaggcgcgc cacaatttca cagtaaggag gtttaactta tgaaaaaatt     900
attattcgca attcctttag ttgttccttt ctattctcac tccgaagtgc aattgctgga     960
```

```
atctggtggt ggtctggtgc agccaggtgg ttctctgcgt ctgtcttgca aggcctctgg   1020
ttacaccttc tcttcttacg ggatgtactg ggtgcgtcag gcaccaggta agggtctgga   1080
atggatcggt tggatcgacc caggcagcgg tggcaccaag tacaacgaaa agttcaaggg   1140
taaggccacc atctccagag acaactctaa gaacaccctg tacttgcaga tgaactctct   1200
gcgtgccgag gacactgcag tgtactactg cgcccgtgaa cgttacggtt actacttcga   1260
ctactggggt cagggtacgc tggtgactgt ctcgagcgca agcaccaaag gcccatcggt   1320
attccccctg gcaccctcct ccaagagcac ctctgggggc acagcggccc tgggctgcct   1380
ggtcaaggac tacttcccc g agccggtgac ggtgtcgtgg aactcaggcg ctctgaccag   1440
cggcgtgcac accttcccgg ctgtcctaca gtcctcagga ctctactccc tcagcagcgt   1500
ggtgactgtg ccctccagca gcttgggcac ccagacctac atctgcaacg tgaatcacaa   1560
gcccagcaac actaaggtgg acaagaaagt tgagcccaaa tcttgtgaca aaactcacac   1620
agcggccgct tatccatacg acgtaccaga ctacgcagga ggtcatcacc atcatcacca   1680
ttaatgaacc tgtgaagtga aaaatggcgc agattgtgcg acatgatcat tgggctgcaa   1740
aacaaaacgg cctcctgtca ggaagccgct tttatcgggt agcctcactg cccgctttcc   1800
agtcgggaaa cctgtcgtgc cagctgcatc agtgaatcgg ccaacgcgcg gggagaggcg   1860
gtttgcgtat tgggagccag ggtggttttt cttttcacca gtgagacggg caacagctga   1920
ttgcccttca ccgcctggcc ctgagagagt gcagcaagc ggtccacgct ggtttgcccc   1980
agcaggcgaa aatcctgttt gatggtggtc agcggcggga tataacatga gctgtcctcg   2040
gtatcgtcgt atcccactac cgagatgtcc gcaccaacgc gcagcccgga ctcggtaatg   2100
gcacgcattg cgcccagcgc catctgatcg ttggcaacca gcatcgcagt gggaacgatg   2160
ccctcattca gcatttgcat ggtttgttga aaaccggaca tggcactcca gtcgccttcc   2220
cgttccgcta tcggctgaat ttgattgcga gtgagatatt tatgccagcc agccagacgc   2280
agacgcgccg agacagaact taatgggcca gctaacagcg cgatttgctg gtggcccaat   2340
gcgaccagat gctccacgcc cagtcgcgta ccgtcctcat gggagaaaat aatactgttg   2400
atgggtgtct ggtcagagac atcaagaaat aacgccggaa cattagtgca ggcagcttcc   2460
acagcaatag catcctggtc atccagcgga tagttaataa tcagcccact gacacgttgc   2520
gcgagaagat tgtgcaccgc cgctttacag gcttcgacgc cgcttcgttc taccatcgac   2580
acgaccacgc tggcacccag ttgatcggcg cgagatttaa tcgccgcgac aatttgcgac   2640
ggcgcgtgca gggccagact ggaggtggca acgccaatca gcaacgactg tttgcccgcc   2700
agttgttgtg ccacgcggtt aggaatgtaa ttcagctccg ccatcgccgc ttccactttt   2760
tcccgcgttt tcgcagaaac gtggctggcc tggttcacca cgcgggaaac ggtctgataa   2820
gagacaccgg catactctgc gacatcgtat aacgttactg gtttcacatt caccaccctg   2880
aattgactct cttccgggcg ctatcatgcc ataccgcgaa aggttttgcg ccattcgatg   2940
tcgacctcga ccaattcgcc ctatagtgag tcgtattacg cgcgctcact ggccgtcgtt   3000
ttacaacgtc gtgactggga aaaccctggc gttacccaac ttaatcgcct tgcagcacat   3060
ccccctttcg ccagctggcg taatagcgaa gaggcccgca ccgatcgccc ttcccaacag   3120
ttgcgcagcc tgaatggcga atgggacgcg ccctgtagcg gcgcattaag cgcggcgggt   3180
gtggtggtta cgcgcagcgt gaccgctaca cttgccagcg ccctagcgcc cgctcctttc   3240
gctttcttcc cttcctttct cgccacgttc gccggctttc cccgtcaagc tctaaatcgg   3300
gggctccctt tagggttccg atttagtgct ttacggcacc tcgaccccaa aaaacttgat   3360
```

-continued

```
tagggtgatg gttcacgtag tgggccatcg ccctgataga cggttttccg cccttttgacg    3420
ttggagtcca cgttctttaa tagtggactc ttgttccaaa ctggaacaac actcaaccct    3480
atctcggtct attcttttga tttataaggg attttgccga tttcggccta ttggttaaaa    3540
aatgagctga tttaacaaaa atttaacgcg aattttaaca aaatattaac gcttacaatt    3600
taggtggcac ttttcgggga aatgtgcgcg gaacccctat ttgtttattt ttctaaatac    3660
attcaaatat gtatccgctc atgagacaat aaccctgata aatgcttcaa taatattgaa    3720
aaaggaagag tatgagtatt caacatttcc gtgtcgccct tattccctt tttgcggcat    3780
tttgccttcc tgttttgct cacccagaaa cgctggtgaa agtaaaagat gctgaagatc    3840
agttgggtgc acgagtgggt tacatcgaac tggatctcaa cagcggtaag atccttgaga    3900
gttttcgccc cgaagaacgt tttccaatga tgagcacttt tgatcagaa aaaaaggatc    3960
atatcgtcaa ttattacctc cacggggaga gcctgagcaa actggcctca ggcatttgag    4020
aagcacacgg tcacactgct tccggtagtc aataaaccgg taaaccagca atagacataa    4080
gcggctattt aacgaccctg ccctgaaccg acgaccgggt cgaatttgct ttcgaatttc    4140
tgccattcat ccgcttatta tcacttattc aggcgtagca accaggcgtt taagggcacc    4200
aataactgcc ttaaaaaaat tacgccccgc cctgccactc atcgcagtac tgttgtaatt    4260
cattaagcat tctgccgaca tggaagccat cacaaacggc atgatgaacc tgaatcgcca    4320
gcggcatcag caccttgtcg ccttgcgtat aatatttgcc catggtgaaa acggggggcga    4380
agaagttgtc catattggcc acgtttaaat caaaactggt gaaactcacc cagggattgg    4440
ctgagacgaa aaacatattc tcaataaacc ctttagggaa ataggccagg ttttcaccgt    4500
aacacgccac atcttgcgaa tatatgtgta gaaactgccg gaaatcgtcg tggtattcac    4560
tccagagcga tgaaaacgtt tcagtttgct catggaaaac ggtgtaacaa gggtgaacac    4620
tatcccatat caccagctca ccgtctttca ttgccatacg taattccgga tgagcattca    4680
tcaggcgggc aagaatgtga ataaaggccg gataaaactt gtgcttattt ttctttacgg    4740
tcttttaaaaa ggccgtaata tccagctgaa cggtctggtt ataggtacat tgagcaactg    4800
actgaaatgc ctcaaaatgt tctttacgat gccattggga tatatcaacg gtggtatatc    4860
cagtgatttt tttctccatt ttagcttcct tagctcctga aaatctcgac aactcaaaaa    4920
atacgcccgg tagtgatctt atttcattat ggtgaaagtt ggaacctctt acgtgccgat    4980
caacgtctca ttttcgccaa aagttggccc agggcttccc ggtatcaaca gggacaccag    5040
gatttattta ttctgcgaag tgatcttccg tcacaggtat ttattcggtc gaaaaggatc    5100
taggtgaaga tccttttga taatctcatg accaaaatcc cttaacgtga gttttcgttc    5160
cactgagcgt cagaccccgt agaaaagatc aaaggatctt cttgagatcc ttttttctg    5220
cgcgtaatct gctgcttgca acaaaaaaa ccaccgctac cagcggtggt ttgtttgccg    5280
gatcaagagc taccaactct ttttccgaag gtaactggct tcagcagagc gcagatacca    5340
aatactgttc ttctagtgta gccgtagtta ggccaccact tcaagaactc tgtagcaccg    5400
cctacatacc tcgctctgct aatcctgtta ccagtggctg ctgccagtgg cgataagtcg    5460
tgtcttaccg ggttggactc aagacgatag ttaccggata aggcgcagcg gtcgggctga    5520
acggggggtt cgtgcacaca gcccagcttg gagcgaacga cctacaccga actgagatac    5580
ctacagcgtg agctatgaga aagcgccacg ctcccgaag ggagaaaggc ggacaggtat    5640
ccggtaagcg gcagggtcgg aacaggagag cgcacgaggg agcttccagg gggaaacgcc    5700
tggtatcttt atagtcctgt cgggtttcgc cacctctgac ttgagcgtcg attttttgtga    5760
```

```
tgctcgtcag gggggcggag cctatggaaa aacgccagca acgcggcctt tttacggttc    5820 ctggccttt t gctggccttt tgctcacatg ttctttcctg cgttatcccc tgattctgtg    5880
gataaccgta ttaccgcctt tgagtgagct gataccgctc gccgcagccg aacgaccgag    5940
cgcagcgagt cagtgagcga ggaagcggaa gagcgcccaa tacgcaaacc gcctctcccc    6000
gcgcgttggc cgattcatta atgcagctgg cacgacaggt ttcccgactg gaaagcgggc    6060
agtga                                                                 6065

<210> SEQ ID NO 647
<211> LENGTH: 6065
<212> TYPE: DNA
<213> ORGANISM: Artificial Sequence
<220> FEATURE:
<223> OTHER INFORMATION: pMAB9-AX132 (complementary) sequence

<400> SEQUENCE: 647
tcactgcccg ctttccagtc gggaaacctg tcgtgccagc tgcattaatg aatcggccaa      60
cgcgcgggga gaggcggttt gcgtattggg cgctcttccg cttcctcgct cactgactcg     120
ctgcgctcgg tcgttcggct gcggcgagcg gtatcagctc actcaaaggc ggtaatacgg     180
ttatccacag aatcagggga taacgcagga agaacatgt gagcaaaagg ccagcaaaag     240
gccaggaacc gtaaaaaggc cgcgttgctg gcgtttttcc ataggctccg ccccctgac     300 gagcatcaca aaaatcgacg ctcaagtcag aggtggcgaa acccgacagg actataaaga     360
taccaggcgt ttccccctgg aagctccctc gtgcgctctc ctgttccgac cctgccgctt     420
accggatacc tgtccgcctt tctcccttcg ggaagcgtgg cgctttctca tagctcacgc     480
tgtaggtatc tcagttcggt gtaggtcgtt cgctccaagc tgggctgtgt gcacgaaccc     540
cccgttcagc ccgaccgctg cgccttatcc ggtaactatc gtcttgagtc aacccggta     600 agacacgact tatcgccact ggcagcagcc actggtaaca ggattagcag agcgaggtat     660
gtaggcggtg ctacagagtt cttgaagtgg tggcctaact acggctacac tagaagaaca     720
gtatttggta tctgcgctct gctgaagcca gttaccttcg gaaaaagagt tggtagctct     780
tgatccggca aacaaaccac cgctggtagc ggtggttttt ttgtttgcaa gcagcagatt     840
acgcgcagaa aaaaggatc tcaagaagat cctttgatct tttctacggg gtctgacgct     900
cagtggaacg aaaactcacg ttaagggatt ttggtcatga gattatcaaa aaggatcttc     960
acctagatcc ttttcgaccg aataaatacc tgtgacggaa gatcacttcg cagaataaat    1020
aaatcctggt gtccctgttg ataccgggaa gccctgggcc aacttttggc gaaaatgaga    1080
cgttgatcgg cacgtaagag gttccaactt tcaccataat gaaataagat cactaccggg    1140 cgtattttt gagttgtcga gattttcagg agctaaggaa gctaaaatgg agaaaaaaat    1200
cactggatat accaccgttg atatatccca atggcatcgt aaagaacatt ttgaggcatt    1260
tcagtcagtt gctcaatgta cctataacca gaccgttcag ctggatatta cggcctttt    1320 aaagaccgta aagaaaaata agcacaagtt ttatccggcc tttattcaca ttcttgcccg    1380
cctgatgaat gctcatccgg aattacgtat ggcaatgaaa gacggtgagc tggtgatatg    1440
ggatagtgtt cacccttgtt acaccgtttt ccatgagcaa actgaaacgt ttcatcgct    1500 ctggagtgaa taccacgacg atttccggca gtttctacac atatattcgc aagatgtggc    1560
gtgttacggt gaaaacctgg cctatttccc taaagggttt attgagaata tgttttcgt    1620 ctcagccaat ccctgggtga gtttcaccag ttttgattta aacgtggcca atatggacaa    1680
cttcttcgcc cccgtttca ccatgggcaa atattatacg caaggcgaca aggtgctgat    1740
```

```
gccgctggcg attcaggttc atcatgccgt ttgtgatggc ttccatgtcg gcagaatgct    1800
taatgaatta caacagtact gcgatgagtg gcagggcggg gcgtaatttt tttaaggcag    1860
ttattggtgc ccttaaacgc ctggttgcta cgcctgaata agtgataata agcggatgaa    1920
tggcagaaat tcgaaagcaa attcgacccg gtcgtcggtt cagggcaggg tcgttaaata    1980
gccgcttatg tctattgctg gtttaccggt ttattgacta ccggaagcag tgtgaccgtg    2040
tgcttctcaa atgcctgagg ccagtttgct caggctctcc ccgtggaggt aataattgac    2100
gatatgatcc ttttttttctg atcaaaaagt gctcatcatt ggaaaacgtt cttcggggcg    2160
aaaactctca aggatcttac cgctgttgag atccagttcg atgtaaccca ctcgtgcacc    2220
caactgatct tcagcatctt ttactttcac cagcgtttct gggtgagcaa aaacaggaag    2280
gcaaaatgcc gcaaaaaagg gaataagggc gacacggaaa tgttgaatac tcatactctt    2340
cctttttcaa tattattgaa gcatttatca gggttattgt ctcatgagcg gatacatatt    2400
tgaatgtatt tagaaaaata aacaaatagg ggttccgcgc acatttcccc gaaaagtgcc    2460
acctaaattg taagcgttaa tattttgtta aaattcgcgt taaattttg ttaaatcagc    2520 tcatttttta accaataggc cgaaatcggc aaaatccctt ataaatcaaa agaatagacc    2580
gagatagggt tgagtgttgt tccagtttgg aacaagagtc cactattaaa gaacgtggac    2640
tccaacgtca aagggcgaaa aaccgtctat cagggcgatg gcccactacg tgaaccatca    2700
ccctaatcaa gttttttggg gtcgaggtgc cgtaaagcac taaatcggaa ccctaaaggg    2760
agcccccgat ttagagcttg acggggaaag ccggcgaacg tggcgagaaa ggaagggaag    2820
aaagcgaaag gagcgggcgc tagggcgctg gcaagtgtag cggtcacgct gcgcgtaacc    2880
accacacccg ccgcgcttaa tgcgccgcta cagggcgcgt cccattcgcc attcaggctg    2940
cgcaactgtt gggaagggcg atcggtgcgg gcctcttcgc tattacgcca gctggcgaaa    3000
gggggatgtg ctgcaaggcg attaagttgg gtaacgccag gttttccca gtcacgacgt    3060 tgtaaaacga cggccagtga gcgcgcgtaa tacgactcac tatagggcga attggtcgag    3120
gtcgacatcg aatggcgcaa aacctttcgc ggtatggcat gatagcgccc ggaagagagt    3180
caattcaggt tggtgaatgt gaaaccagta acgttatacg atgtcgcaga gtatgccggt    3240
gtctcttatc agaccgtttc ccgcgtggtg aaccaggcca gccacgtttc tgcgaaaacg    3300
cgggaaaaag tggaagcggc gatggcggag ctgaattaca ttcctaaccg cgtggcacaa    3360
caactggcgg gcaaacagtc gttgctgatt ggcgttgcca cctccagtct ggccctgcac    3420
gcgccgtcgc aaattgtcgc ggcgattaaa tctcgcgccg atcaactggg tgccagcgtg    3480
gtcgtgtcga tggtagaacg aagcggcgtc gaagcctgta aagcggcggt gcacaatctt    3540
ctcgcgcaac gtgtcagtgg gctgattatt aactatccgc tggatgacca ggatgctatt    3600
gctgtggaag ctgcctgcac taatgttccg gcgttatttc ttgatgtctc tgaccagaca    3660
cccatcaaca gtattatttt ctcccatgag gacggtacgc gactgggcgt ggagcatctg    3720
gtcgcattgg gccaccagca aatcgcgctg ttagctggcc cattaagttc tgtctcggcg    3780
cgtctgcgtc tggctggctg gcataaatat ctcactcgca atcaaattca gccgatagcg    3840
gaacgggaag gcgactggag tgccatgtcc ggttttcaac aaaccatgca aatgctgaat    3900
gagggcatcg ttcccactgc gatgctggtt gccaacgatc agatggcgct gggcgcaatg    3960
cgtgccatta ccgagtccgg gctgcgcgtt ggtgcggaca tctcggtagt gggatacgac    4020
gataccgagg acagctcatg ttatatcccg ccgctgacca ccatcaaaca ggattttcgc    4080
ctgctggggc aaaccagcgt ggaccgcttg ctgcaactct ctcagggcca gcggtgaag    4140
```

```
ggcaatcagc tgttgcccgt ctcactggtg aaaagaaaaa ccaccctggc tcccaatacg   4200
caaaccgcct ctccccgcgc gttggccgat tcactgatgc agctggcacg acaggtttcc   4260
cgactggaaa gcgggcagtg aggctacccg ataaaagcgg cttcctgaca ggaggccgtt   4320
ttgttttgca gcccaatgat catgtcgcac aatctgcgcc atttttcact tcacaggttc   4380
attaatggtg atgatggtga tgacctcctg cgtagtctgg tacgtcgtat ggataagcgg   4440
ccgctgtgtg agttttgtca caagatttgg gctcaacttt cttgtccacc ttagtgttgc   4500
tgggcttgtg attcacgttg cagatgtagg tctgggtgcc caagctgctg gagggcacag   4560
tcaccacgct gctgagggag tagagtcctg aggactgtag gacagccggg aaggtgtgca   4620
cgccgctggt cagagcgcct gagttccacg acaccgtcac cggctcgggg aagtagtcct   4680
tgaccaggca gcccagggcc gctgtgcccc cagaggtgct cttggaggag ggtgccaggg   4740
ggaataccga tgggcctttg gtgcttgcgc tcgagacagt caccagcgta ccctgacccc   4800
agtagtcgaa gtagtaaccg taacgttcac gggcgcagta gtacactgca gtgtcctcgg   4860
cacgcagaga gttcatctgc aagtacaggg tgttcttaga gttgtctctg gagatggtgg   4920
ccttacccct gaacttttcg ttgtacttgg tgccaccgct gcctgggtcg atccaaccga   4980
tccattccag acccttacct ggtgcctgac gcacccagta catcccgtaa gaagagaagg   5040
tgtaaccaga ggccttgcaa gacagacgca gagaaccacc tggctgcacc agaccaccac   5100
cagattccag caattgcact tcggagtgag aatagaaagg aacaactaaa ggaattgcga   5160
ataataattt tttcataagt taaacctcct tactgtgaaa ttgtggcgcg ccttatcaac   5220
actctcccct gttgaagctc tttgtgacgg gcgagctcag gccctgatgg gtgacttcgc   5280
aggcgtagac tttgtgtttc tcgtagtctg ctttgctcag cgtcagggtg ctgctgaggc   5340
tgtaggtgct gtccttgctg tcctgctctg tgacactctc ctgggagtta cccgattgga   5400
gggcgttatc caccttccac tgtactttgg cctctctggg atagaagtta ttcagcaggc   5460
acacaacaga ggcagttcca gatttcaact gctcatcaga tggcgggaag atgaagacag   5520
atggtgcagc caccgtacgt ttgatctcca ctttggtacc accaccgaac accacaggag   5580
gagagctgtc ccatacctgg cagtagtaca cggcgaagtc ttctggttcc agagaagaga   5640
tggtcagggt gaagtcggtg ccagaaccag aaccagagaa acgggctggg ataccggtgg   5700
cacggttaga ggcgtcgtag atcagcagac gtggcgcctg acctggcttc tgctgatacc   5760
agttcaggta gctgccgaca tactgagagg cacggcaggt gatggtggca cgttccccgg   5820
gagacagaga cagggtggct ggagactggg tcagcacgat ttcagcgaag cttagcatcg   5880
gaacgagggt agcaacggct acggaggctt tgaggactaa agactttttc attttttaat   5940
tcctccttaa agaaccggta aattgttatc cgctcacaat tccacacaac atacgagccg   6000
gaagcataaa gtgtaaagcc tggggtgcct aatgagtgag ctaactcaca ttaattgcgt   6060
tgcgc                                                              6065
```